United States Patent
Yoshida et al.

(10) Patent No.: US 12,312,317 B2
(45) Date of Patent: May 27, 2025

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Tokyo (JP)

(72) Inventors: Kei Yoshida, Sodegaura (JP); Masatoshi Saito, Sodegaura (JP); Masato Nakamura, Sodegaura (JP); Sayaka Mizutani, Sodegaura (JP); Masato Mitani, Sodegaura (JP); Yoshinori Aoyama, Sodegaura (JP); Ryota Takahashi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 18/050,171

(22) Filed: Oct. 27, 2022

(65) Prior Publication Data
US 2023/0167072 A1   Jun. 1, 2023

Related U.S. Application Data

(63) Continuation of application No. PCT/JP2022/002577, filed on Jan. 25, 2022.

(30) Foreign Application Priority Data

Feb. 25, 2021  (JP) .................................. 2021-029020
Nov. 4, 2021   (JP) .................................. 2021-180251

(51) Int. Cl.
*C07D 239/26*   (2006.01)
*C07D 401/04*   (2006.01)
(Continued)

(52) U.S. Cl.
CPC ......... *C07D 239/26* (2013.01); *C07D 401/04* (2013.01); *C07D 401/10* (2013.01);
(Continued)

(58) Field of Classification Search
CPC ............................ C07D 239/26; H10K 85/622
See application file for complete search history.

(56) References Cited

U.S. PATENT DOCUMENTS 9,960,363 B2   5/2018   Eum et al.
10,074,809 B2  9/2018   Jang et al.
(Continued)

FOREIGN PATENT DOCUMENTS

CN    106478535 A    3/2017
CN    107188857 A    9/2017
(Continued)

OTHER PUBLICATIONS

Office Action issued Jan. 10, 2023, in Japanese Application No. 2022-568999 (w/attached Concise Explanation of Relevance of Non-English Document).

(Continued)

*Primary Examiner* — Sean M DeGuire
(74) *Attorney, Agent, or Firm* — Oblon, McClelland, Maier & Neustadt, L.L.P.

(57) ABSTRACT

A compound that further improves the capability of an organic electroluminescent device, an organic electroluminescent device having a further improved device capability, and an electronic device including the organic electroluminescent device are provided. A compound represented by the following formula (1):

(Continued)

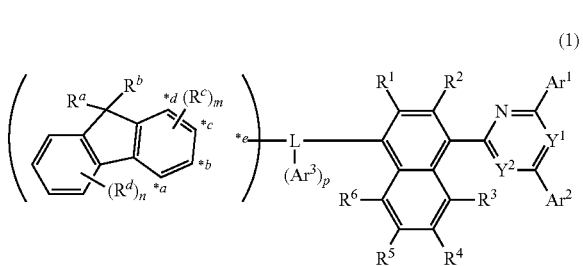

(1)

wherein the symbols in the formula (1) are defined in the description, an organic electroluminescent device including the compound, and an electronic device including the organic electroluminescent device.

10 Claims, 1 Drawing Sheet

(51) Int. Cl.
  C07D 401/10 (2006.01)
  C07D 403/04 (2006.01)
  C07D 405/04 (2006.01)
  C07D 409/04 (2006.01)
  H10K 50/16 (2023.01)
  H10K 50/18 (2023.01)
  H10K 85/60 (2023.01)
(52) U.S. Cl.
  CPC ......... *C07D 403/04* (2013.01); *C07D 405/04* (2013.01); *C07D 409/04* (2013.01); *H10K 50/16* (2023.02); *H10K 50/18* (2023.02); *H10K 85/615* (2023.02); *H10K 85/622* (2023.02); *H10K 85/654* (2023.02); *C07B 2200/05* (2013.01)

(56) References Cited

U.S. PATENT DOCUMENTS

| | | |
|---|---|---|
| 10,367,149 B2 | 7/2019 | Han et al. |
| 10,435,390 B2 | 10/2019 | Jung et al. |
| 10,930,853 B2 | 2/2021 | Kim et al. |
| 11,063,226 B1 | 7/2021 | Lee et al. |
| 11,069,861 B2 | 7/2021 | Maeda et al. |
| 2016/0211454 A1 | 7/2016 | Kim et al. |
| 2017/0098777 A1 | 4/2017 | Huh et al. |
| 2017/0104163 A1 | 4/2017 | Lee et al. |
| 2017/0179402 A1 | 6/2017 | Kim et al. |
| 2017/0222160 A1 | 8/2017 | Lee et al. |
| 2017/0244043 A1 | 8/2017 | Kim et al. |
| 2017/0317294 A1 | 11/2017 | Kim et al. |
| 2018/0053898 A1 | 2/2018 | Kim et al. |
| 2018/0053900 A1* | 2/2018 | Eum ............... C07D 239/26 |
| 2018/0114921 A1 | 4/2018 | Rothe et al. |
| 2018/0222872 A1 | 8/2018 | Jatsch et al. |
| 2018/0226587 A1 | 8/2018 | Parham et al. |
| 2019/0027698 A1 | 1/2019 | Bae et al. |
| 2019/0051835 A1 | 2/2019 | Takahashi et al. |
| 2019/0097140 A1 | 3/2019 | Kim et al. |
| 2019/0106391 A1 | 4/2019 | Wucherer-Plietker et al. |
| 2019/0214571 A1 | 7/2019 | Huh et al. |
| 2019/0378981 A1 | 12/2019 | Yoo et al. |
| 2019/0389810 A1 | 12/2019 | Cha et al. |
| 2019/0393426 A1 | 12/2019 | Masuda et al. |
| 2020/0168805 A1* | 5/2020 | Park ............... C07D 401/10 |
| 2020/0227644 A1 | 7/2020 | Lee et al. |
| 2020/0235303 A1 | 7/2020 | Kim et al. |
| 2020/0235307 A1 | 7/2020 | Cho et al. |
| 2020/0388767 A1 | 12/2020 | Masuda et al. |
| 2020/0388768 A1 | 12/2020 | Masuda et al. |
| 2021/0013422 A1 | 1/2021 | Heo et al. |
| 2021/0013439 A1 | 1/2021 | Sado et al. |
| 2021/0028365 A1 | 1/2021 | Tasaki et al. |
| 2021/0050528 A1 | 2/2021 | Cha et al. |
| 2021/0074918 A1 | 3/2021 | Kim et al. |
| 2021/0074925 A1 | 3/2021 | Yoshizaki et al. |
| 2021/0119137 A1 | 4/2021 | Cha et al. |
| 2021/0130336 A1 | 5/2021 | Shirasaki et al. |
| 2021/0143328 A1 | 5/2021 | Kim et al. |
| 2021/0296589 A1 | 9/2021 | Song et al. |
| 2021/0305516 A1 | 9/2021 | Heo et al. |
| 2021/0320265 A1 | 10/2021 | Song et al. |
| 2021/0359216 A1 | 11/2021 | Kim et al. |
| 2021/0359217 A1 | 11/2021 | Yoshida et al. |
| 2021/0367164 A1 | 11/2021 | Song et al. |
| 2022/0020929 A1 | 1/2022 | Song et al. |
| 2022/0052271 A1 | 2/2022 | Kim et al. |
| 2022/0059775 A1 | 2/2022 | Nakano et al. |
| 2022/0069232 A1 | 3/2022 | Haketa et al. |
| 2022/0085298 A1 | 3/2022 | Lee et al. |
| 2022/0165964 A1 | 5/2022 | Itoi et al. |
| 2022/0165965 A1 | 5/2022 | Itoi et al. |
| 2022/0173334 A1 | 6/2022 | Itoi et al. |
| 2022/0173335 A1 | 6/2022 | Itoi et al. |
| 2022/0181558 A1 | 6/2022 | Jun et al. |
| 2022/0199911 A1 | 6/2022 | Lee et al. |
| 2022/0223798 A1 | 7/2022 | Shiomi et al. |
| 2022/0231227 A1 | 7/2022 | Nakano et al. |
| 2022/0231231 A1 | 7/2022 | Nakamura et al. |
| 2022/0238814 A1 | 7/2022 | Yamada et al. |
| 2022/0251086 A1 | 8/2022 | Wolleb et al. |
| 2022/0255009 A1 | 8/2022 | Ryu et al. |
| 2022/0255016 A1 | 8/2022 | Aoyama et al. |
| 2022/0263032 A1 | 8/2022 | Saito et al. |
| 2022/0278294 A1 | 9/2022 | Kim et al. |
| 2022/0285625 A1 | 9/2022 | Tsasaki et al. |
| 2022/0289704 A1 | 9/2022 | Itoi et al. |
| 2022/0289726 A1 | 9/2022 | Itoi et al. |
| 2022/0310930 A1 | 9/2022 | Tasaki et al. |
| 2022/0393113 A1 | 12/2022 | Tasaki et al. |
| 2023/0026288 A1 | 1/2023 | Takahashi et al. |

FOREIGN PATENT DOCUMENTS

| | | |
|---|---|---|
| CN | 109503466 A | 3/2019 |
| CN | 109956897 A | 7/2019 |
| CN | 110964021 A | 4/2020 |
| CN | 111057005 A | 4/2020 |
| CN | 113121514 A | 7/2021 |
| CN | 114751892 | 7/2022 |
| EP | 3 527 558 A1 | 8/2019 |
| EP | 3 667 753 A2 | 6/2020 |
| EP | 3 694 012 A1 | 8/2020 |
| EP | 4 033 556 A1 | 7/2022 |
| JP | 2022/123991 | 8/2022 |
| KR | 10-2013-0135516 A | 12/2013 |
| KR | 10-2016-0085603 A | 7/2016 |
| KR | 10-2016-0111780 A | 9/2016 |
| KR | 10-2017-0086211 A | 7/2017 |
| KR | 10-2017-0086243 A | 7/2017 |
| KR | 10-2017-0086277 A | 7/2017 |
| KR | 10-2017-0086329 A | 7/2017 |
| KR | 10-2017-0093273 A | 8/2017 |
| KR | 10-2017-0111387 A | 10/2017 |
| KR | 10-2017-0136440 A | 12/2017 |
| KR | 10-2017-0141144 A | 12/2017 |
| KR | 10-2018-0063709 A | 6/2018 |
| KR | 10-2018-0063710 A | 6/2018 |
| KR | 10-2018-0123657 A | 11/2018 |
| KR | 10-1933209 B1 | 12/2018 |
| KR | 10-2019-0005522 A | 1/2019 |
| KR | 10-2019-0007789 A | 1/2019 |
| KR | 10-2019-0010500 A | 1/2019 |
| KR | 10-2019-0097713 A | 8/2019 |
| KR | 10-2019-0135398 A | 12/2019 |
| KR | 10-2020-0014189 A | 2/2020 |
| KR | 10-2020-0017727 A | 2/2020 |
| KR | 10-2020-0026079 A | 3/2020 |
| KR | 10-2020-0026754 A | 3/2020 |

(56) References Cited

FOREIGN PATENT DOCUMENTS

| | | |
|---|---|---|
| KR | 10-2084989 B1 | 3/2020 |
| KR | 10-2020-0052075 A | 5/2020 |
| KR | 10-2020-0052081 A | 5/2020 |
| KR | 10-2020-0081976 A | 7/2020 |
| KR | 10-2020-0081983 A | 7/2020 |
| KR | 10-2020-0081985 A | 7/2020 |
| KR | 10-2020-0081986 A | 7/2020 |
| KR | 10-2020-0095730 A | 8/2020 |
| KR | 10-2148056 B1 | 8/2020 |
| KR | 10-2020-0125080 A | 11/2020 |
| KR | 10-2020-0129334 A | 11/2020 |
| KR | 10-2020-0129993 | 11/2020 |
| KR | 10-2020-0129993 A | 11/2020 |
| KR | 10-2020-0131681 A | 11/2020 |
| KR | 10-2020-0133423 | 11/2020 |
| KR | 10-2020-0134877 | 12/2020 |
| KR | 10-2020-0141385 | 12/2020 |
| KR | 10-2020-0145198 | 12/2020 |
| KR | 10-2020-0145223 | 12/2020 |
| KR | 10-2020-0145270 | 12/2020 |
| KR | 10-2021-0015723 A | 2/2021 |
| KR | 10-2021-0015724 A | 2/2021 |
| KR | 10-2021-0032184 A | 3/2021 |
| KR | 10-2238703 B1 | 4/2021 |
| KR | 10-2252291 B1 | 5/2021 |
| KR | 10-2021-0077686 A | 6/2021 |
| KR | 10-2021-0077690 A | 6/2021 |
| KR | 10-2021-0080655 A | 7/2021 |
| KR | 10-2021-0085530 A | 7/2021 |
| KR | 10-2021-0095582 A | 8/2021 |
| KR | 10-2021-0096630 A | 8/2021 |
| KR | 10-2022-0020313 | 2/2022 |
| KR | 10-2022-0020447 | 2/2022 |
| WO | WO 2015/152633 A1 | 10/2015 |
| WO | WO 2016/105141 A2 | 6/2016 |
| WO | WO 2017/131380 A1 | 8/2017 |
| WO | WO 2017/157983 A1 | 9/2017 |
| WO | WO 2018/225940 A1 | 12/2018 |
| WO | WO 2018/236040 A1 | 12/2018 |
| WO | WO 2019/017616 A1 | 1/2019 |
| WO | WO 2019/156405 A1 | 8/2019 |
| WO | WO 2020/050217 A1 | 3/2020 |
| WO | WO 2020/050372 A1 | 3/2020 |
| WO | WO 2020/080720 A1 | 4/2020 |
| WO | WO 2020/096012 A1 | 5/2020 |
| WO | WO 2020/096021 A1 | 5/2020 |
| WO | WO 2020/115933 A1 | 6/2020 |
| WO | WO 2020/153758 A1 | 7/2020 |
| WO | WO 2020/209292 A1 | 10/2020 |
| WO | WO 2020/209293 A1 | 10/2020 |
| WO | WO 2020/209299 A1 | 10/2020 |
| WO | WO 2020/209307 A1 | 10/2020 |
| WO | WO 2020/209309 A1 | 10/2020 |
| WO | WO 2020/209310 A1 | 10/2020 |
| WO | WO 2020/241580 A1 | 12/2020 |
| WO | WO 2021/025162 A1 | 2/2021 |
| WO | WO 2021/025163 A1 | 2/2021 |
| WO | WO 2021/049651 A1 | 3/2021 |
| WO | WO 2021/049653 A1 | 3/2021 |
| WO | WO 2021/049654 A1 | 3/2021 |
| WO | WO 2021/049655 A1 | 3/2021 |
| WO | WO 2021/049660 A1 | 3/2021 |
| WO | WO 2021/049661 A1 | 3/2021 |
| WO | WO 2021/049662 A1 | 3/2021 |
| WO | WO 2021/049663 A1 | 3/2021 |
| WO | WO 2021/090930 A1 | 5/2021 |
| WO | WO 2021/090931 A1 | 5/2021 |
| WO | WO 2021/090932 A1 | 5/2021 |
| WO | WO 2021/090933 A1 | 5/2021 |
| WO | WO 2021/090934 A1 | 5/2021 |
| WO | WO 2021/132535 A1 | 7/2021 |
| WO | WO 2021/150048 A1 | 7/2021 |
| WO | WO 2021/172292 | 9/2021 |
| WO | WO 2021/250277 | 12/2021 |
| WO | WO 2021/250279 | 12/2021 |
| WO | WO 2021/256564 | 12/2021 |
| WO | WO 2021/256565 | 12/2021 |
| WO | WO 2022/010302 | 1/2022 |
| WO | WO 2022/025021 | 2/2022 |
| WO | WO 2022/082764 | 4/2022 |
| WO | WO 2022/091691 | 5/2022 |
| WO | WO 2022/114115 | 6/2022 |
| WO | WO 2022/114156 | 6/2022 |
| WO | WO 2022/118867 | 6/2022 |
| WO | WO 2022/138107 | 6/2022 |
| WO | WO 2022/138948 | 6/2022 |
| WO | WO 2022/138950 | 6/2022 |
| WO | WO 2022/139445 | 6/2022 |
| WO | WO 2022/149476 | 7/2022 |
| WO | WO 2022/154030 | 7/2022 |
| WO | WO 2022/158578 | 7/2022 |
| WO | WO 2022/163626 | 8/2022 |

OTHER PUBLICATIONS

International Search Report dated Mar. 22, 2022, in PCT/JP2022/002577 (3 pages).
Official Communication issued Mar. 26, 2024, in Korean Patent Application No. 10-2022-7041460 (with English language translation).
Communication issued in EP Application 22759199.7 on Dec. 23, 2024 (12 pages).
Official communication issued in EP application 22759199.7 on Mar. 21, 2025 (12 pages).

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

TECHNICAL FIELD

The present invention relates to a compound, a material for an organic electroluminescent device, an organic electroluminescent device, and an electronic device including the organic electroluminescent device.

BACKGROUND ART

In general, an organic electroluminescent device (which may be hereinafter referred to as an "organic EL device") is constituted by an anode, a cathode, and an organic layer intervening between the anode and the cathode. In application of a voltage between both the electrodes, electrons from the cathode side and holes from the anode side are injected into the light emitting region, and the injected electrons and holes are recombined in the light emitting region to generate an excited state, which then returns to the ground state to emit light. Accordingly, development of a material that efficiently transports electrons or holes into the light emitting region, and promotes recombination of the electrons and holes is important for providing a high-performance organic EL device.

PTLs 1 to 12 describe compounds used for a material for an organic electroluminescent device.

CITATION LIST

Patent Literatures

PTL 1: WO 2016/105141
PTL 2: WO 2015/152633
PTL 3: WO 2017/157983
PTL 4: WO 2018/236040
PTL 5: KR 10-2018-0063709 A
PTL 6: CN 109956897 A
PTL 7: WO 2020/080720
PTL 8: KR 10-2019-135398 A
PTL 9: WO 2018/225940
PTL 10: KR 10-2013-135516 A
PTL 11: KR 10-2019-97713 A
PTL 12: KR 10-2017-136440 A

Technical Problem

Various compounds for organic EL devices have been reported, but a compound that further enhances the capability of an organic EL device has been still demanded.

The present invention has been made for solving the problem, and an object thereof is to provide a compound that further improves the capability of an organic EL device, an organic EL device having a further improved device capability, and an electronic device including the organic EL device.

In the present invention, the "further improvement of the capability of an organic EL device" means the prolongation of the lifetime, the enhancement of the efficiency, the decrease of the driving voltage, and the like, but is not limited thereto.

Solution to Problem

As a result of the earnest investigations by the present inventors on the capabilities of organic EL devices containing the compounds described in PTLs 1 to 12, it has been found that an organic EL device including a compound represented by the following formula (1) has a further improved capability.

In one embodiment, the present invention provides a compound represented by the following formula (1):

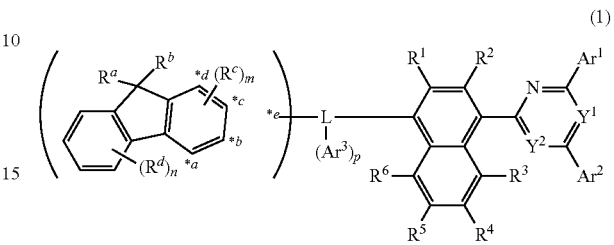

wherein in the formula (1),
any one of $Y^1$ and $Y^2$ represents a nitrogen atom, and the other one thereof represents $CR^{10}$,
$Ar^1$ to $Ar^3$ each independently represent a substituted or unsubstituted aryl group having 6 to 30 ring carbon atoms or a substituted or unsubstituted heterocyclic group having 5 to 30 ring atoms,
L represents a single bond or a substituted or unsubstituted (2+p)-valent aromatic hydrocarbon ring having 6 to 30 ring carbon atoms,
p represents an integer of 0 to 3, in which p represents 0 in the case where L represents a single bond, and p represents an integer of 0 to 3 in the case where L represents a substituted or unsubstituted (2+p)-valent aromatic hydrocarbon ring having 6 to 30 ring carbon atoms,
in the case where two or more groups represented by $Ar^3$ exist, the two or more groups represented by $Ar^3$ are the same as or different from each other,
$R^1$ to $R^6$, $R^{10}$, $R^c$, and $R^d$ each independently represent
a hydrogen atom,
a halogen atom,
a cyano group,
a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a group represented by $—Si(R_{901})(R_{902})(R_{903})$,
a group represented by $—O—(R_{904})$,
a group represented by $—S—(R_{905})$,
a group represented by $—N(R_{906})(R_{907})$,
a substituted or unsubstituted aryl group having 6 to 50 ring carbon atoms, or
a substituted or unsubstituted heterocyclic group having 5 to 50 ring atoms,
$R_{901}$ to $R_{907}$ each independently represent
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or a substituted or unsubstituted heterocyclic group having 5 to 50 ring atoms, in the case where two or more groups represented by $R_{901}$ exist, the two or more groups represented by $R_{901}$ are the same as or different from each other, in the case where two or more groups represented by $R_{902}$ exist, the two or more groups represented by $R_{902}$ are the same as or different from each other, in the case where two or more groups represented by $R_{903}$ exist, the two or more groups represented by $R_{903}$ are the same as or different from each other, in the case where two or more groups represented by $R_{904}$ exist, the two or more groups represented by $R_{904}$ are the same as or different from each other, in the case where two or more groups represented by $R_{905}$ exist, the two or more groups represented by $R_{905}$ are the same as or different from each other, in the case where two or more groups represented by $R_{906}$ exist, the two or more groups represented by $R_{906}$ are the same as or different from each other, in the case where two or more groups represented by $R_{907}$ exist, the two or more groups represented by $R_{907}$ are the same as or different from each other, $R^a$ and $R^b$ each independently represent a hydrogen atom, a substituted or unsubstituted alkyl group having 1 to 50 carbon atoms, or a substituted or unsubstituted aryl group having 6 to 50 ring carbon atoms, $R^1$ and $R^2$, $R^a$ and $R^b$, and two groups represented by $R^c$ adjacent to each other each are not bonded to each other to form a ring, in one or more combination selected from $R^3$ and $R^4$, $R^4$ and $R^5$, $R^5$ and $R^6$, and two groups represented by $R^d$ adjacent to each other, two groups adjacent to each other may be bonded to each other to form a substituted or unsubstituted ring, m represents 3, n represents 4, groups represented by $R^c$ are the same as or different from each other, groups represented by $R^d$ are the same as or different from each other, and e is bonded to any one selected from carbon atoms *a, *b, *c, and *d.

In another embodiment, the present invention provides a material for an organic EL device, containing the compound represented by the formula (1).

In still another embodiment, the present invention provides an organic electroluminescent device including an anode, a cathode, and organic layers intervening between the anode and the cathode, the organic layers including a light emitting layer, at least one layer of the organic layers containing the compound represented by the formula (1).

In further another embodiment, the present invention provides an electronic device including the organic electroluminescent device.

Advantageous Effects of Invention

An organic EL device containing the compound represented by the formula (1) shows an improved device capability.

DESCRIPTION OF EMBODIMENTS

Definitions

Figure 1:
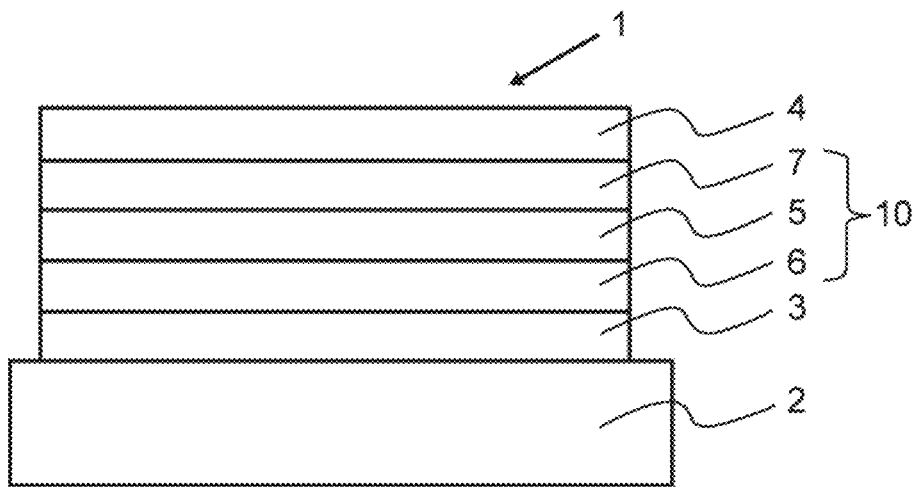
FIG. 1 is a schematic illustration showing an example of the layer configuration of the organic EL device according to one embodiment of the present invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly, a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly, a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly, a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly, a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A)

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenarenyl group,
a pyrenyl group, a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
monovalent aryl groups derived by removing one hydrogen atom from each of the ring structures represented by the following general formulae (TEMP-1) to (TEMP-15):

(TEMP-1)
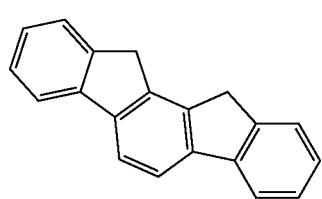

(TEMP-2)
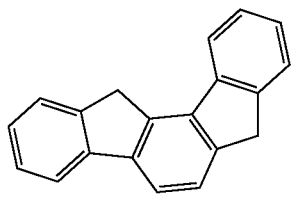

(TEMP-3)
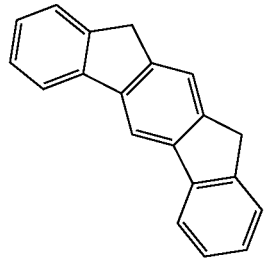

(TEMP-4)
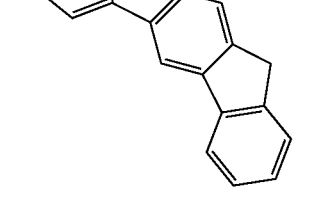

(TEMP-5)
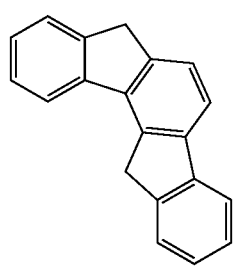

(TEMP-6)
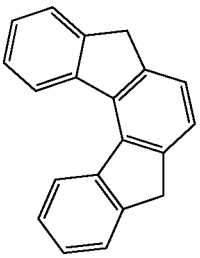

(TEMP-7)
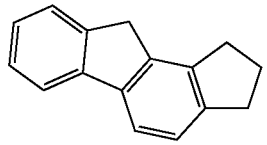

(TEMP-8)
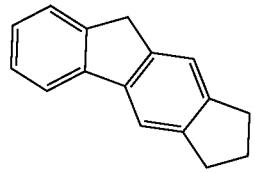

(TEMP-9)
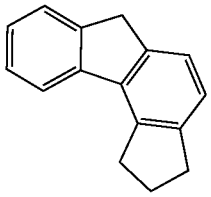

(TEMP-10)
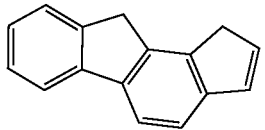

(TEMP-11)
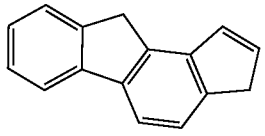

(TEMP-12)
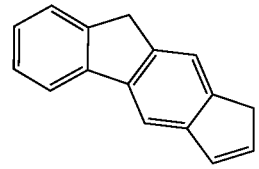

(TEMP-13)
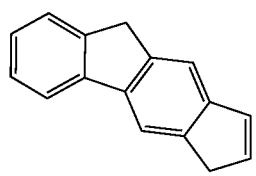

-continued

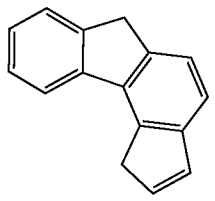
(TEMP-14)

(TEMP-15)

Substituted Aryl Group (Set of Specific Examples G1B)

an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
a o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G32B4).

Unsubstituted Heterocyclic Group Containing Nitrogen Atom (Set of Specific Examples G2A1)

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group, a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing
Oxygen Atom (Set of Specific Examples G2A2)

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing
Sulfur Atom (Set of Specific Examples G2A3)

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group Derived by
Removing One Hydrogen Atom from Ring
Structures Represented by General Formulae
(TEMP-16) to (TEMP-33) (Set of Specific
Examples G2A4)

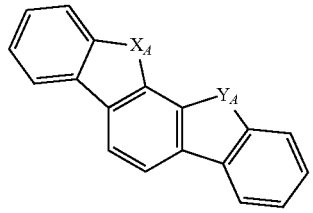

(TEMP-16)

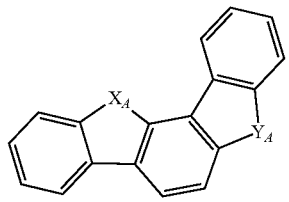

(TEMP-17)

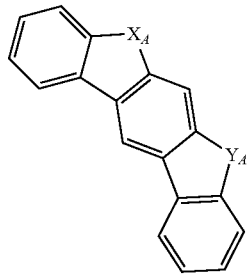

(TEMP-18)

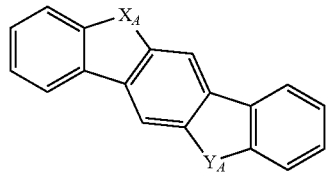

(TEMP-19)

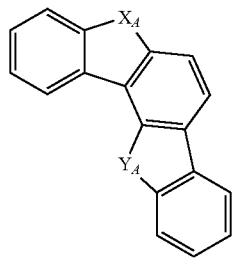

(TEMP-20)

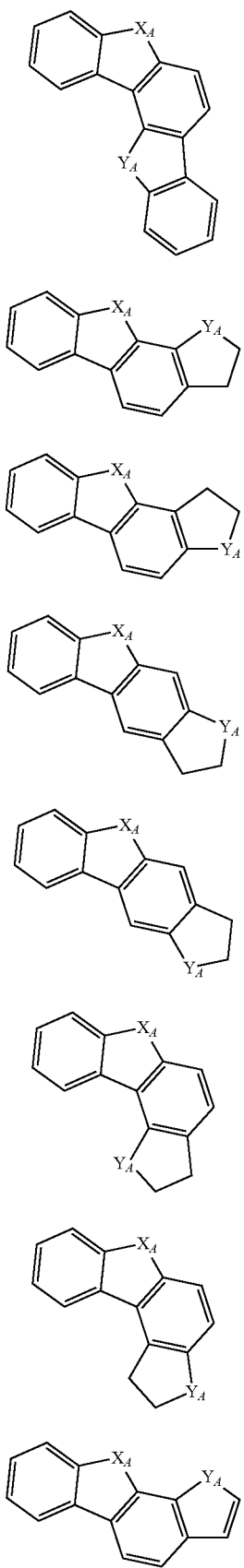
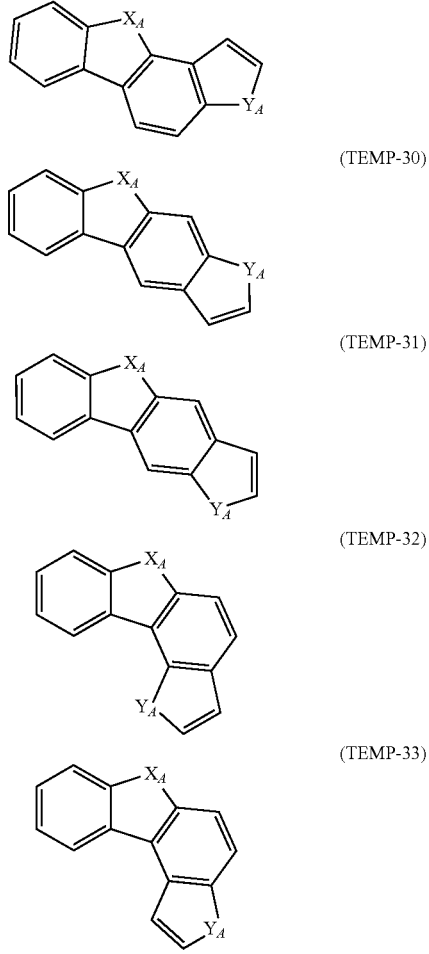

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group Containing Nitrogen Atom (Set of Specific Examples G2B1)

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenyltriazinyl group,
a diphenyltriazinyl group,
a phenylquinazolinyl group, and
a biphenylquinazolinyl group.

Substituted Heterocyclic Group Containing Oxygen
Atom (Set of Specific Examples G2B2)

a phenyldibenzofuranyl group,
a methyldibenzofuranyl group,
a t-butyldibenzofuranyl group, and
a monovalent residual group of spiro[9H-xanthene-9,9'-[9H]fluorene].

Substituted Heterocyclic Group Containing Sulfur
Atom (Set of Specific Examples G2B3)

a phenyldibenzothiophenyl group,
a methyldibenzothiophenyl group,
a t-butyldibenzothiophenyl group, and
a monovalent residual group of spiro[9H-thioxanthene-9,9'-[9H]fluorene].

Group Formed by Substituting One or More
Hydrogen Atom of Monovalent Heterocyclic Group
Derived from Ring Structures Represented by
General Formulae (TEMP-16) to (TEMP-33) by
Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$ represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly, the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific
Examples G3A)

a methyl group,
an ethyl group,
a n-propyl group,
an isopropyl group,
a n-butyl group,
an isobutyl group,
a s-butyl group, and
a t-butyl group.

Substituted Alkyl Group (Set of Specific Examples
G3B)

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific
Examples G4A)

a vinyl group,
an allyl group,
a 1-butenyl group,
a 2-butenyl group, and
a 3-butenyl group.

Substituted Alkenyl Group (Set of Specific
Examples G4B)

a 1,3-butanedienyl group,
a 1-methylvinyl group,
a 1-methylallyl group,
a 1,1-dimethylallyl group, a 2-methylallyl group, and a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5A) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5A) by a substituent.

Unsubstituted Alkynyl Group (Set of Specific Examples G5A)

an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6A) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A)

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Set of Specific Examples G6B)

a 4-methylcyclohexyl group.

Group Represented by $-Si(R_{901})(R_{902})(R_{903})$

In the description herein, specific examples (set of specific examples G7) of the group represented by $-Si(R_{901})(R_{902})(R_{903})$ include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group Represented by $-O-(R_{904})$

In the description herein, specific examples (set of specific examples G8) of the group represented by $-O-(R_{904})$ include:

—O(G1),
—O(G2),
—O(G3), and
—O(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by $-S-(R_{905})$

In the description herein, specific examples (set of specific examples G9) of the group represented by $-S-(R_{905})$ include:

—S(G1),
—S(G2),

—S(G3), and
—S(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —N($R_{906}$)($R_{907}$)

In the description herein, specific examples (set of specific examples G10) of the group represented by —N($R_{906}$)($R_{907}$) include:

—N(G1)(G1),
—N(G2)(G2),
—N(G1)(G2),
—N(G3)(G3), and
—N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)

(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a 6-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

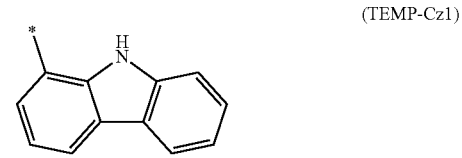
(TEMP-Cz1)

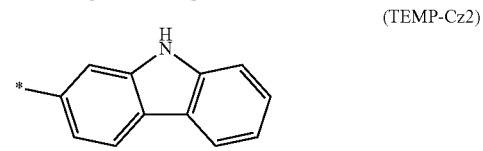
(TEMP-Cz2)

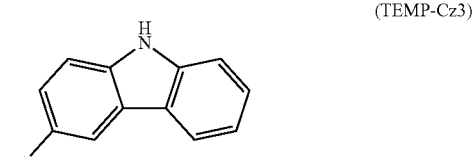
(TEMP-Cz3)

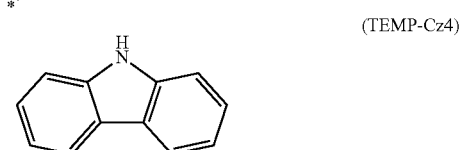
(TEMP-Cz4)

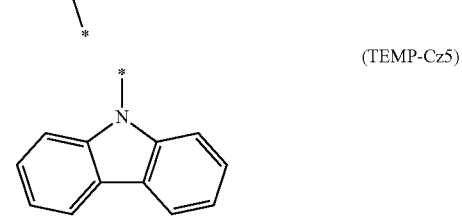
(TEMP-Cz5)

In the description herein, the (9-phenyl)carbazolyl group is specifically any one of the following groups unless otherwise indicated in the description.

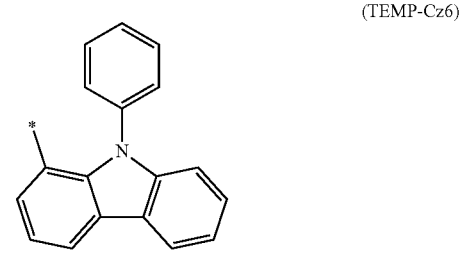
(TEMP-Cz6)

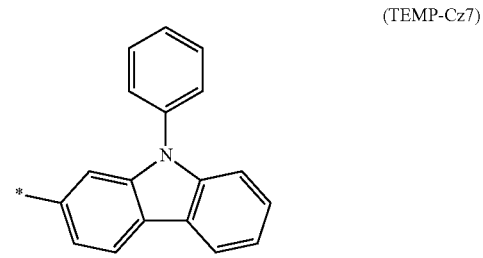
(TEMP-Cz7)

(TEMP-Cz8)

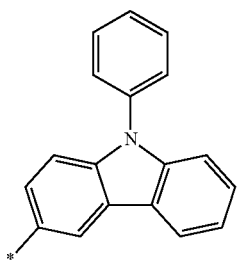

(TEMP-Cz9)

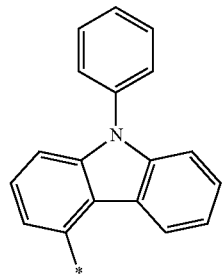

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

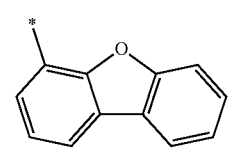

(TEMP-35)

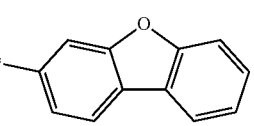

(TEMP-36)

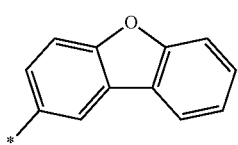

(TEMP-37)

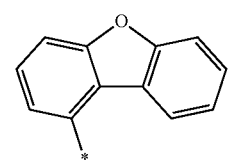

(TEMP-38)

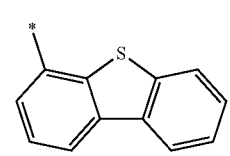

(TEMP-39)

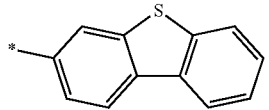

(TEMP-40)

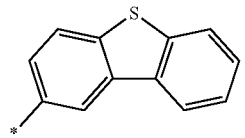

(TEMP-41)

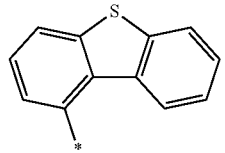

In the general formulae (TEMP-34) to (TEMP-41), * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

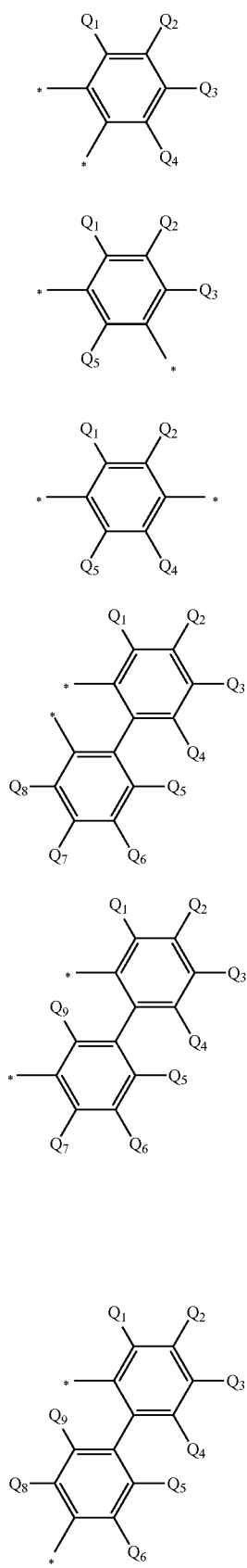
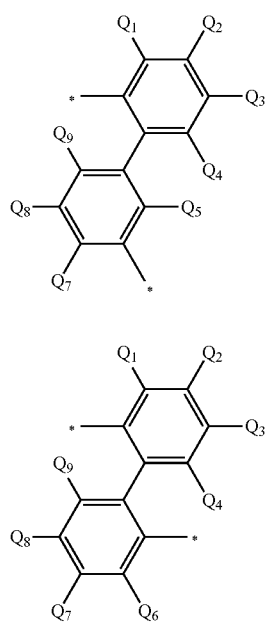
In the general formulae (TEMP-42) to (TEMP-52), $Q_1$ to $Q_{10}$ each independently represent a hydrogen atom or a substituent.
In the general formulae (TEMP-42) to (TEMP-52), * represents a bonding site.

(TEMP-53) 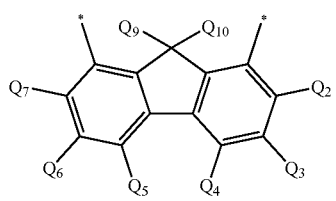
(TEMP-54) 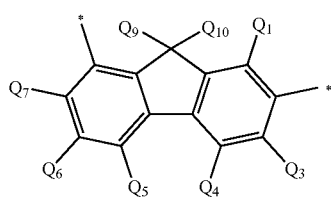
(TEMP-55) 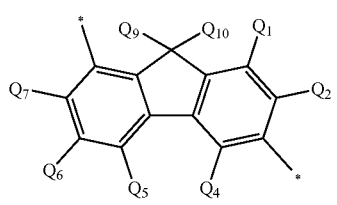
(TEMP-56) 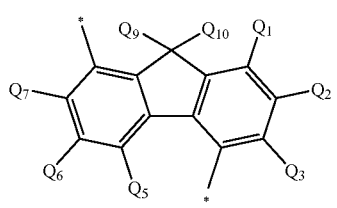
(TEMP-57) 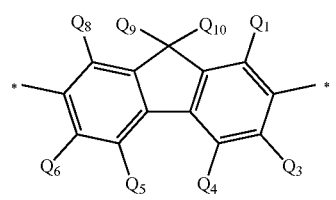
(TEMP-58) 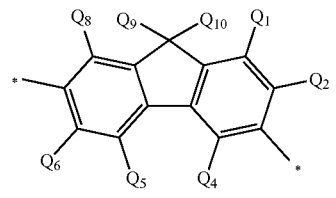
(TEMP-59) 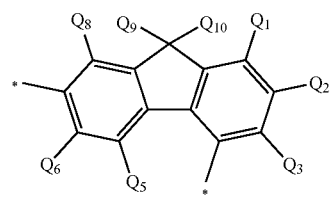
(TEMP-60) 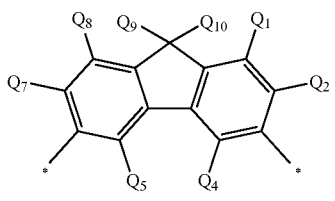
(TEMP-61) 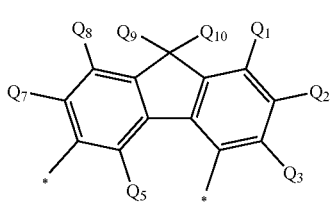
(TEMP-62) 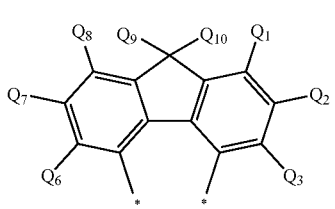
In the general formulae (TEMP-53) to (TEMP-62), $Q_1$ to $Q_{10}$ each independently represent a hydrogen atom or a substituent.
The formulae $Q_9$ and $Q_{10}$ may be bonded to each other to form a ring via a single bond.
In the general formulae (TEMP-53) to (TEMP-62), * represents a bonding site.
(TEMP-63) 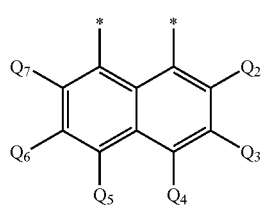
(TEMP-64) 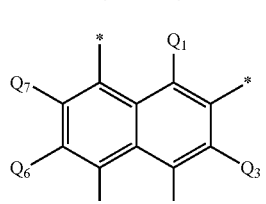
(TEMP-65) 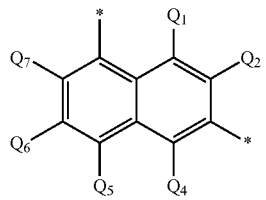

(TEMP-66)
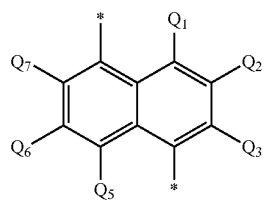

(TEMP-67)
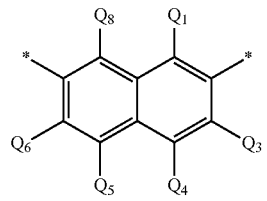

(TEMP-68)
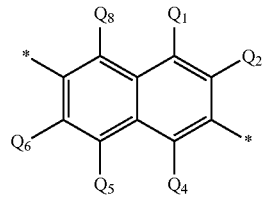

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

(TEMP-69)
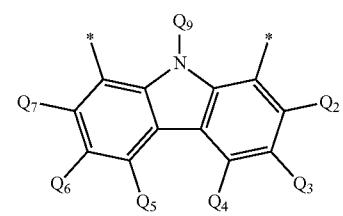

(TEMP-70)
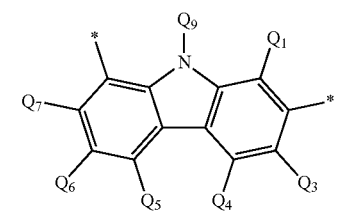

(TEMP-71)
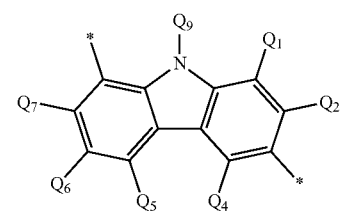

(TEMP-72)
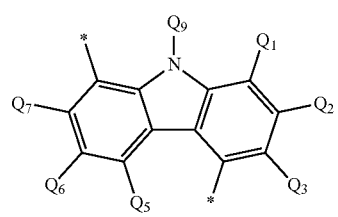

(TEMP-73)
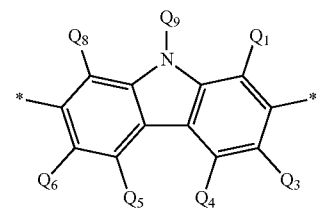

(TEMP-74)
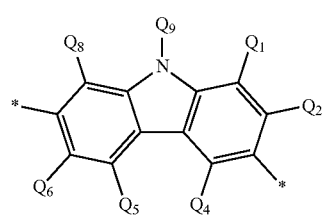

(TEMP-75)
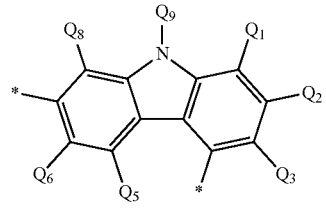

(TEMP-76)
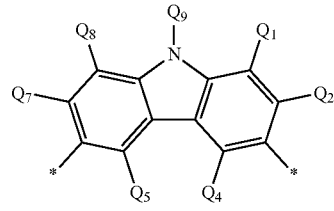

(TEMP-77)
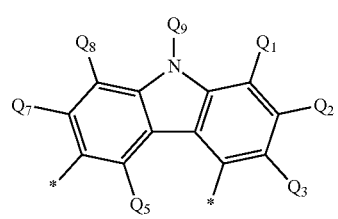

(TEMP-78)
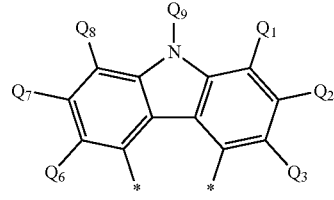

(TEMP-79)
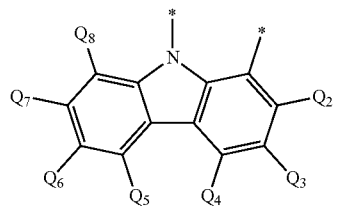
(TEMP-80)
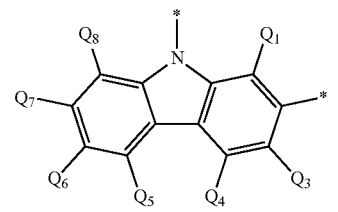
(TEMP-81)
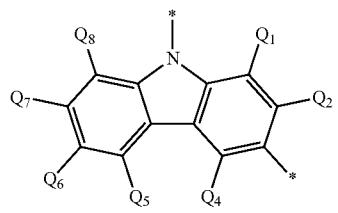
(TEMP-82)
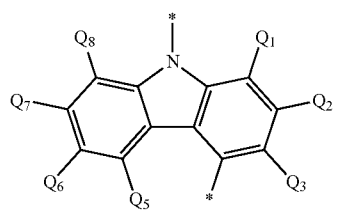
In the general formulae (TEMP-69) to (TEMP-82), $Q_1$ to $Q_9$ each independently represent a hydrogen atom or a substituent.
(TEMP-83)
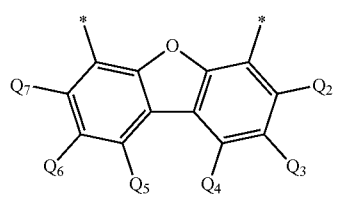
(TEMP-84)
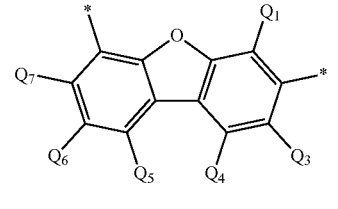
(TEMP-85)
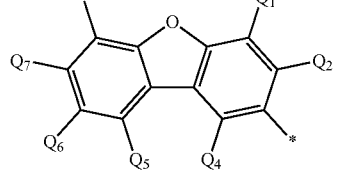
(TEMP-86)
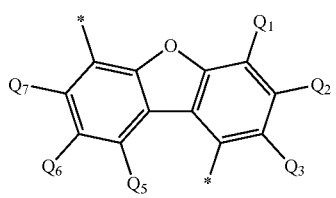
(TEMP-87)
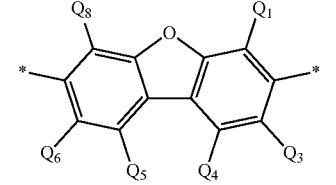
(TEMP-88)
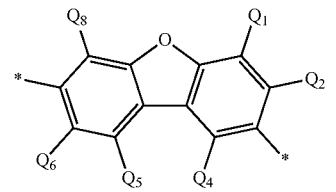
(TEMP-89)
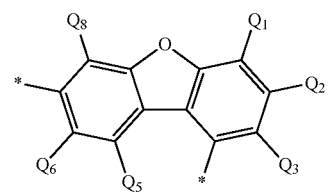
(TEMP-90)
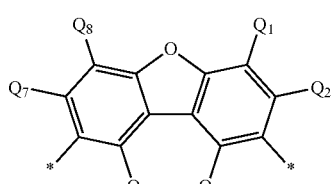
(TEMP-91)
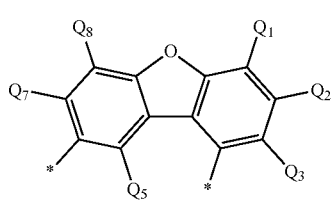
(TEMP-92)
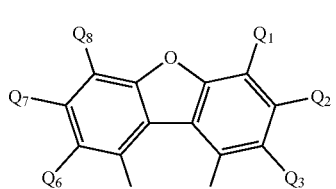
(TEMP-93)
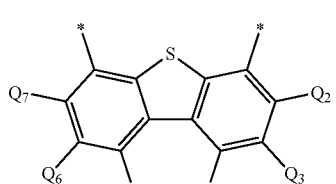

(TEMP-94)
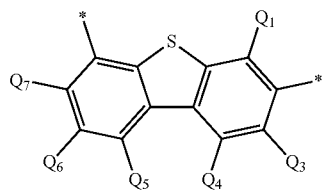

(TEMP-95)
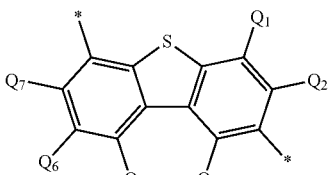

(TEMP-96)
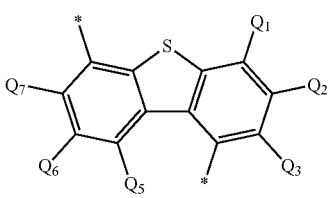

(TEMP-97)
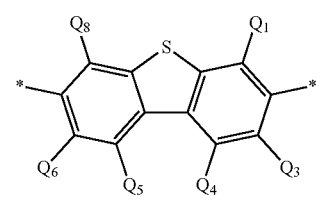

(TEMP-98)
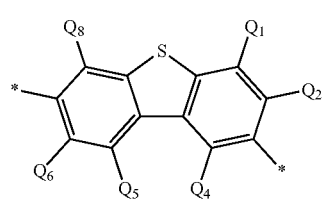

(TEMP-99)
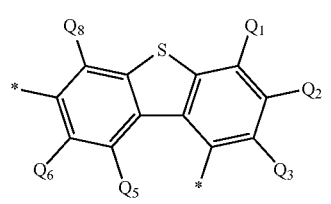

(TEMP-100)
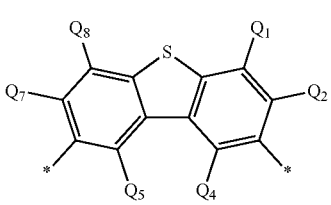

(TEMP-101)
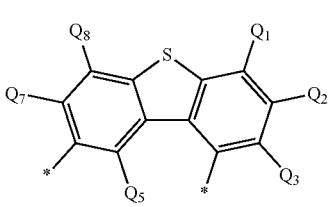

(TEMP-102)
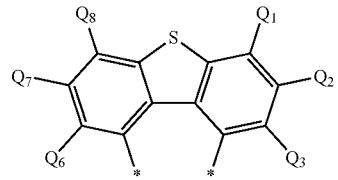

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)
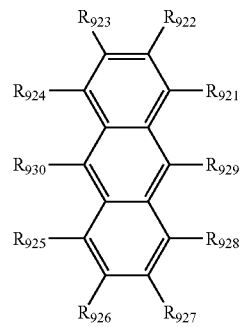

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

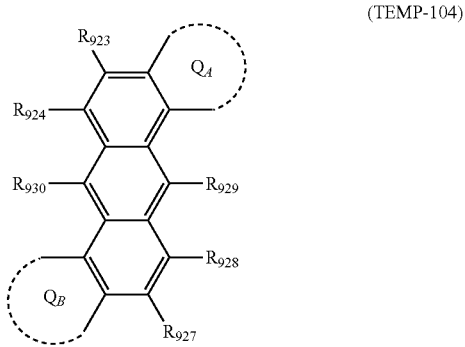

(TEMP-104)

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

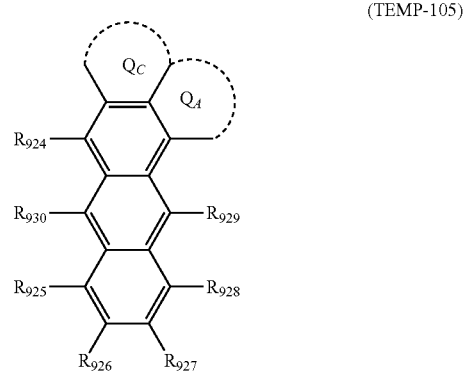

(TEMP-105)

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TEMP-104) is a benzene ring, the ring $Q_A$ is a monocyclic ring. In the case where the ring $Q_A$ in the general formula (TEMP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group having 6 to 50 ring carbon atoms, and
an unsubstituted heterocyclic group having 5 to 50 ring atoms, wherein $R_{901}$ to $R_{907}$ each independently represent
a hydrogen atom.
a substituted or unsubstituted alkyl group having 1 to 50 carbon atoms
a substituted or unsubstituted cycloalkyl group having 3 to 50 ring carbon atoms,
a substituted or unsubstituted aryl group having 6 to 50 ring carbon atoms, or
a substituted or unsubstituted heterocyclic group having 5 to 50 ring atoms.

In the case where two or more groups each represented by $R_{901}$ exist, the two or more groups each represented by $R_{901}$ are the same as or different from each other,
in the case where two or more groups each represented by $R_{902}$ exist, the two or more groups each represented by $R_{902}$ are the same as or different from each other,
in the case where two or more groups each represented by $R_{903}$ exist, the two or more groups each represented by $R_{903}$ are the same as or different from each other,
in the case where two or more groups each represented by $R_{904}$ exist, the two or more groups each represented by $R_{904}$ are the same as or different from each other,
in the case where two or more groups each represented by $R_{905}$ exist, the two or more groups each represented by $R_{905}$ are the same as or different from each other,
in the case where two or more groups each represented by $R_{906}$ exist, the two or more groups each represented by $R_{906}$ are the same as or different from each other, and
in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of
an alkyl group having 1 to 50 carbon atoms,
an aryl group having 6 to 50 ring carbon atoms, and
a heterocyclic group having 5 to 50 ring atoms.

In one embodiment, the substituent for the case of "substituted or unsubstituted" may be a group selected from the group consisting of
an alkyl group having 1 to 18 carbon atoms,
an aryl group having 6 to 18 ring carbon atoms, and
a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will be described below.

The compound according to one embodiment of the present invention is represented by the following formula (1).

In the following description, the compounds of the present invention represented by the formula (1) and the subordinate formulae of the formula (1) described later each may be referred simply to as an "inventive compound (1)" or an "inventive compound".

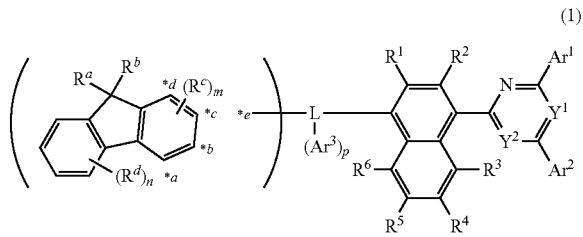

(1)

The symbols in the formula (1) and the subordinate formulae of the formula (1) described later will be explained below. The same symbols have the same meaning.

In the formula (1),
any one of $Y^1$ and $Y^2$ represents a nitrogen atom, and the other one thereof represents $CR^{10}$, and preferably a methine group (CH).

It is preferred that $Y^1$ represents a nitrogen atom, and $Y^2$ represents $CR^{10}$, and preferably a methine group (CH).

In the formula (1),
$Ar^1$ to $Ar^3$ each independently represent a substituted or unsubstituted aryl group having 6 to 30 ring carbon atoms or a substituted or unsubstituted heterocyclic group having 5 to 30 ring atoms.

The details of the substituted or unsubstituted aryl group having 6 to 30 ring carbon atoms represented by $Ar^1$ to $Ar^3$ have been described in the section "Substituents in Description" above.

The unsubstituted aryl group represented by $Ar^1$ to $Ar^3$ is preferably a phenyl group, a biphenylyl group, a naphthyl group, or a fluorenyl group.

The details of the substituted or unsubstituted heterocyclic group having 5 to 30 ring atoms represented by $Ar^1$ to $Ar^3$ have been described in the section "Substituents in Description" above.

The unsubstituted heterocyclic group represented by $Ar^1$ to $Ar^3$ is preferably a pyridyl group, a quinolyl group, a dibenzofuranyl group, or a dibenzothiophenyl group.

$Ar^1$ preferably represents a substituted or unsubstituted aryl group having 6 to 30 ring carbon atoms, more preferably a phenyl group, a biphenylyl group, a naphthyl group, or a fluorenyl group, and more preferably a phenyl group.

In another embodiment, $Ar^1$ preferably represents a substituted or unsubstituted heterocyclic group having 5 to 30 ring atoms, and more preferably a pyridyl group, a quinolyl group, a dibenzofuranyl group, or a dibenzothiophenyl group.

In one embodiment, $Ar^2$ preferably represents a substituted or unsubstituted aryl group having 6 to 30 ring carbon atoms, more preferably a phenyl group, a biphenylyl group, a naphthyl group, or a fluorenyl group, and more preferably a phenyl group.

In another embodiment, $Ar^2$ preferably represents a substituted or unsubstituted heterocyclic group having 5 to 30 ring atoms, and more preferably a pyridyl group, a quinolyl group, a dibenzofuranyl group, or a dibenzothiophenyl group.

$Ar^3$ preferably represents a phenyl group, a naphthyl group, a pyridyl group, a dibenzofuranyl group, or a dibenzothiophenyl group, and more preferably a phenyl group or a naphthyl group.

In the case where two or more groups represented by $Ar^3$ exist, the two or more groups represented by $Ar^3$ are the same as or different from each other.

$Ar^1$ and $Ar^2$ are preferably different from each other, and more preferably each represent an aryl group and are different from each other.

One of $Ar^1$ and $Ar^2$ preferably has a terphenyl structure shown below.

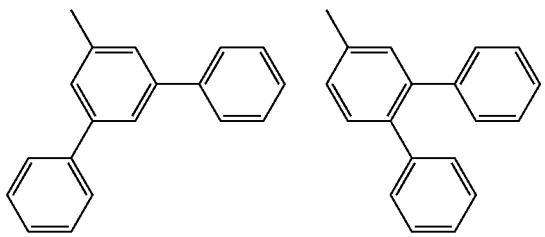

L represents a single bond or a substituted or unsubstituted (2+p)-valent aromatic hydrocarbon ring having 6 to 30 ring carbon atoms.

In one embodiment of the present invention, L preferably represents a single bond. In another embodiment, L preferably represents a substituted or unsubstituted (2+p)-valent aromatic hydrocarbon ring having 6 to 30 ring carbon atoms.

Examples of the substituted or unsubstituted (2+p)-valent aromatic hydrocarbon ring having 6 to 30 ring carbon atoms represented by L include a phenylene group, a biphenylyldiyl group, a terphenylylene group, a naphthylene group, an anthrylene group, a benzoanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluorantenylene group, or a fluorenylene group.

The substituted or unsubstituted (2+p)-valent aromatic hydrocarbon ring having 6 to 30 ring carbon atoms represented by L is preferably a phenylene group, a biphenylene group, or a naphthylene group, and more preferably a phenylene group or a naphthylene group.

p represents an integer of 0 to 3, in which p represents 0 in the case where L represents a single bond, and p represents an integer of 0 to 3 in the case where L represents a substituted or unsubstituted (2+p)-valent aromatic hydrocarbon ring having 6 to 30 ring carbon atoms.

p preferably represents 0 or 1, and more preferably 0.

$R^1$ to $R^6$, $R^{10}$, $R^c$, and $R^d$ each independently represent a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aryl group having 6 to 50 ring carbon atoms, or a substituted or unsubstituted heterocyclic group having 5 to 50 ring atoms, in which $R_{901}$ to $R_{907}$ each independently represent a hydrogen atom a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, in which in the case where two or more groups represented by $R_{901}$ exist, the two or more groups represented by $R_{901}$ are the same as or different from each other, in the case where two or more groups represented by $R_{902}$ exist, the two or more groups represented by $R_{902}$ are the same as or different from each other, in the case where two or more groups represented by $R_{903}$ exist, the two or more groups represented by $R_{903}$ are the same as or different from each other, in the case where two or more groups represented by $R_{904}$ exist, the two or more groups represented by $R_{904}$ are the same as or different from each other, in the case where two or more groups represented by $R_{905}$ exist, the two or more groups represented by $R_{905}$ are the same as or different from each other, in the case where two or more groups represented by $R_{906}$ exist, the two or more groups represented by $R_{906}$ are the same as or different from each other, and in the case where two or more groups represented by $R_{907}$ exist, the two or more groups represented by $R_{907}$ are the same as or different from each other.

$R^a$ and $R^b$ each independently represent a hydrogen atom, a substituted or unsubstituted alkyl group having 1 to 50 carbon atoms, or a substituted or unsubstituted aryl group having 6 to 50 ring carbon atoms.

$R^1$ and $R^2$, $R^a$ and $R^b$, and two groups represented by $R^c$ adjacent to each other each are not bonded to each other to form a ring, and in one or more combination selected from $R^3$ and $R^4$, $R^4$ and $R^5$, $R^5$ and $R^6$, and two groups represented by $R^d$ adjacent to each other, two groups adjacent to each other may be bonded to each other to form a substituted or unsubstituted ring.

m represents 3, n represents 4, groups represented by $R^c$ are the same as or different from each other, and groups represented by $R^d$ are the same as or different from each other.

$R^1$ to $R^6$, $R^c$, and $R^d$ each independently preferably represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, more preferably a hydrogen atom or a substituted or unsubstituted alkyl group having 1 to 50 carbon atoms, and further preferably a hydrogen atom.

$R^a$ and $R^b$ each independently preferably represent a substituted or unsubstituted alkyl group having 1 to 50 carbon atoms or a substituted or unsubstituted aryl group having 6 to 50 ring carbon atoms.

Both $R^a$ and $R^b$ may be substituted or unsubstituted alkyl groups having 1 to 50 carbon atoms. Both $R^a$ and $R^b$ may be substituted or unsubstituted aryl groups having 6 to 50 ring carbon atoms. It is possible that one of $R^a$ and $R^b$ is a substituted or unsubstituted alkyl group having 1 to 50 carbon atoms, and the other of $R^a$ and $R^b$ is a substituted or unsubstituted aryl group having 6 to 50 ring carbon atoms.

The details of the halogen atom represented by $R^1$ to $R^6$, $R^c$, and $R^d$ have been described in the section "Substituents in Description" above, and a fluorine atom is preferred.

The details of the substituted or unsubstituted alkyl group having 1 to 50 carbon atoms represented by $R^1$ to $R^6$, $R^a$, $R^b$, $R^c$, and $R^d$ have been described in the section "Substituents in Description" above.

The unsubstituted alkyl group represented by $R^1$ to $R^6$, $R^a$, $R^b$, $R^c$, and $R^d$ is preferably a methyl group, an ethyl group, a n-propyl group, an isopropyl group, a n-butyl group, an isobutyl group, a s-butyl group, or a t-butyl group, more preferably a methyl group, an ethyl group, an isopropyl group, or a t-butyl group, and further preferably a methyl group or a t-butyl group.

The details of the substituted or unsubstituted alkenyl group having 2 to 50 ring carbon atoms represented by $R^1$ to $R^6$, $R^c$, and $R^d$ have been described in the section "Substituents in Description" above.

The details of the substituted or unsubstituted alkynyl group having 2 to 50 ring carbon atoms represented by $R^1$ to $R^6$, $R^c$, and $R^d$ have been described in the section "Substituents in Description" above.

The details of the substituted or unsubstituted cycloalkyl group having 3 to 50 ring carbon atoms represented by $R^1$ to $R^6$, $R^c$, and $R^d$ have been described in the section "Substituents in Description" above.

The cycloalkyl group represented by $R^1$ to $R^6$, $R^c$, and $R^d$ is preferably a cyclopropyl group, a cyclobutyl group, a cyclopentyl group, a cyclohexyl group, a 1-adamantyl group, a 2-adamantyl group, a 1-norbornyl group, or a 2-norbornyl group, more preferably a cyclopropyl group, a cyclobutyl group, a cyclopentyl group, or a cyclohexyl group, and further preferably a cyclopentyl group or a cyclohexyl group.

The details of the group represented by —Si($R_{901}$)($R_{902}$)($R_{903}$), the group represented by —O—($R_{904}$), the group represented by —S—($R_{905}$), and the group represented by —N($R_{906}$)($R_{907}$) represented by $R^1$ to $R^6$, $R^c$, and $R^d$ have been described in the section "Substituents in Description" above.

The details of the substituted or unsubstituted aryl group having 6 to 50 ring carbon atoms represented by $R^1$ to $R^6$, $R^a$, $R^b$, $R^c$, and $R^d$ have been described in the section "Substituents in Description" above.

The unsubstituted aryl group represented by $R^1$ to $R^6$, $R^a$, $R^b$, $R^c$, and $R^d$ is preferably a phenyl group, a biphenylyl group, a naphthyl group, or a phenanthryl group, more preferably a phenyl group, a biphenylyl group, or a naphthyl group, and further preferably a phenyl group.

The details of the substituted or unsubstituted heterocyclic group having 5 to 50 ring atoms represented by $R^1$ to $R^6$, $R^c$, and $R^d$ have been described in the section "Substituents in Description" above.

The unsubstituted heterocyclic group is preferably a dibenzofuranyl group or a dibenzothiophenyl group.

The details of the optional substituted or unsubstituted ring formed by bonding the two groups adjacent to each other in one or more combination selected from $R^3$ and $R^4$, $R^4$ and $R^5$, $R^5$ and $R^6$, and two groups represented by $R^d$ adjacent to each other have been described in the section "Substituents in Description" above, and the substituted or unsubstituted ring may be selected from a substituted or unsubstituted aromatic hydrocarbon ring, a substituted or unsubstituted aliphatic hydrocarbon ring, a substituted or unsubstituted aromatic heterocyclic ring, and a substituted or unsubstituted non-aromatic heterocyclic ring.

The aromatic hydrocarbon ring is, for example, a benzene ring, a biphenyl ring, a naphthalene ring, or a fluorene ring, and preferably a naphthalene ring or a fluorene ring.

The aliphatic hydrocarbon ring is, for example, a cyclopentene ring, a cyclopentadiene ring, a cyclohexene ring, a cyclohexadiene ring, or a hydrocarbon ring obtained by partially hydrogenating the aromatic hydrocarbon ring.

The aromatic heterocyclic ring is, for example, a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, or a benzocarbazole ring, and preferably a dibenzofuran ring or a dibenzothiophene ring.

The non-aromatic heterocyclic ring is, for example, a heterocyclic ring obtained by partially hydrogenating the aromatic heterocyclic ring.

In the present invention, in one or more combination selected from $R^3$ and $R^4$, $R^4$ and $R^5$, $R^5$ and $R^6$, and two groups represented by $R^d$ adjacent to each other, two groups adjacent to each other may not be bonded to each other to form a substituted or unsubstituted ring.

In the present invention, in one or more combination selected from two groups represented by $R^d$ adjacent to each other, two groups adjacent to each other are preferably bonded to each other to form a substituted or unsubstituted ring, and in one combination selected from two groups represented by $R^d$ adjacent to each other, two groups adjacent to each other are more preferably bonded to each other to form a substituted or unsubstituted ring. In the preferred case and the more preferred case, two groups represented by $R^d$ adjacent to each other are further preferably bonded to each other to form a benzene ring. $R^d$ preferably represents an aryl group.

m represents 3.

n represents 4.

e is bonded to any one selected from carbon atoms *a, *b, *c, and *d.

In one embodiment of the present invention, *e is preferably bonded to a carbon atom *a. In another embodiment, *e is preferably bonded to a carbon atom *b. In still another embodiment, *e is preferably bonded to a carbon atom *c. In further another embodiment, *e is preferably bonded to a carbon atom *d.

The inventive compound (1) represented by the formula (1) is preferably represented by any of the following formulae (1A) to (1D).

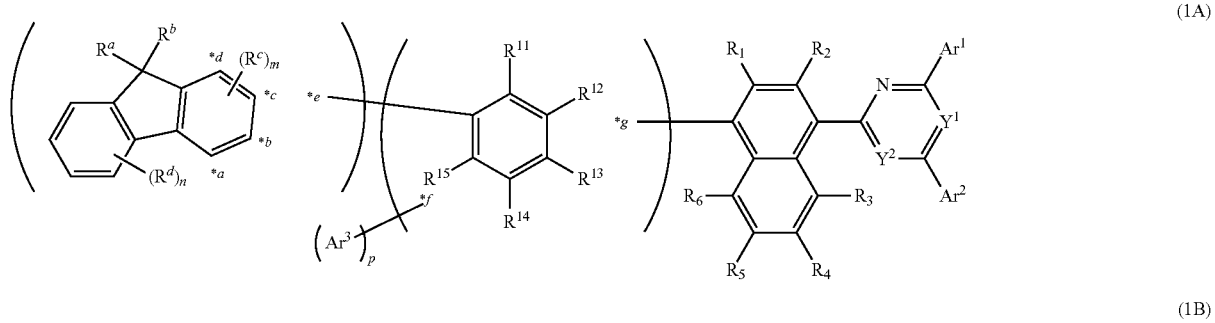

(1A)

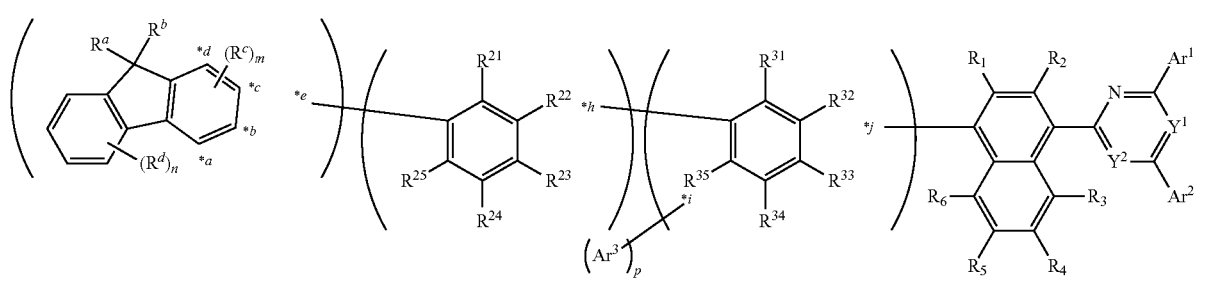

(1B)

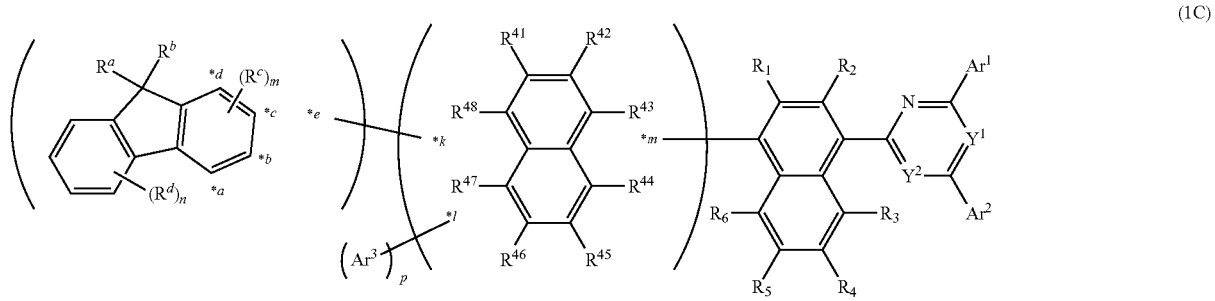

(1C)

-continued (1D)

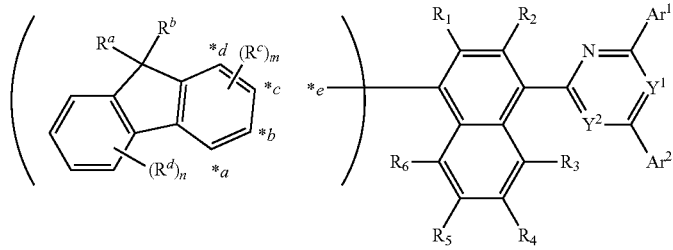

In the formulae (1A) to (1D),
$R^{11}$ to $R^{15}$, $R^{21}$ to $R^{25}$, $R^{31}$ to $R^{38}$, and $R^{41}$ to $R^{48}$ each independently represent
a hydrogen atom,
a halogen atom,
a cyano group,
a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a group represented by —Si($R_{901}$)($R_{902}$)($R_{903}$),
a group represented by —O—($R_{904}$),
a group represented by —S—($R_{905}$),
a group represented by —N($R_{906}$)($R_{907}$),
a substituted or unsubstituted aryl group having 6 to 50 ring carbon atoms, or
a substituted or unsubstituted heterocyclic group having 5 to 50 ring atoms.

In the formula (1A),
in the case where p is 0, one selected from $R^{11}$ to $R^{15}$ represents a single bond bonded to *g,
in the case where p is 1, one selected from $R^{11}$ to $R^{15}$ represents a single bond bonded to *f, and another one selected from $R^{11}$ to $R^{15}$ represents a single bond bonded to *g,
in the case where p is 2, two selected from $R^{11}$ to $R^{15}$ represent single bonds bonded to *f, and another one selected from $R^{11}$ to $R^{15}$ represents a single bond bonded to *g, and
in the case where p is 3, three selected from $R^{11}$ to $R^{15}$ represent single bonds bonded to *f, and another one selected from $R^{11}$ to $R^{15}$ represents a single bond bonded to *g.

In the formula (1B),
in the case where p is 0, one selected from $R^{21}$ to $R^{28}$ represents a single bond bonded to *h, and one selected from $R^{31}$ to $R^{35}$ represents a single bond bonded to *j,
in the case where p is 1, one selected from $R^{21}$ to $R^{25}$ represents a single bond bonded to *h, one selected from $R^{31}$ to $R^{35}$ represents a single bond bonded to *i, and another one selected from $R^{31}$ to $R^{35}$ represents a single bond bonded to *j,
in the case where p is 2, one selected from $R^{21}$ to $R^{25}$ represents a single bond bonded to *h, two selected from $R^{31}$ to $R^{35}$ represent single bonds bonded to *i, and another one selected from $R^{31}$ to $R^{35}$ represents a single bond bonded to *j, and in the case where p is 3, one selected from $R^{21}$ to $R^{25}$ represents a single bond bonded to *h, three selected from $R^{31}$ to $R^{35}$ represent single bonds bonded to *i, and another one selected from $R^{31}$ to $R^{35}$ represents a single bond bonded to *j.

In the formula (1C),
in the case where p is 0, one selected from $R^{41}$ to $R^{48}$ represents a single bond bonded to *k, and another one selected from $R^{41}$ to $R^{48}$ represents a single bond bonded to *m,
in the case where p is 1, one selected from $R^{41}$ to $R^{48}$ represents a single bond bonded to *l, another one selected from $R^{41}$ to $R^{48}$ represents a single bond bonded to *k, and still another one selected from $R^{41}$ to $R^{48}$ represents a single bond bonded to *m,
in the case where p is 2, two selected from $R^{41}$ to $R^{48}$ represent single bonds bonded to *l, another one selected from $R^{41}$ to $R^{48}$ represents a single bond bonded to *k, and still another one selected from $R^{41}$ to $R^{48}$ represents a single bond bonded to *m, and
in the case where p is 3, three selected from $R^{41}$ to $R^{48}$ represent single bonds bonded to *l, another one selected from $R^{41}$ to $R^{48}$ represents a single bond bonded to *k, and still another one selected from $R^{41}$ to $R^{48}$ represents a single bond bonded to *m.

$Y^1$, $Y^2$, $Ar^1$ to $Ar^3$, p, $R^1$ to $R^6$, $R^a$, $R^b$, $R^c$, $R^d$, *a, *b, *c, *d, *e, n, m, and $R_{901}$ to $R_{907}$ have the same definitions as in the formula (1).

$R^{11}$ to $R^{15}$, $R^{21}$ to $R^{25}$, $R^{31}$ to $R^{35}$, and $R^{41}$ to $R^{48}$ each independently preferably represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, more preferably a hydrogen atom or a substituted or unsubstituted alkyl group having 1 to 50 carbon atoms, and further preferably a hydrogen atom.

The details of the groups represented by $R^{11}$ to $R^{15}$, $R^{21}$ to $R^{25}$, $R^{31}$ to $R^{35}$, and $R^{41}$ to $R^{48}$ are the same as the details of the corresponding groups described for $R^1$ to $R^6$, $R^a$, $R^b$, $R^c$, and $R^d$, and the preferred groups and the like thereof are also the same.

The inventive compound (1) represented by the formula (1) is preferably represented by the following formula (1A-1), (1B-1), or (1C-1).

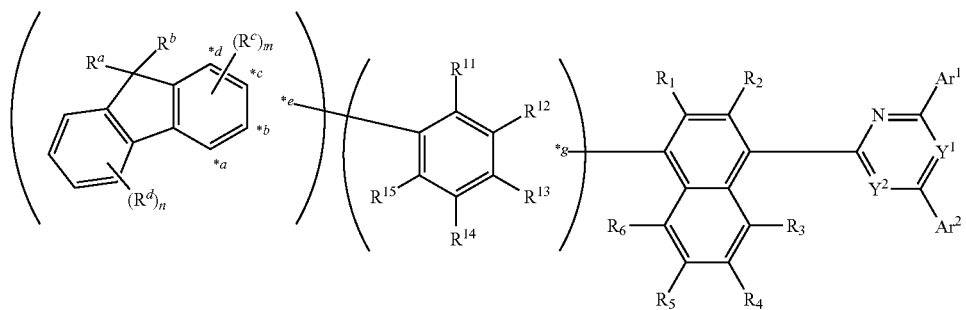

(1A-1)

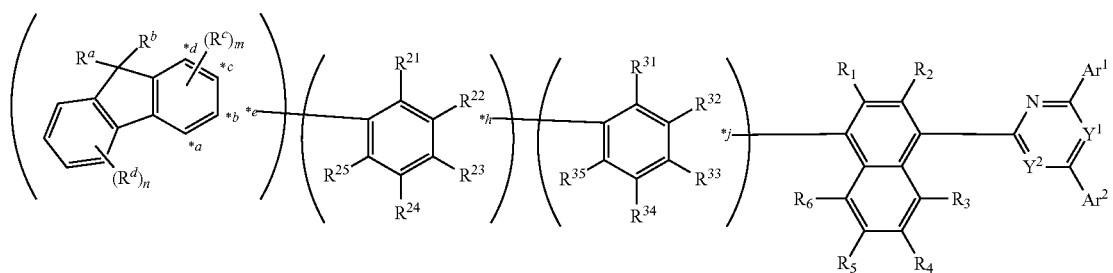

(1B-1)

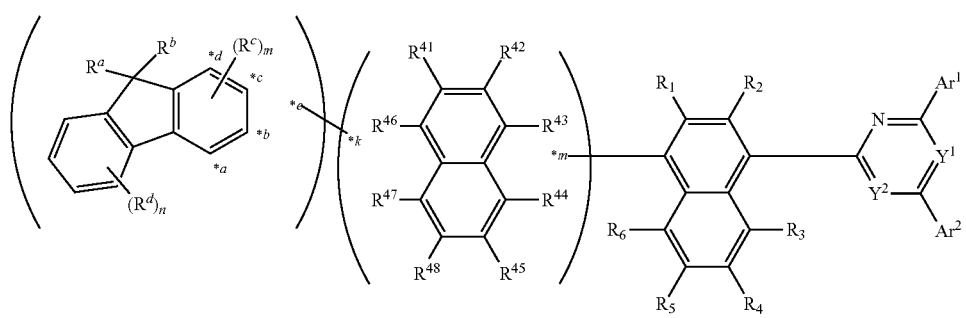

(1C-1)

In the formulae (1A-1), (1B-1), and (1C-1), $Y^1$, $Y^2$, $Ar^1$, $Ar^2$, $R^1$ to $R^6$, $R^a$, $R^b$, $R^c$, $R^d$, *a, *b, *c, *d, *e, n, and m have the same definitions as in the formula (1), $R^{11}$ to $R^{15}$ and *g have the same definitions as in the formula (1A), $R^{21}$ to $R^{25}$, $R^{31}$ to $R^{35}$, *h, and *j have the same definitions as in the formula (1B), and $R^{41}$ to $R^{48}$, *k, and *m have the same definitions as in the formula (1C).

The inventive compound (1) represented by the formula (1) is preferably represented by the following formula (1A-1a) or (1A-1b).

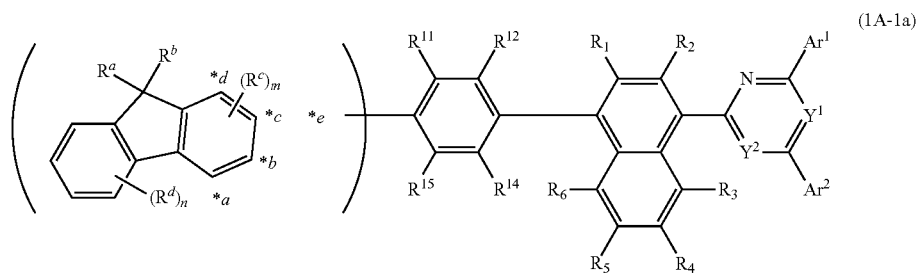

(1A-1a)

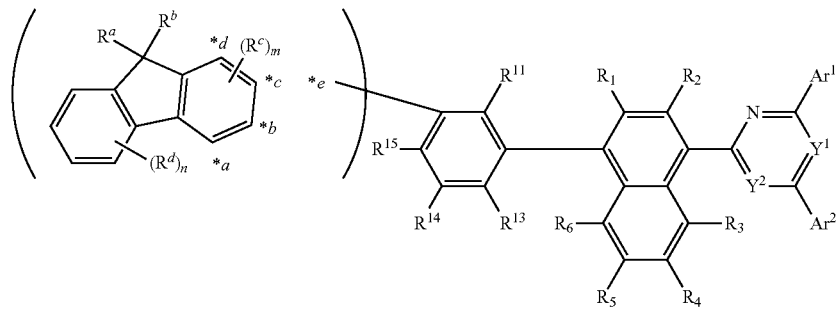

(1A-1b)

In the formulae (1A-1a) and (1A-1b),
$Y^1$, $Y^2$, $Ar^1$, $Ar^2$, $R^1$ to $R^6$, $R^a$, $R^b$, $R^c$, $R^d$, *a, *b, *c, *d, *e, n, and m have the same definitions as in the formula (1), and $R^{11}$ to $R^{15}$ have the same definitions as in the formula (1A).

The inventive compound (1) represented by the formula (1) is preferably represented by the following formula (1A-1c).

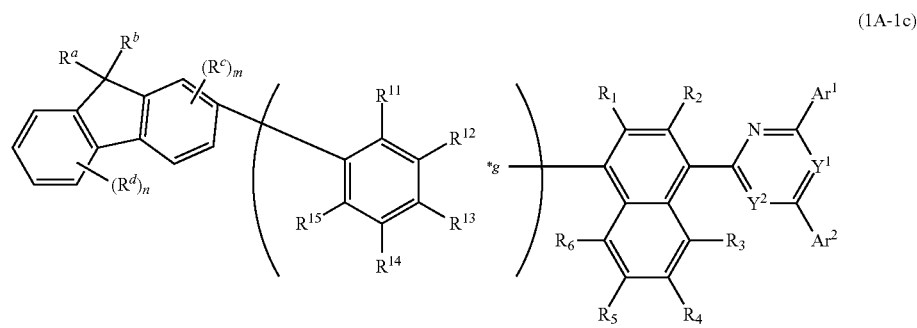

(1A-1c)

In the formula (1A-1c),
$Y^1$, $Y^2$, $Ar^1$, $Ar^2$, $R^1$ to $R^6$, $R^a$, $R^b$, $R^c$, $R^d$, n, and m have the same definitions as in the formula (1), and $R^{11}$ to $R^{15}$ and *g have the same definitions as in the formula (1A).

The inventive compound (1) represented by the formula (1) is preferably represented by the following formula (1D-1a).

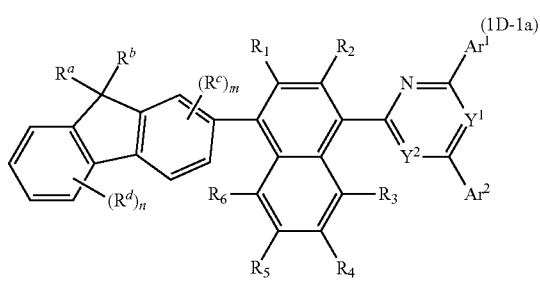

(1D-1a)

In the formula (1D-1a),
$Y^1$, $Y^2$, $Ar^1$, $Ar^2$, $R^1$ to $R^6$, $R^a$, $R^b$, $R^c$, $R^d$, n, and m have the same definitions as in the formula (1).

In one embodiment of the present invention,
(1-1) all $R^1$ to $R^6$ and $R^{10}$ may be hydrogen atoms,
(1-2) both $R^c$ and $R^d$ may be hydrogen atoms,
(1-3) in the formula (1A), all $R^{11}$ to $R^{15}$ that are not single bonds bonded to *f and *g may be hydrogen atoms,
(1-4) in the formula (1B), all $R^{21}$ to $R^{25}$ that are not a single bond bonded to *h may be hydrogen atoms,
(1-5) in the formula (1B), all $R^{31}$ to $R^{35}$ that are not single bonds bonded to *i and *j may be hydrogen atoms,
(1-6) in the formula (1C), all $R^{41}$ to $R^{48}$ that are not single bonds bonded to *k, *l, and *m may be hydrogen atoms,
(1-7) in the formula (1A-1), all $R^{11}$ to $R^{15}$ that are not a single bond bonded to *g may be hydrogen atoms,
(1-8) in the formula (1B-1), all $R^{21}$ to $R^{25}$ that are not a single bond bonded to *h may be hydrogen atoms,
(1-9) in the formula (1B-1), all $R^{31}$ to $R^{35}$ that are not a single bond bonded to *j may be hydrogen atoms, (1-10) in the formula (1C-1), all $R^{41}$ to $R^{48}$ that are not single bonds bonded to *k and *m may be hydrogen atoms, (1-11) in the formula (1A-1a), all $R^{11}$, $R^{12}$, $R^{14}$, and $R^{15}$ may be hydrogen atoms, (1-12) in the formula (1A-1b), all $R^{11}$ and $R^{13}$ to $R^{15}$ may be hydrogen atoms, and (1-13) in the formula (1A-1c), all $R^{11}$ to $R^{15}$ that are not a single bond bonded to *g may be hydrogen atoms.

As described above, the "hydrogen atom" referred in the description herein encompasses a protium atom, a deuterium atom, and tritium atom. Accordingly, the inventive compound may contain a naturally derived deuterium atom.

A deuterium atom may be intentionally introduced into the inventive compound by using a deuterated compound as a part or the whole of the raw material. Accordingly, in one embodiment of the present invention, the inventive compound contains at least one deuterium atom. Accordingly, the inventive compound (1) may be a compound represented by the formula (1), in which at least one hydrogen atom contained in the compound is a deuterium atom.

In the compound represented by the formula (1), at least one hydrogen atom selected from hydrogen atoms of the substituted or unsubstituted aryl group or the substituted or unsubstituted heterocyclic group represented by $Ar^1$ to $Ar^3$;

hydrogen atoms of the substituted or unsubstituted (2+p)-valent aromatic hydrocarbon ring having 6 to 30 ring carbon atoms represented by L;

hydrogen atoms represented by $R^1$ to $R^6$, $R^{10}$, $R^c$ and $R^d$; hydrogen atoms of the substituted or unsubstituted alkyl group, alkenyl group, alkynyl group, cycloalkyl group, aryl group, or heterocyclic group represented by $R^1$ to $R^6$, $R^c$, and $R^d$;

hydrogen atoms represented by $R_{901}$ to $R_{907}$ in $R^1$ to $R^6$, $R^c$, and $R^d$; hydrogen atoms of the substituted or unsubstituted alkyl group, cycloalkyl group, aryl group, or heterocyclic group represented by $R_{901}$ to $R_{907}$ in $R^1$ to $R^6$, $R^c$, and $R^d$;

hydrogen atoms of the substituted or unsubstituted alkyl group or aryl group represented by $R^a$ and $R^b$;

hydrogen atoms of the pyrimidine ring constituting the formula (1); and hydrogen atoms other than $R^a$ to $R^d$ contained in the structure represented by the following formula (1-x) constituting the formula (1) may be a deuterium atom.

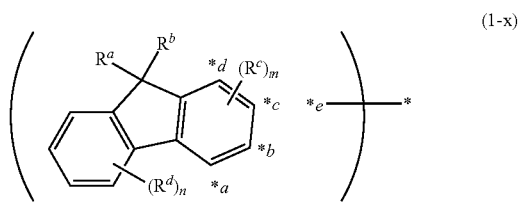

In the formula (1-x), * represents a bonding site to L, and $R^a$ to $R^d$, *a, *b, *c, *d, and *e have the same definitions as in the formula (1).

The deuteration rate of the inventive compound depends on the deuteration rates of the raw material compounds used. Even though a raw material having a prescribed deuteration rate is used, a naturally derived protium isotope may be contained at a certain proportion. Accordingly, the embodiments of the deuteration rate of the inventive compound shown below include the proportion in consideration of a slight amount of the naturally derived isotopes, with respect to the proportion obtained by counting the number of deuterium atoms shown in the chemical formula.

The deuteration rate of the inventive compound is preferably 1% or more, more preferably 3% or more, further preferably 5% or more, still further preferably 10% or more, and still more further preferably 50% or more.

The inventive compound may be a mixture of a deuterated compound and a non-deuterated compound, or a mixture of two or more compounds having different deuteration rates from each other. The deuteration rate of the mixture is preferably 1% or more, more preferably 3% or more, further preferably 5% or more, still further preferably 10% or more, and still more further preferably 50% or more, and is less than 100%.

The proportion of the number of deuterium atoms with respect to the number of all the hydrogen atoms in the inventive compound is preferably 1% or more, more preferably 3% or more, further preferably 5% or more, and still further preferably 10% or more, and is 100% or less.

The details of the substituent (optional substituent) in the case of "substituted or unsubstituted" included in the definitions for the formulae have been described in the "Substituent for 'Substituted or Unsubstituted'" above.

The inventive compound can be readily produced by a person skilled in the art according to Synthesis Examples described later or the known synthesis methods.

Specific examples of the inventive compound of the present invention will be described below, but the inventive compound is not limited to the example compounds below.

In the following specific examples, D represents a deuterium atom.

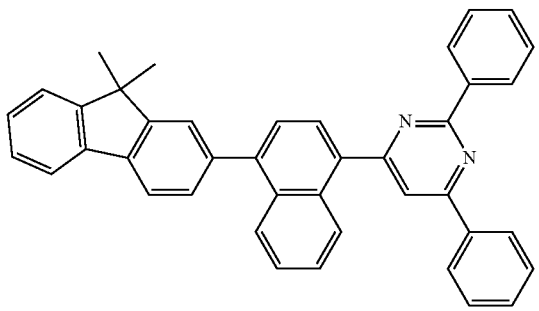

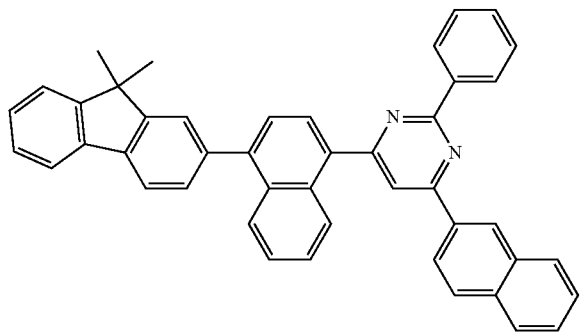

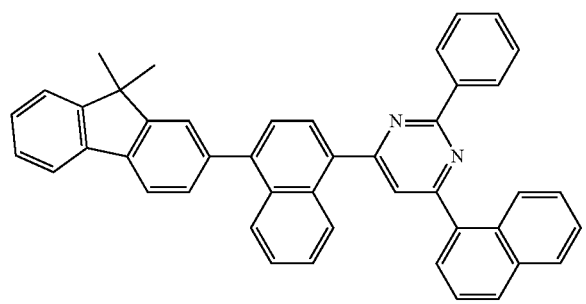

-continued
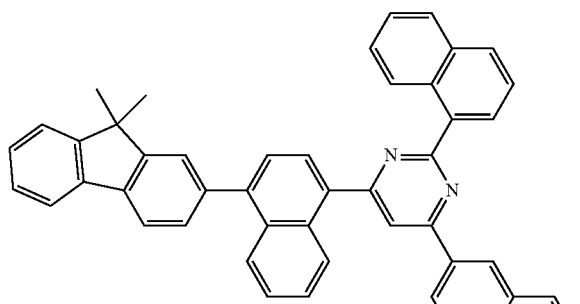
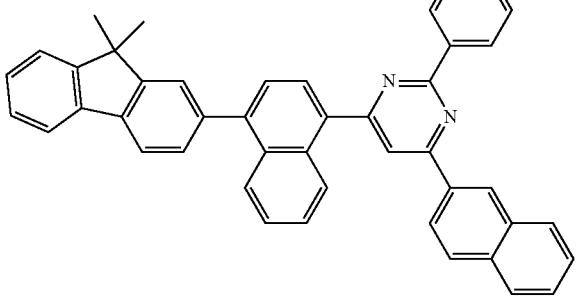
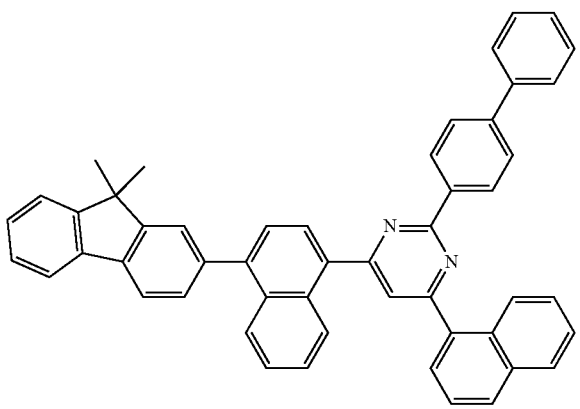
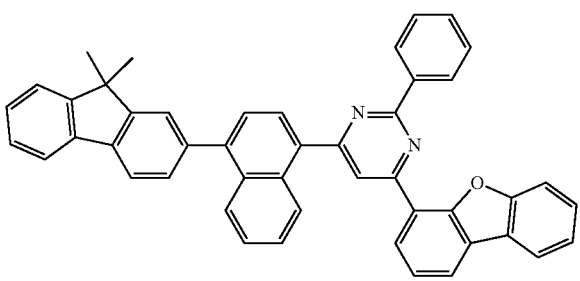
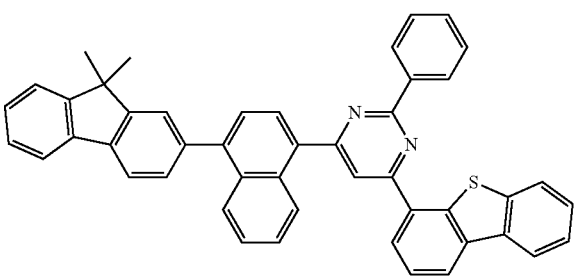
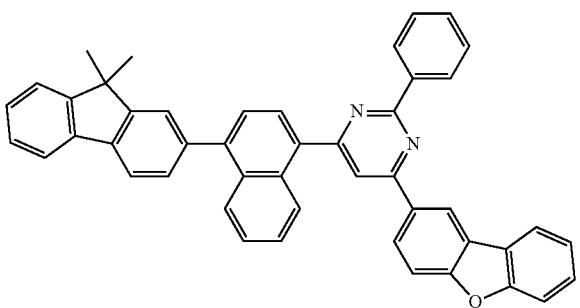
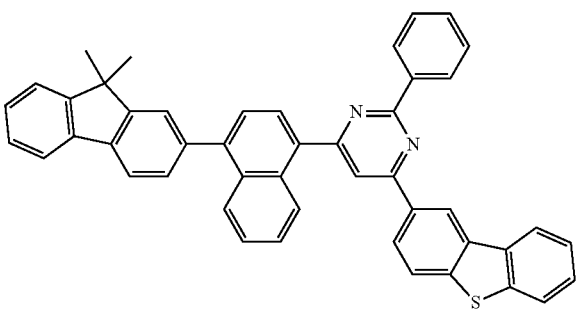

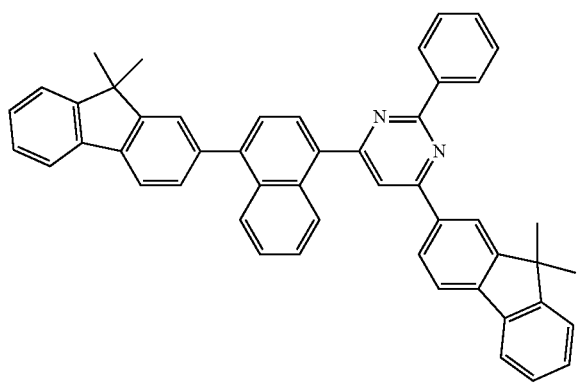
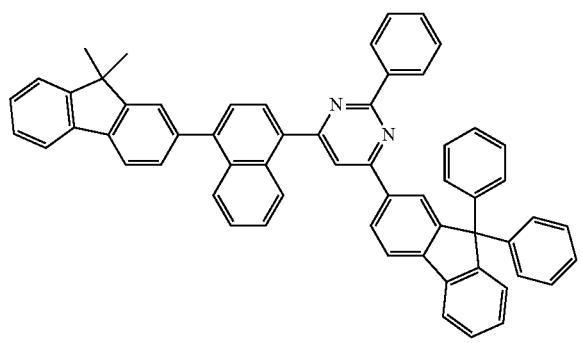
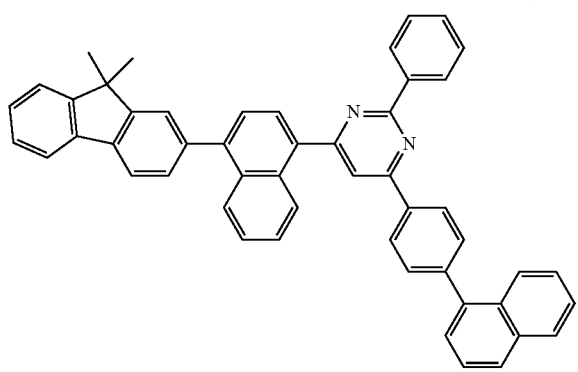
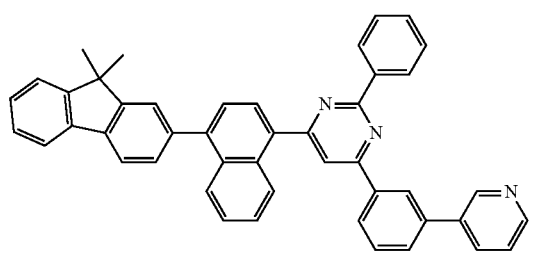
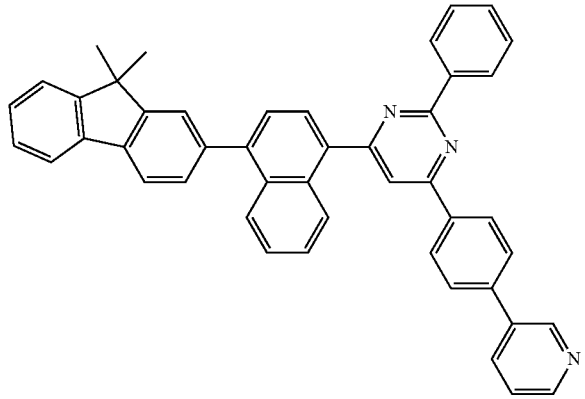
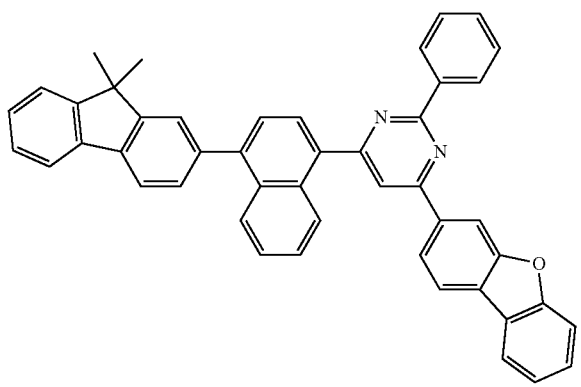
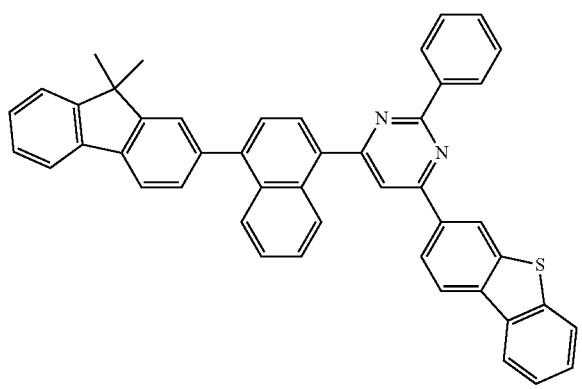
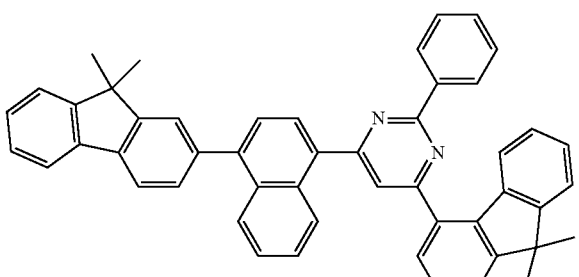

59
60
-continued
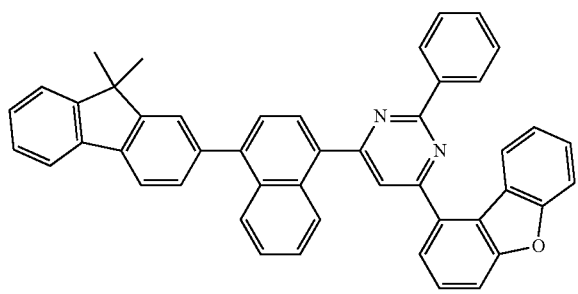
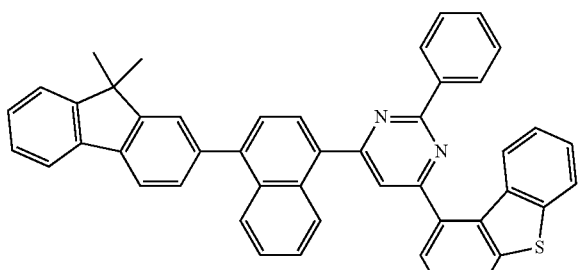
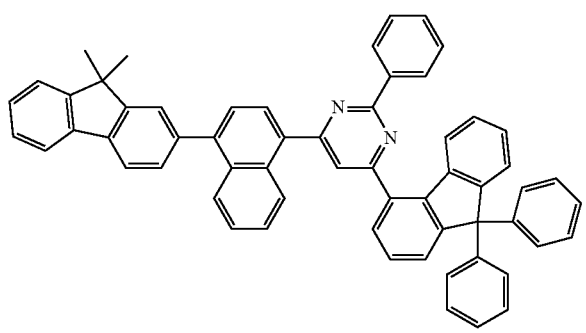
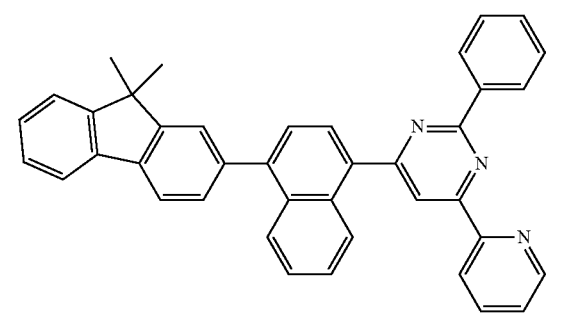
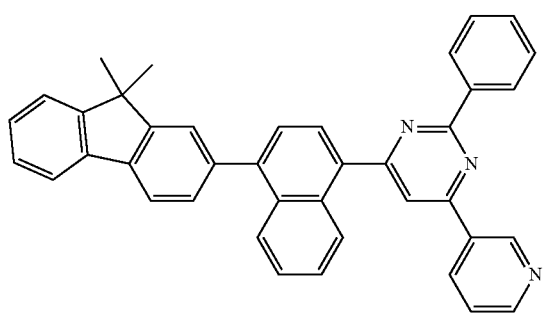
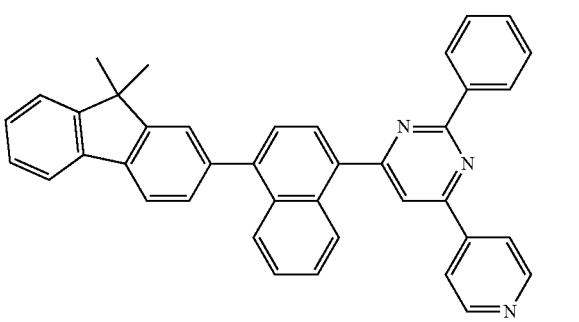
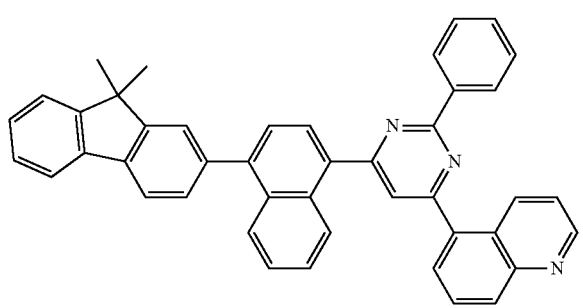
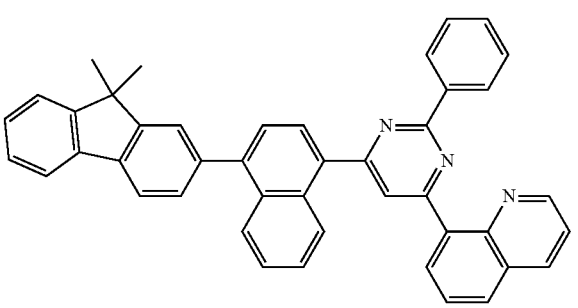
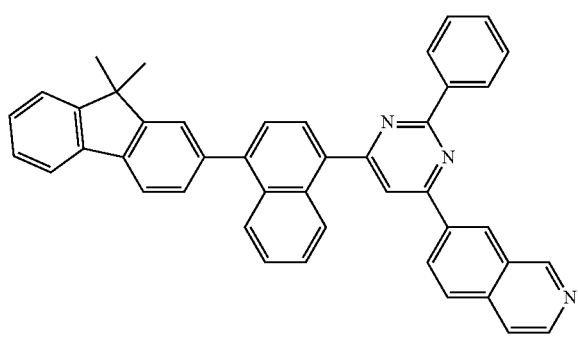
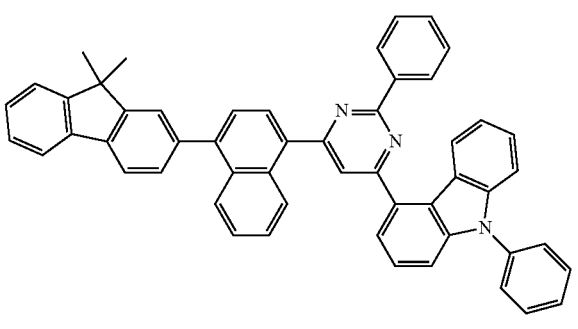

-continued
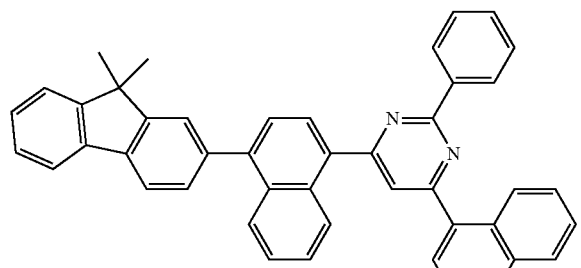
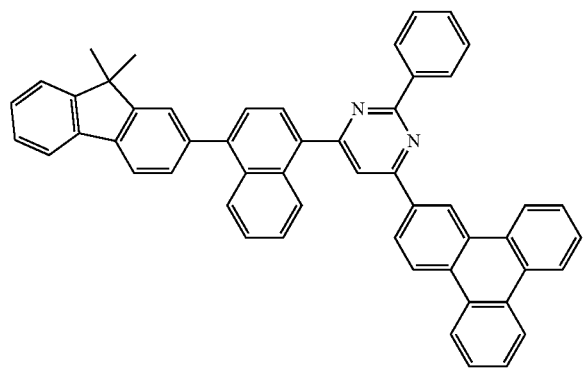
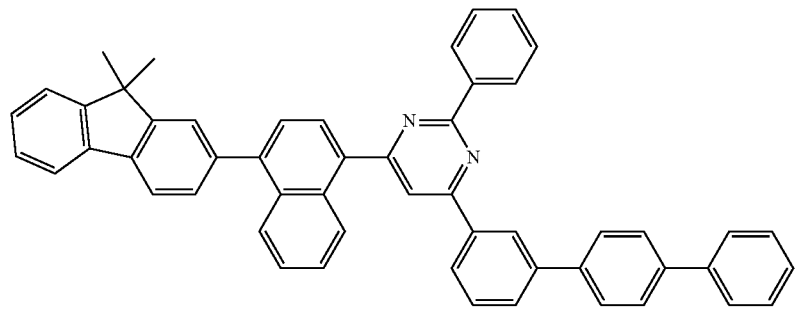
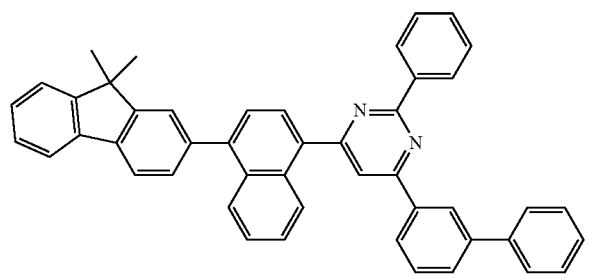
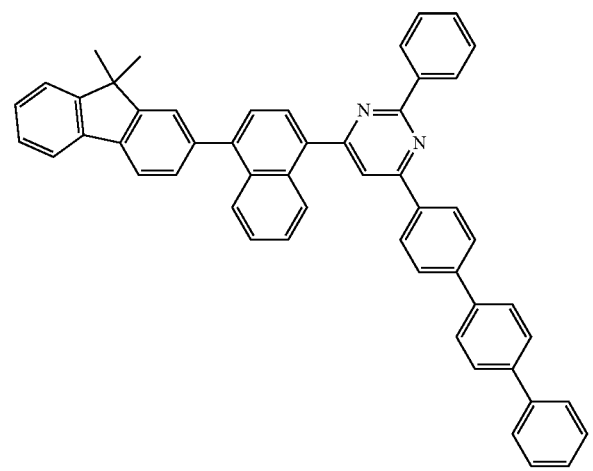
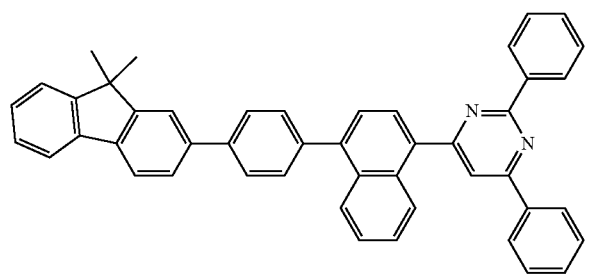
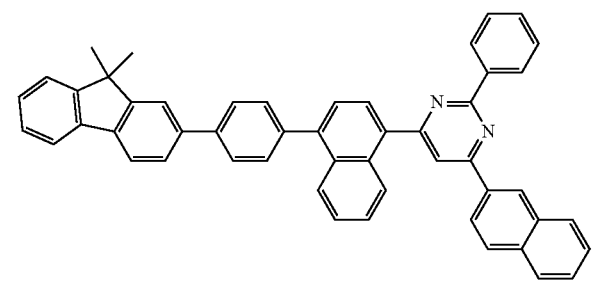
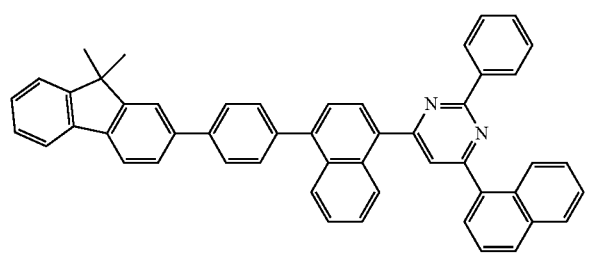

-continued
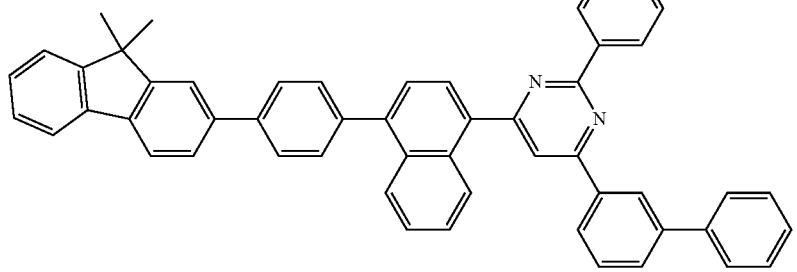
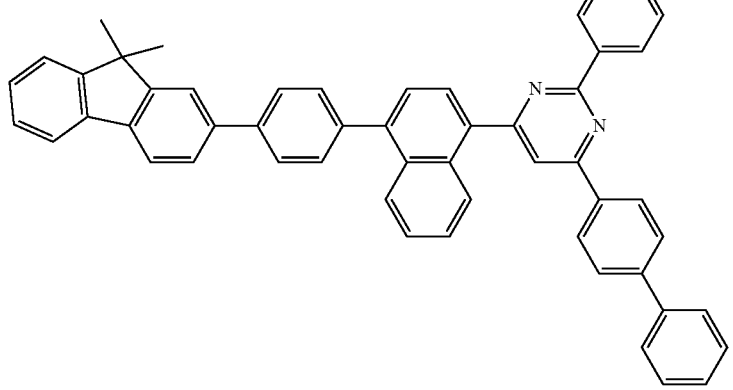
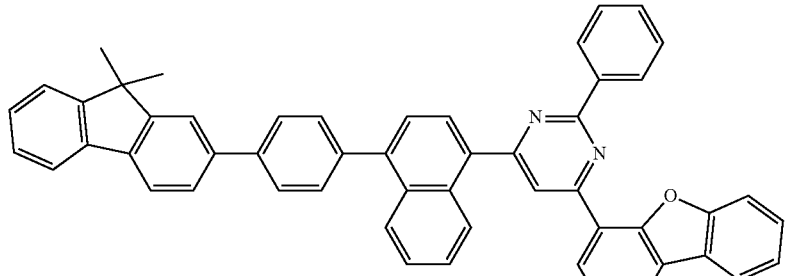
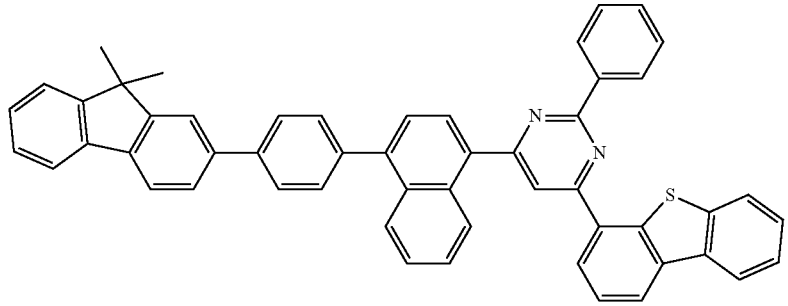
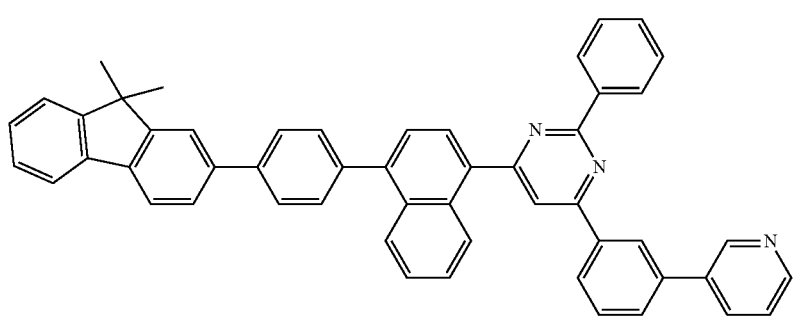

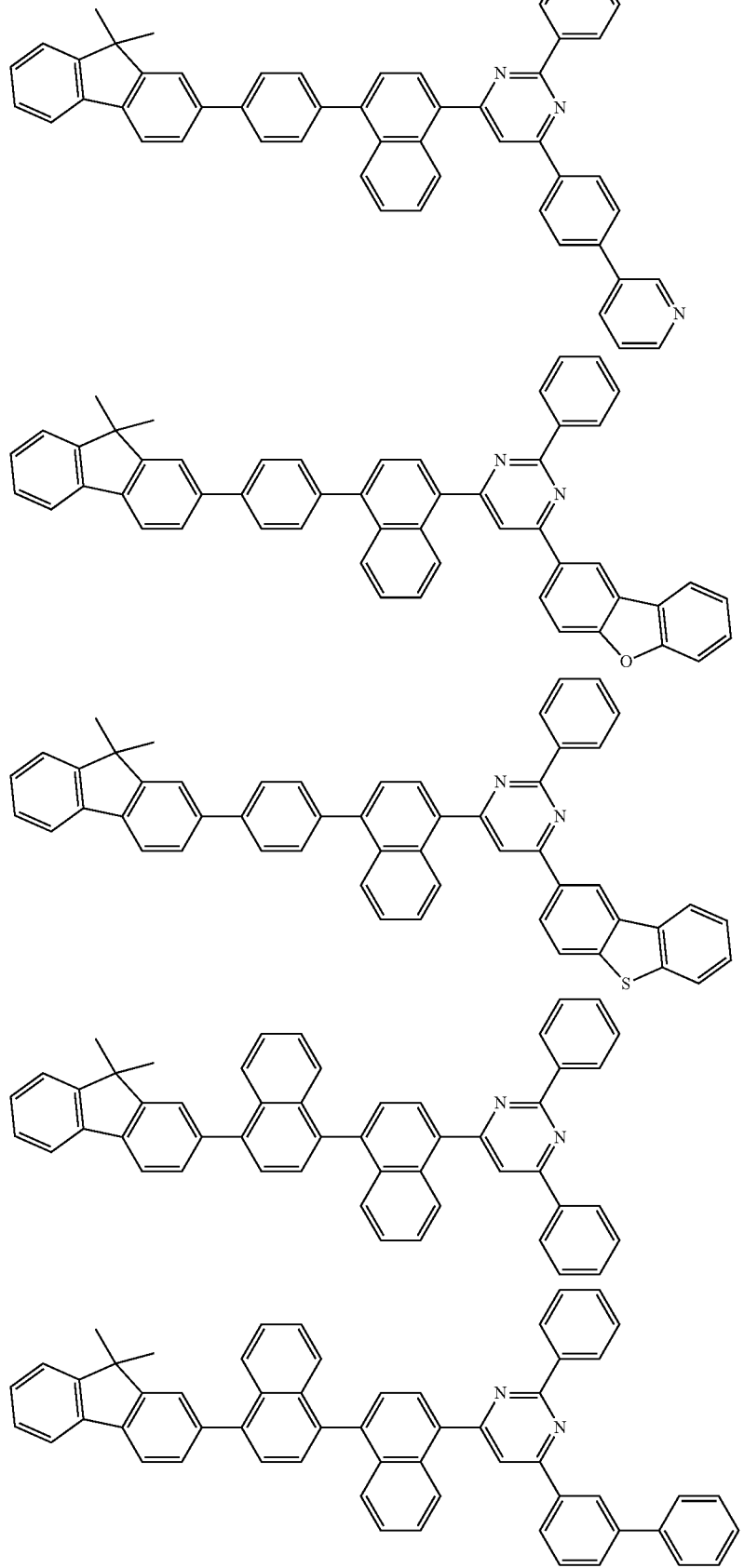

-continued
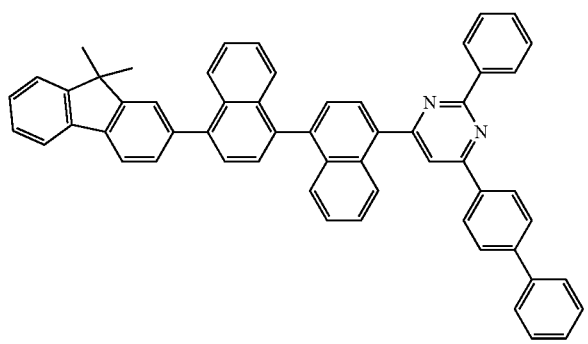
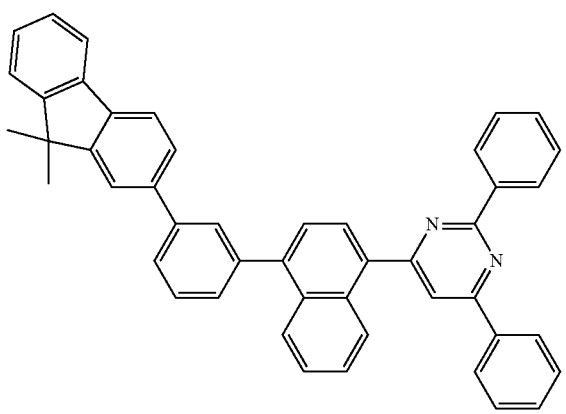
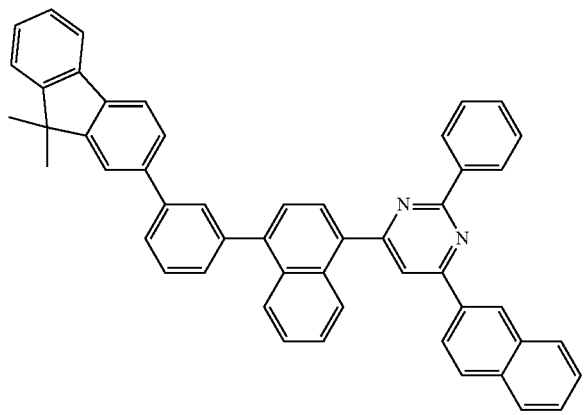
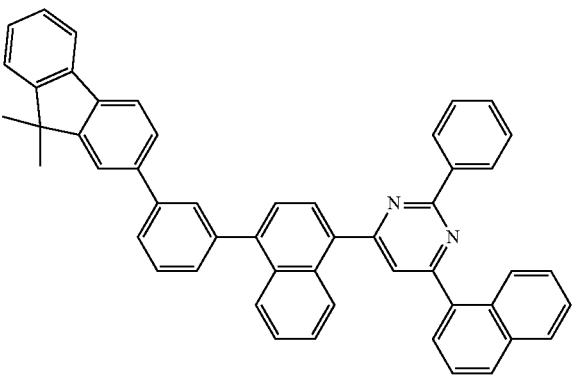
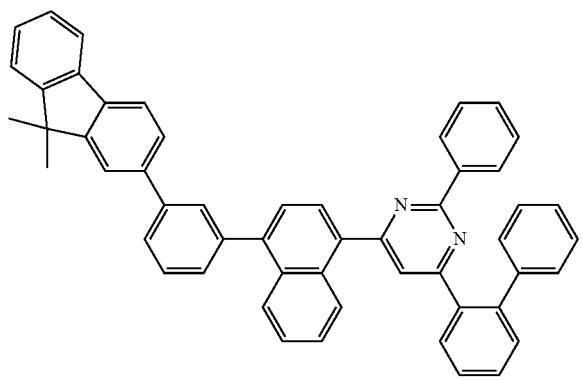
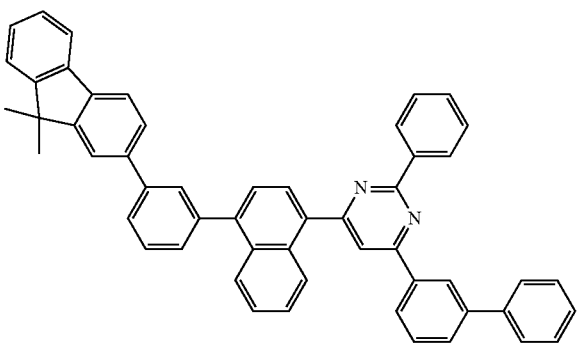
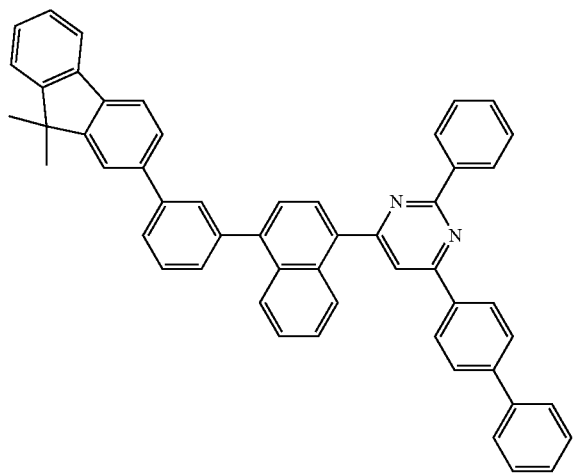
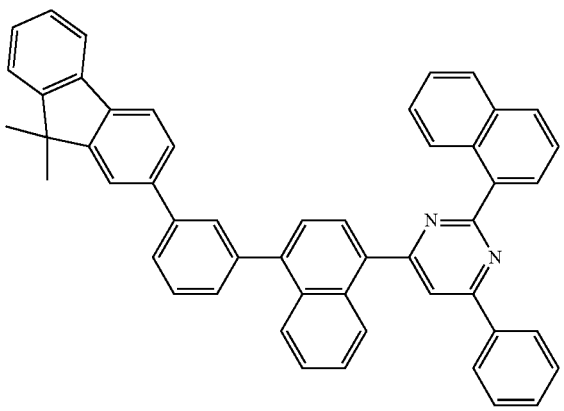

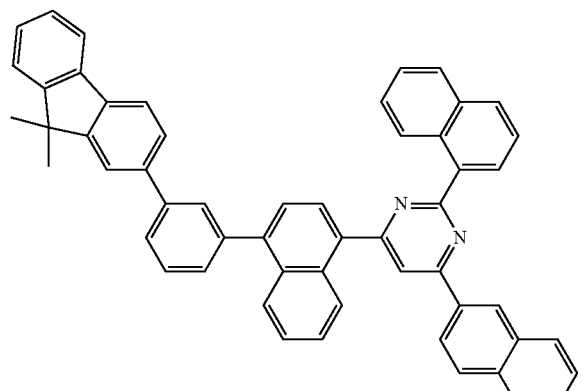

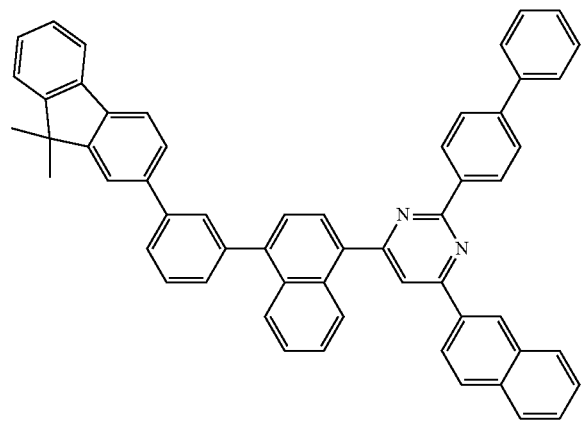
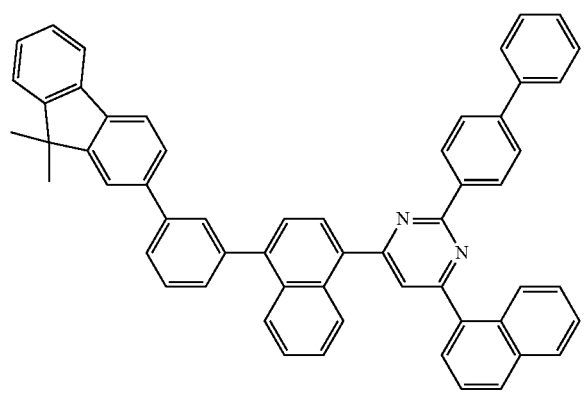
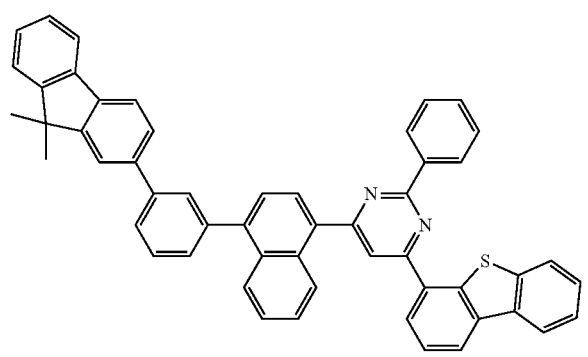
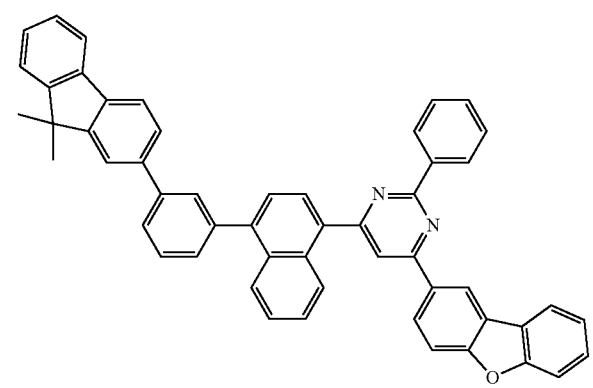

-continued
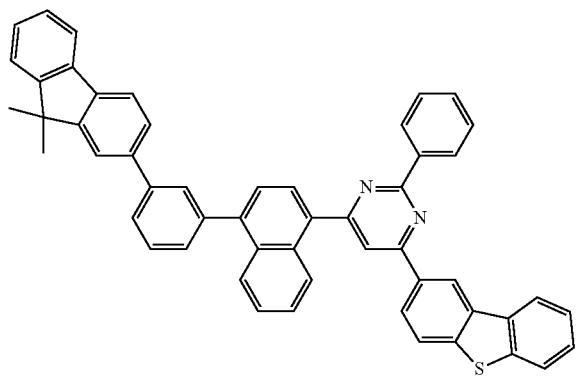
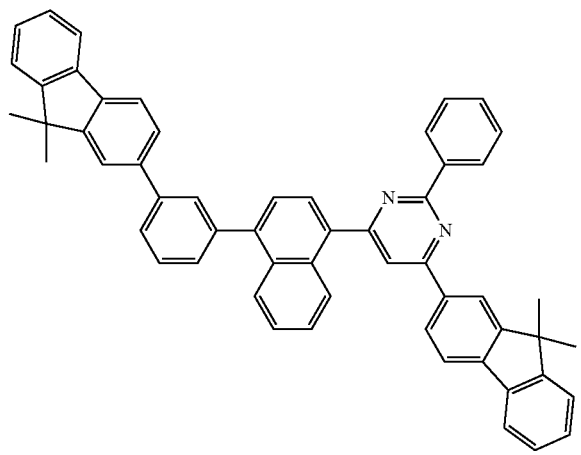
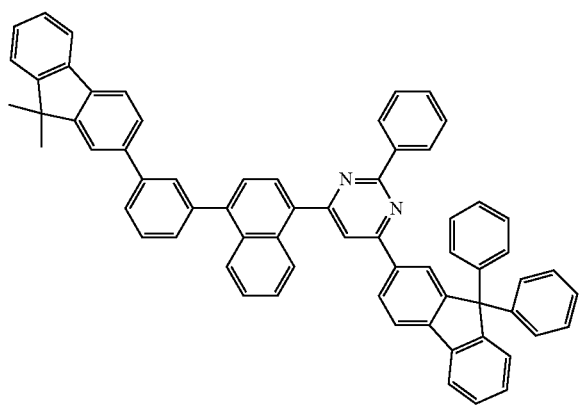
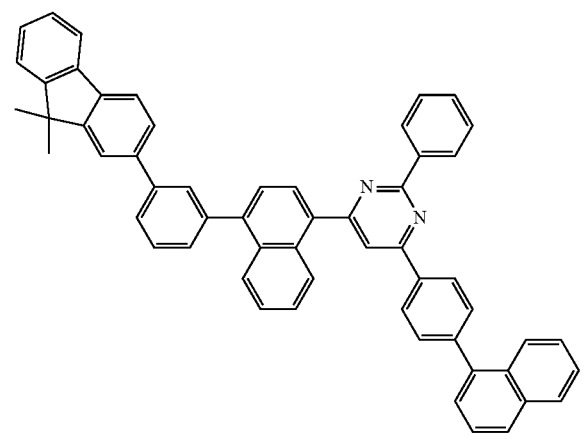
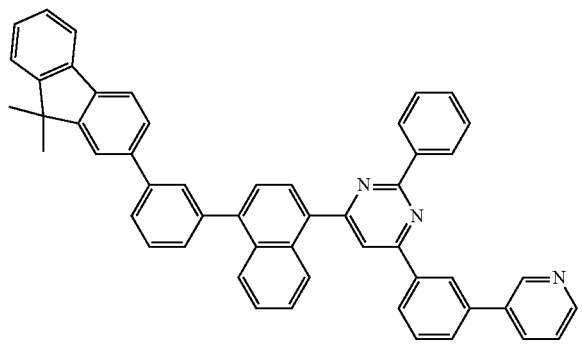
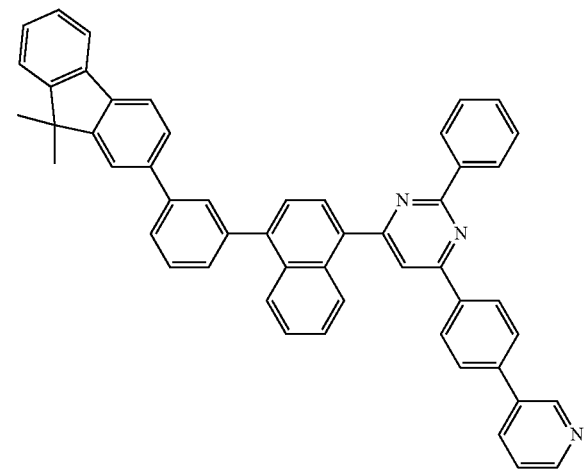
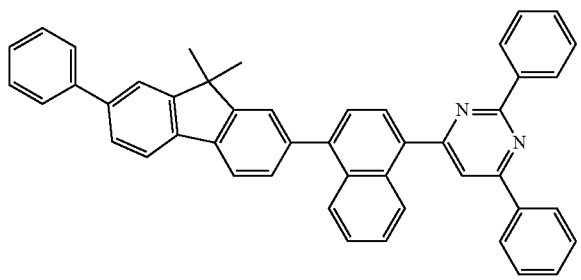

-continued
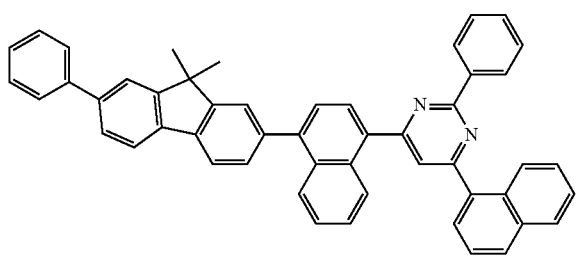
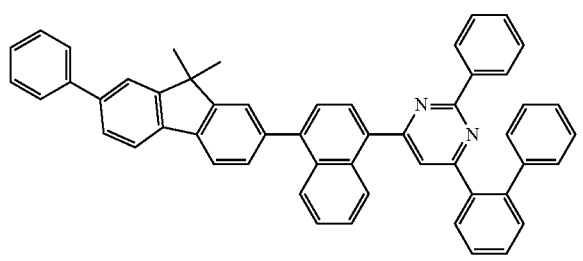
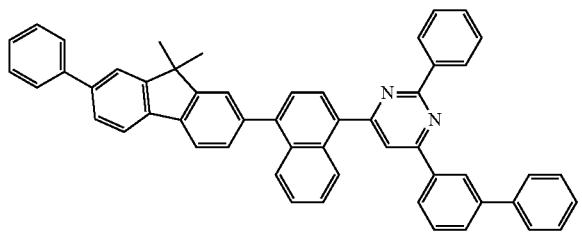
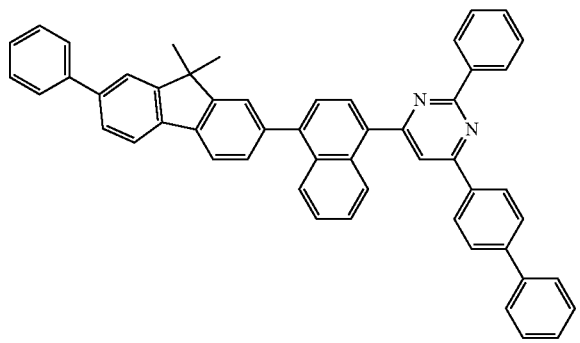
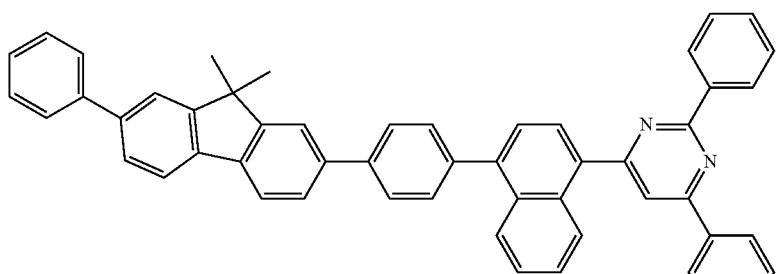
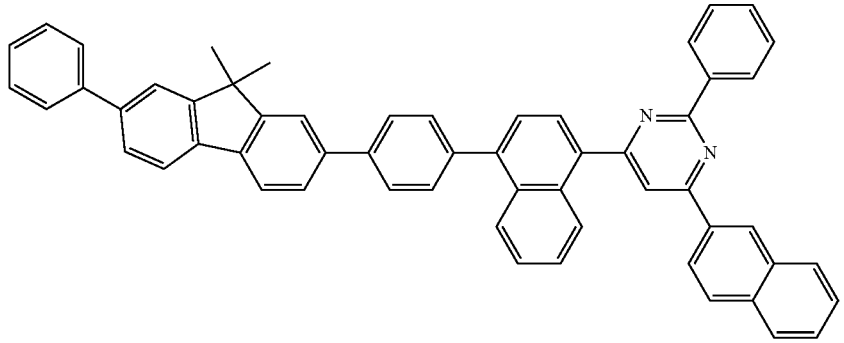
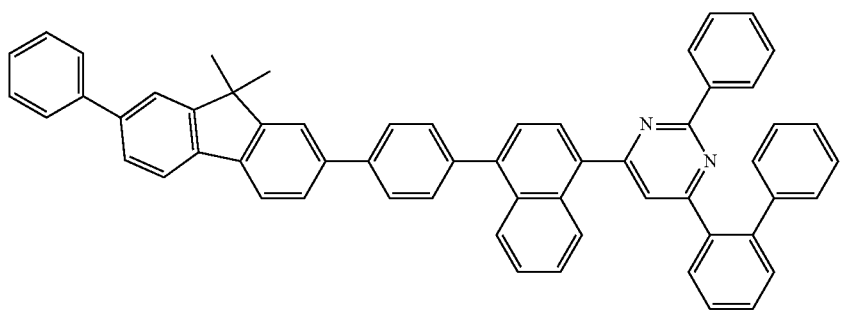

-continued
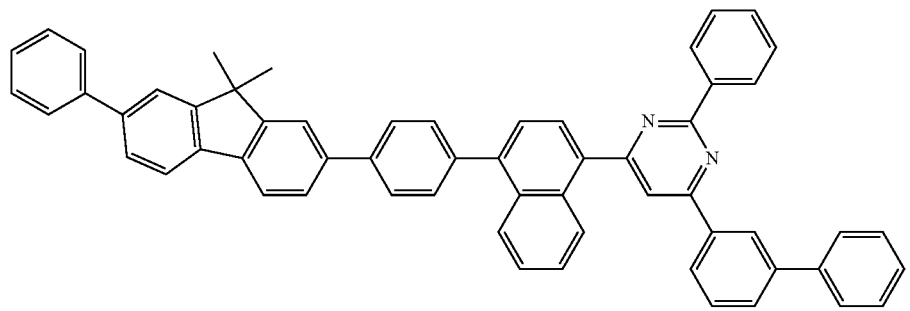
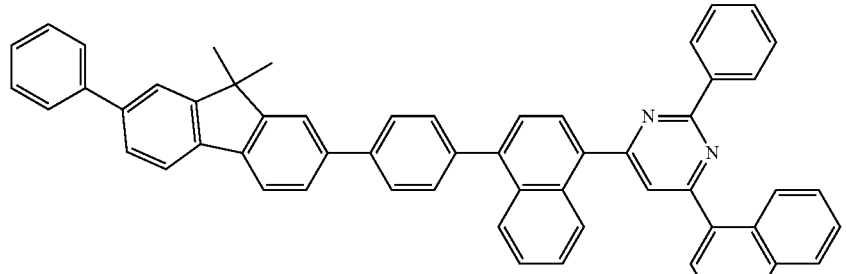
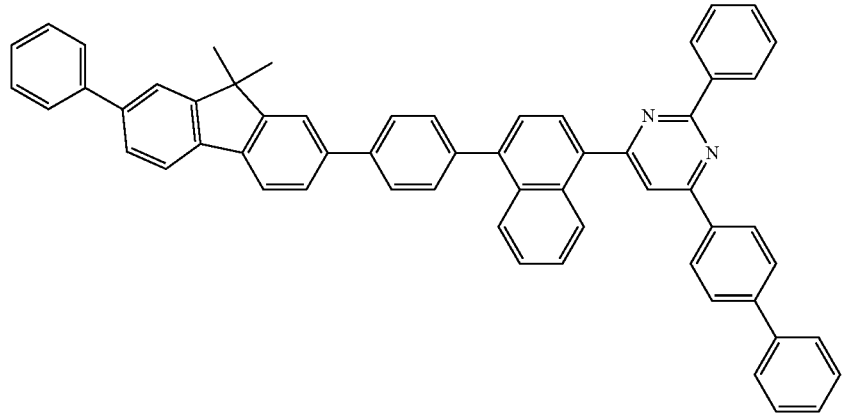
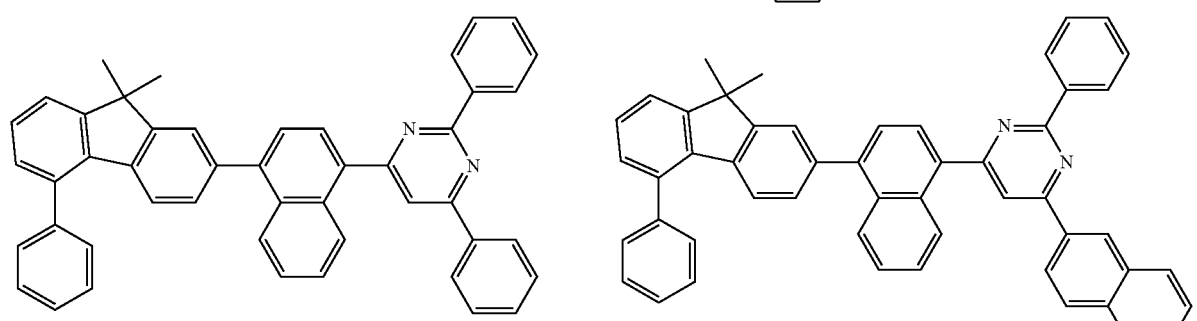
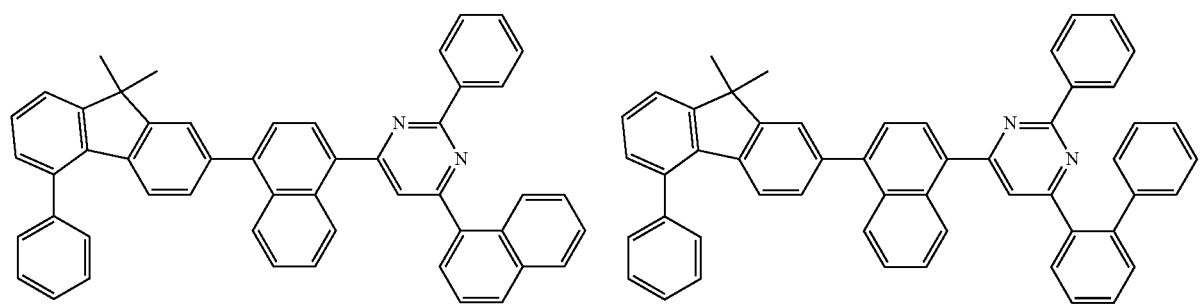

-continued
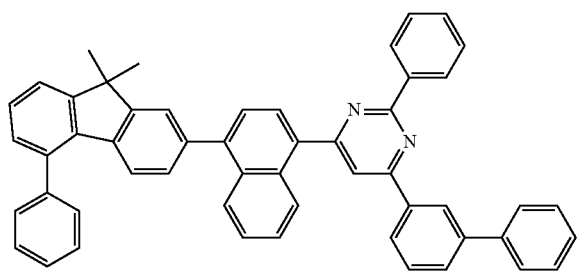
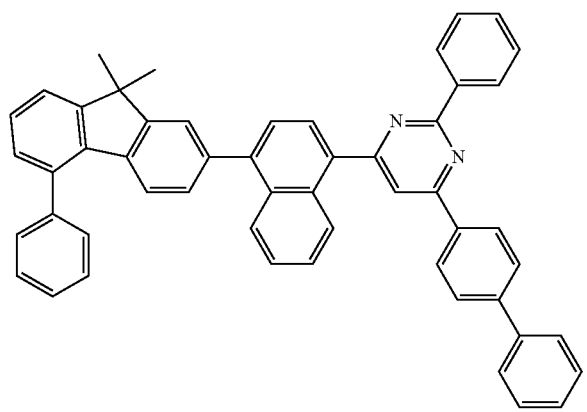
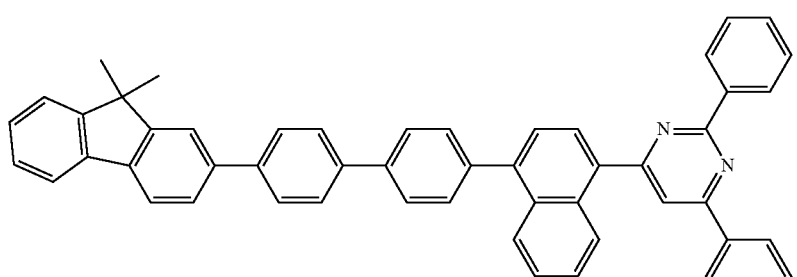
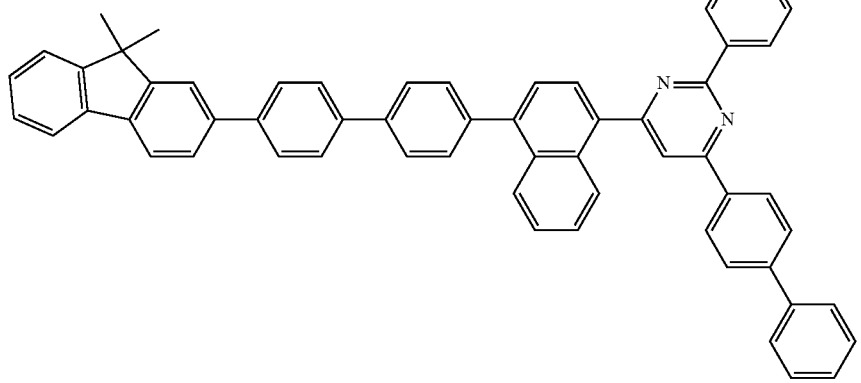
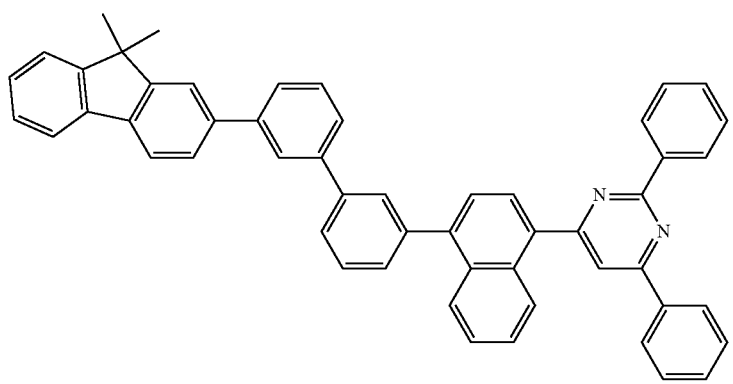

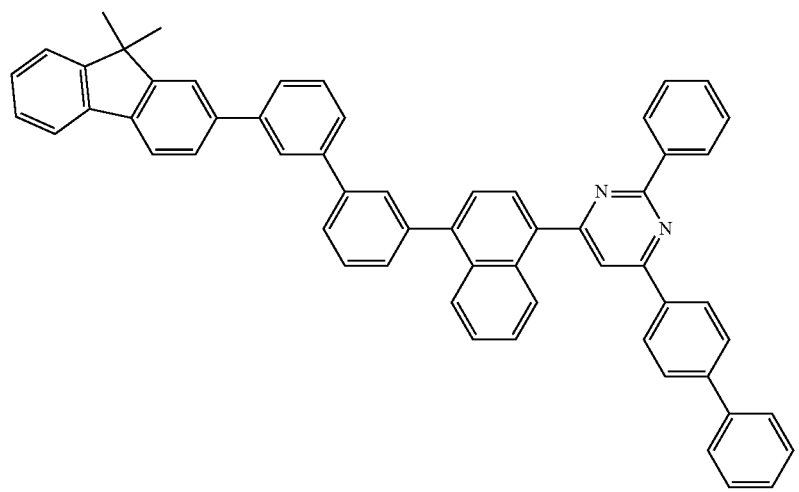
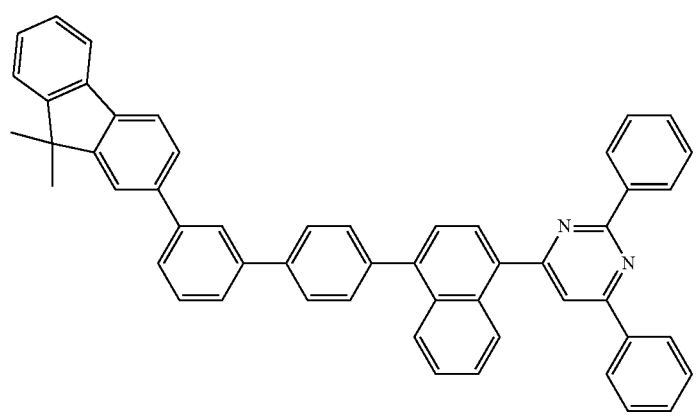
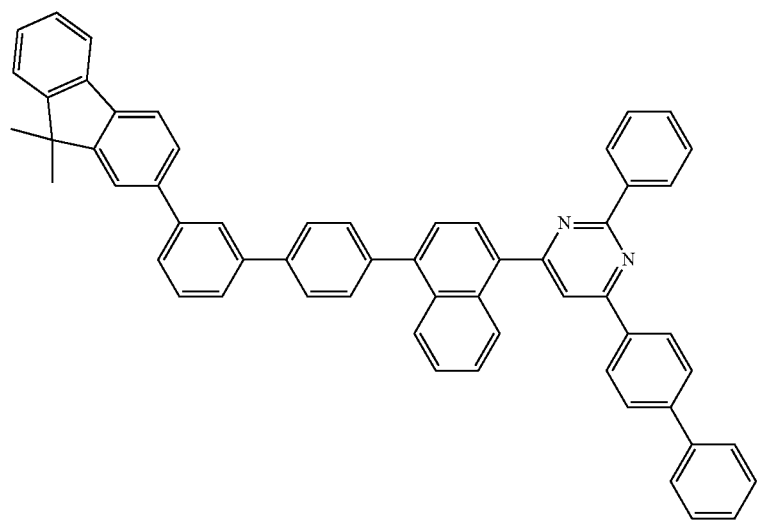

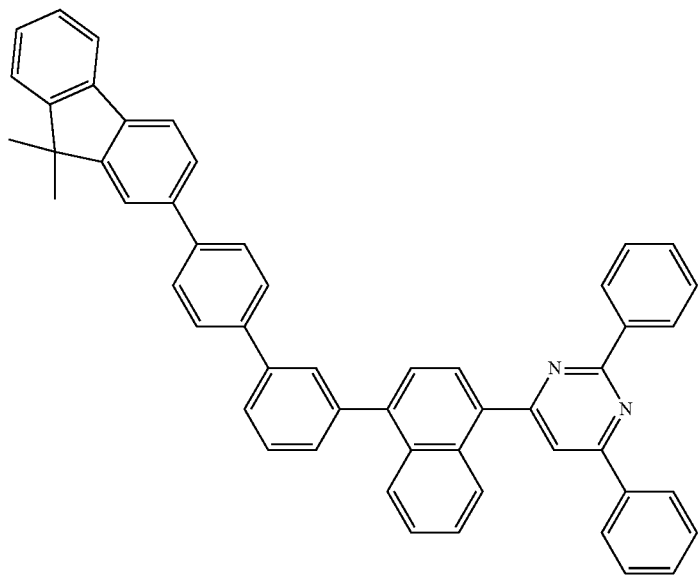
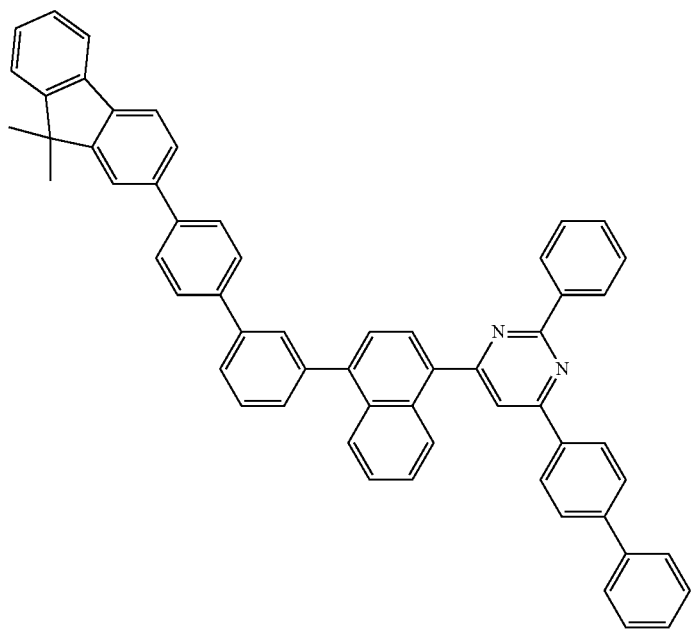
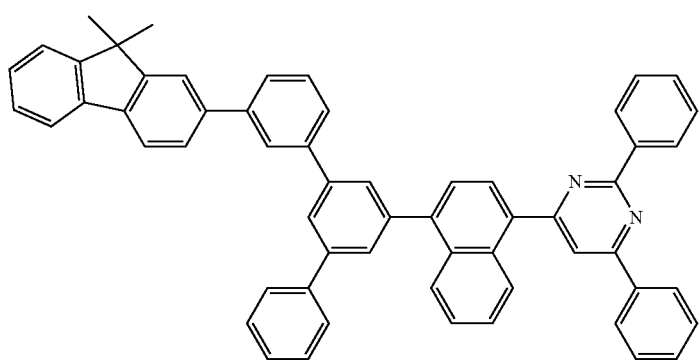

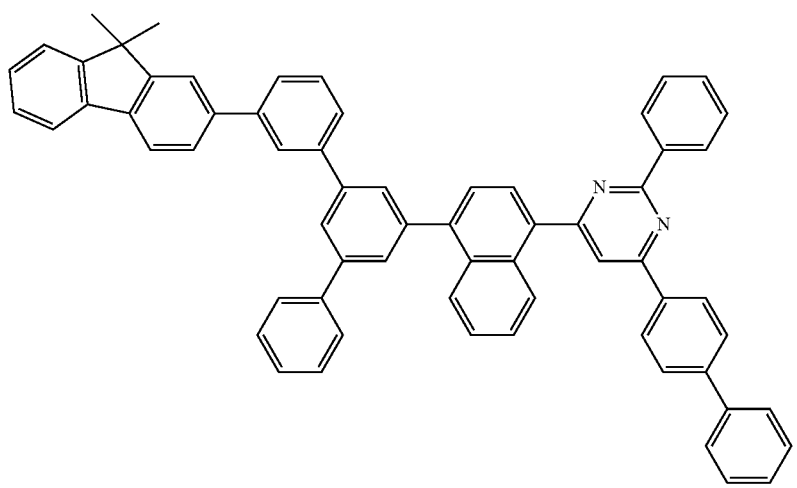 [SMILES: CC1(C)c2ccccc2-c2ccc(-c3cccc(-c4cc(-c5ccccc5)cc(-c5ccc(-c6cc(-c7ccc(-c8ccccc8)cc7)nc(-c7ccccc7)n6)c6ccccc56)c4)c3)cc21]
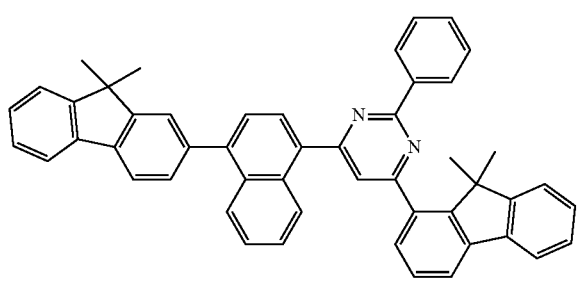
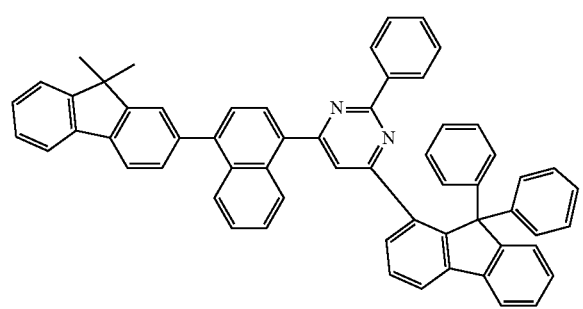
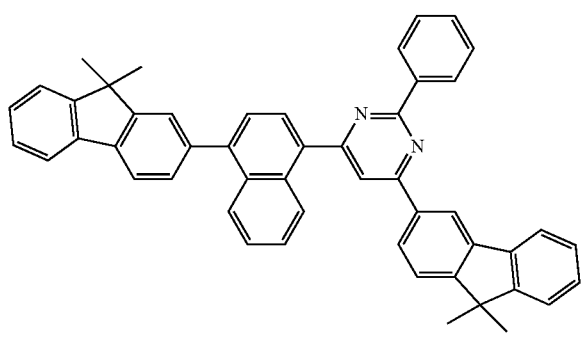
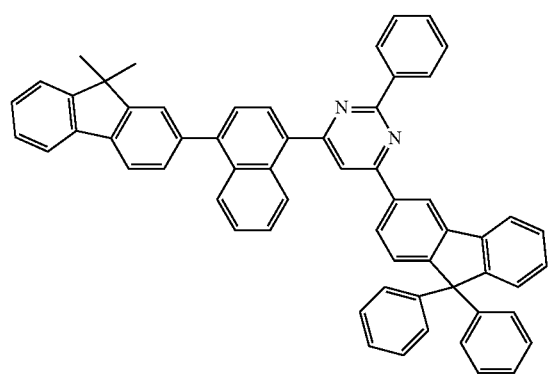
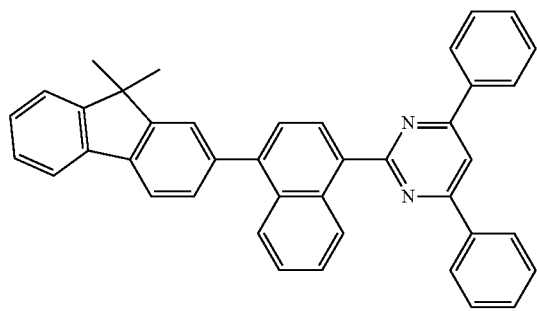
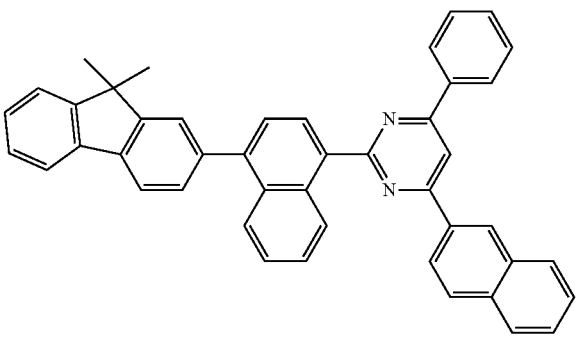

-continued
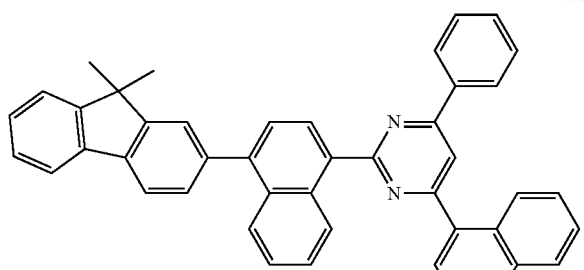
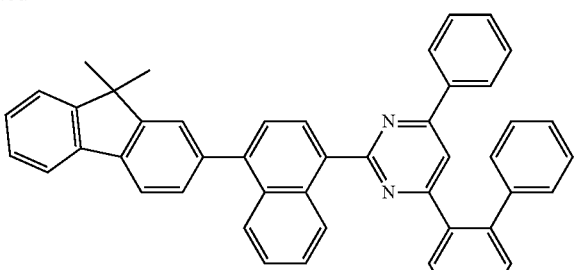
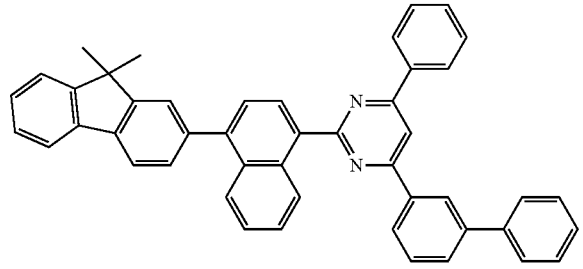
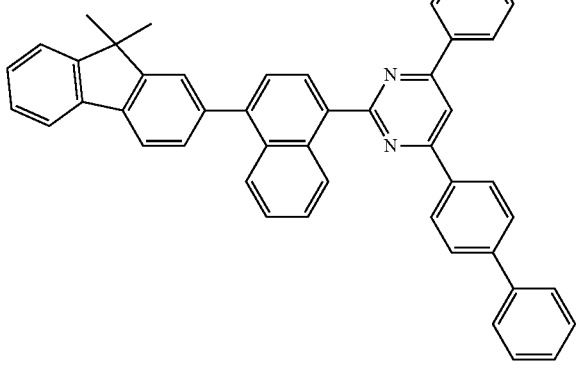
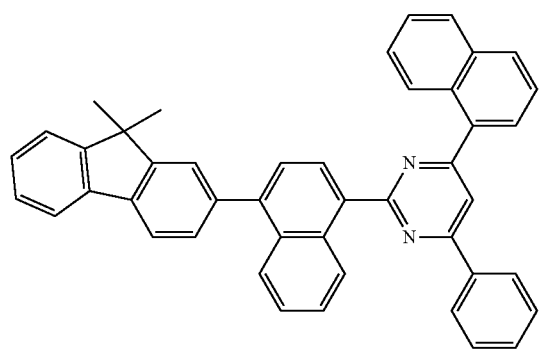
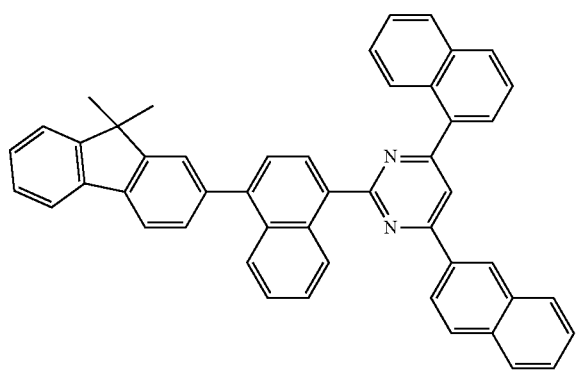
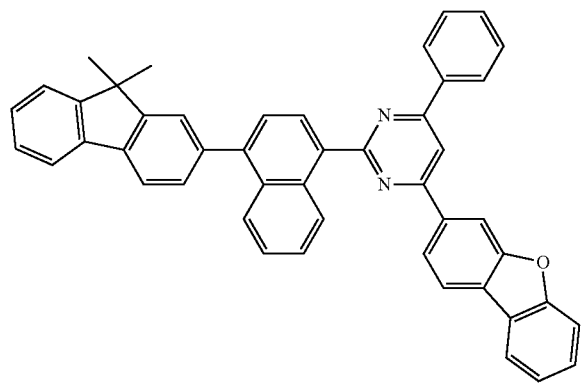
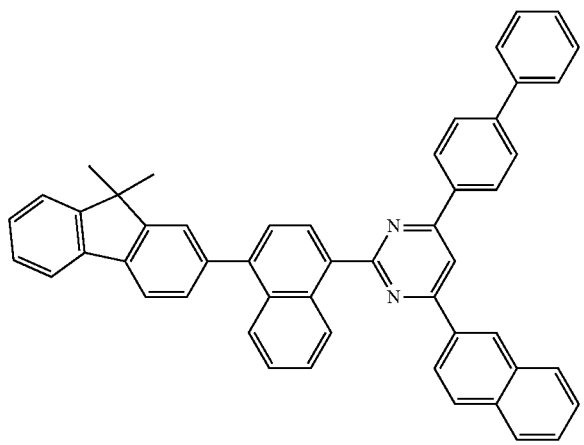

-continued
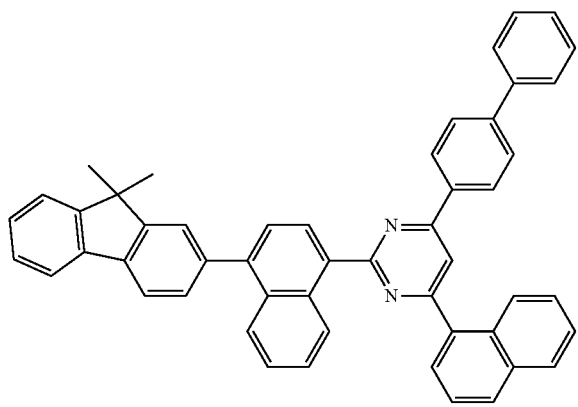 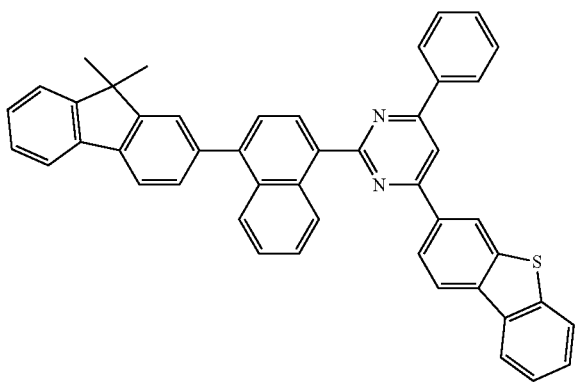
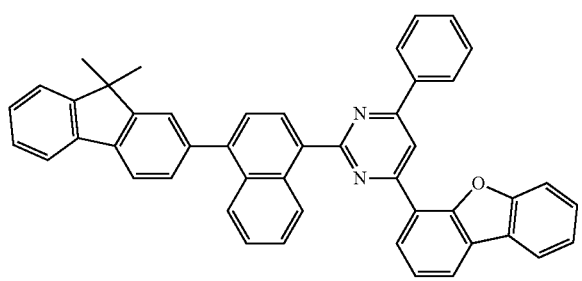 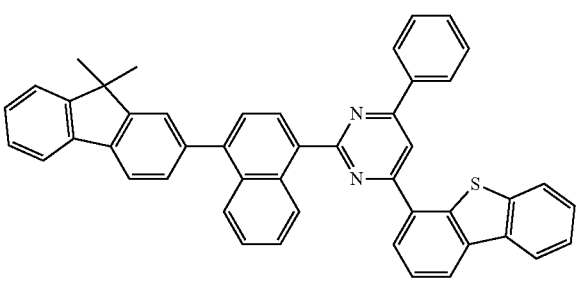
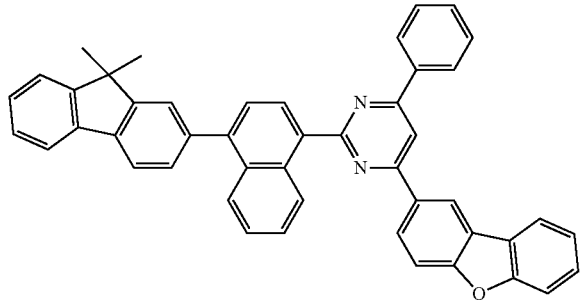 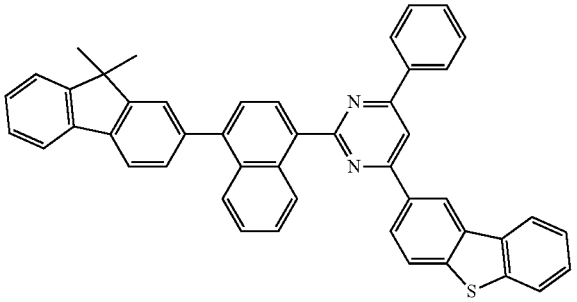
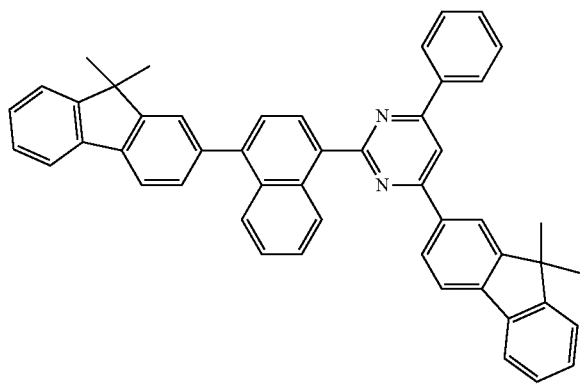 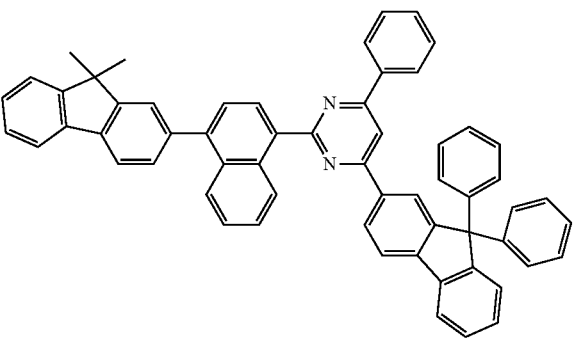
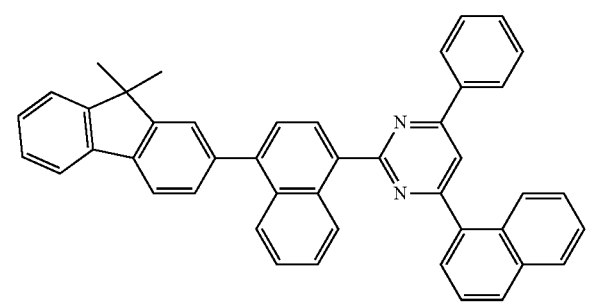 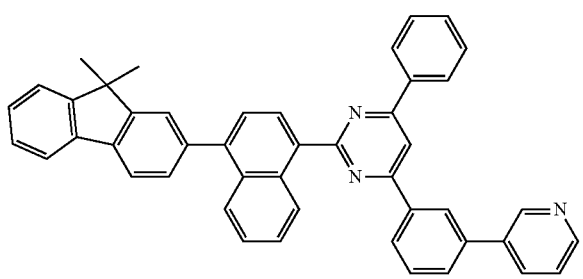

-continued
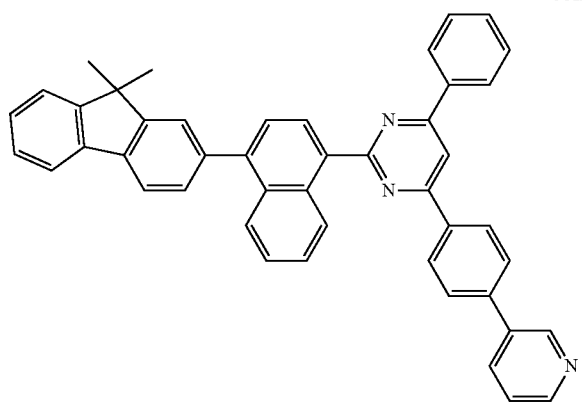
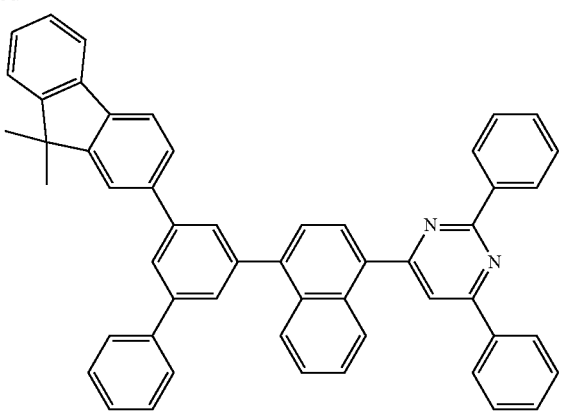
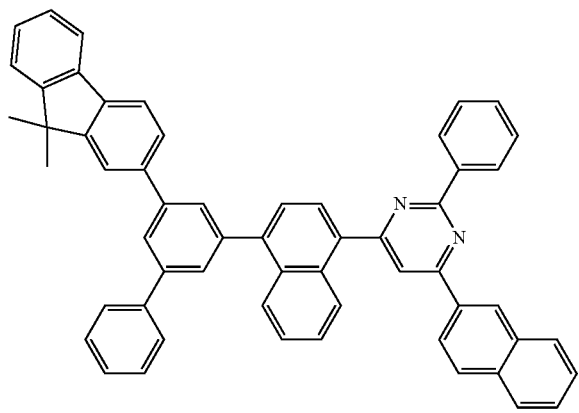
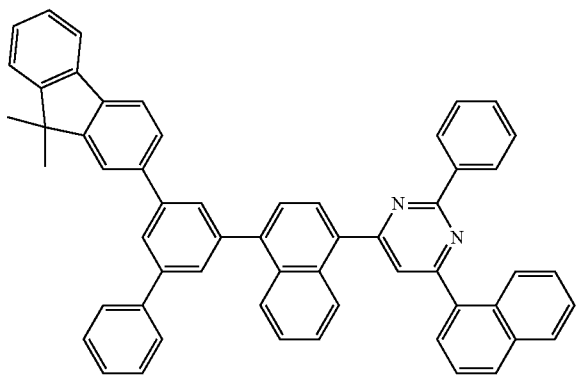
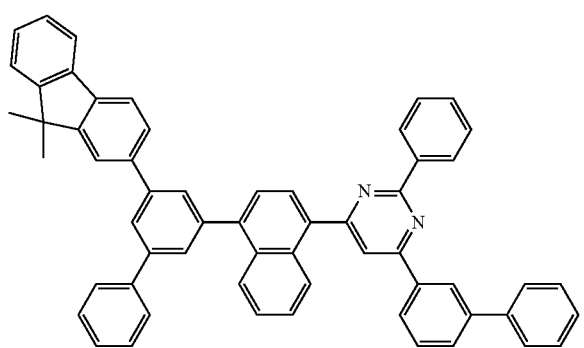
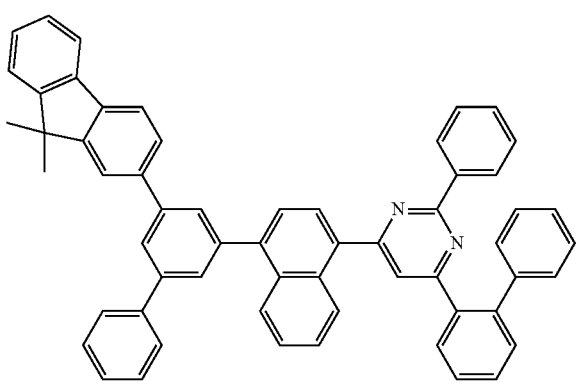
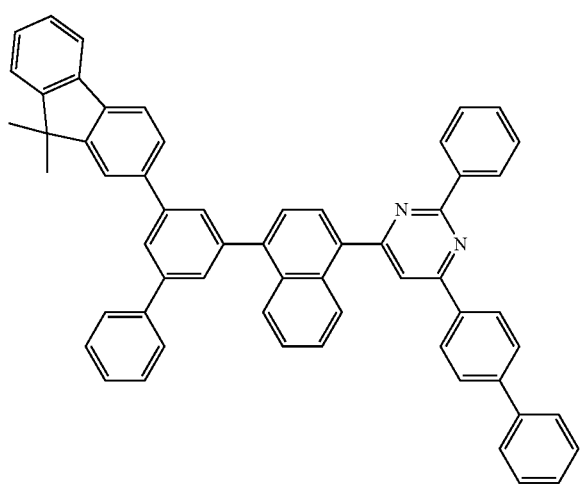
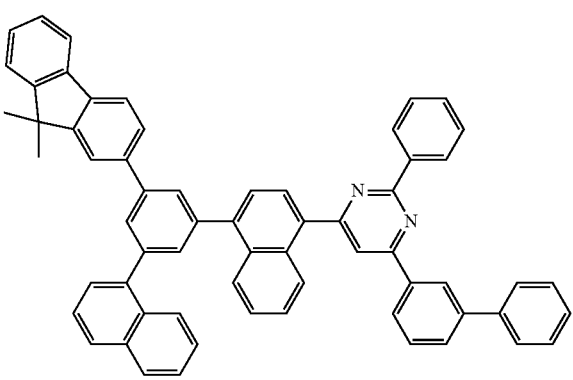

-continued
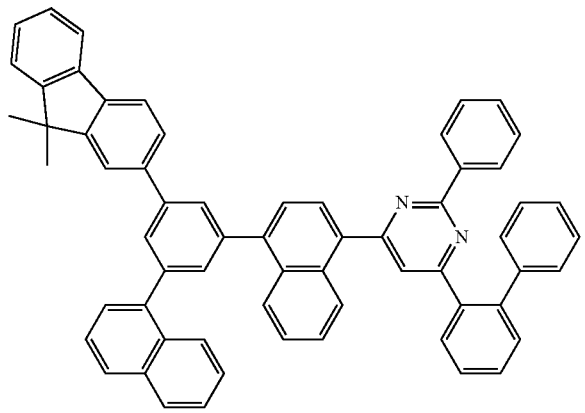
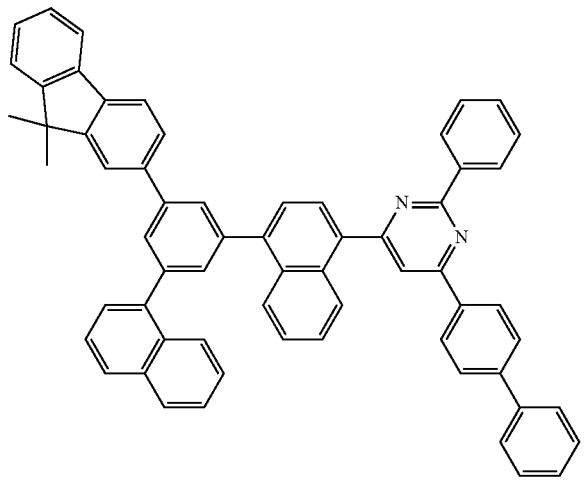
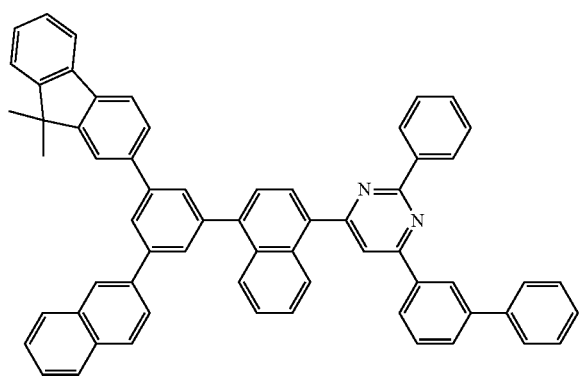
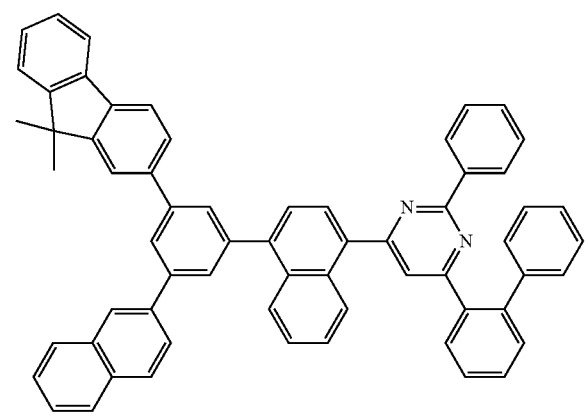
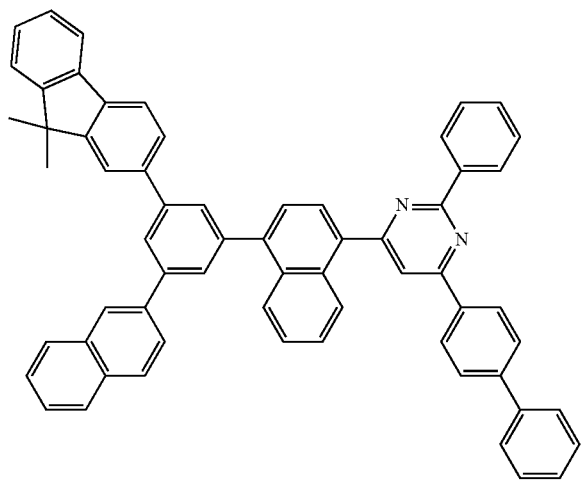
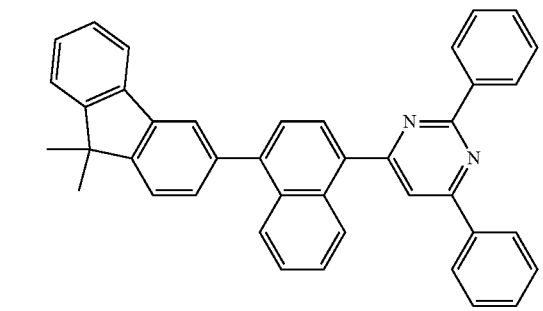
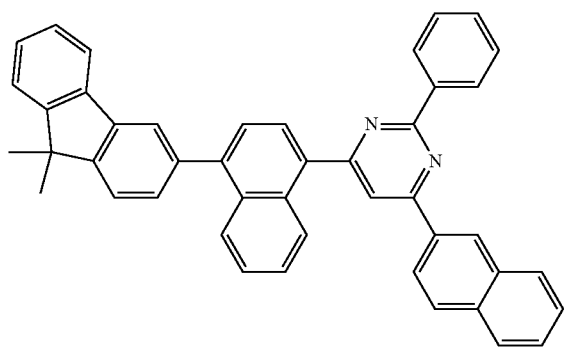
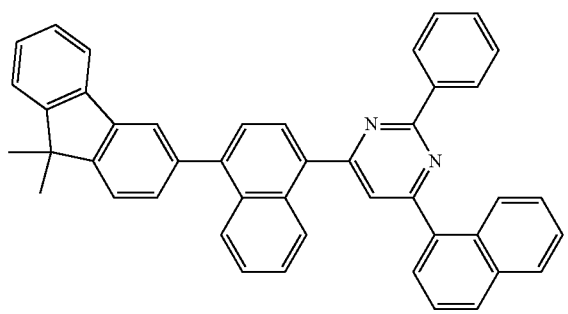

-continued
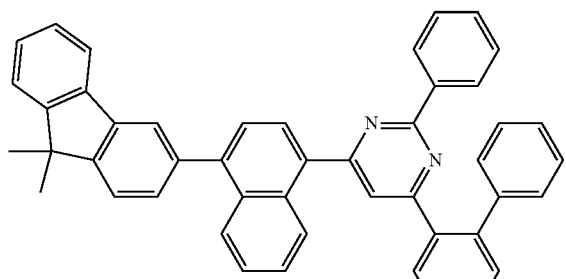
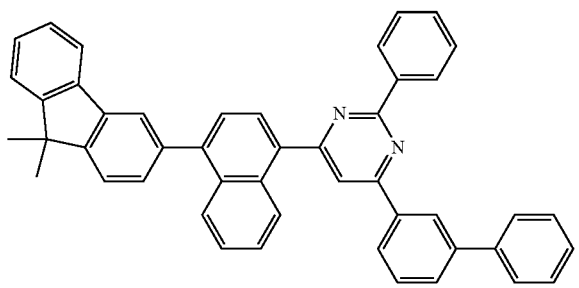
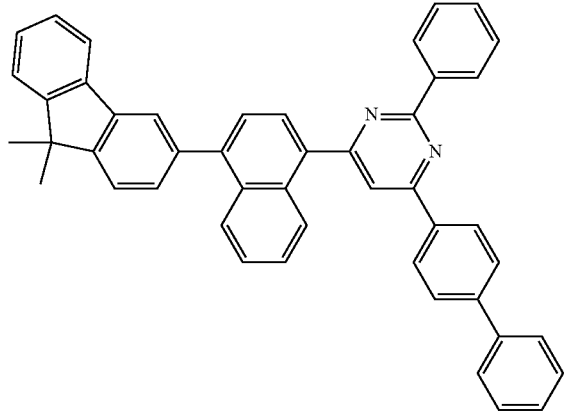
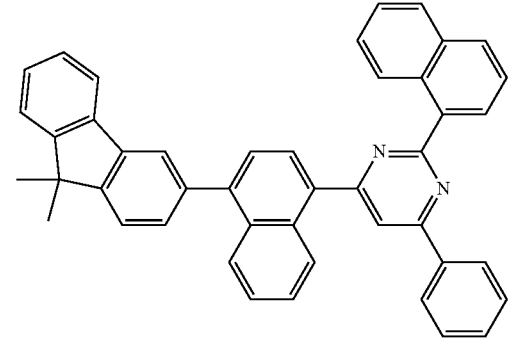
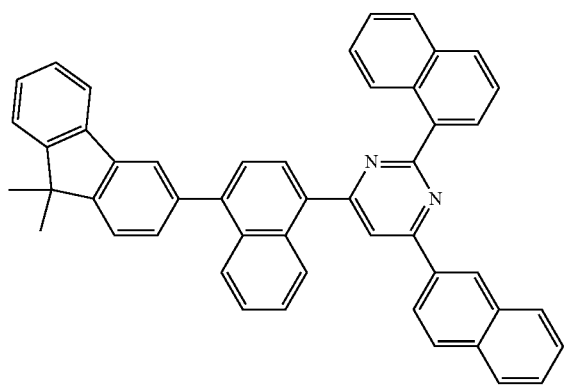
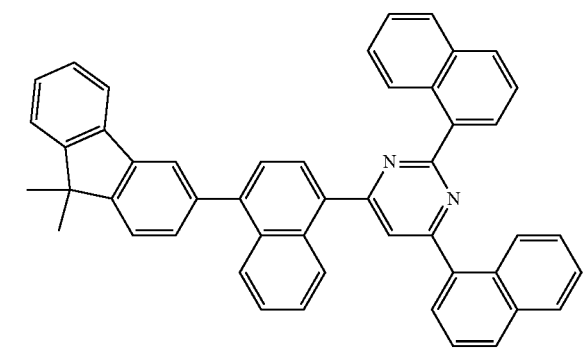
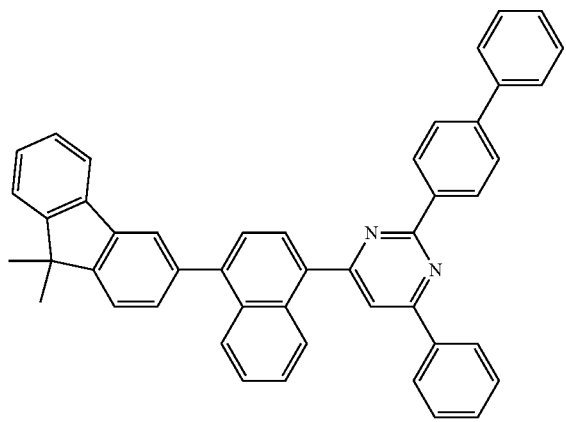
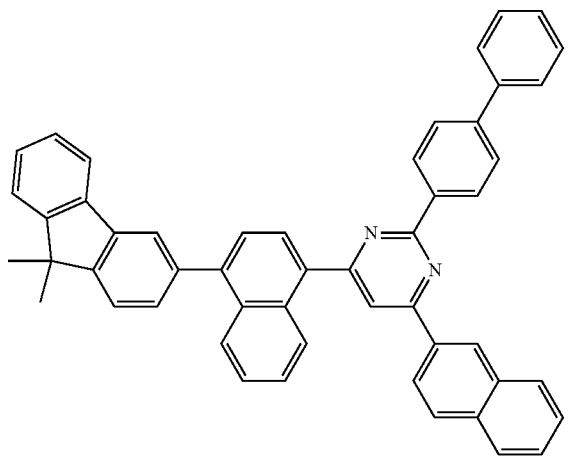

-continued
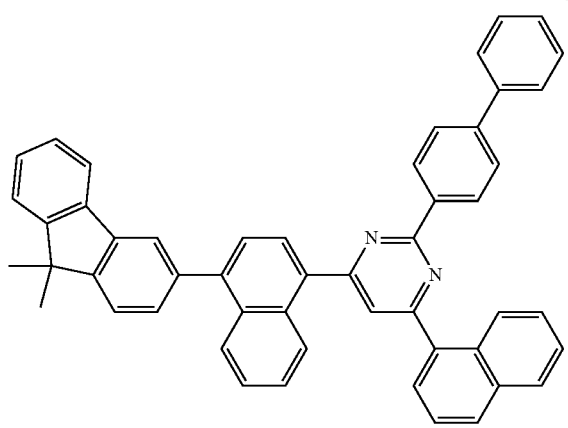
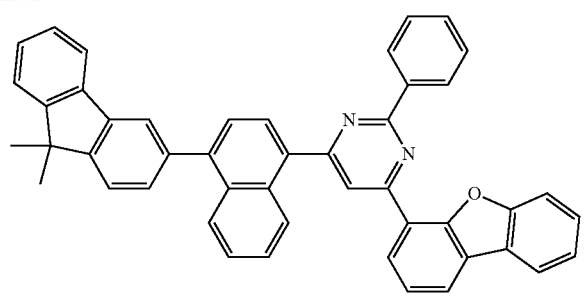
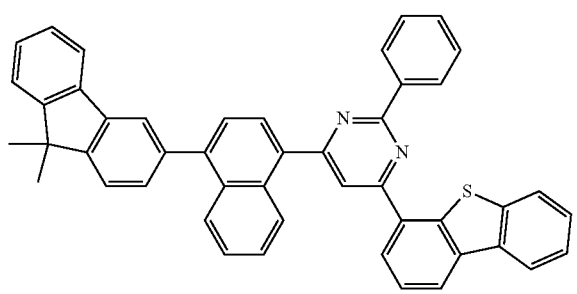
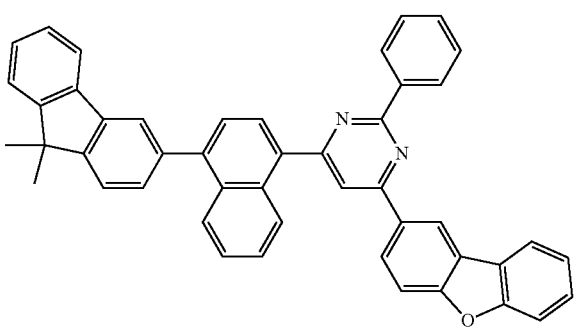
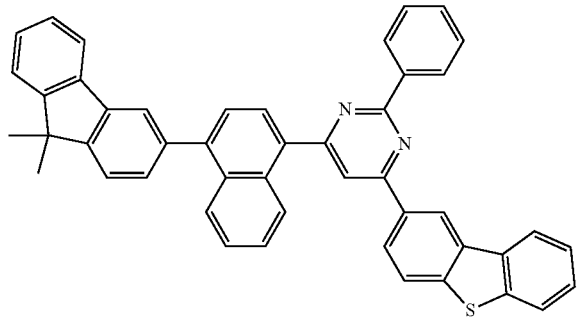
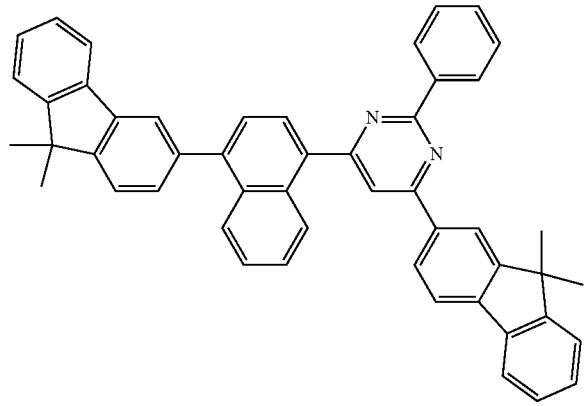
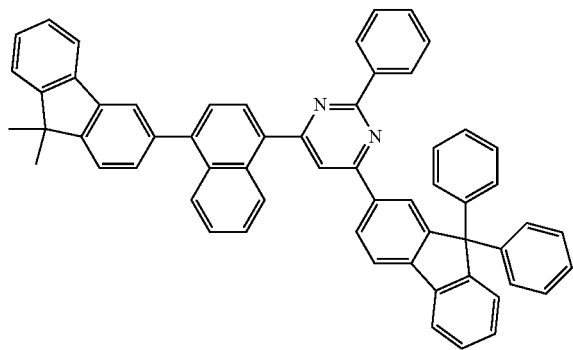
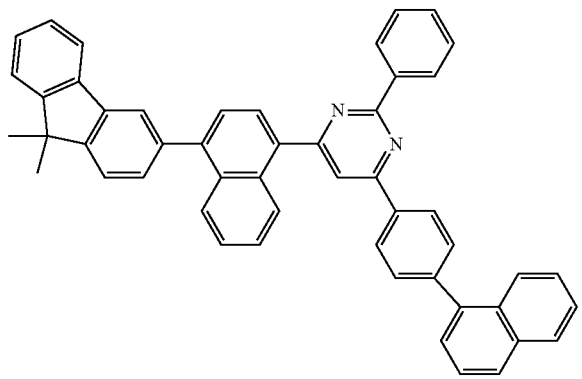

| 97 | 98 |
|---|---|
| 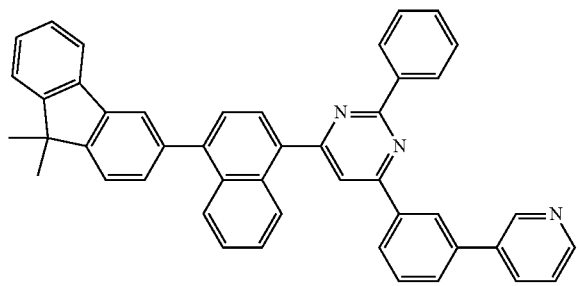 | 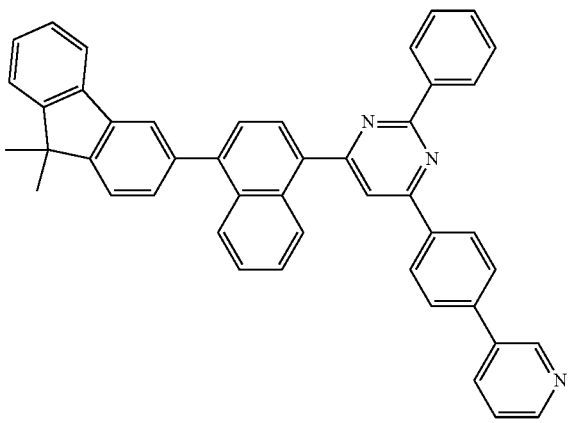 |
| 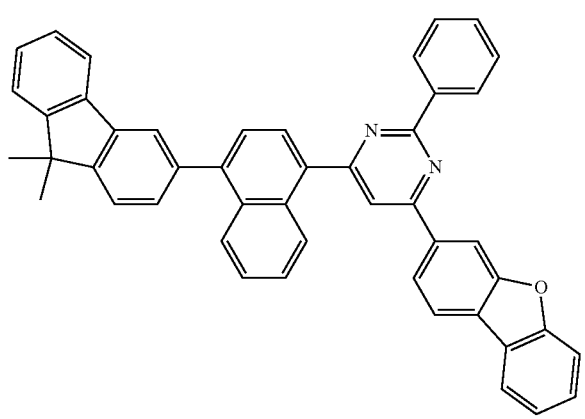 | 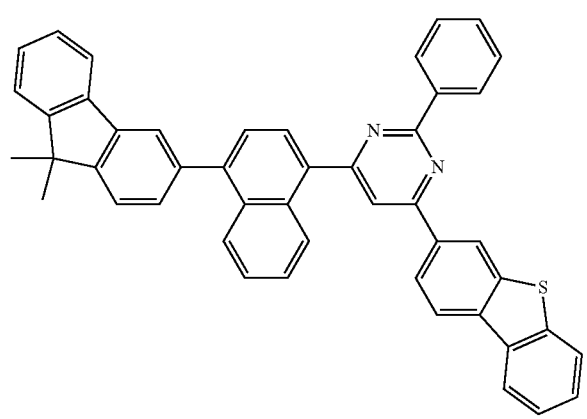 |
| 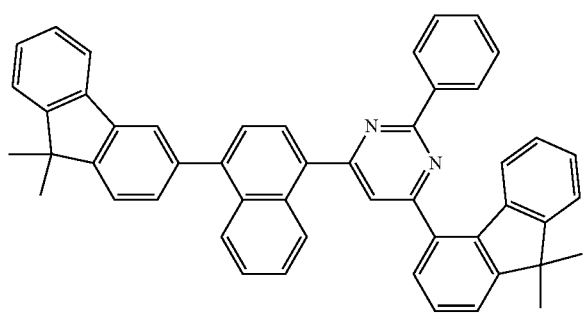 | 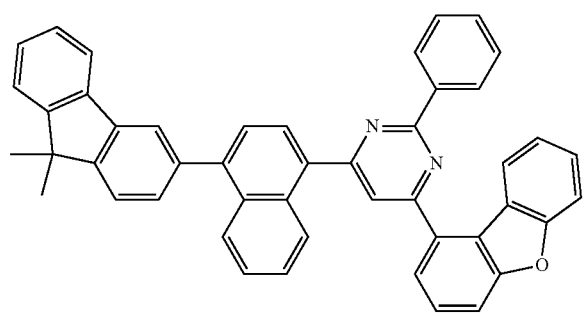 |
| 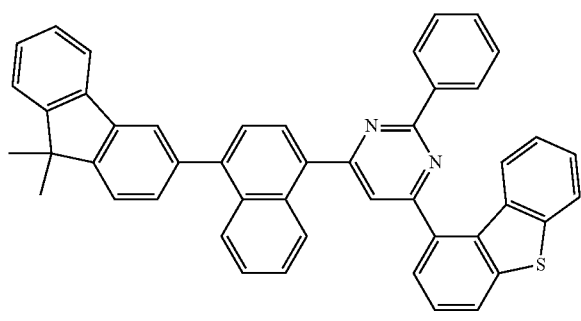 | 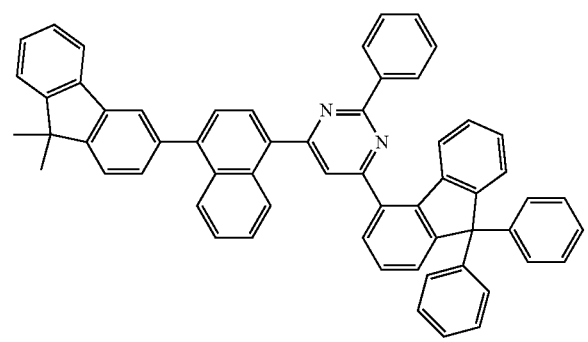 |

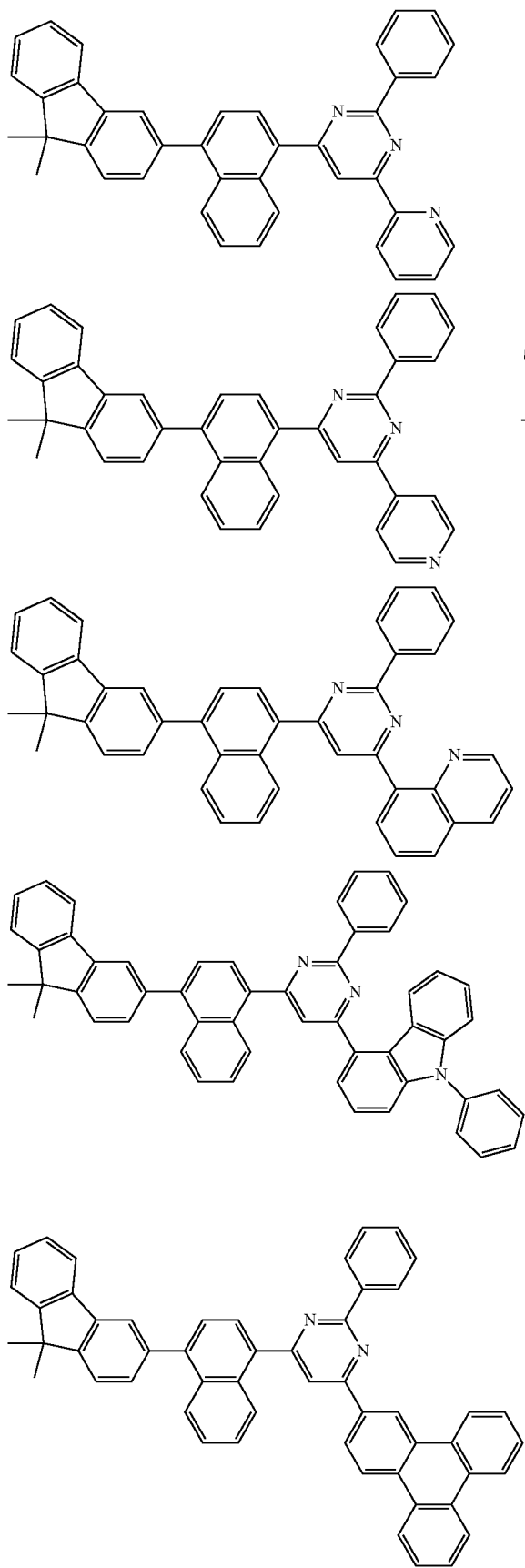

-continued
| 101 | 102 |
|---|---|
| 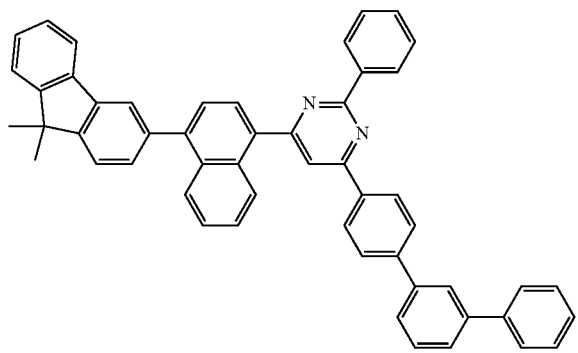 | 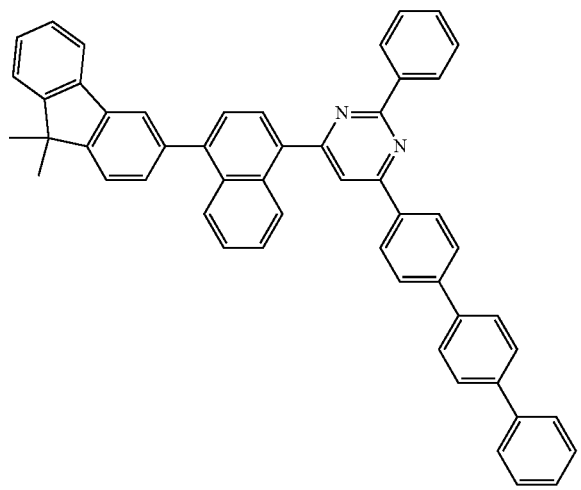 |
| 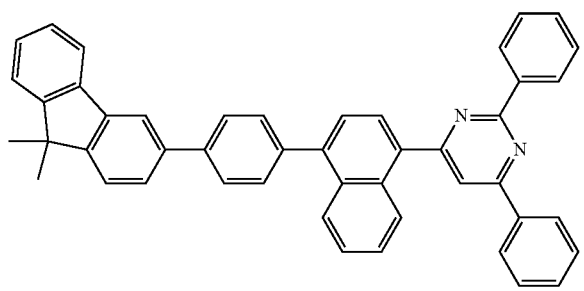 | 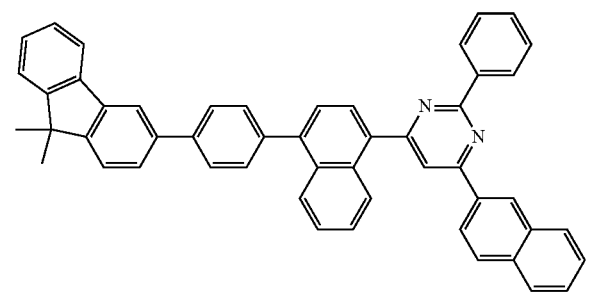 |
| 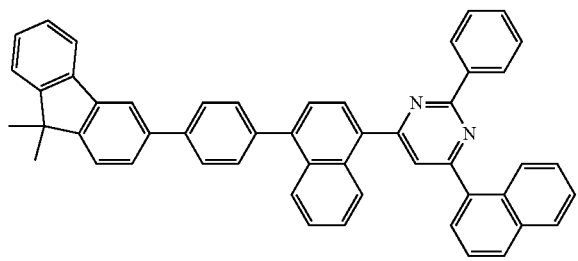 | 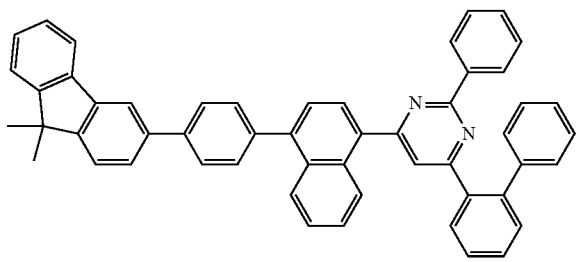 |
| 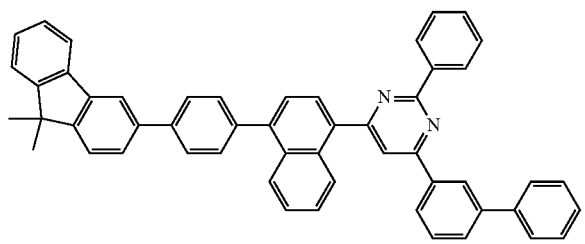 | 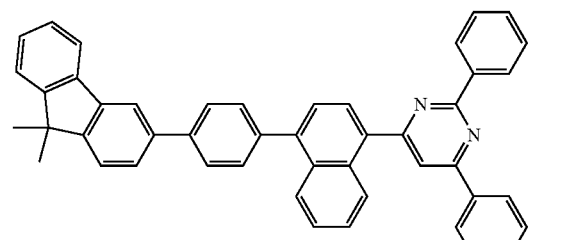 |
| 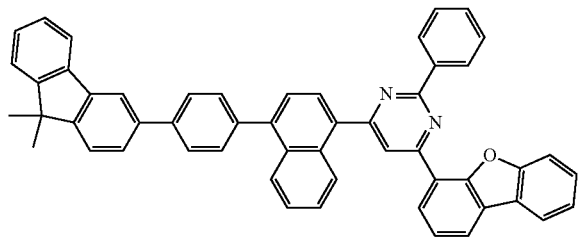 | 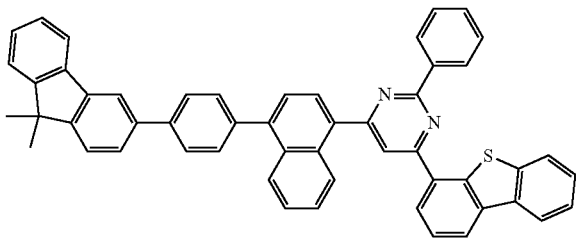 |

-continued
| 103 | 104 |
|---|---|
| 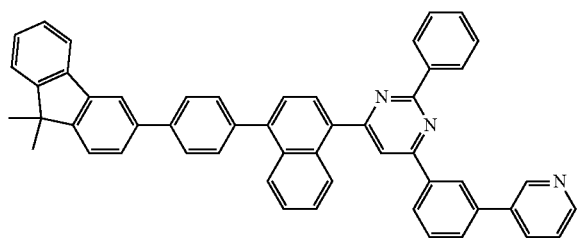 | 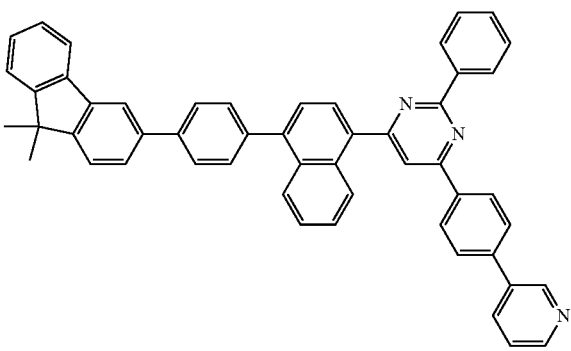 |
| 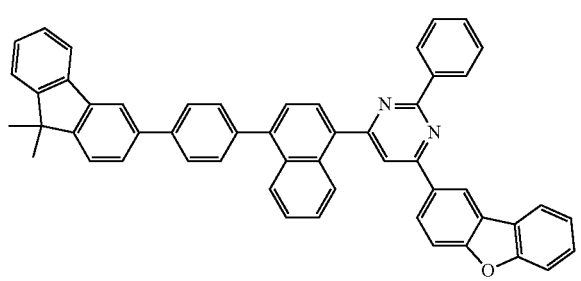 | 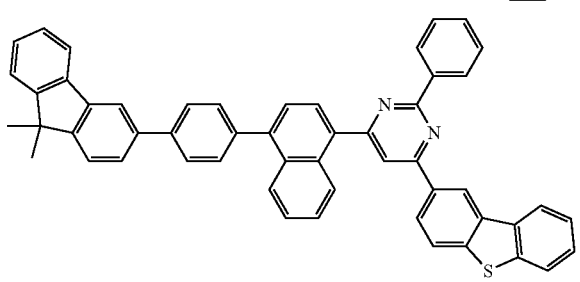 |
| 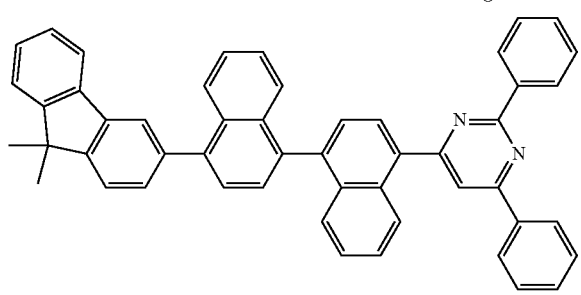 | 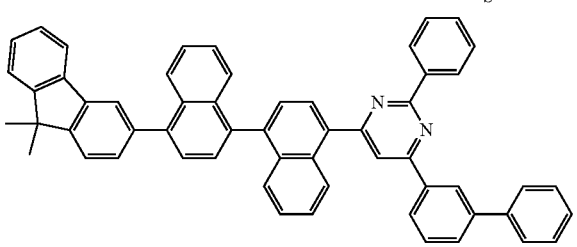 |
| 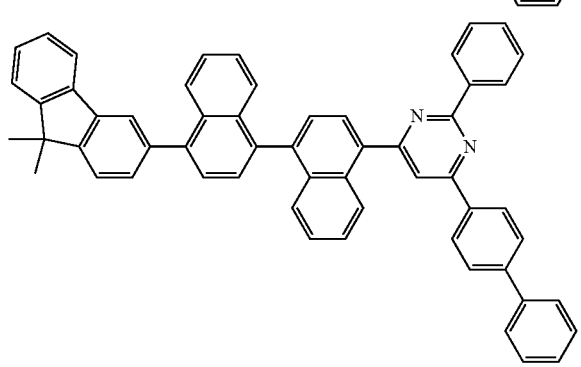 | 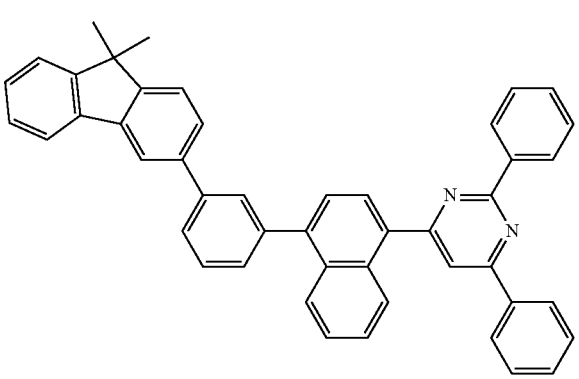 |
| 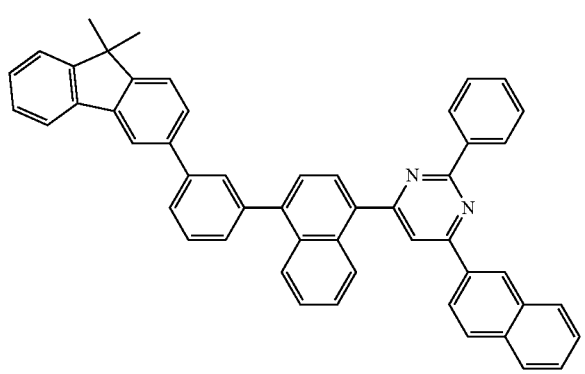 | 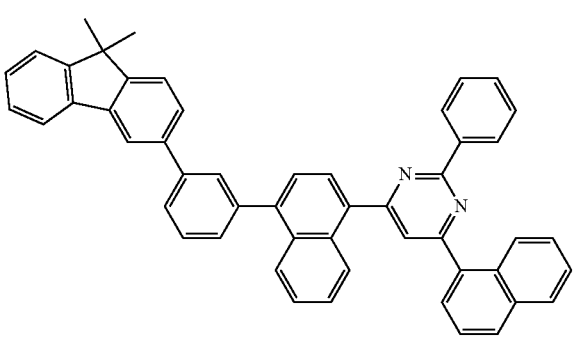 |

-continued
| 105 | 106 |
|---|---|
| 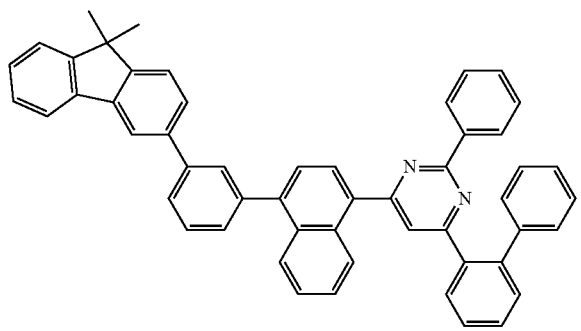 | 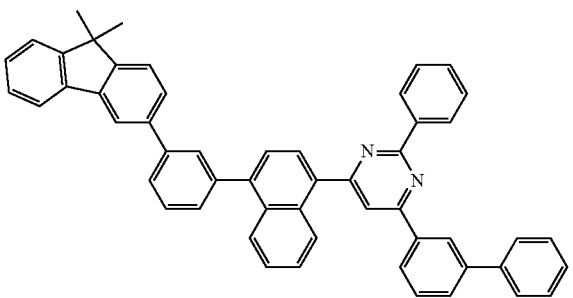 |
| 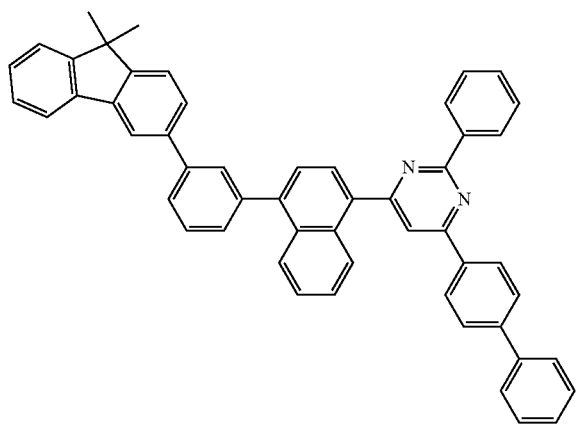 | 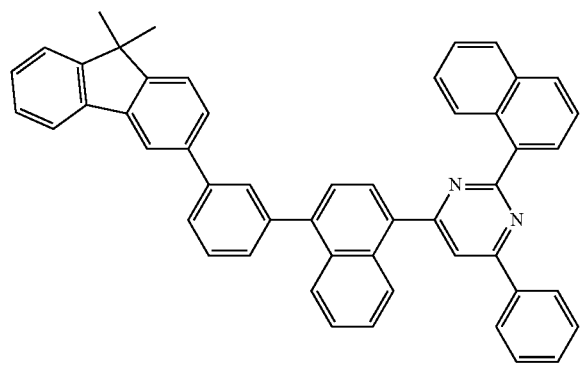 |
| 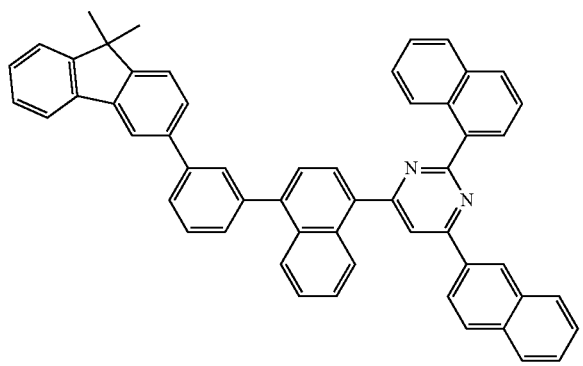 | 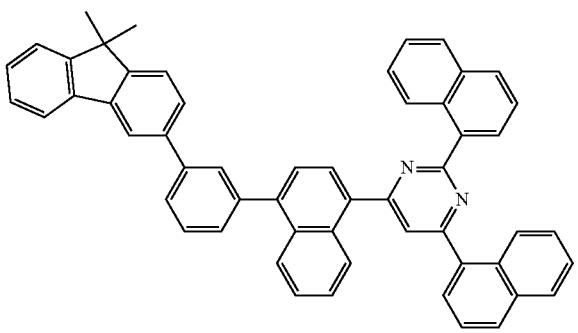 |
| 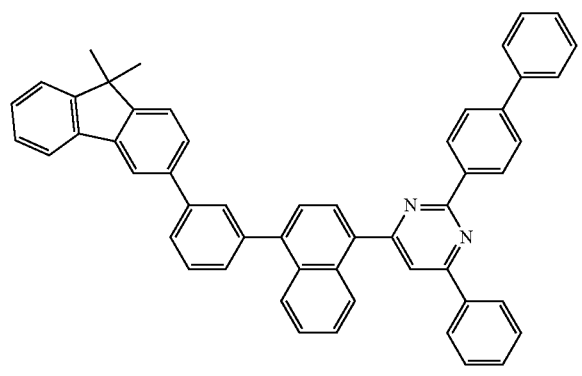 | 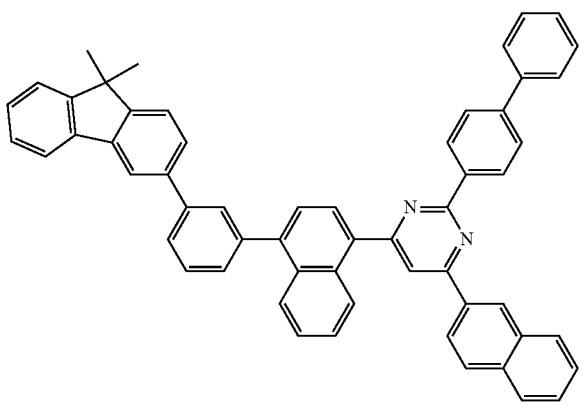 |

-continued
107
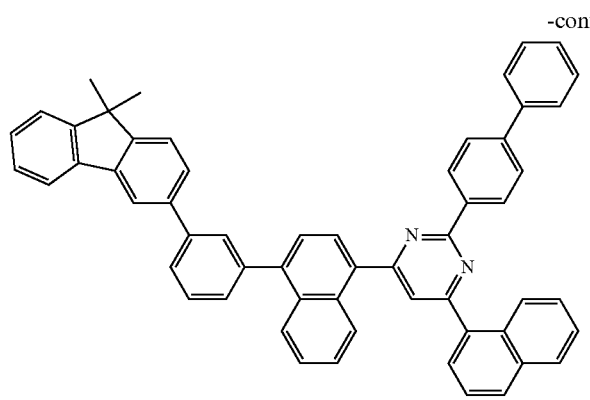
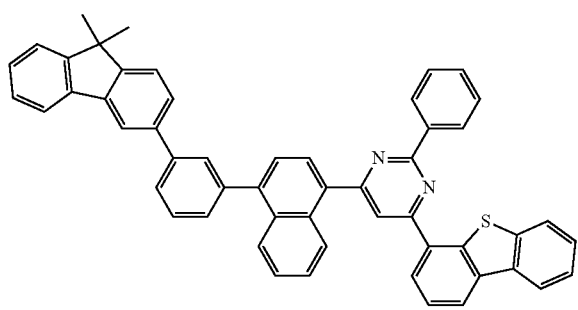
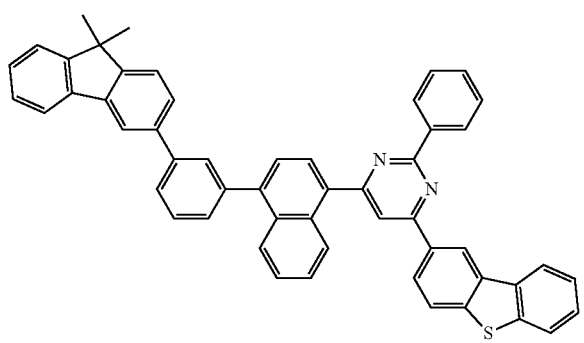
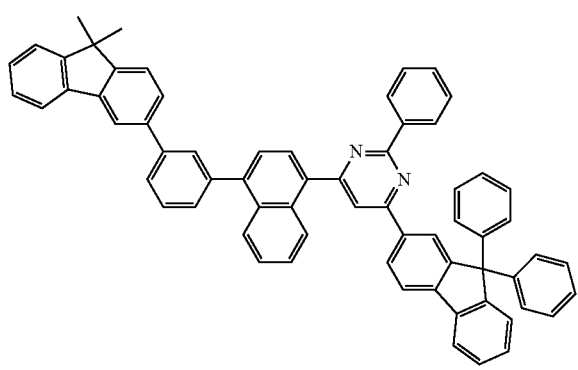
108
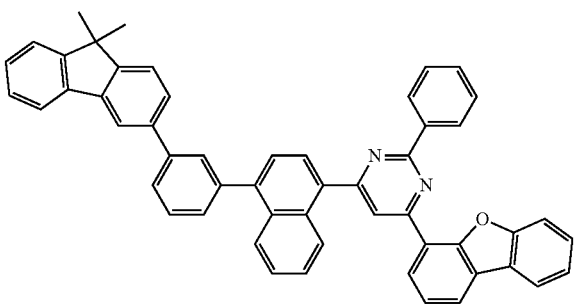
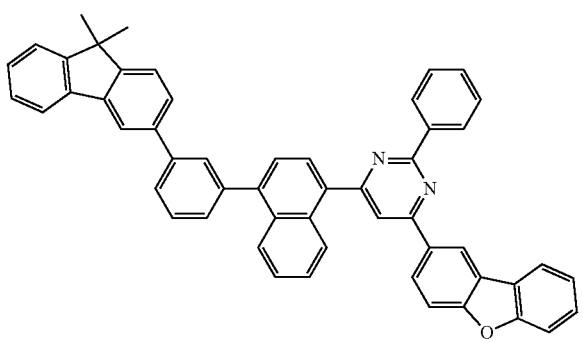
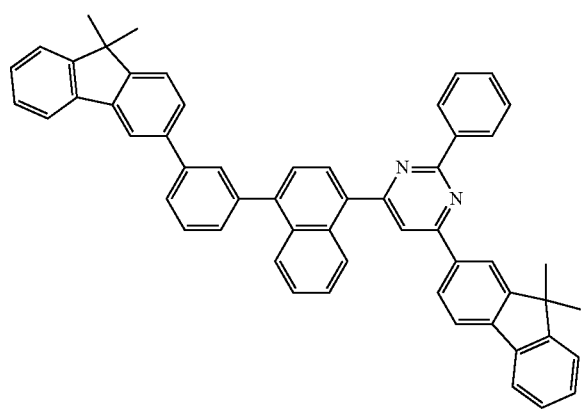
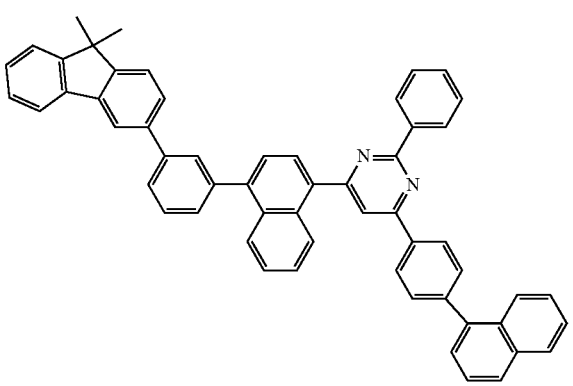

109
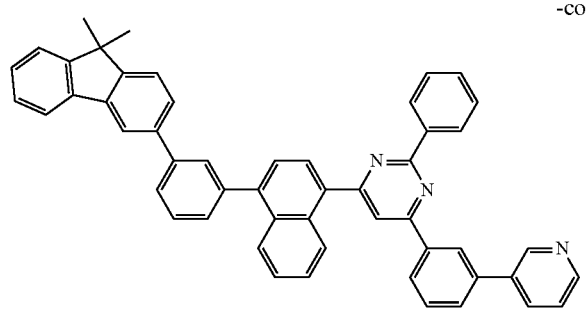
110
-continued
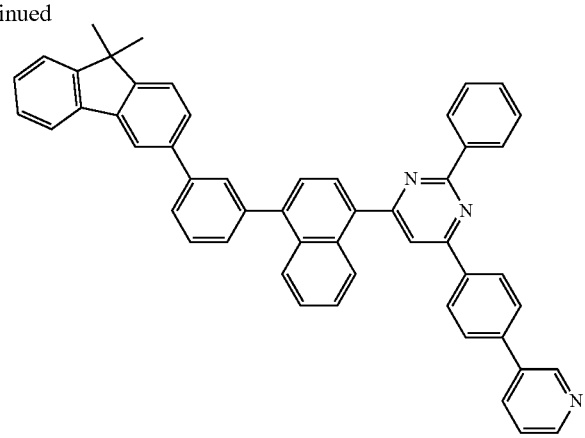
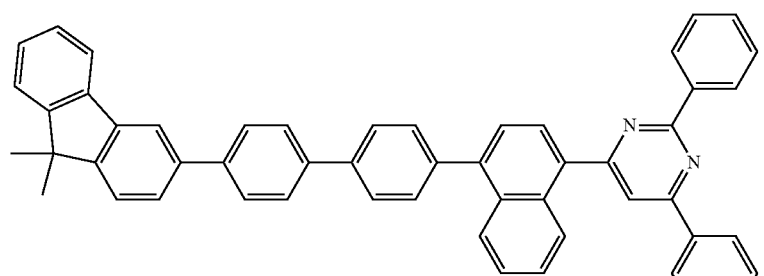
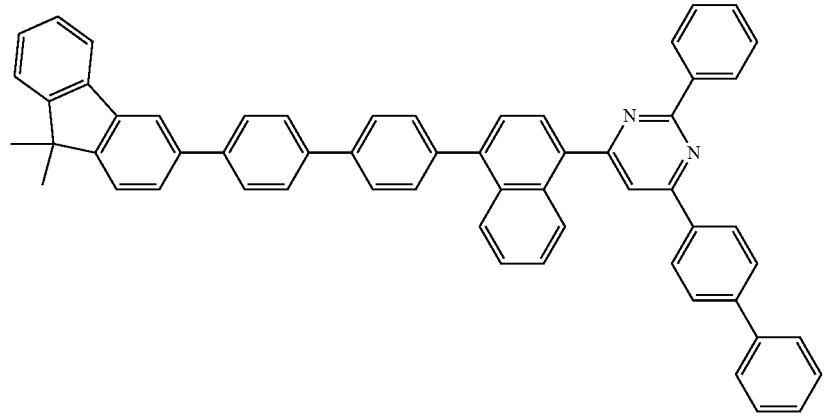
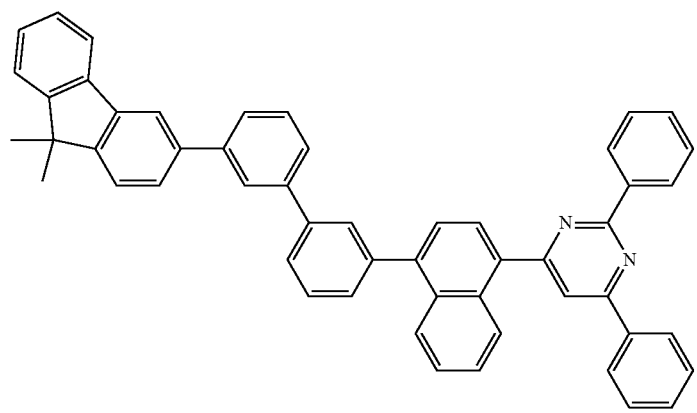

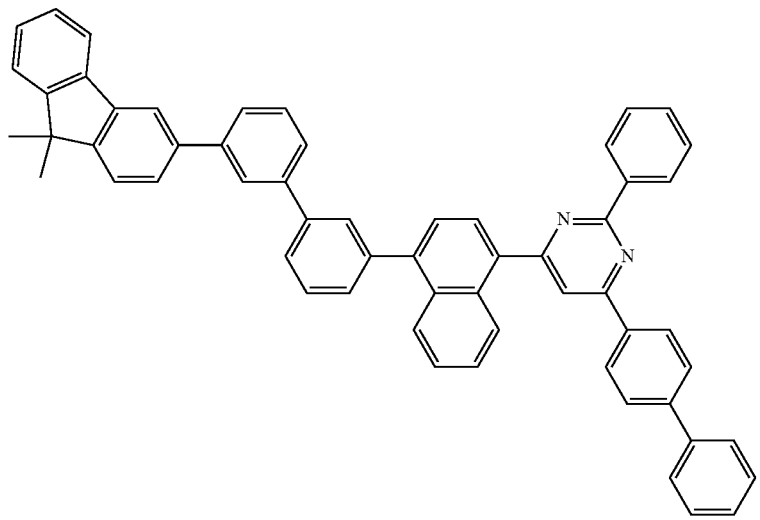
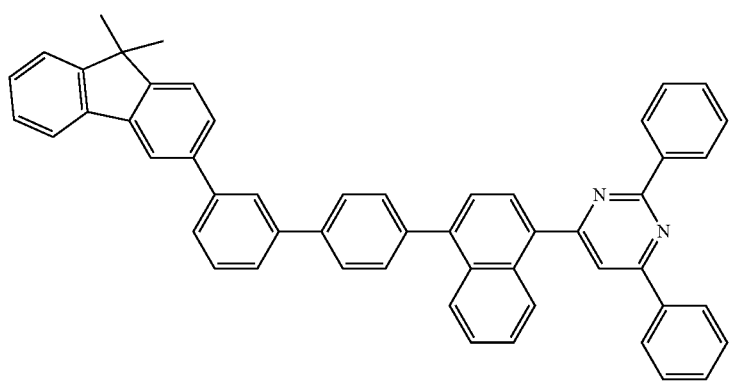
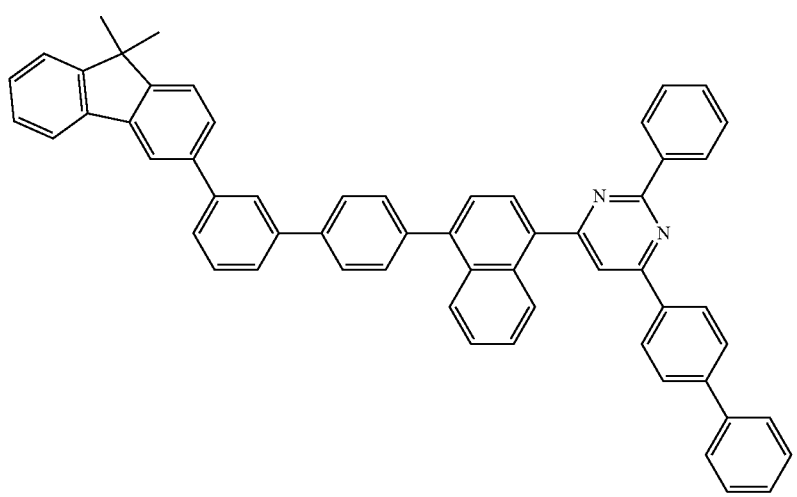

-continued
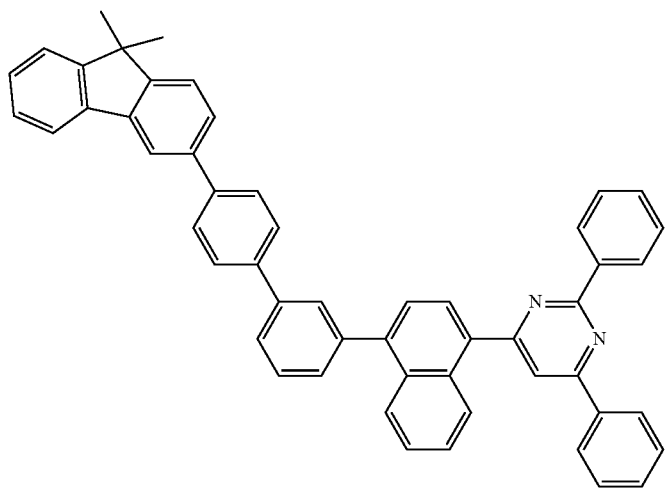
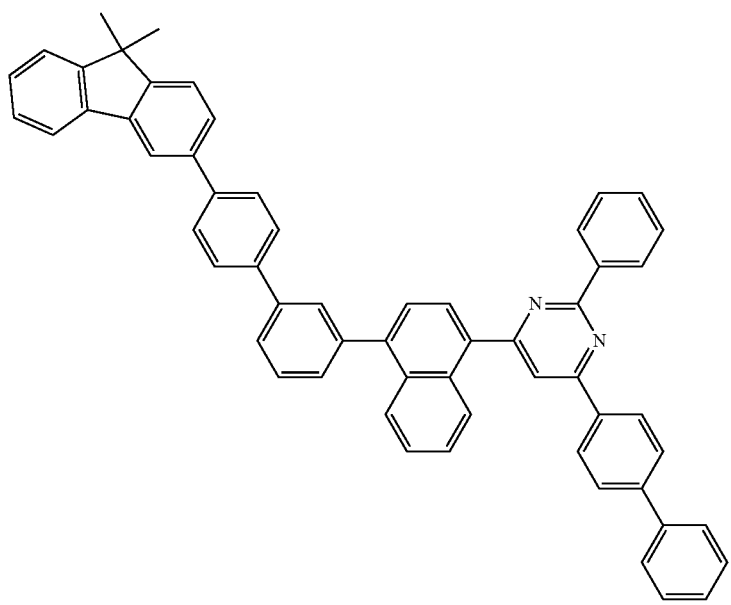
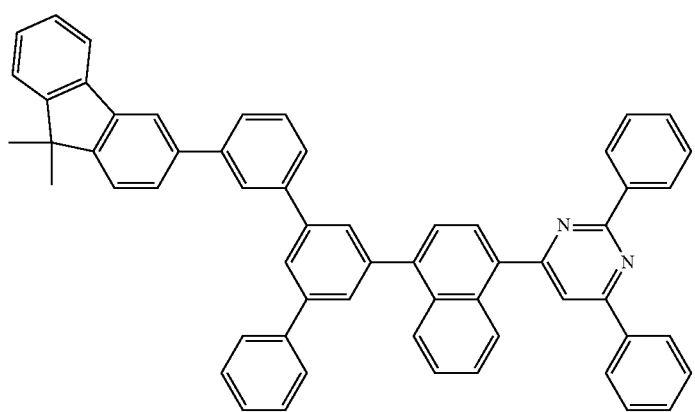

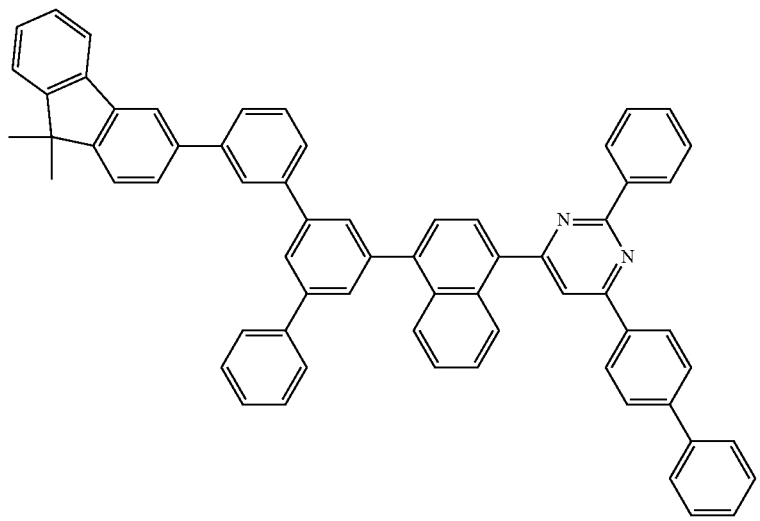
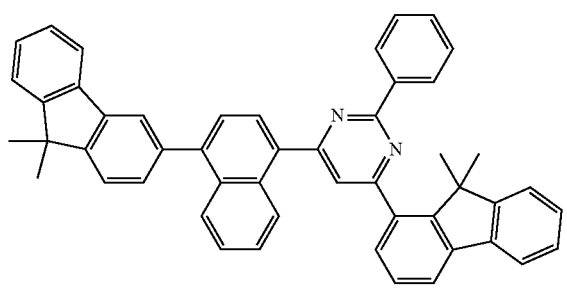
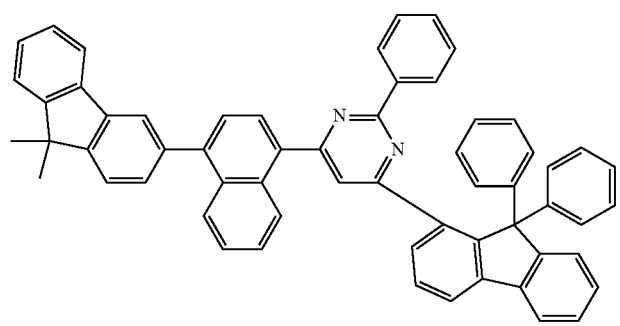
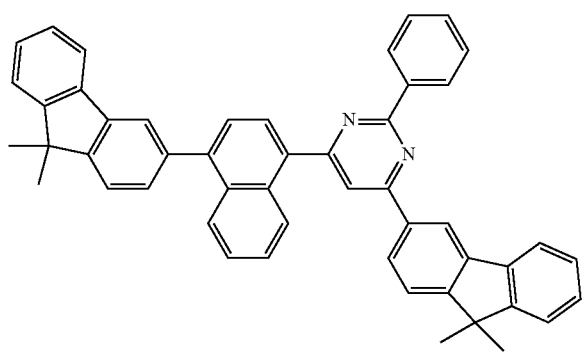
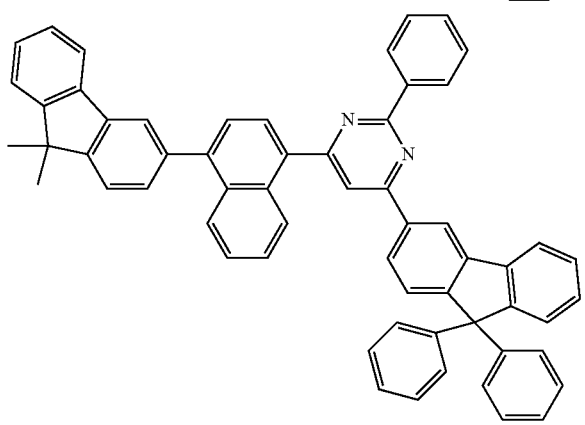
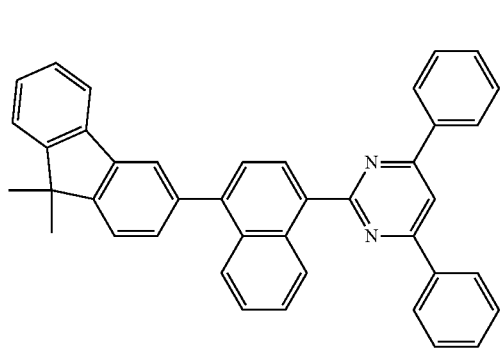
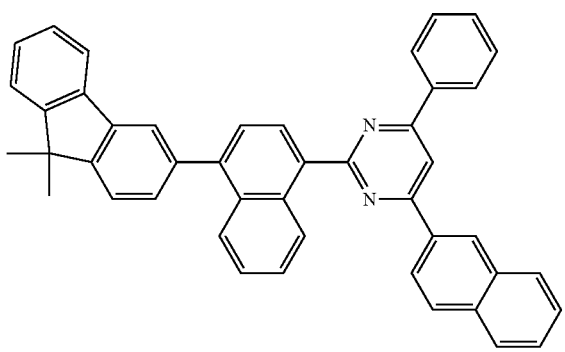

-continued
117
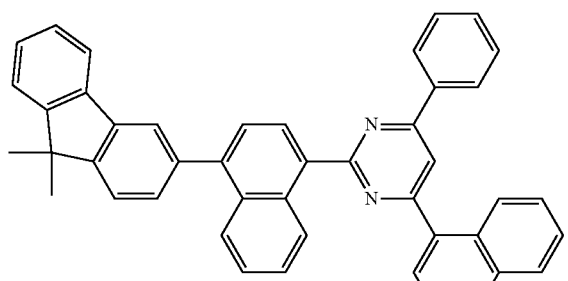
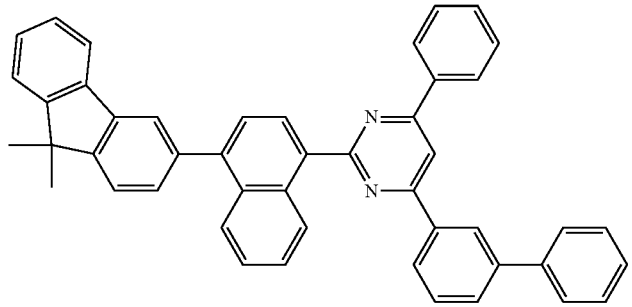
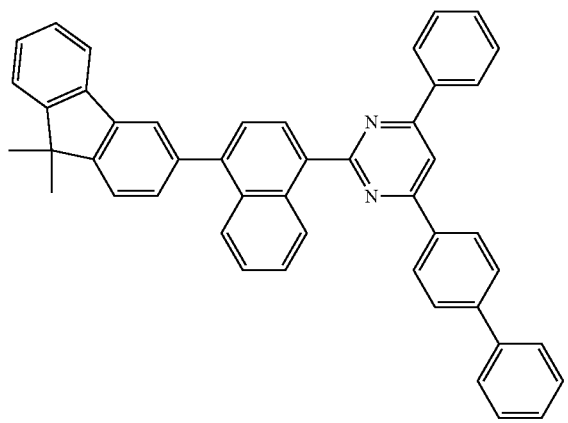
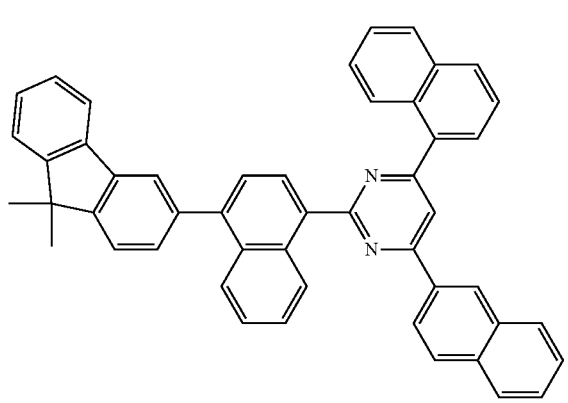
118
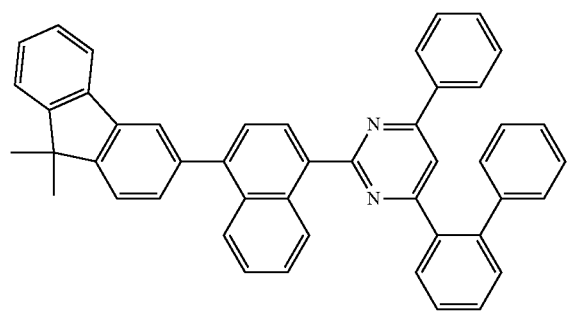
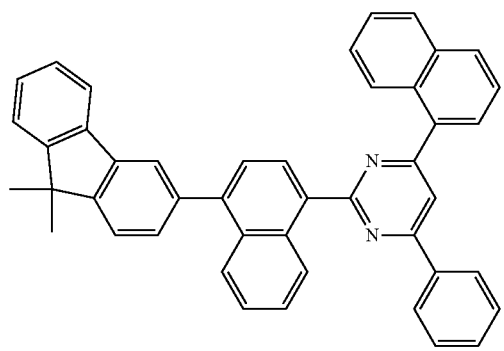
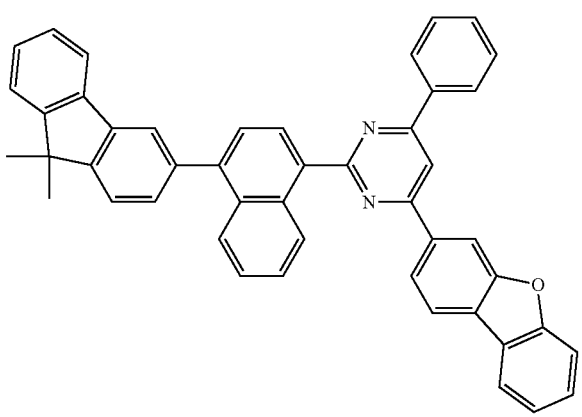

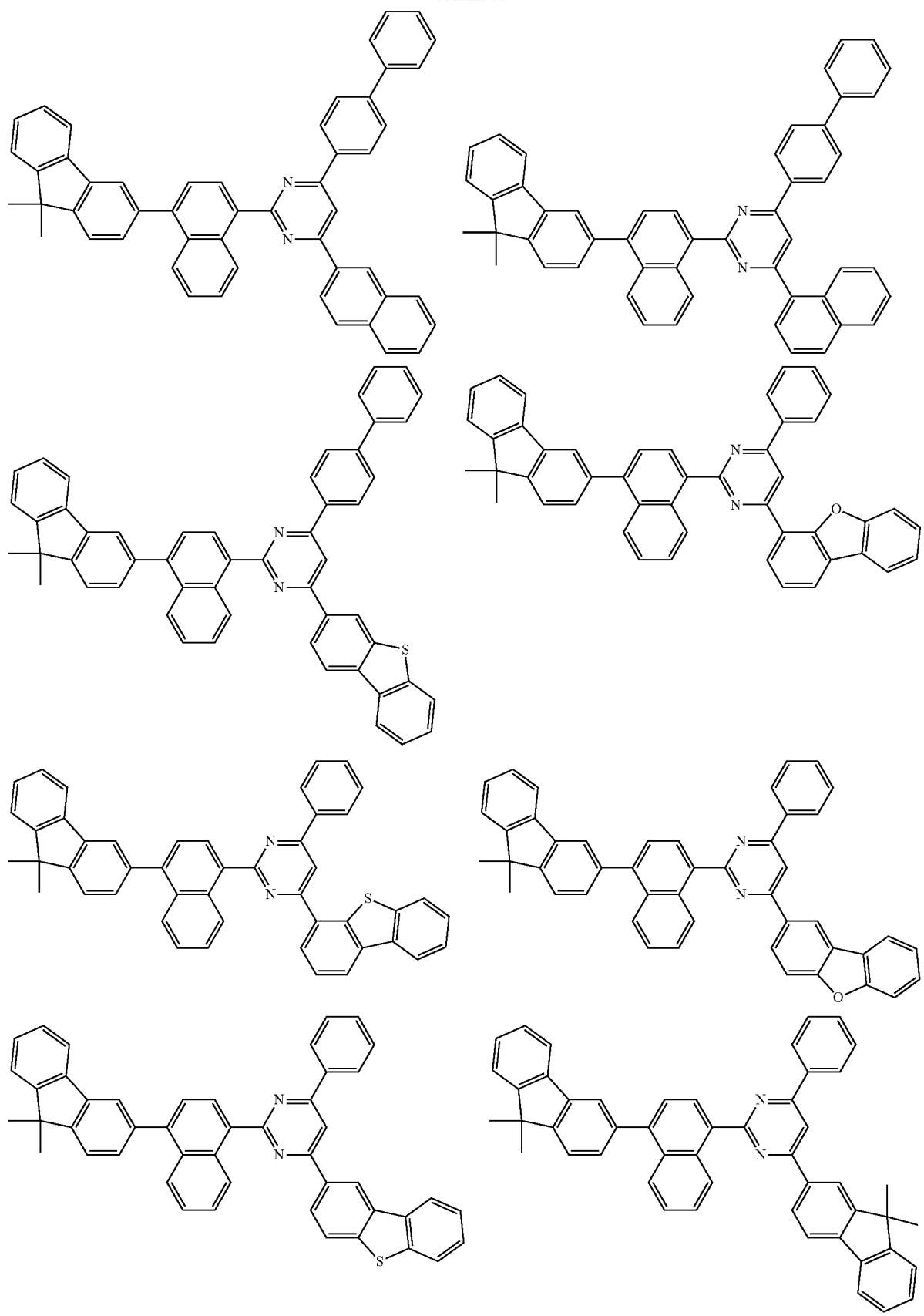

-continued
121
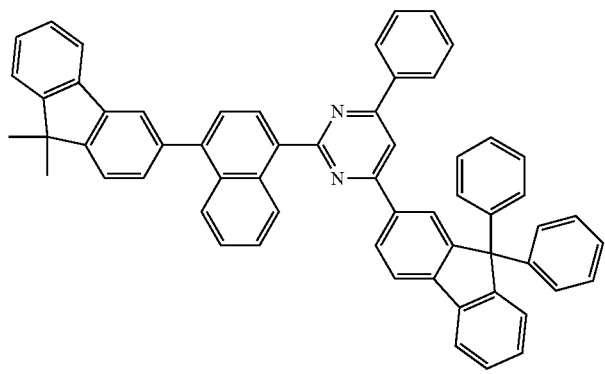
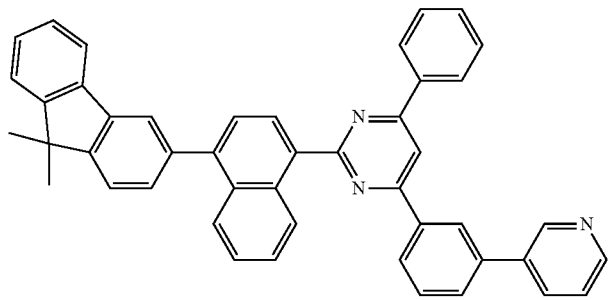
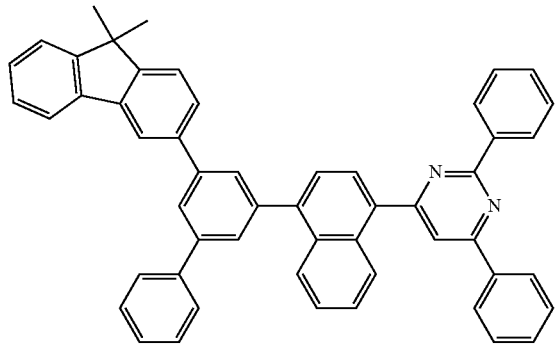
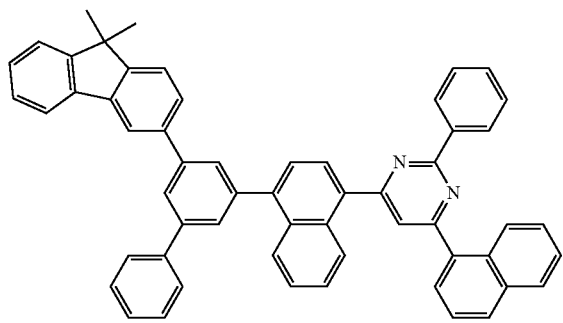
122
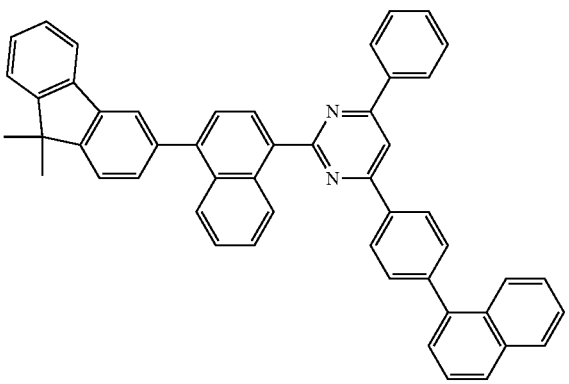
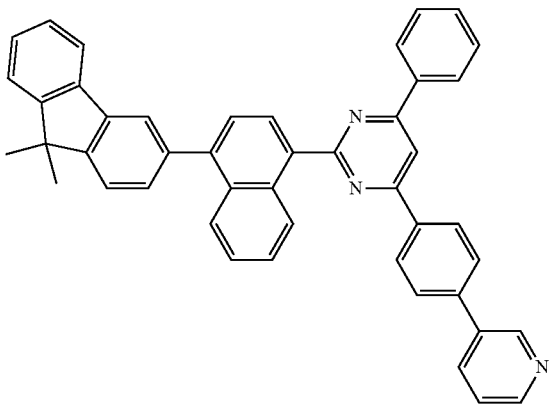
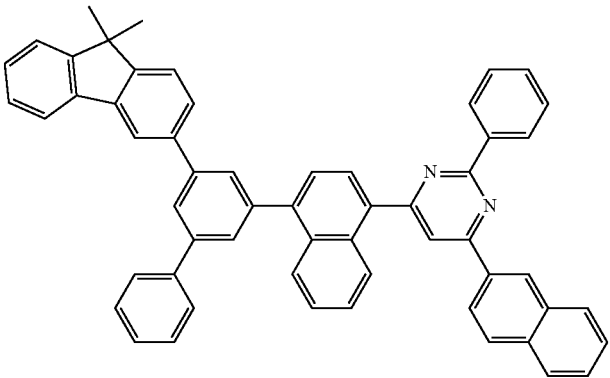
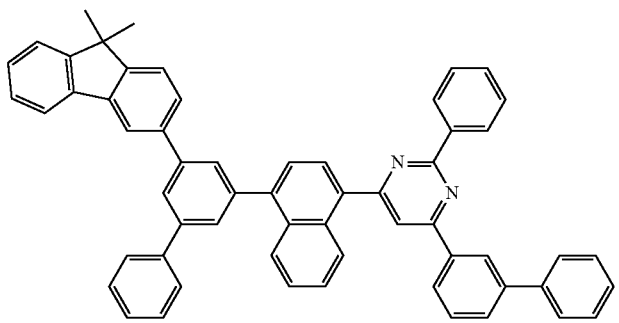

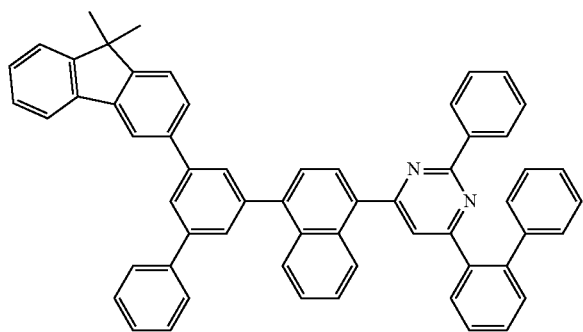
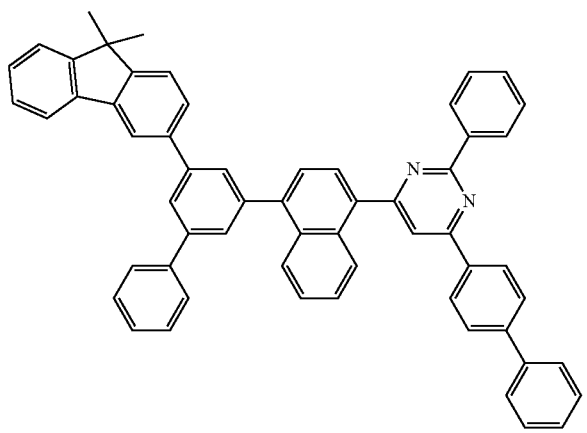
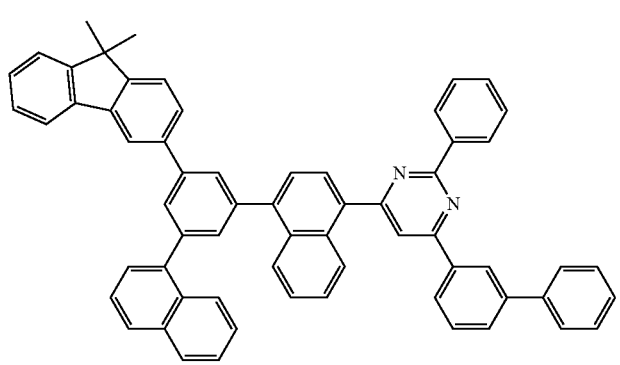
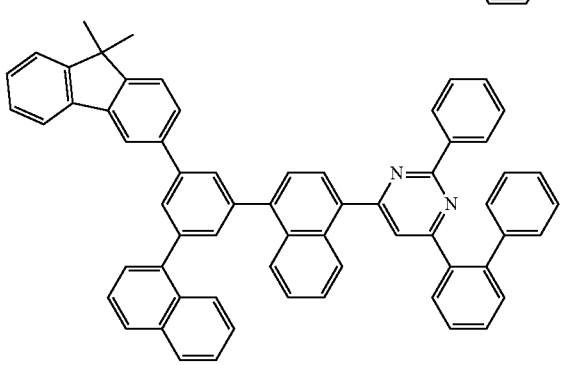
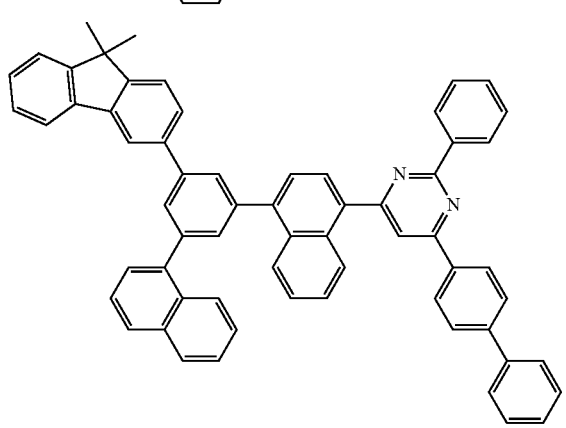
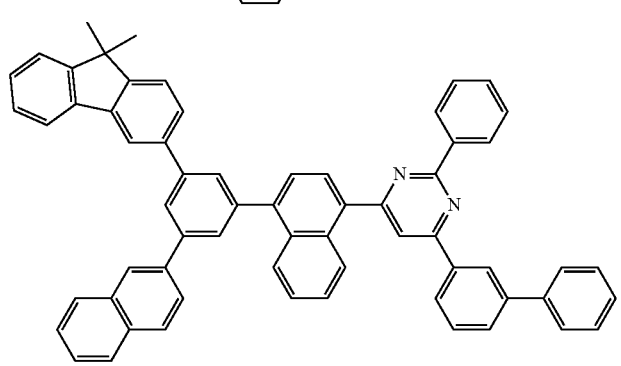
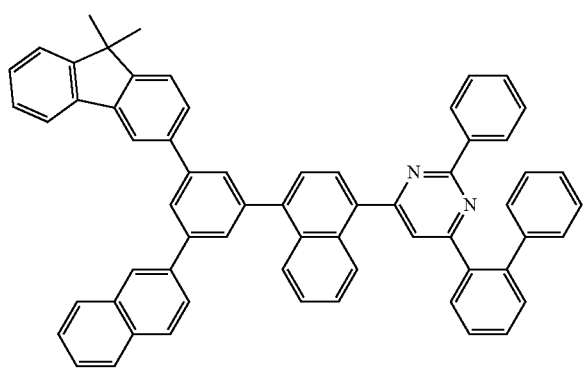
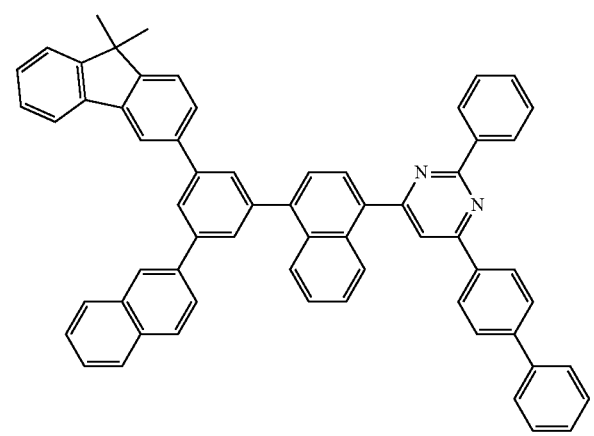

-continued
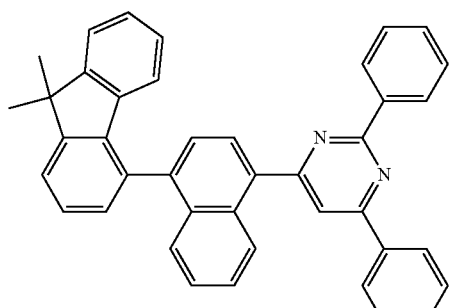
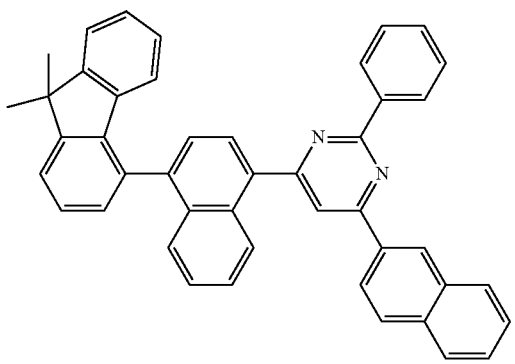
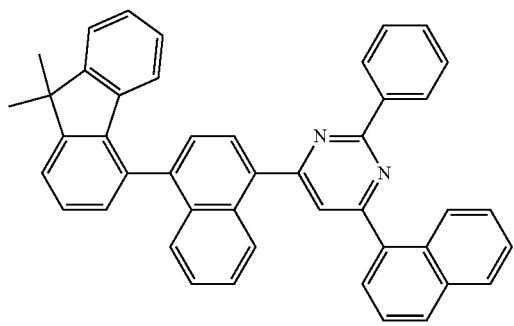
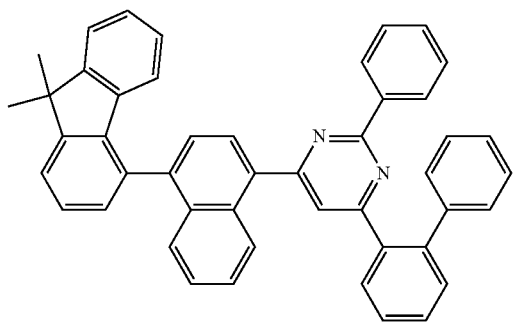
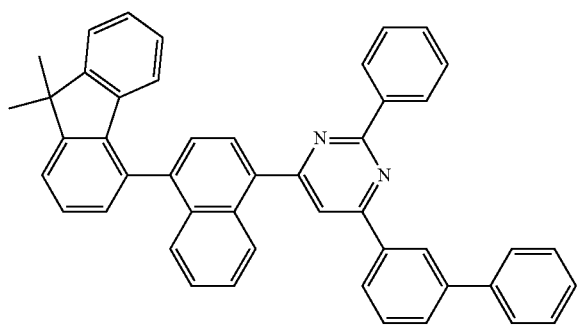
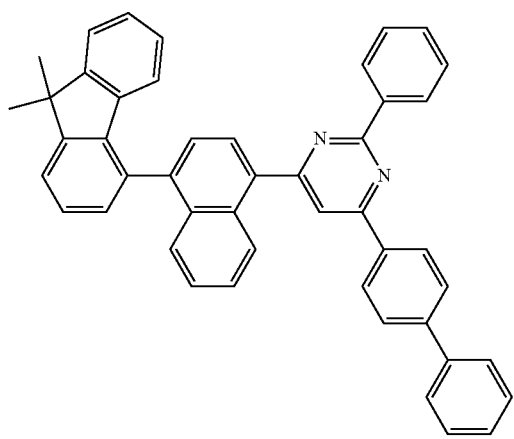
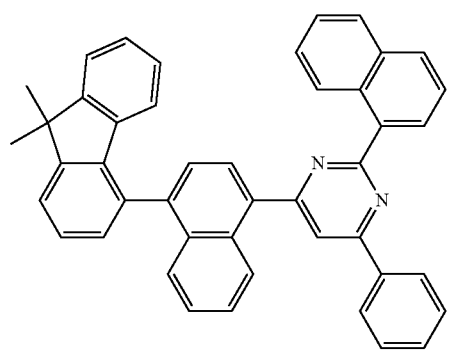

127
128
-continued
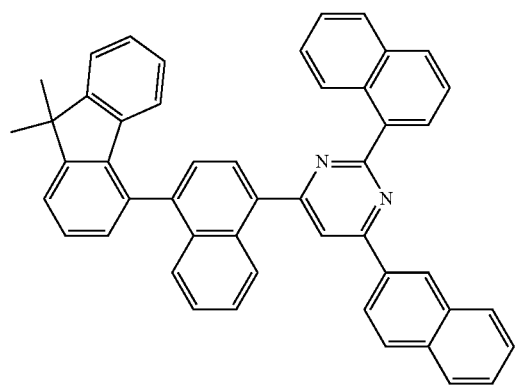
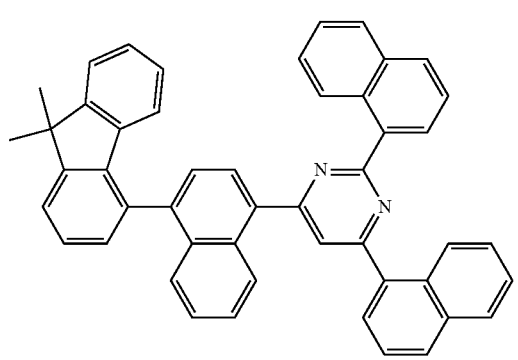
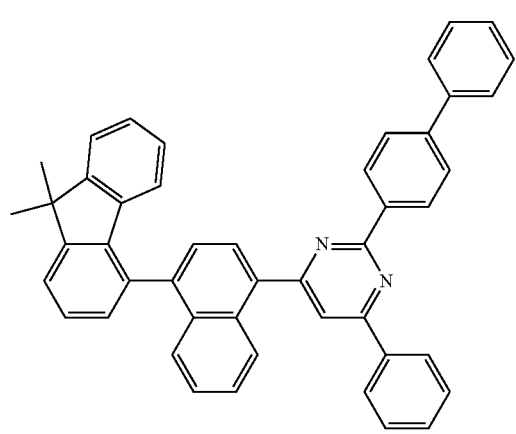
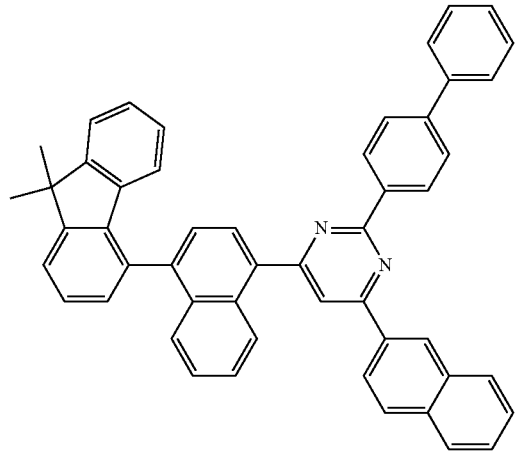
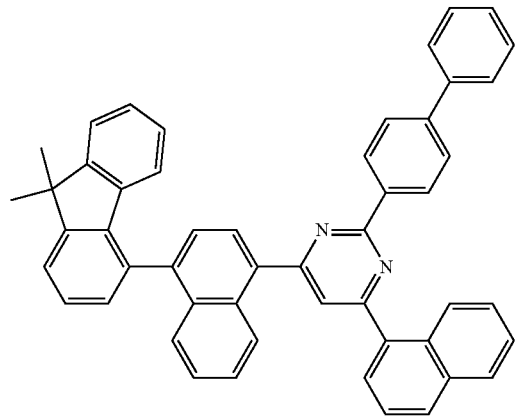
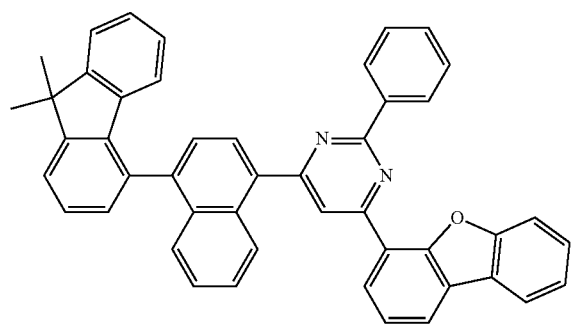
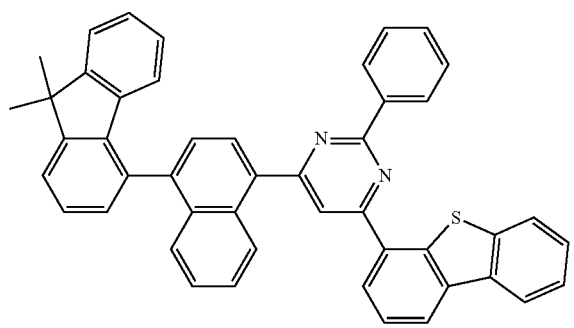

129
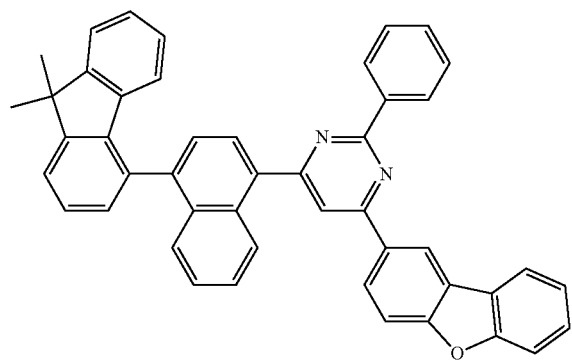
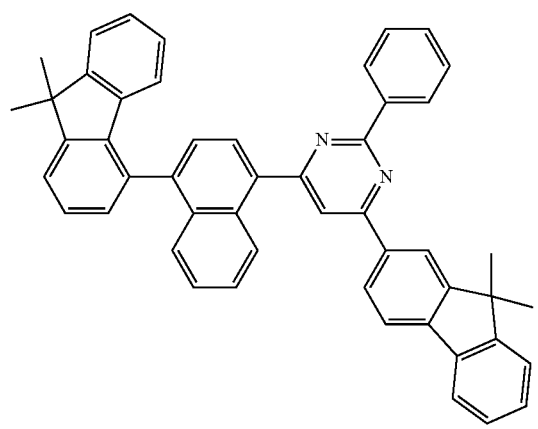
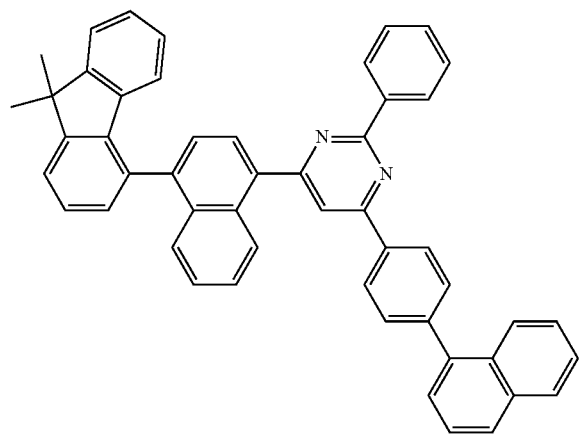
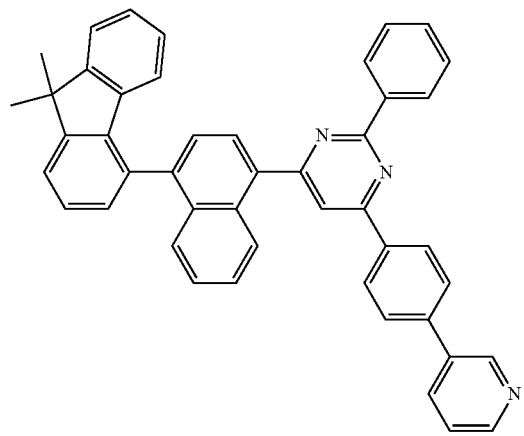
130
-continued
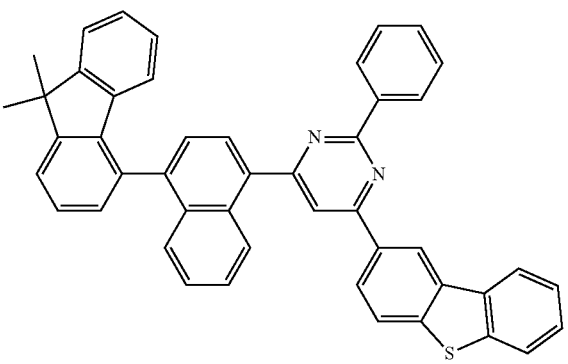
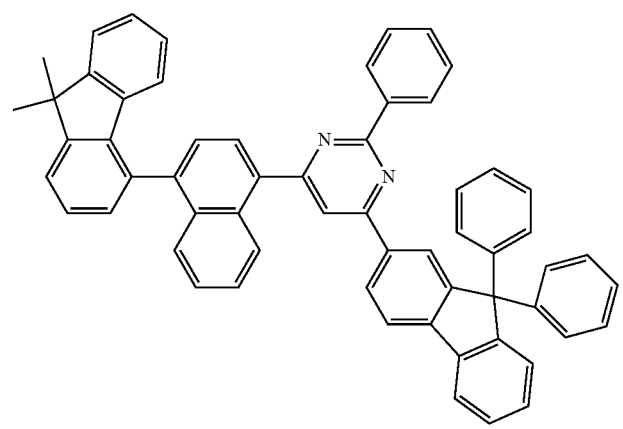
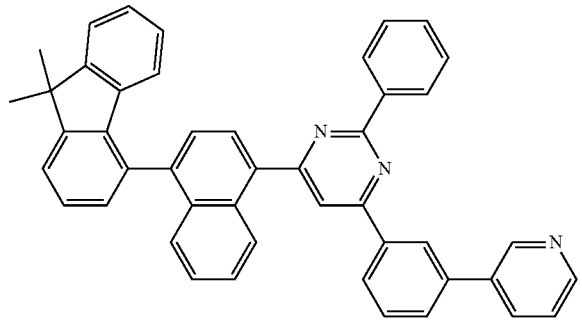
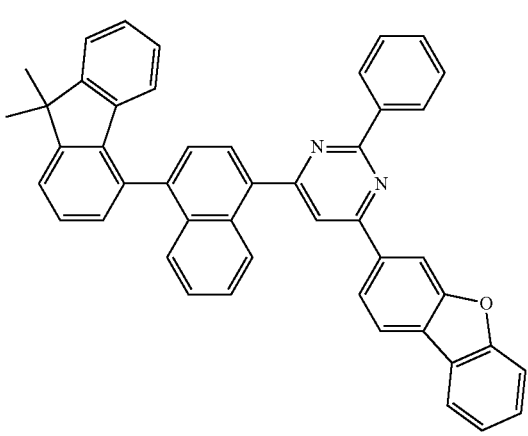

131
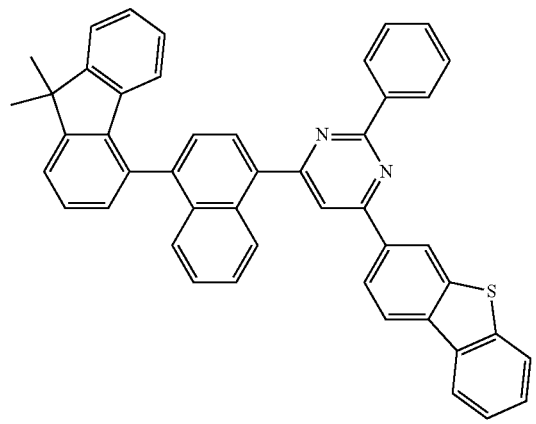
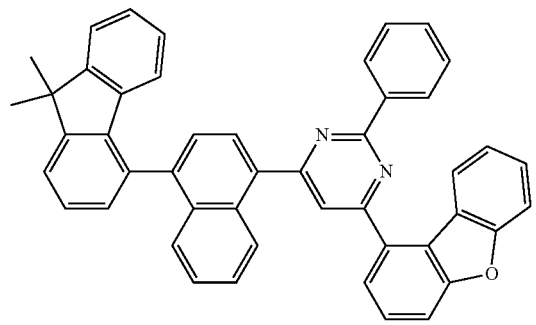
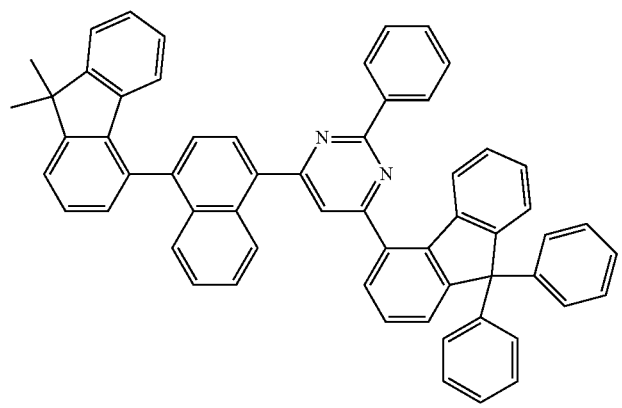
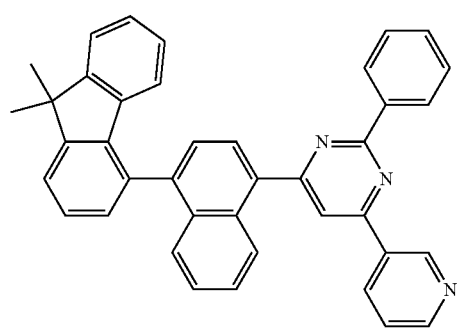
132
-continued
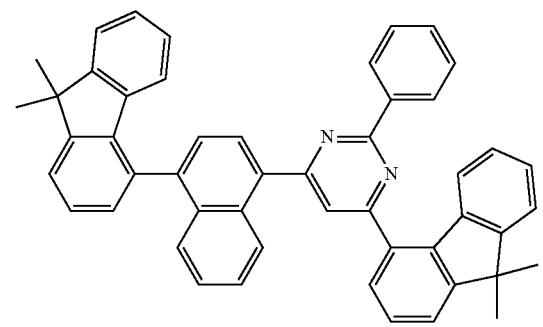
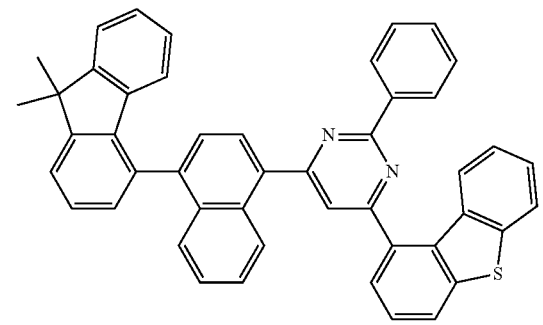
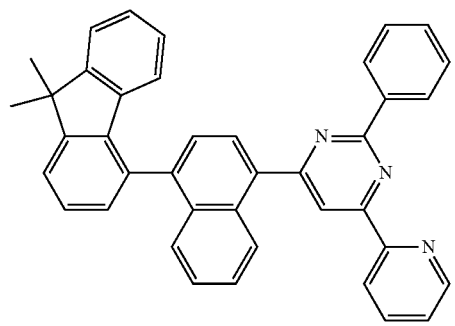
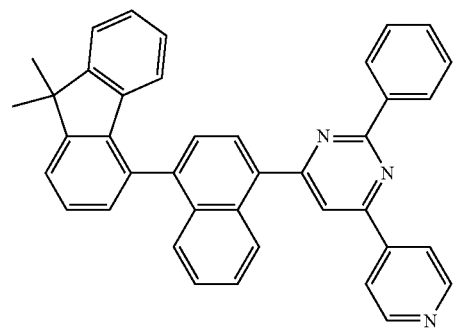

133
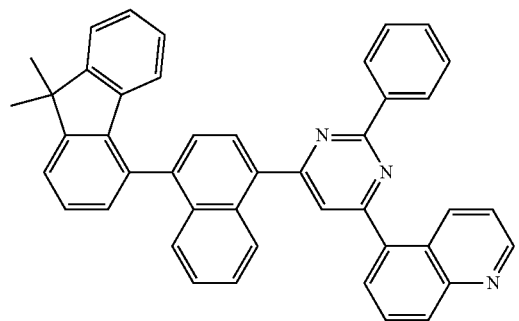
134
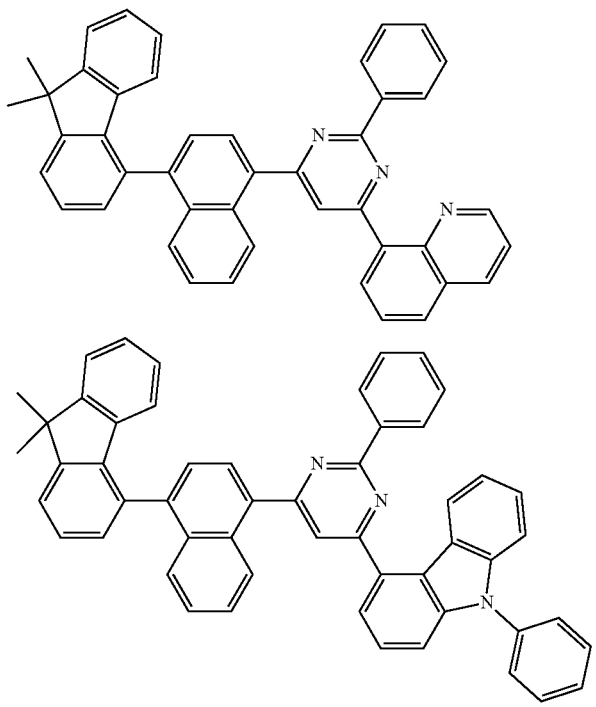
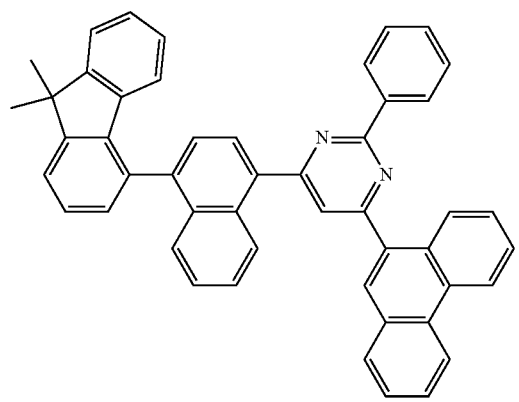
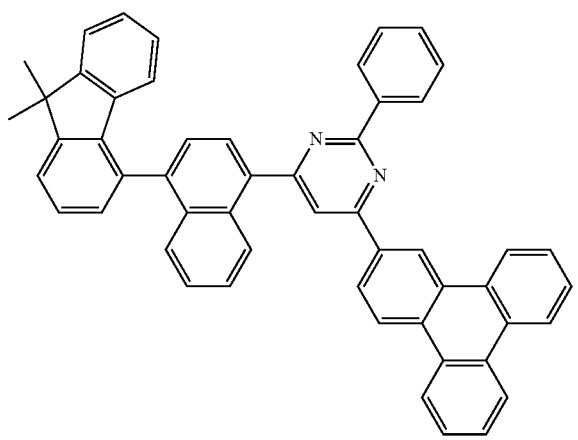
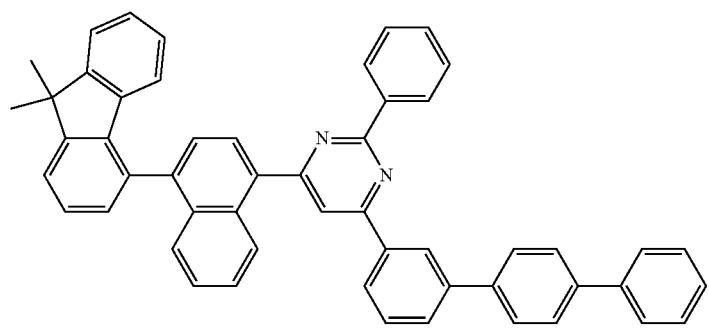

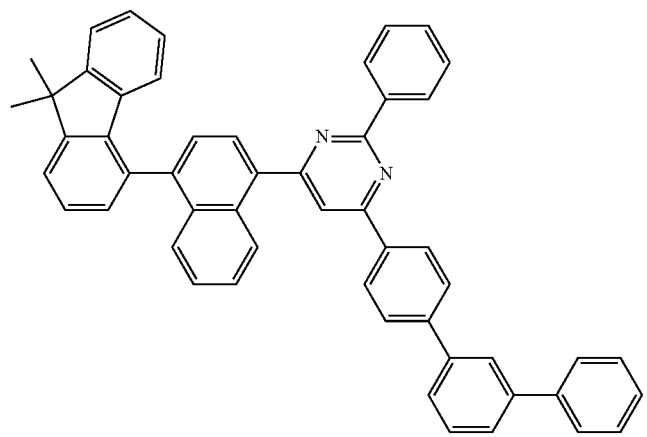
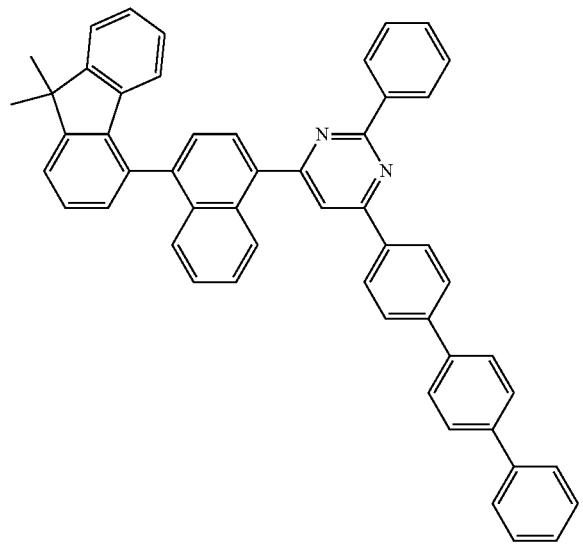
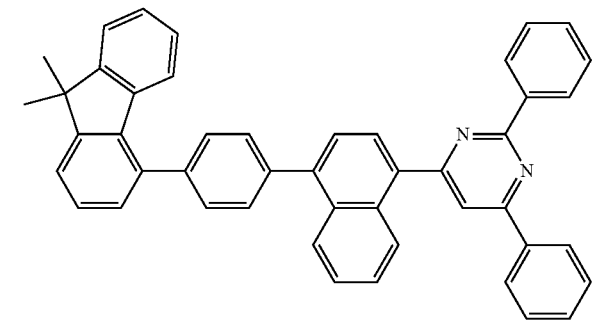
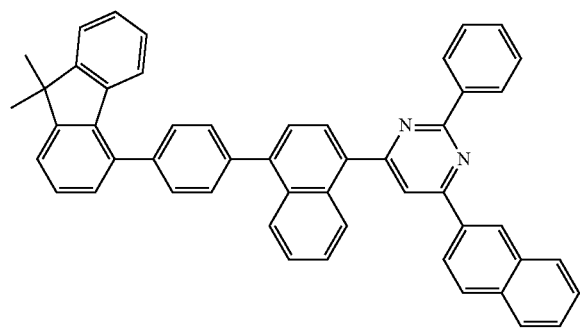
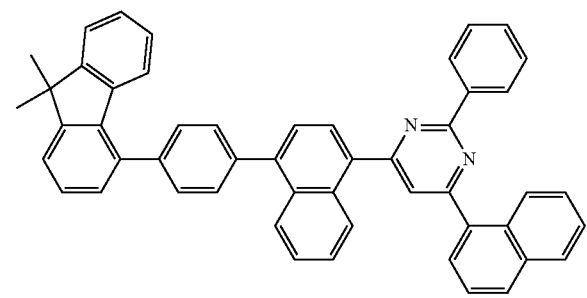
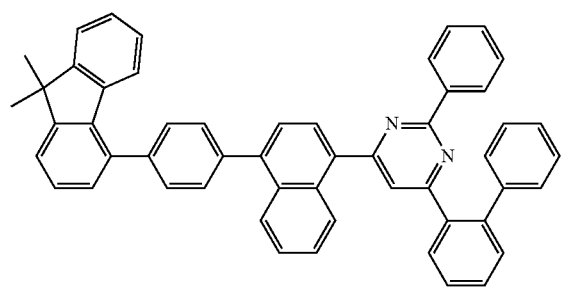
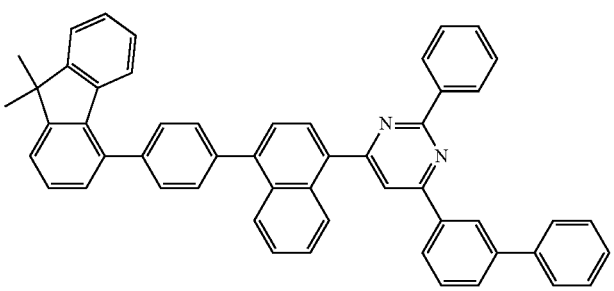

-continued
137
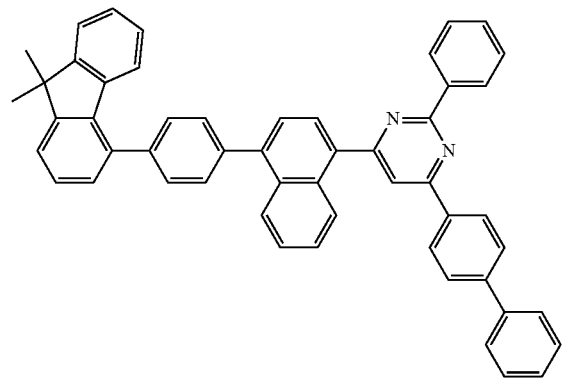
138
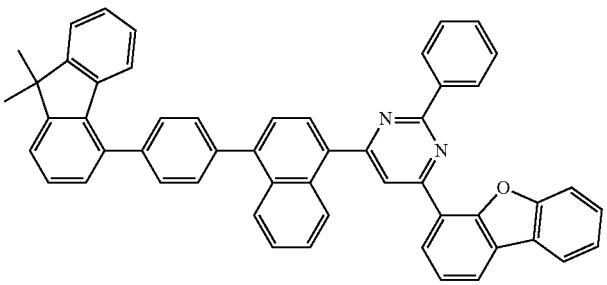
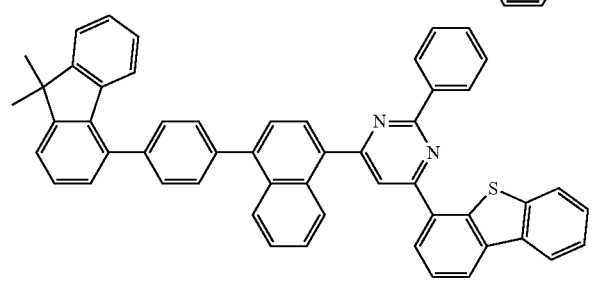
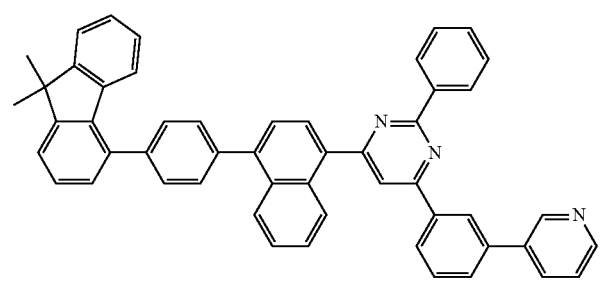
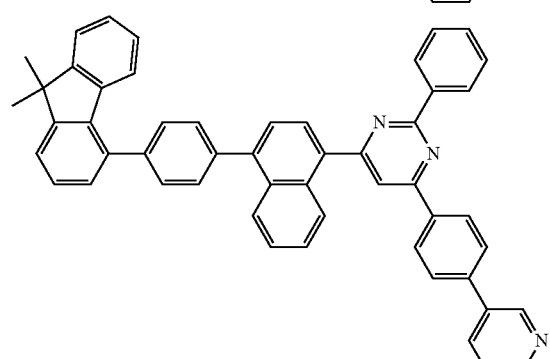
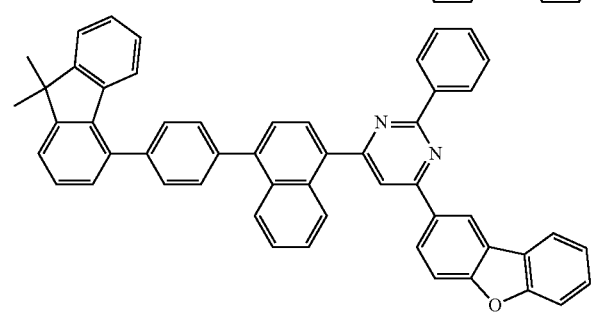
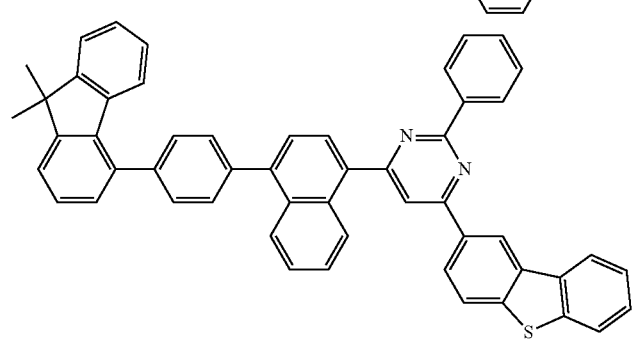
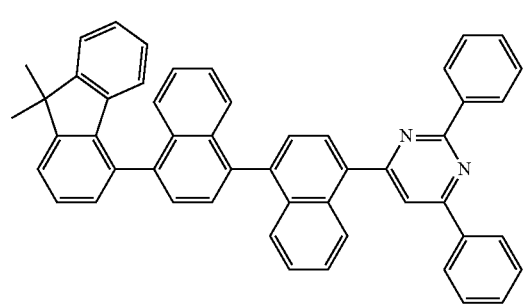
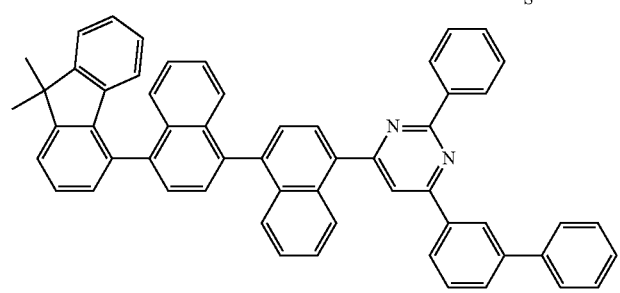
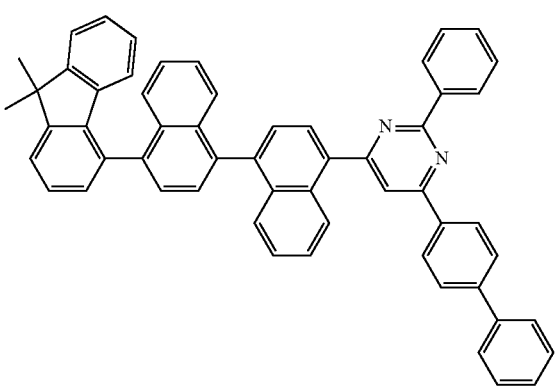

-continued
139
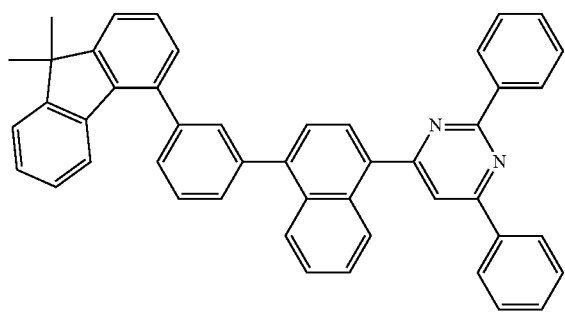
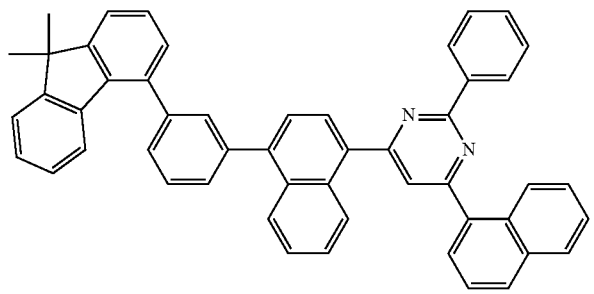
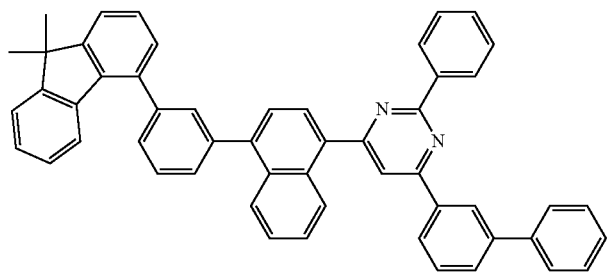
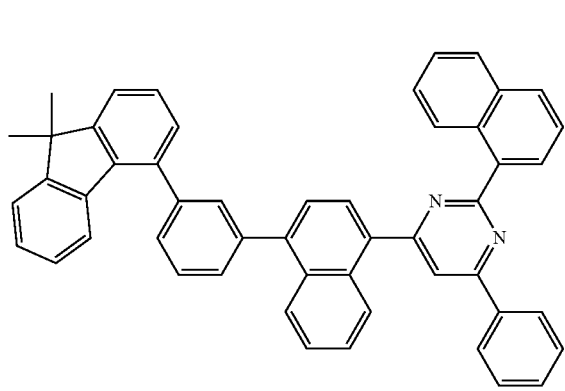
140
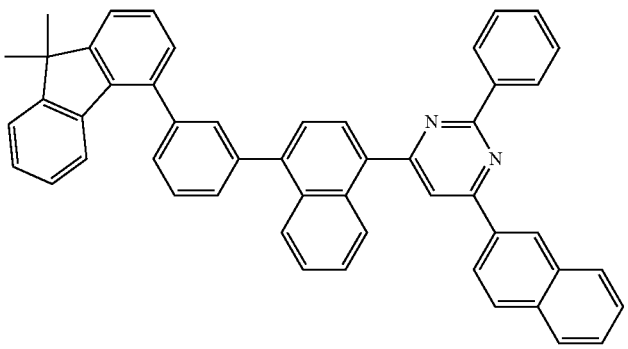
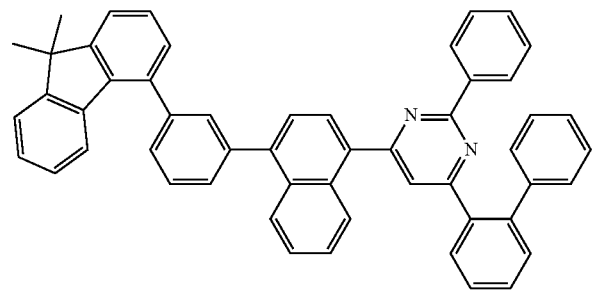
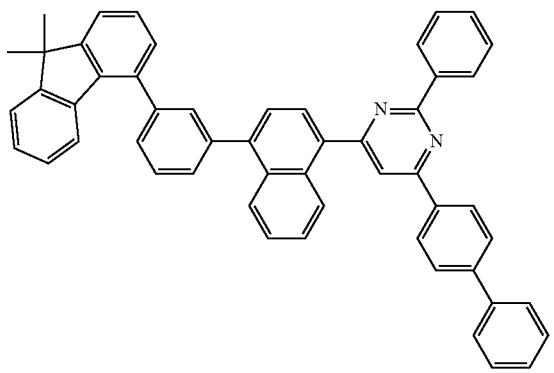
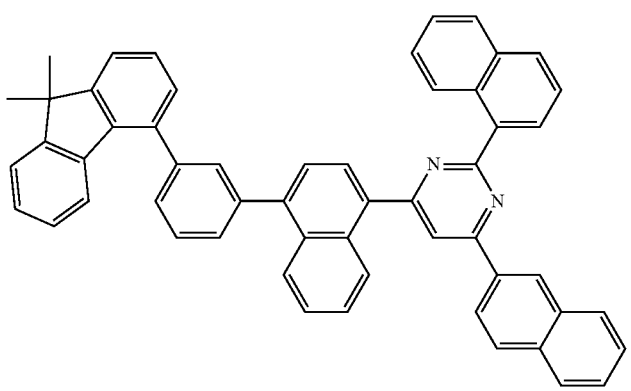

-continued
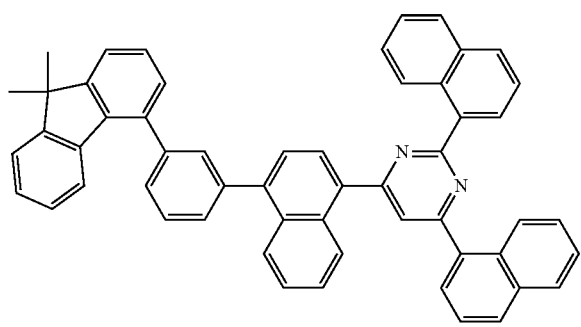
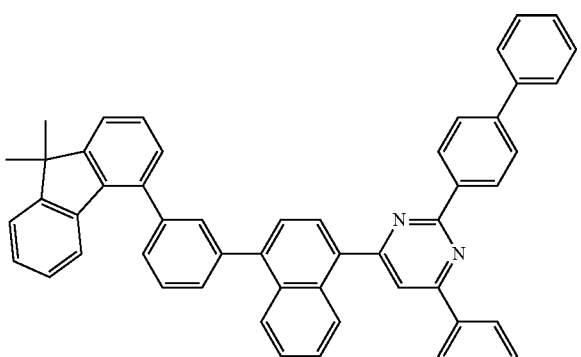
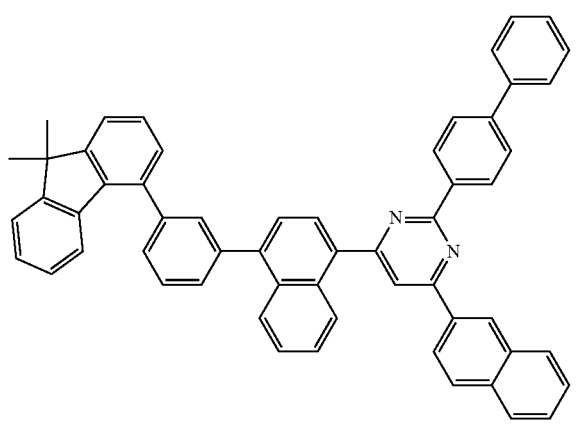
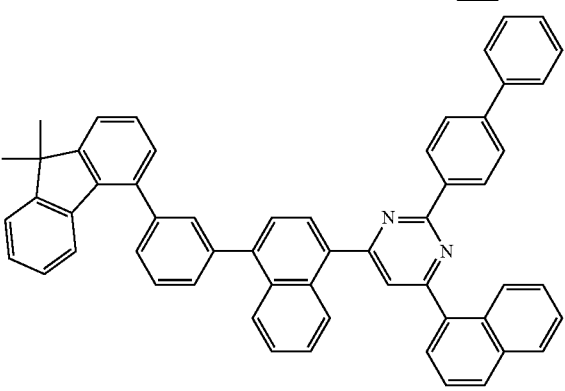
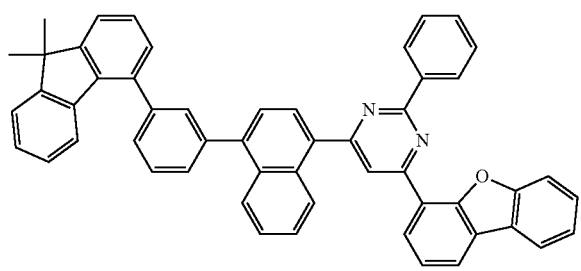
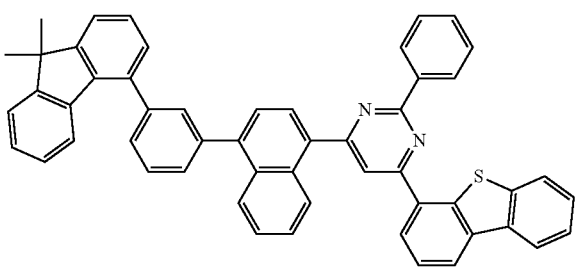
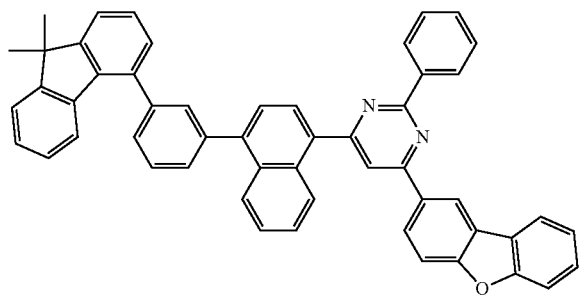
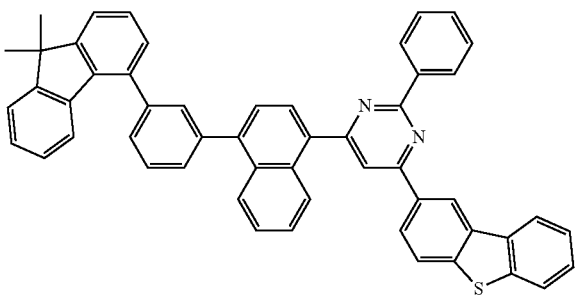

-continued
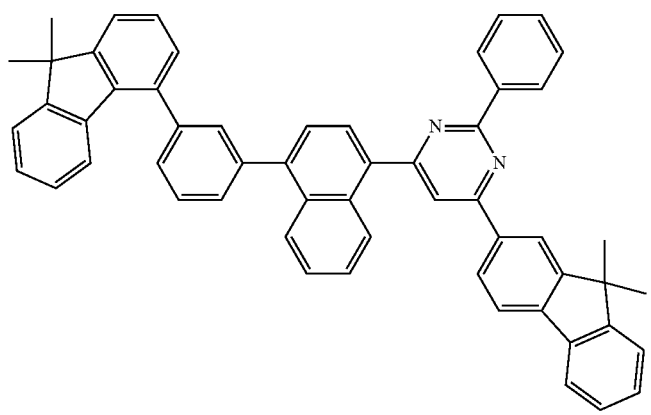
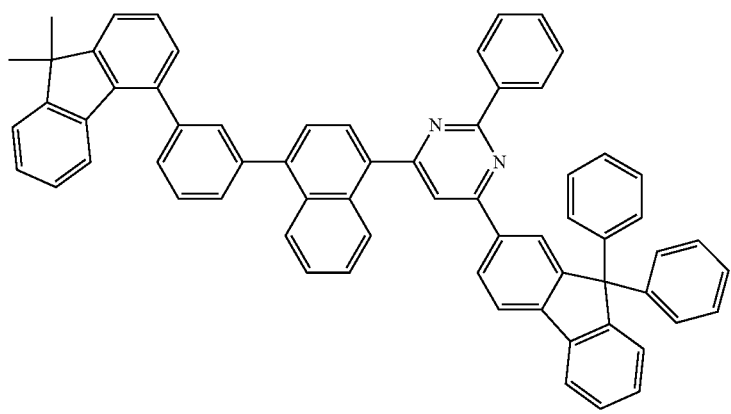
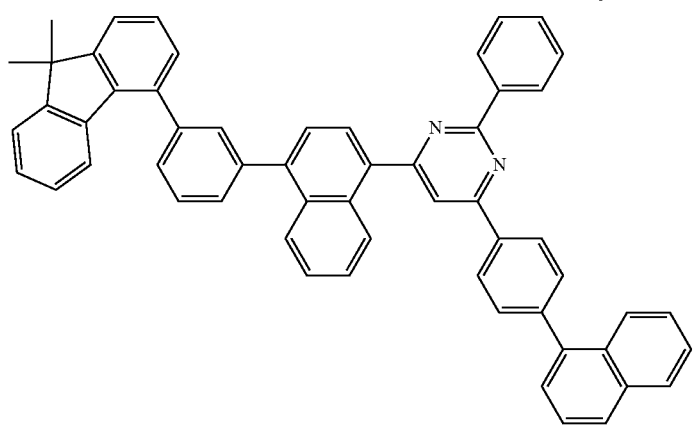

-continued
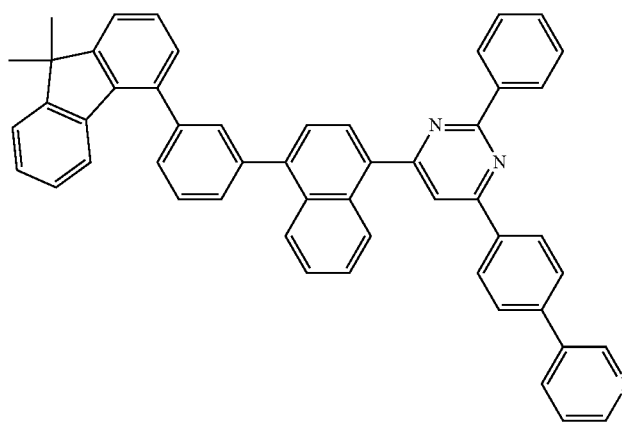
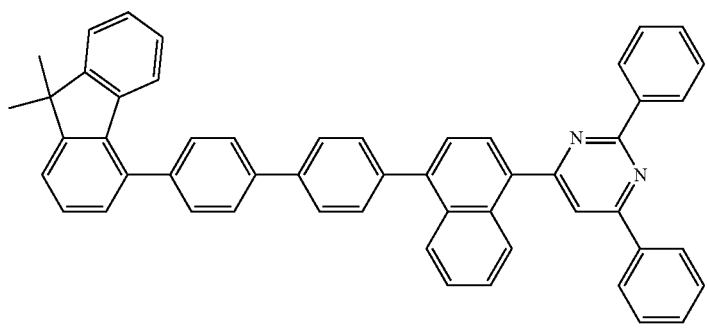
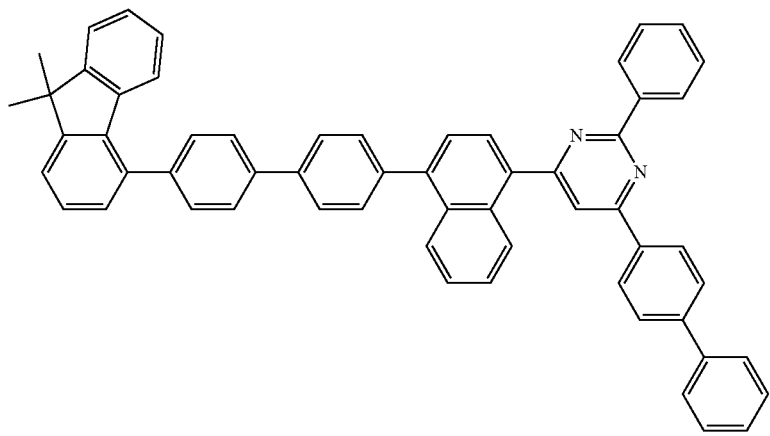
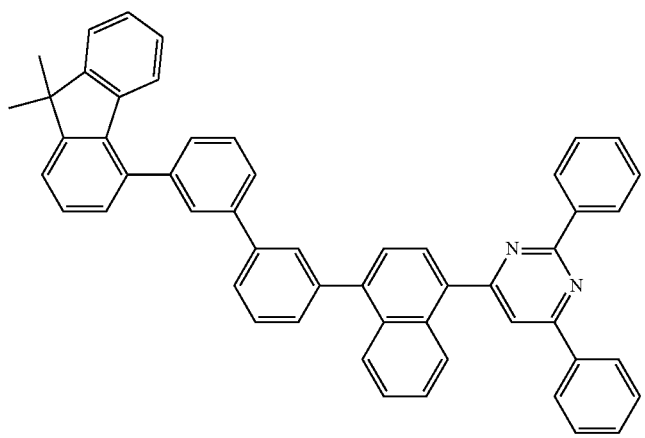

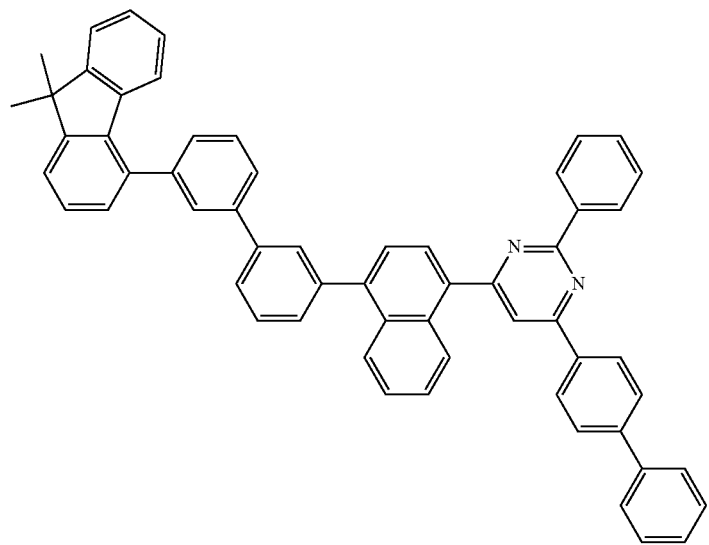
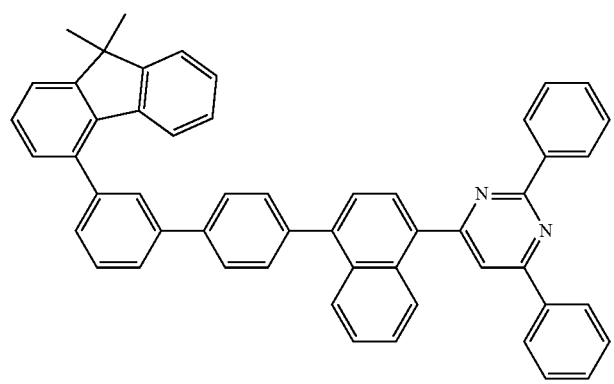
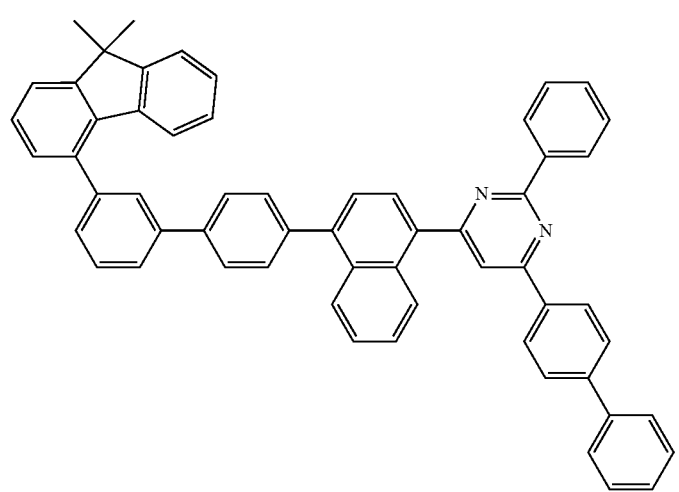

-continued
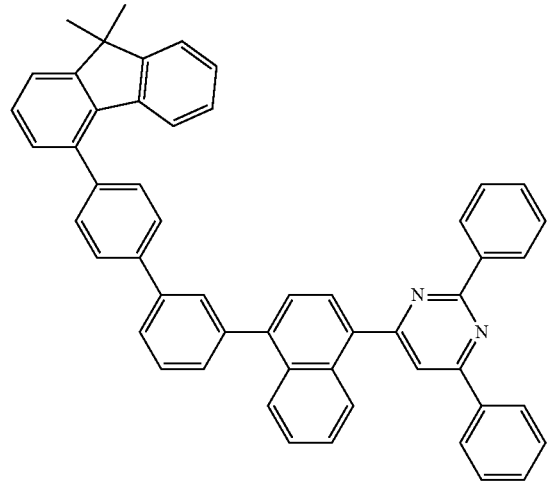
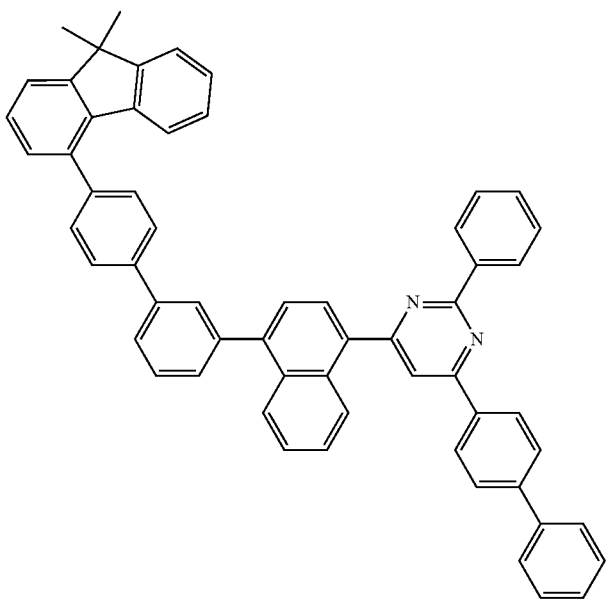
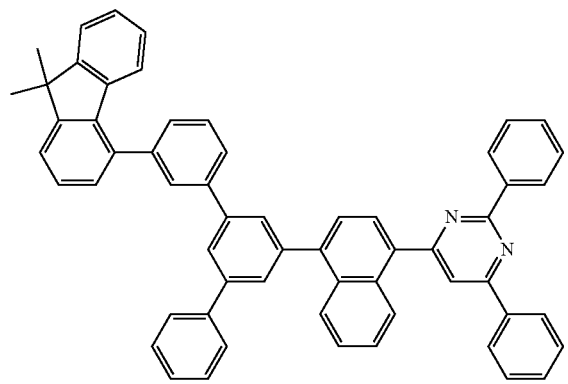
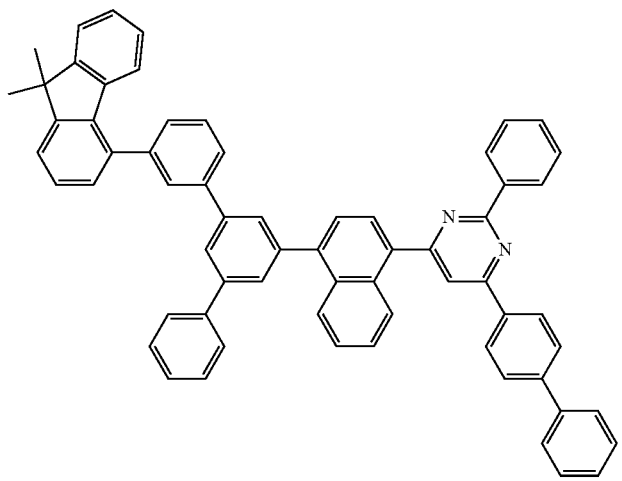
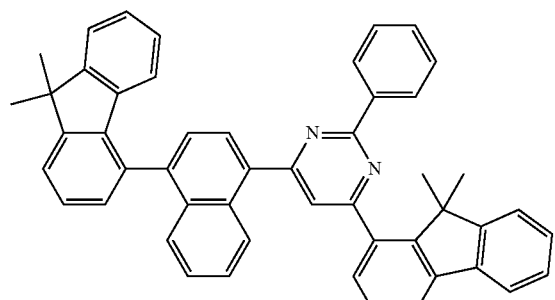
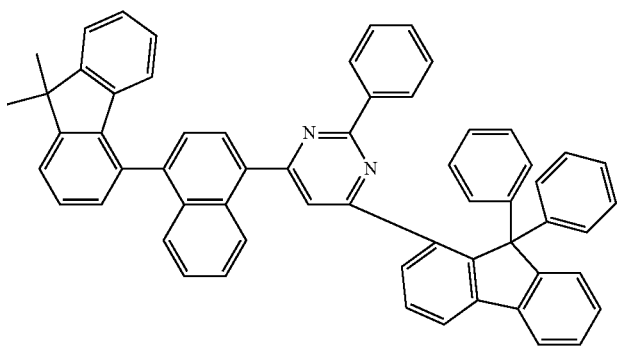

151
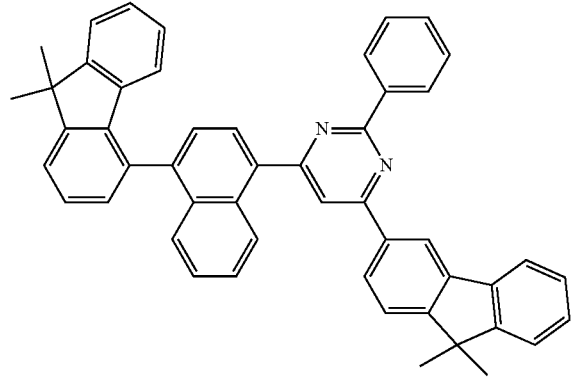
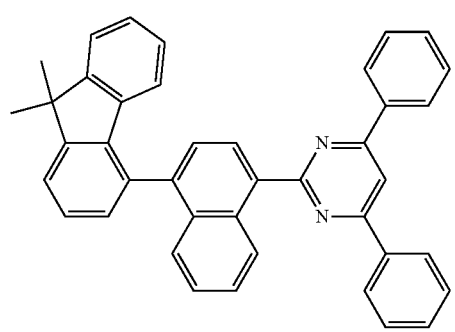
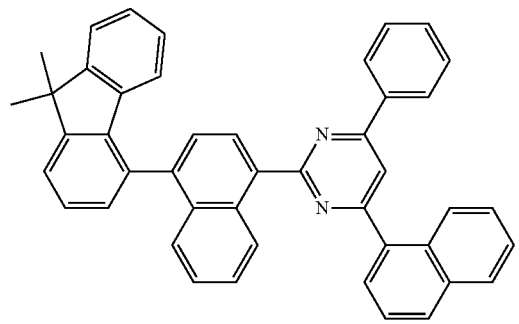
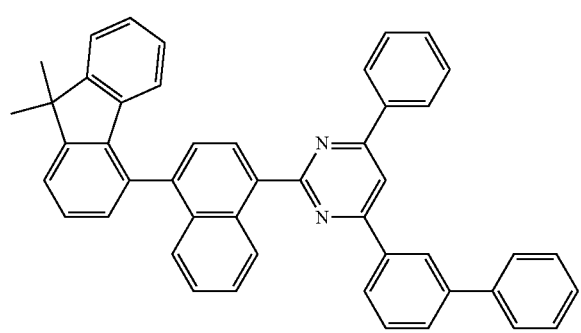
152
-continued
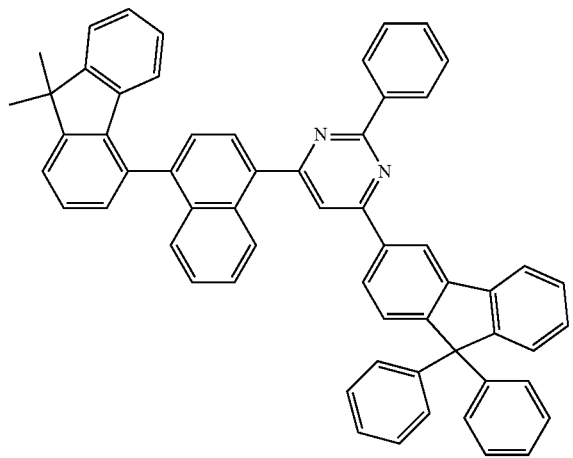
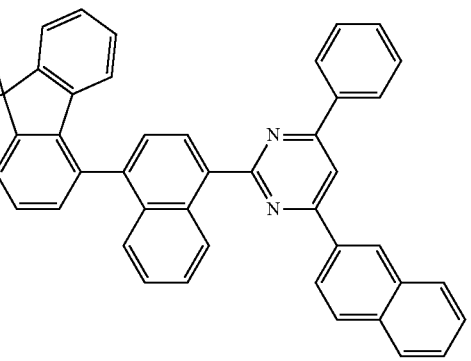
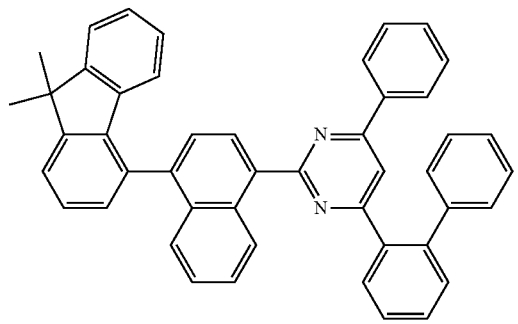
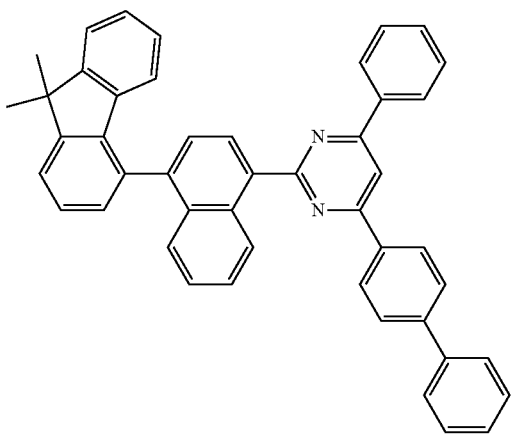

153
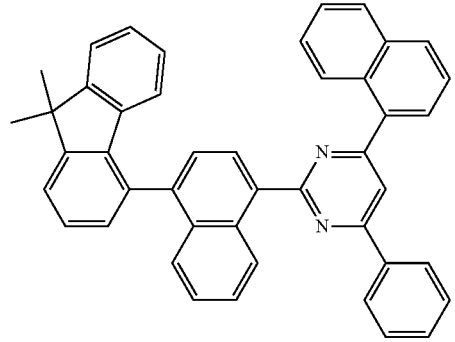
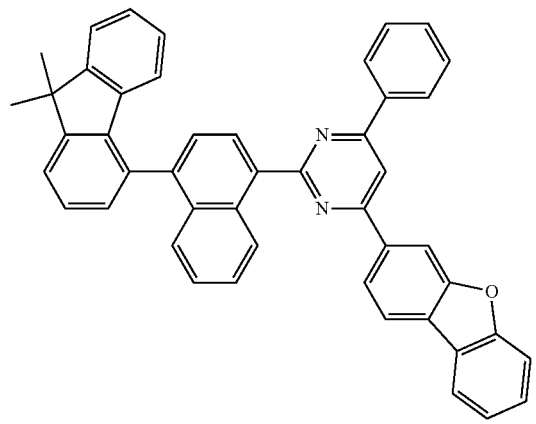
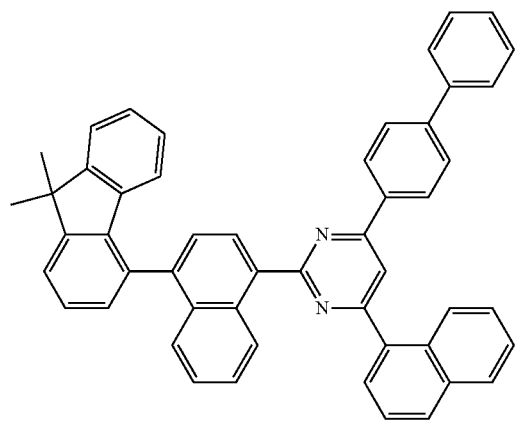
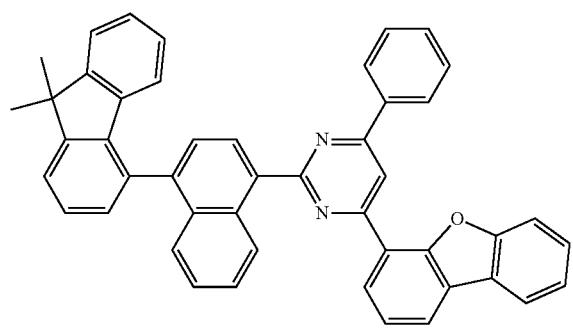
154
-continued
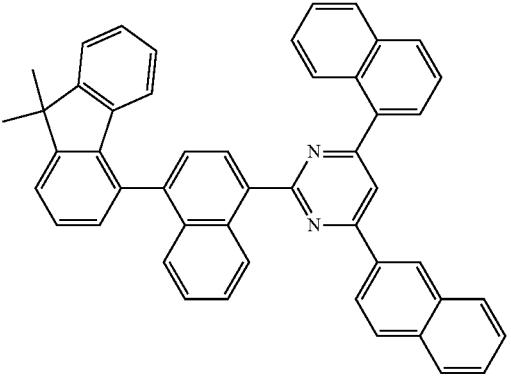
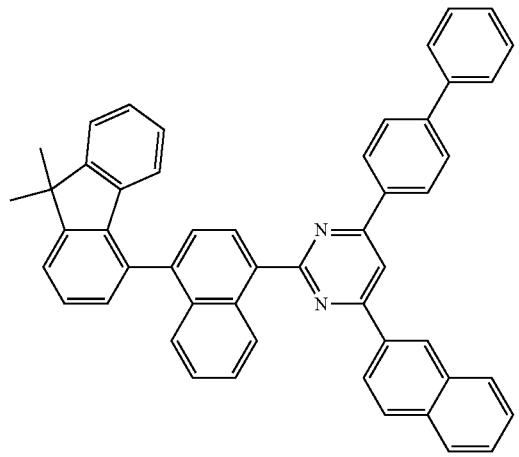
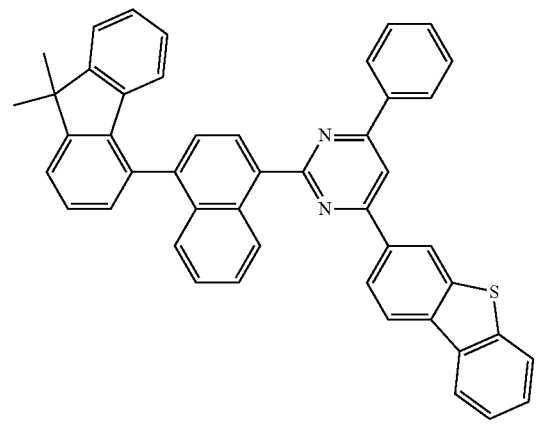
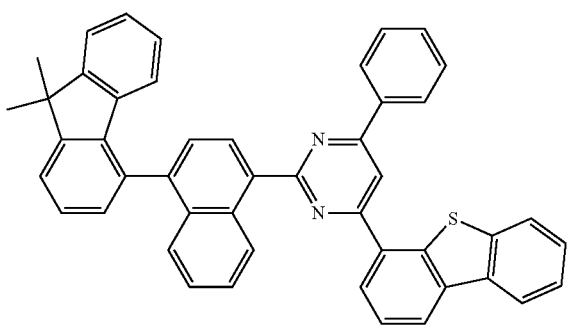

155
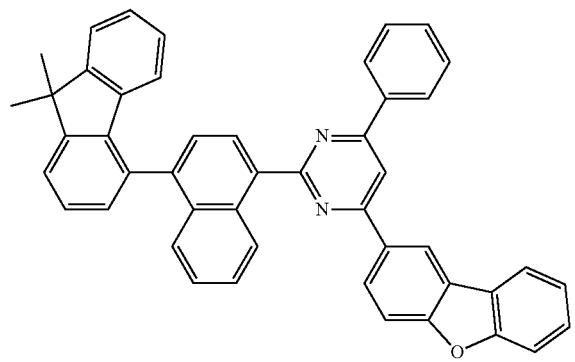
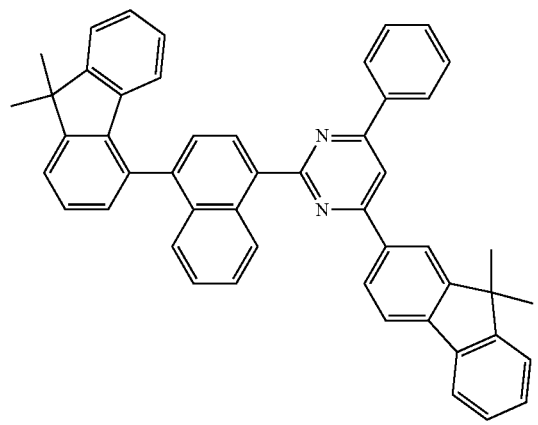
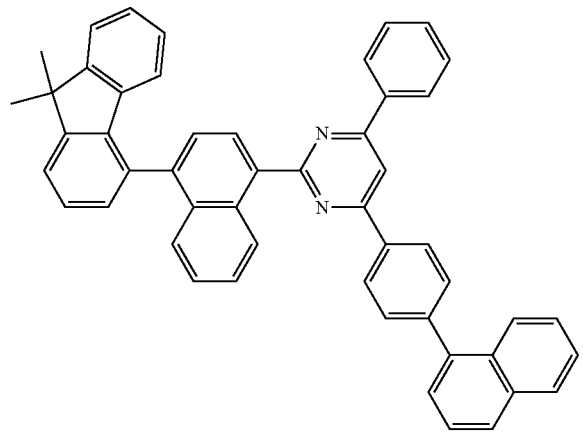
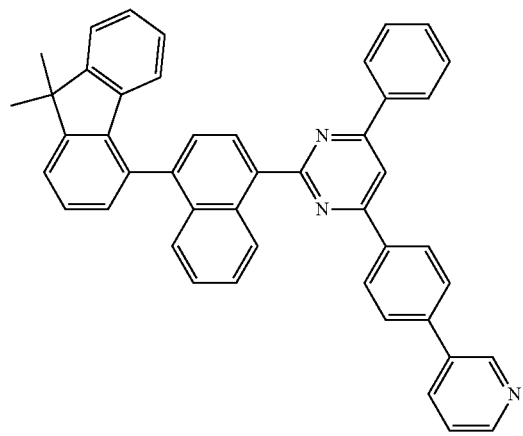
156
-continued
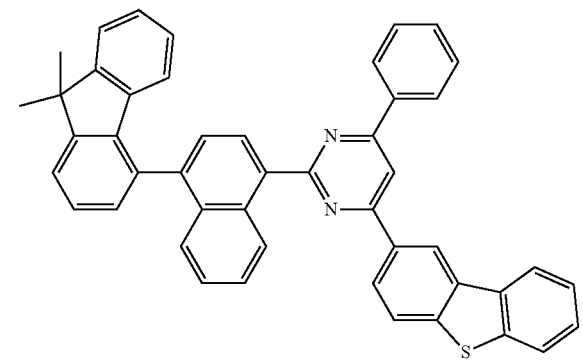
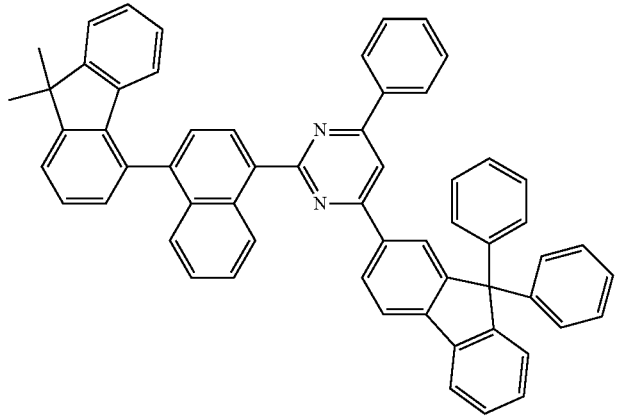
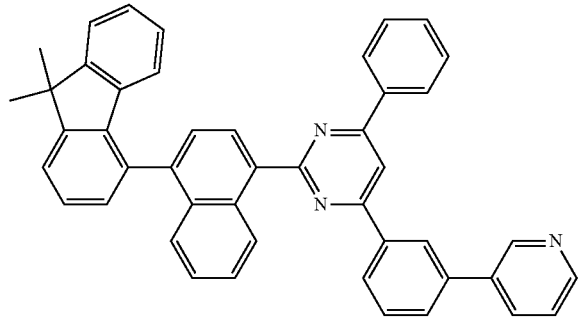
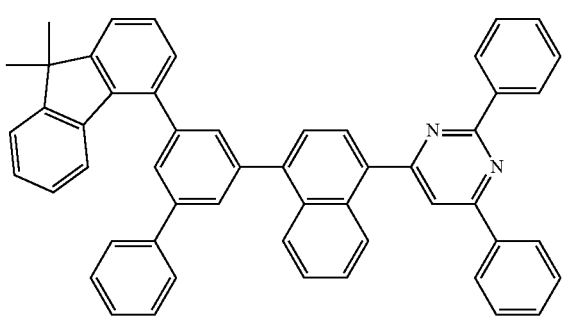

-continued
157
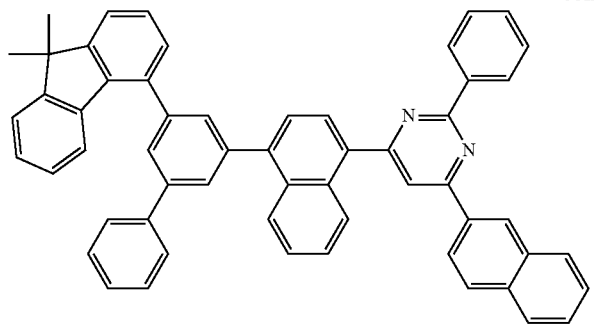
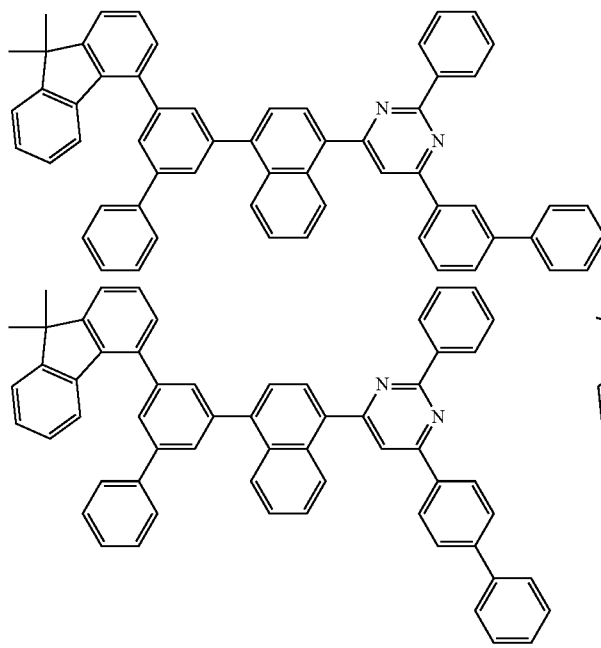
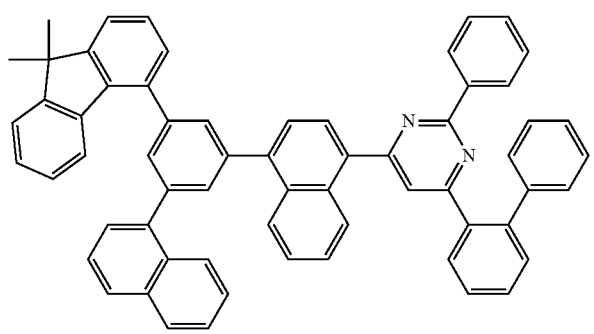
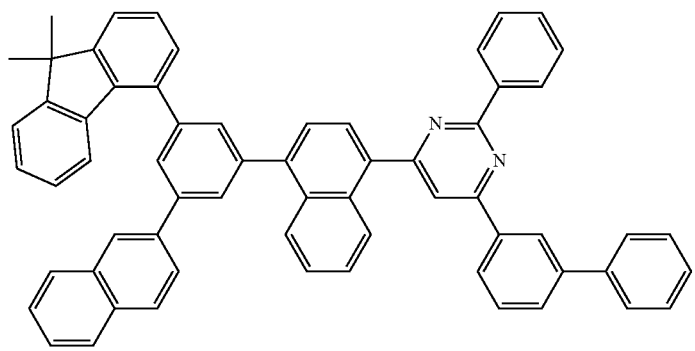
158
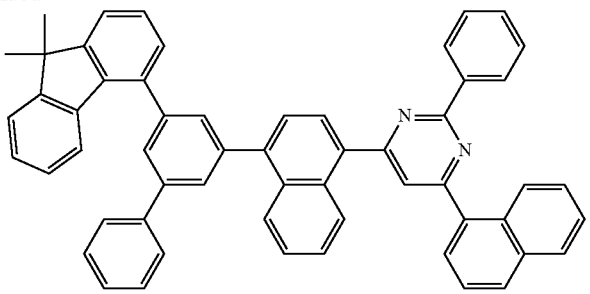
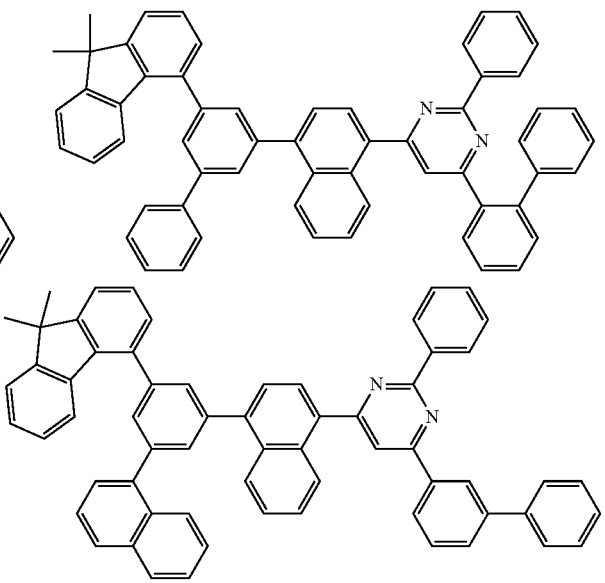
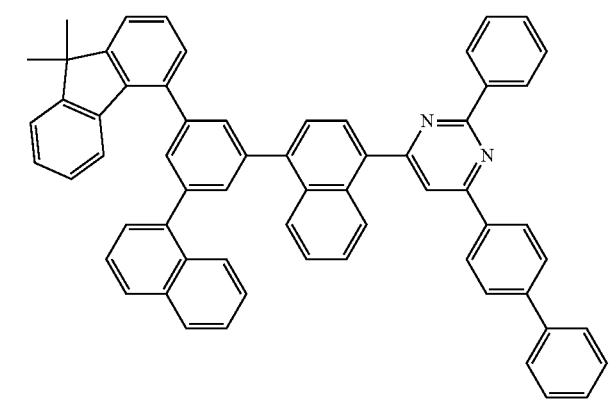

-continued
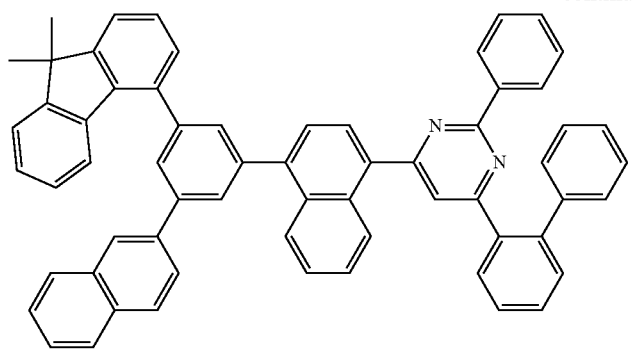
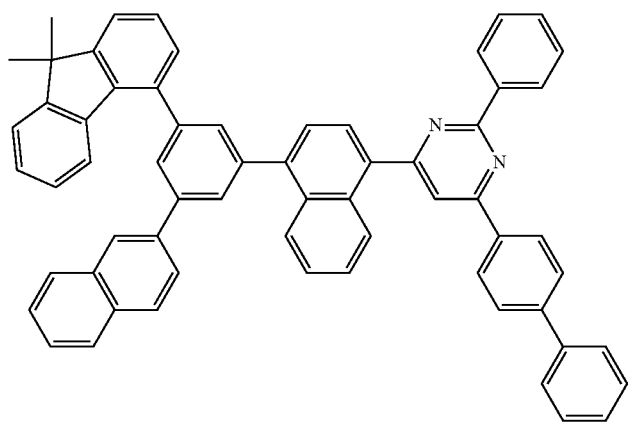
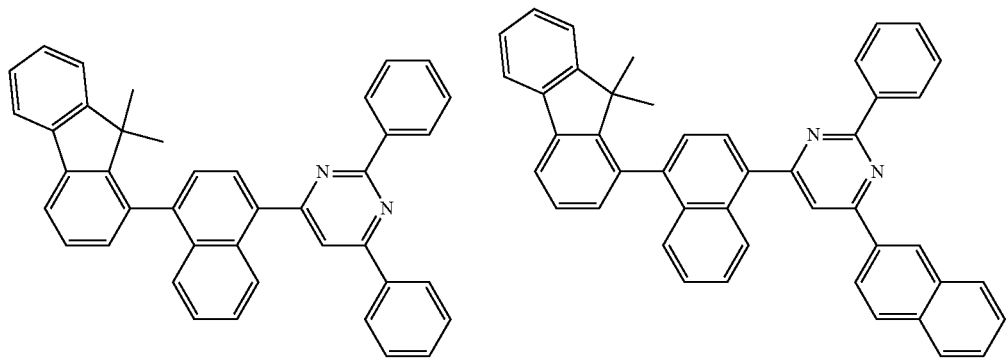
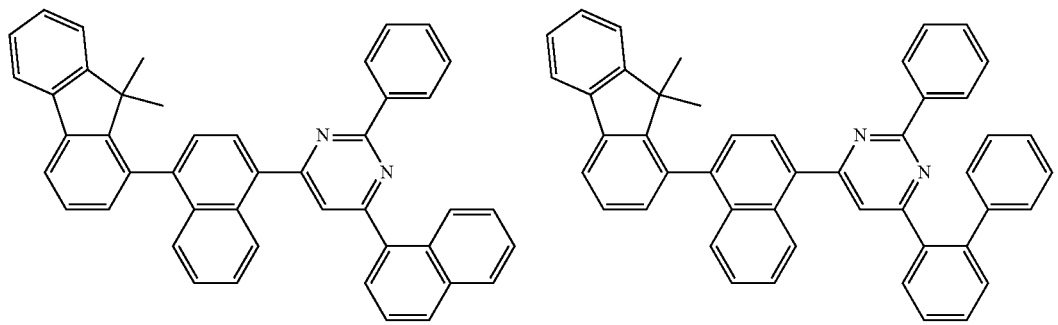

-continued
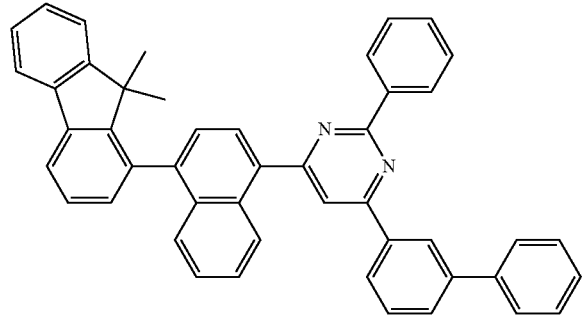
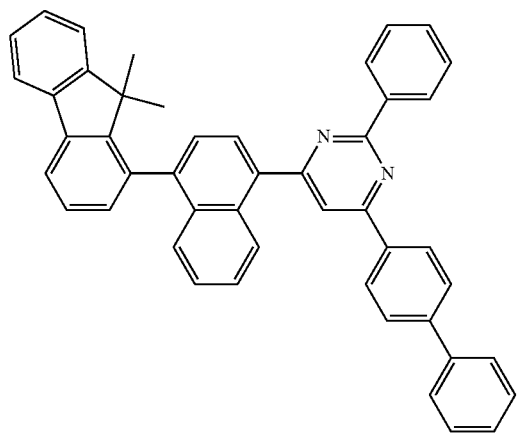
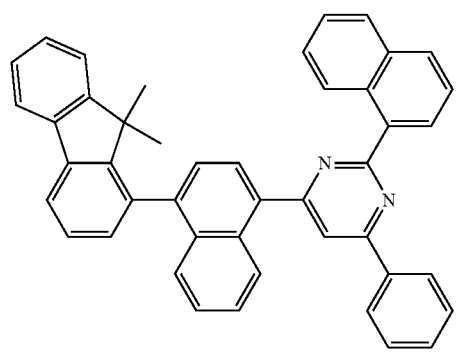
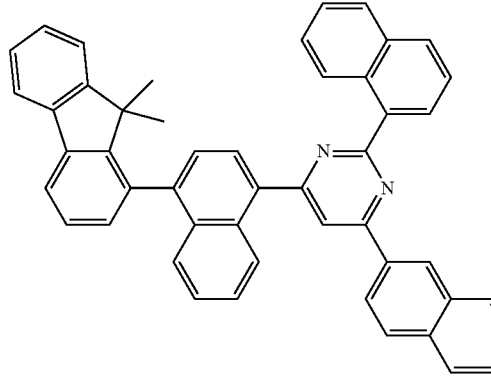
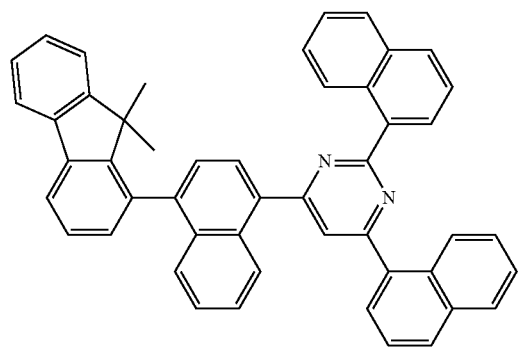
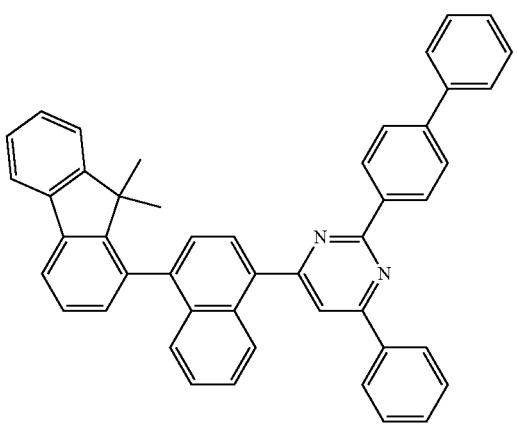
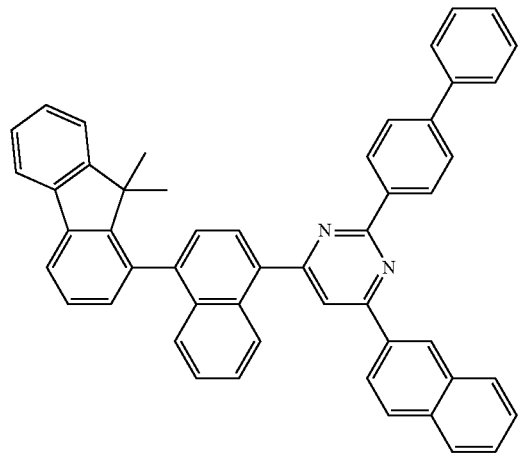
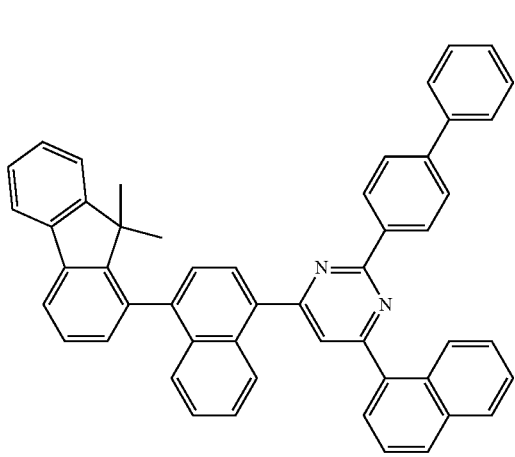

163
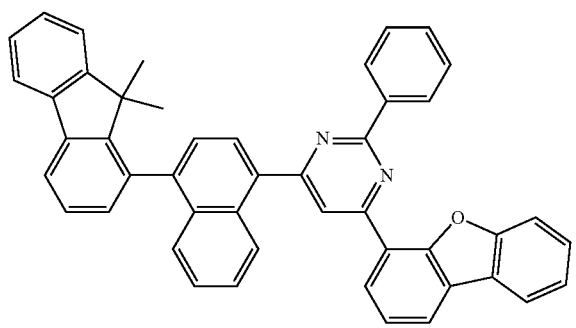
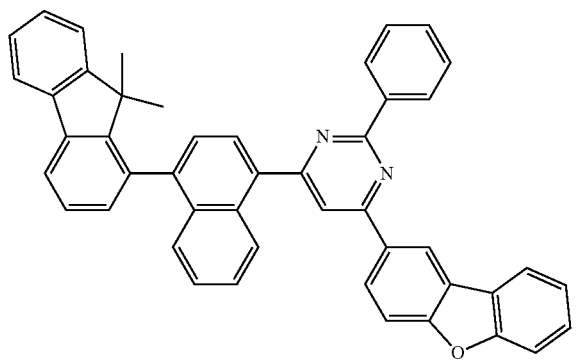
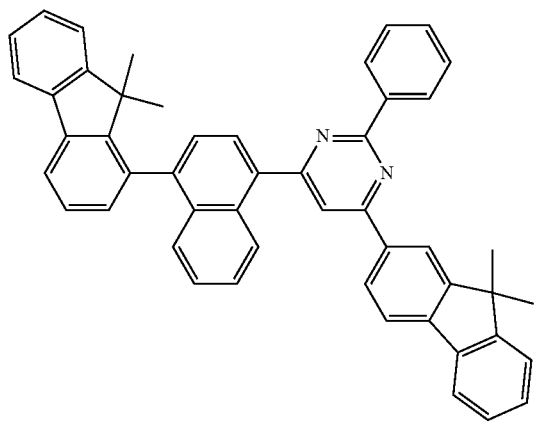
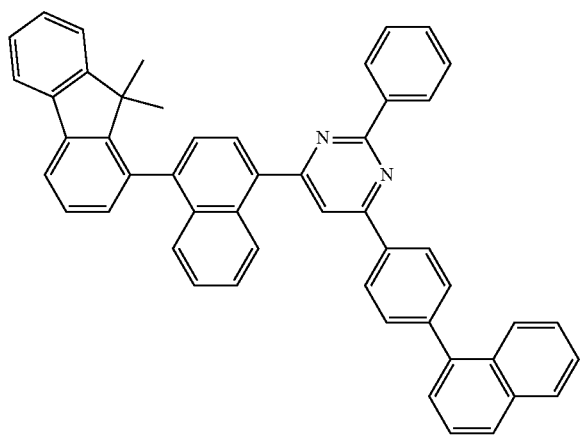
164
-continued
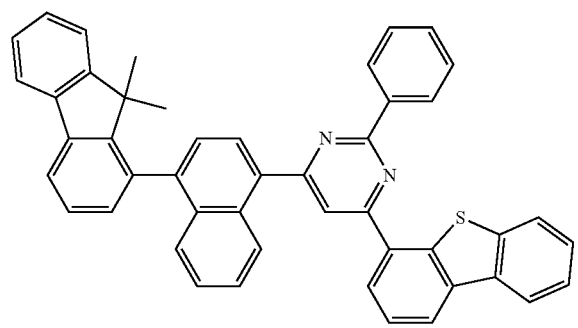
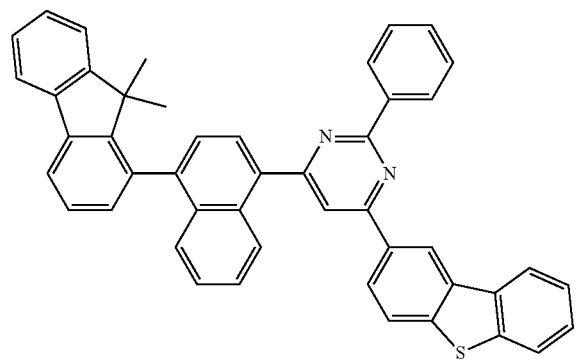
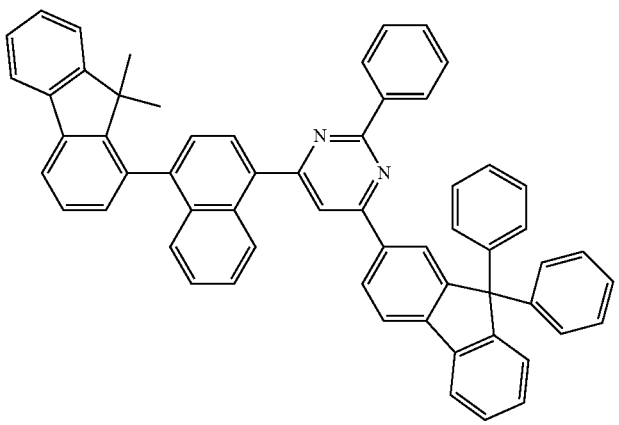
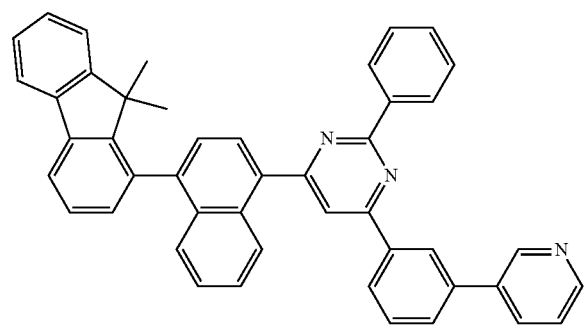

-continued
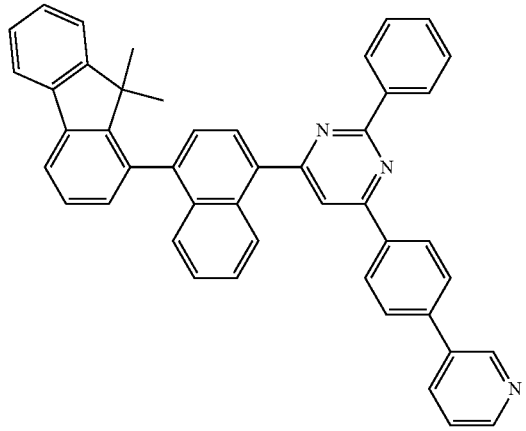

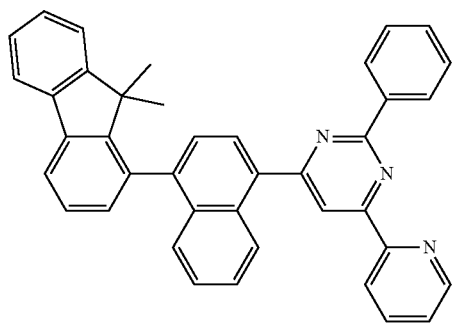 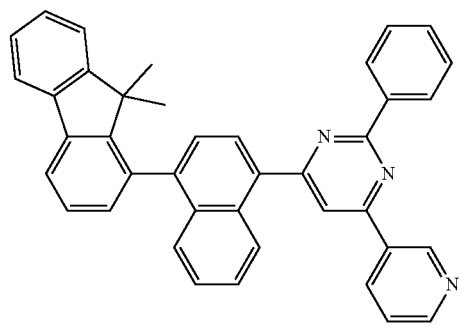
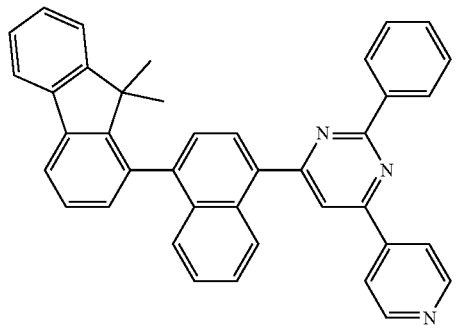 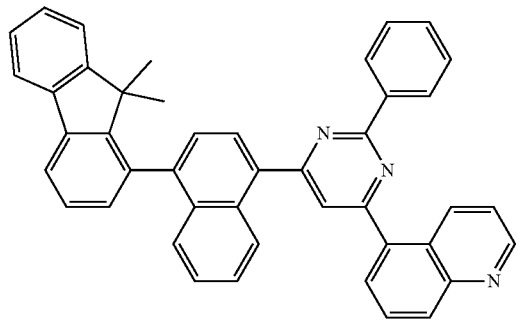
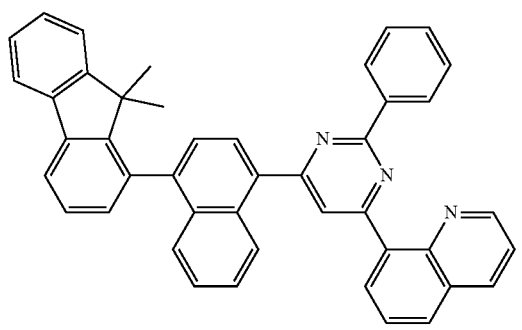 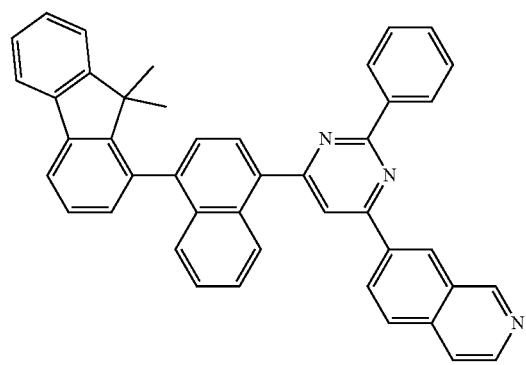
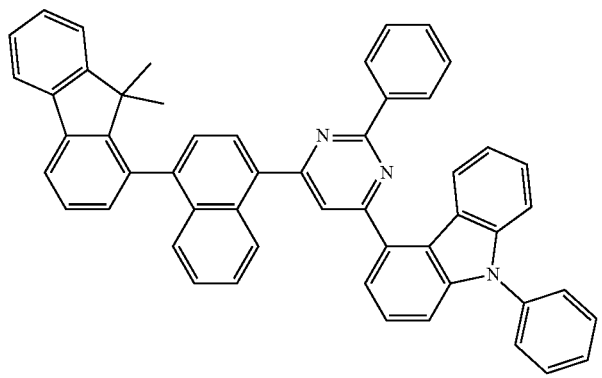 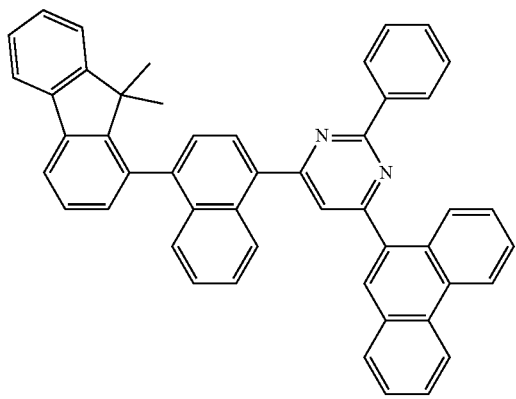

-continued
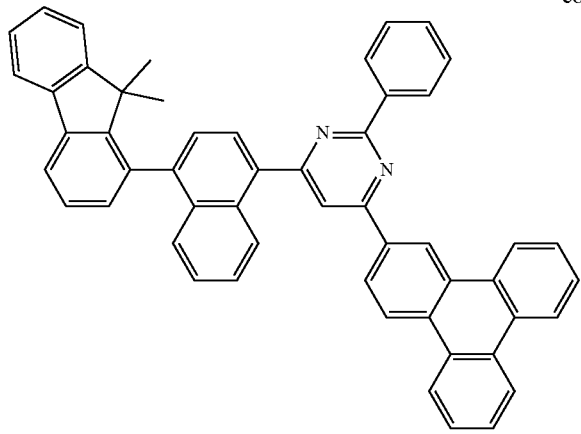
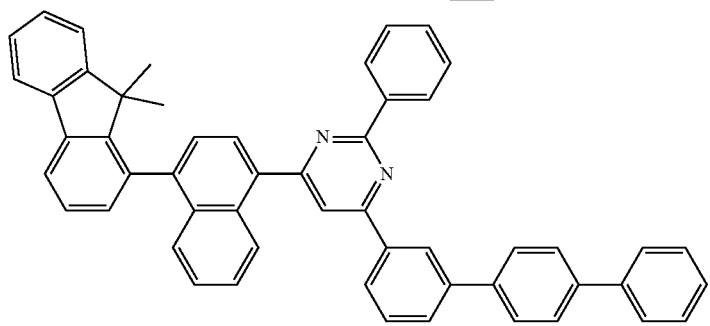
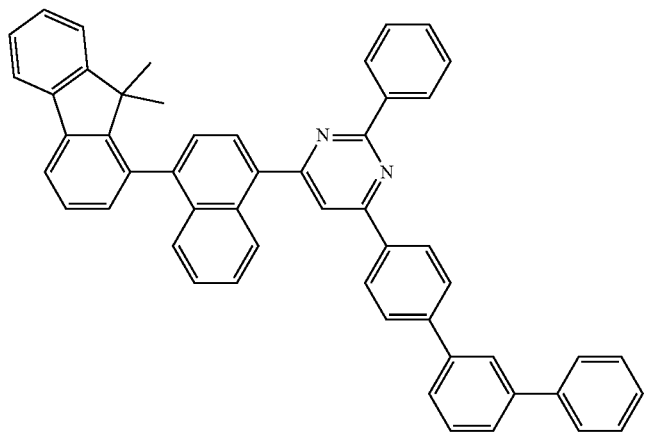
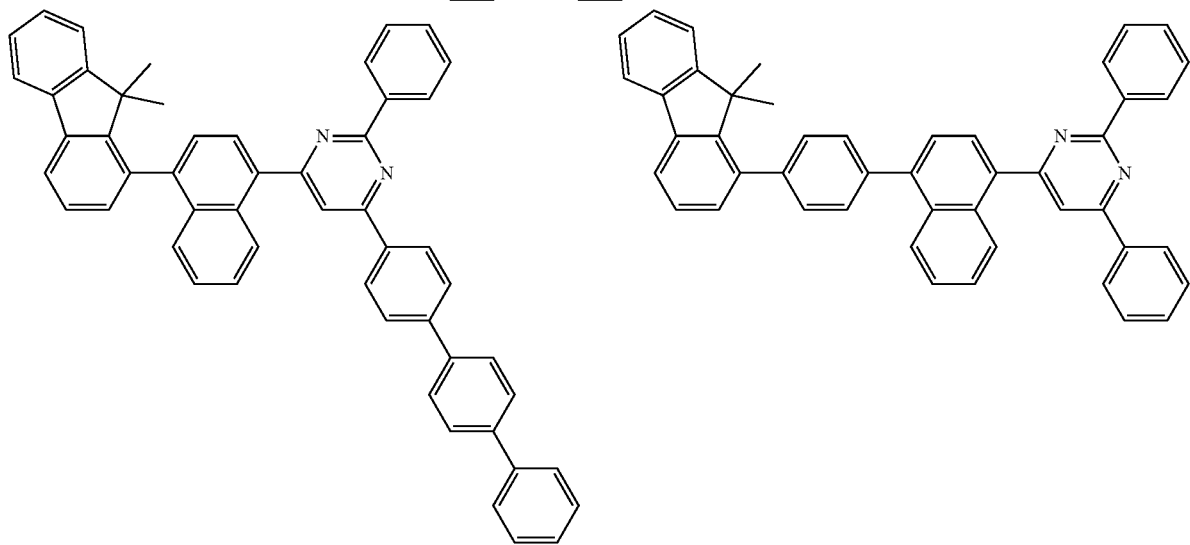

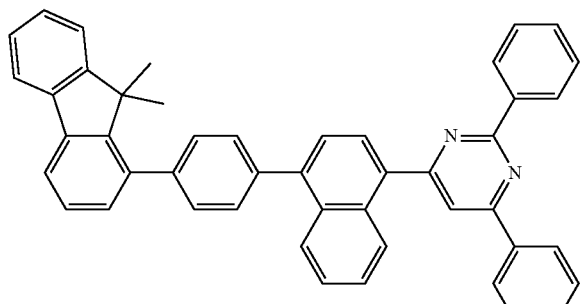
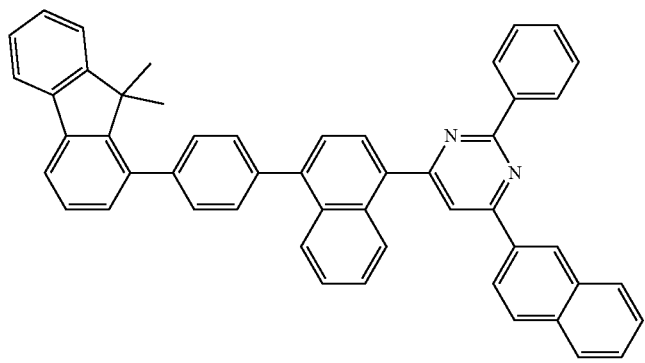
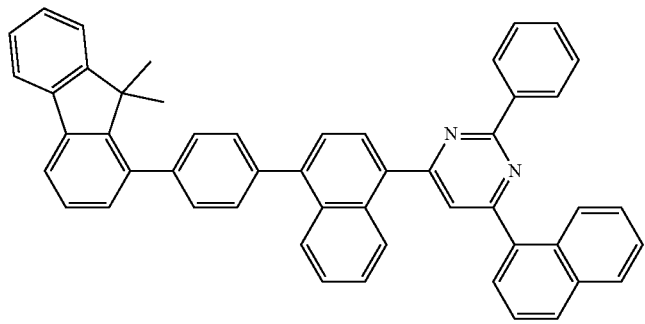
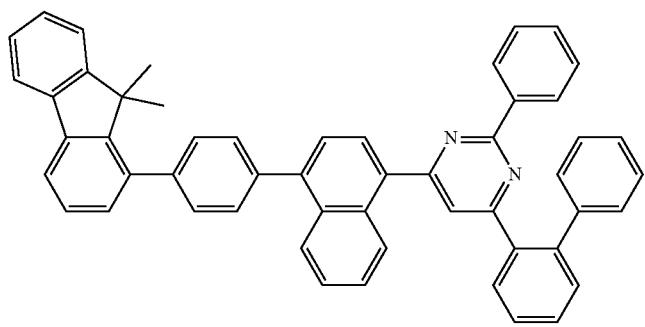
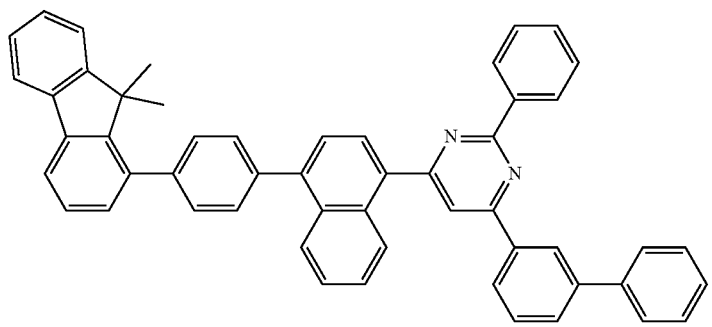

-continued
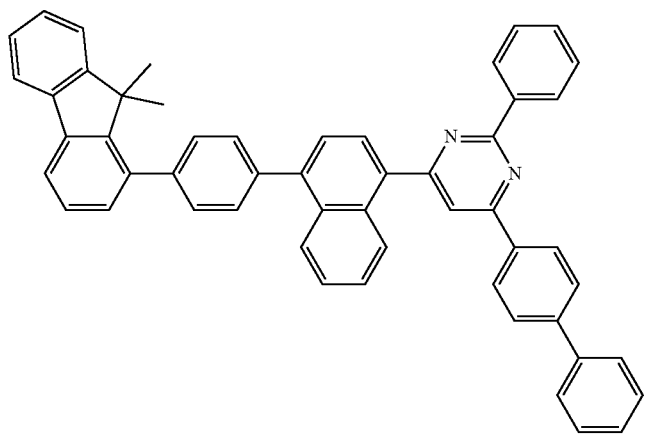
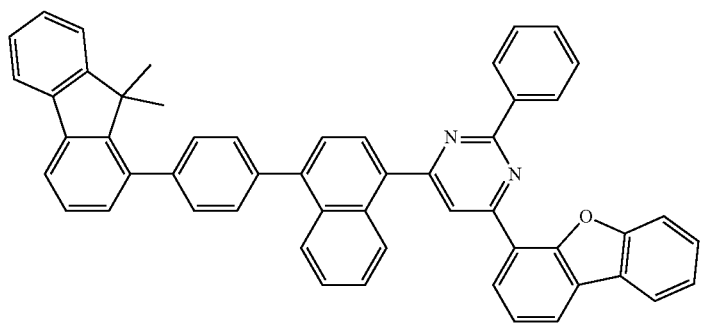
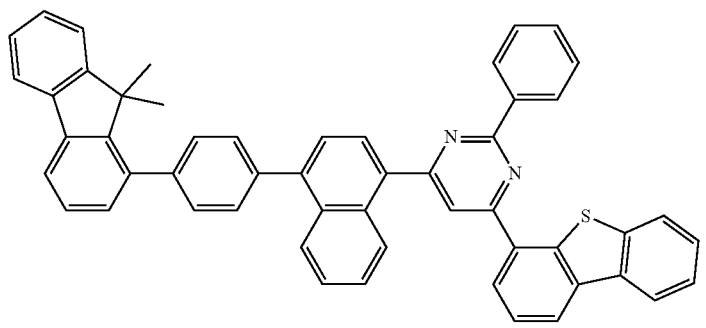
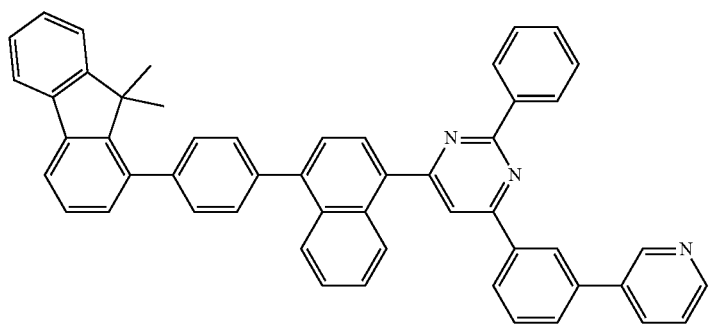

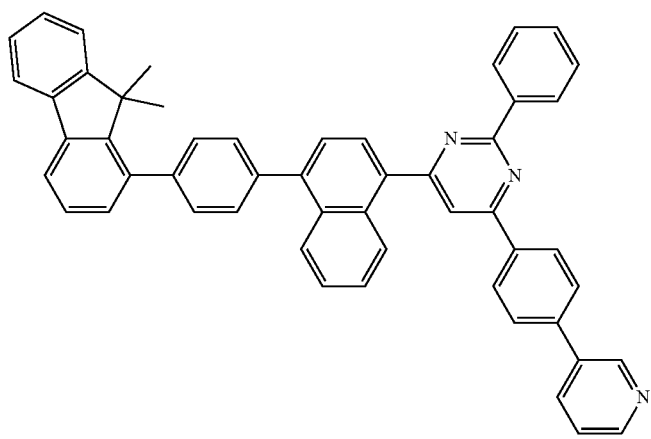
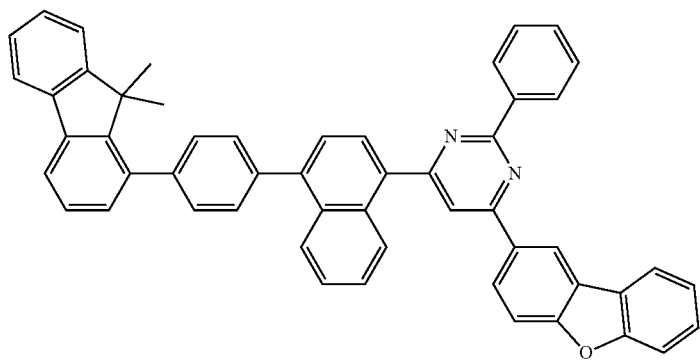
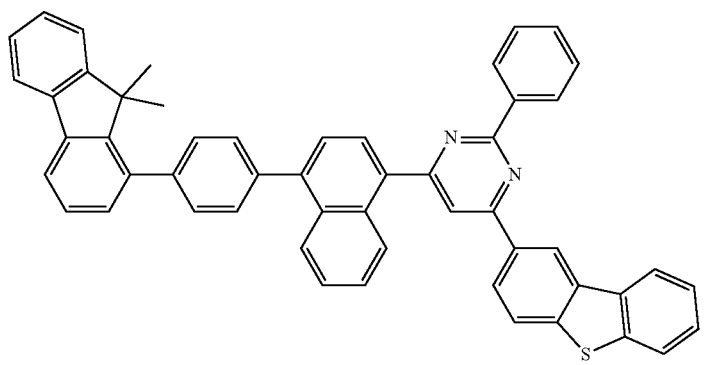
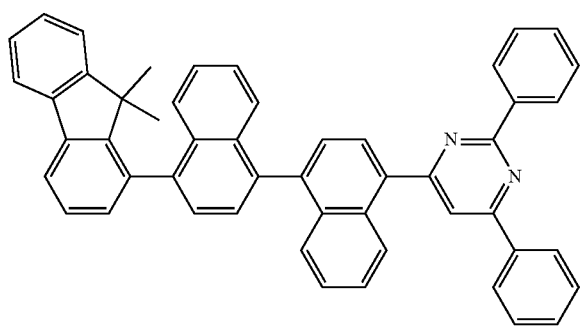

-continued
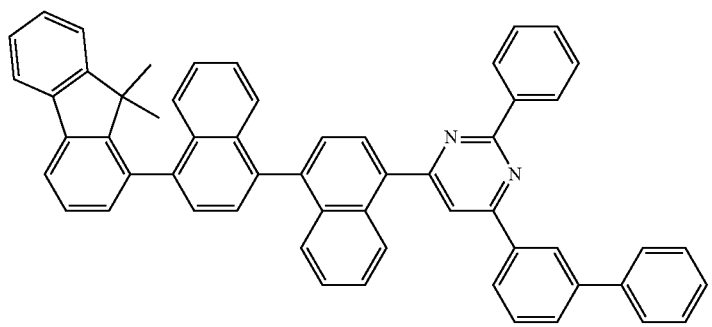
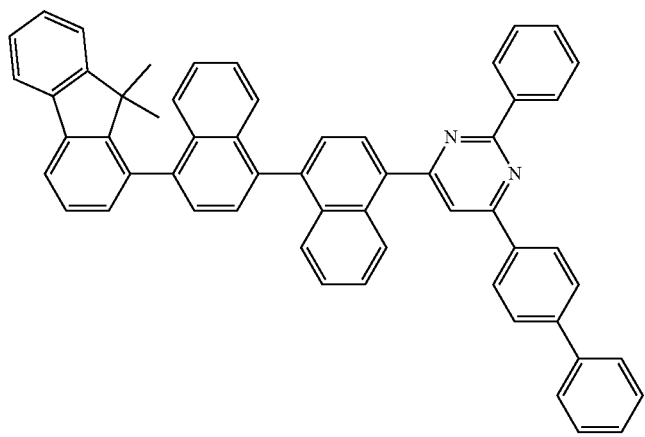
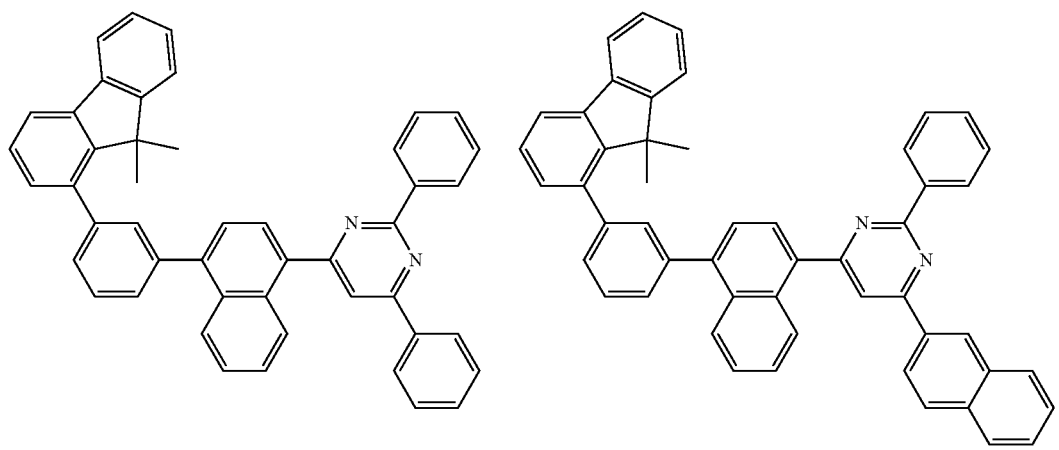
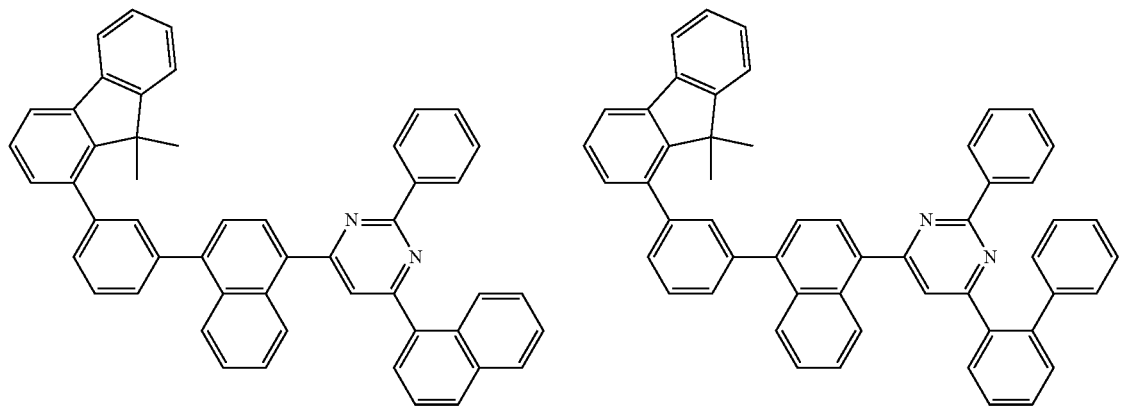

-continued
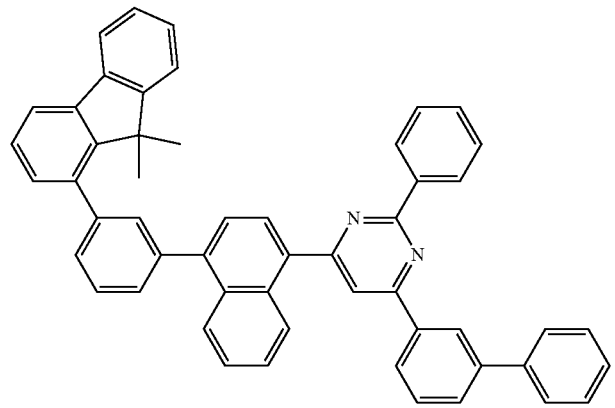
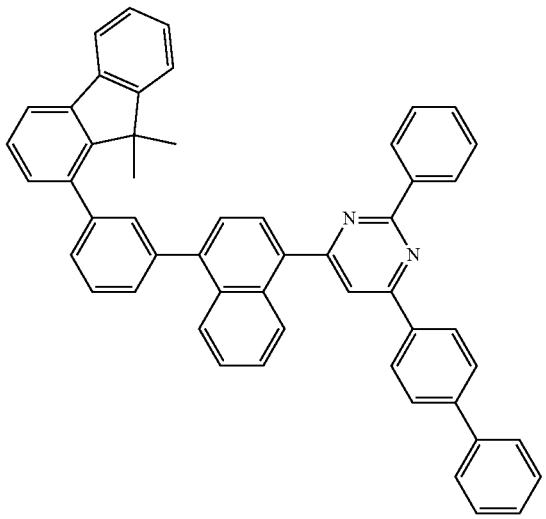
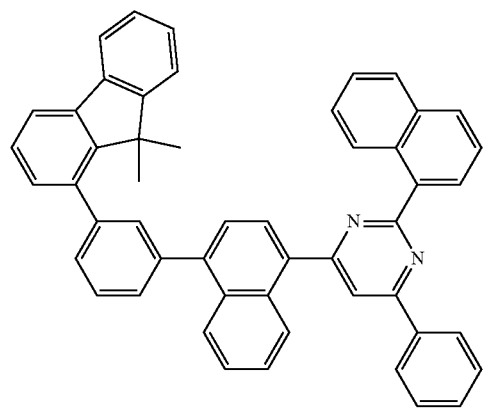
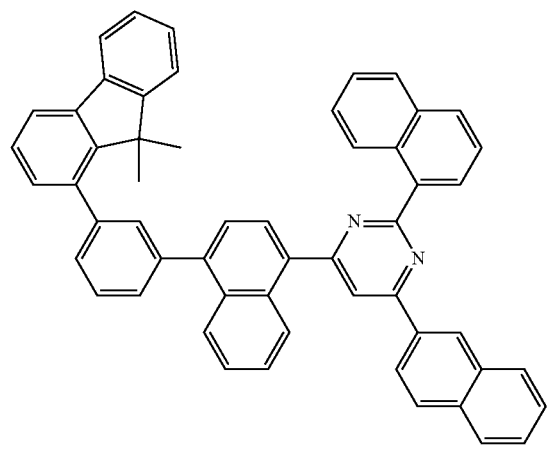
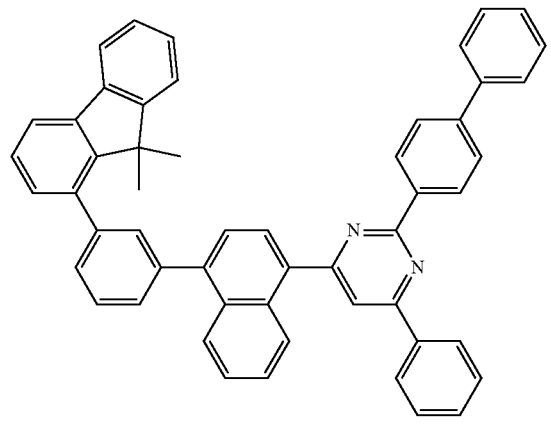
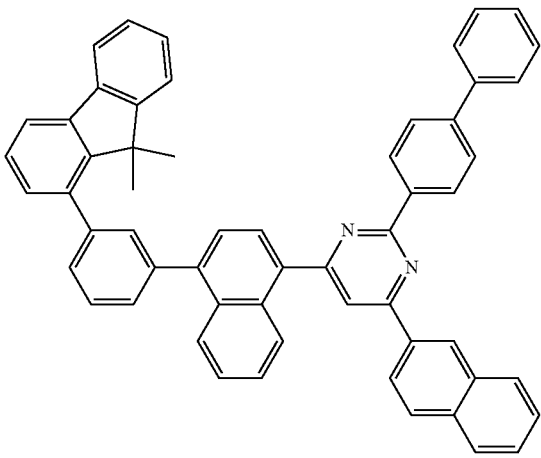

-continued
181
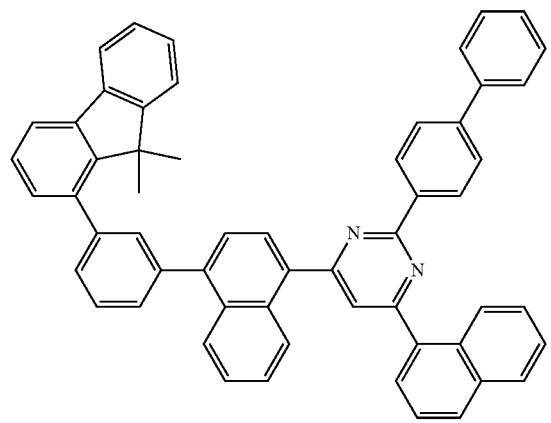
182
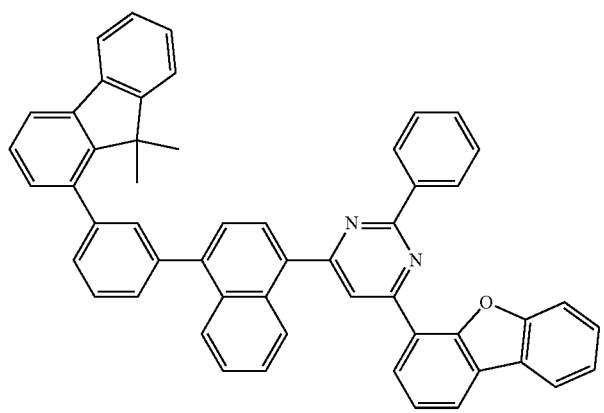
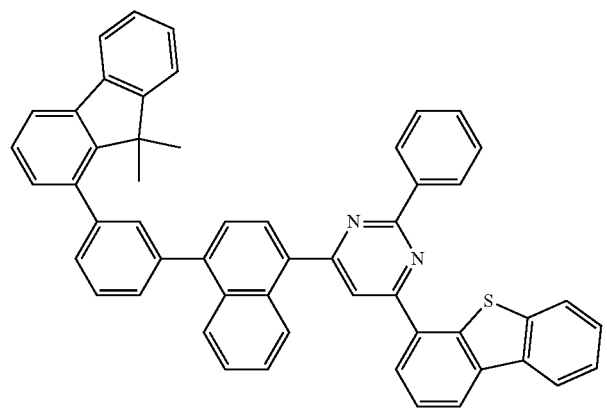
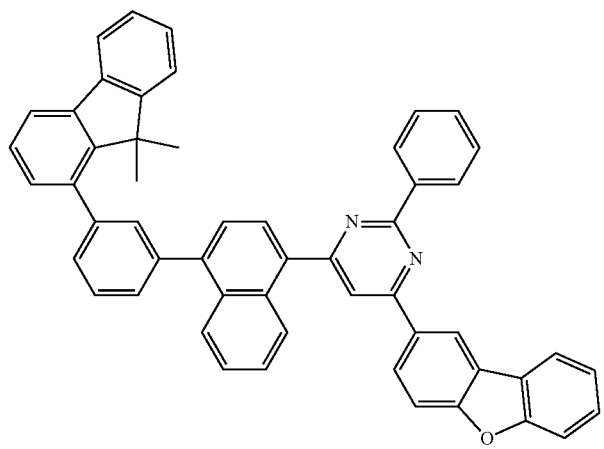
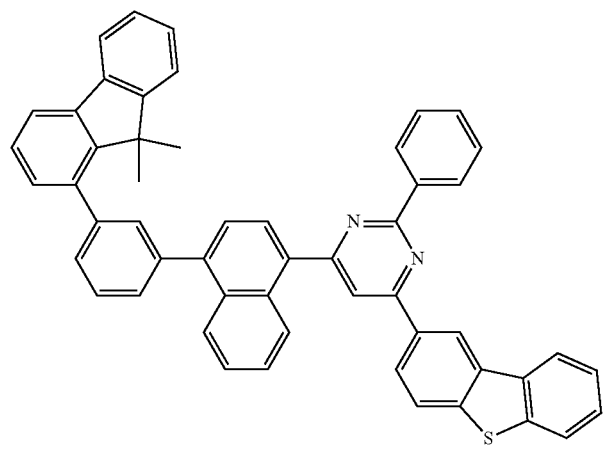
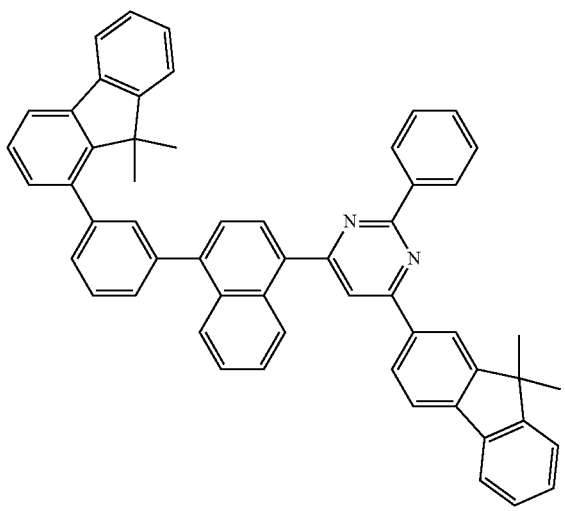

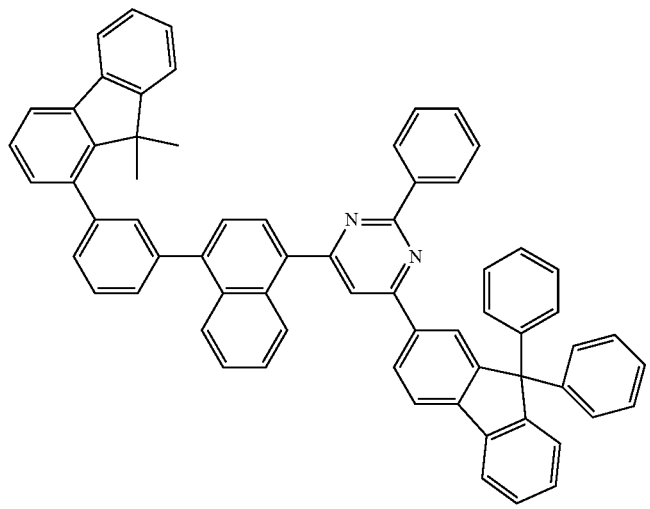
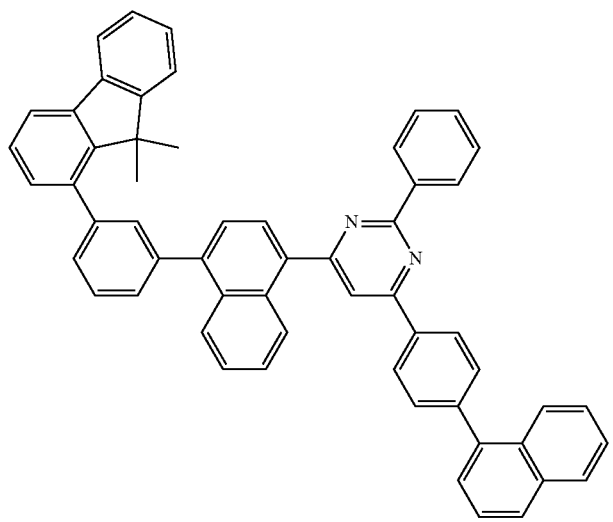
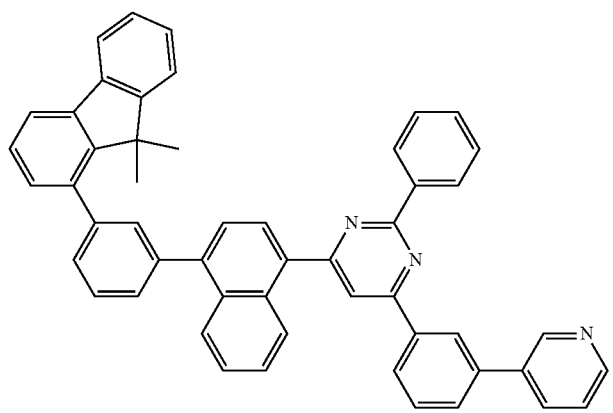
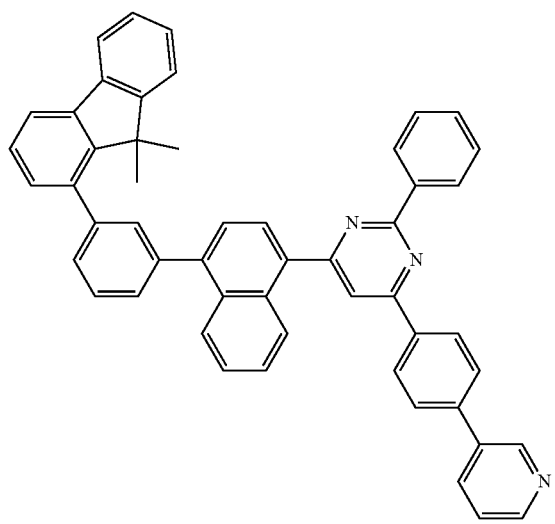

-continued
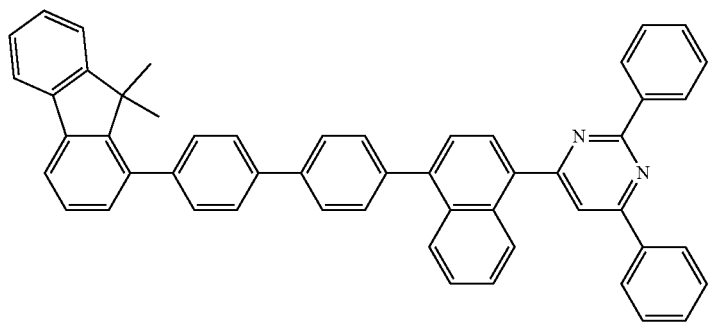
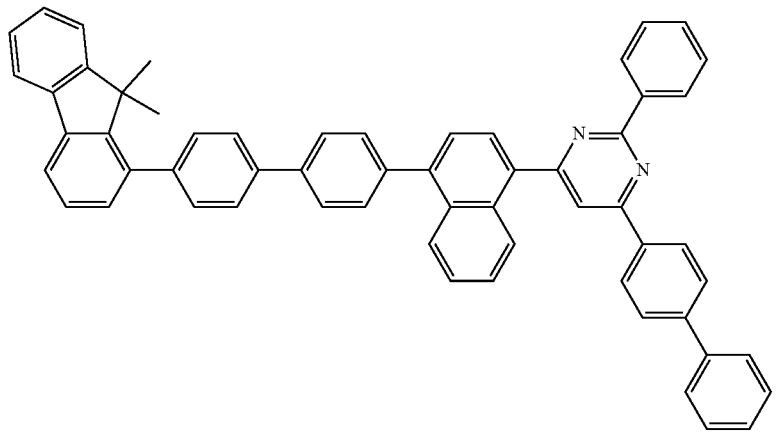
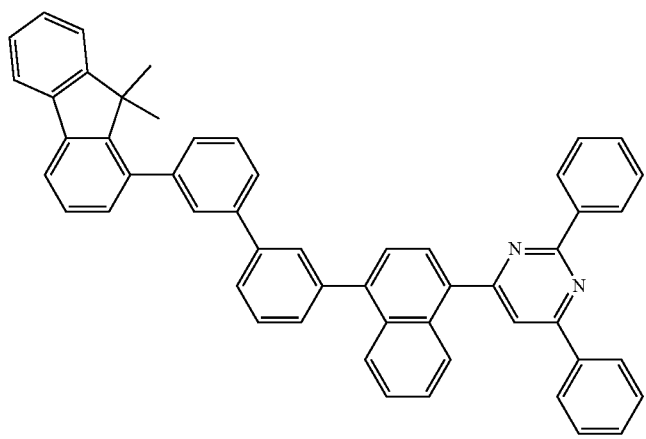
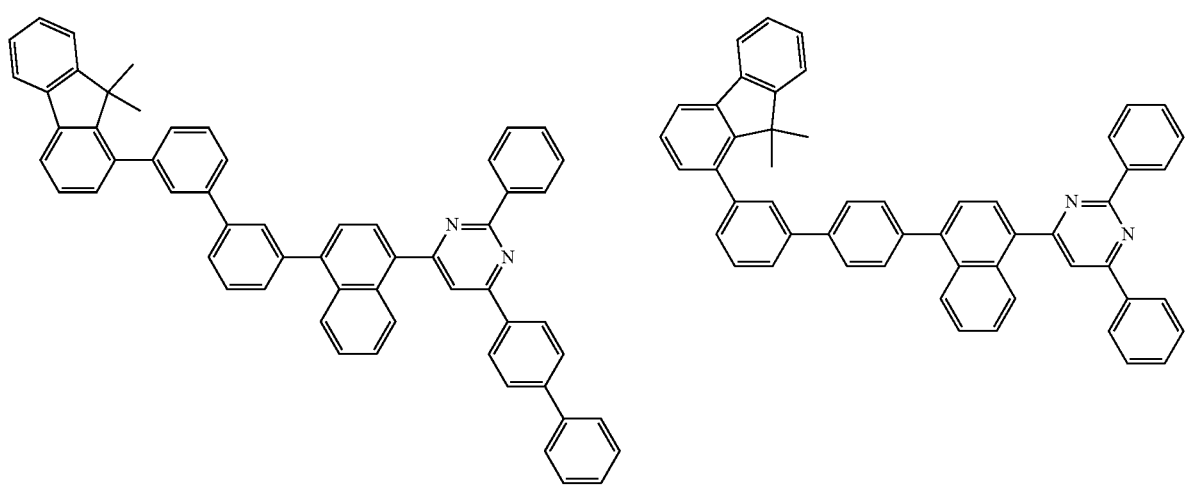

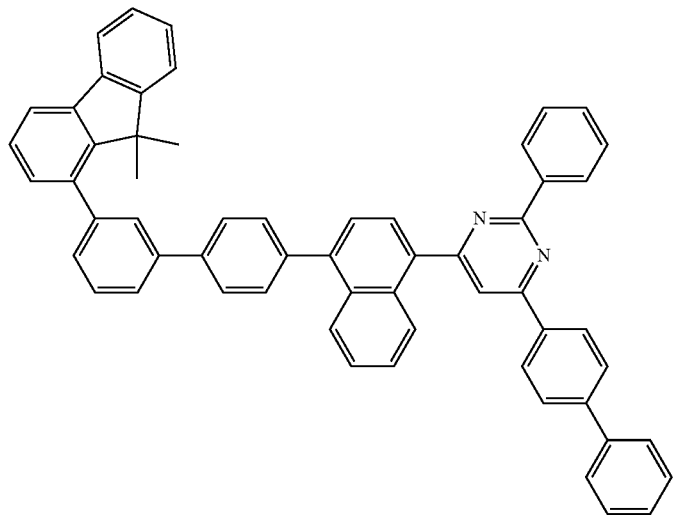
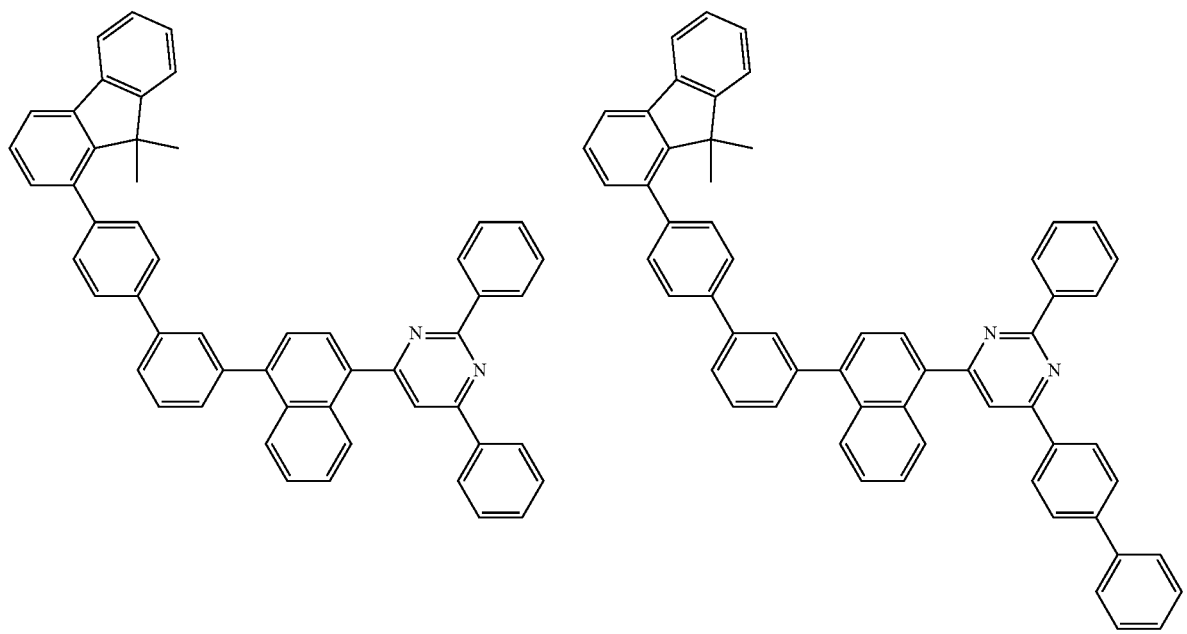
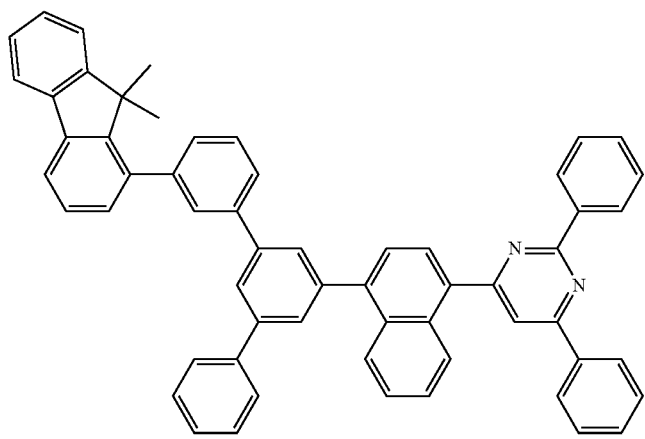

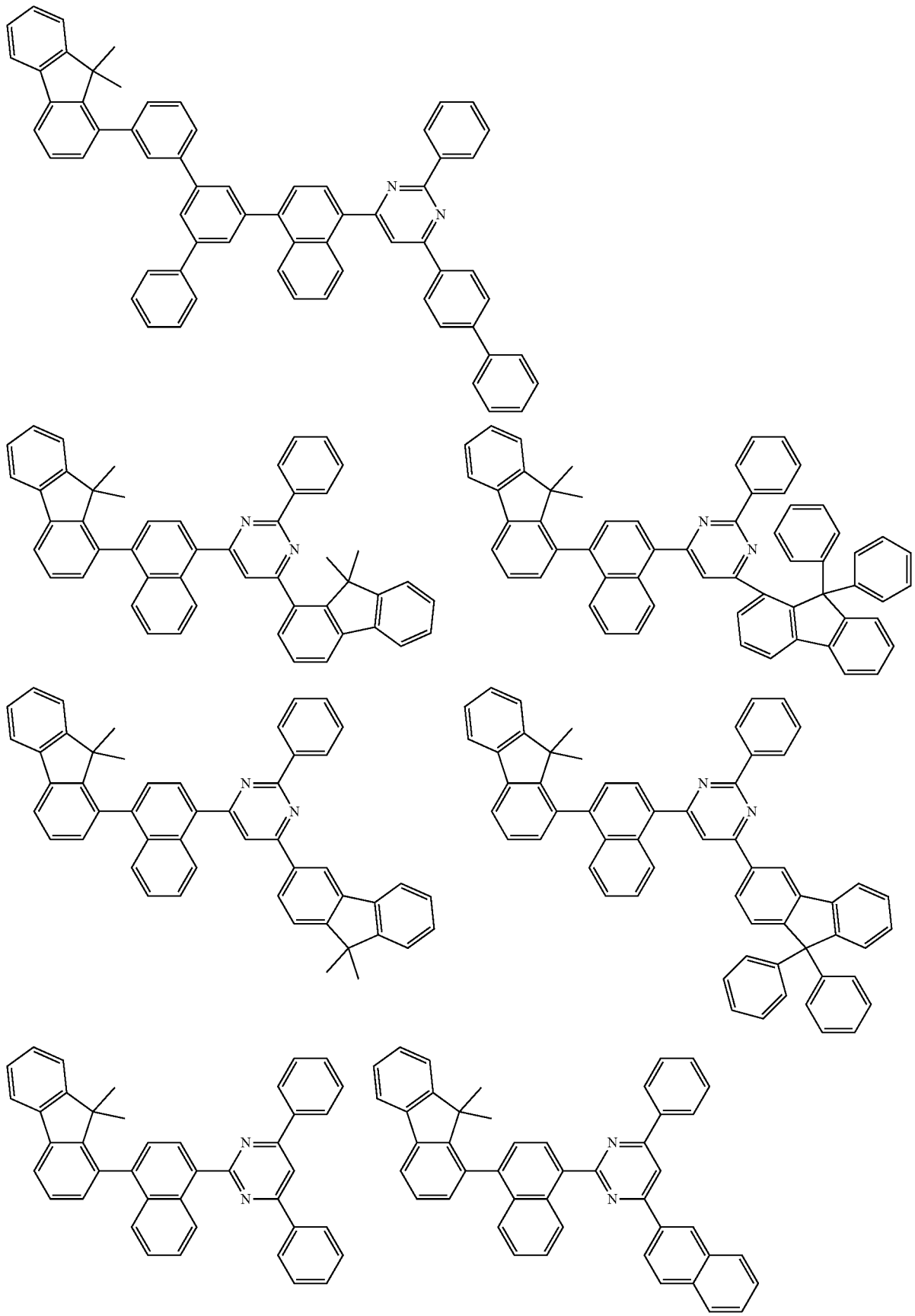

-continued
| 191 | 192 |
|---|---|
| 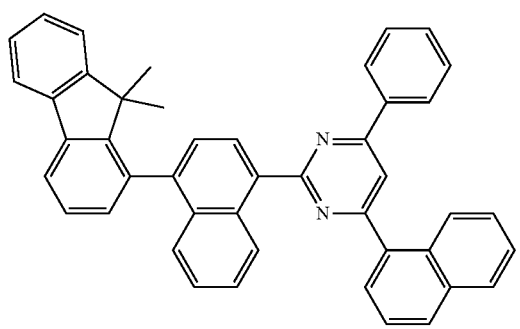 | 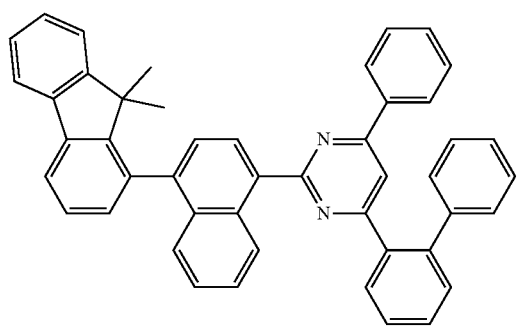 |
| 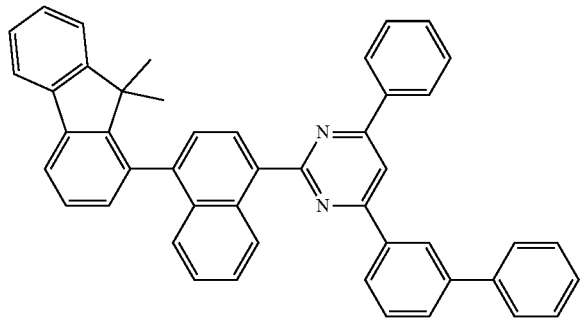 | 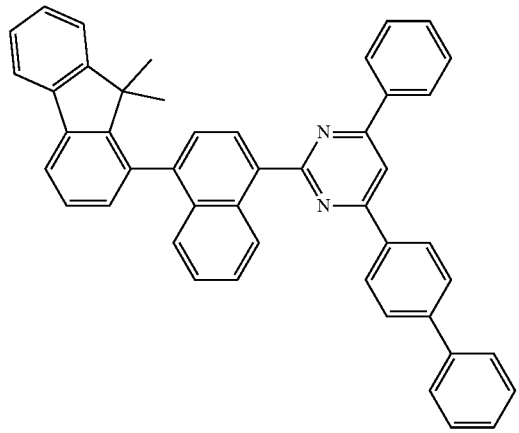 |
| 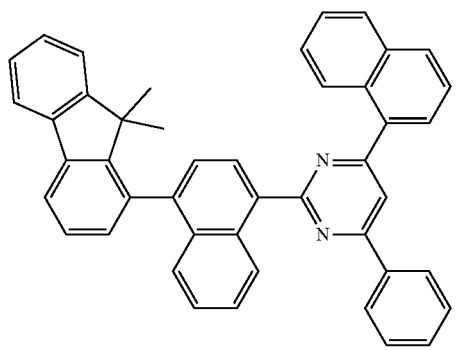 | 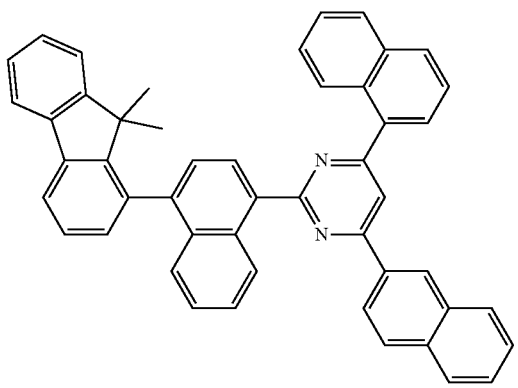 |
| 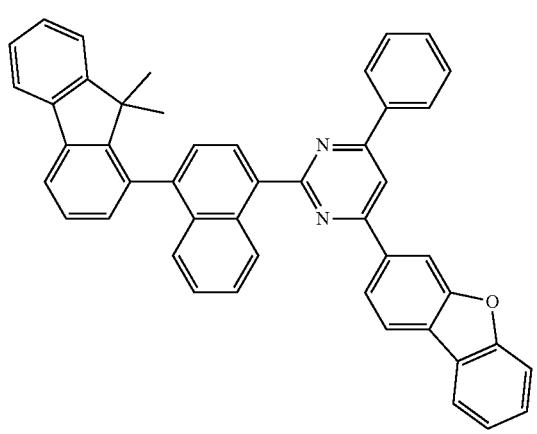 | 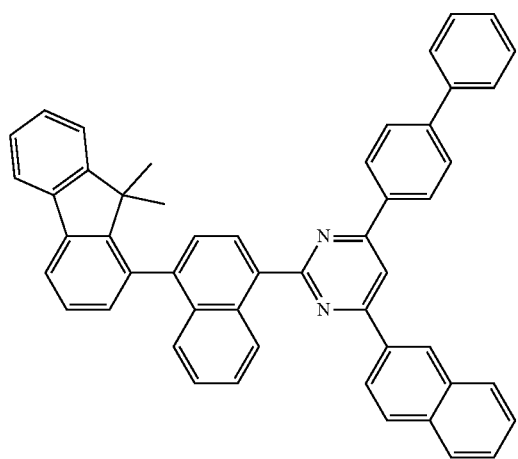 |

-continued
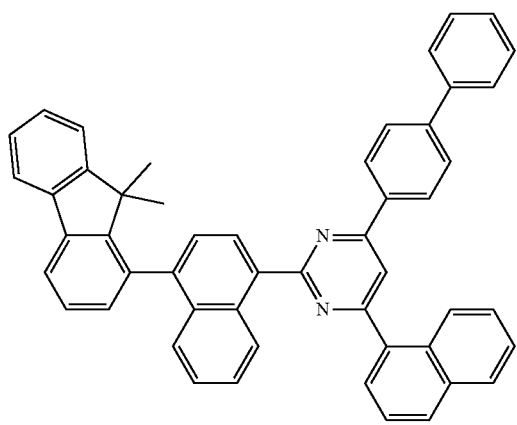
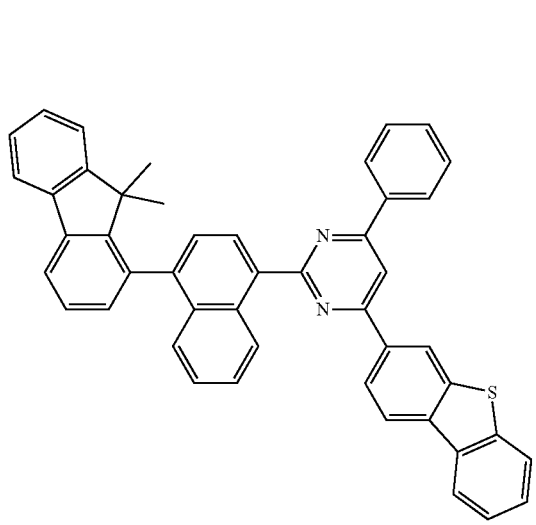
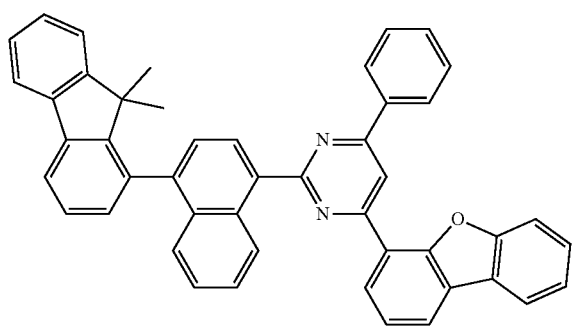
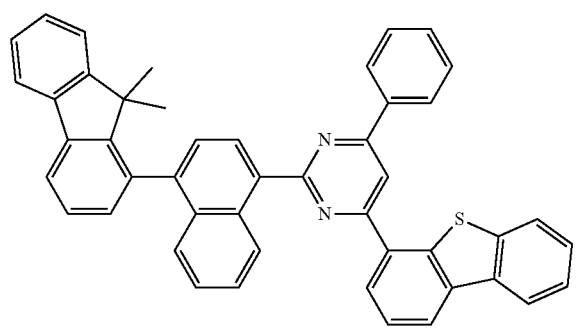
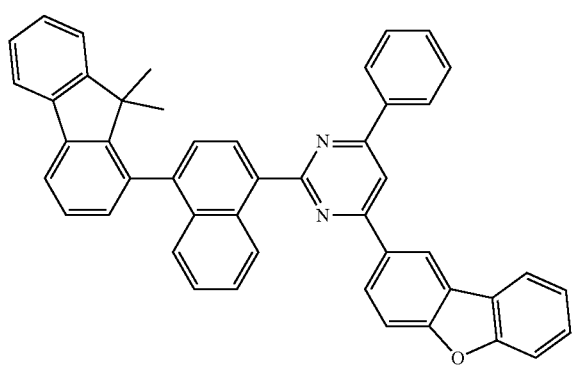
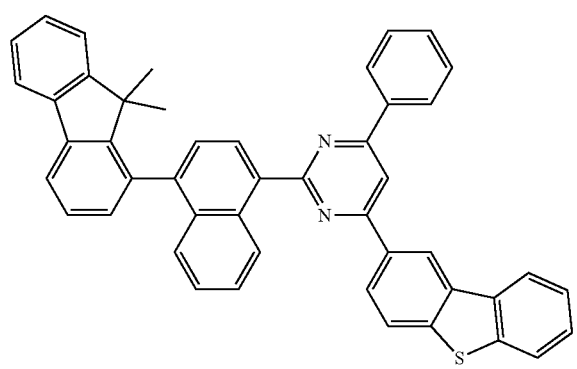
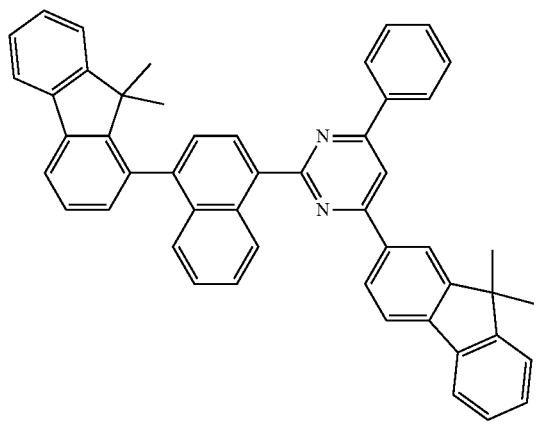
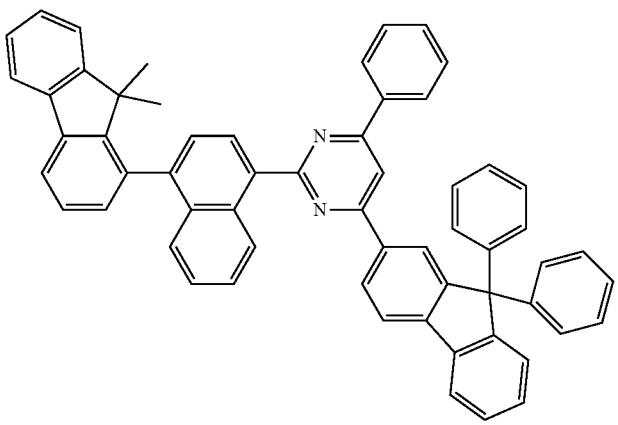

195 196
-continued
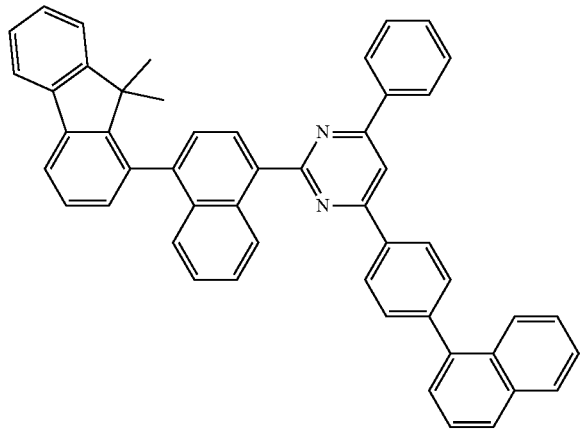

-continued
| 197 | 198 |
|---|---|
| 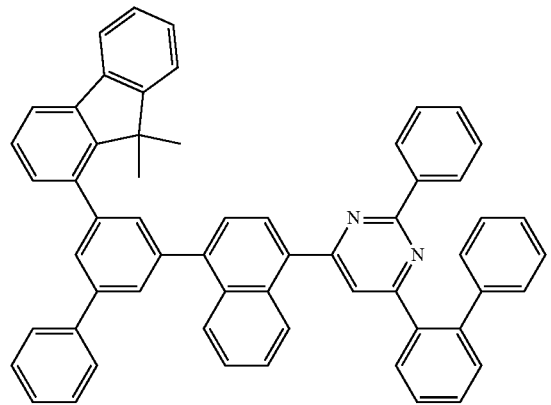 | 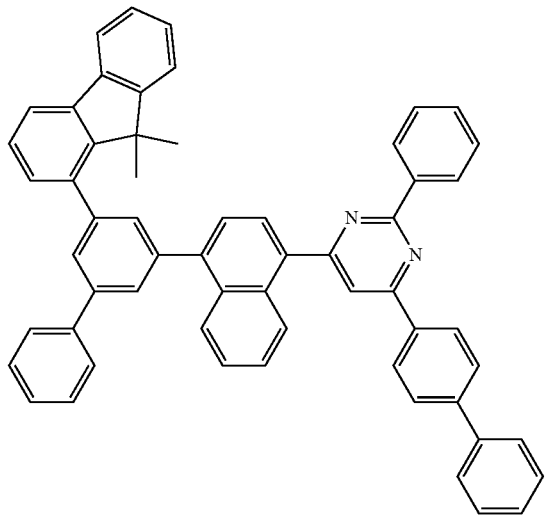 |
| 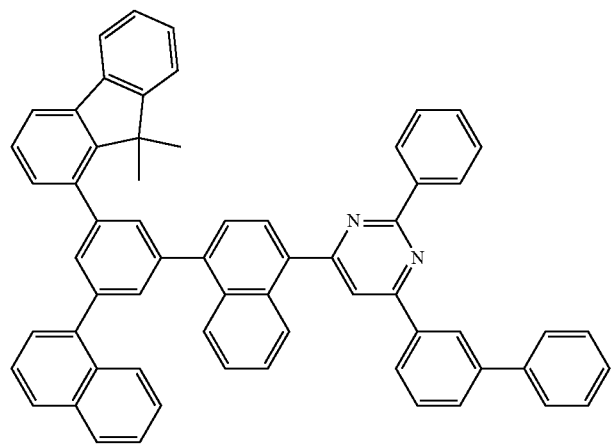 | 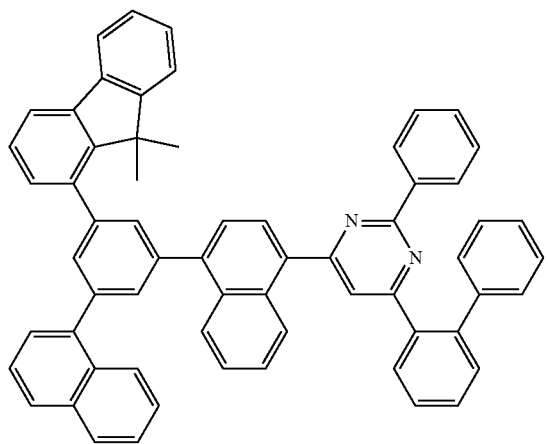 |
| 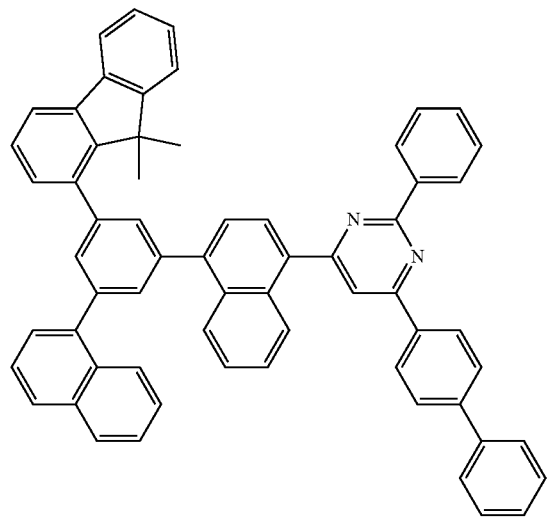 | 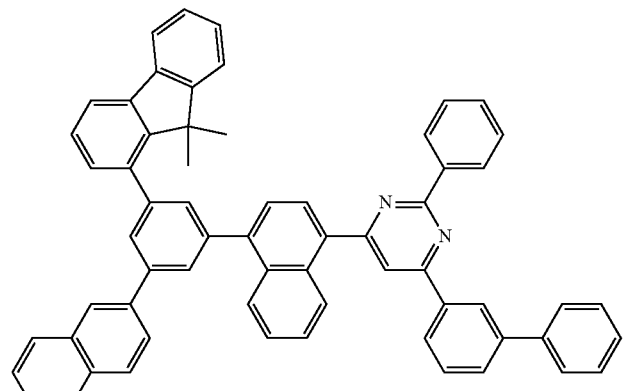 |

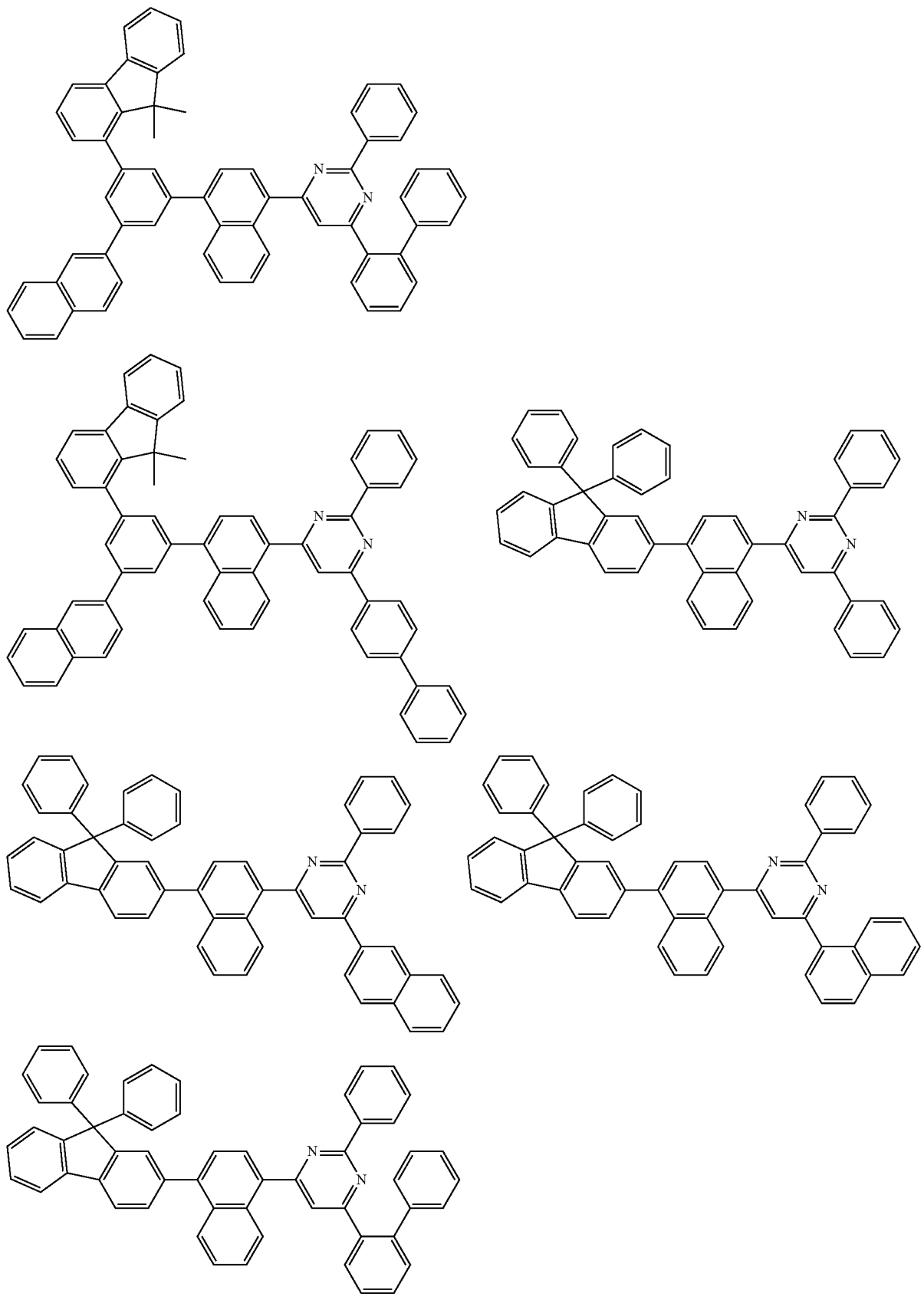

-continued
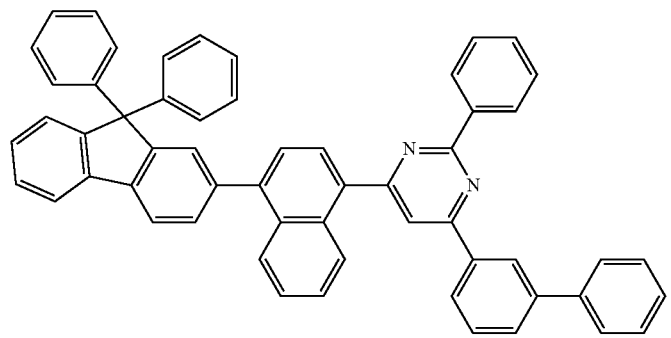
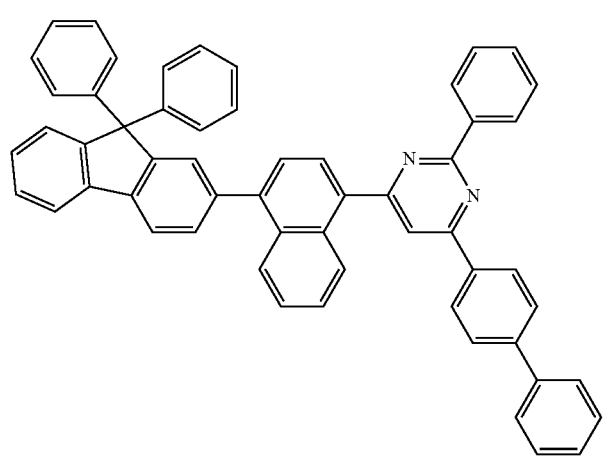
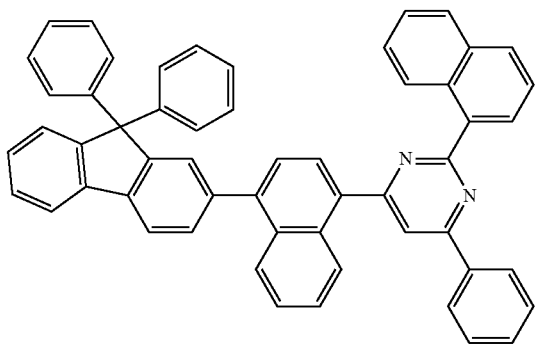
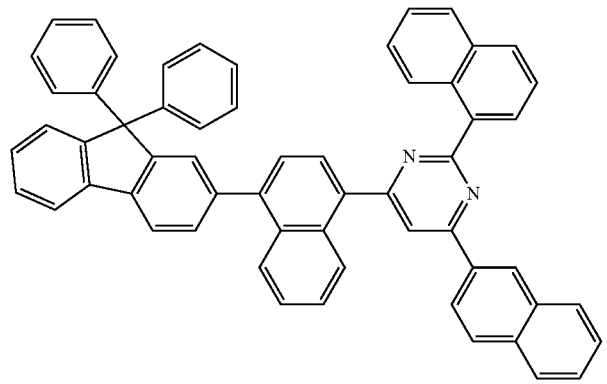
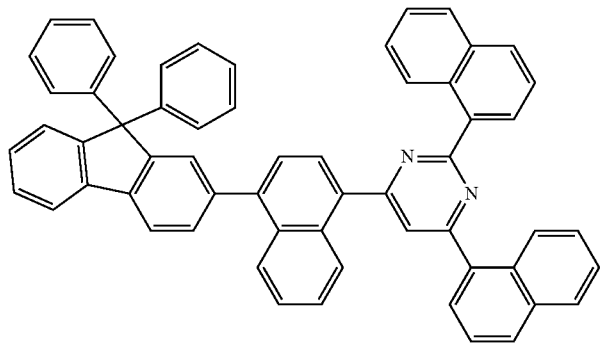
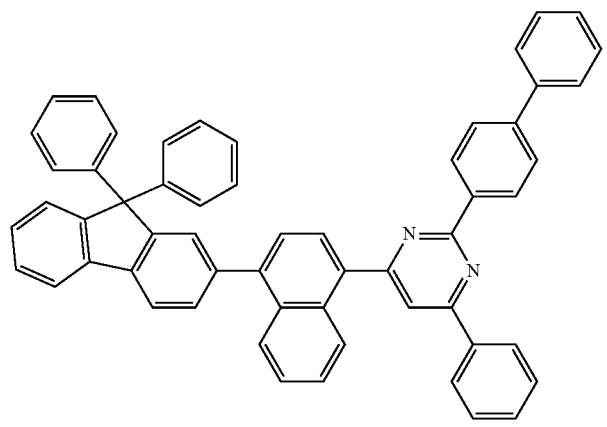
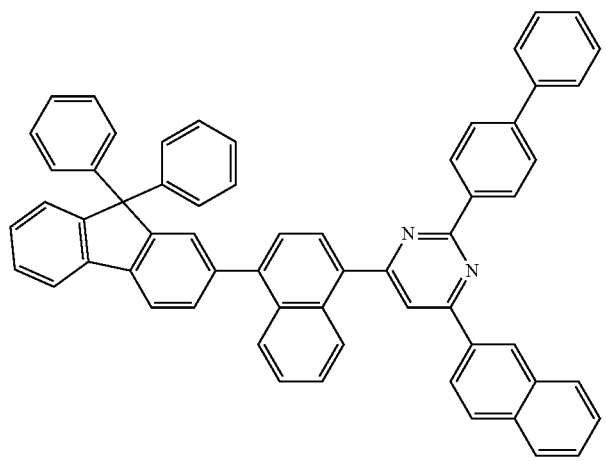

-continued
| 203 | 204 |
|---|---|
| 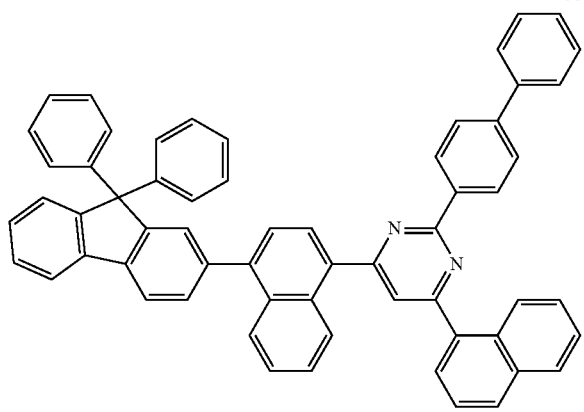 | 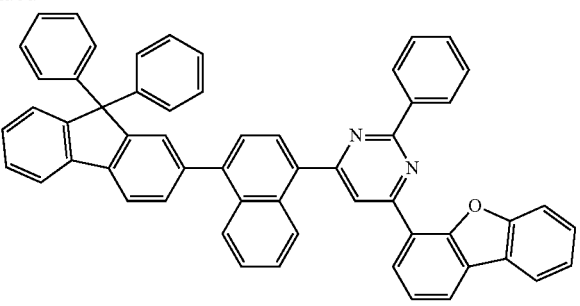 |
| 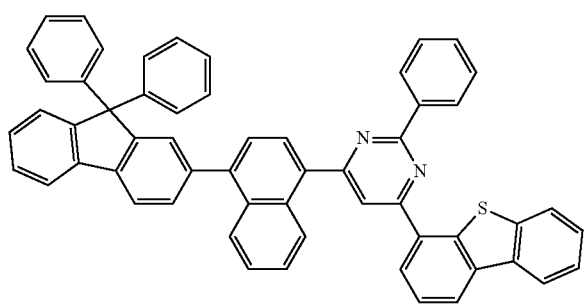 | 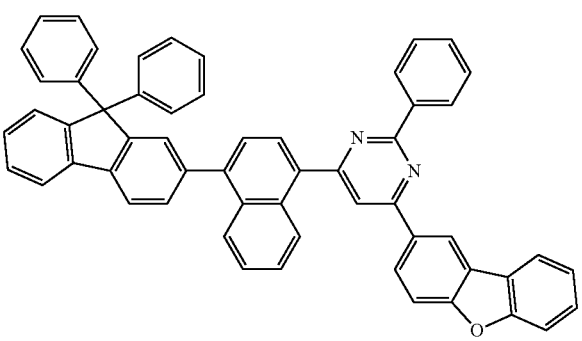 |
| 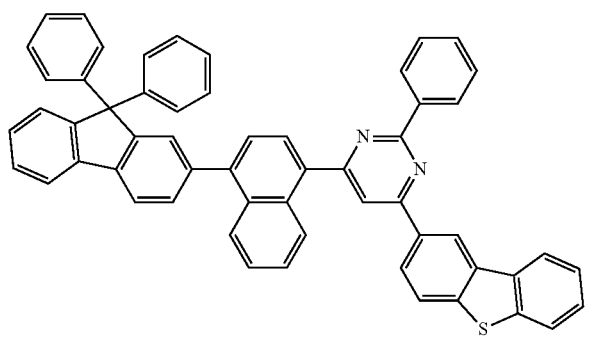 | 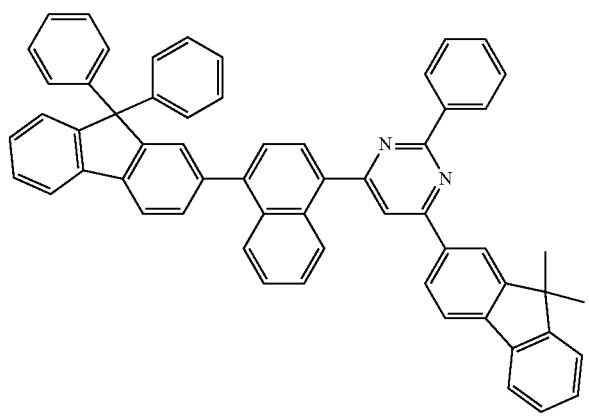 |
| 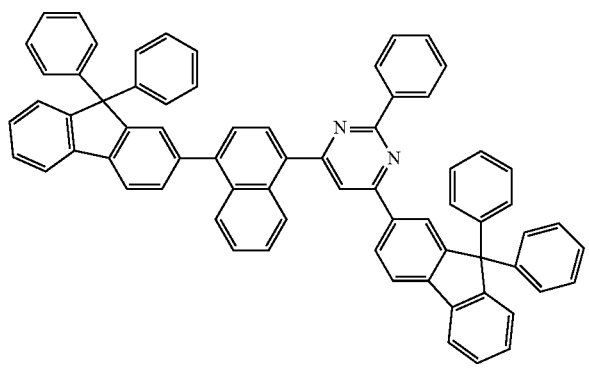 | 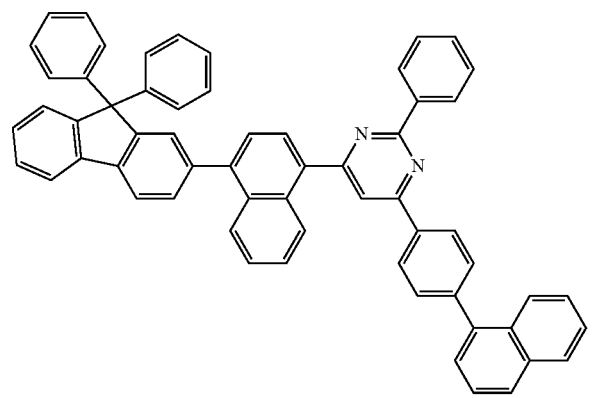 |

205
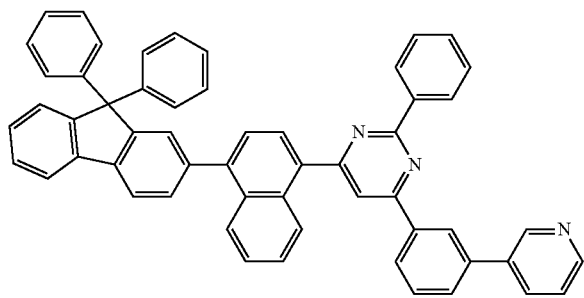
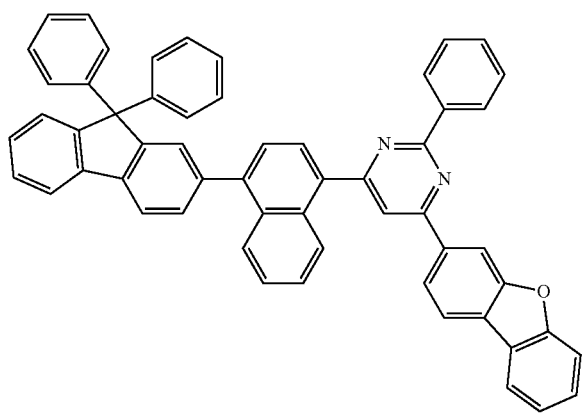
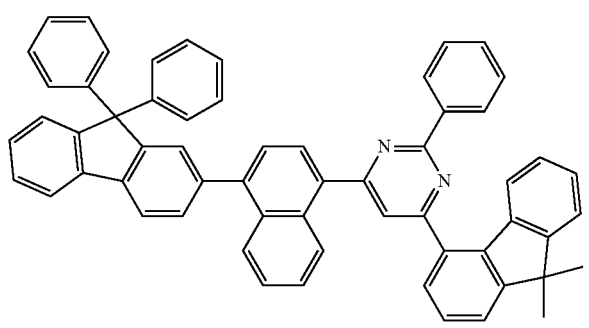
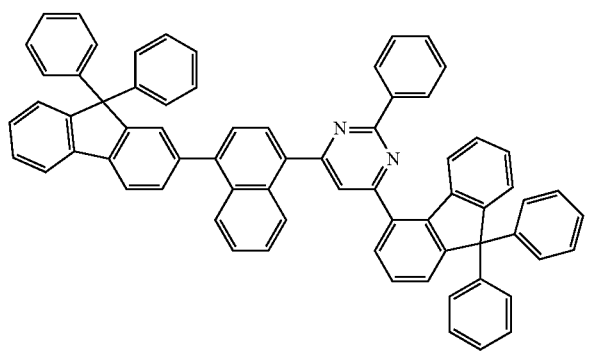
206
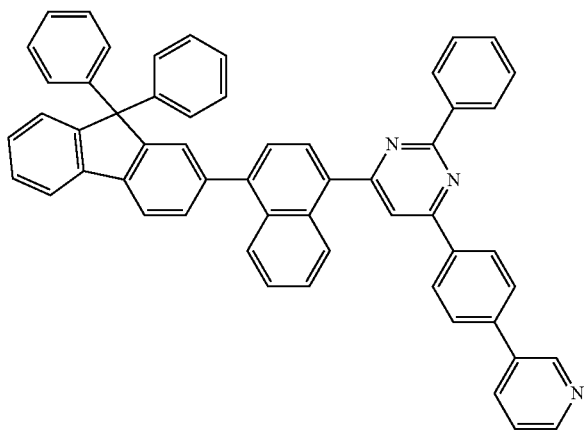
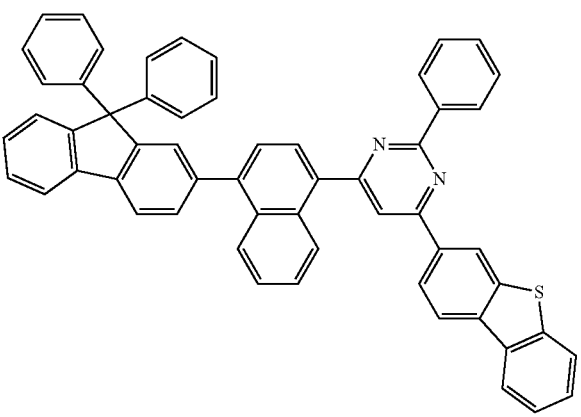
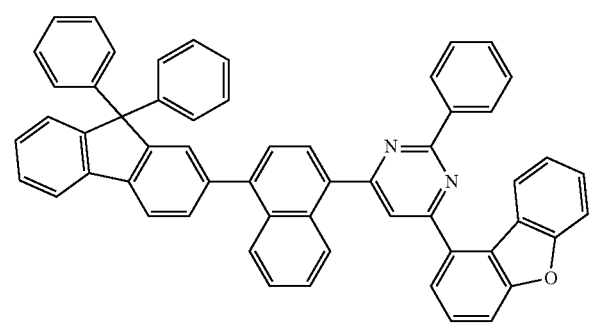
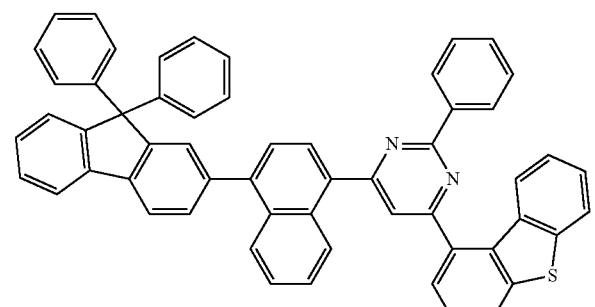

-continued
| 207 | 208 |
|---|---|
| 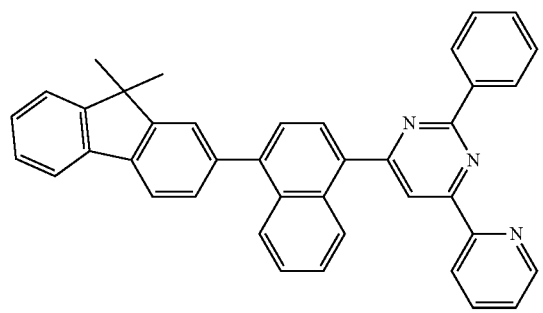 | 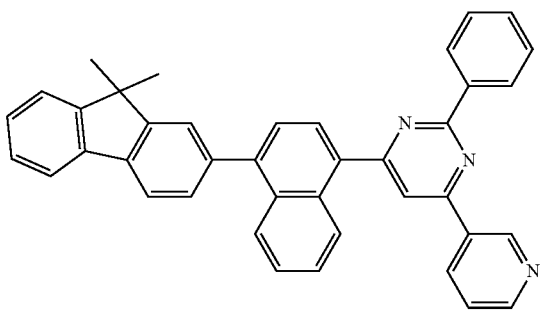 |
| 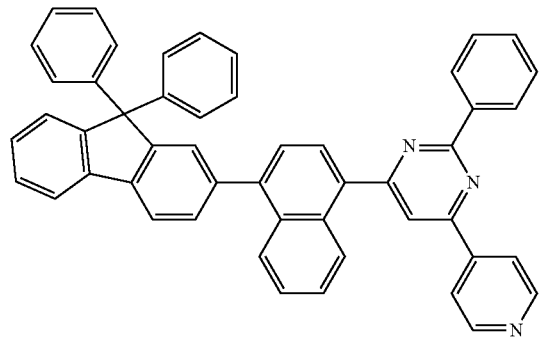 | 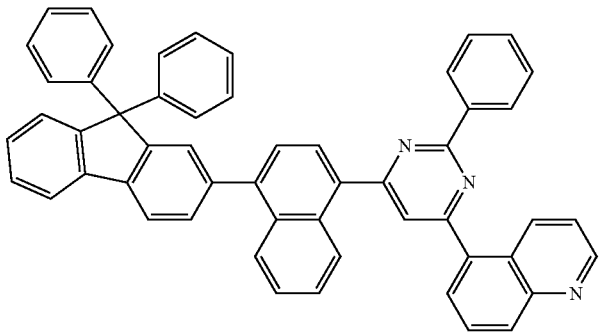 |
| 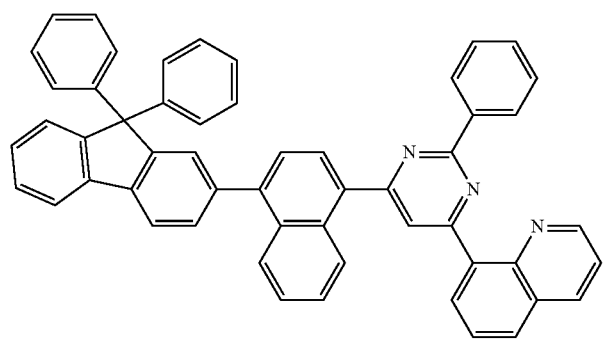 | 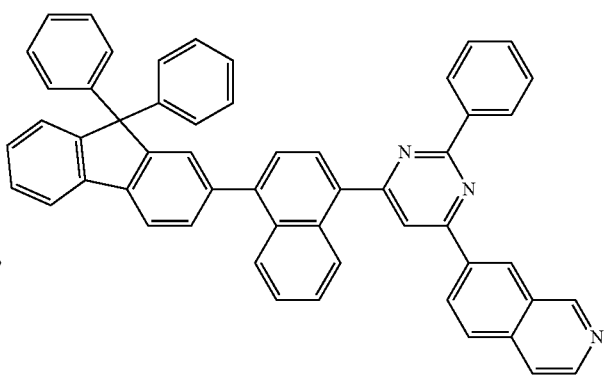 |
| 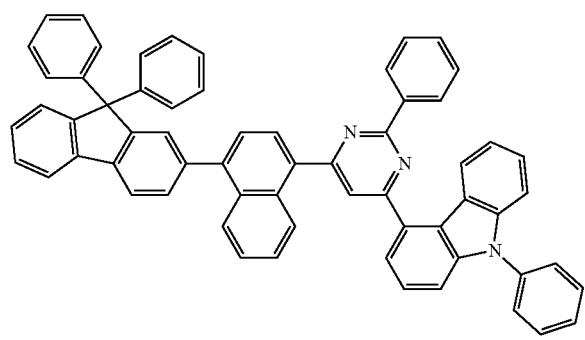 | 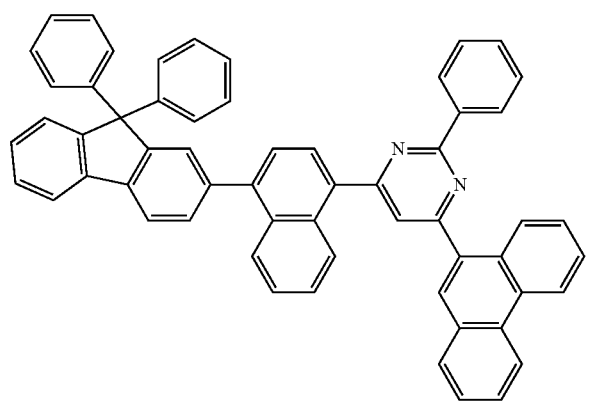 |

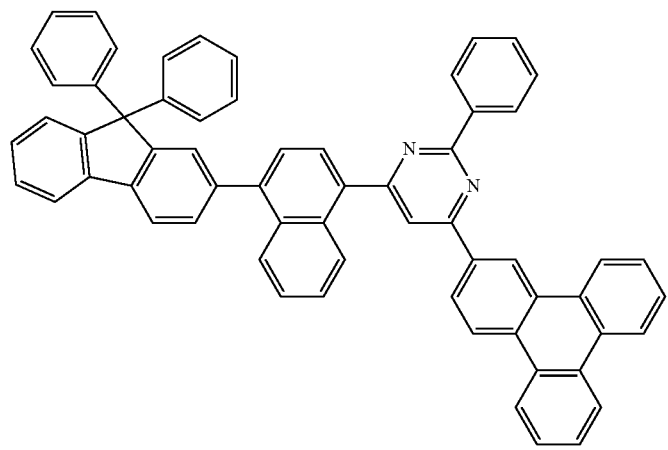
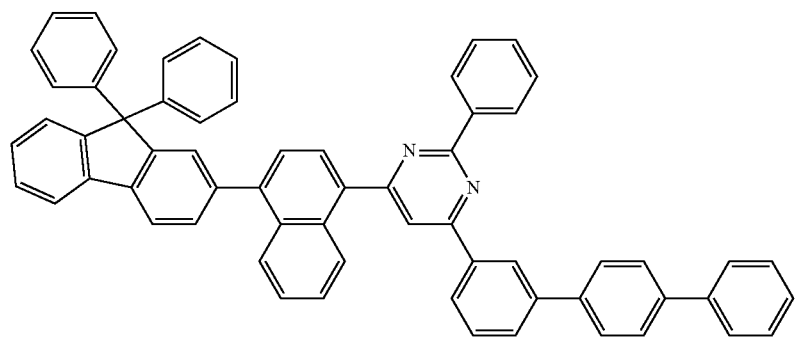
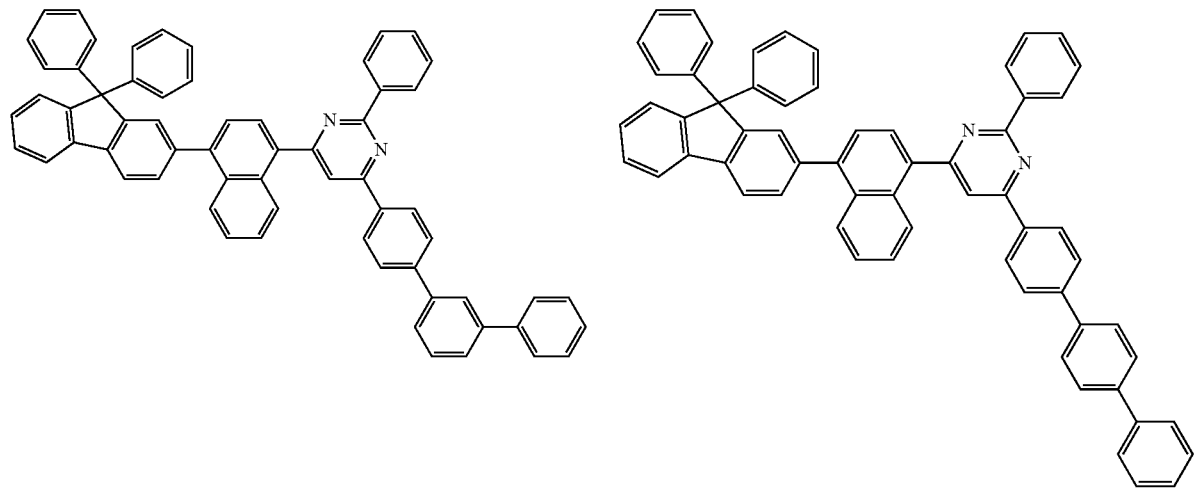
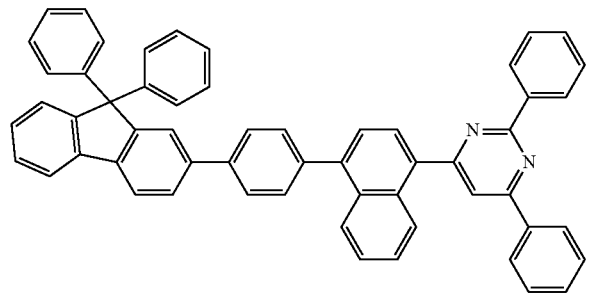
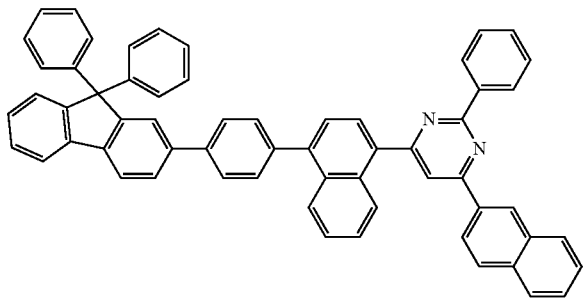

-continued
| 211 | 212 |
|---|---|
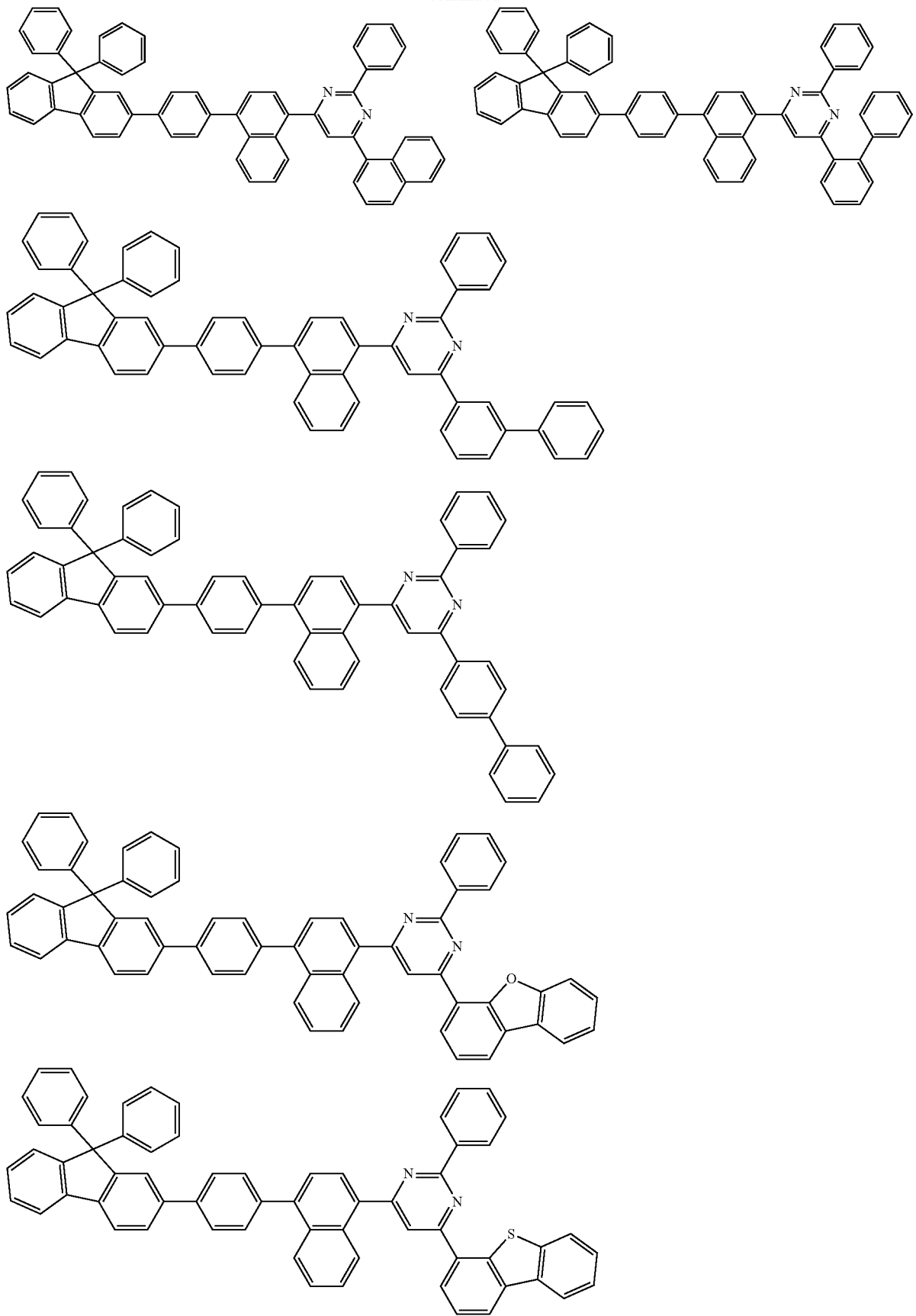

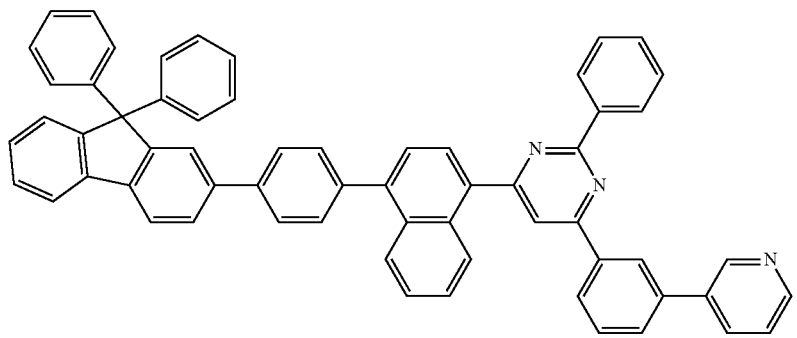

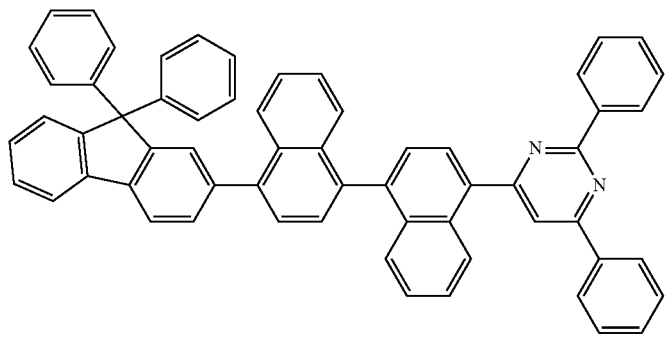
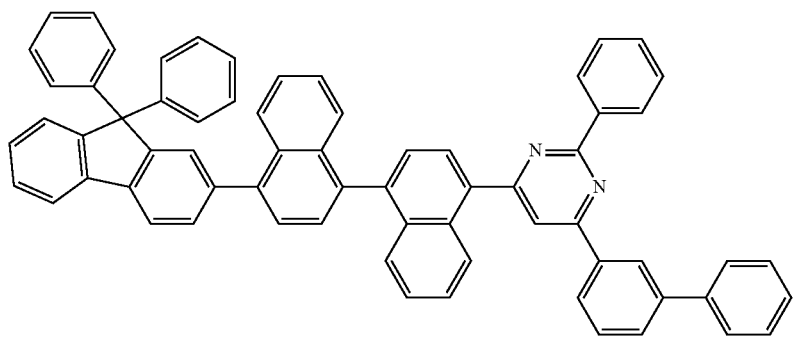
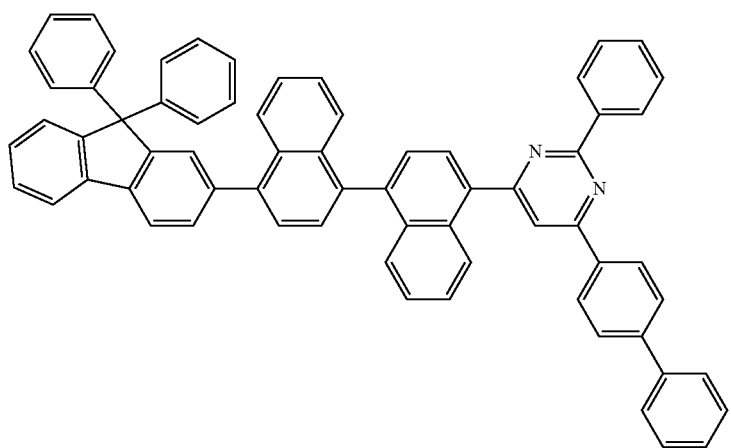
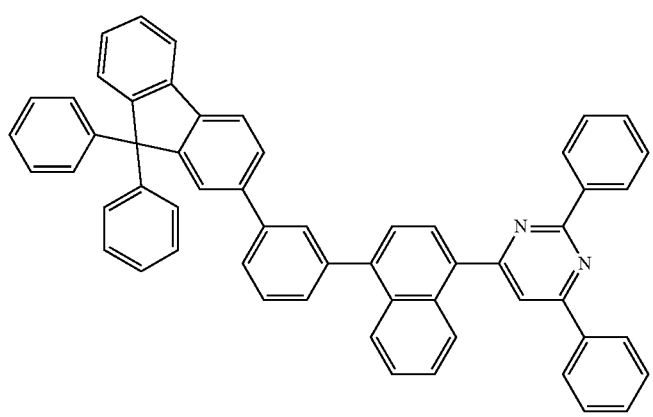

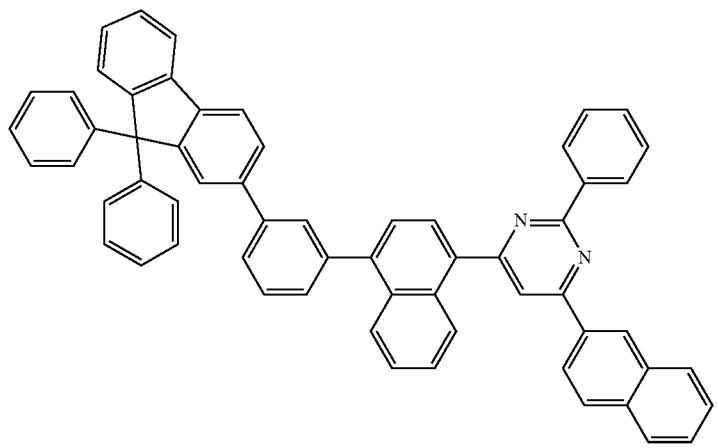
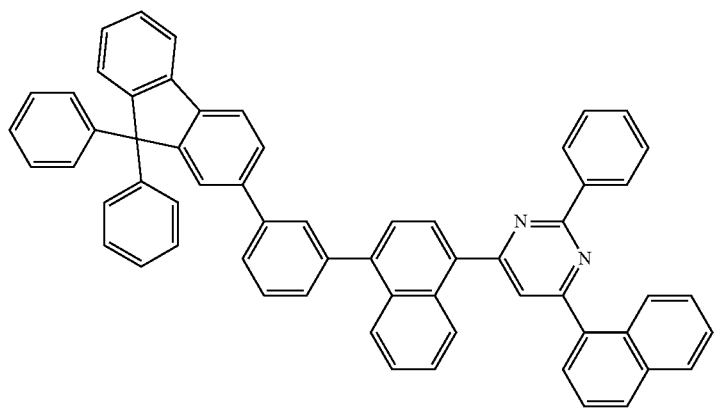
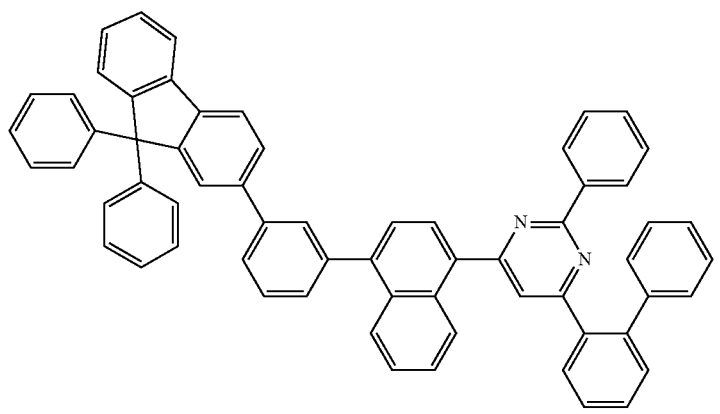
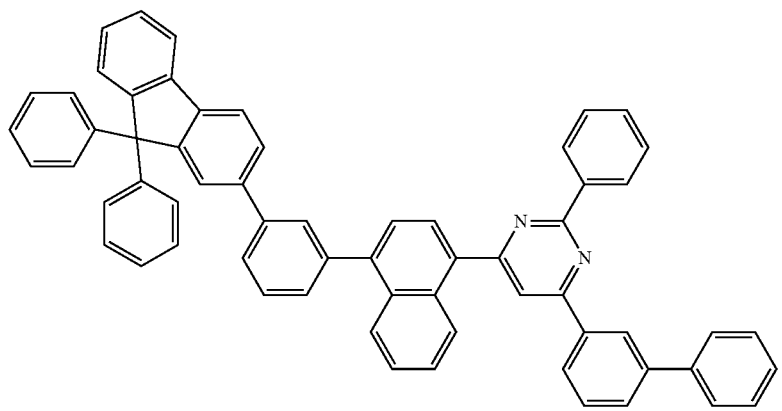

-continued
| 219 | 220 |
|---|---|
| 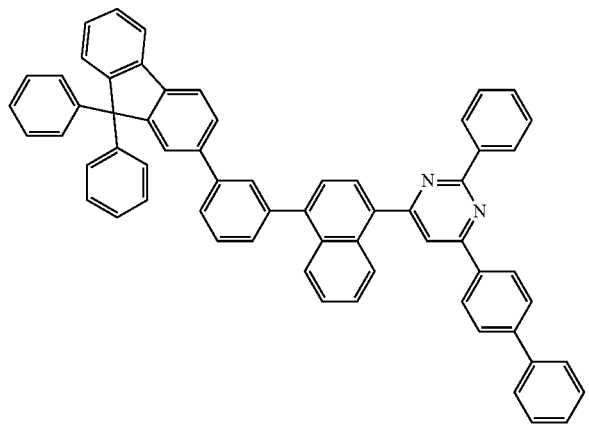 | 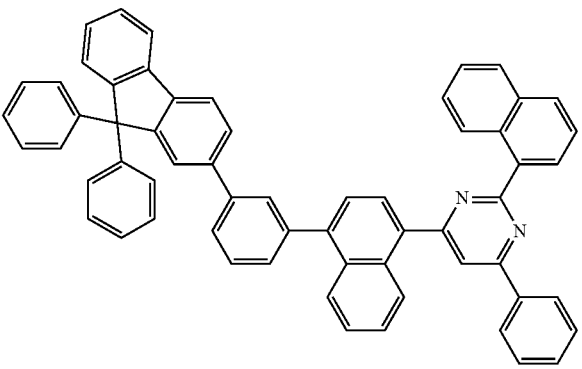 |
| 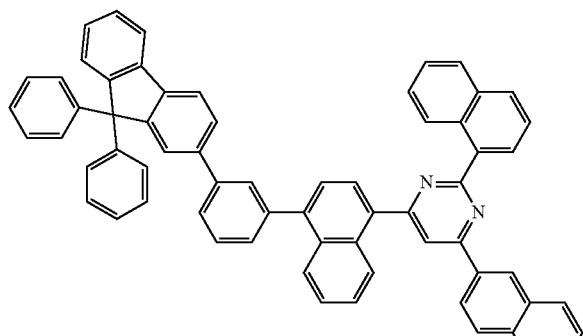 | 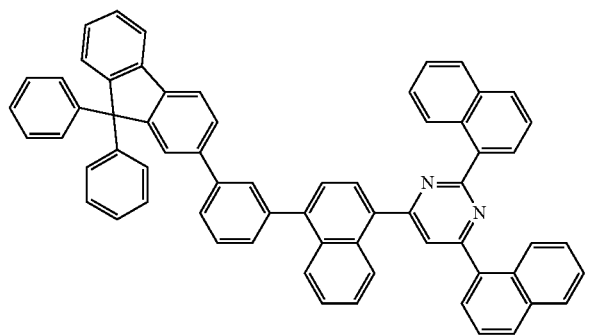 |
| 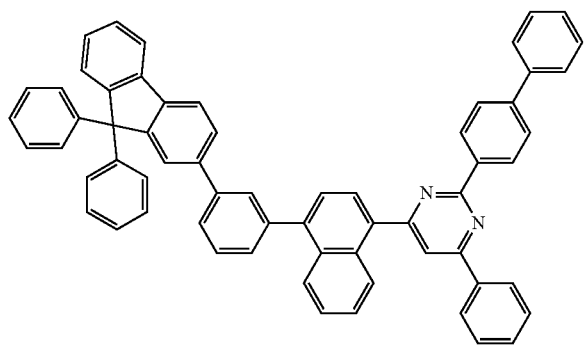 | 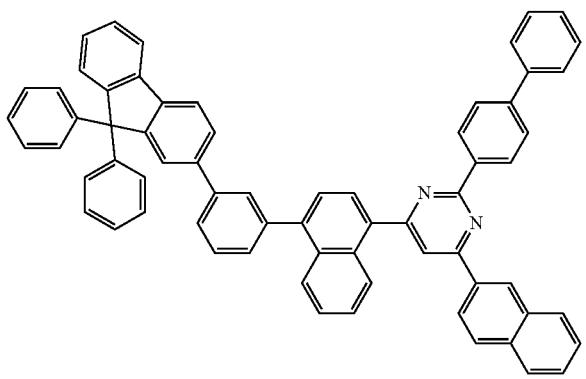 |
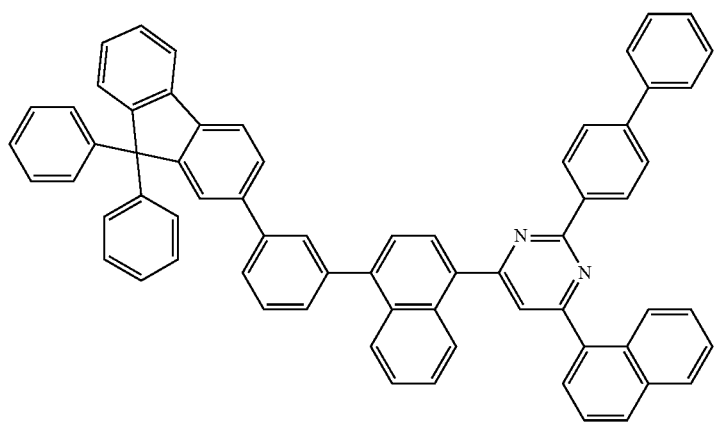

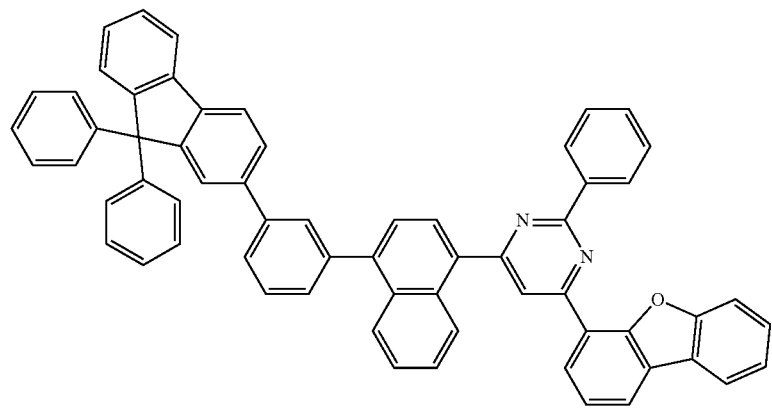
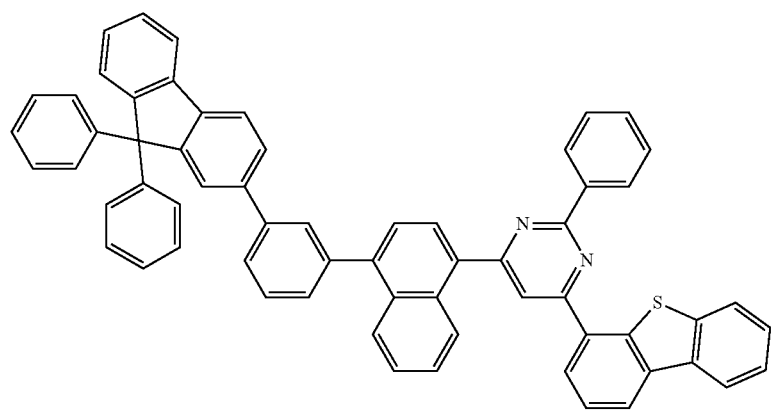
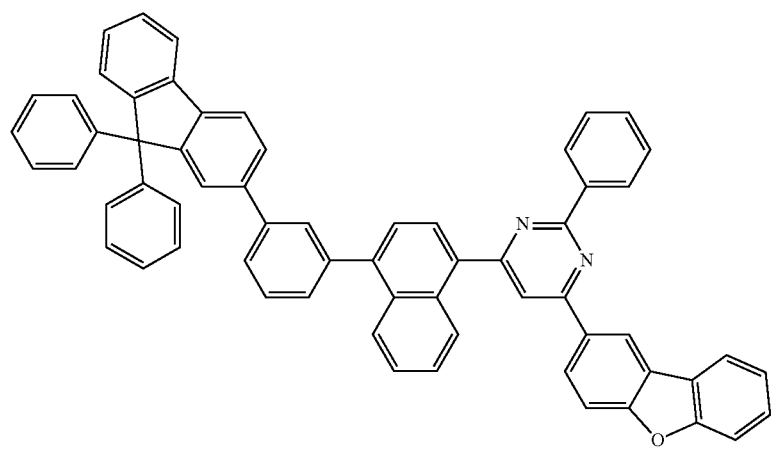
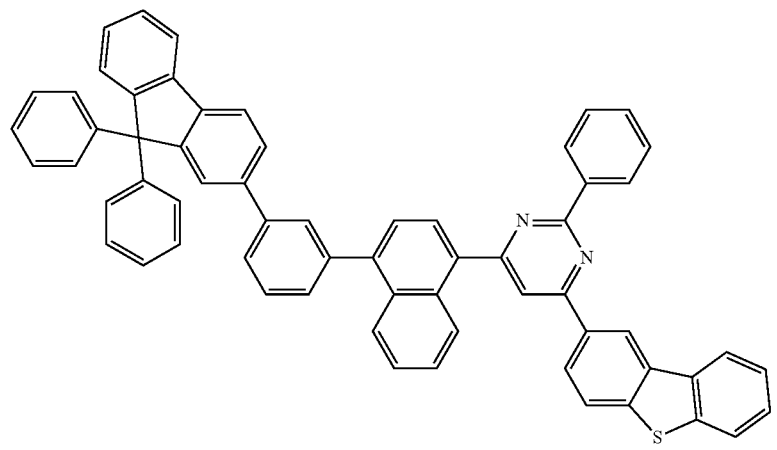

-continued
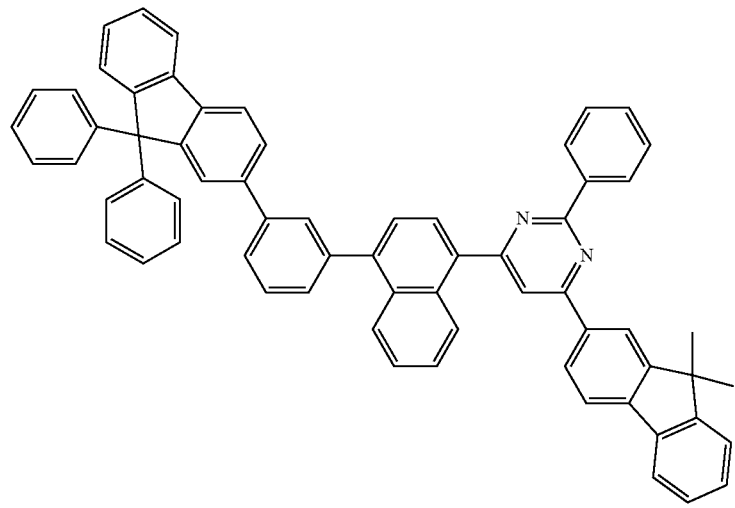
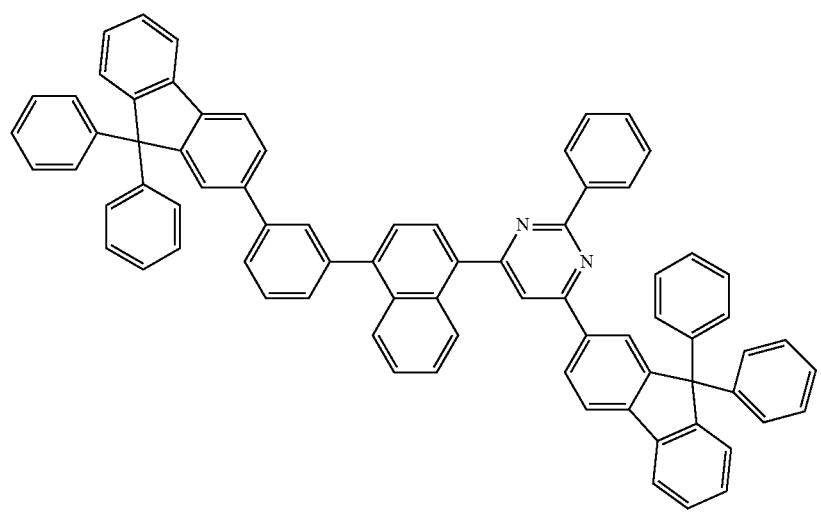
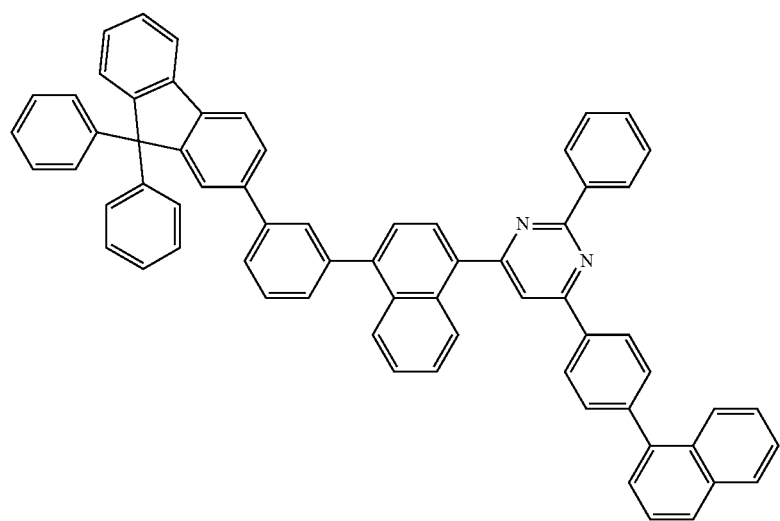

-continued
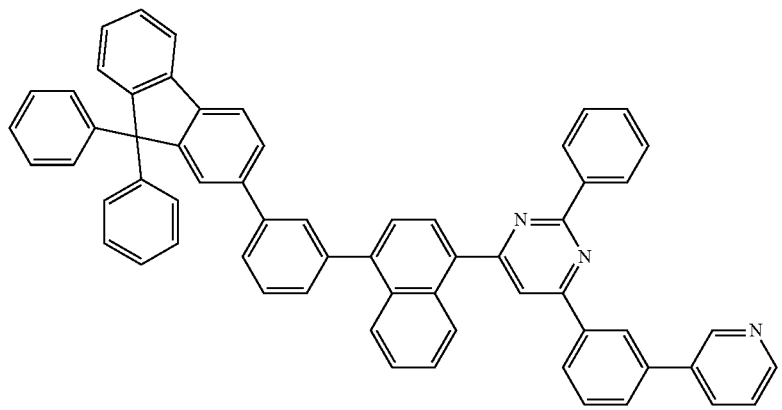
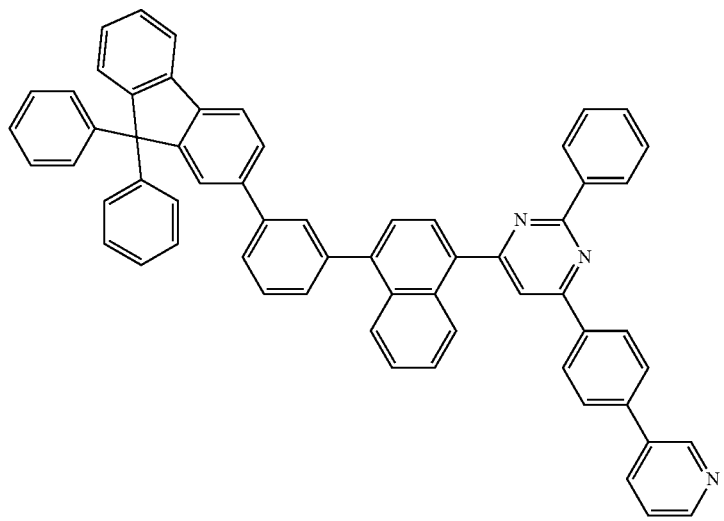
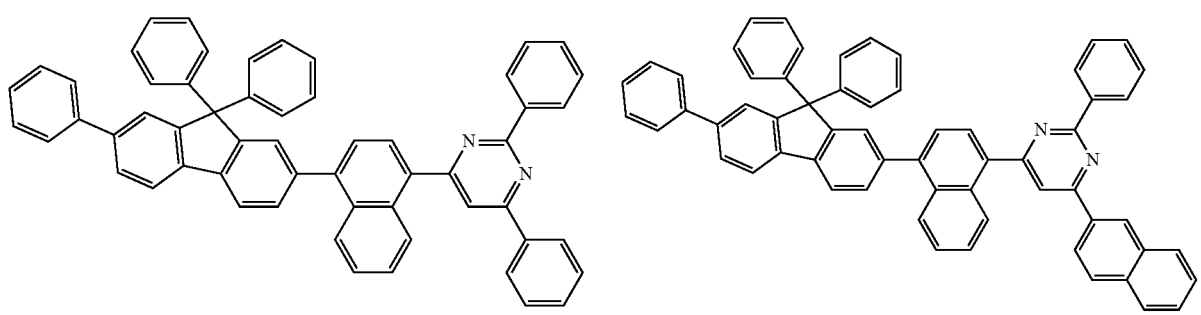
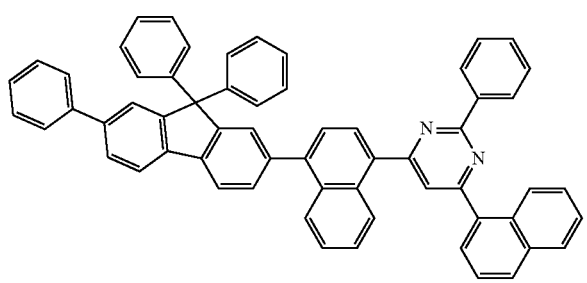
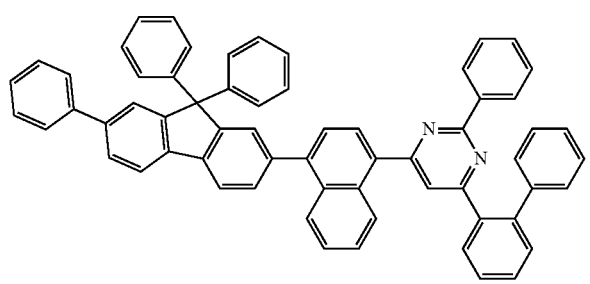

-continued
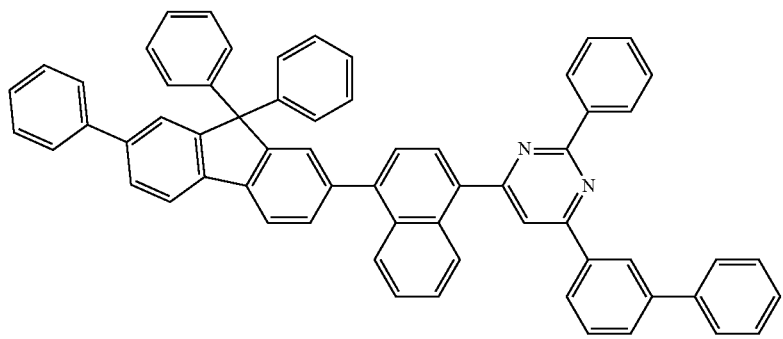
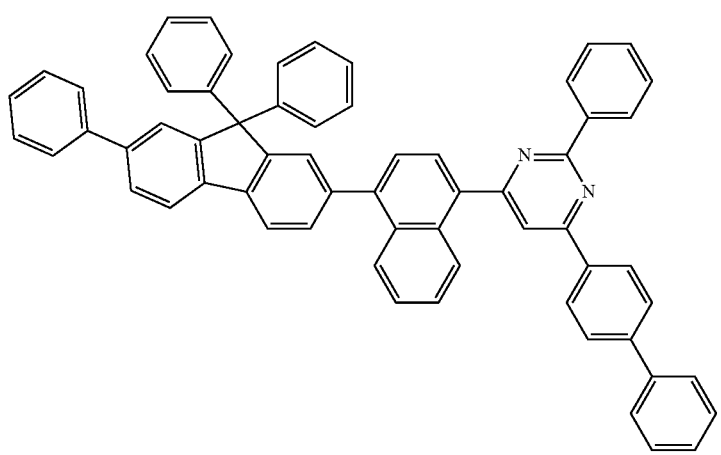
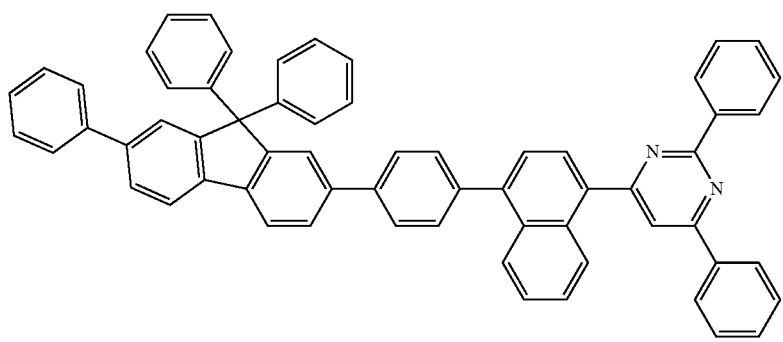
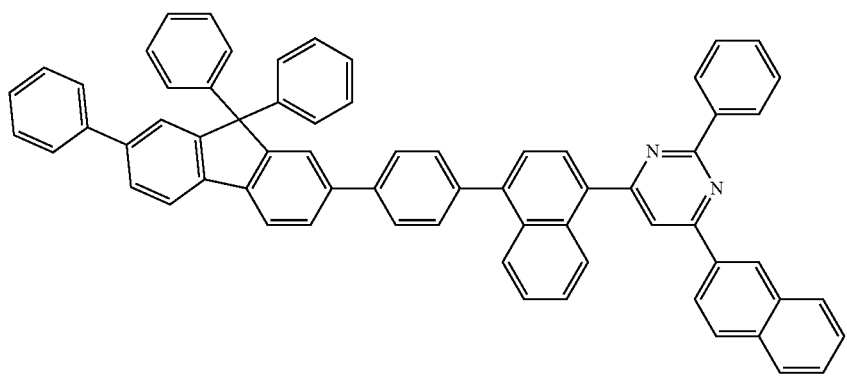

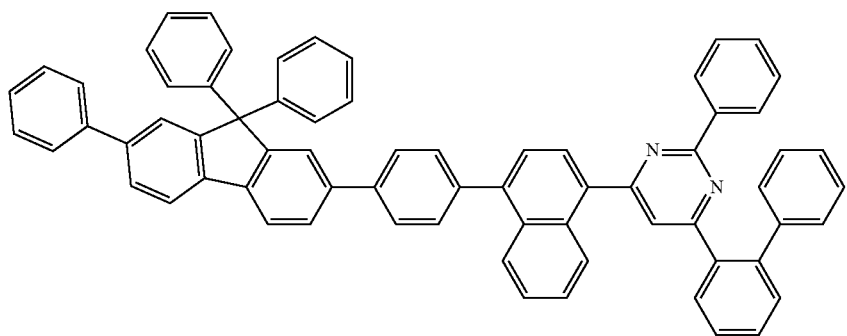
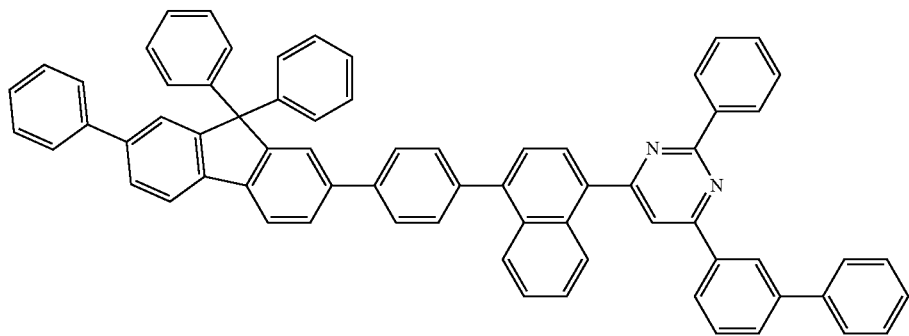
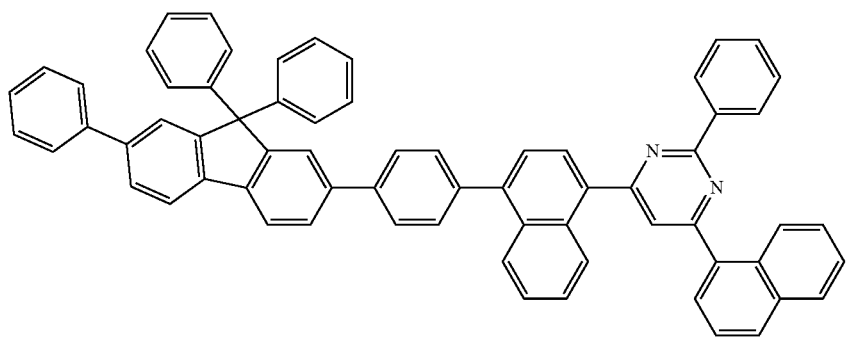
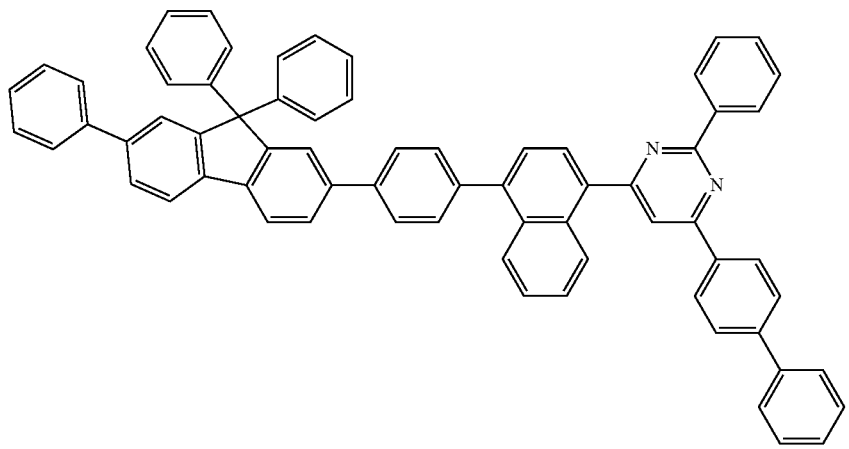

231
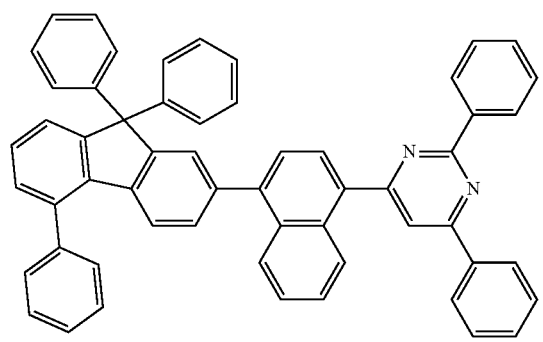
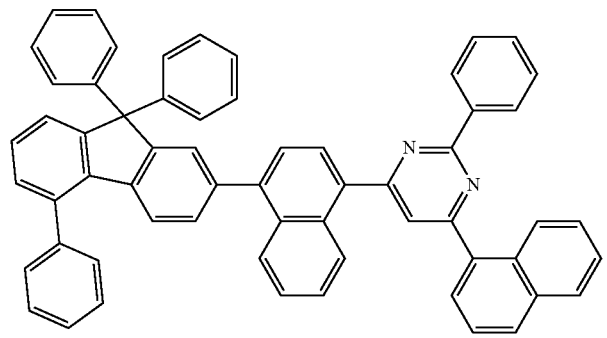
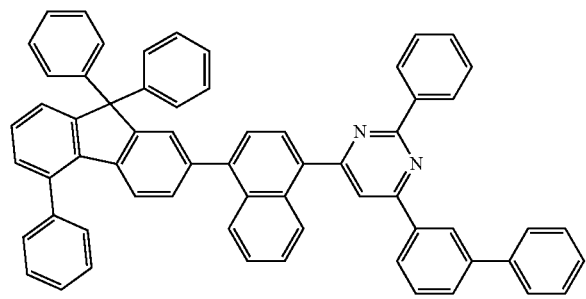
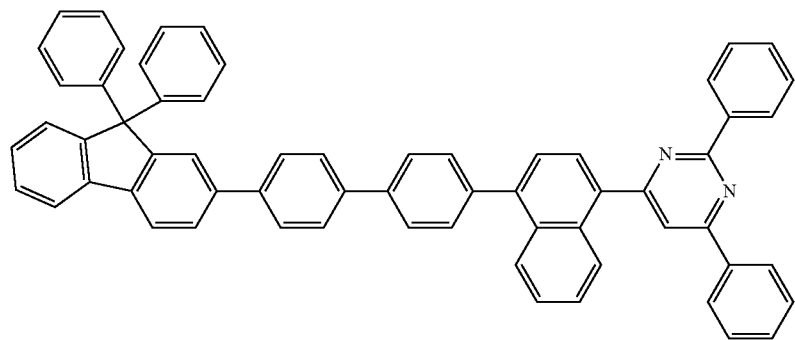
-continued
232
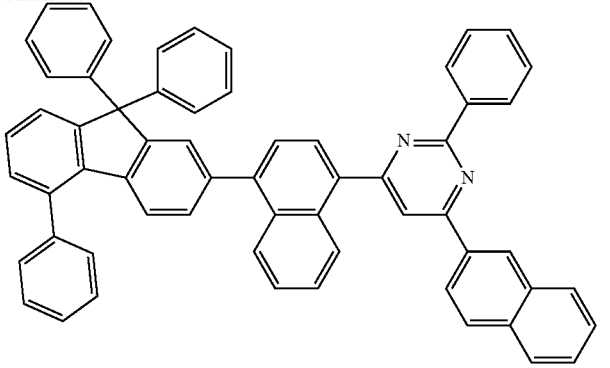
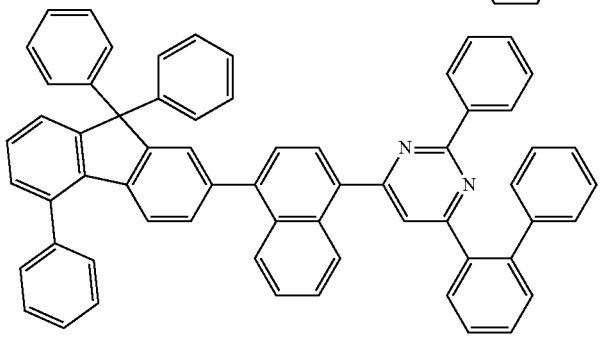
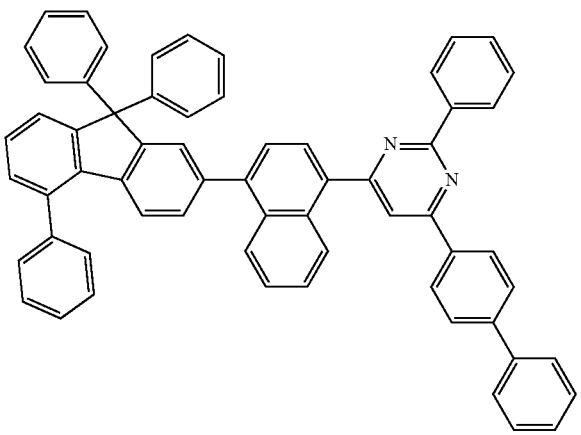

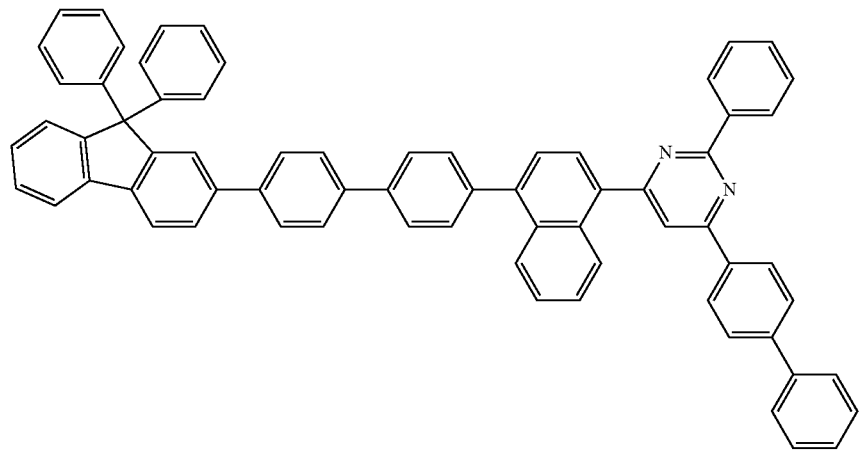
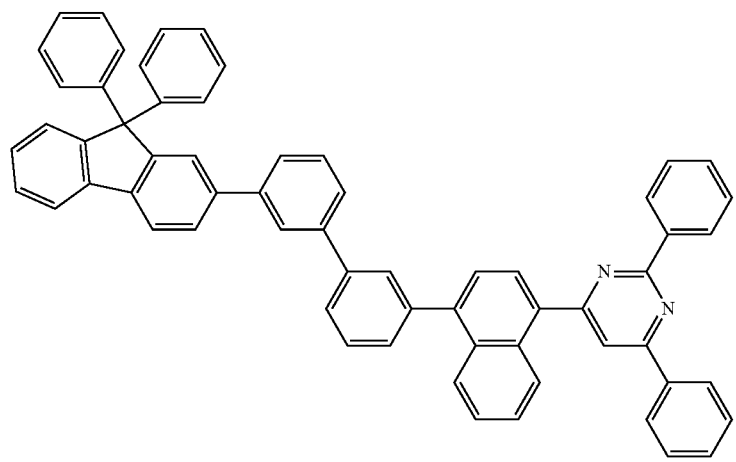
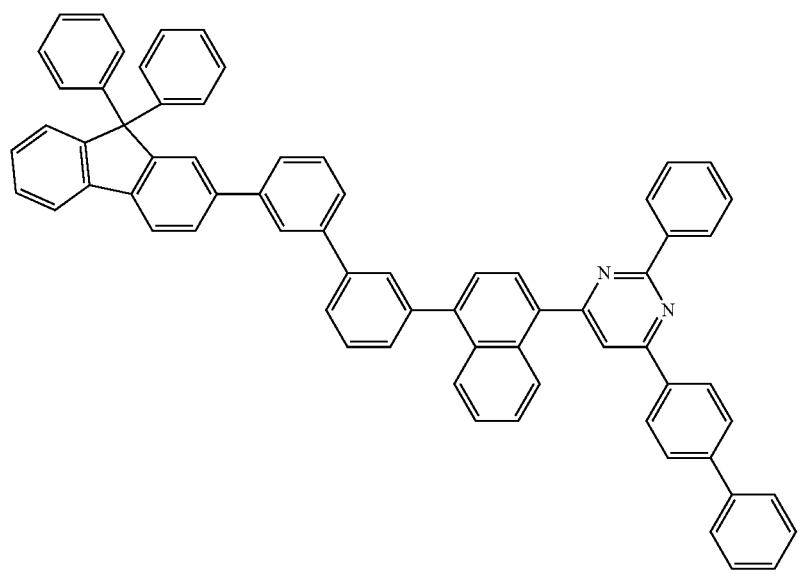

-continued
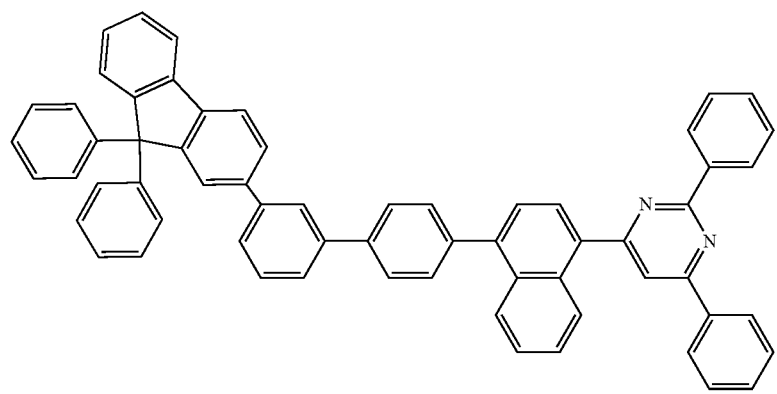
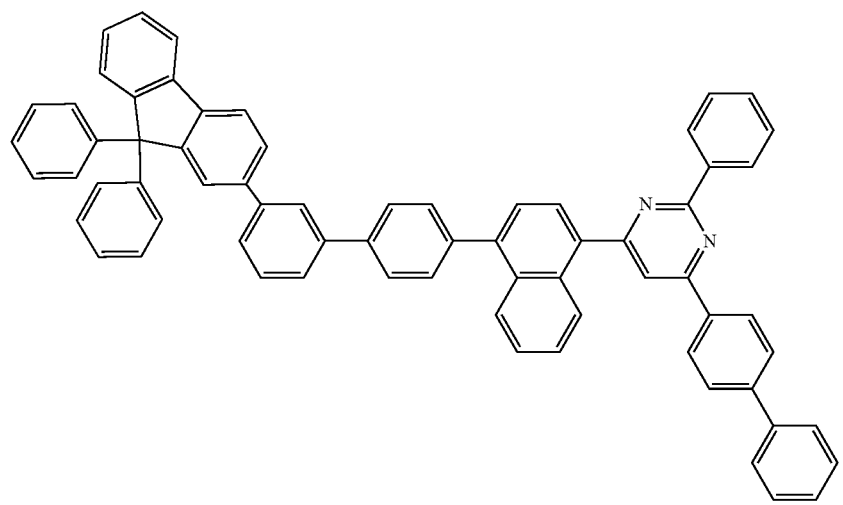
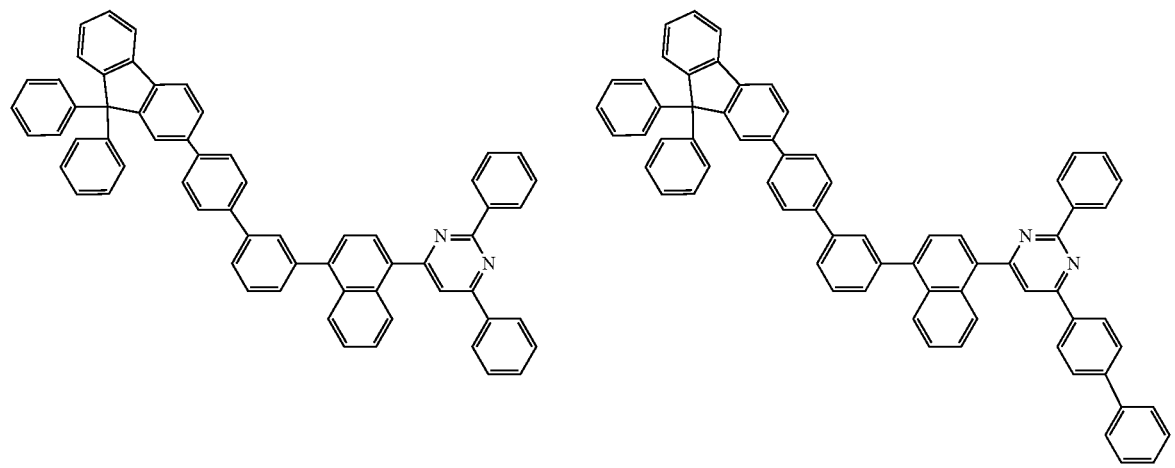

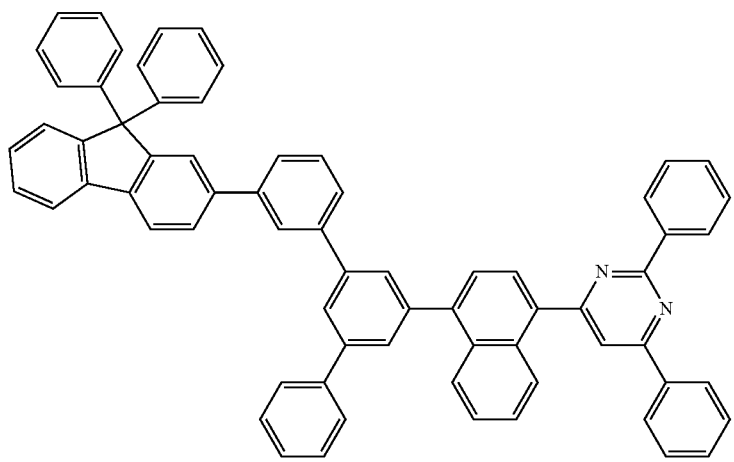
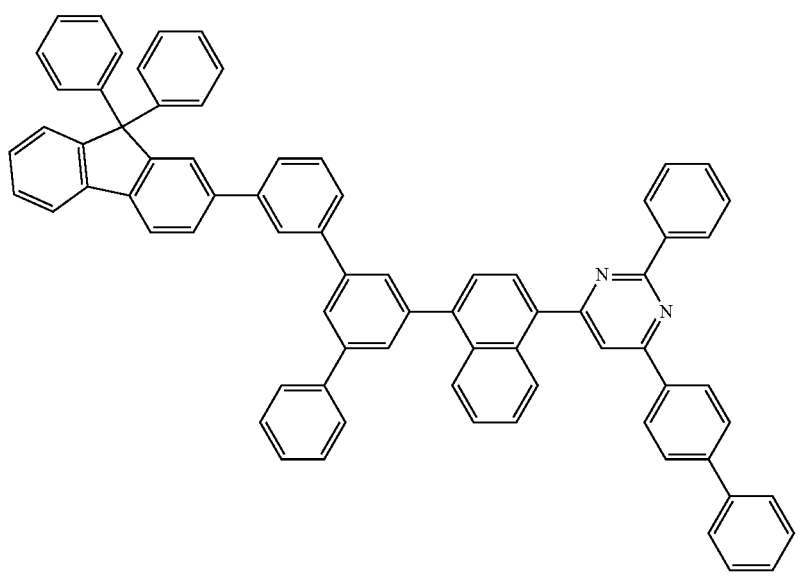
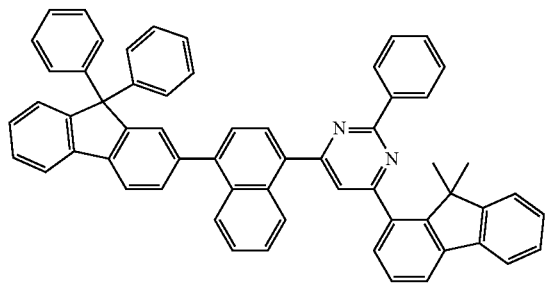
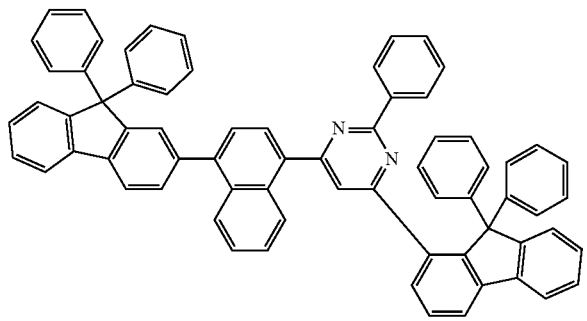

-continued
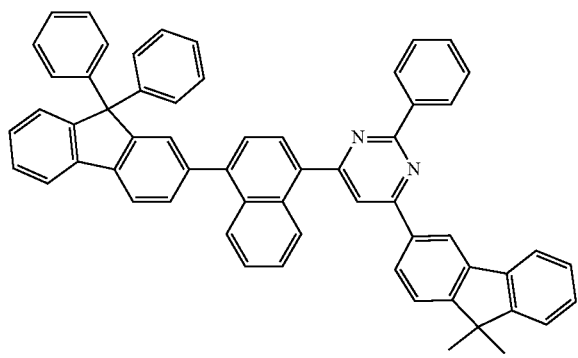
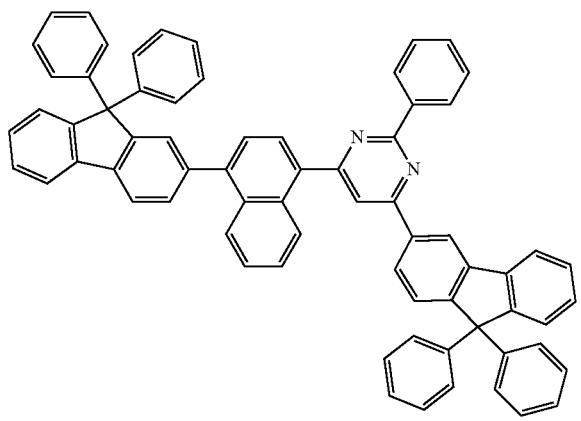
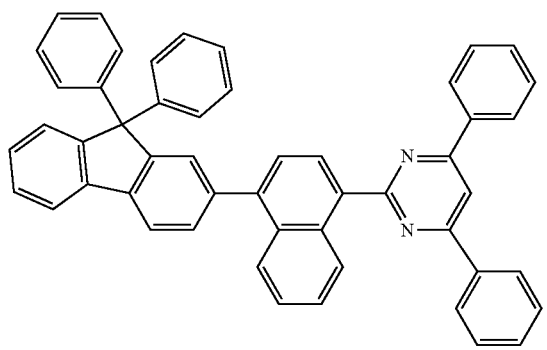
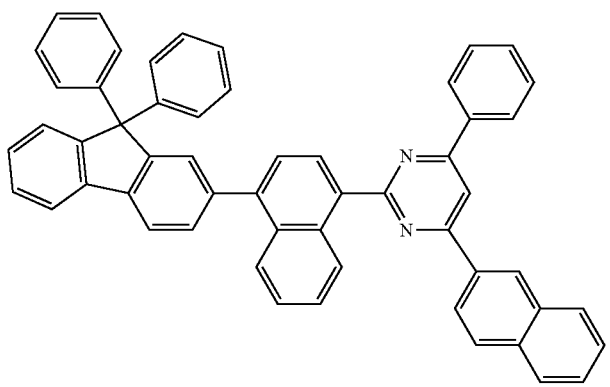
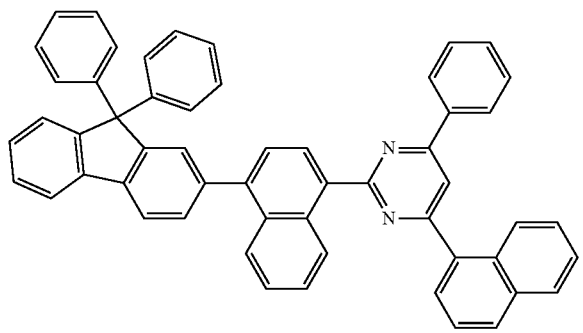
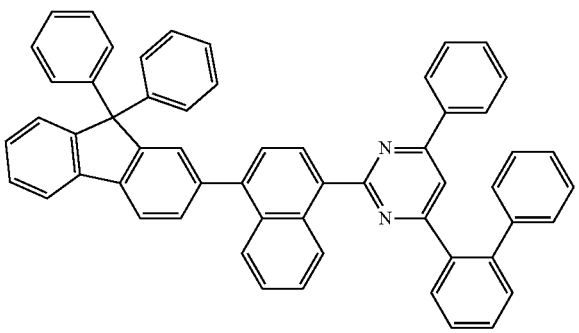
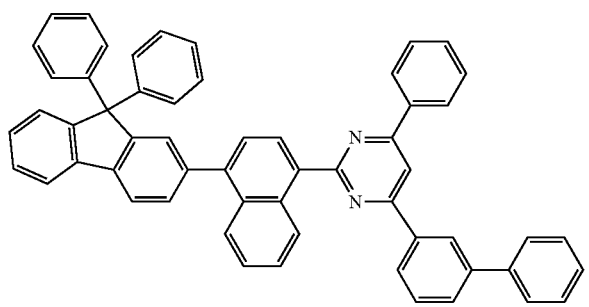
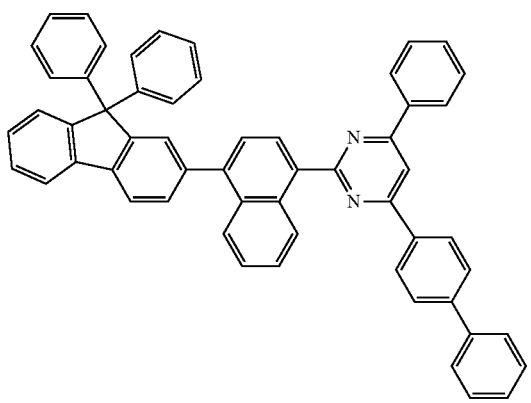

241
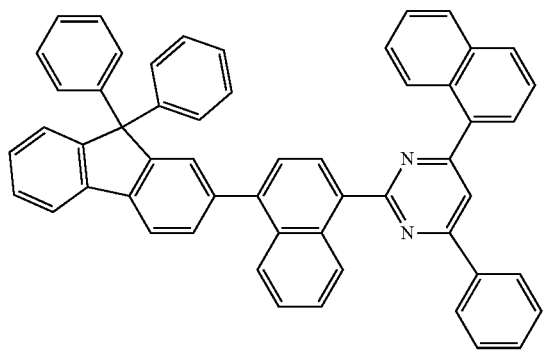
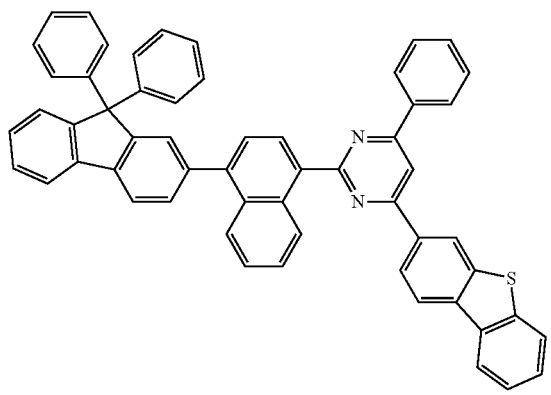
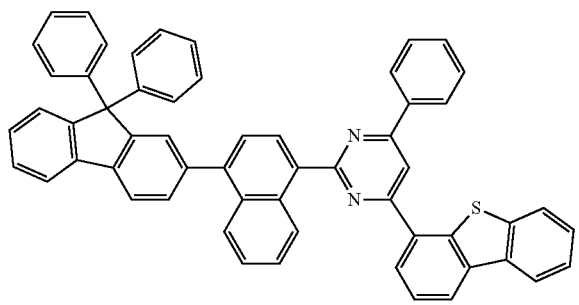
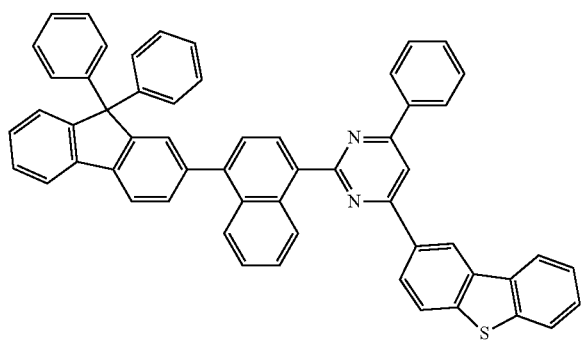
242
-continued
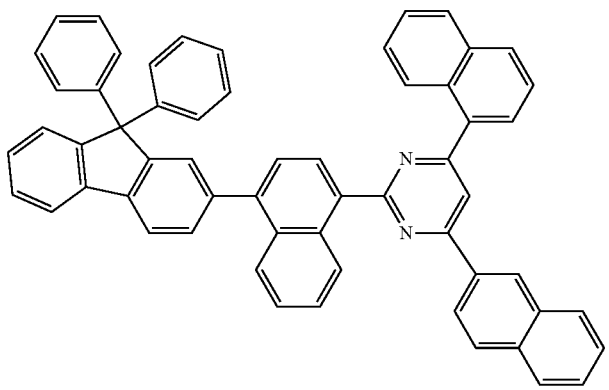
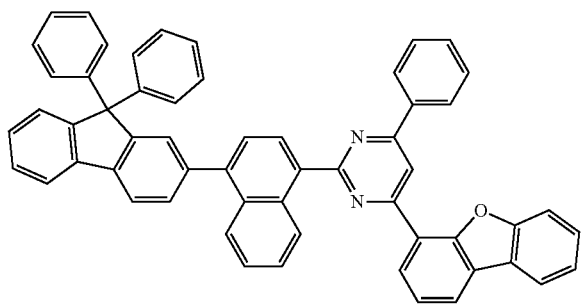
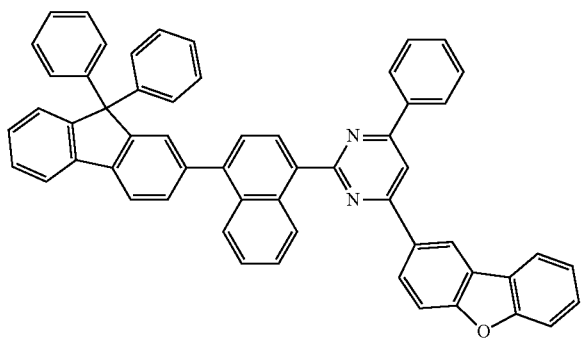
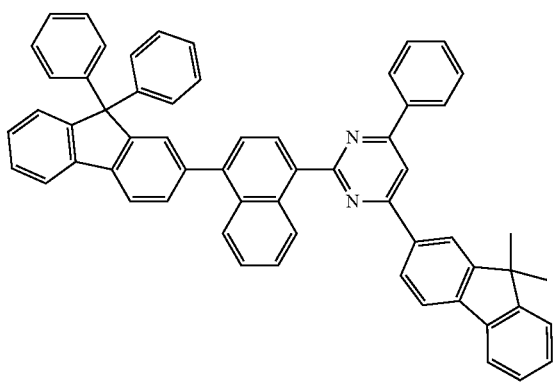

-continued
| 243 | 244 |
|---|---|
| 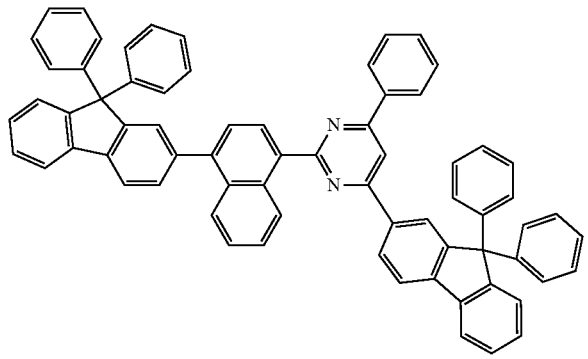 | 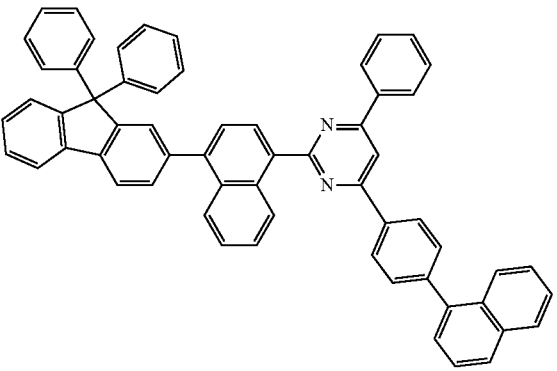 |
| 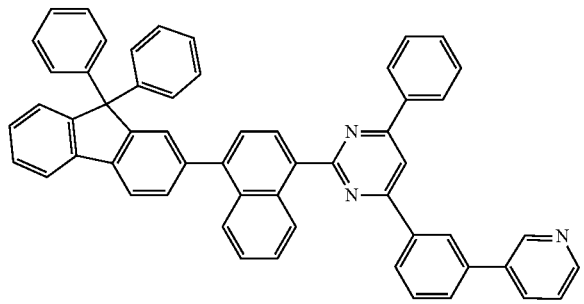 | 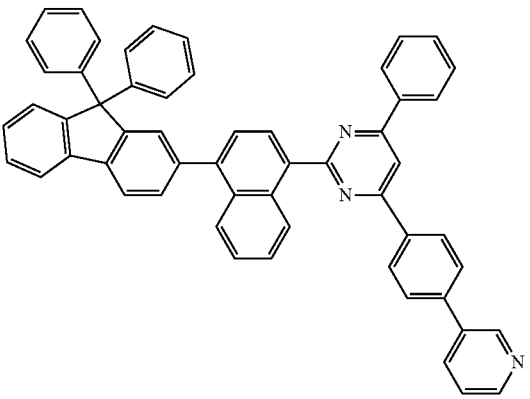 |
| 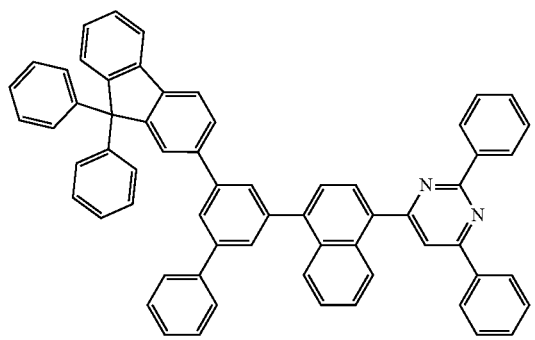 | 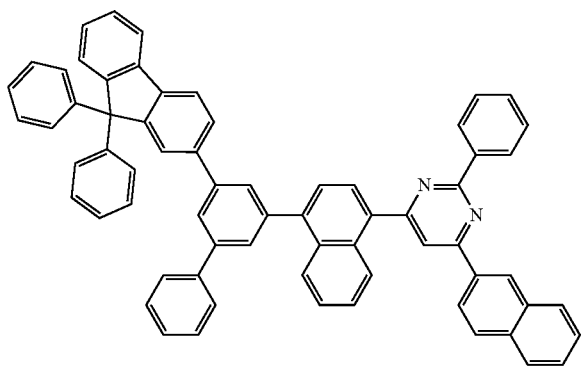 |
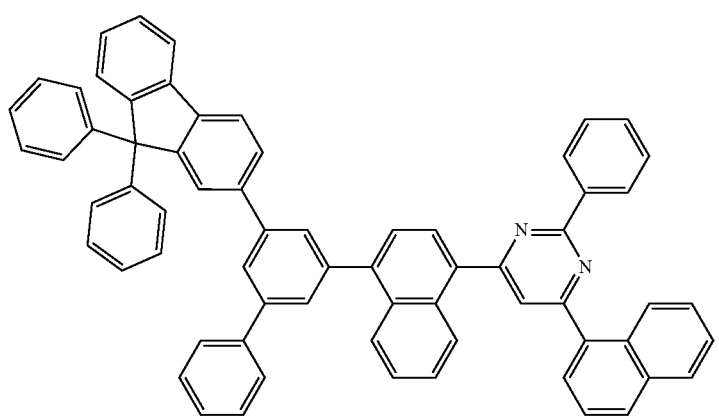

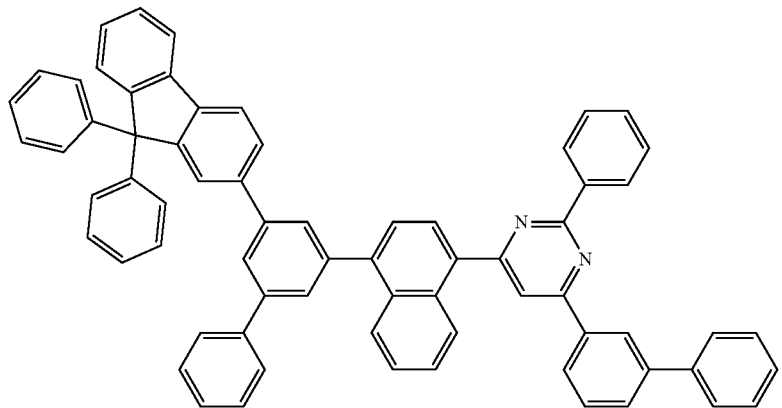
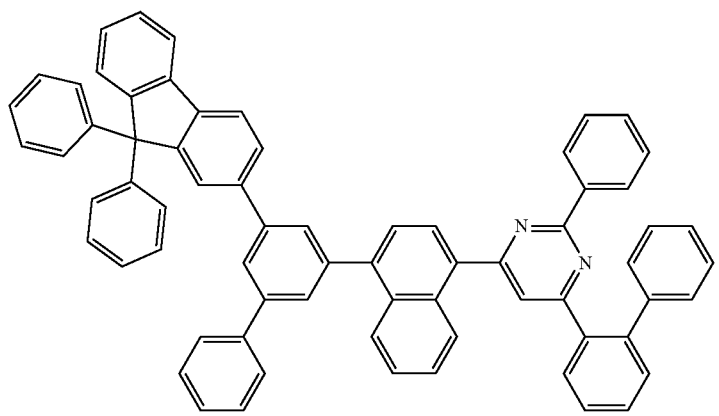
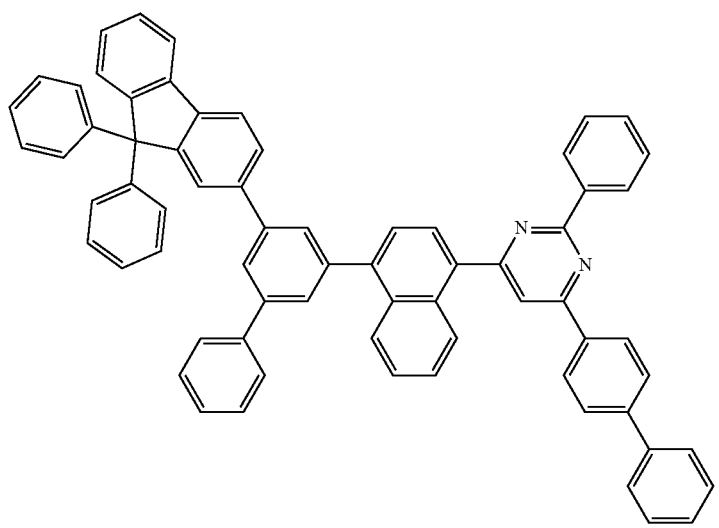

-continued
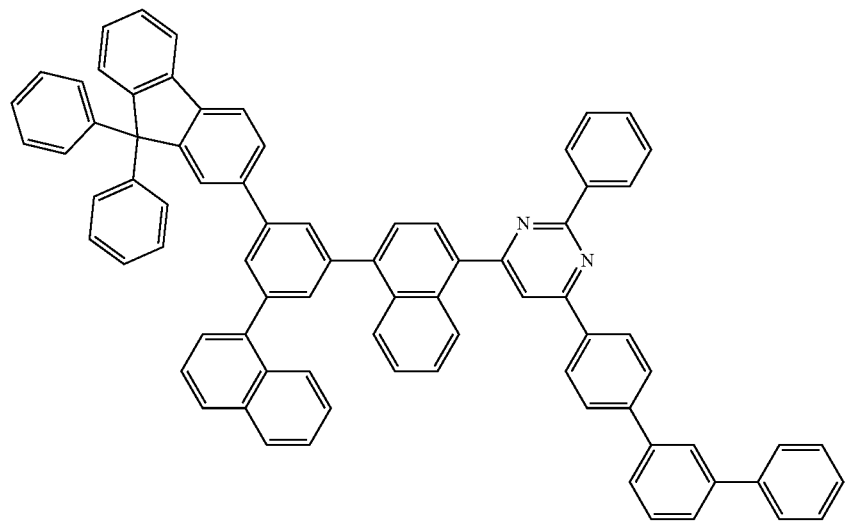
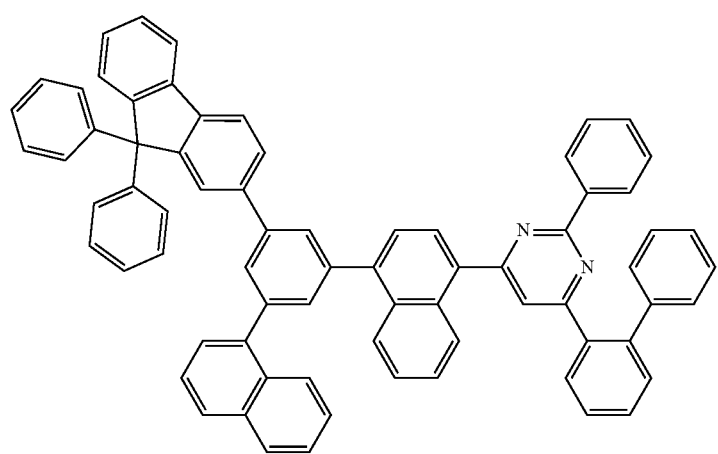
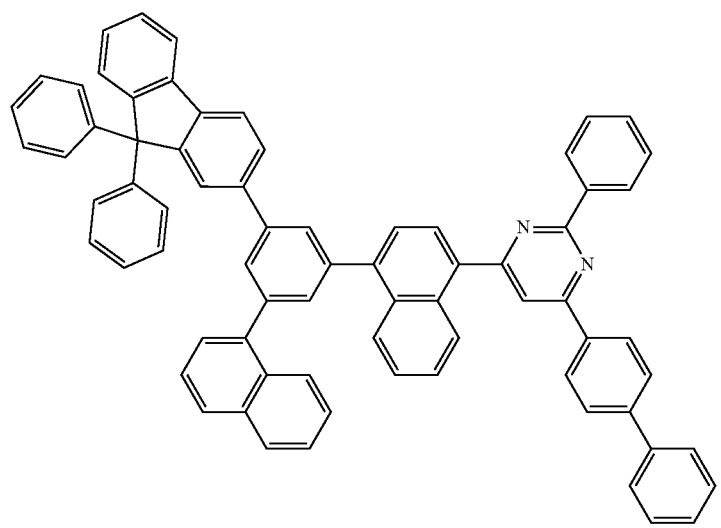

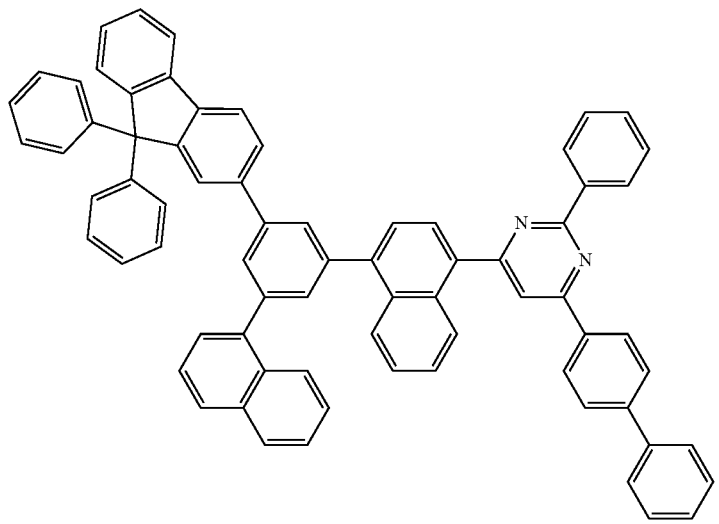
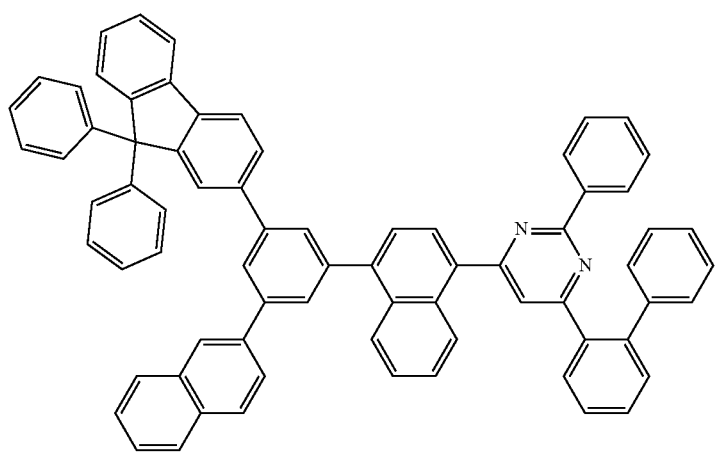
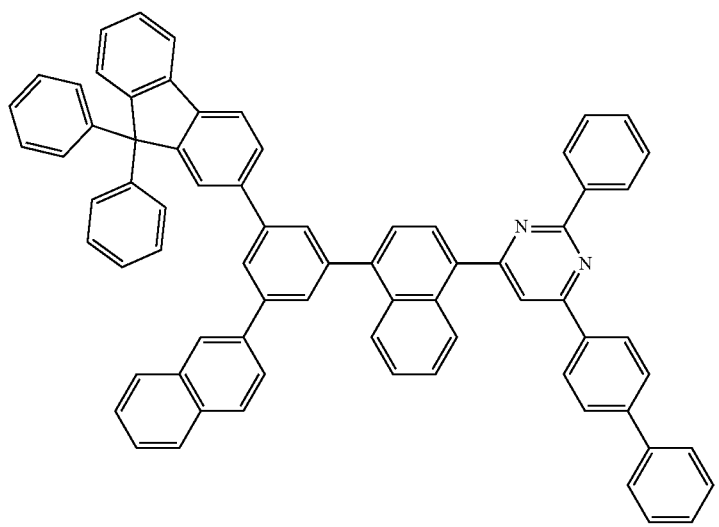

-continued
251
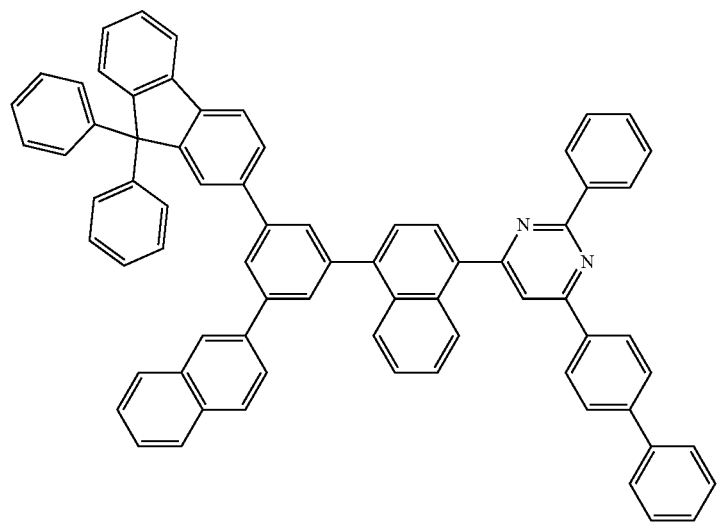
252
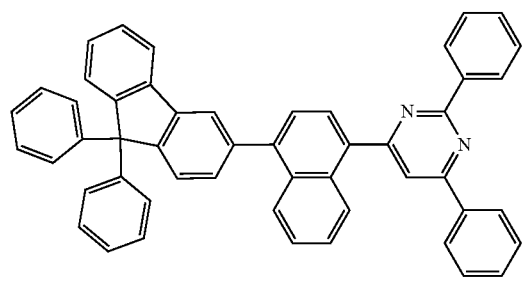
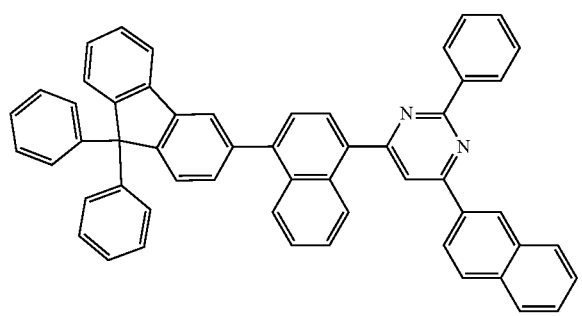
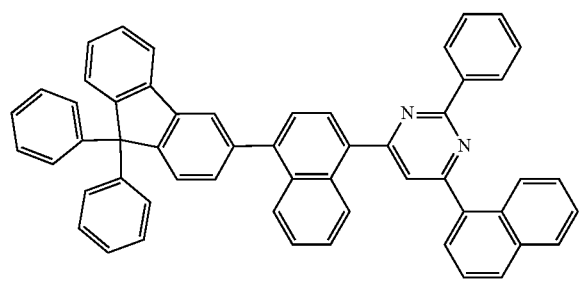
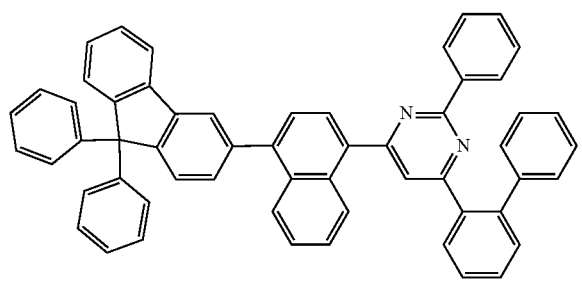
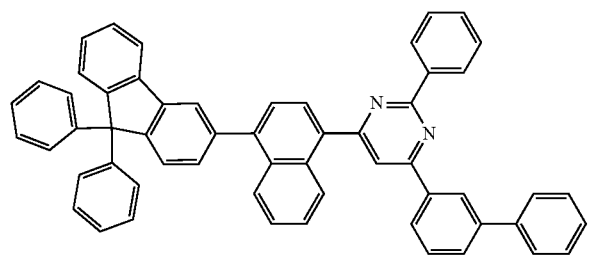
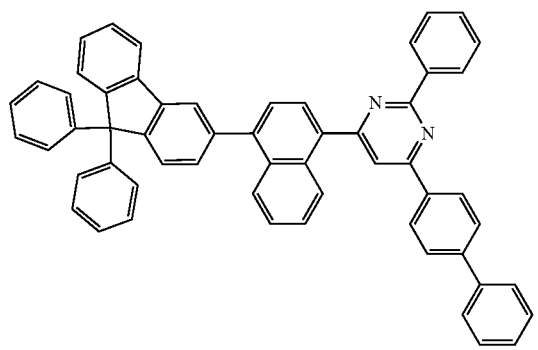

-continued
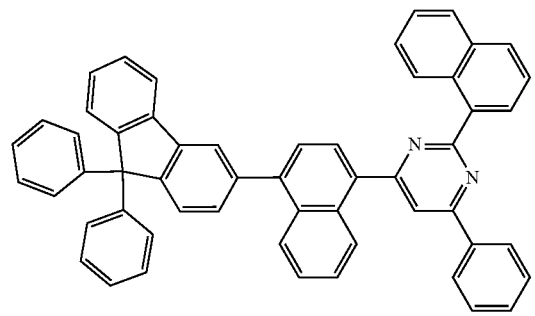
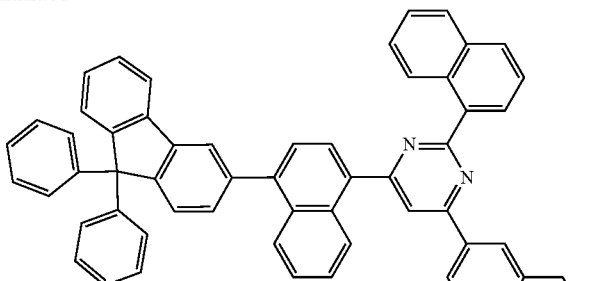
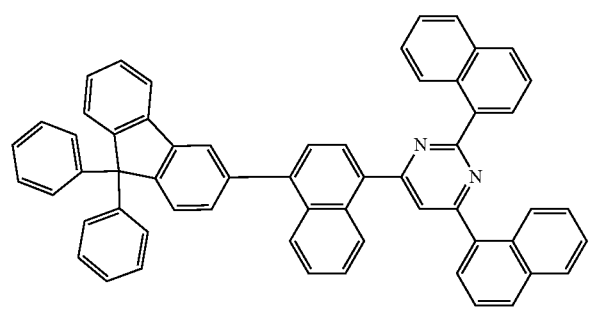
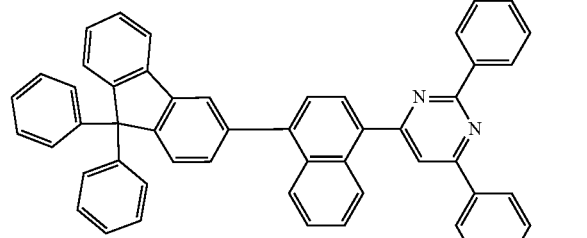
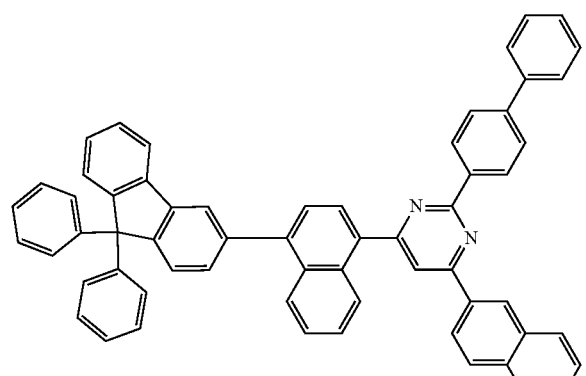
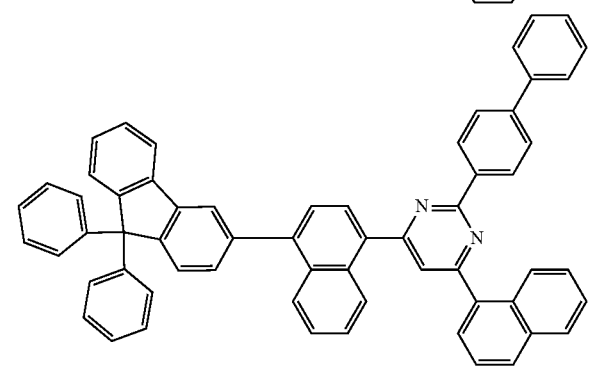
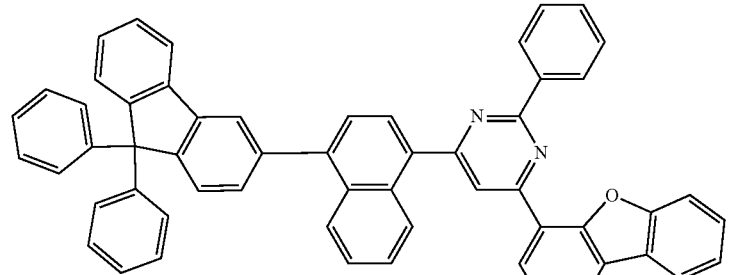
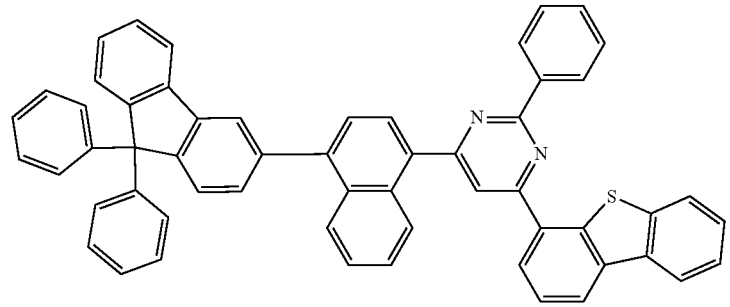

-continued
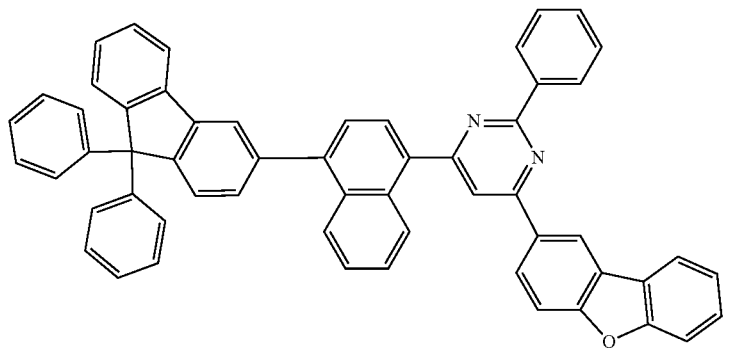
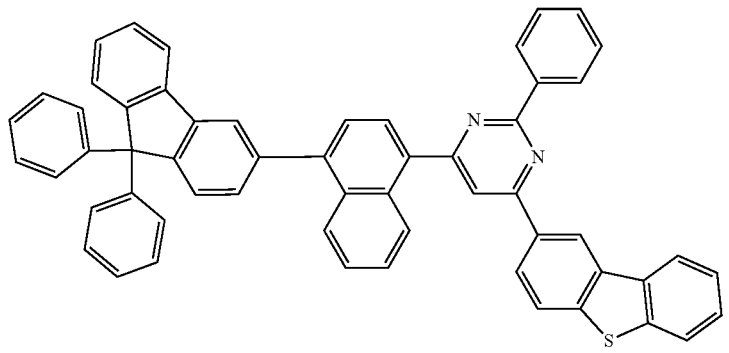
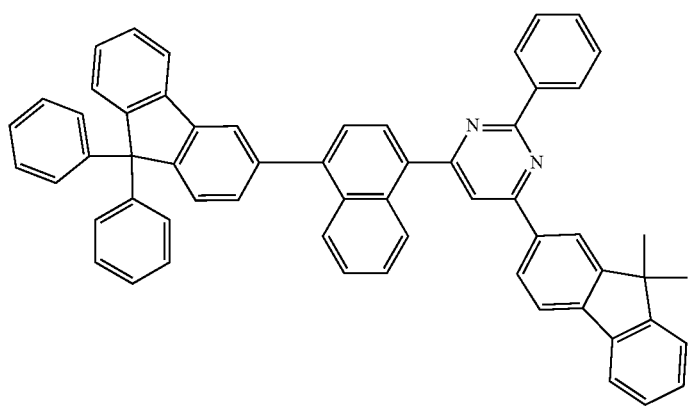
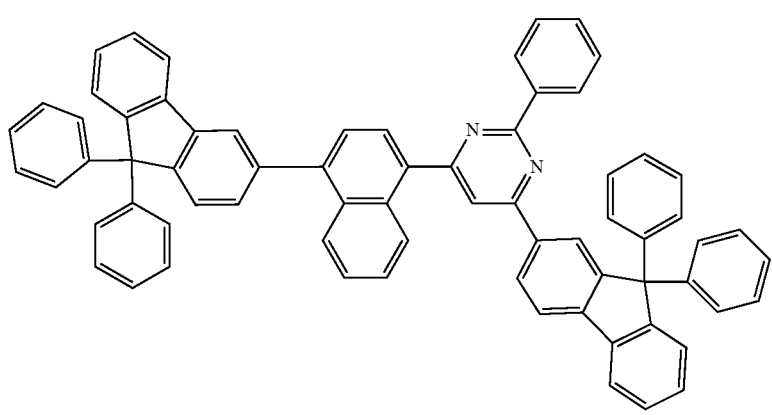

-continued
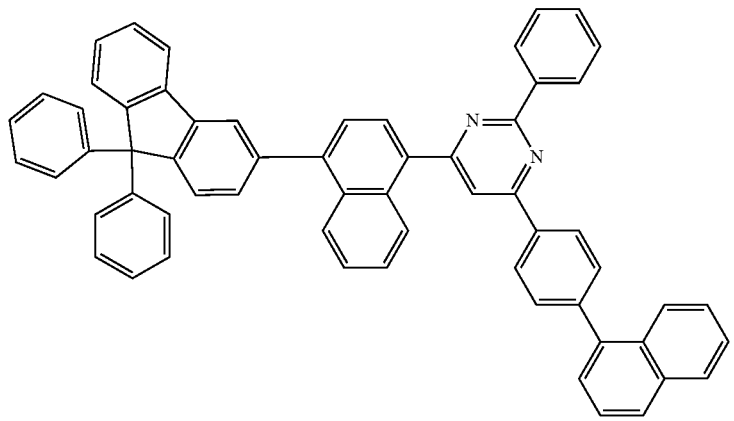
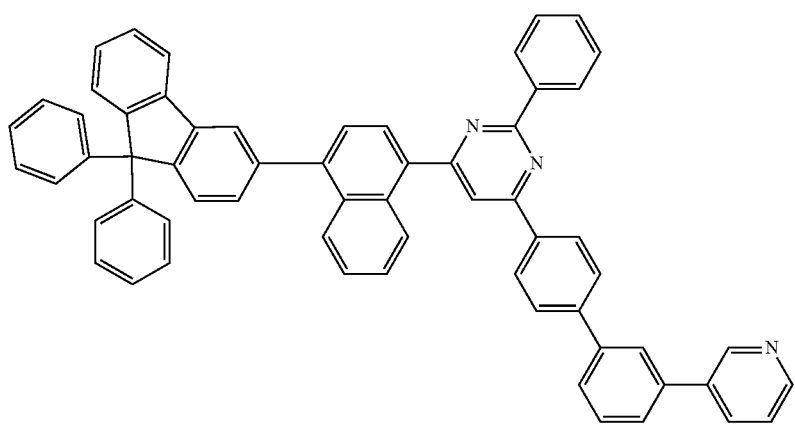
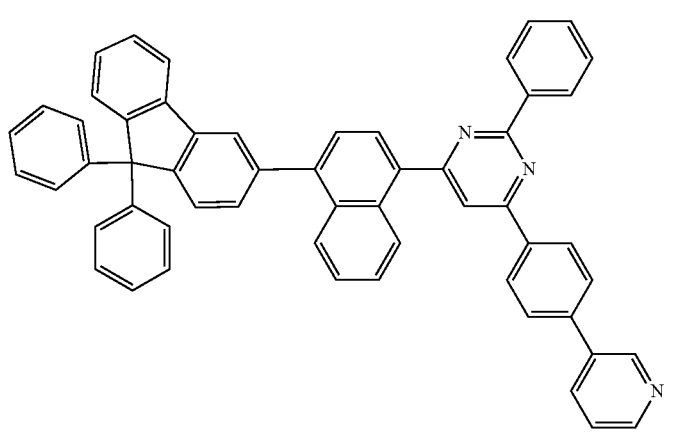
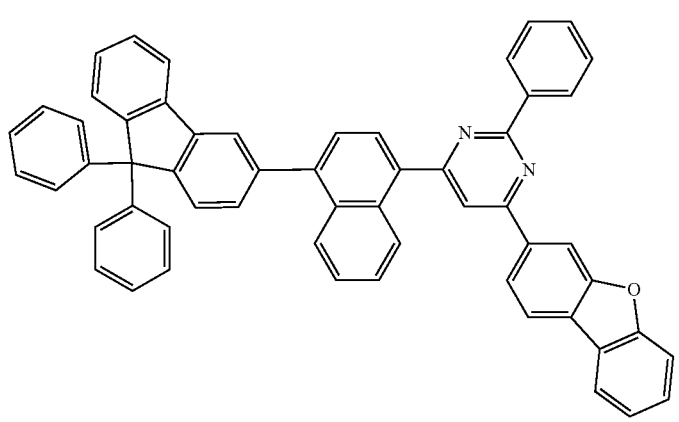

-continued
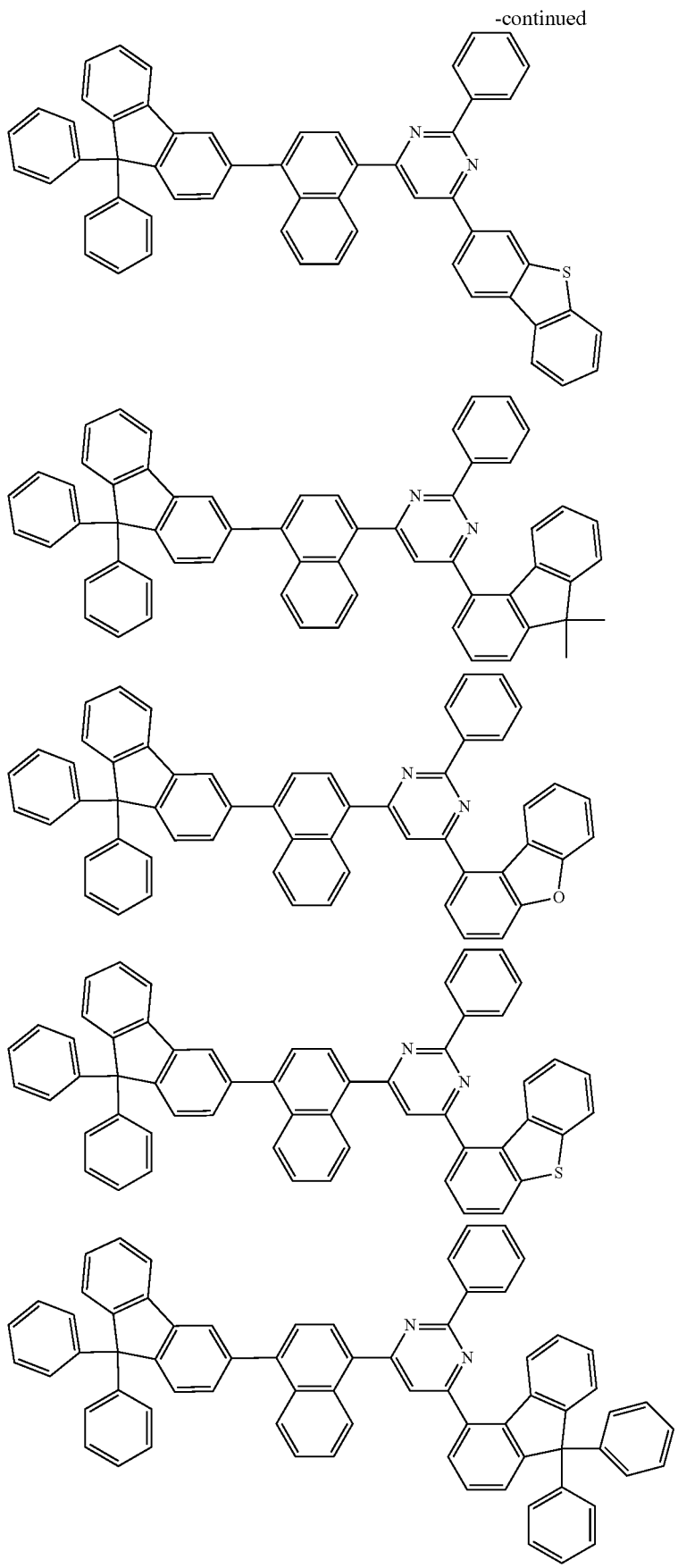

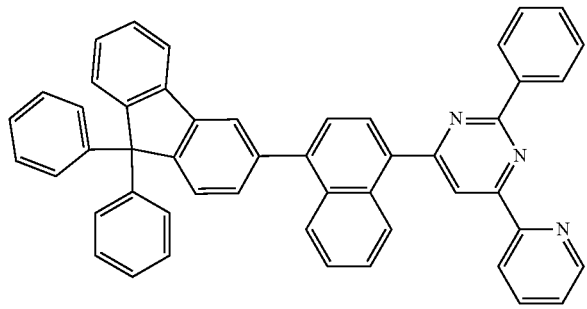
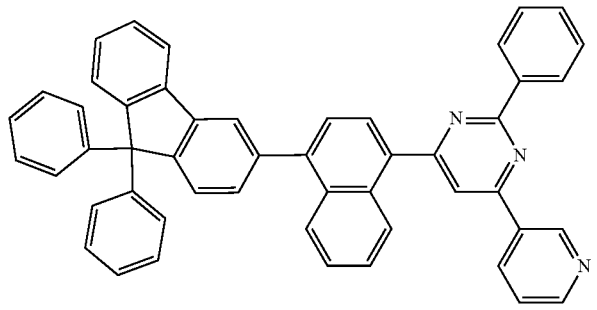
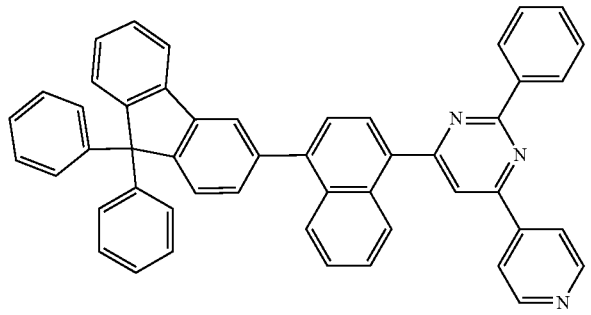
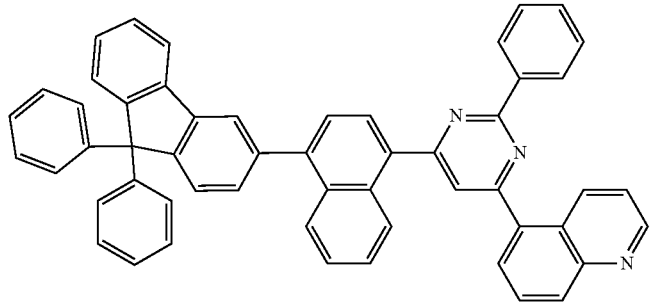
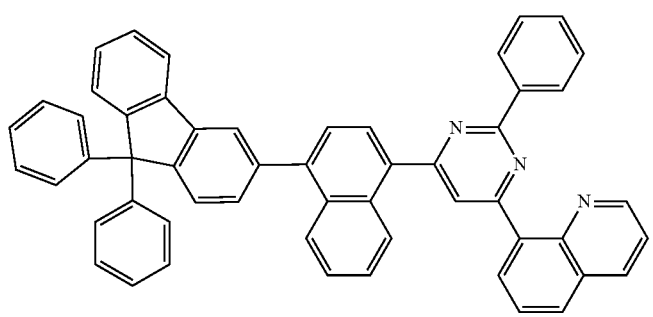

-continued
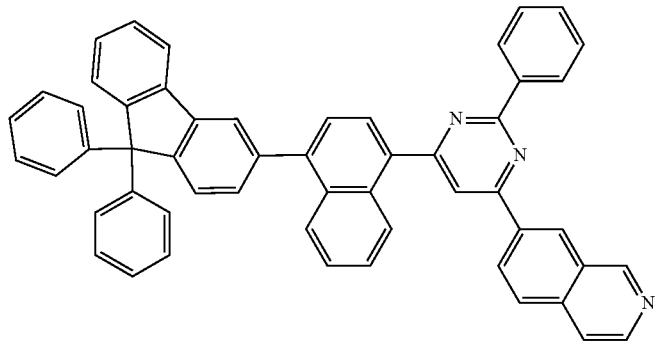
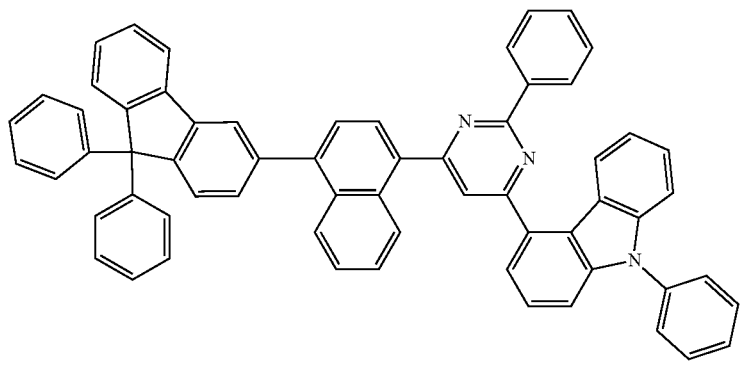
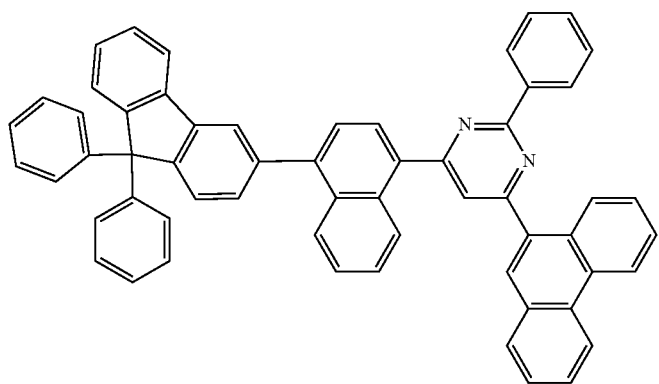
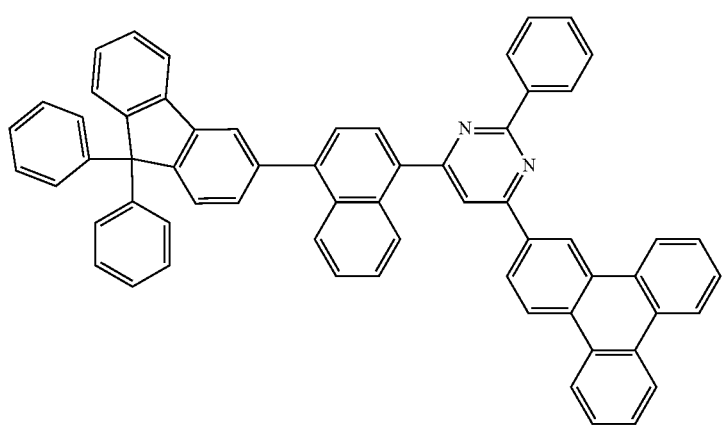

-continued
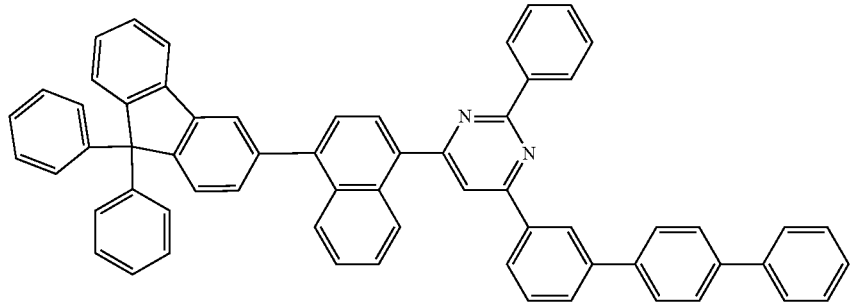
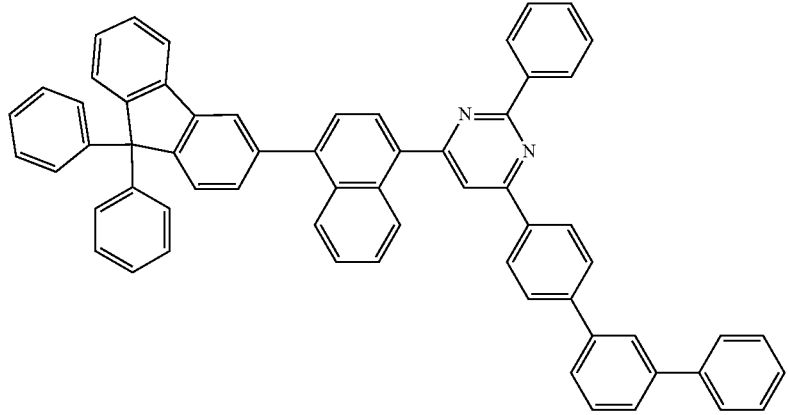
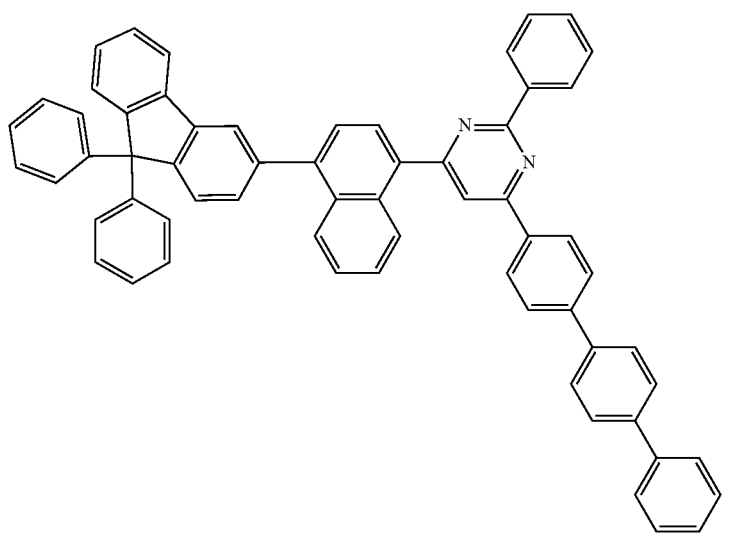
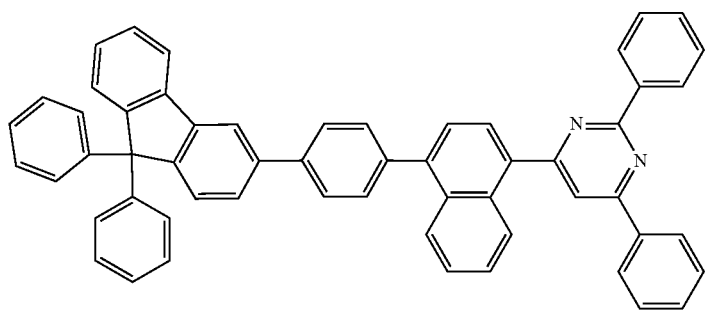

-continued
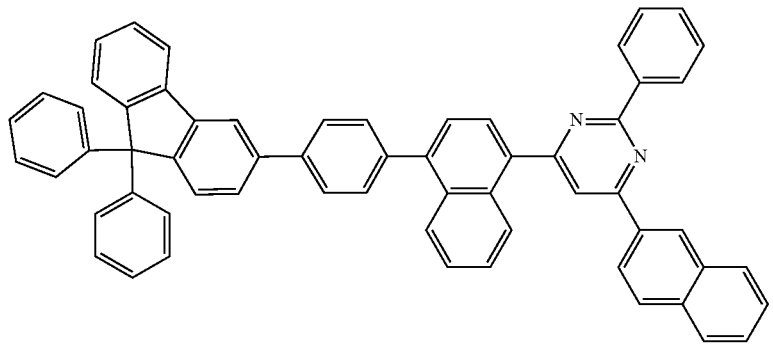
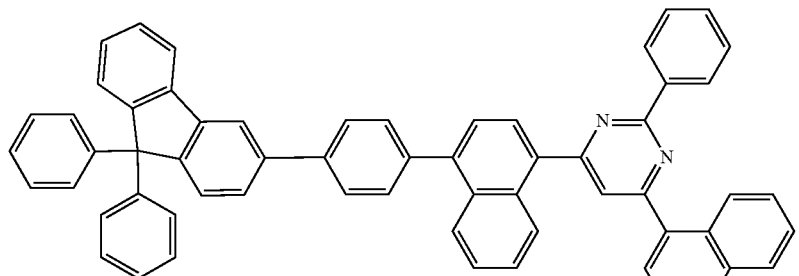
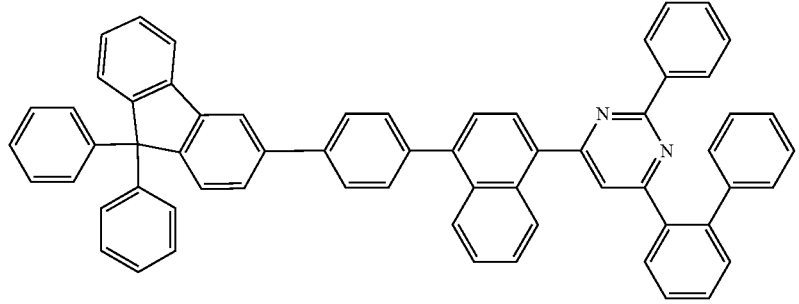
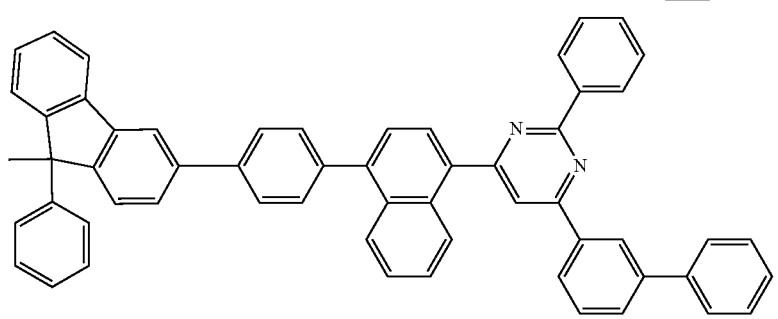
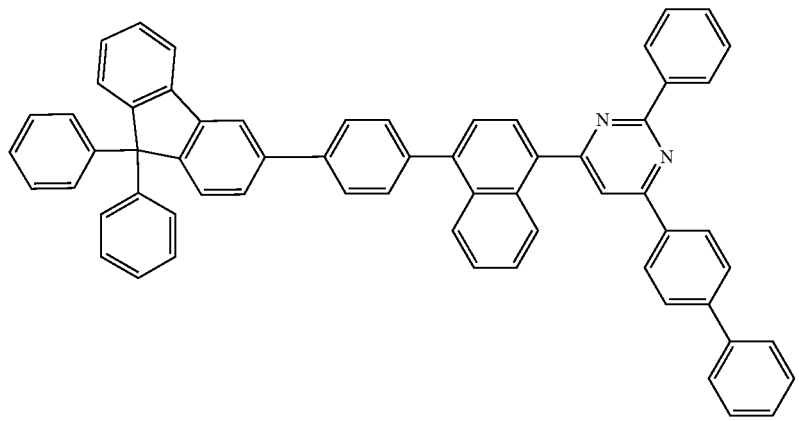

-continued
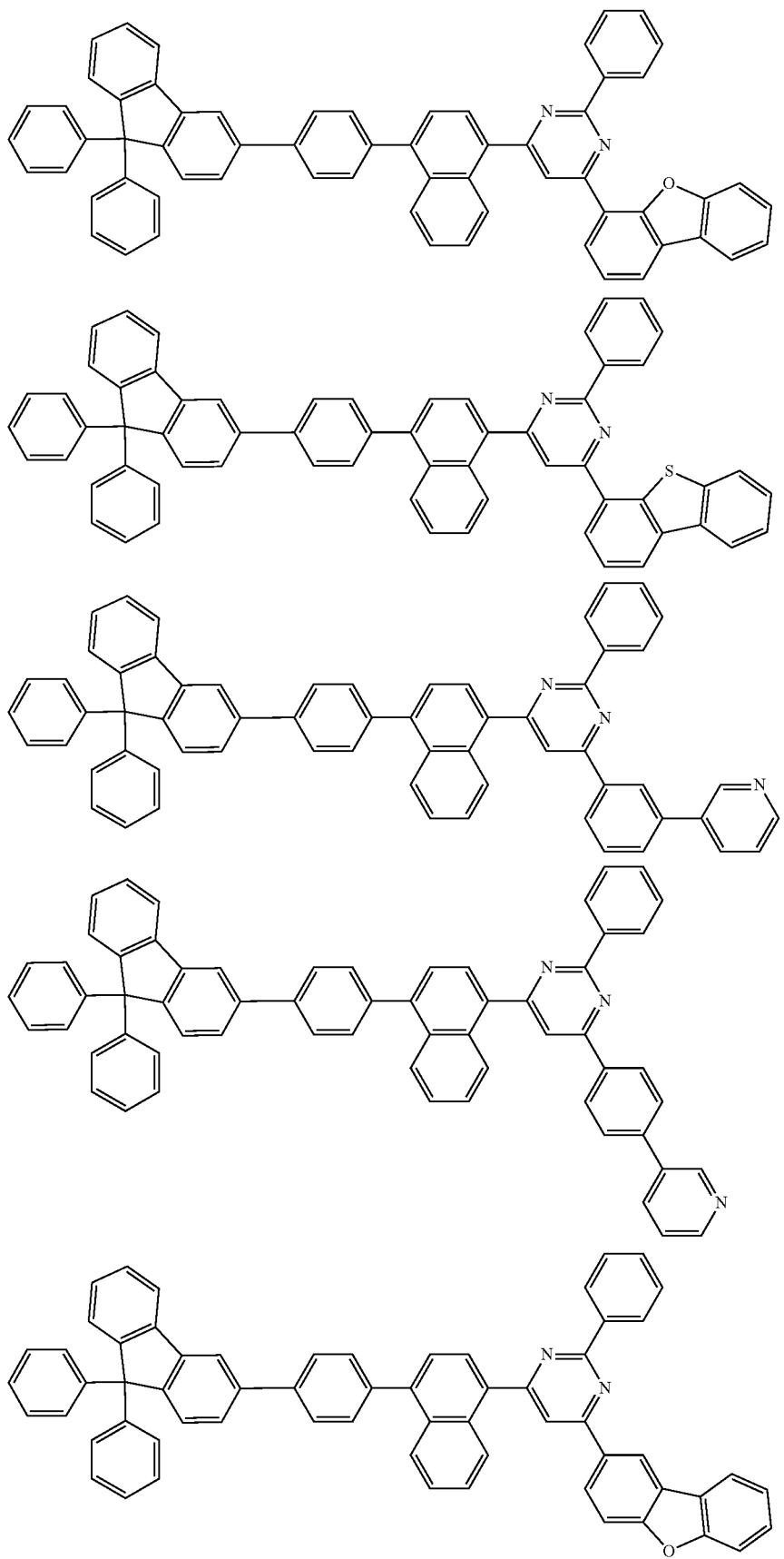

-continued
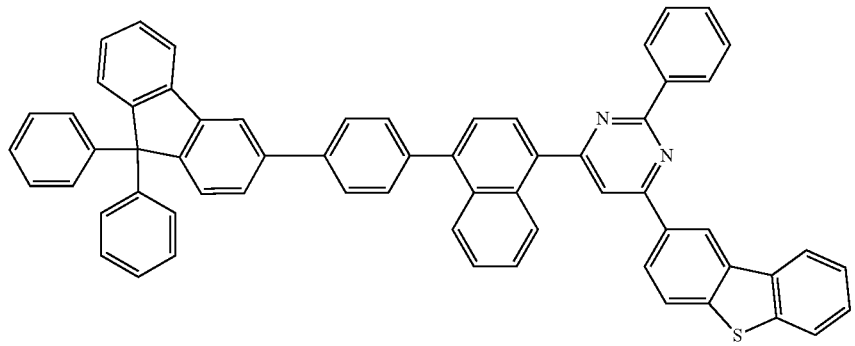
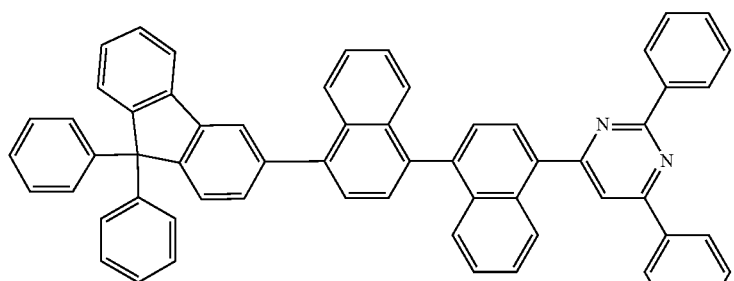
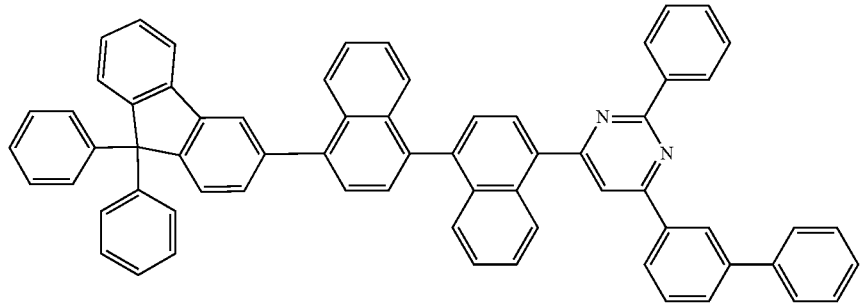
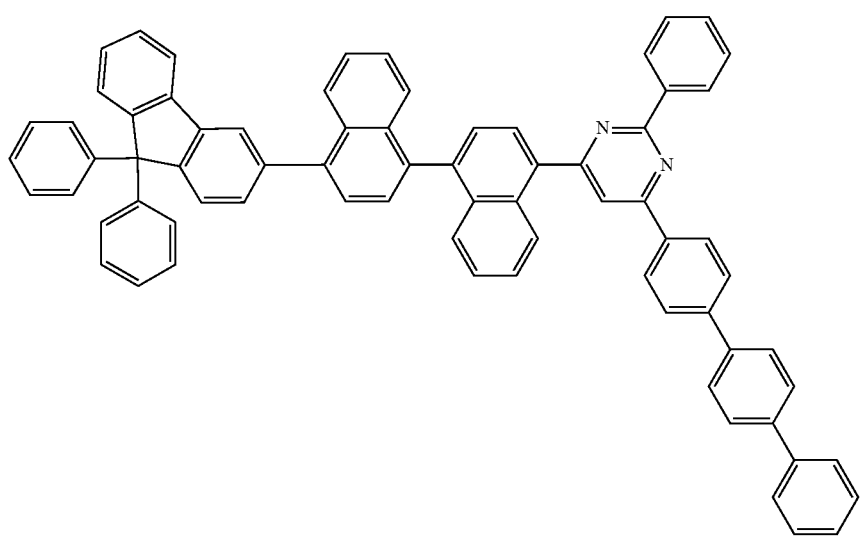

273
274
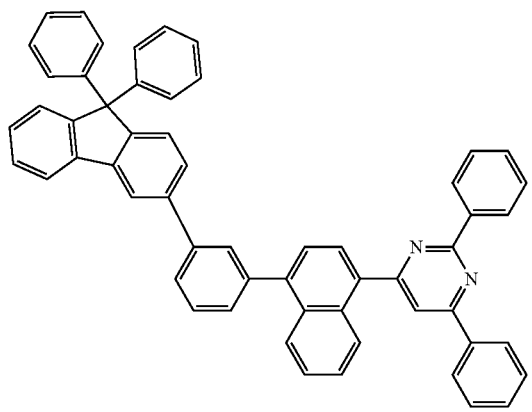
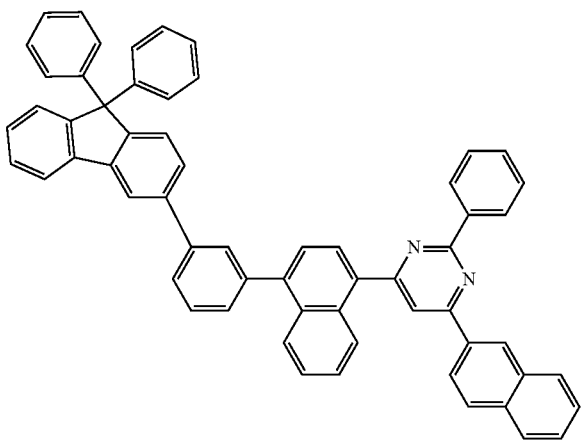
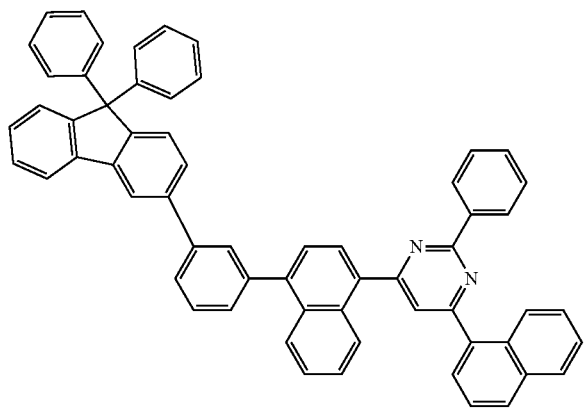
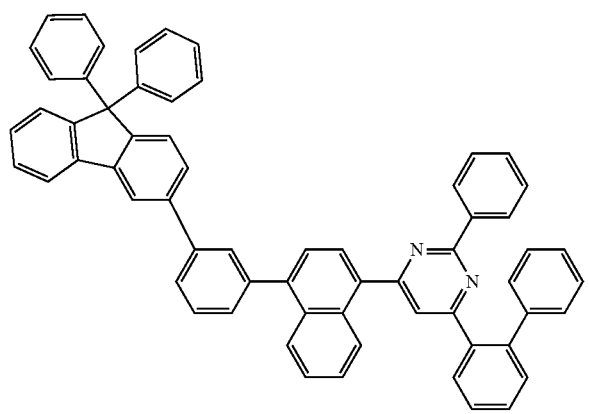
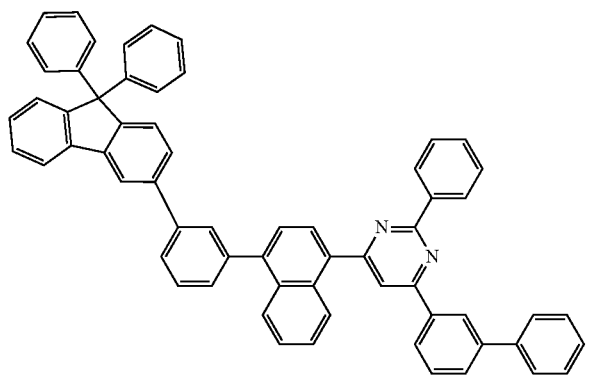
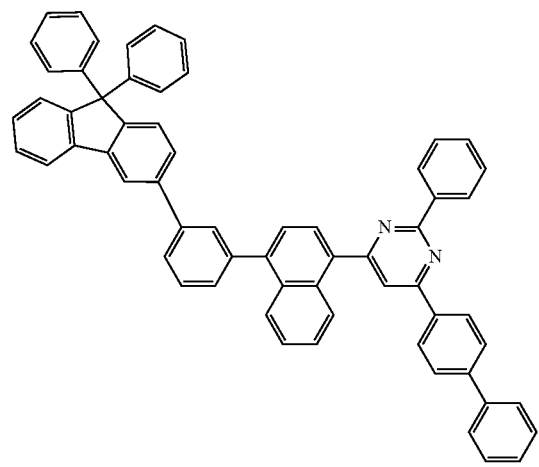

275
276
-continued
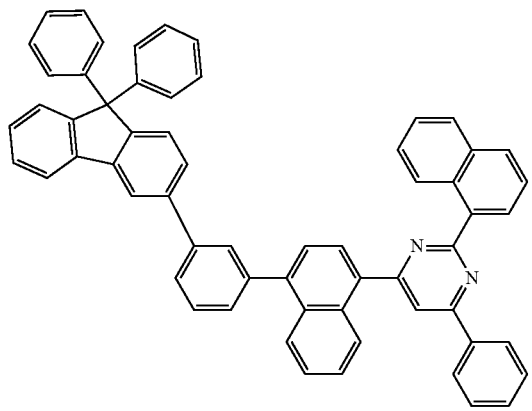
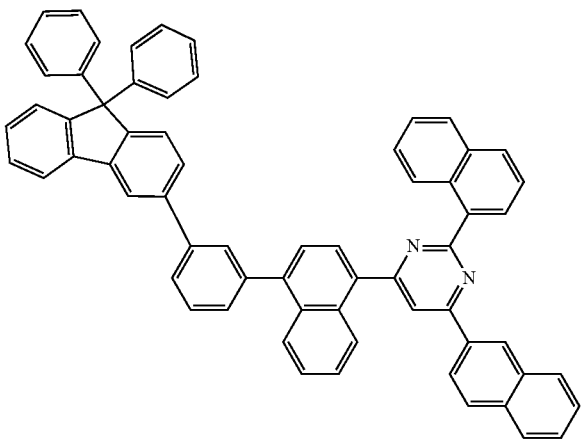
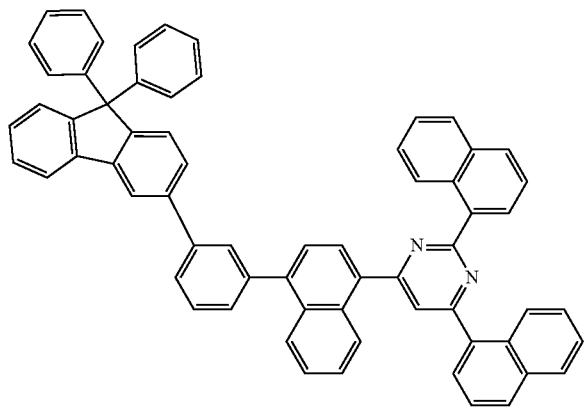
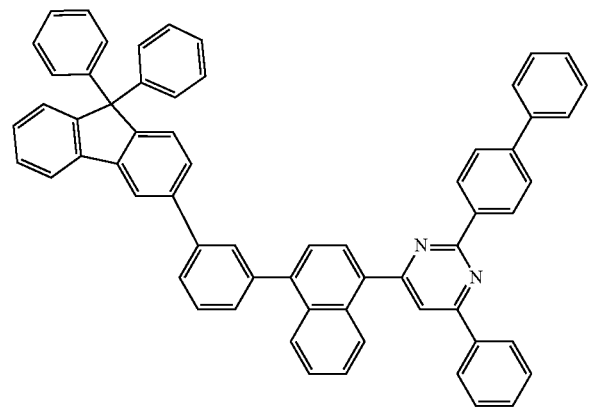
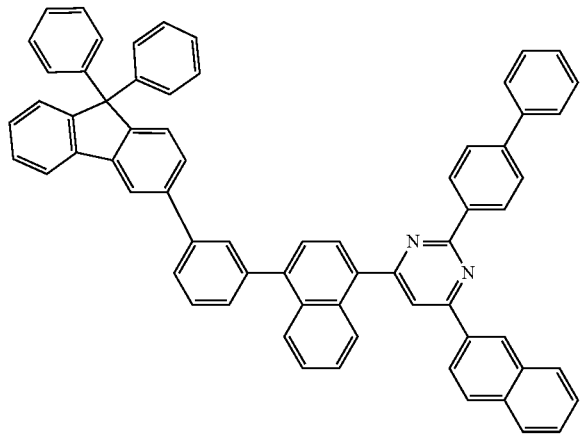
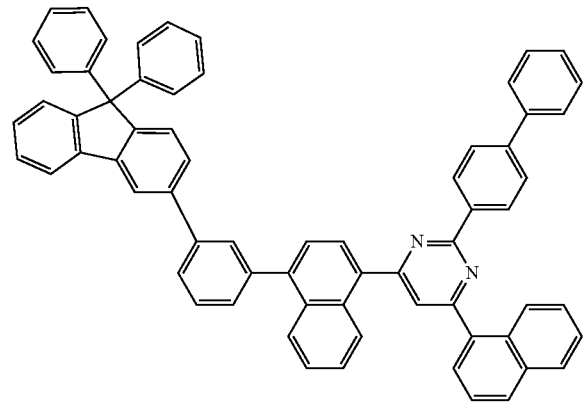
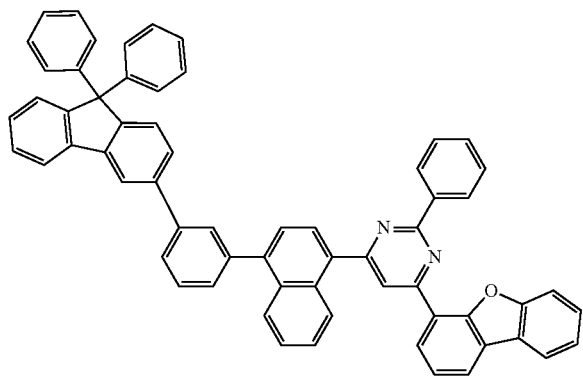
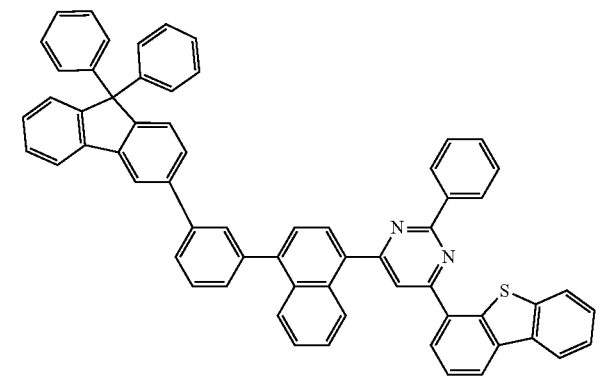

-continued
277
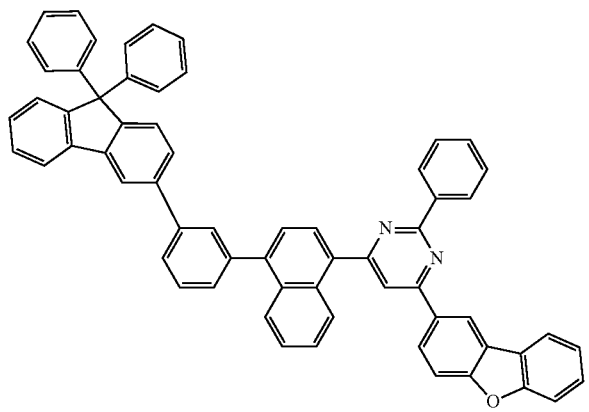
278
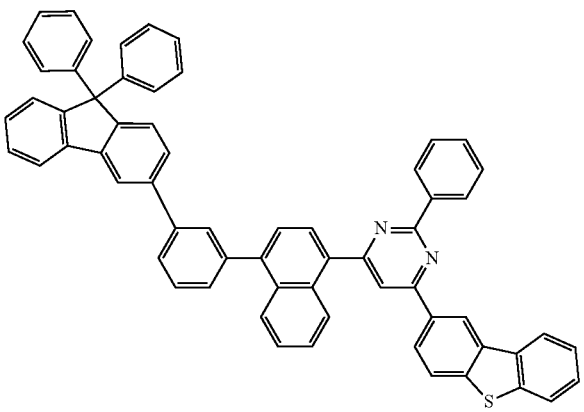
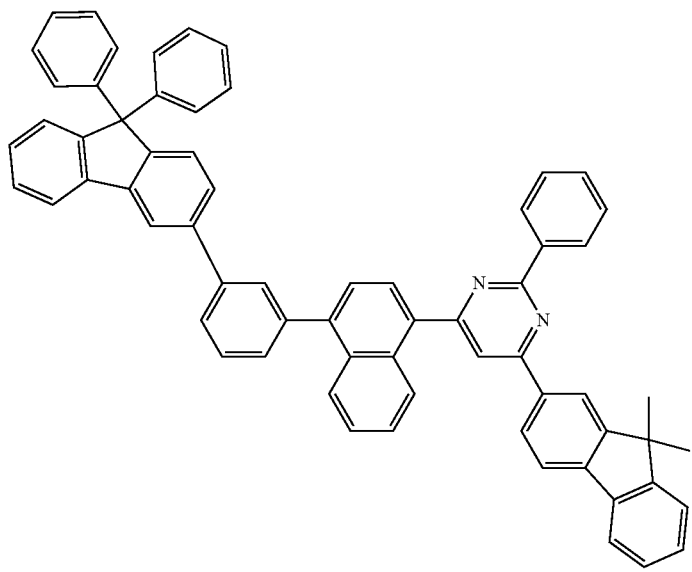
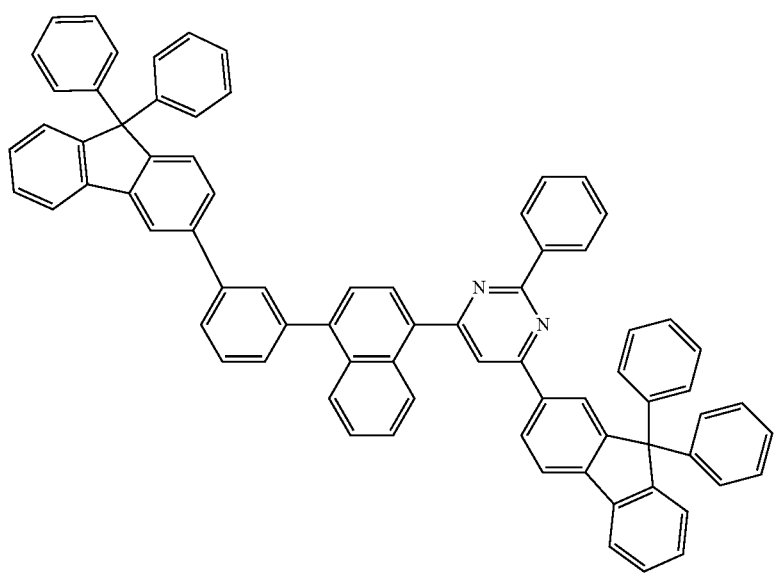

-continued
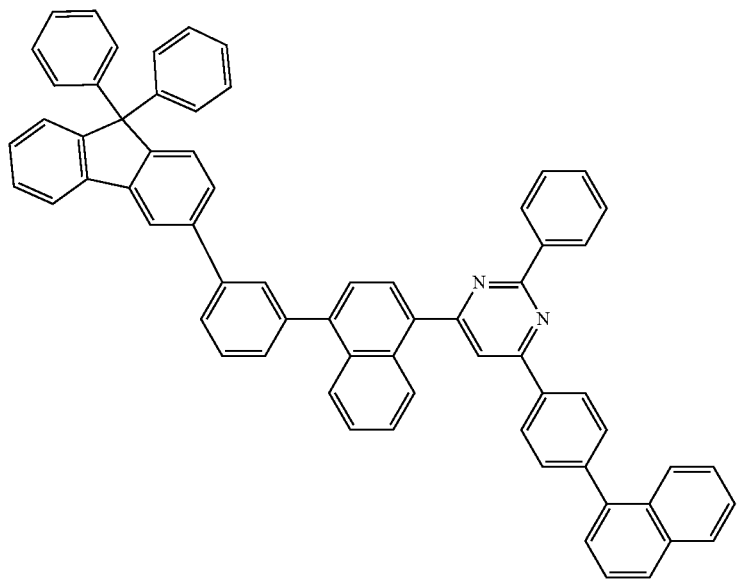
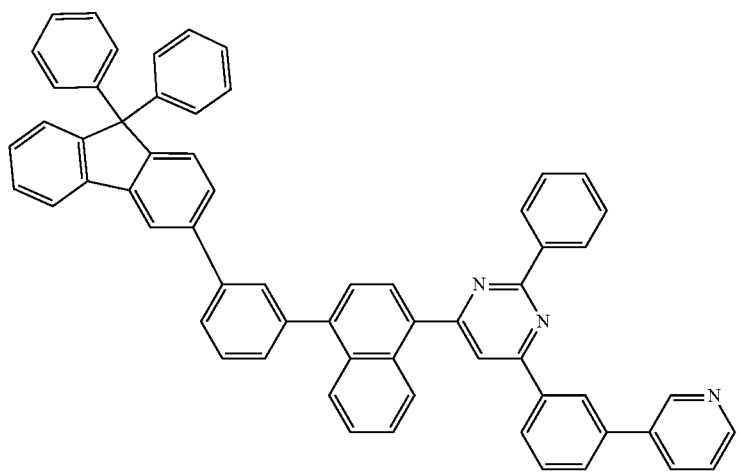
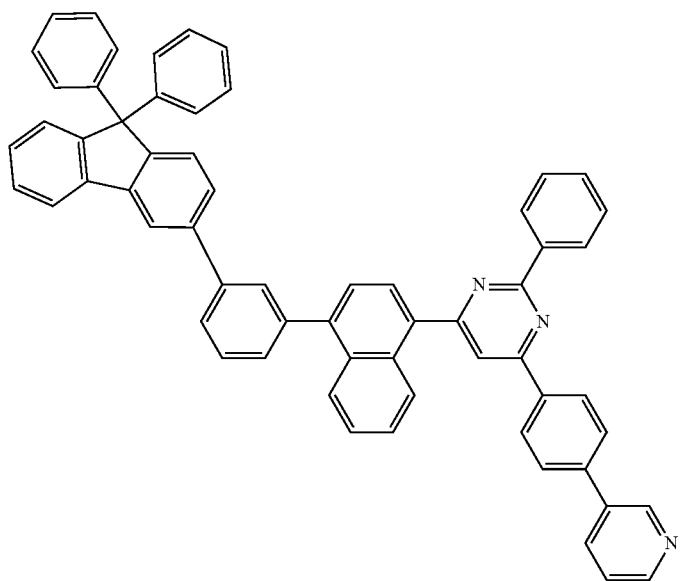

-continued
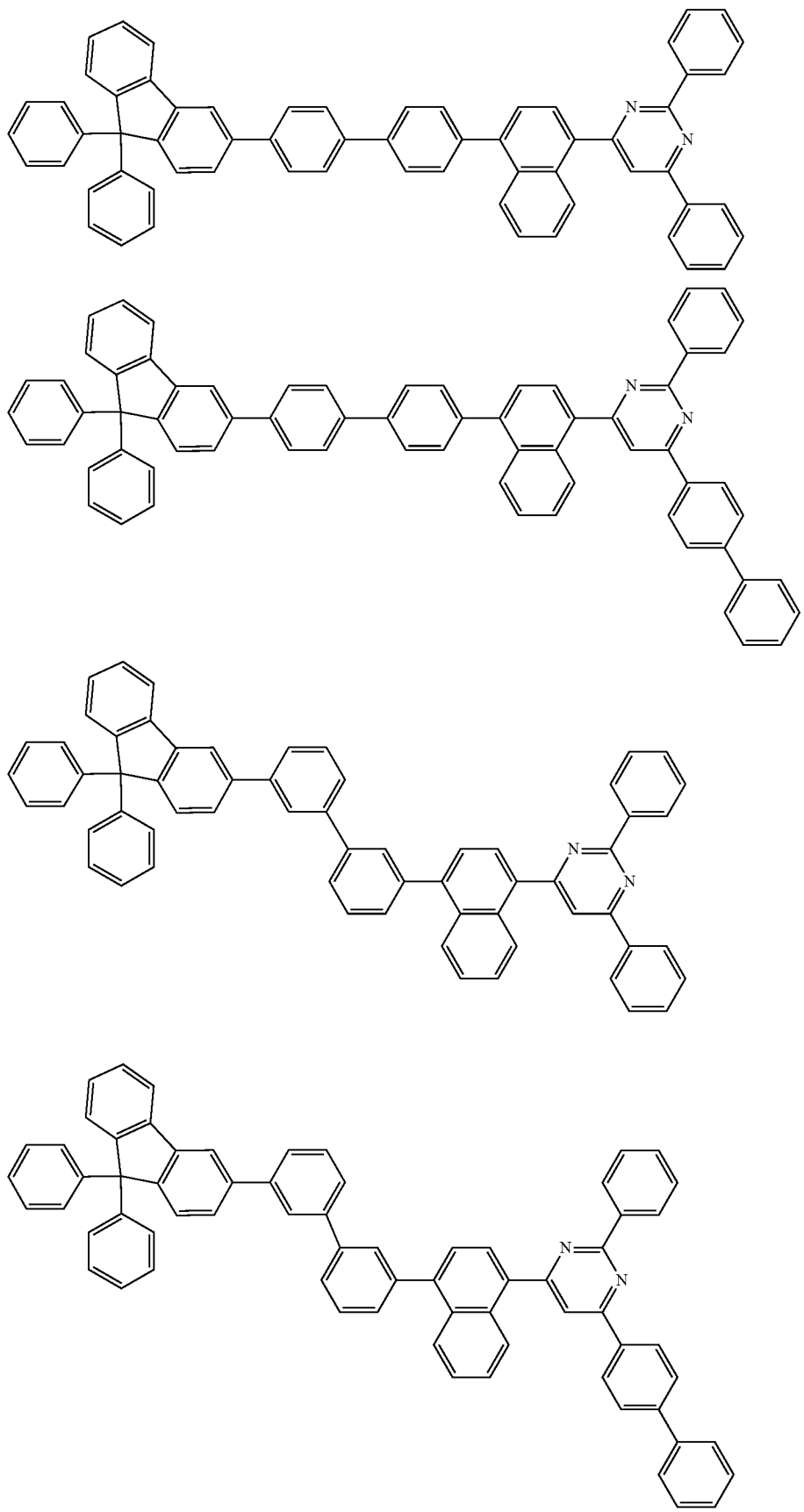

-continued
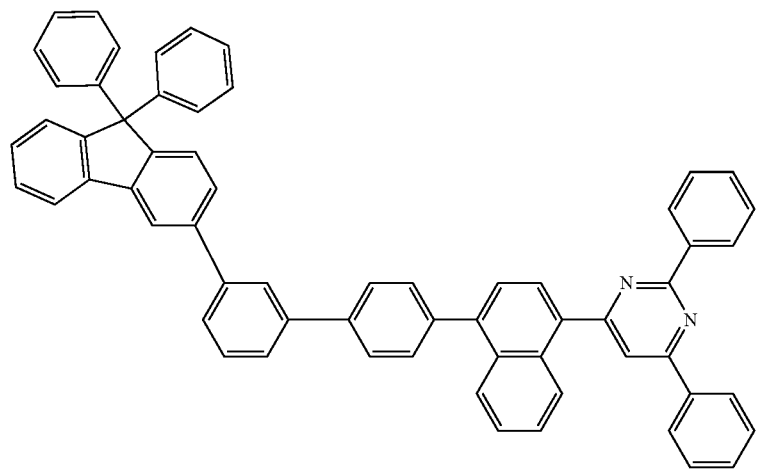
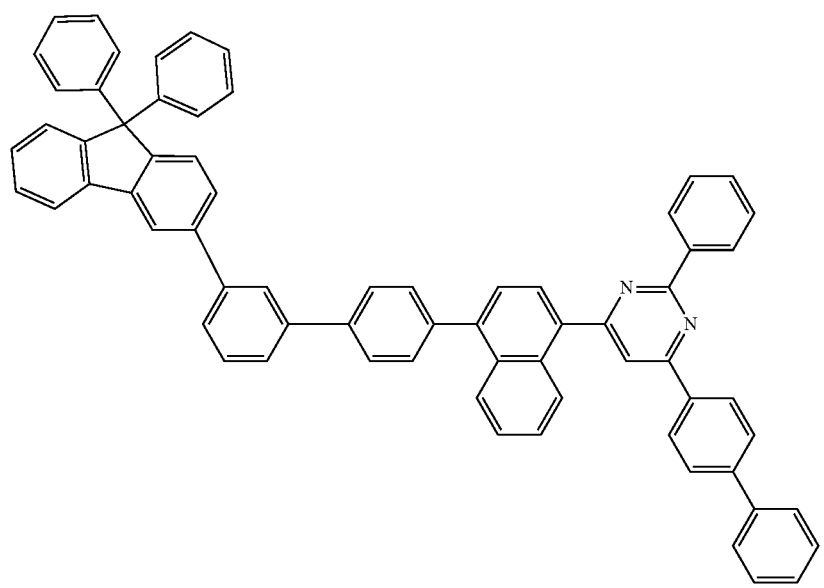
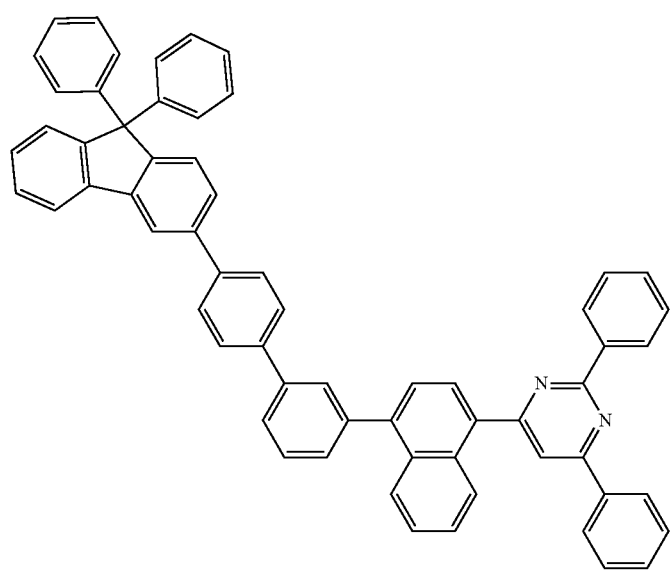

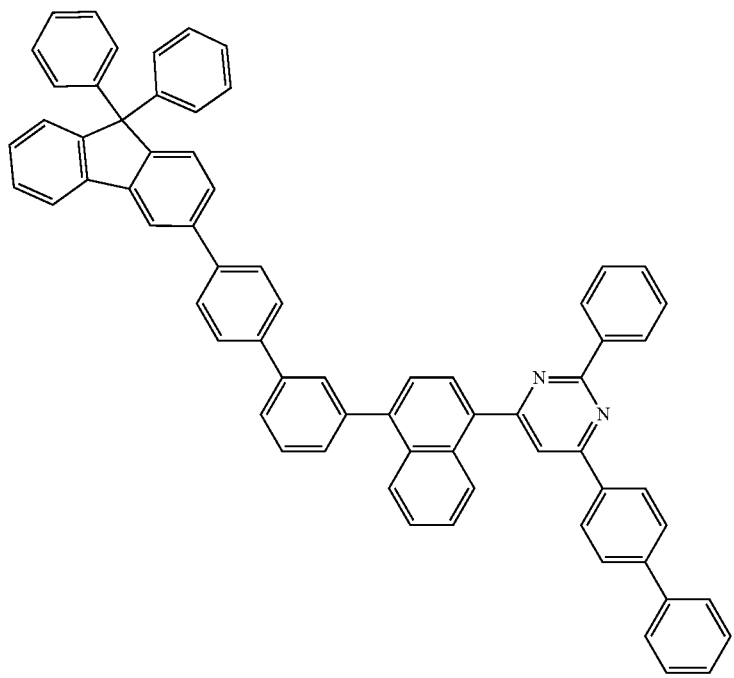
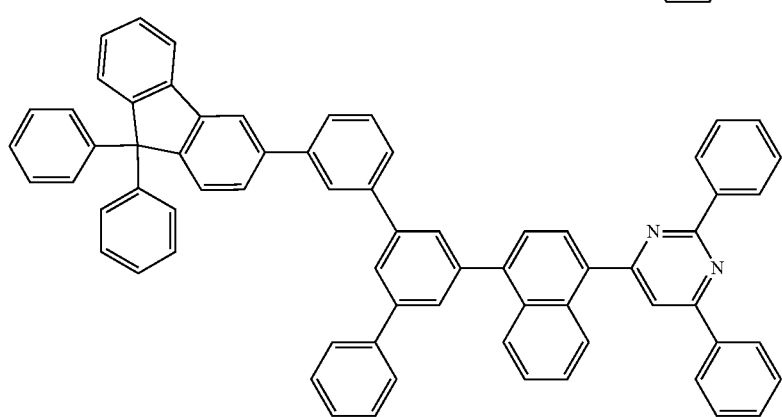
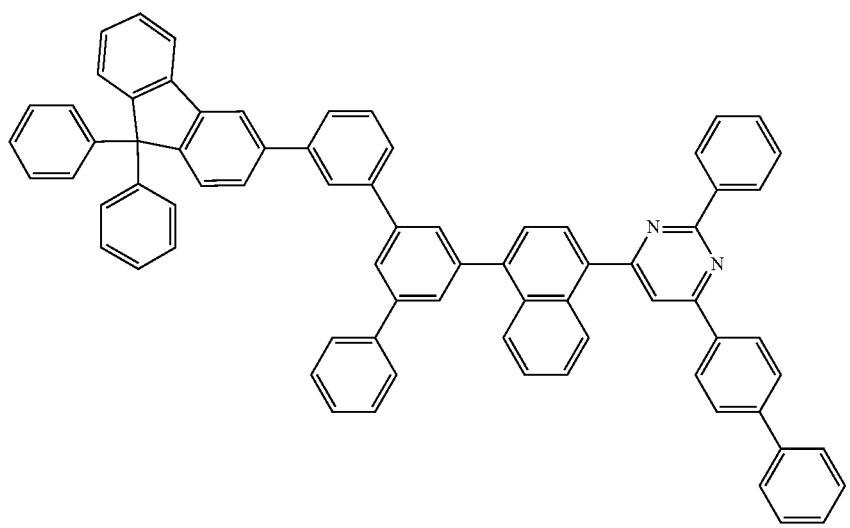

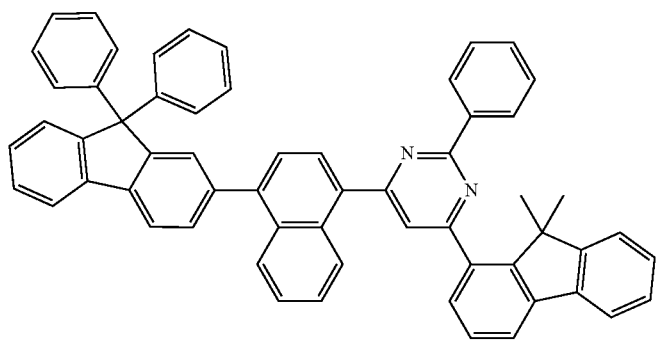
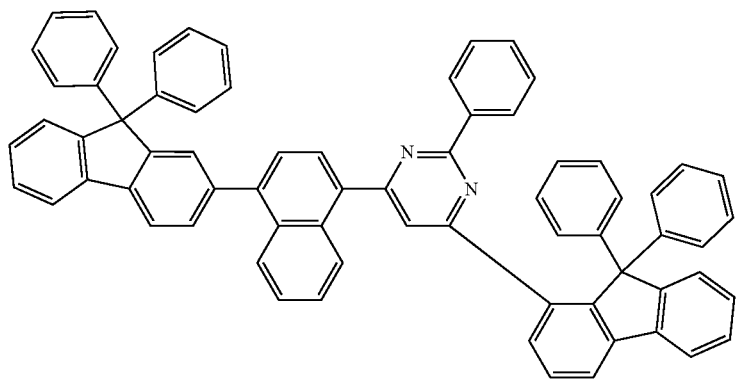
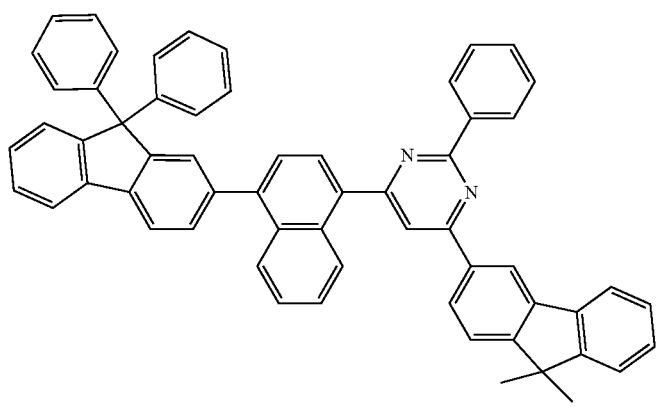
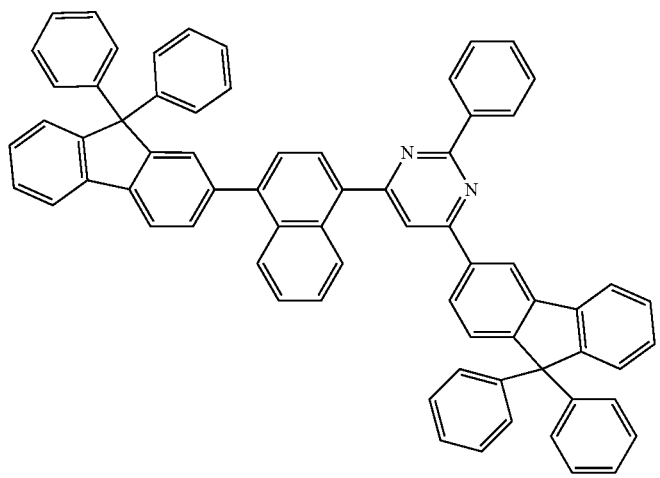

-continued
289 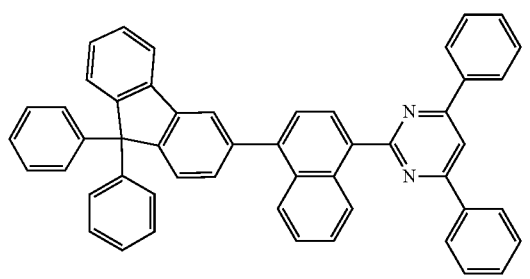
290 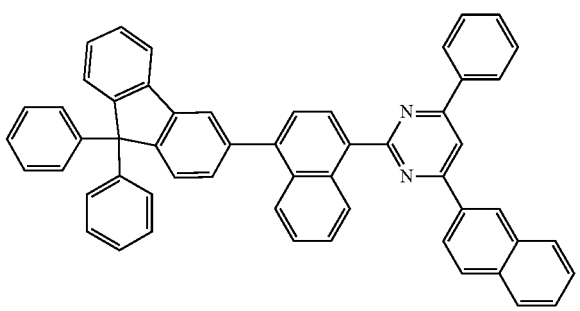
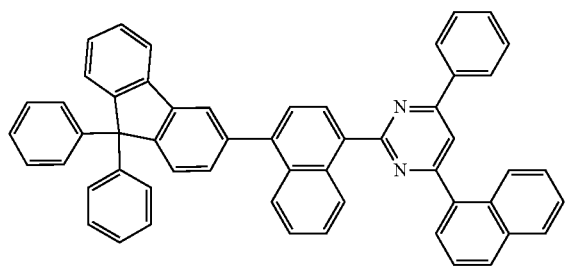
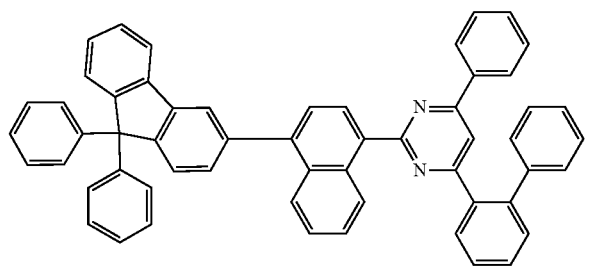
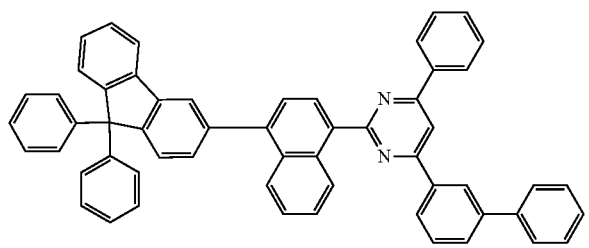
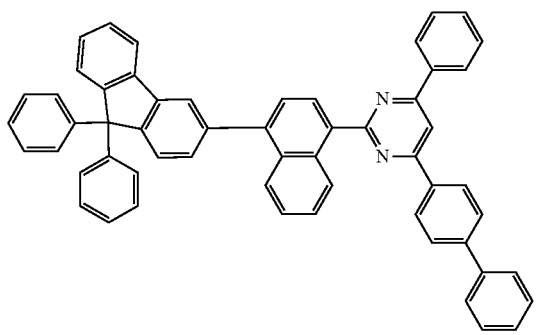
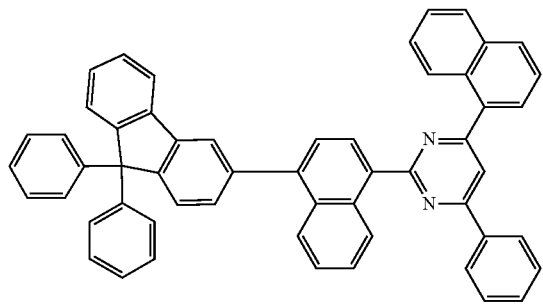
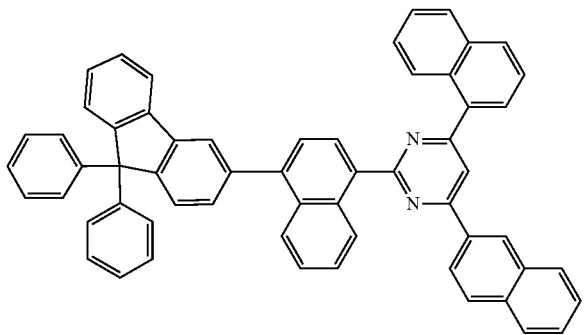
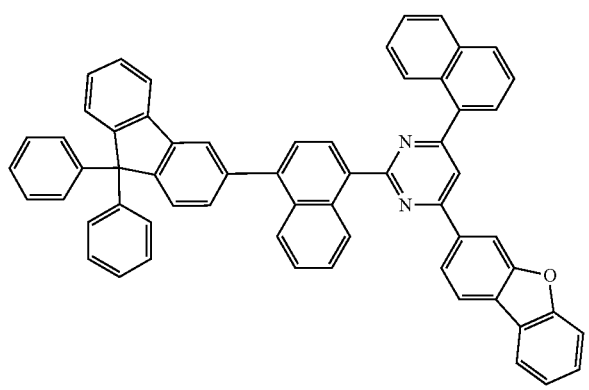
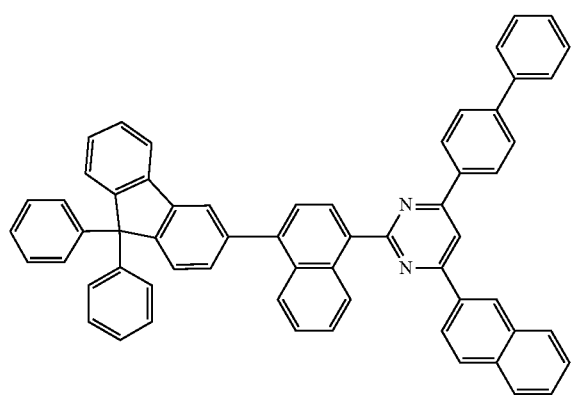

291 292
-continued
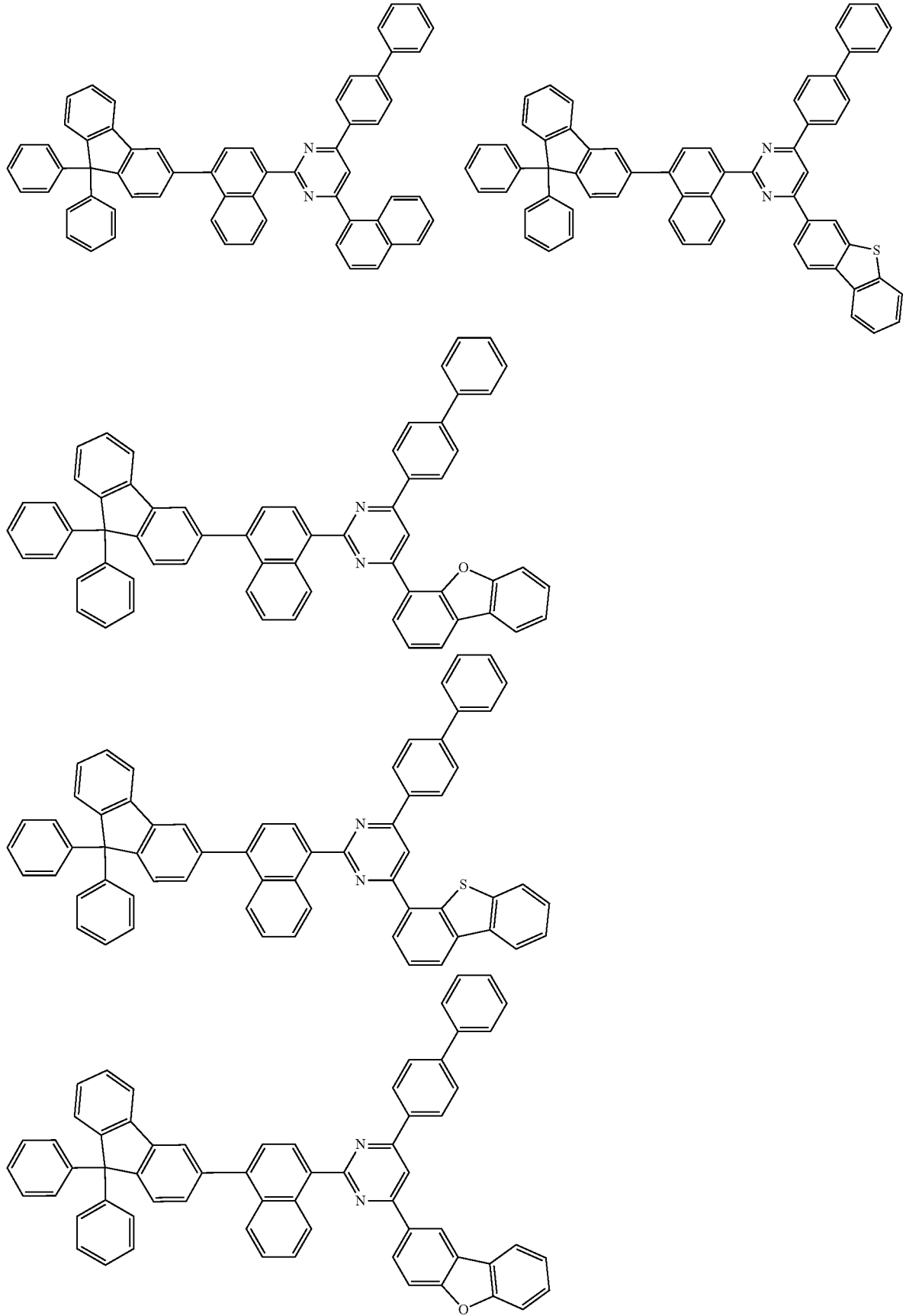

-continued
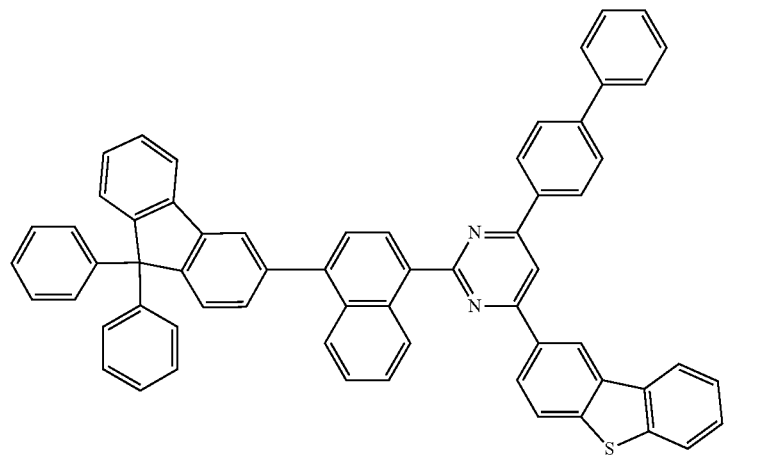
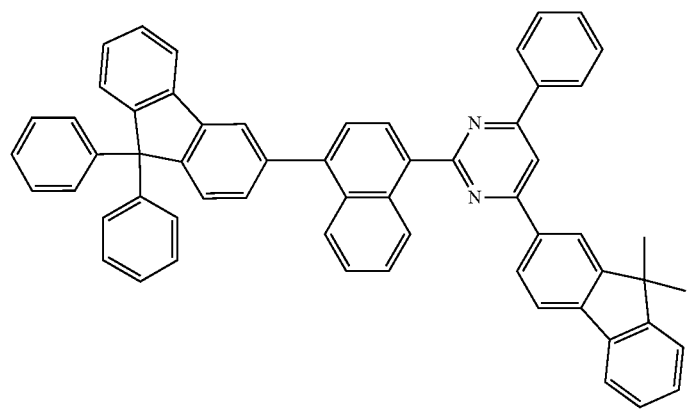
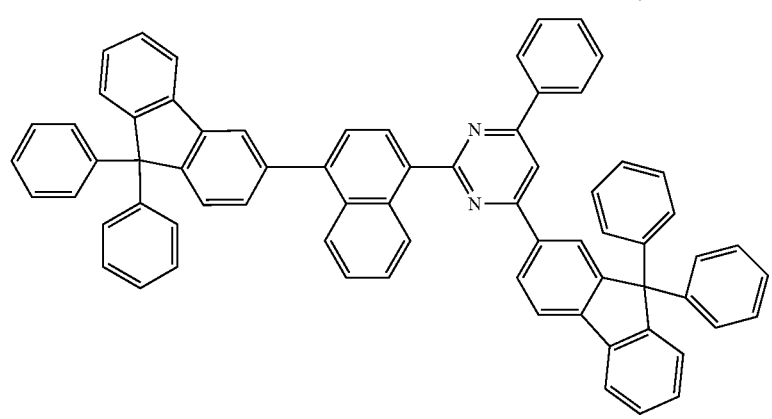
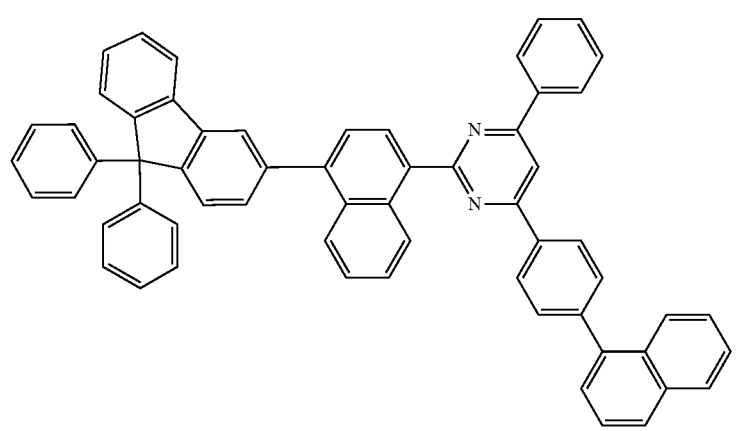

-continued
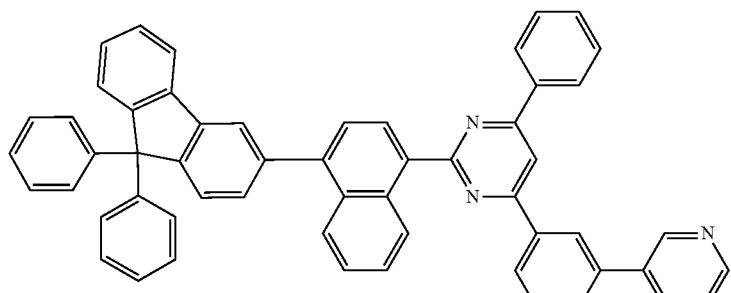
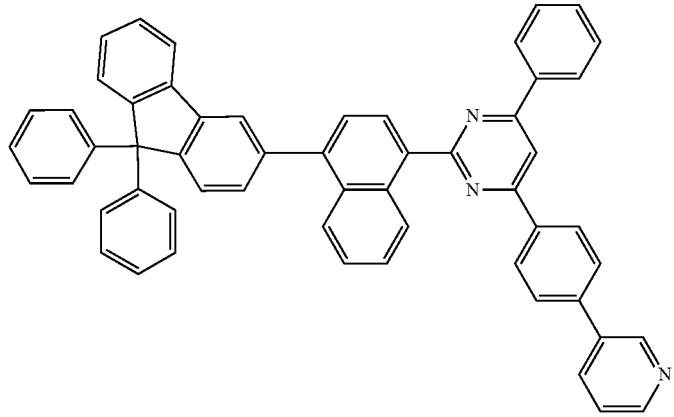
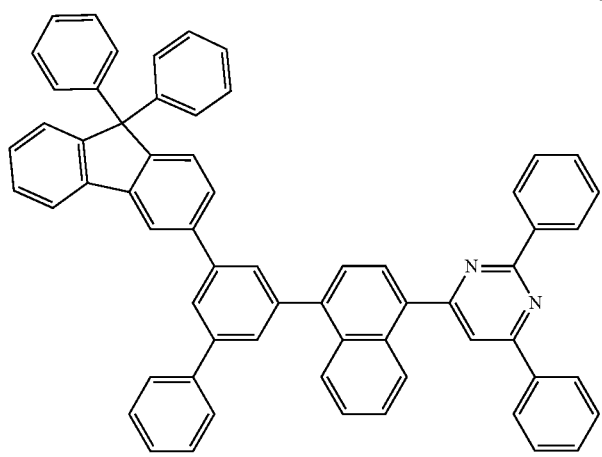
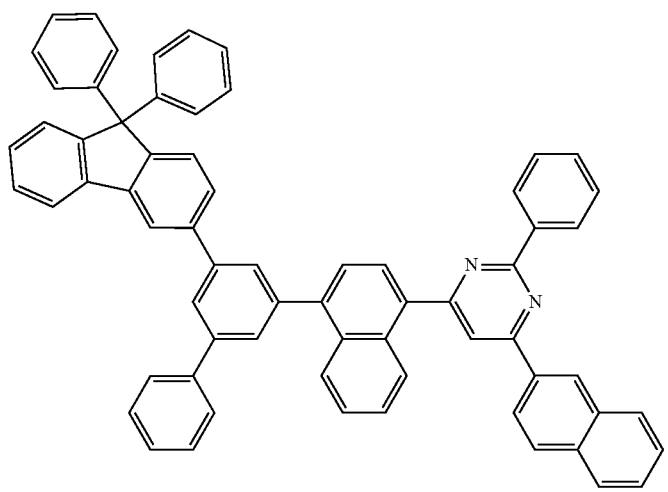

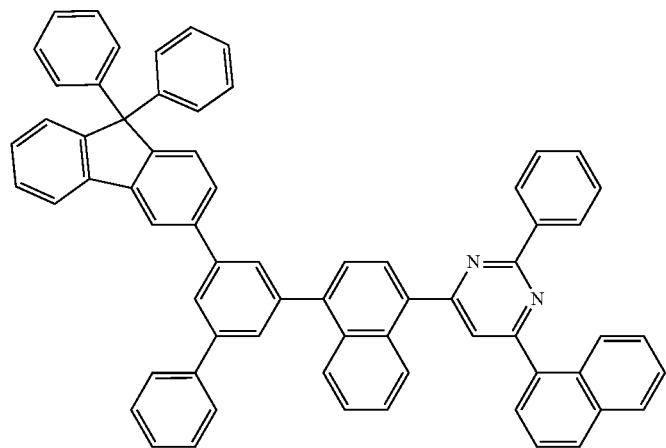
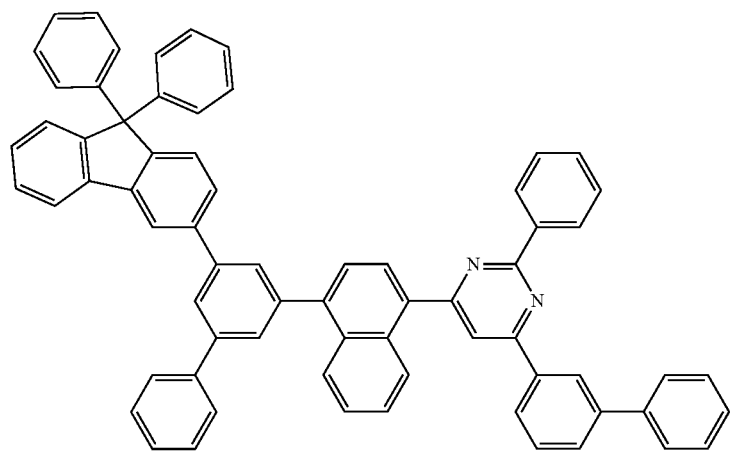
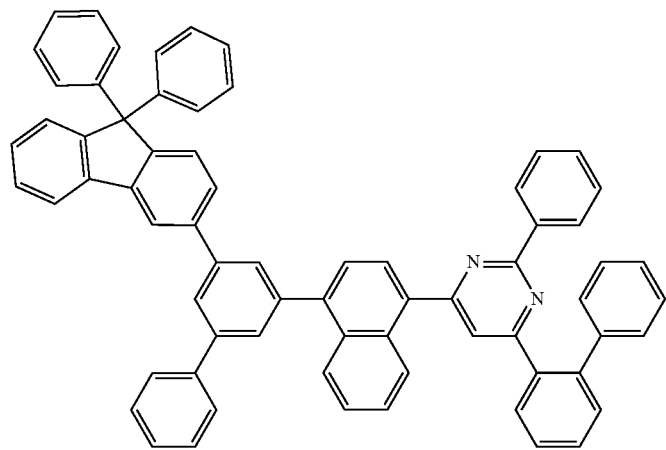

-continued
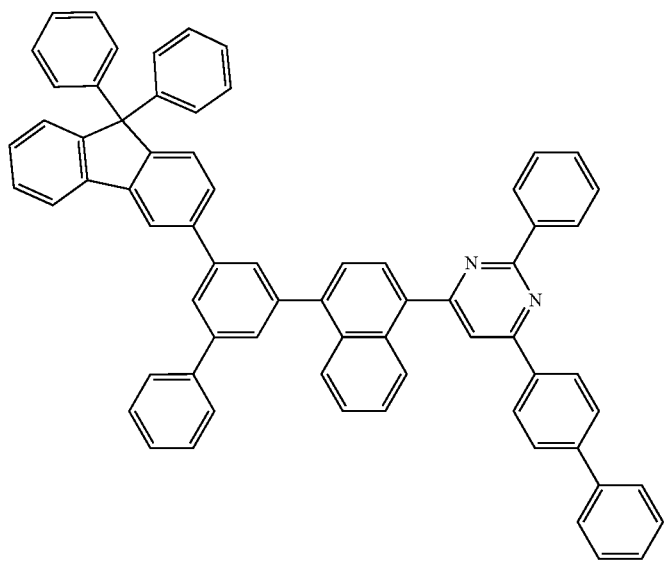
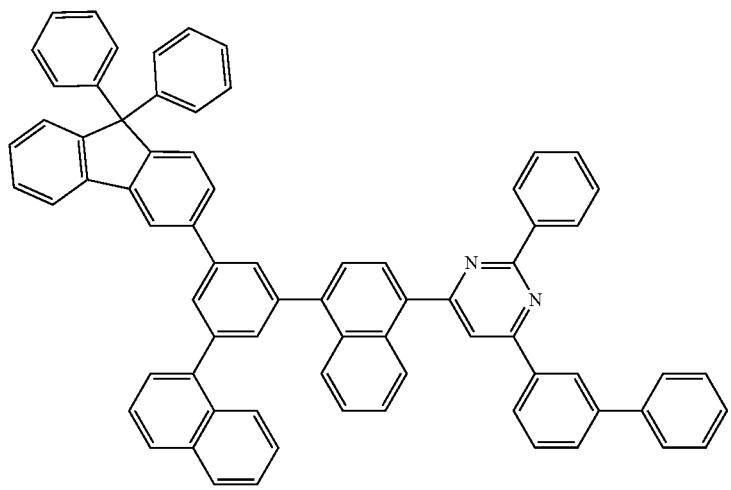
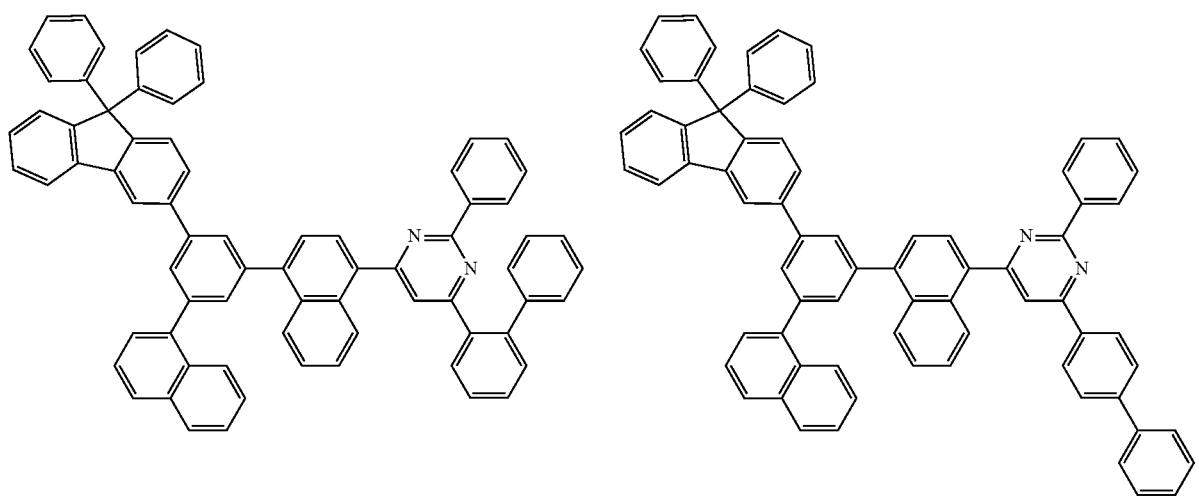

-continued
| 301 | 302 |
|---|---|
| 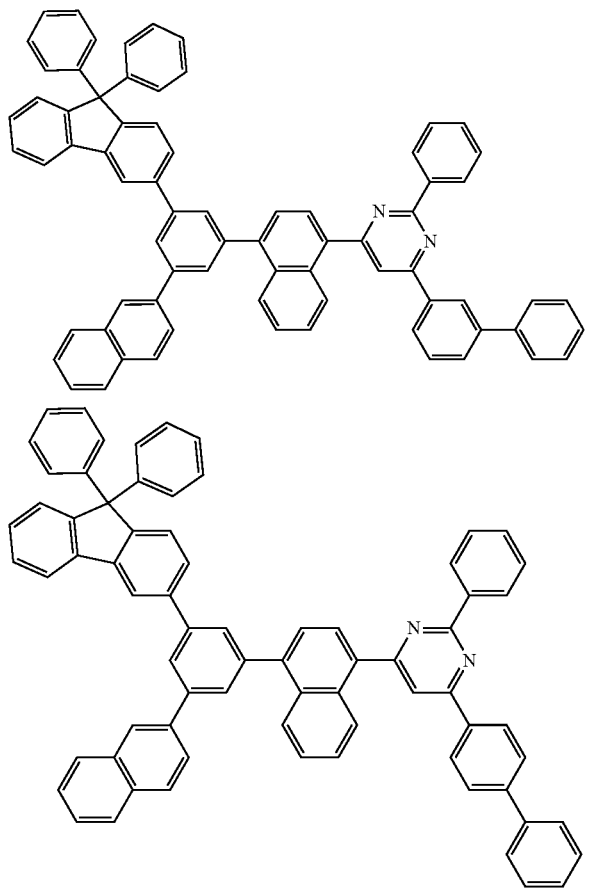 | 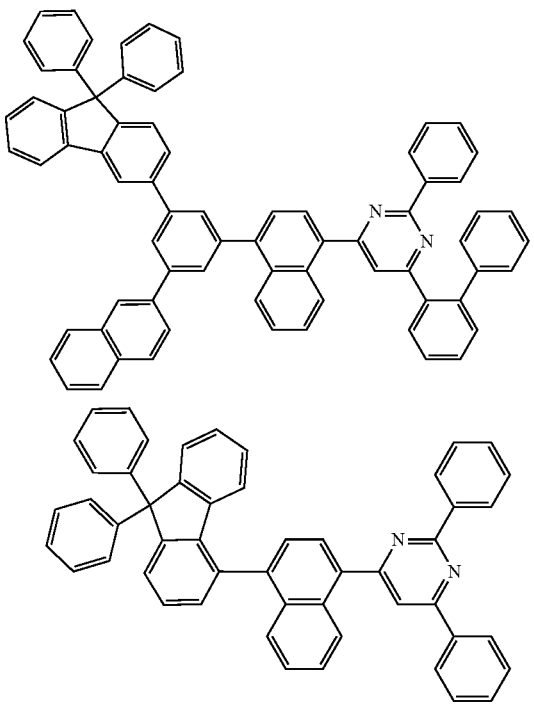 |
| 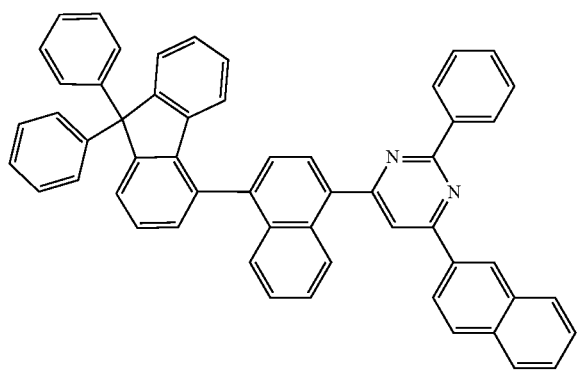 | 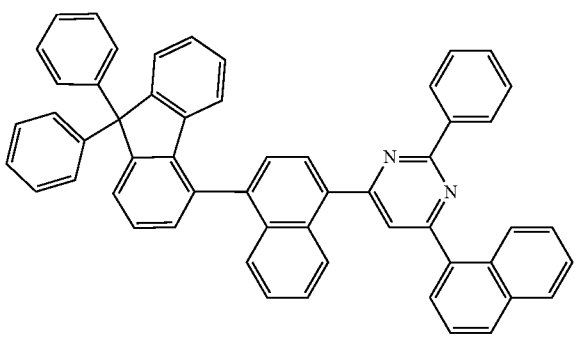 |
| 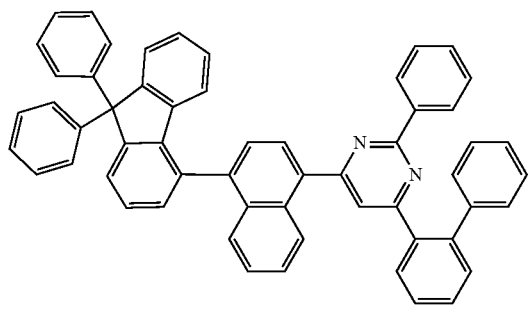 | 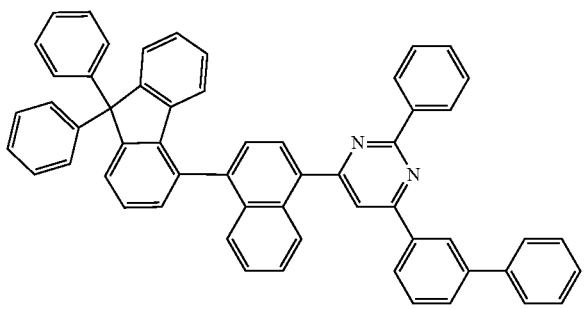 |

-continued
| 303 | 304 |
|---|---|
| 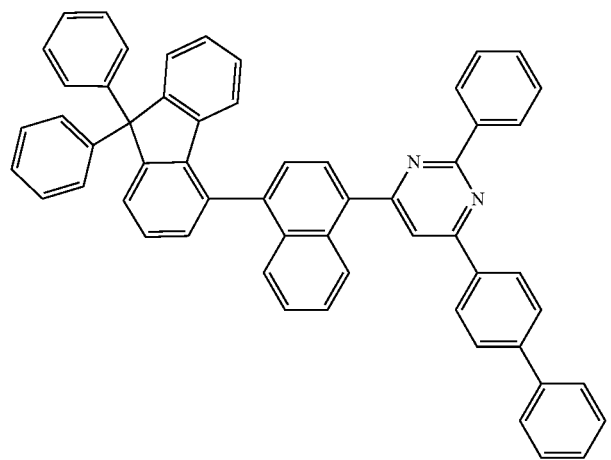 | 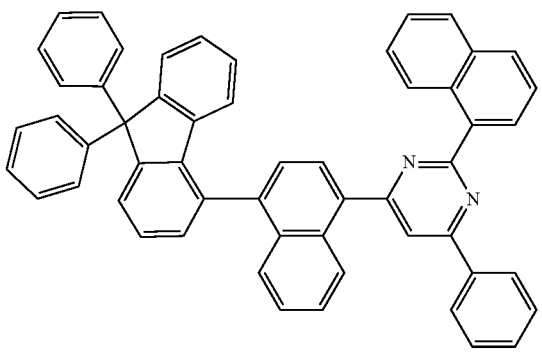 |
| 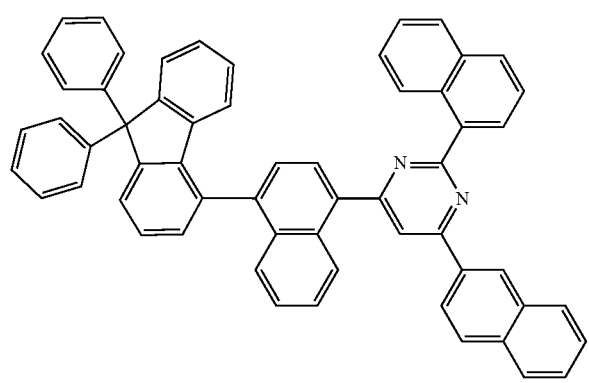 | 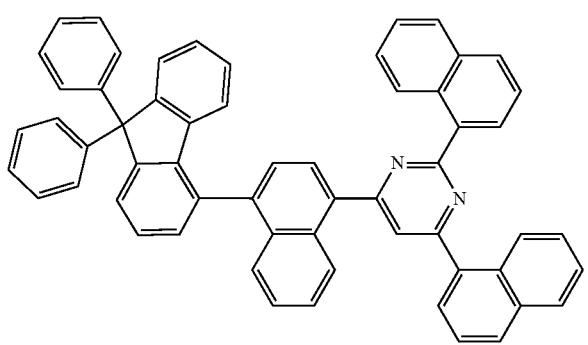 |
| 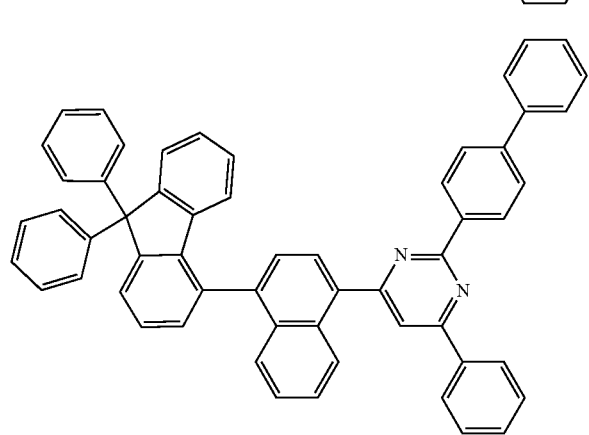 | 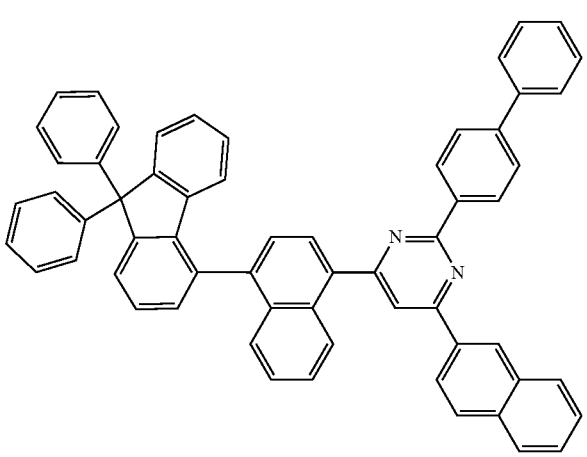 |
| 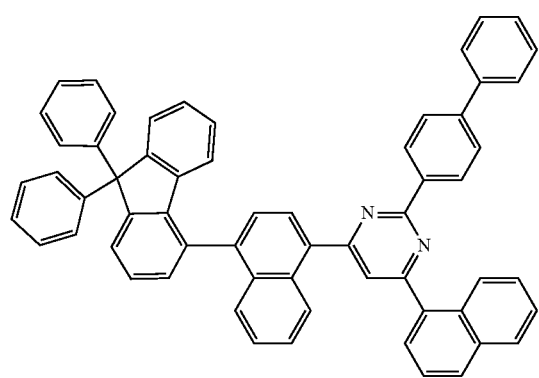 | 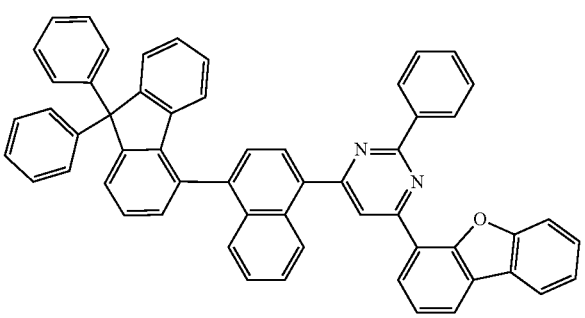 |

-continued
305
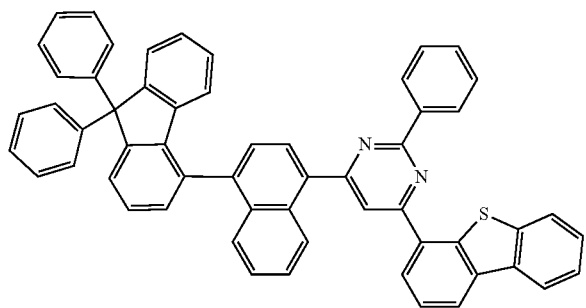
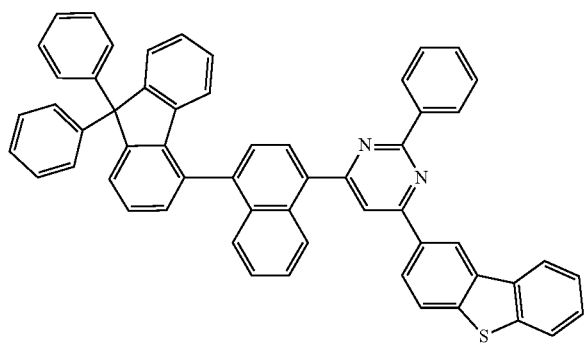
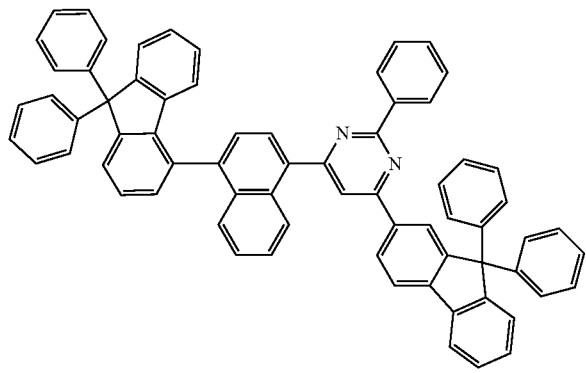
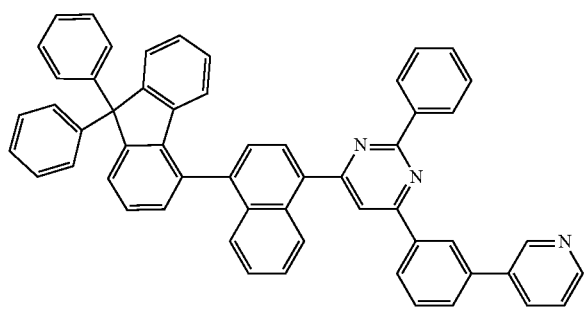
306
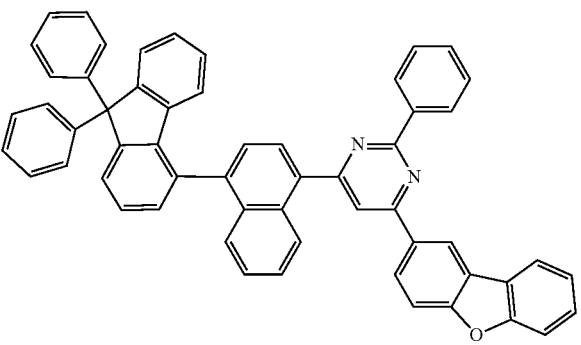
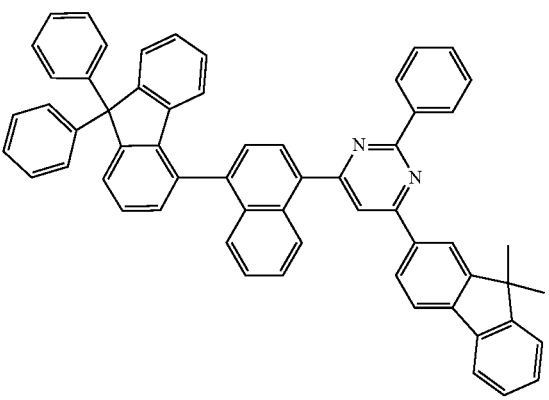
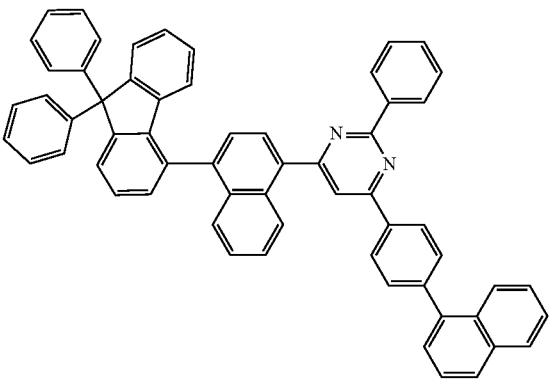
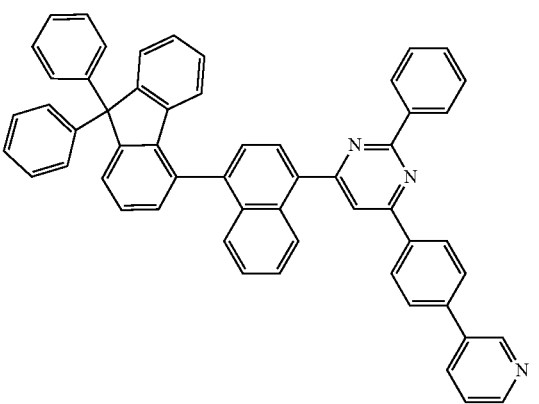

307
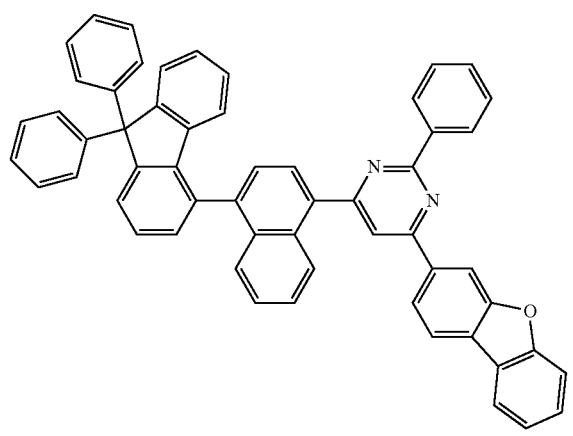
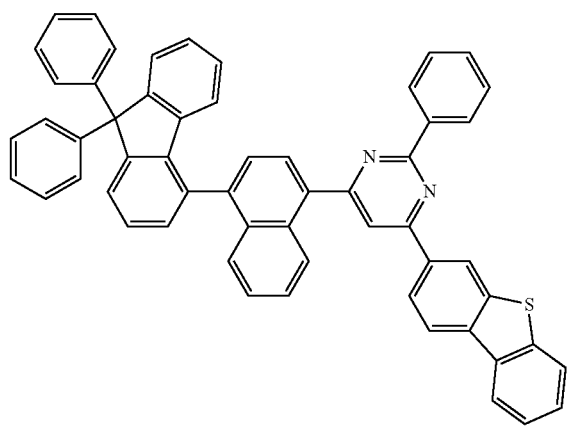
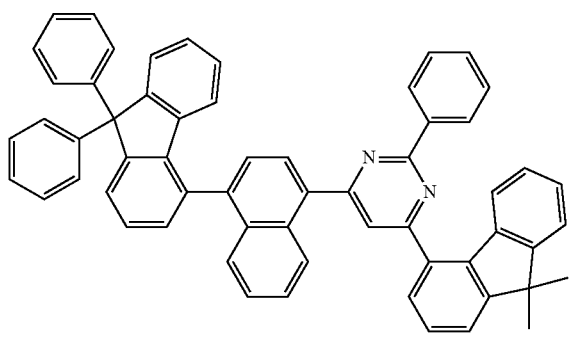
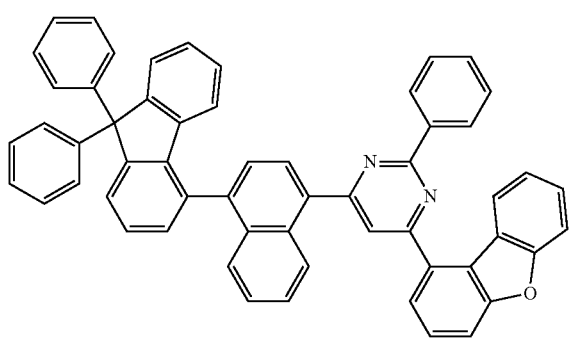
308
-continued
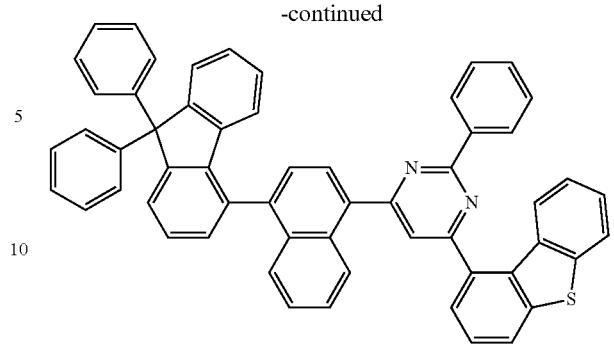
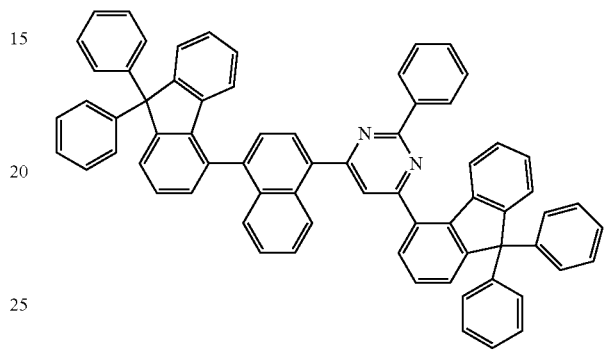
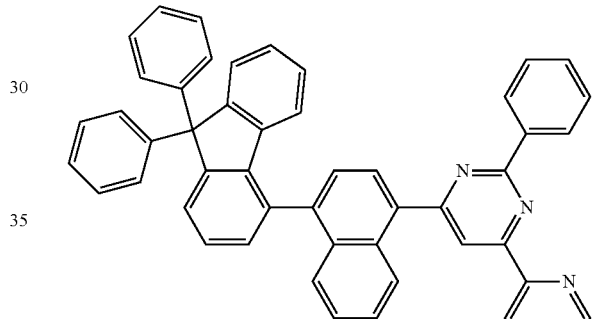
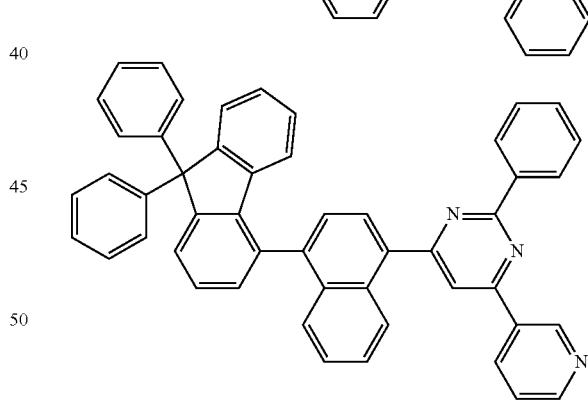
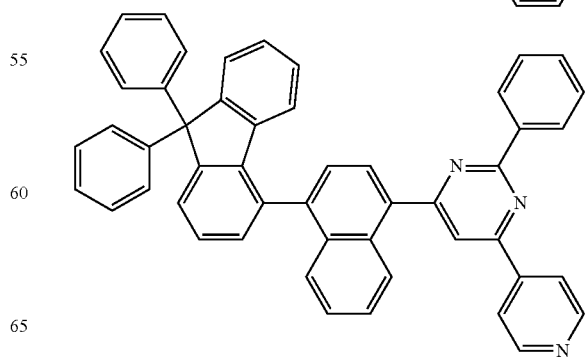

309
-continued
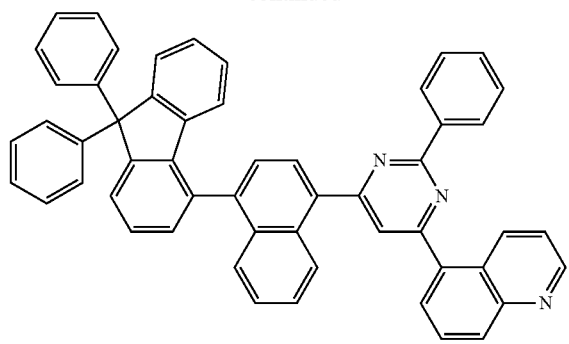
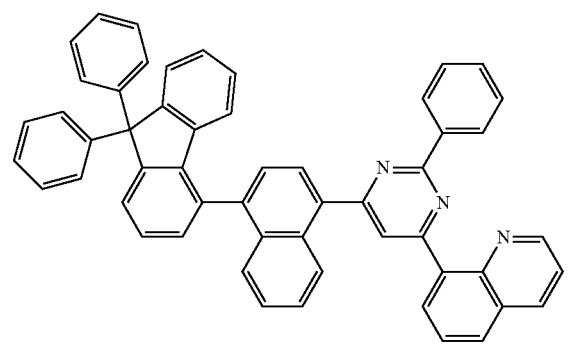
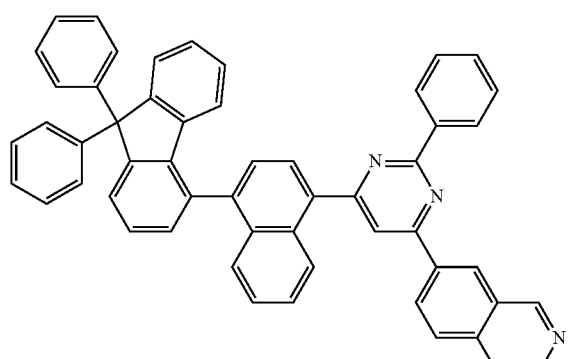
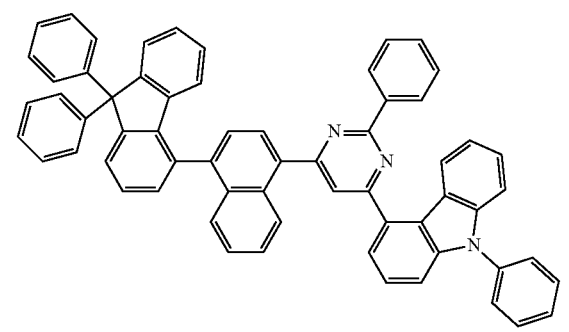
310
-continued
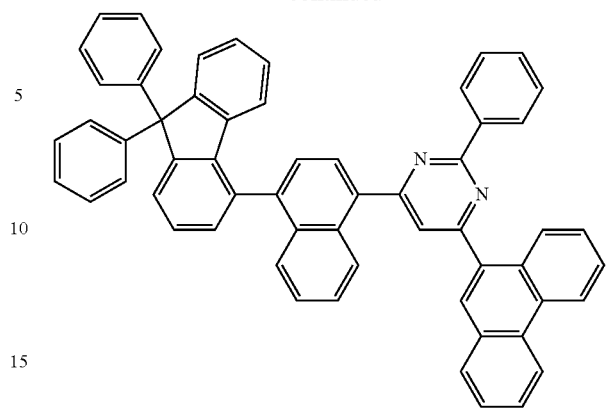
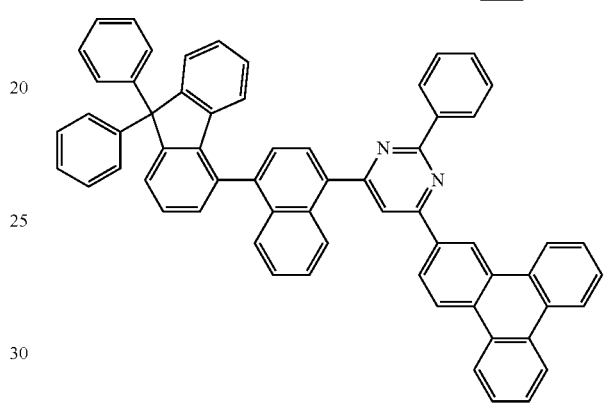
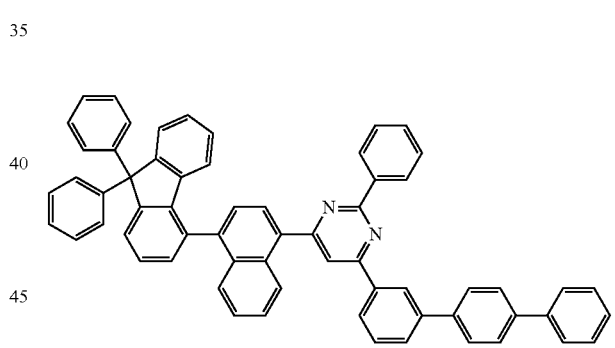
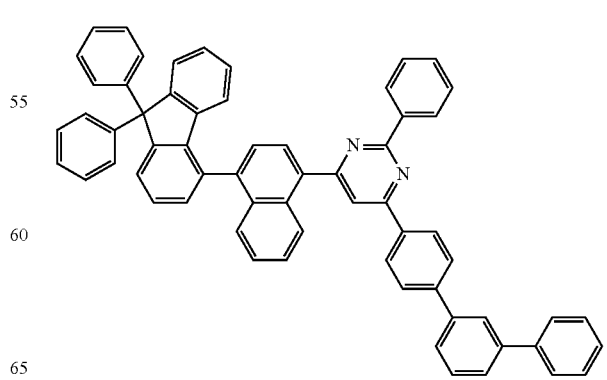

311
-continued
312
-continued
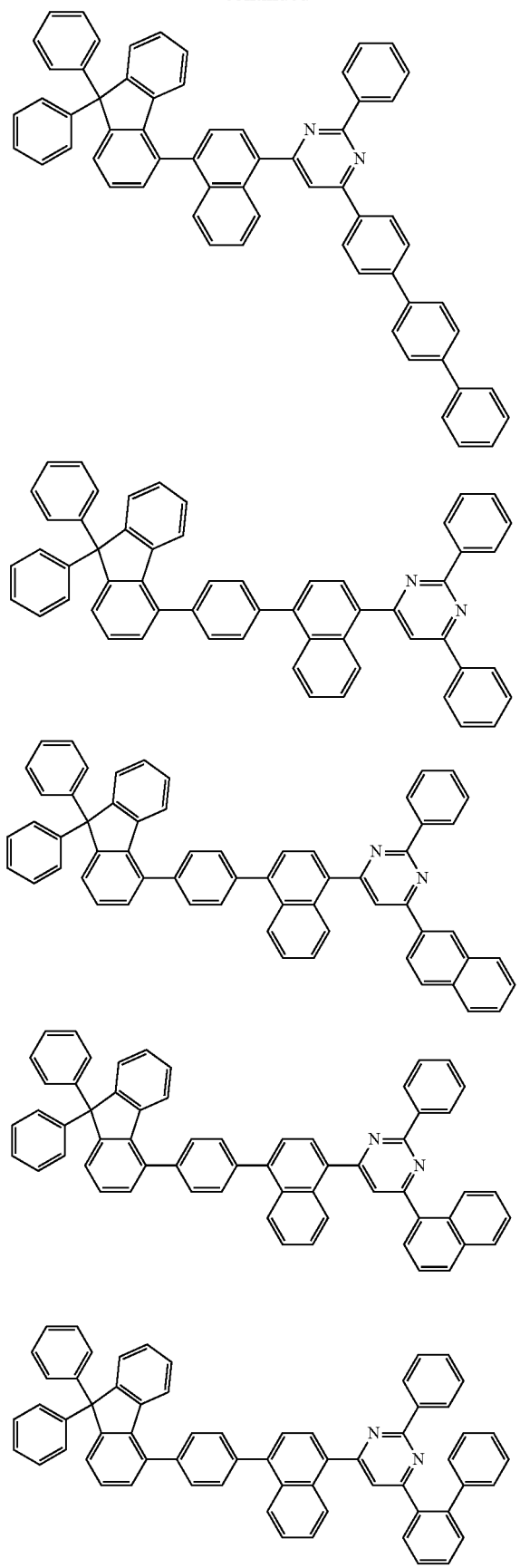

313
-continued
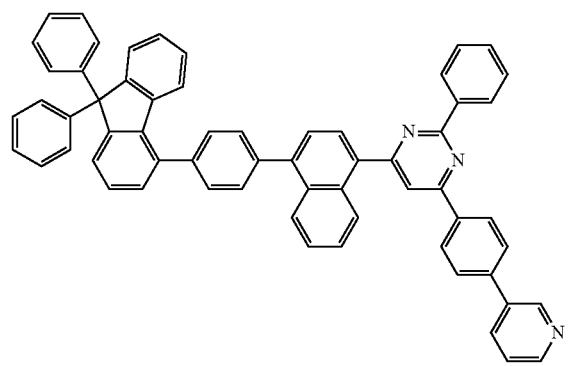
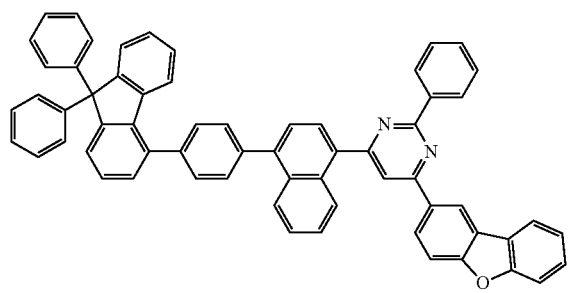
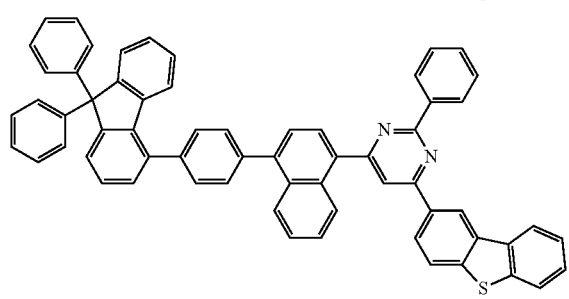
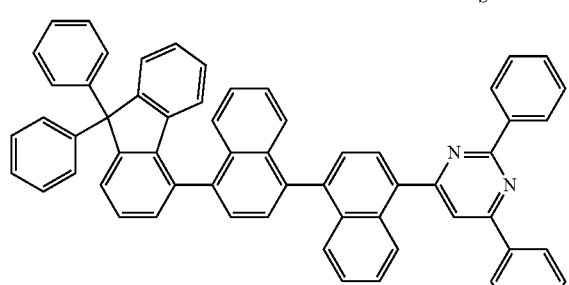
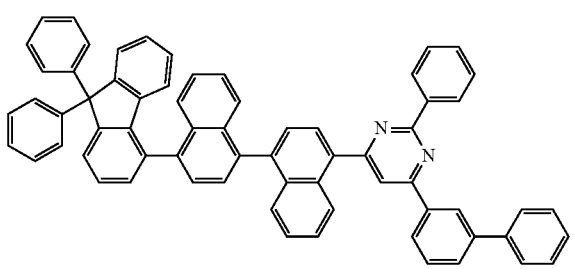
314
-continued
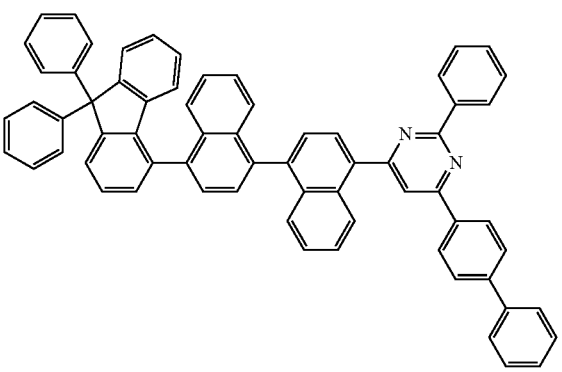
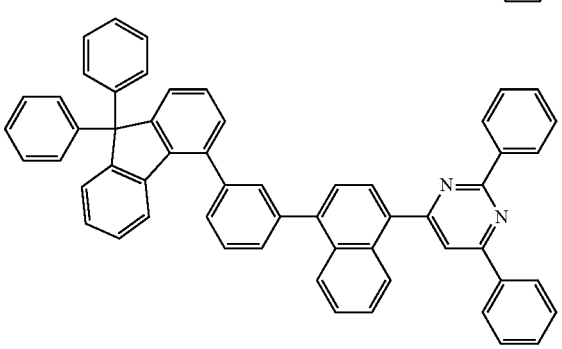
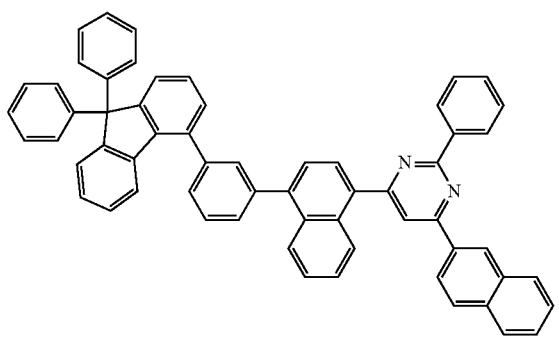
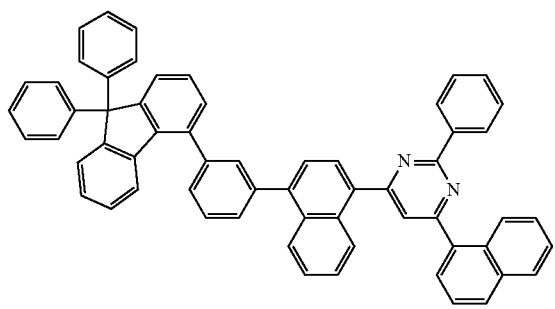
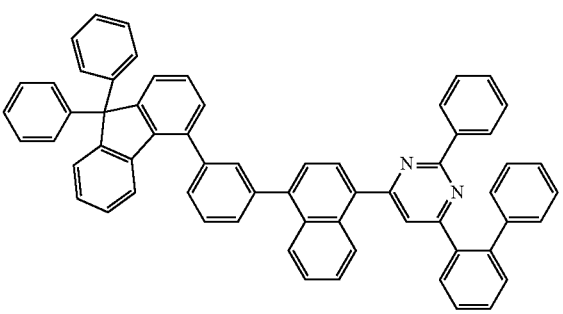

315
-continued
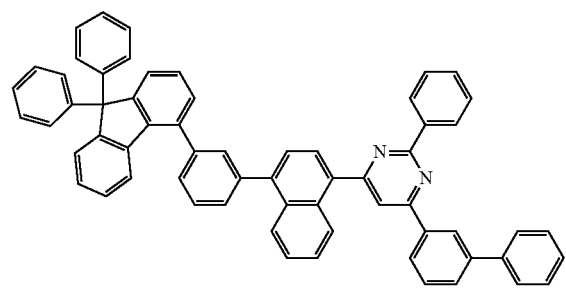
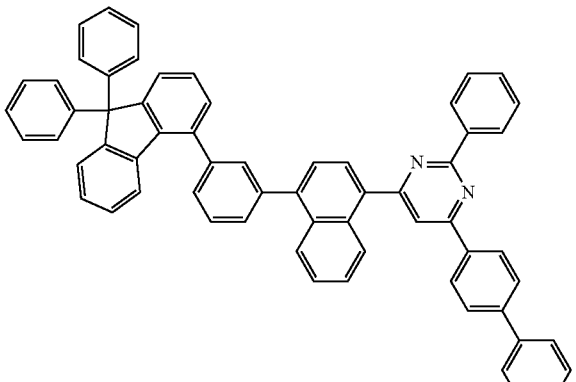
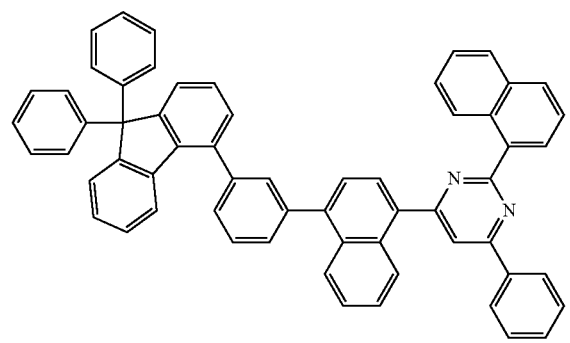
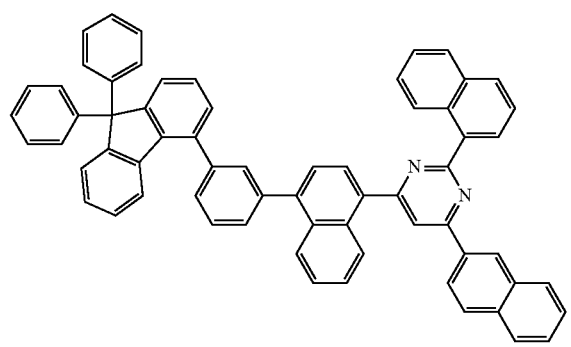
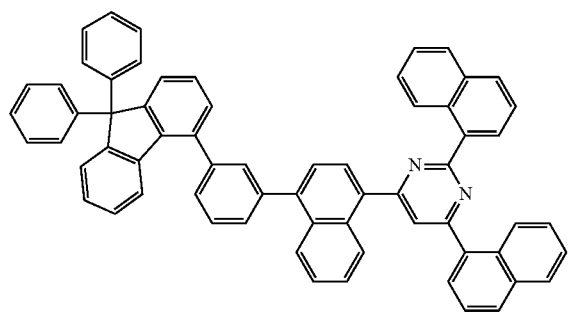
316
-continued
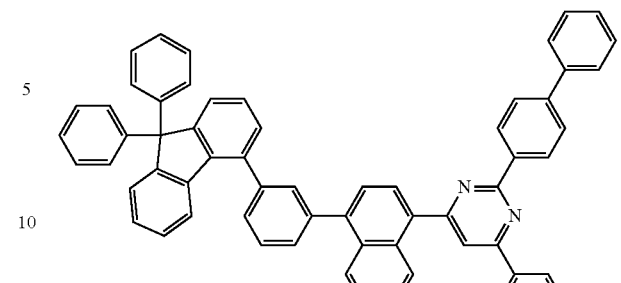
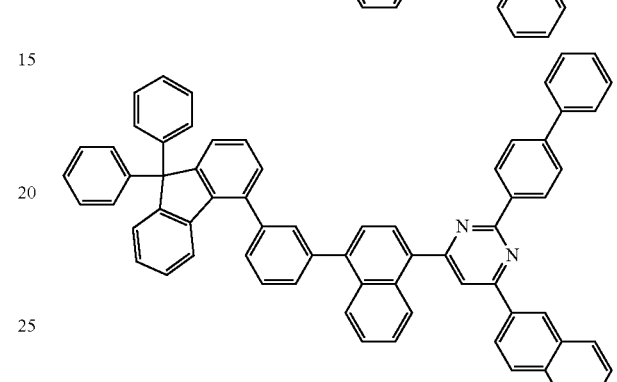
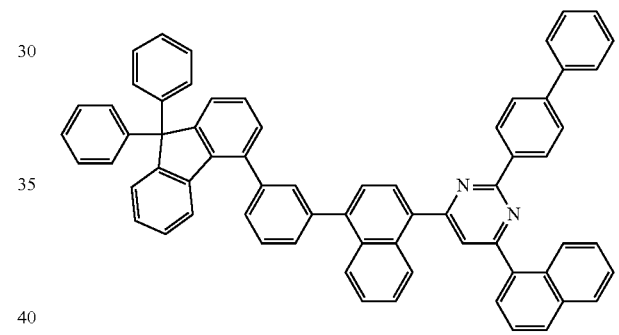
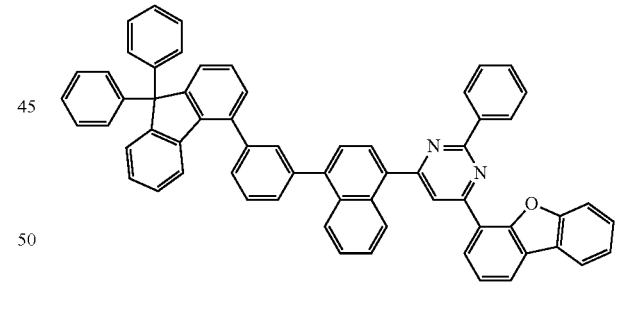
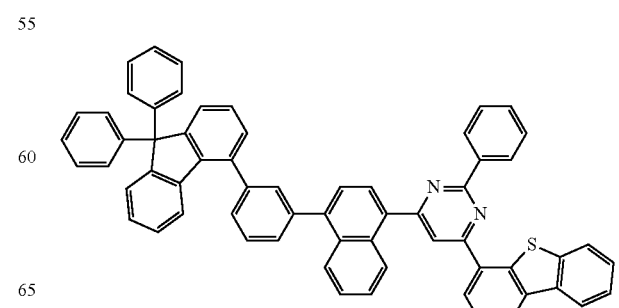

317
-continued
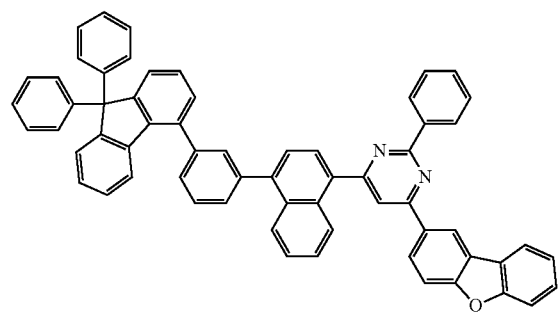
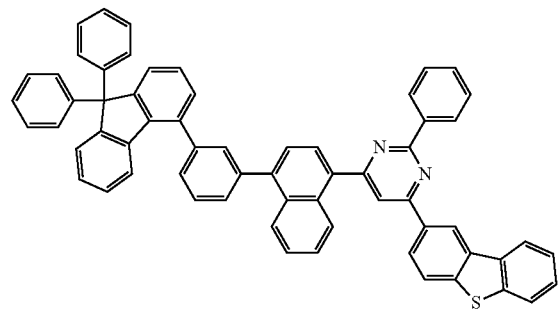
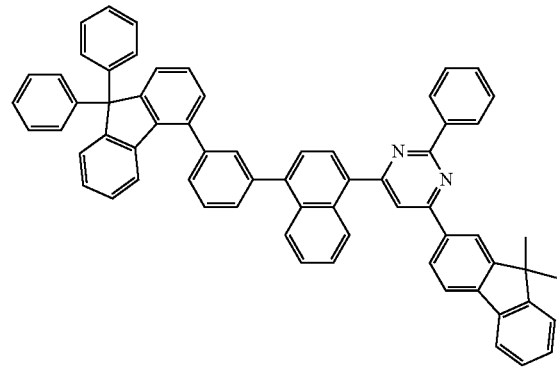
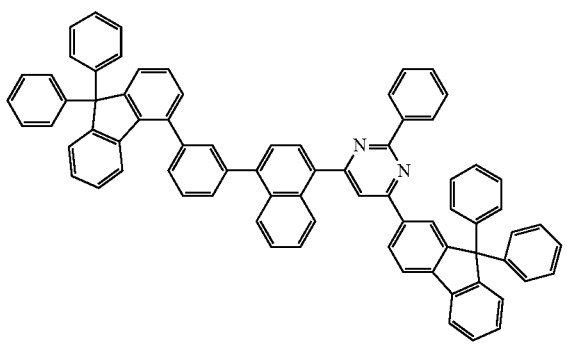
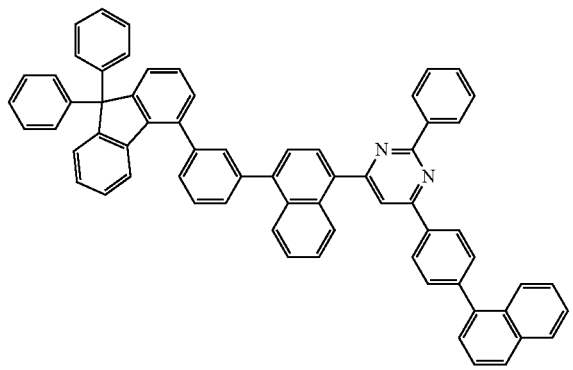
318
-continued
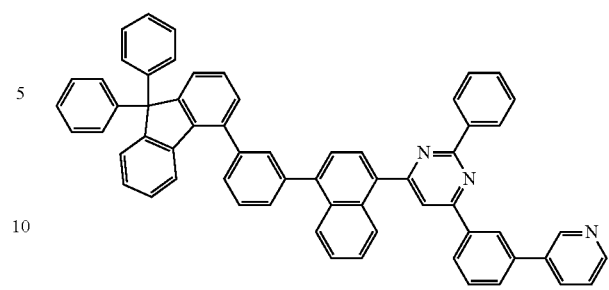
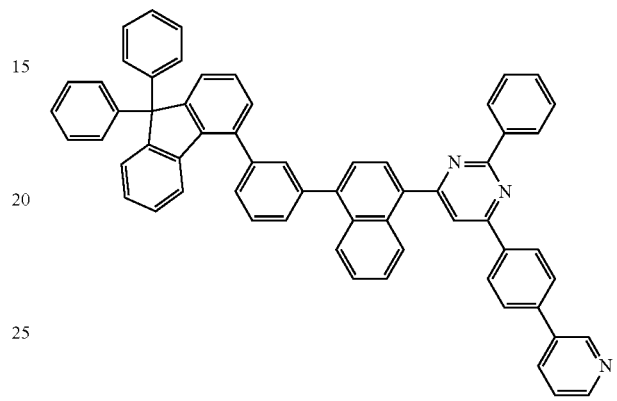
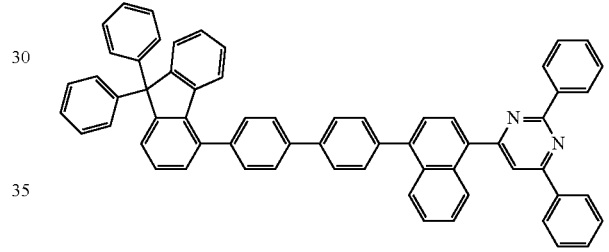
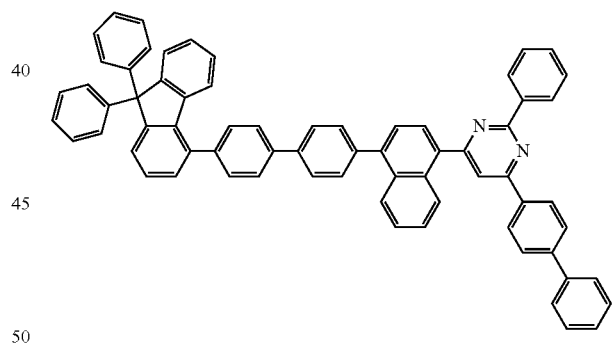
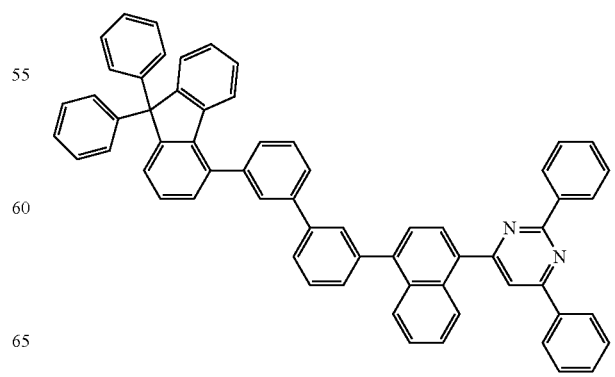

319
-continued
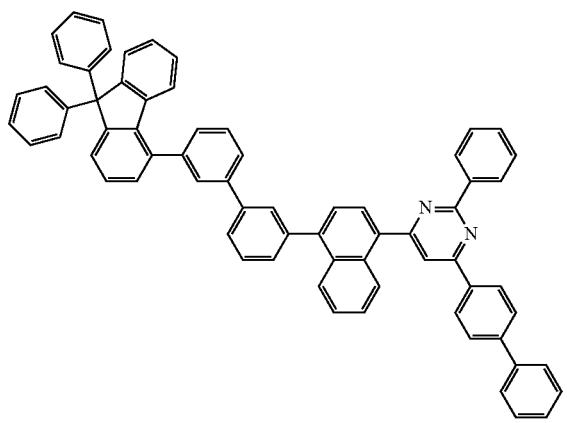
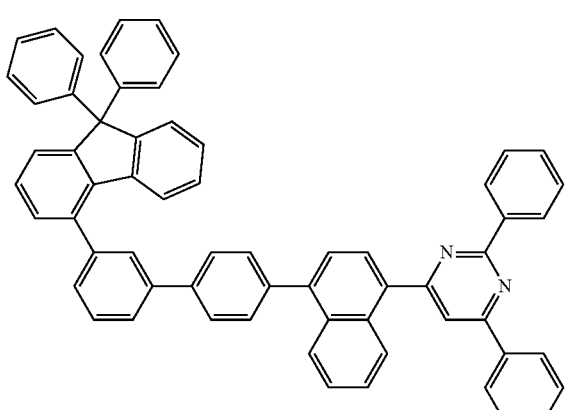
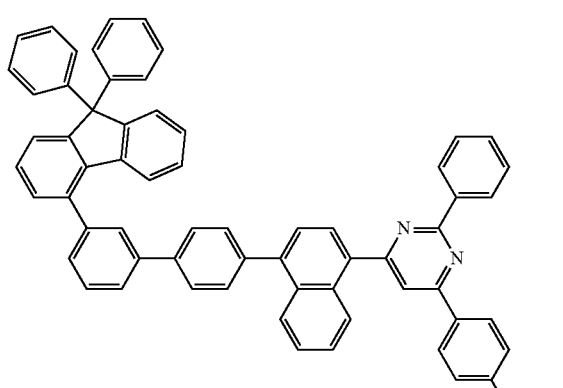
320
-continued
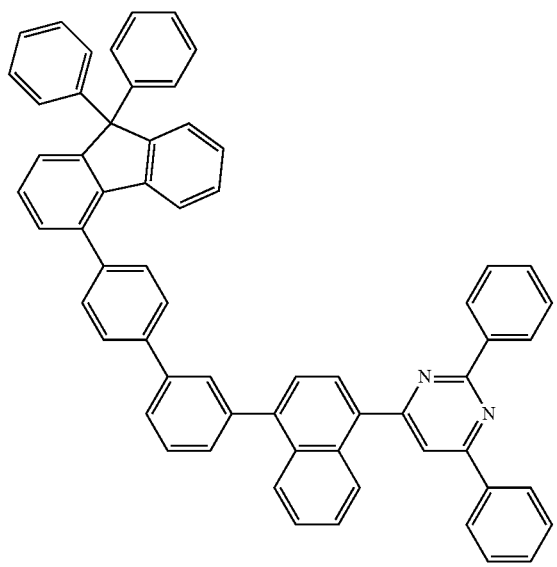
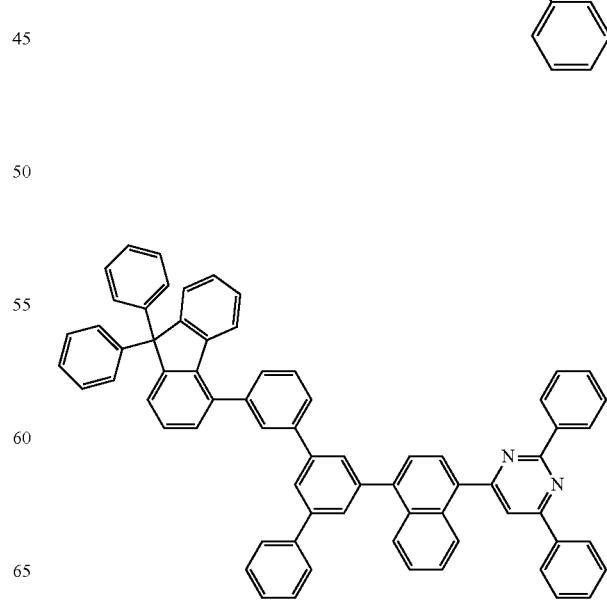

321
-continued
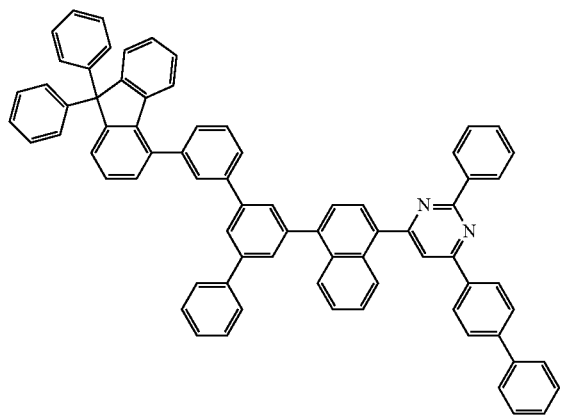
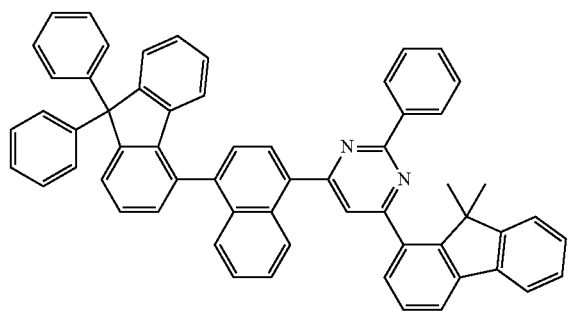
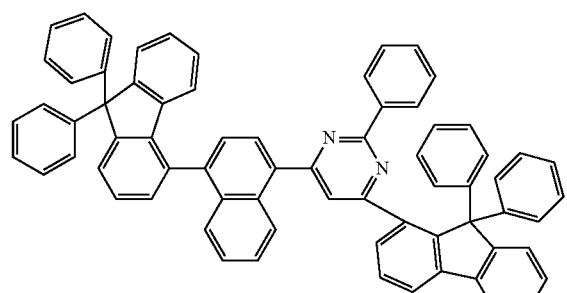
322
-continued
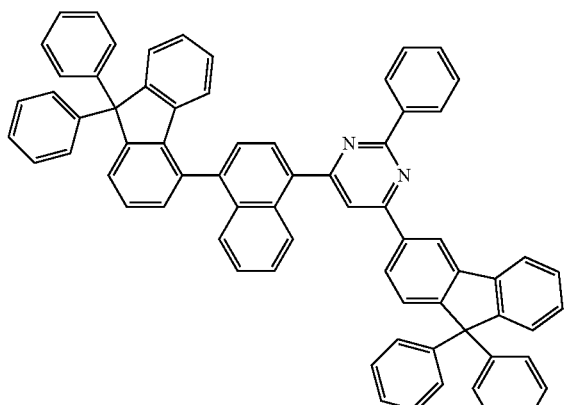
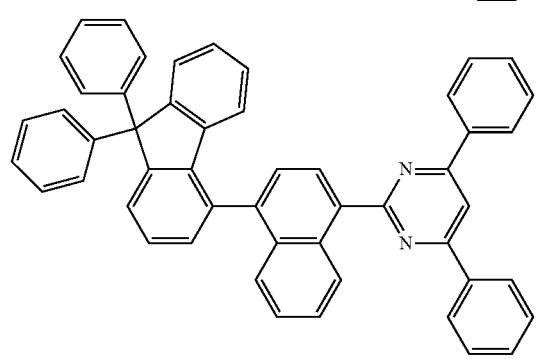
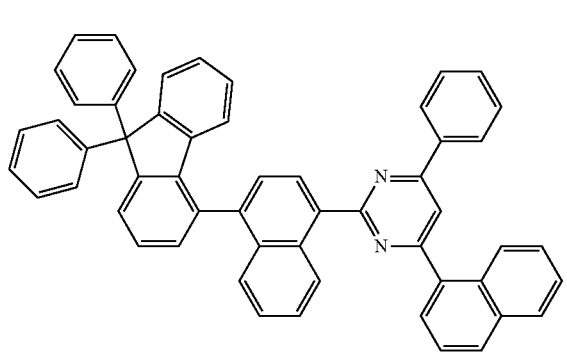

323
-continued
324
-continued
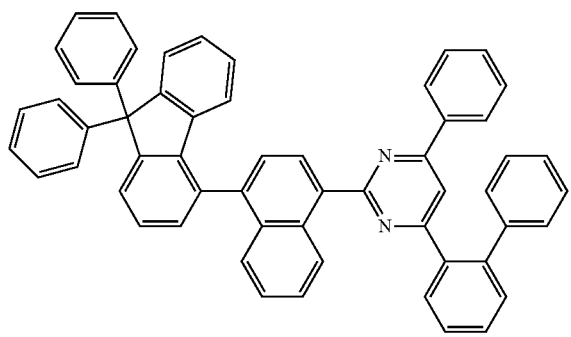
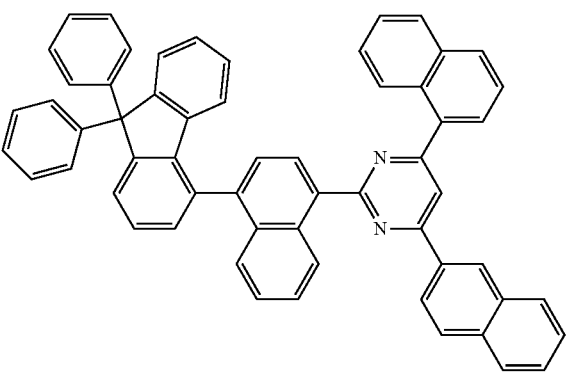
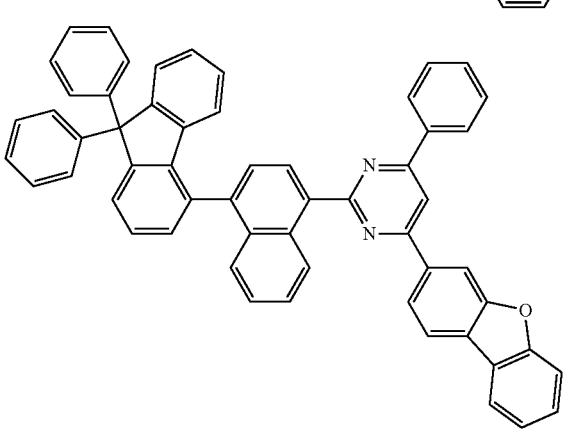
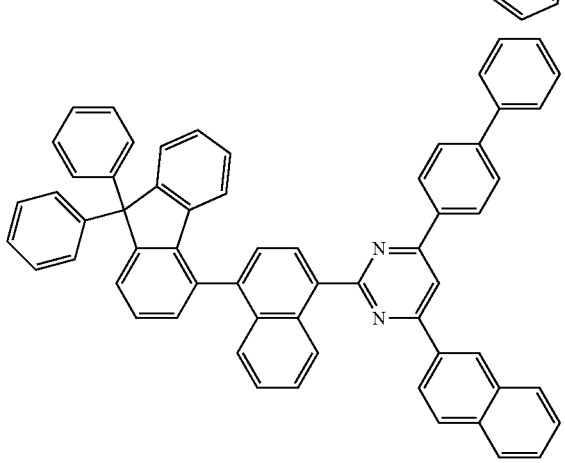
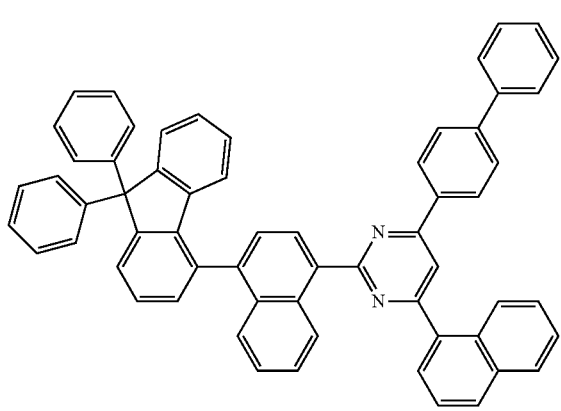

325
-continued
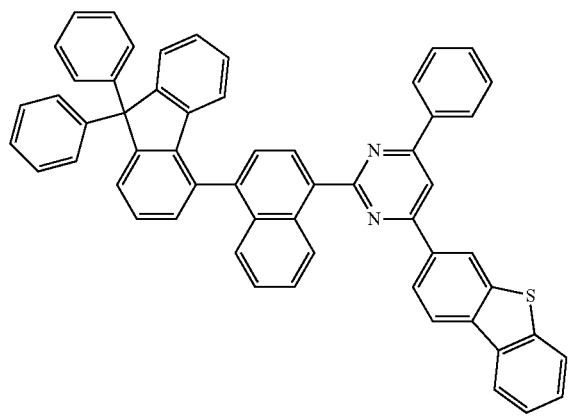
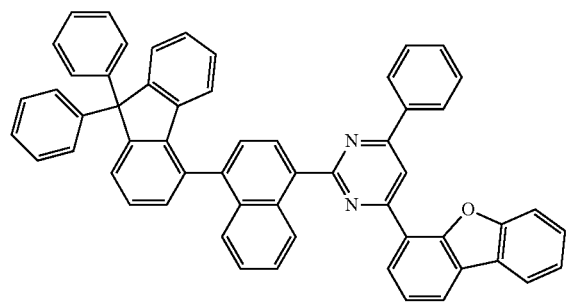
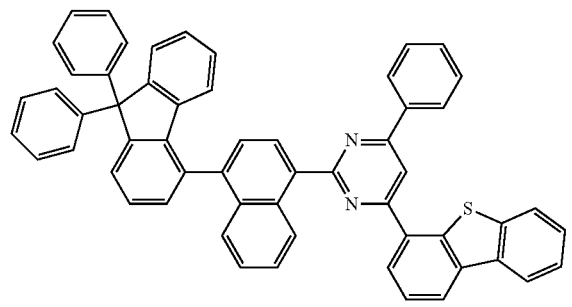
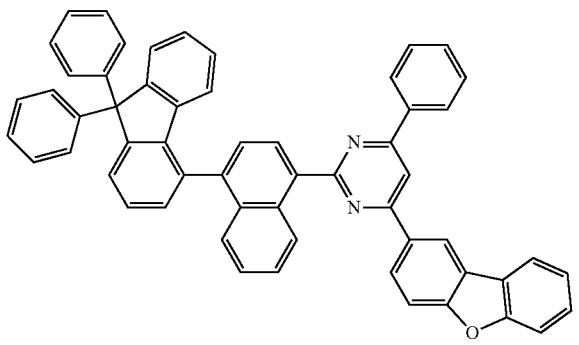
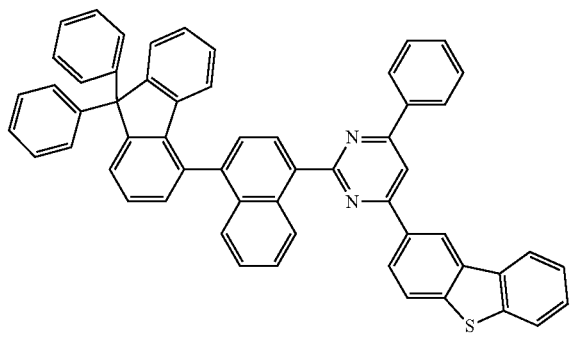
326
-continued
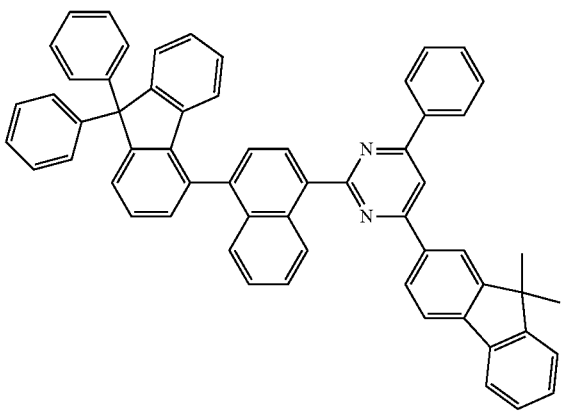
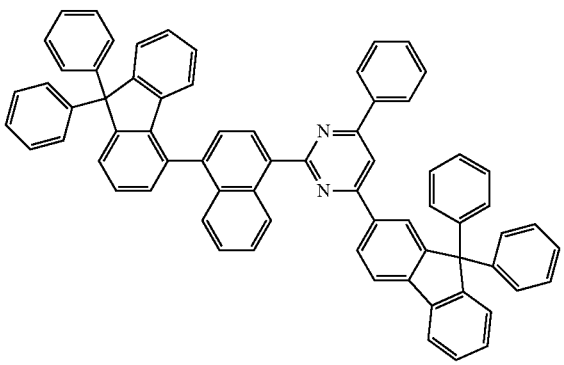
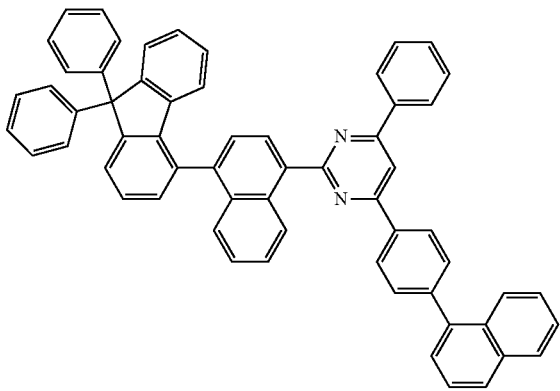
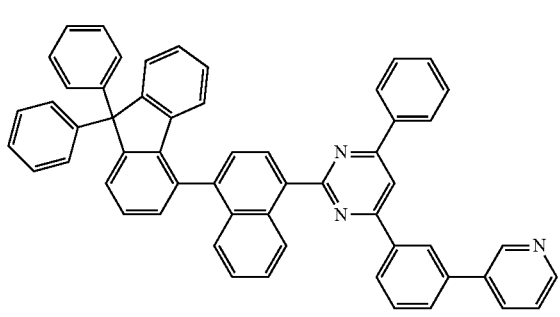

327 -continued
328 -continued
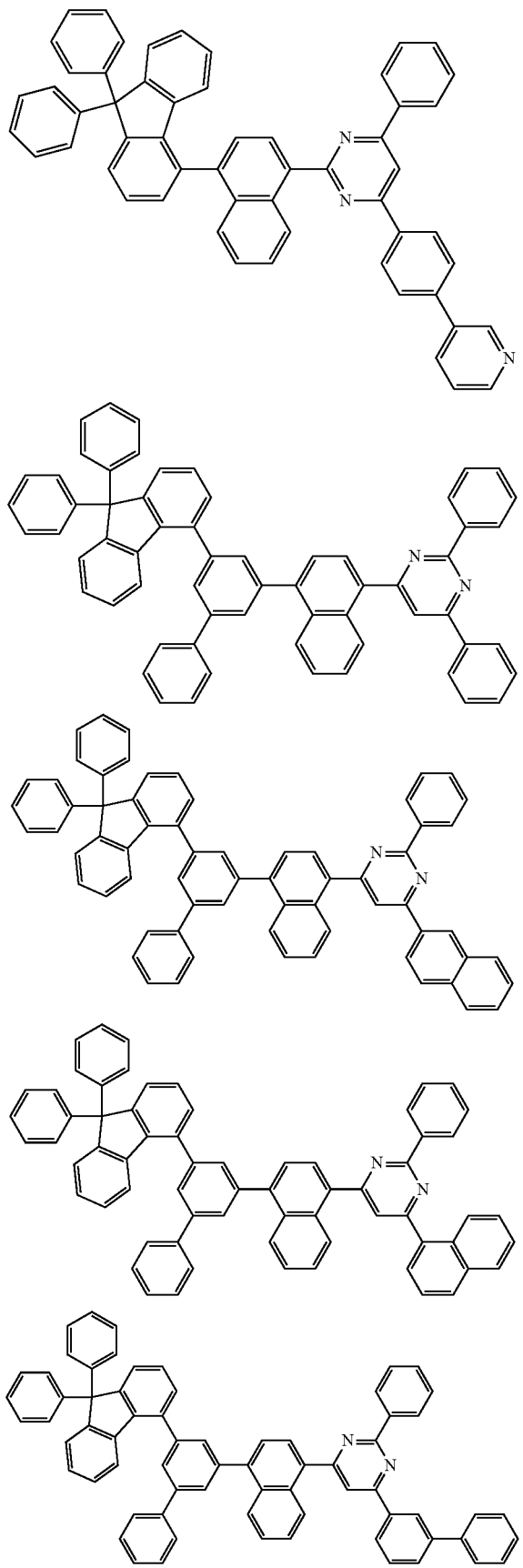
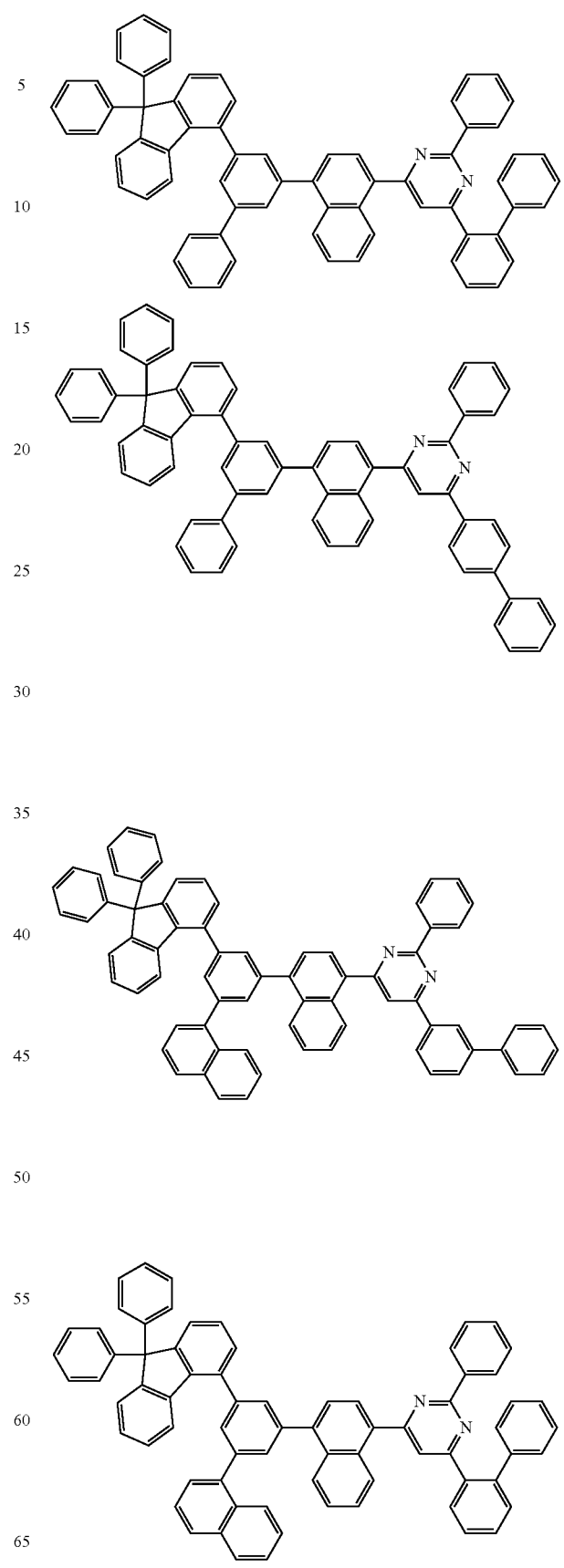

329
-continued
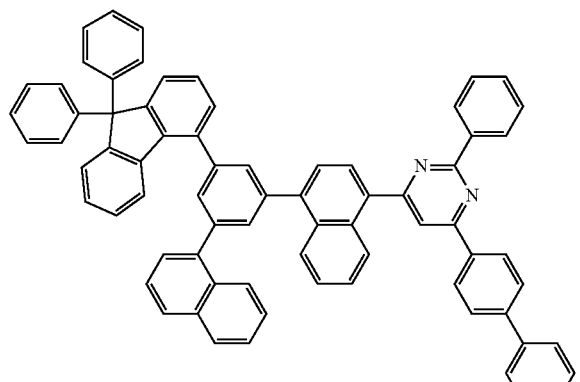
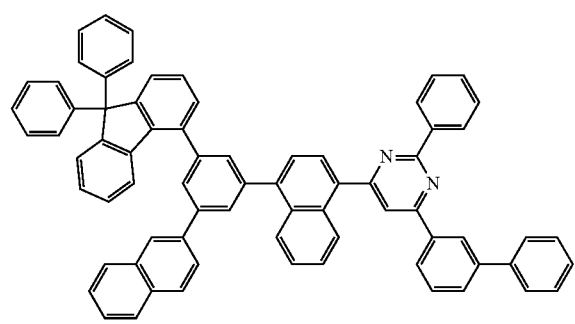
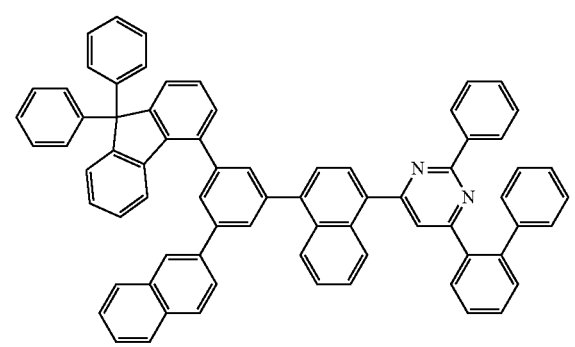
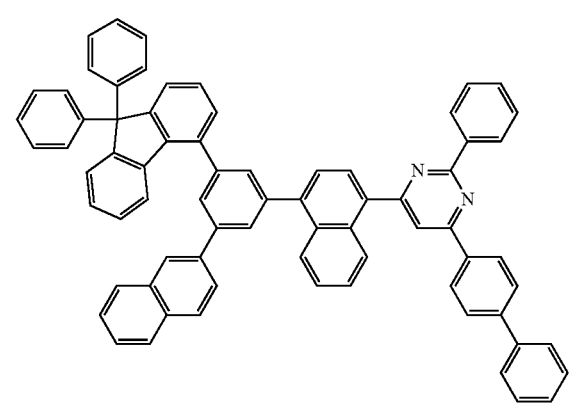
330
-continued
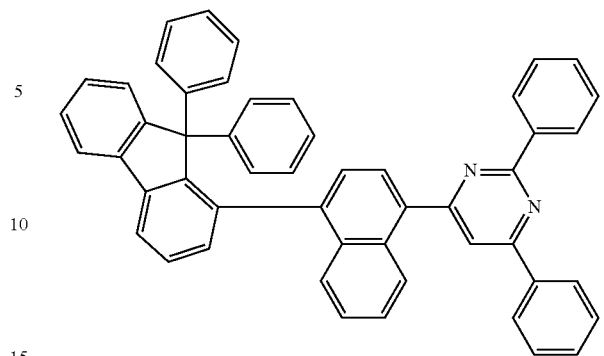
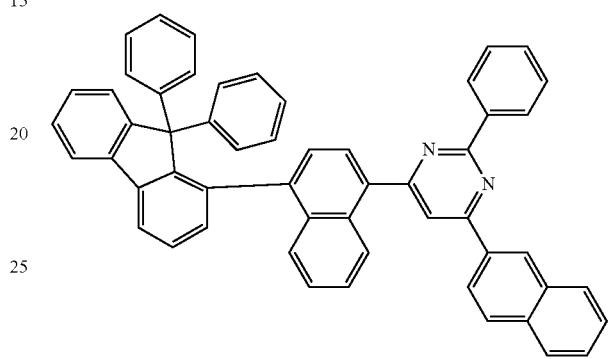
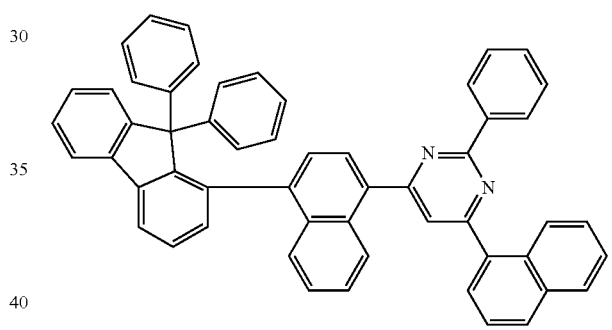
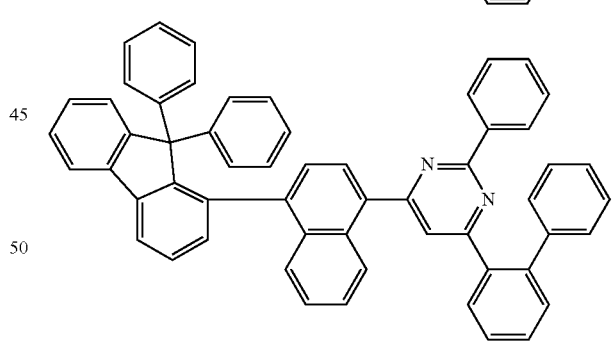

331
-continued
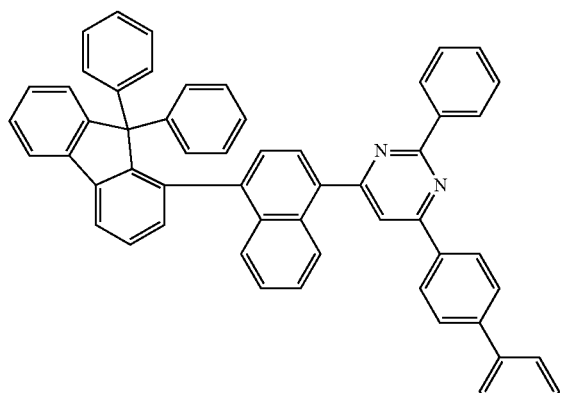
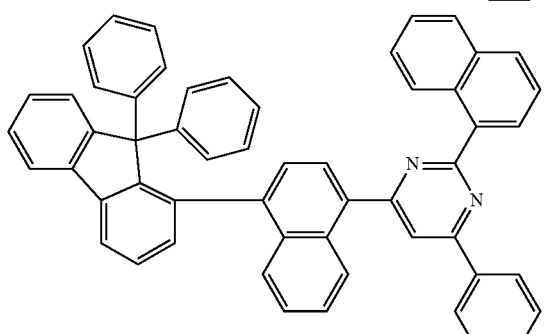
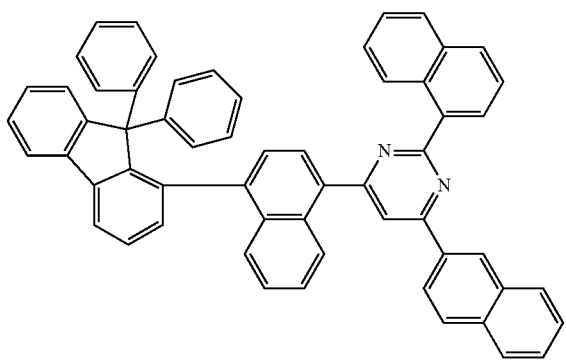
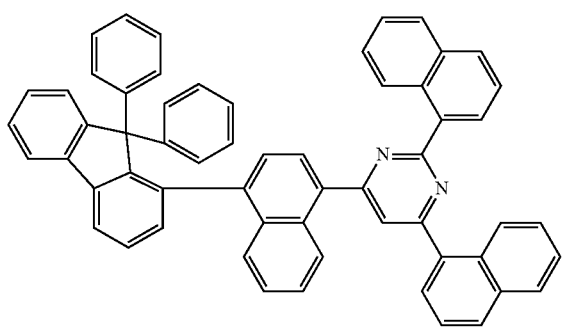
332
-continued
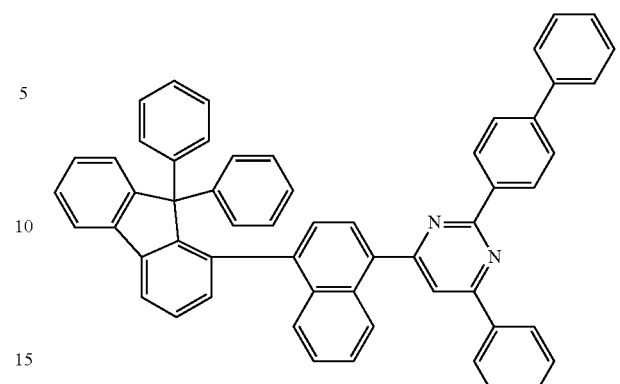
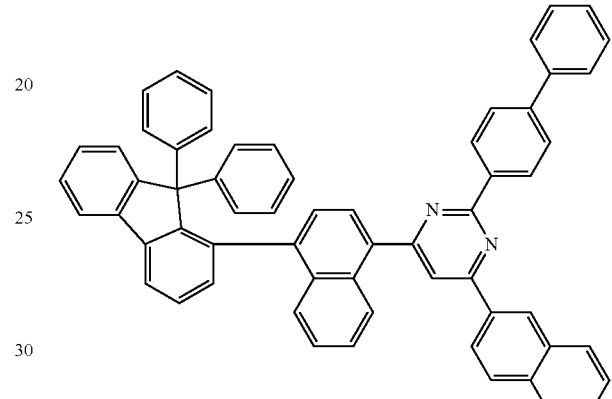
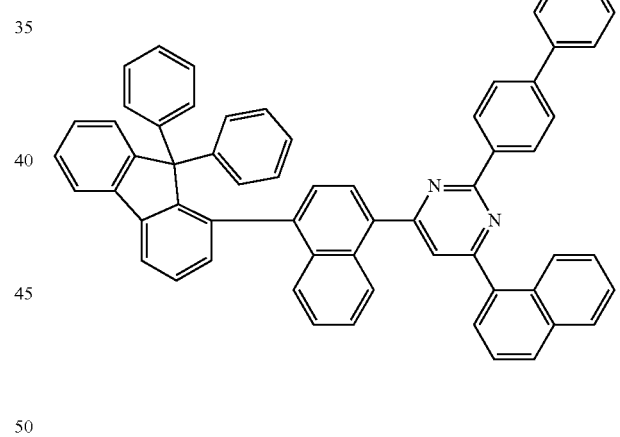
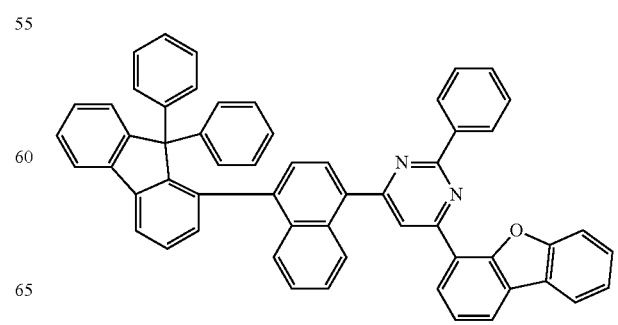

333
-continued
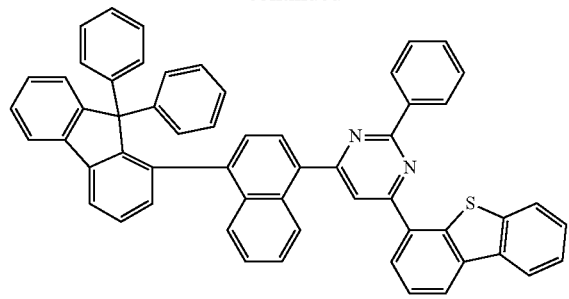
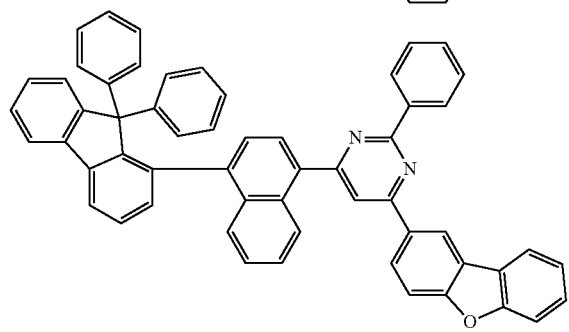
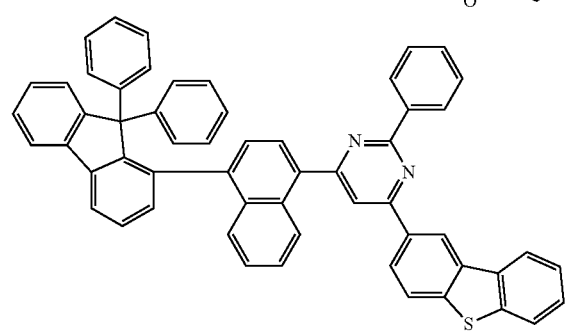
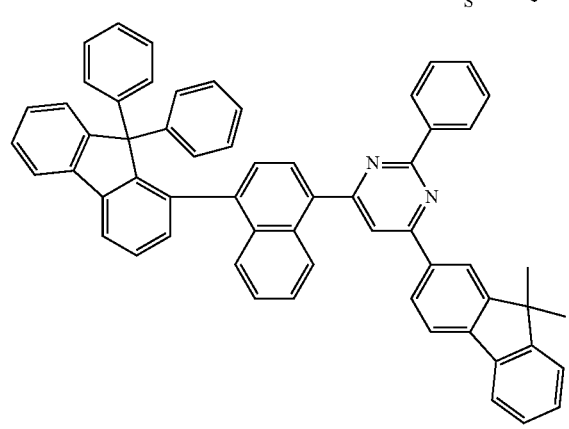
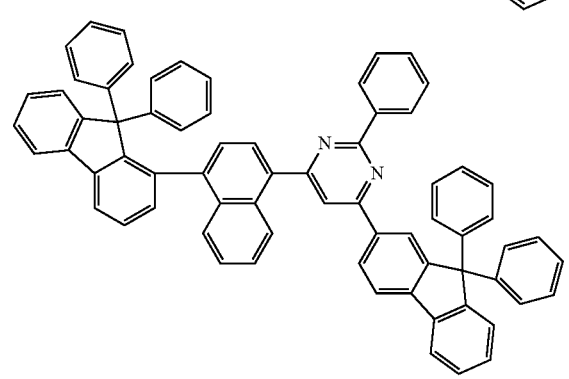
334
-continued
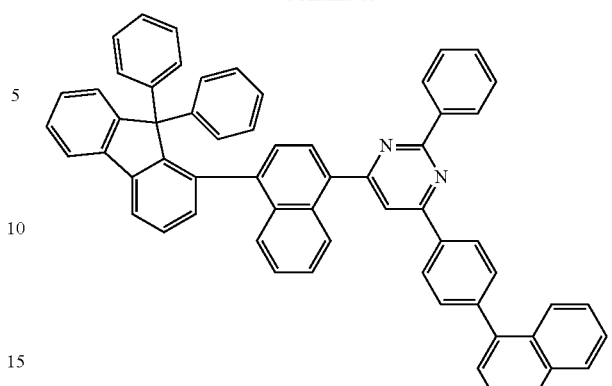
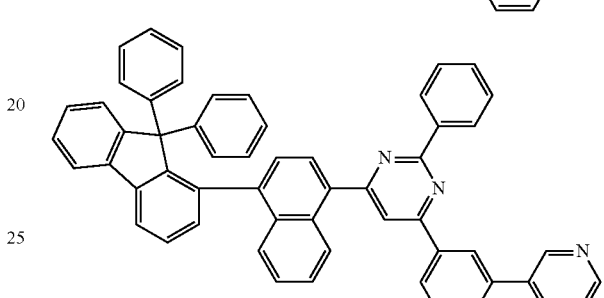
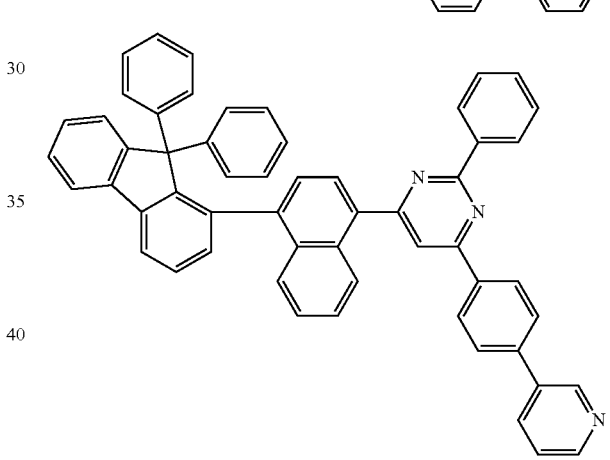
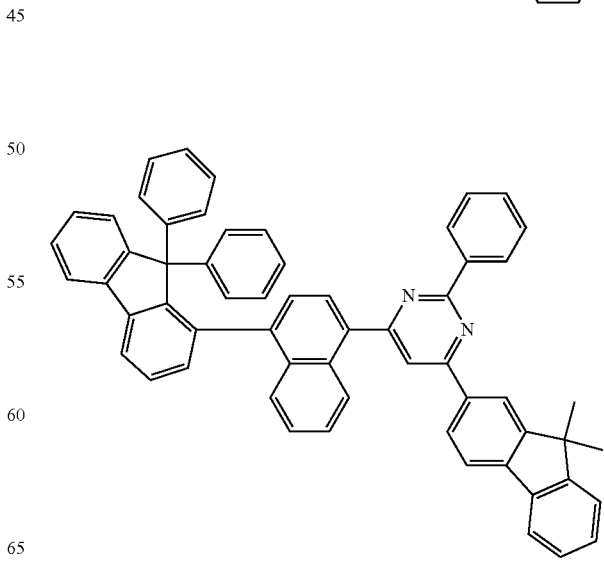

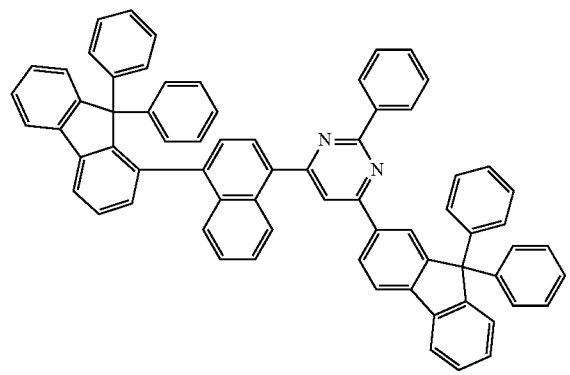
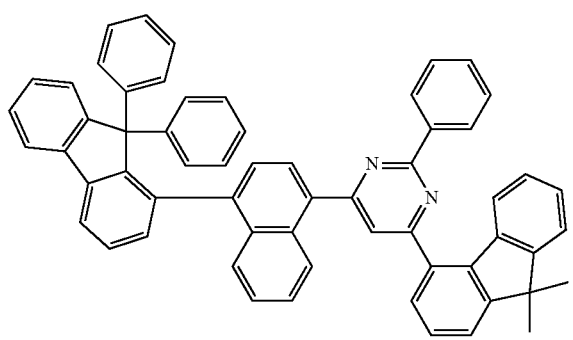
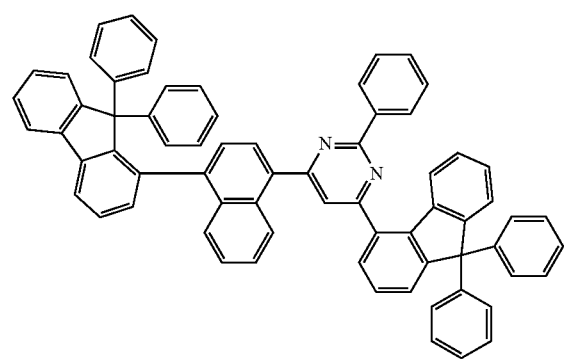
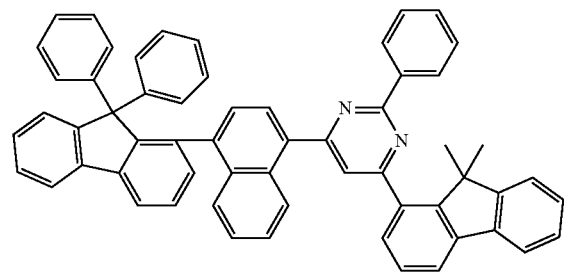
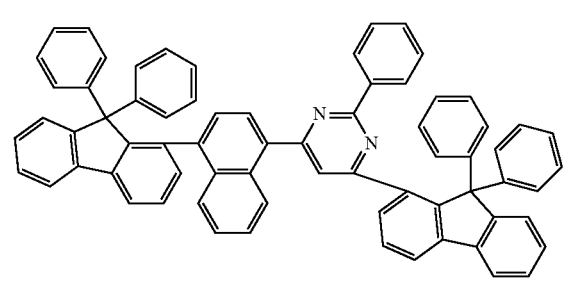
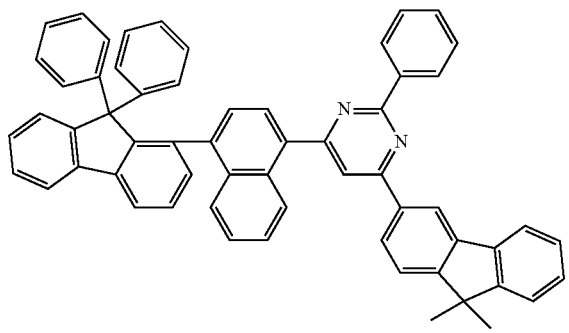
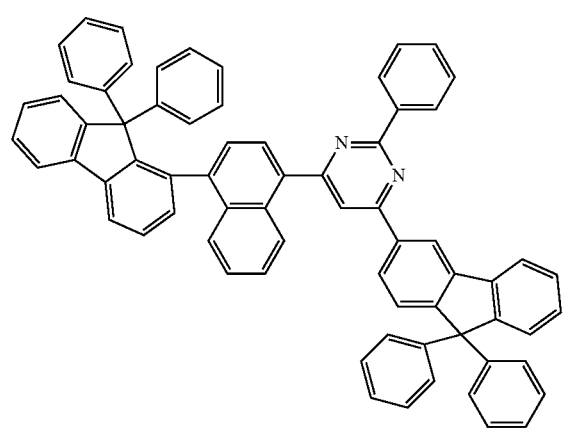
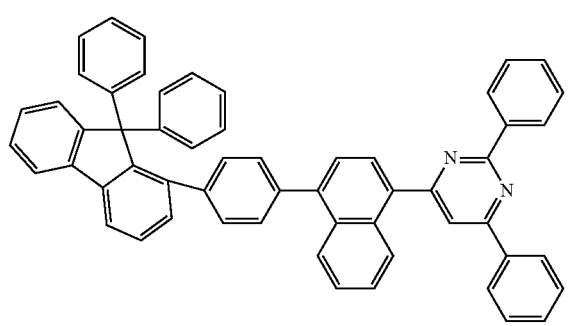
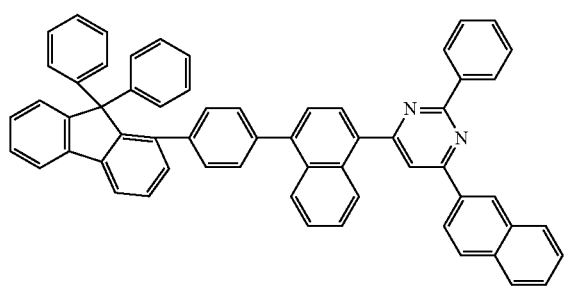
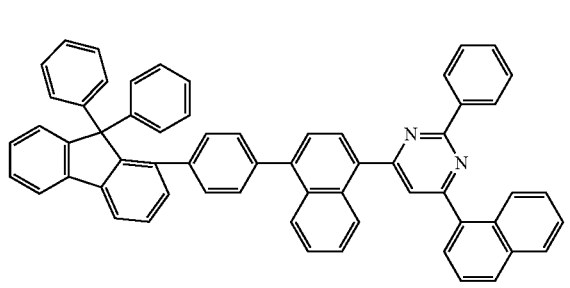

337
-continued
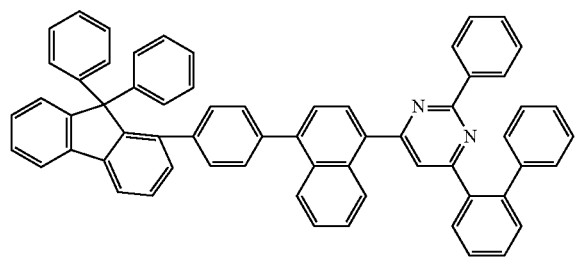
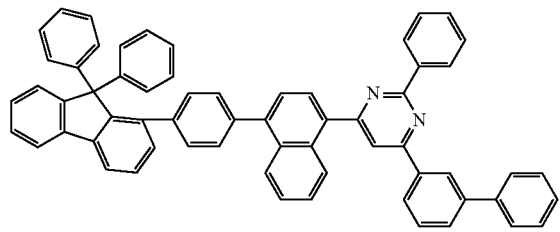
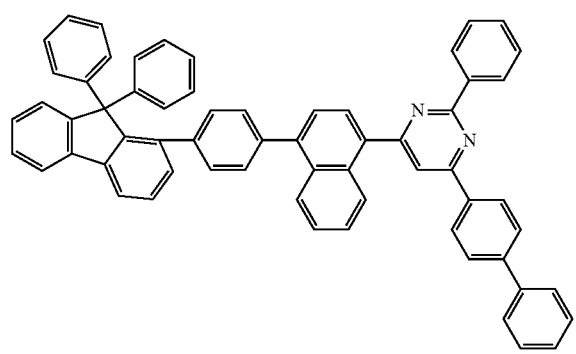
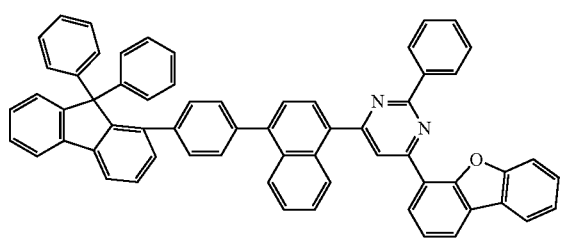
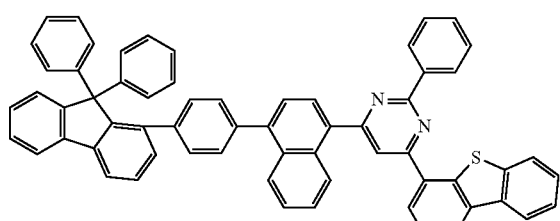
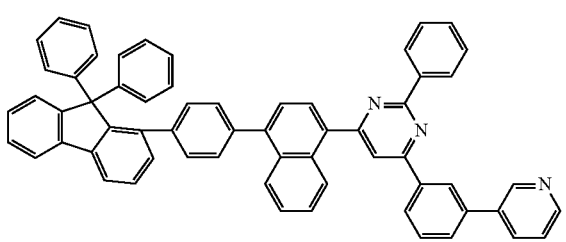
338
-continued
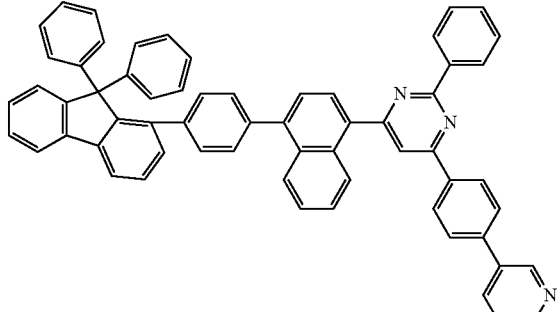
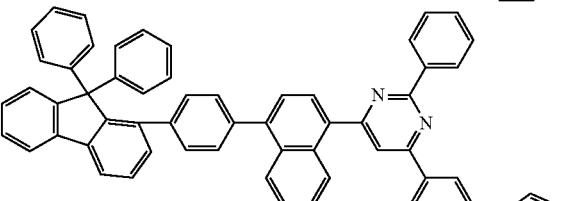
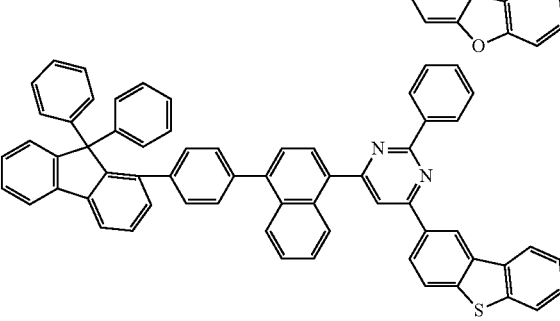
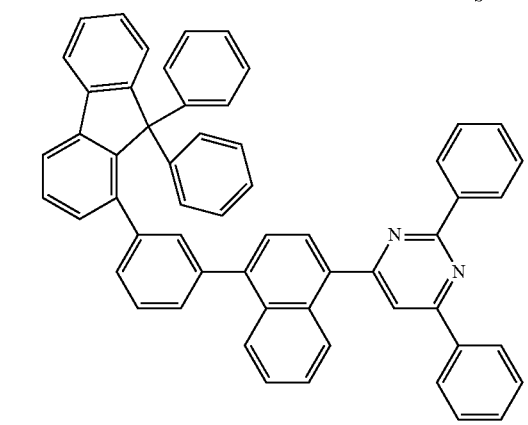
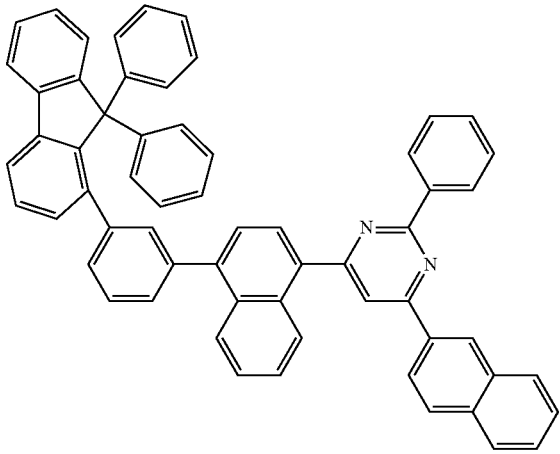

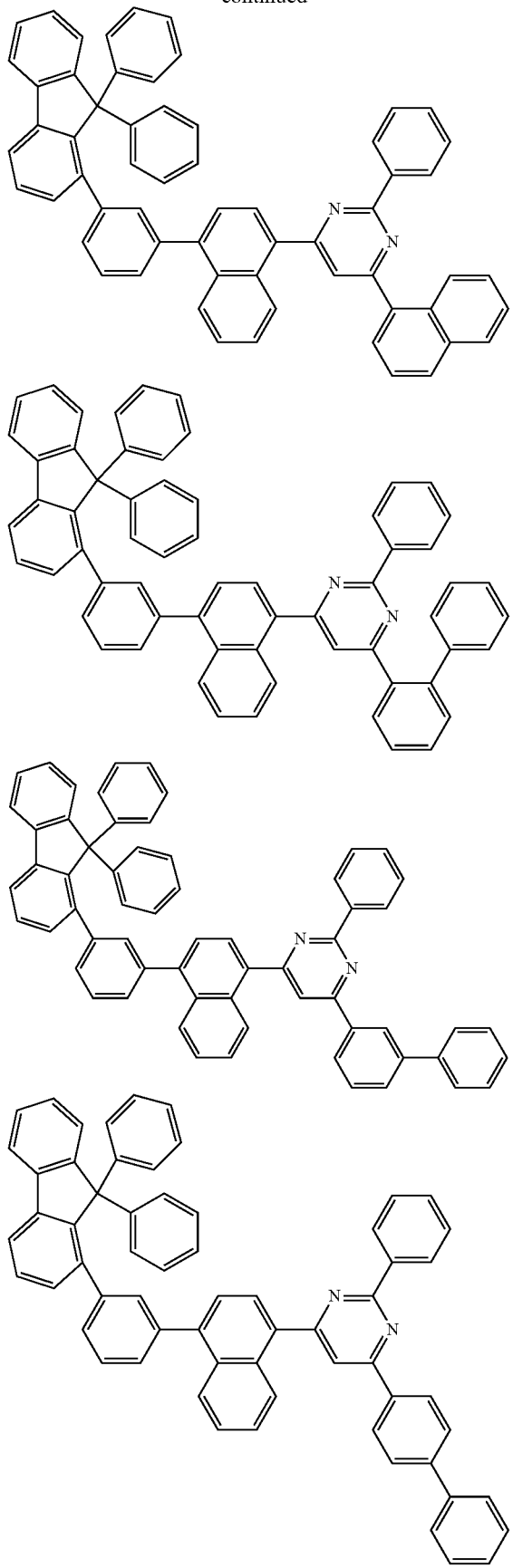
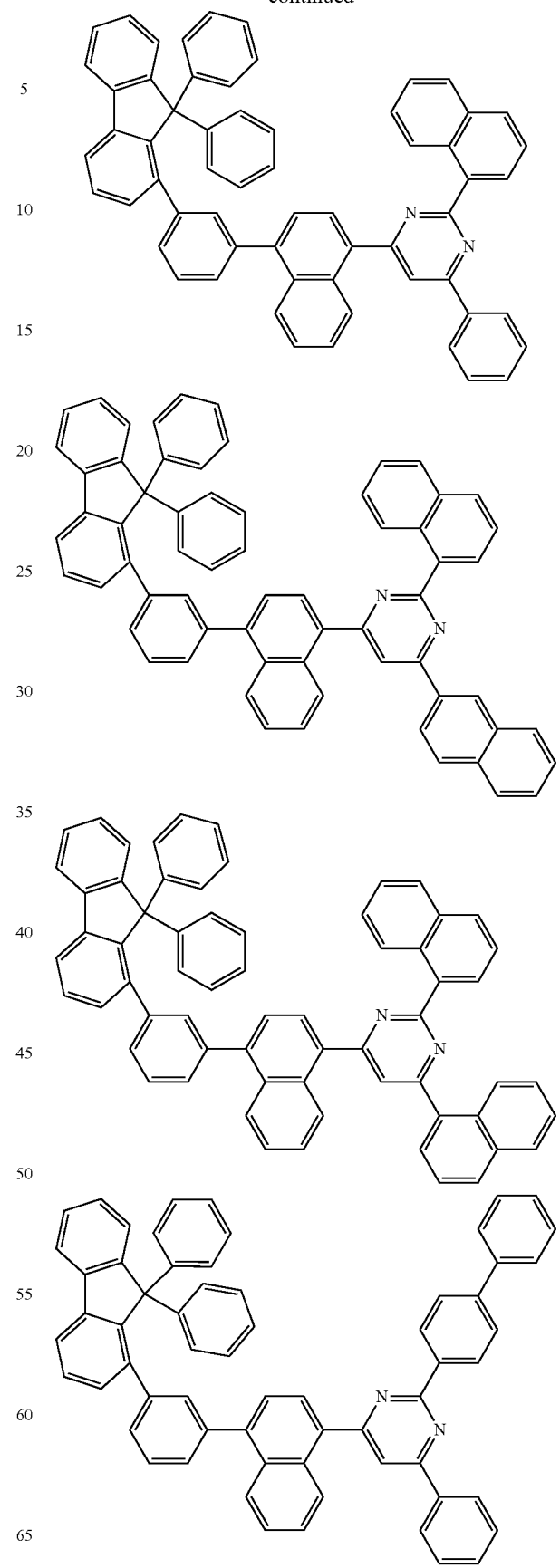

341
-continued
342
-continued
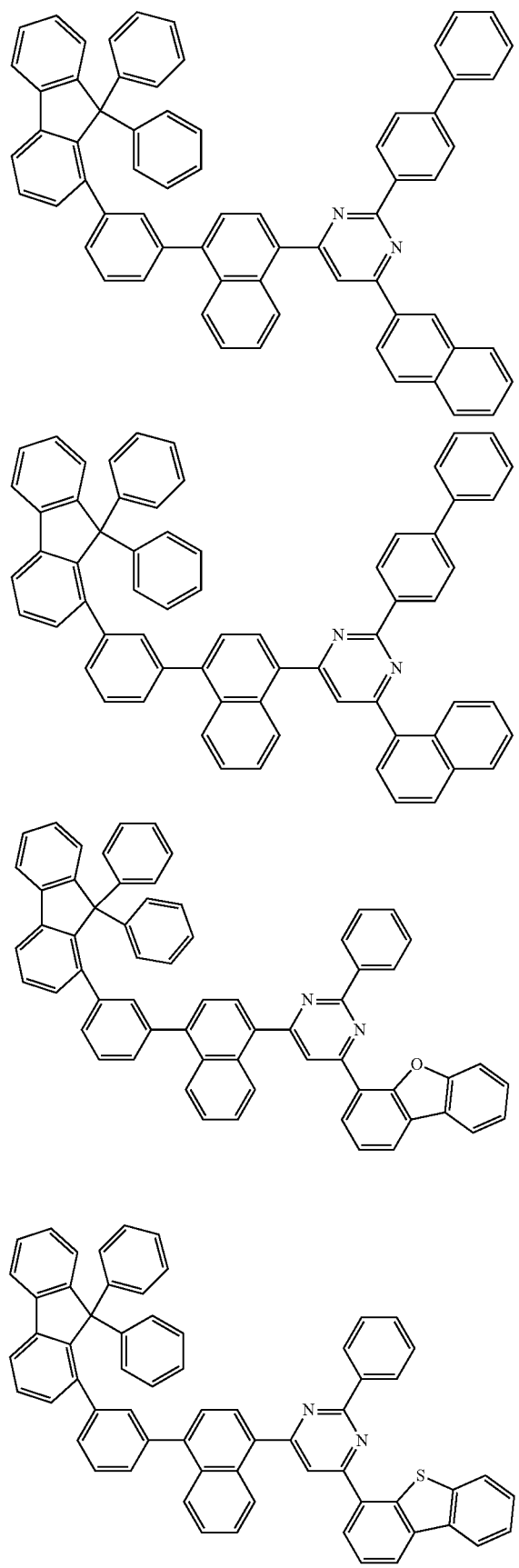
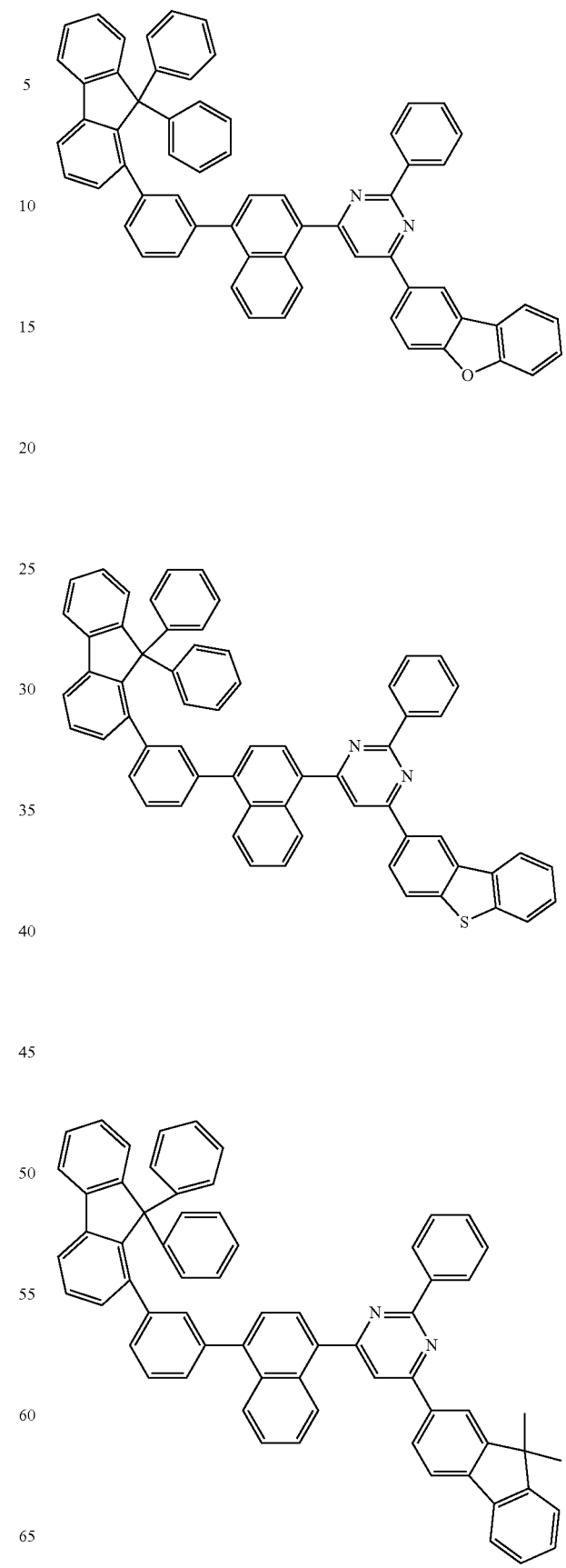

343
-continued
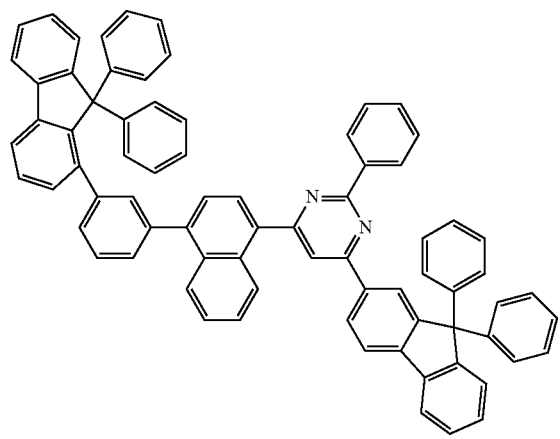
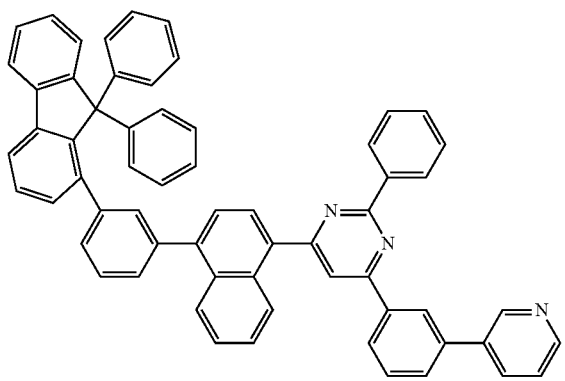
344
-continued
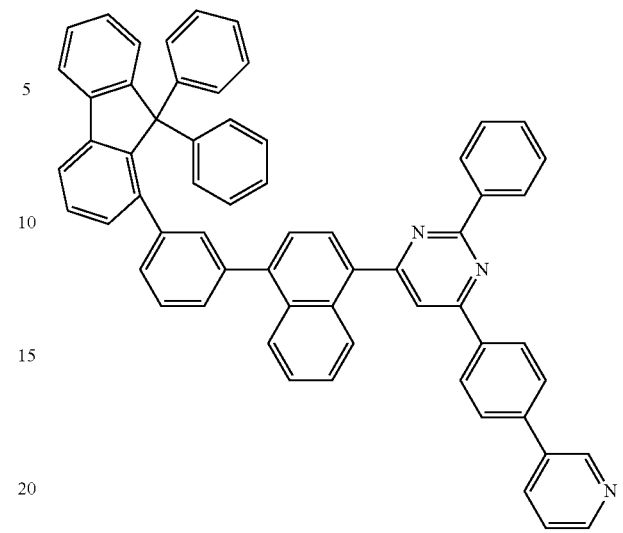
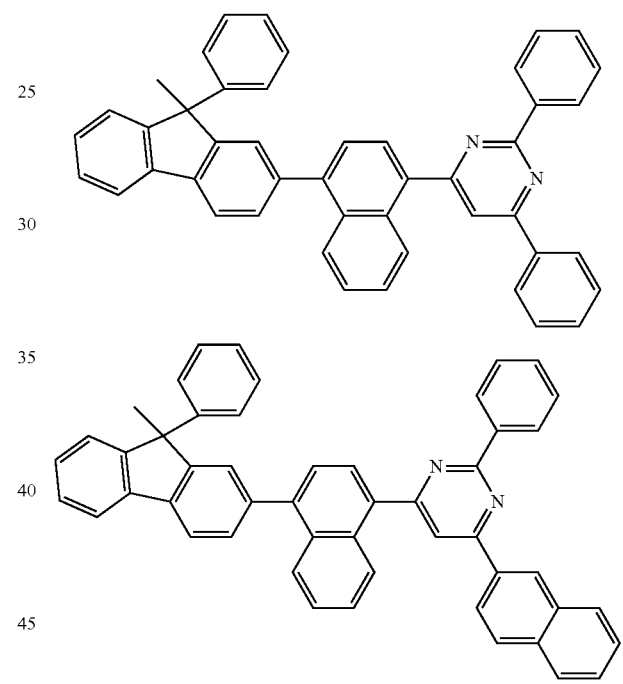
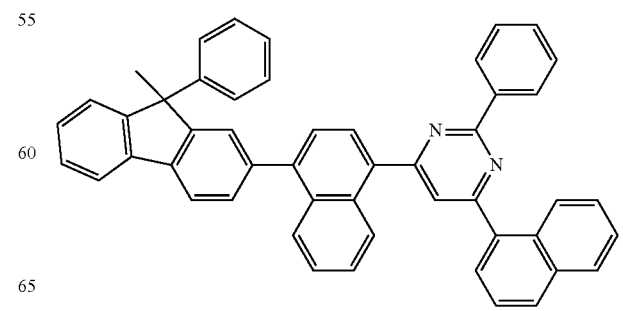

345
-continued
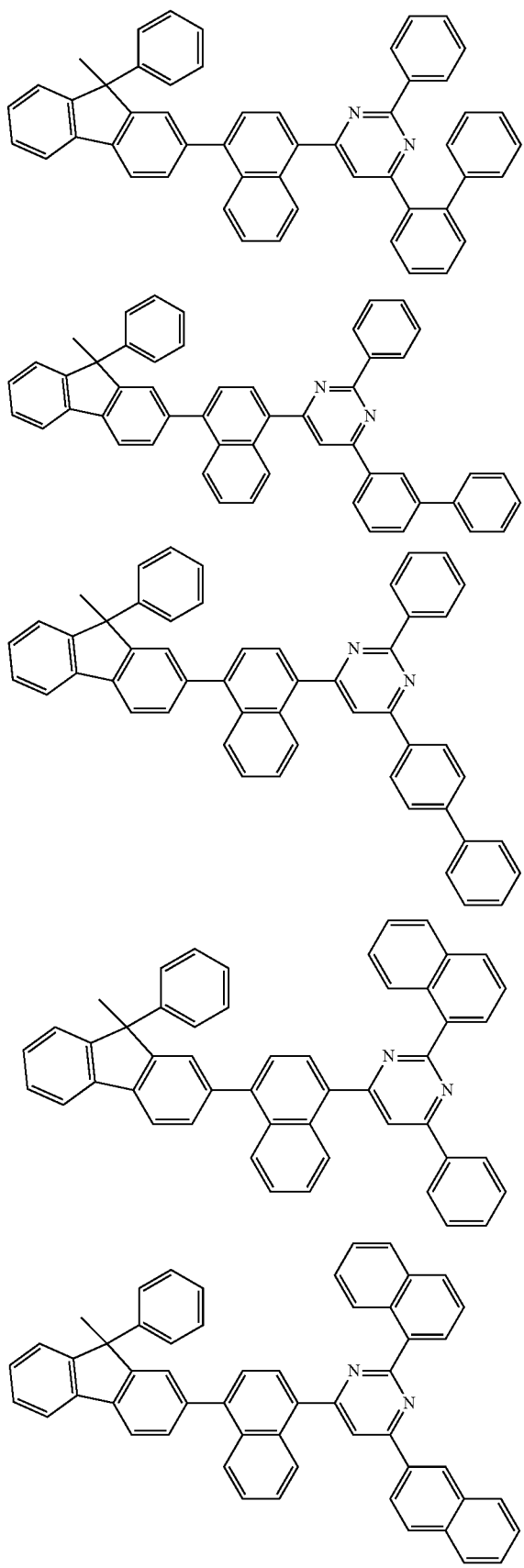
346
-continued
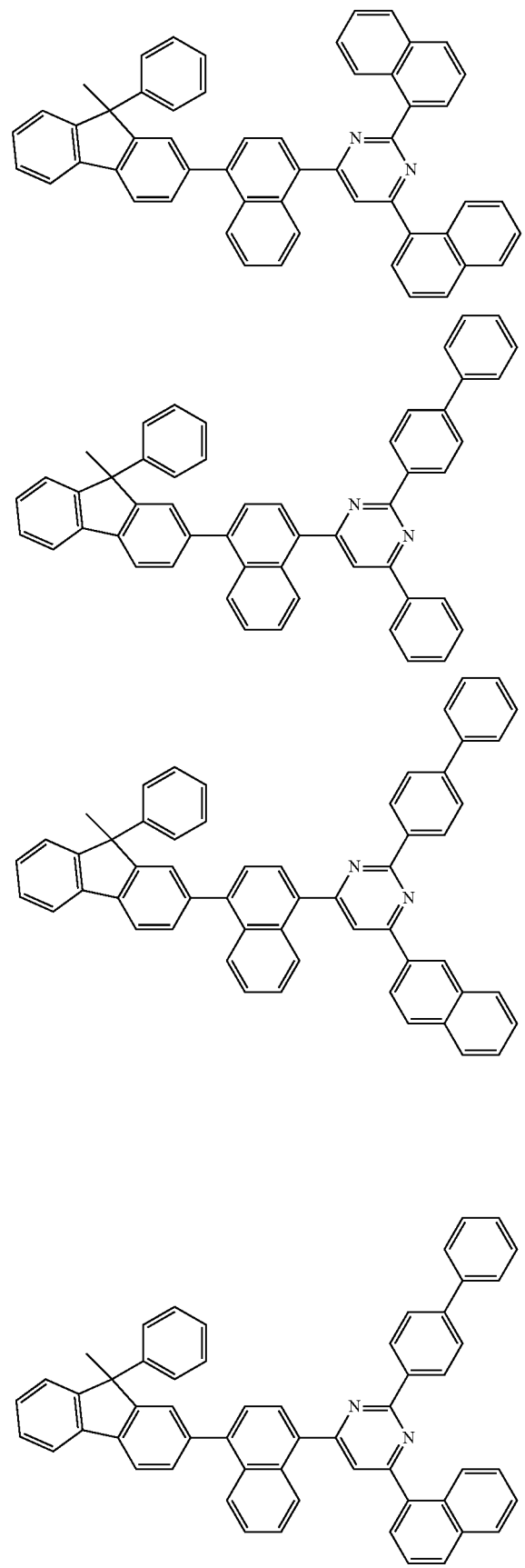

347
-continued
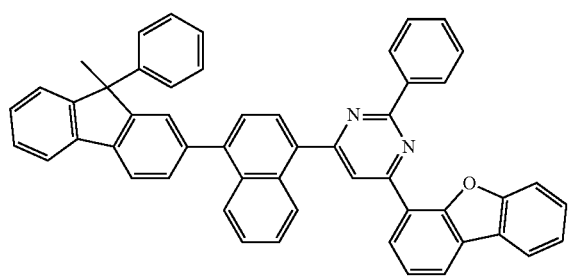
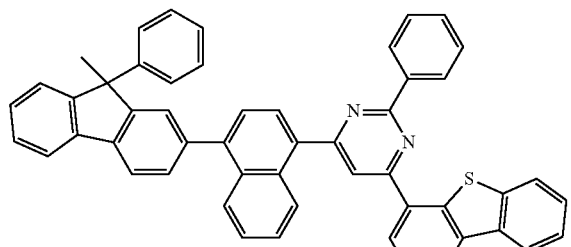
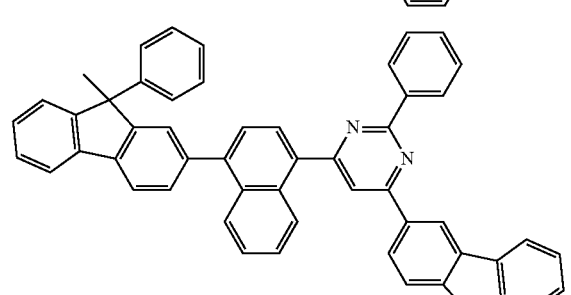
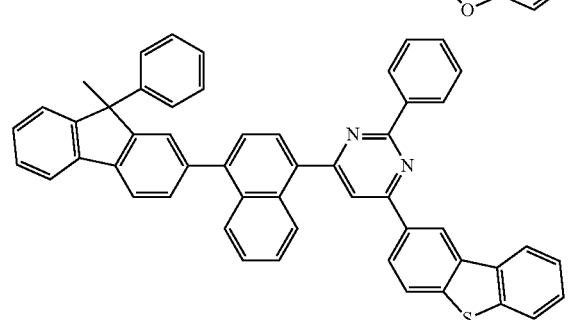
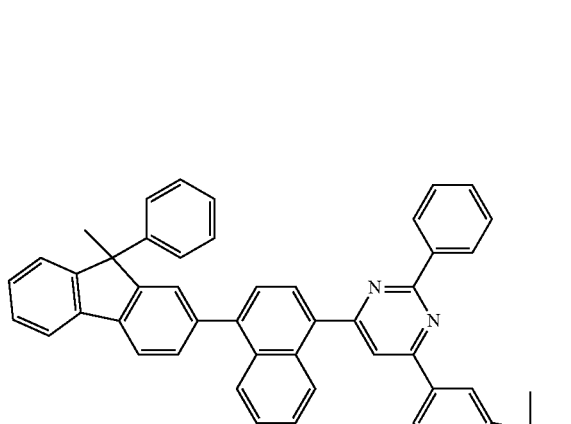
348
-continued
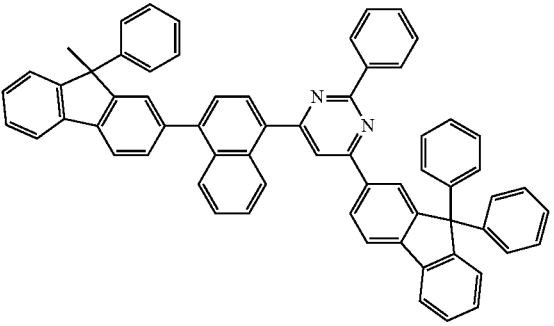
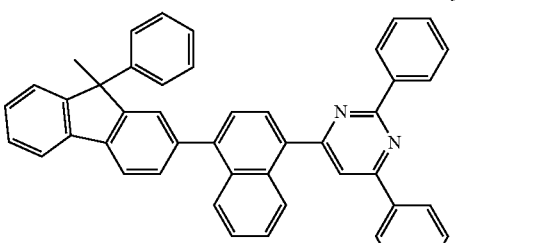
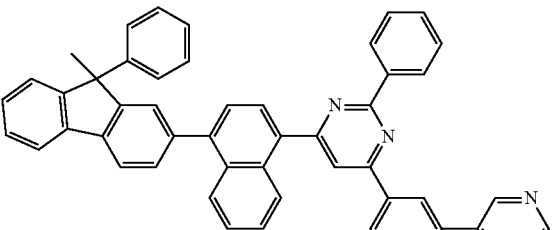
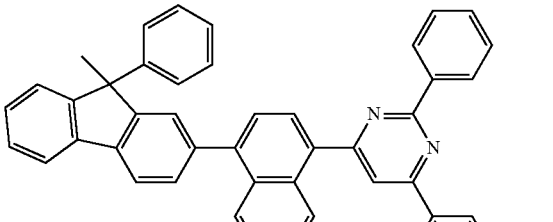
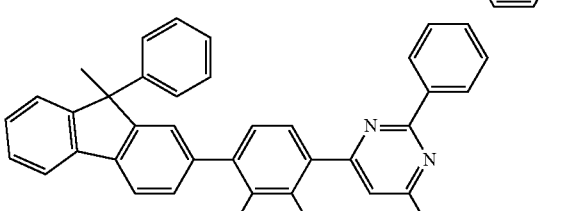
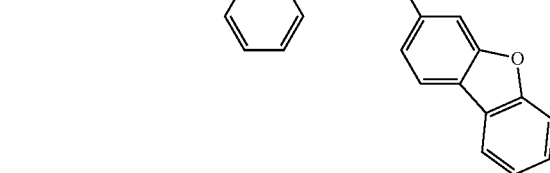

349
-continued
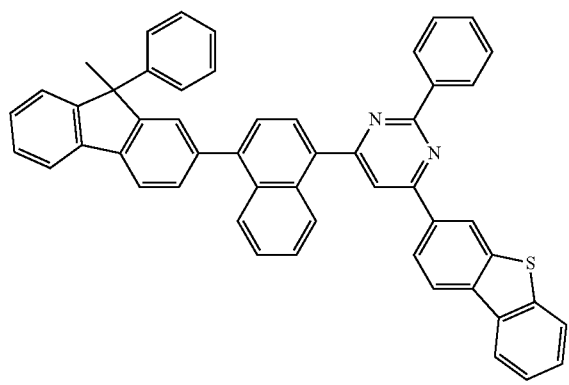
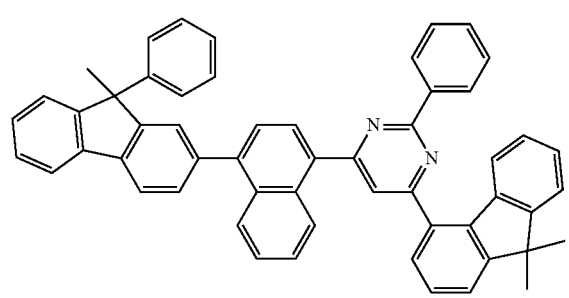
350
-continued
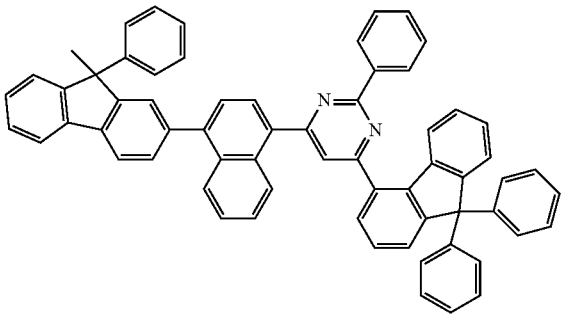
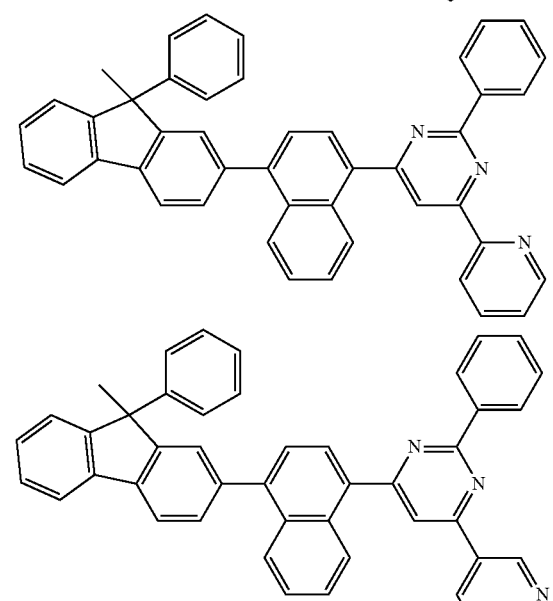
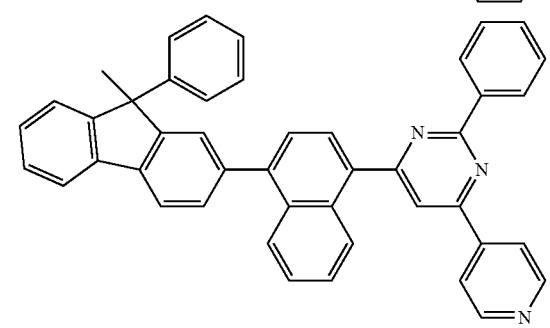
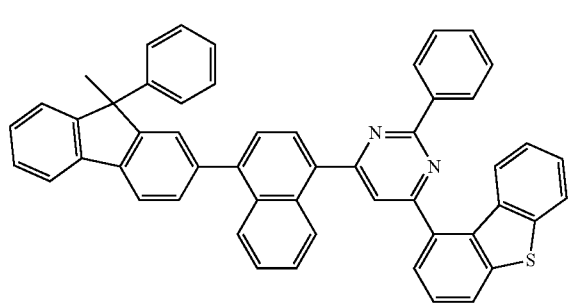
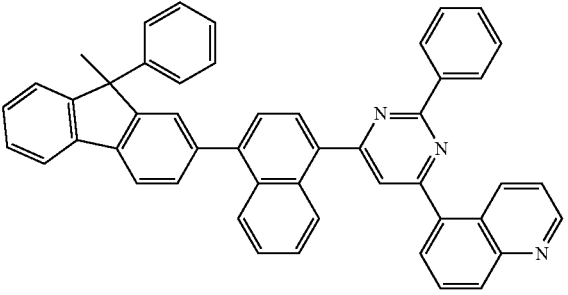

351
-continued
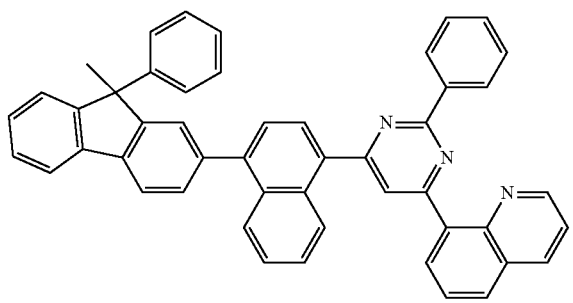
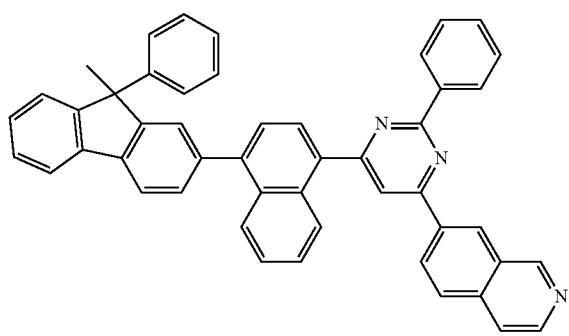
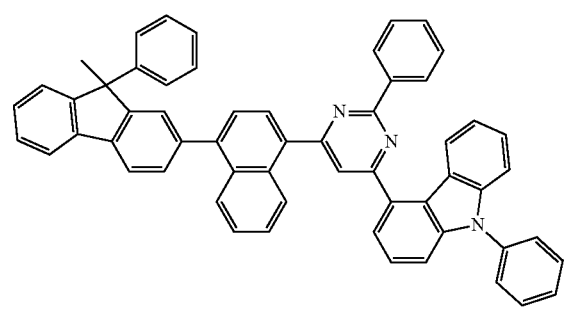
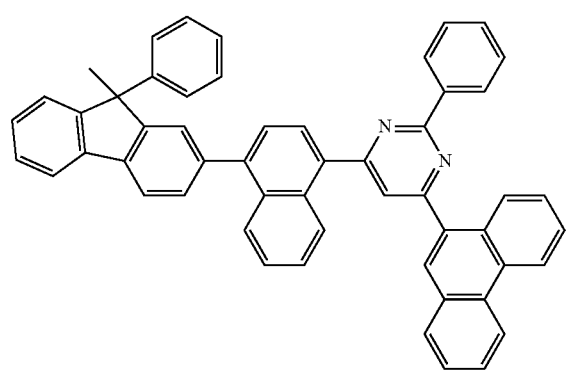
352
-continued
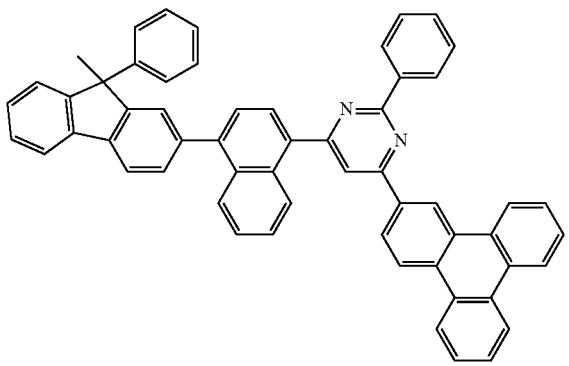
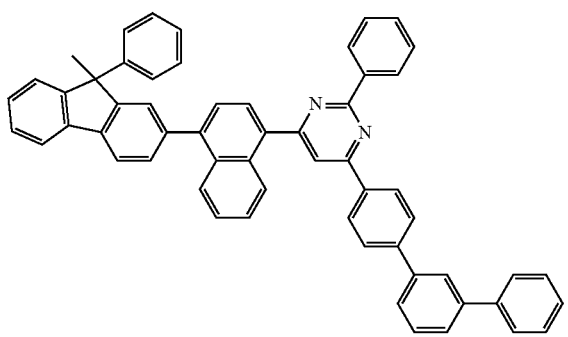
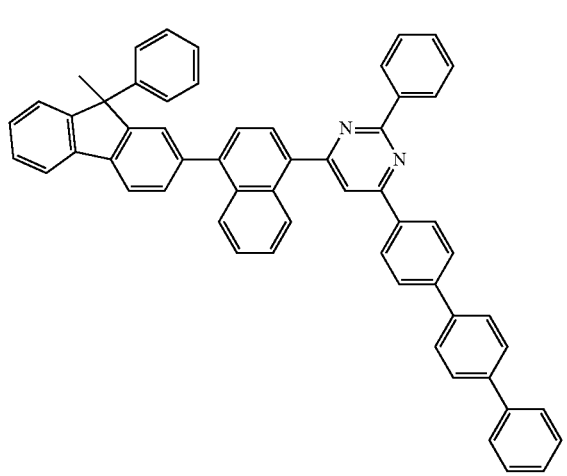

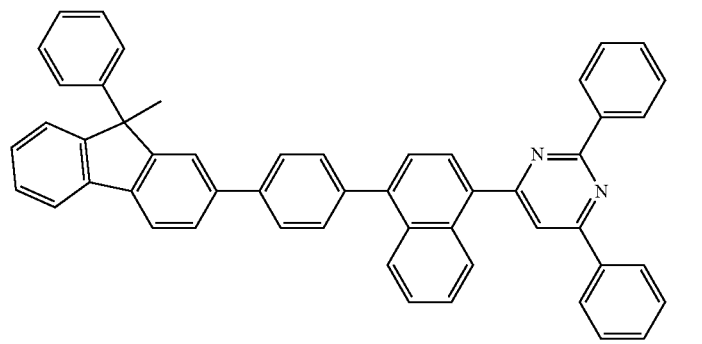
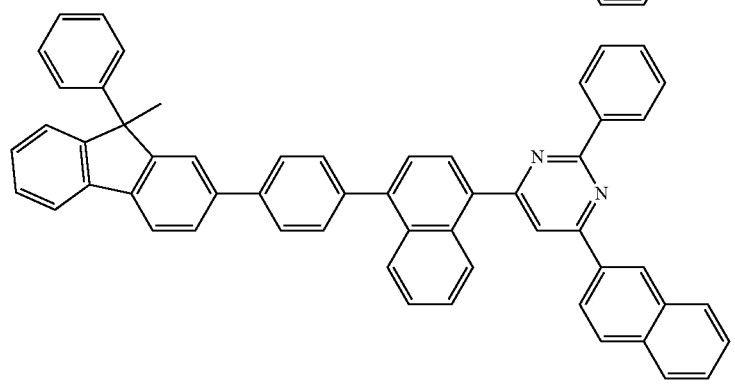
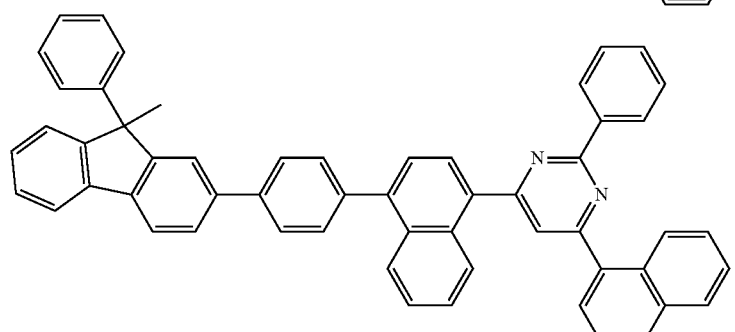
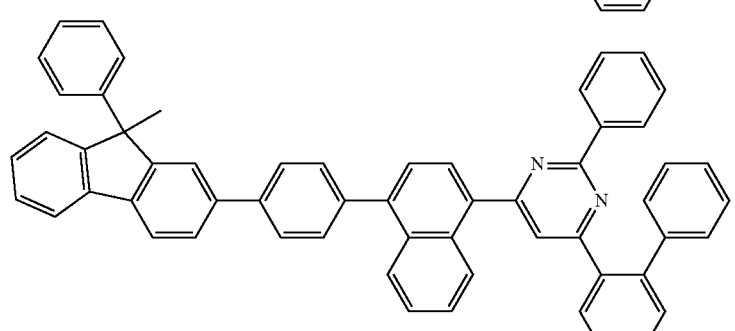
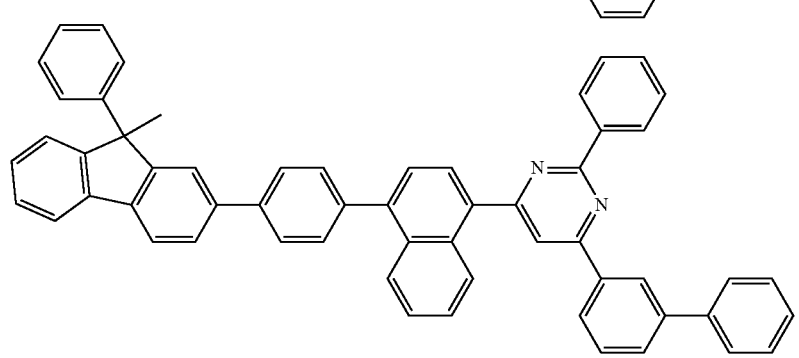

-continued
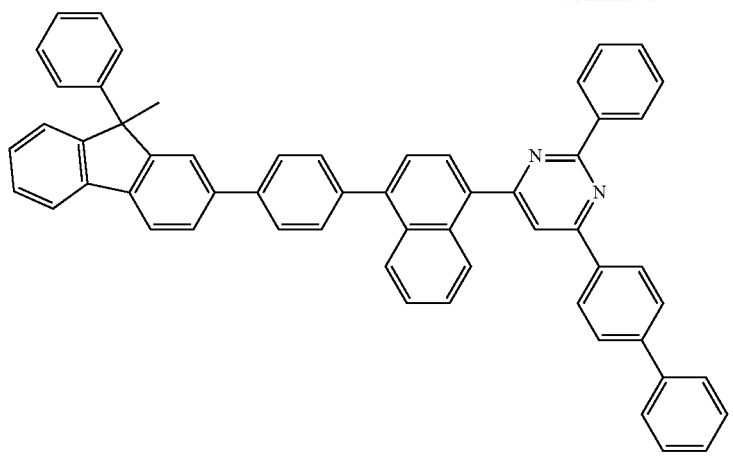
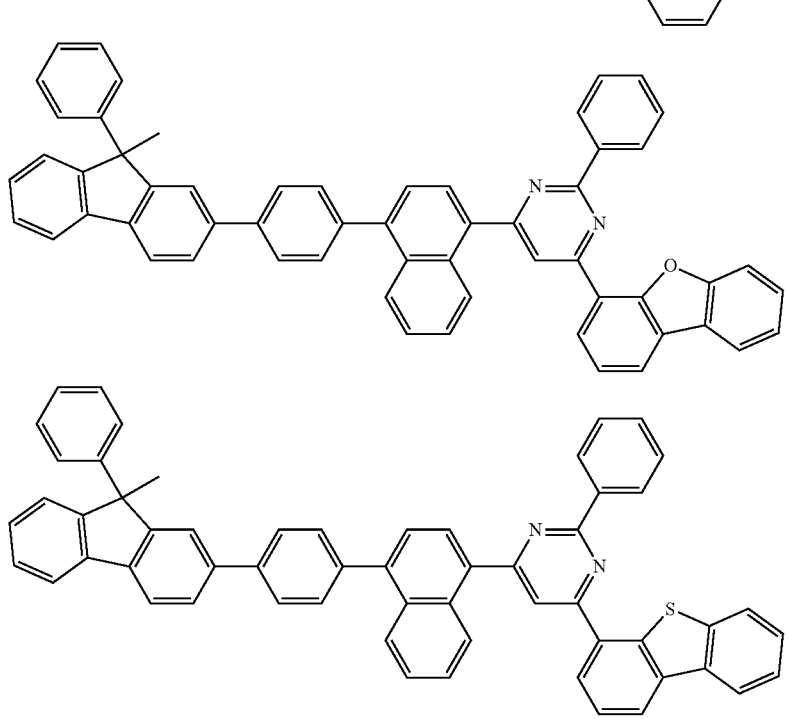
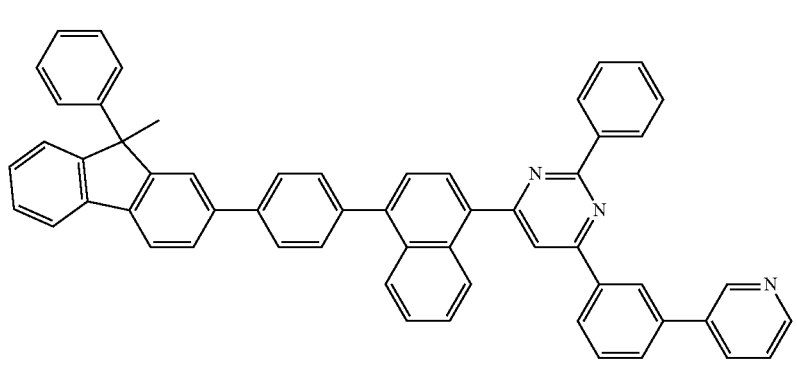

-continued
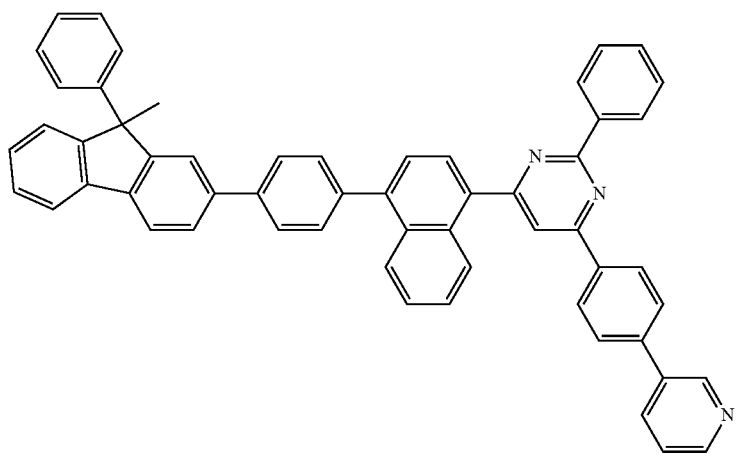
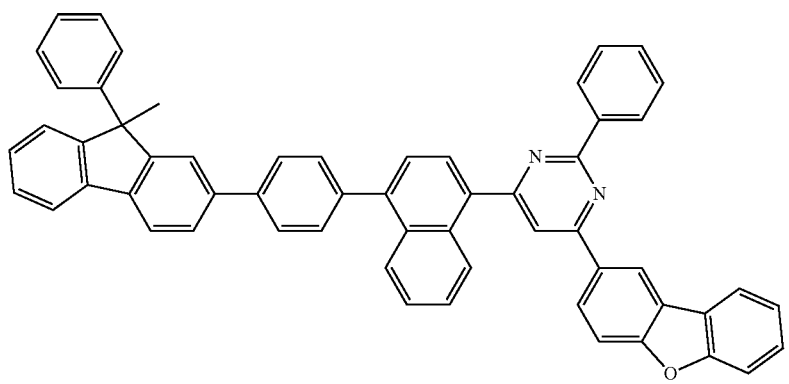
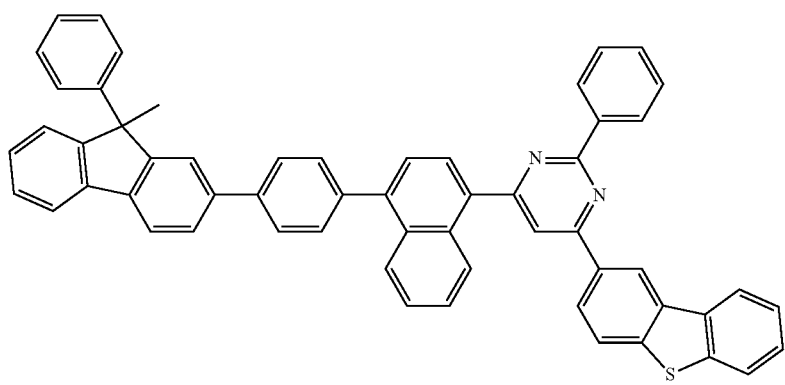
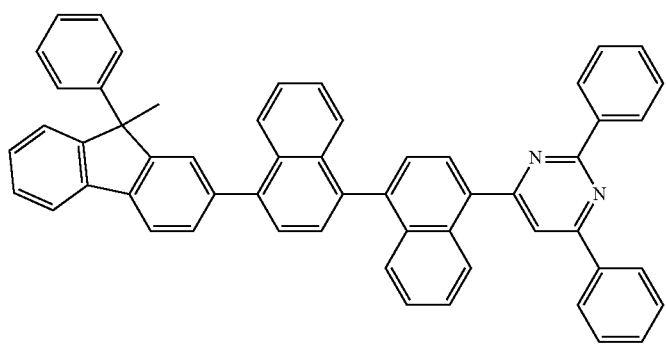

-continued
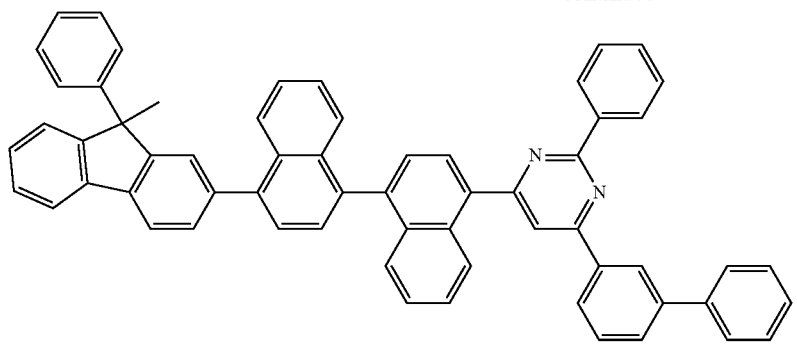
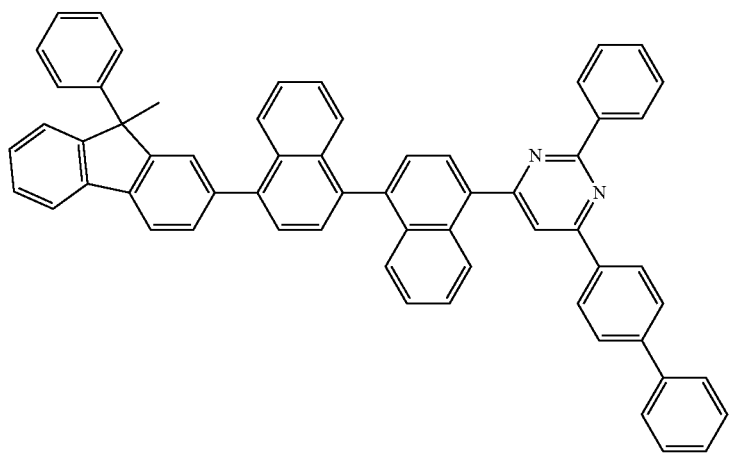
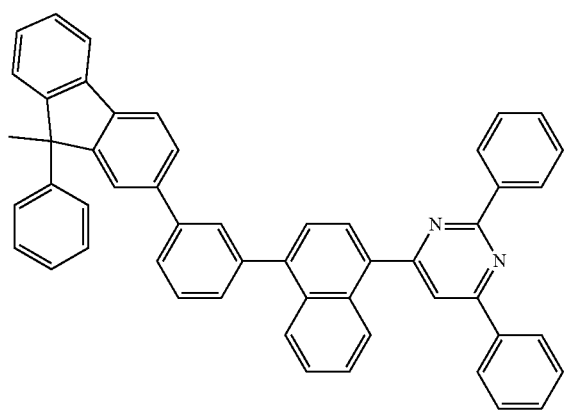
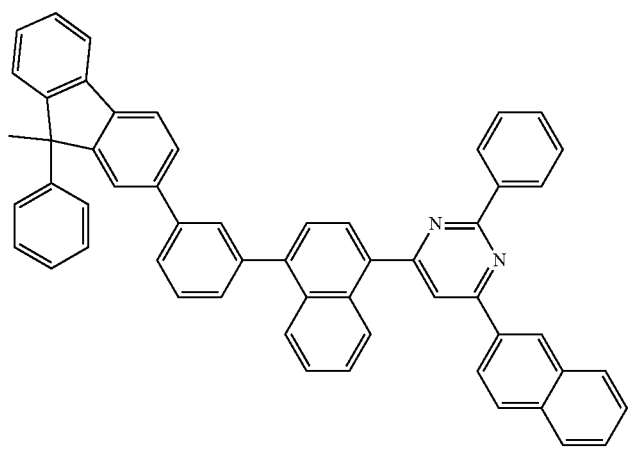

-continued
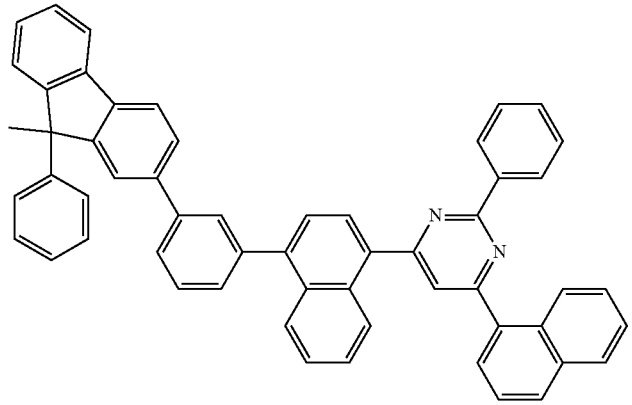
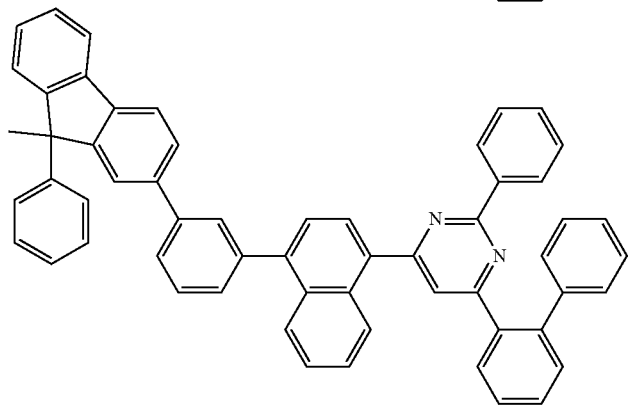
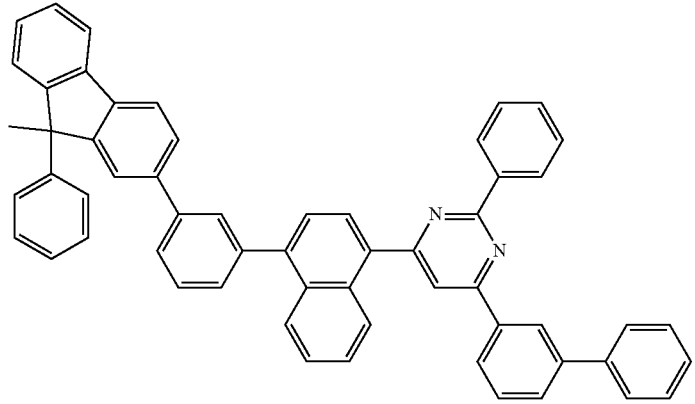
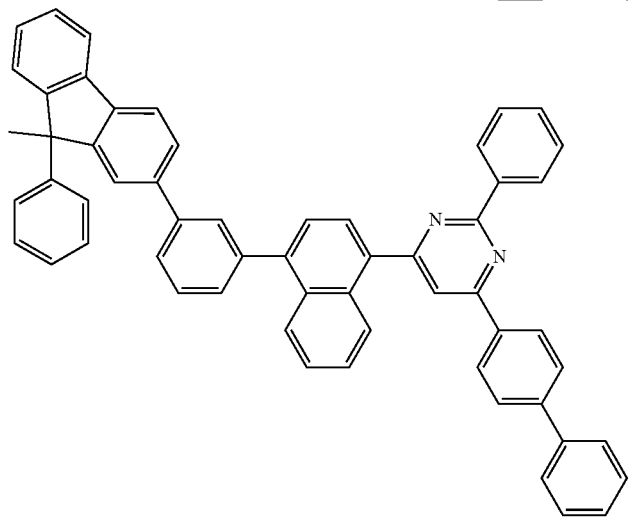

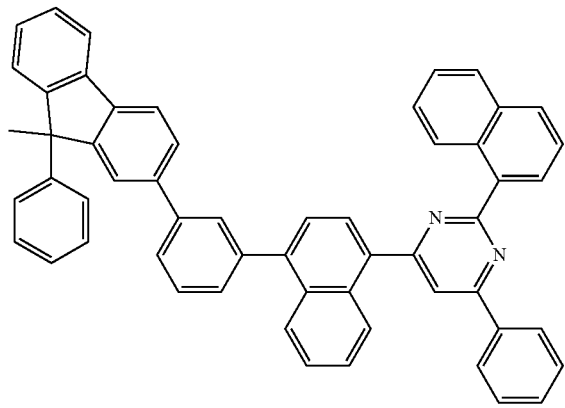
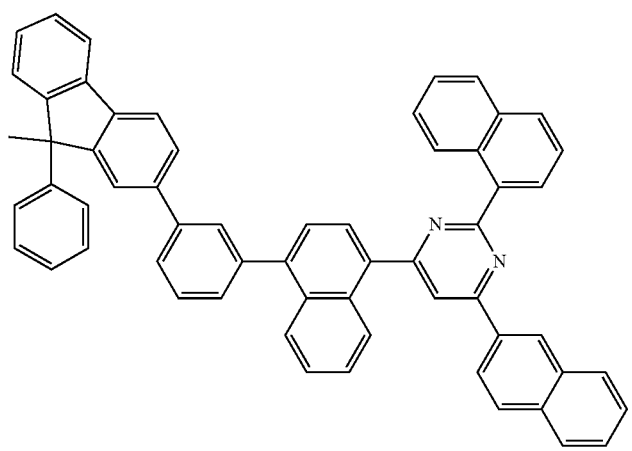
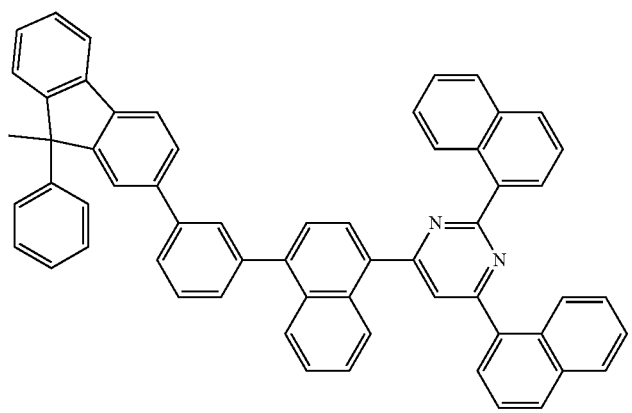
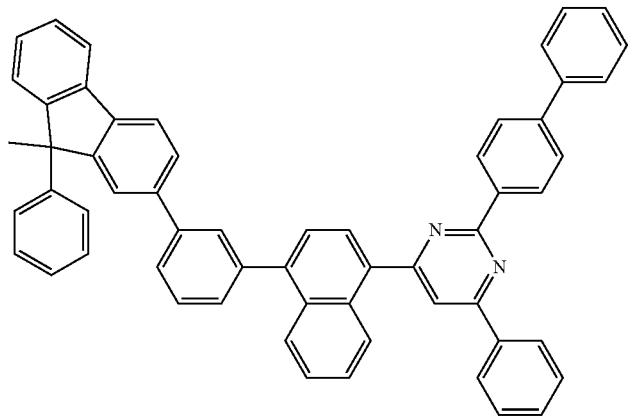

-continued
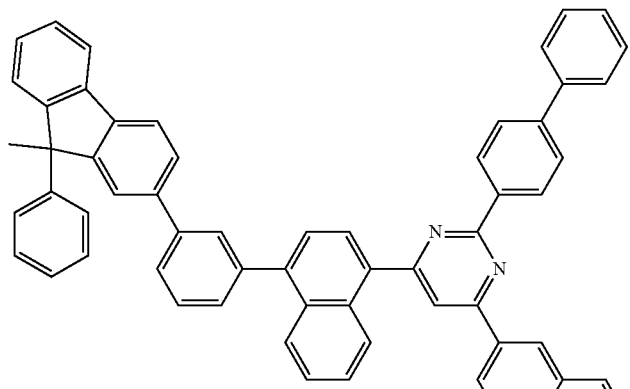
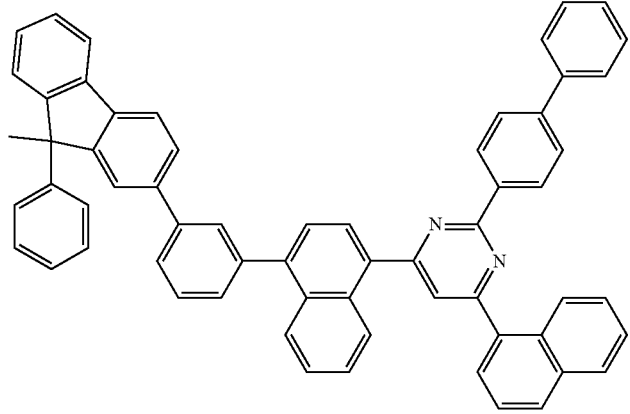
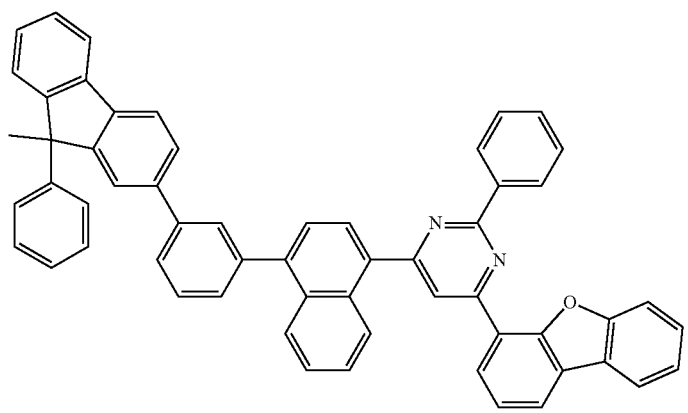
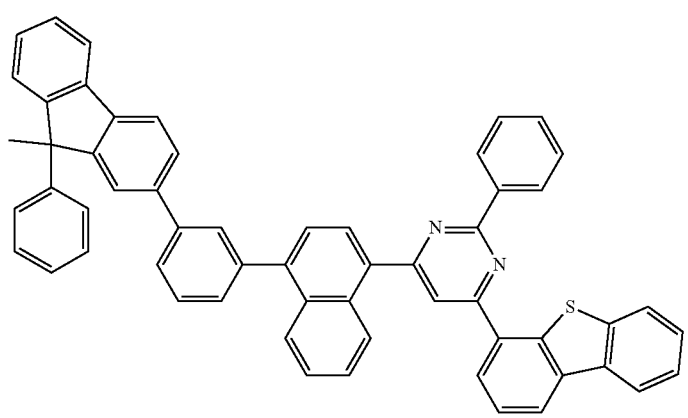

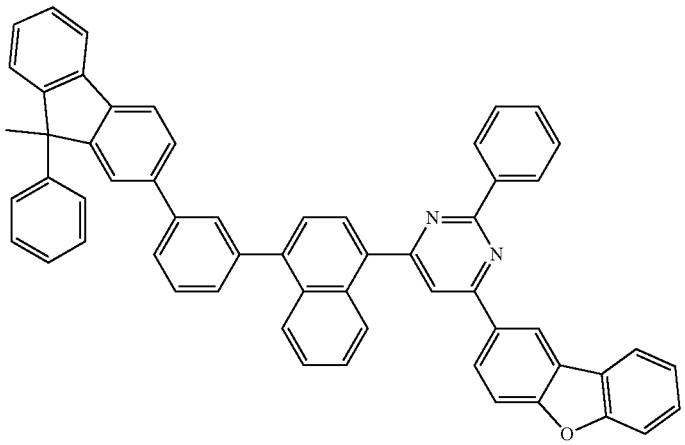
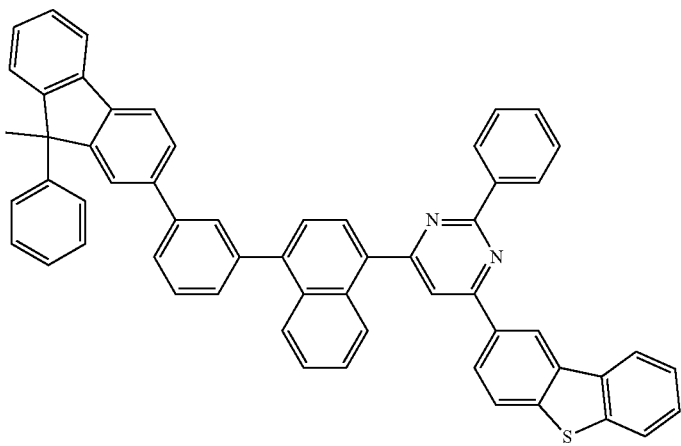
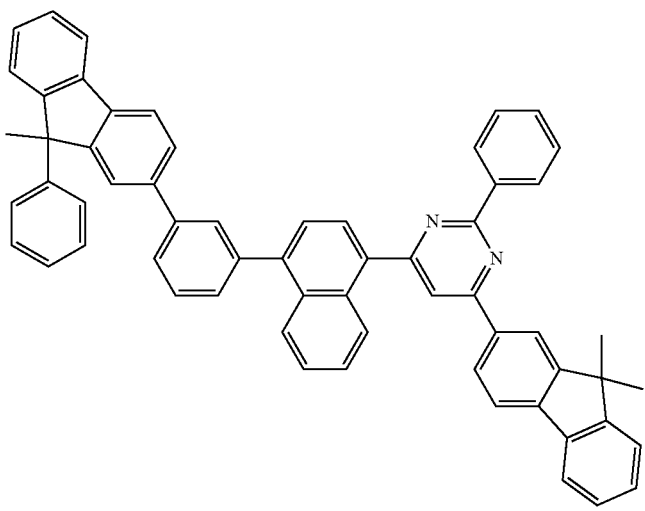

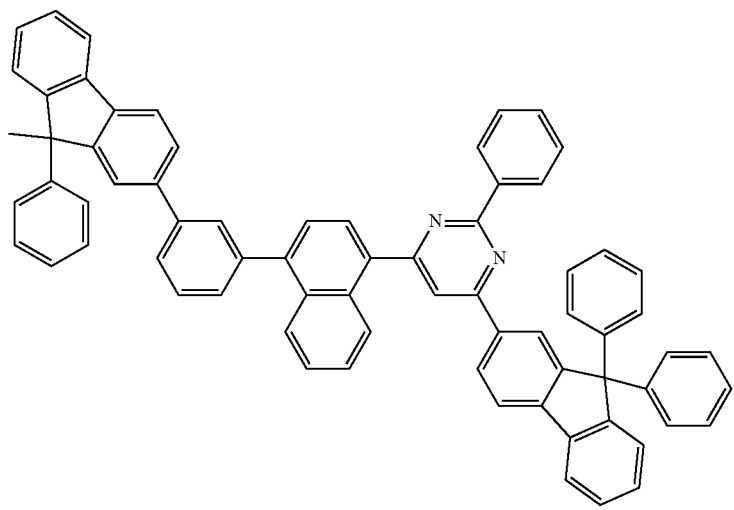
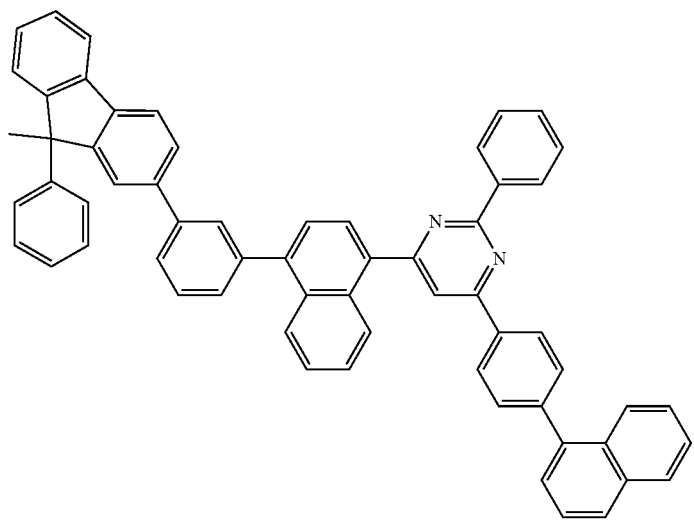
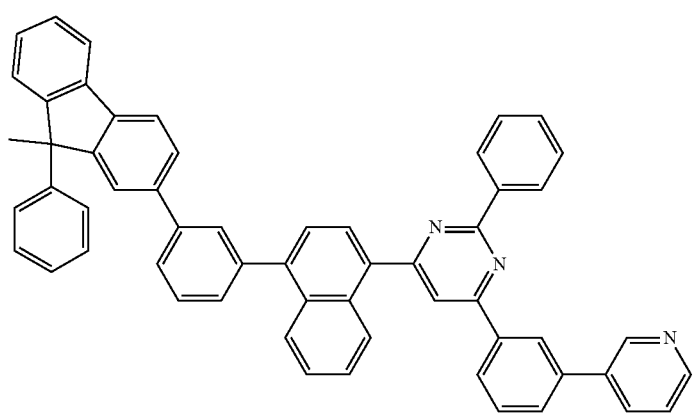

-continued
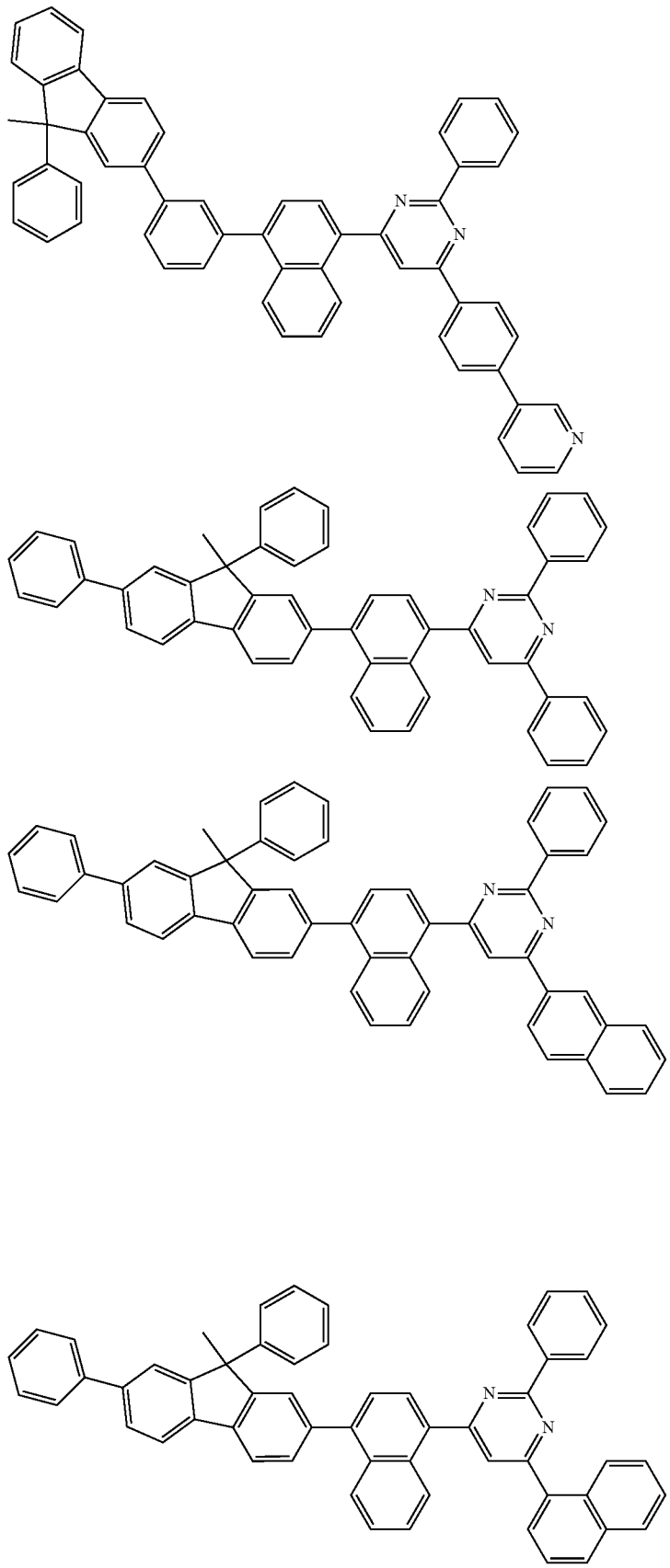

-continued
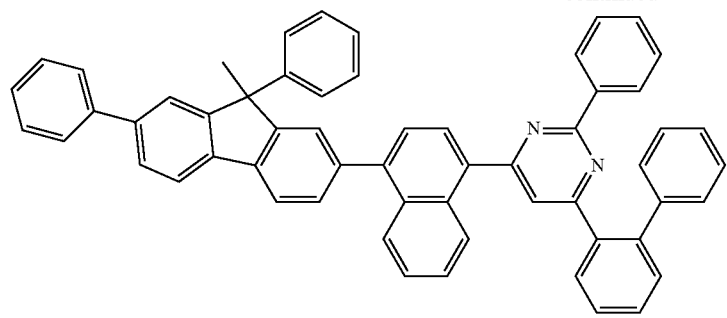
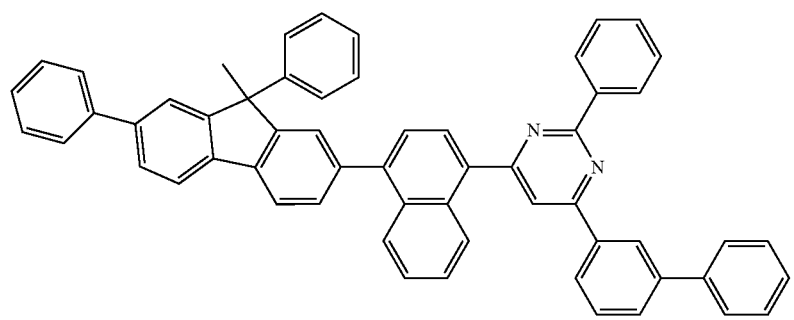
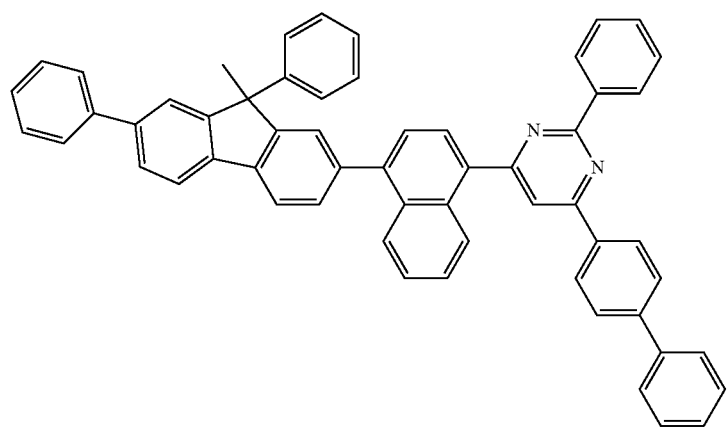
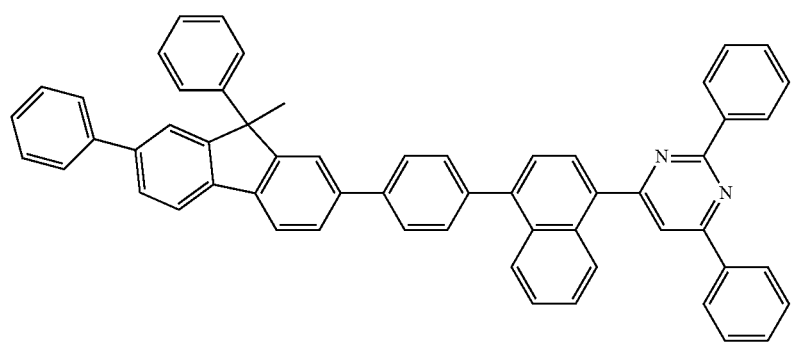

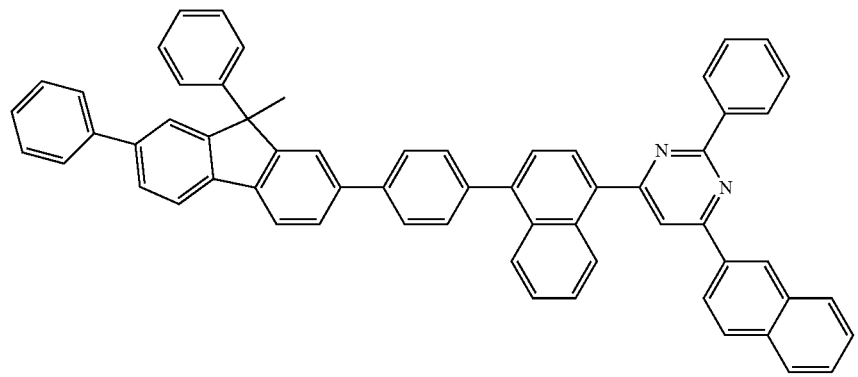
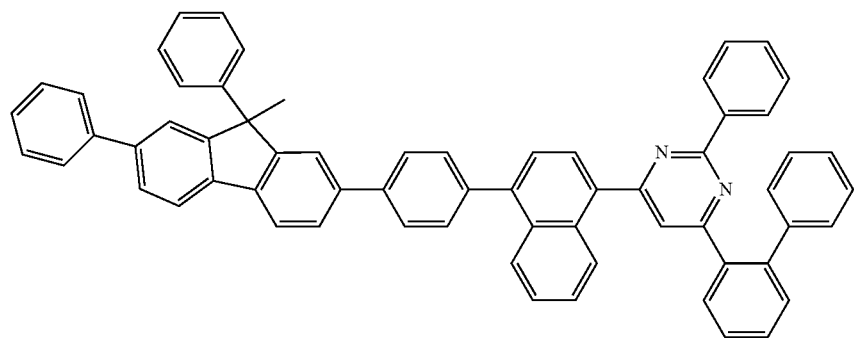
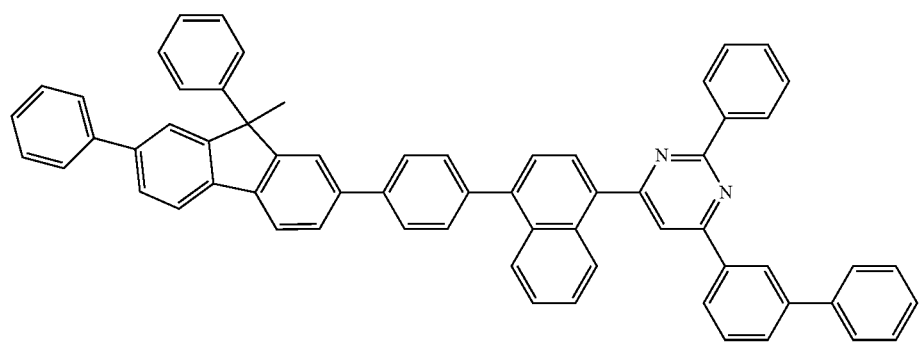
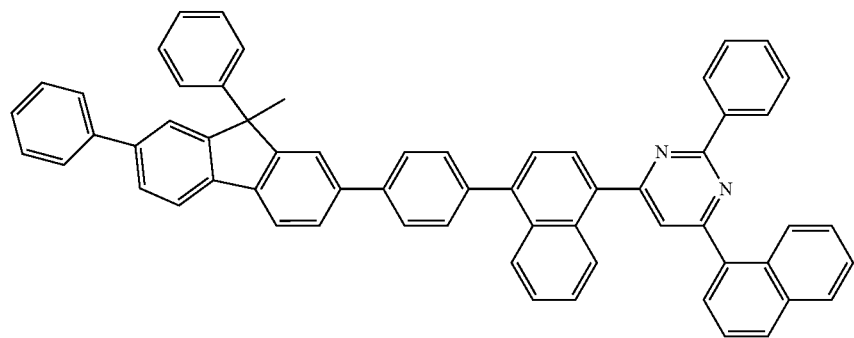

-continued
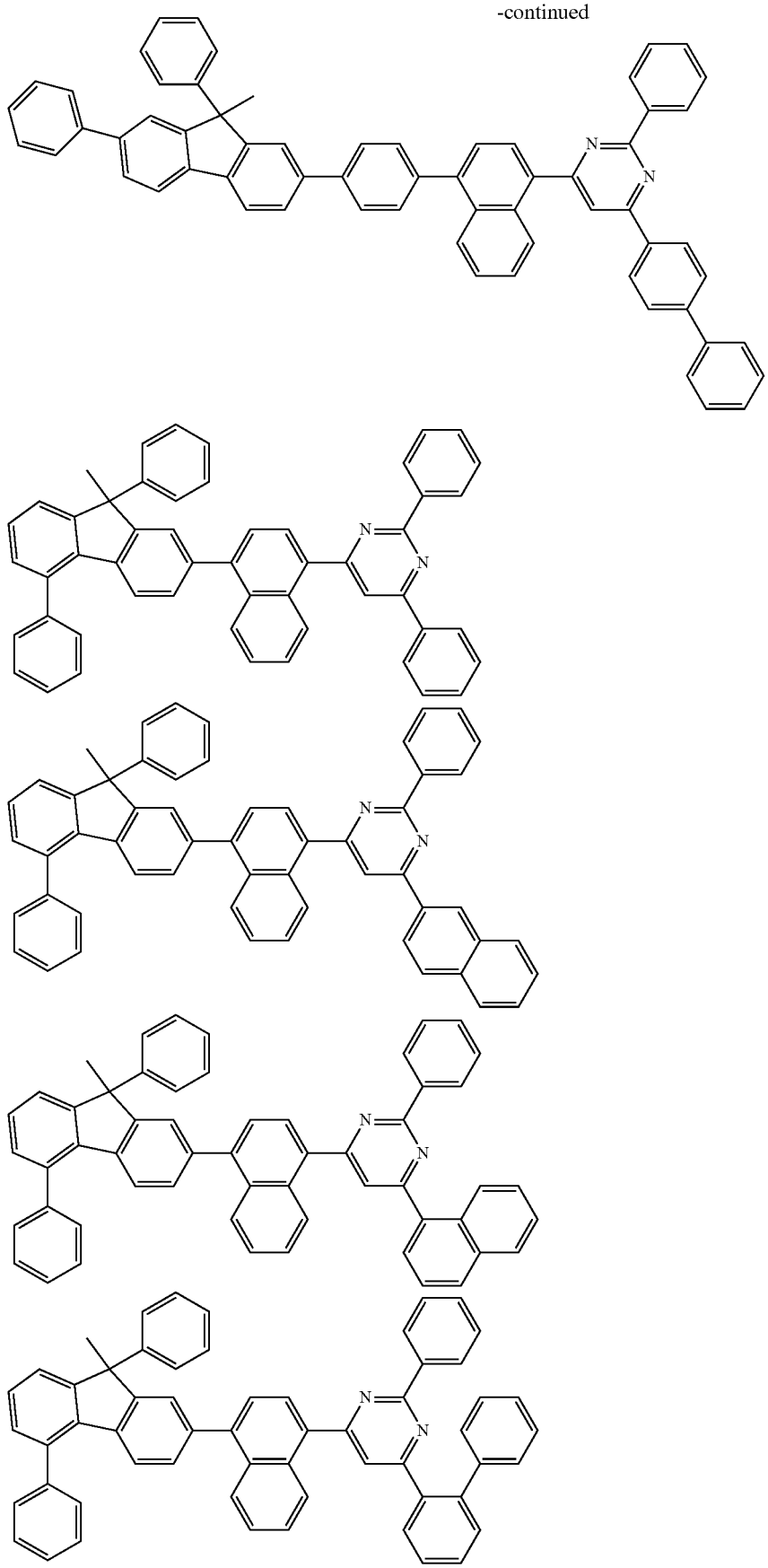

-continued
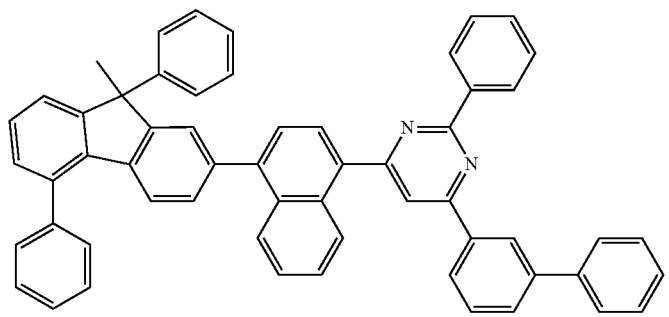
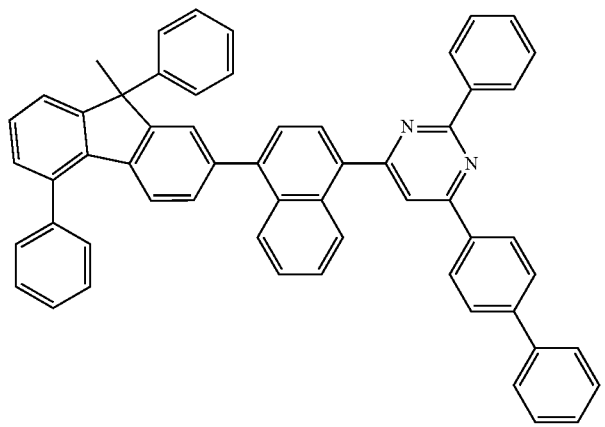
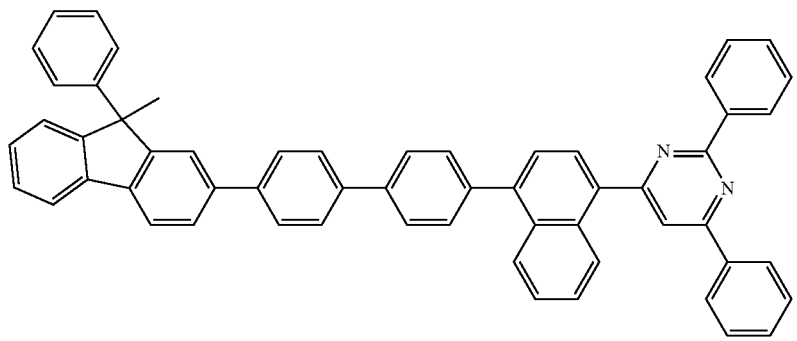
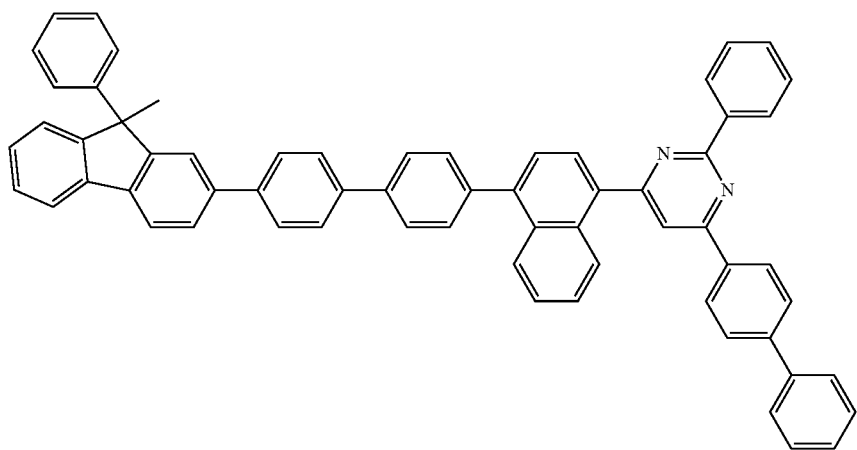

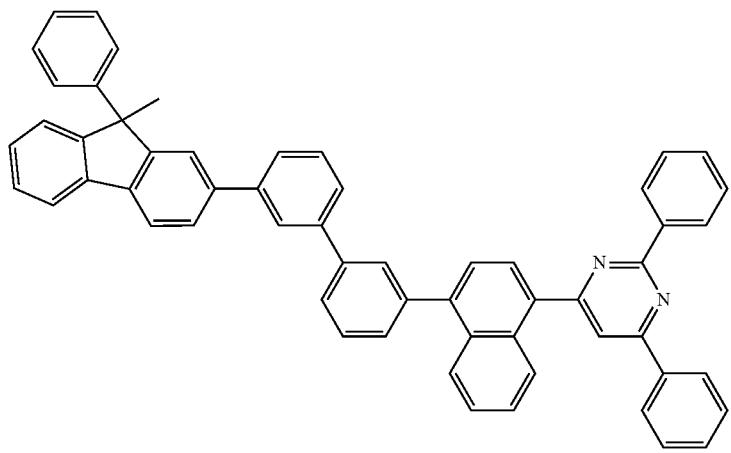
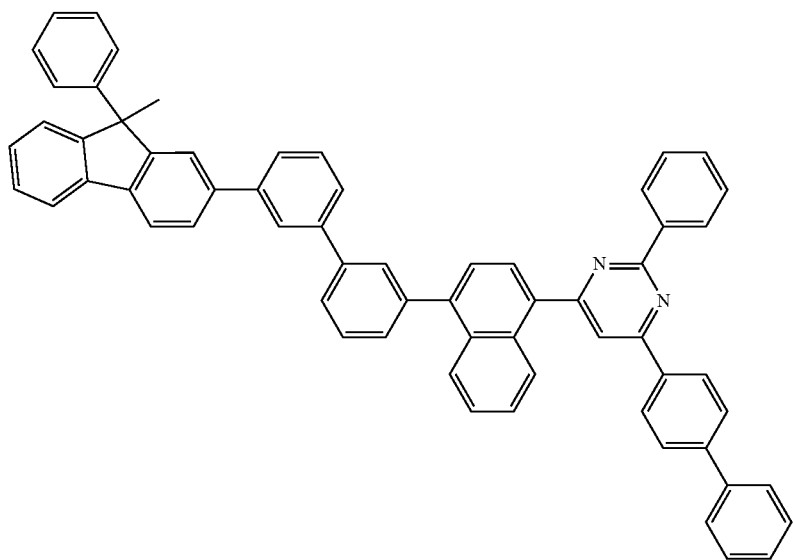
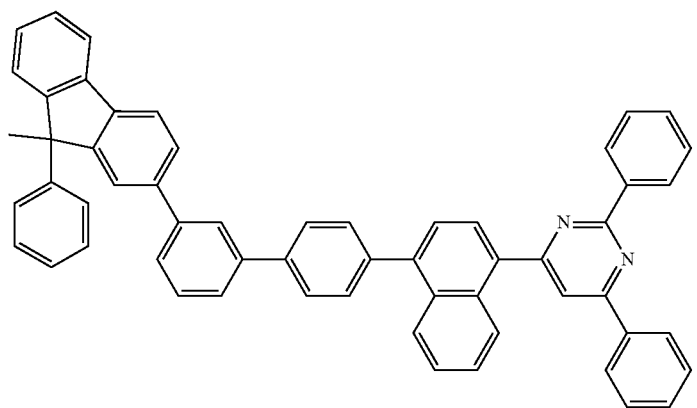

-continued
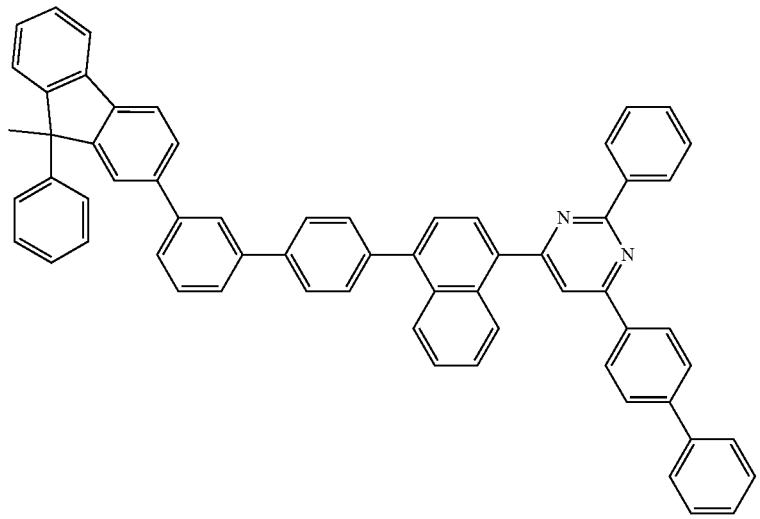
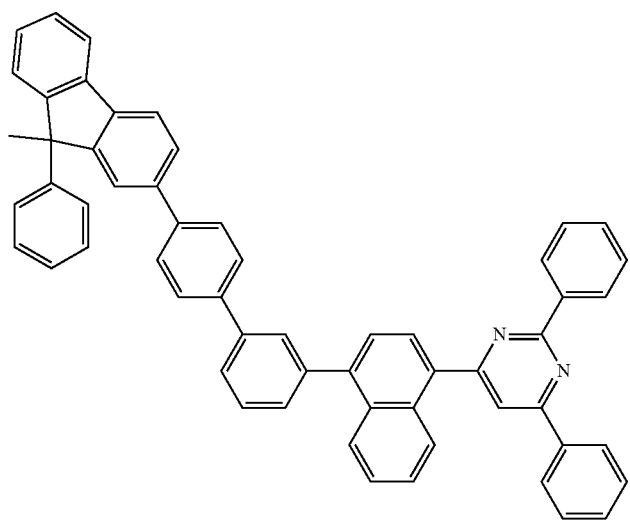
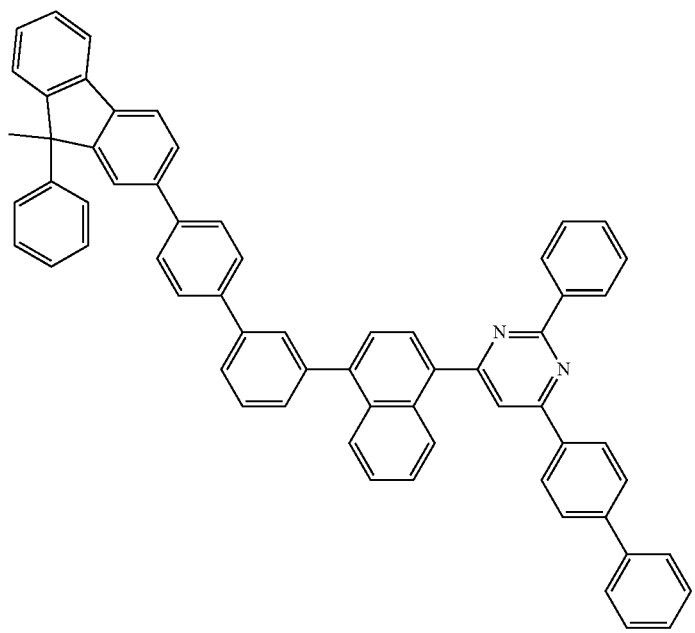

-continued
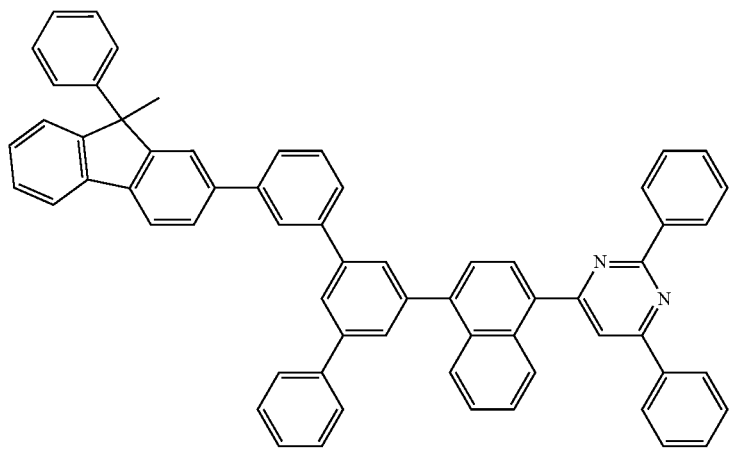
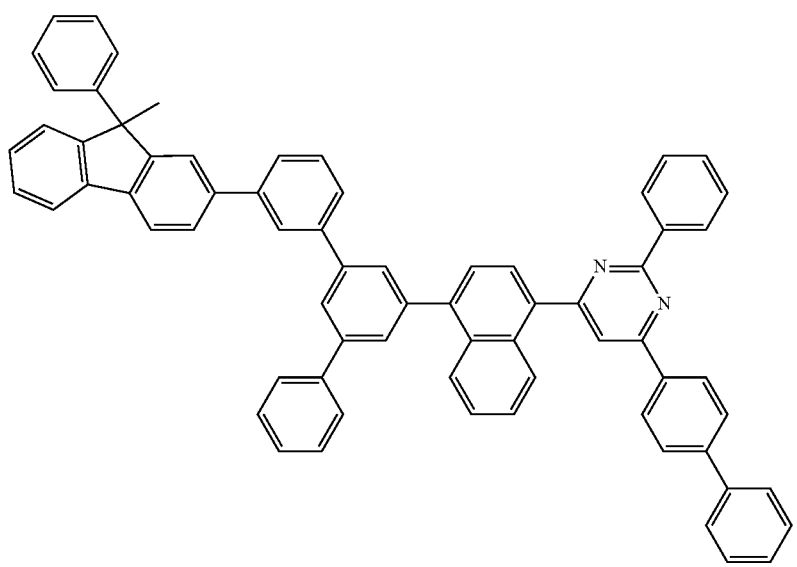
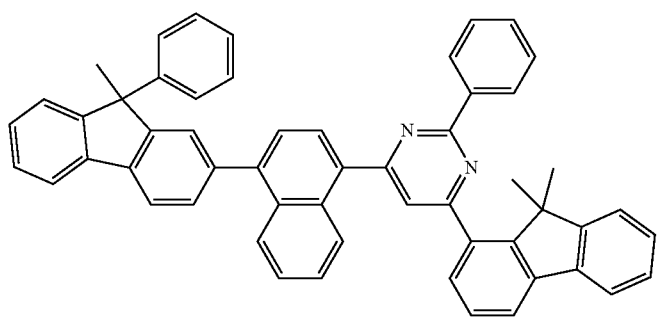
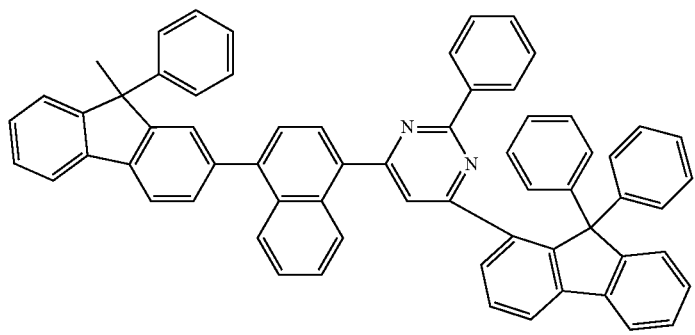

-continued
| 387 | 388 |
|---|---|
| 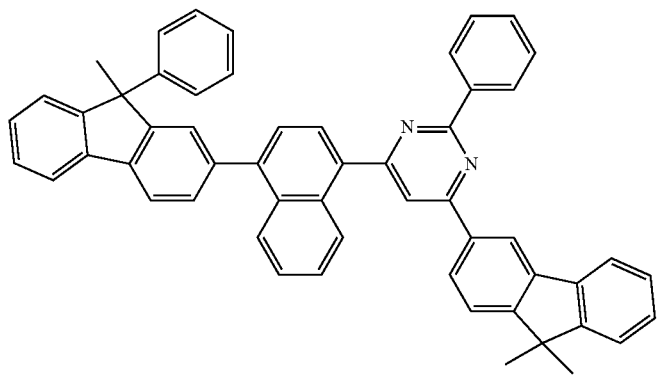 | |
| 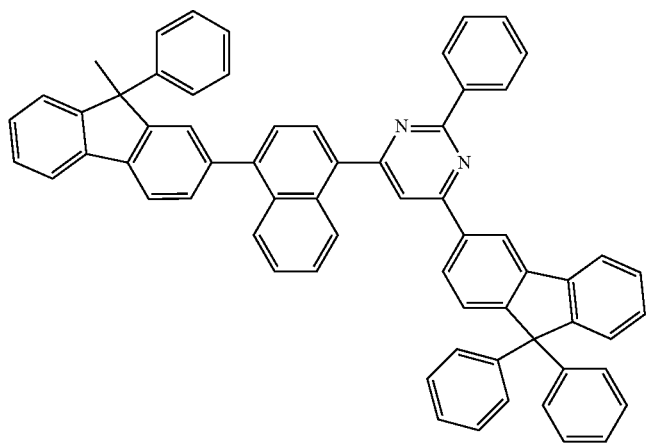 | 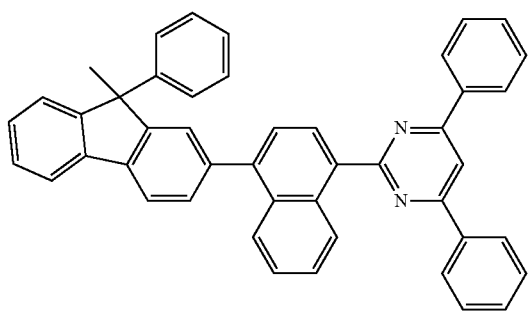 |
| 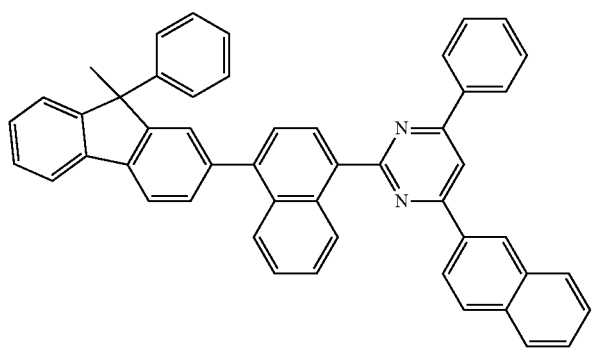 | 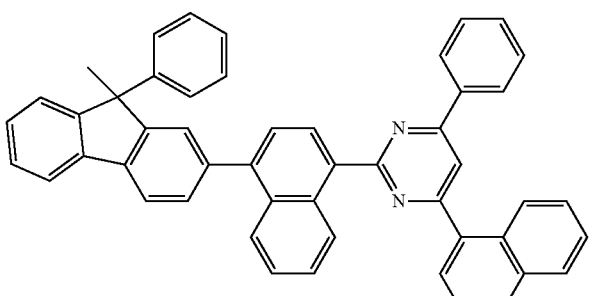 |
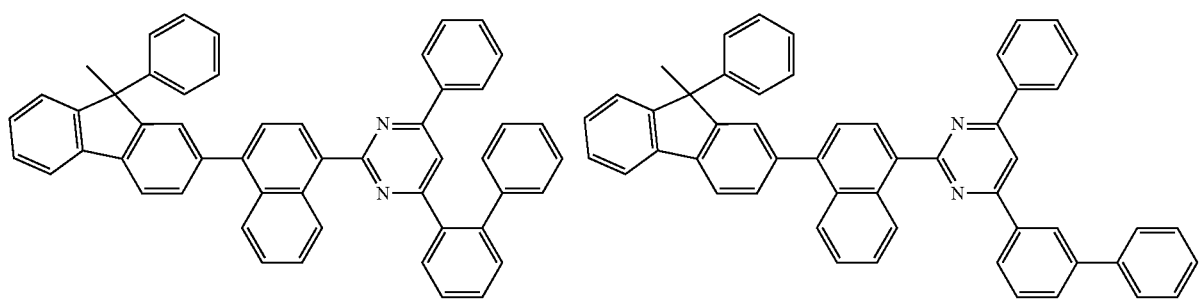

-continued
389
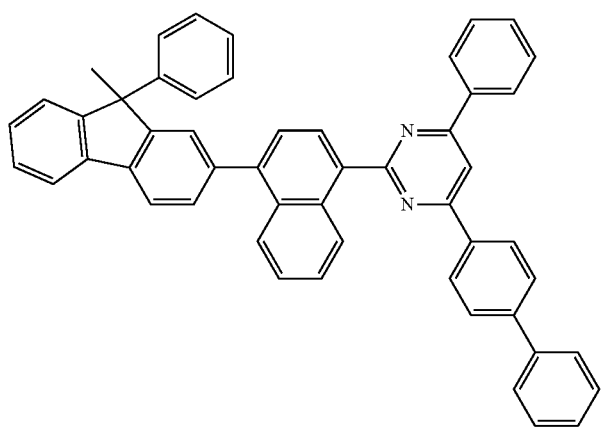
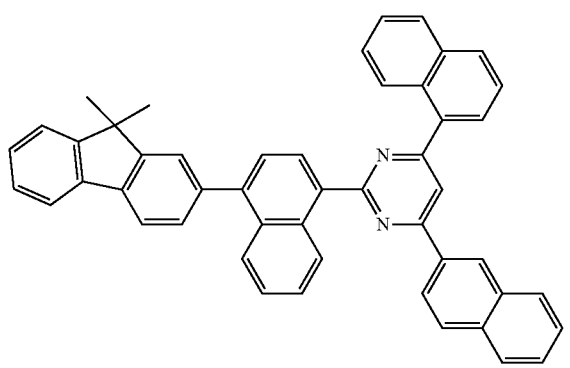
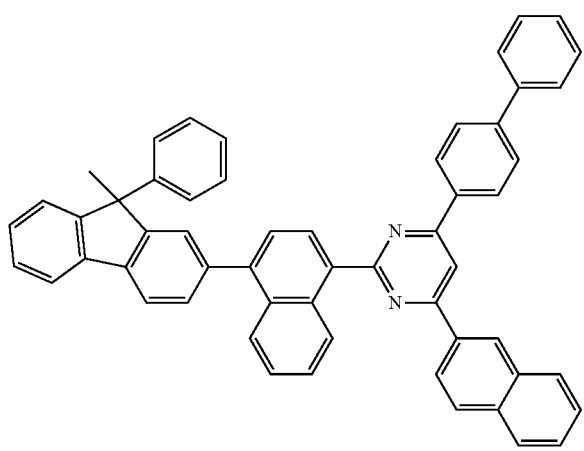
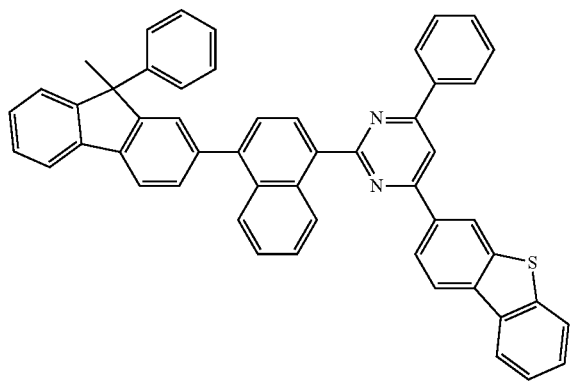
390
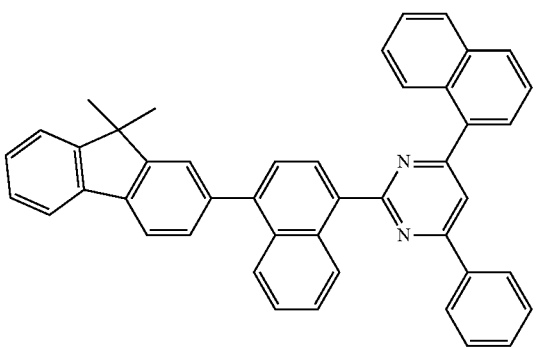
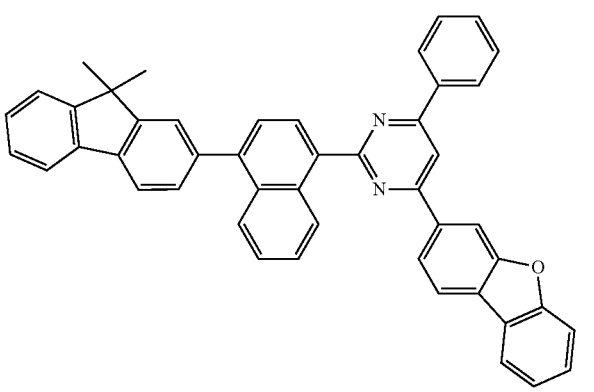
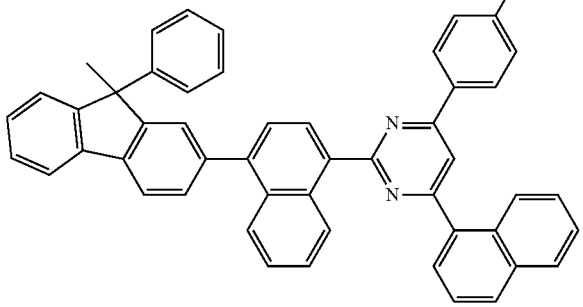
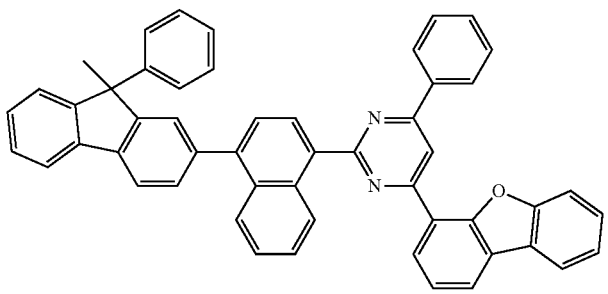

391 392
-continued
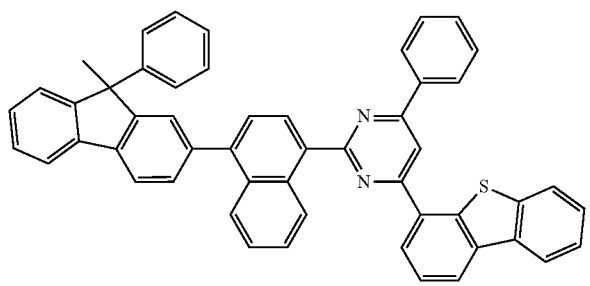
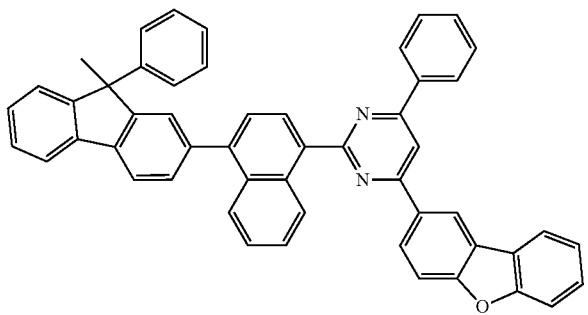
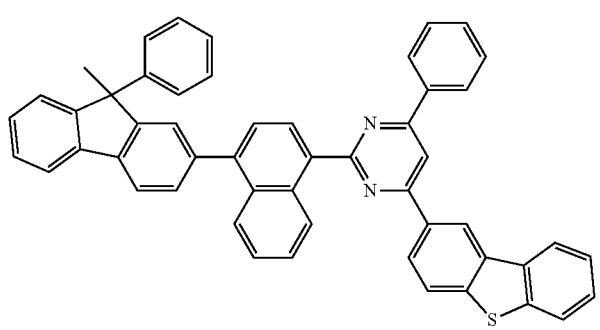
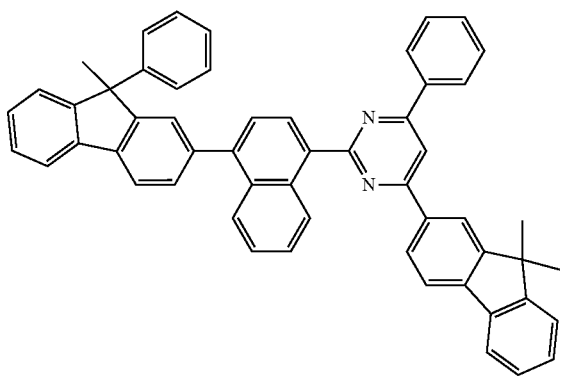
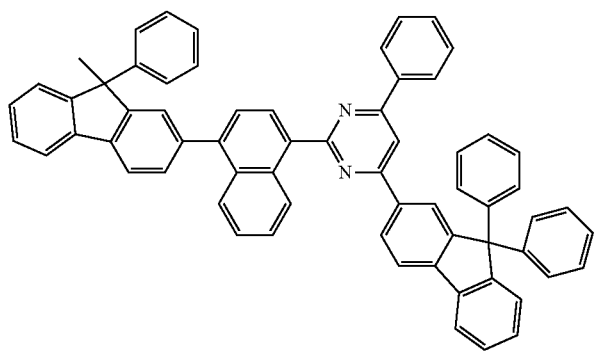
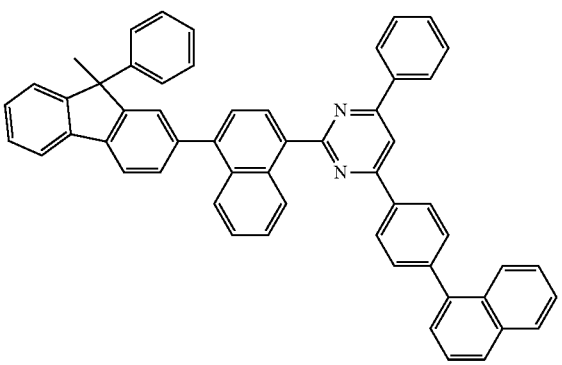
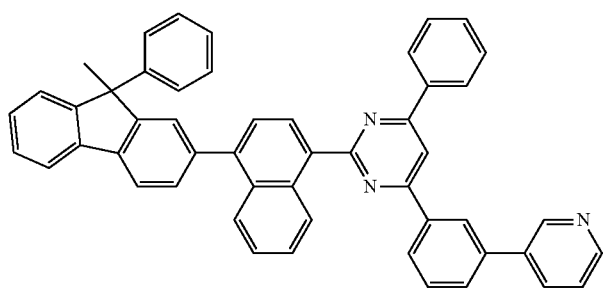
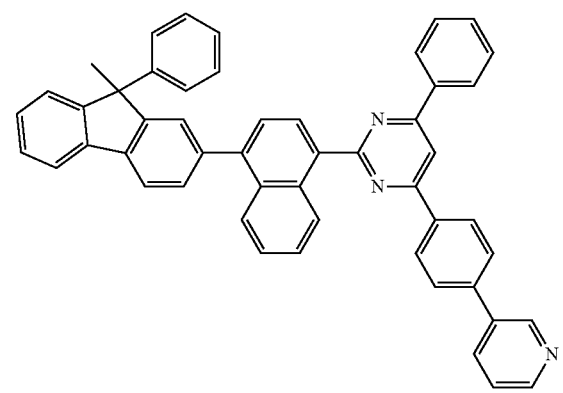

393
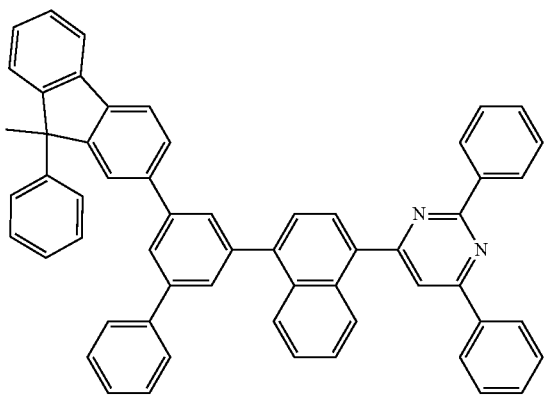
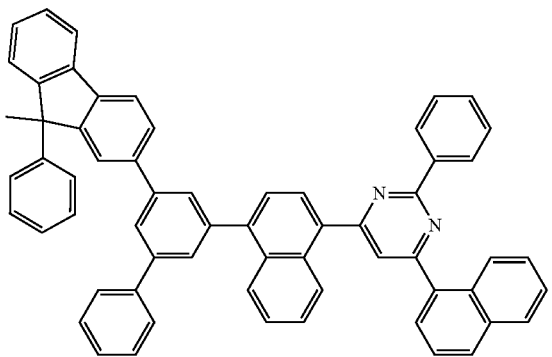
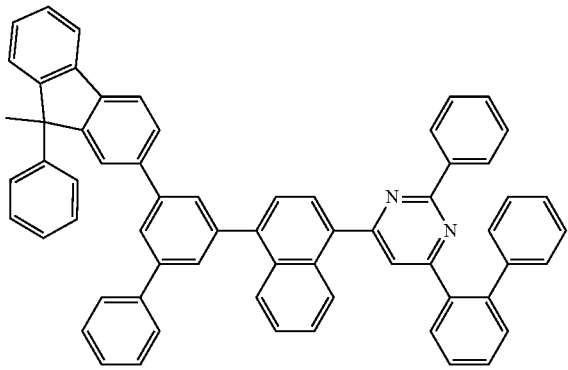
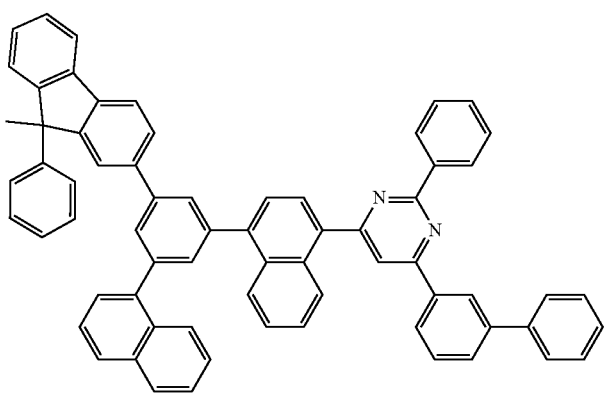
394
-continued
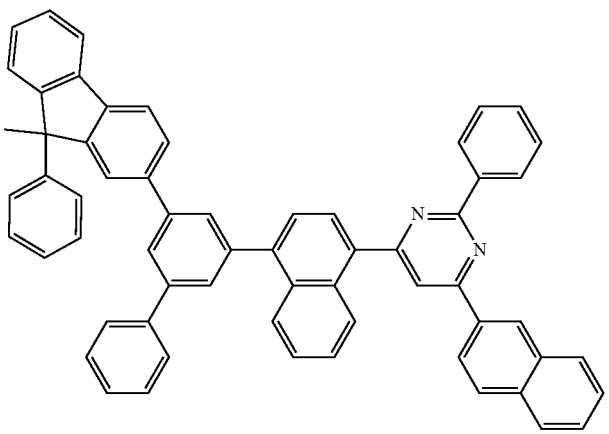
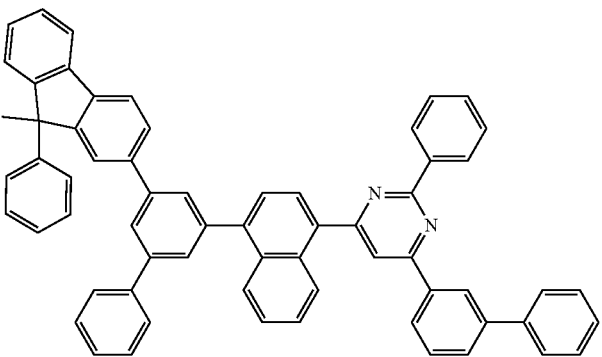
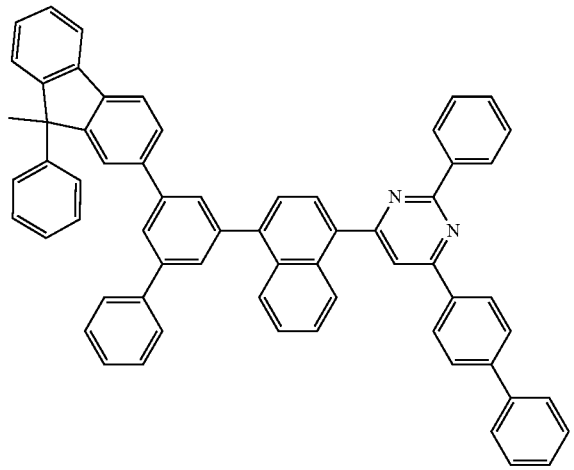
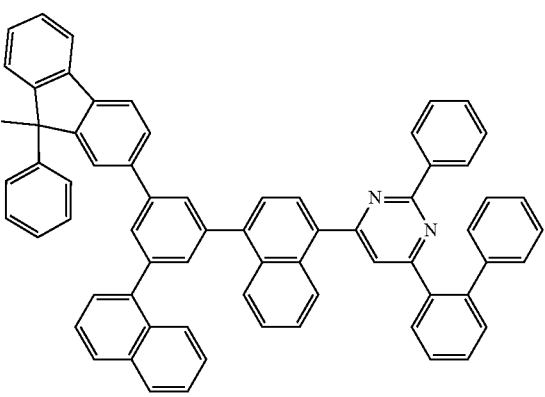

395
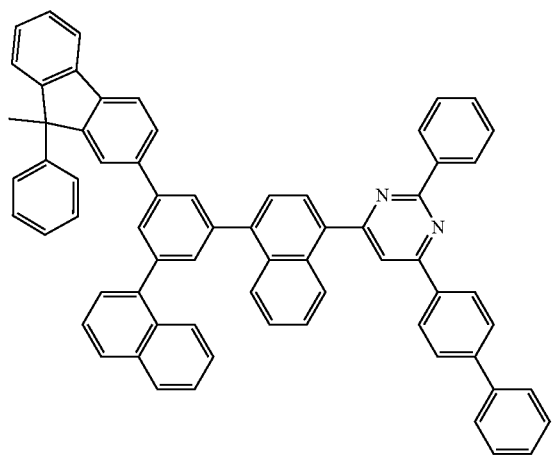
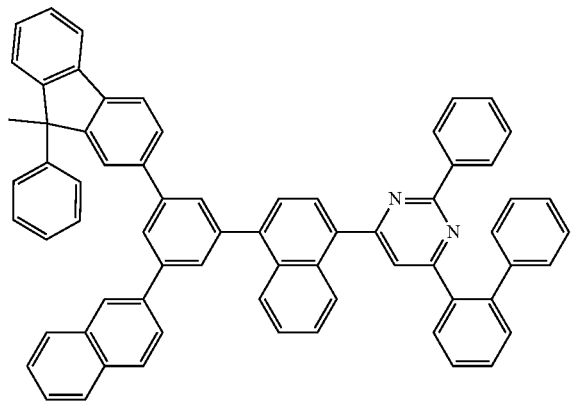
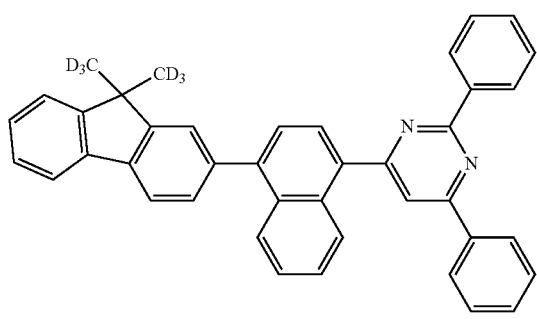
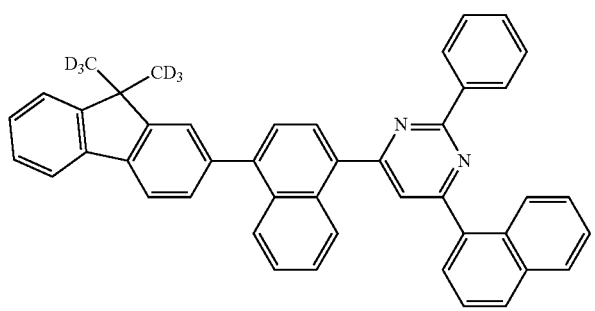
396
-continued
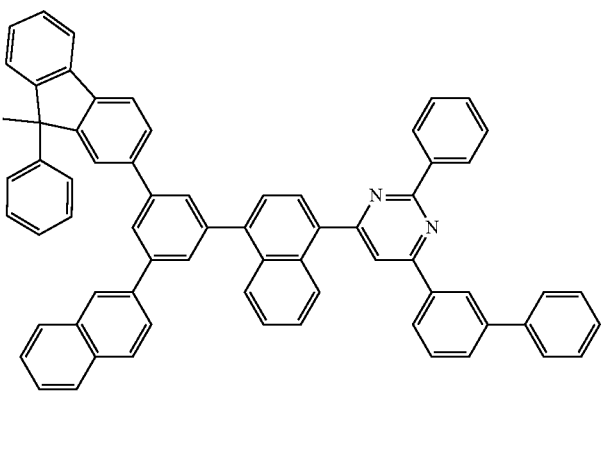
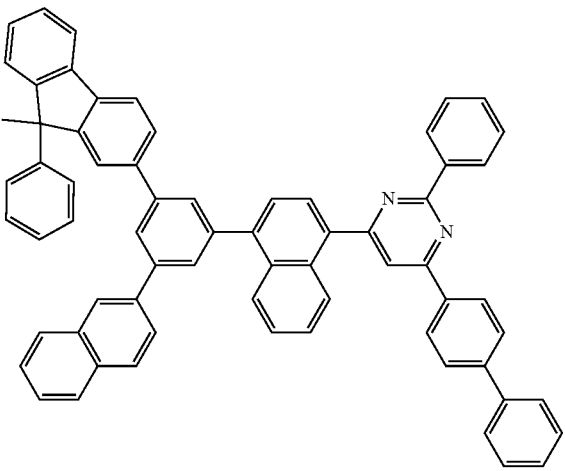
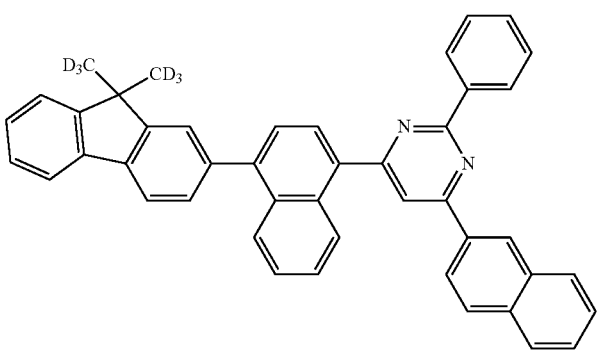
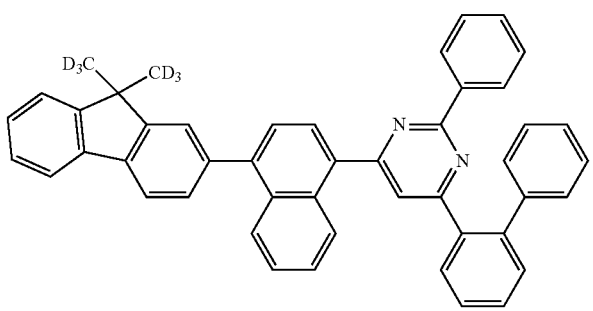

| 397 | 398 |
|---|---|
| 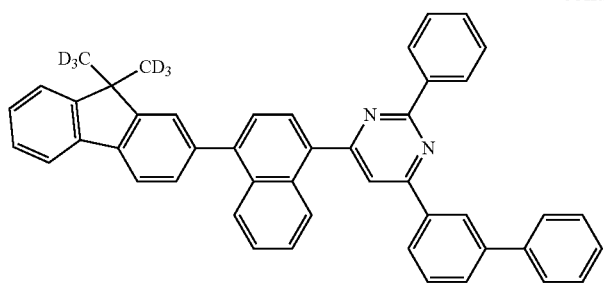 | 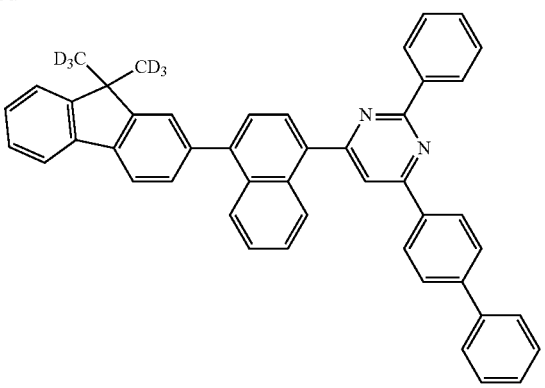 |
| 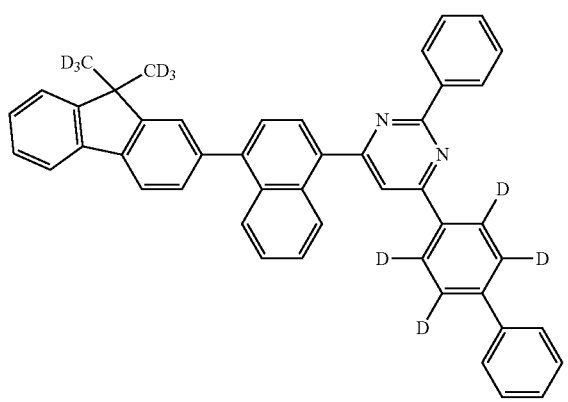 | 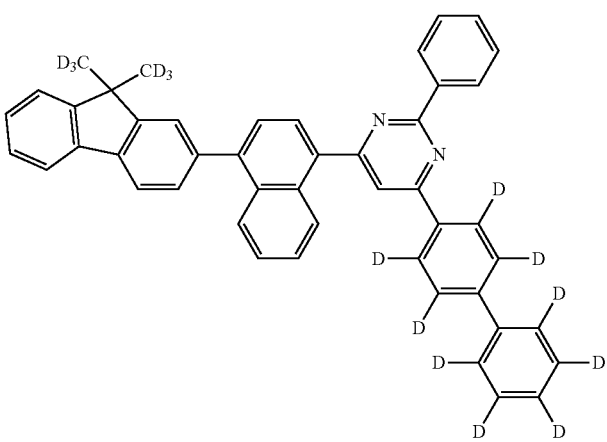 |
| 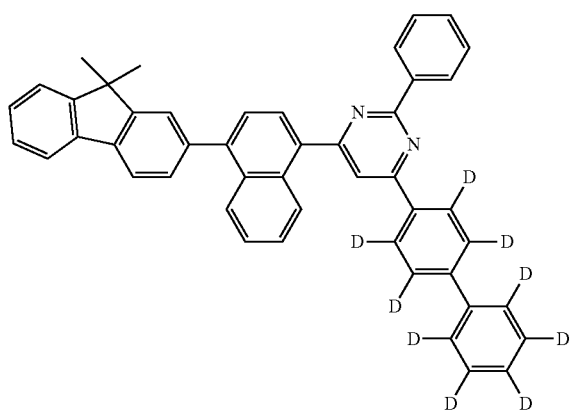 | 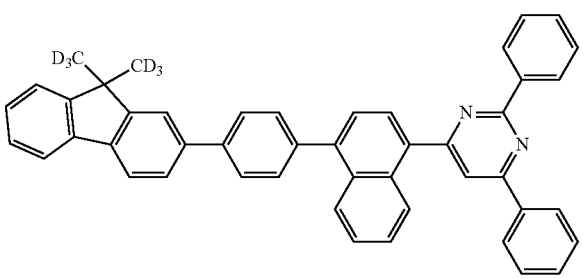 |
| 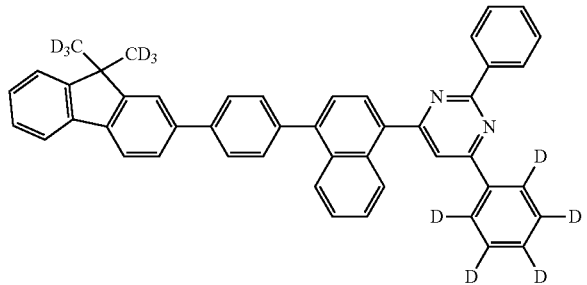 | 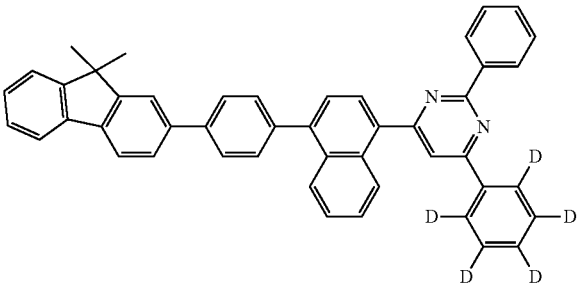 |
-continued 399
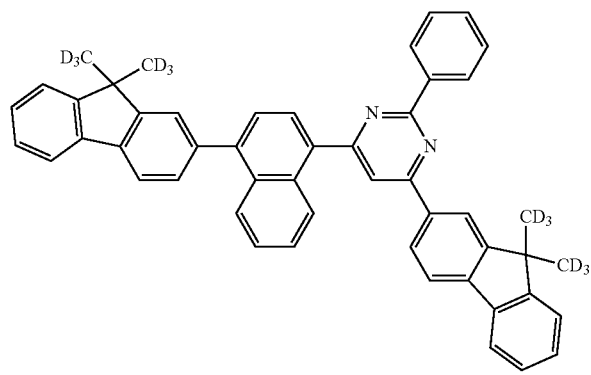
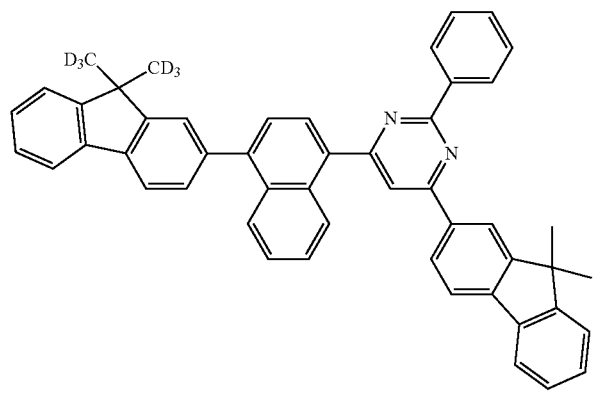
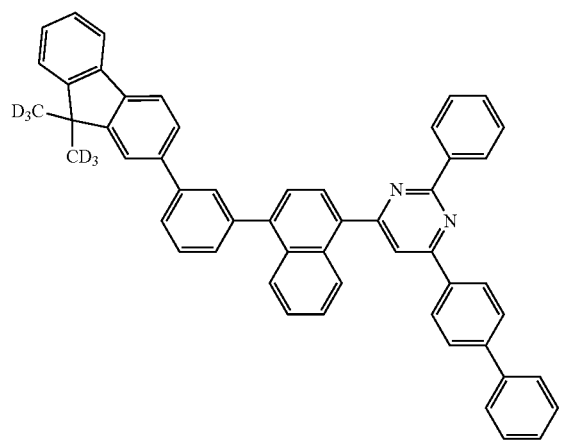
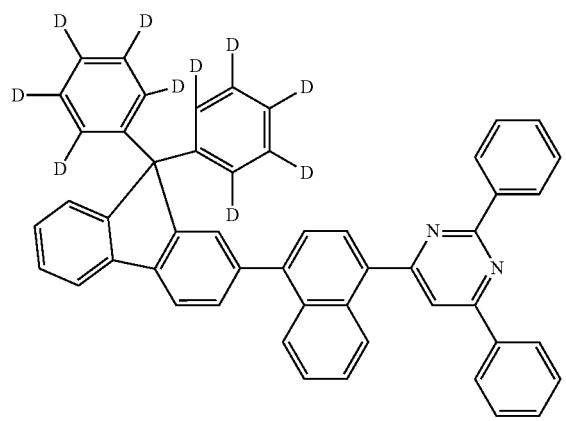
400
-continued
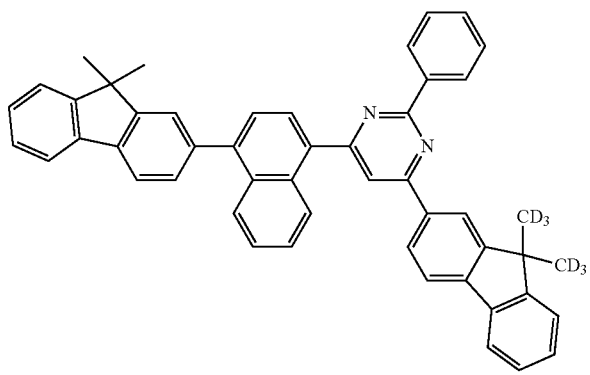
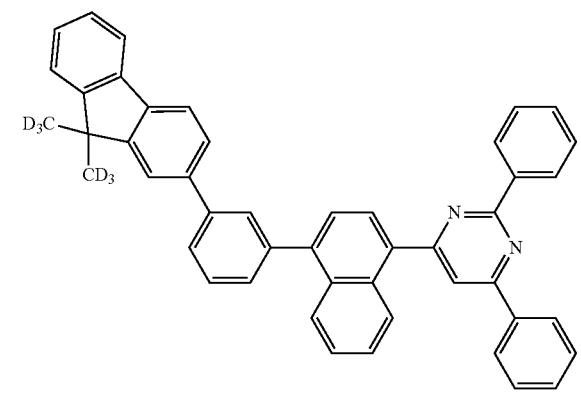
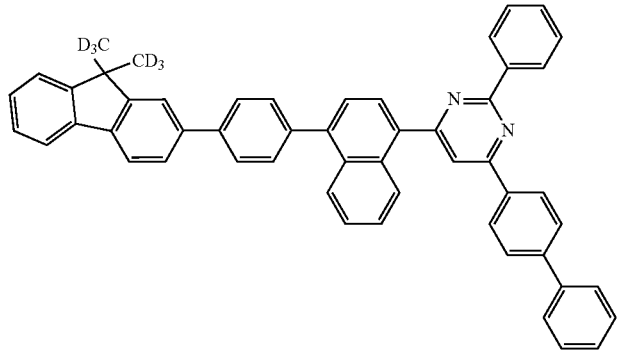
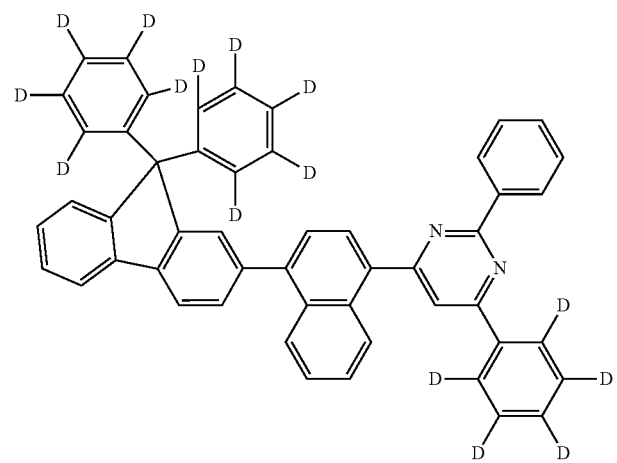

-continued
401
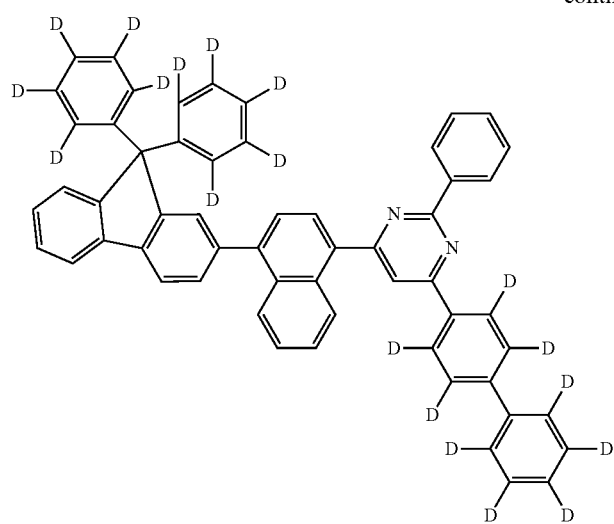
402
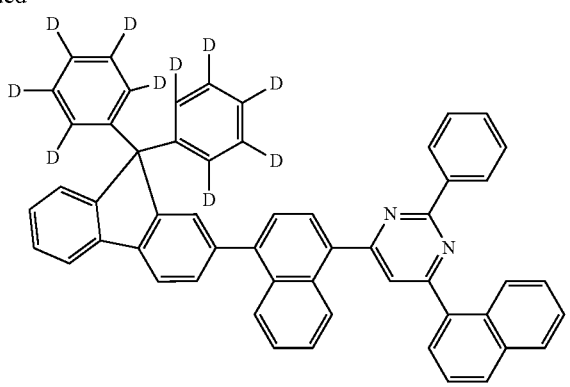
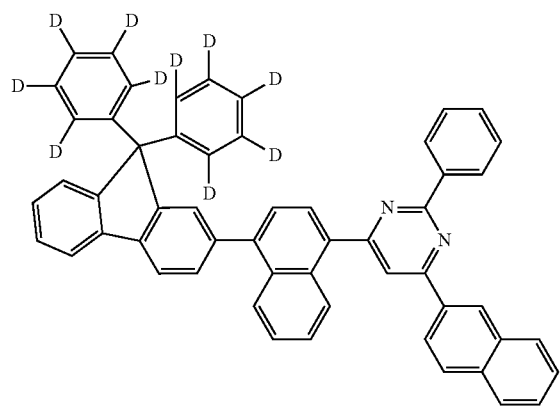
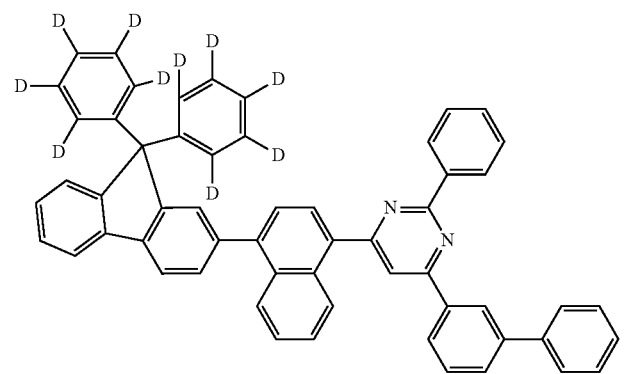
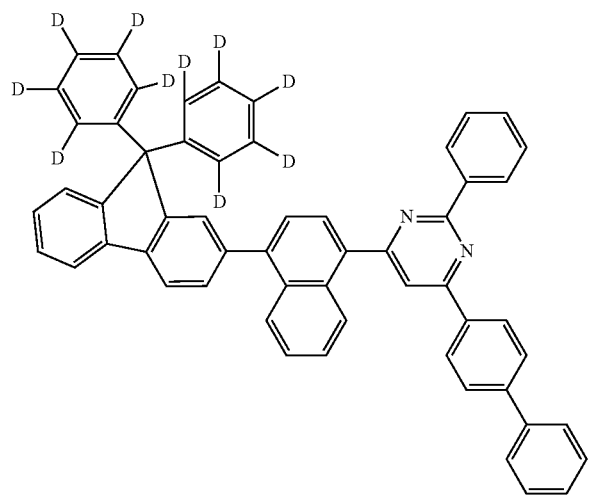
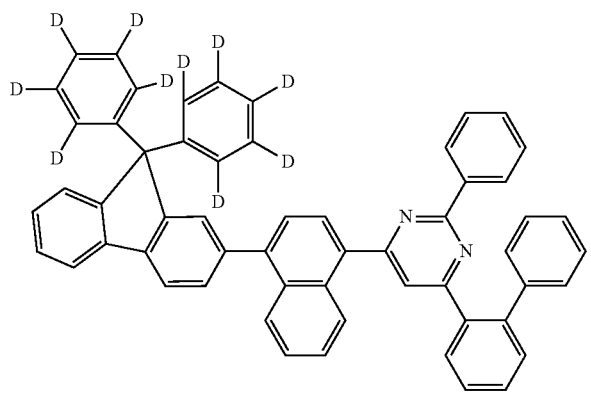

403 404
-continued
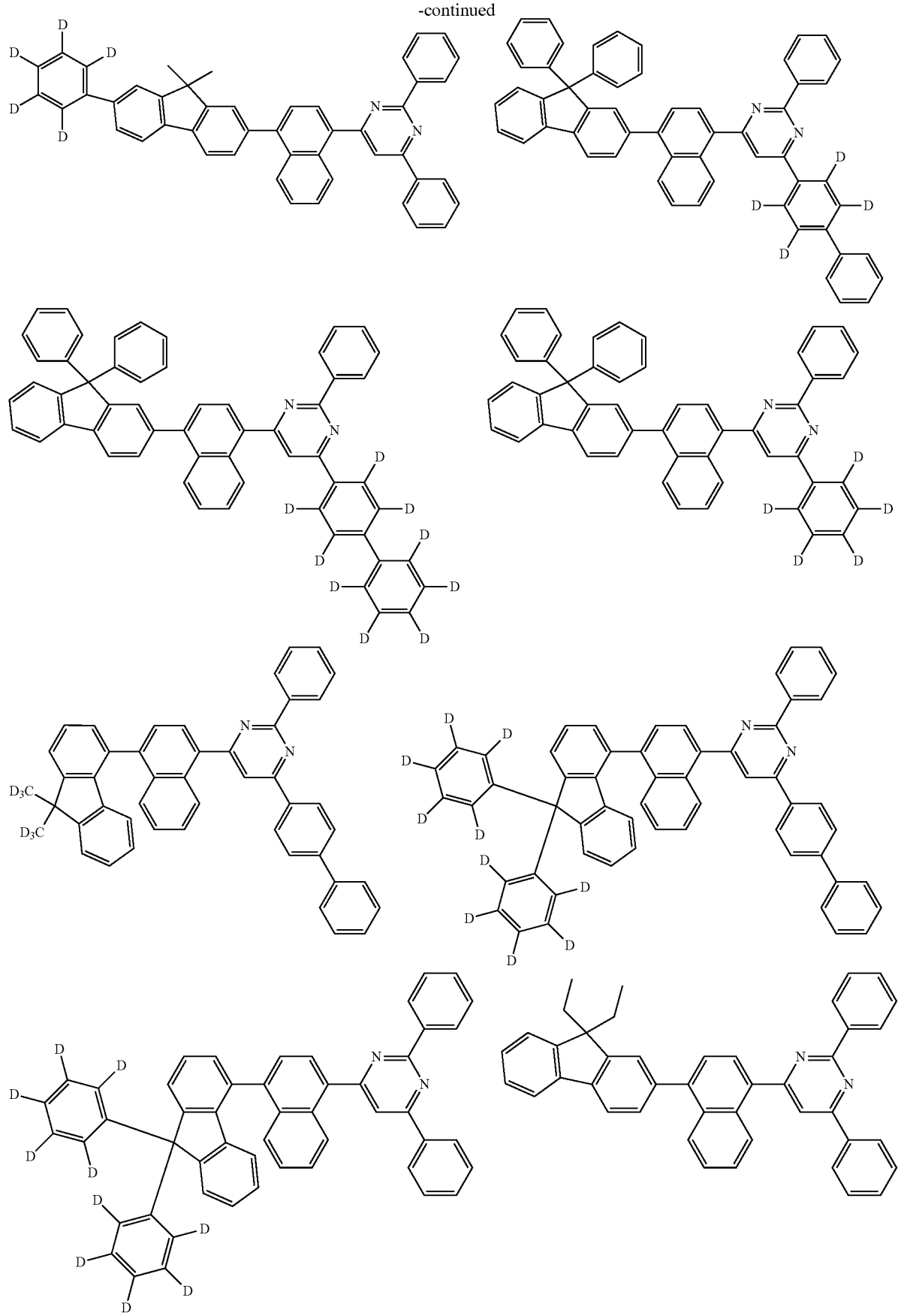

-continued
| 405 | 406 |
|---|---|
| 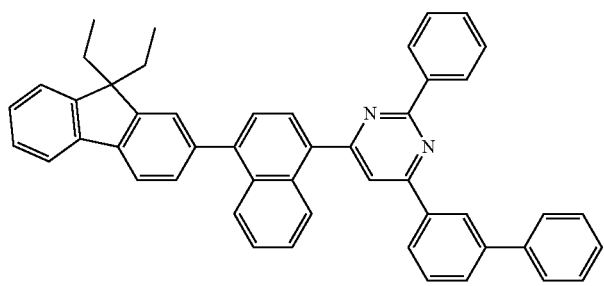 | 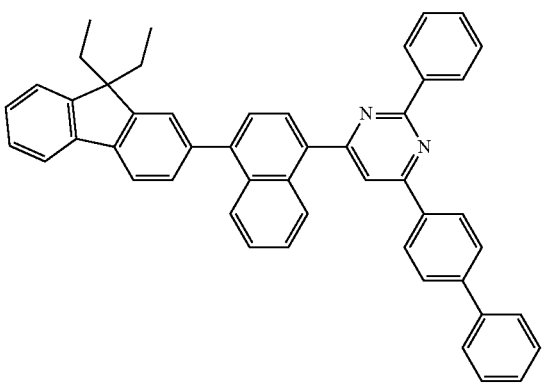 |
| 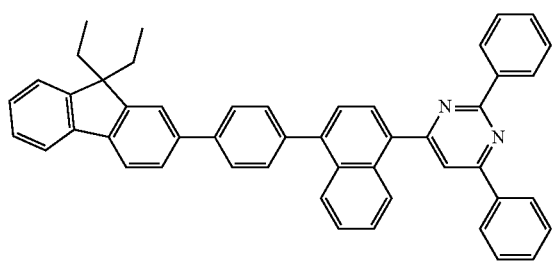 | 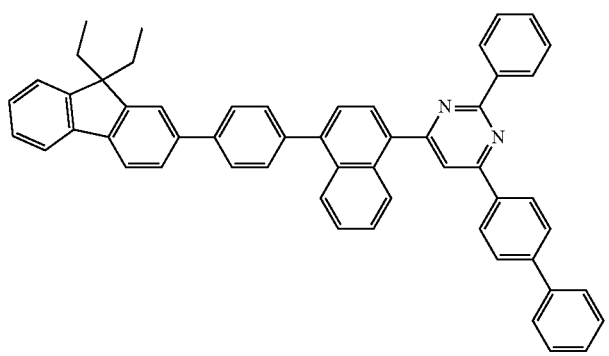 |
| 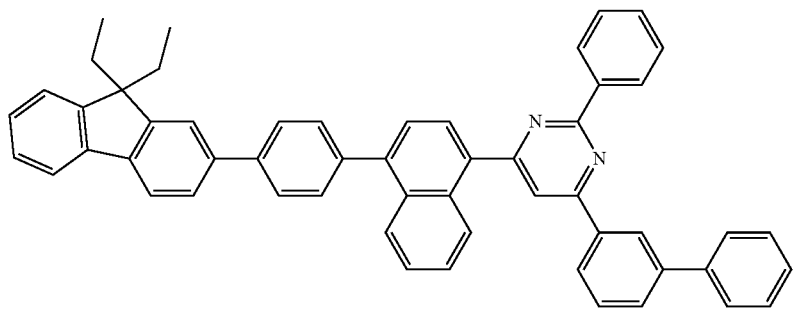 | |
| 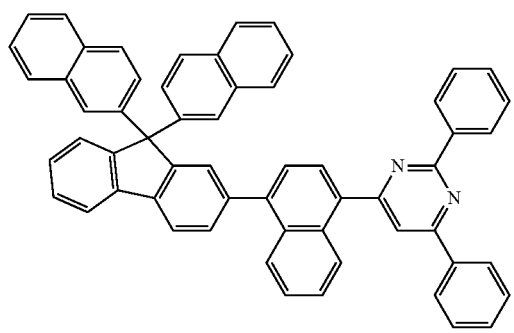 | 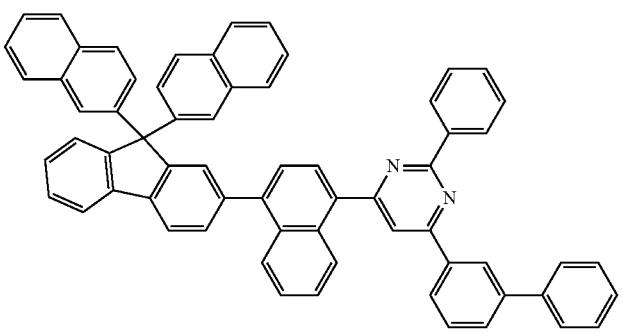 |

-continued
| 407 | 408 |
|---|---|
| 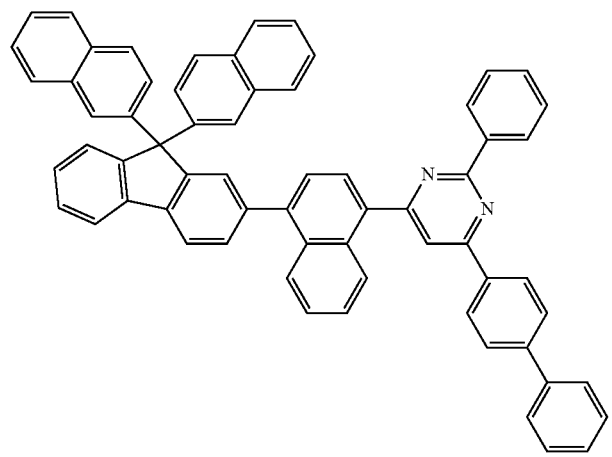 | 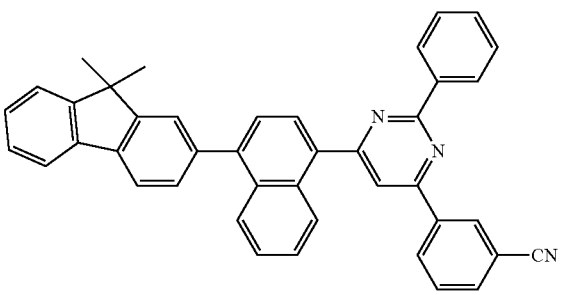 |
| 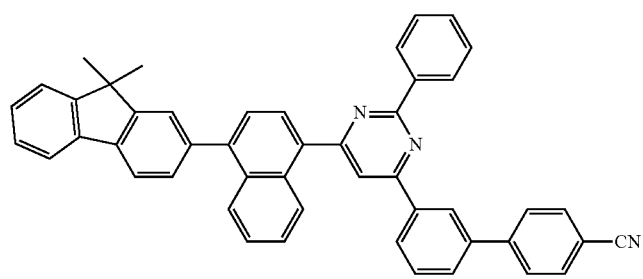 | 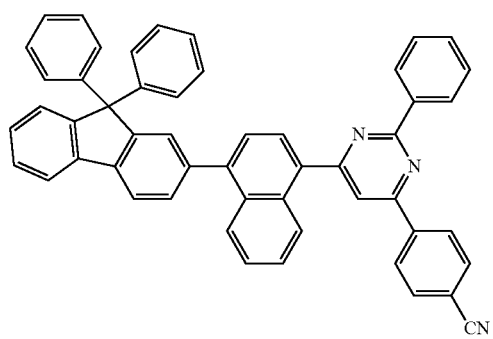 |
| 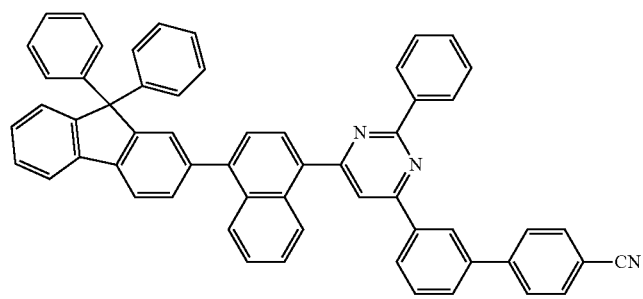 | 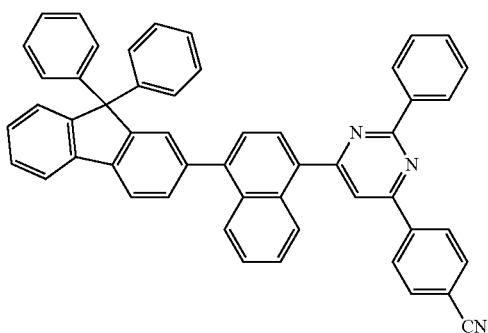 |
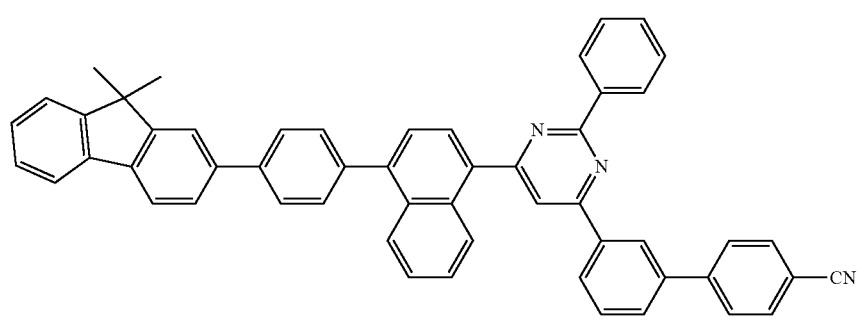 [SMILES: CC1(C)c2ccccc2-c2ccc(-c3ccc(-c4ccc(-c5cc(-c6cccc(-c7ccc(C#N)cc7)c6)nc(-c6ccccc6)n5)c5ccccc45)cc3)cc21]

409
-continued
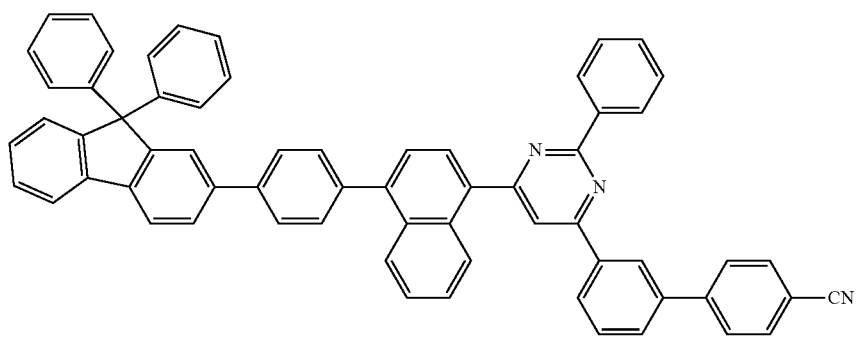
410
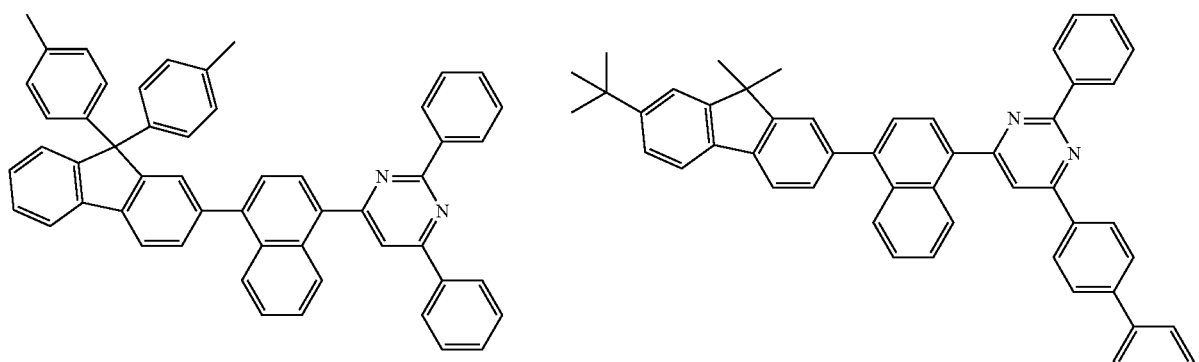
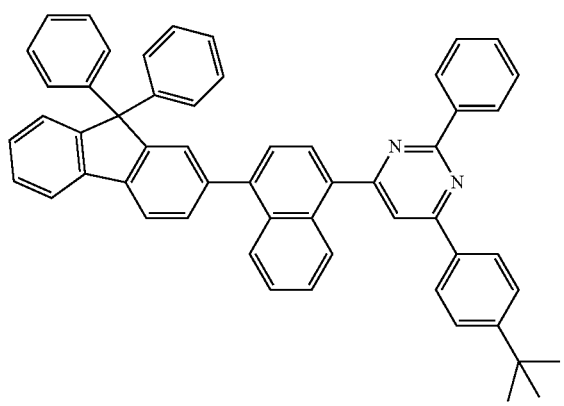
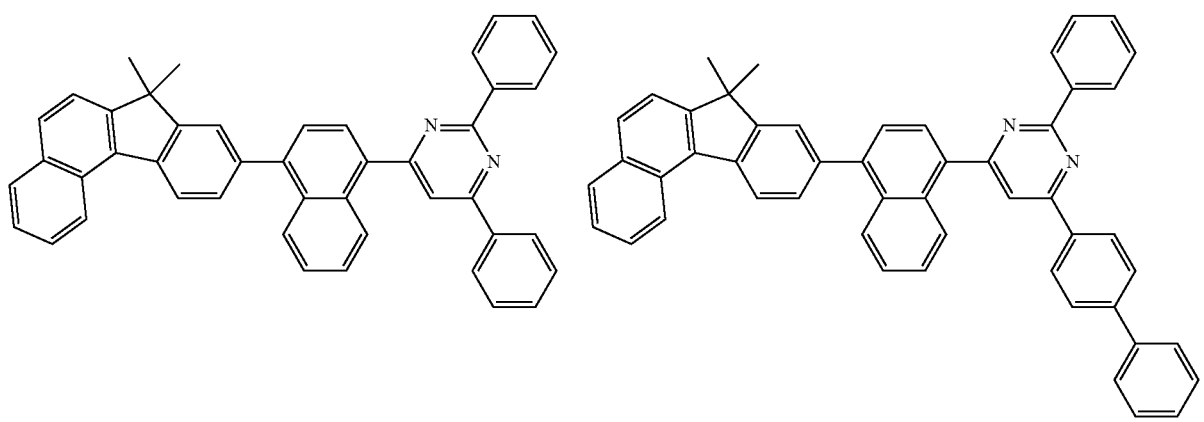

-continued
411
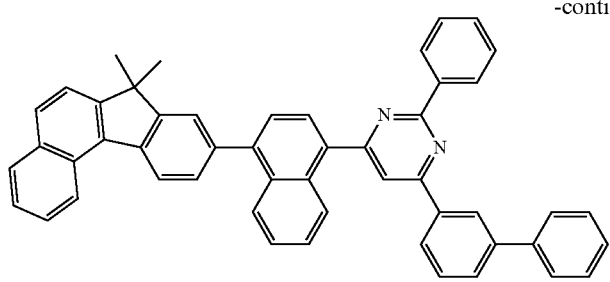
412
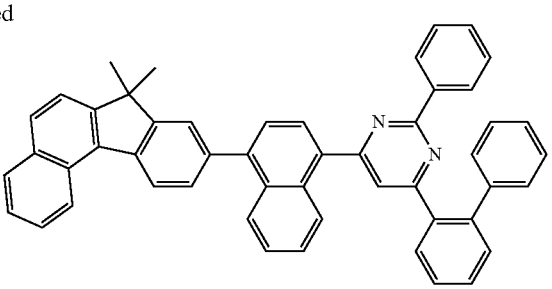
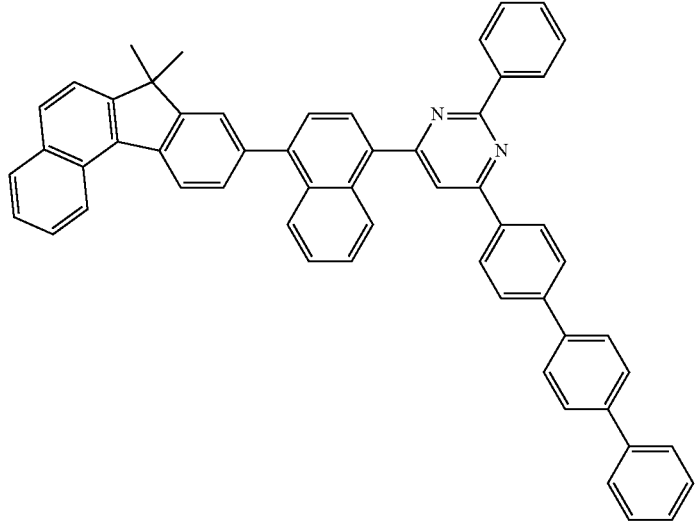
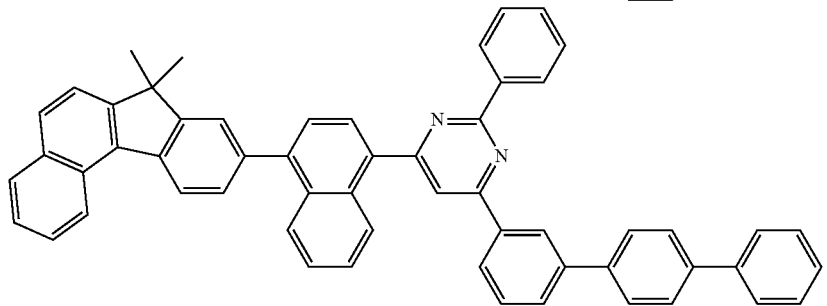
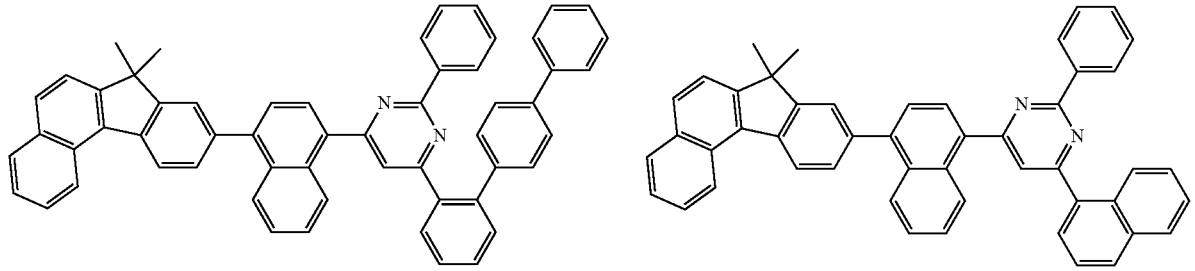
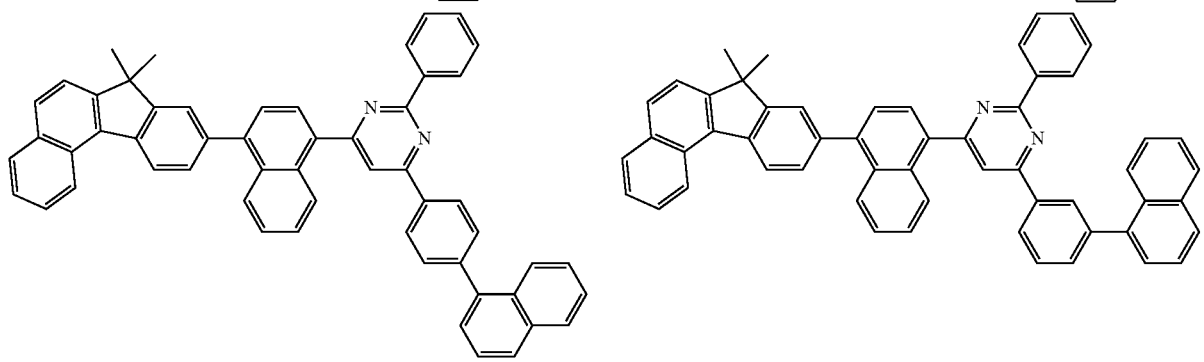

-continued
413 414
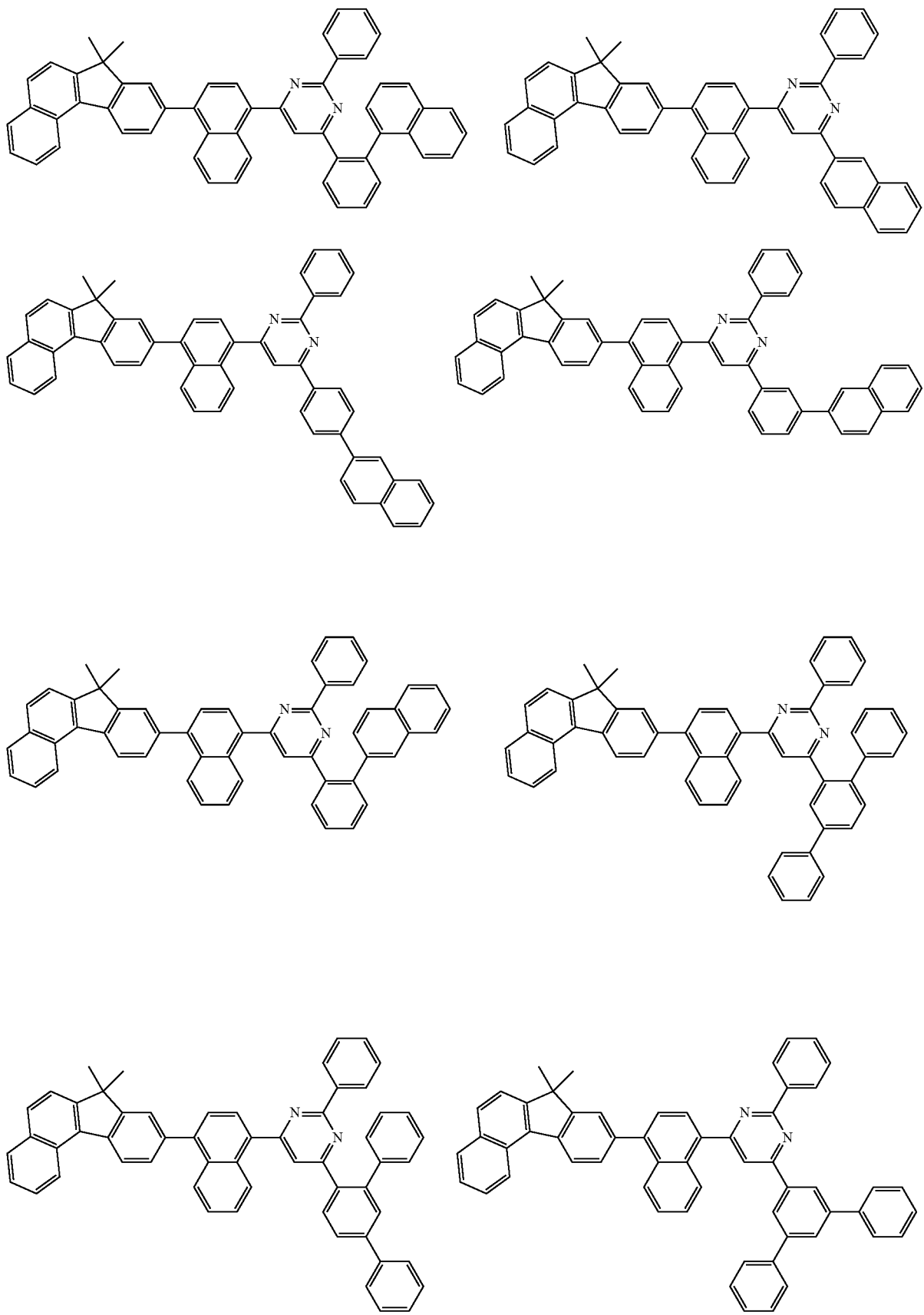

-continued
415
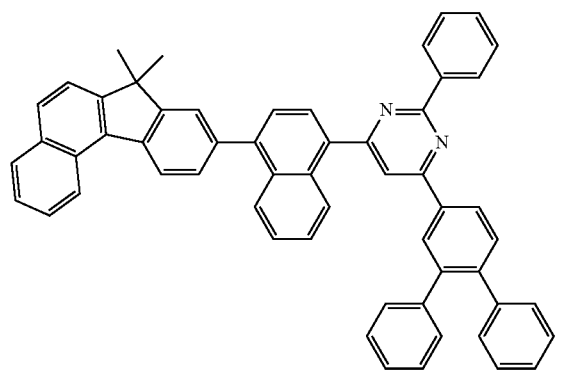
416
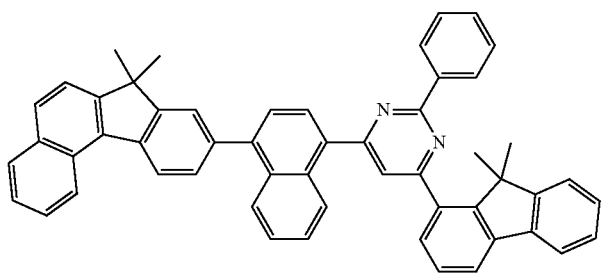
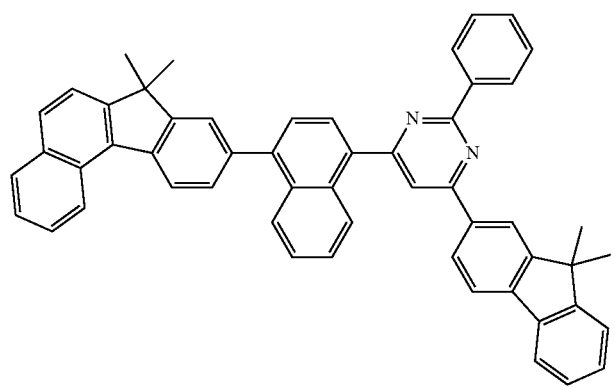
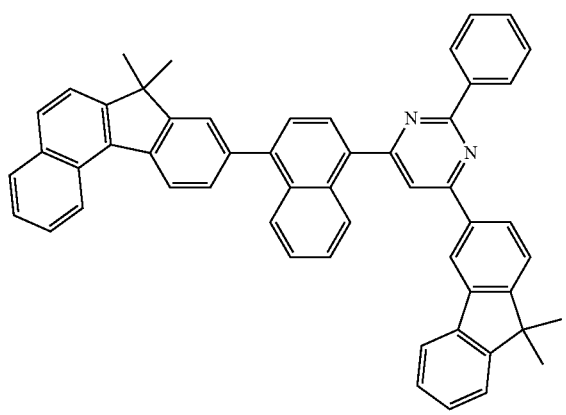
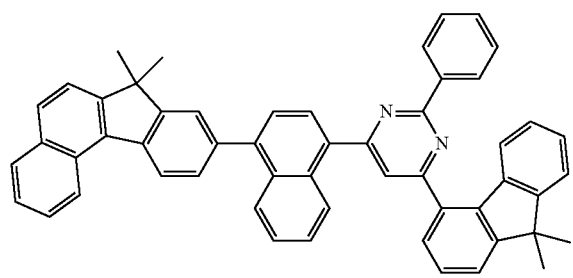
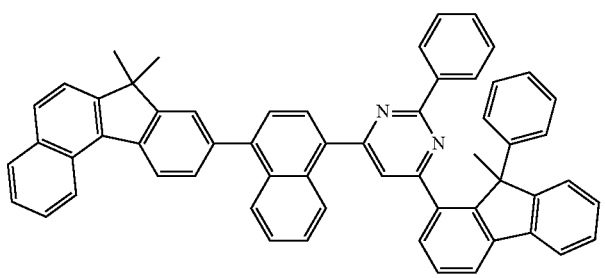
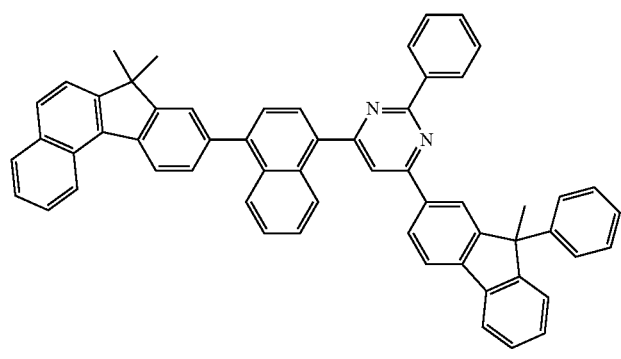
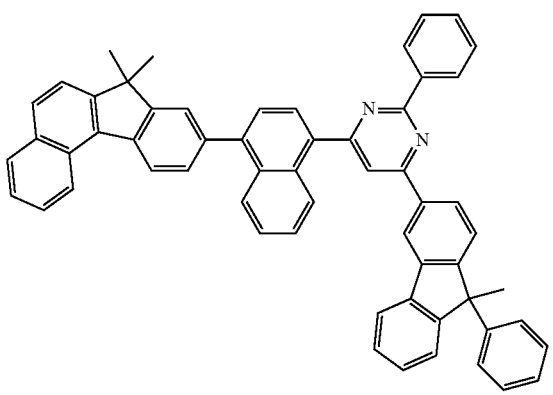

-continued
| 417 | 418 |
|---|---|
| 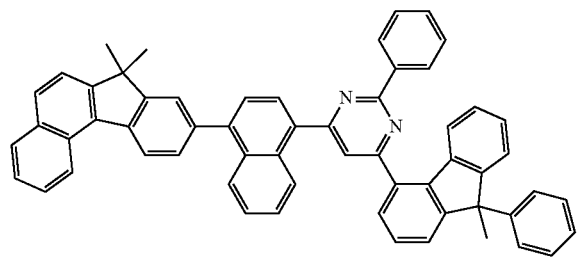 | 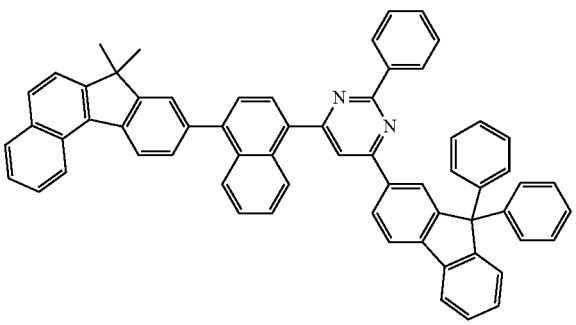 |
| 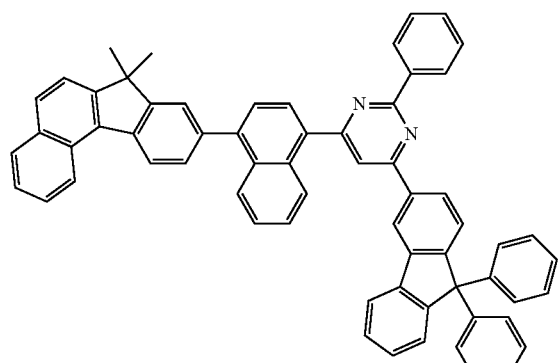 | 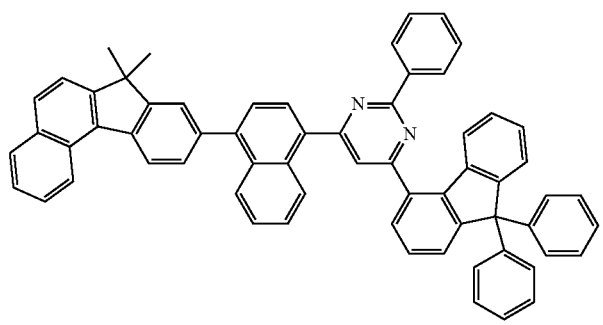 |
| 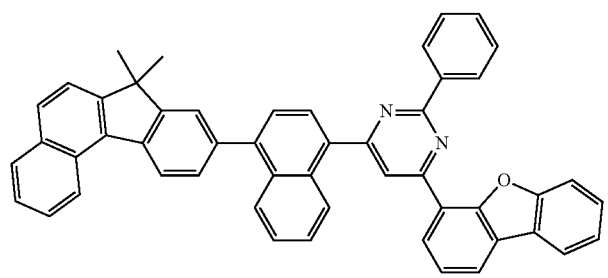 | 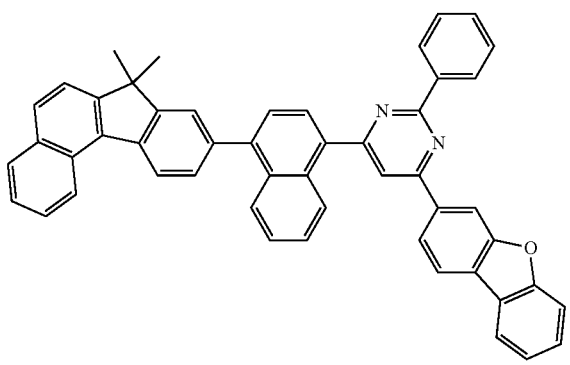 |
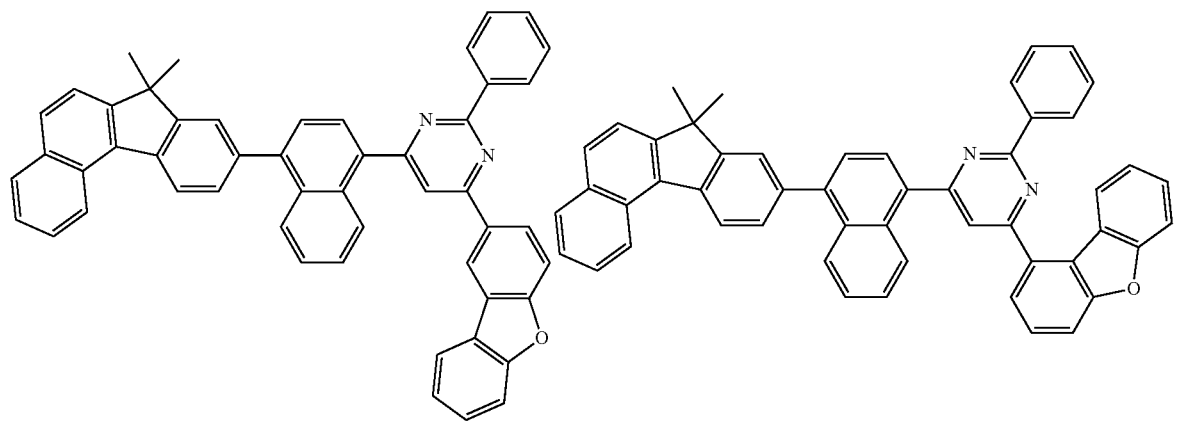

419 420
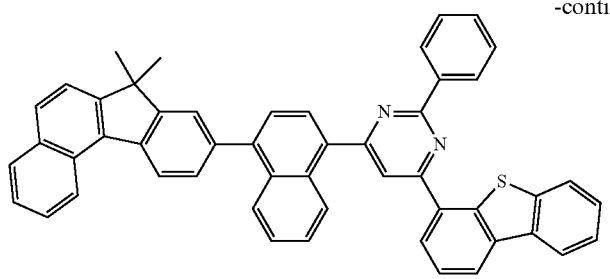
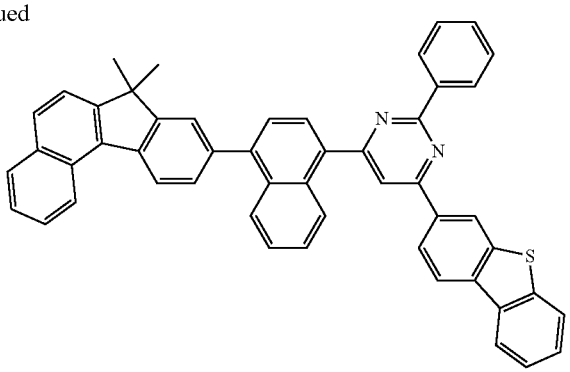
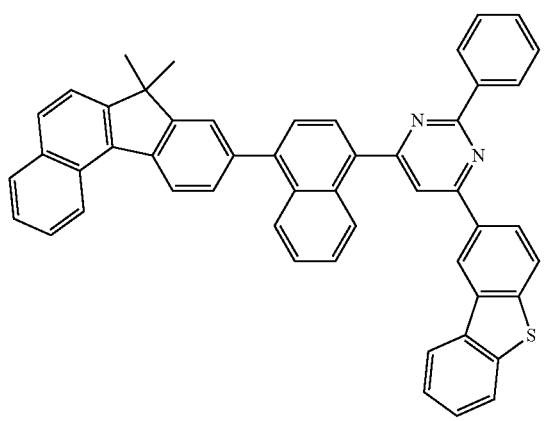
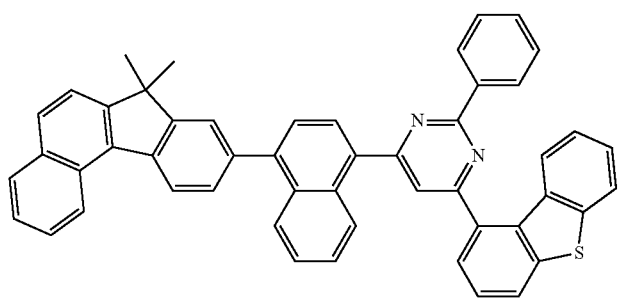
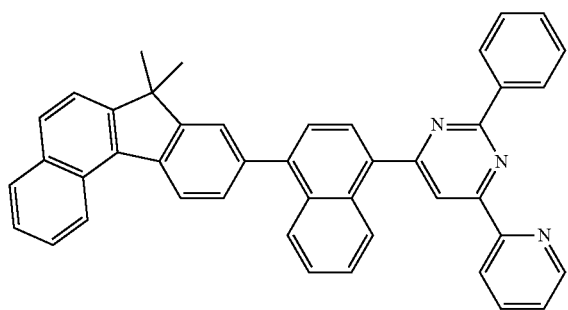
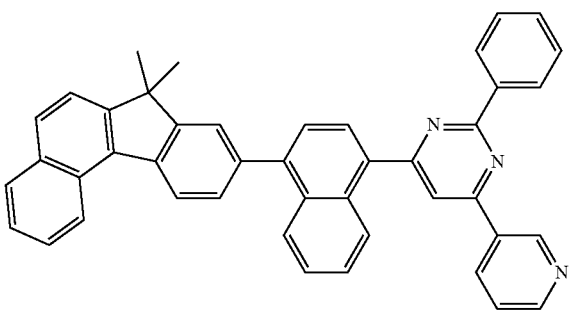
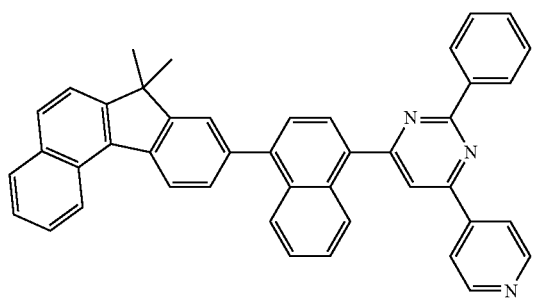
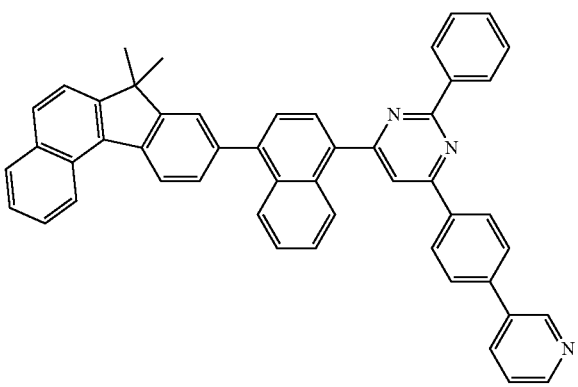

421
422
-continued
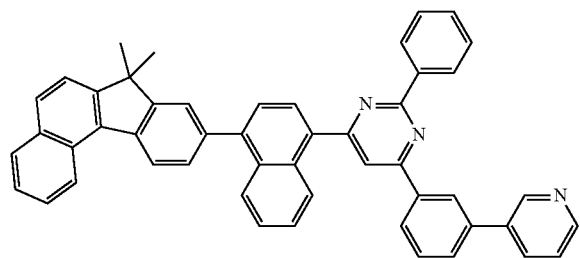
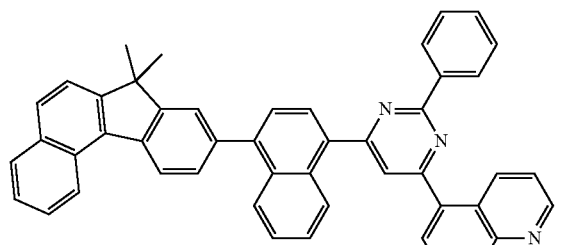
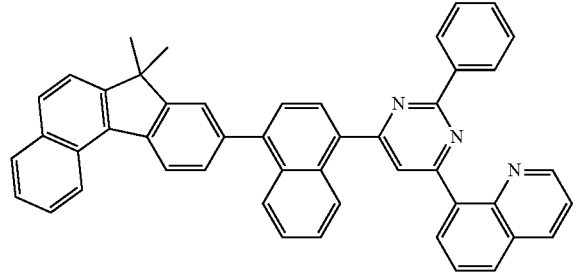
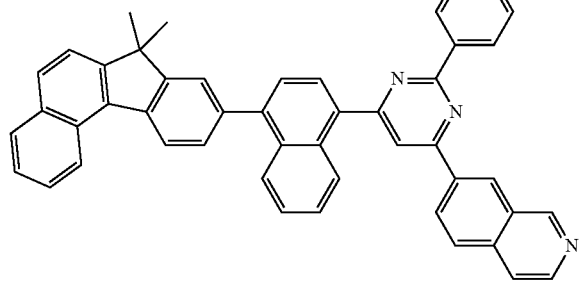
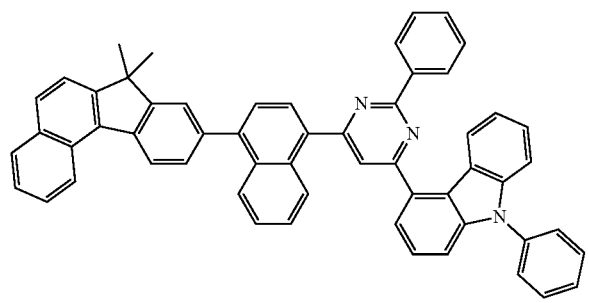
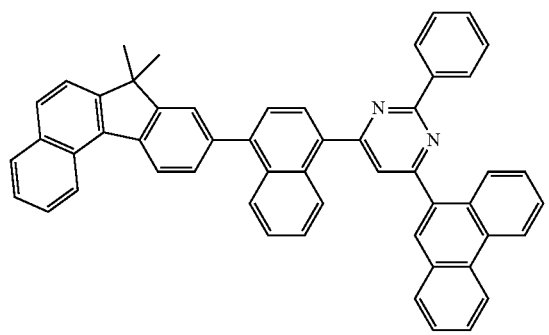
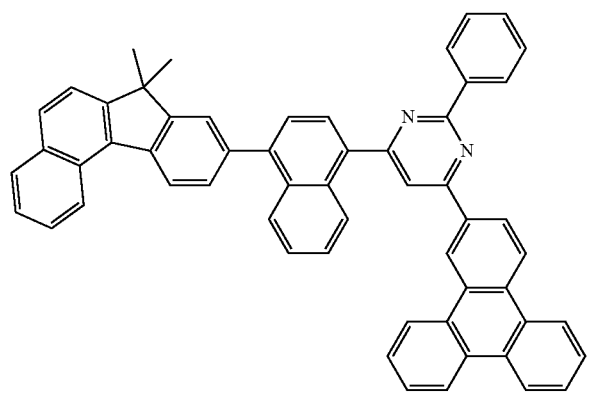
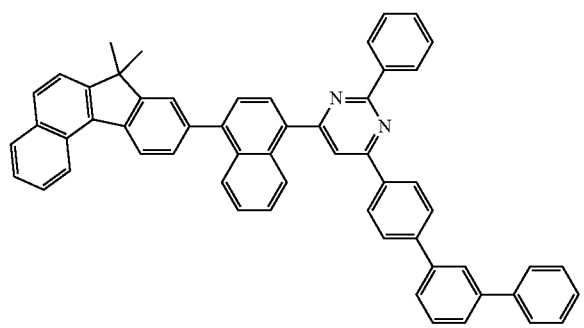
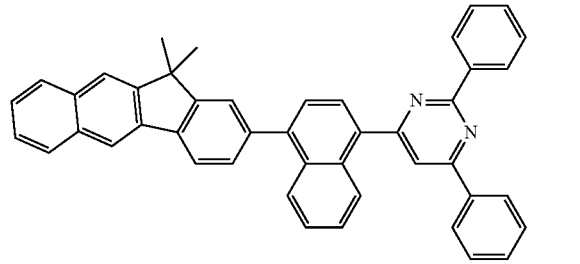
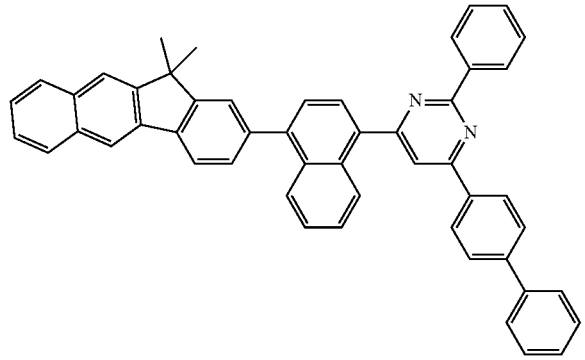

| 423 | 424 |
|---|---|
| 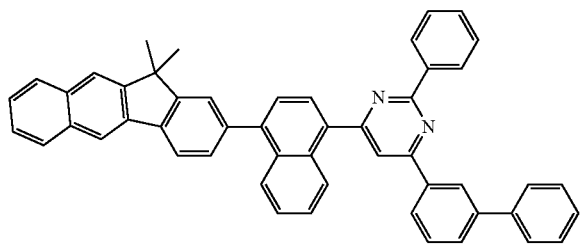 | 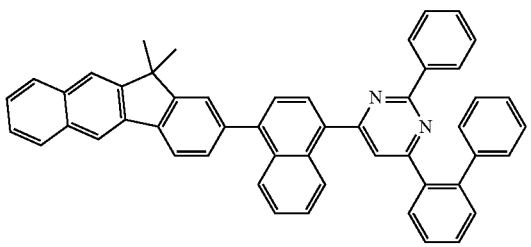 |
-continued
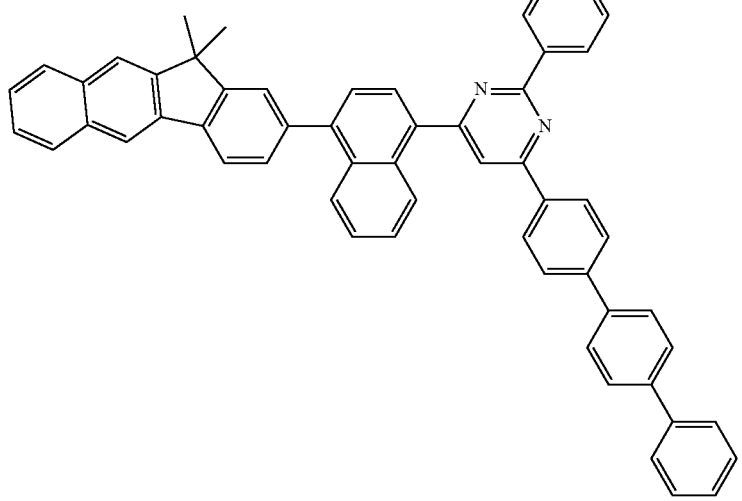
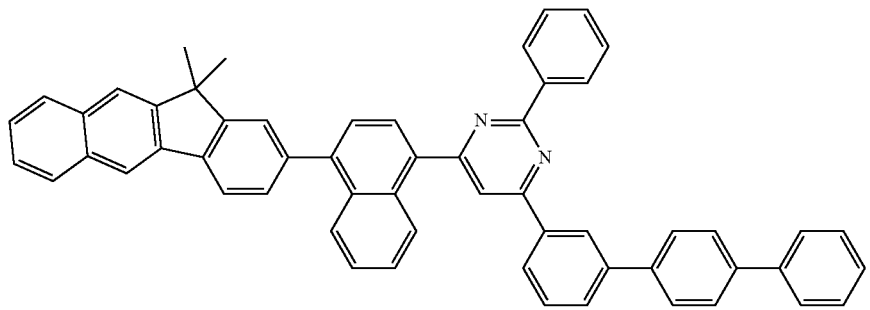
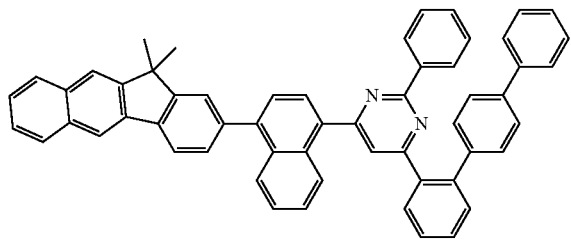
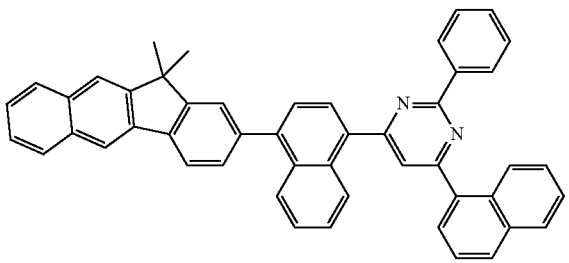
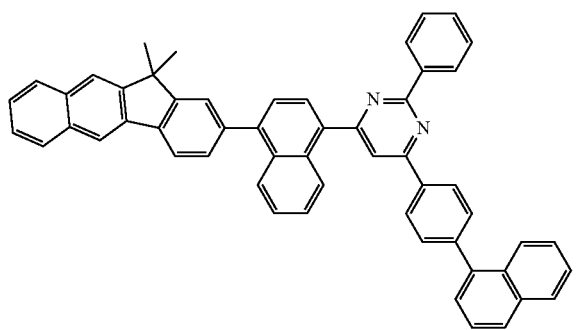
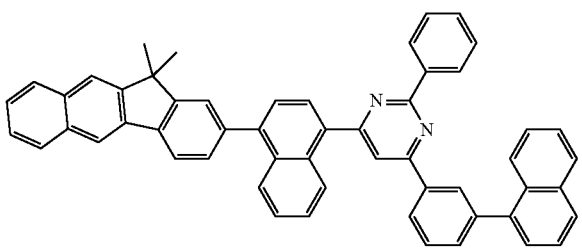

-continued
| 425 | 426 |
|---|---|
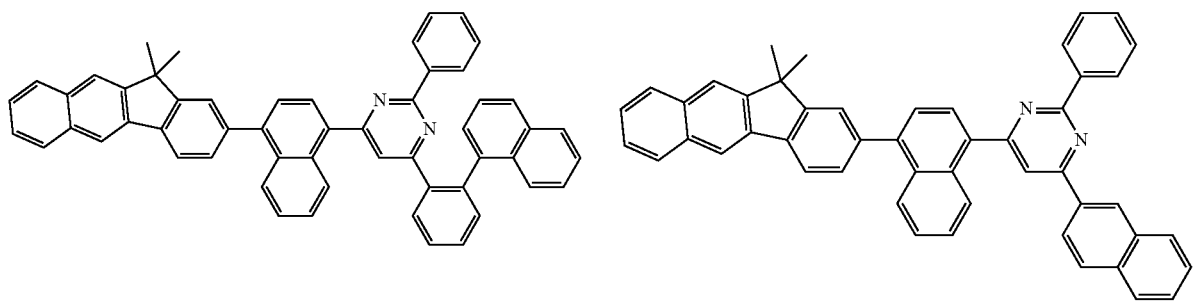
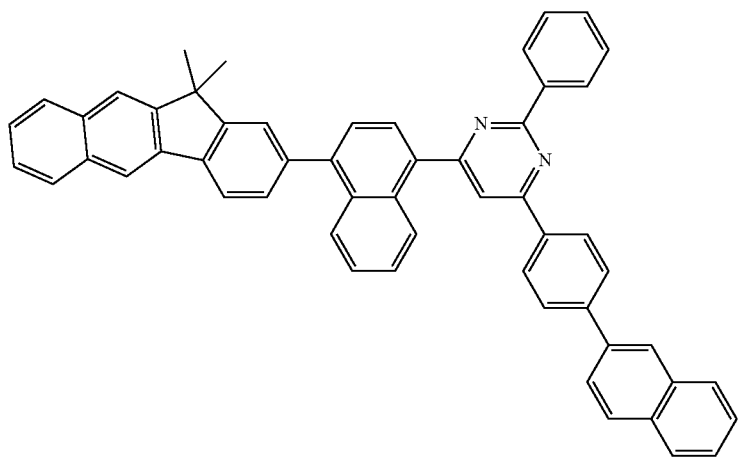
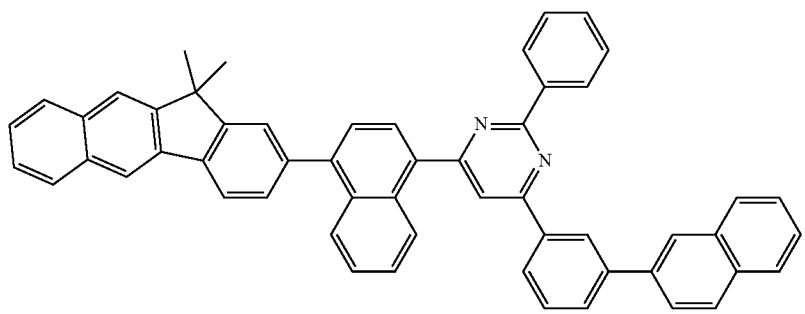
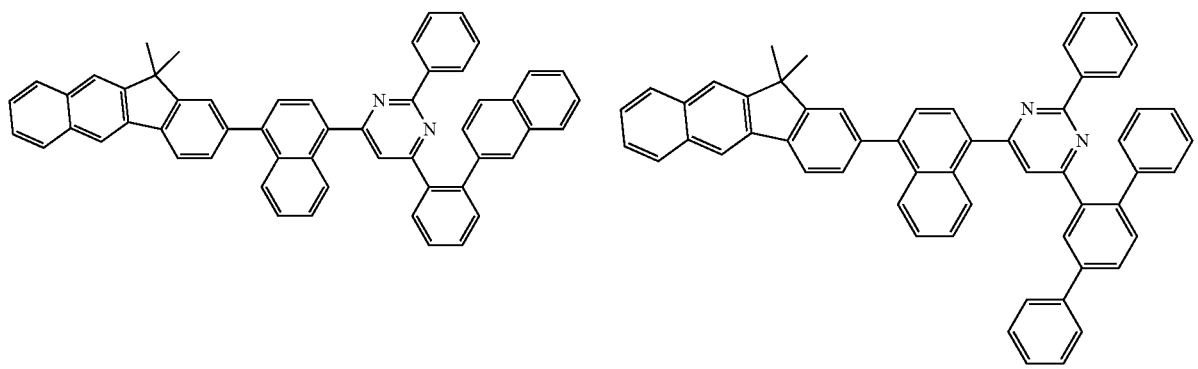

-continued
427 428
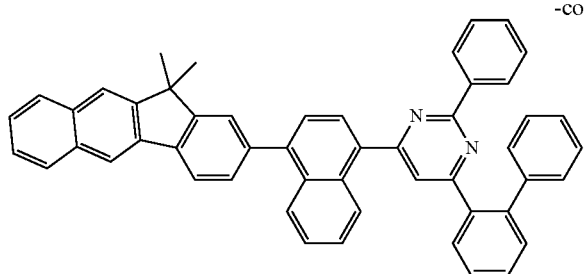 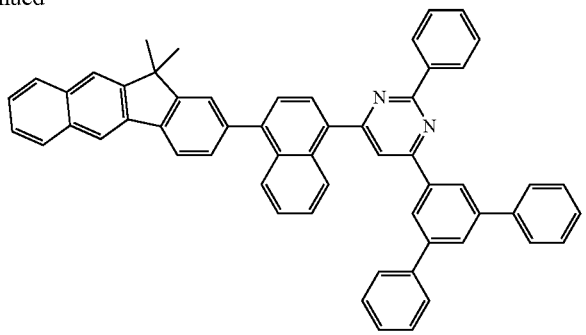
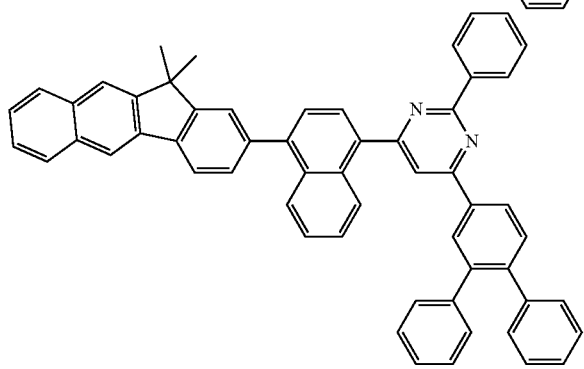 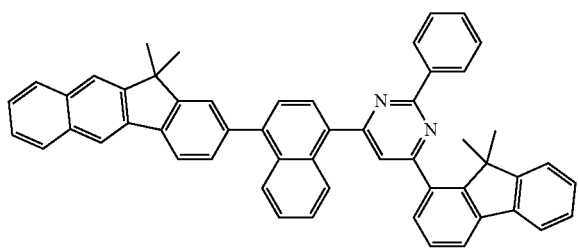
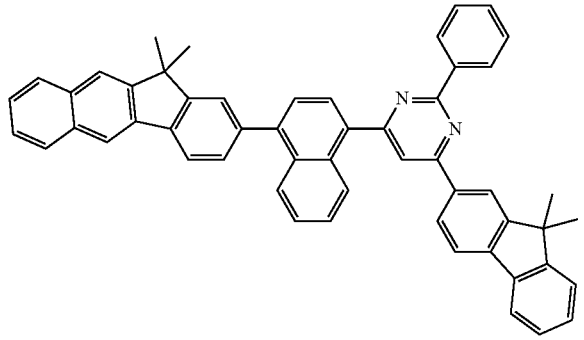 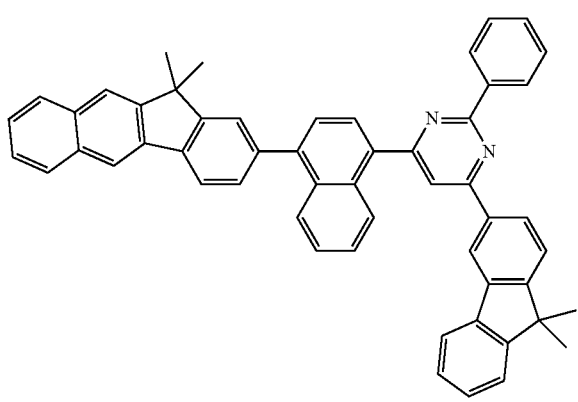
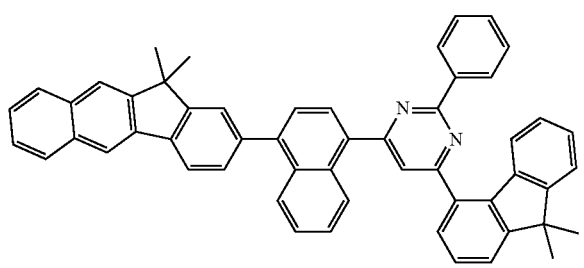 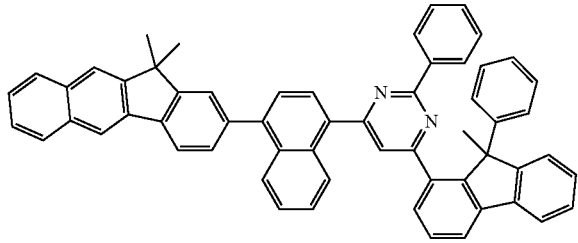
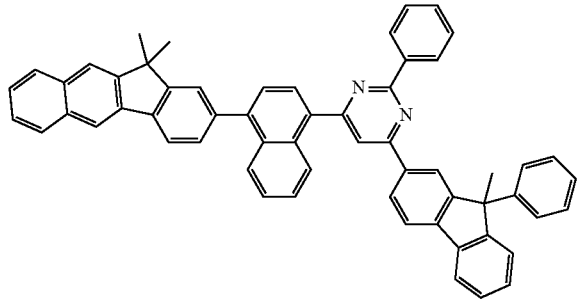 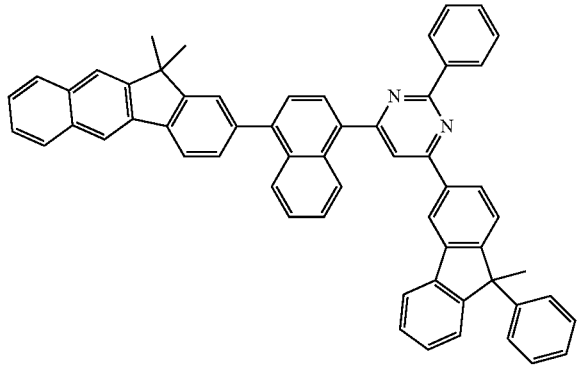

-continued
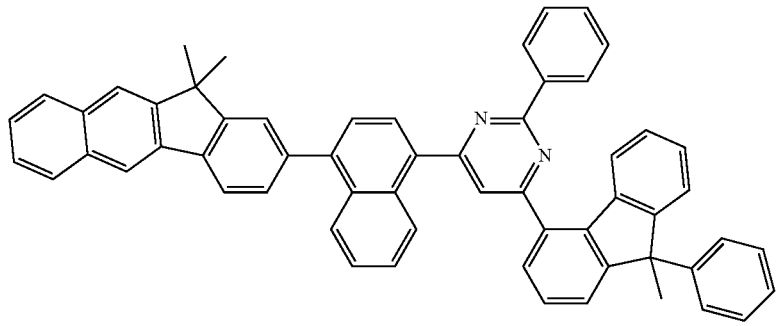
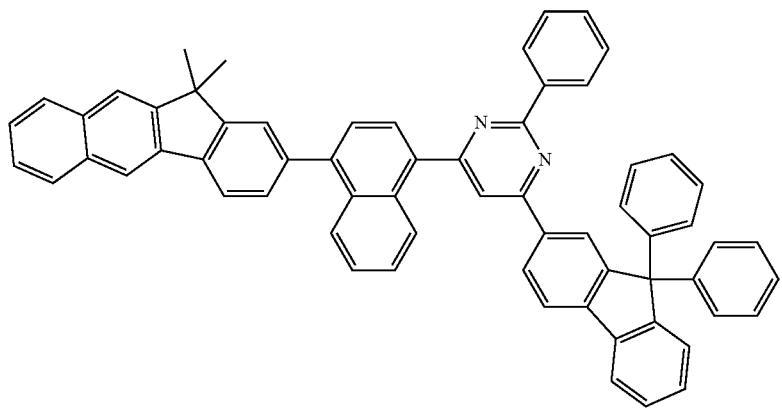
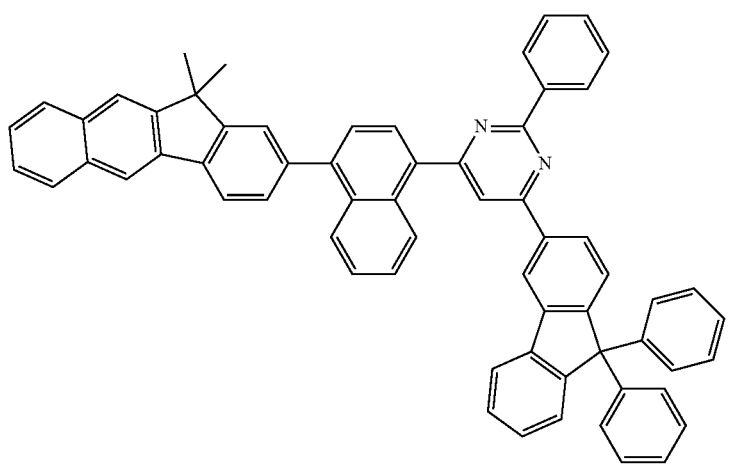
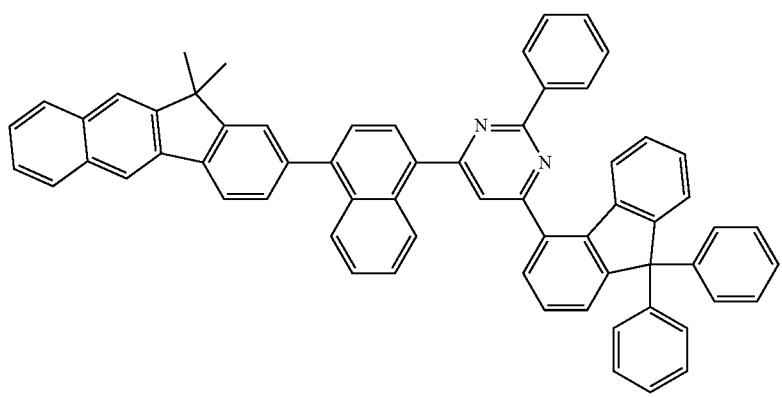

-continued
431 432
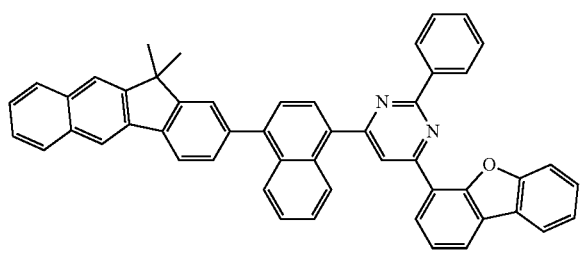
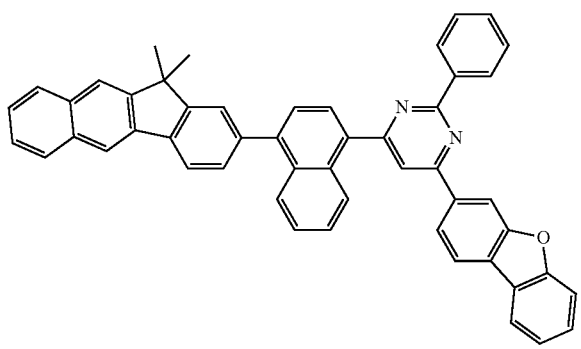
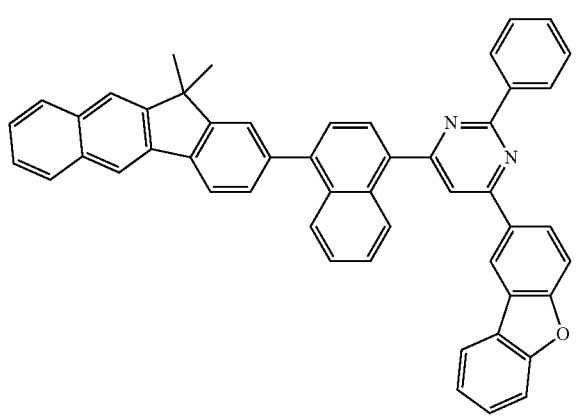
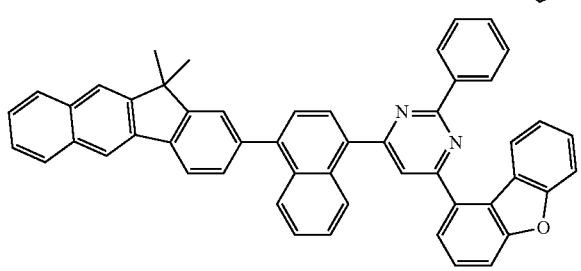
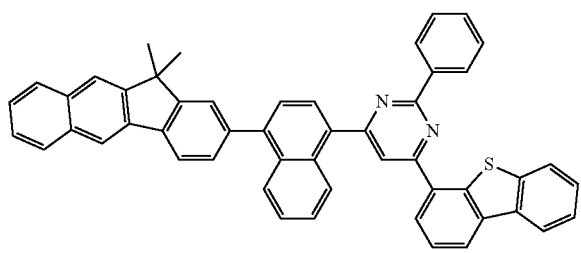
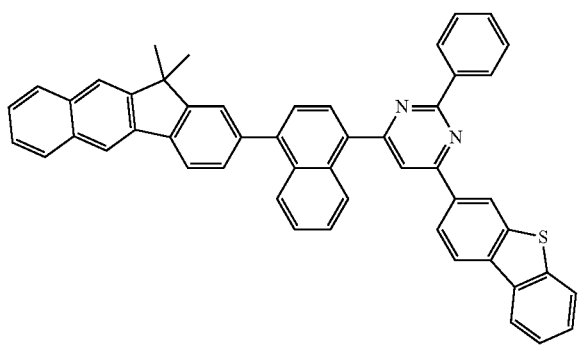
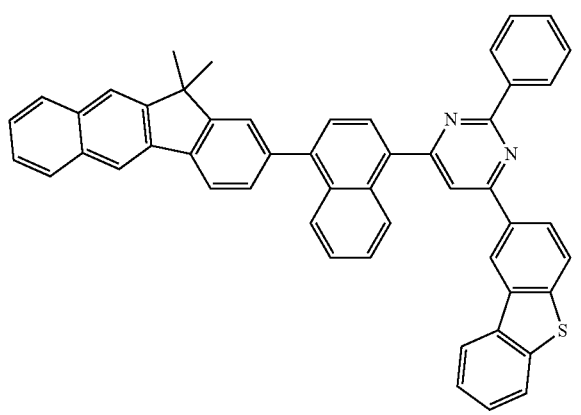
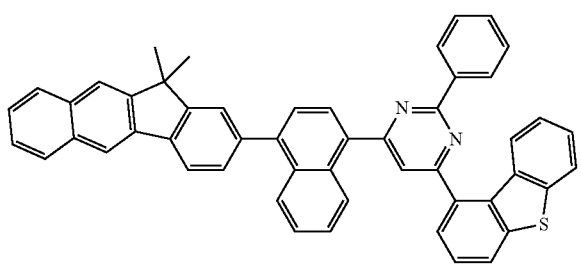

433 434
-continued
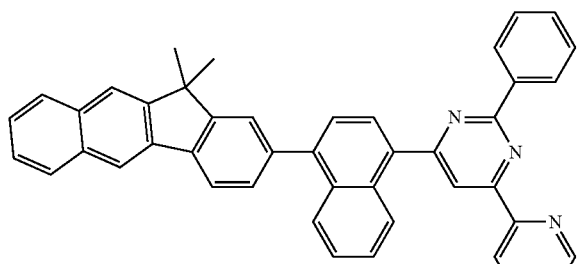
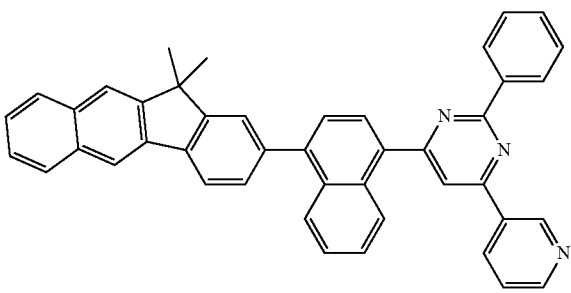
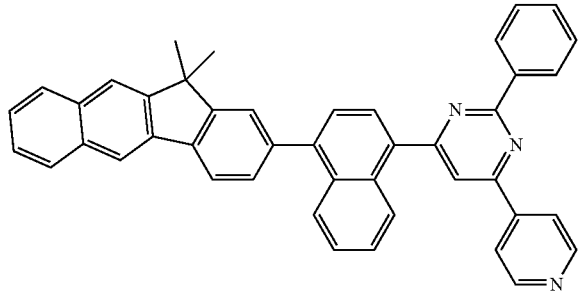
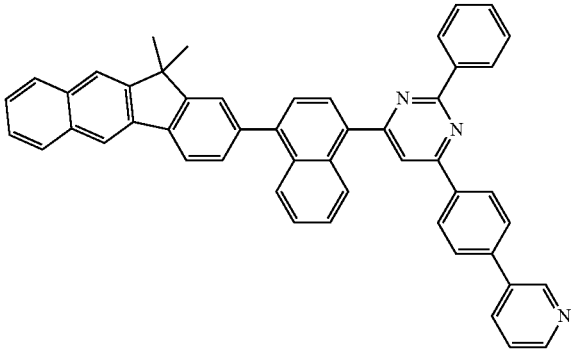
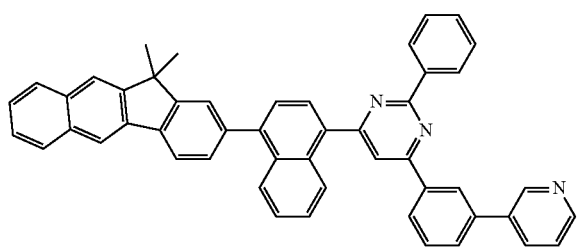
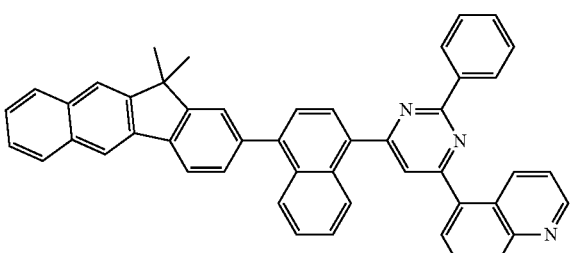
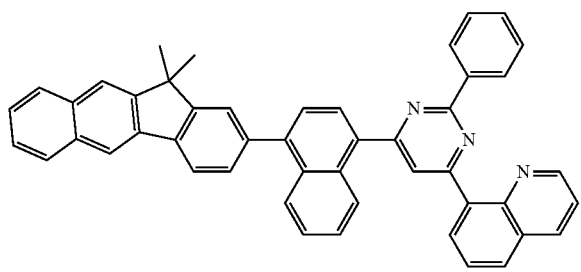
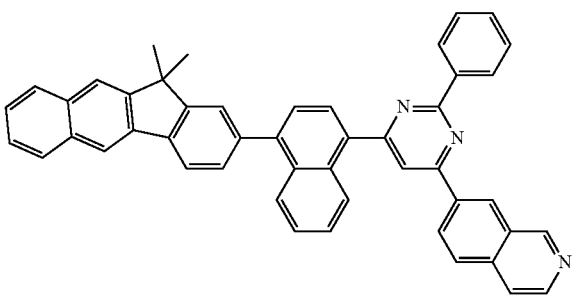
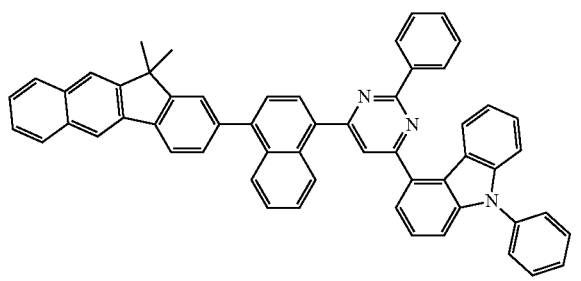
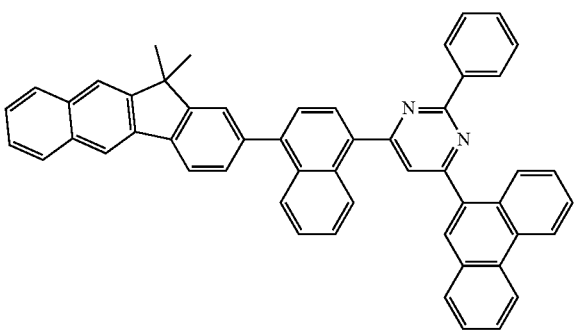

435
-continued
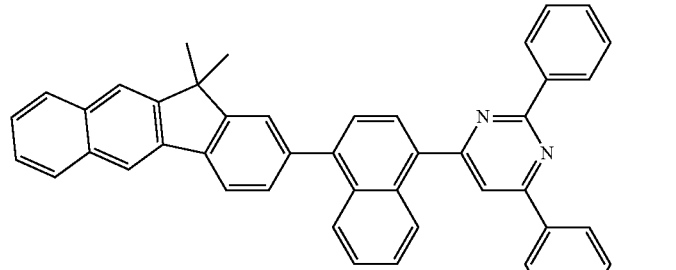
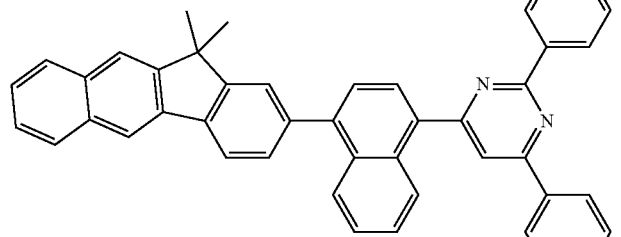
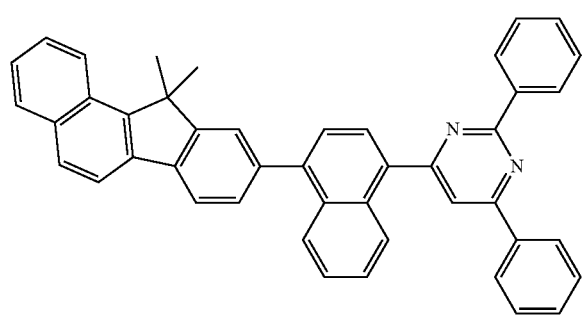
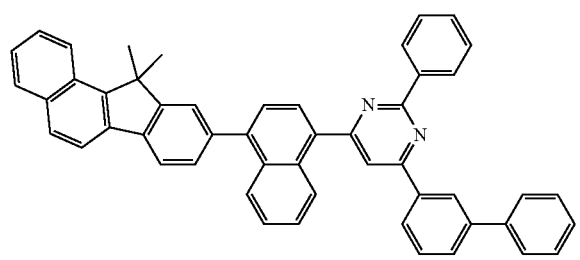
436
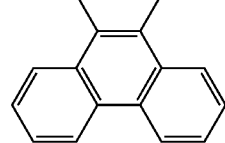
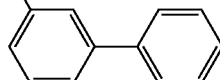
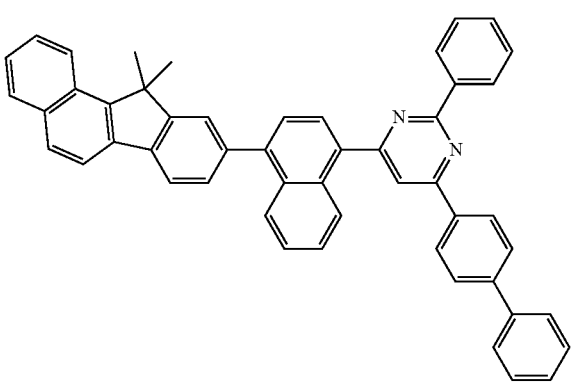
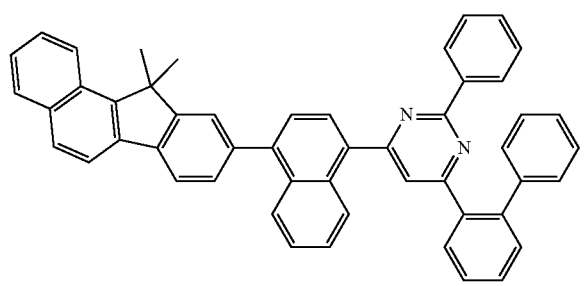

437                                                      438
-continued
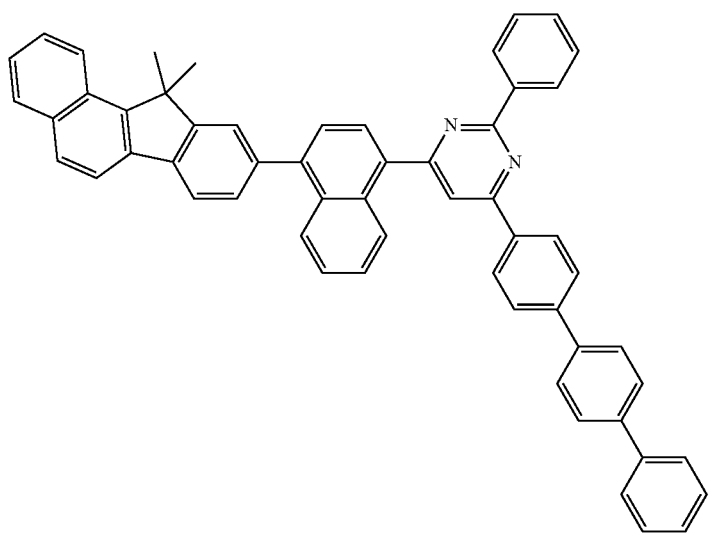
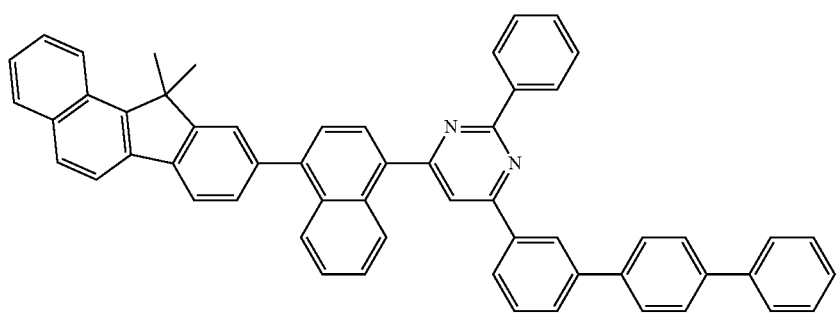
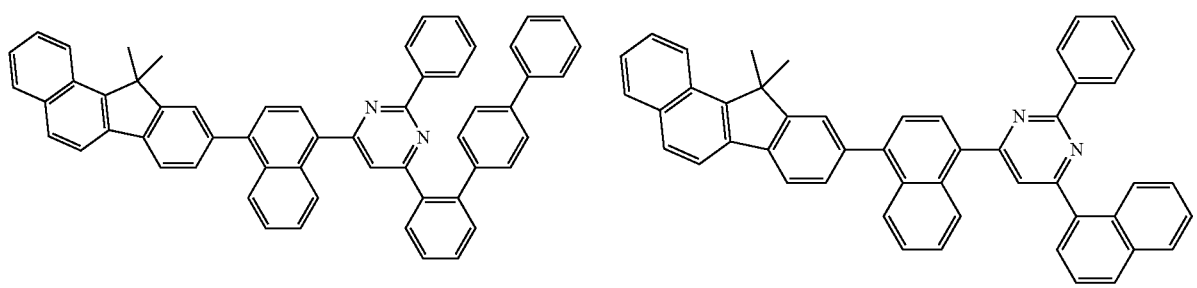
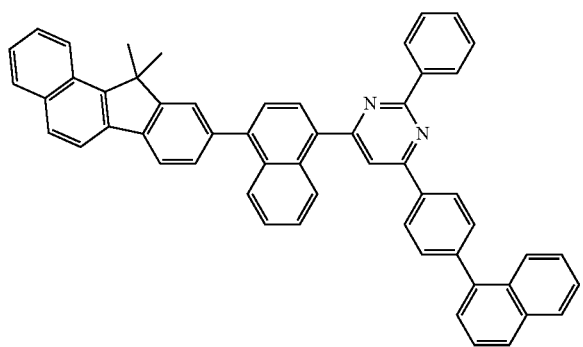
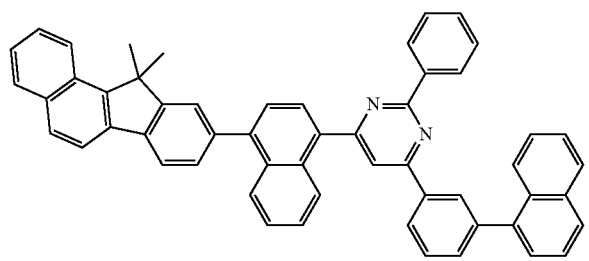

439 440
-continued
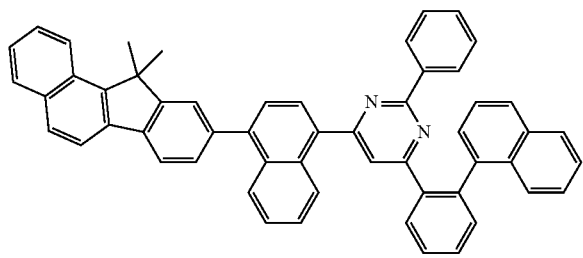
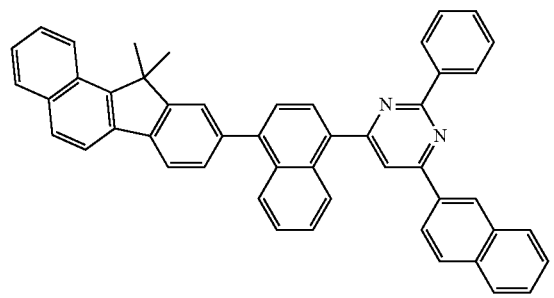
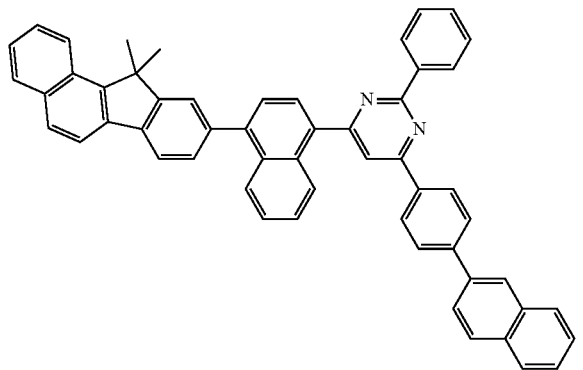
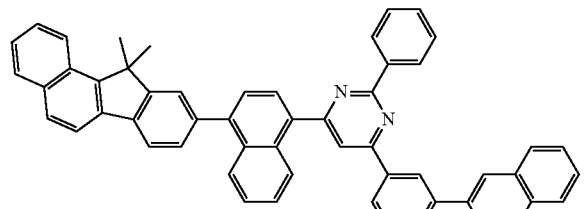
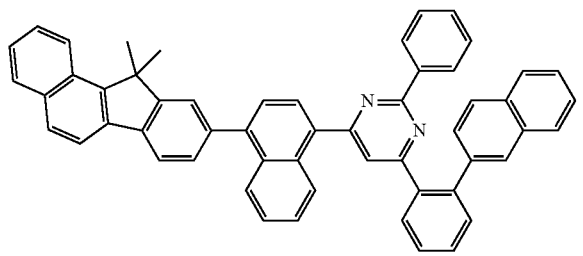
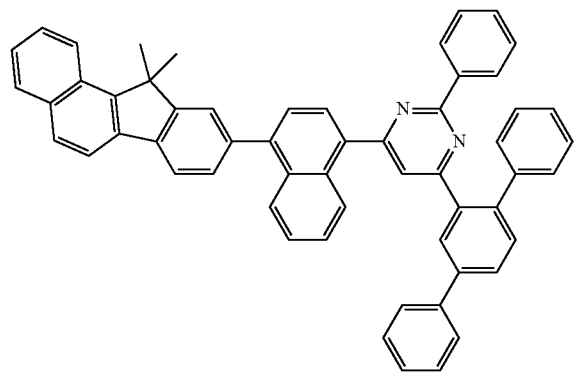
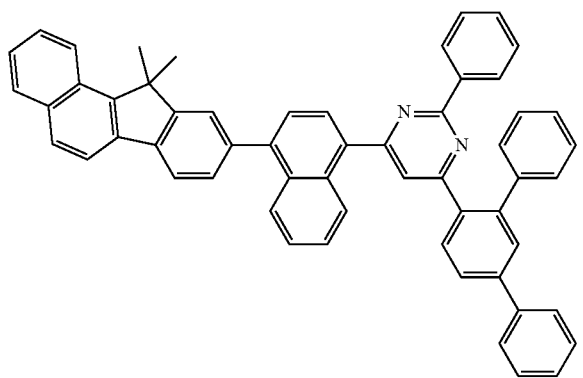
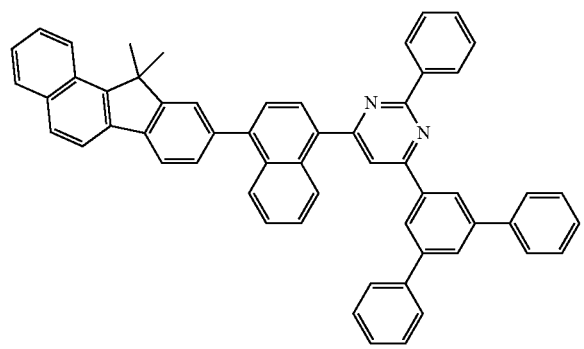

-continued
441 442
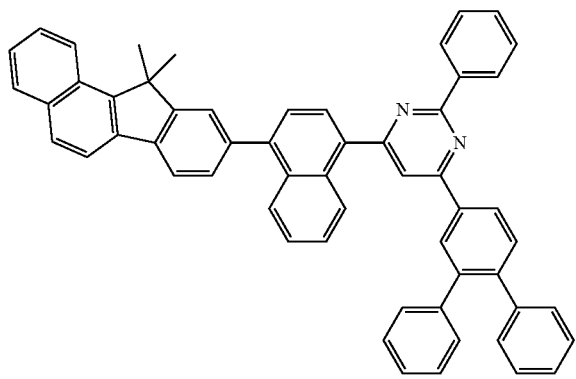
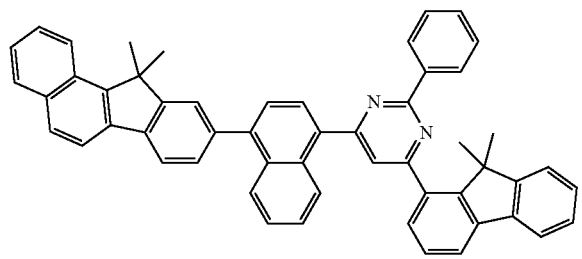
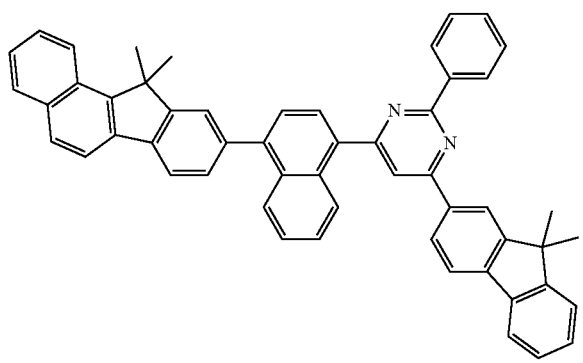
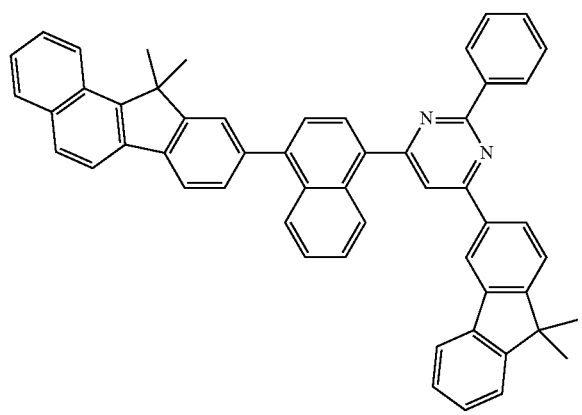
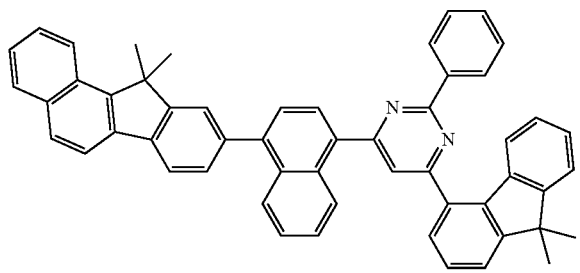
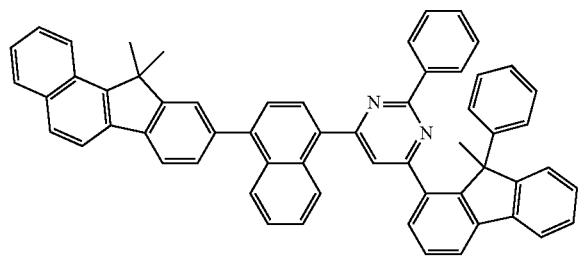
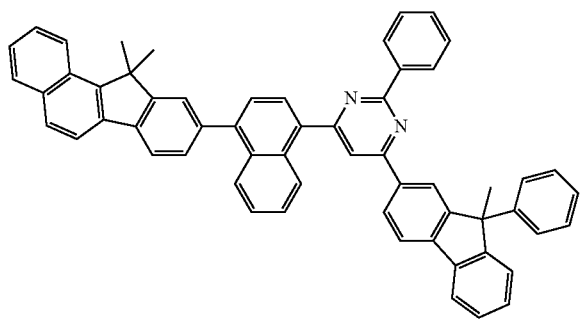
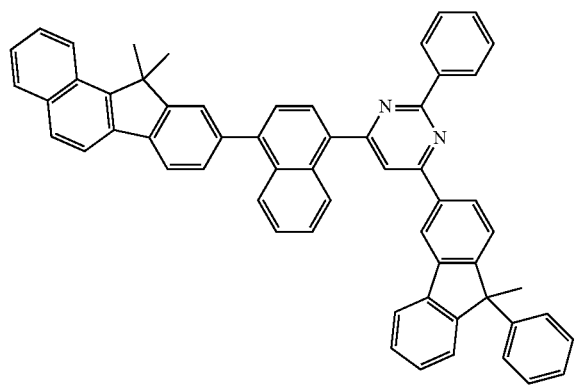

-continued
| 443 | 444 |
|---|---|
| 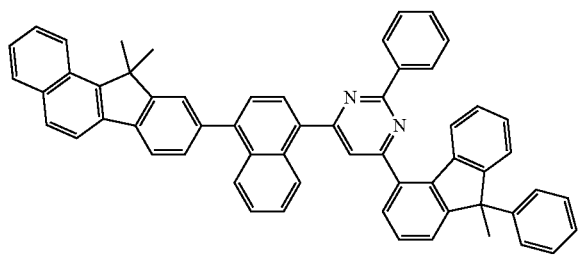 | 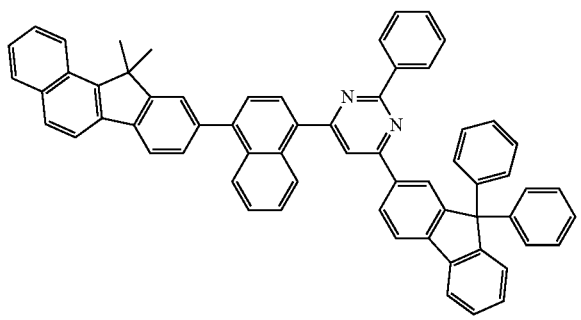 |
| 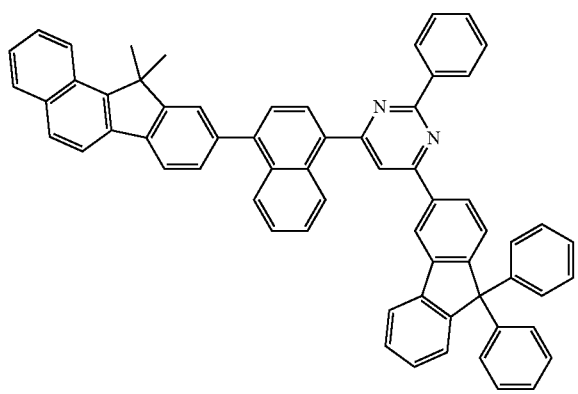 | 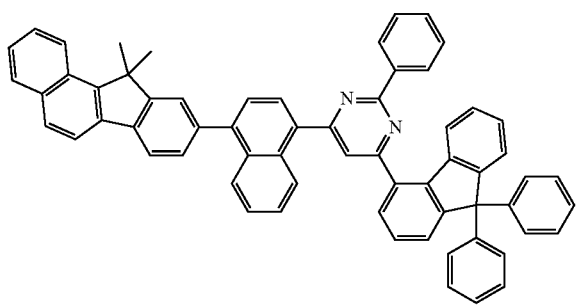 |
| 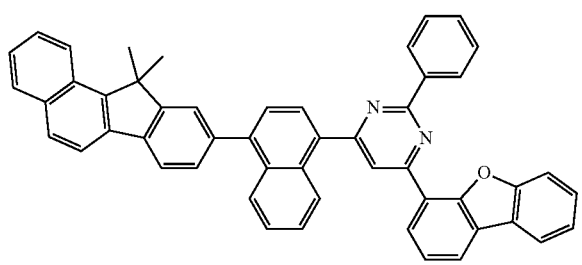 | 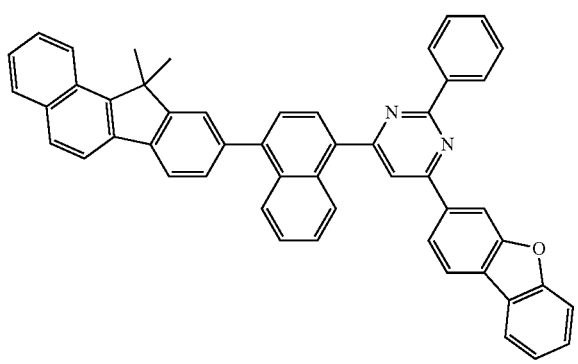 |
| 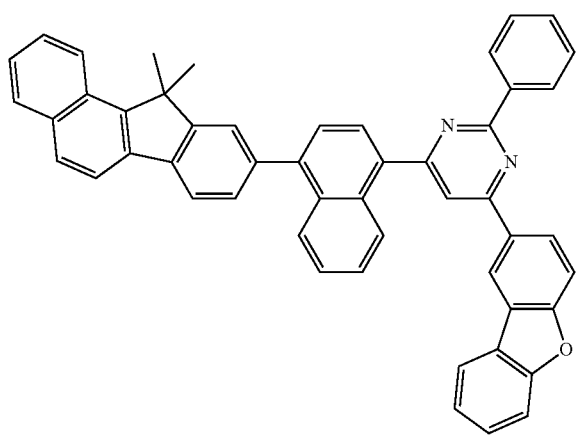 | 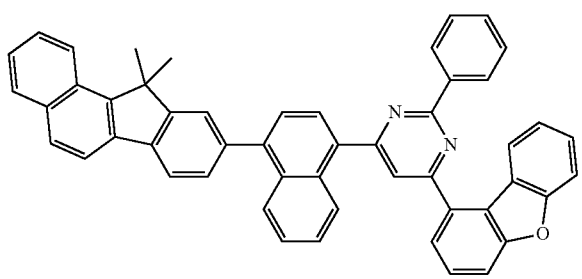 |

445
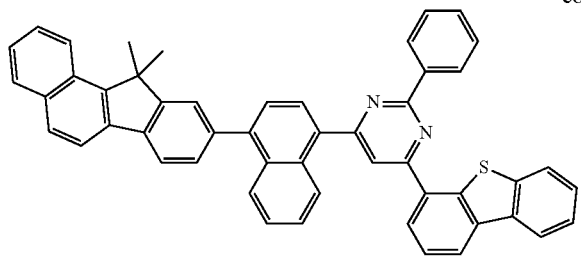
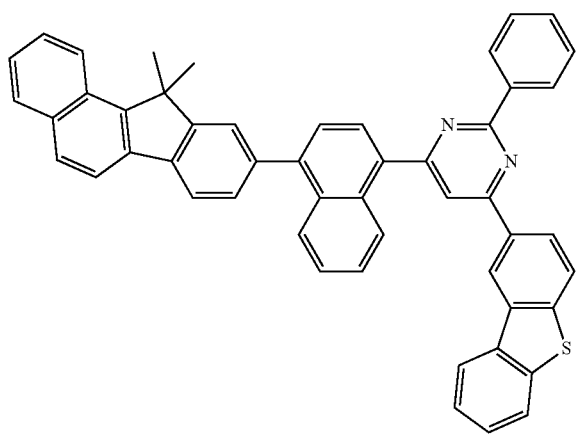
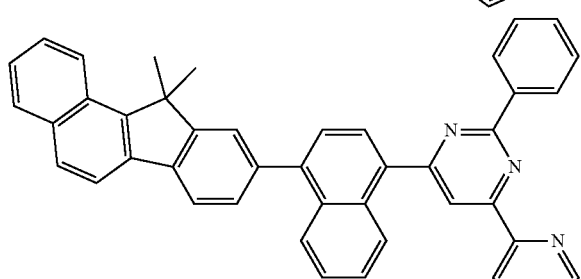
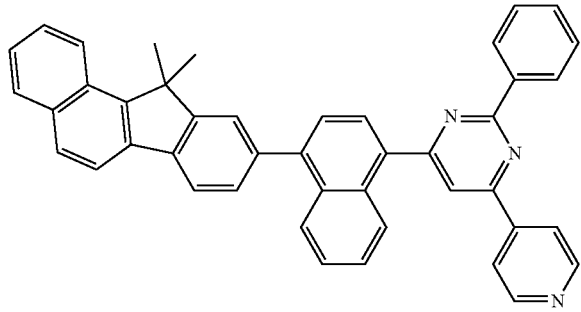
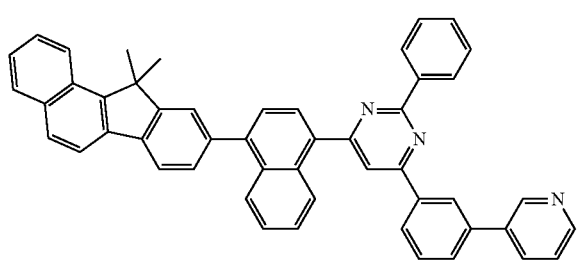
446
-continued
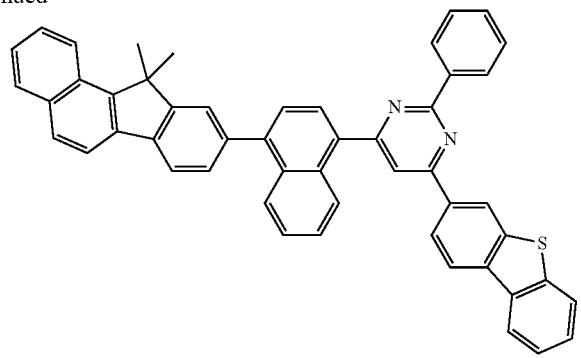
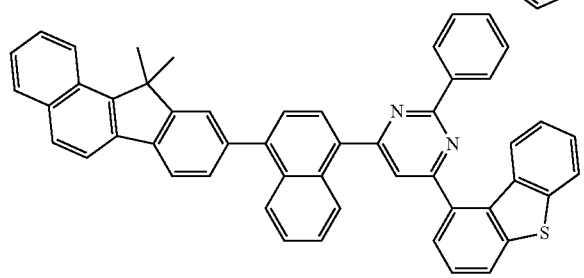
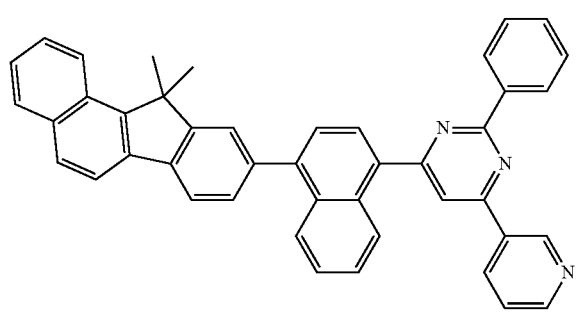
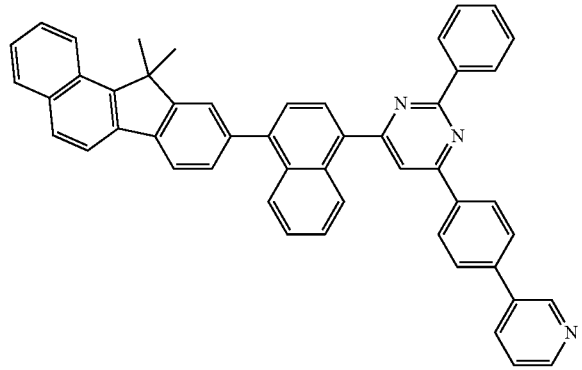
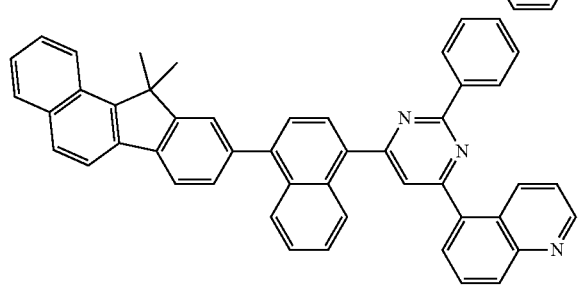

-continued
| 447 | 448 |
|---|---|
| 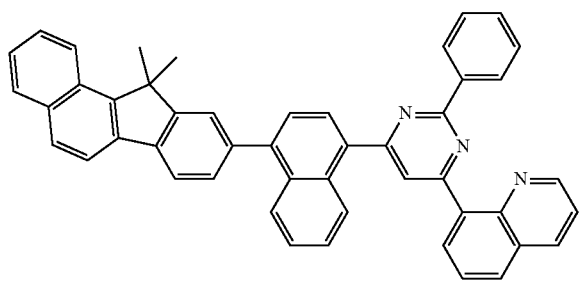 | 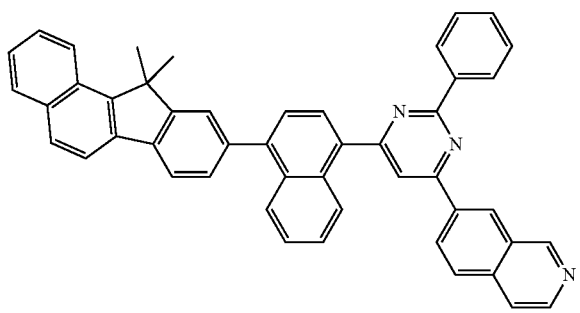 |
| 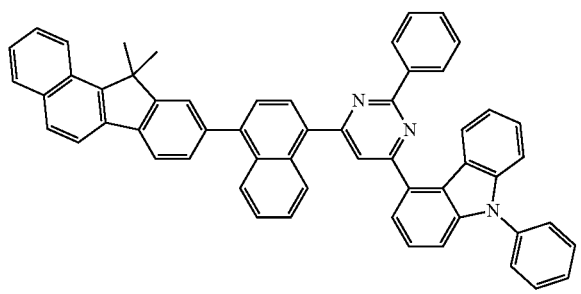 | 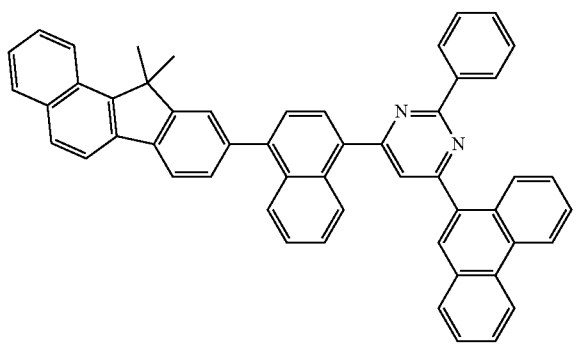 |
| 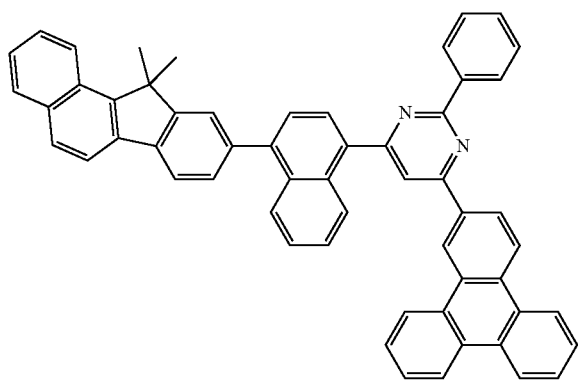 | 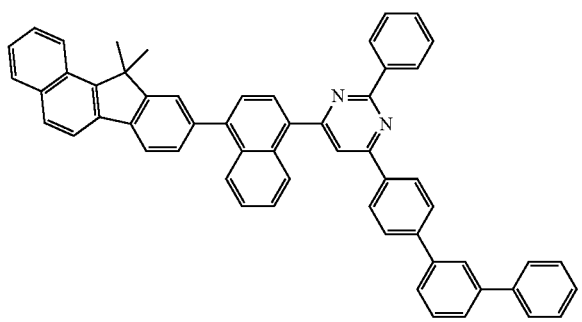 |
| 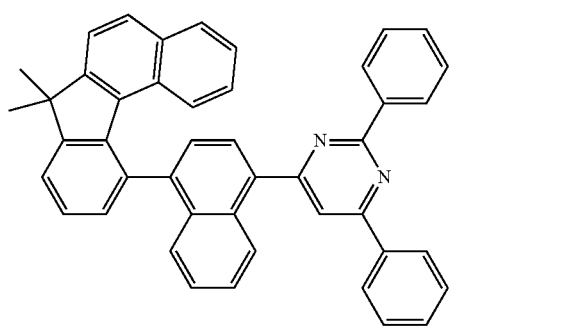 | 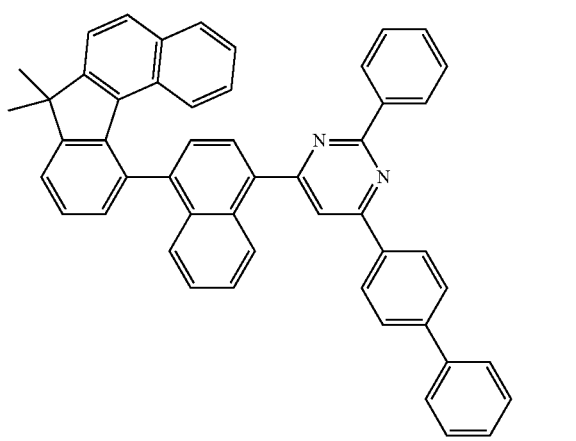 |

449
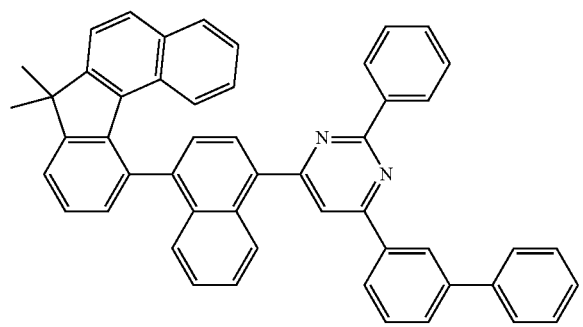
450
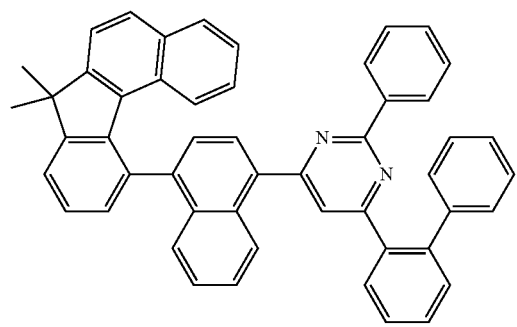
-continued
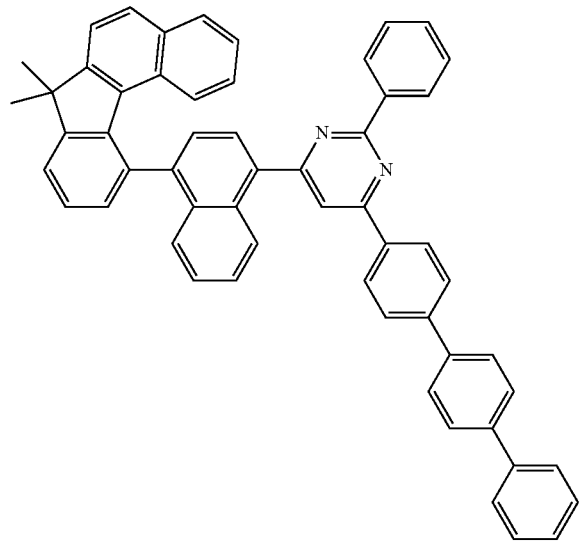
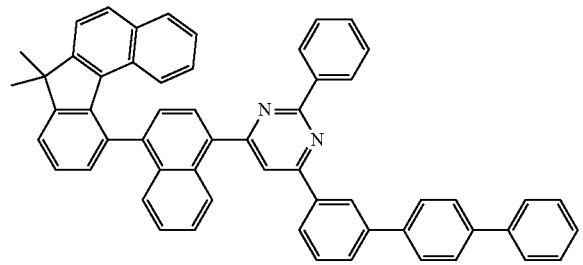
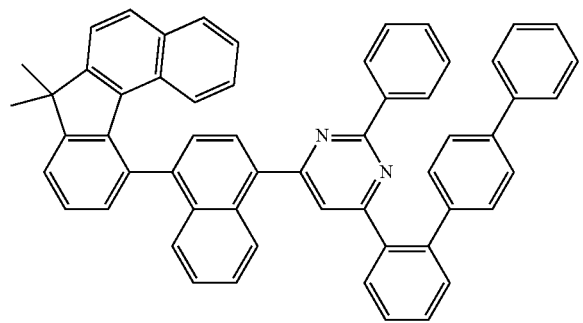
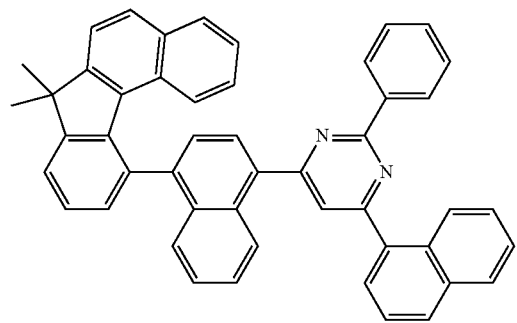
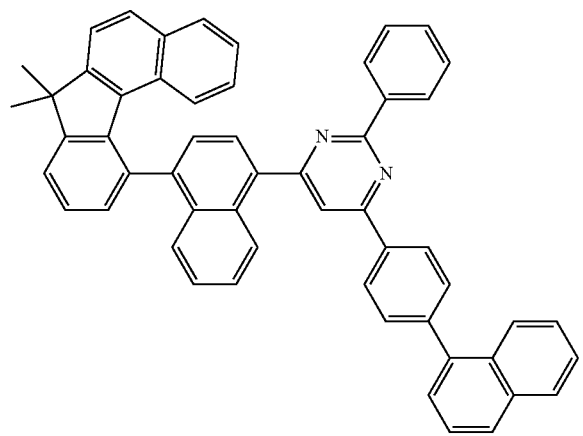
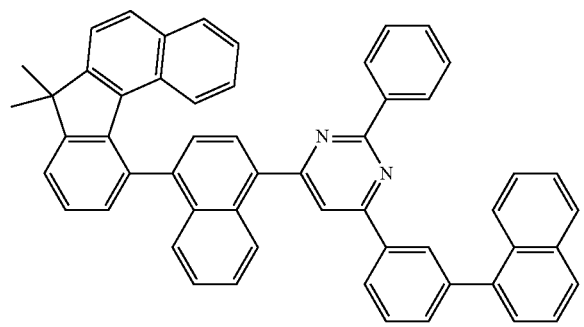

451
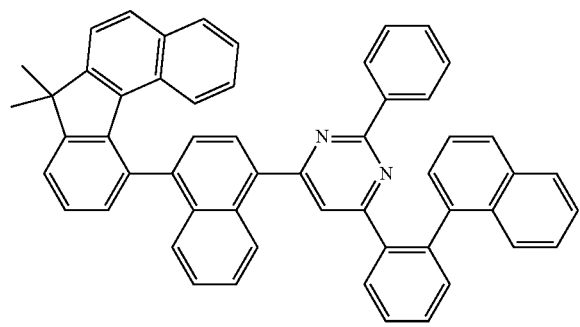
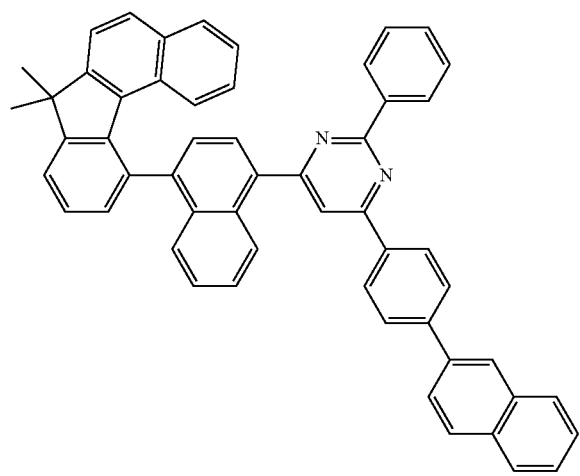
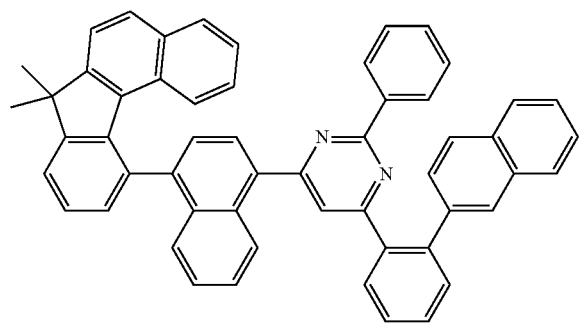
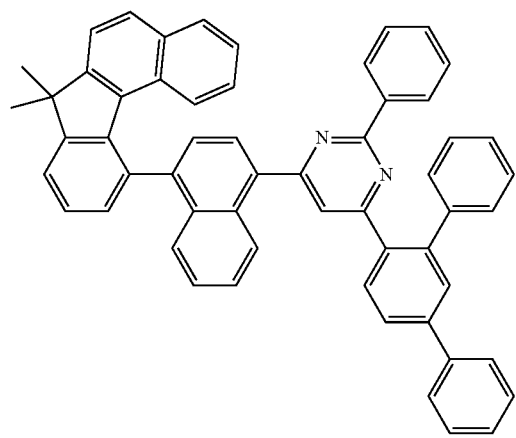
452
-continued
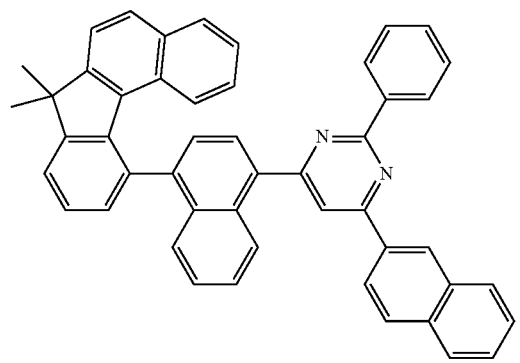
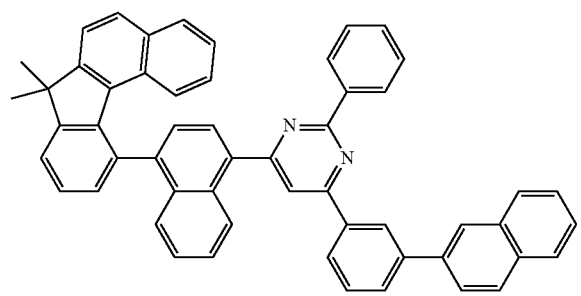
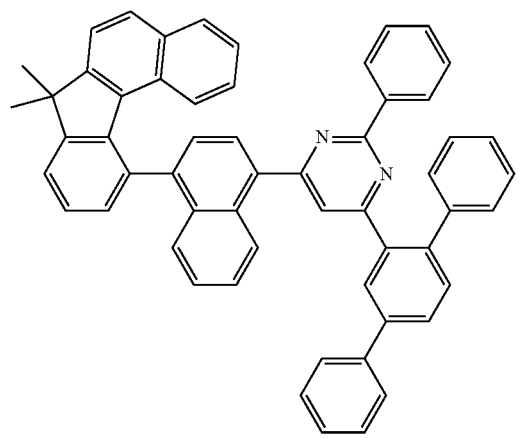
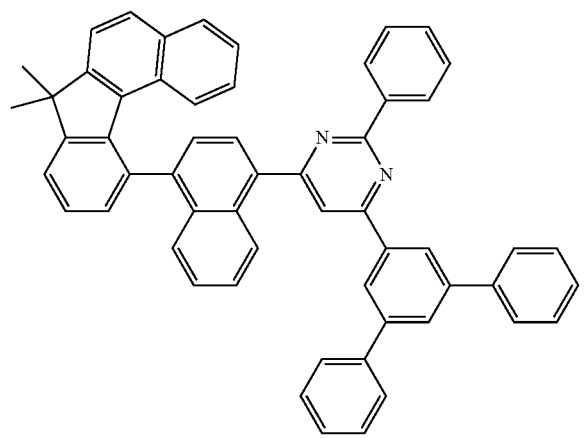

453
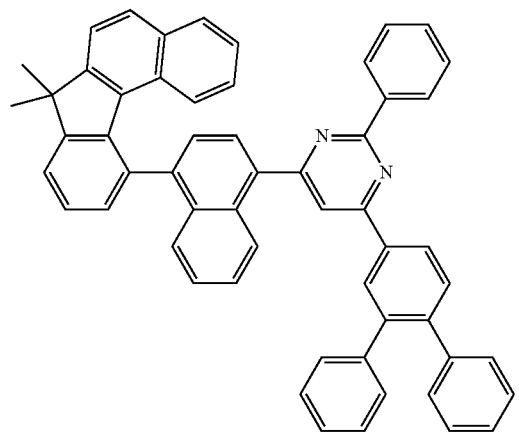
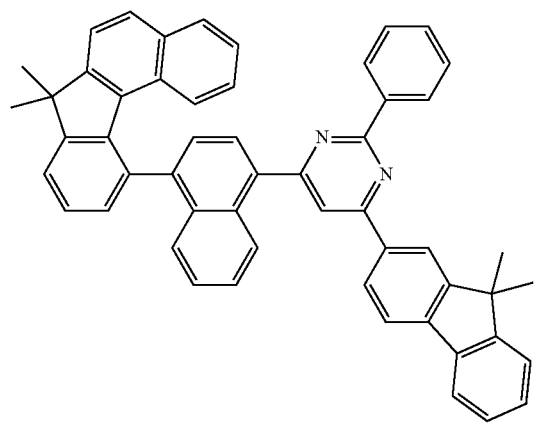
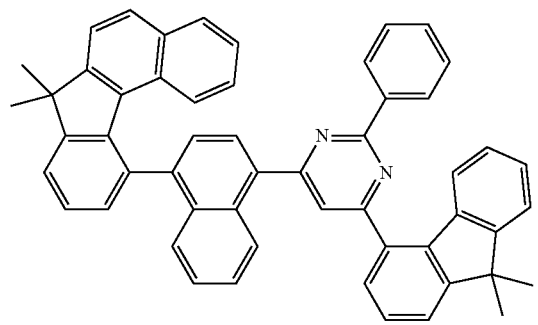
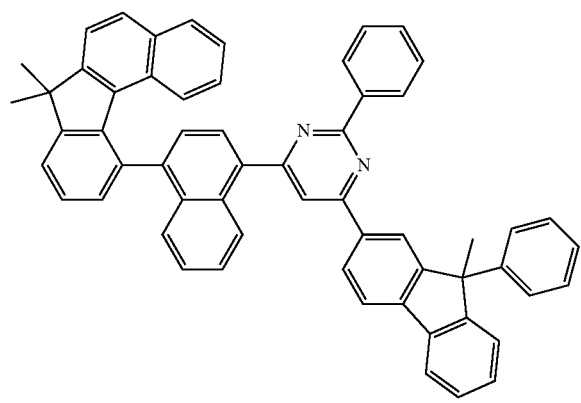
454
-continued
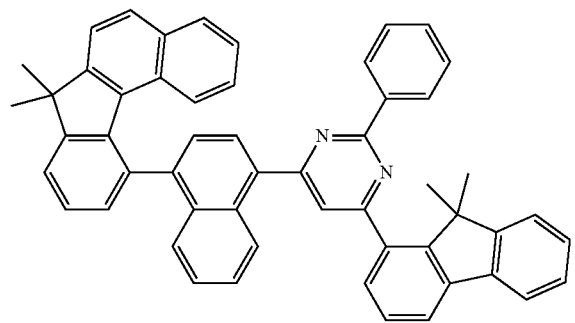
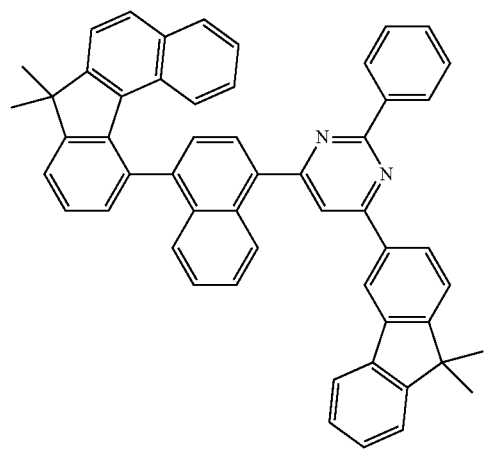
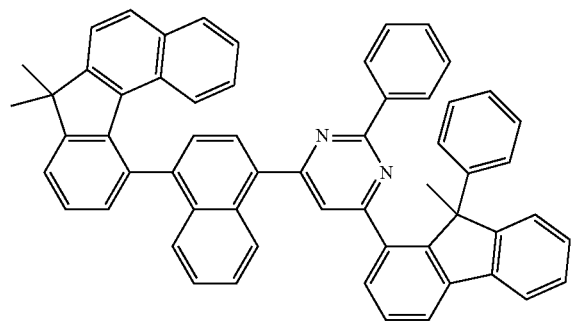
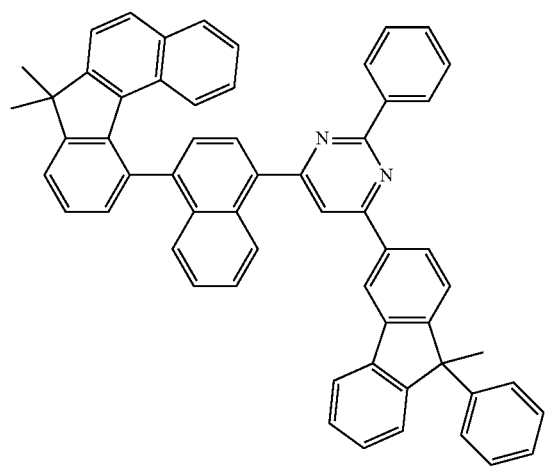

455
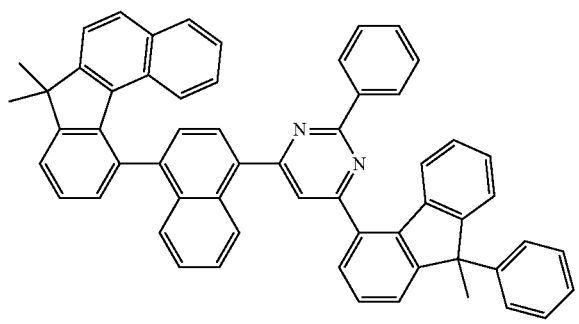
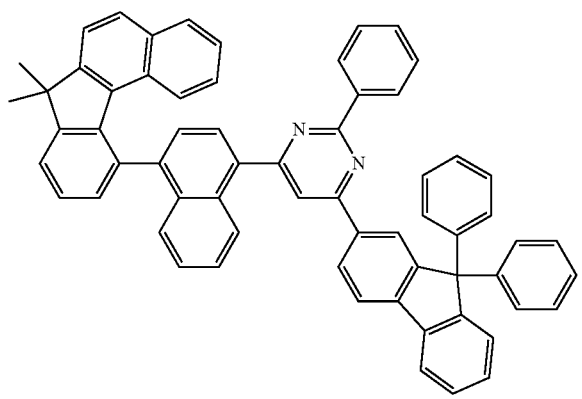
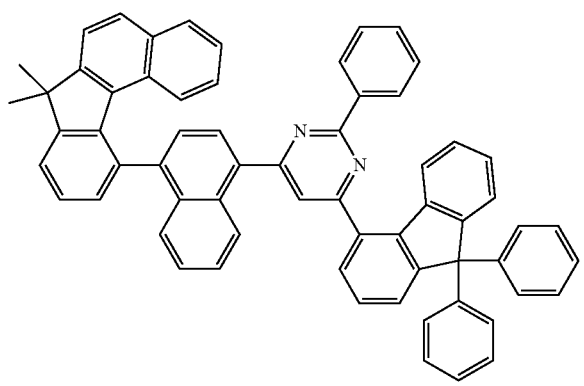
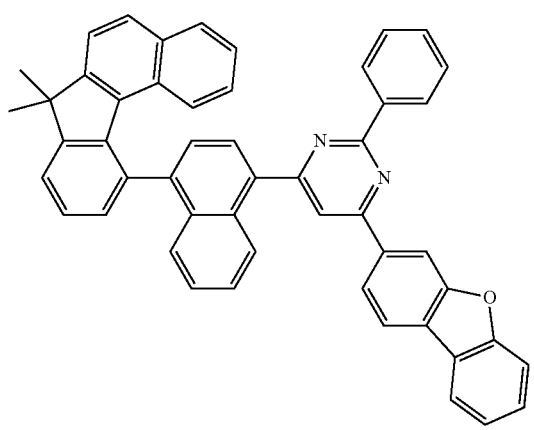
-continued
456
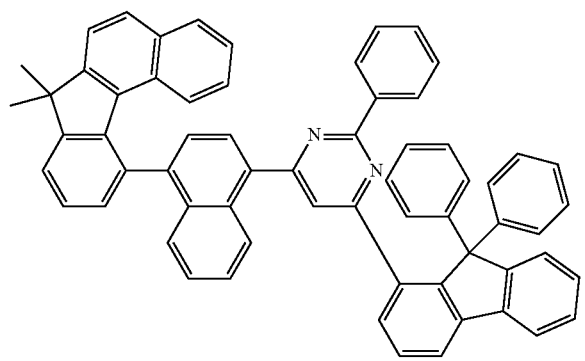
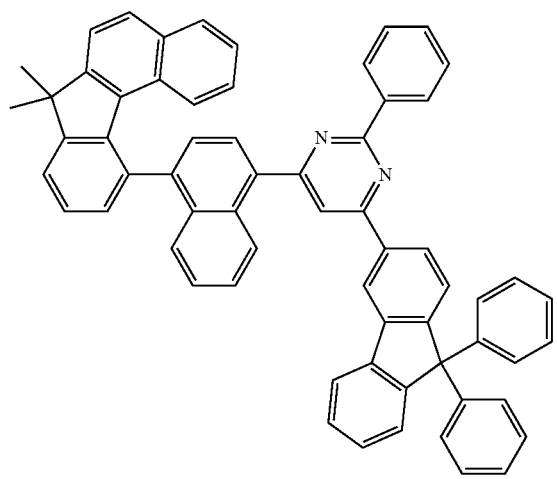
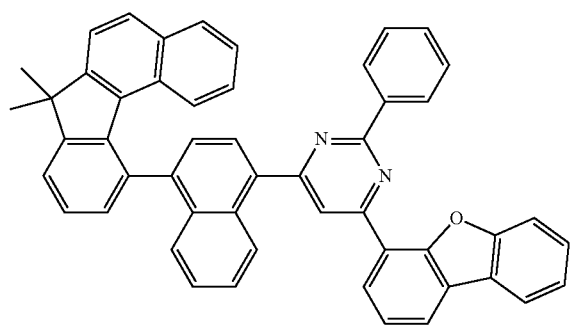
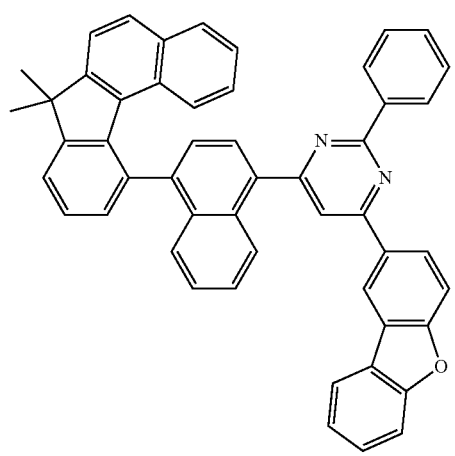

457 458
-continued
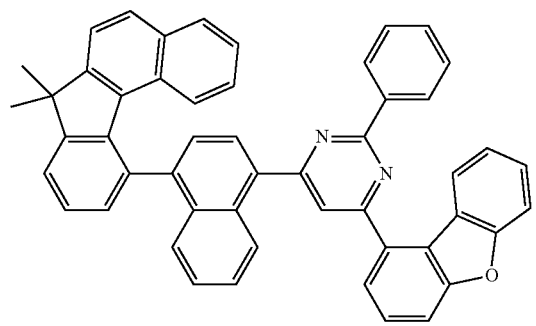
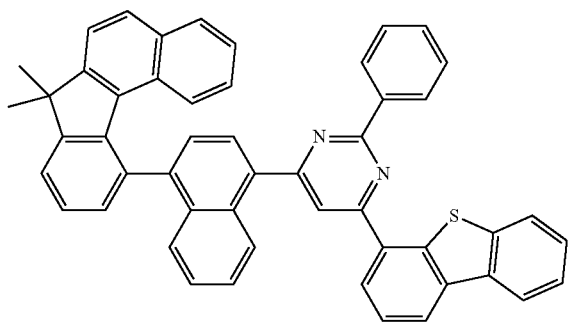
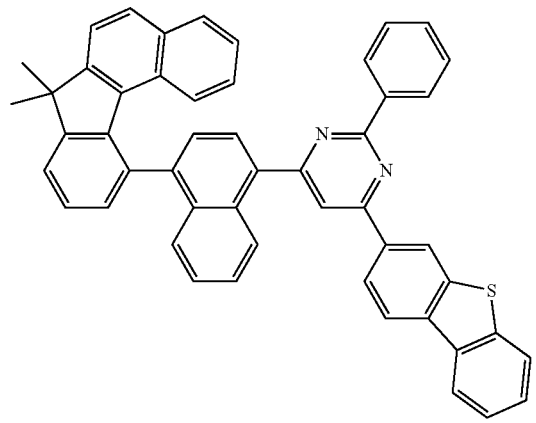
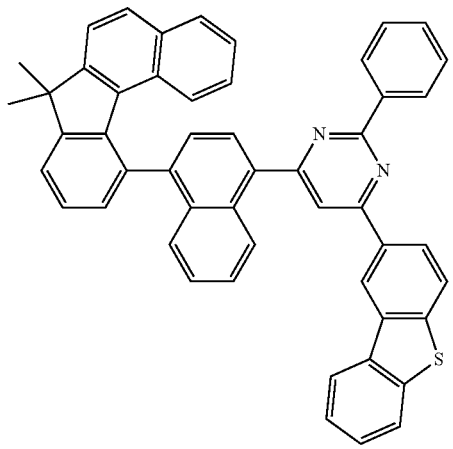
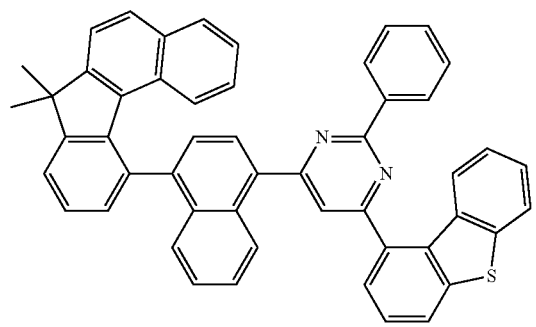
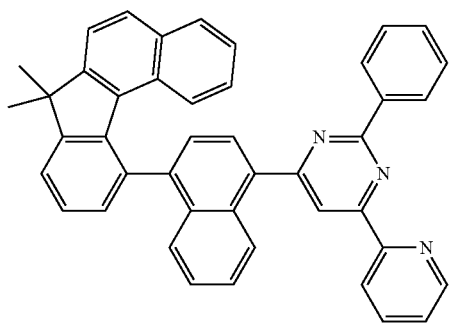
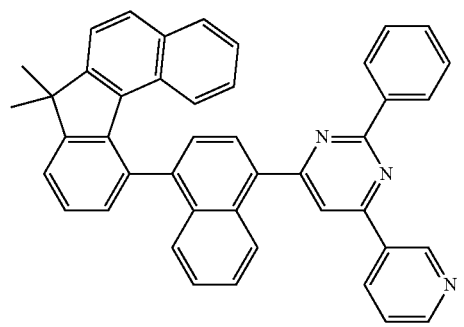
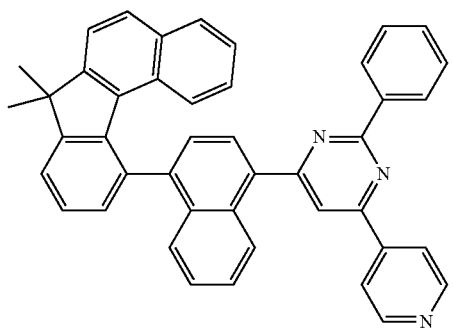

459 460
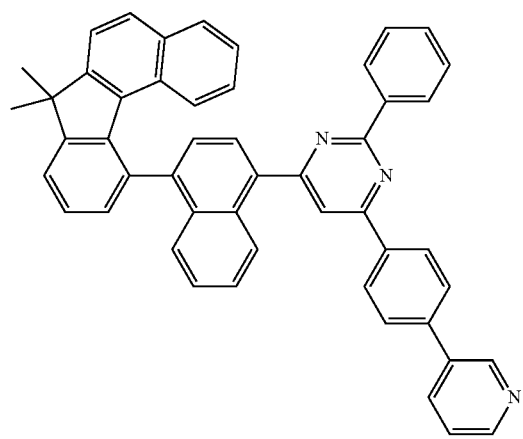
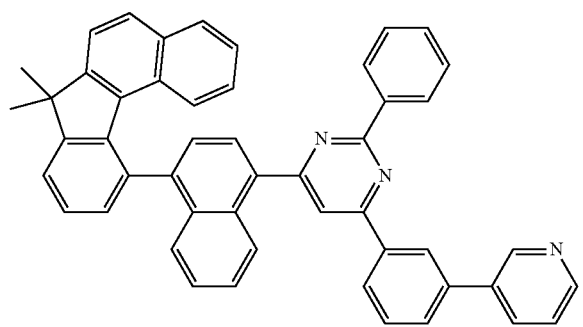
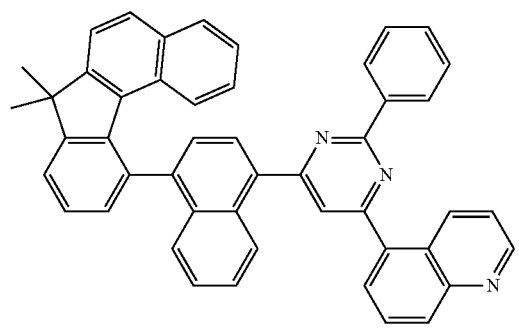
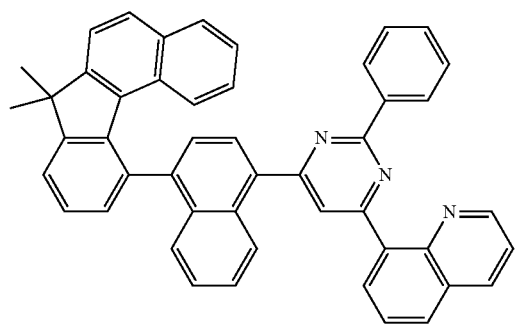
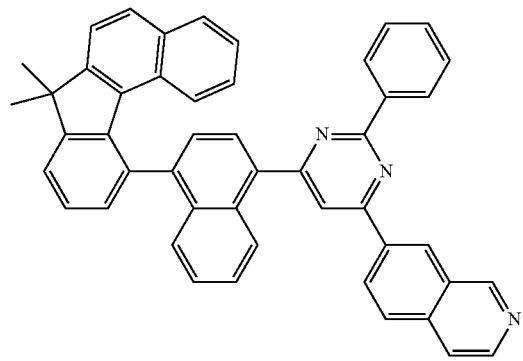
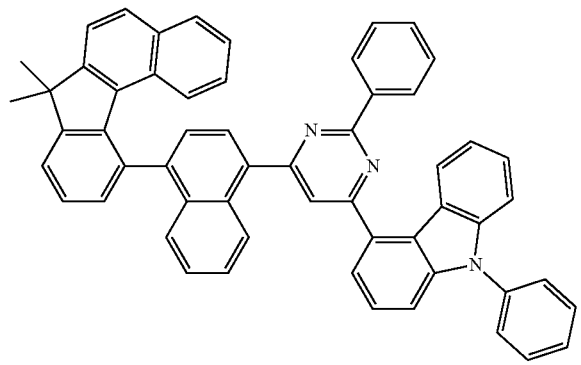
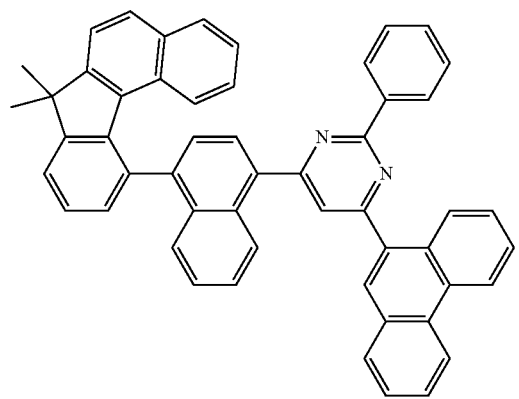
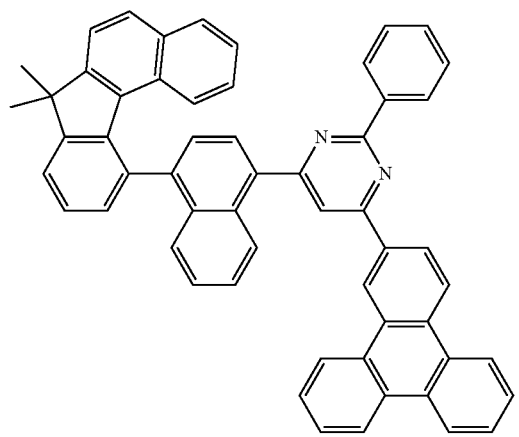

-continued
| 461 | 462 |
|---|---|
| 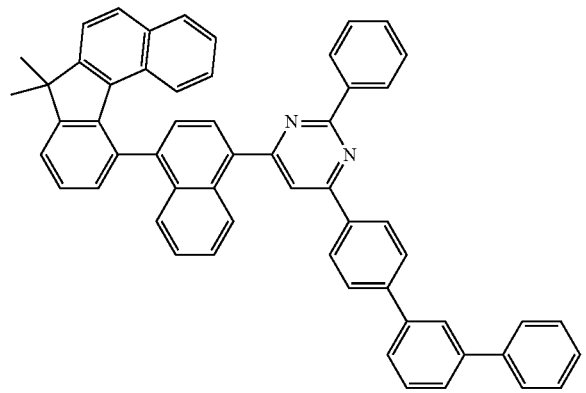 | 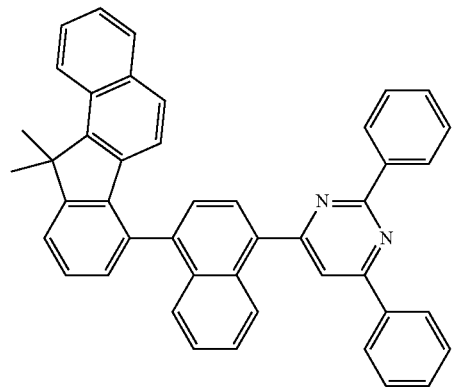 |
| 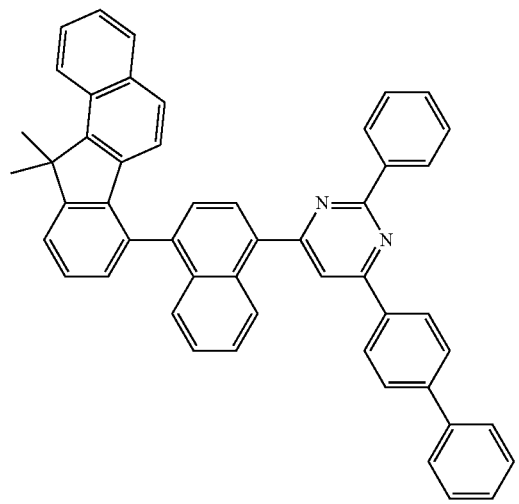 | 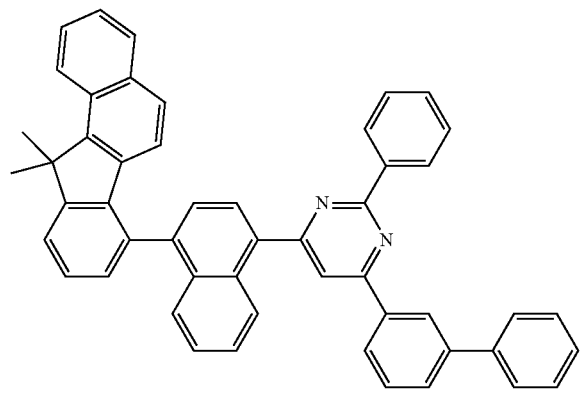 |
| 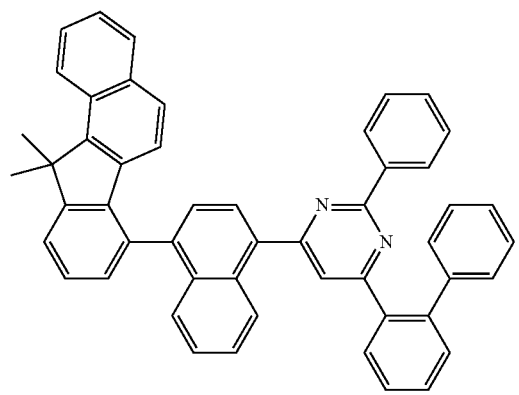 | 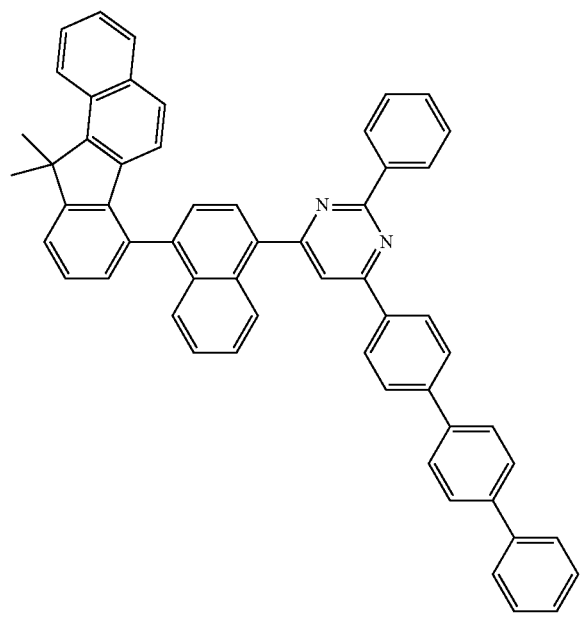 |

-continued
463
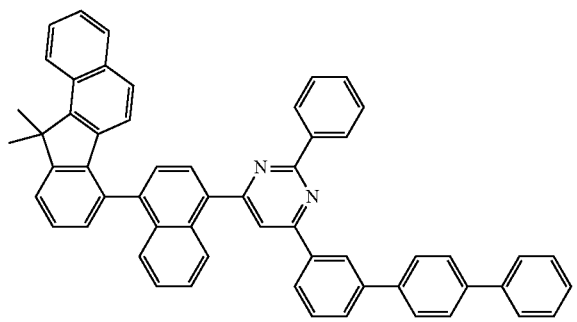
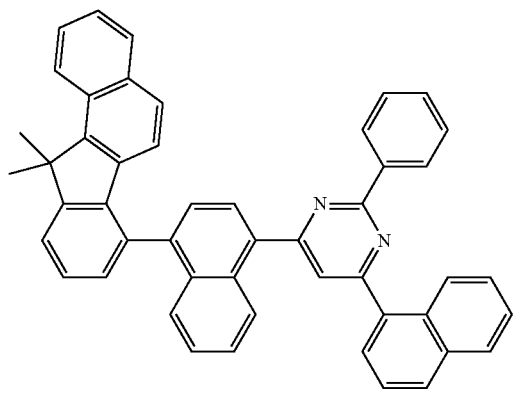
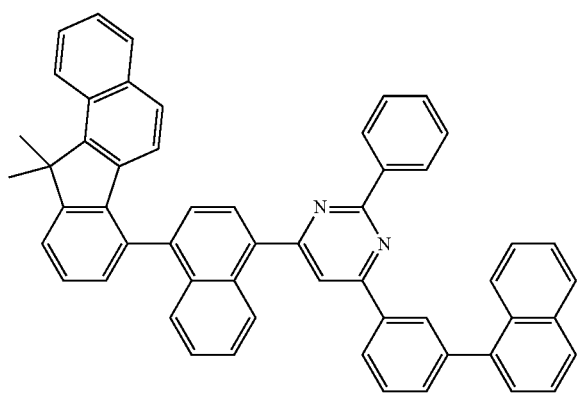
464
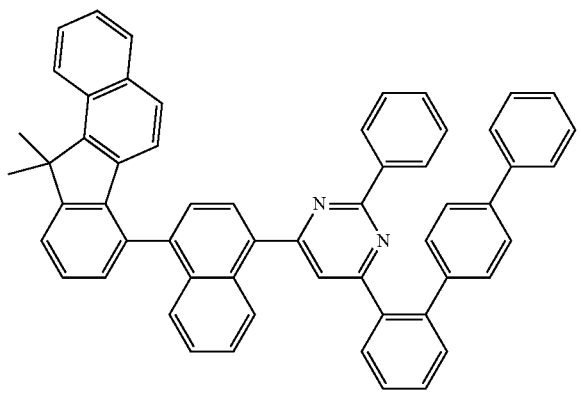
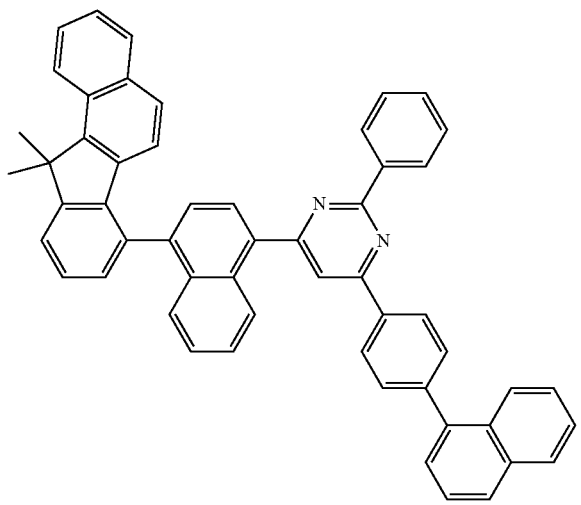
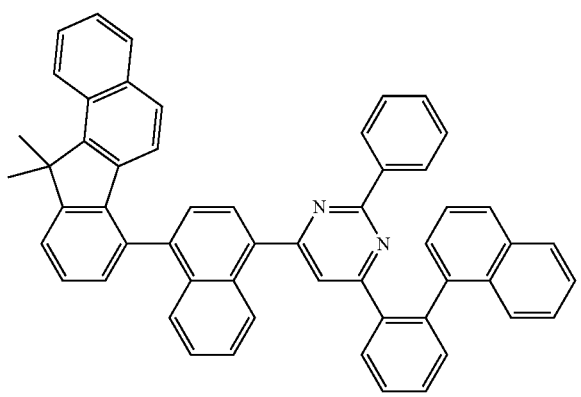

465
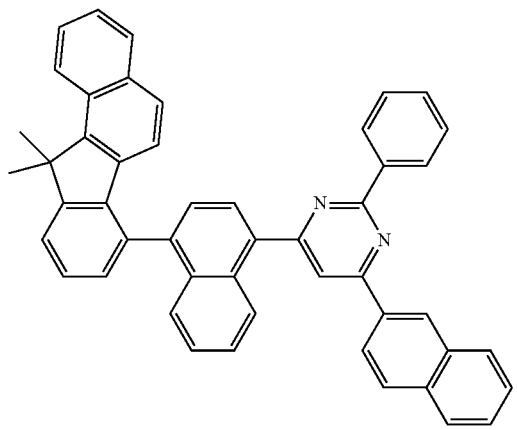
466
-continued
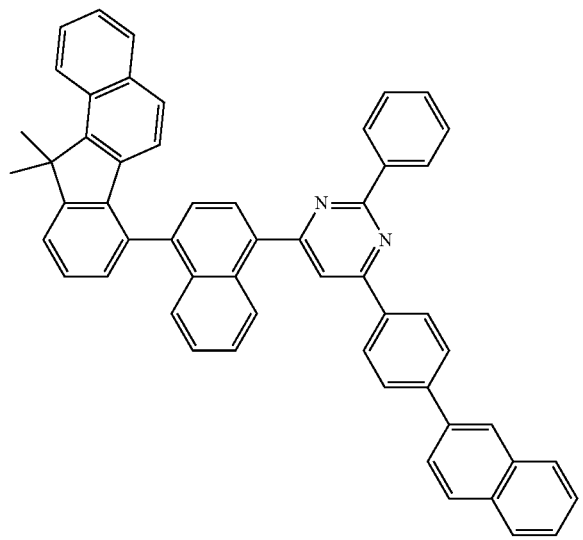
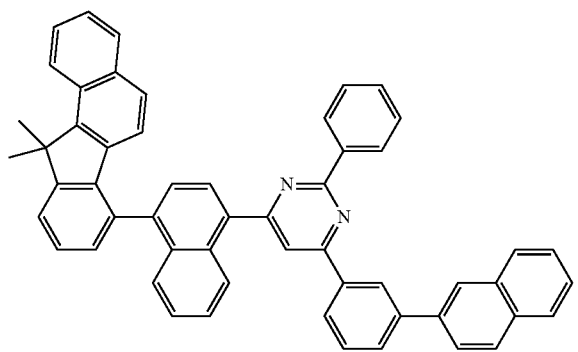
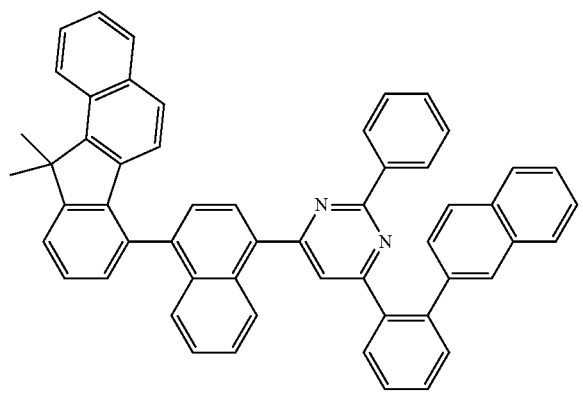
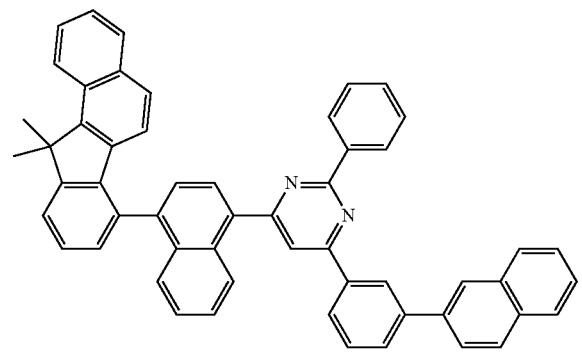

467
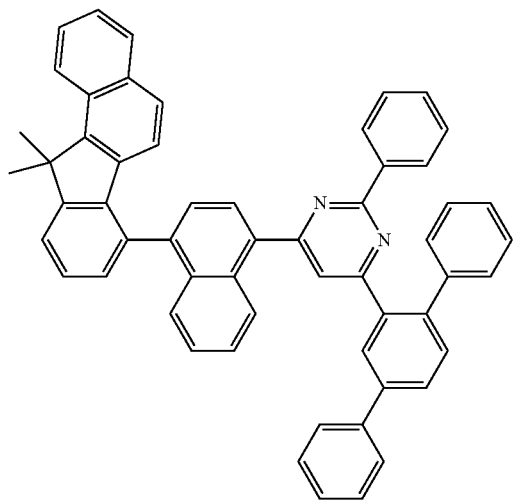
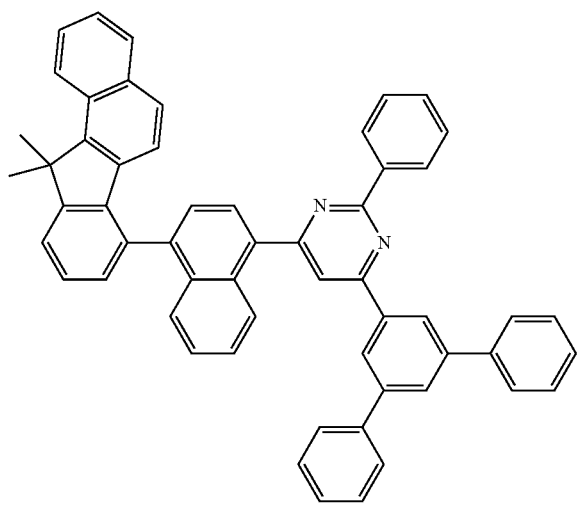
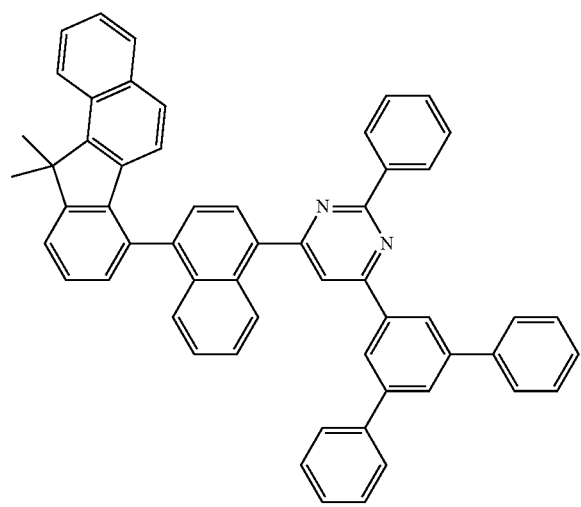
468
-continued
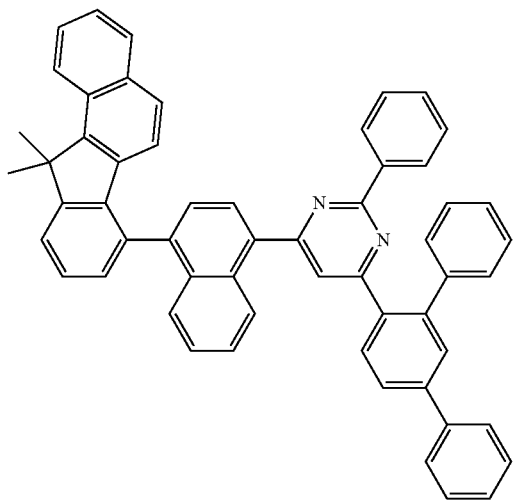
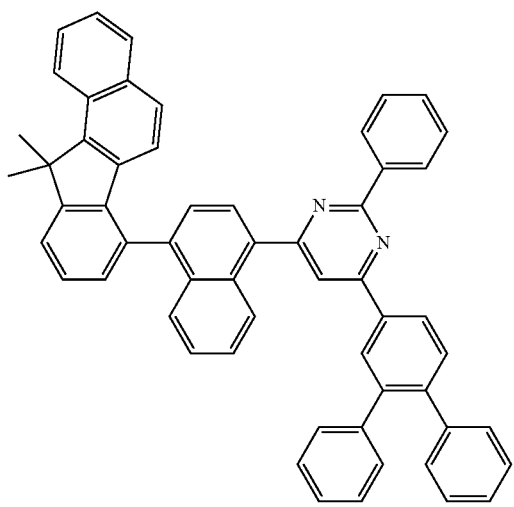

469
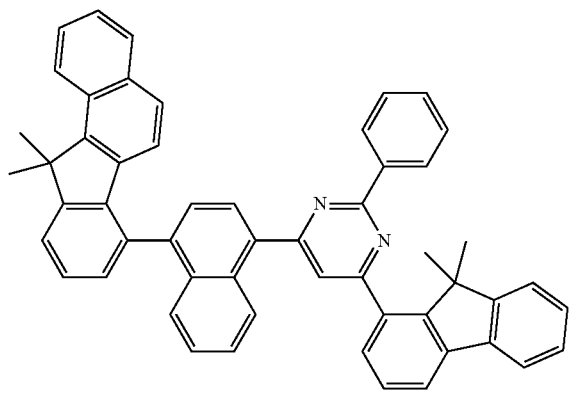
470
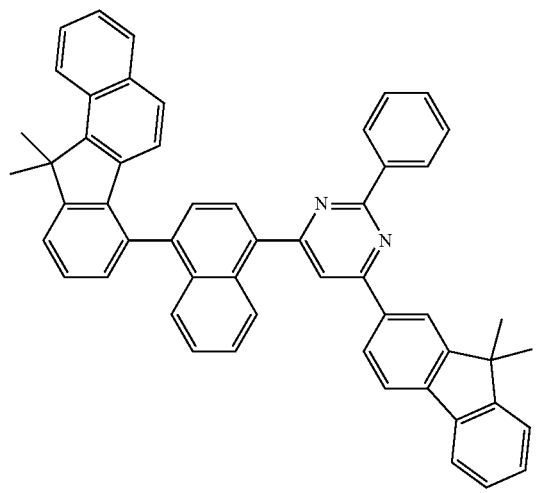
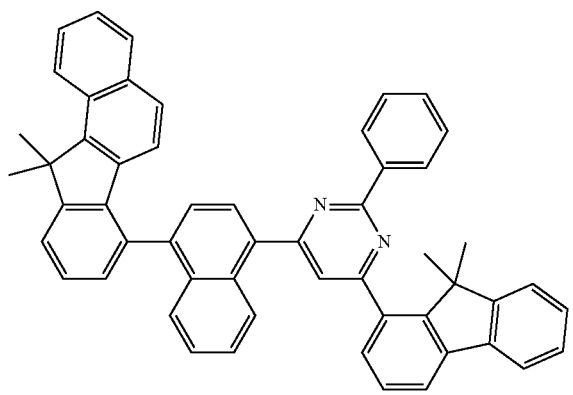
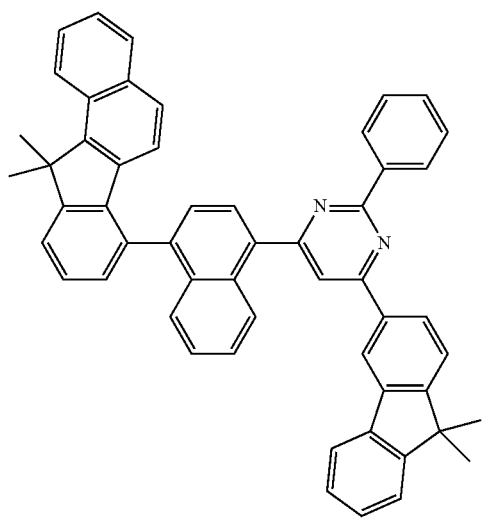
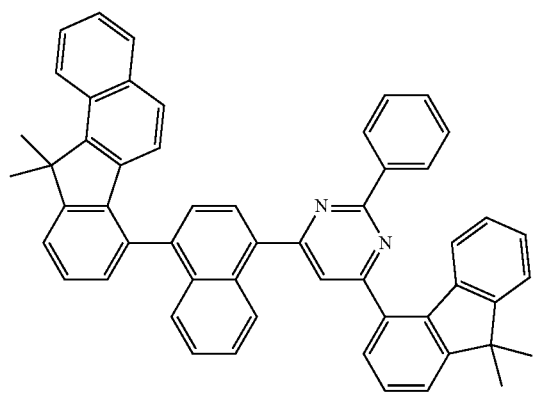

-continued
| 471 | 472 |
|---|---|
| 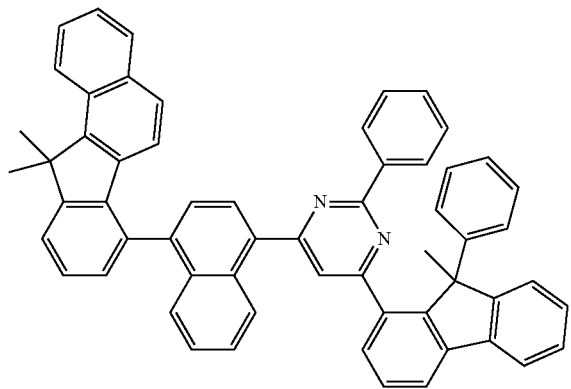 | 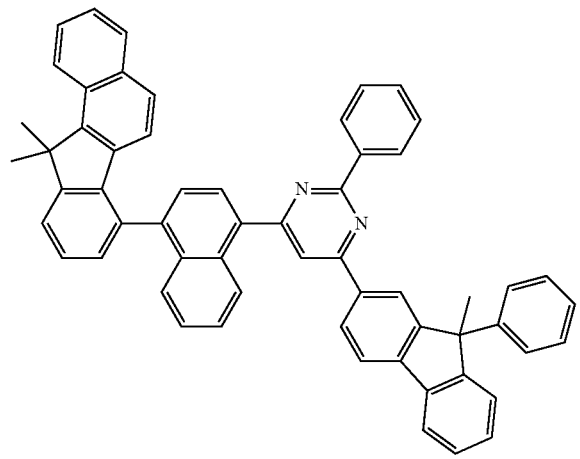 |
| 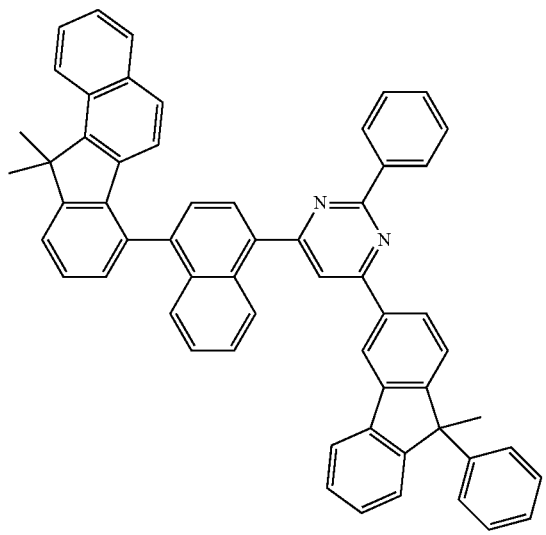 | 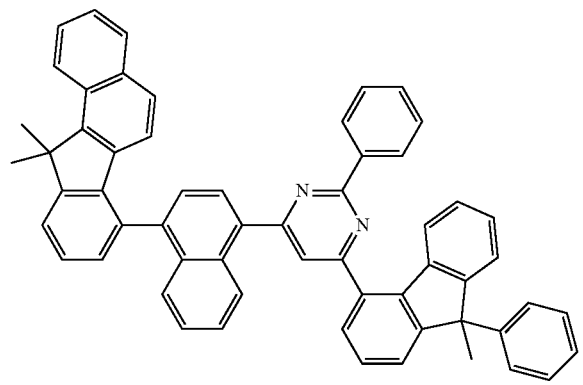 |
| 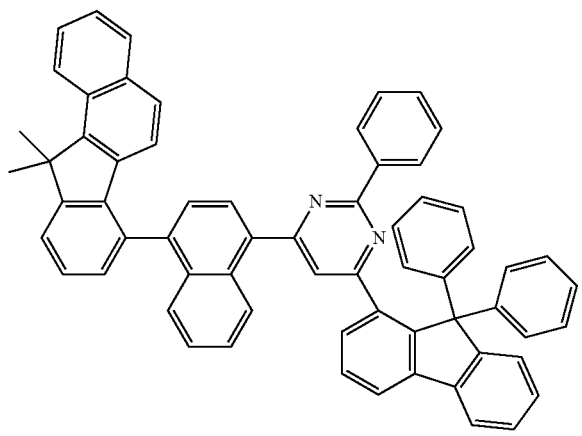 | 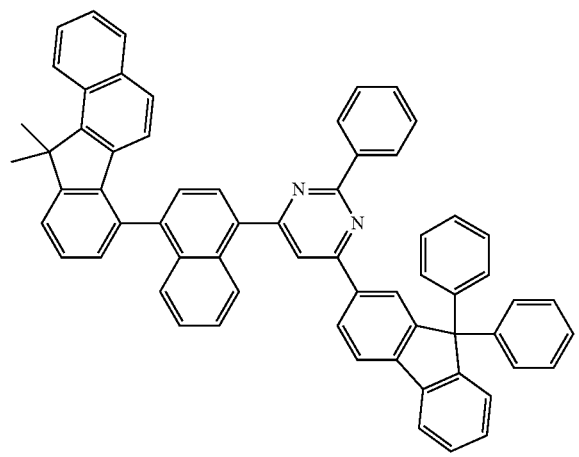 |

-continued
| 473 | 474 |
|---|---|
| 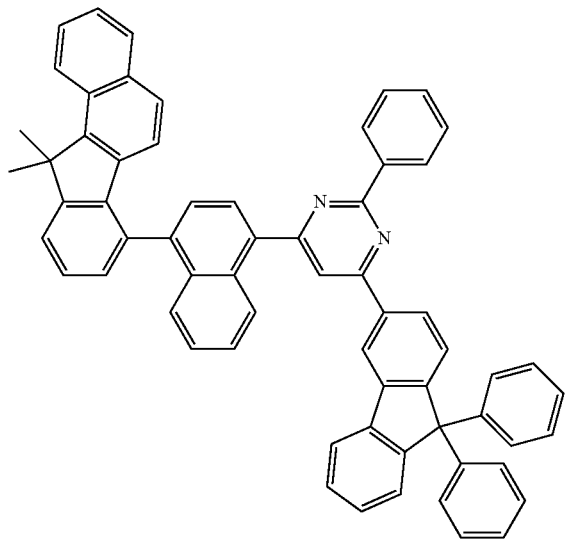 | 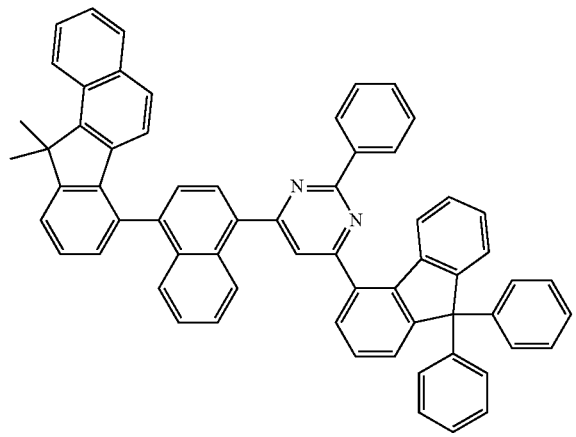 |
| 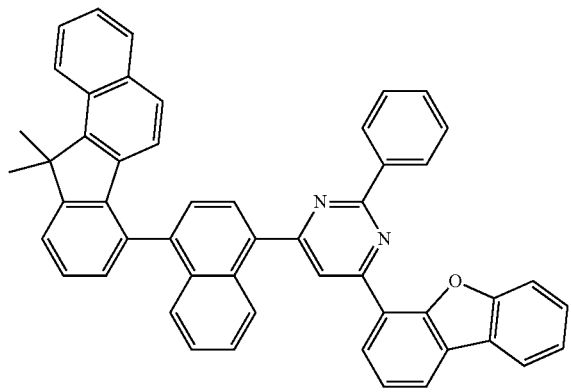 | 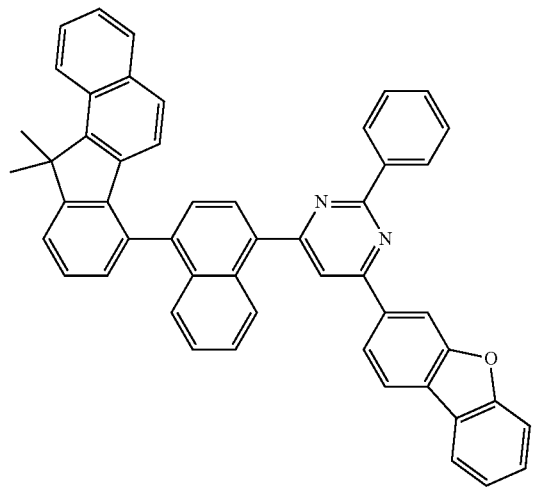 |
| 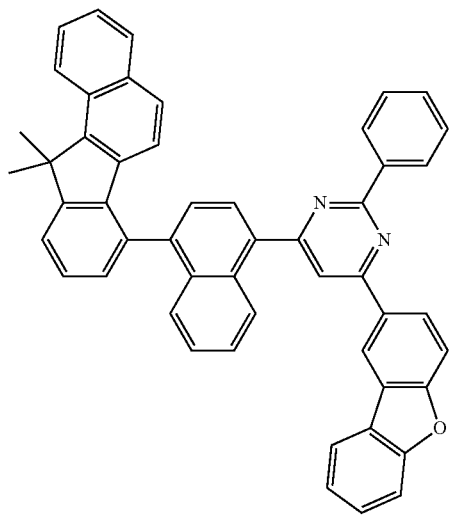 | 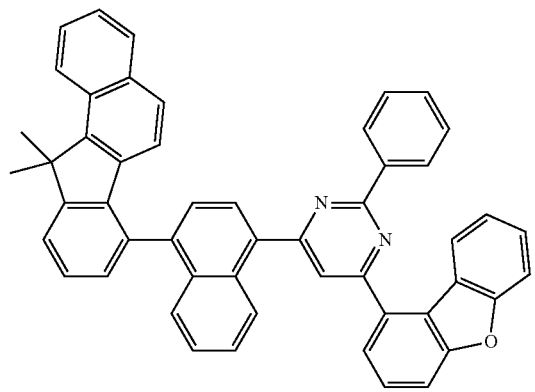 |

-continued
475
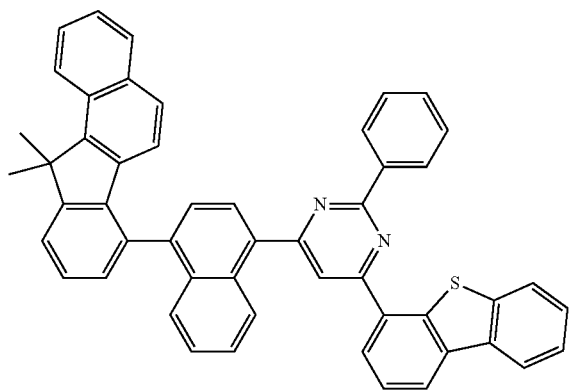
476
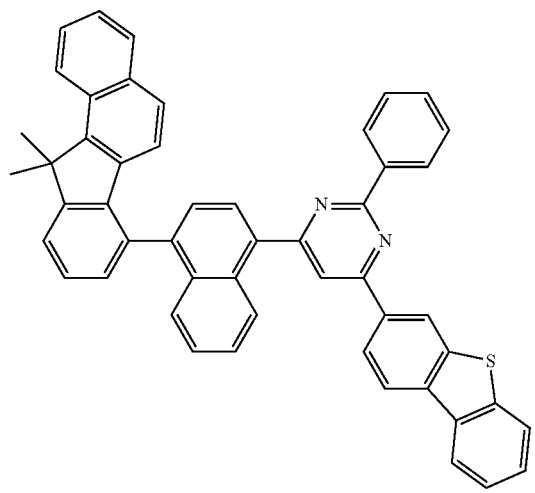
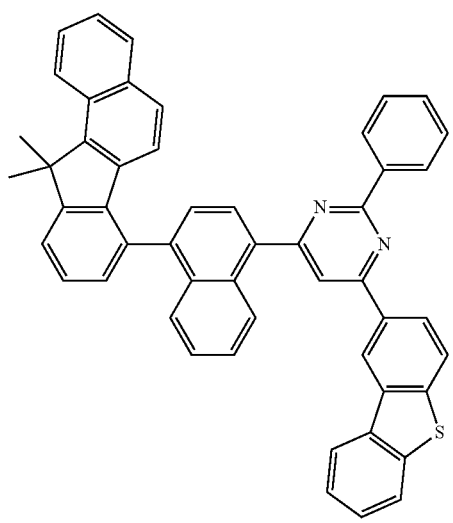
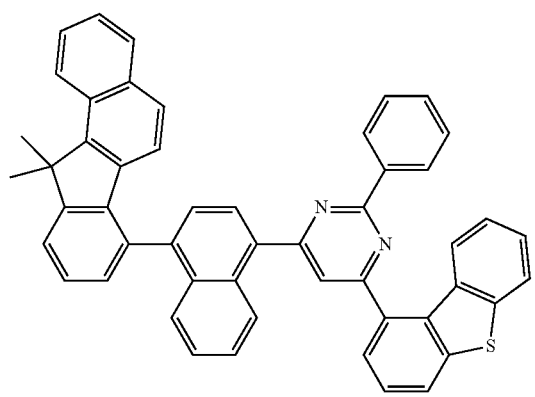
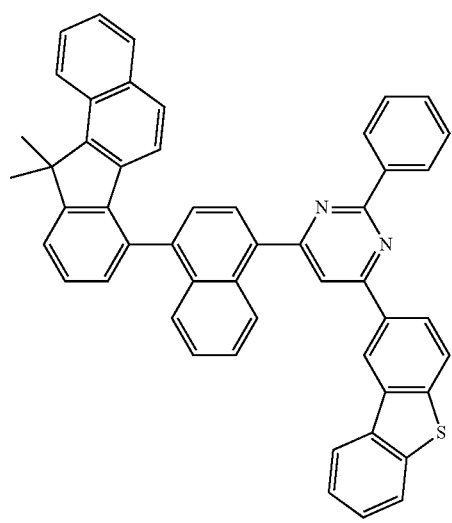

-continued
| 477 | 478 |
|---|---|
| 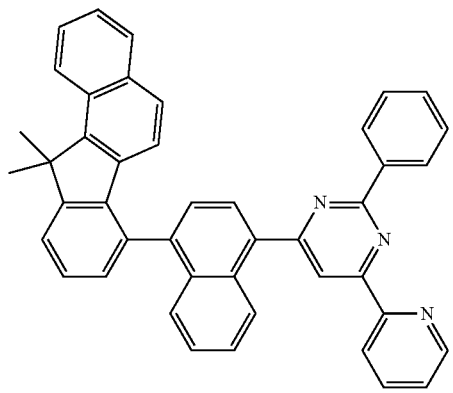 | 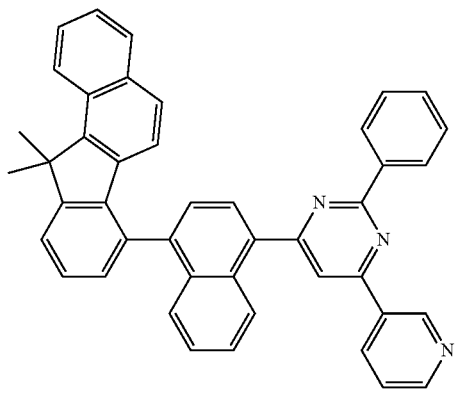 |
| 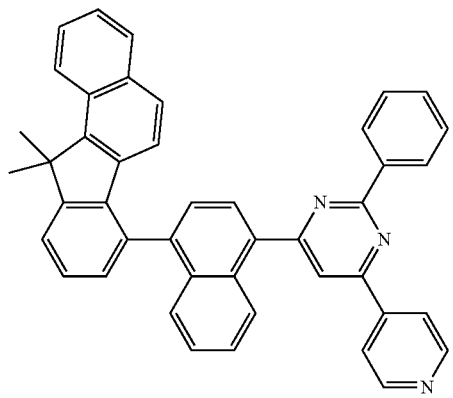 | 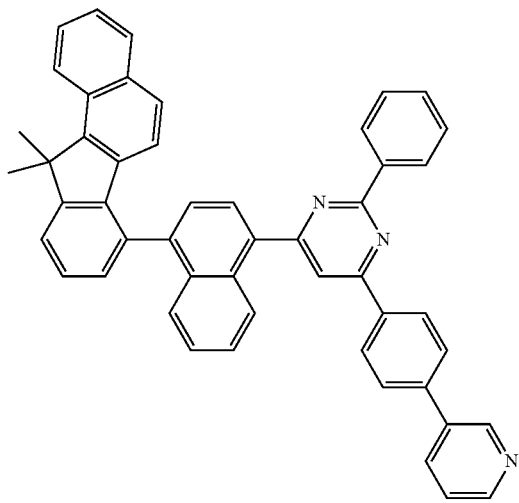 |
| 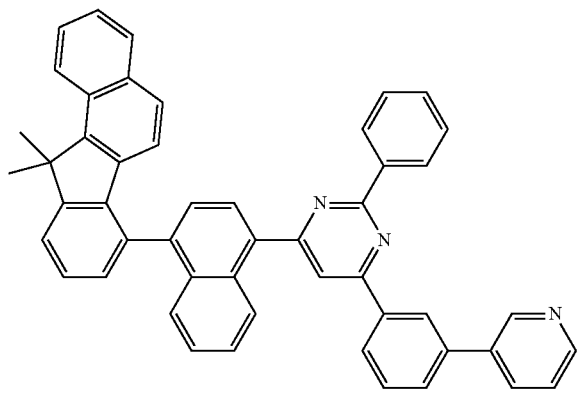 | 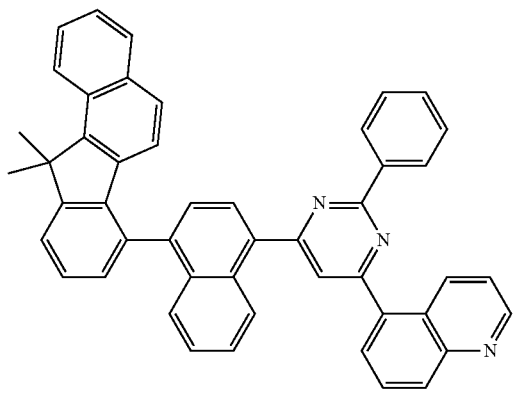 |
| 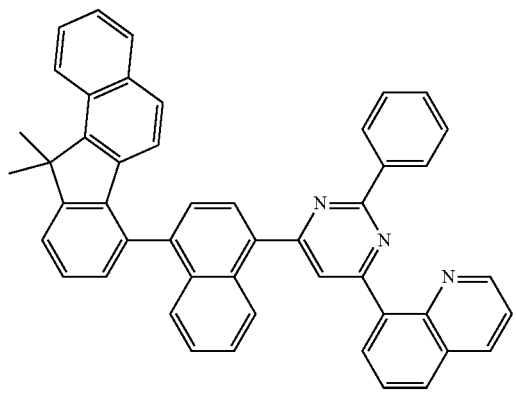 | 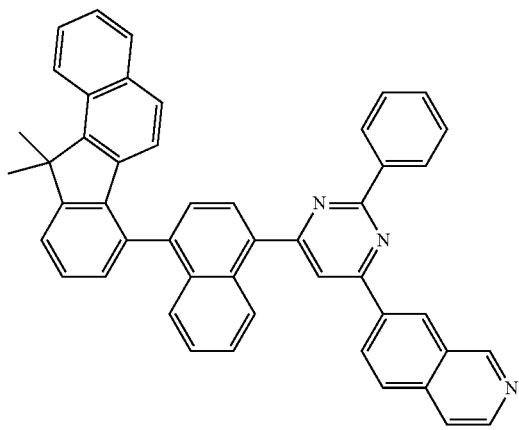 |

-continued
| 479 | 480 |
|---|---|
| 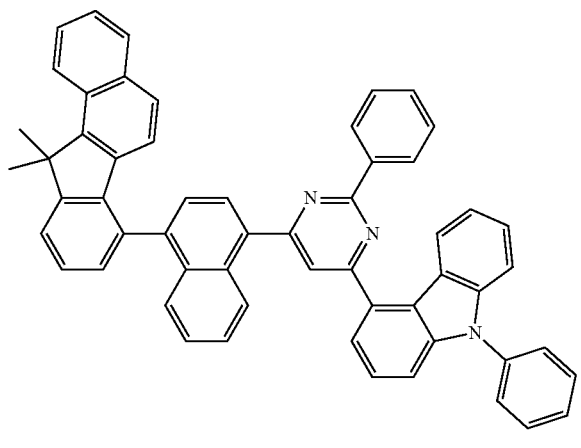 | 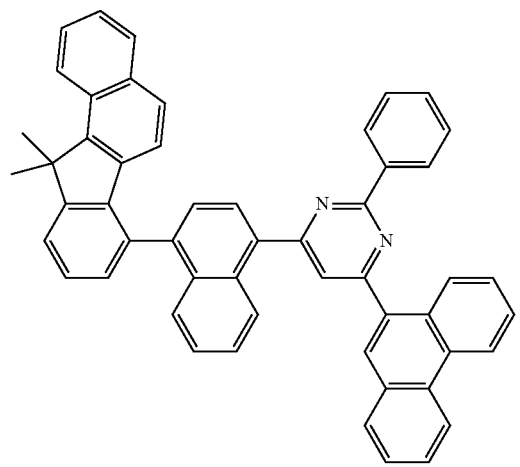 |
| 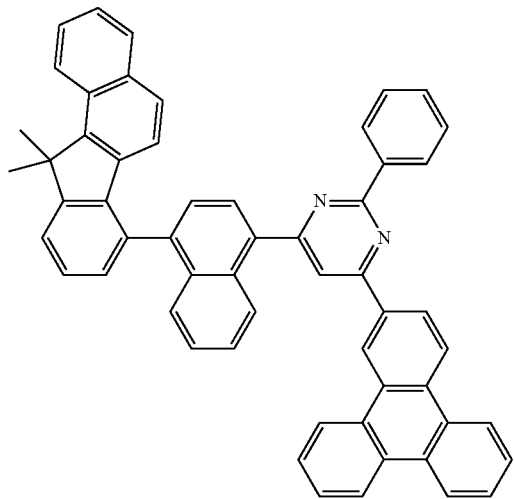 | 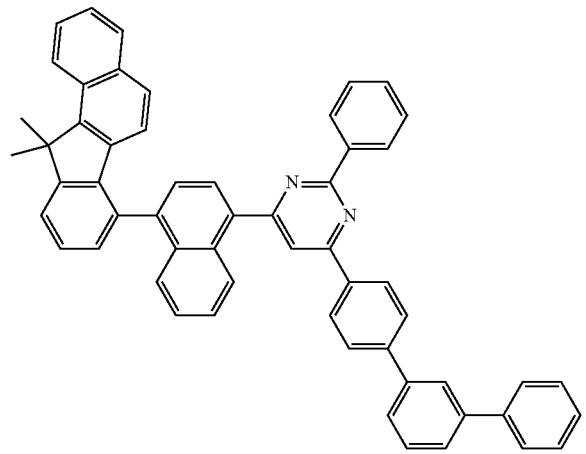 |
| 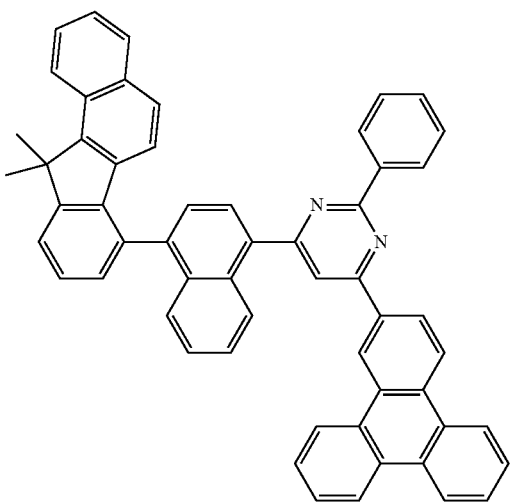 | |

-continued
481
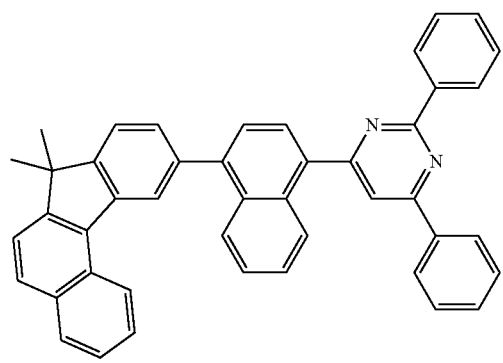
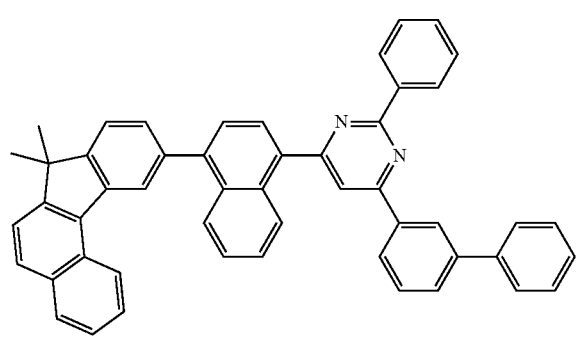
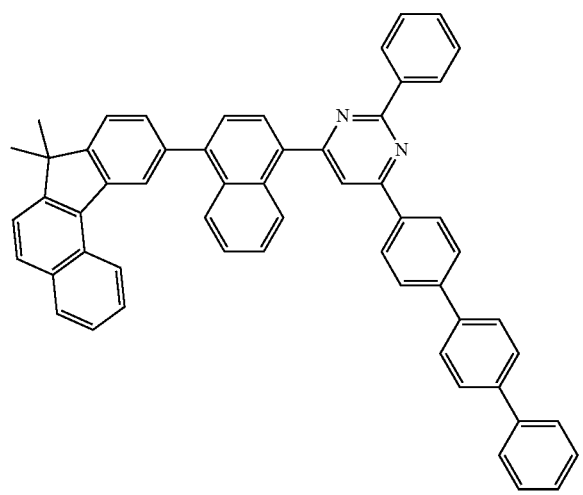
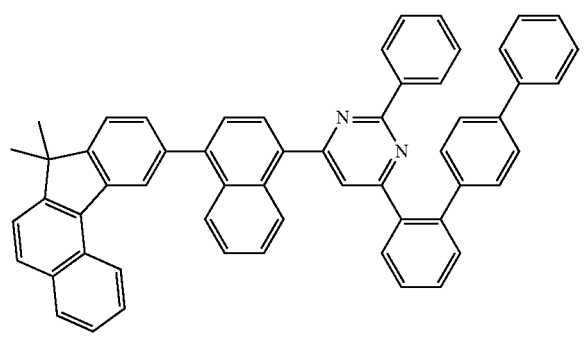
482
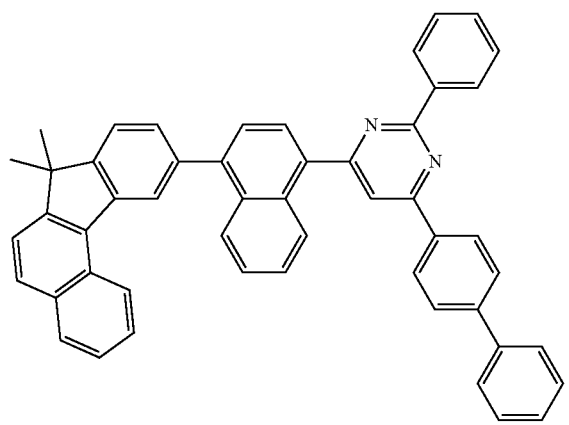
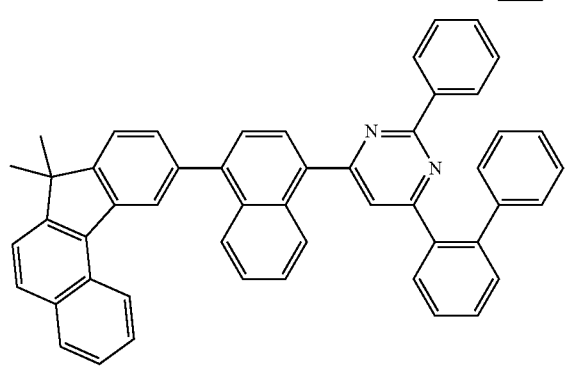
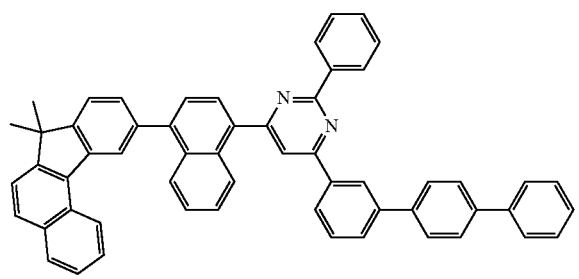
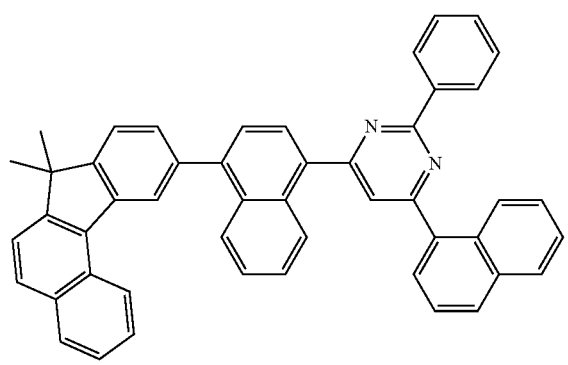

483
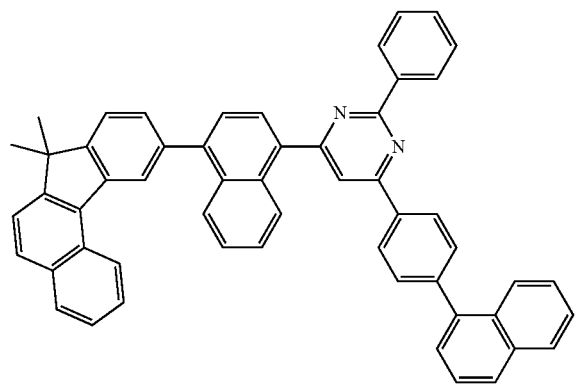
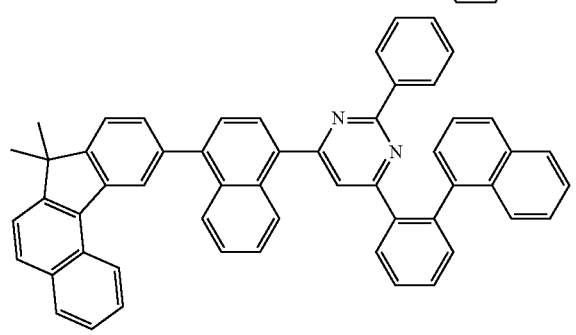
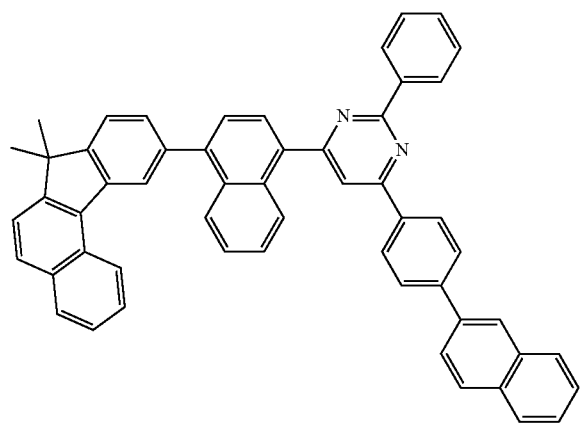
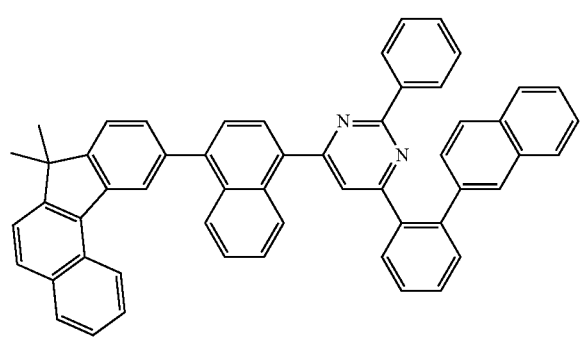
484
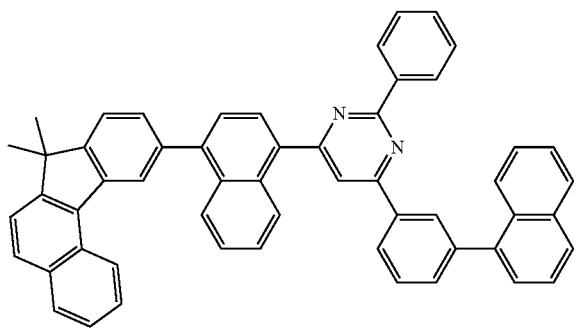
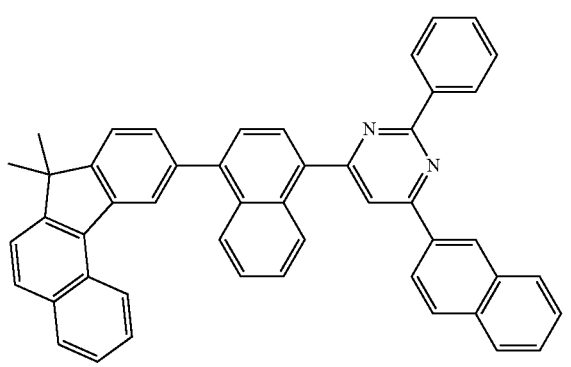
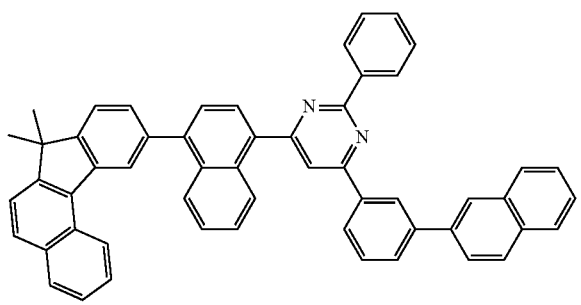
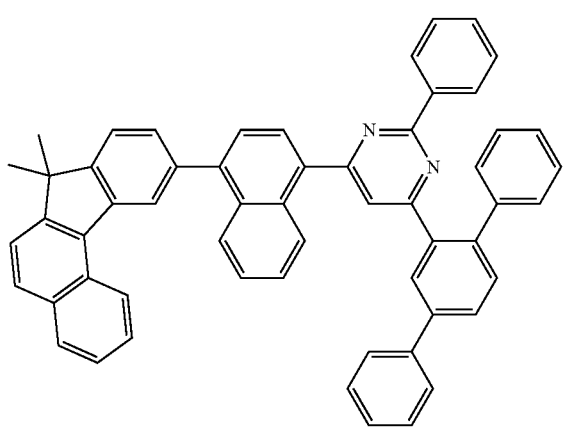

485
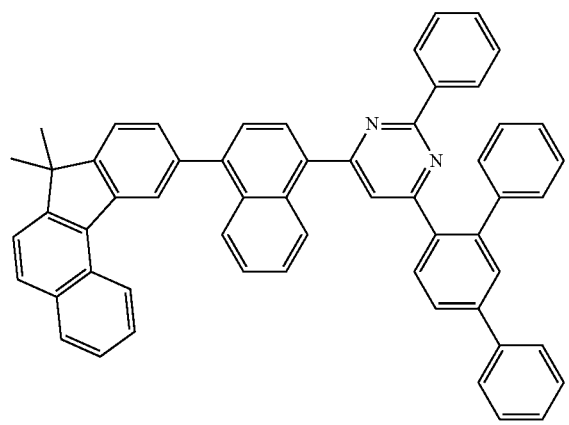
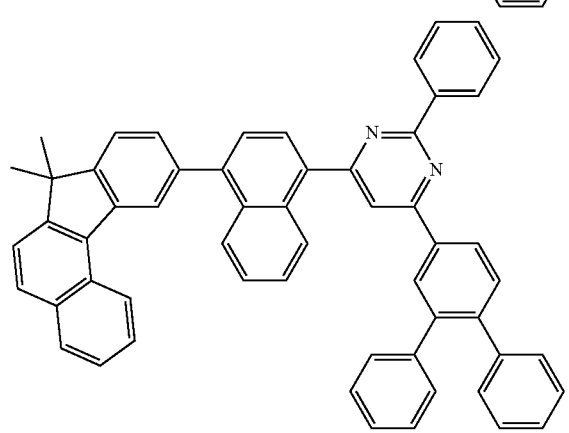
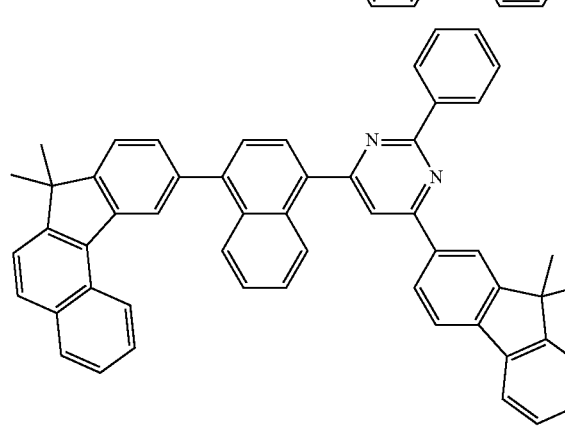
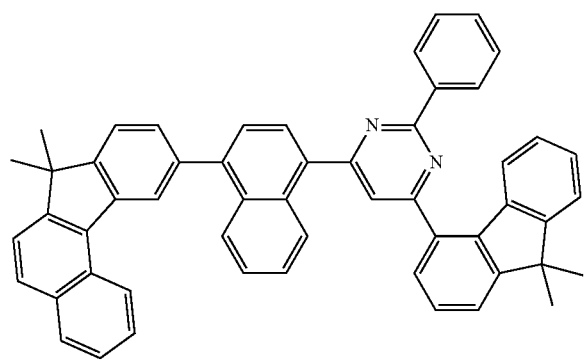
486
-continued
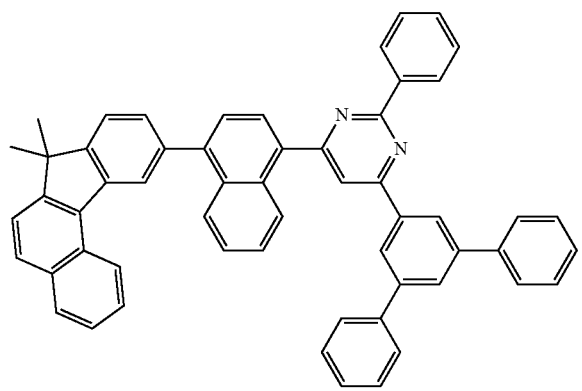
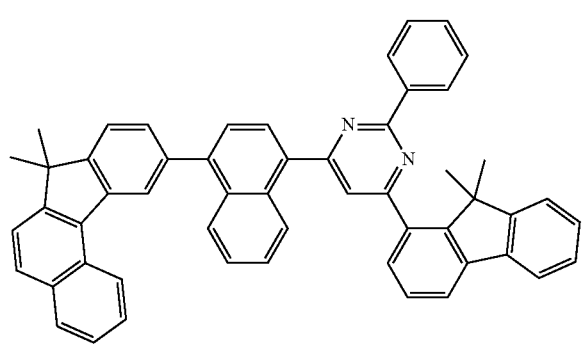
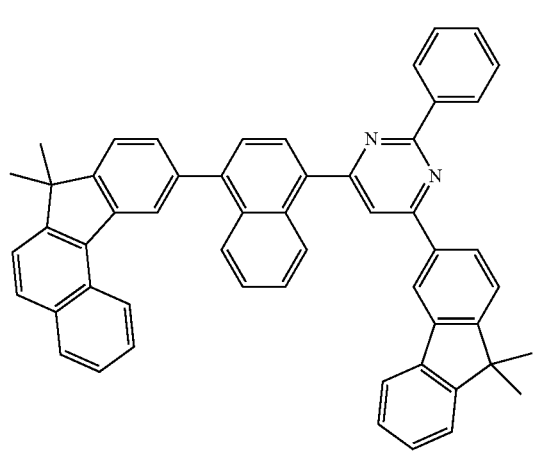
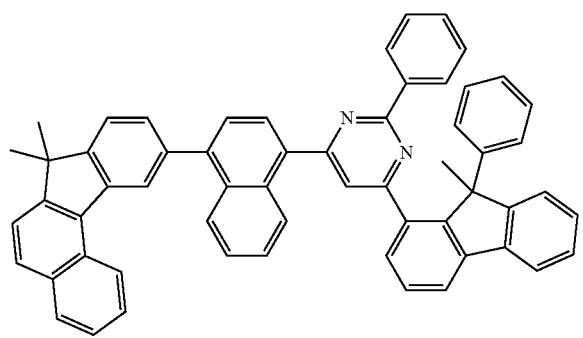

487 488
-continued
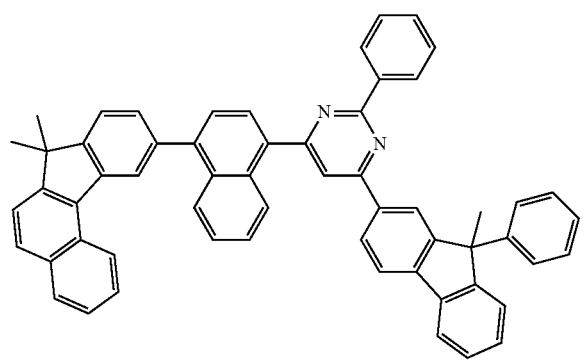
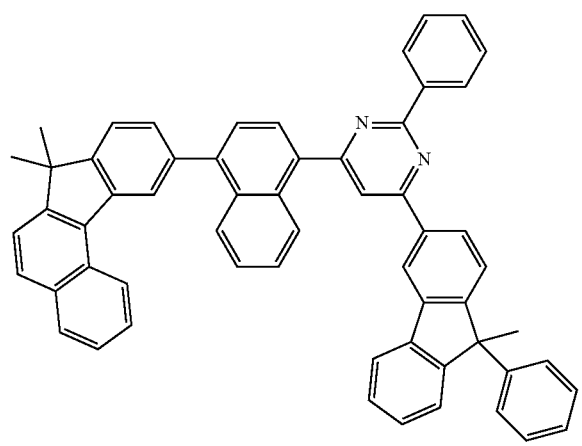
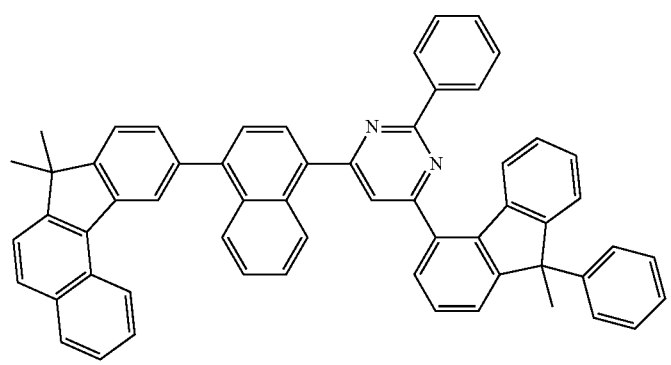
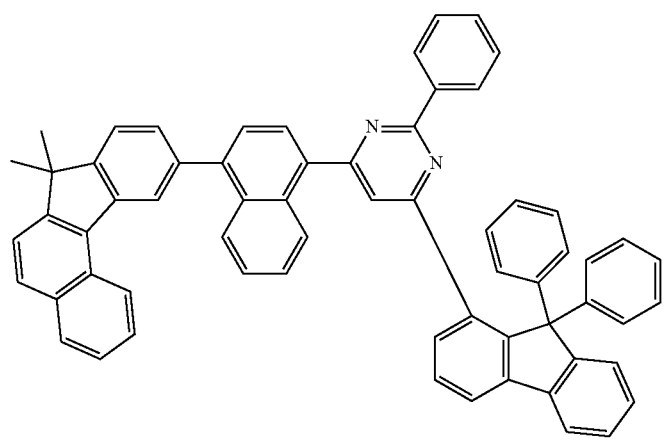

489    490
-continued
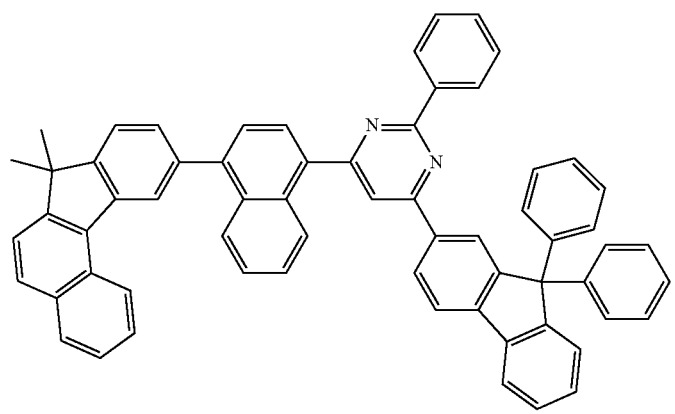
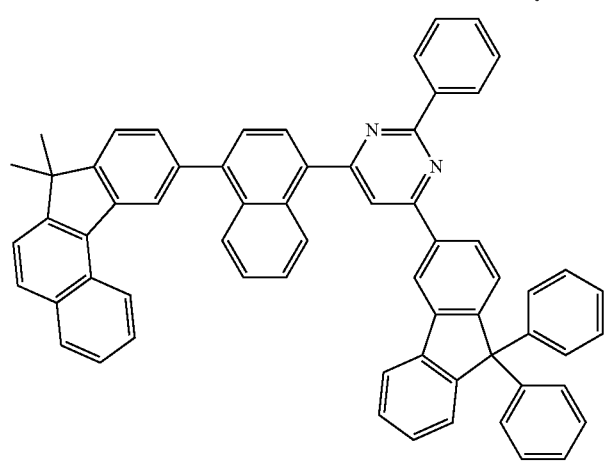
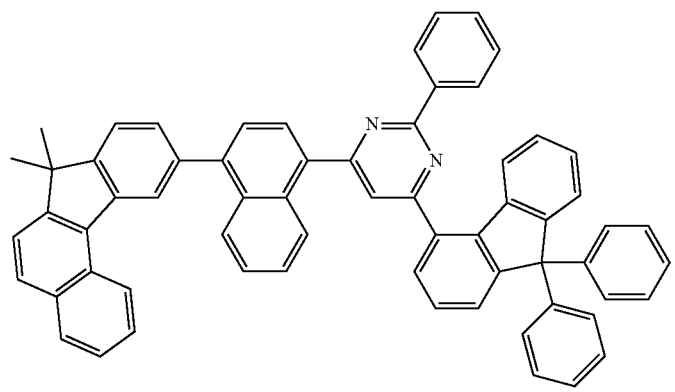
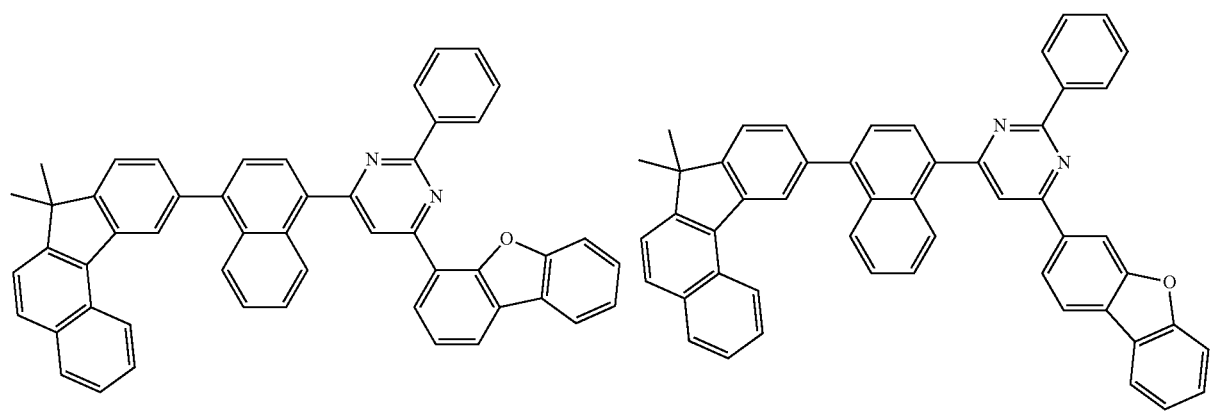

491
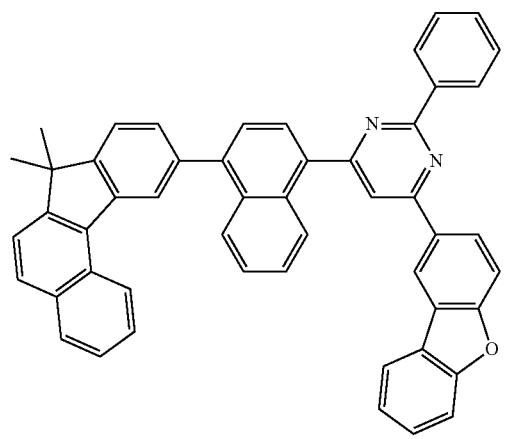
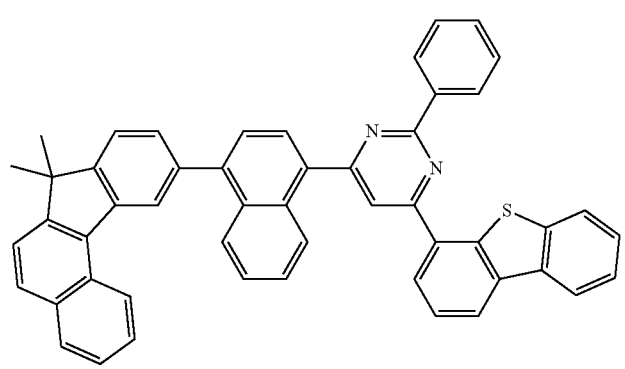
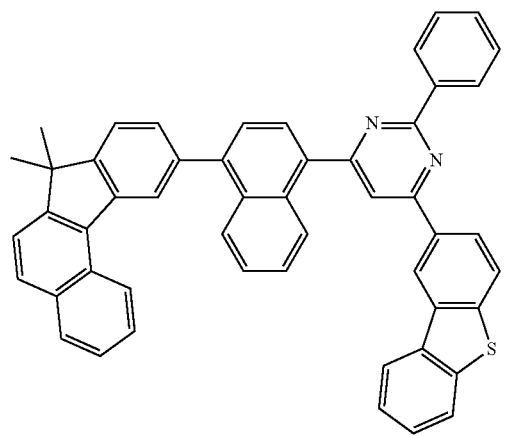
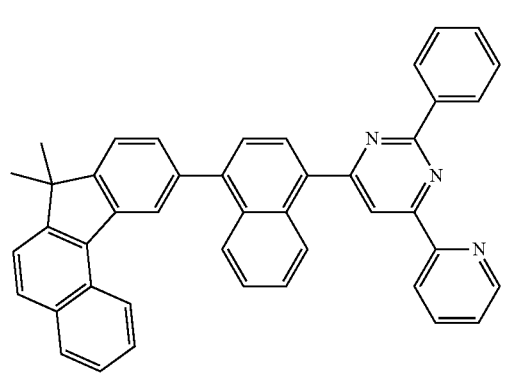
492
-continued
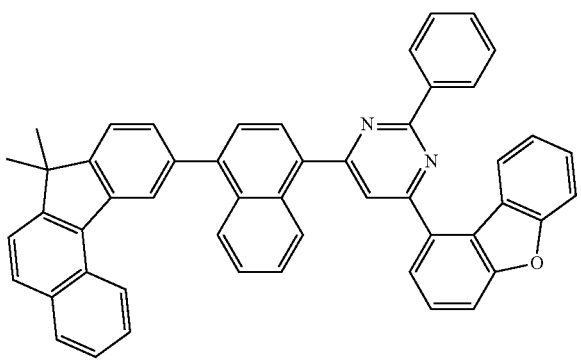
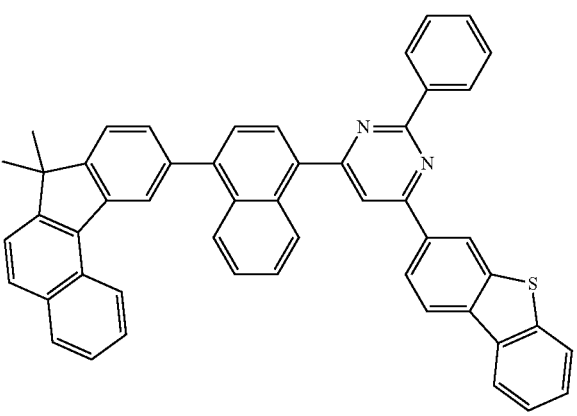
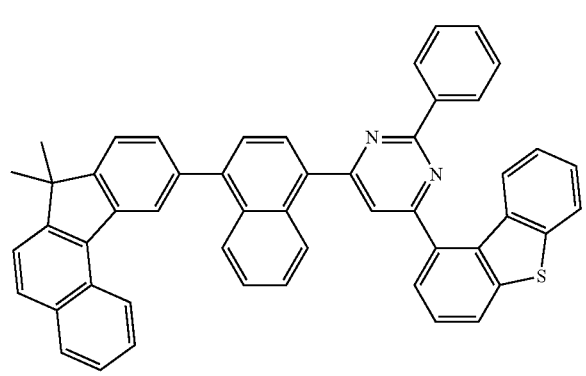
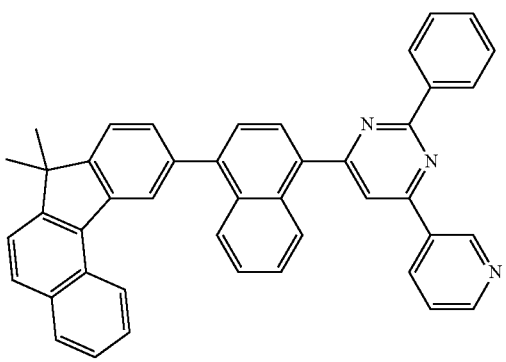

493
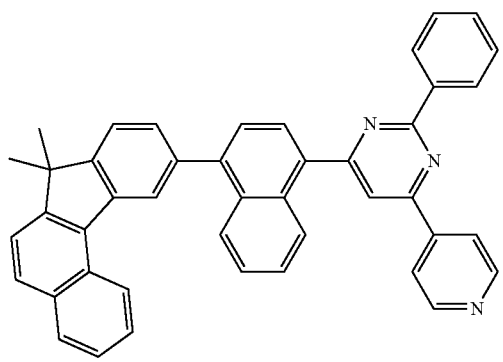
494
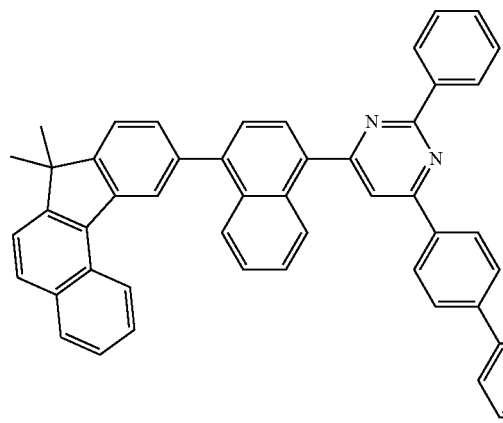
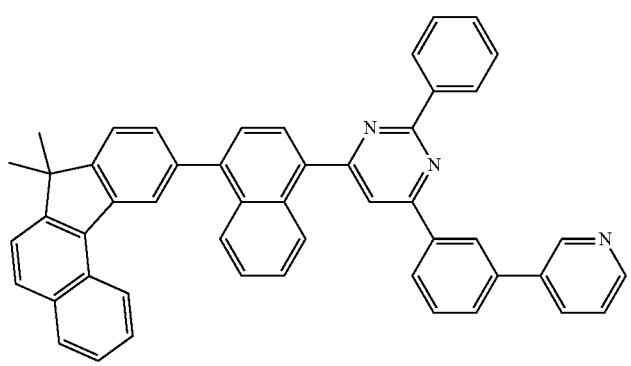
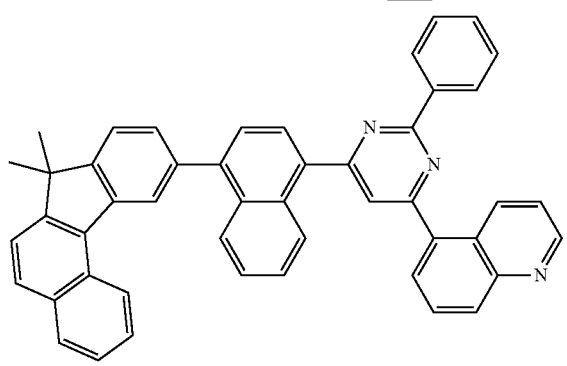
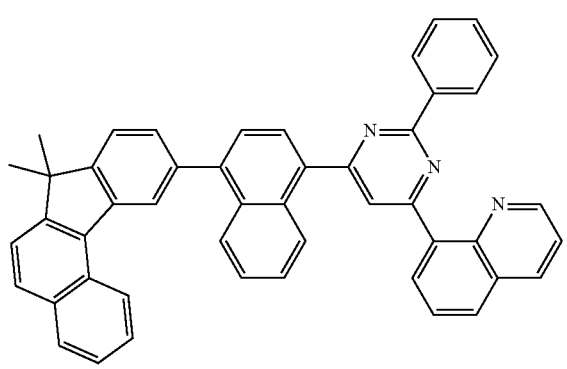
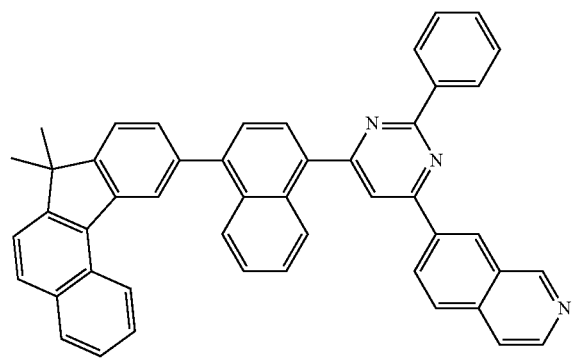
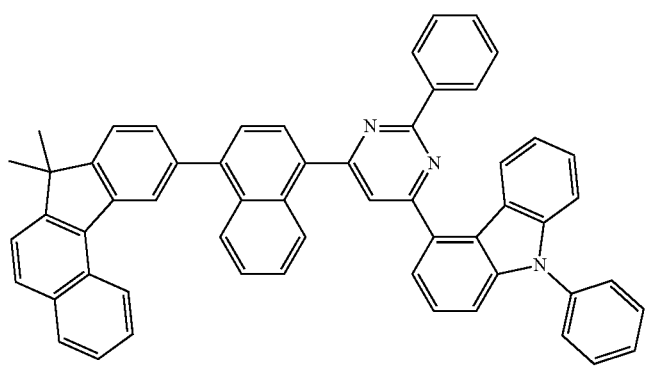

495 496
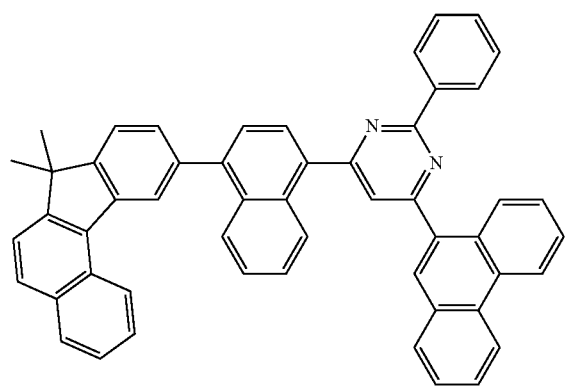
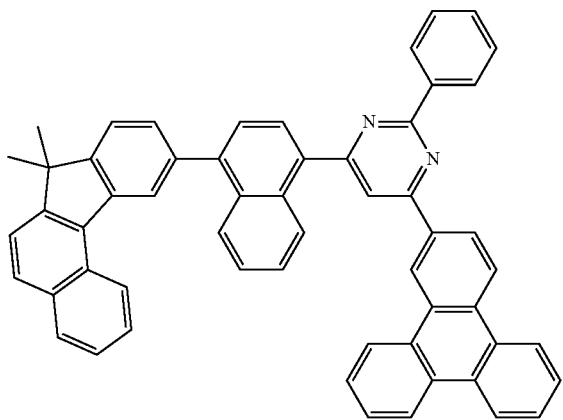
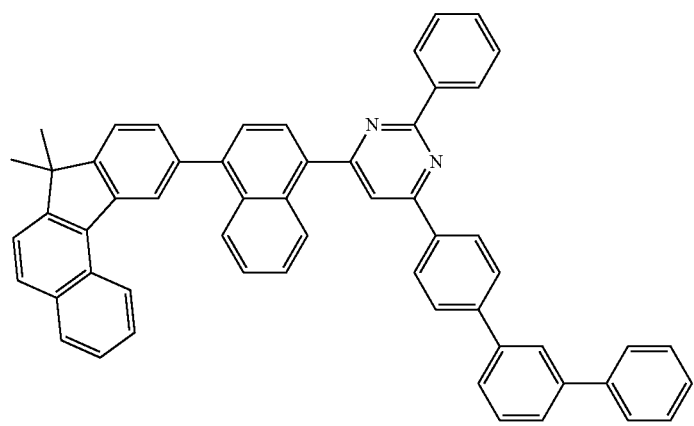
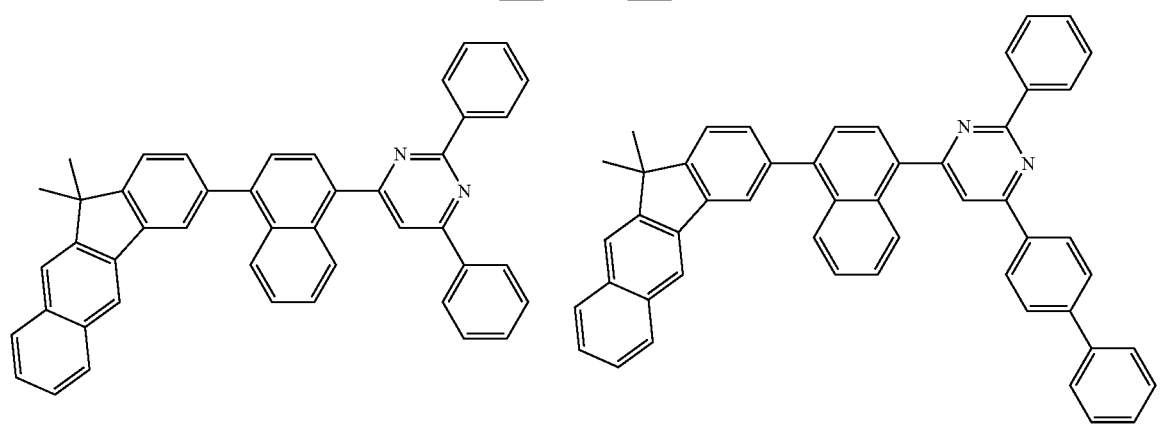
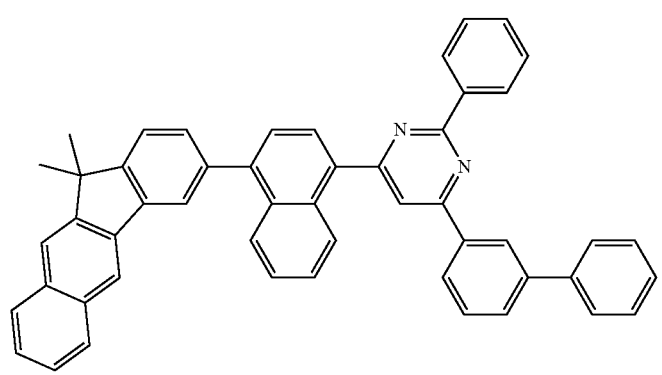

-continued
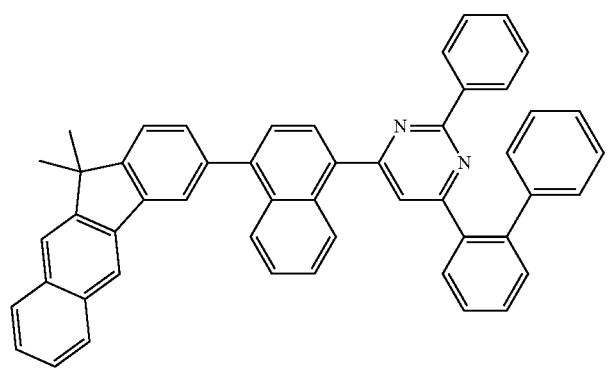
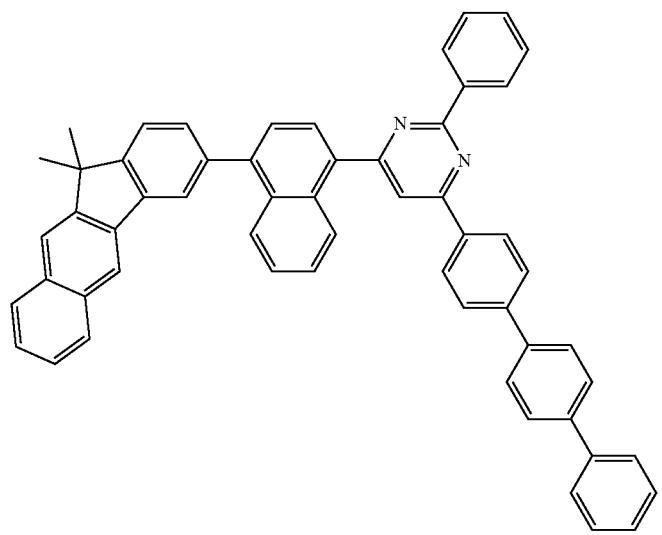
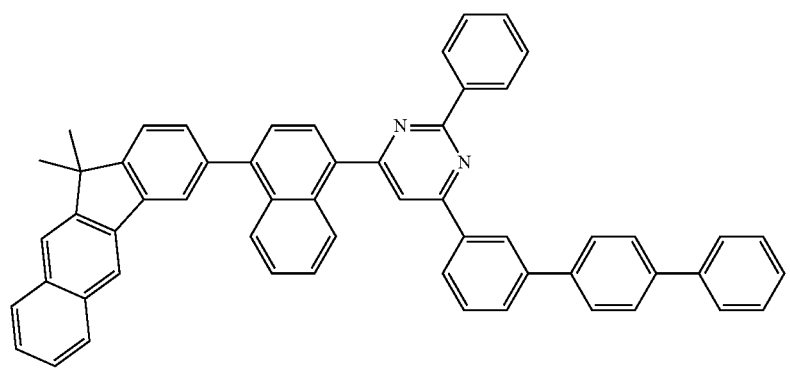
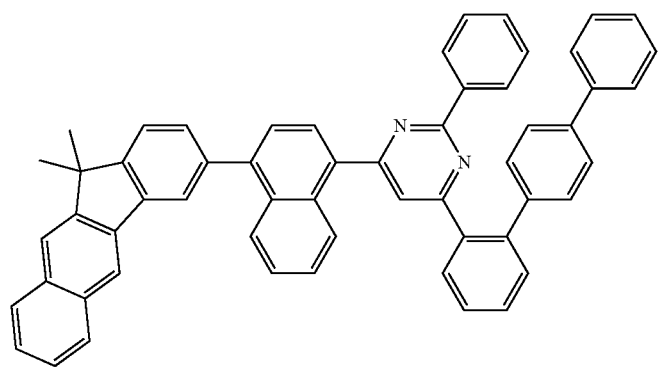

-continued
| 499 | 500 |
|---|---|
| 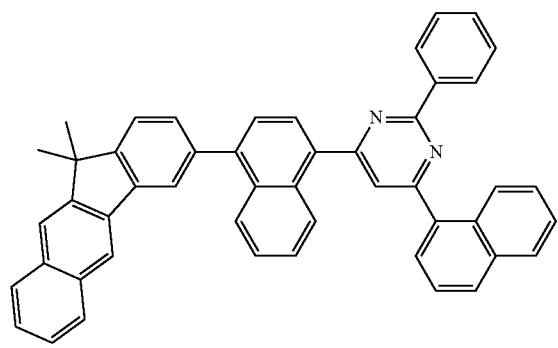 | 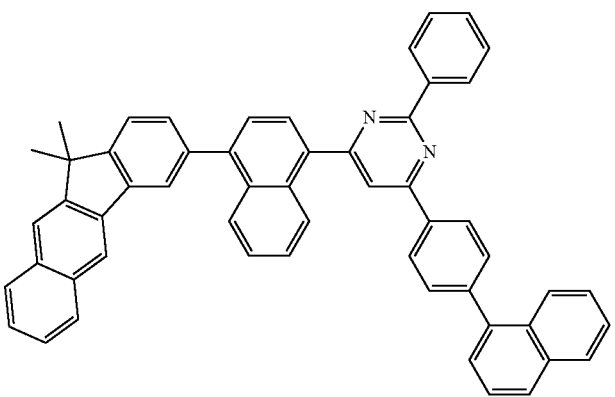 |
| 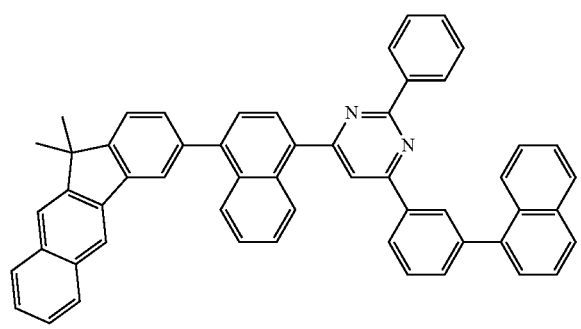 | 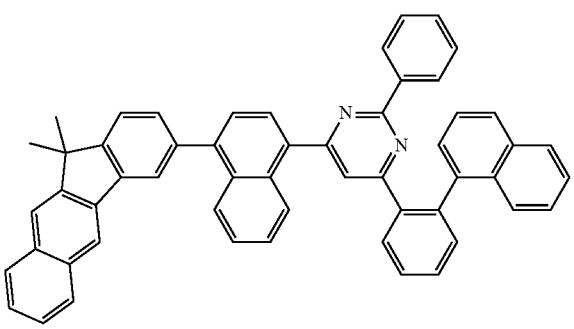 |
| 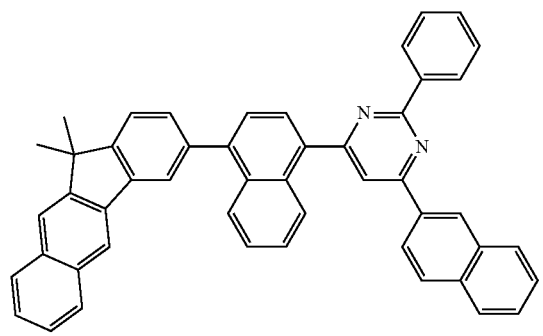 | 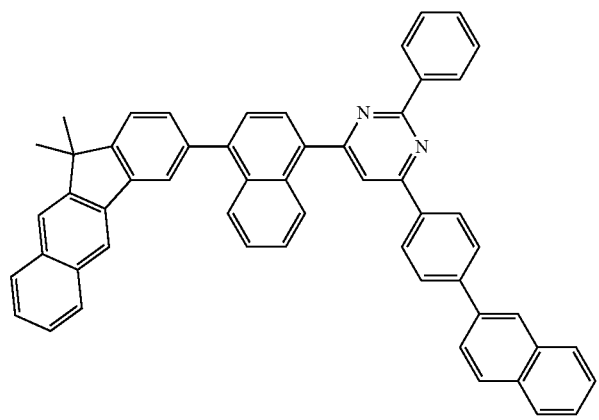 |
| 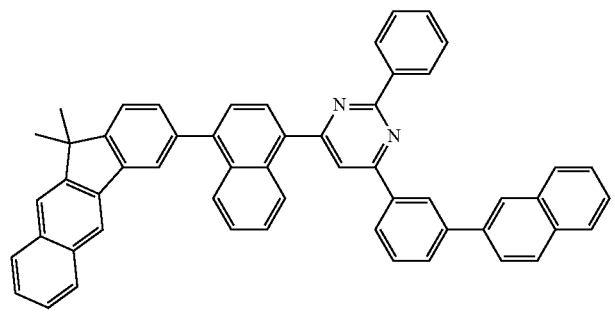 | 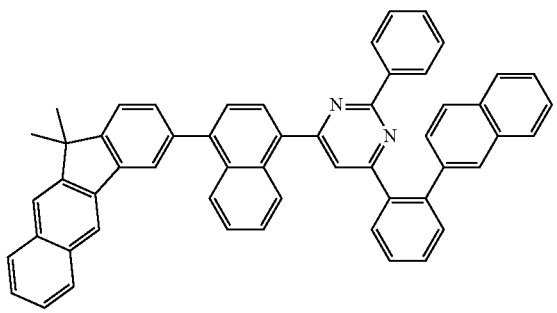 |

501 502
-continued
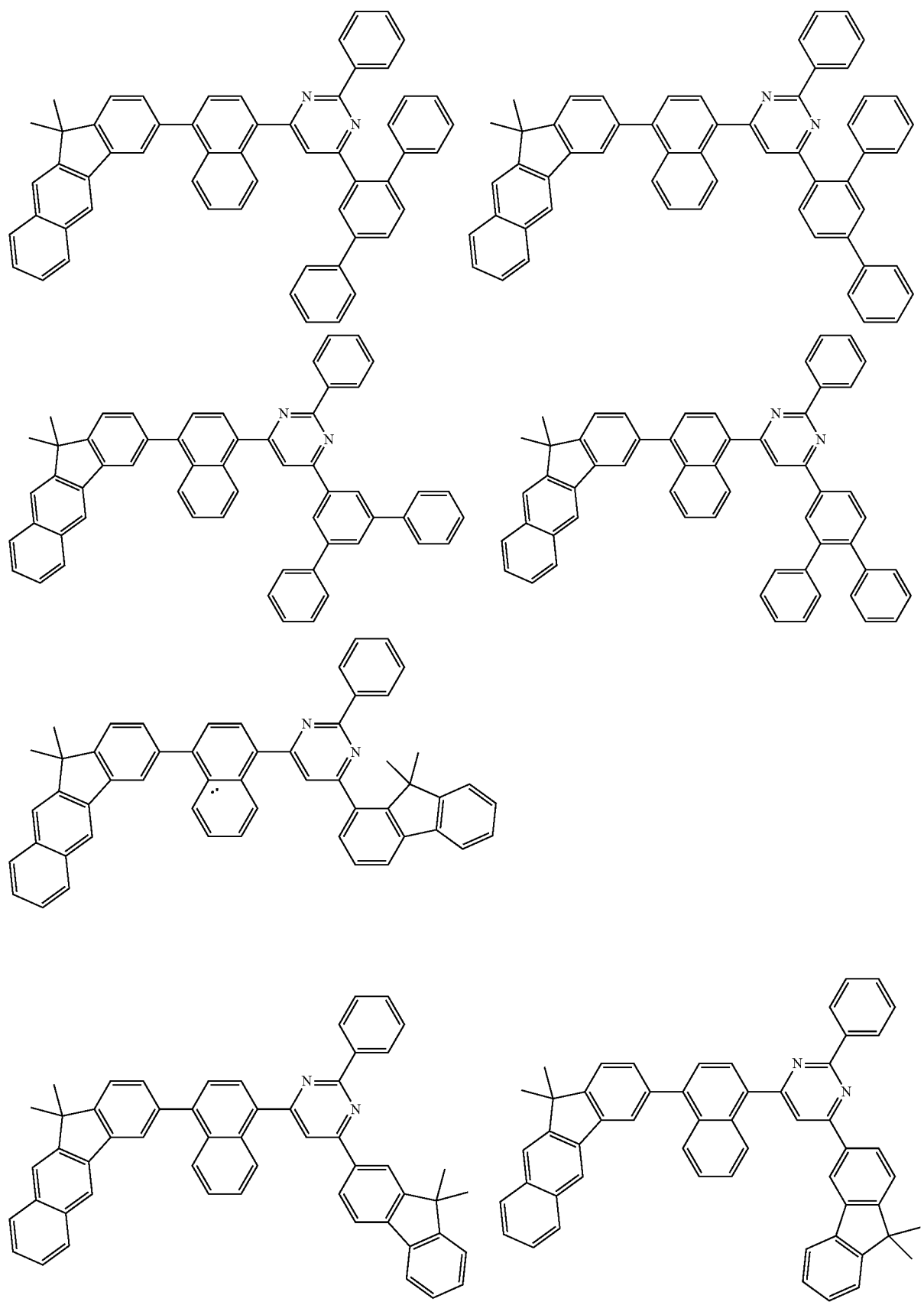

-continued
503 504
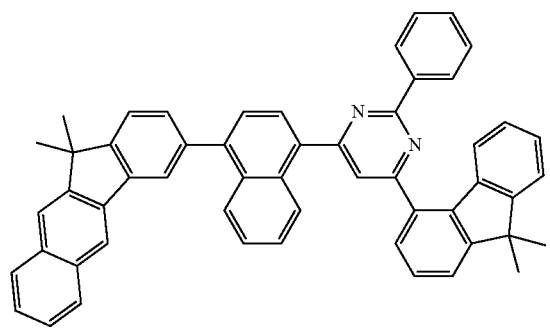
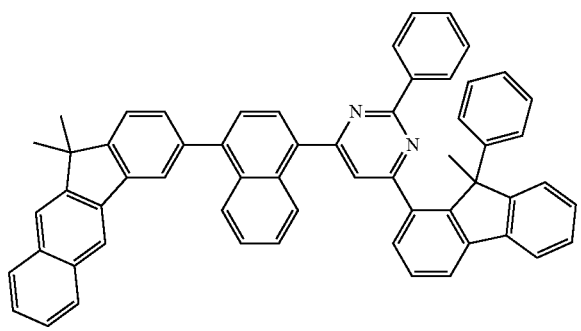
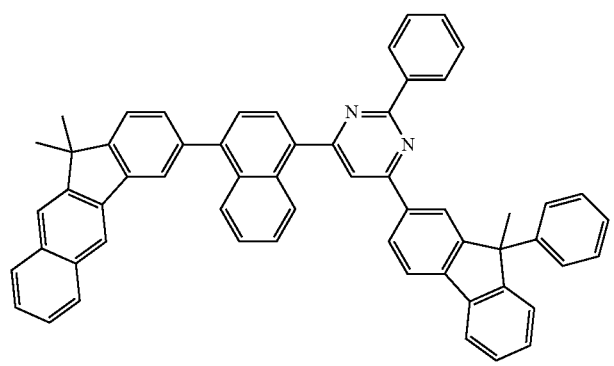
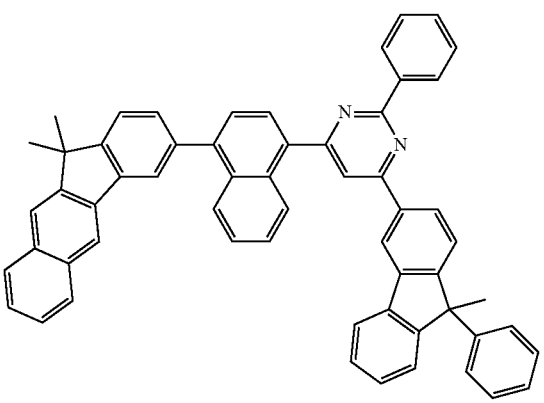
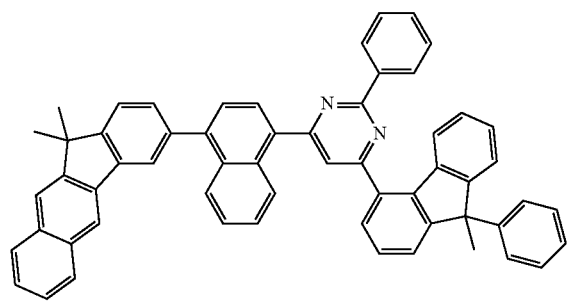
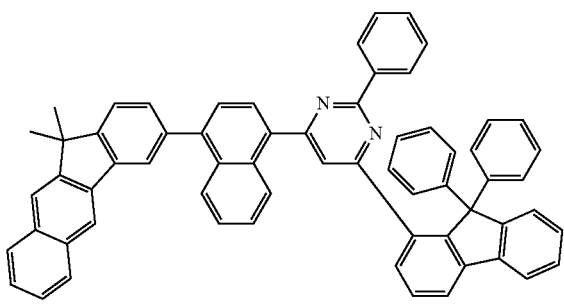
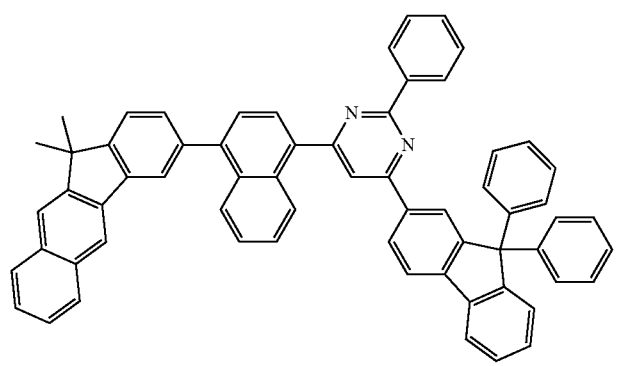
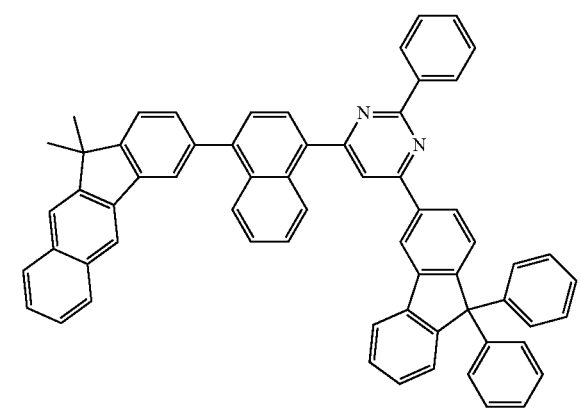

505 506
-continued
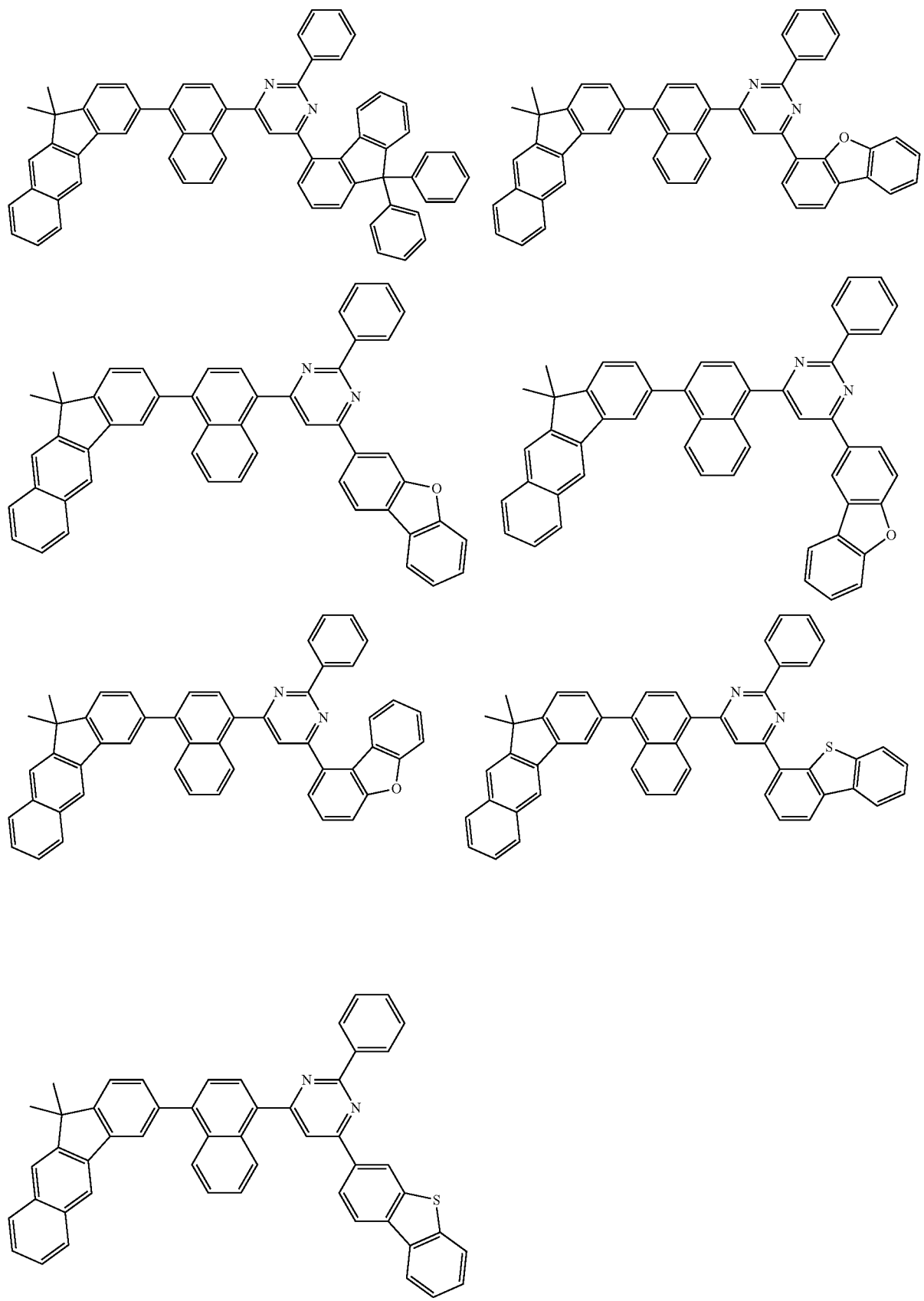

-continued
507
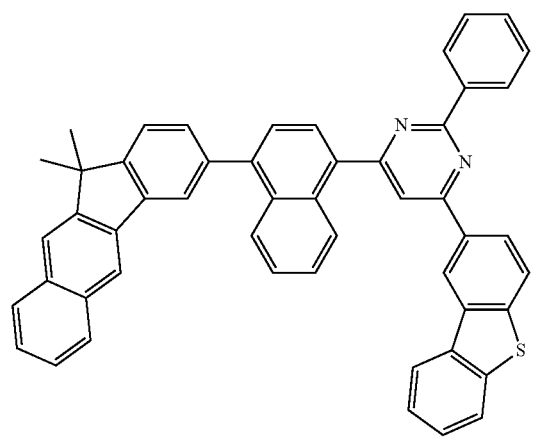
508
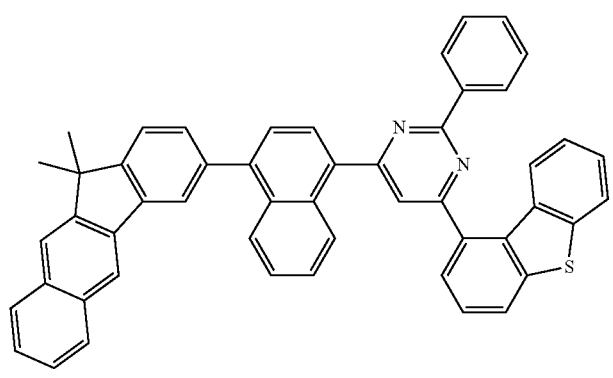
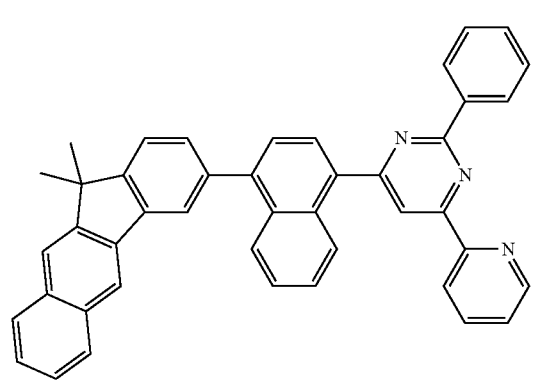
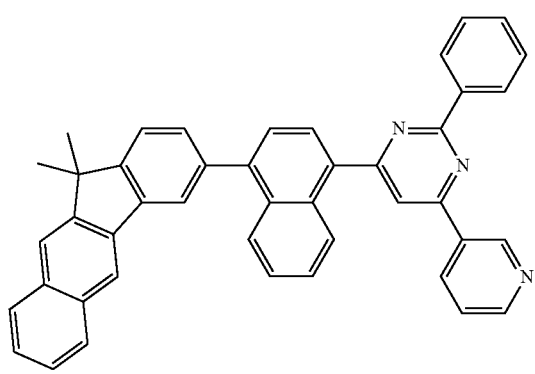
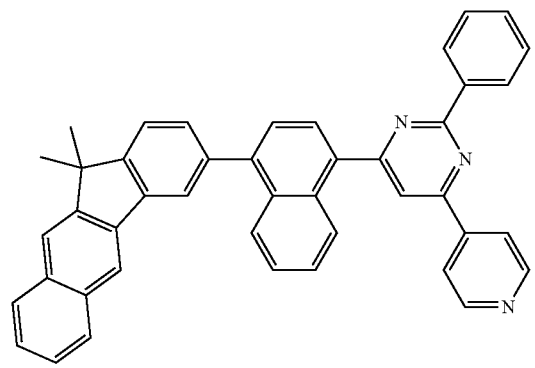
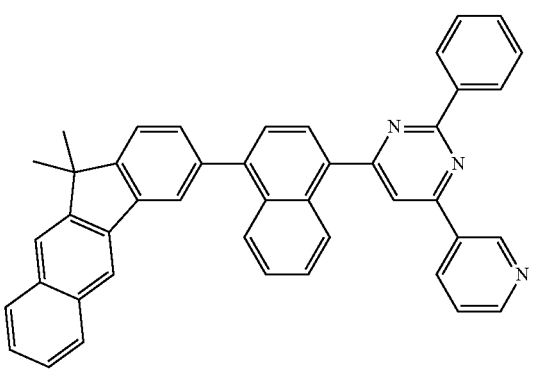
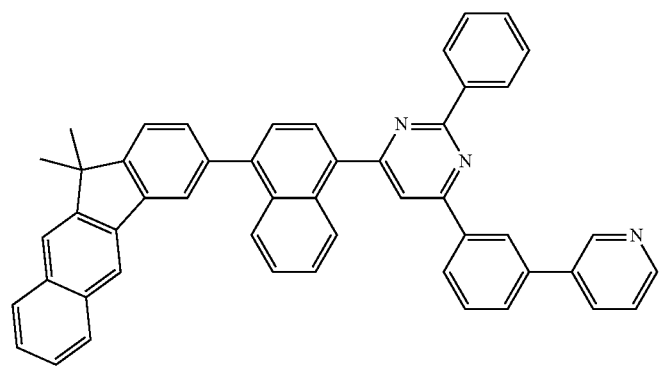

509 510
-continued
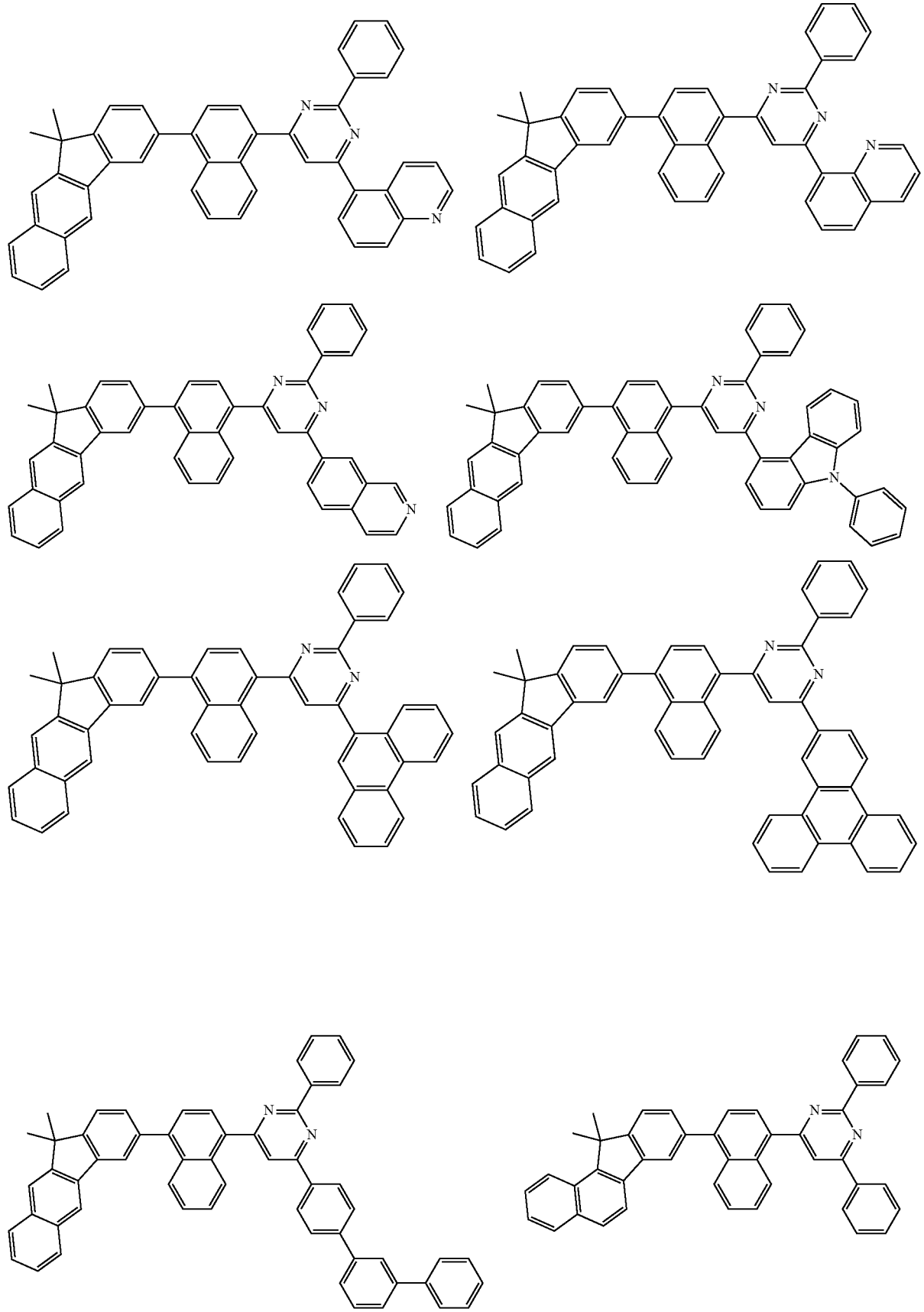

511 512
-continued
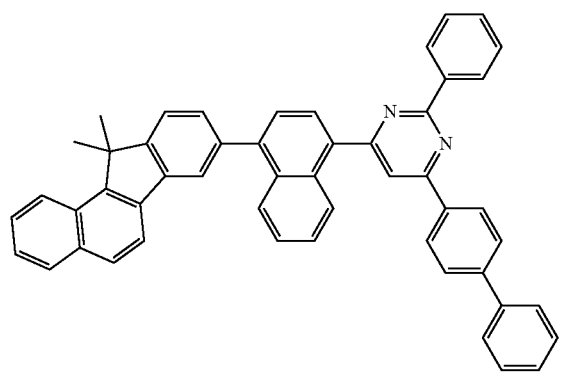 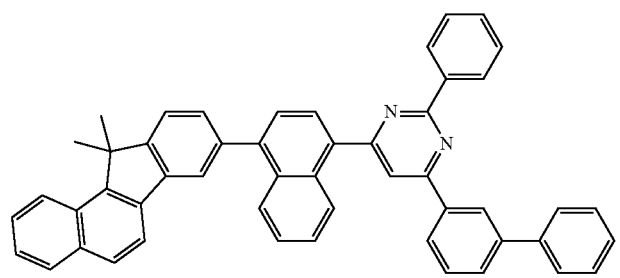
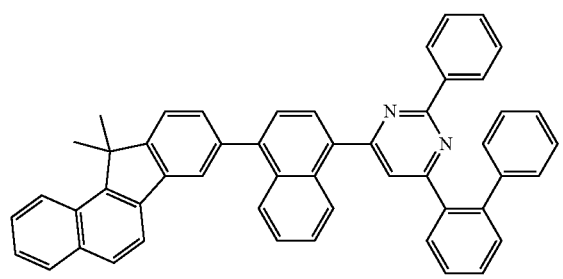 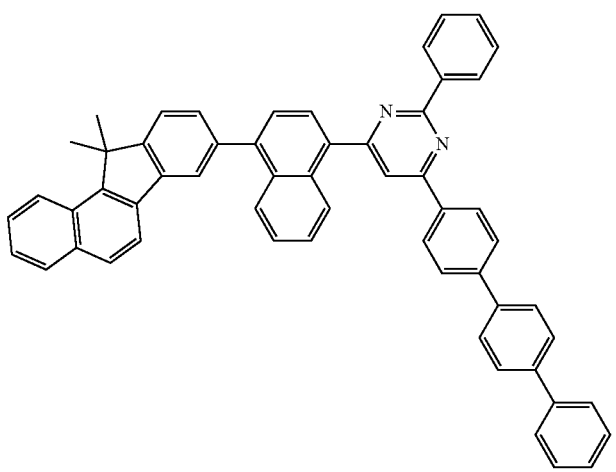
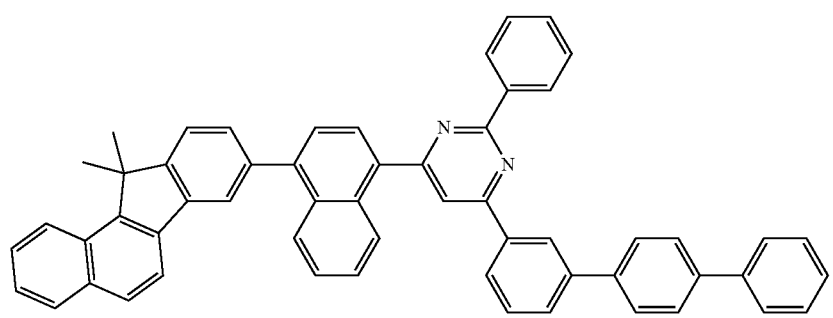
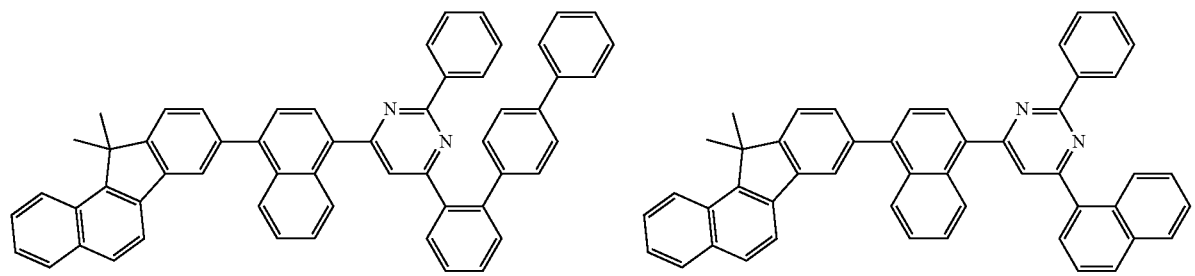

513
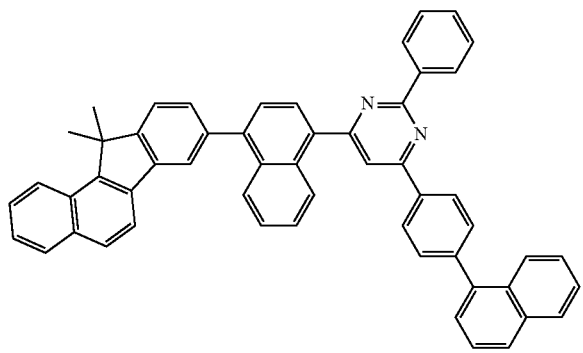
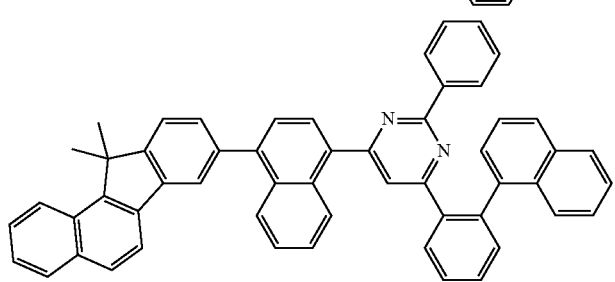
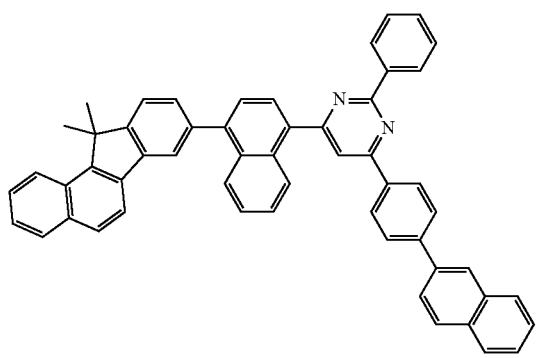
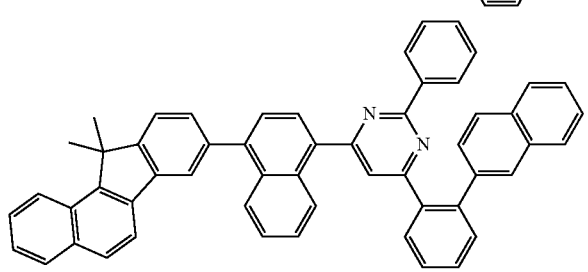
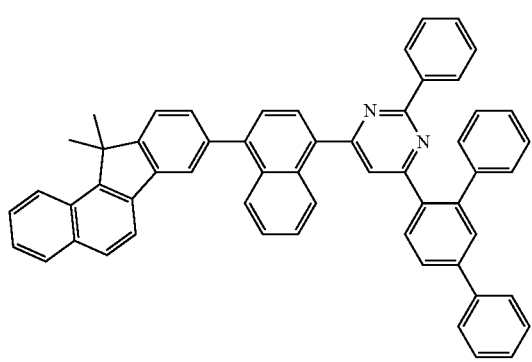
514
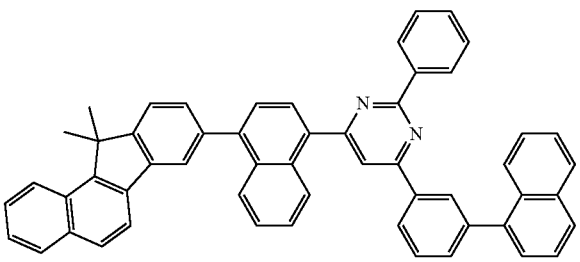
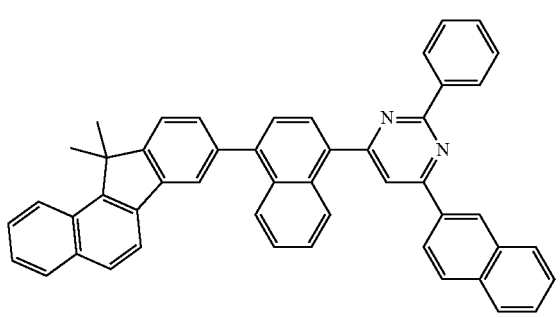
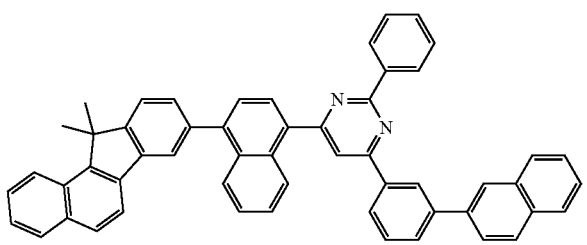
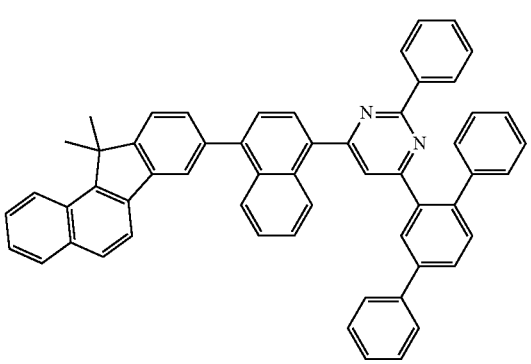
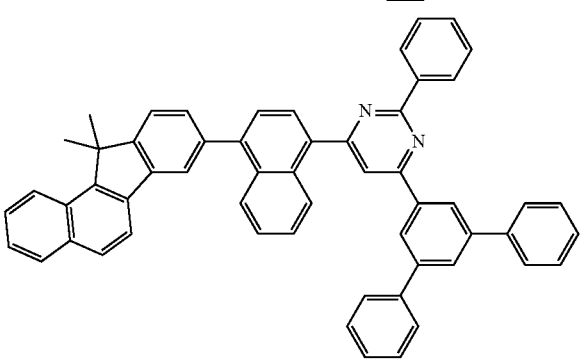

515
516
-continued
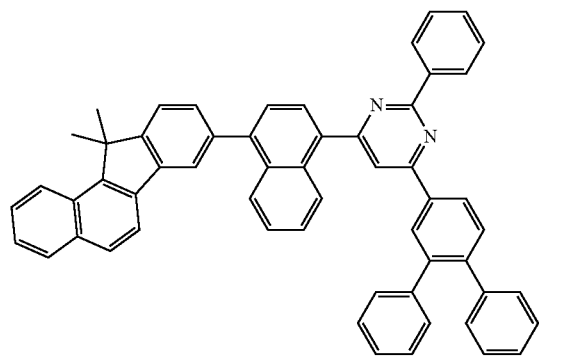
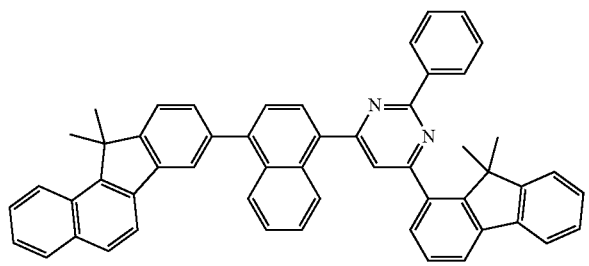
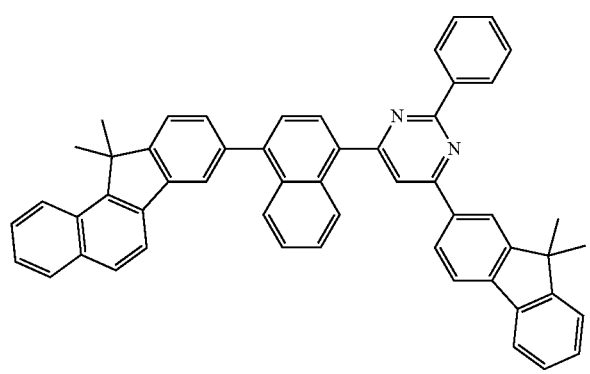
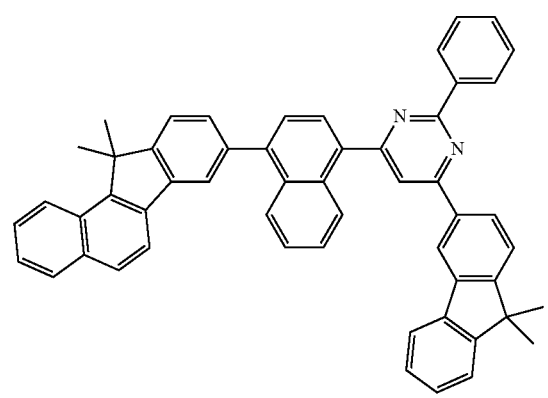
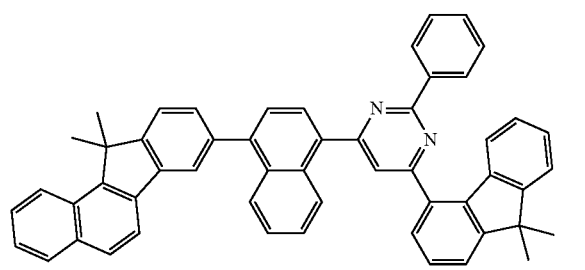
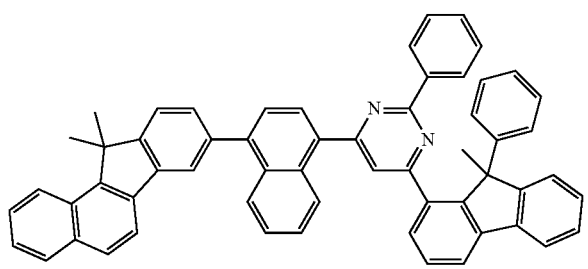
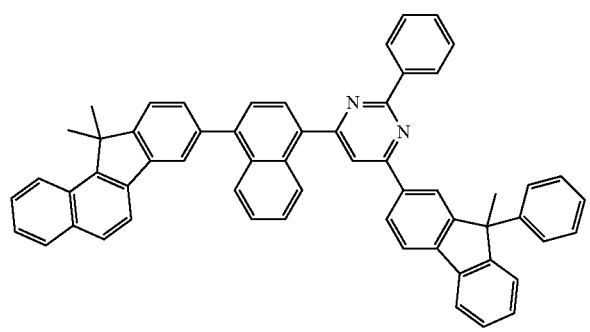
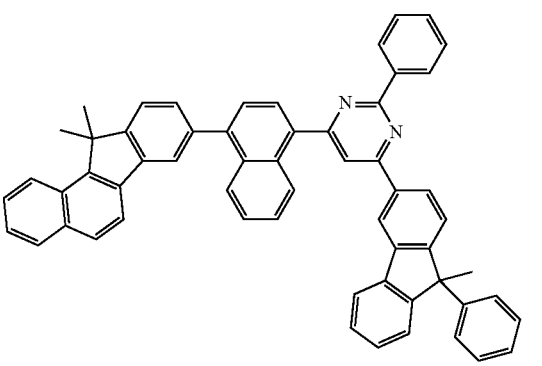
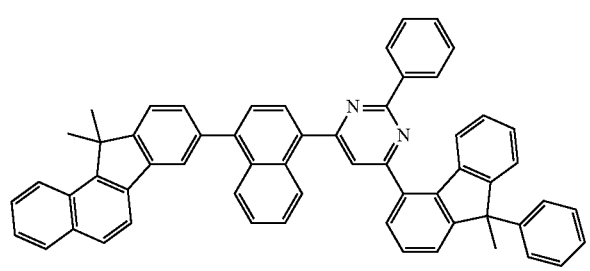
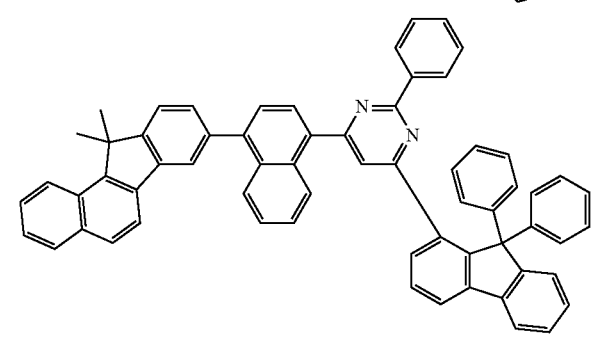

| 517 | 518 |
|---|---|
| 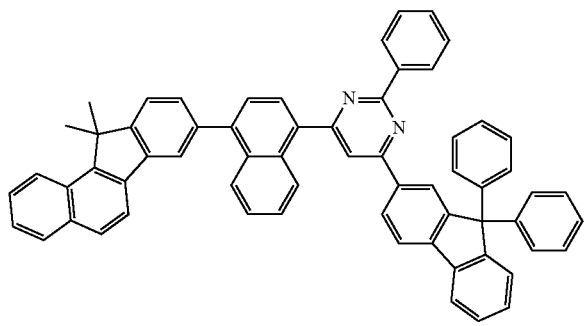 | 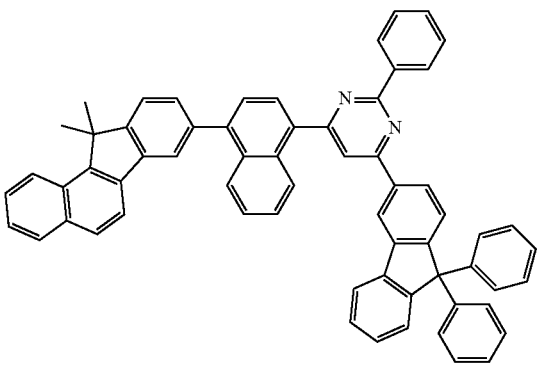 |
| 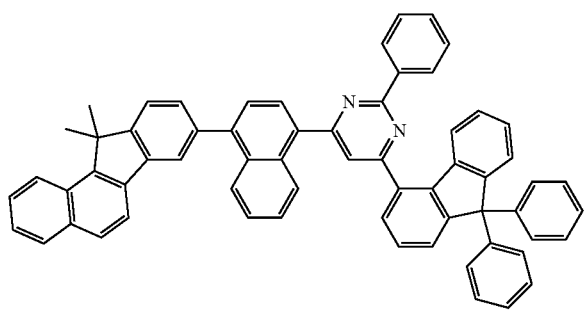 | 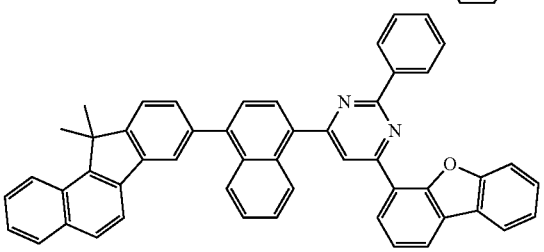 |
| 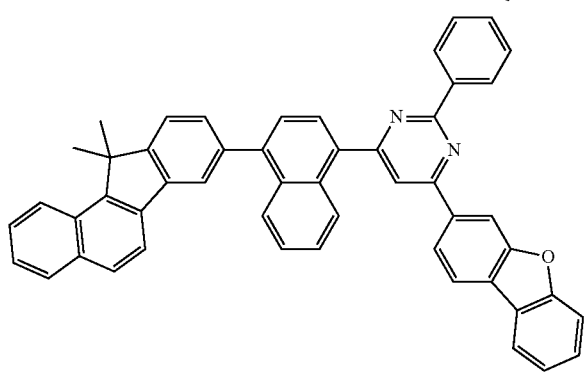 | 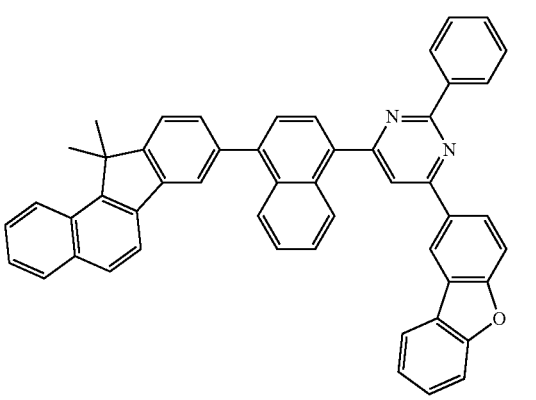 |
| 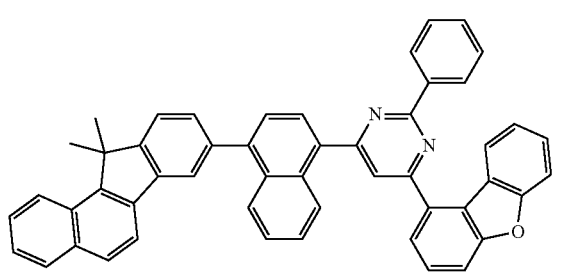 | 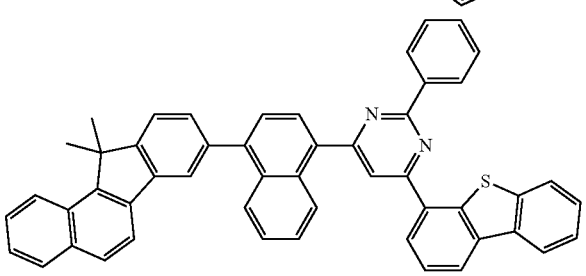 |
| 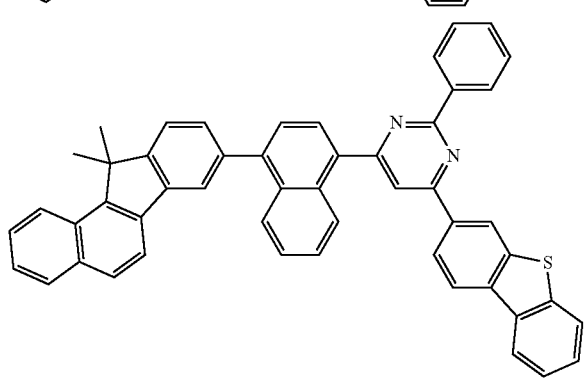 | 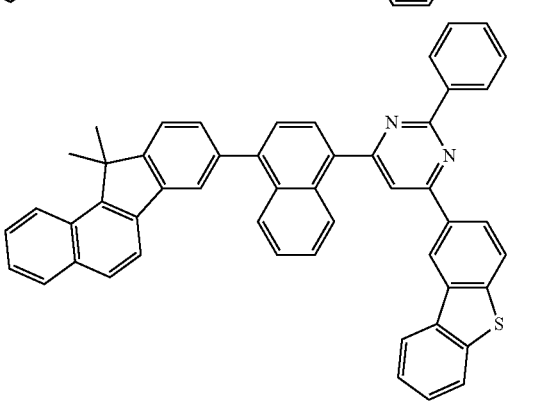 |

519 520
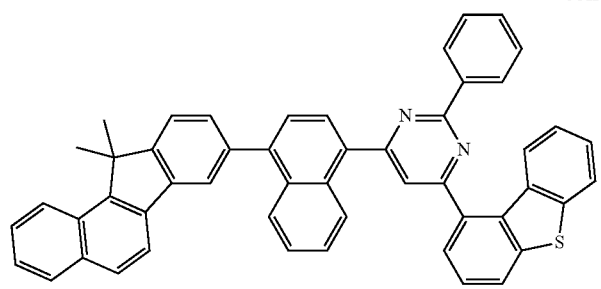
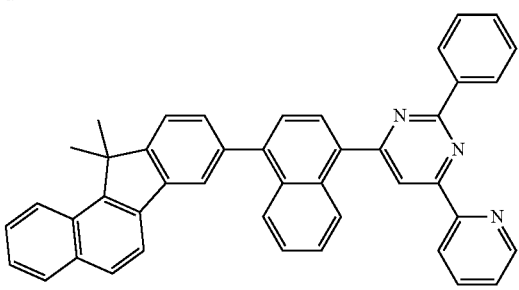
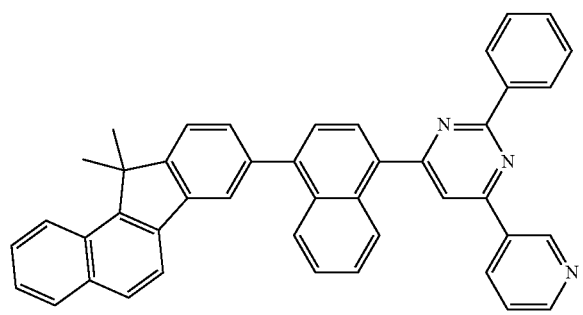
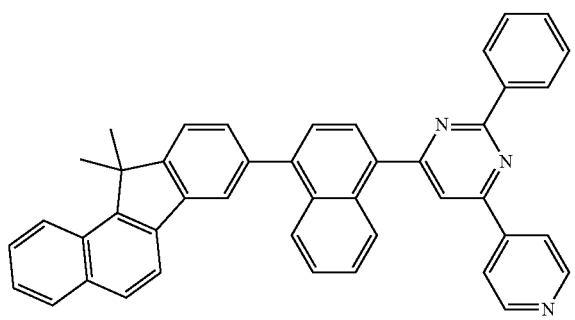
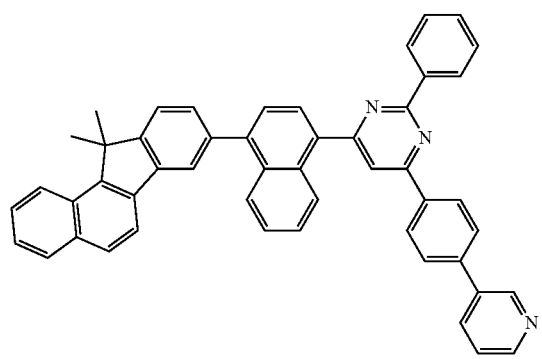
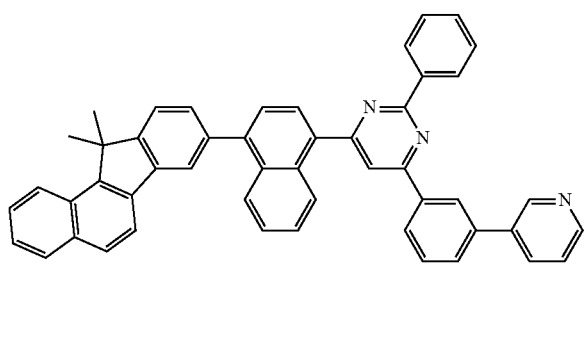
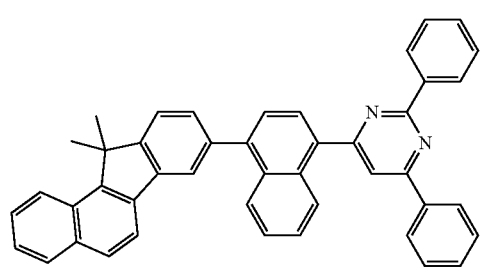
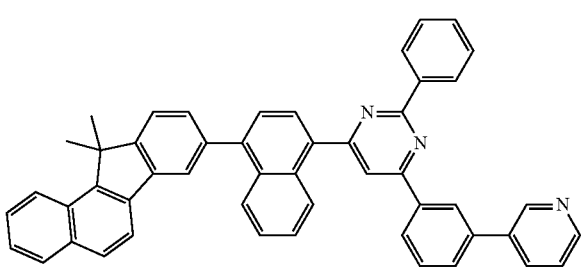
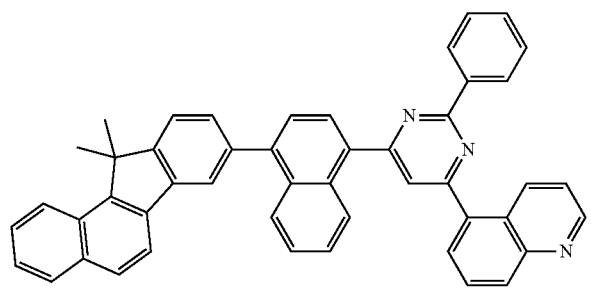
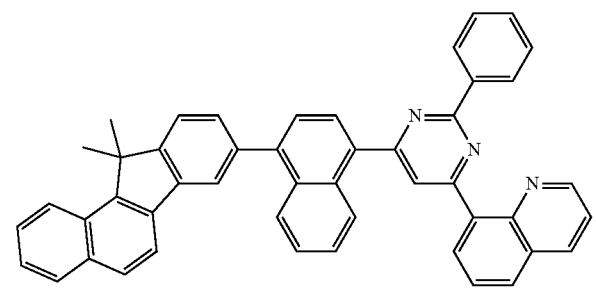

-continued
| 521 | 522 |
|---|---|
| 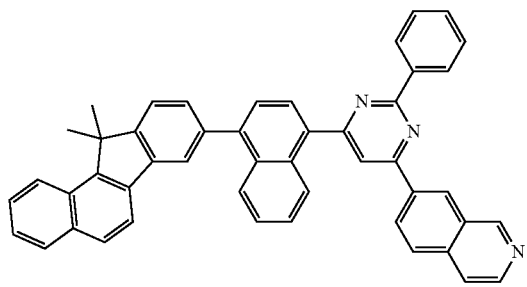 | 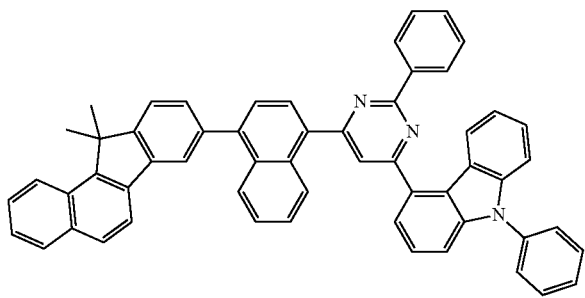 |
| 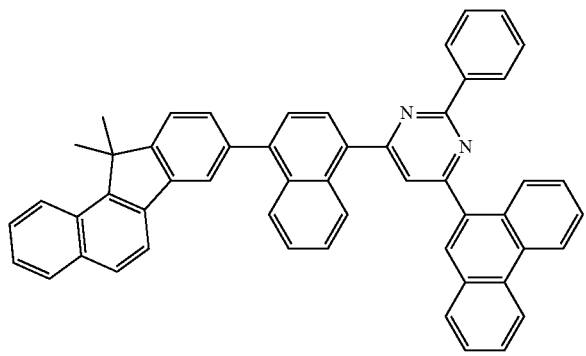 | 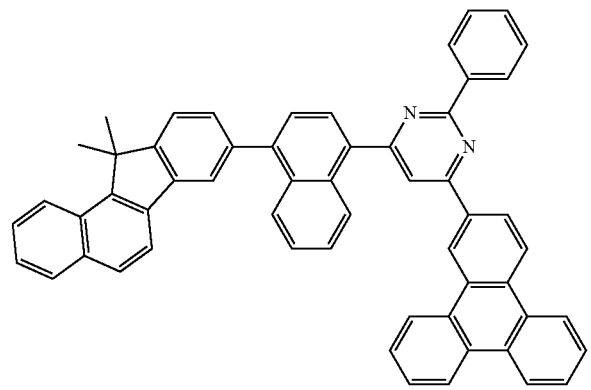 |
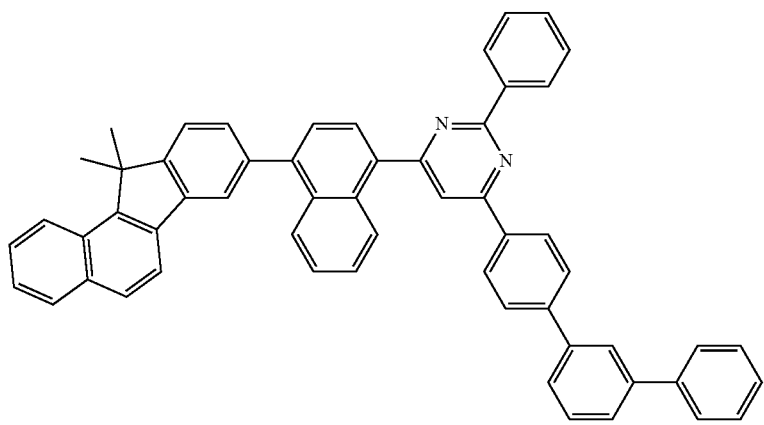
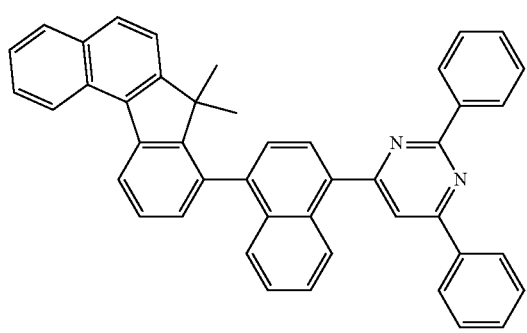
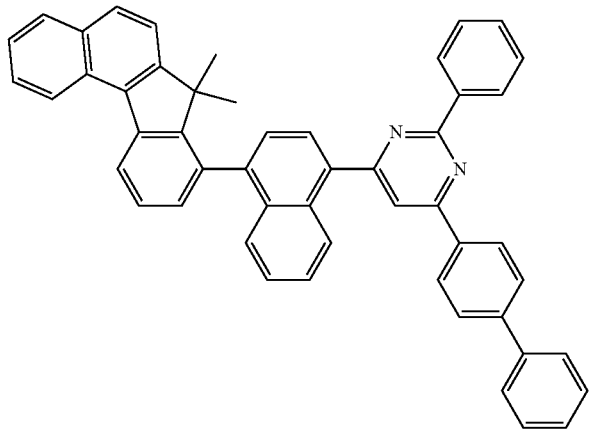

-continued
523
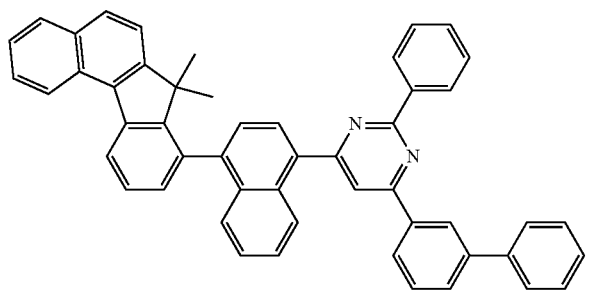
524
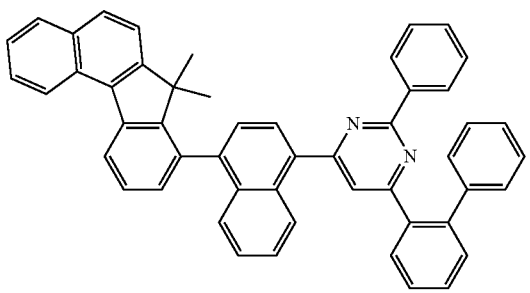
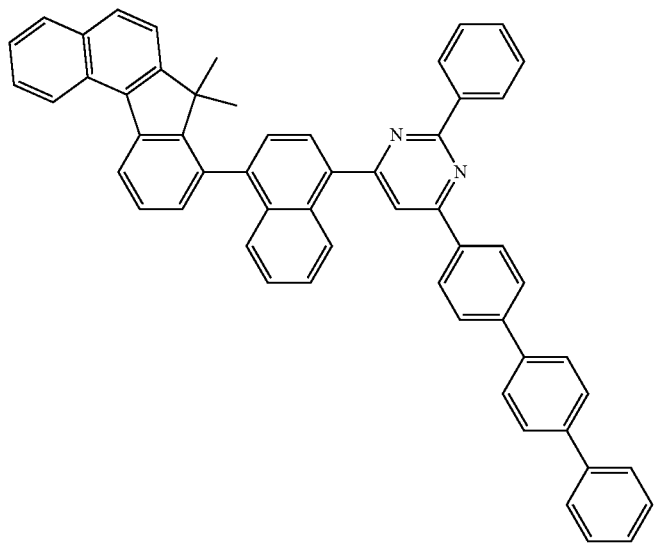
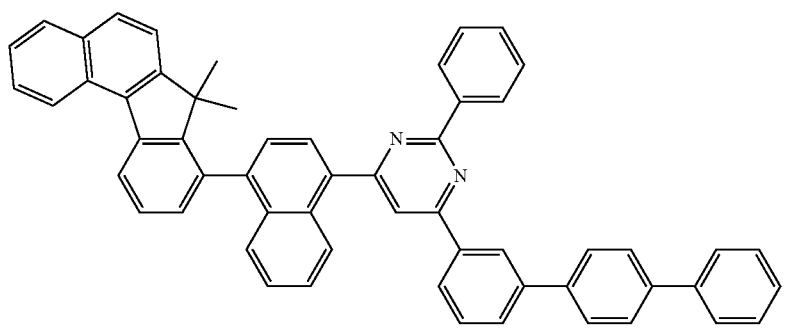
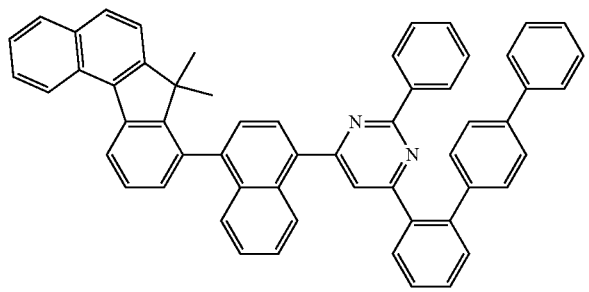
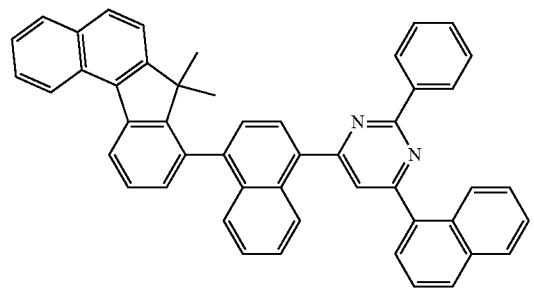

-continued
| 525 | 526 |
|---|---|
| 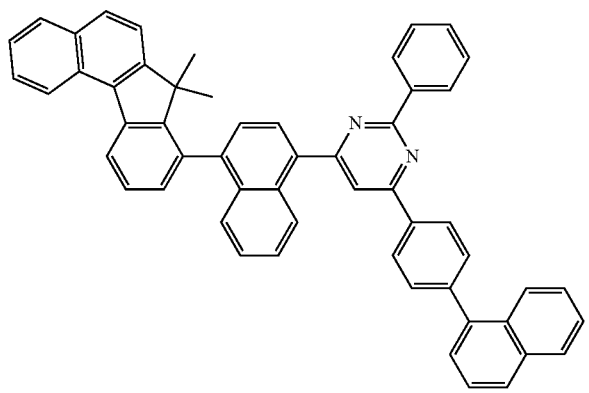 | 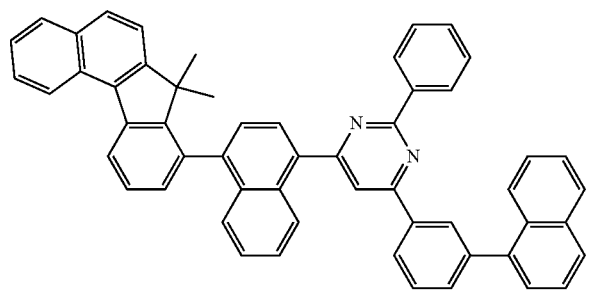 |
| 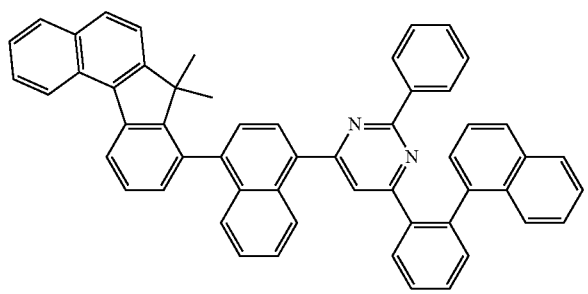 | 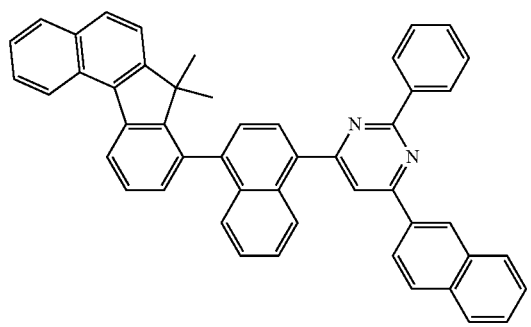 |
| 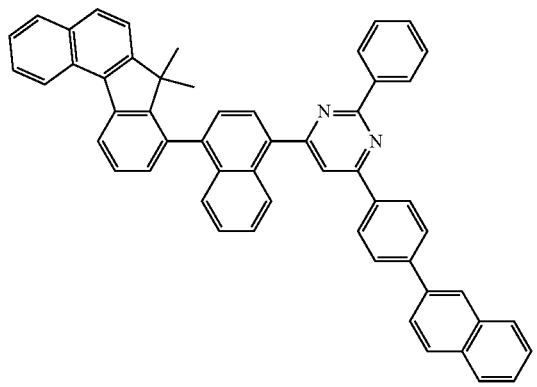 | 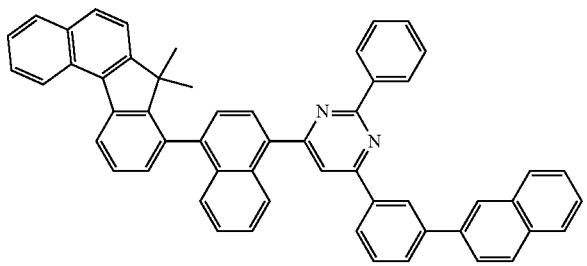 |
| 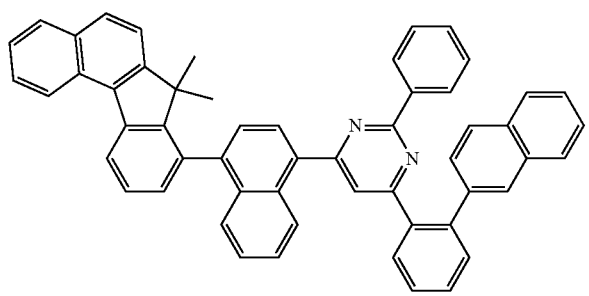 | 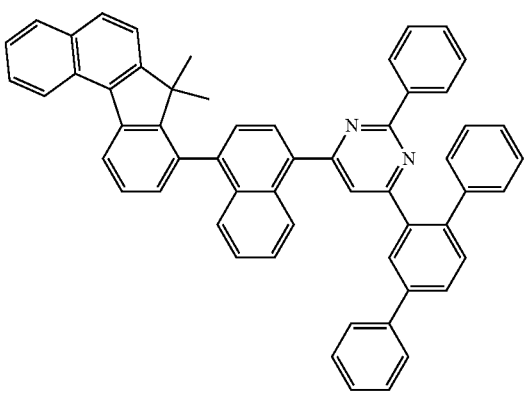 |

-continued
| 527 | 528 |
|---|---|
| 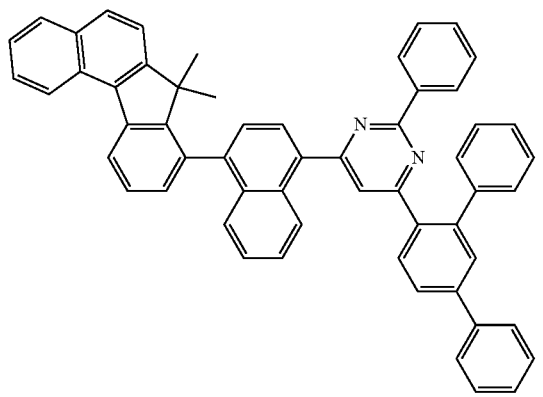 | 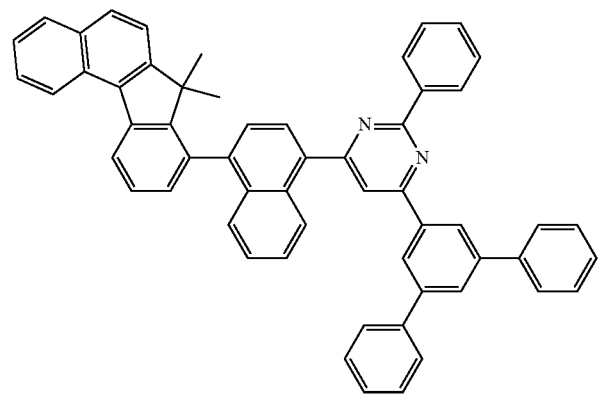 |
| 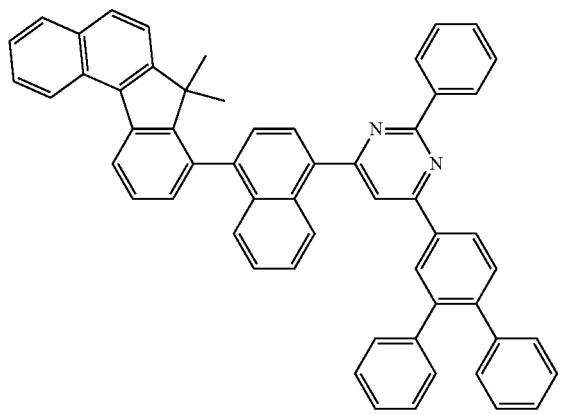 | 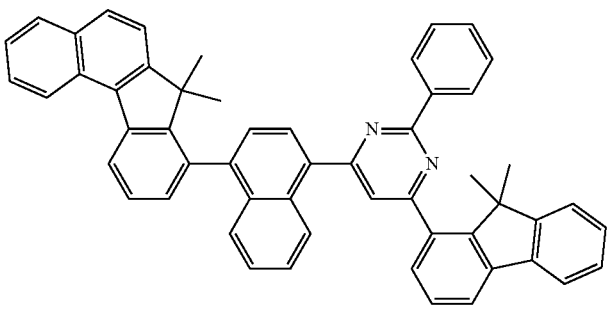 |
| 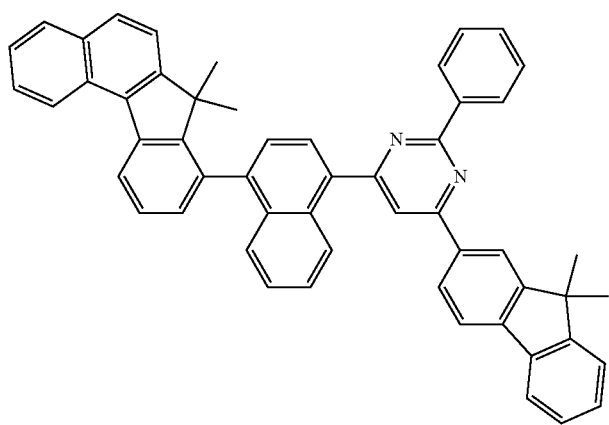 | 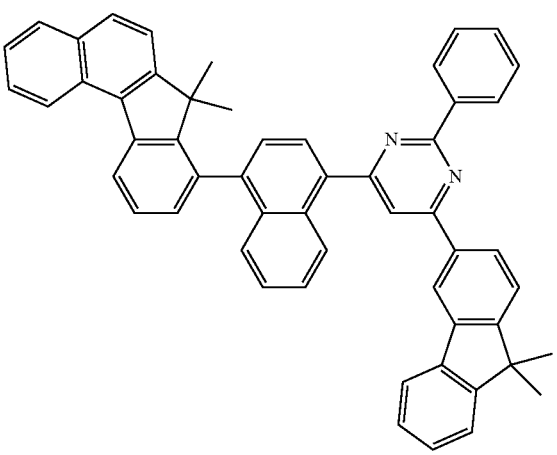 |
| 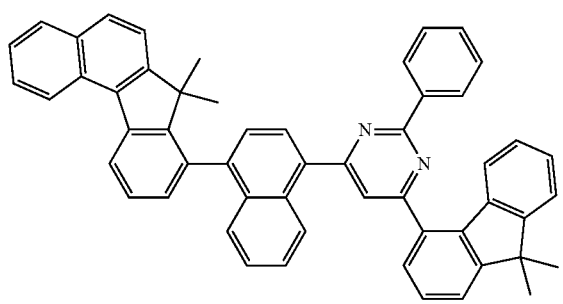 | 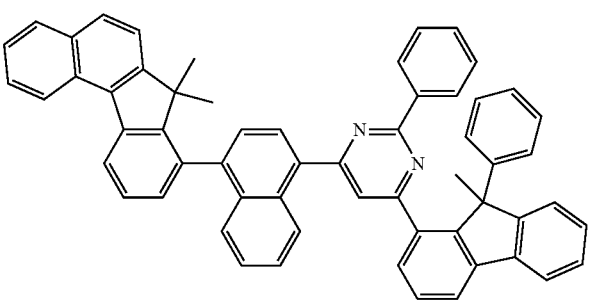 |

-continued
| 529 | 530 |
|---|---|
| 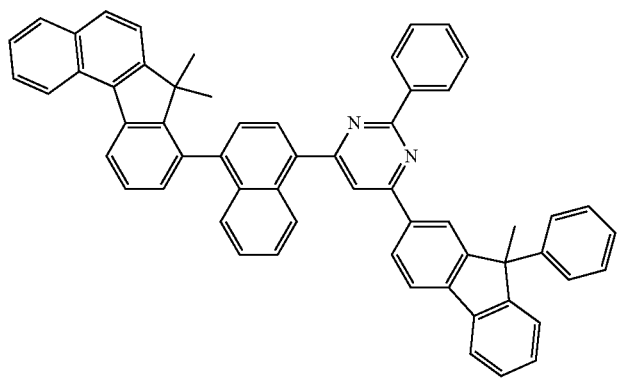 | 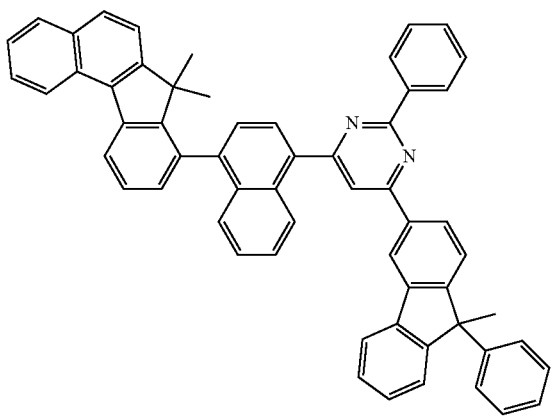 |
| 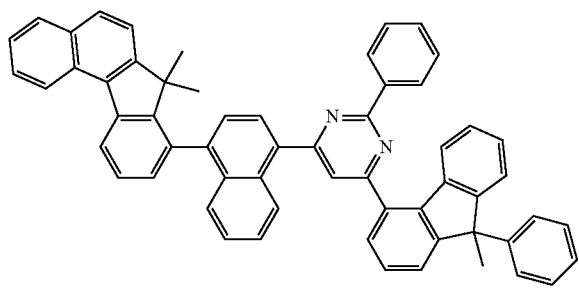 | 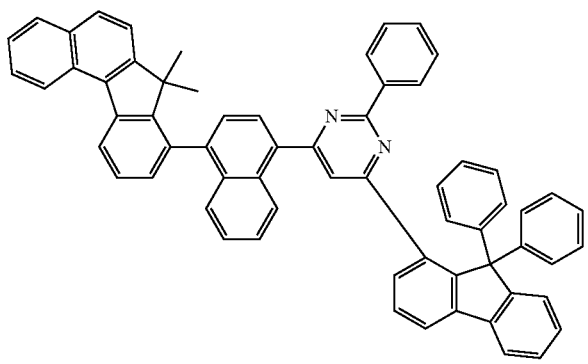 |
| 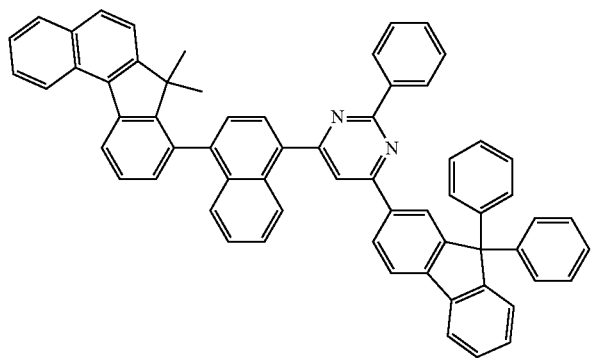 | 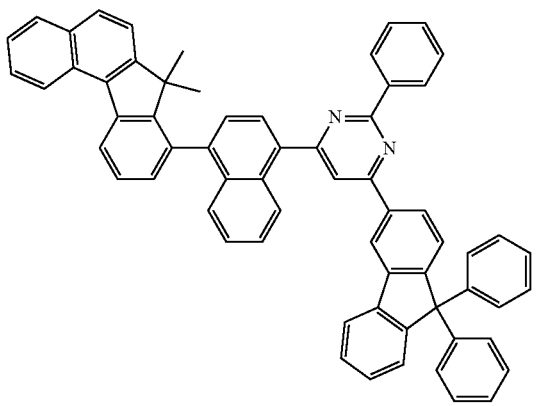 |
| 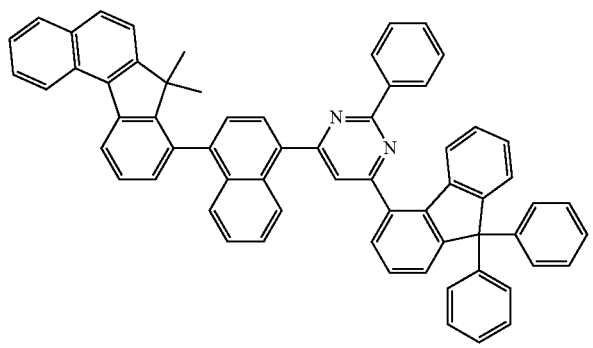 | 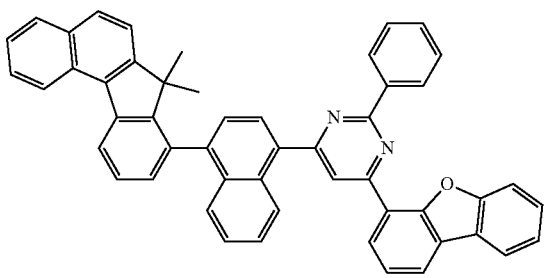 |

531
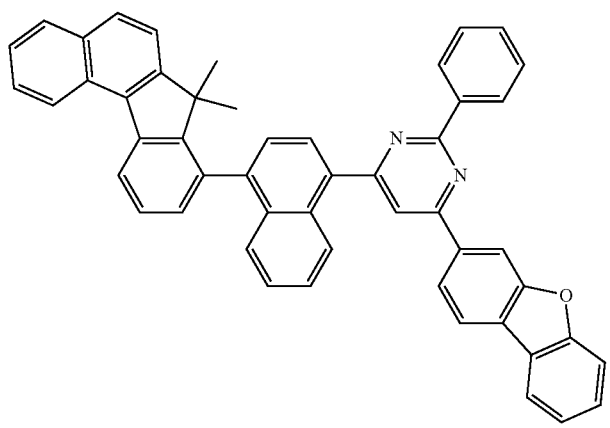
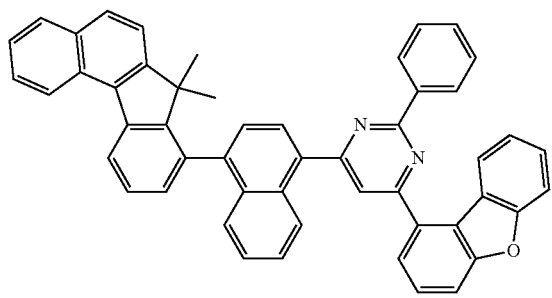
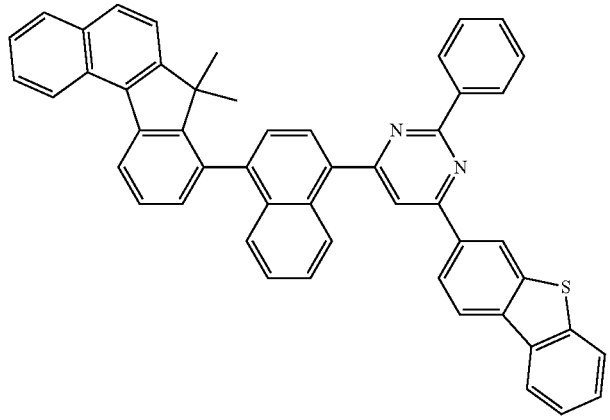
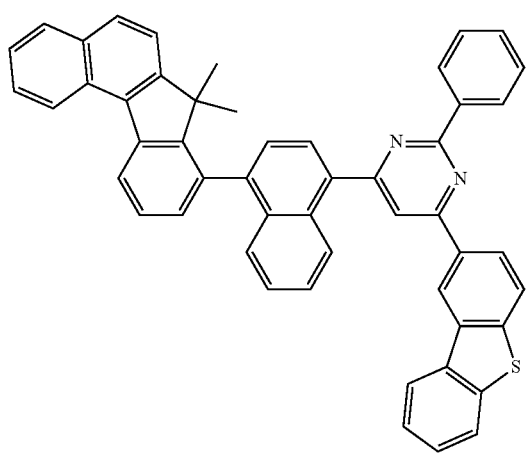
532
-continued
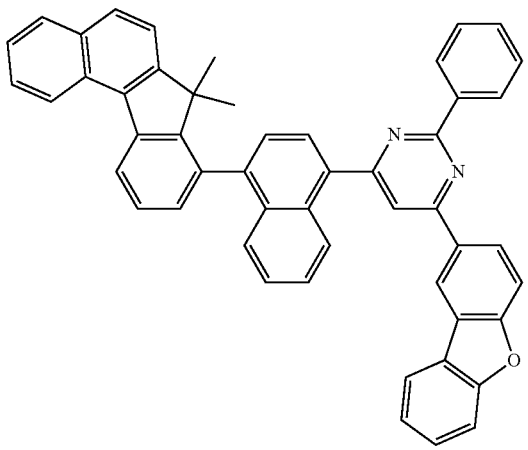
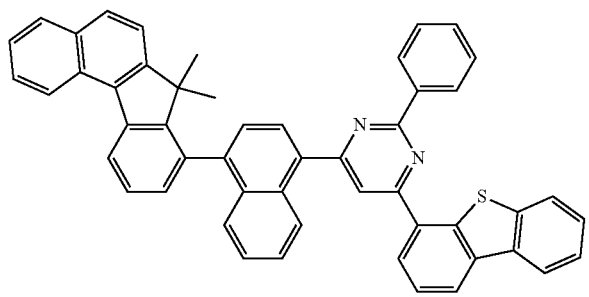
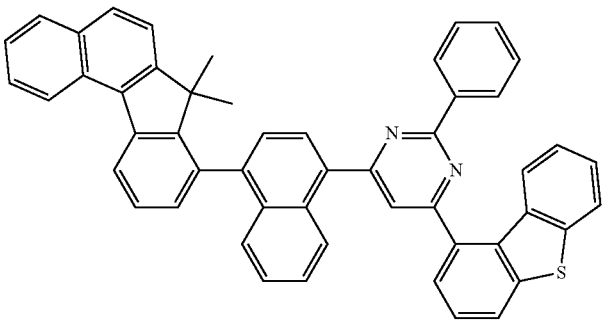

533 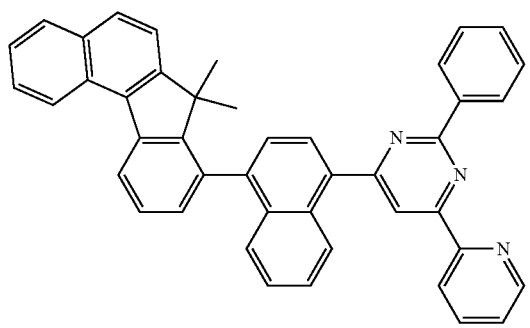 534 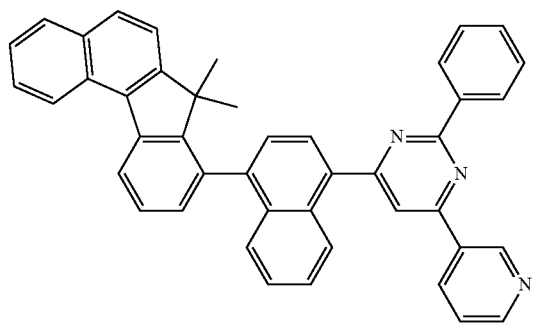
-continued
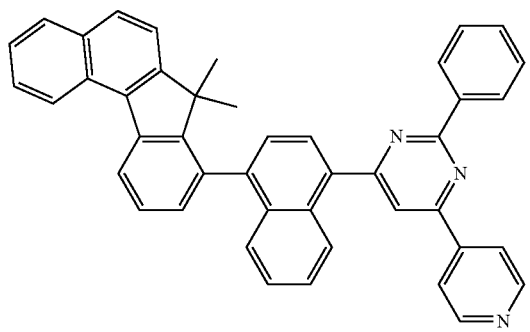 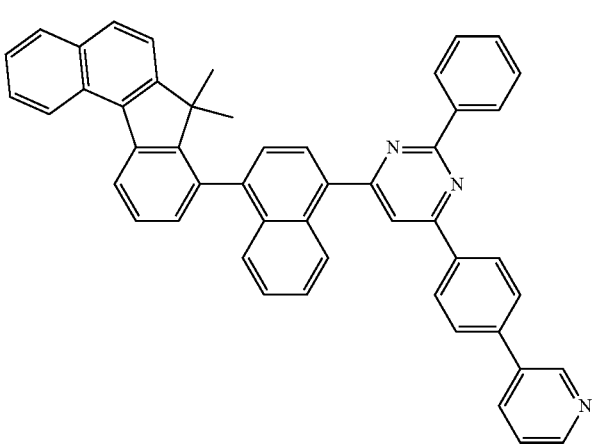
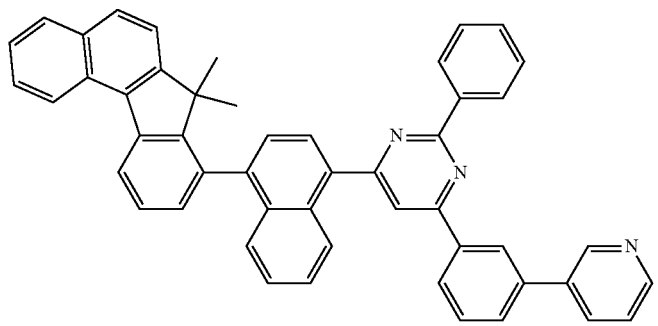
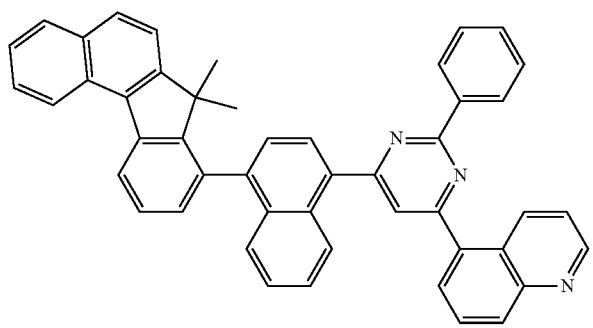 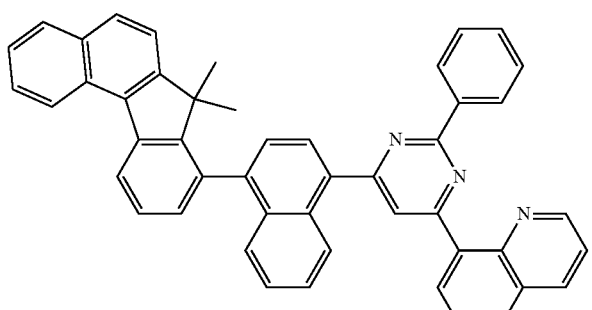

-continued
535
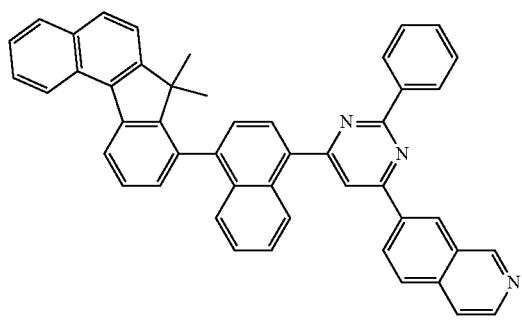
536
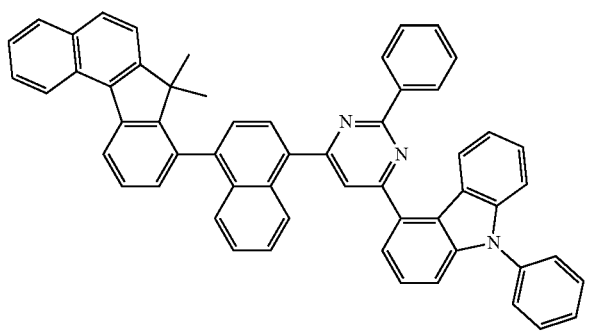
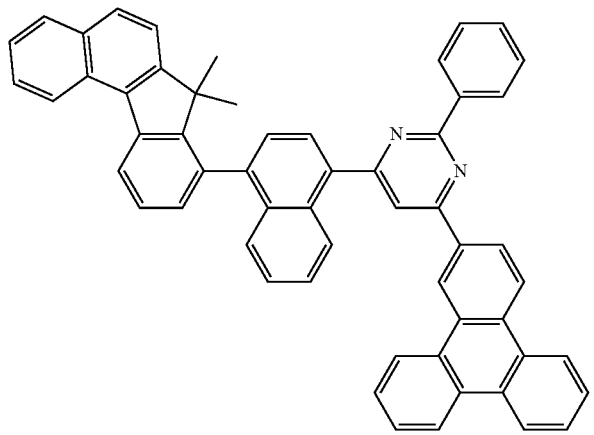
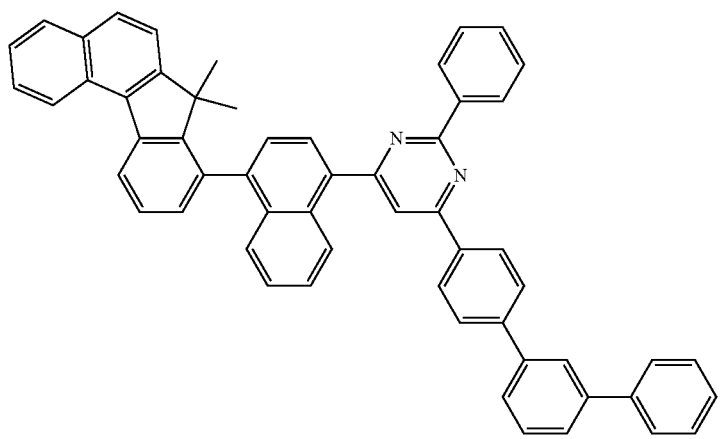
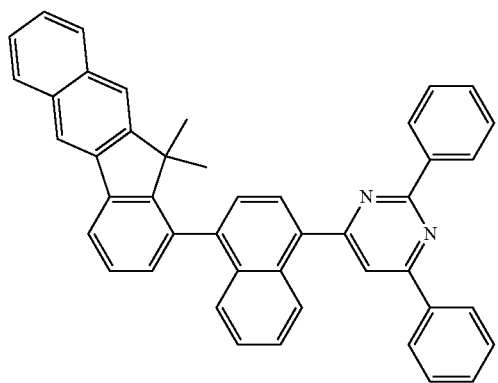
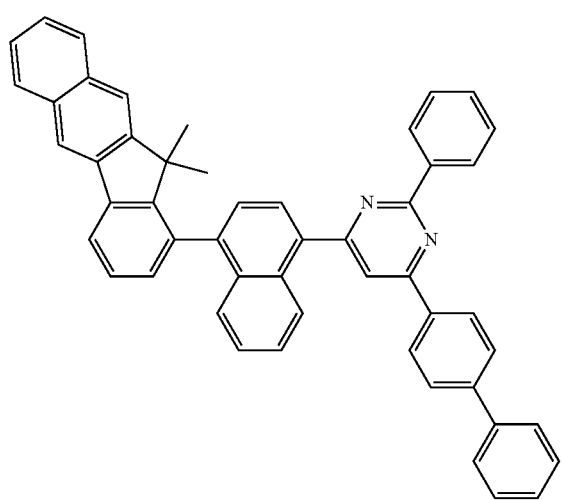

537 538
-continued
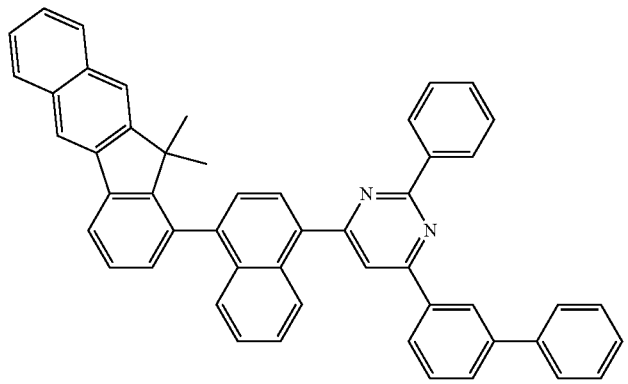
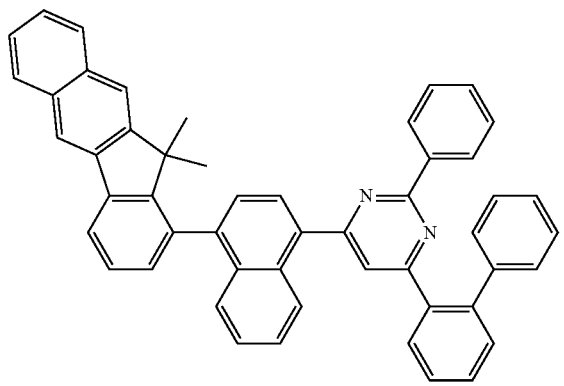
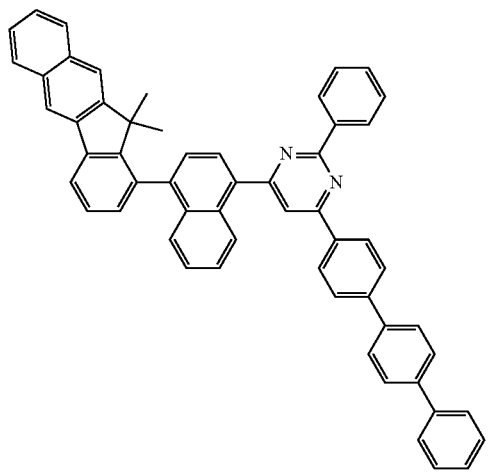
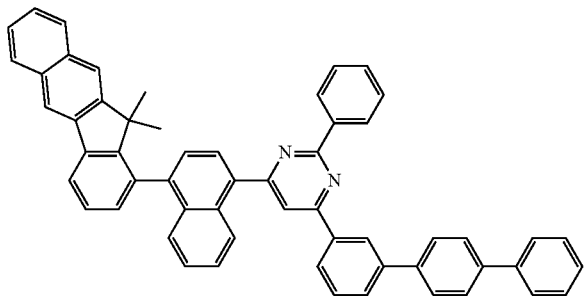
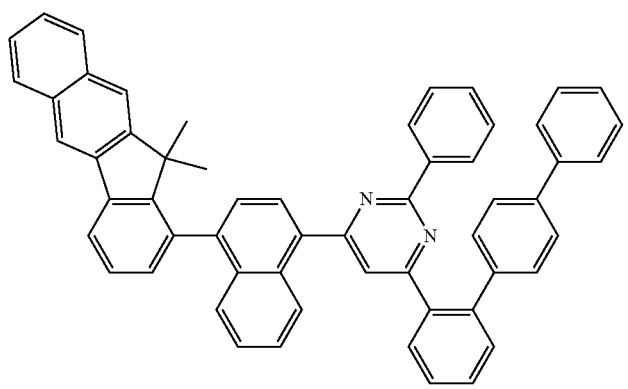
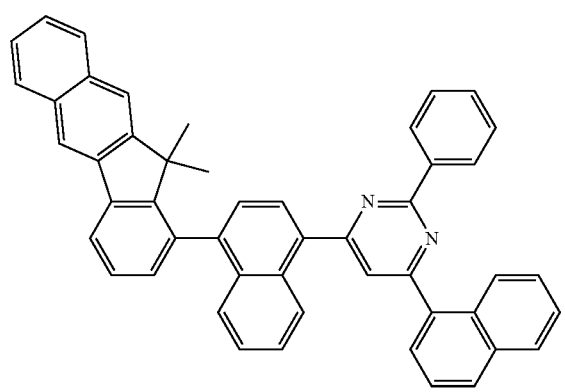
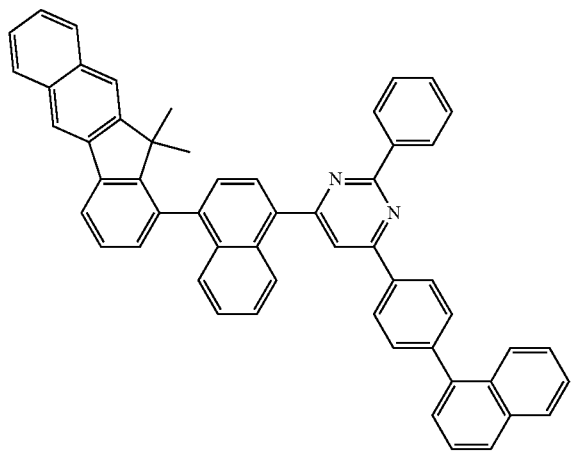
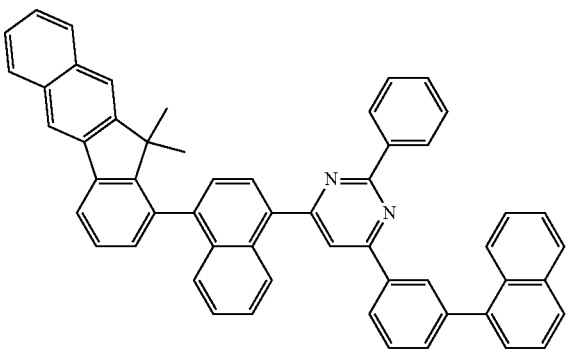

539
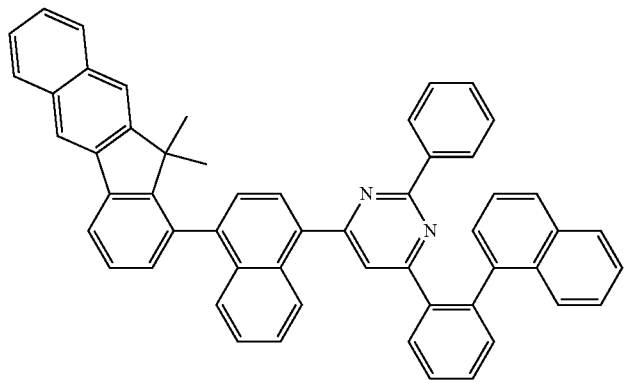
540 -continued
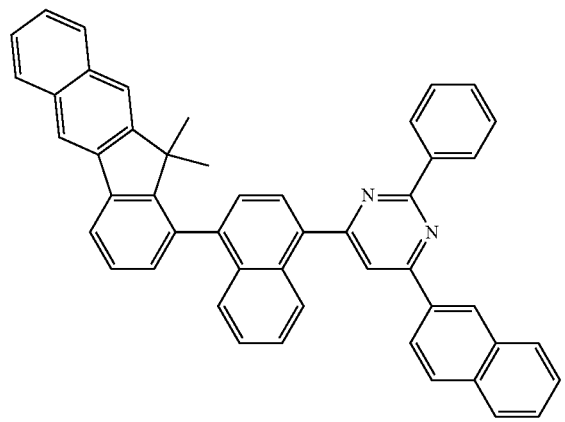
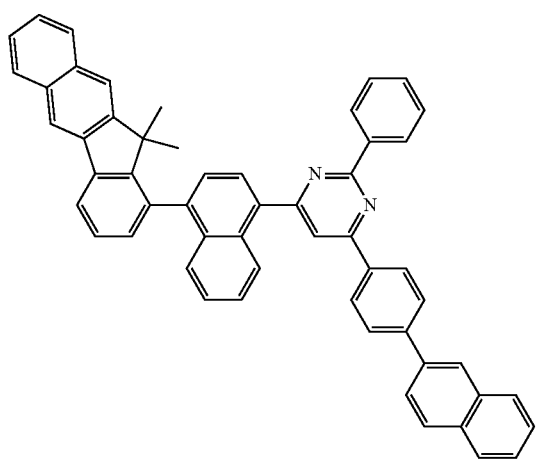
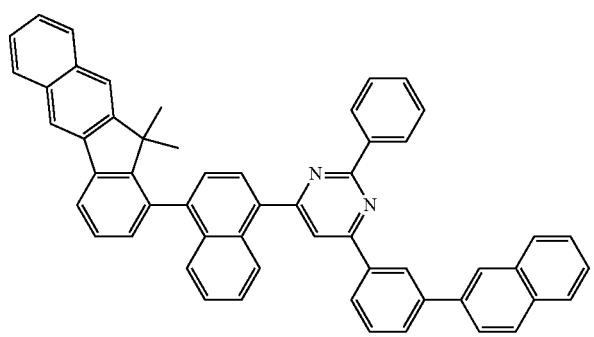
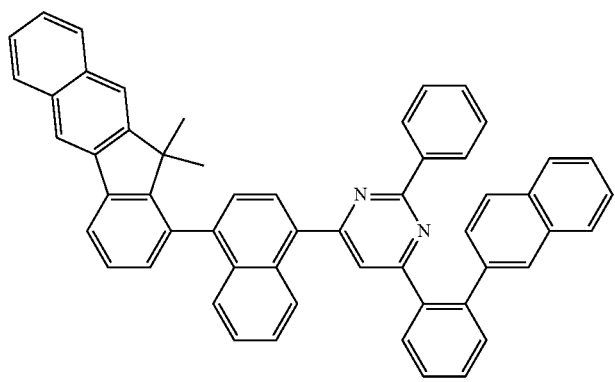
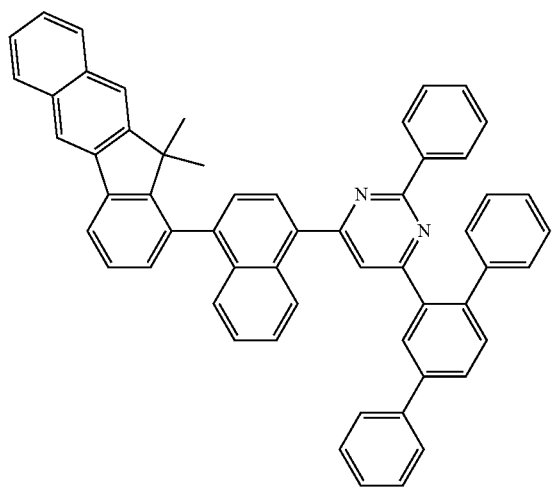

-continued
| 541 | 542 |
|---|---|
| 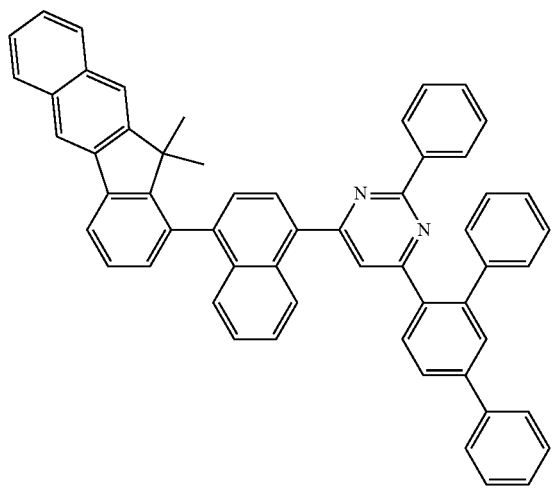 | 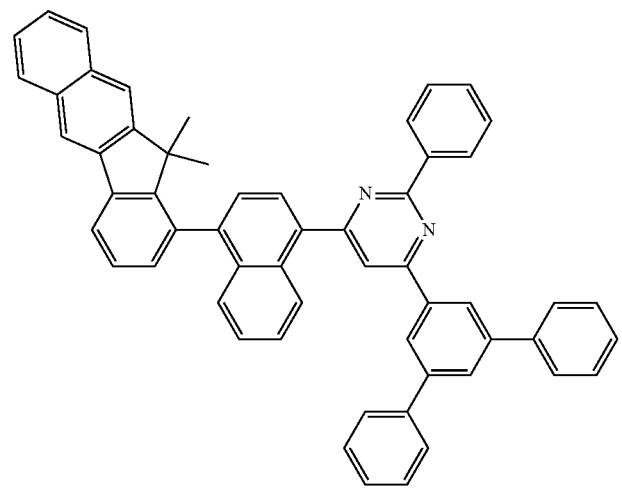 |
| 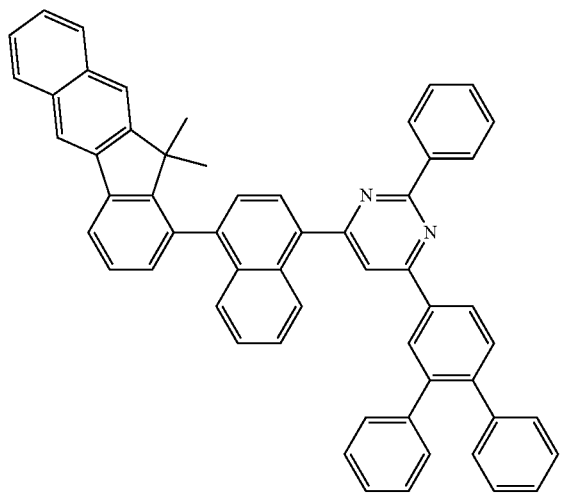 | 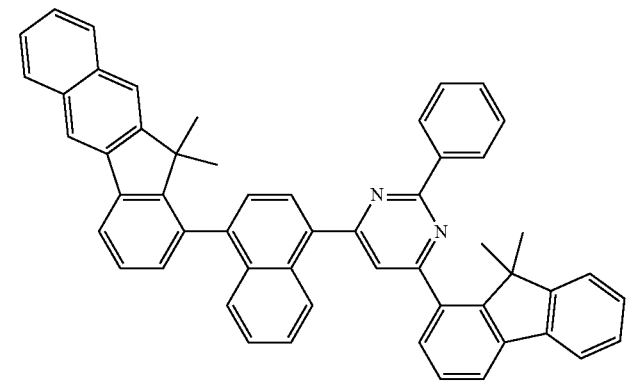 |
| 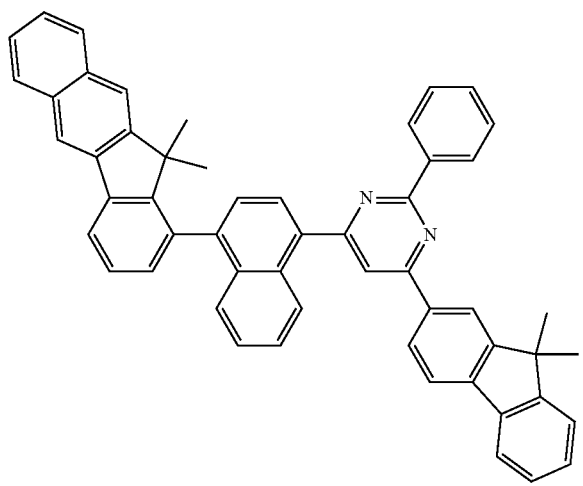 | 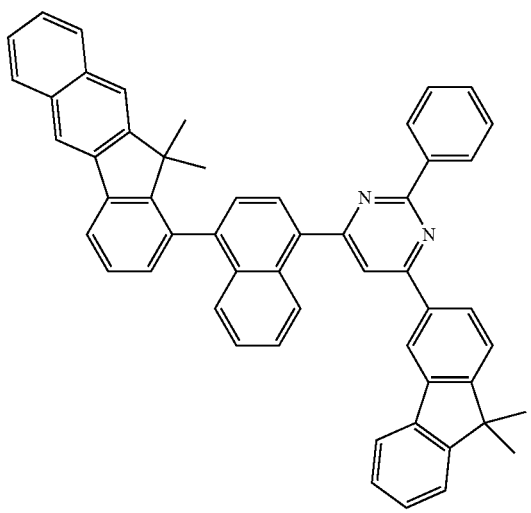 |

543
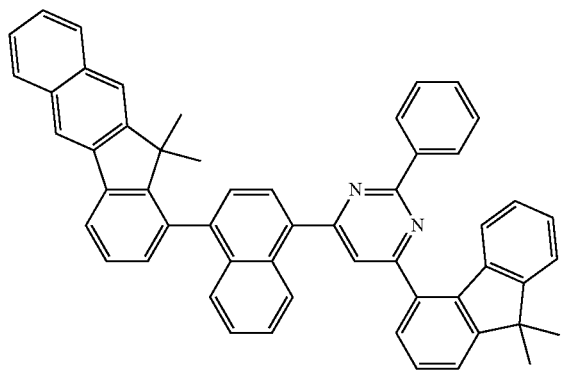
544
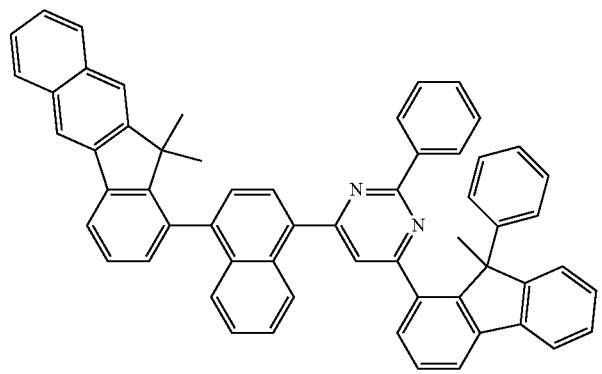
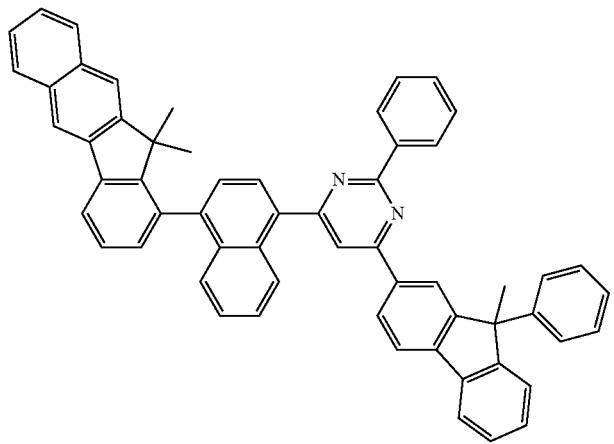
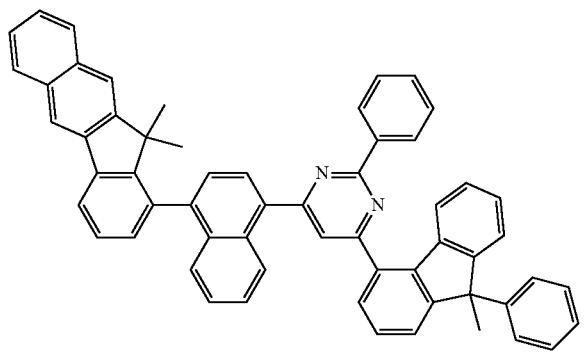
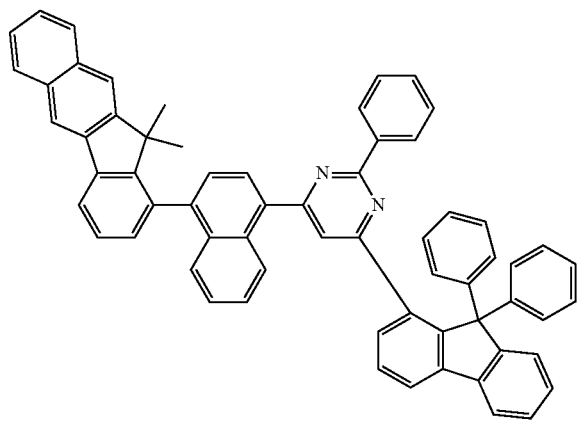

-continued
545
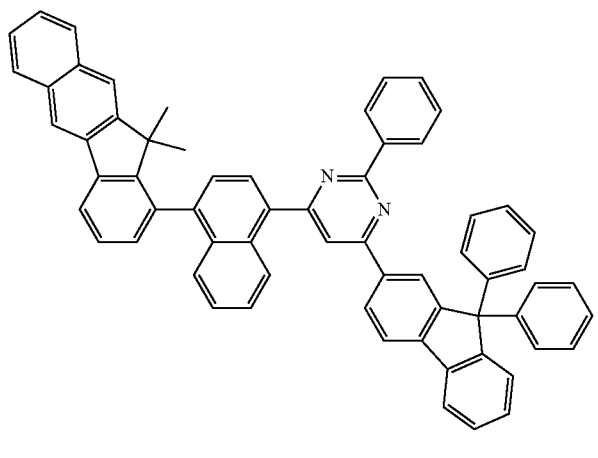
546
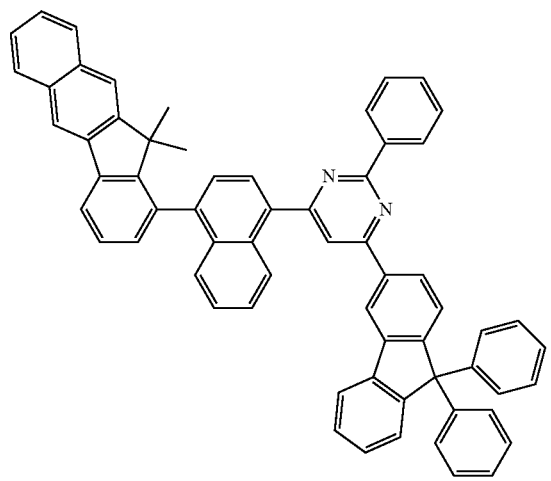
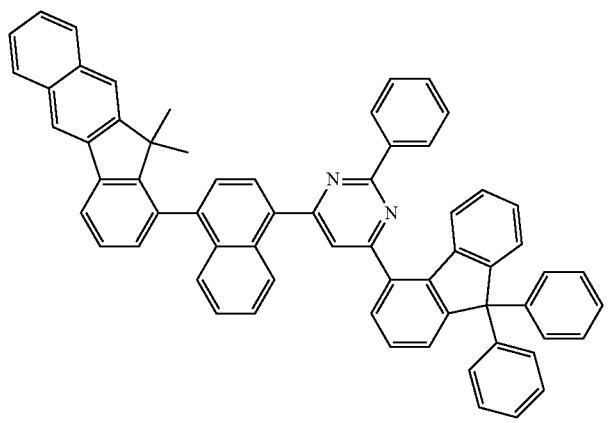
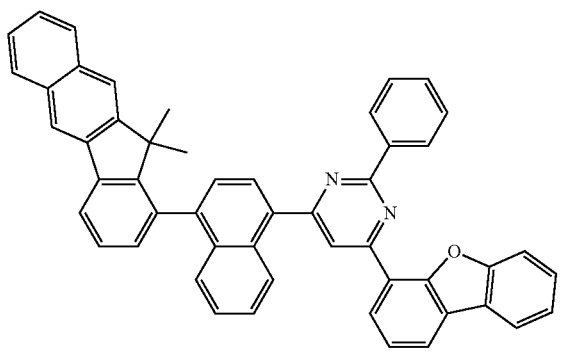
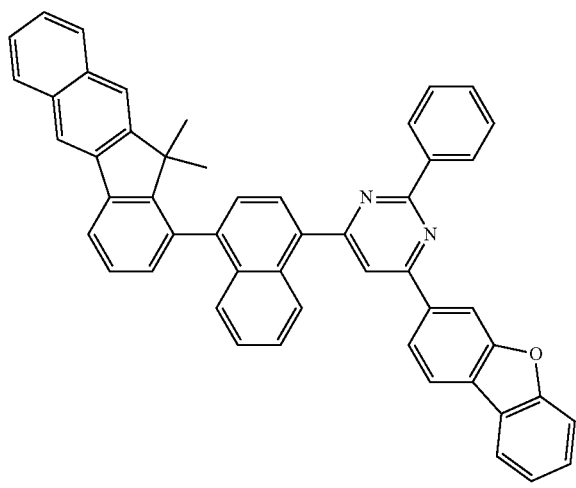
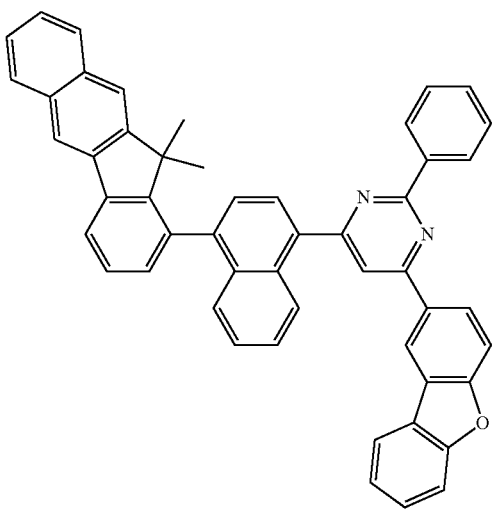

| 547 | 548 |
|---|---|
| 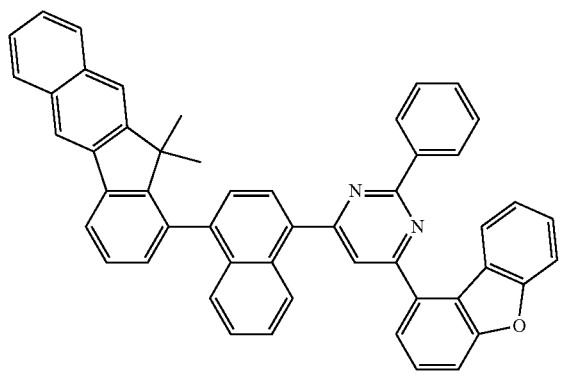 | 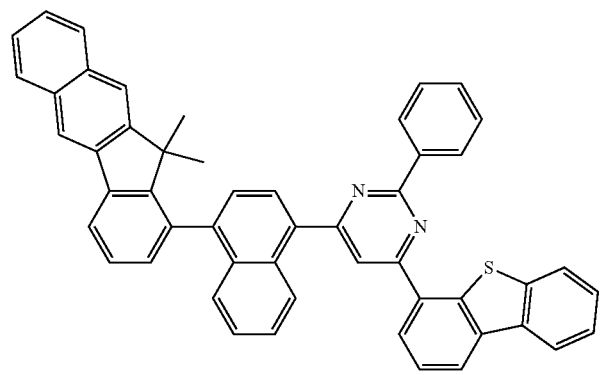 |
| 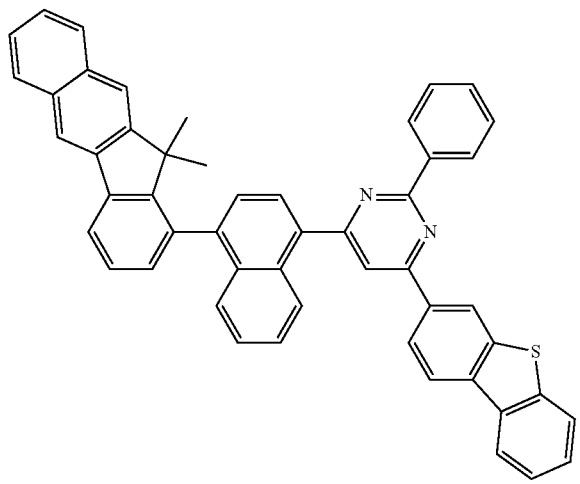 | 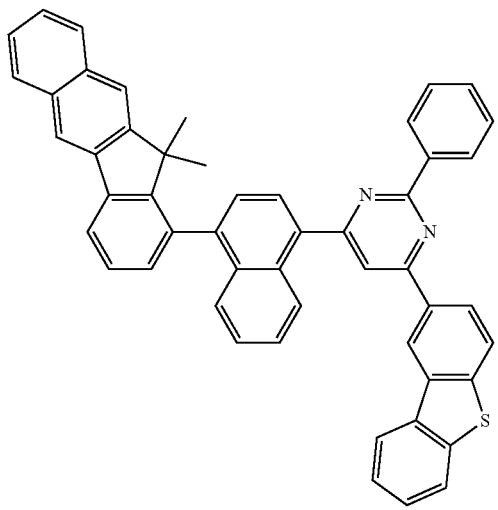 |
| 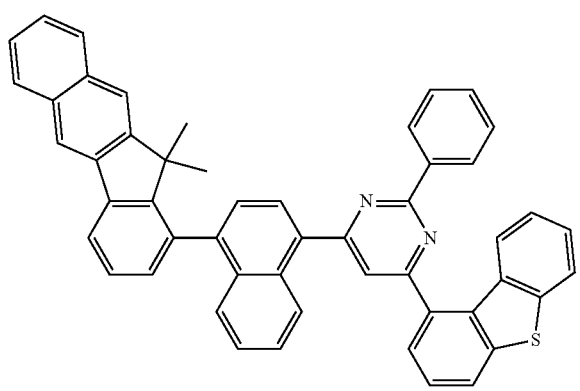 | 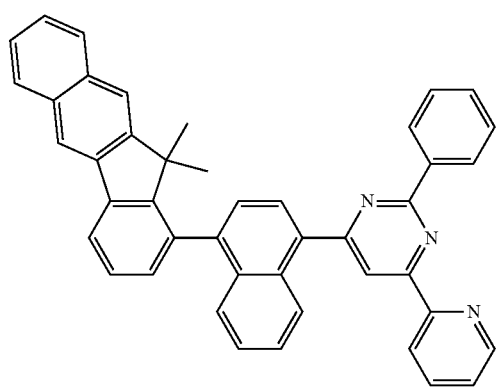 |
| 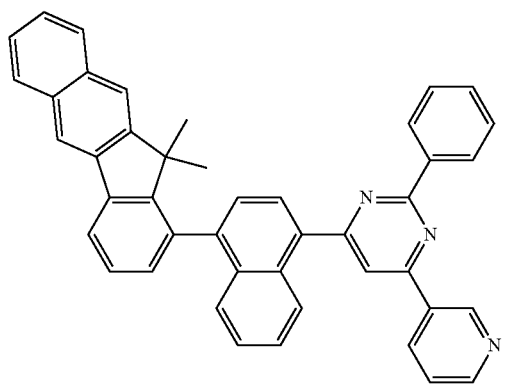 | 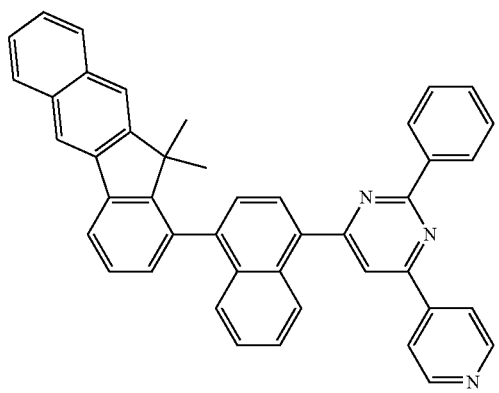 |

549
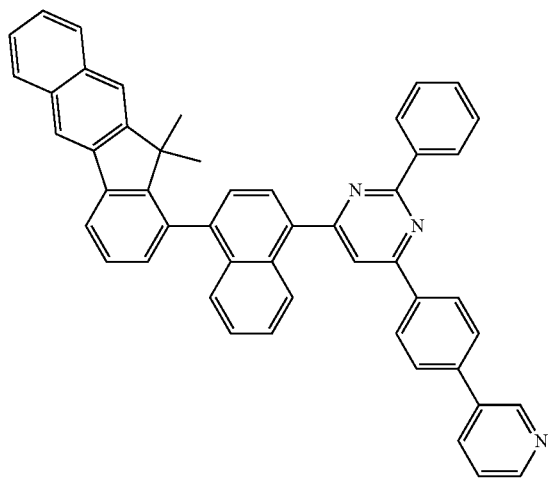
550
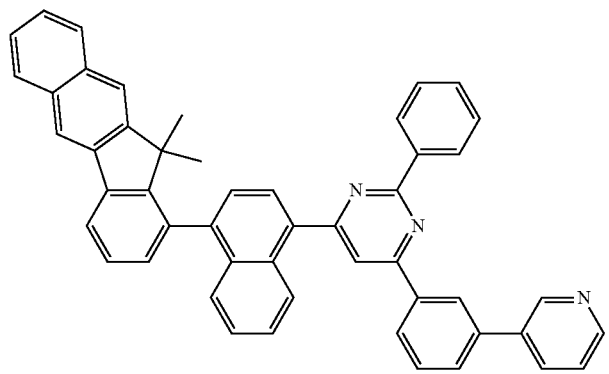
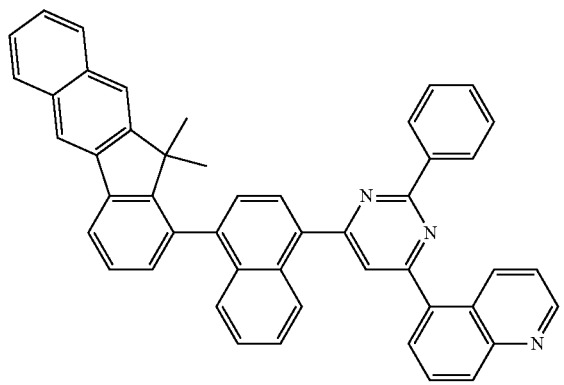
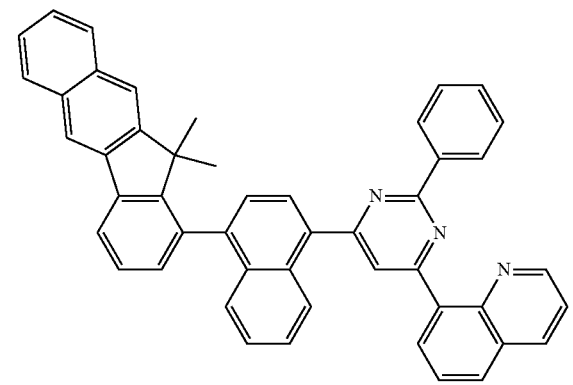
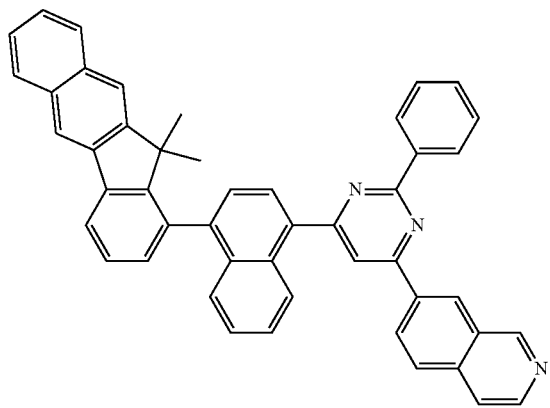
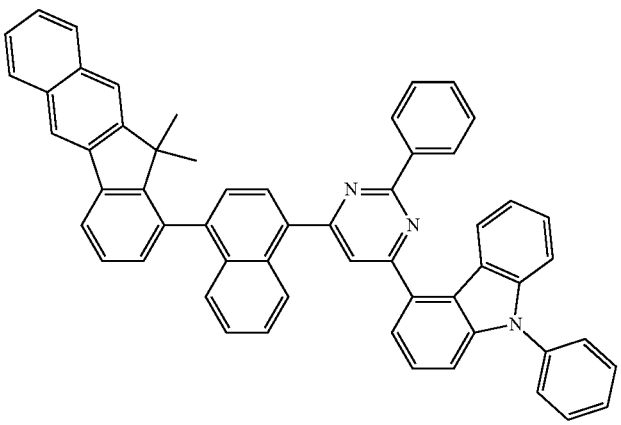

551
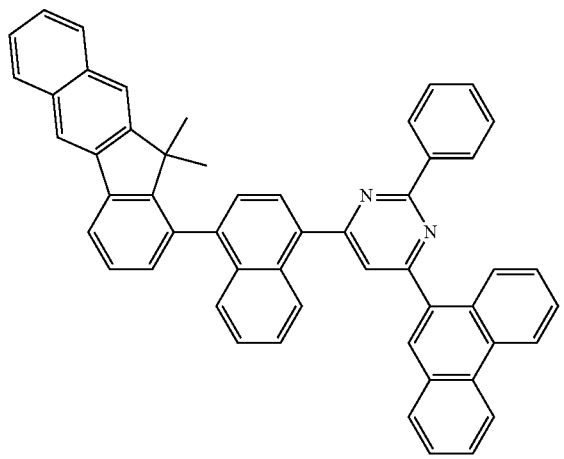
552
-continued
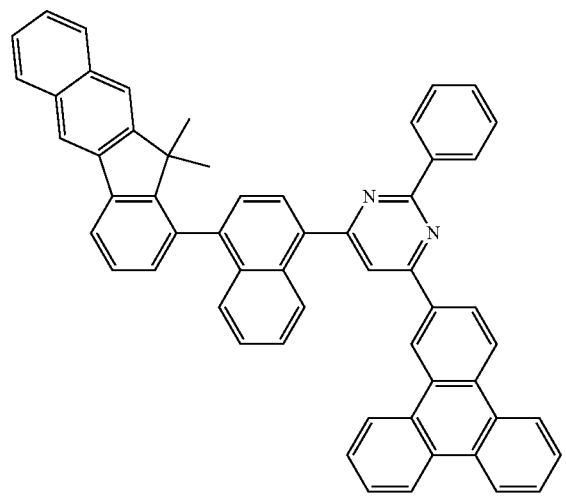
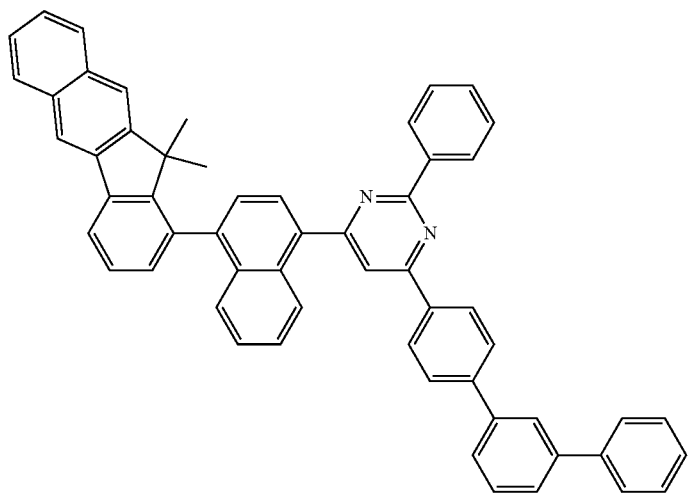
-continued
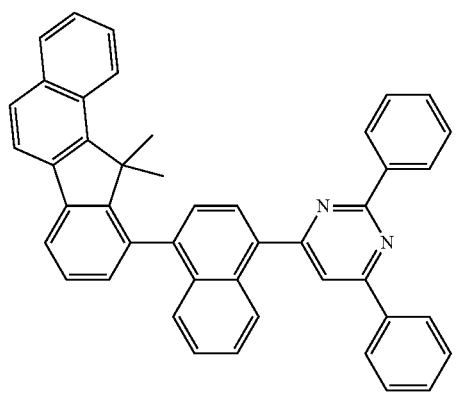
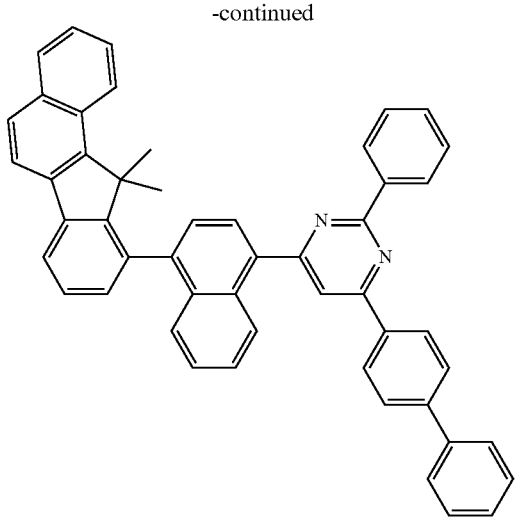

553
-continued
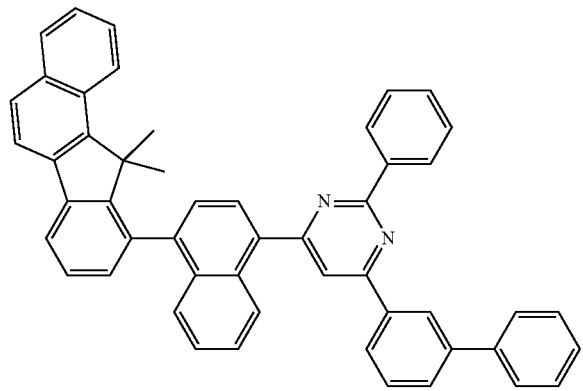
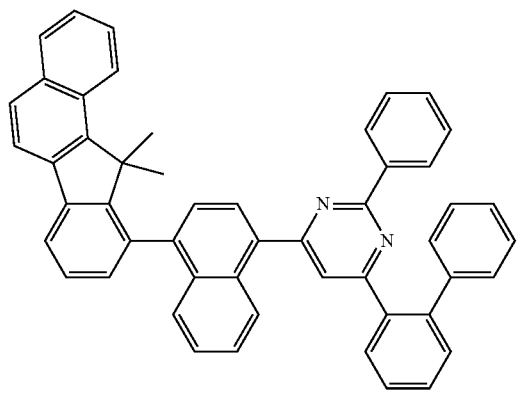
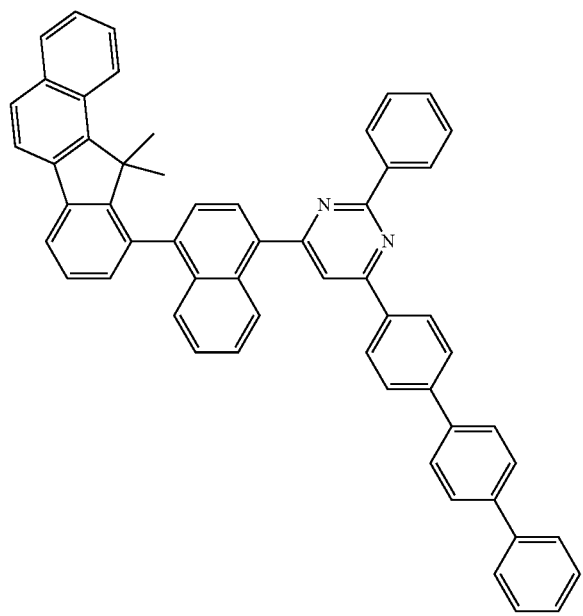
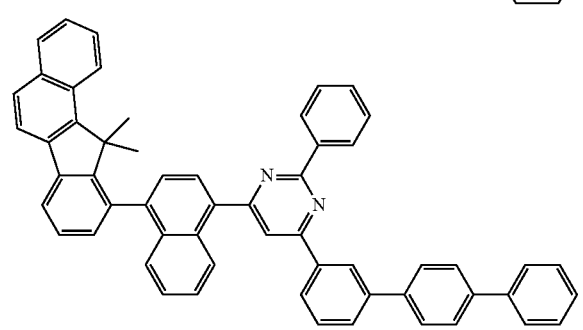
554
-continued
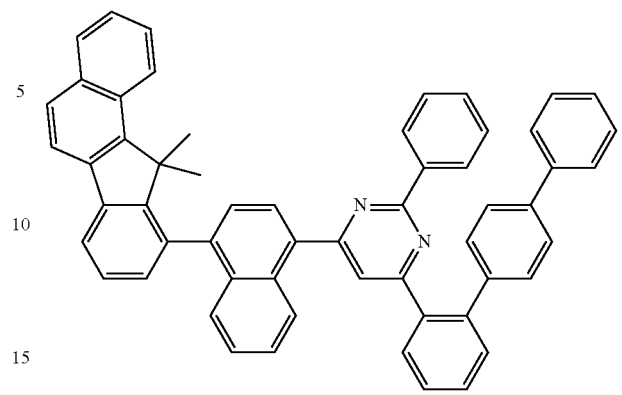
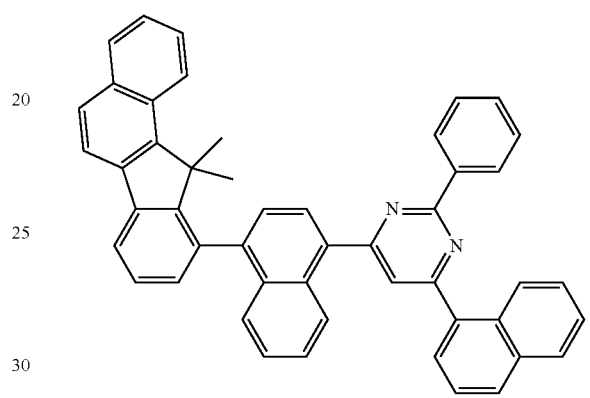
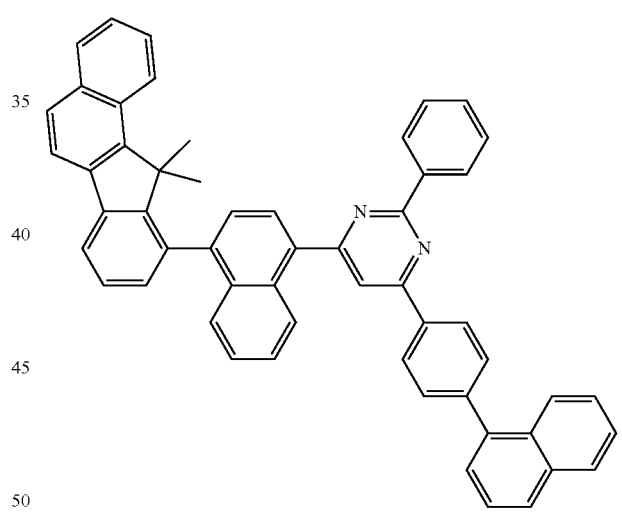
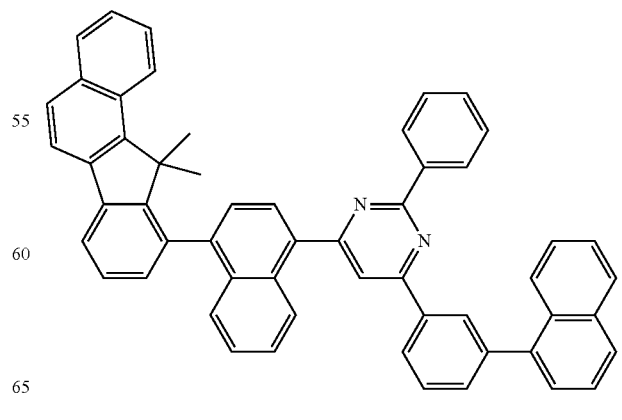

555
-continued
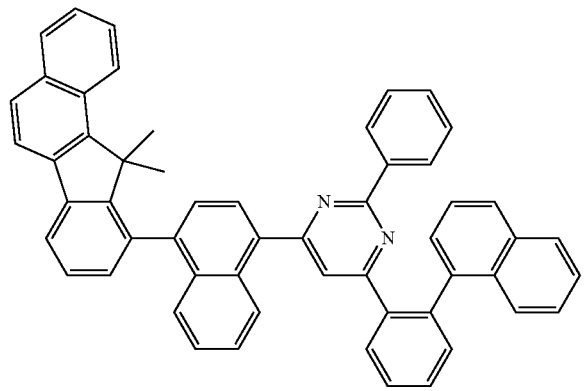
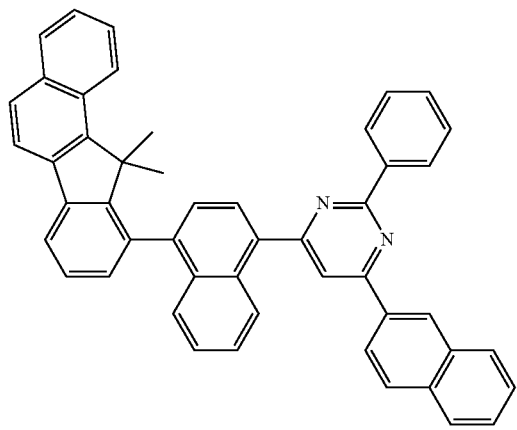
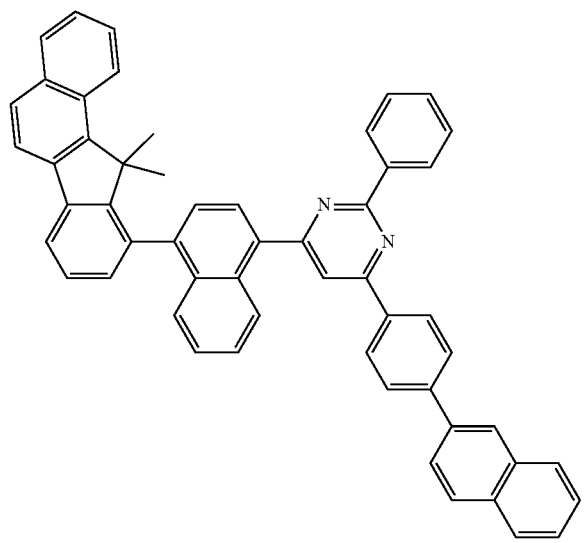
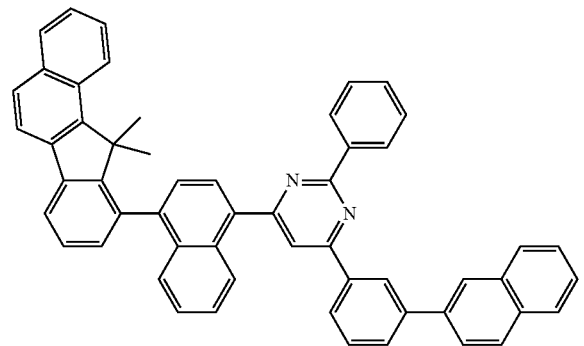
556
-continued
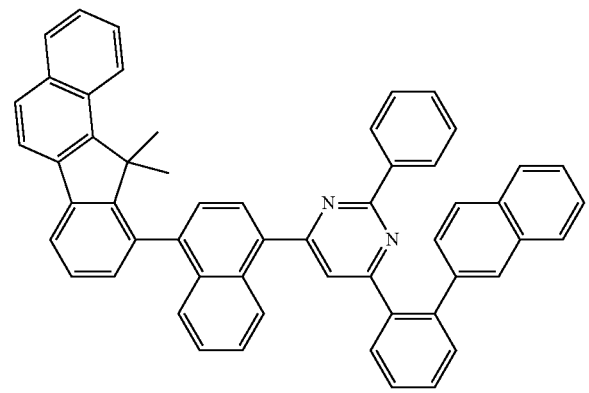
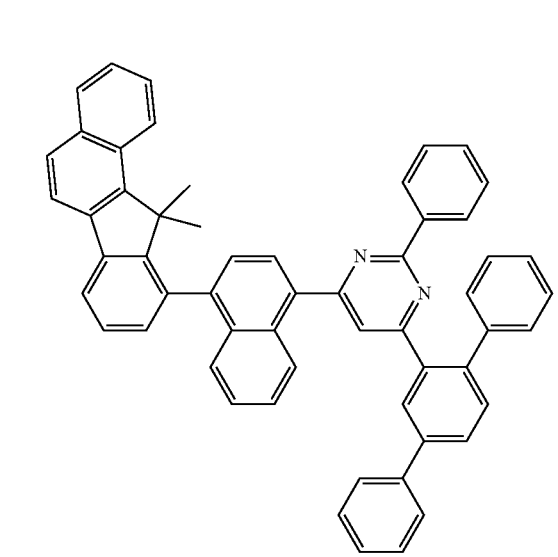
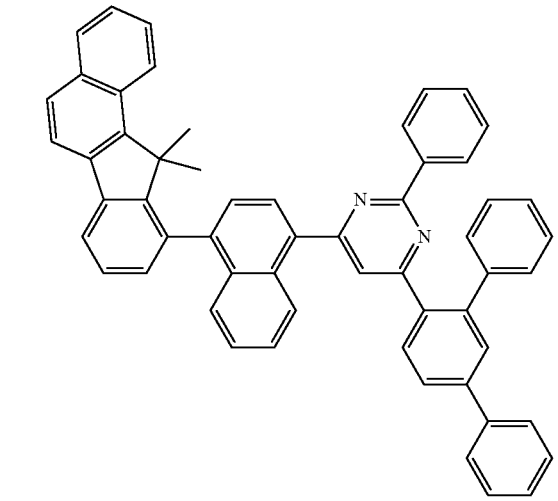

557
-continued
558
-continued
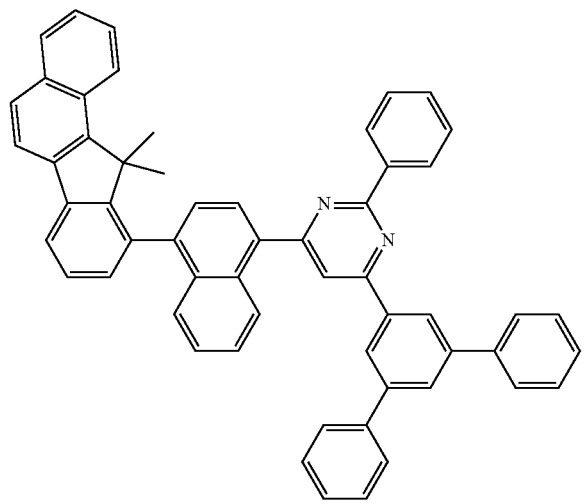
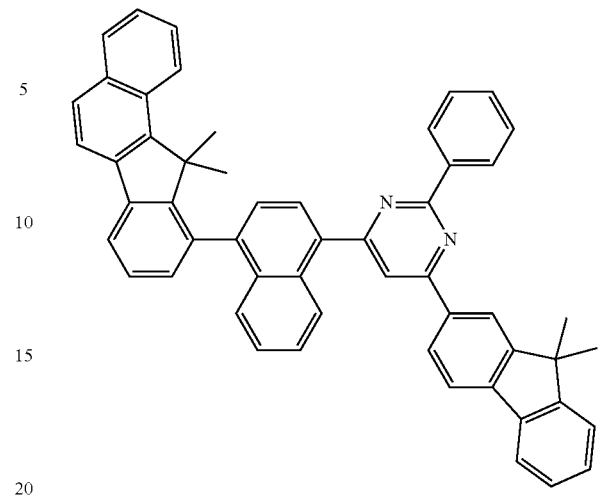
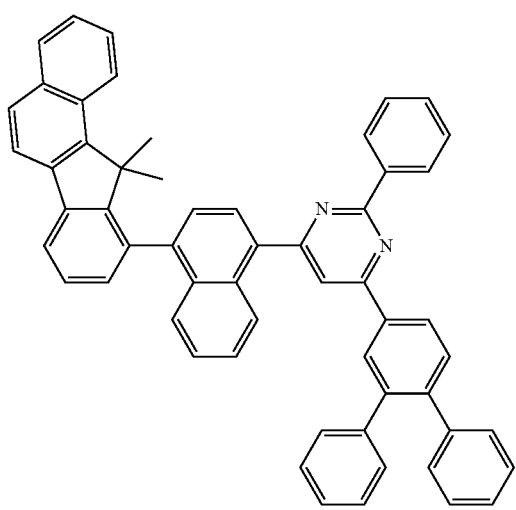
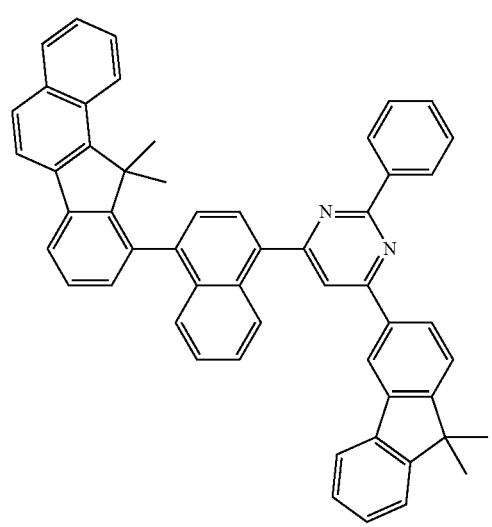
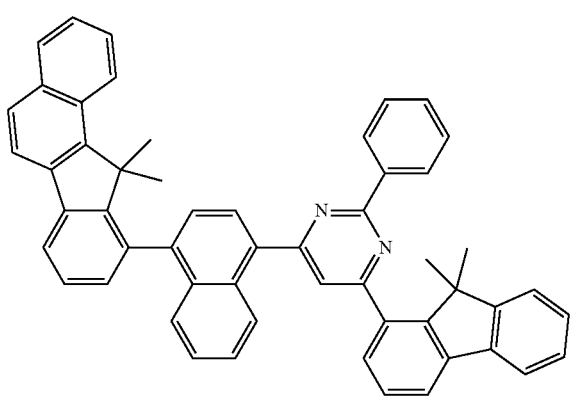
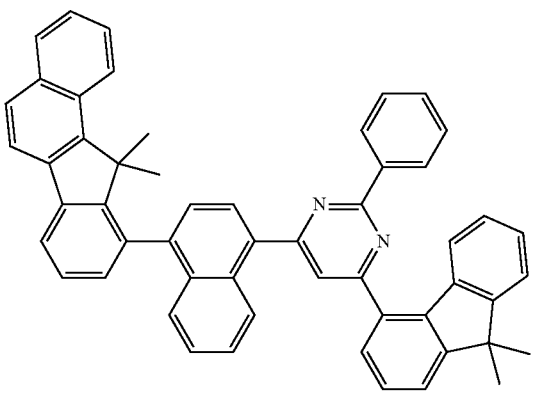

559
-continued
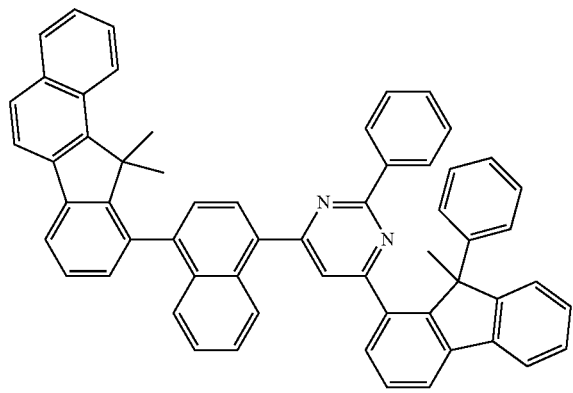
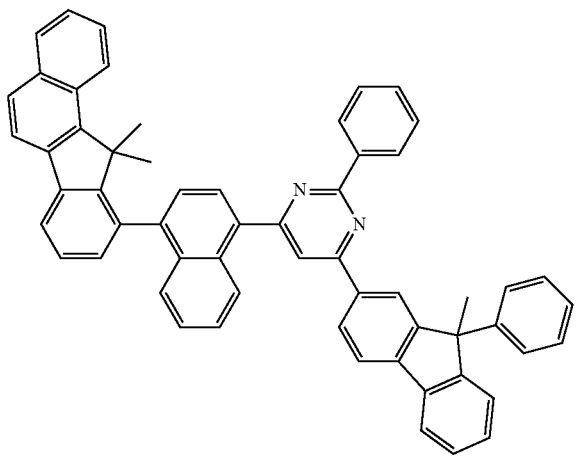
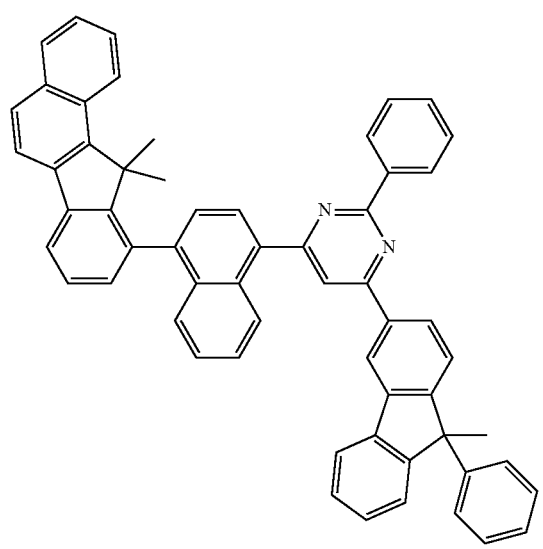
560
-continued
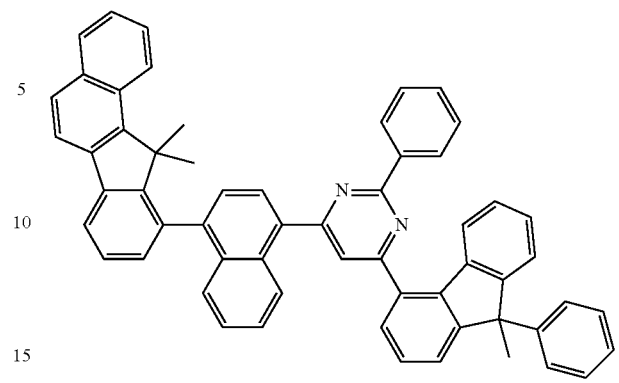
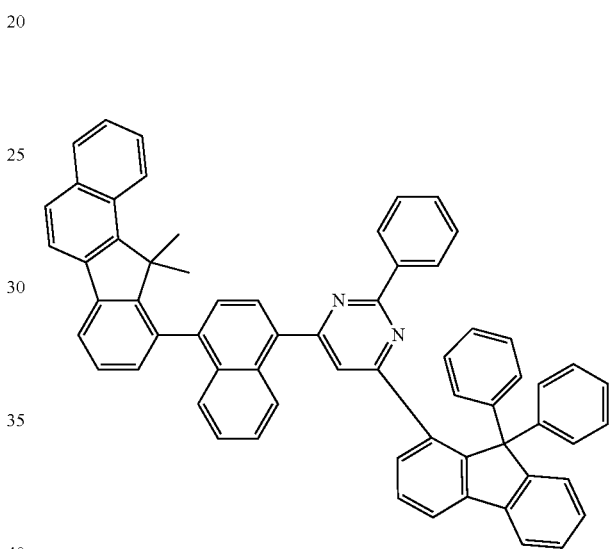

561
-continued
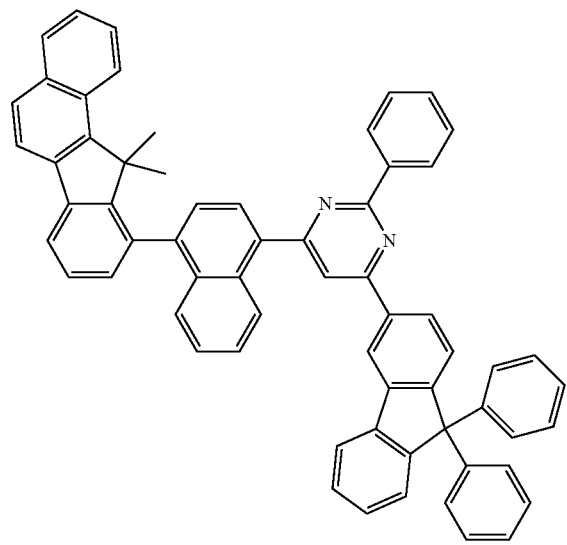
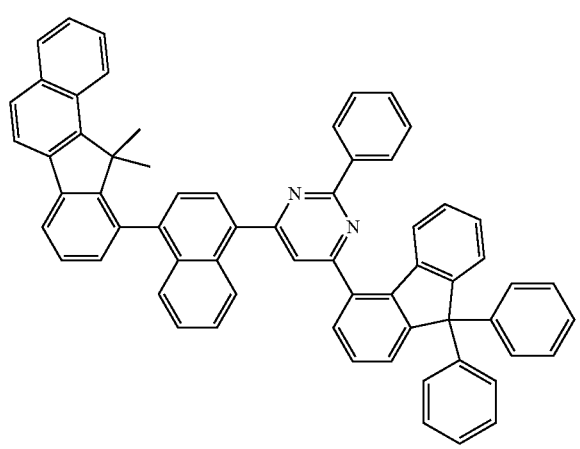
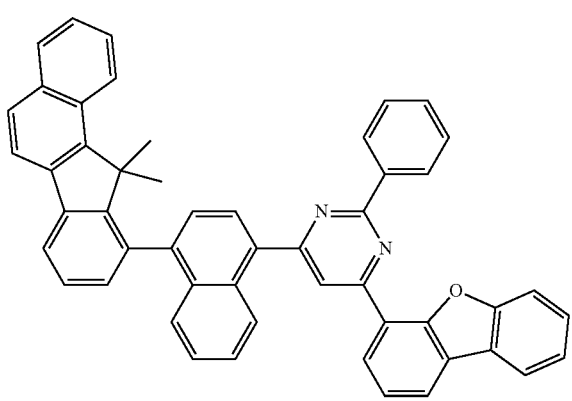
562
-continued
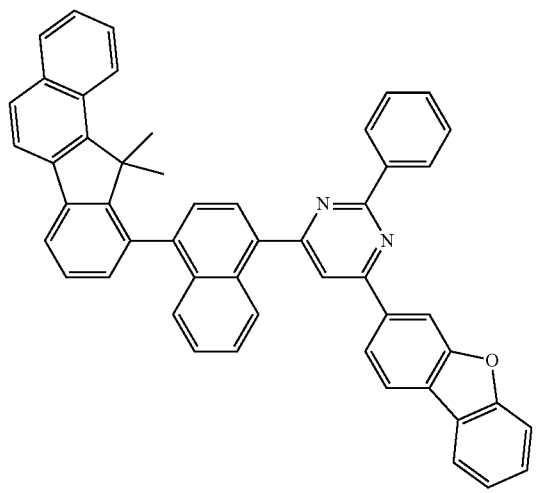
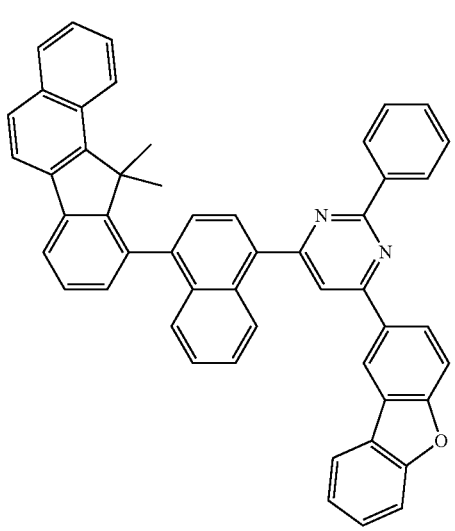
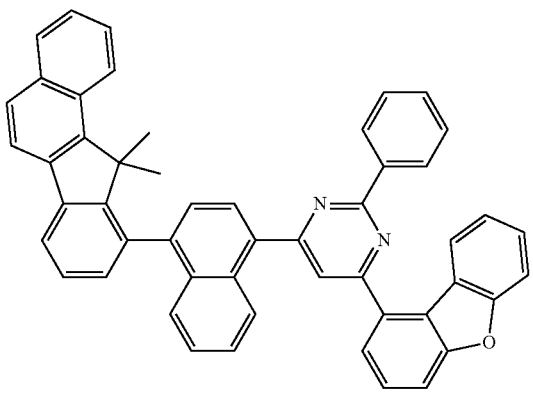

563
-continued
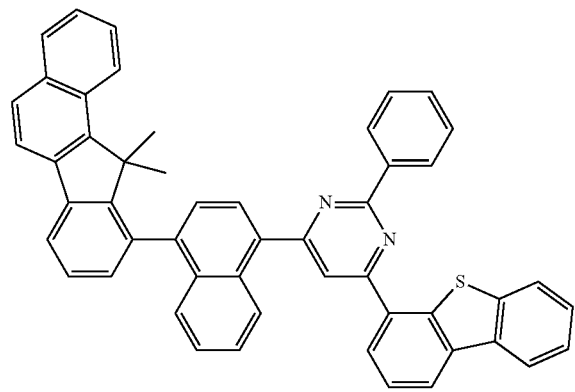
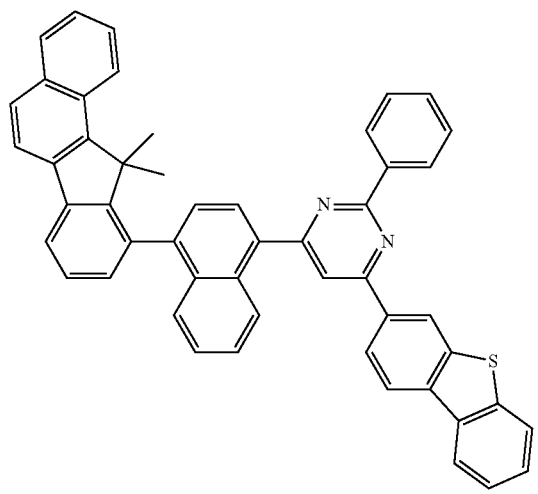
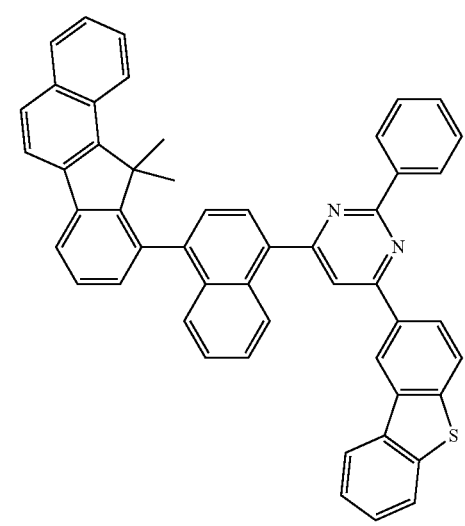
564
-continued
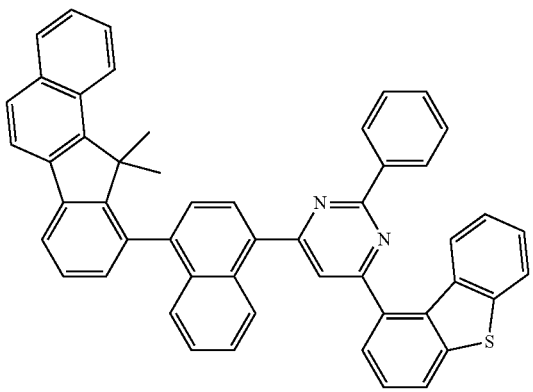
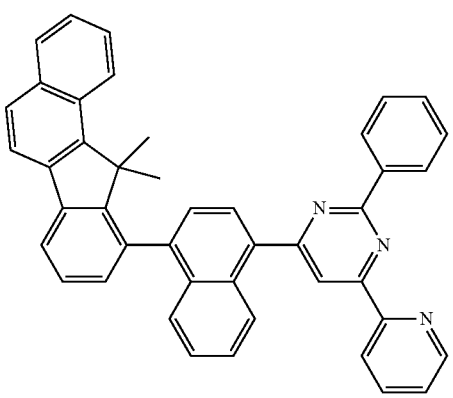
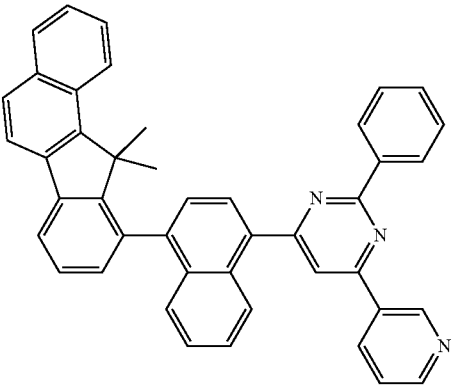
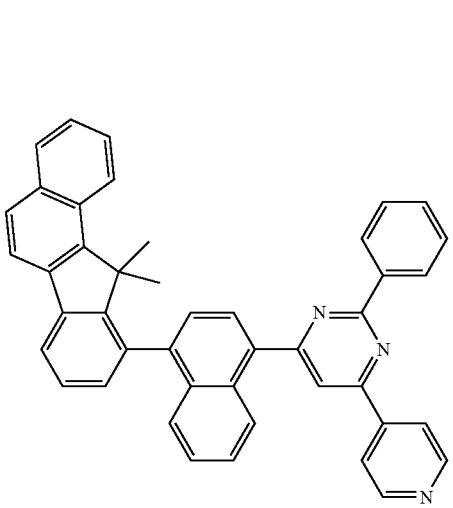

565
-continued
566
-continued
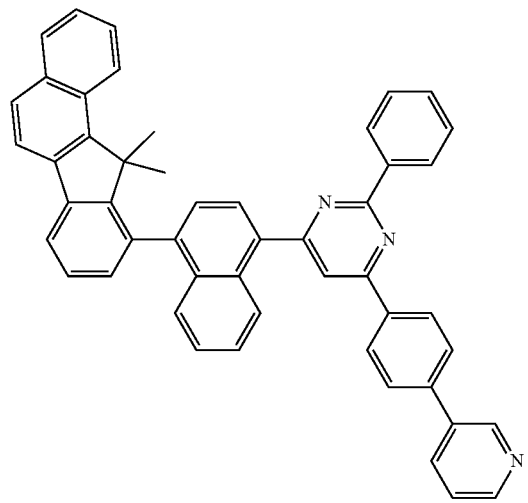
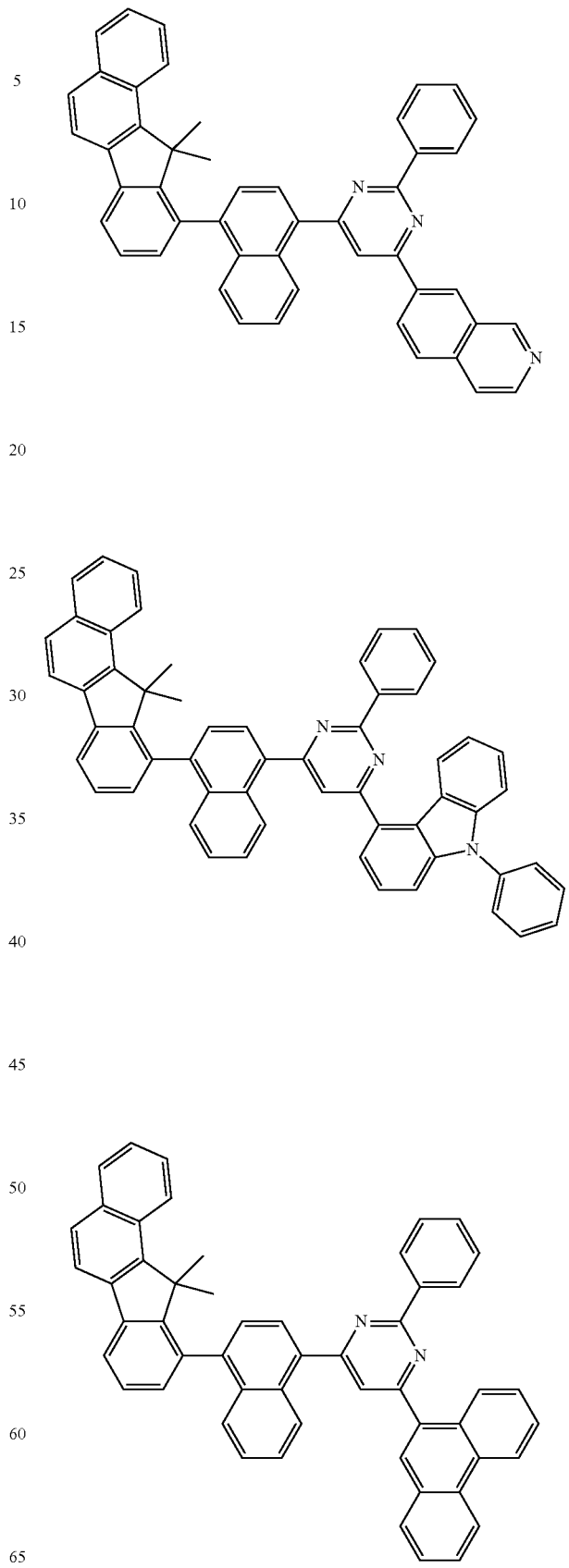

567
-continued
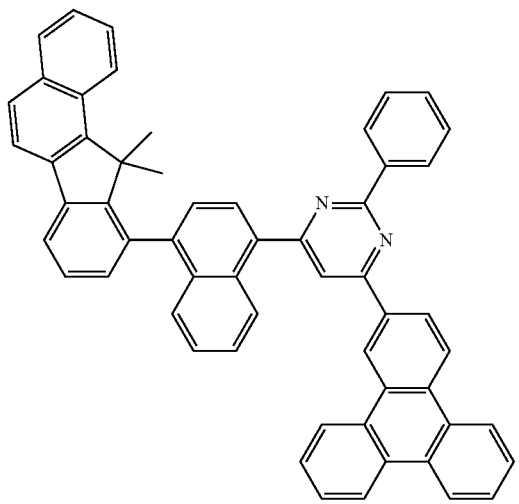
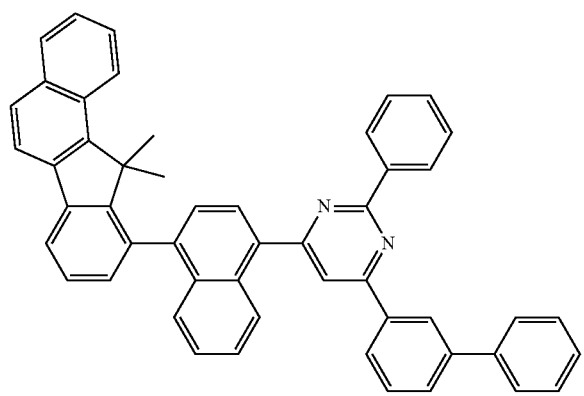
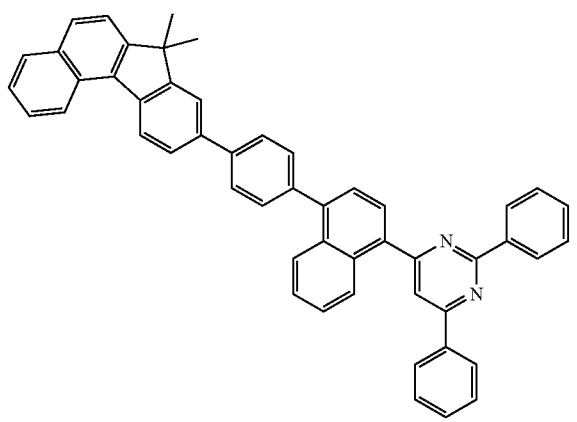
568
-continued
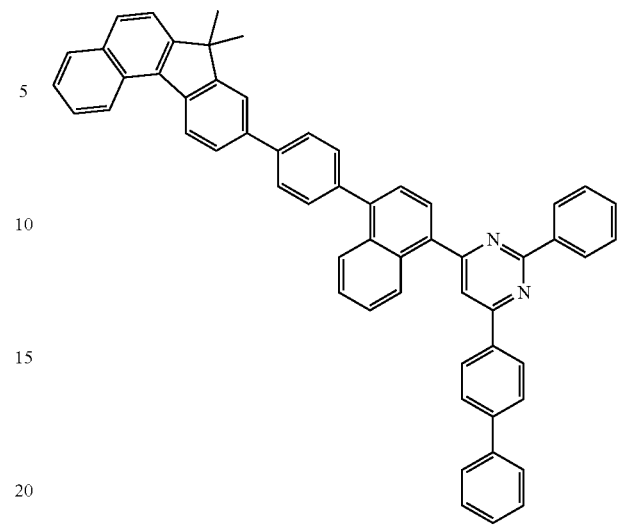
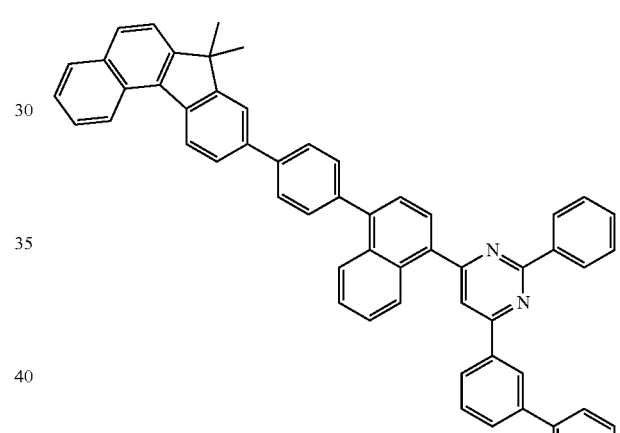
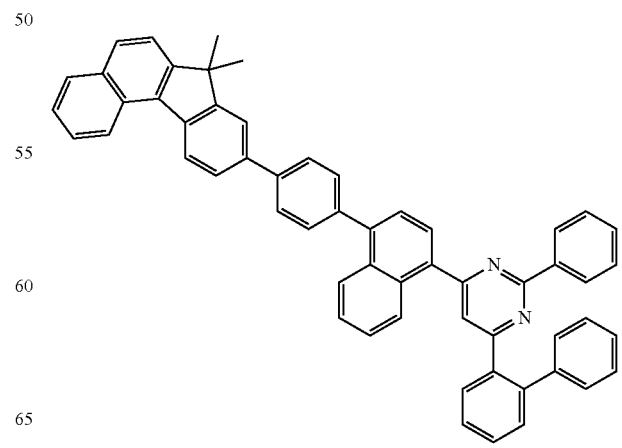

569
-continued
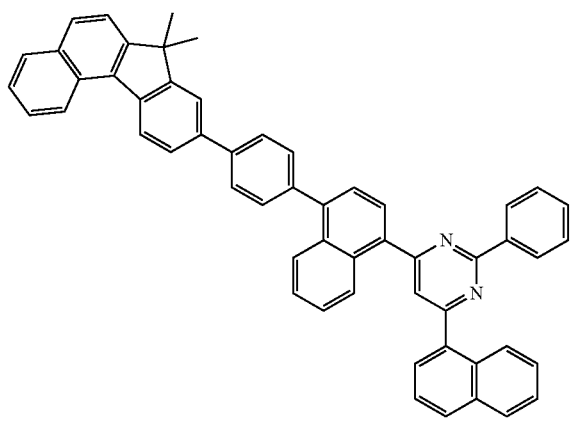
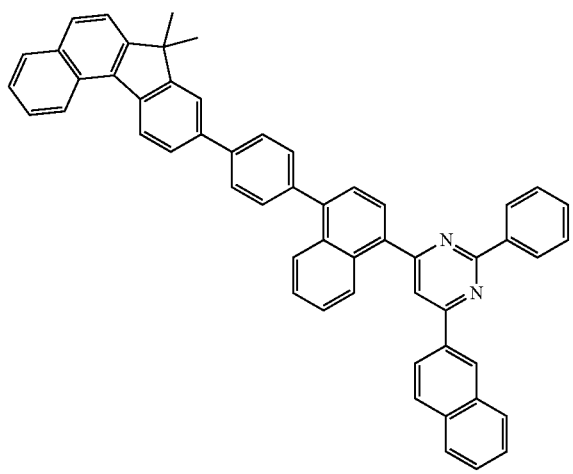
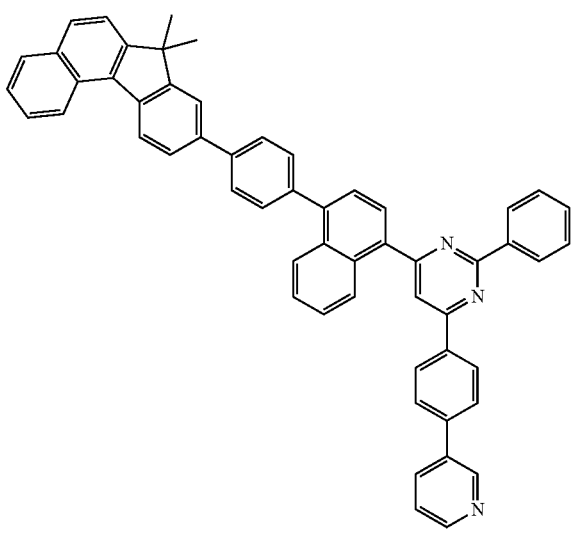
570
-continued
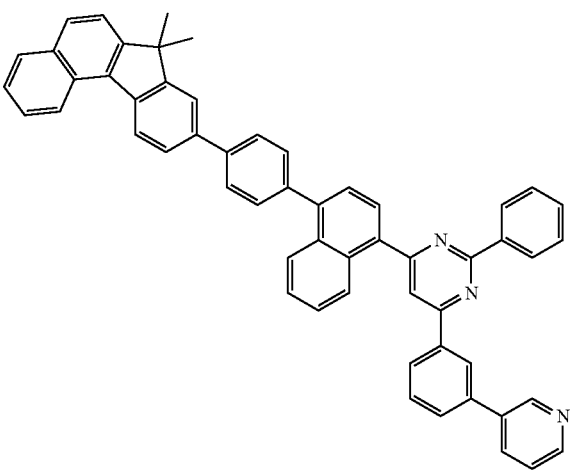
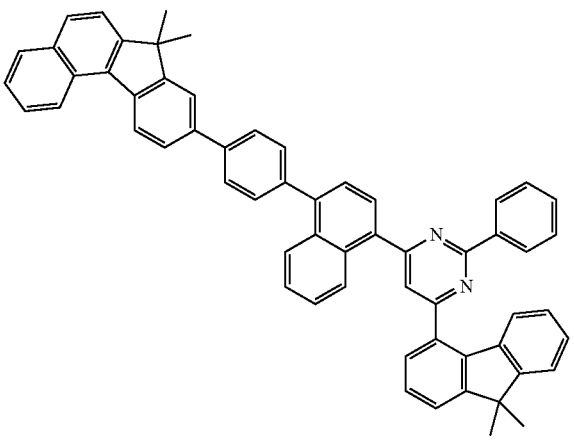
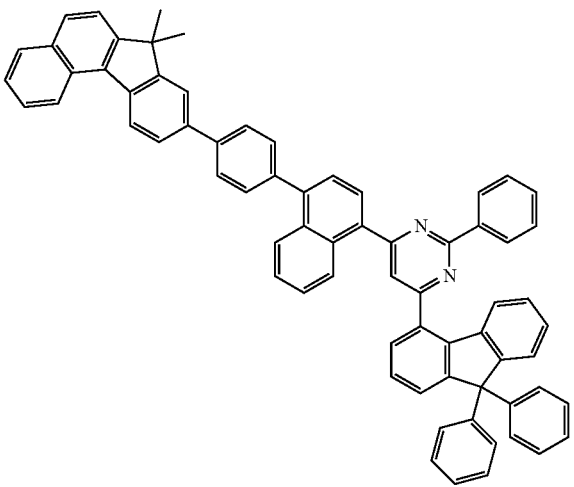

571
-continued
572
-continued
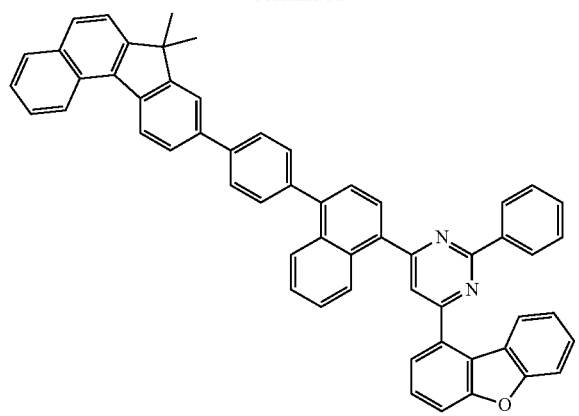
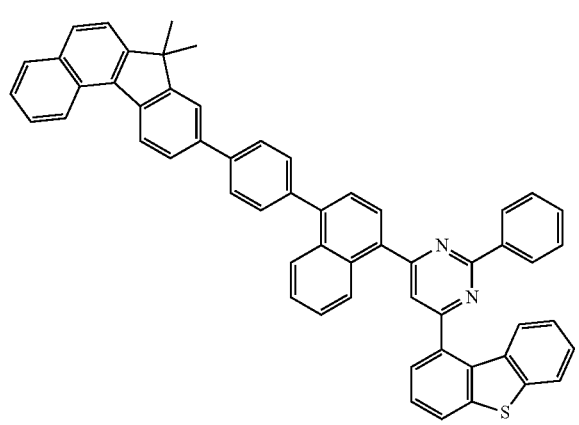
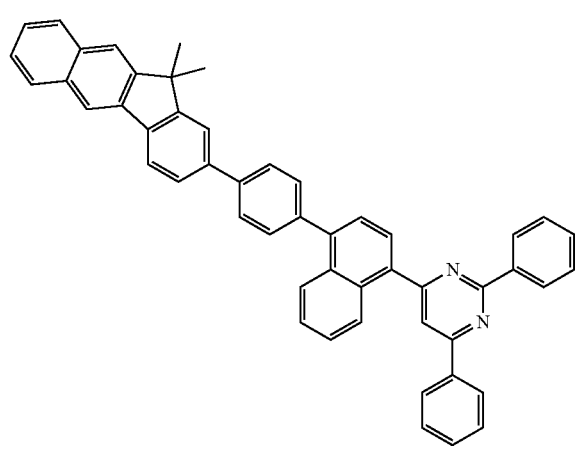
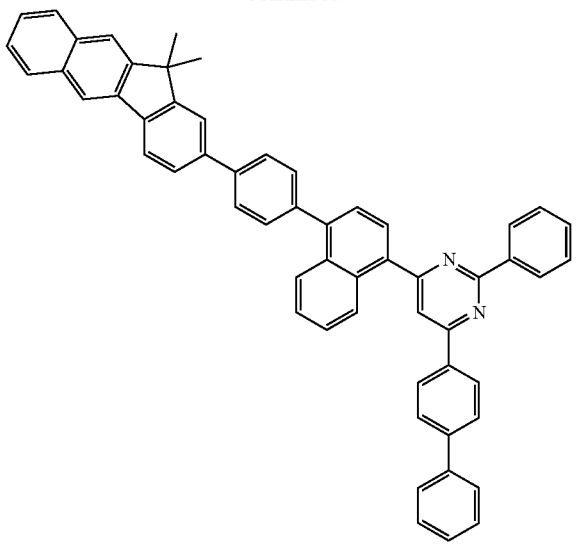
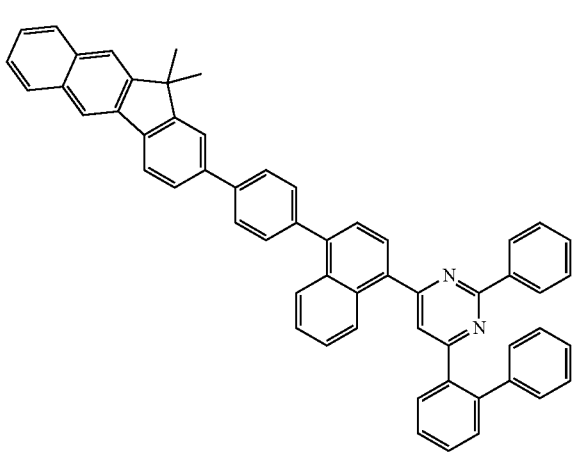

573
-continued
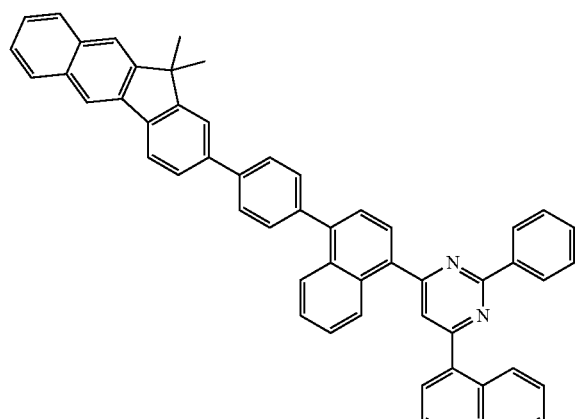
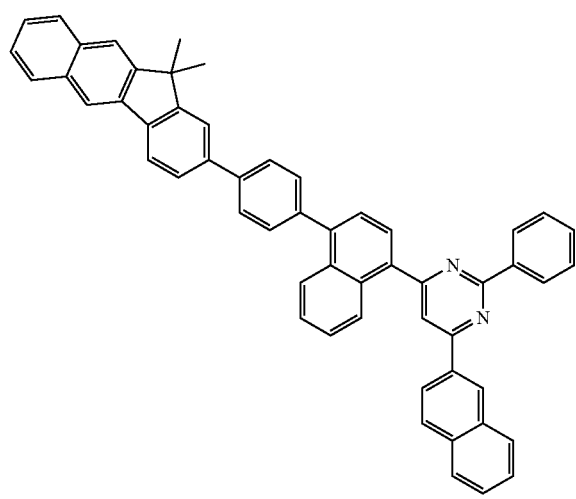
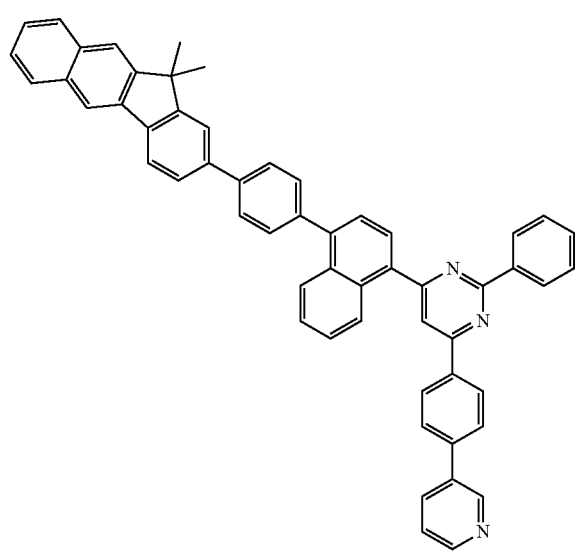
574
-continued
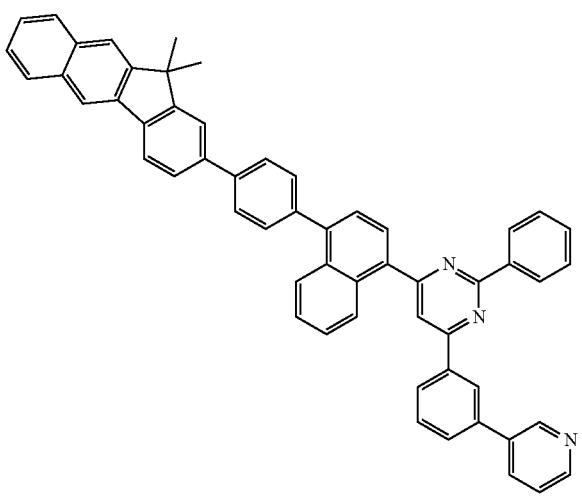
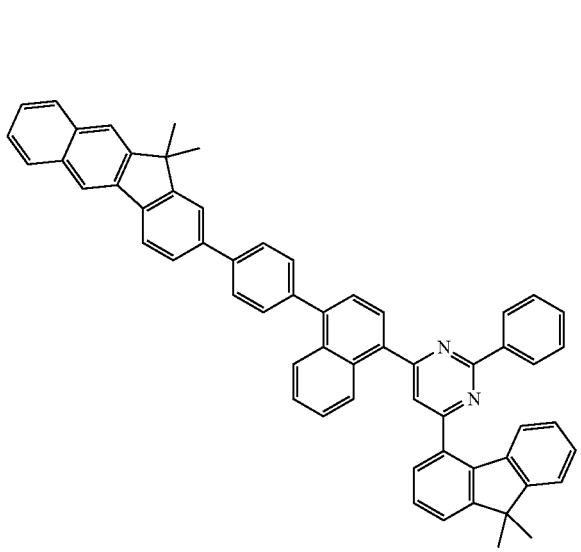
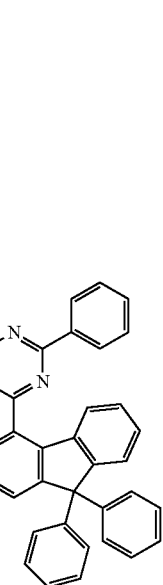

575
-continued
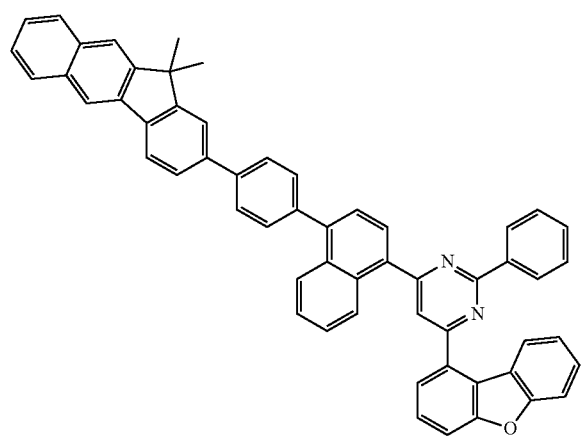
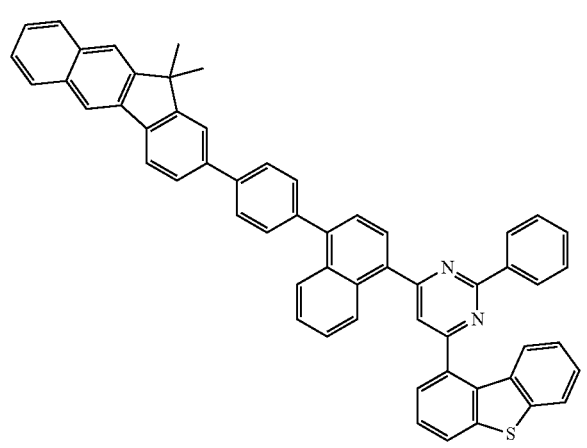
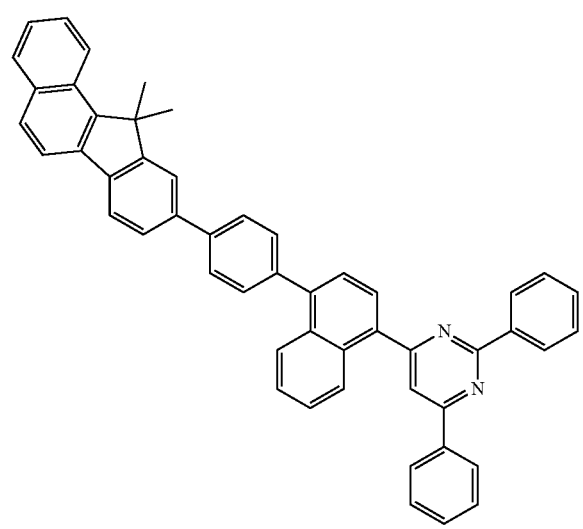
576
-continued
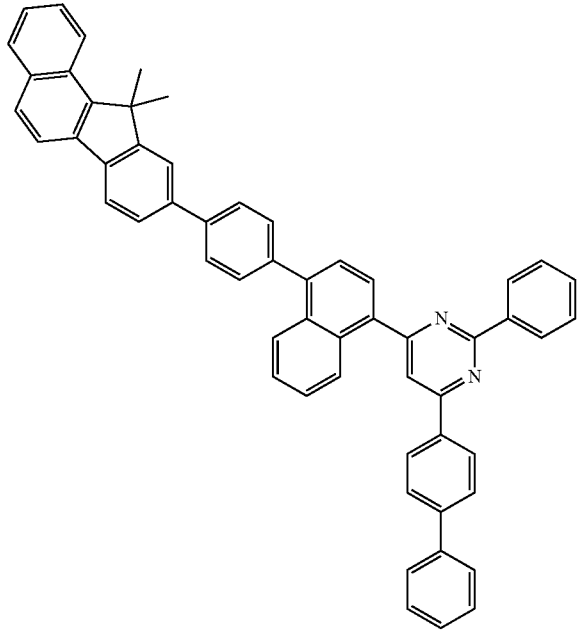
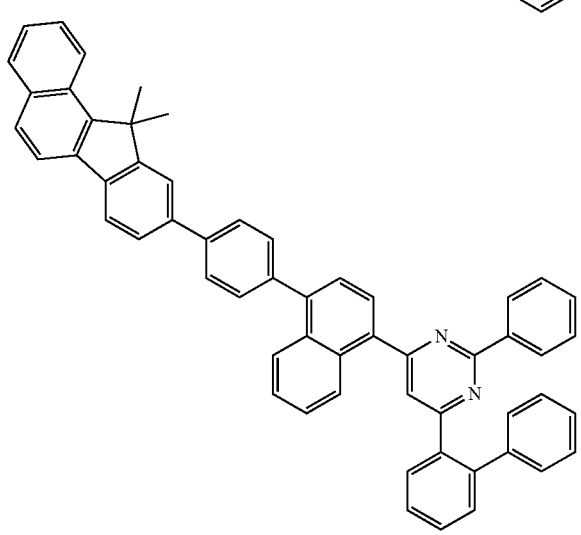

577
-continued
578
-continued
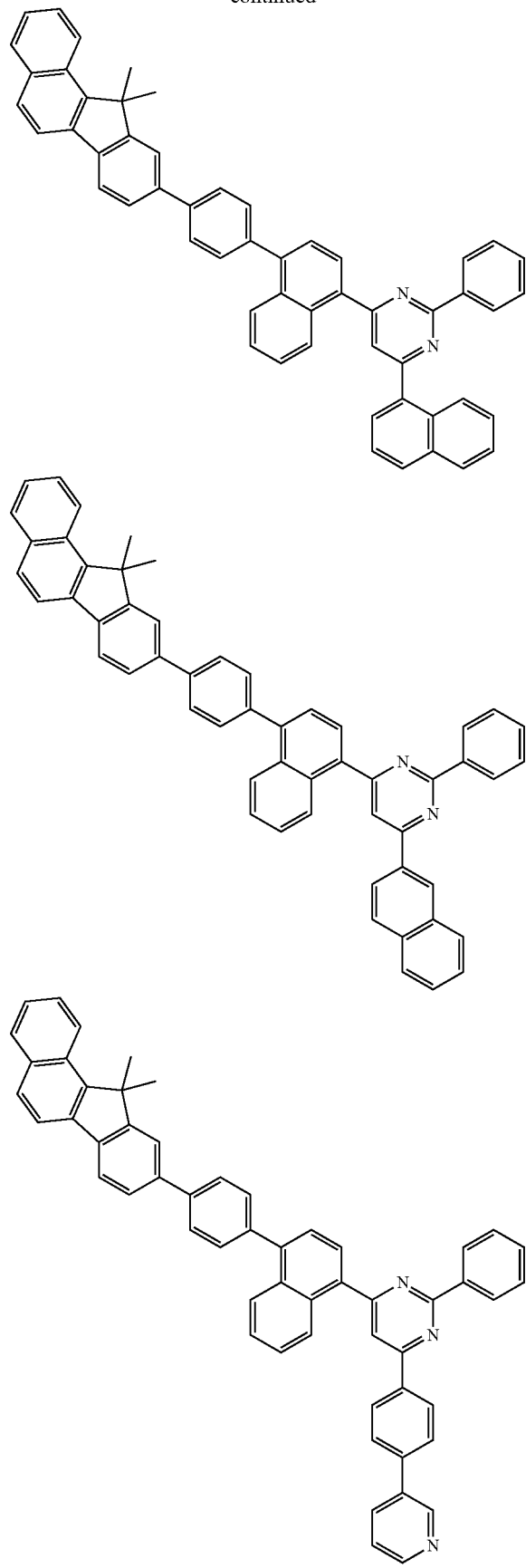
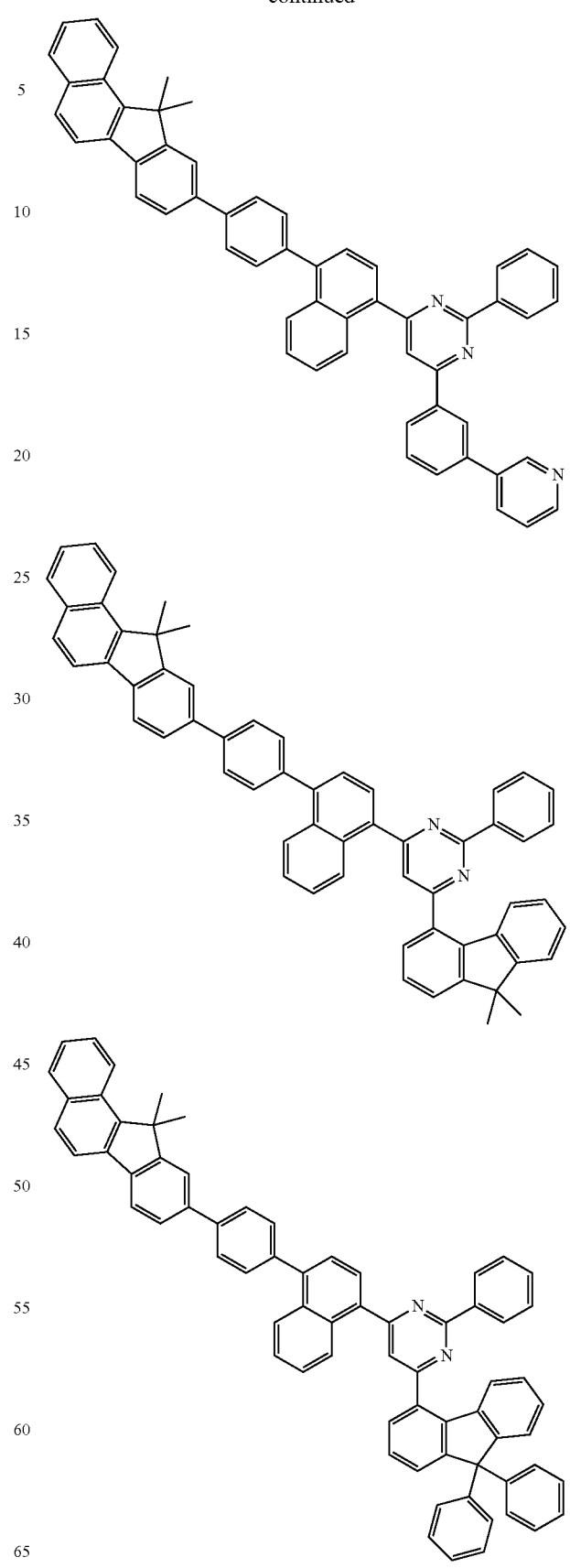

579
-continued
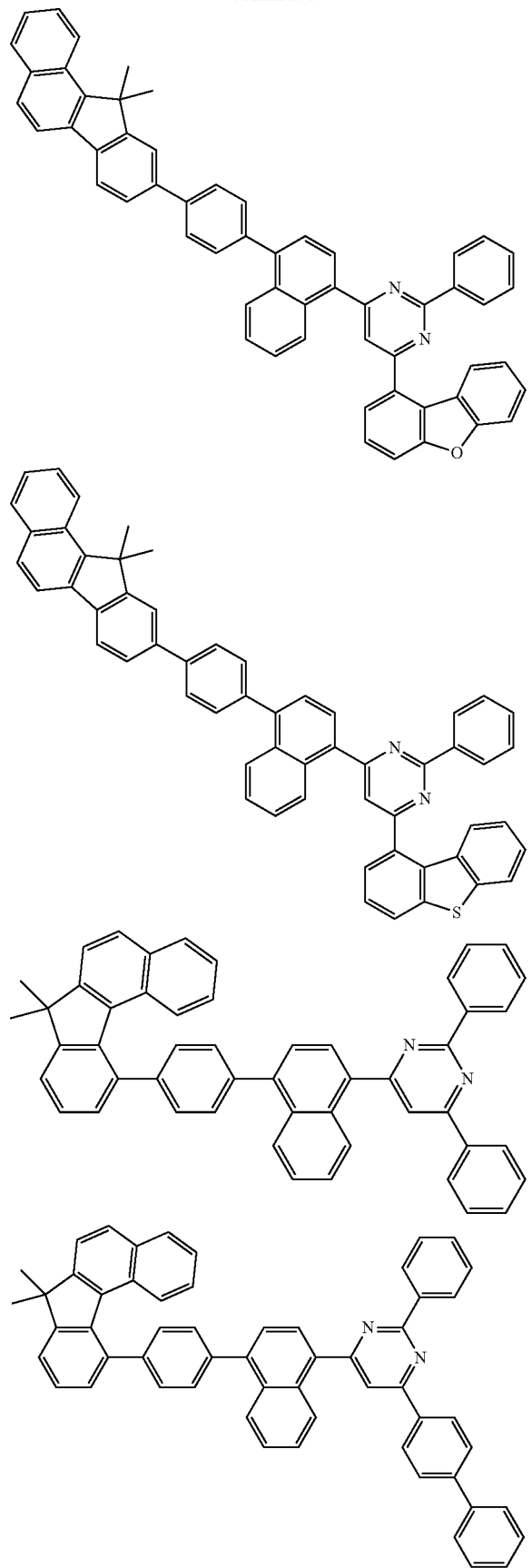
580
-continued
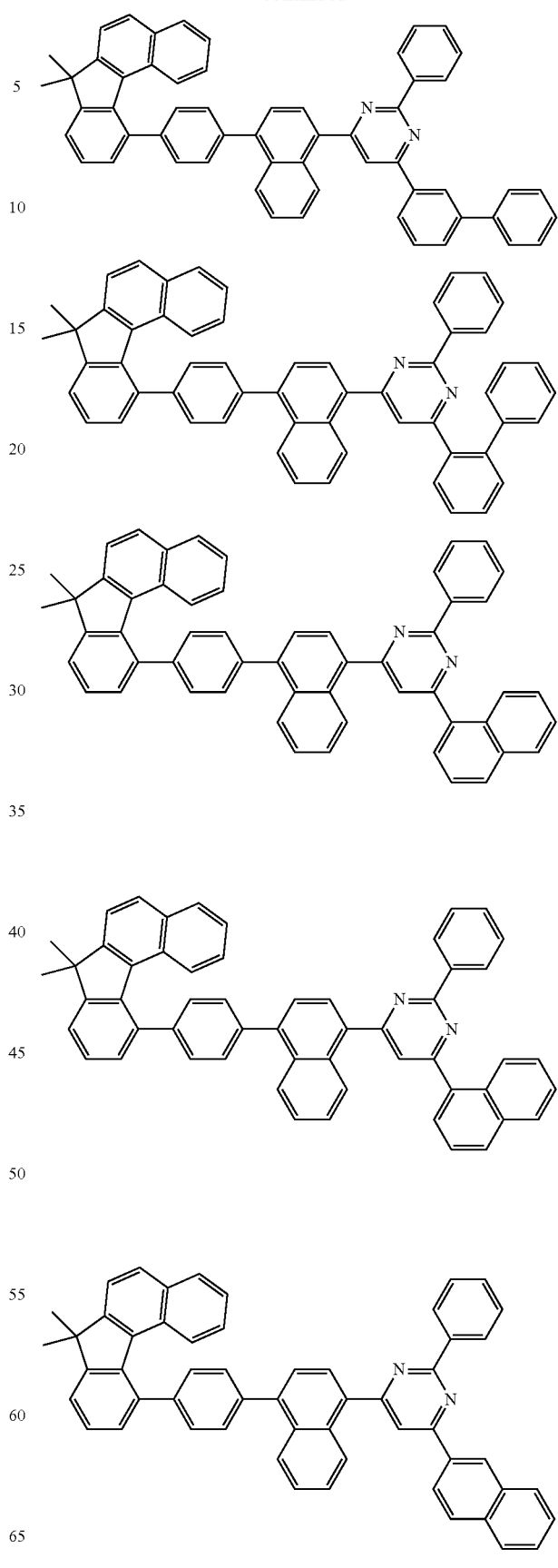

581
-continued
582
-continued
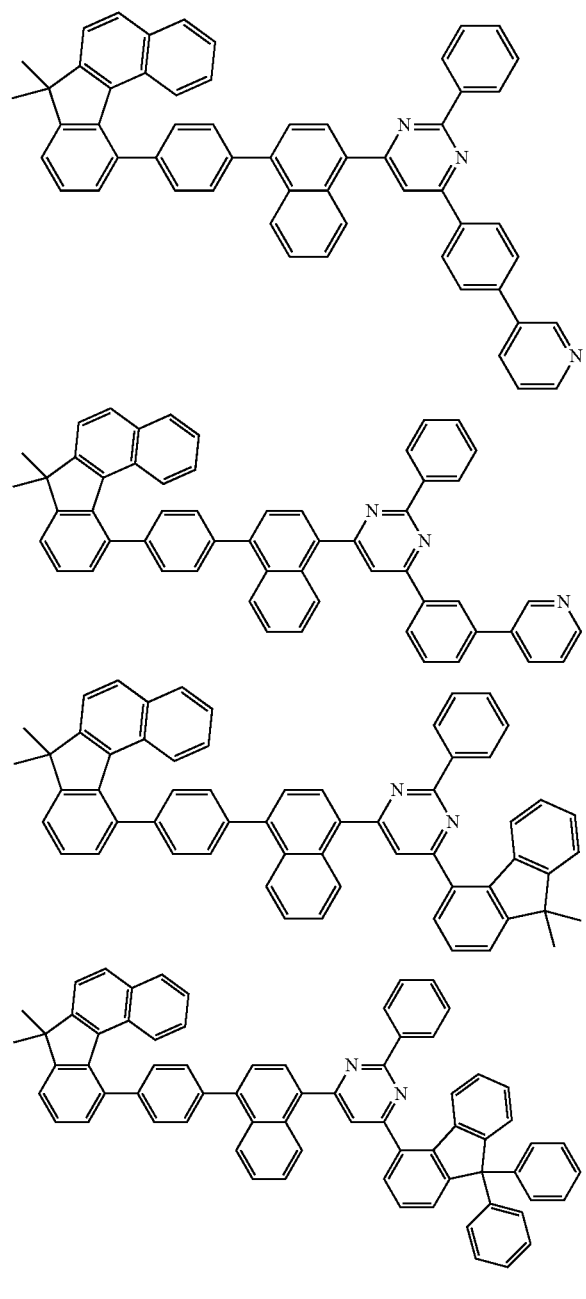
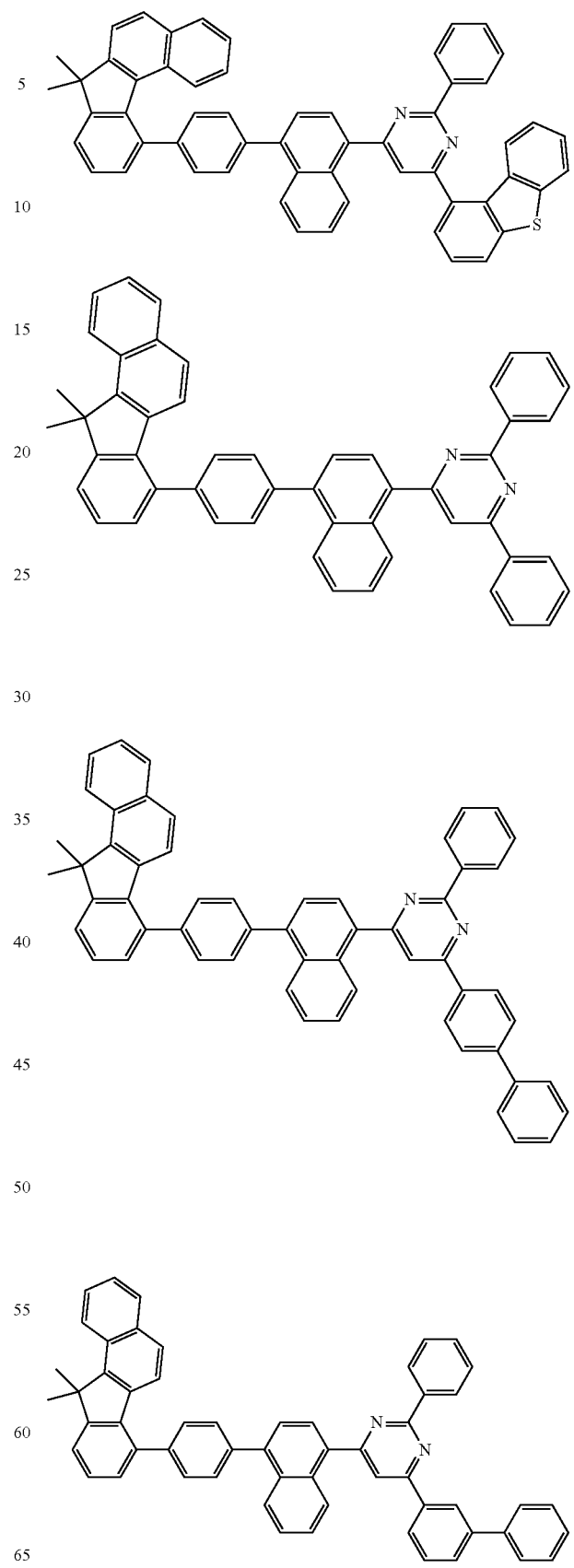

583
-continued
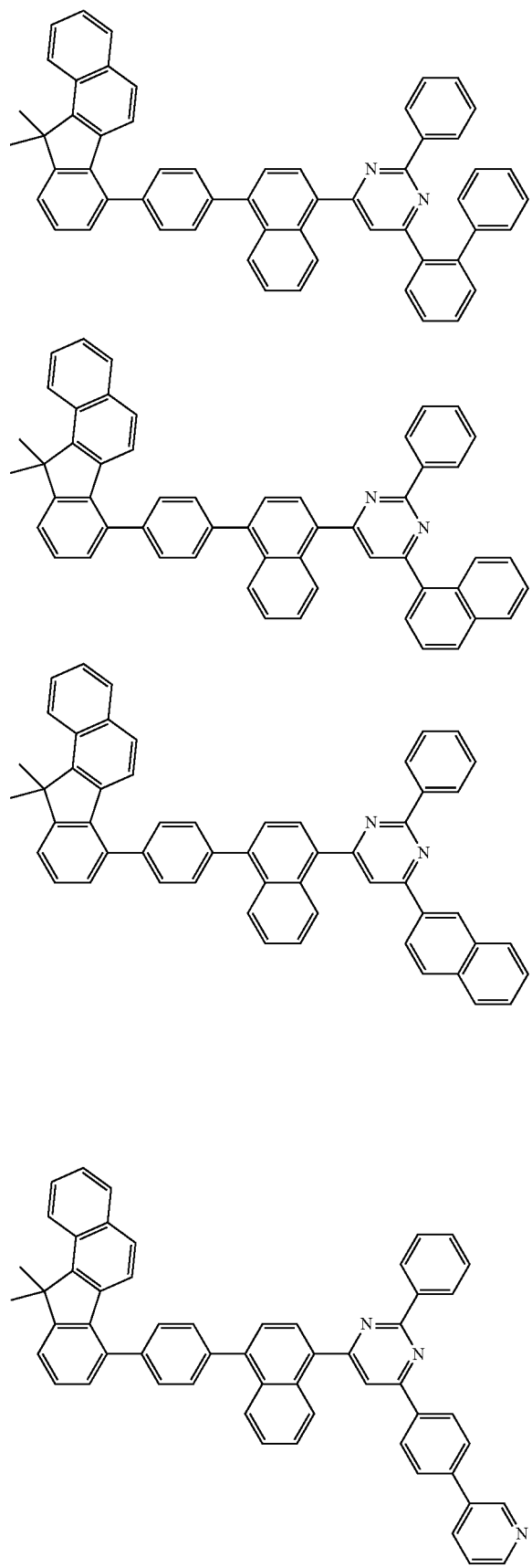
584
-continued
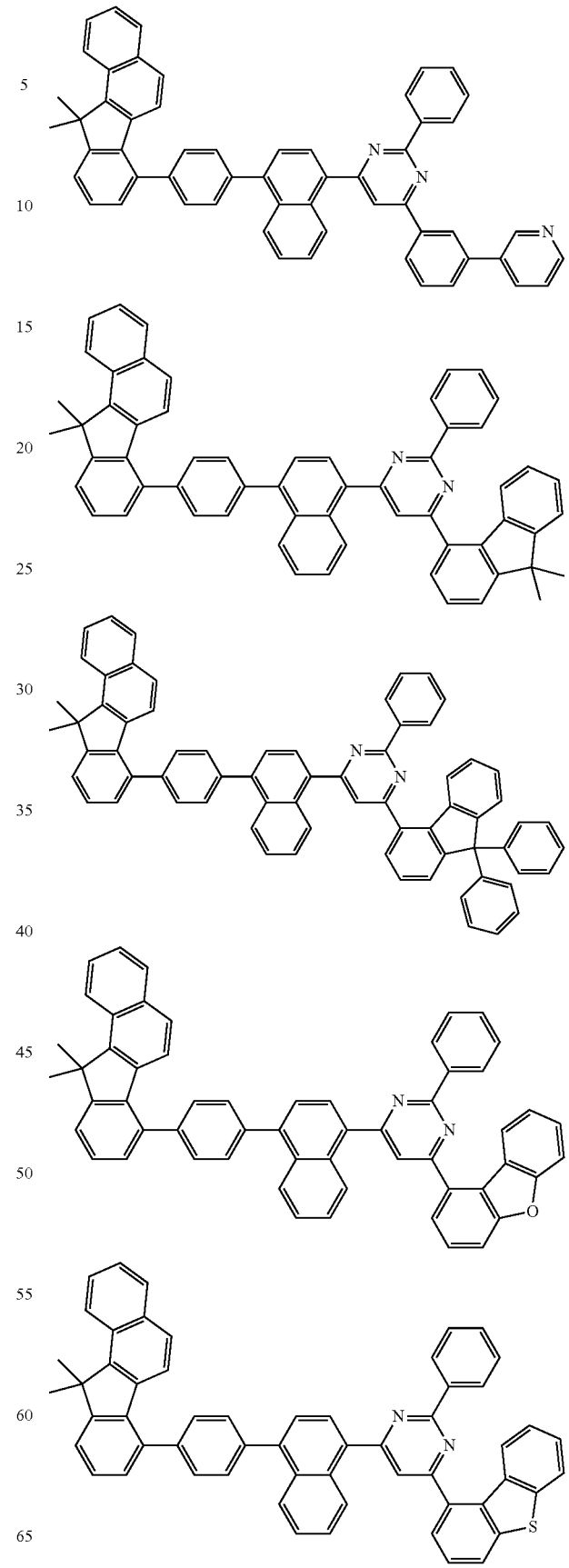

585
-continued
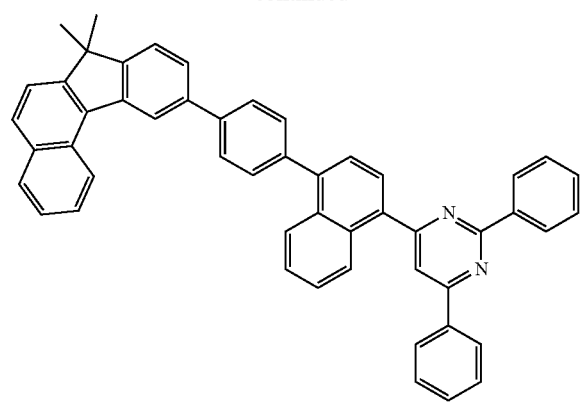
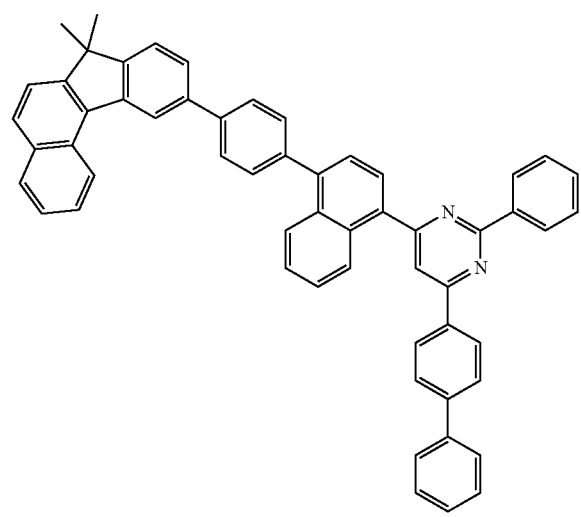
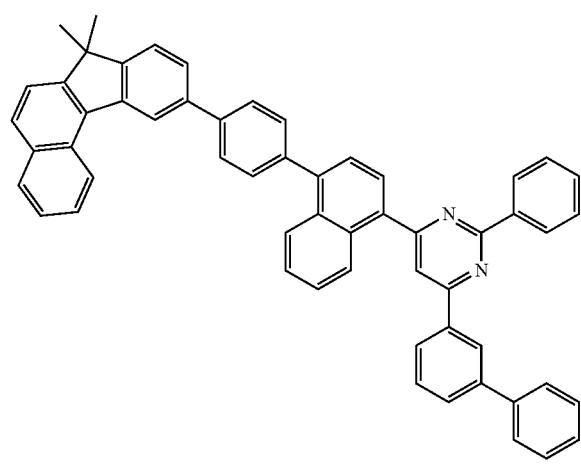
586
-continued
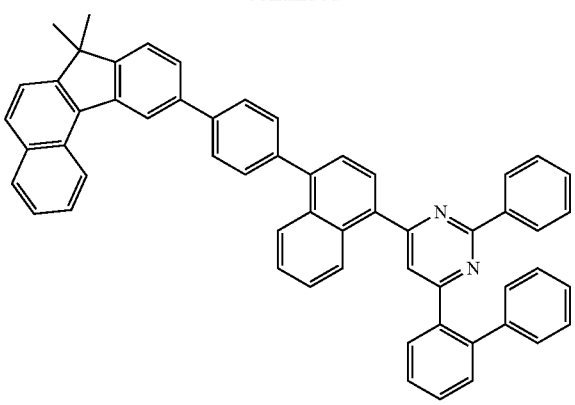
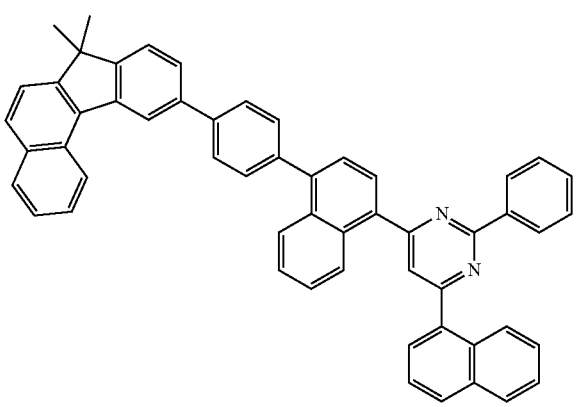
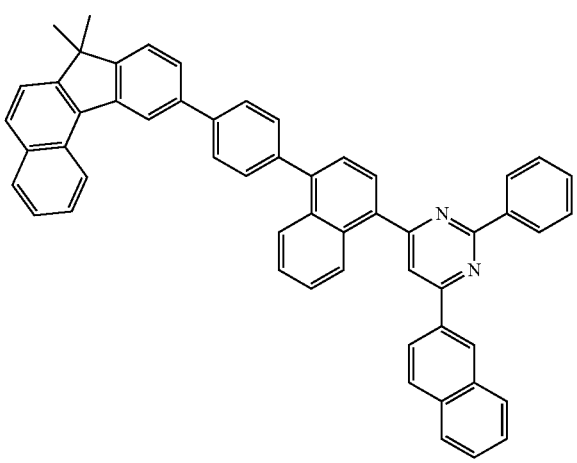

587
-continued
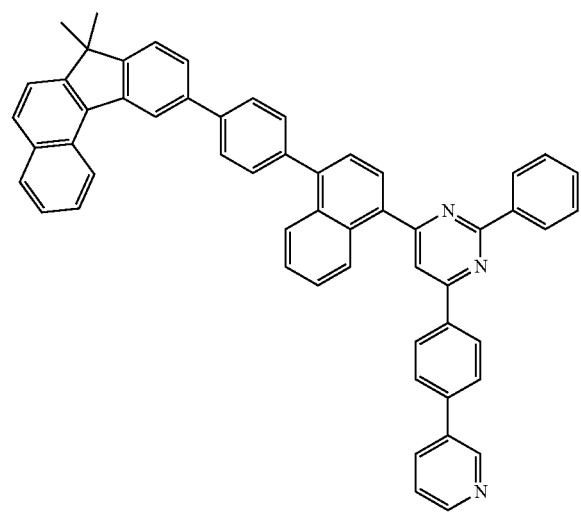
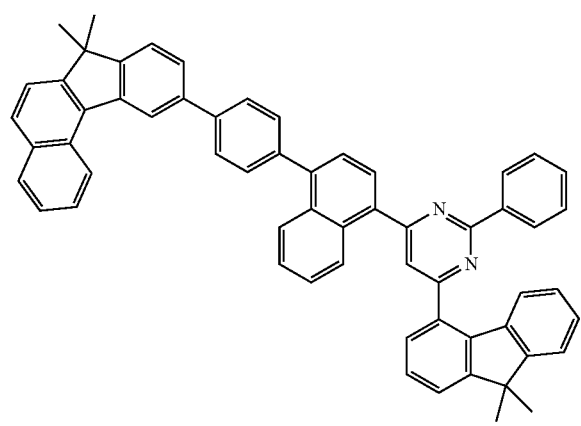
588
-continued
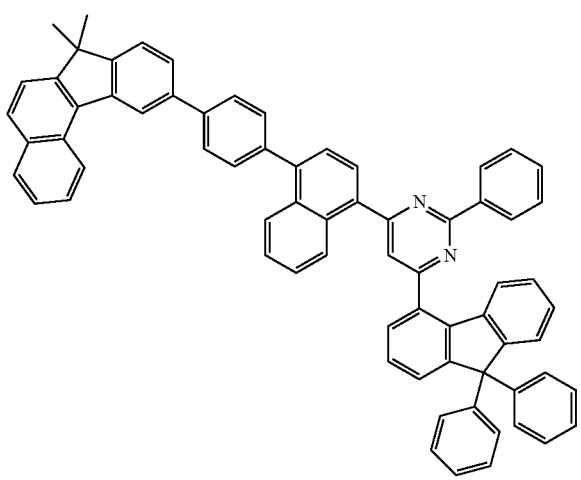
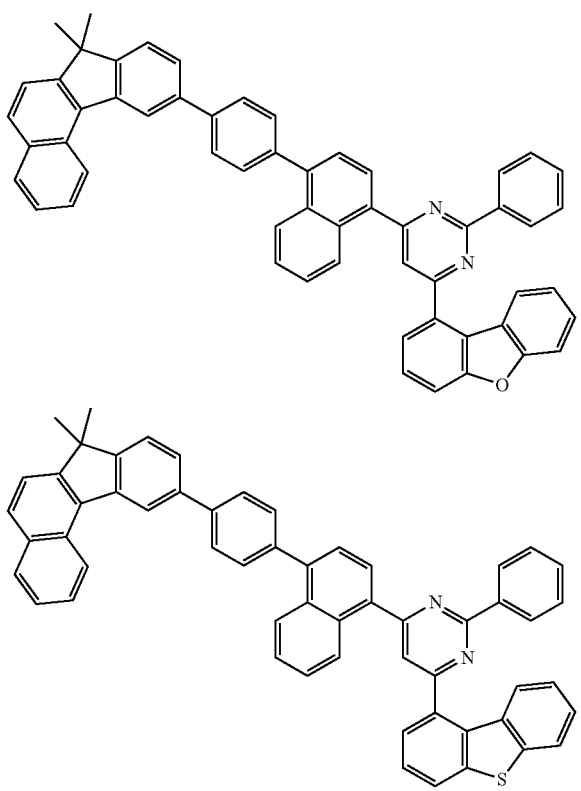
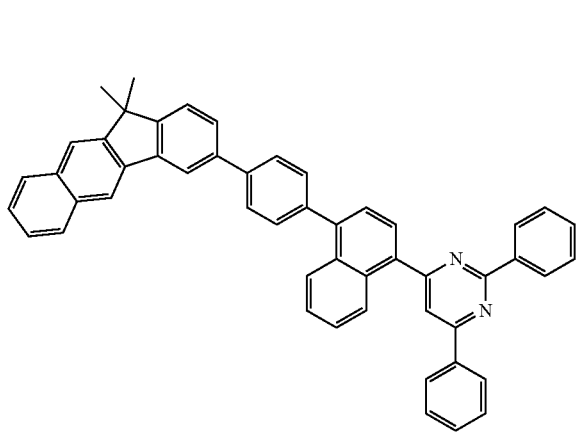

589
-continued
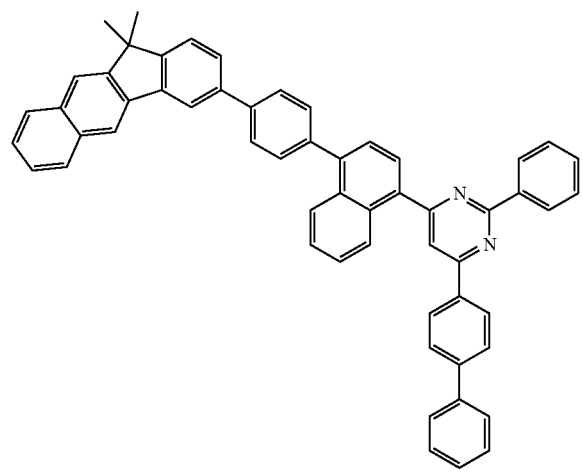
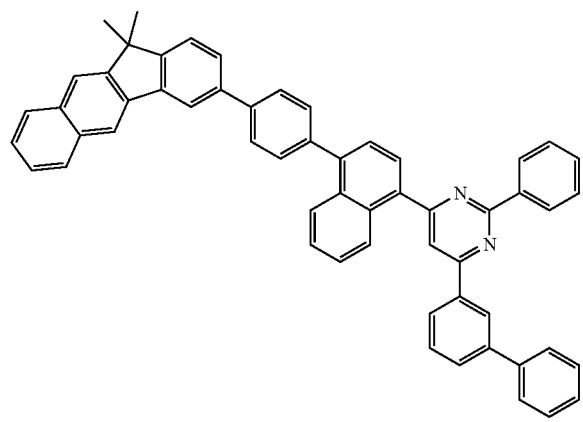
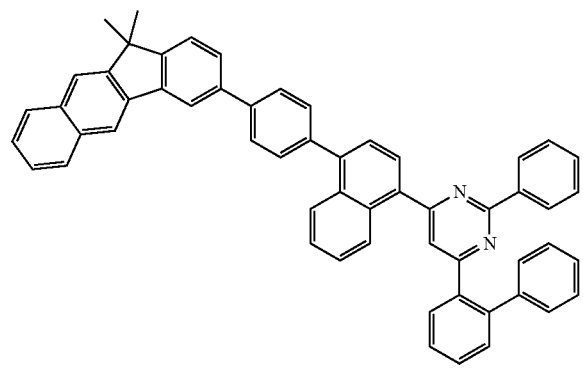
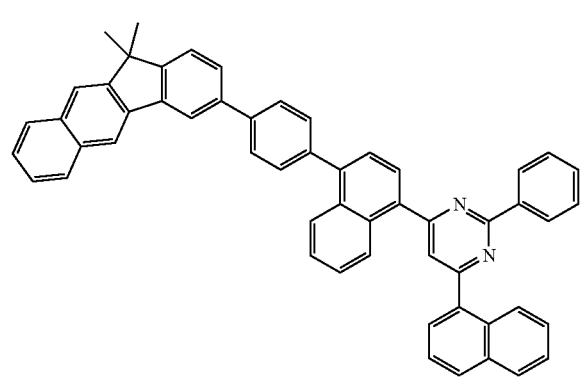
590
-continued
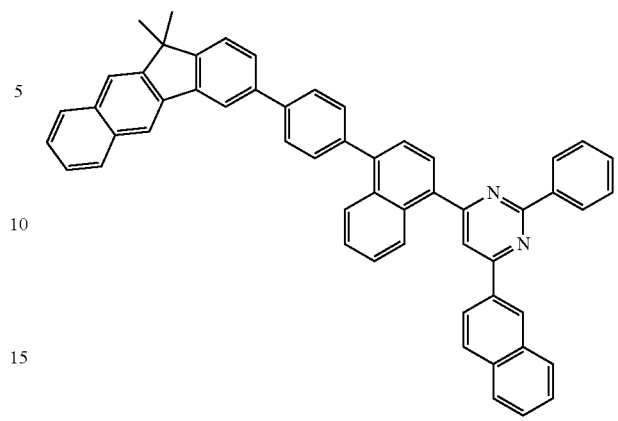
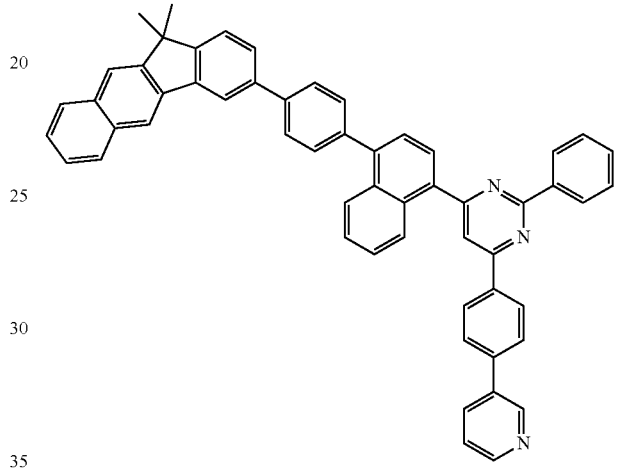
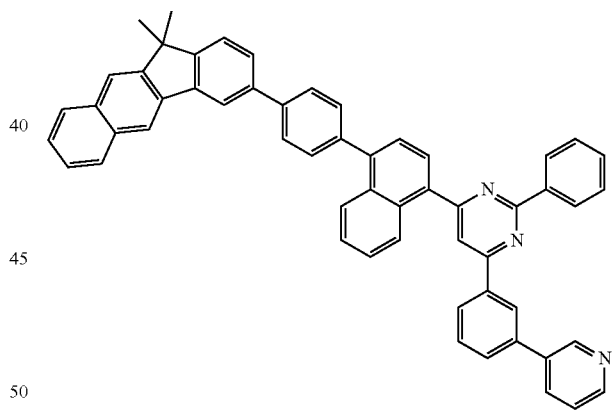
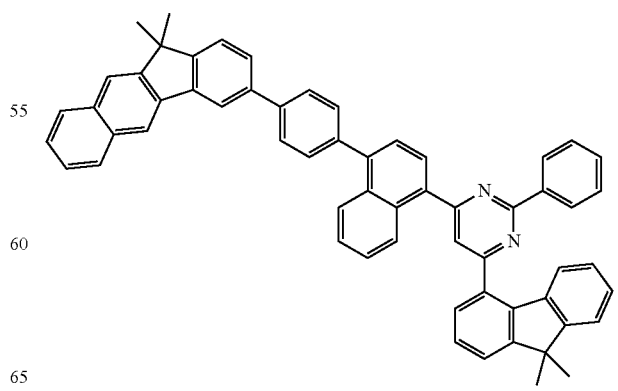

591
-continued
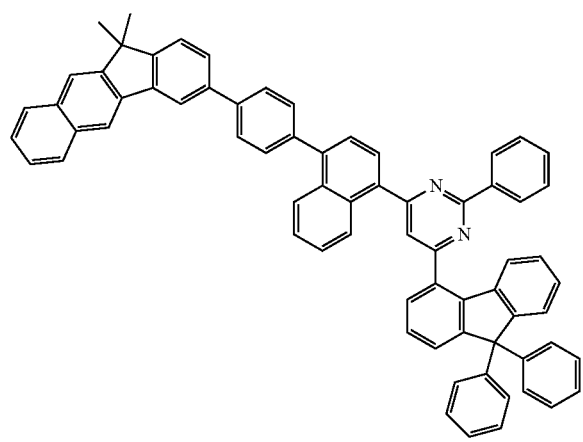
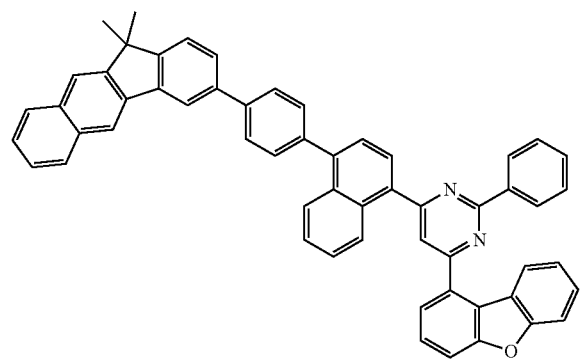
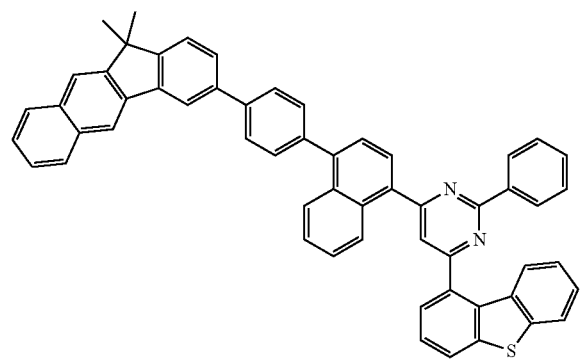
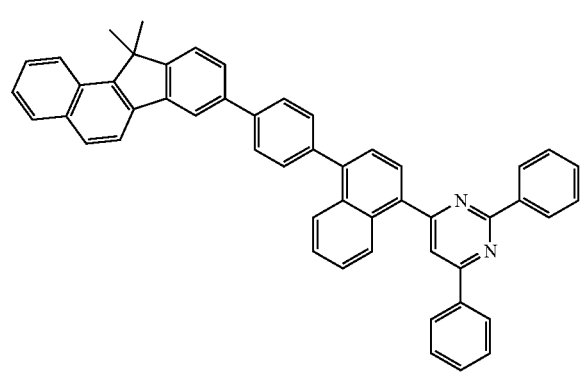
592
-continued
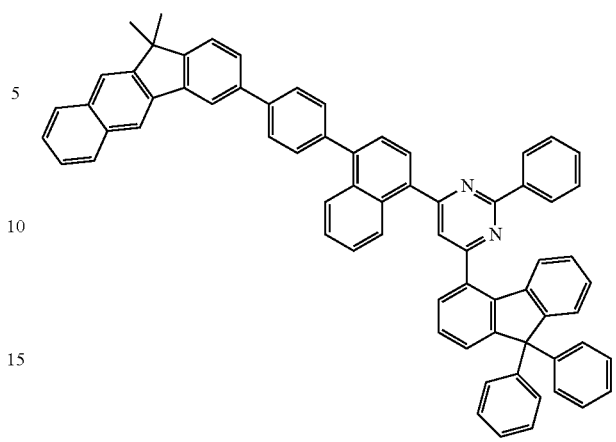
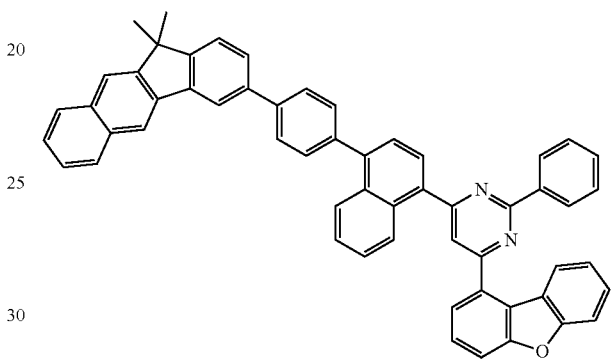
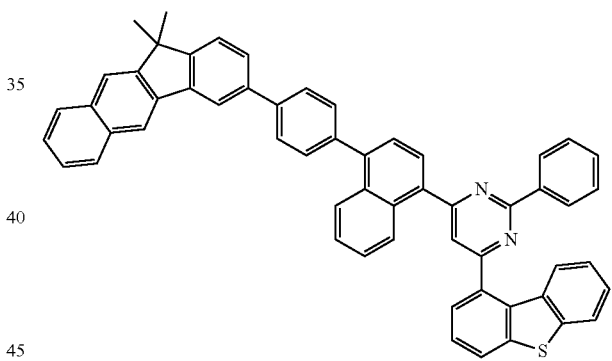
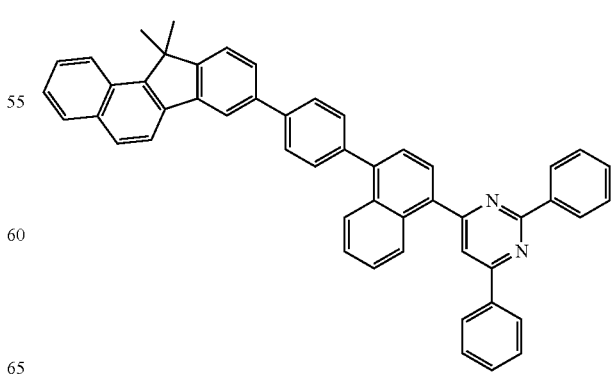

593
-continued
594
-continued
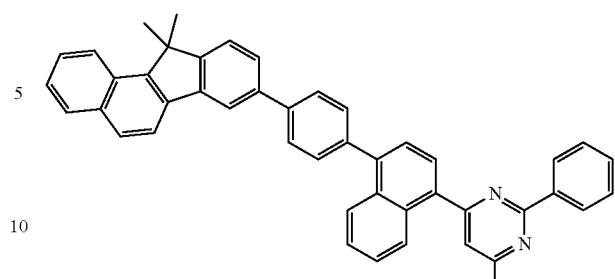
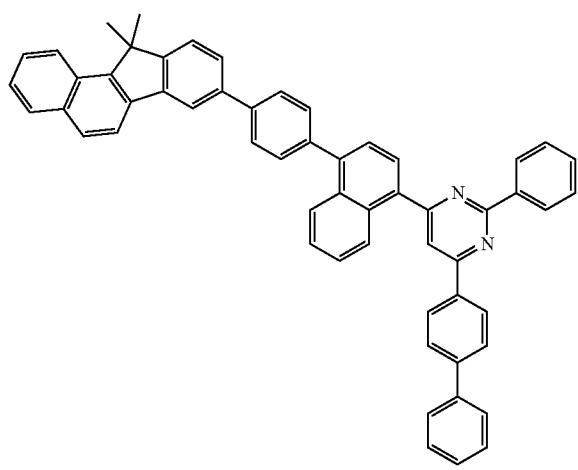
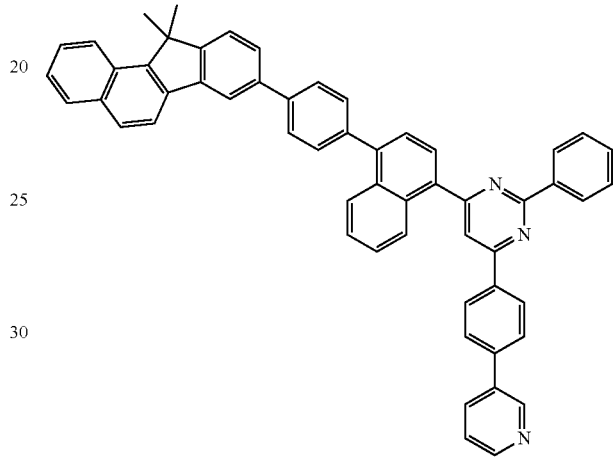
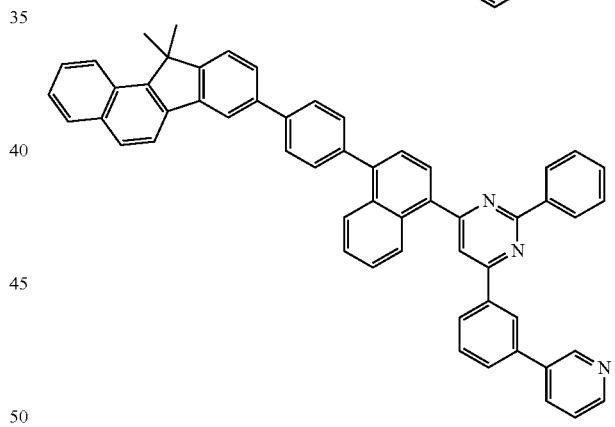
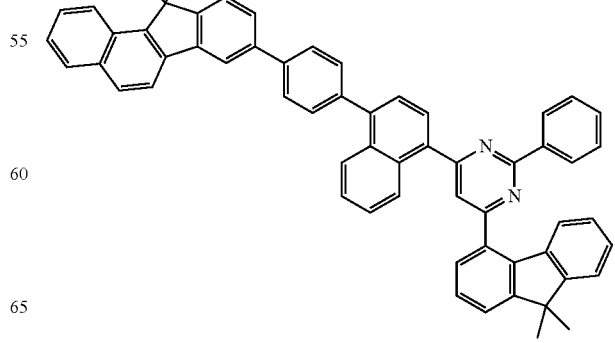

595
-continued
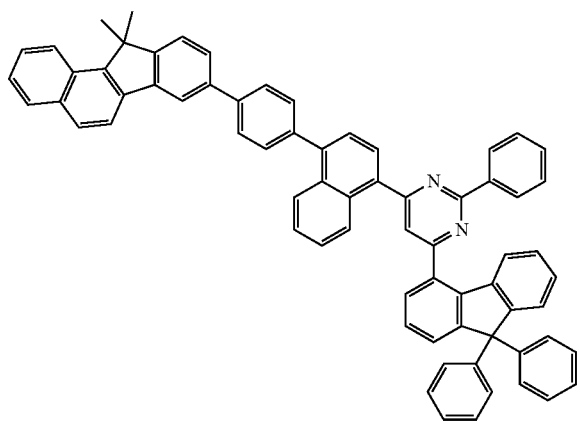
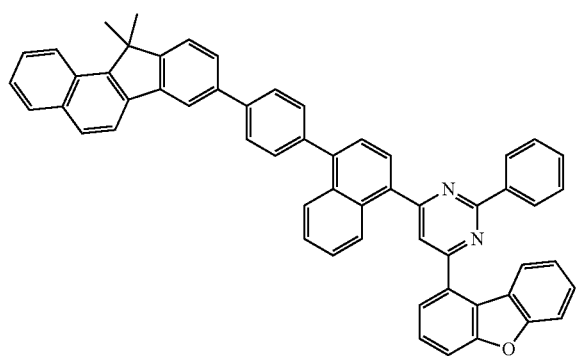
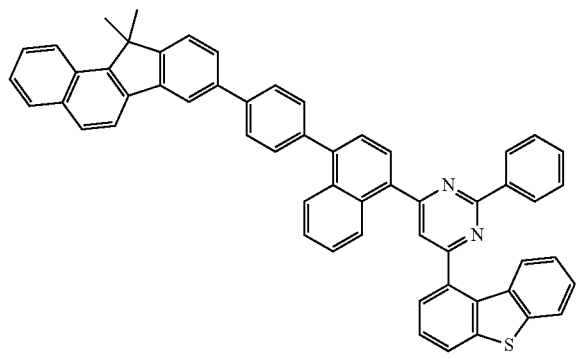
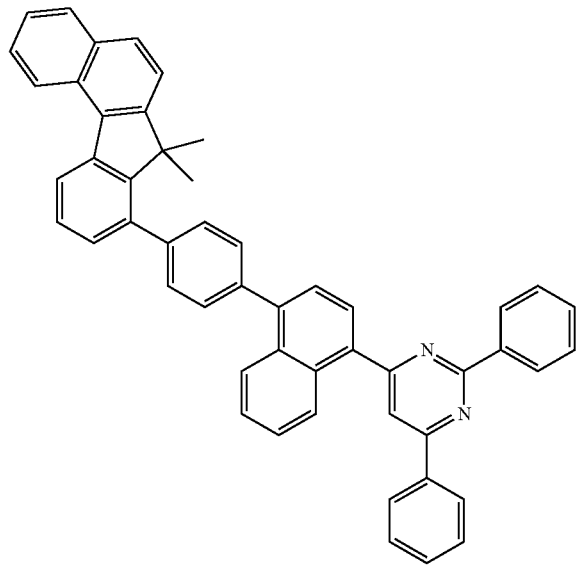
596
-continued
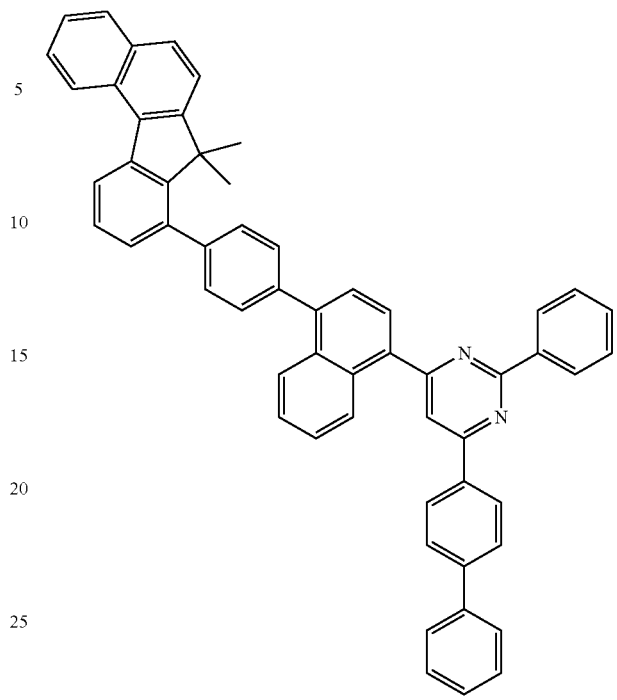
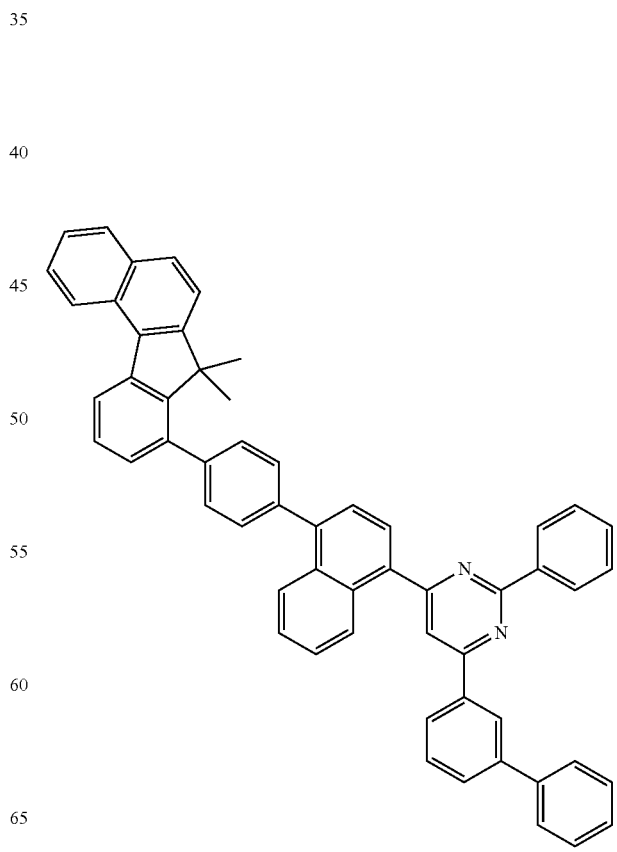

597
-continued
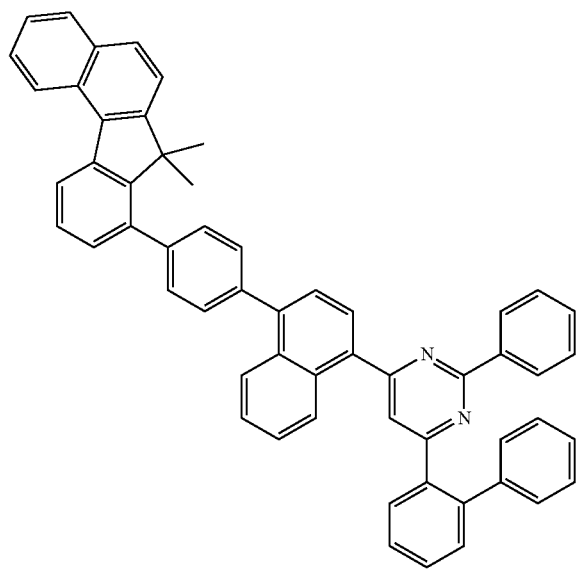
598
-continued
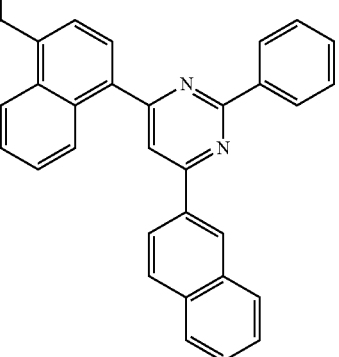
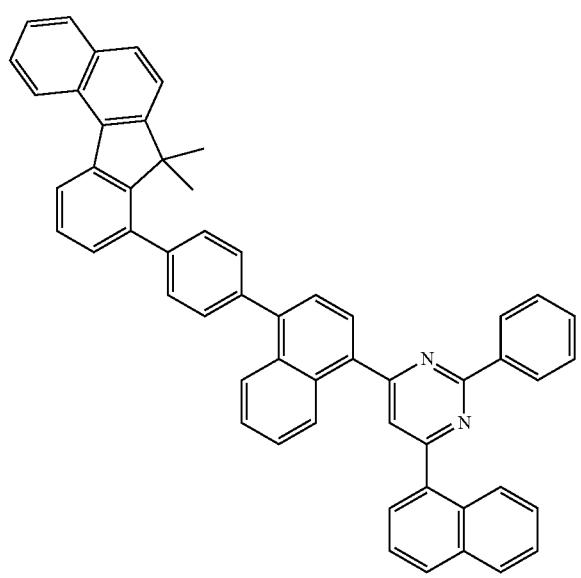
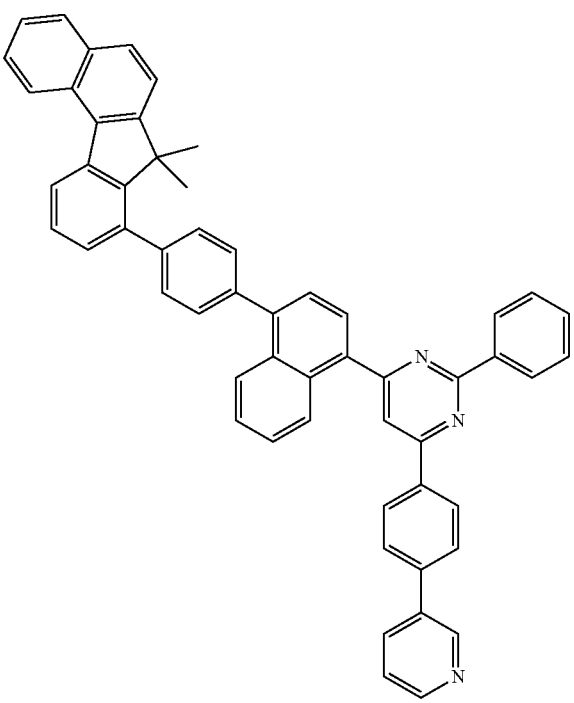

599
-continued
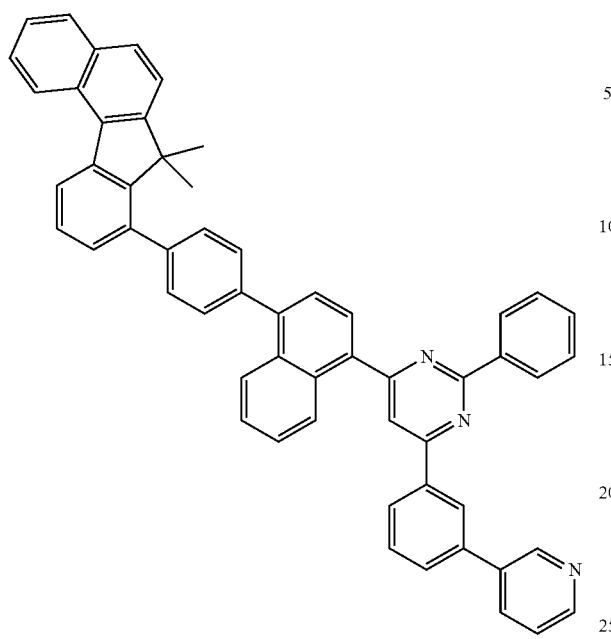
600
-continued
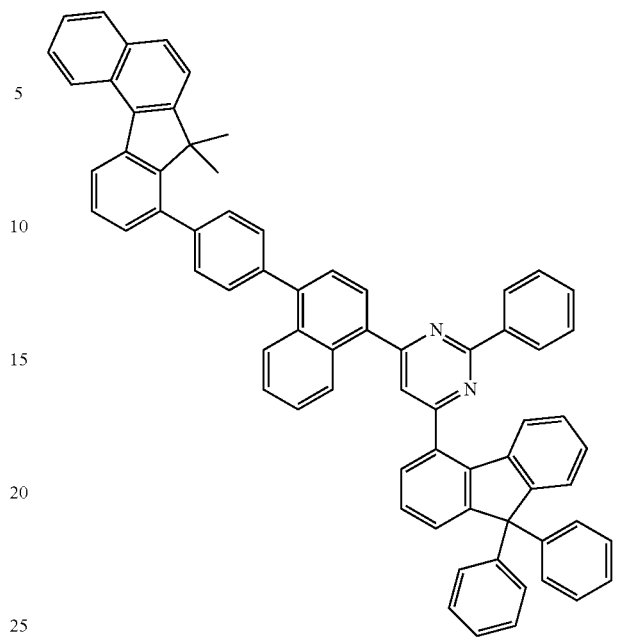
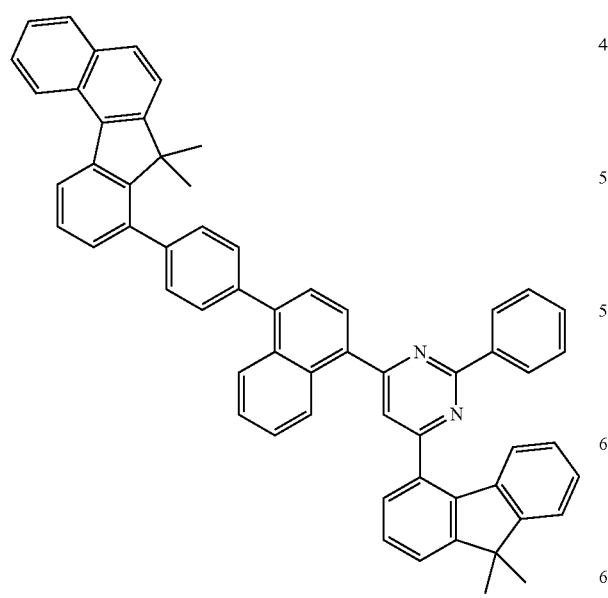
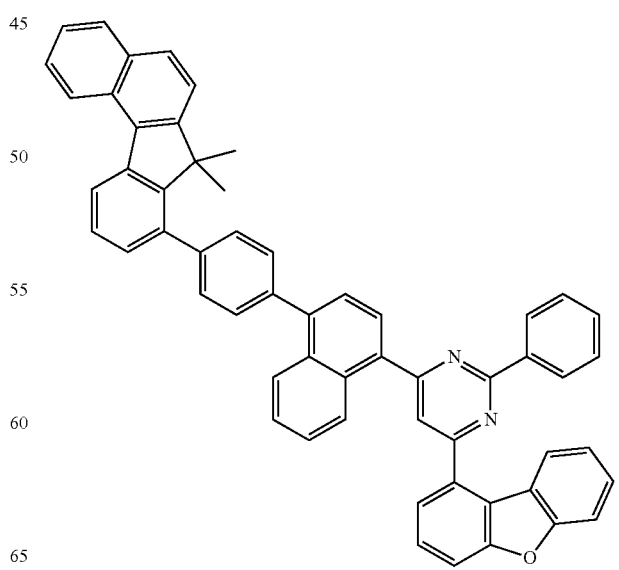

601
-continued
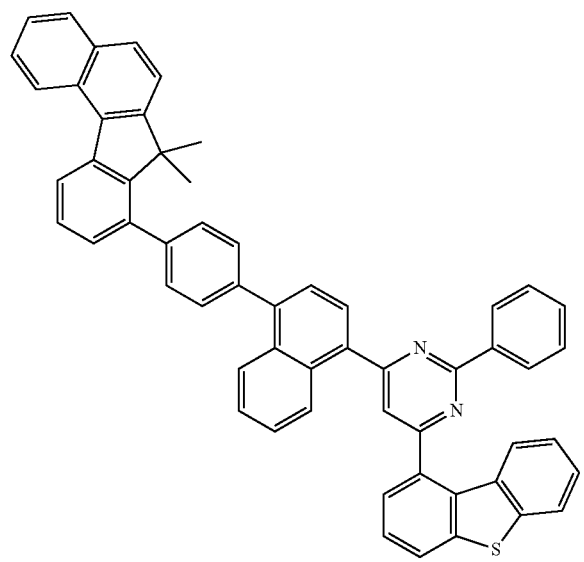
602
-continued
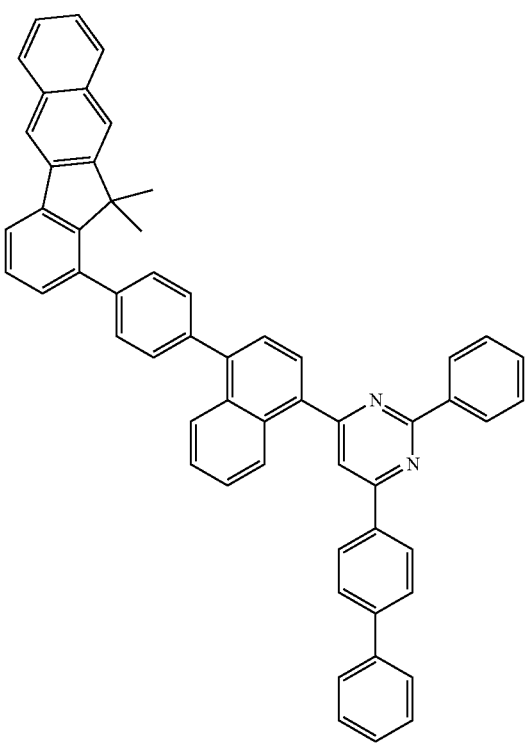
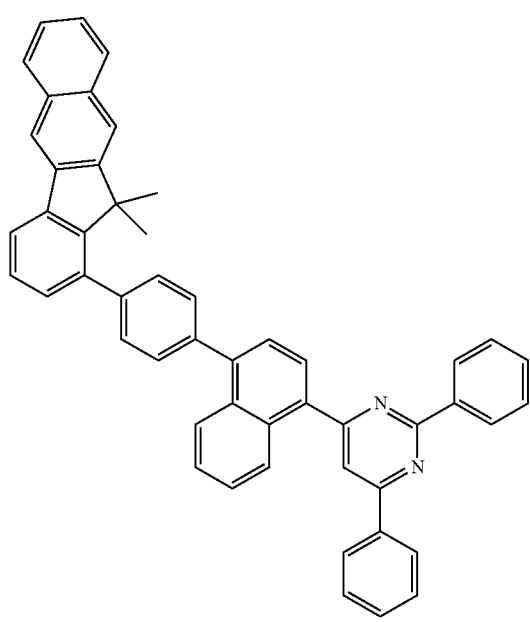
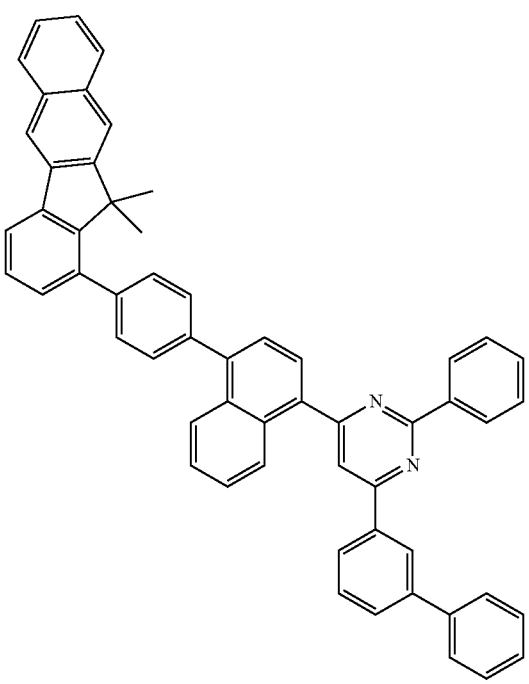

603
-continued
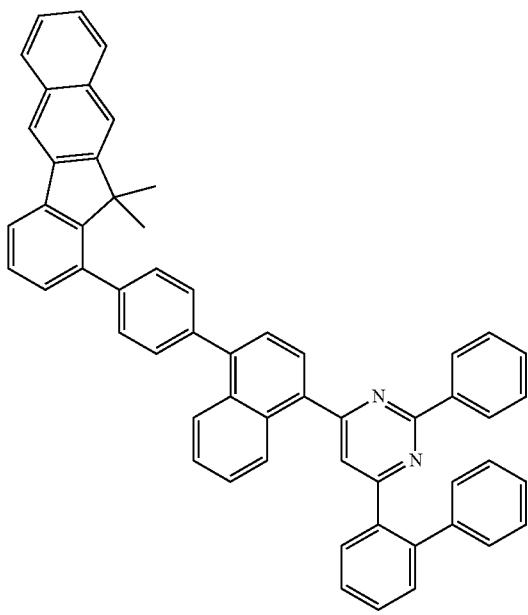
604
-continued
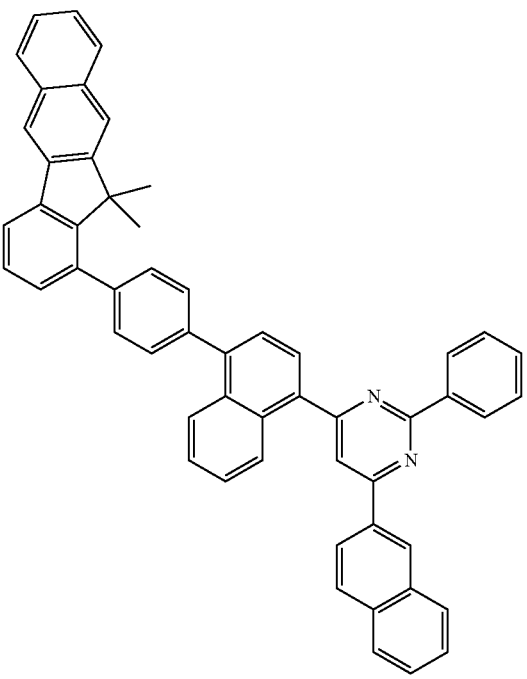
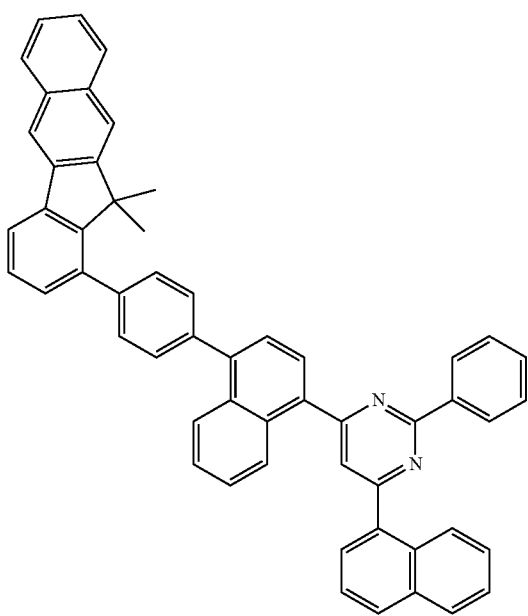
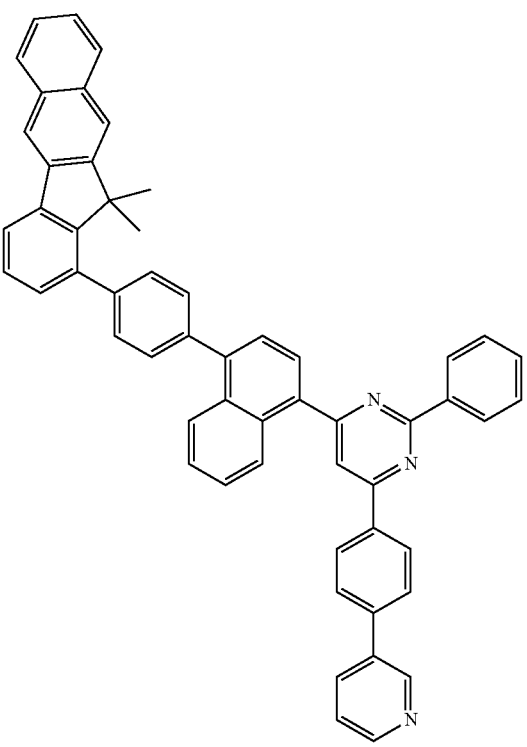

605
-continued
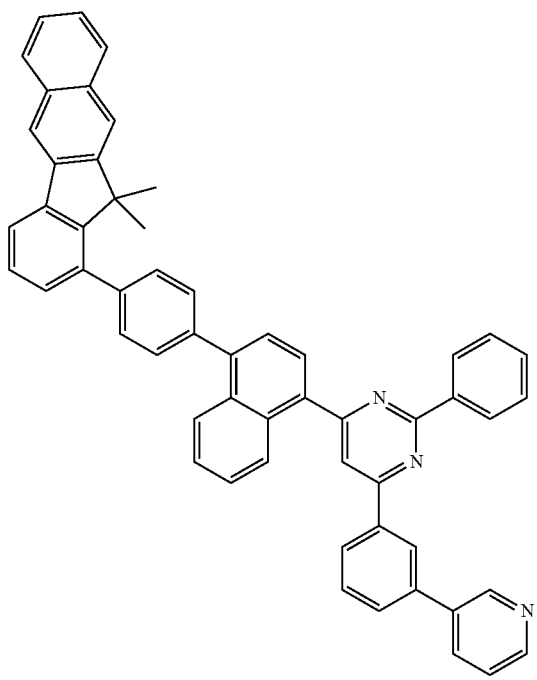
606
-continued
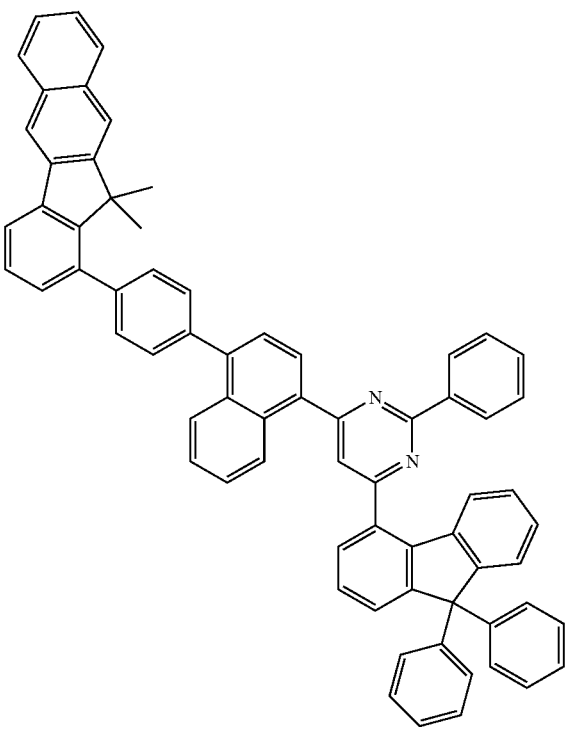
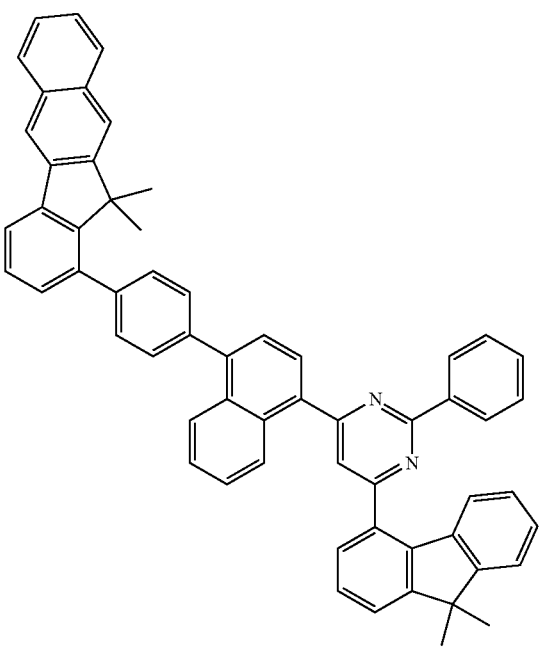
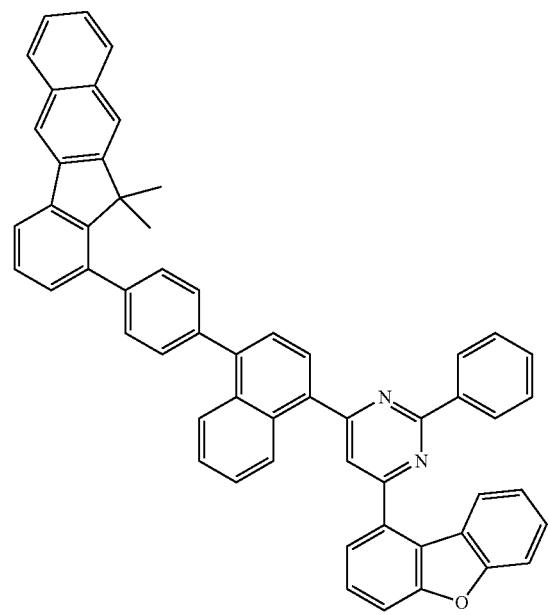

607
-continued
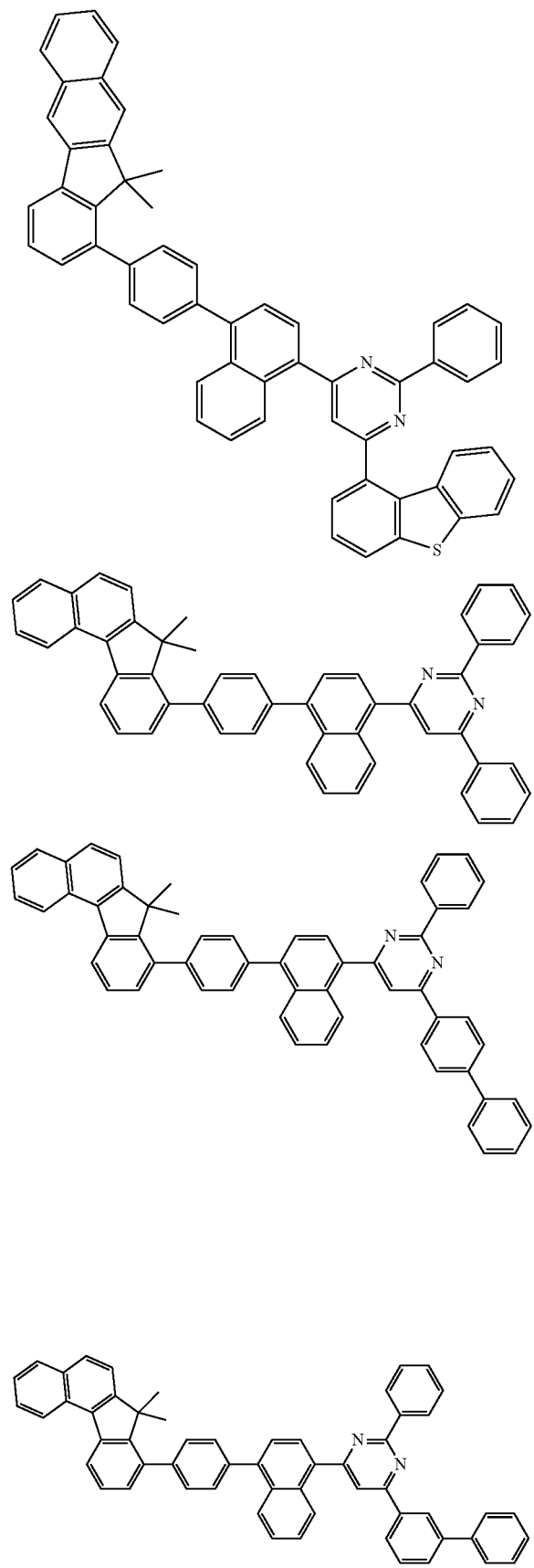
608
-continued
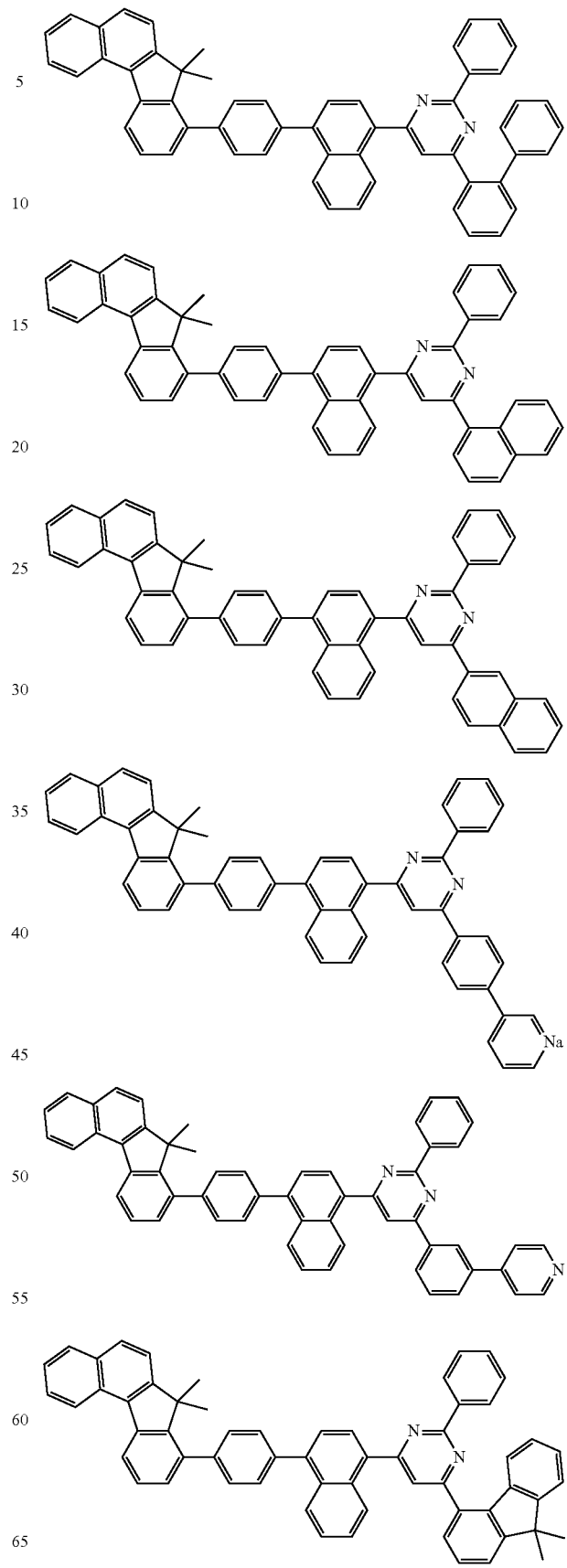

609
-continued
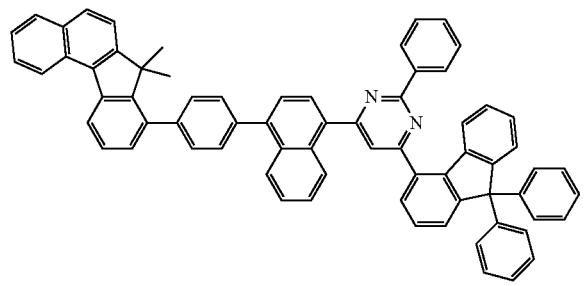
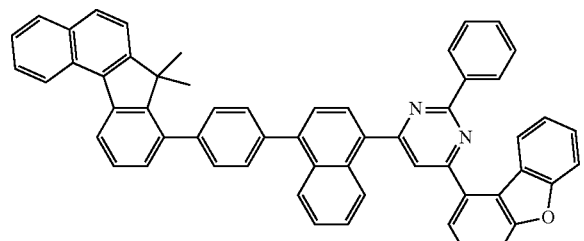
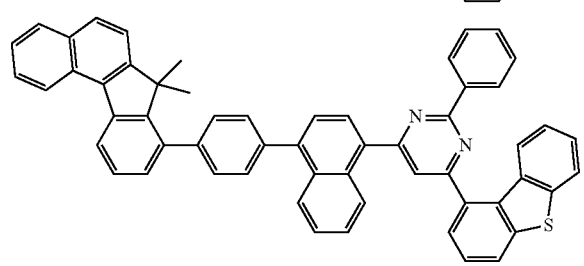
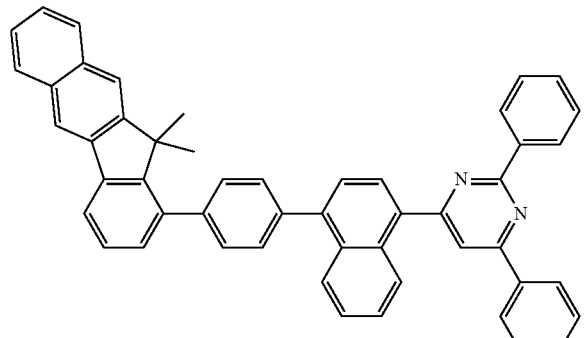
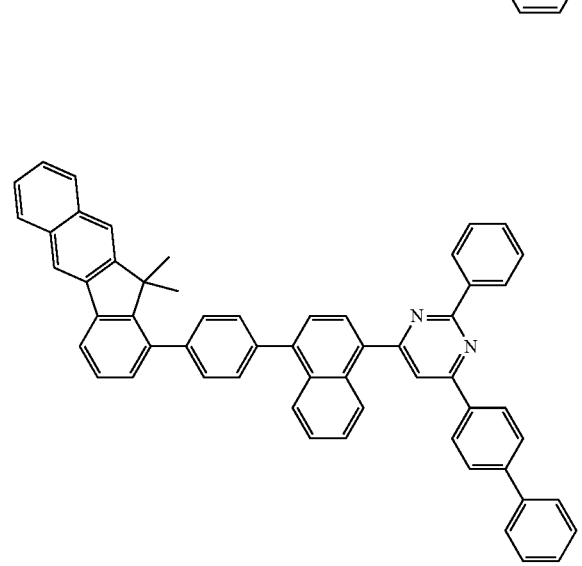
610
-continued
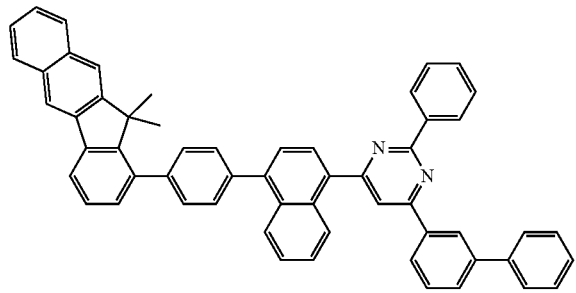
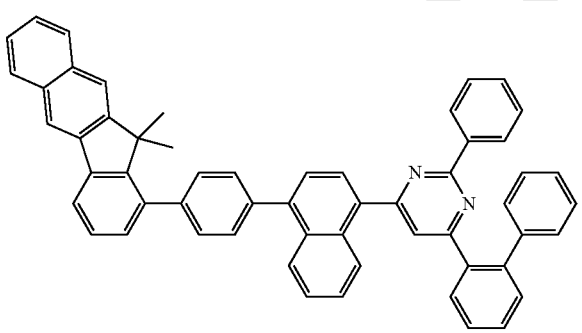
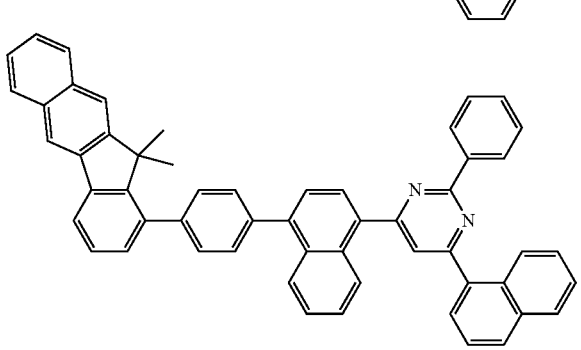
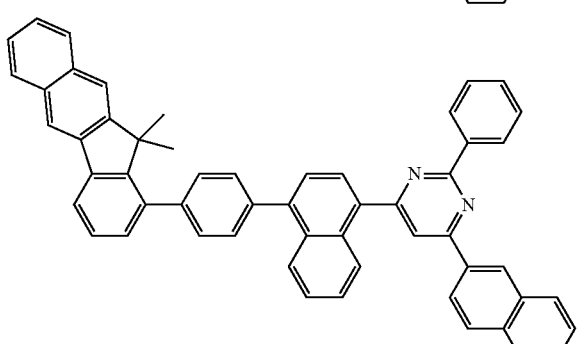
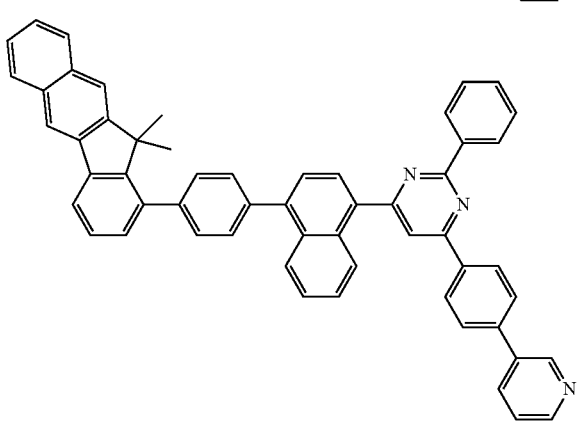

611
-continued
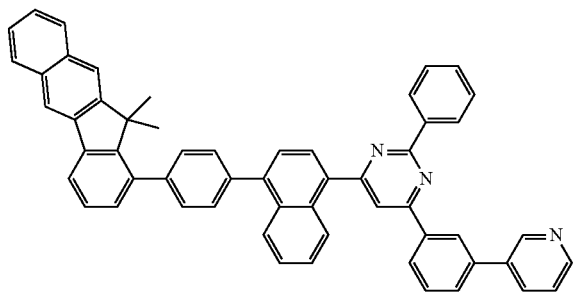
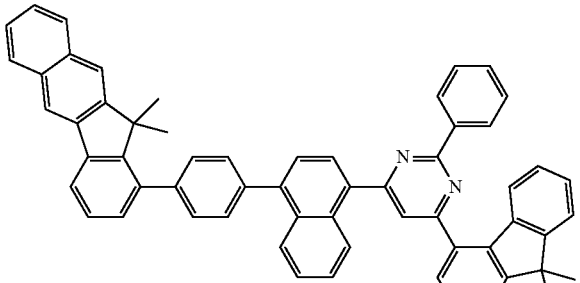
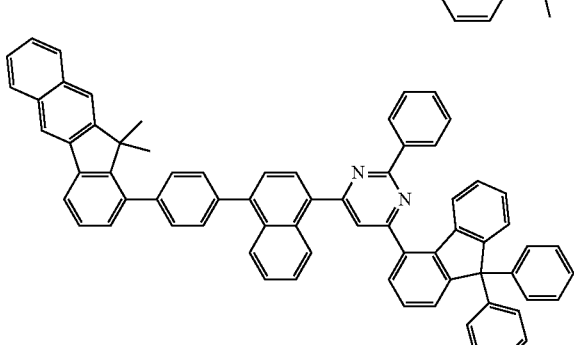
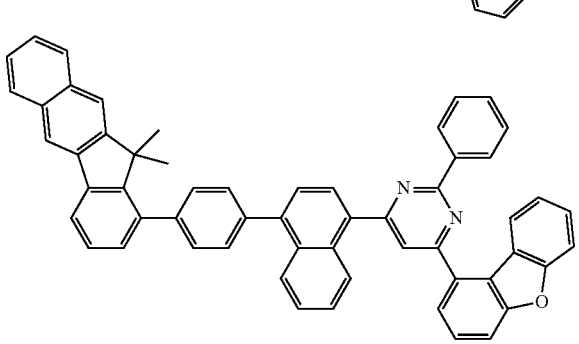
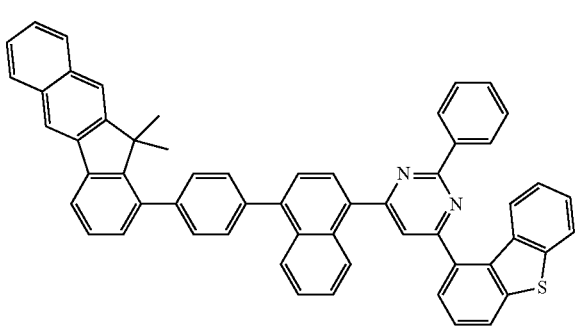
612
-continued
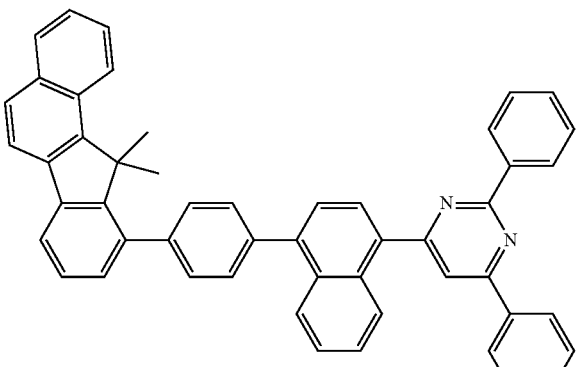
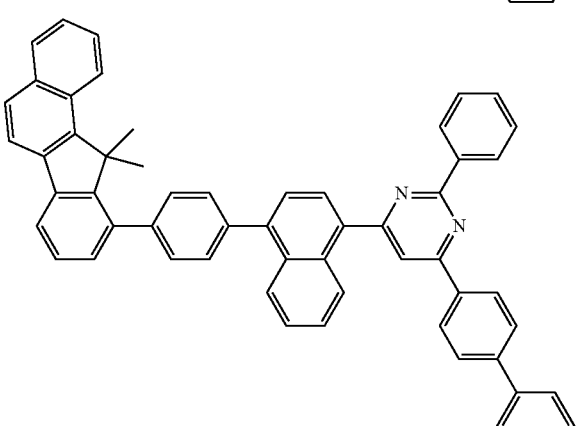
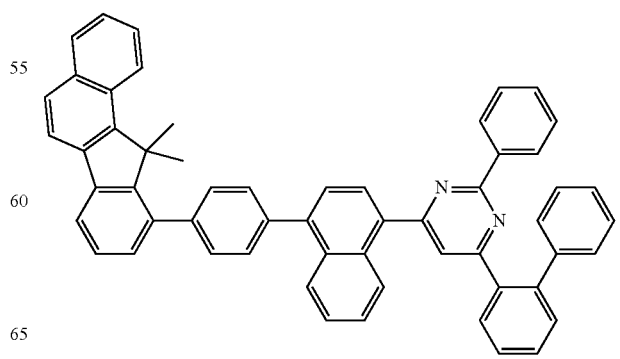

613
-continued
614
-continued
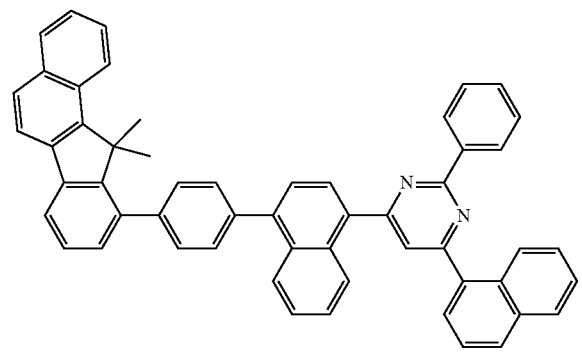
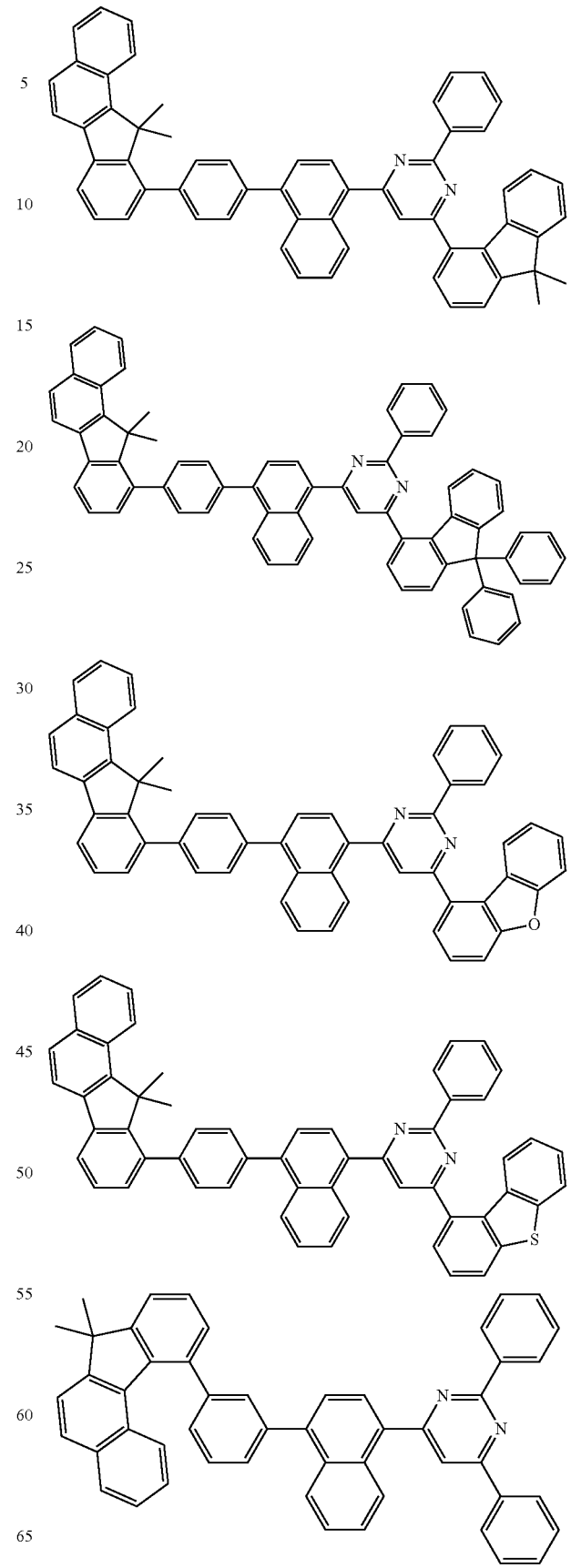

615
-continued
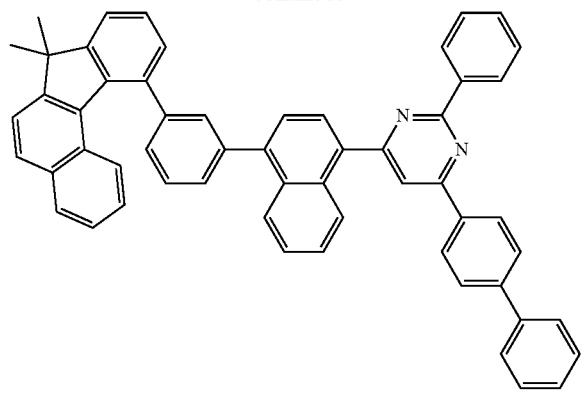
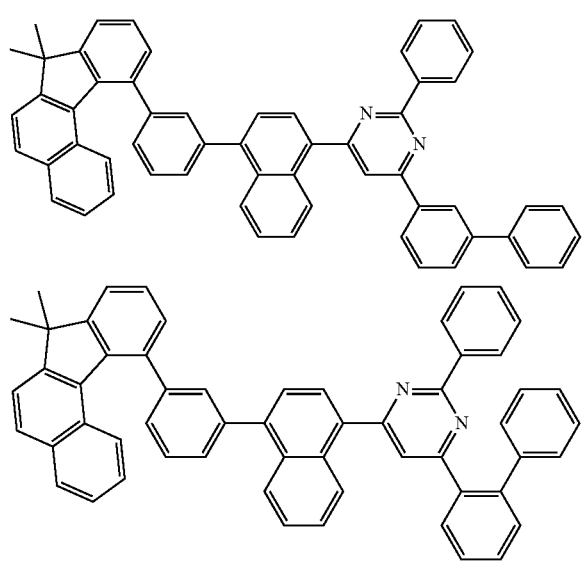
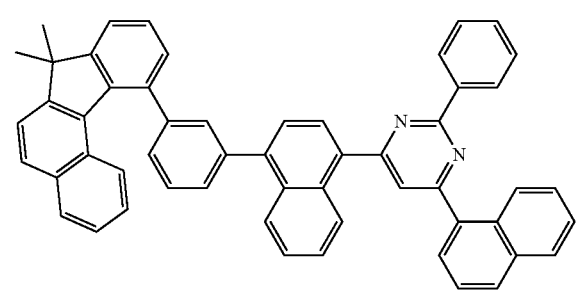
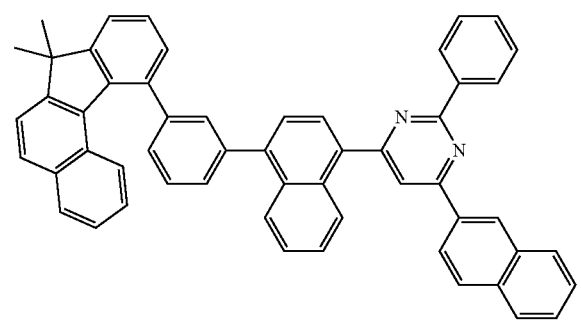
616
-continued
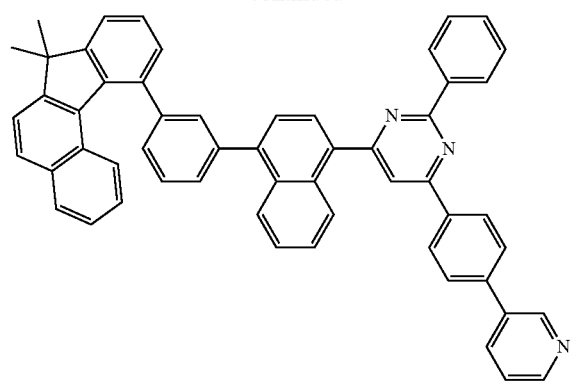
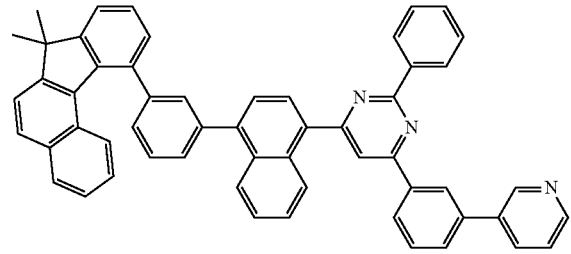
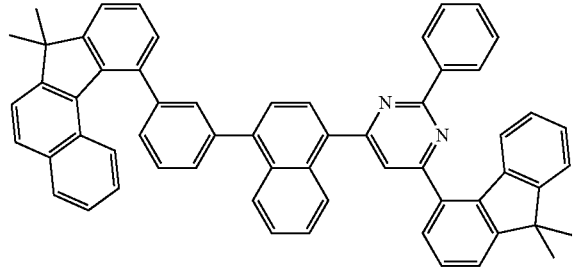
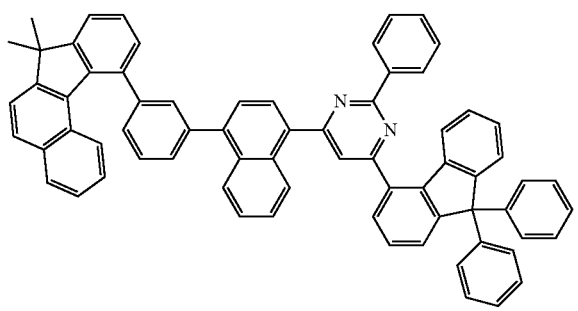
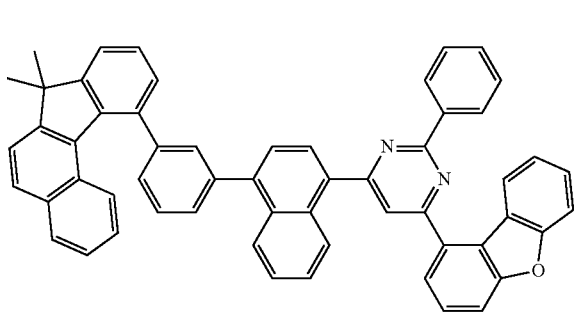

617
-continued
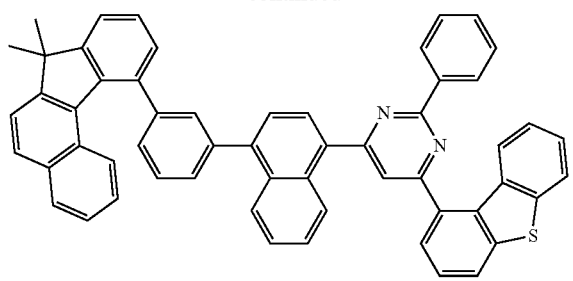
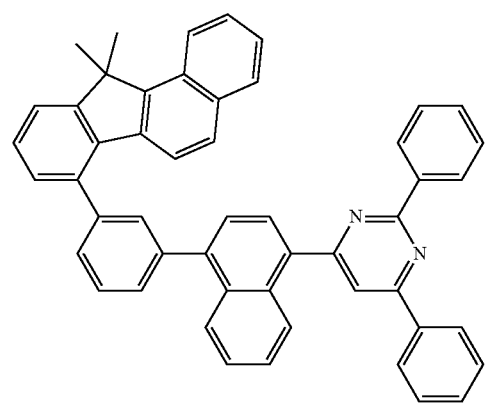
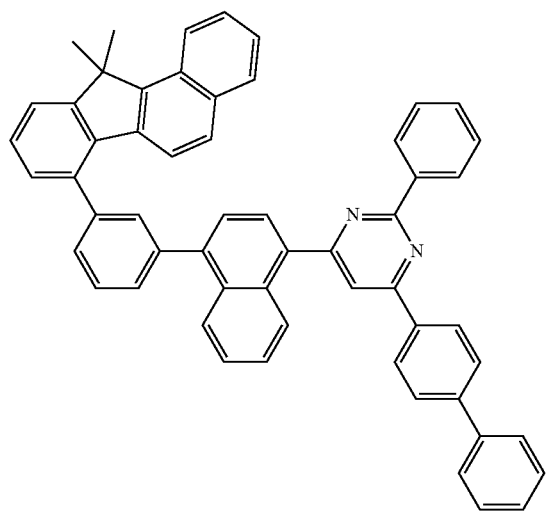
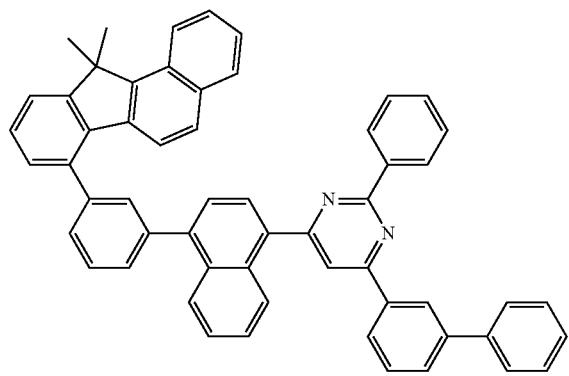
618
-continued
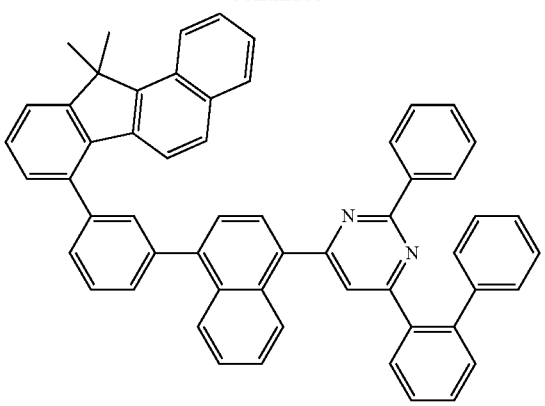
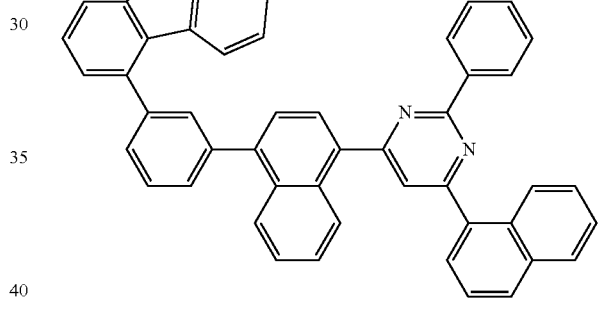
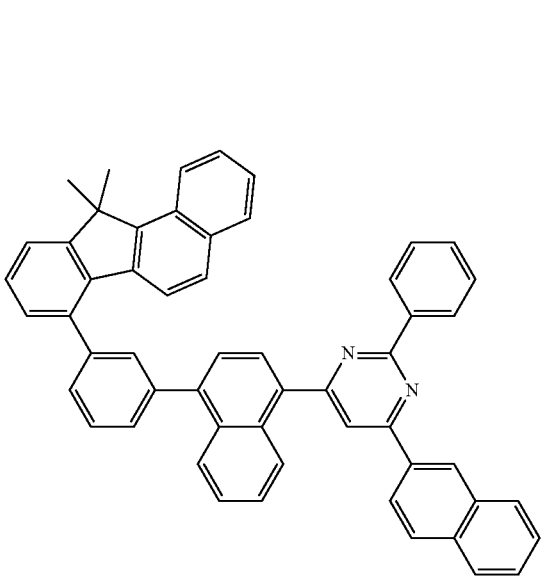

619
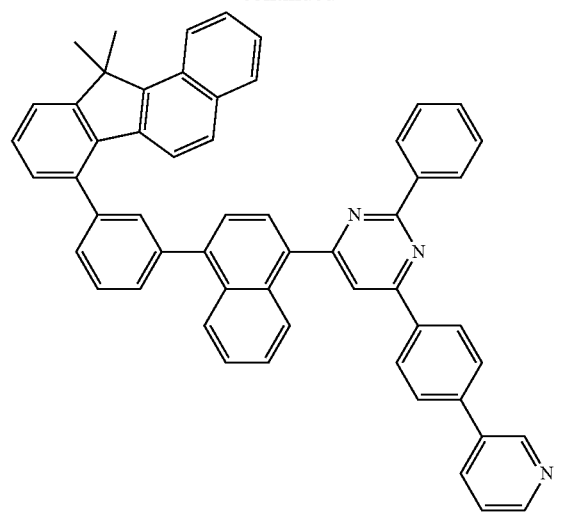
620
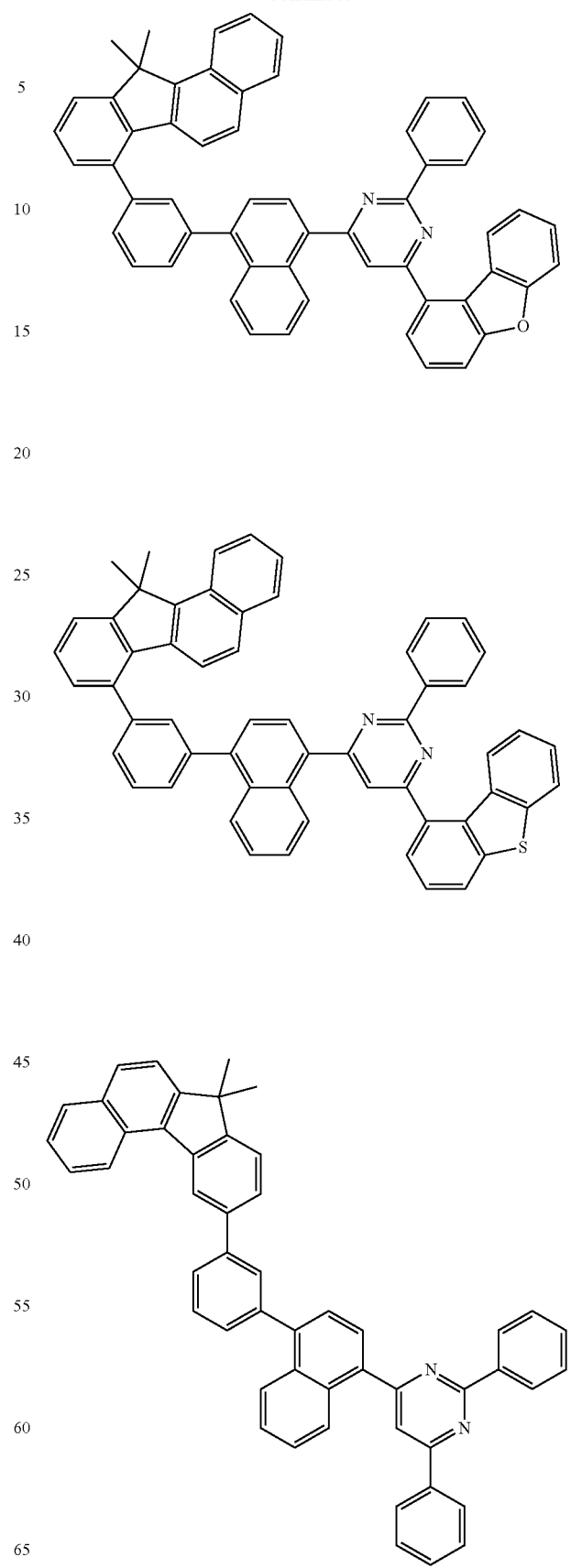

621
-continued
622
-continued
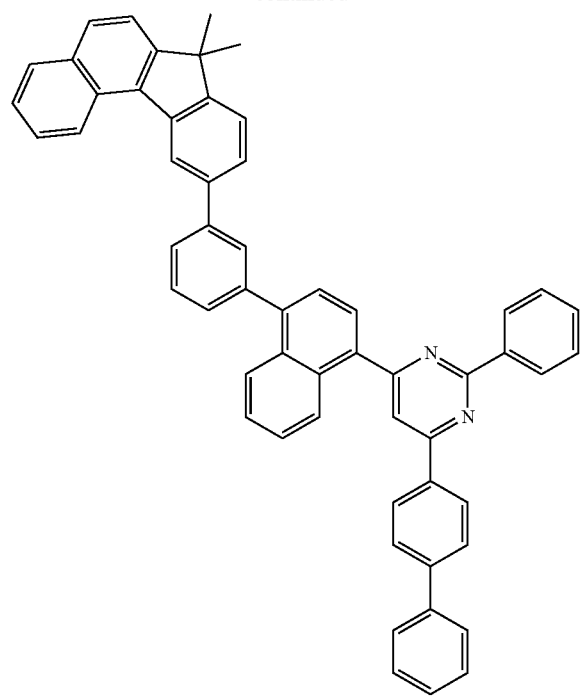
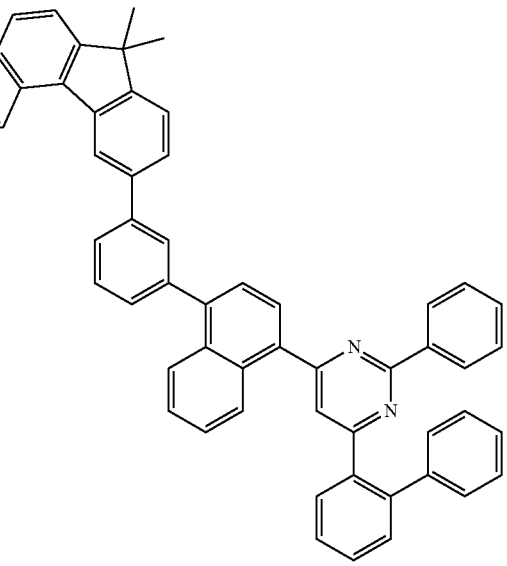
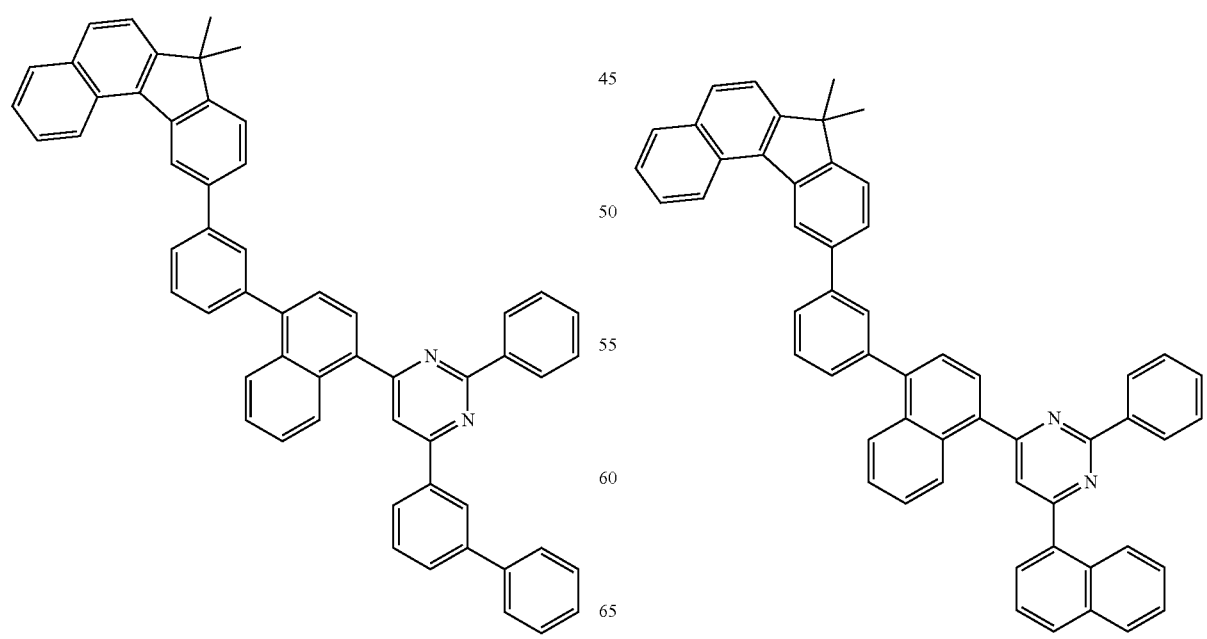

623
-continued
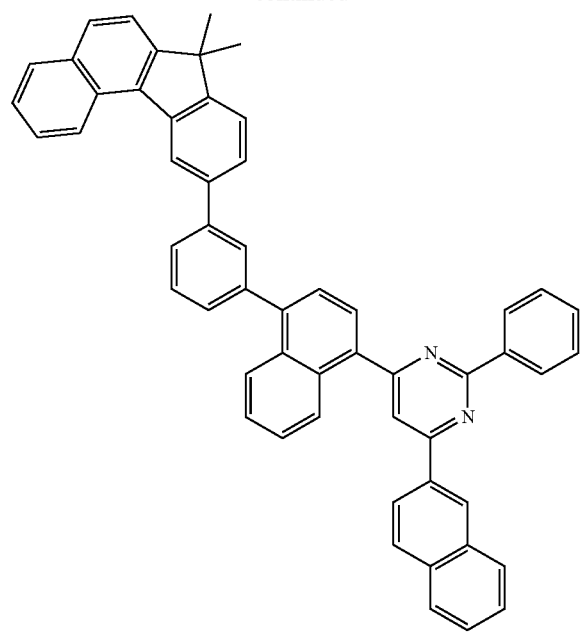
624
-continued
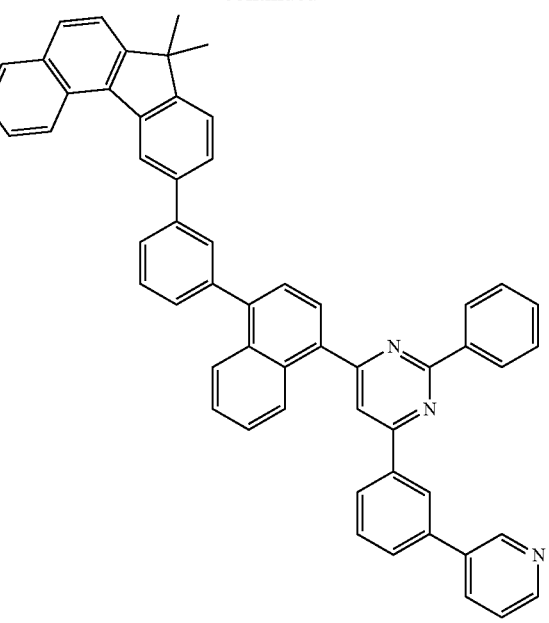
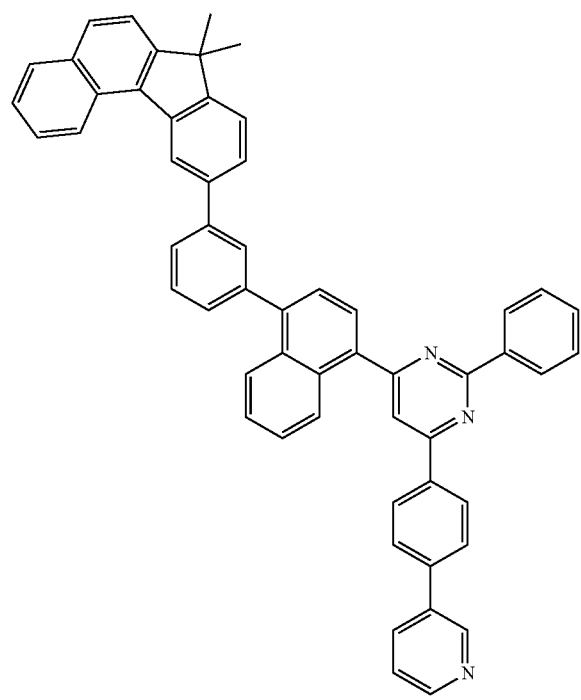
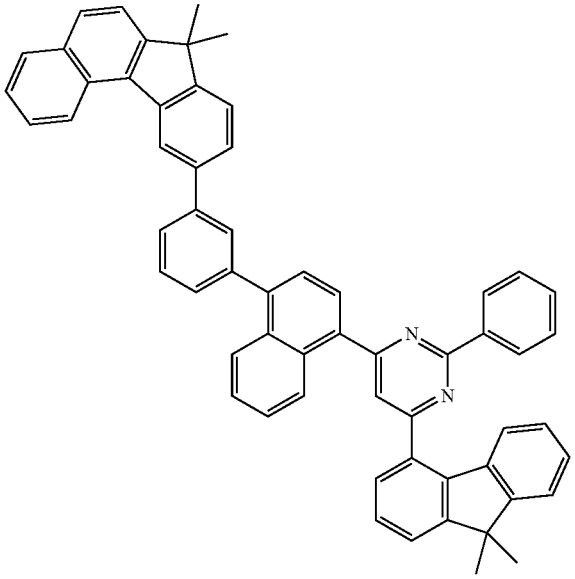

625
-continued
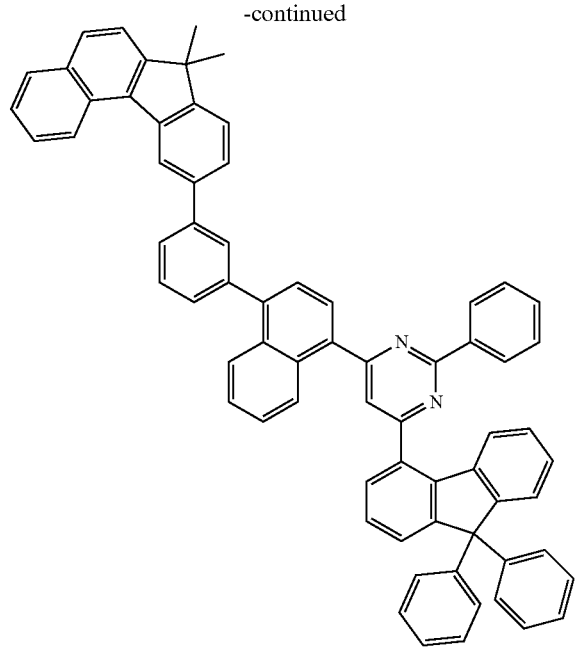
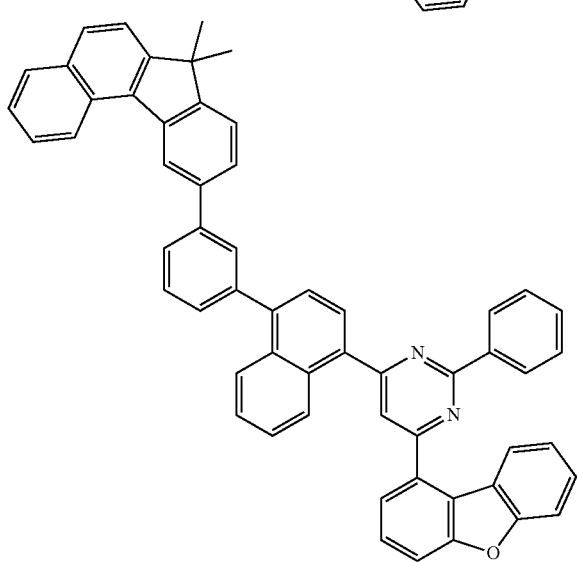
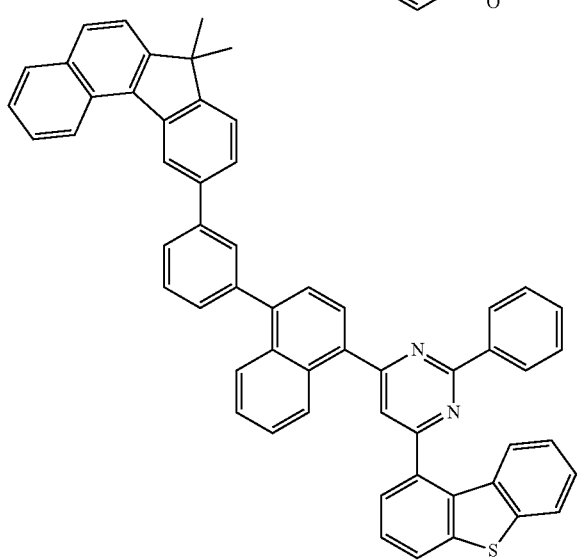
626
-continued
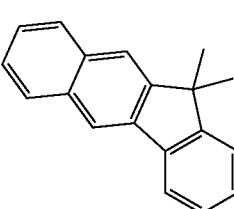
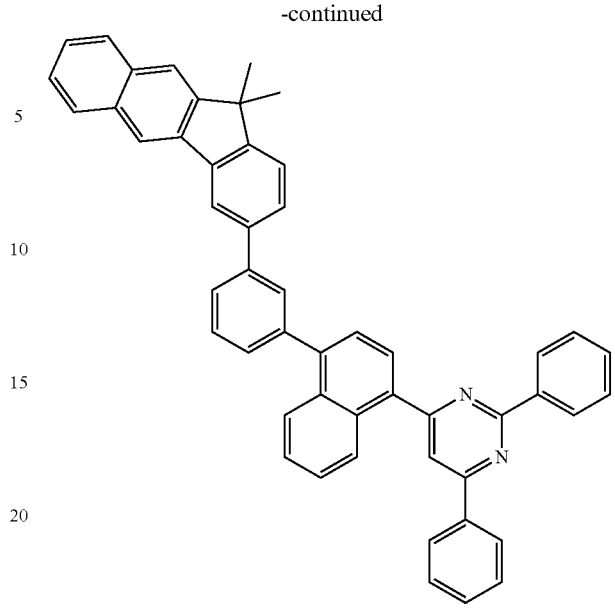
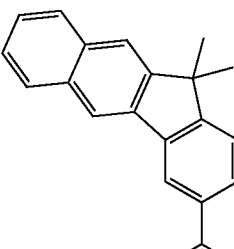

627
-continued
628
-continued
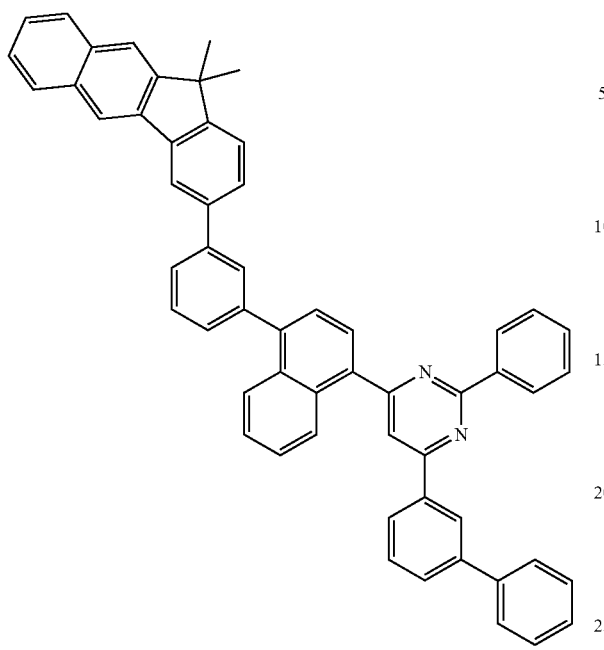
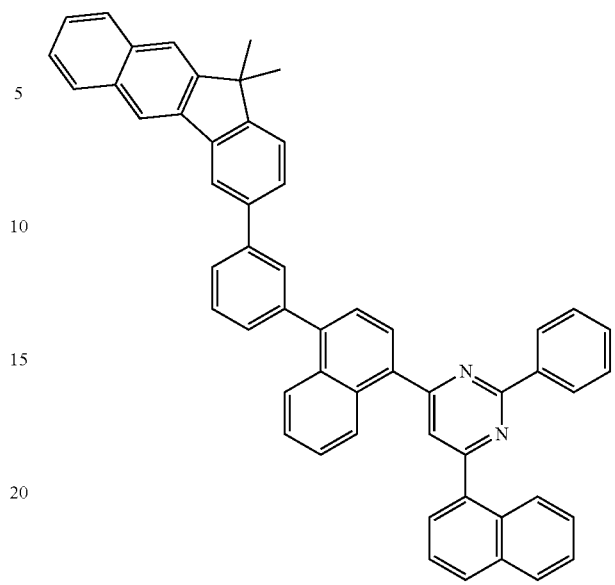
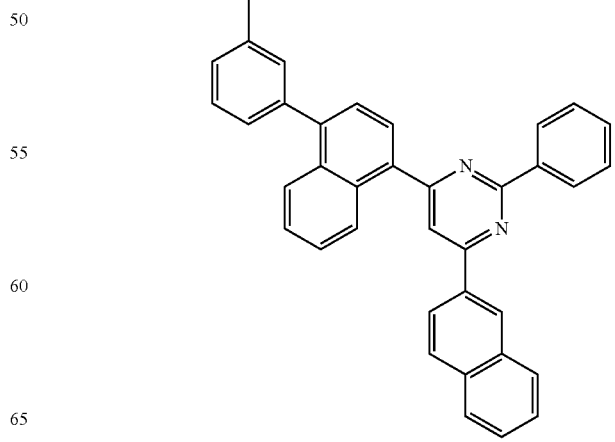

629
-continued
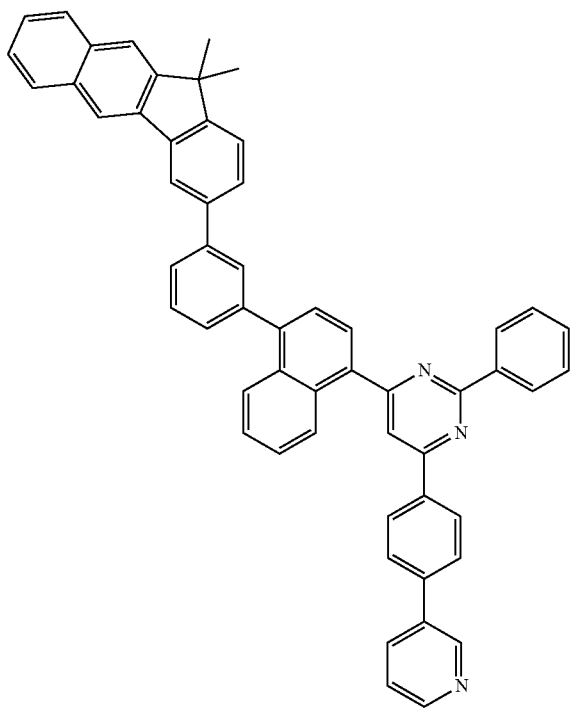
630
-continued
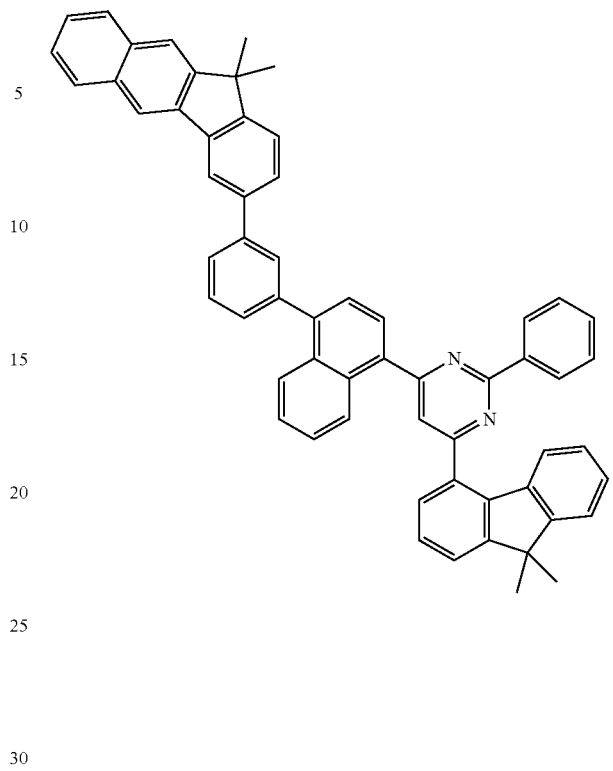
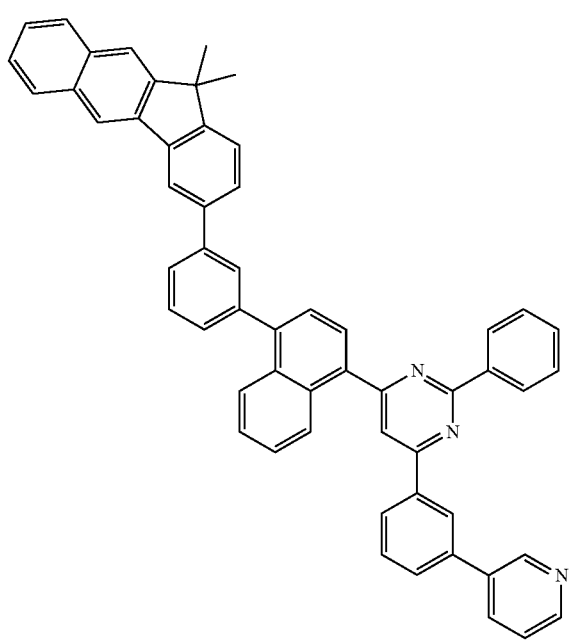
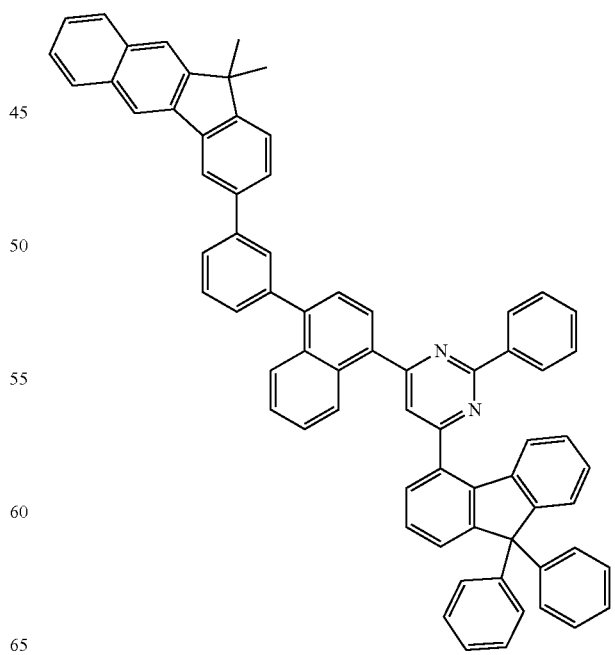

631
-continued
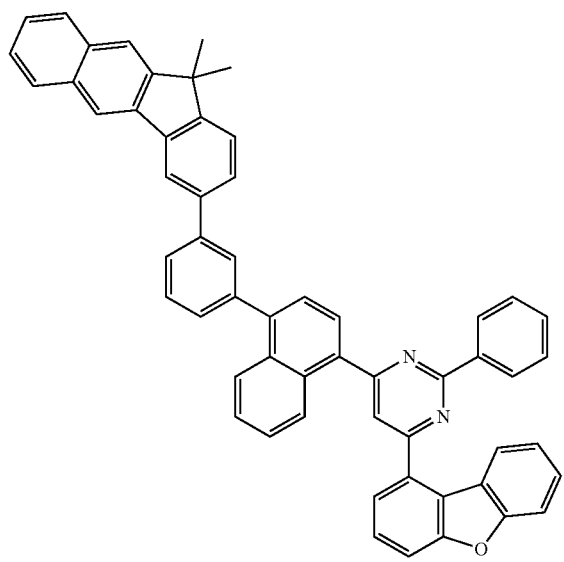
632
-continued
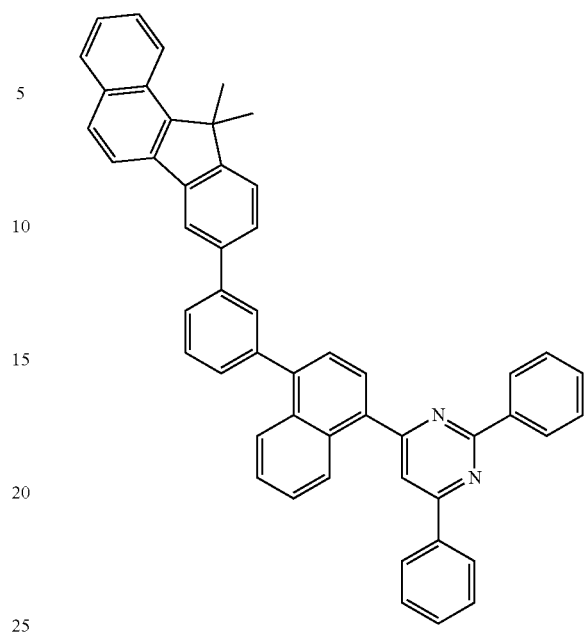
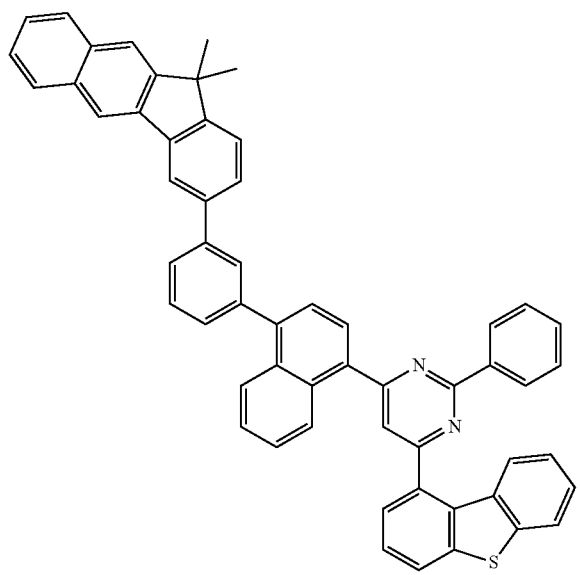
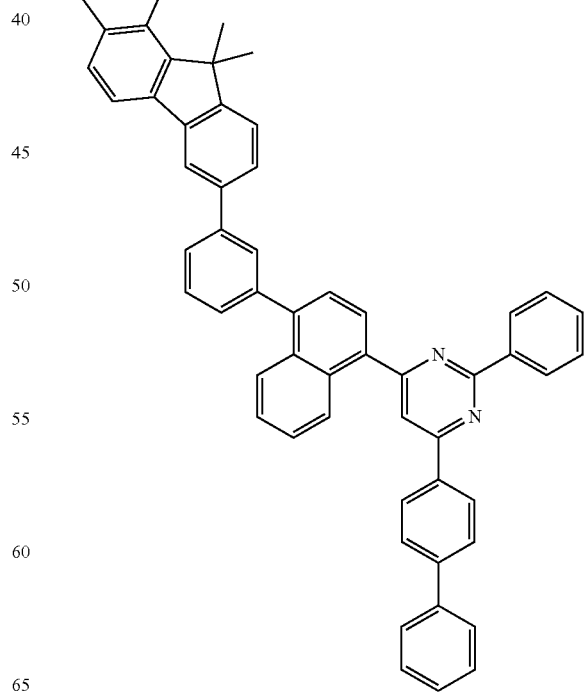

633
-continued
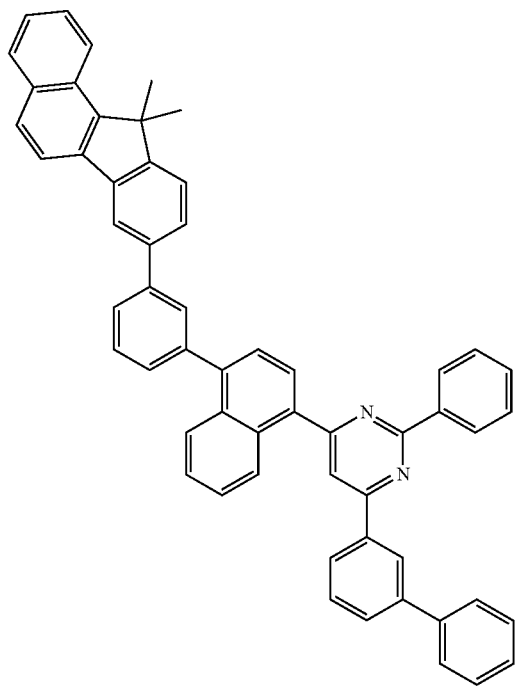
634
-continued
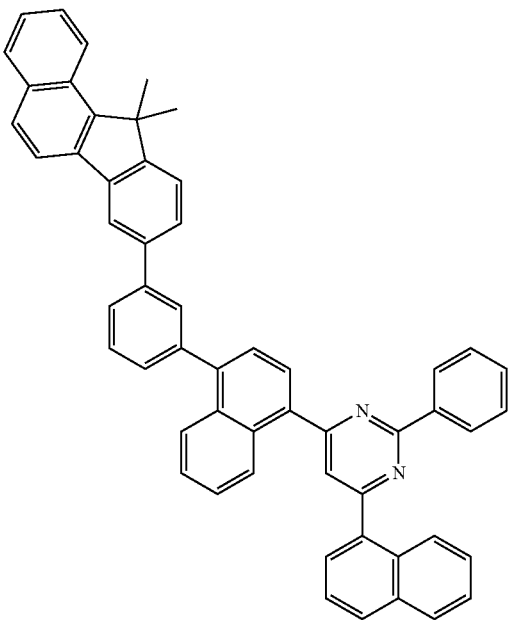
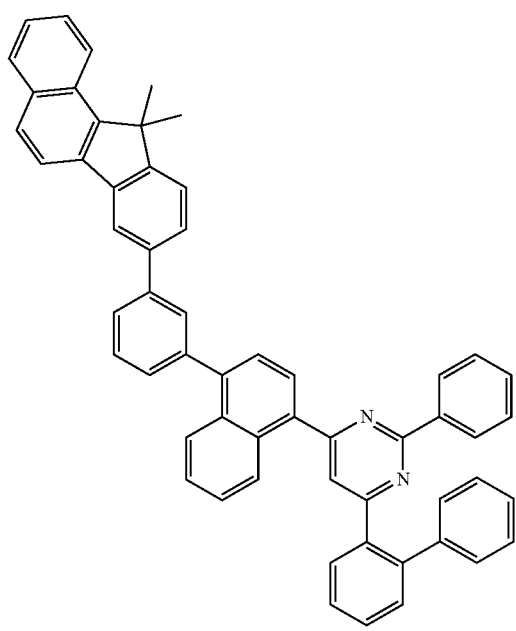
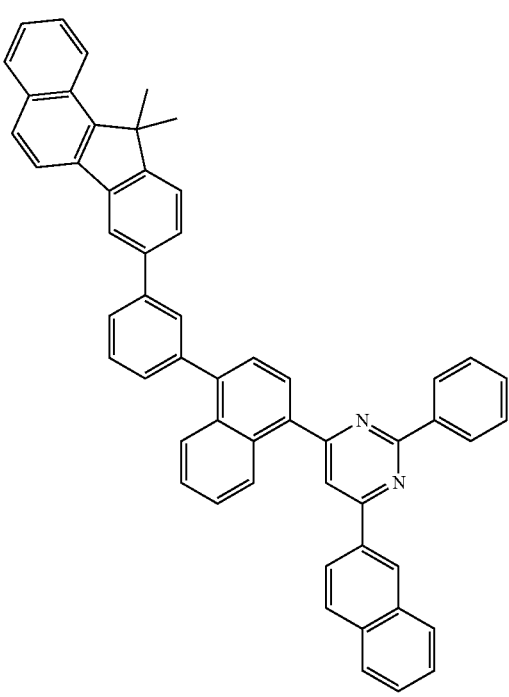

635
-continued
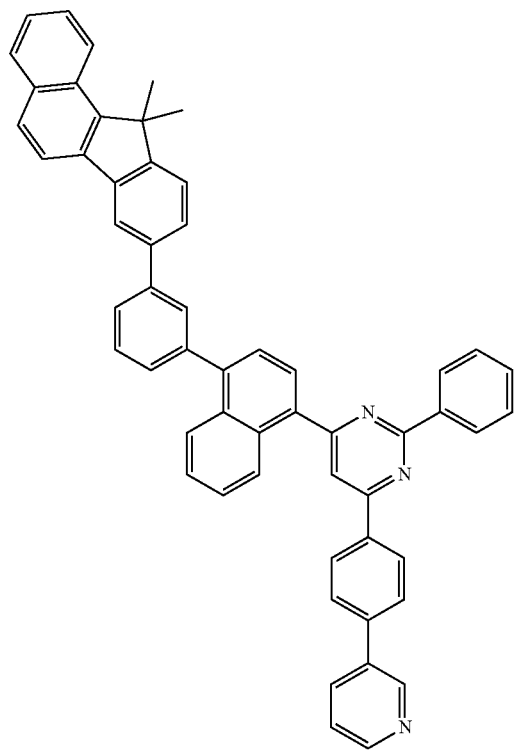
636
-continued
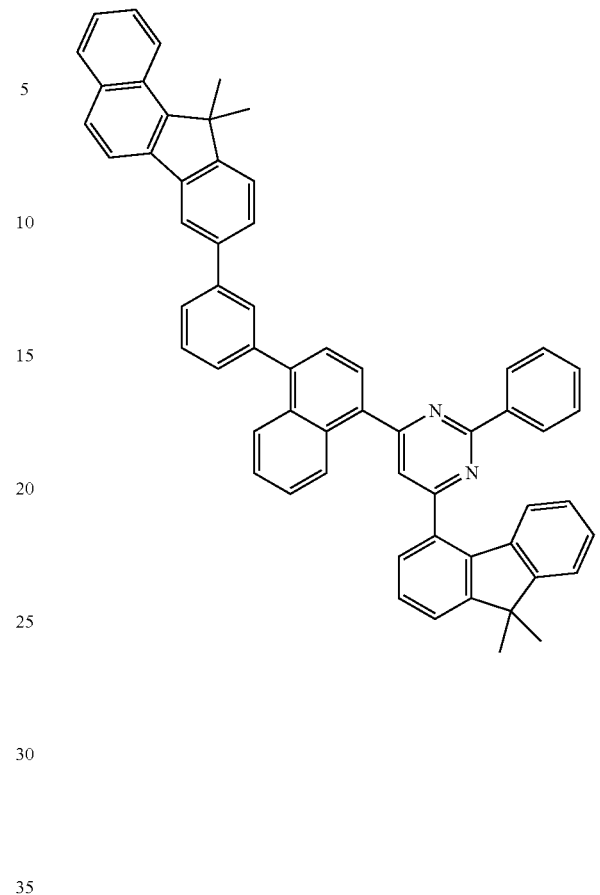
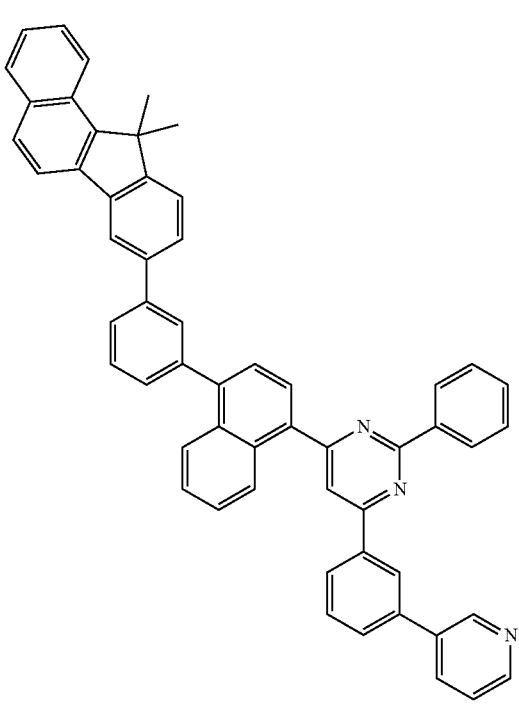
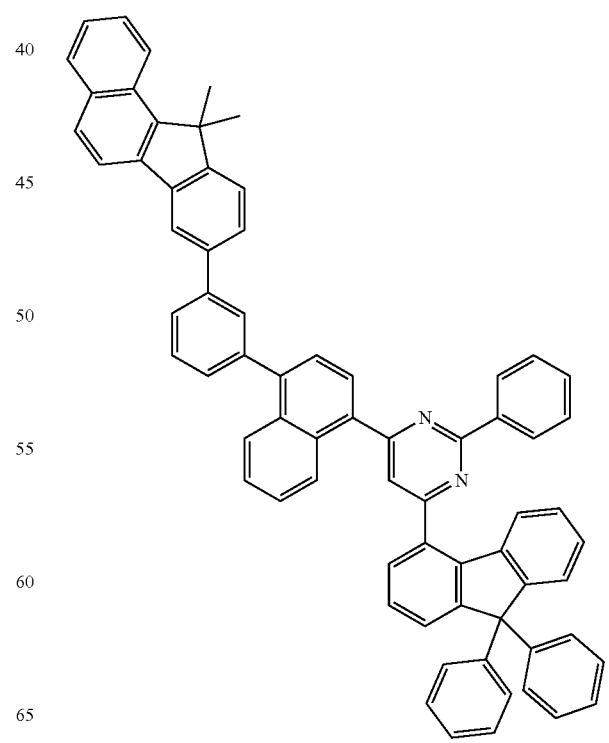

637
-continued
638
-continued
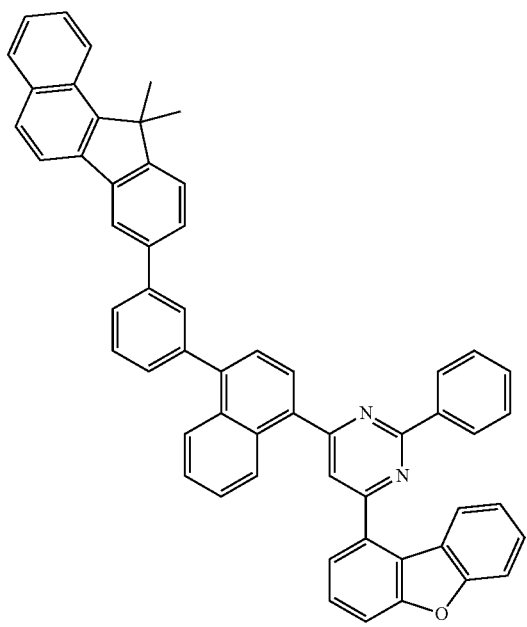
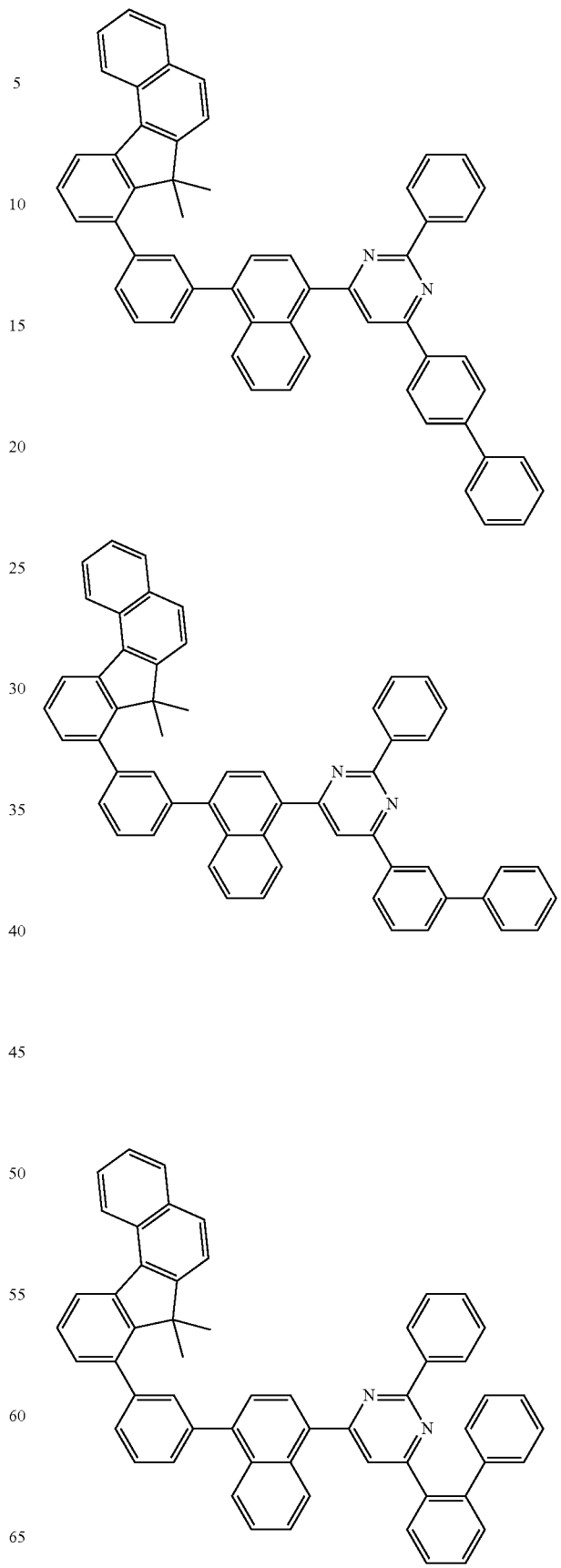

639
-continued
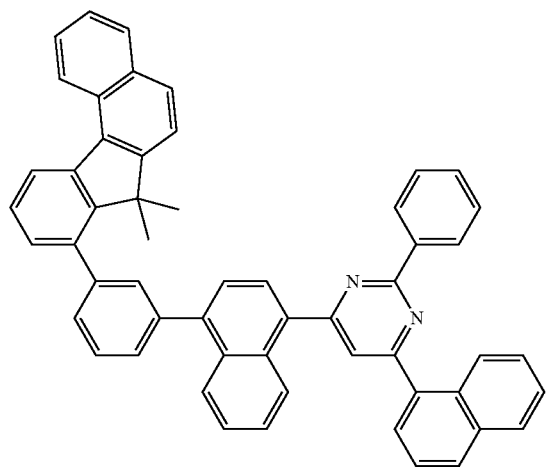
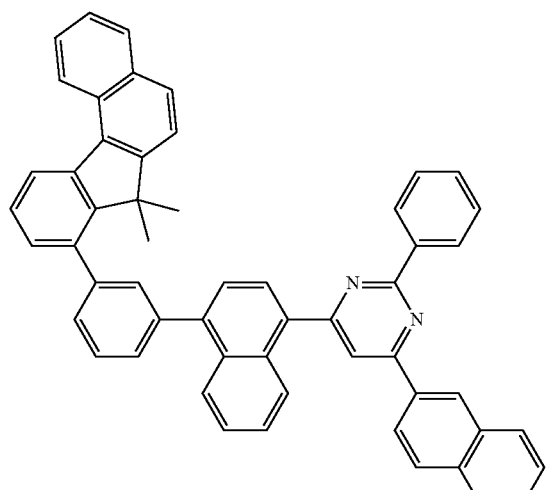
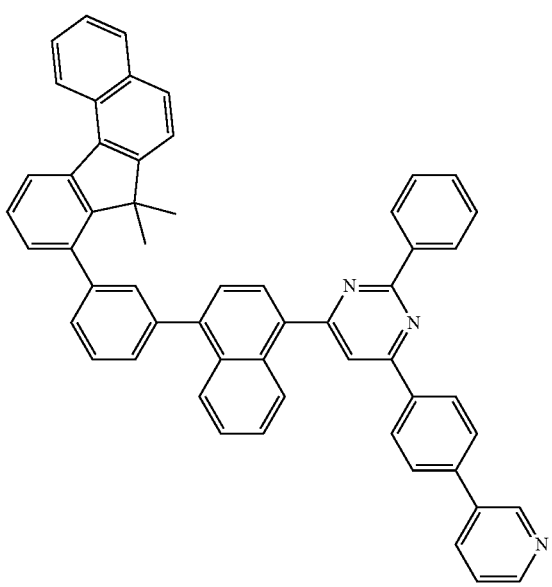
640
-continued
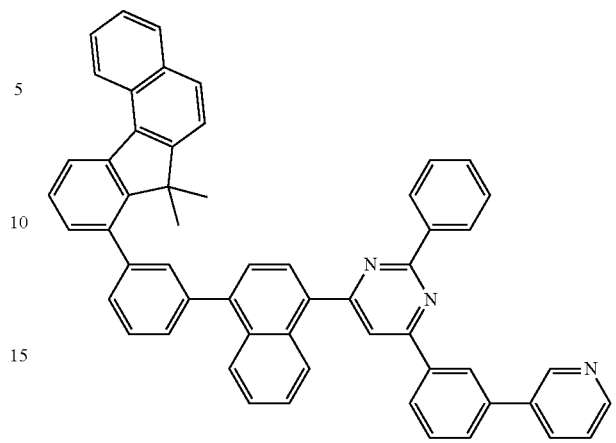
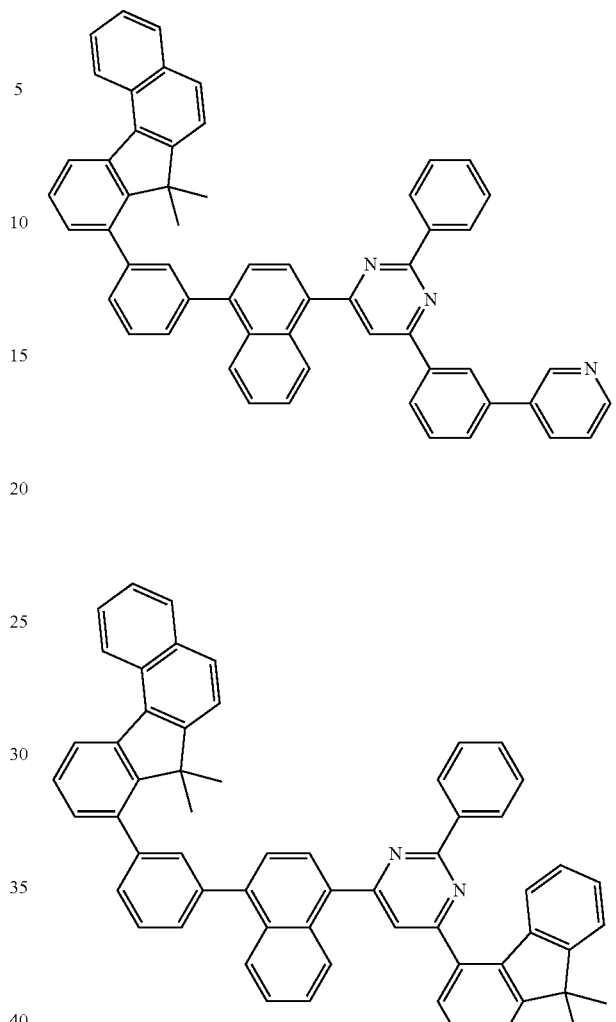
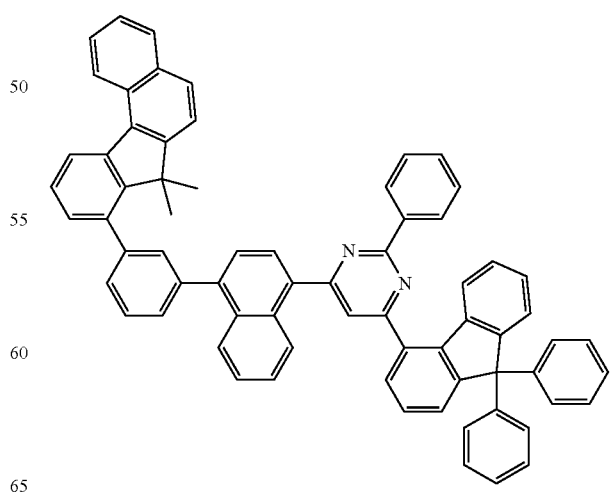

641
-continued
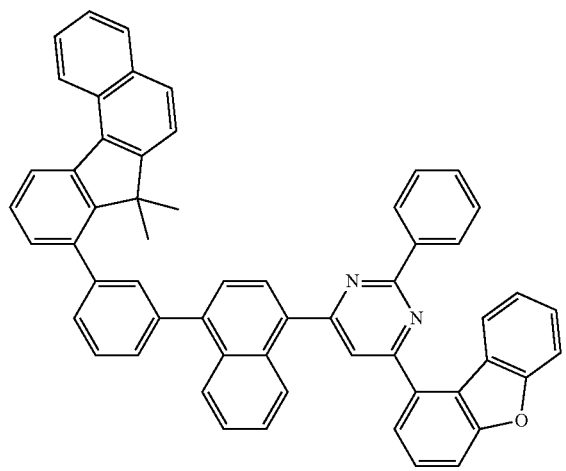
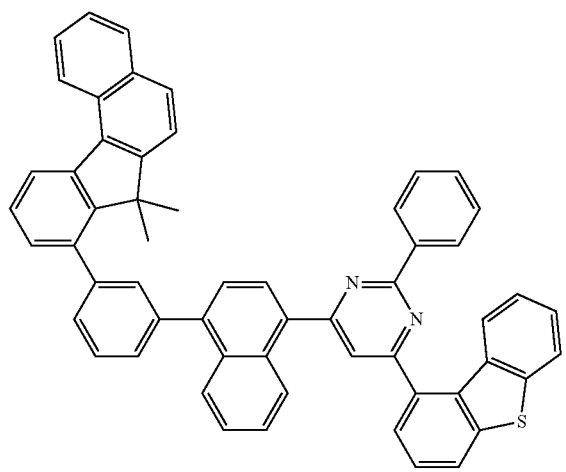
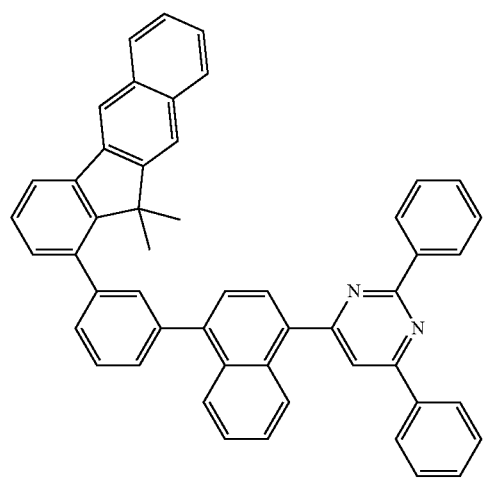
642
-continued
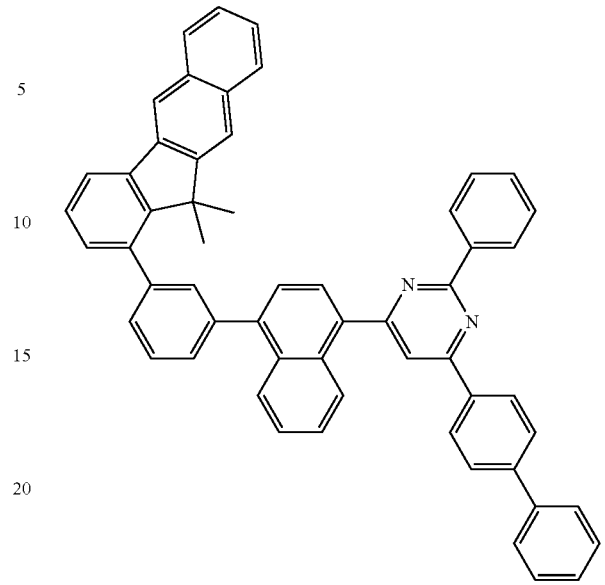
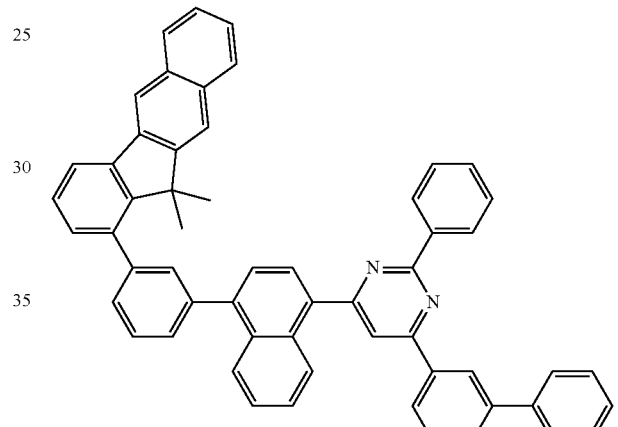
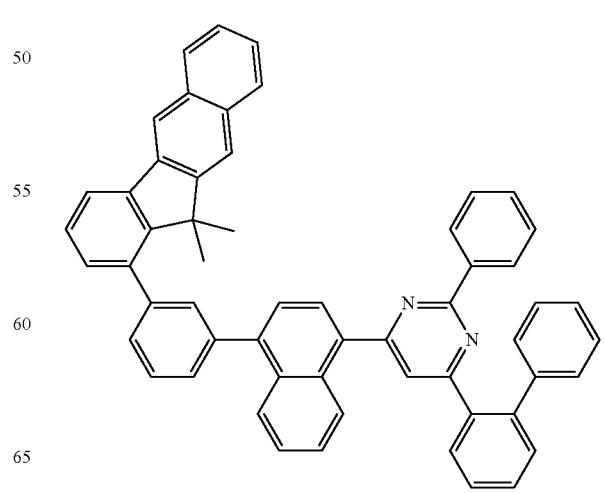

643
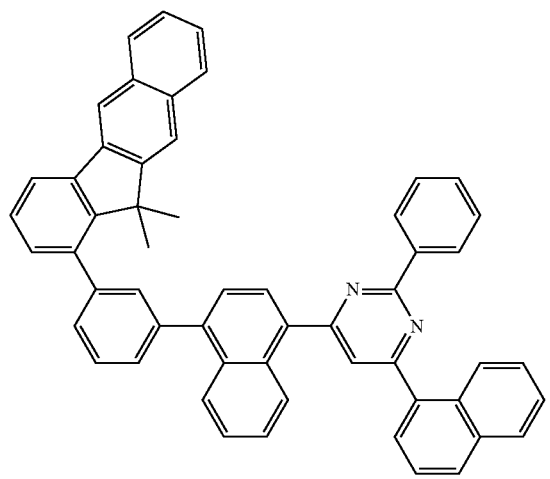
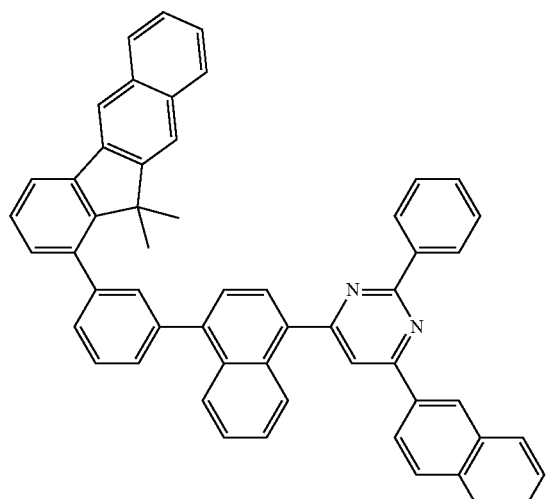
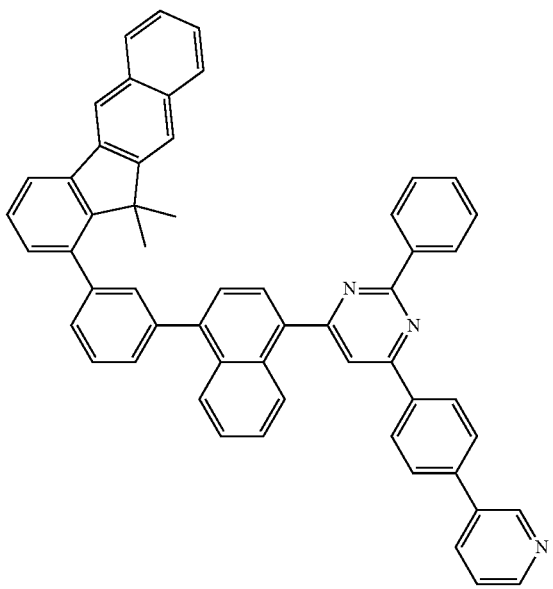
644
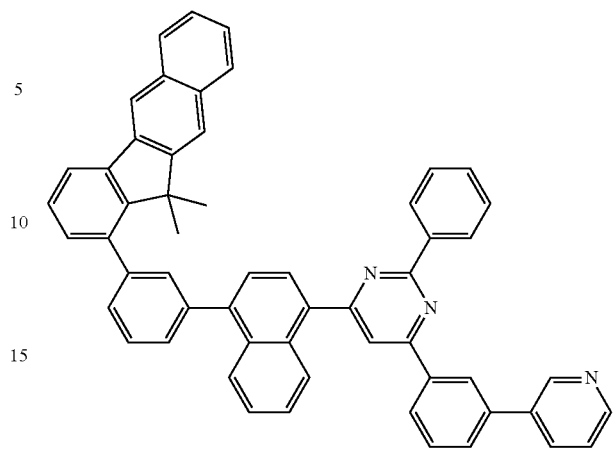
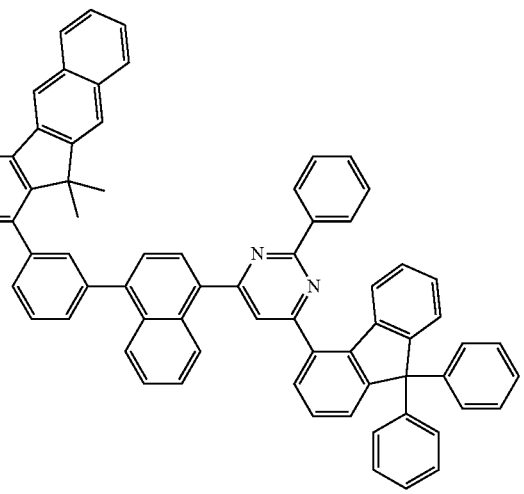

645
-continued
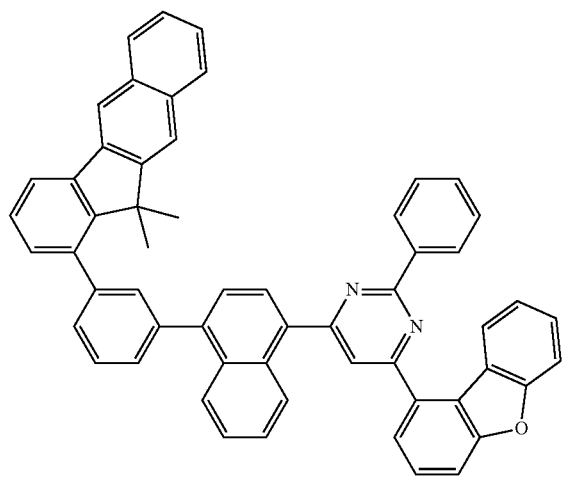
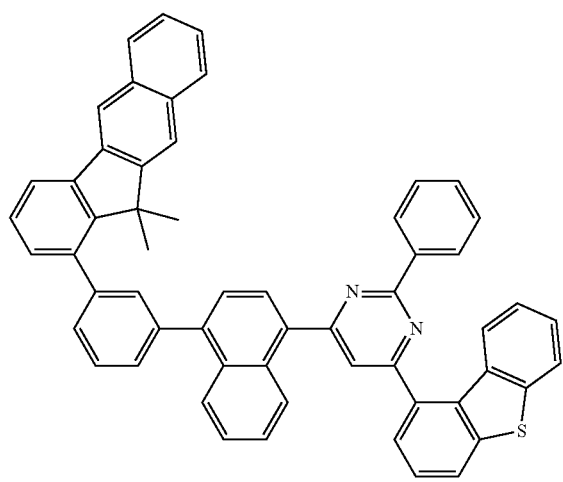
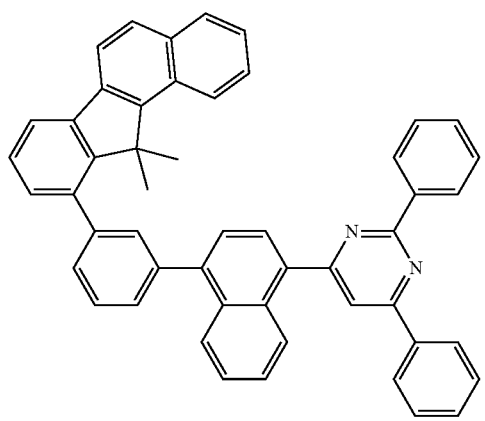
646
-continued
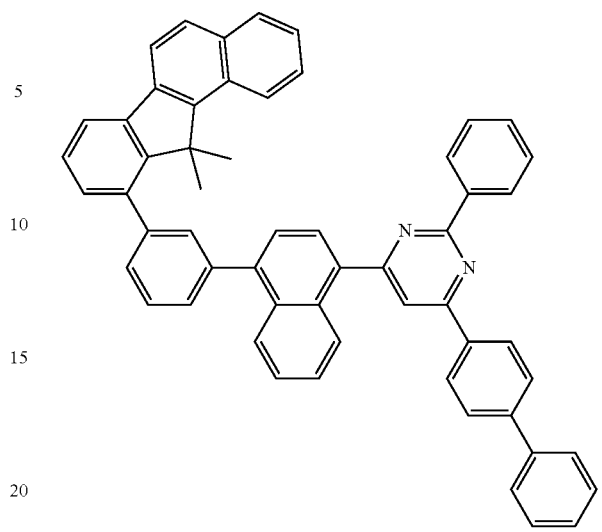
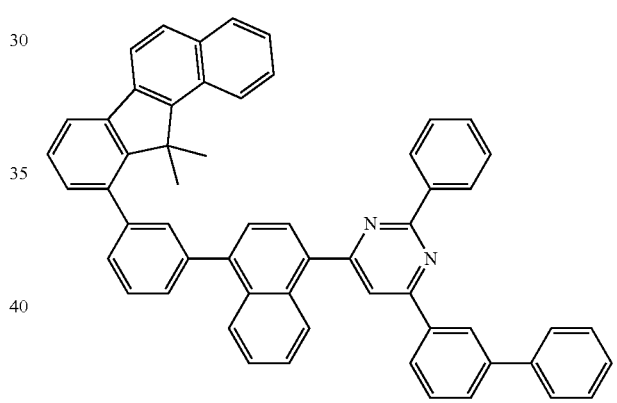
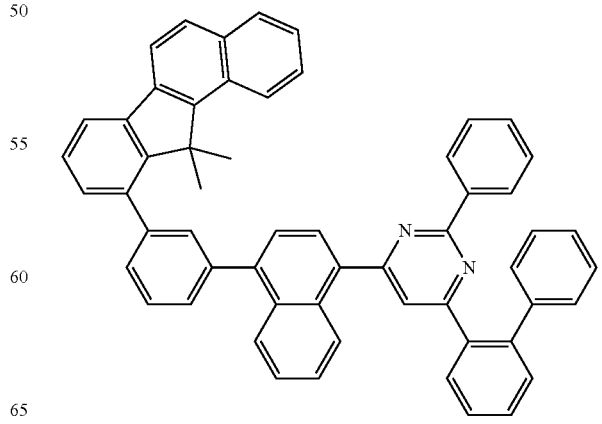

647
-continued
648
-continued
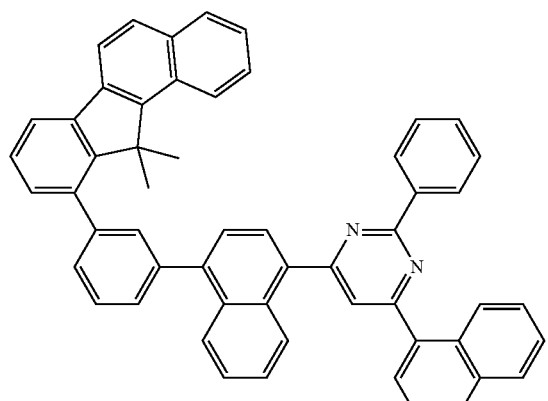
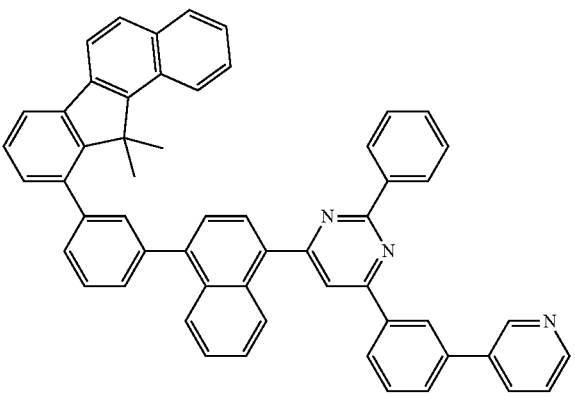
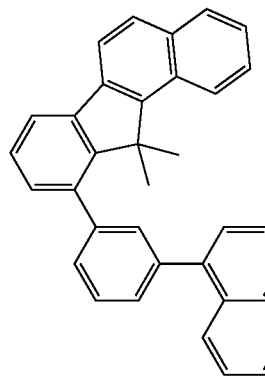
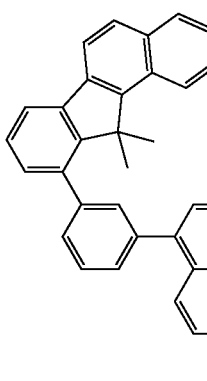
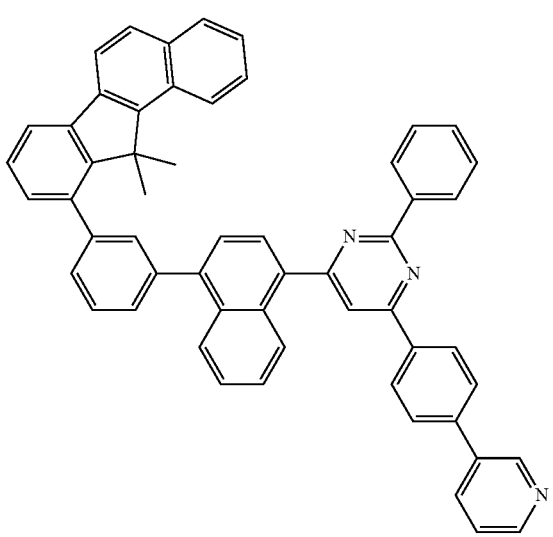
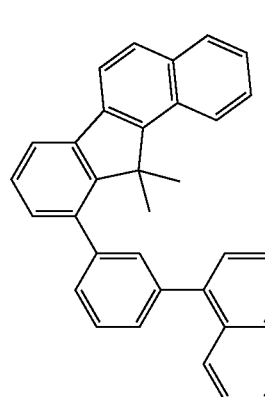

649
-continued
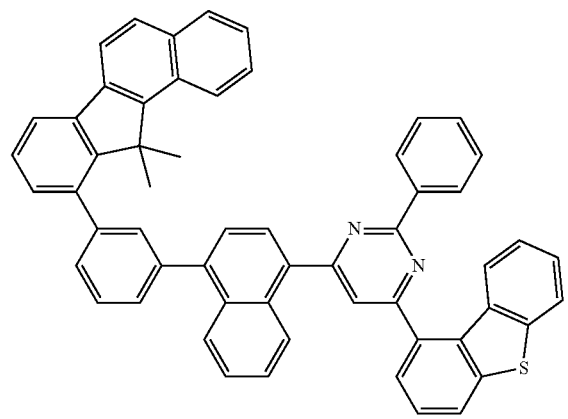
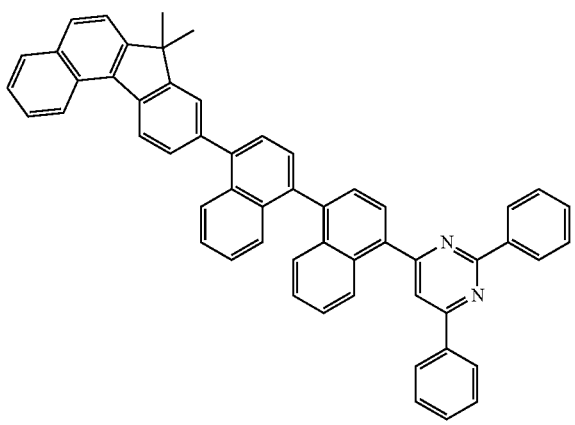
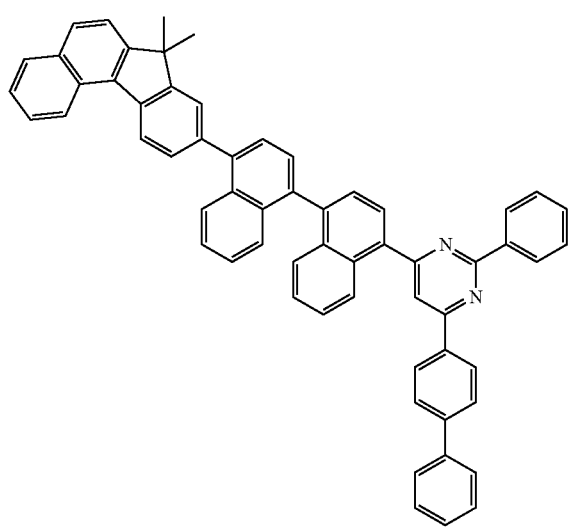
650
-continued
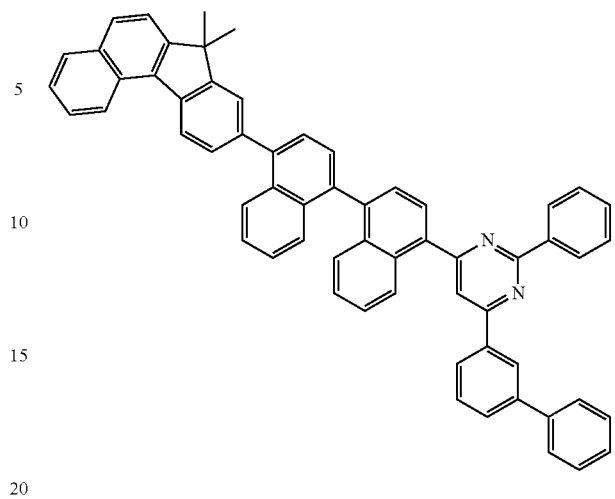
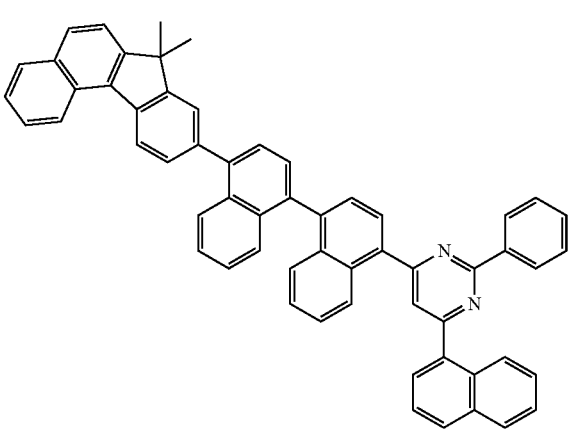

651
-continued
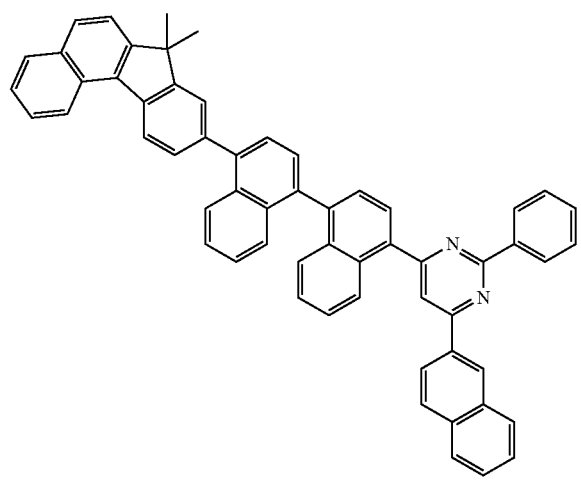
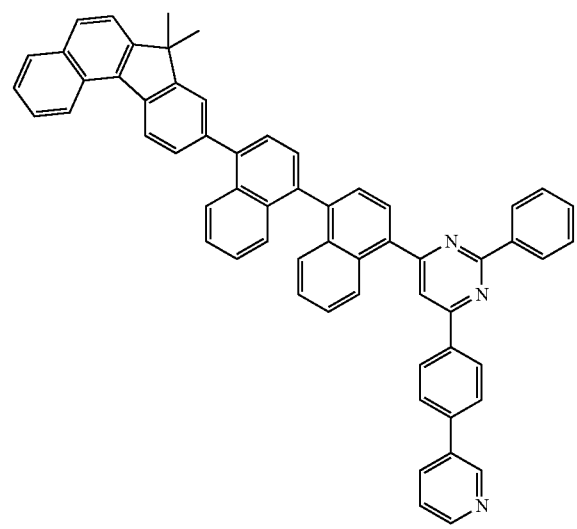
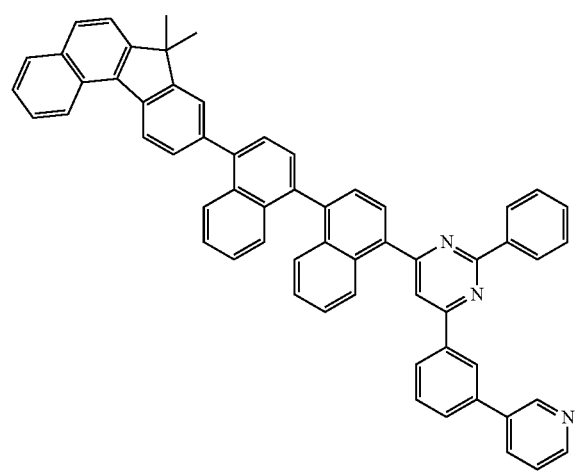
652
-continued
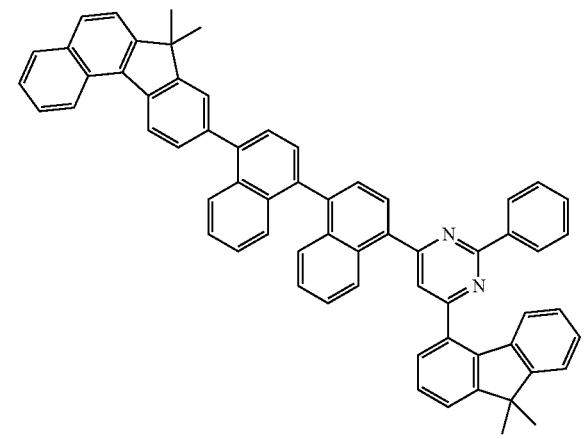
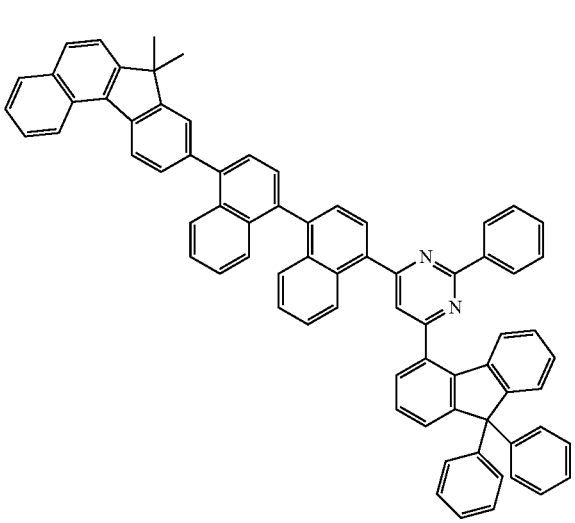
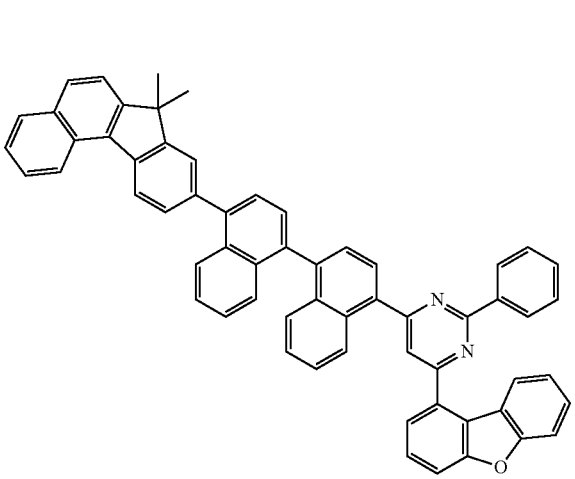

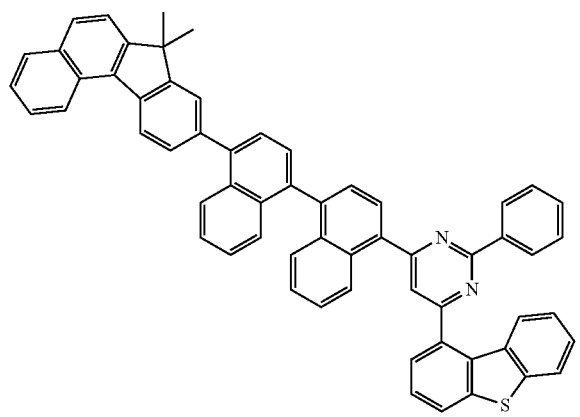
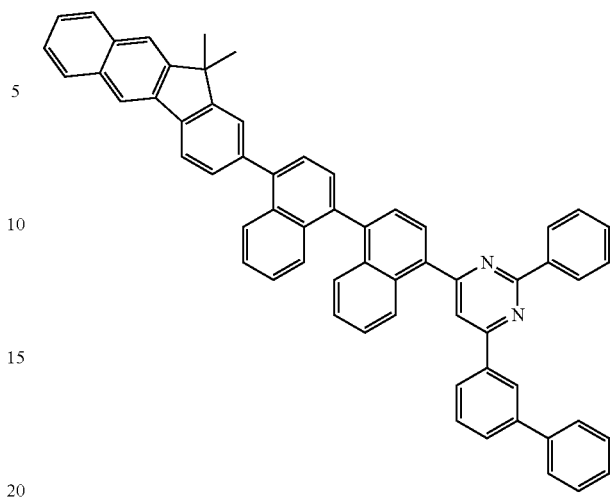
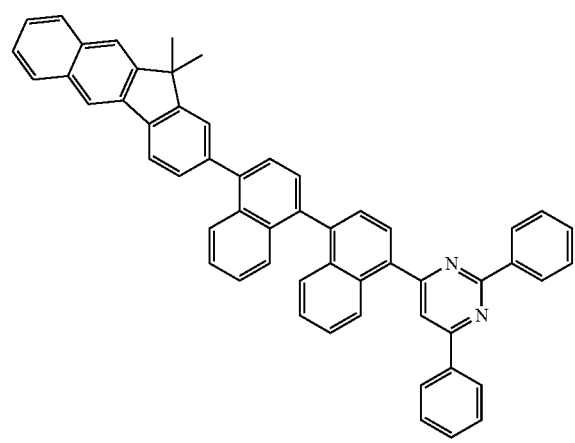
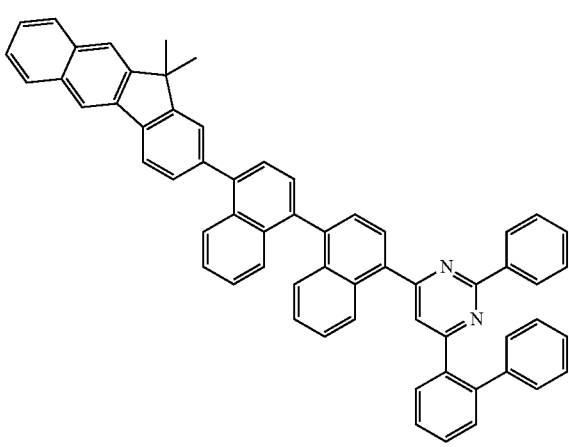
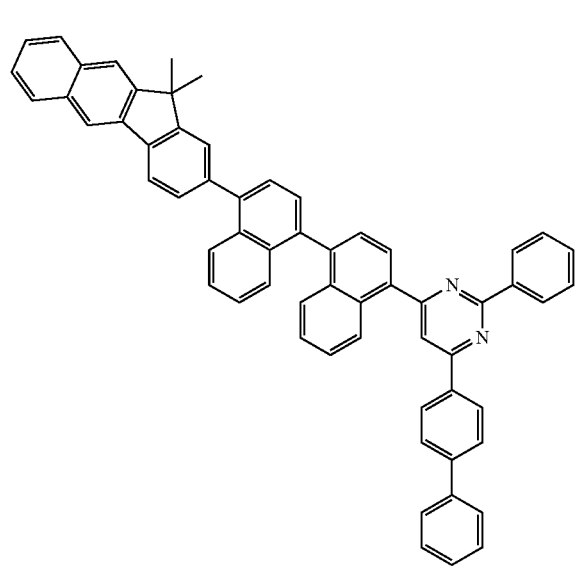
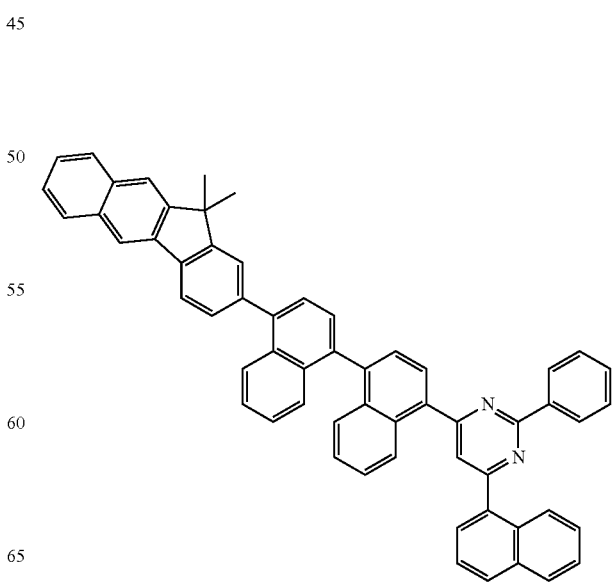

655
-continued
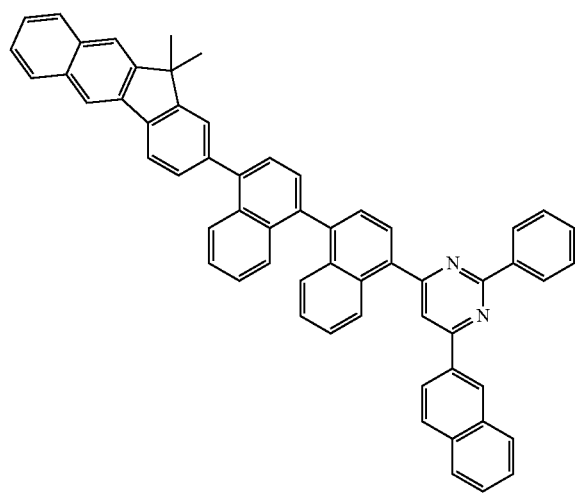
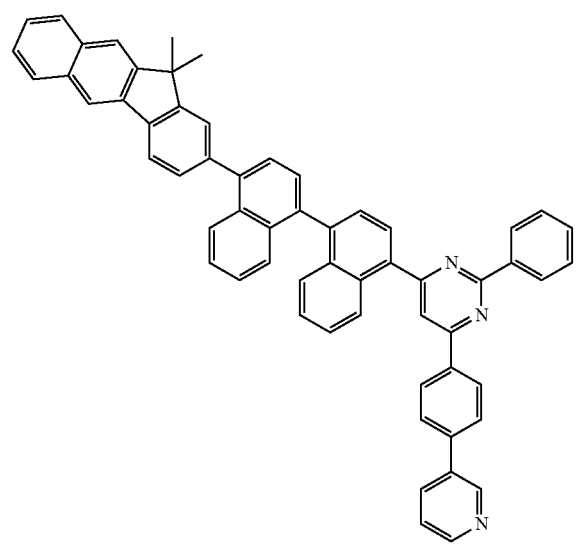
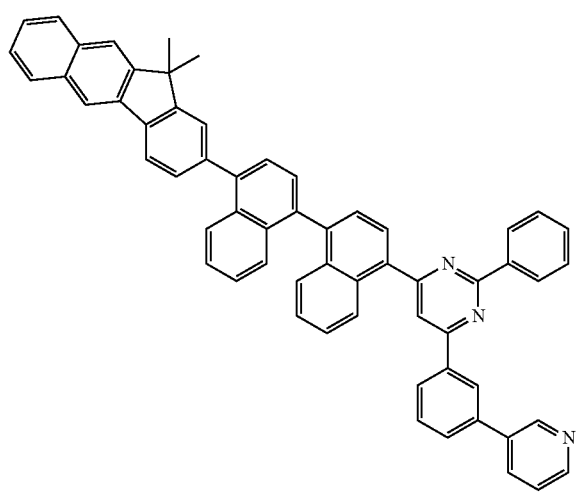
656
-continued
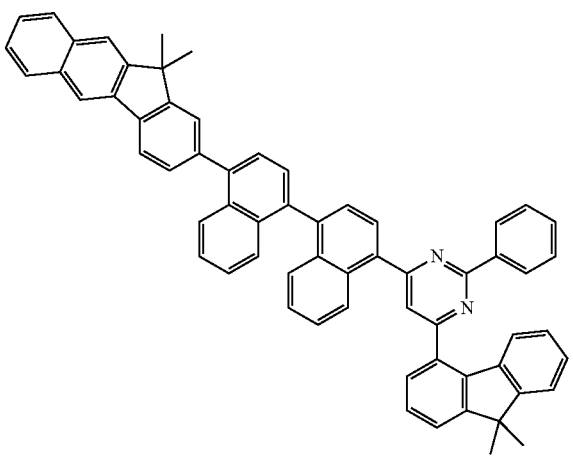
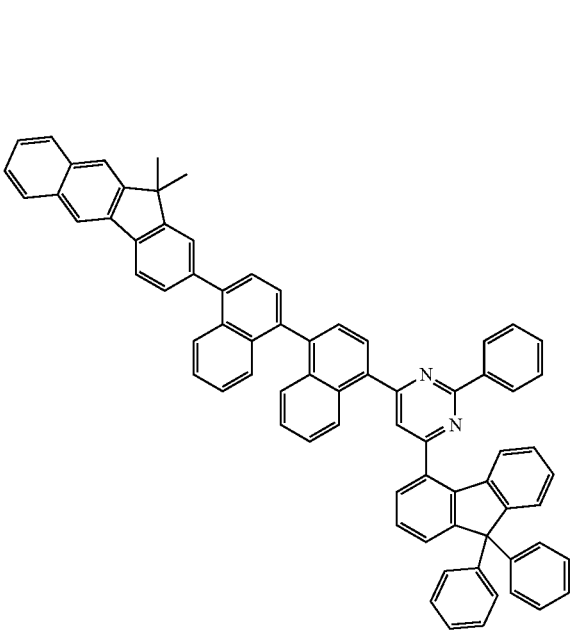
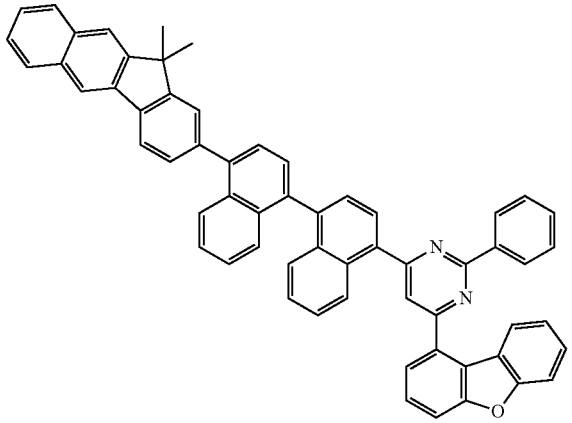

657
-continued
658
-continued
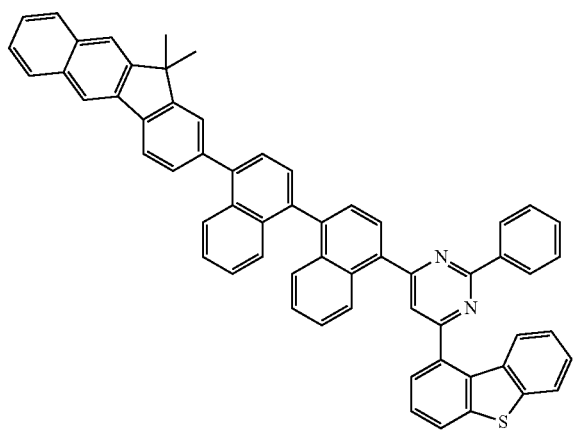
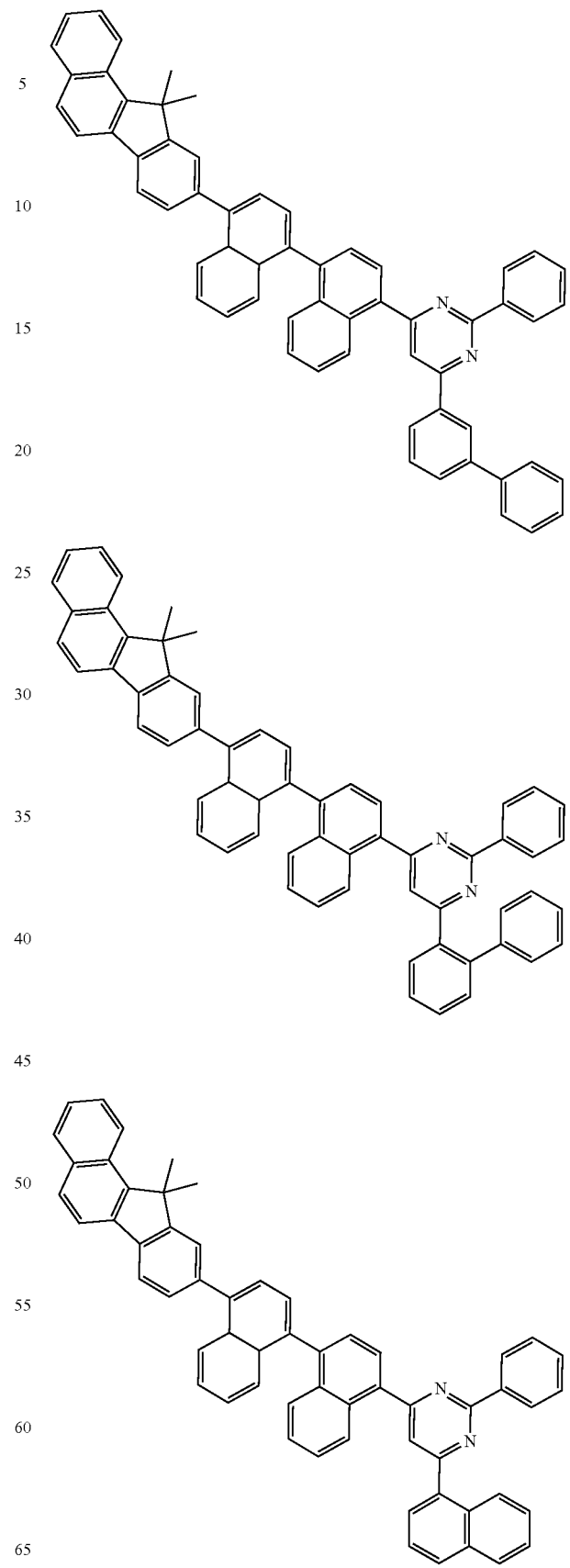

659
-continued
660
-continued
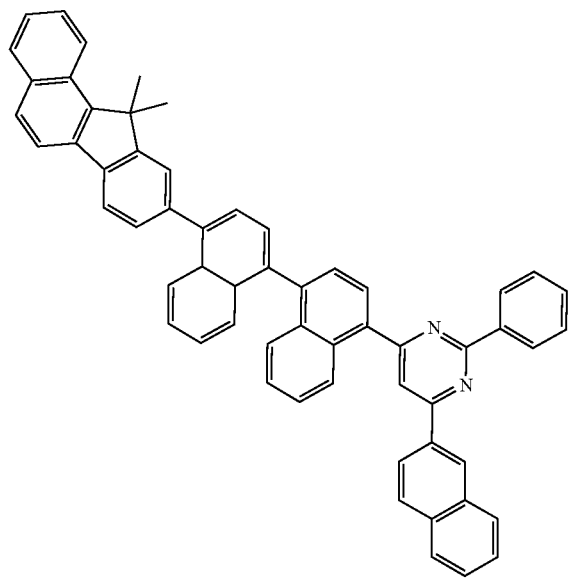
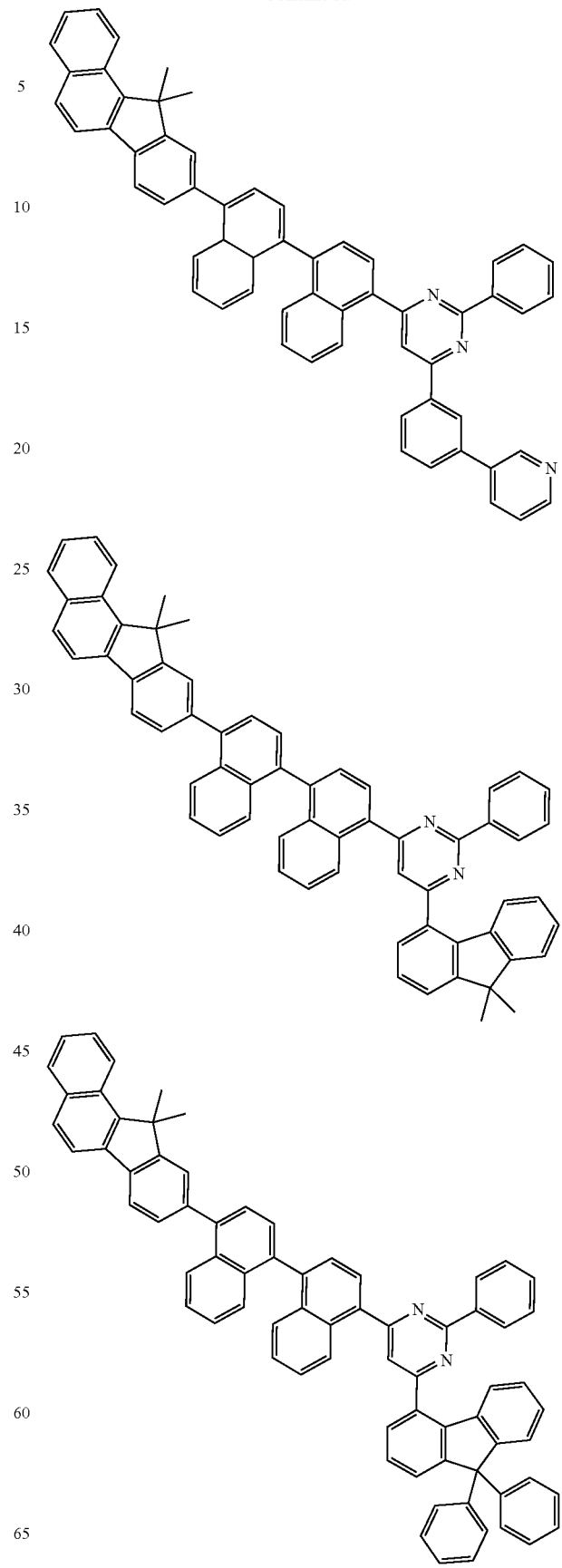

661
-continued
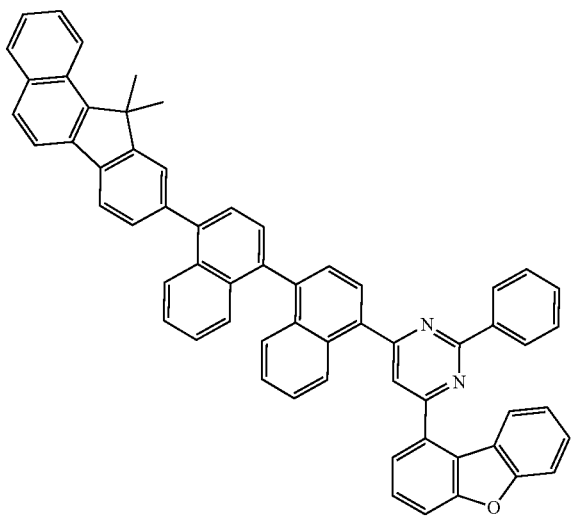
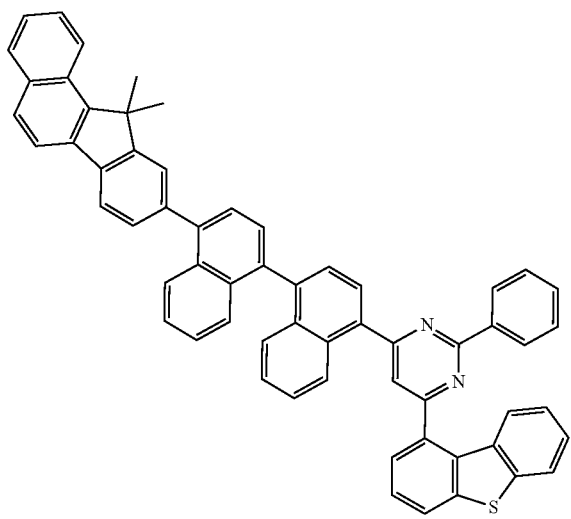
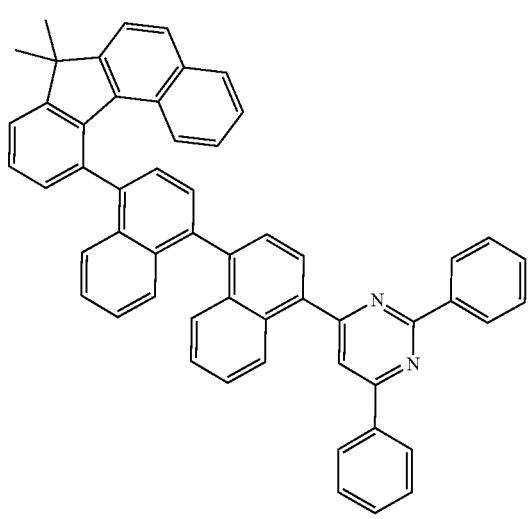
662
-continued
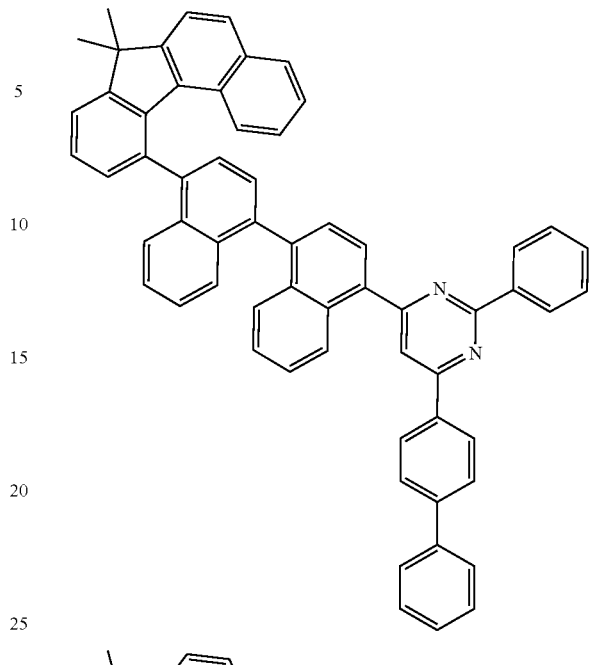
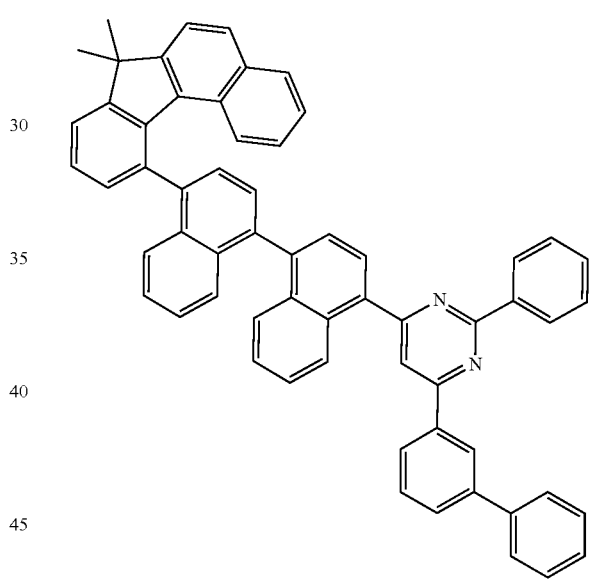
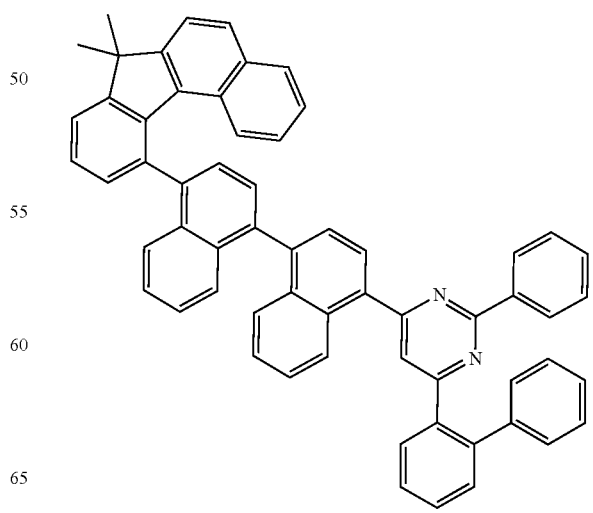

663
-continued
664
-continued
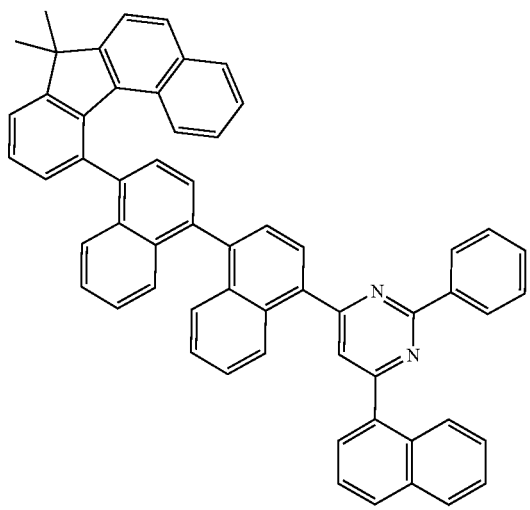
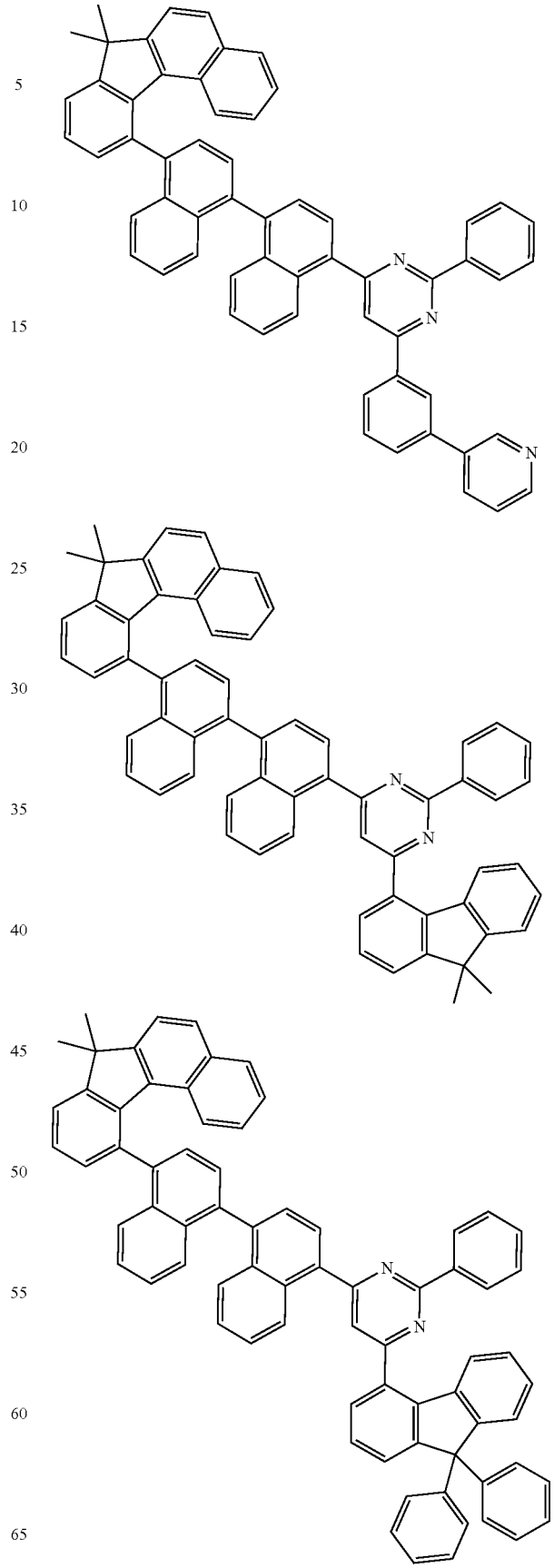

665
-continued
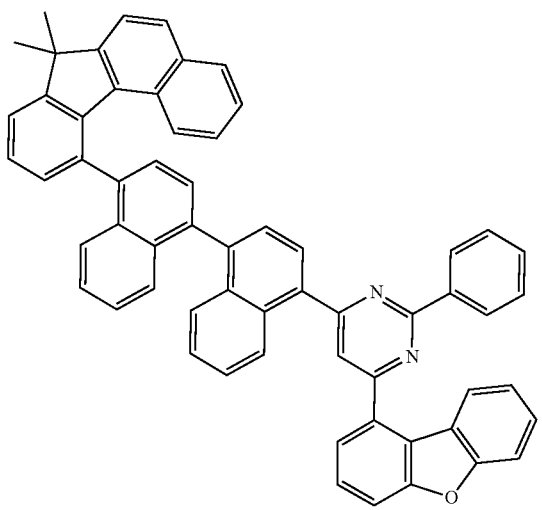
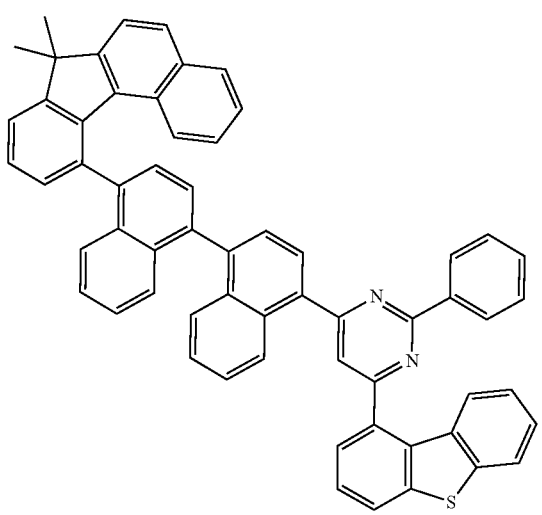
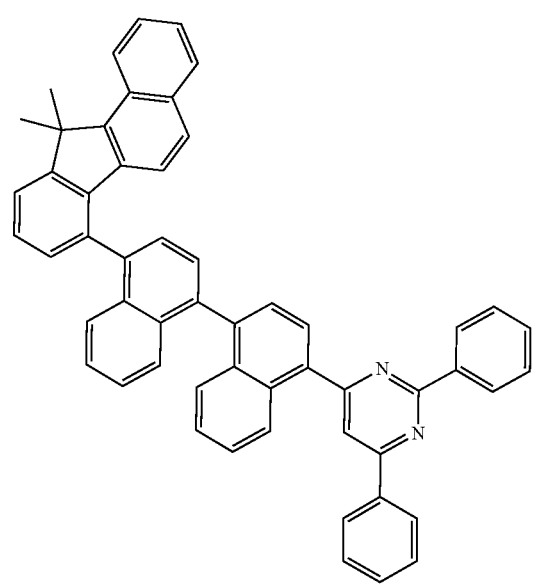
666
-continued
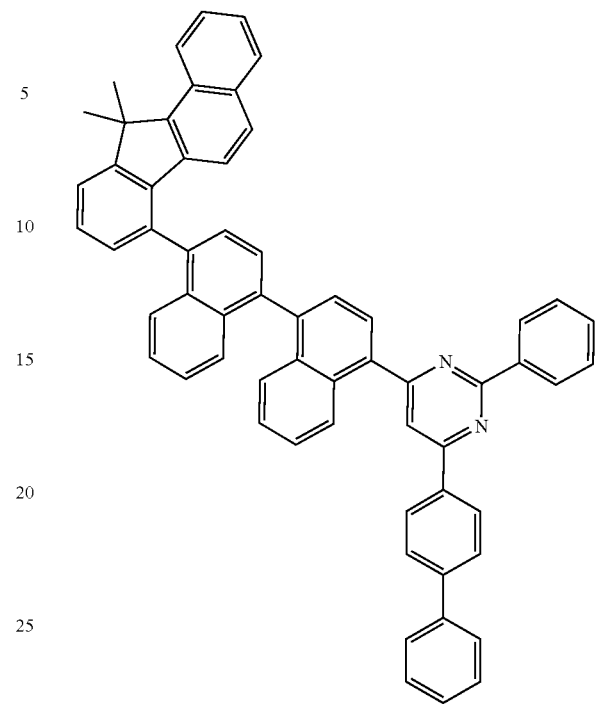
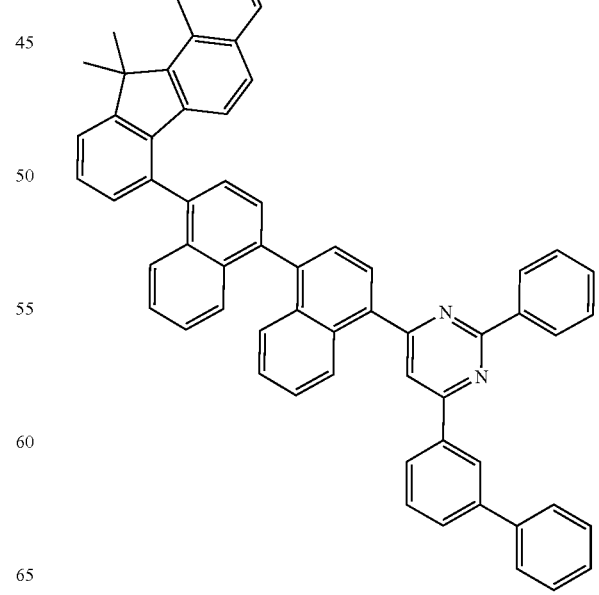

667
-continued
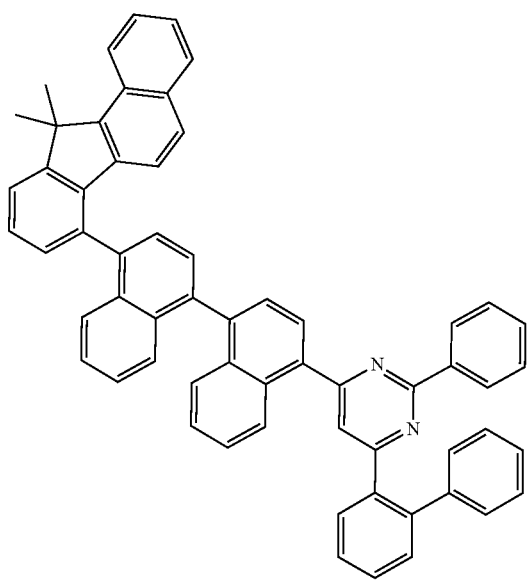
668
-continued
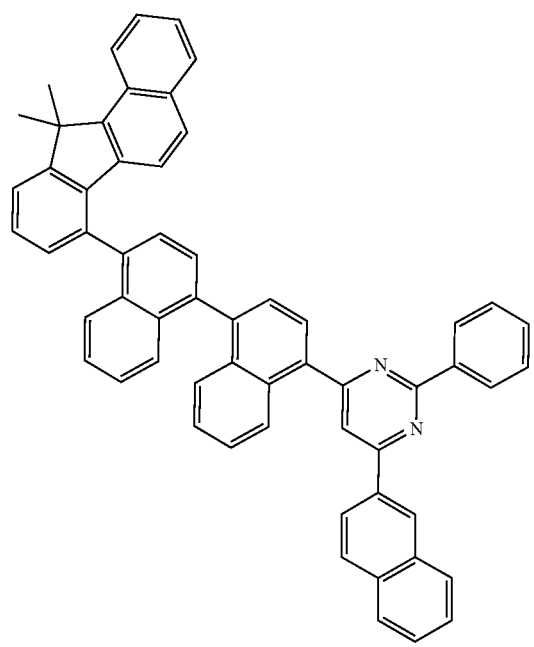
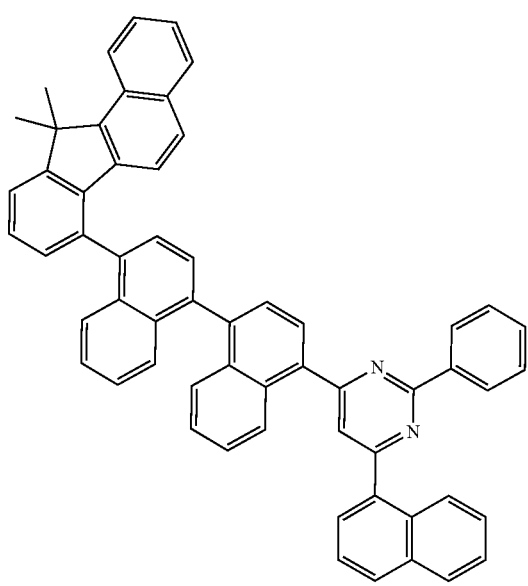
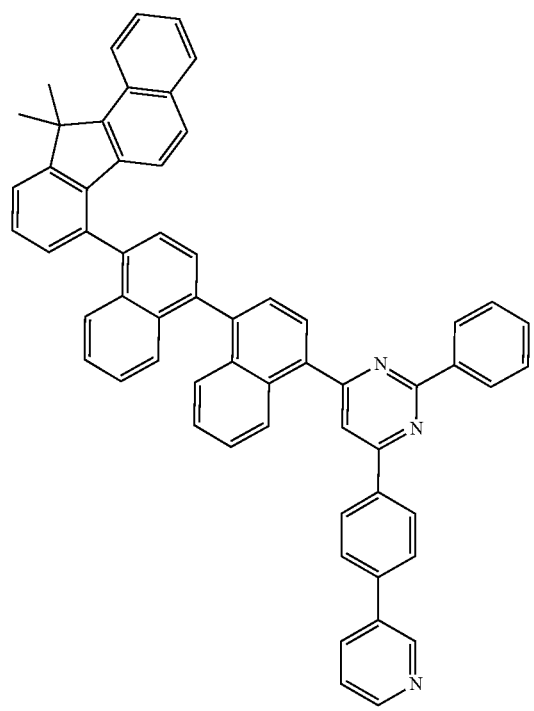

669
-continued
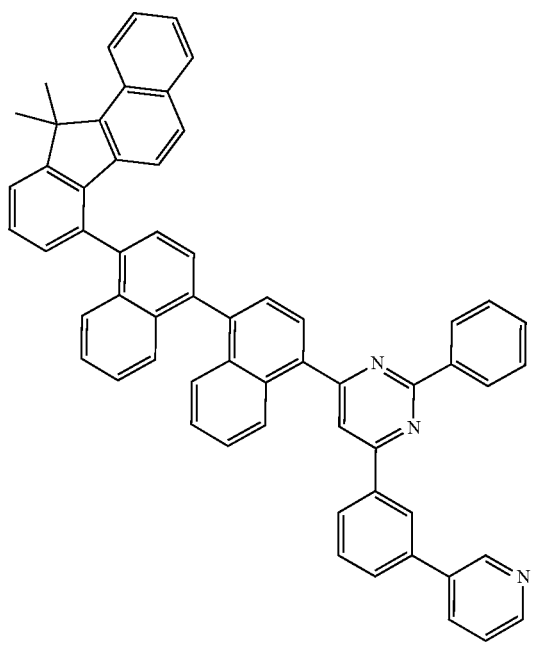
670
-continued
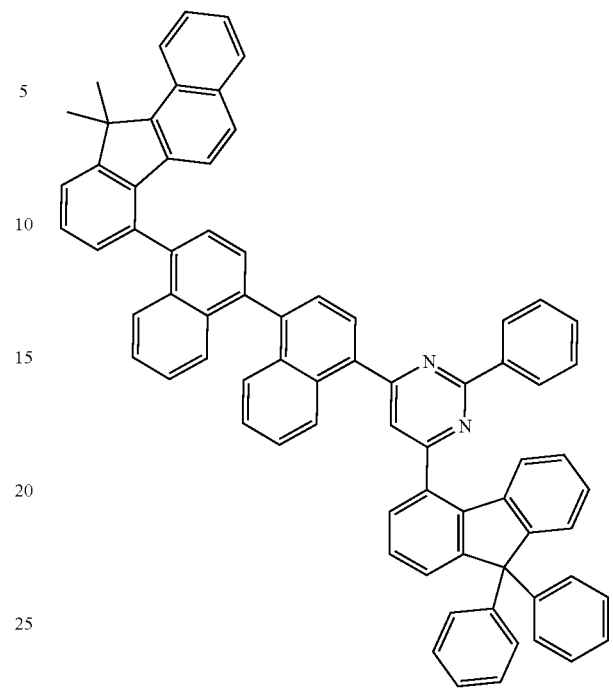
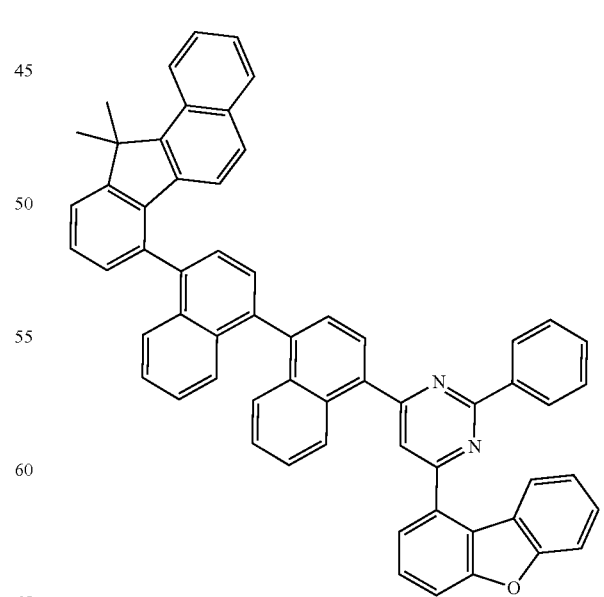

671
-continued
672
-continued
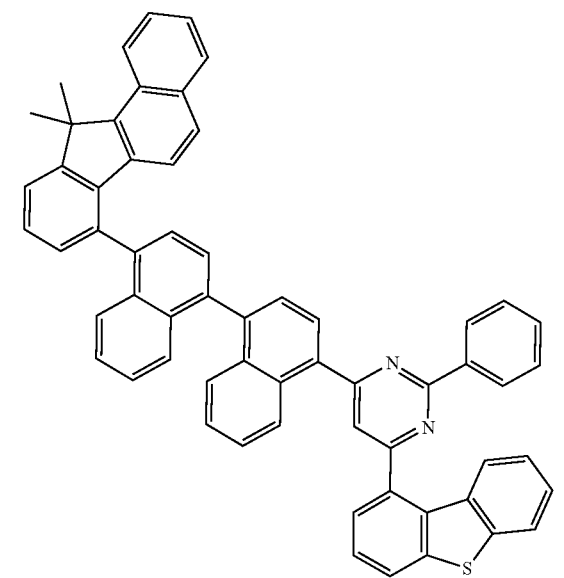
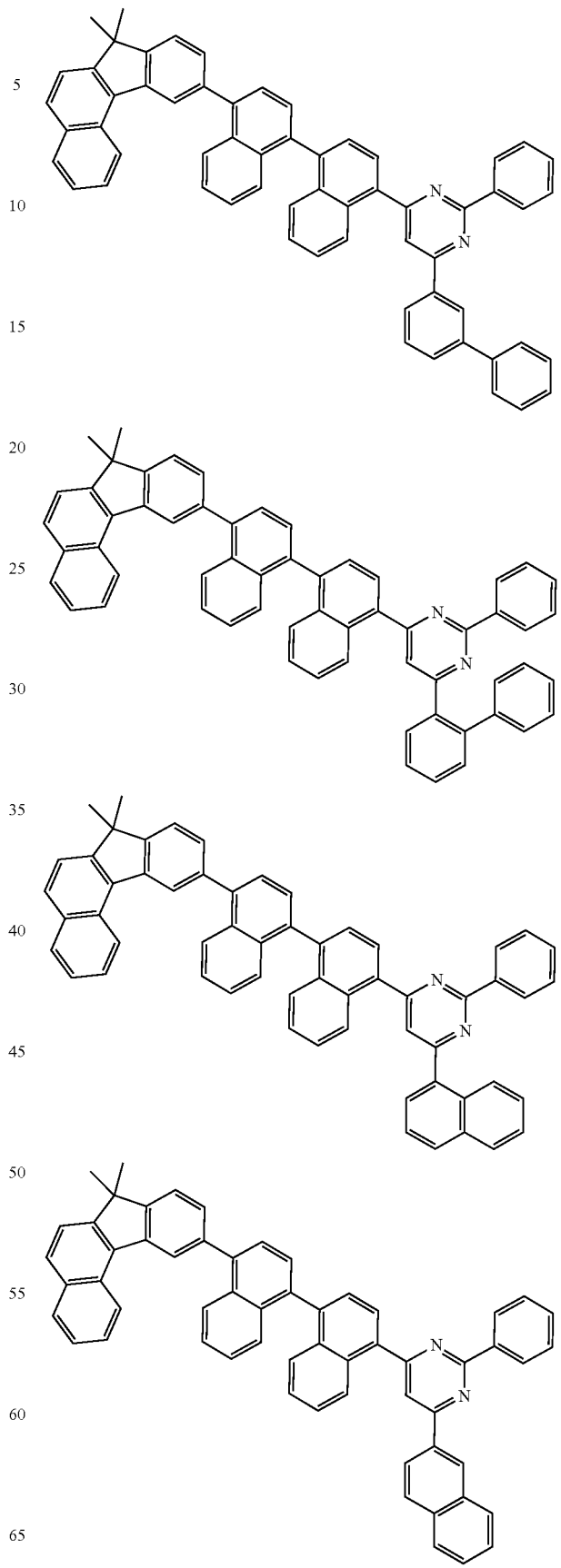

673
-continued
674
-continued
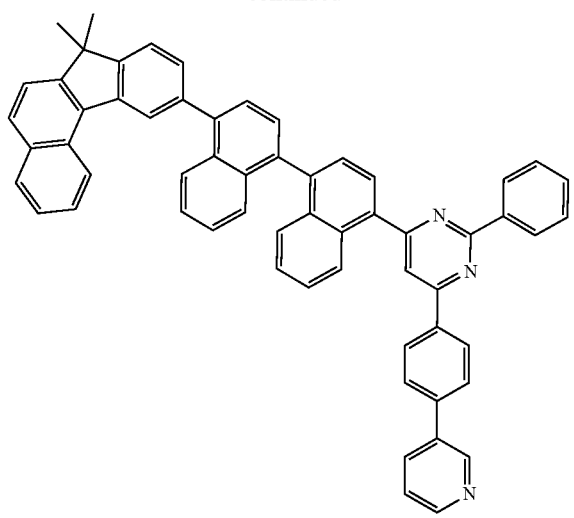
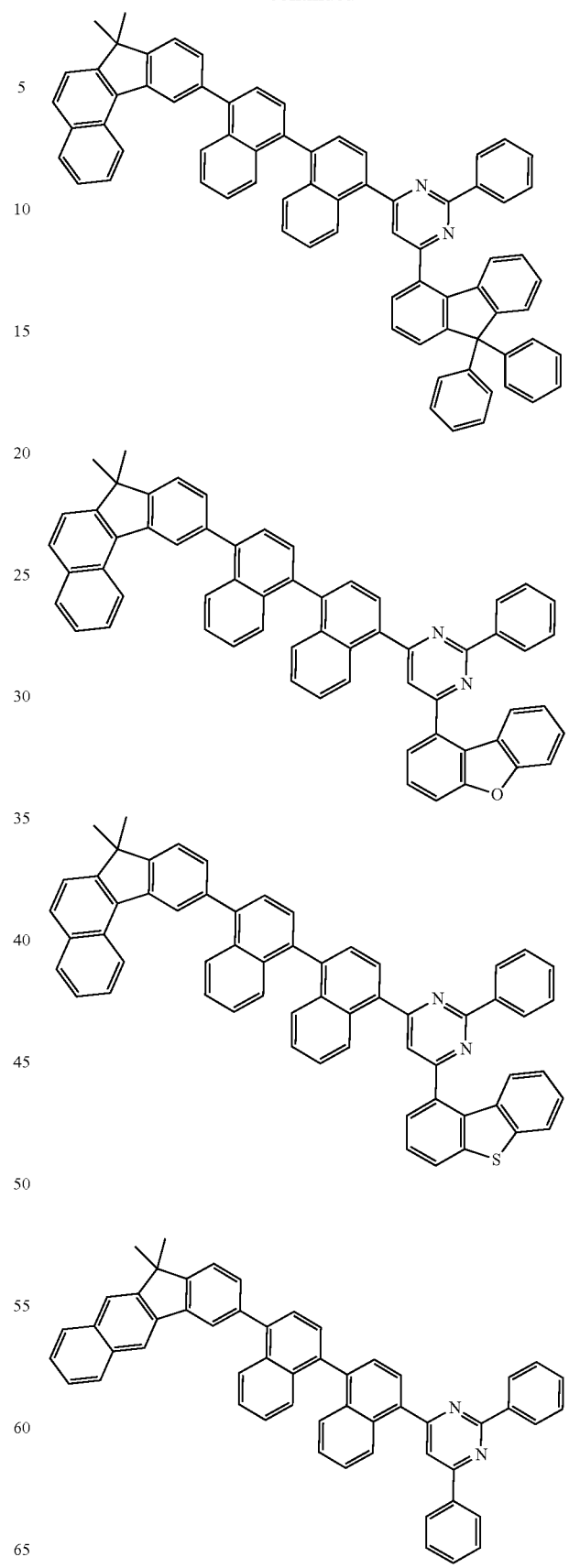

675
-continued
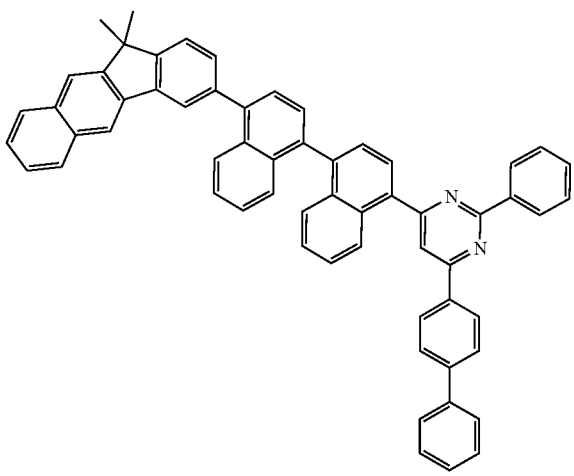
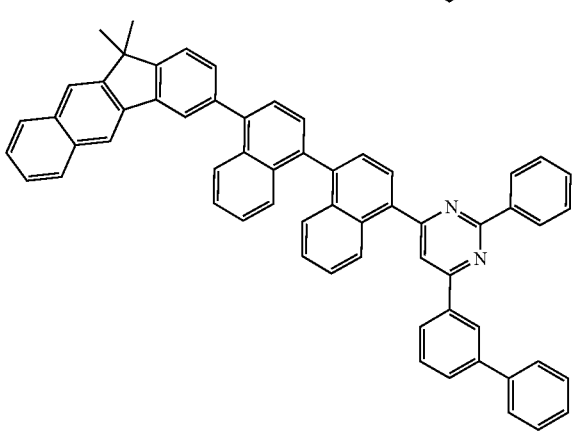
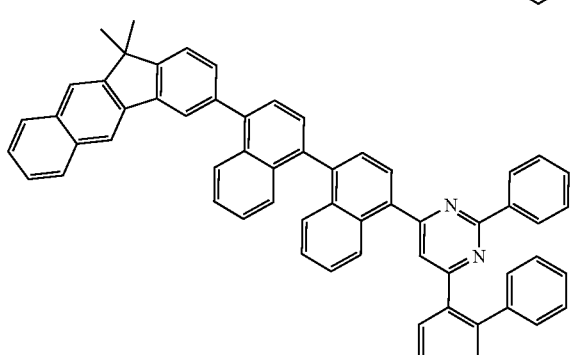
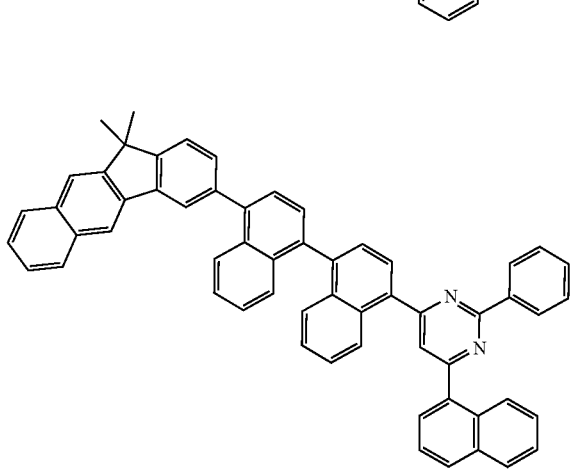
676
-continued
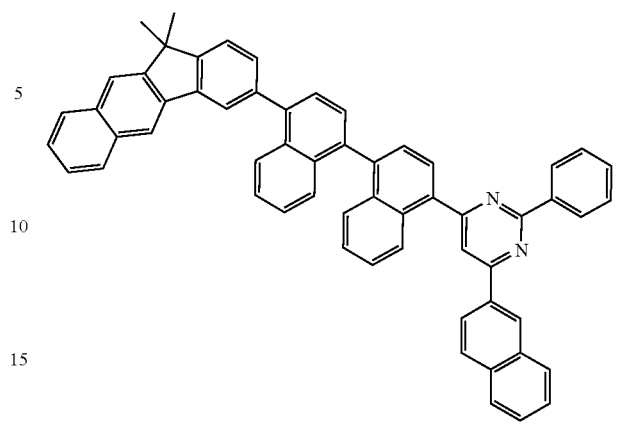
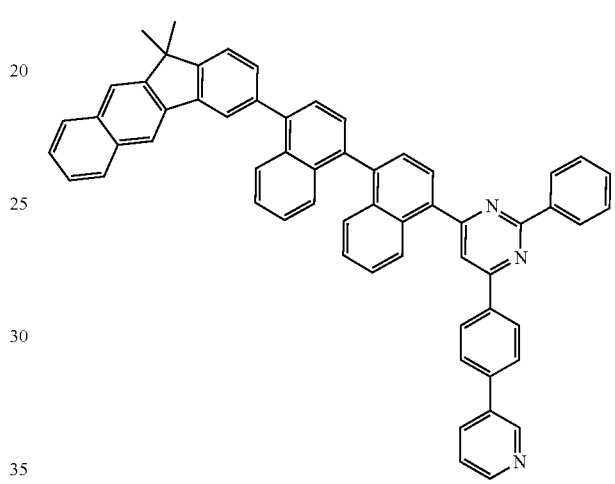
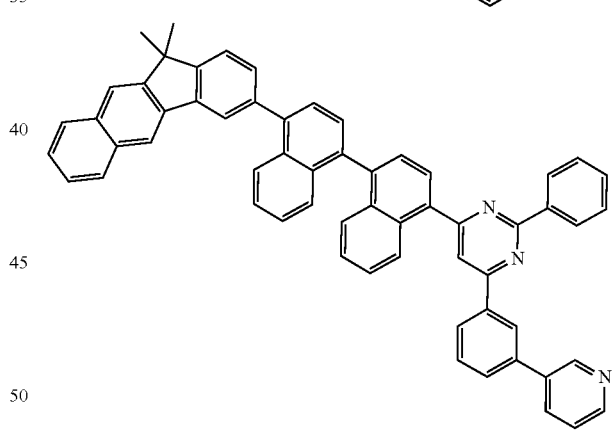
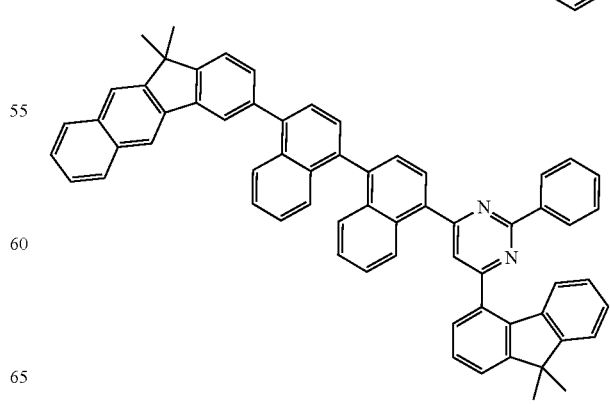

677
-continued
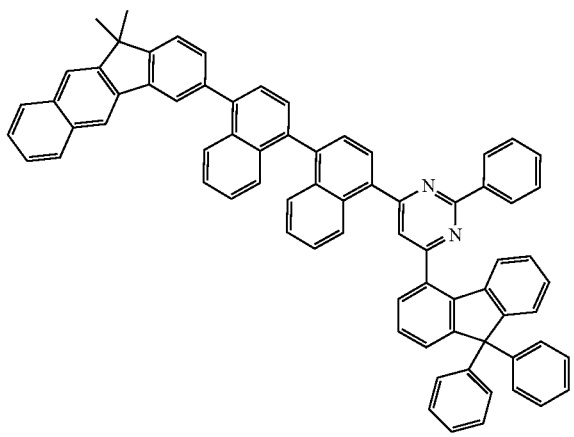
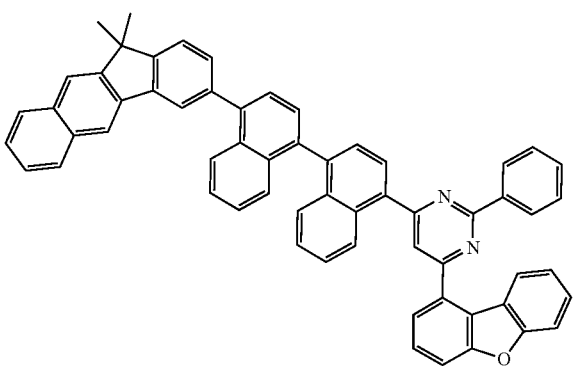
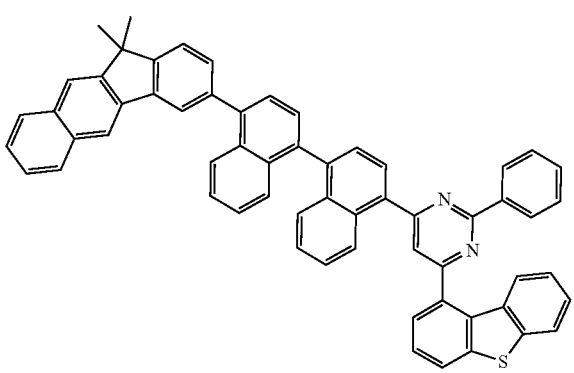
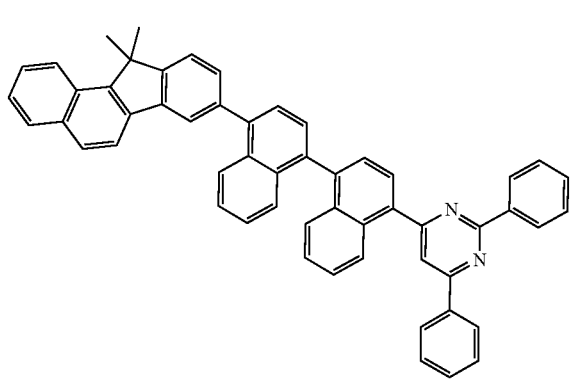
678
-continued
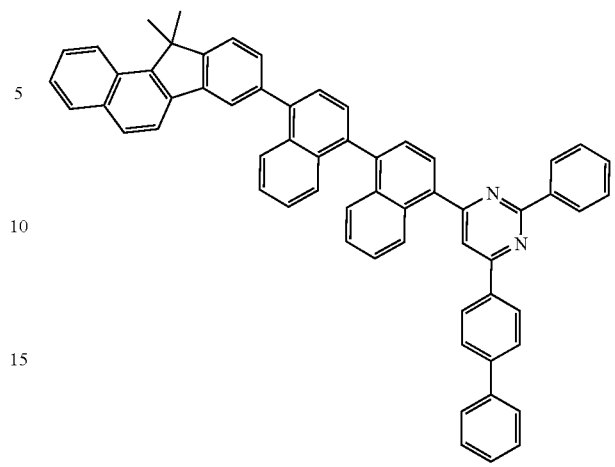
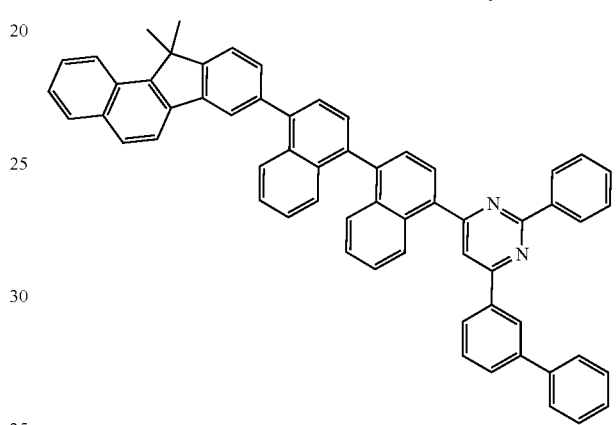
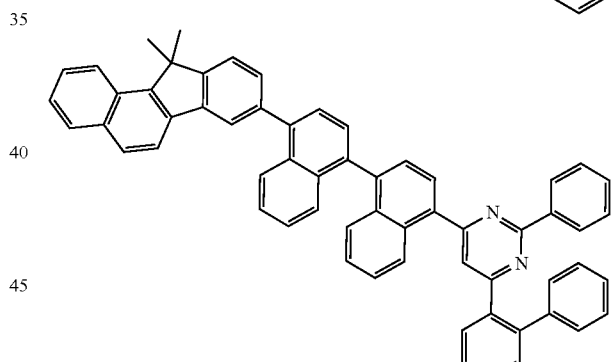
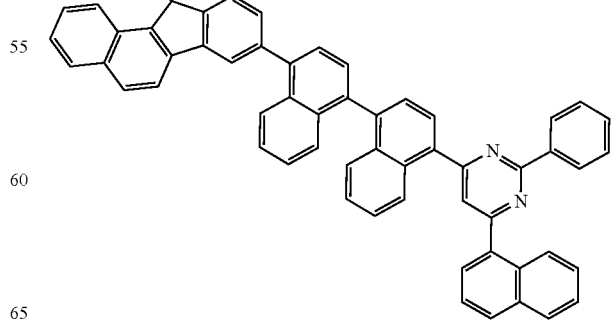

679
-continued
680
-continued
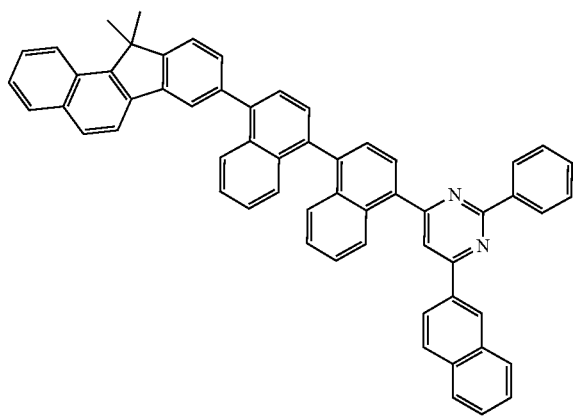
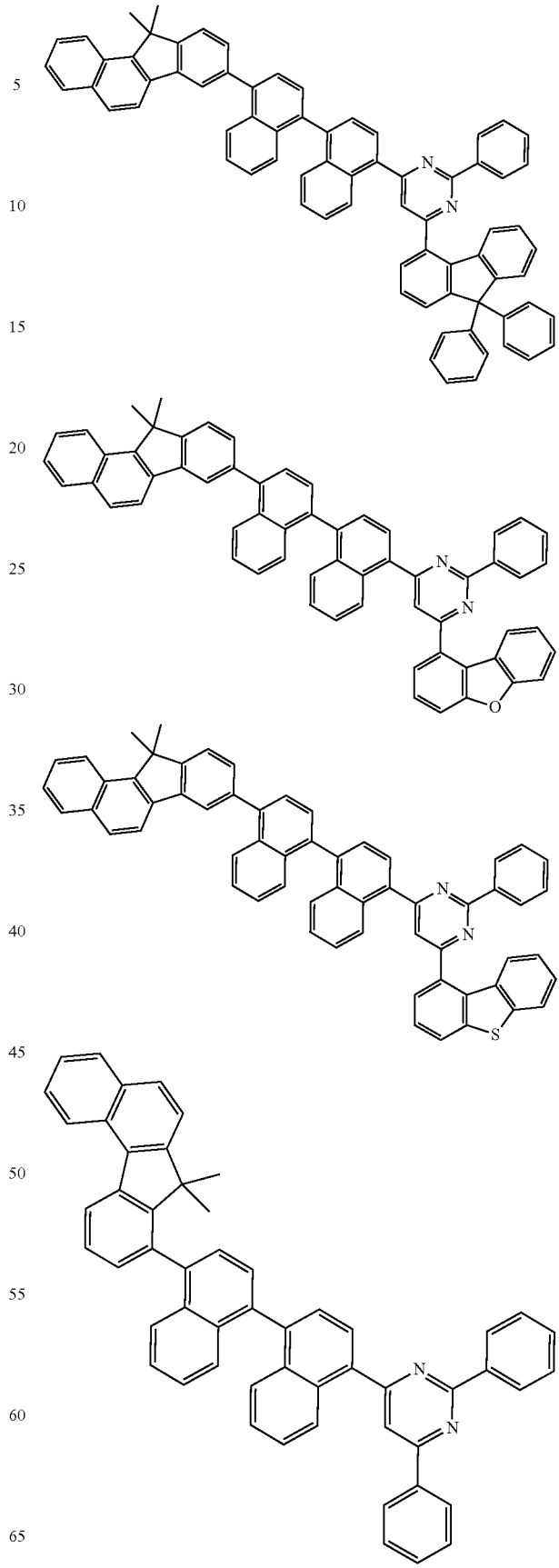

681
-continued
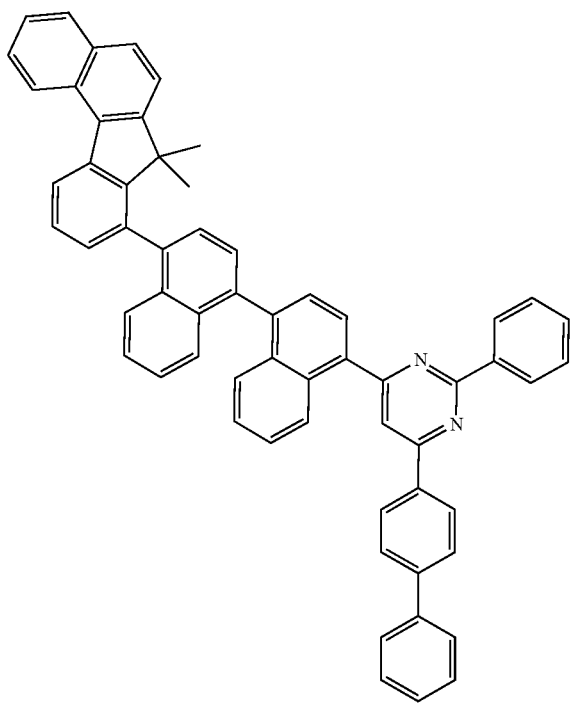
682
-continued
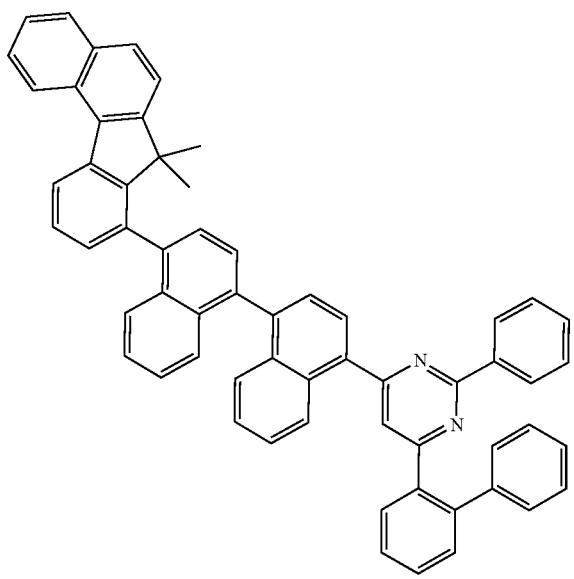
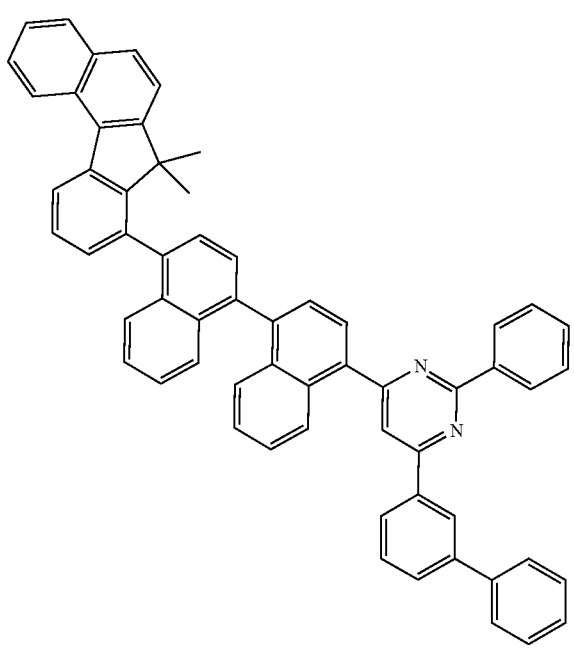
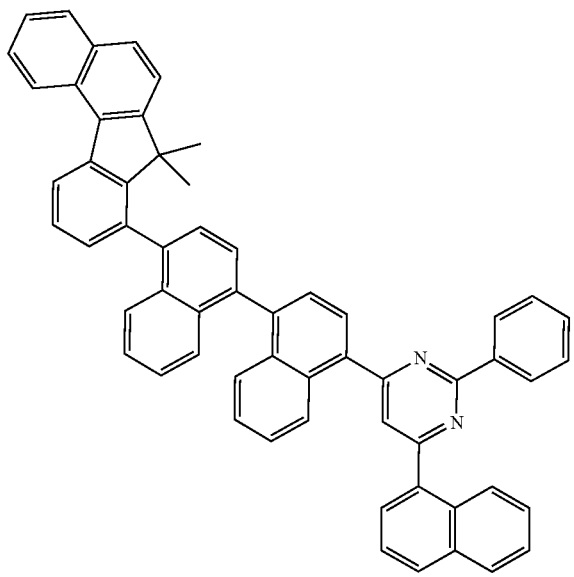

683
-continued
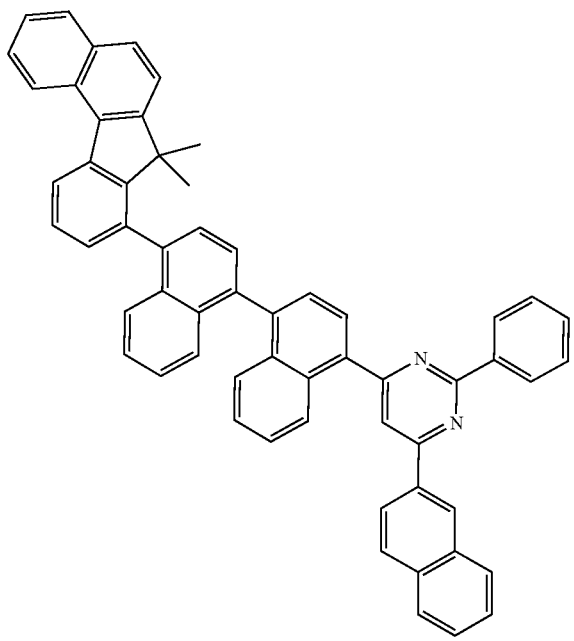
684
-continued
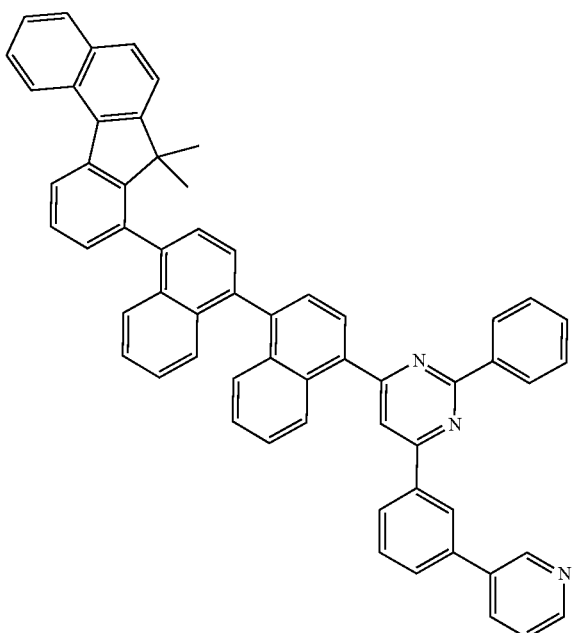
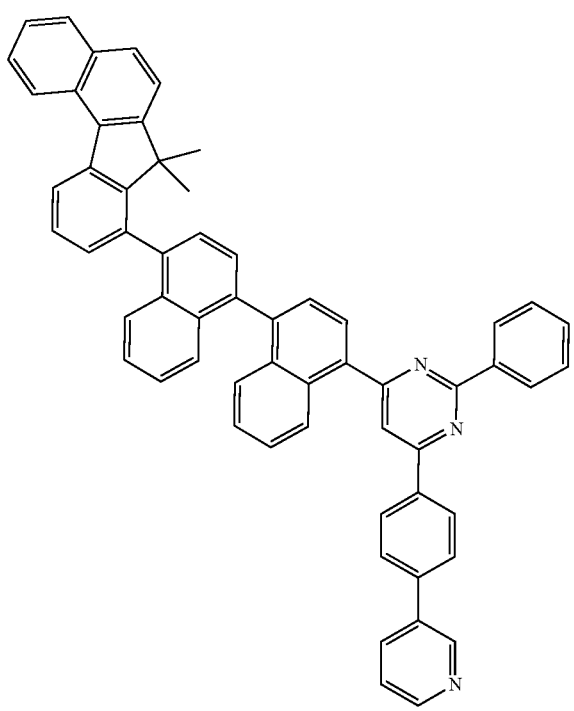
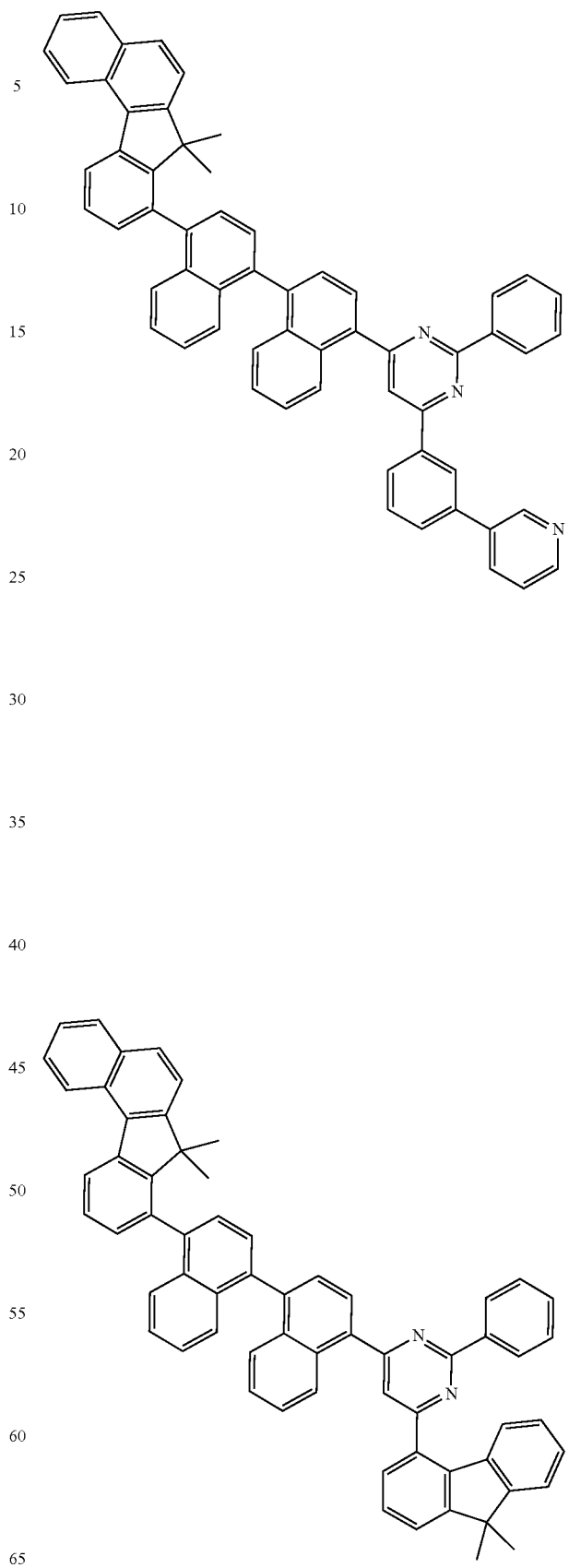

685
-continued
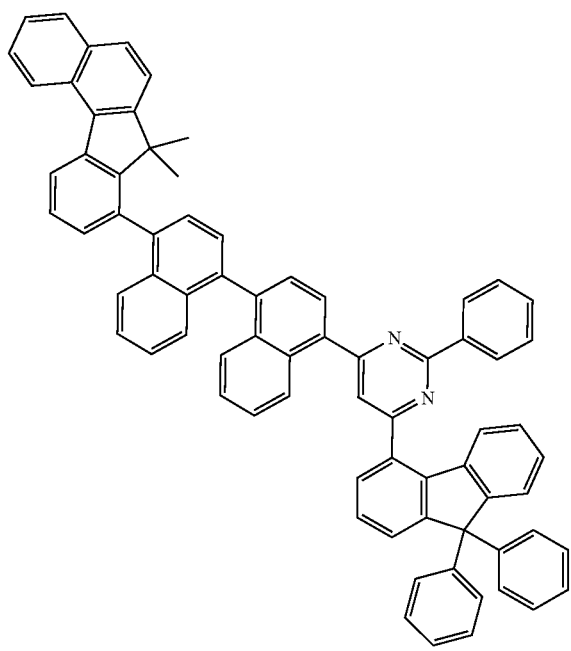
686
-continued
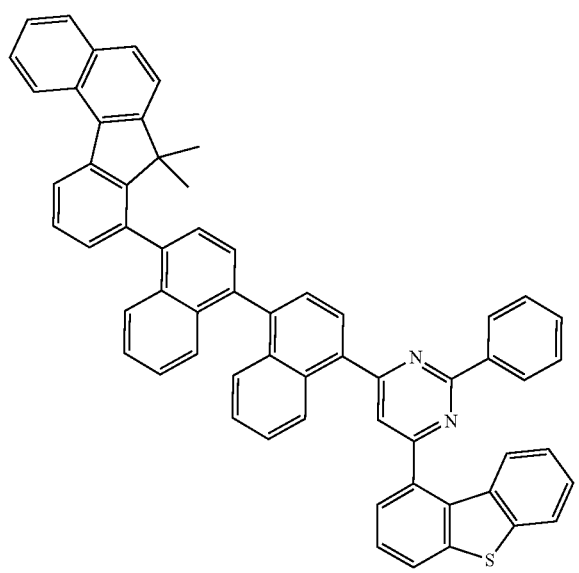
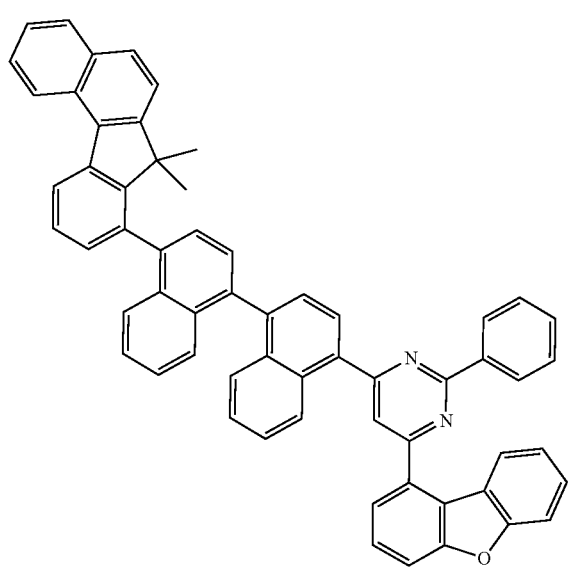

687
-continued
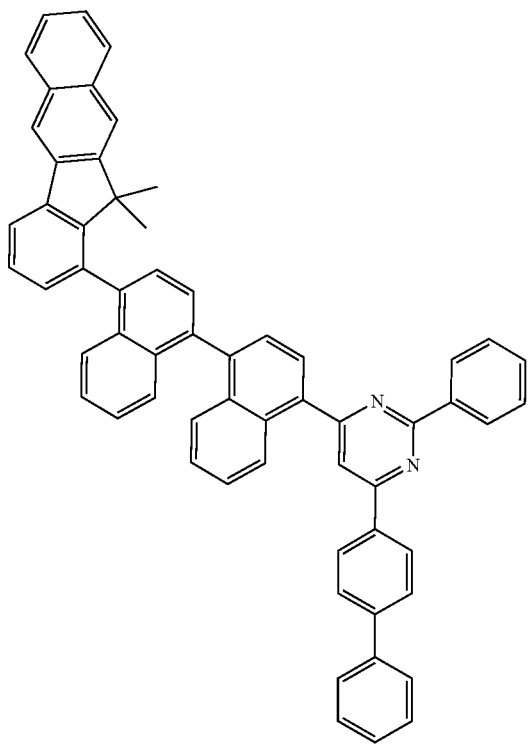
688
-continued
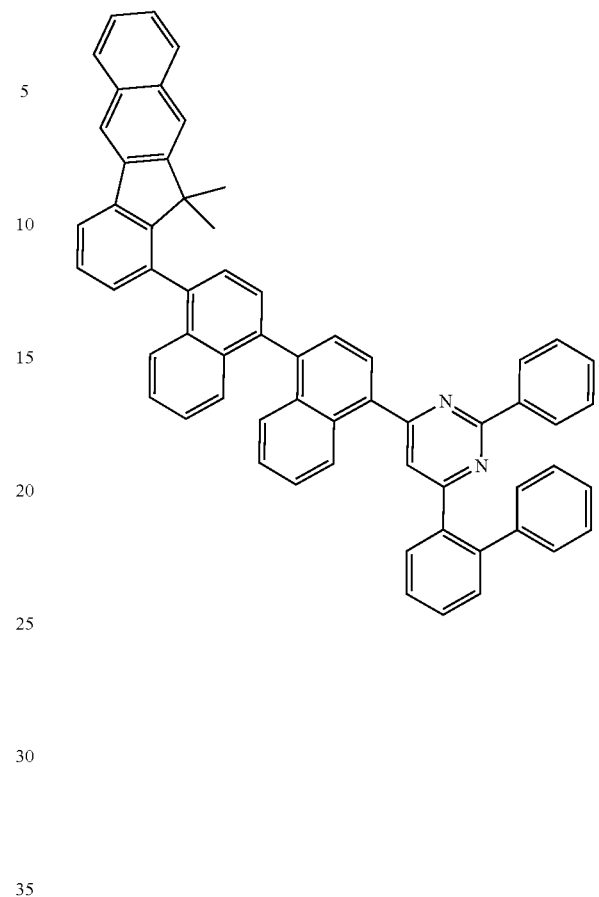
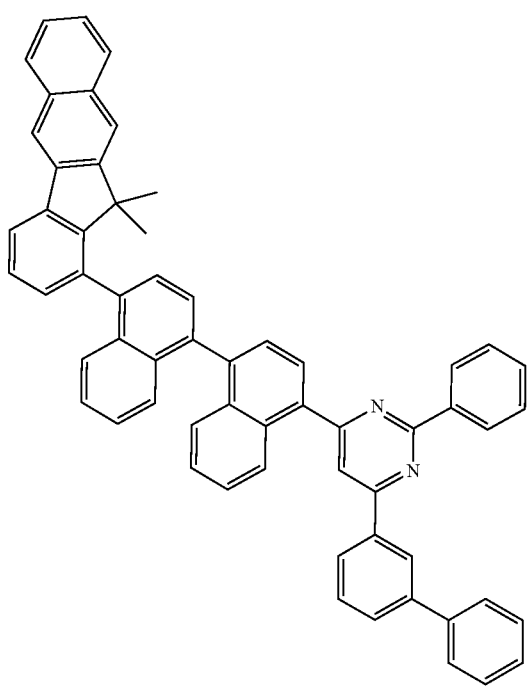

689
-continued
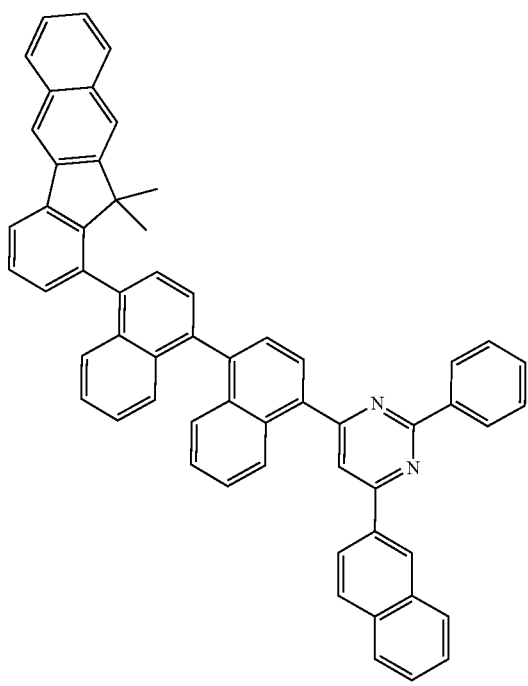
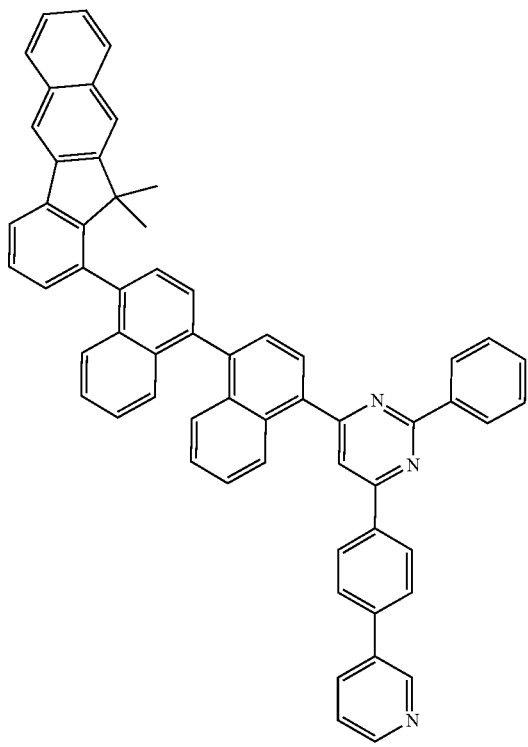
690
-continued
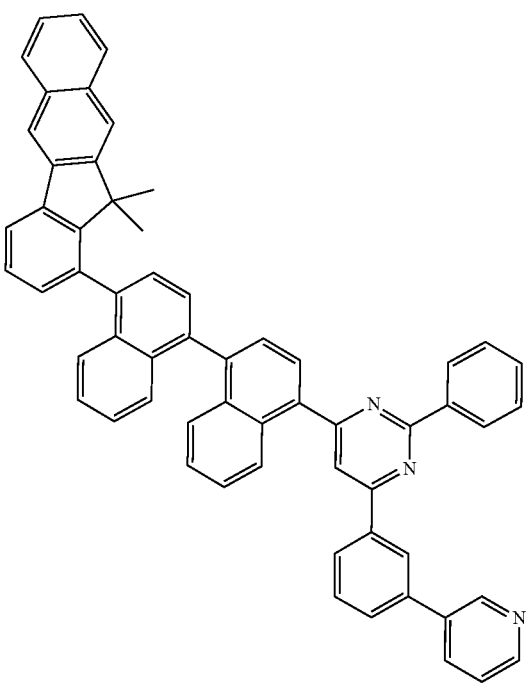
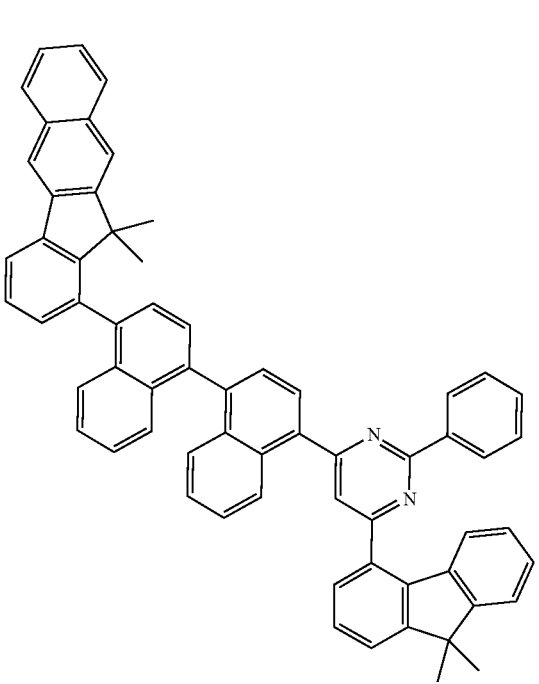

691
-continued
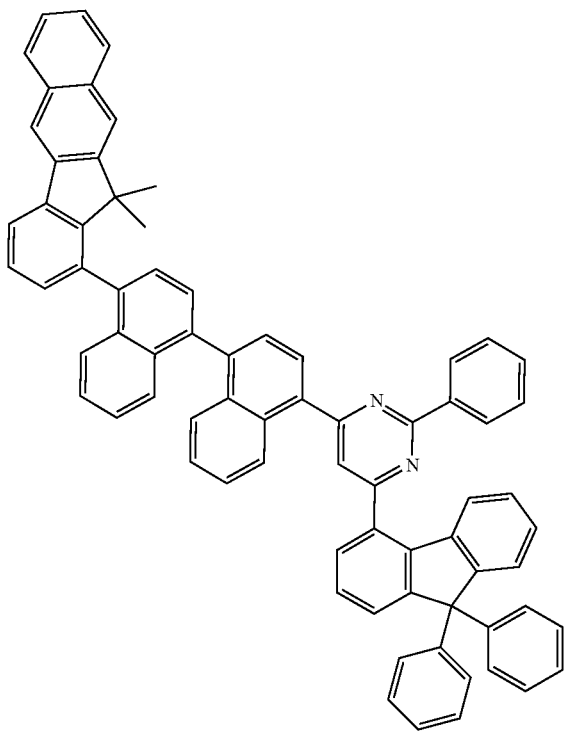
692
-continued
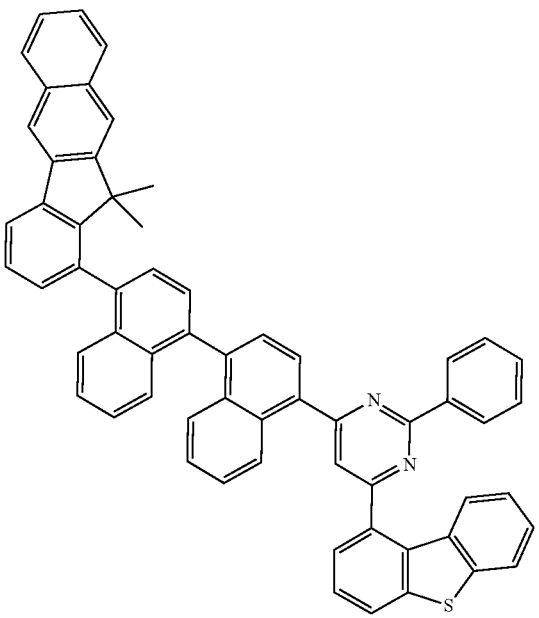
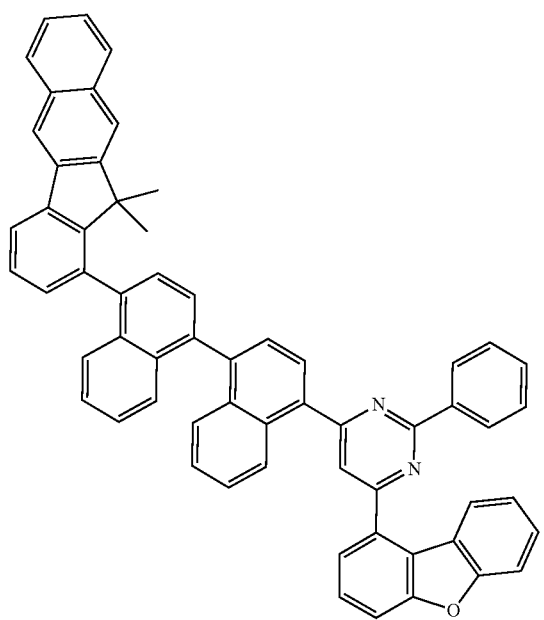

693
-continued
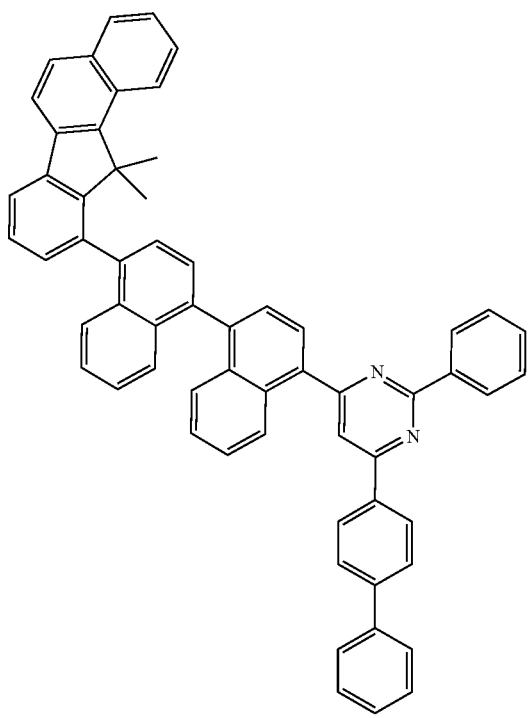
694
-continued
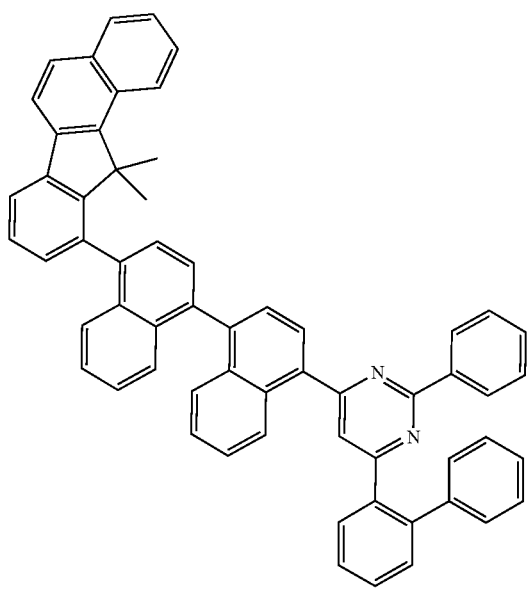
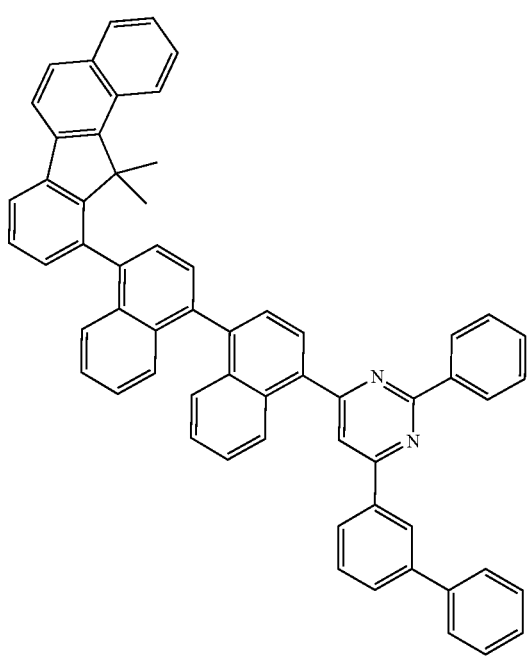
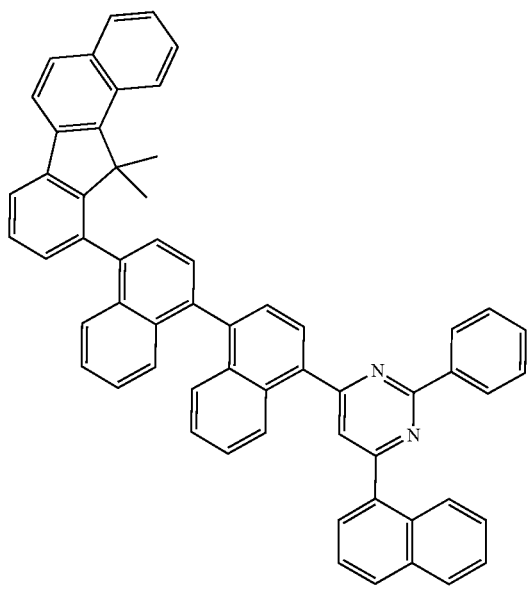

695
-continued
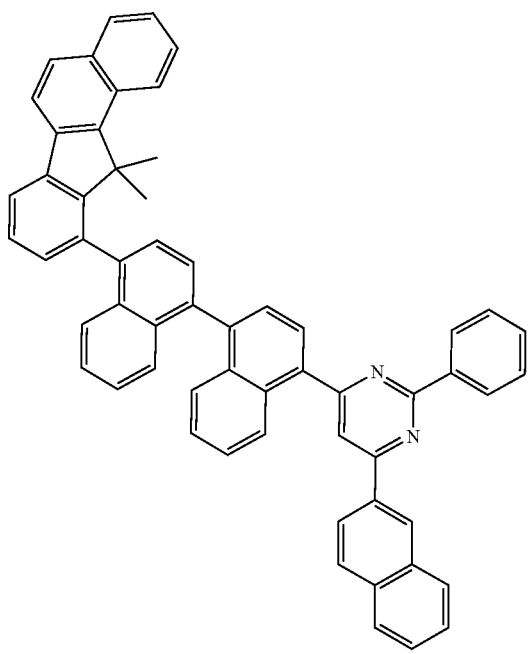
696
-continued
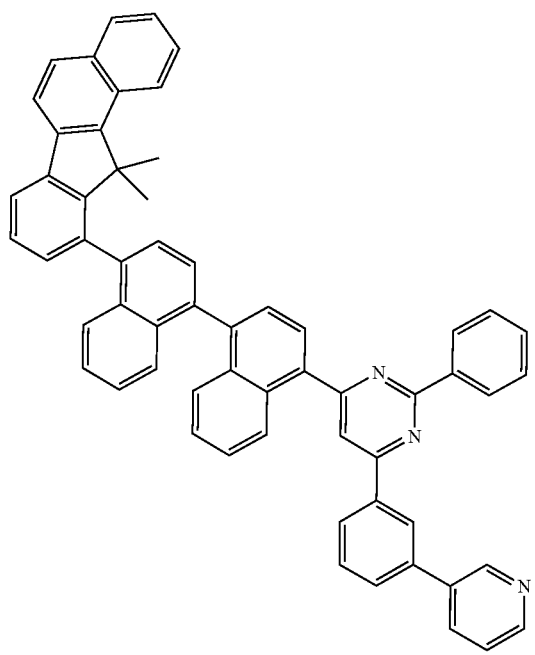
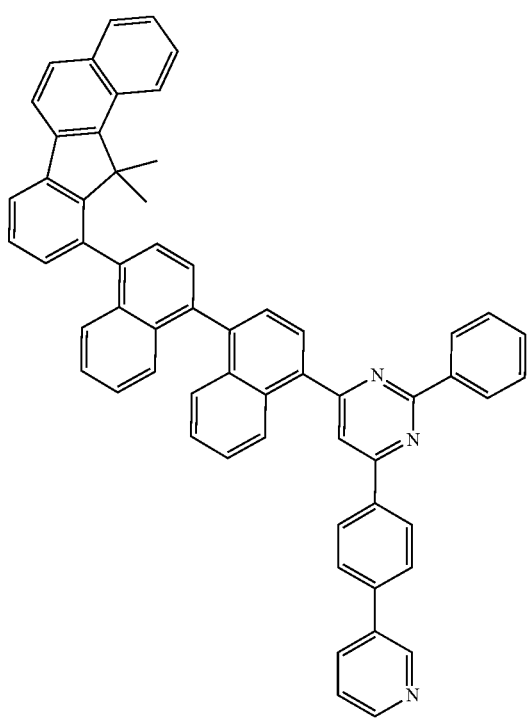
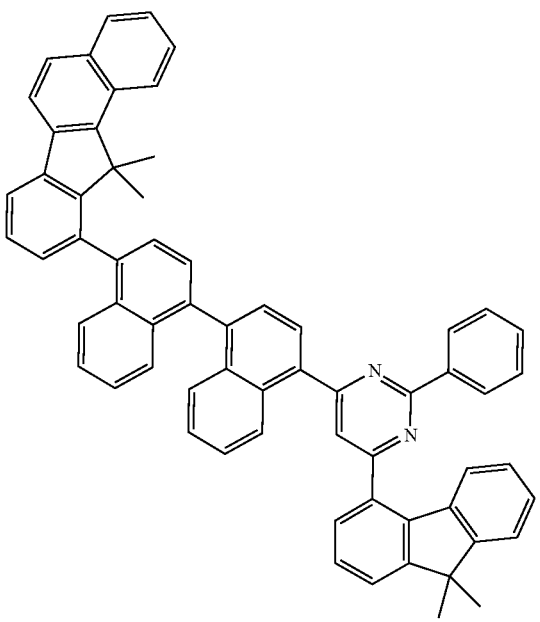

697
-continued
698
-continued
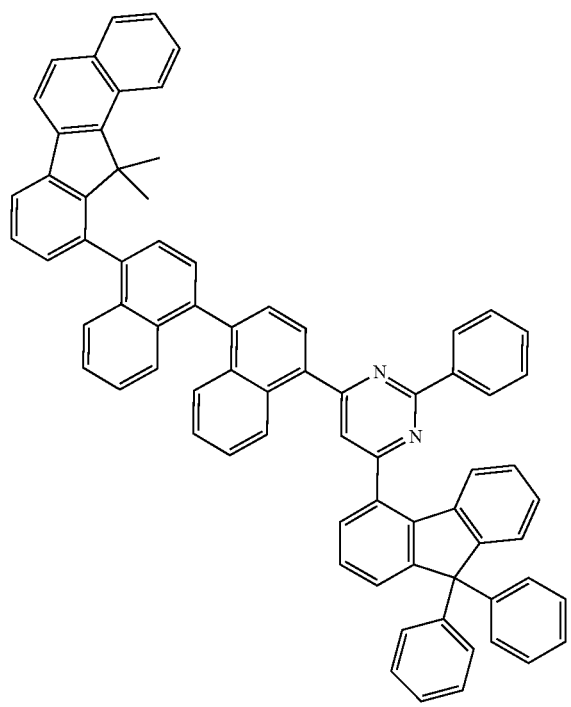
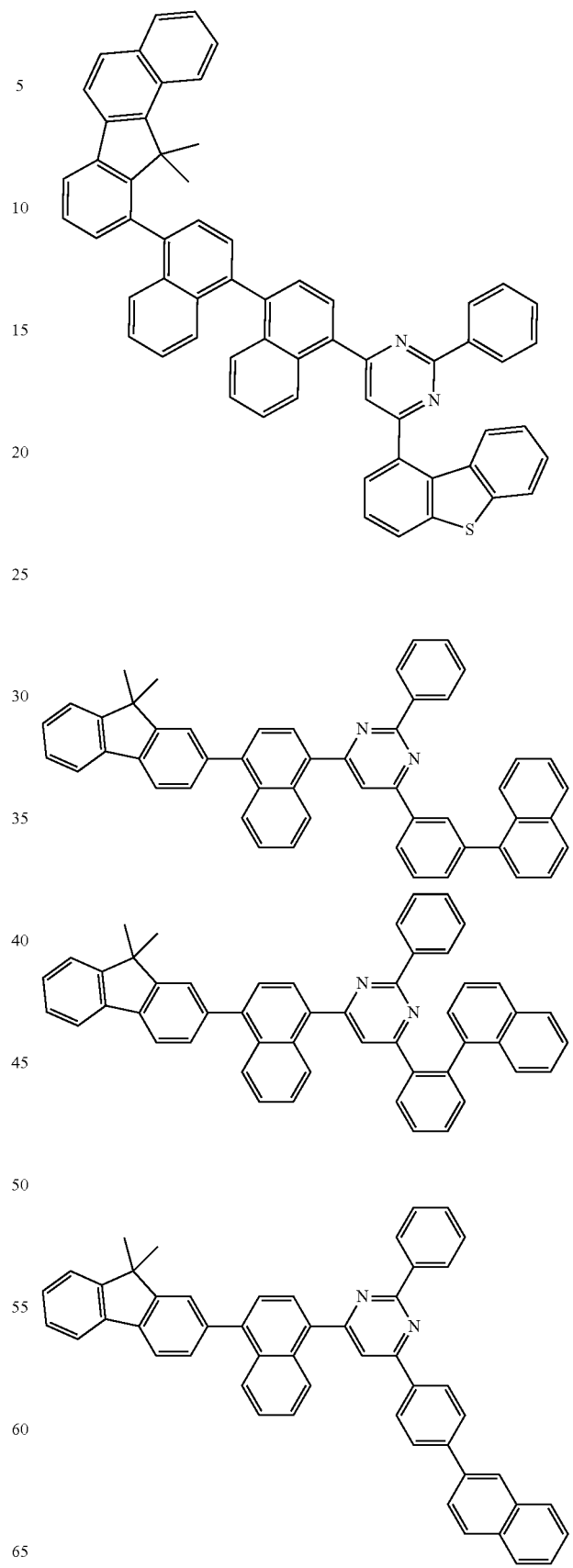

699
-continued
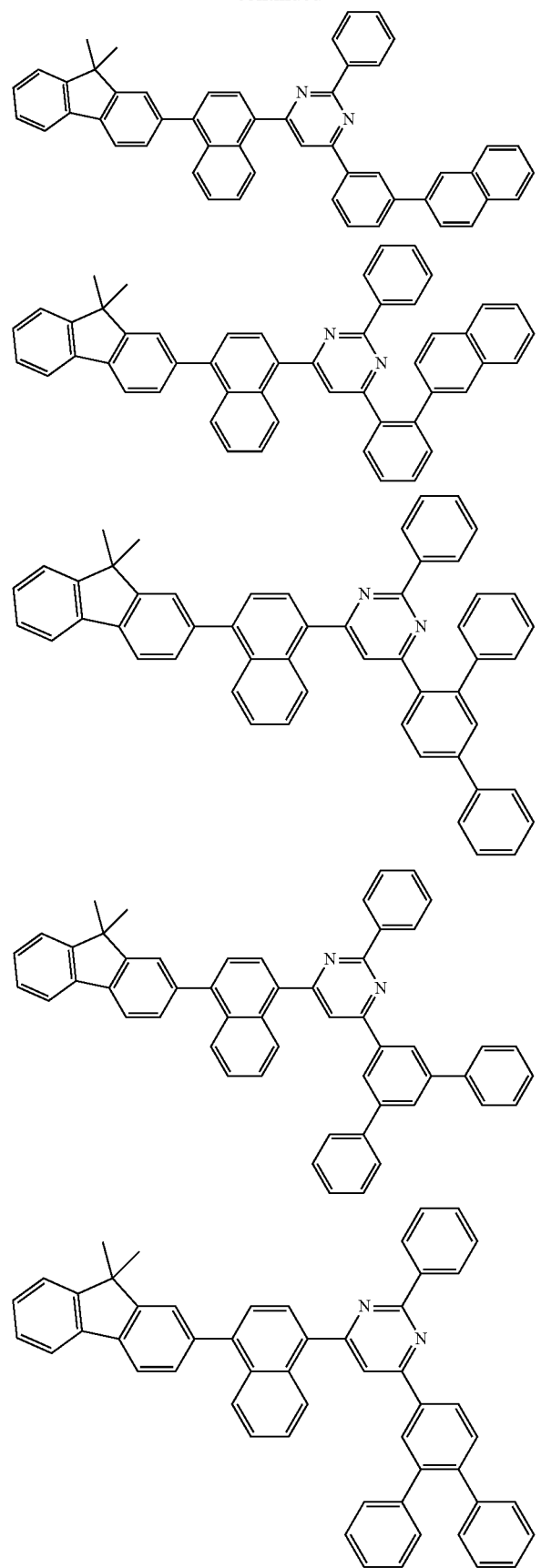
700
-continued
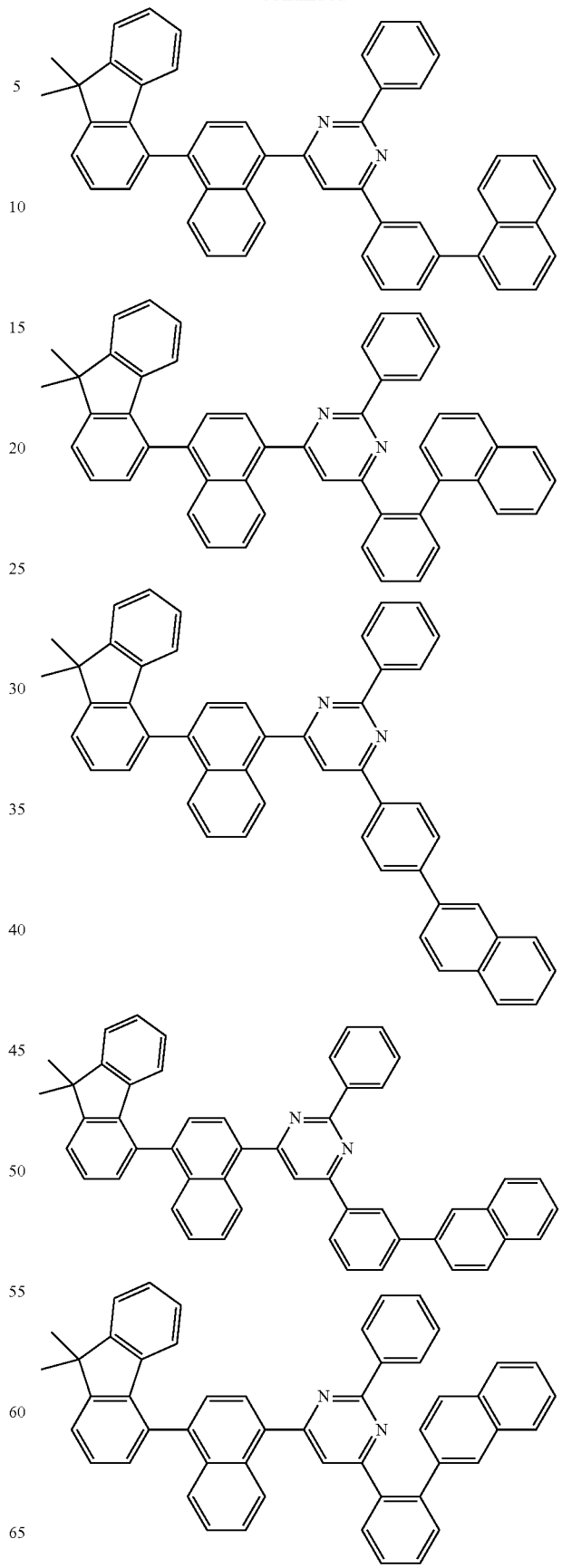

701
-continued
702
-continued
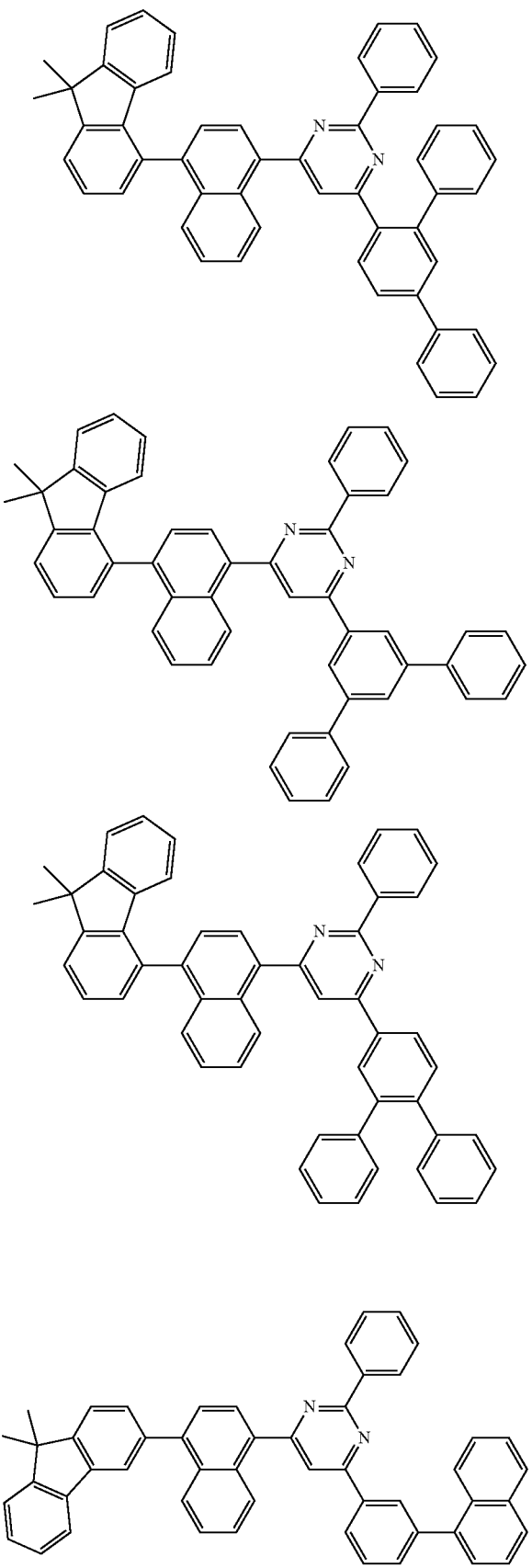
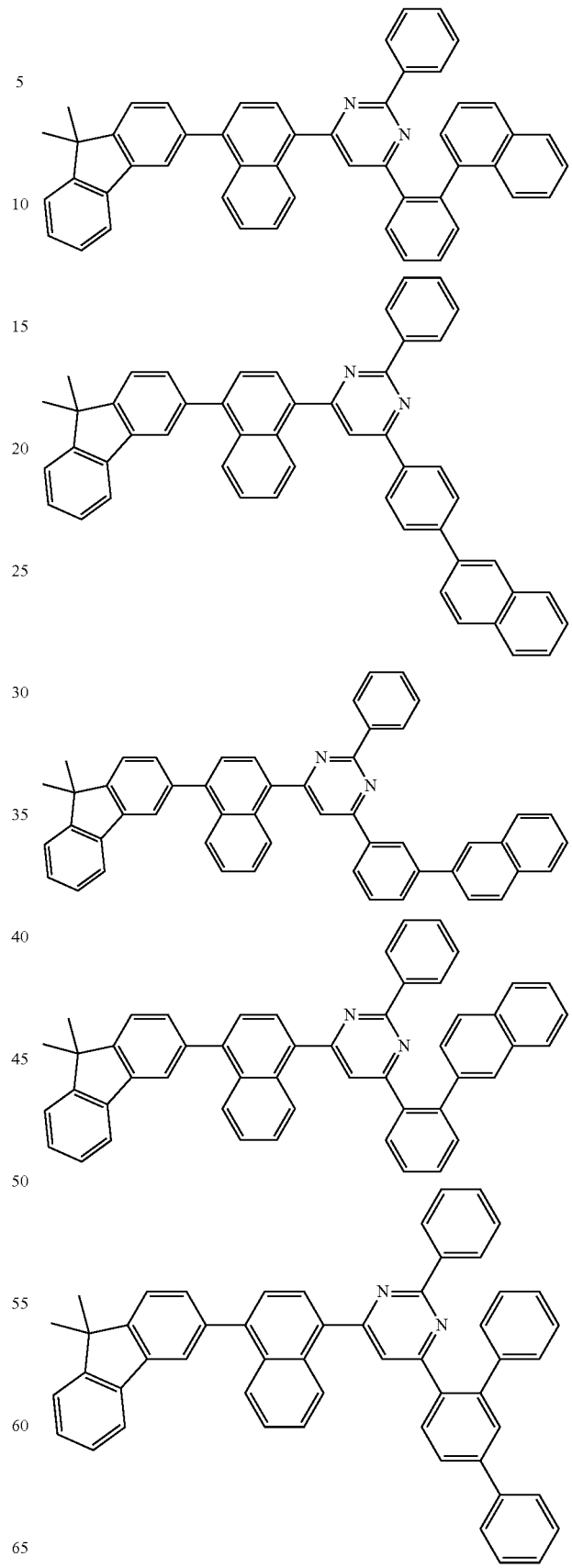

703
-continued
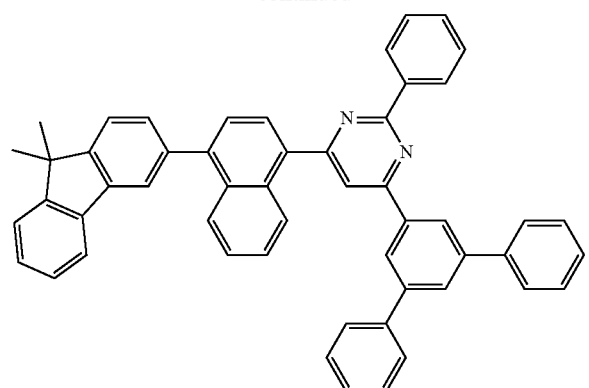
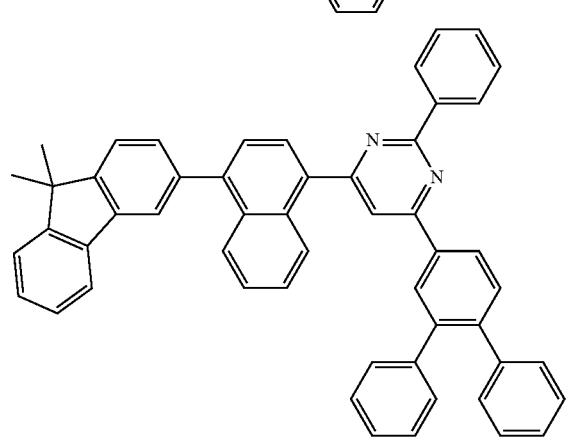
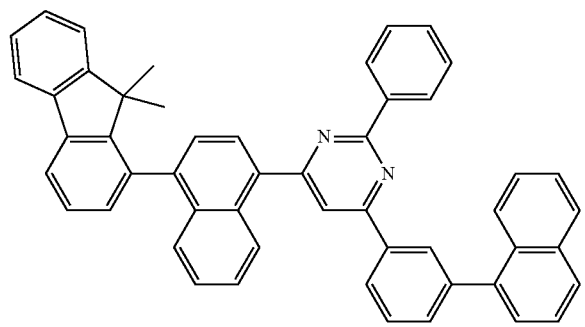
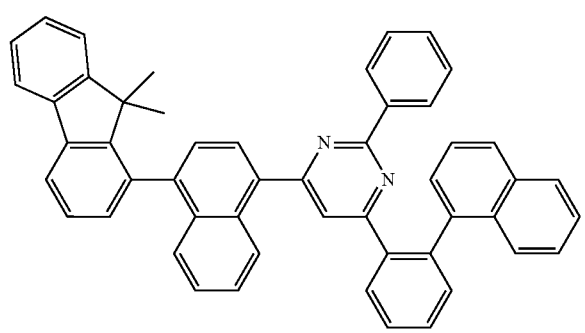
704
-continued
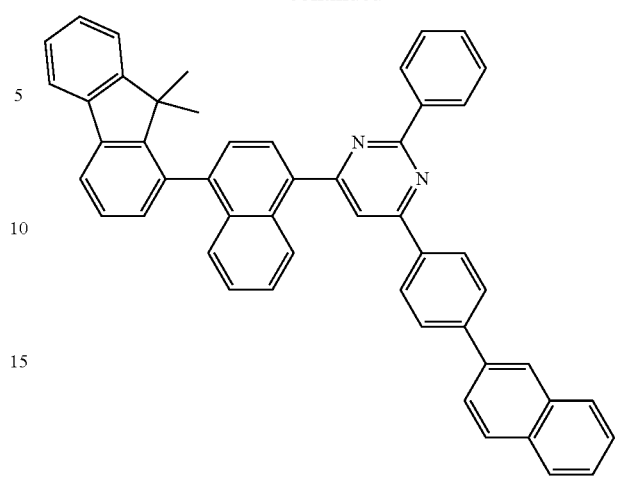
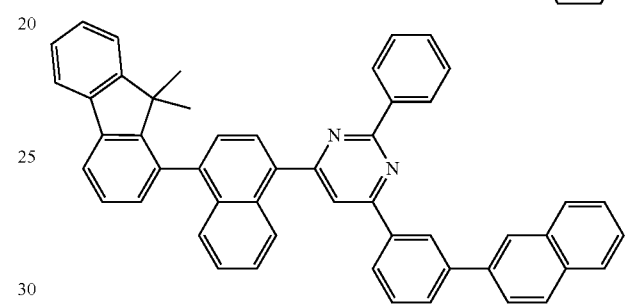
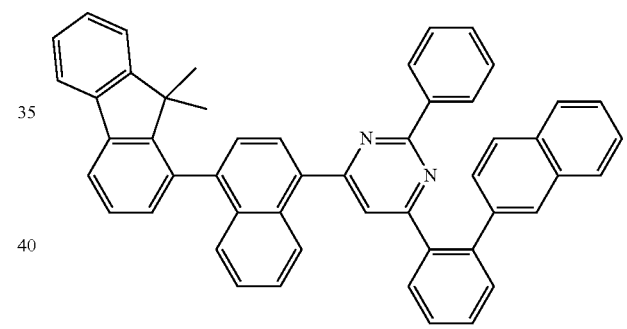
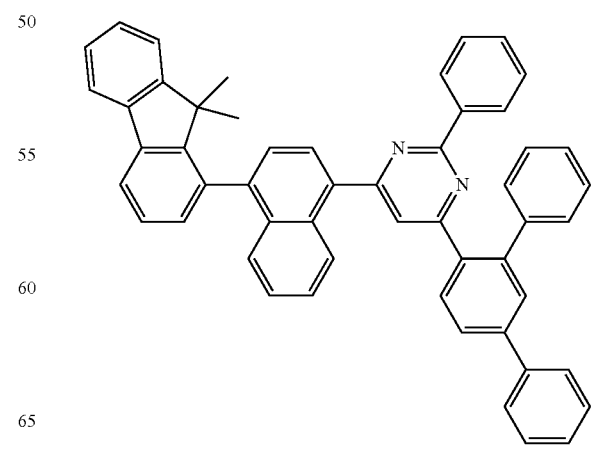

705
-continued
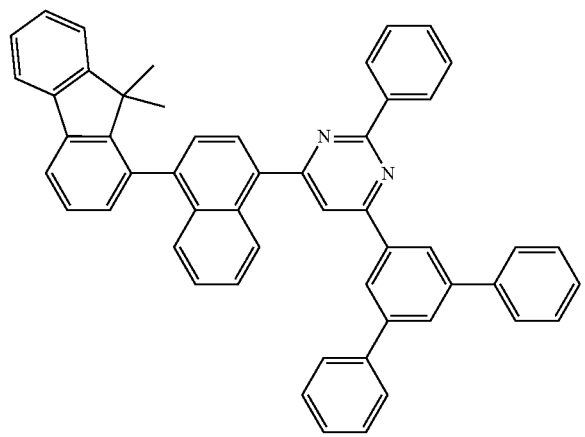
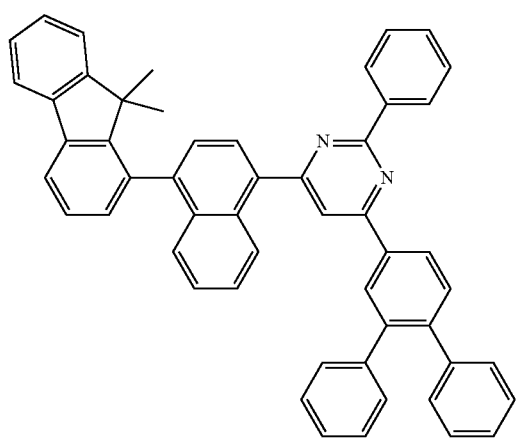
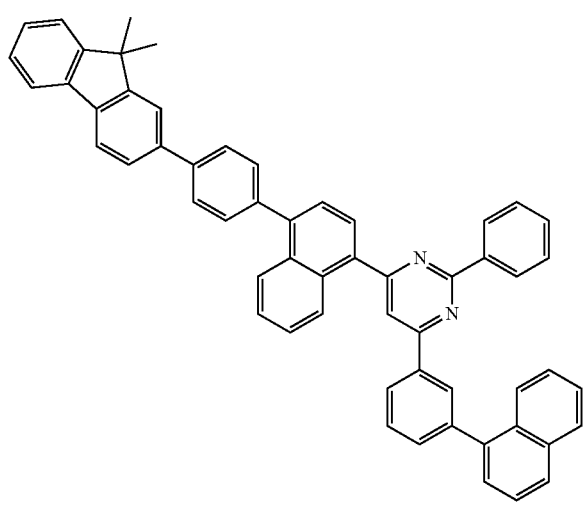
706
-continued
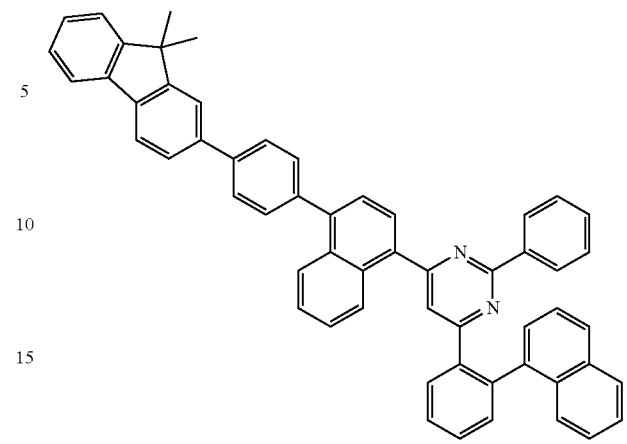
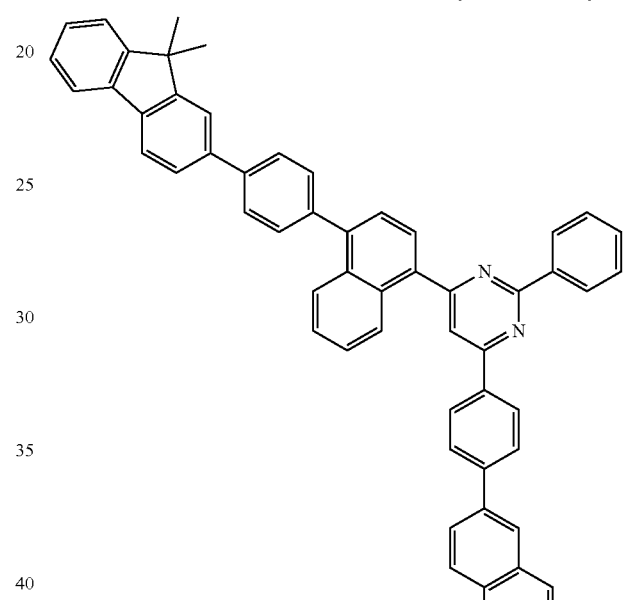
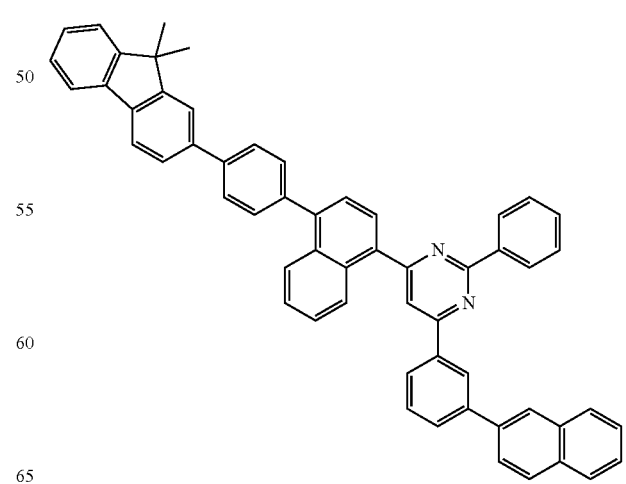

707
-continued
708
-continued
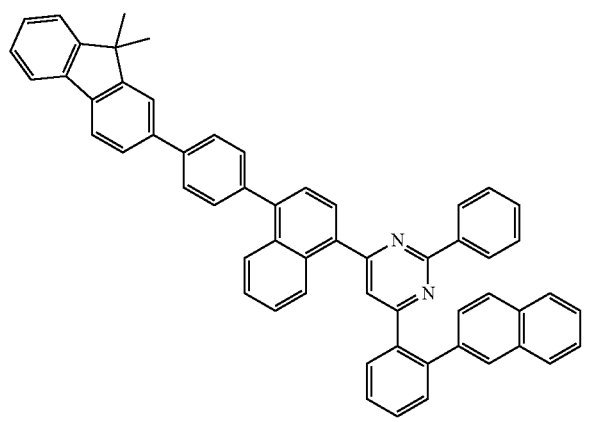
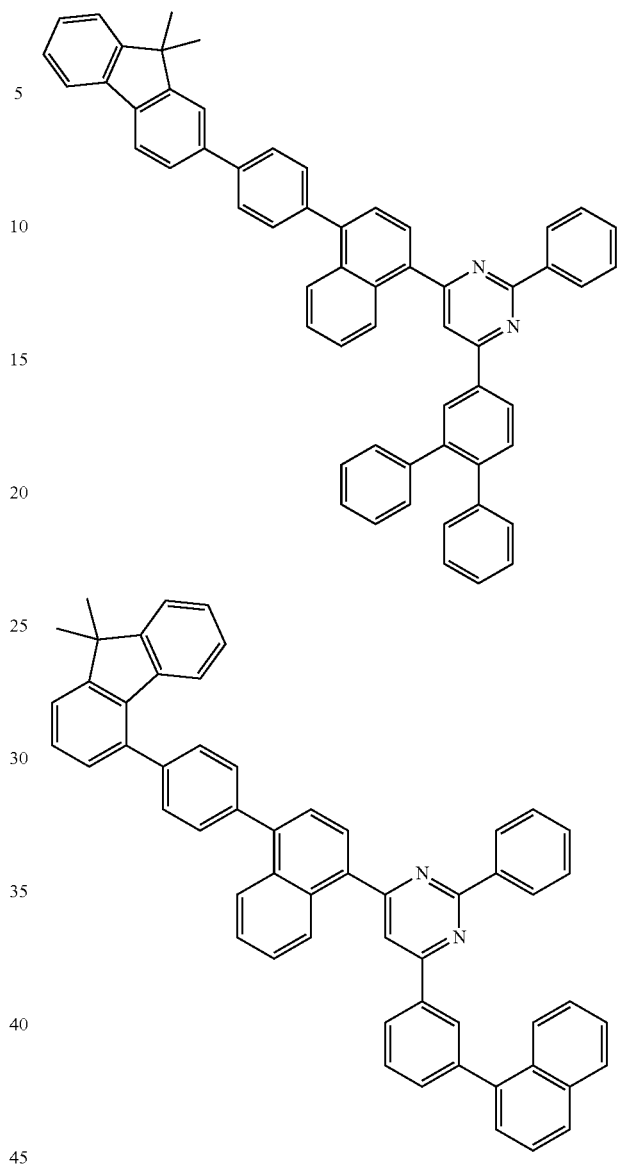
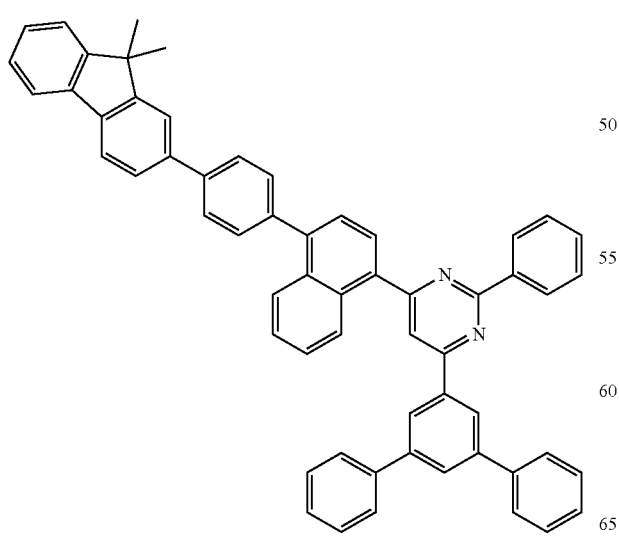

709
-continued
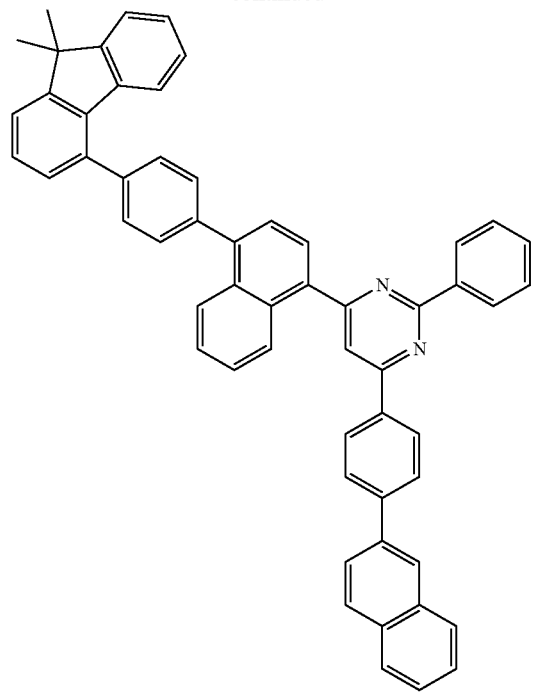
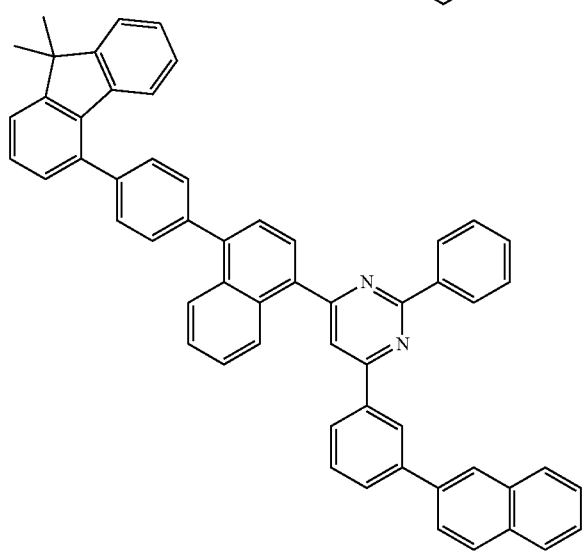
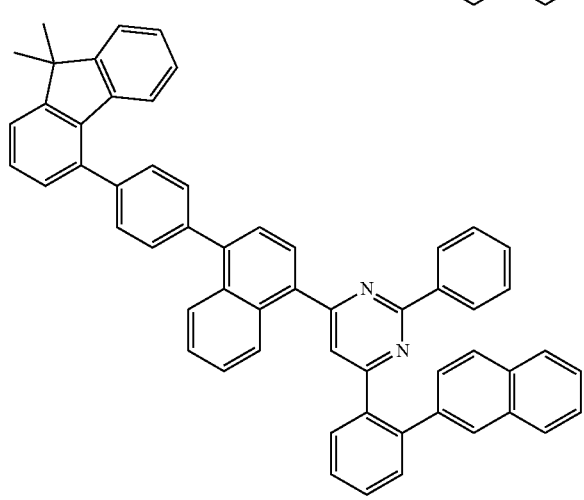
710
-continued
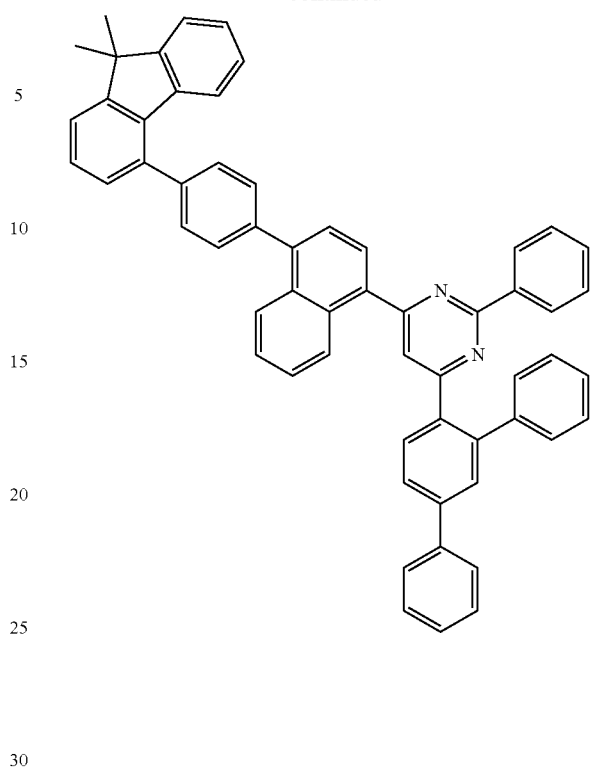
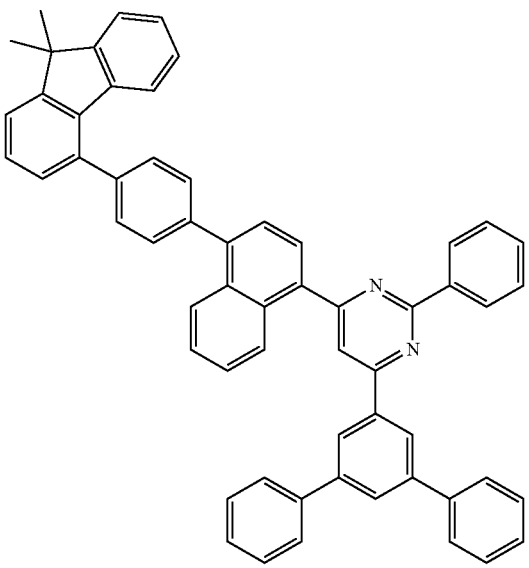

711
-continued
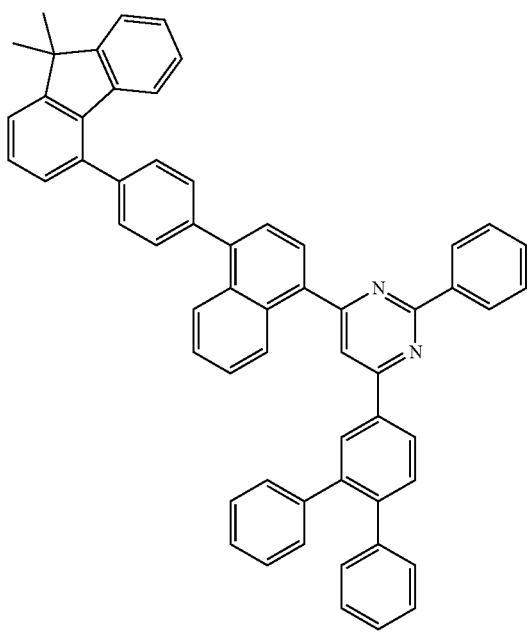
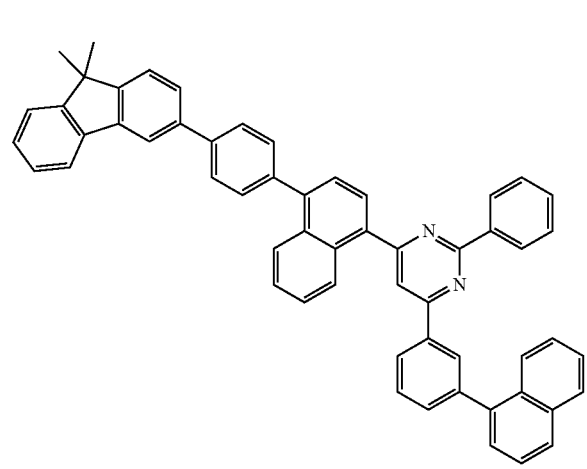
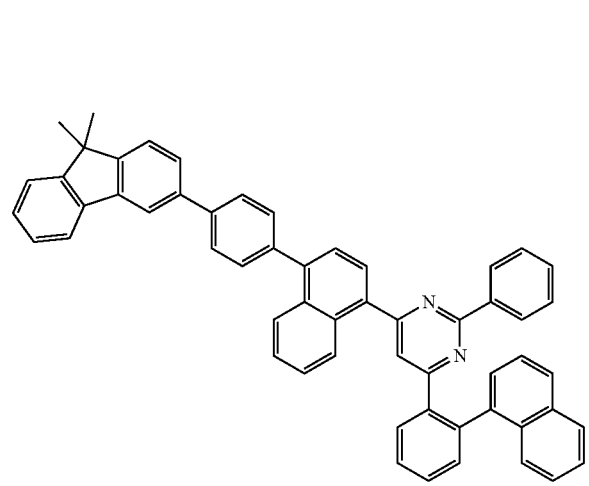
712
-continued
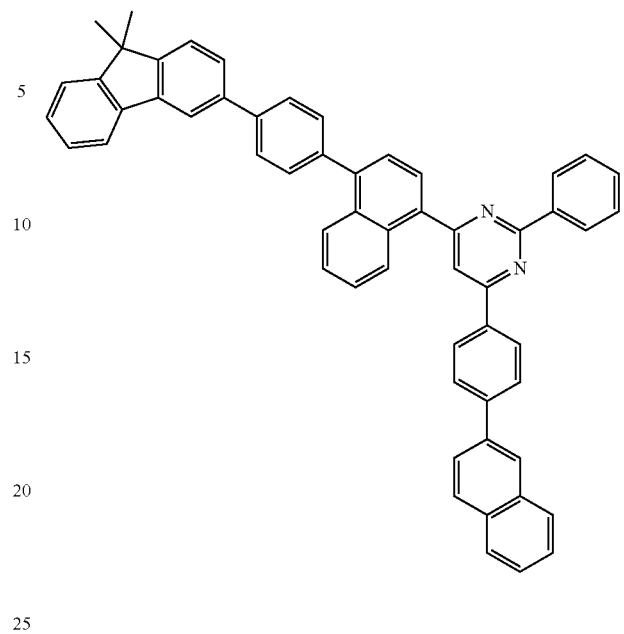
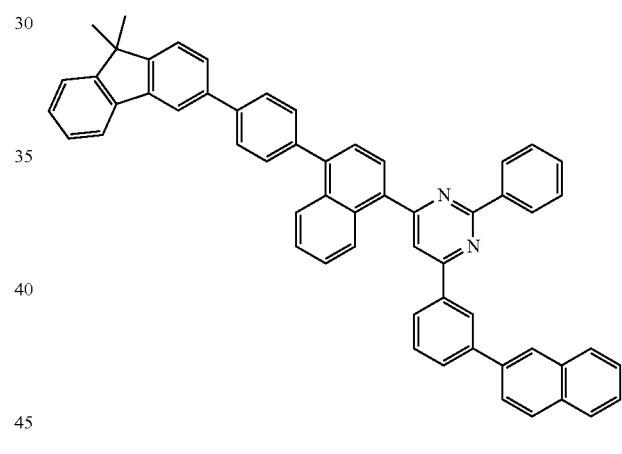
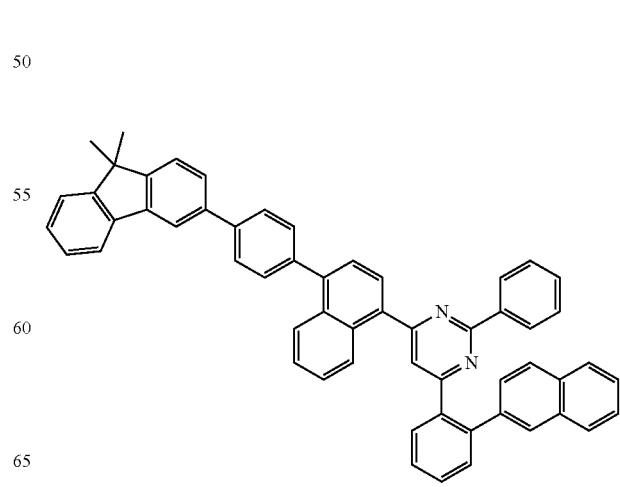

713
-continued
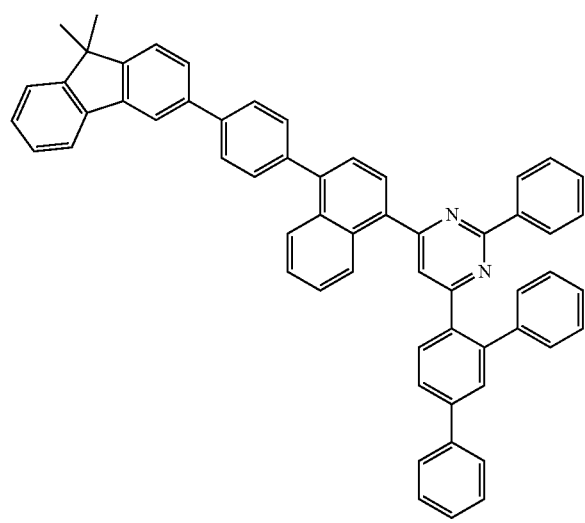
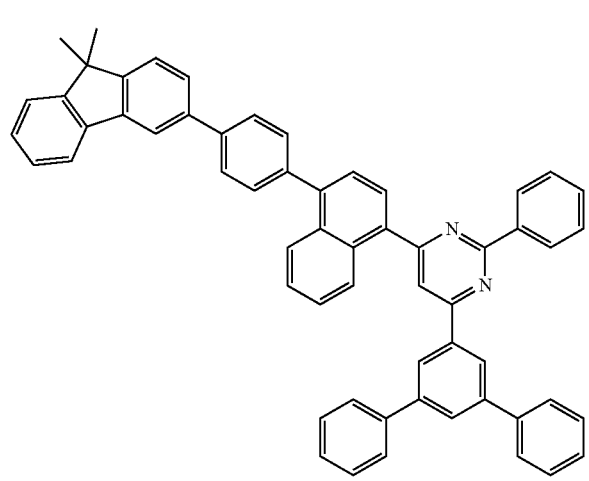
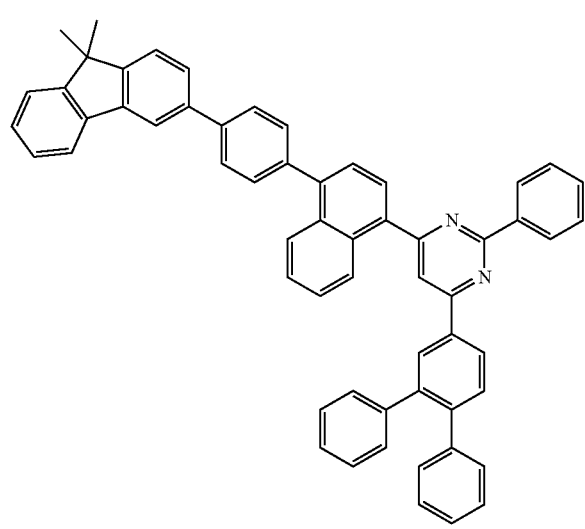
714
-continued
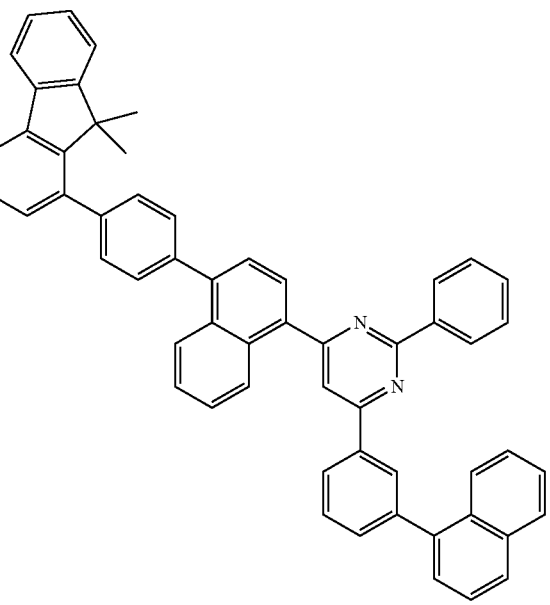
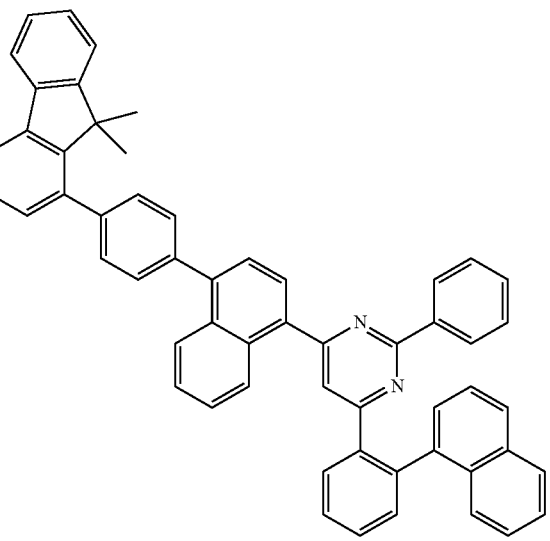

715
-continued
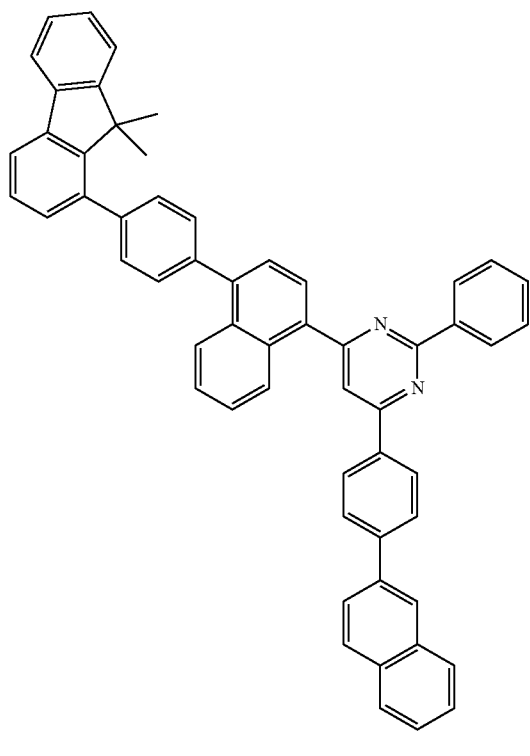
716
-continued
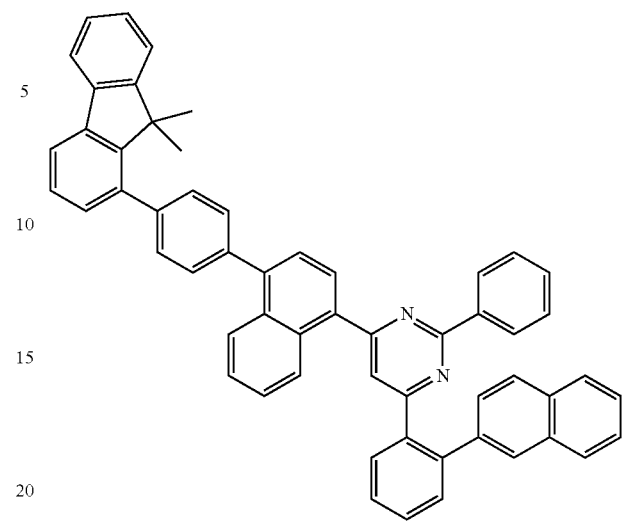
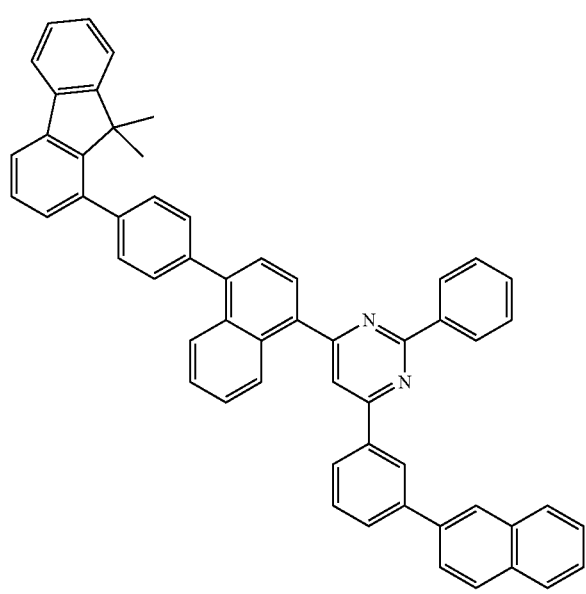

717
-continued
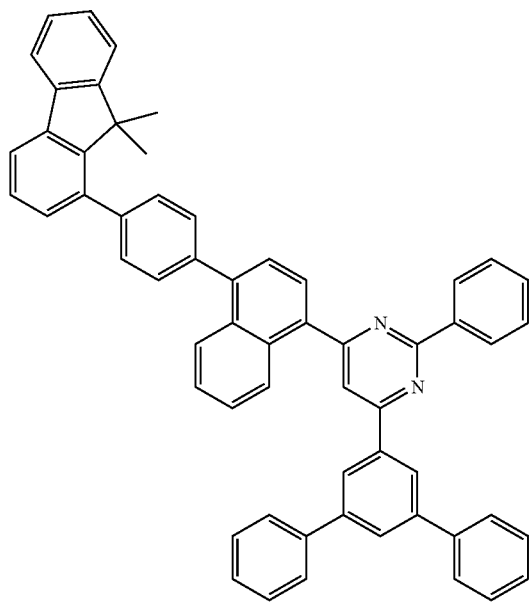
718
-continued
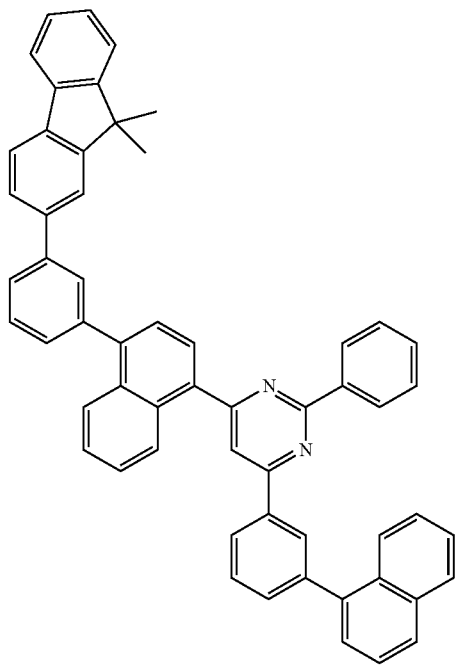
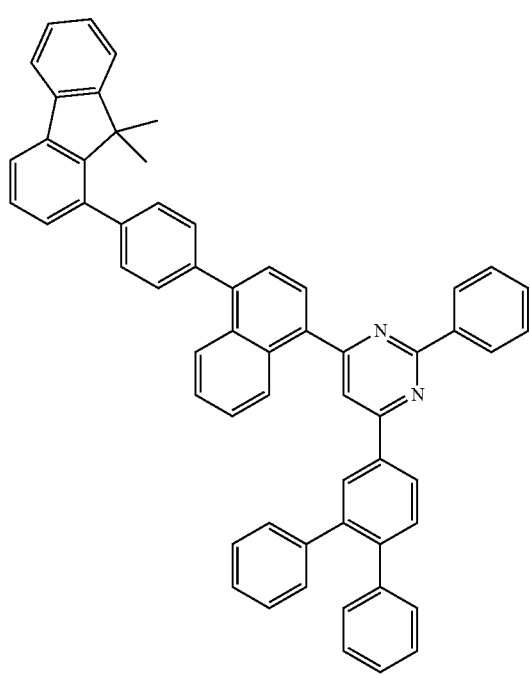
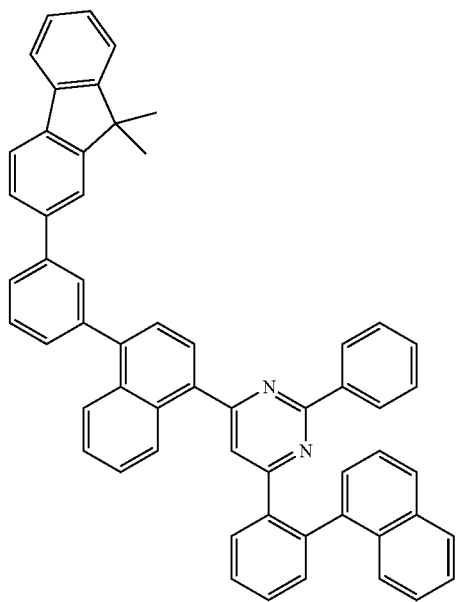

719
-continued
720
-continued
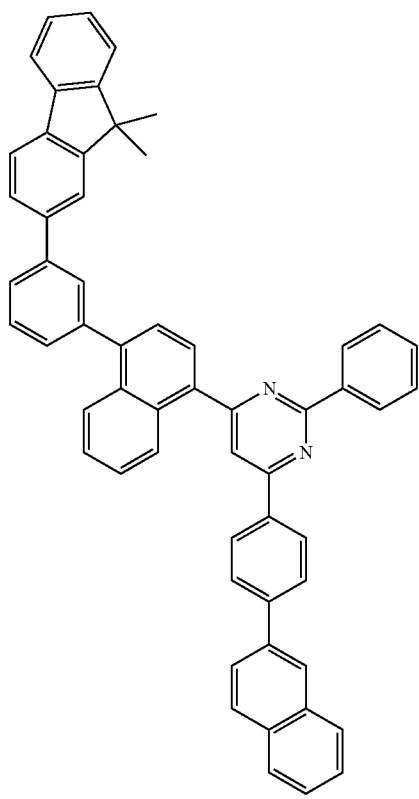
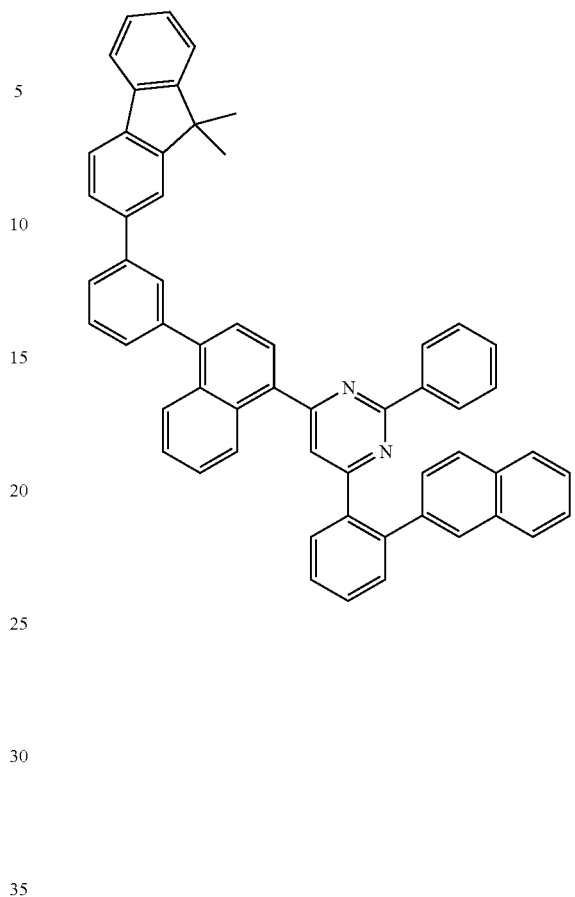
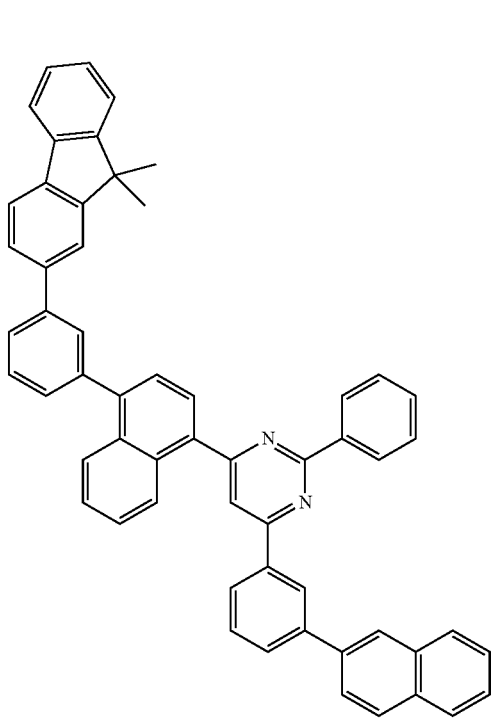

721
-continued
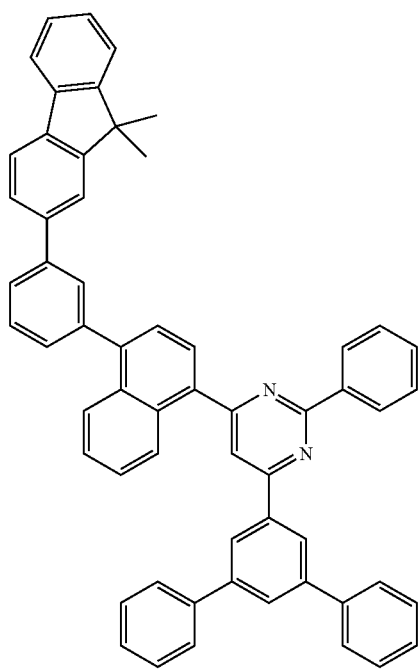
722
-continued
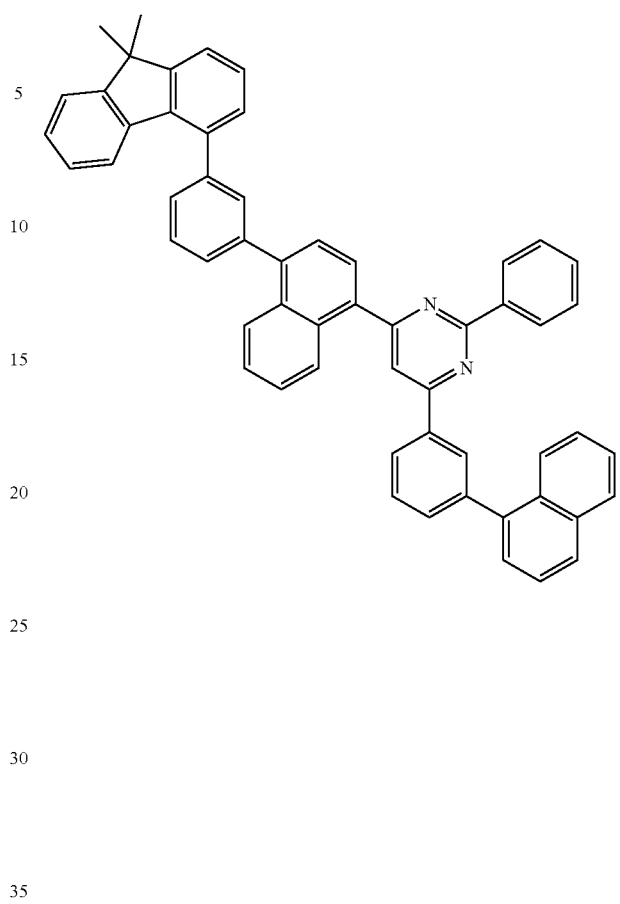
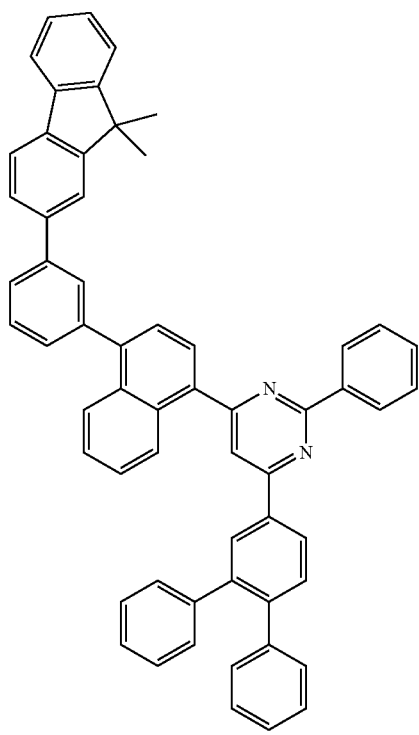
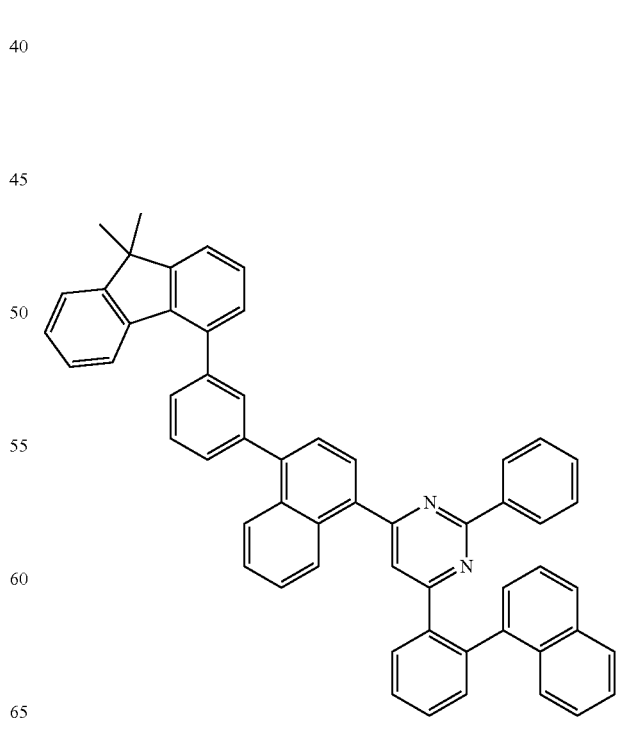

723
-continued
724
-continued
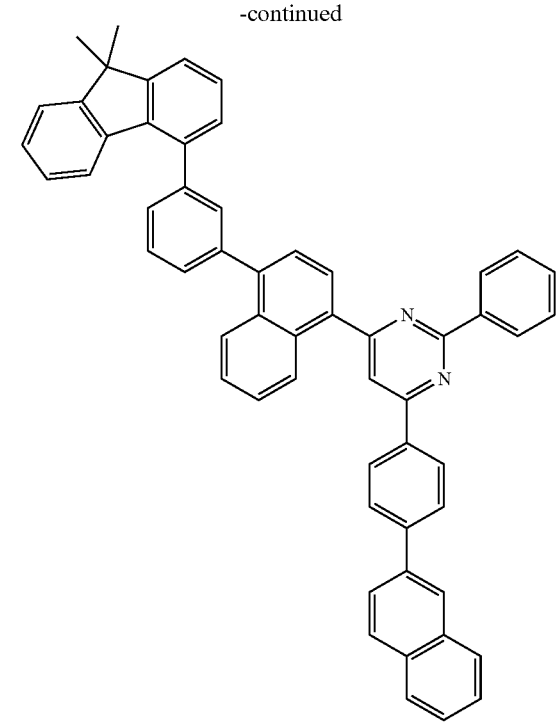
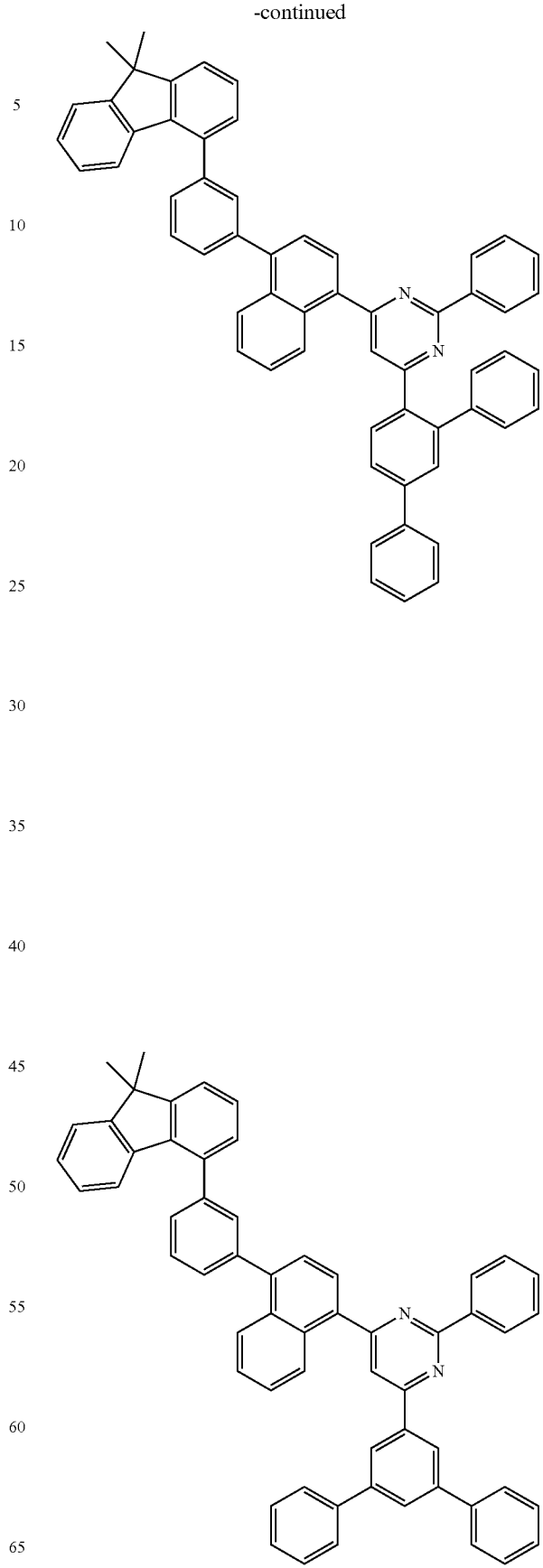

725
-continued
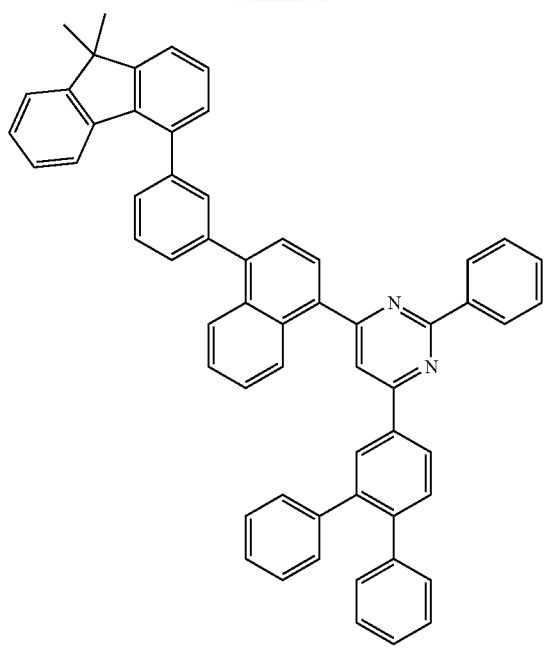
726
-continued
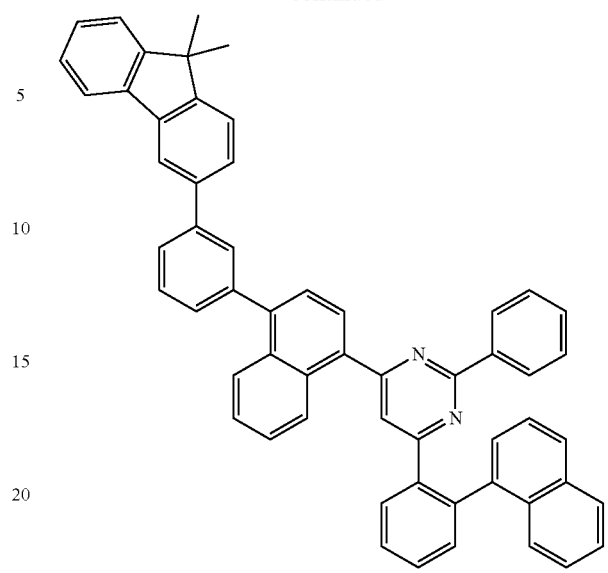
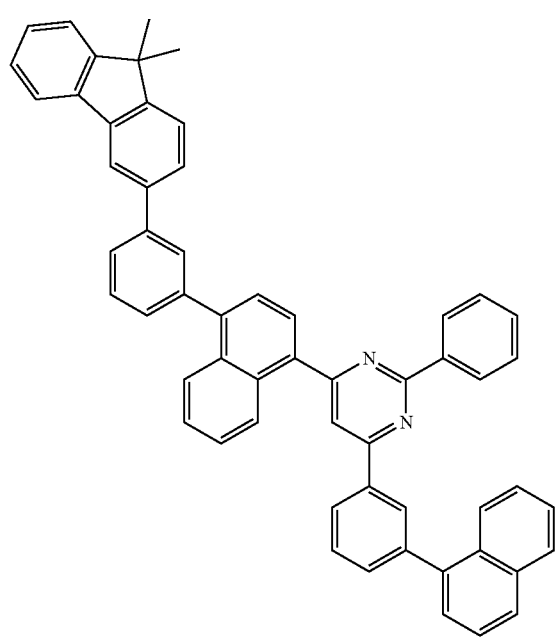
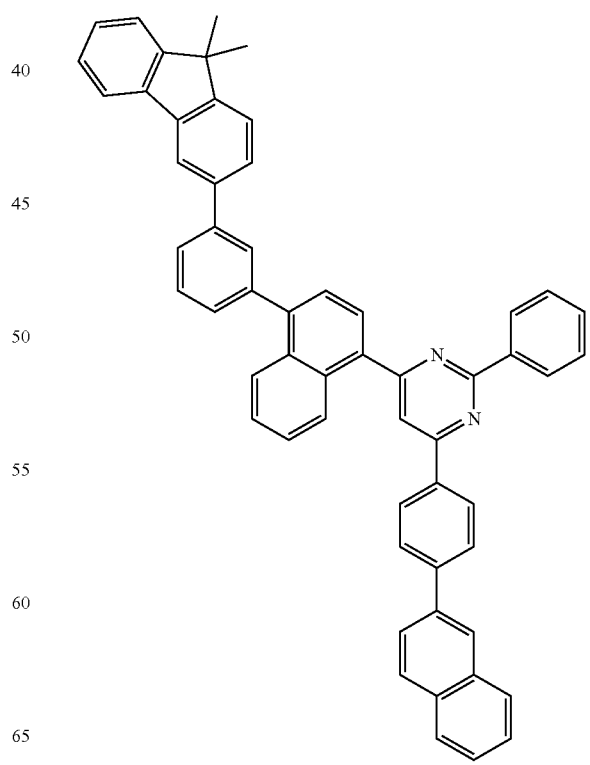

727
-continued
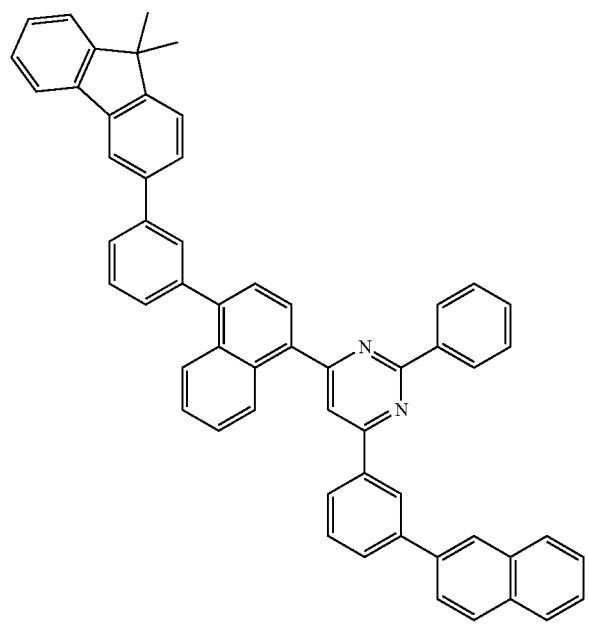
728
-continued
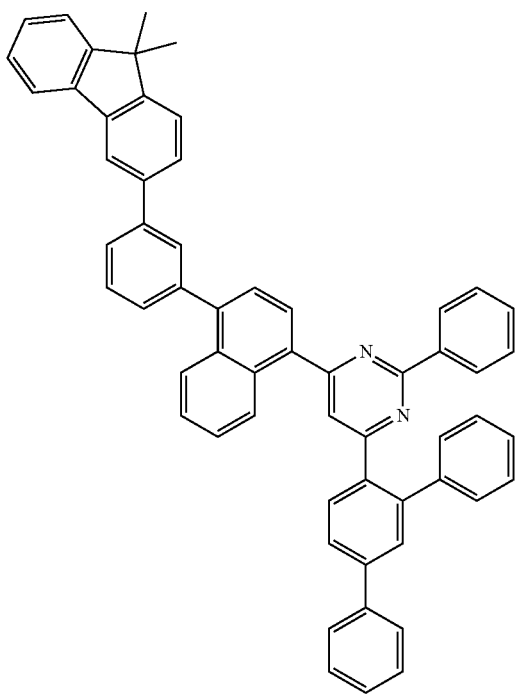
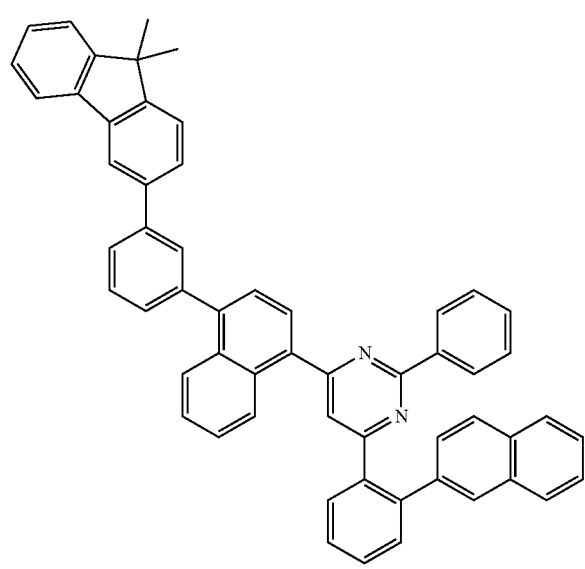
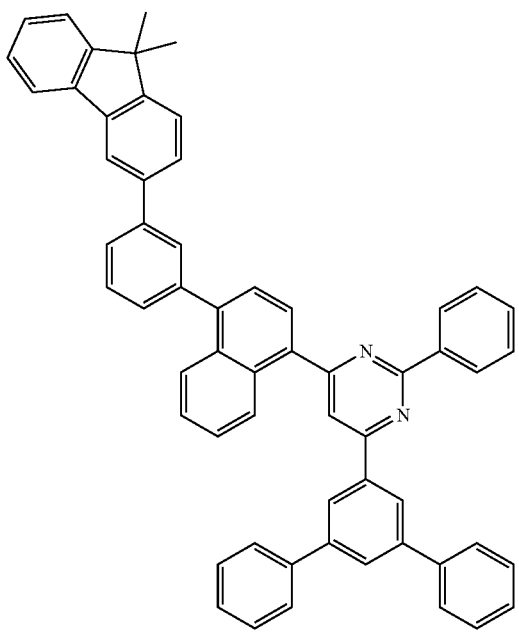

729
-continued
730
-continued
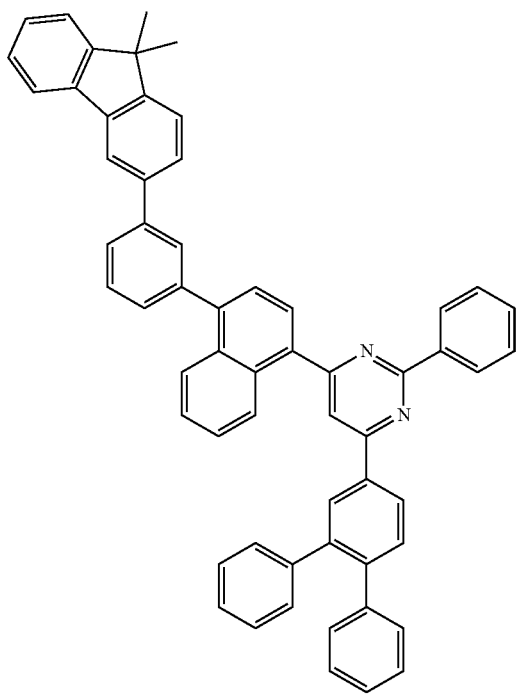
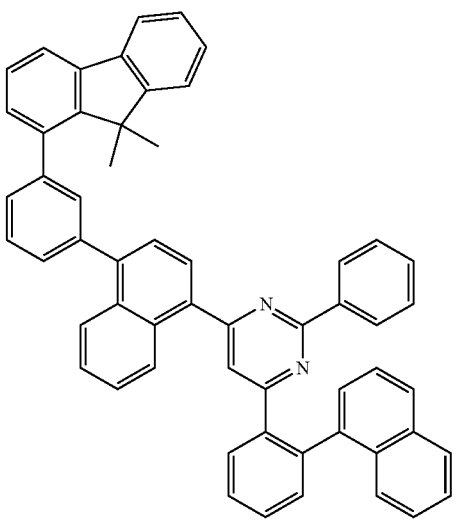
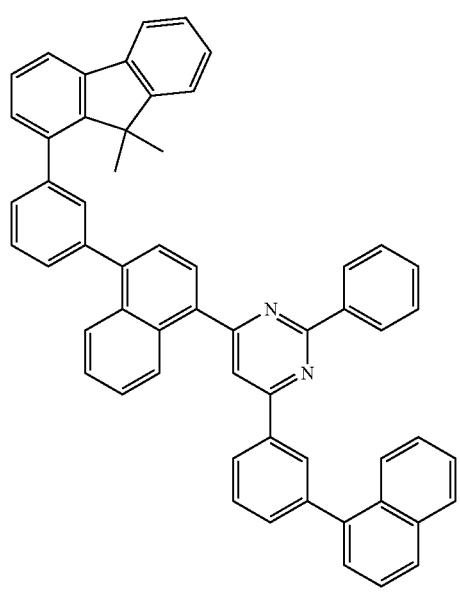

731
-continued
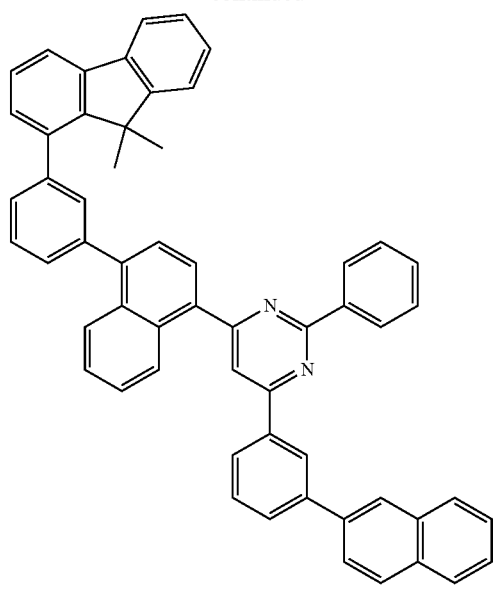
732
-continued
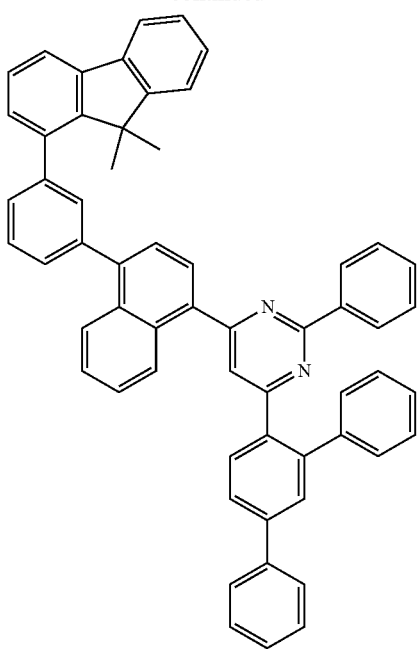
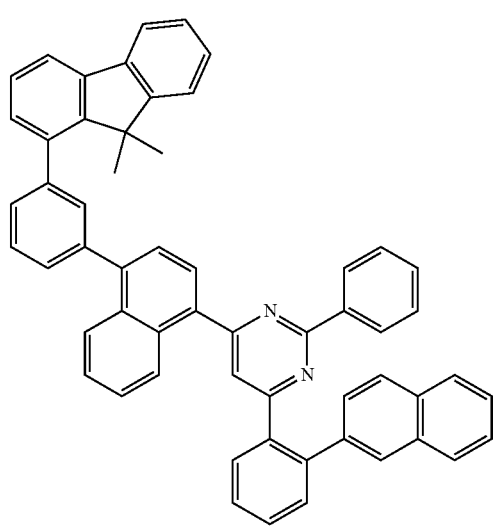
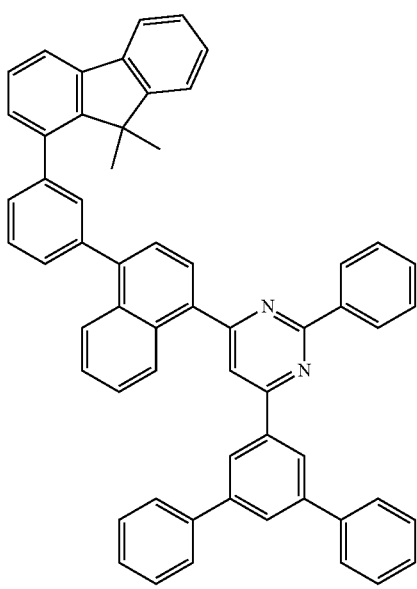

733
-continued
734
-continued
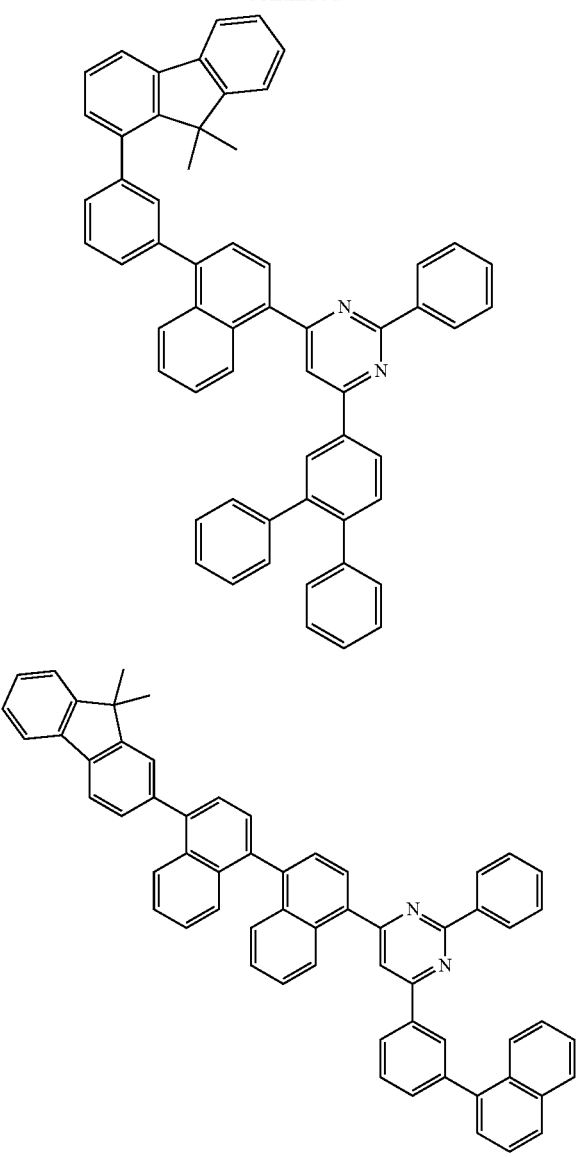
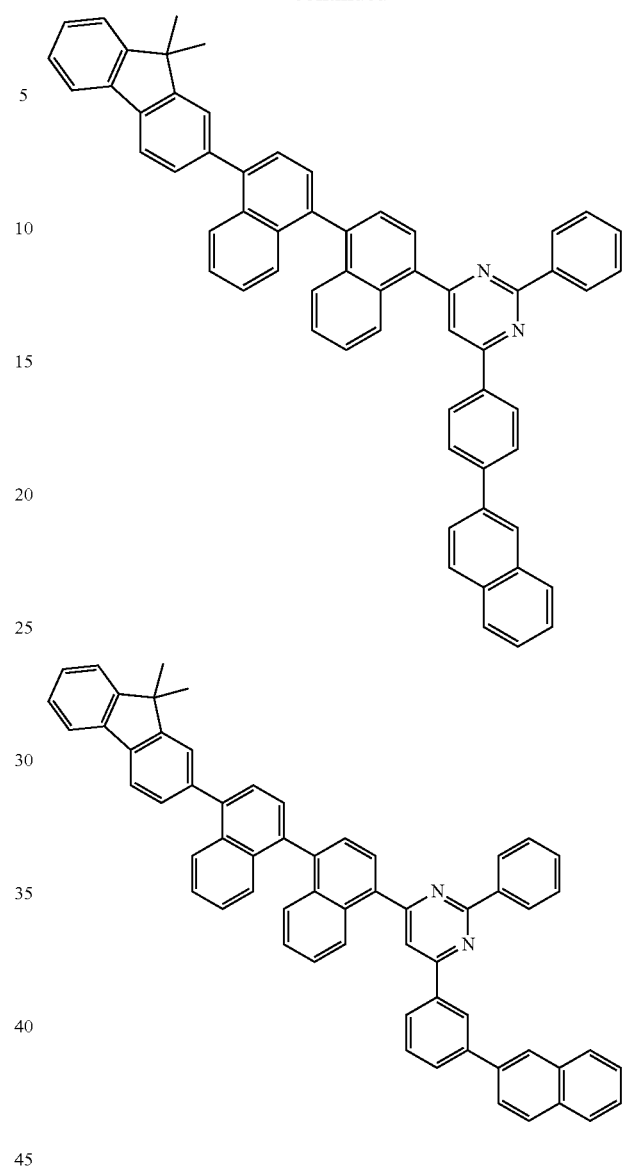
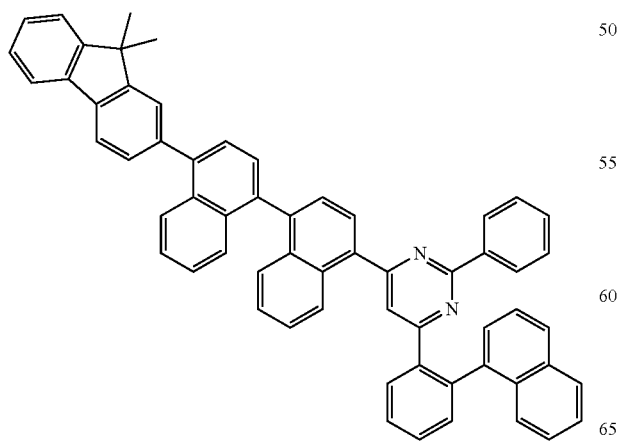

735
-continued
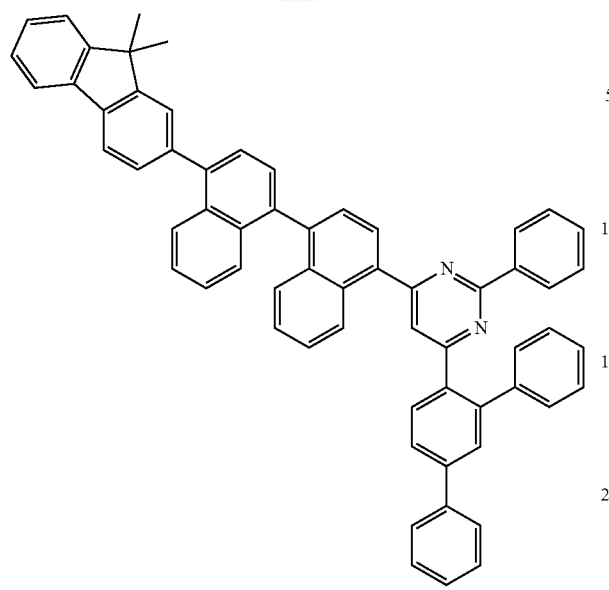
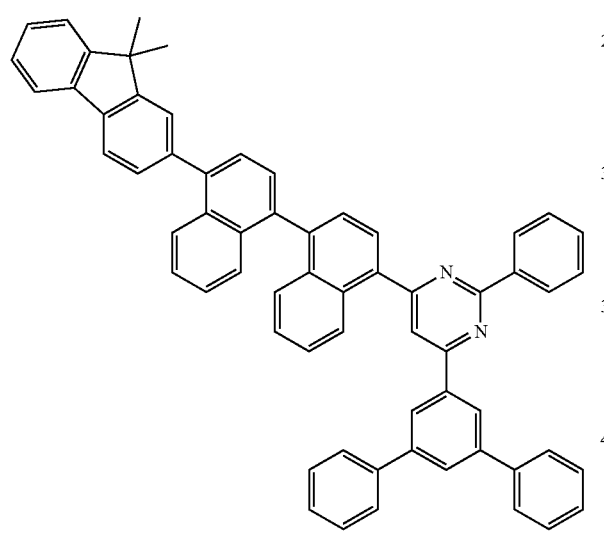
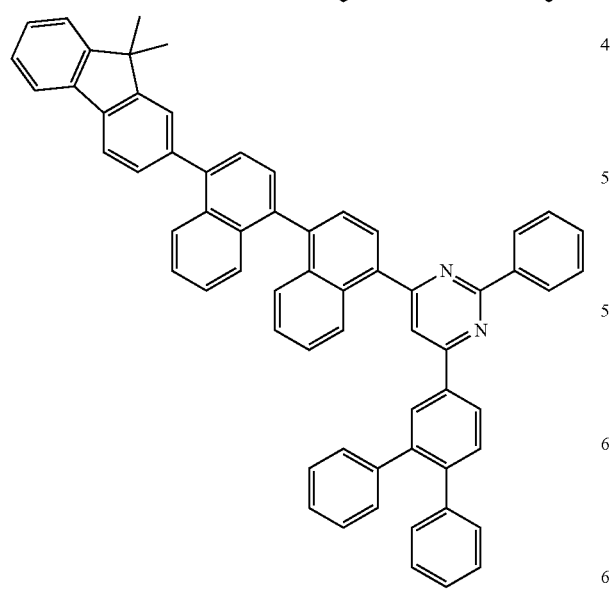
736
-continued
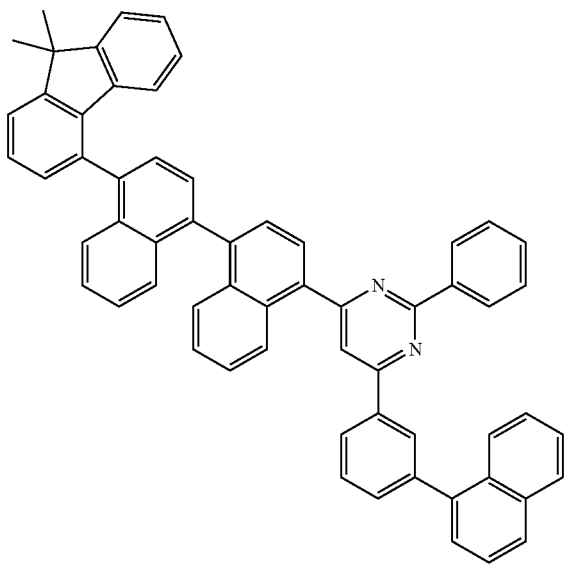
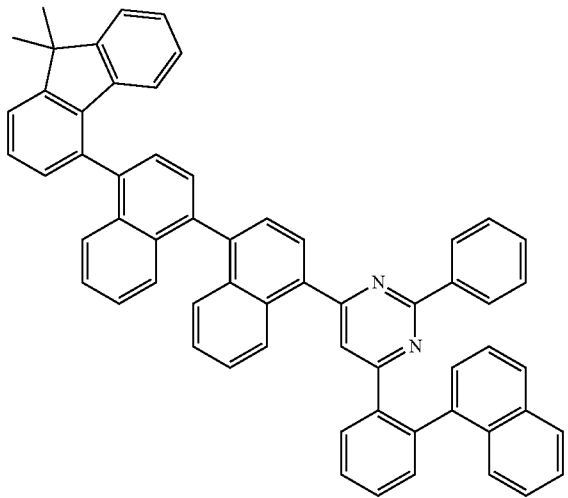

737
-continued
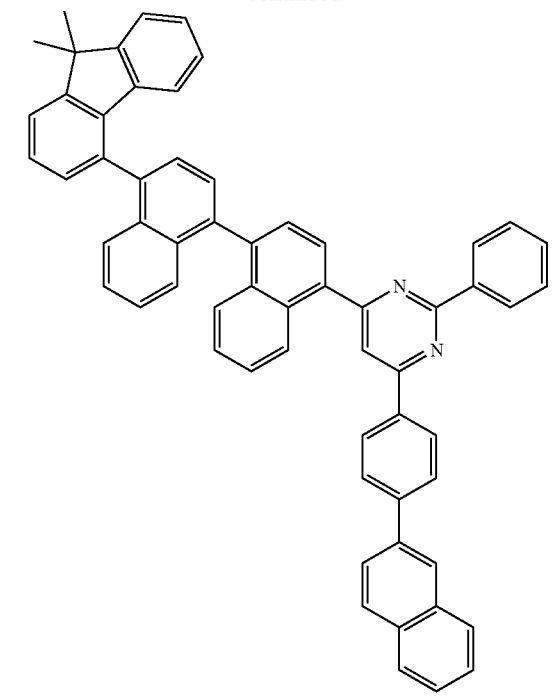
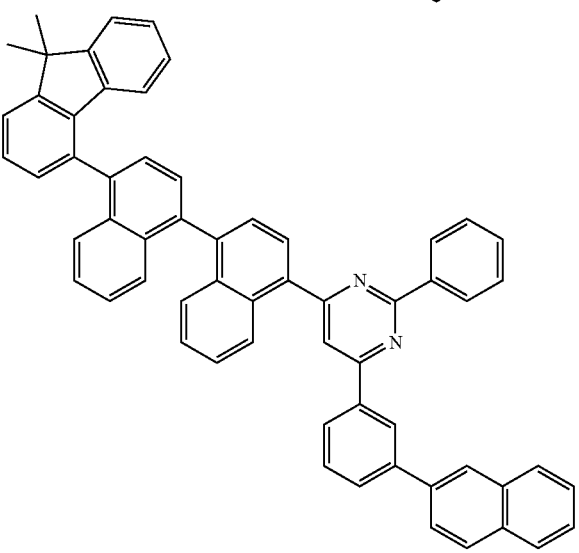
738
-continued
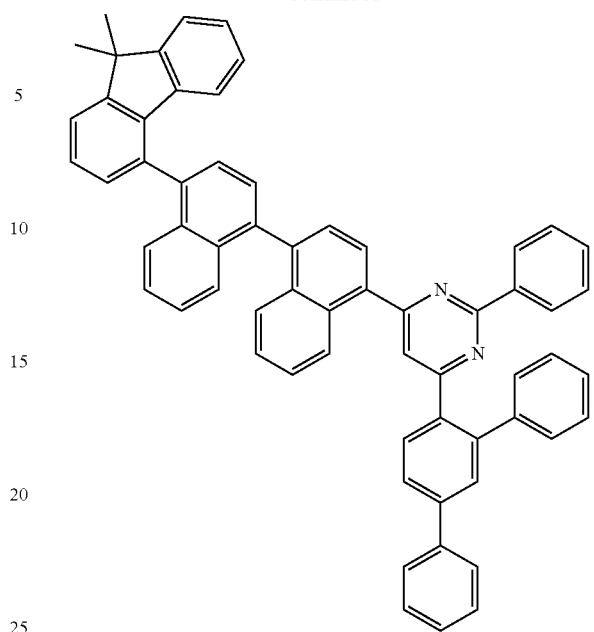
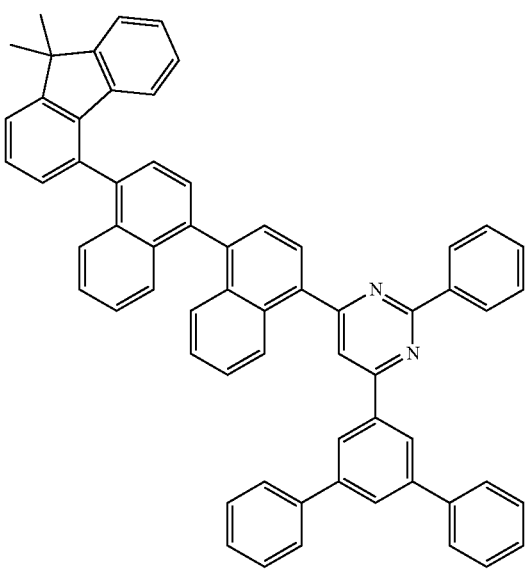

739
-continued
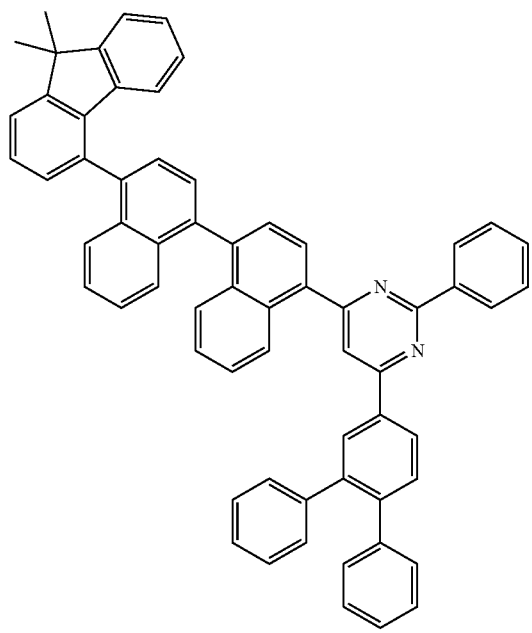
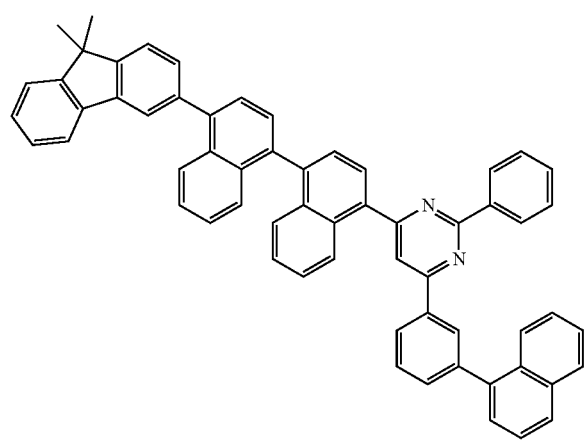
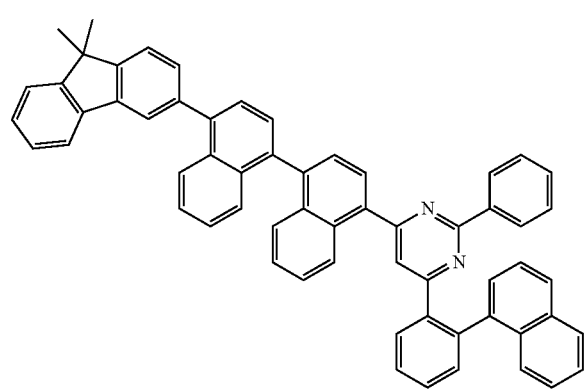
740
-continued
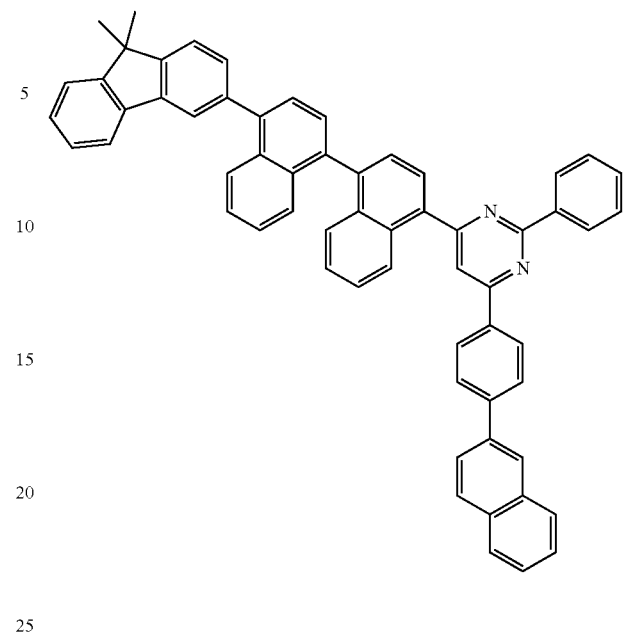
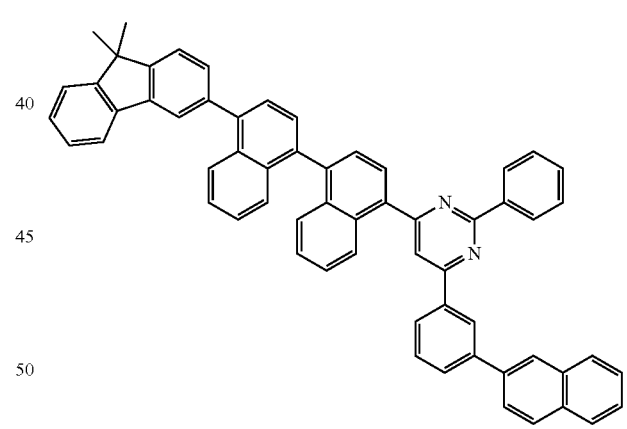
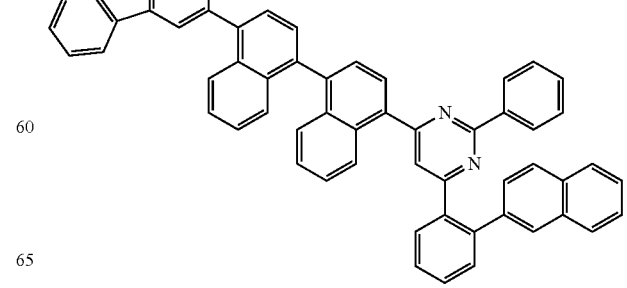

741
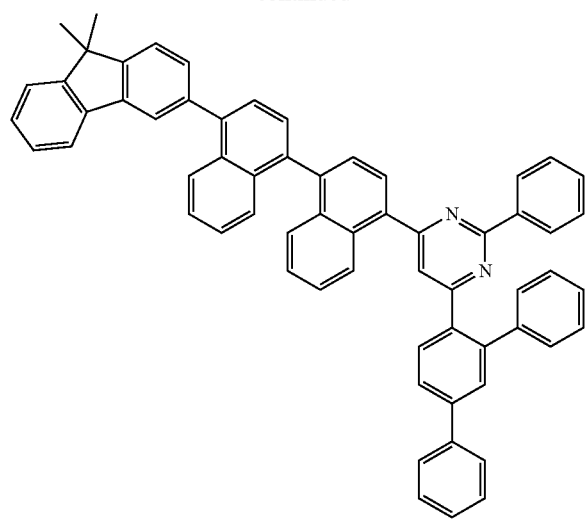
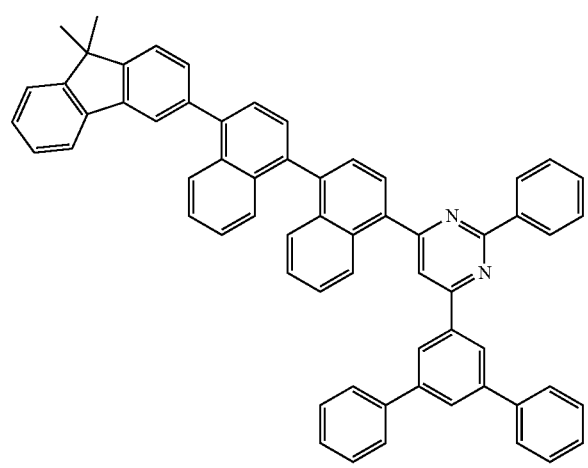
742
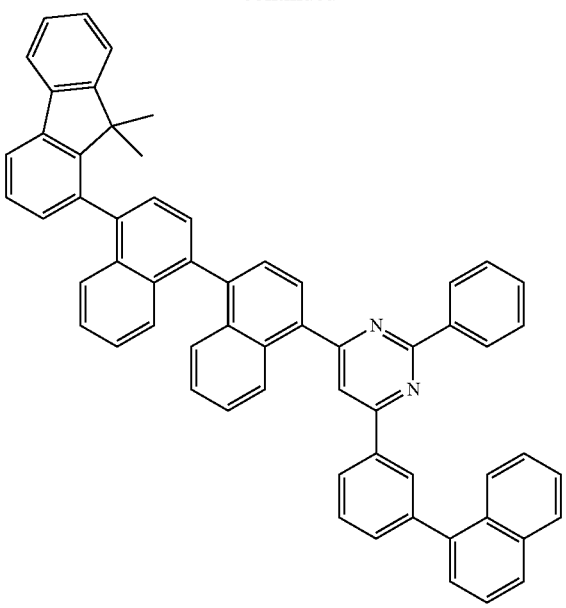
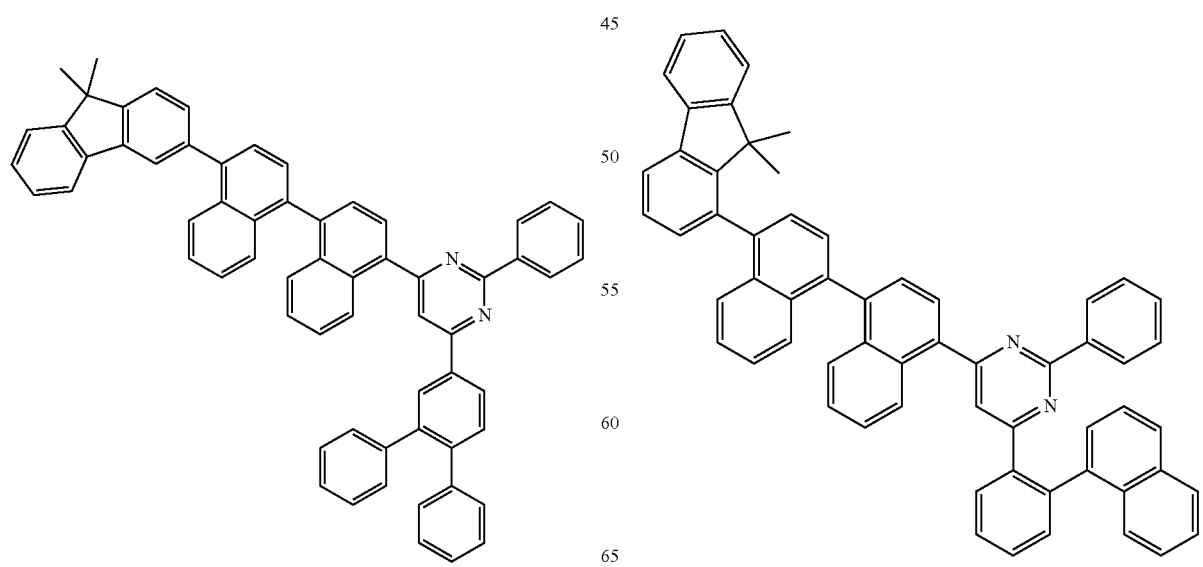

743
-continued
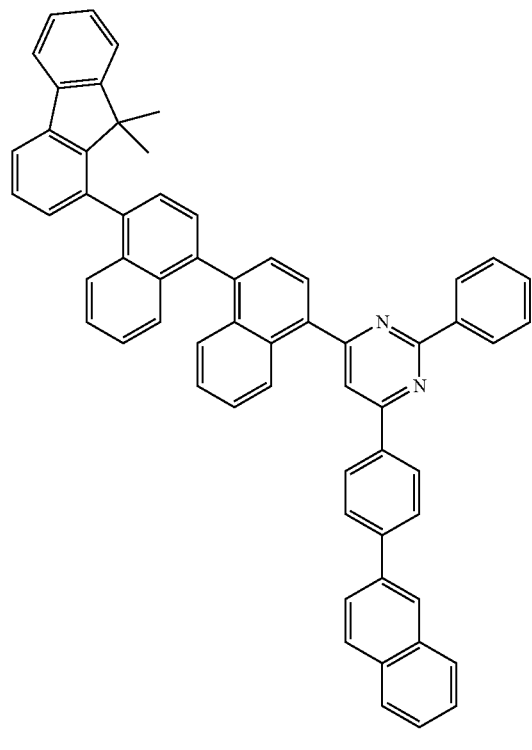
744
-continued
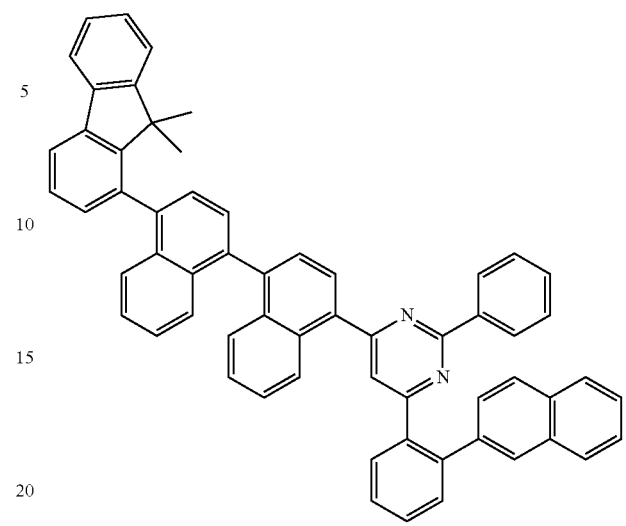
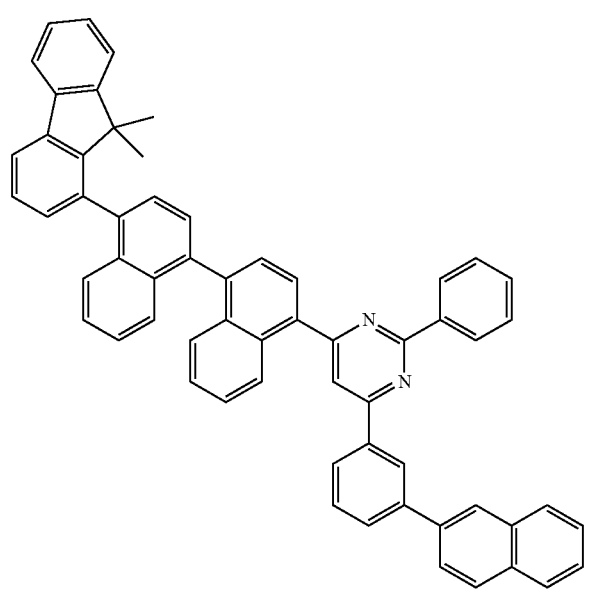
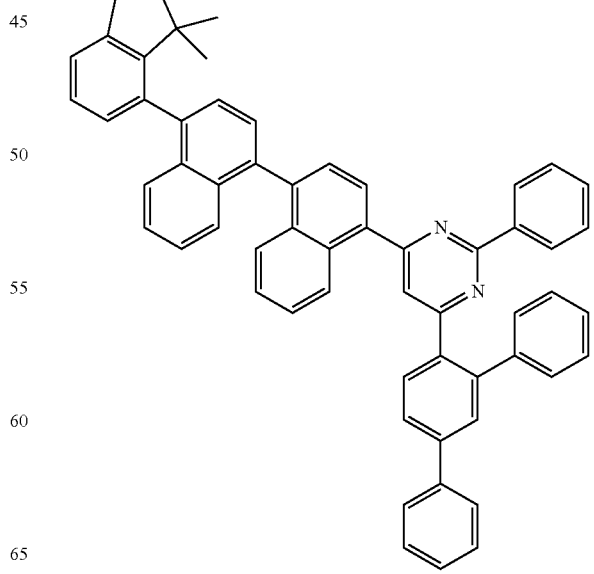

745
-continued
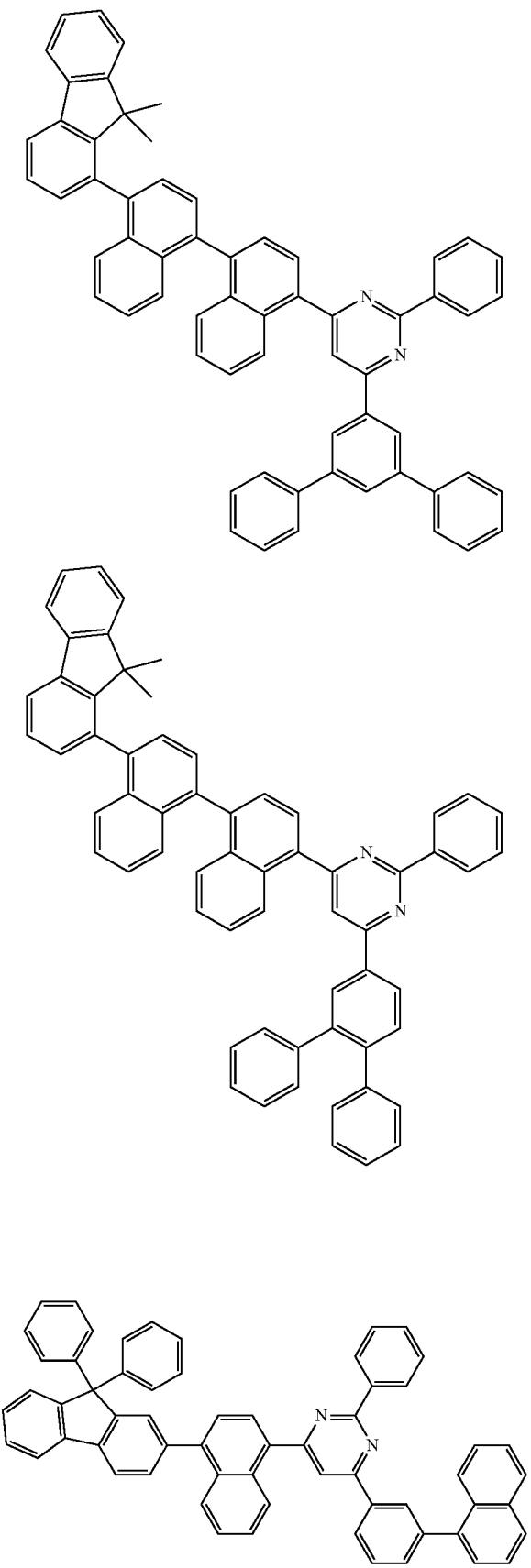
746
-continued
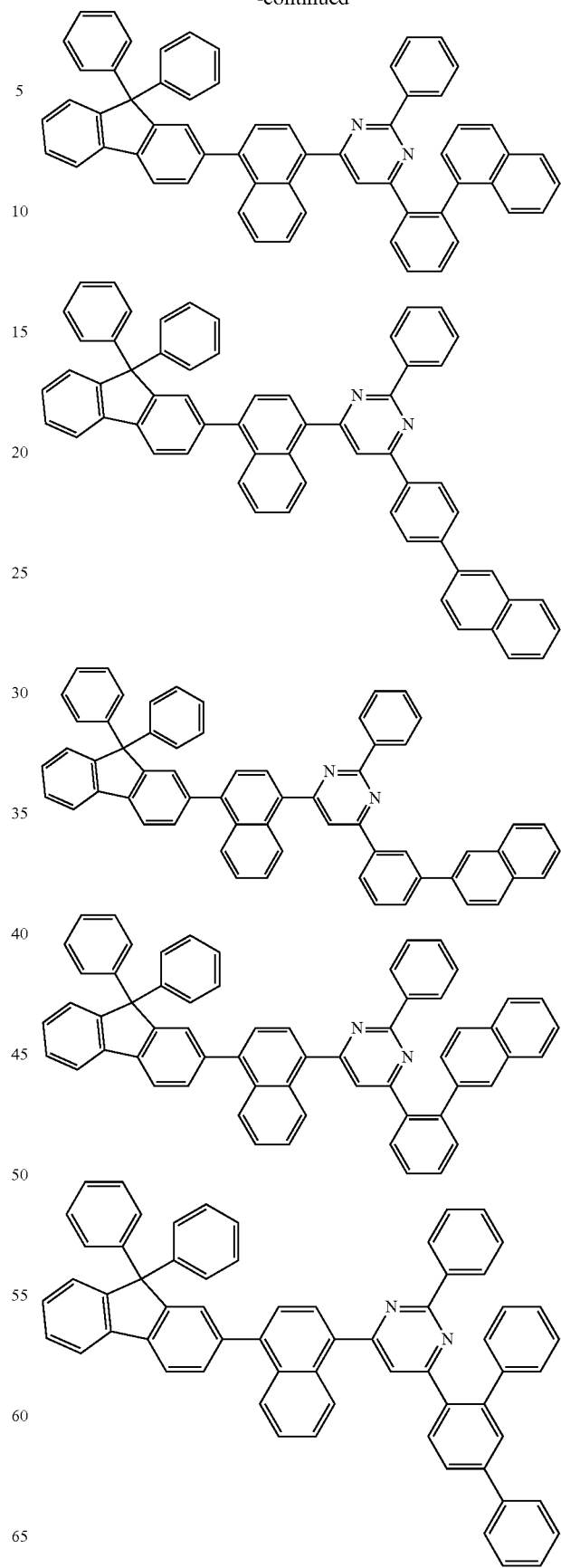

747
-continued
748
-continued
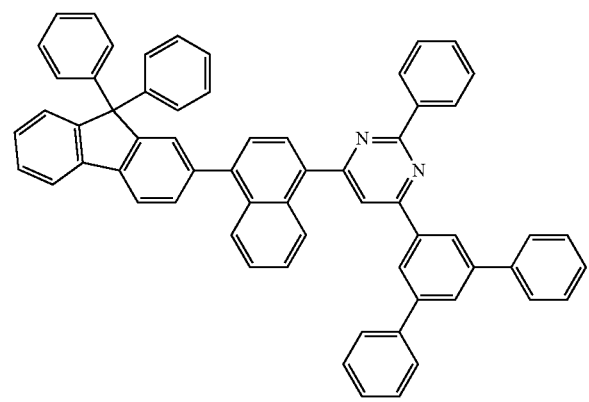
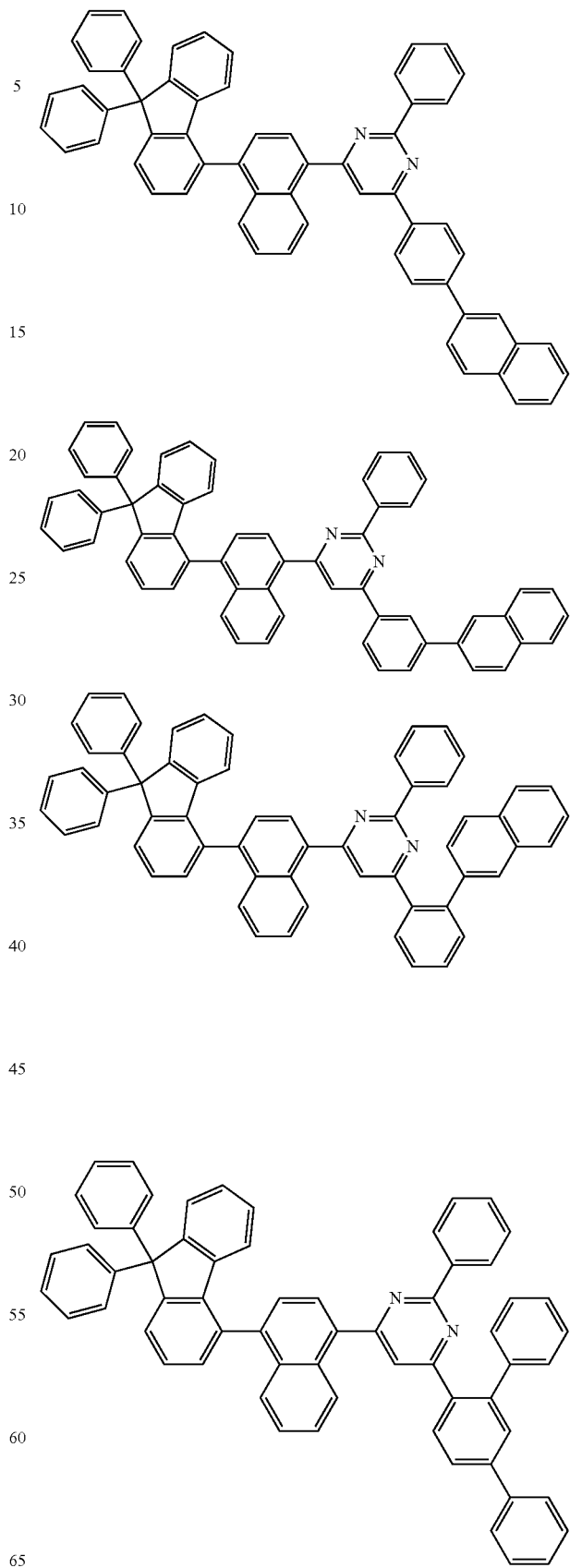

749
-continued
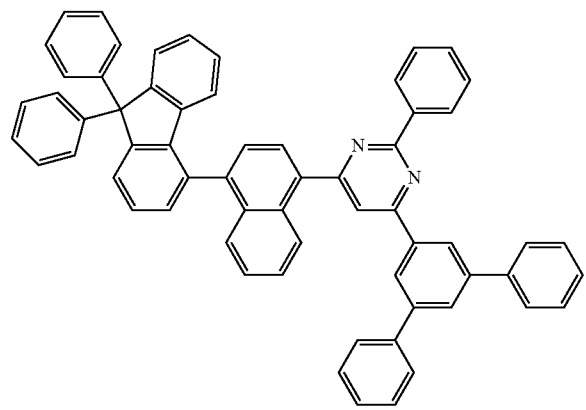
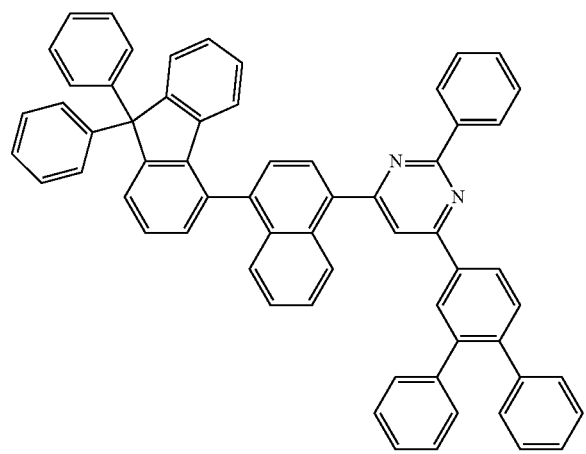
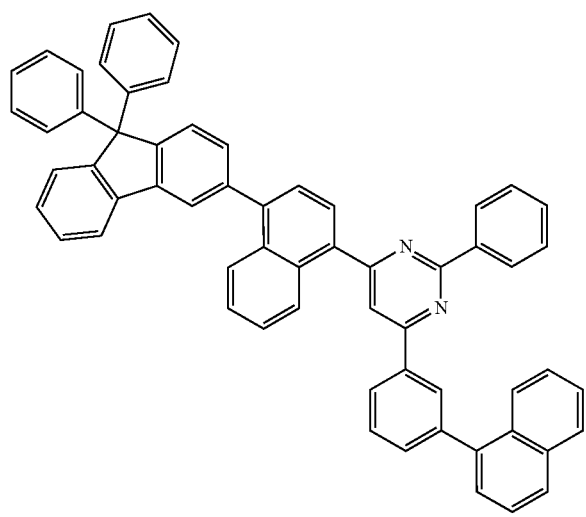
750
-continued
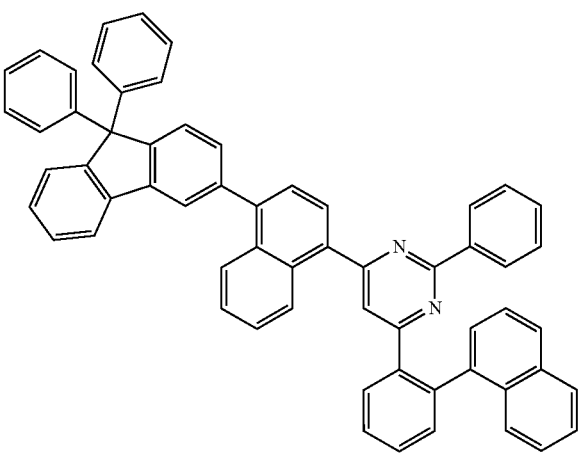
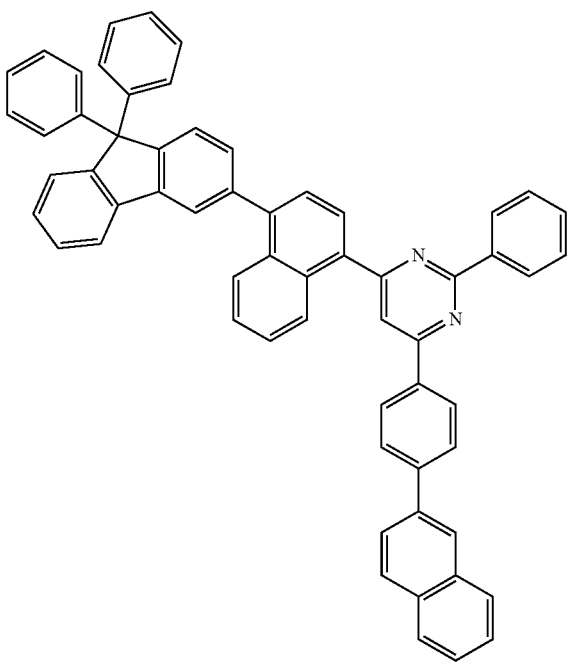
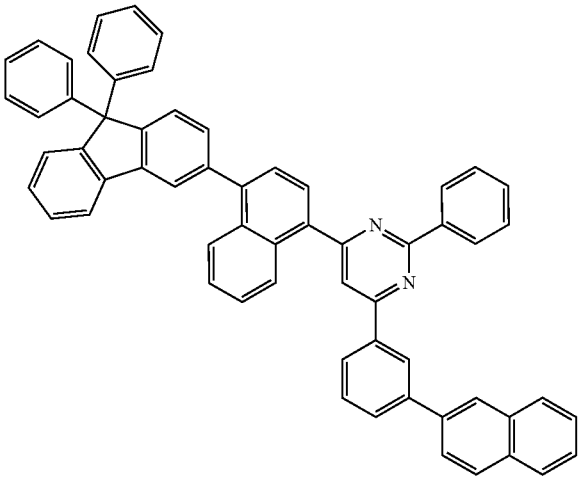

751
-continued
752
-continued
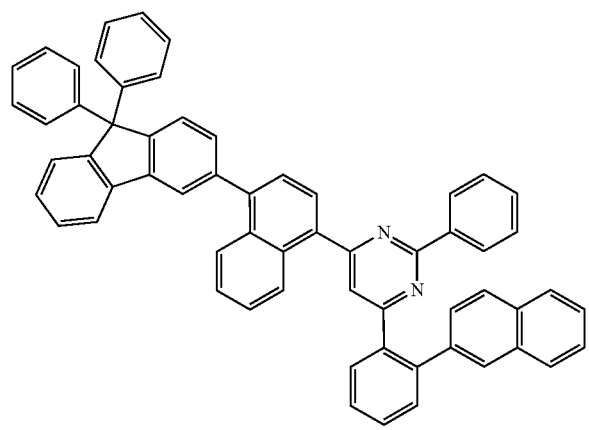
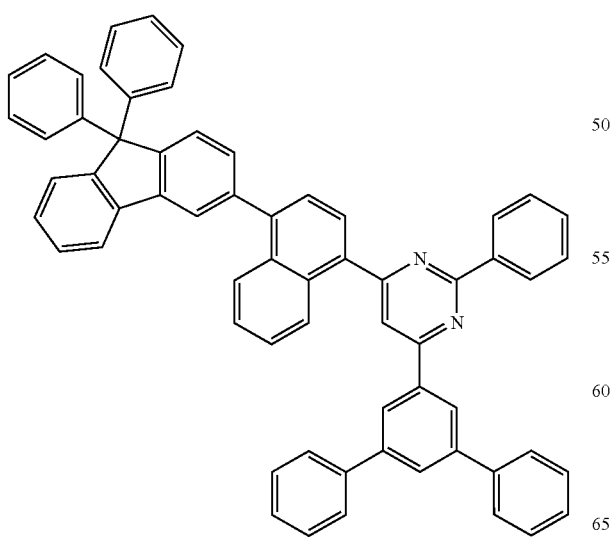
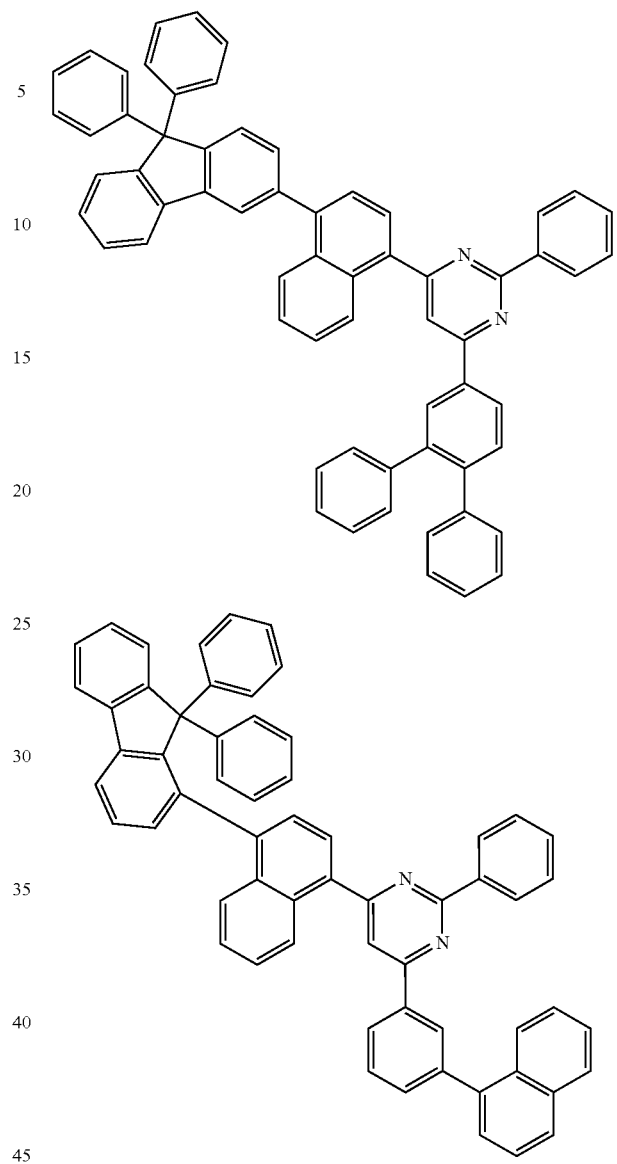

753
-continued
754
-continued
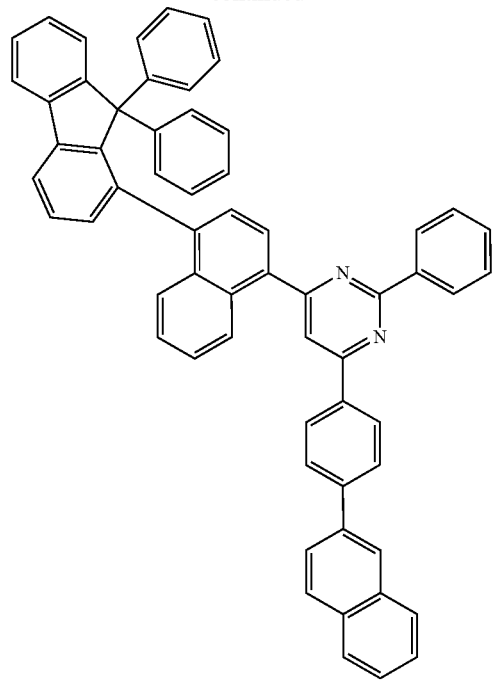
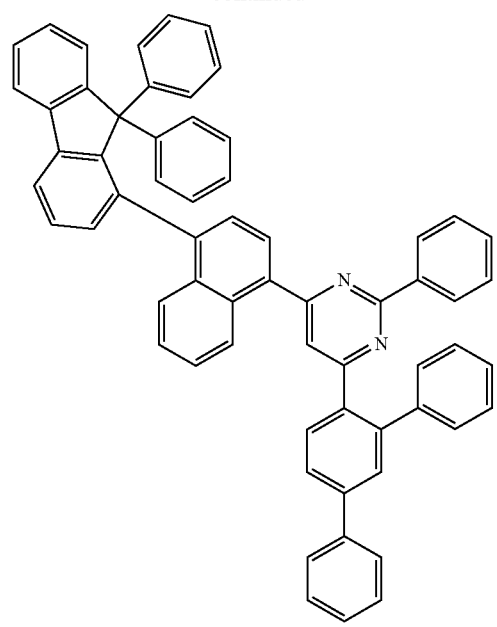
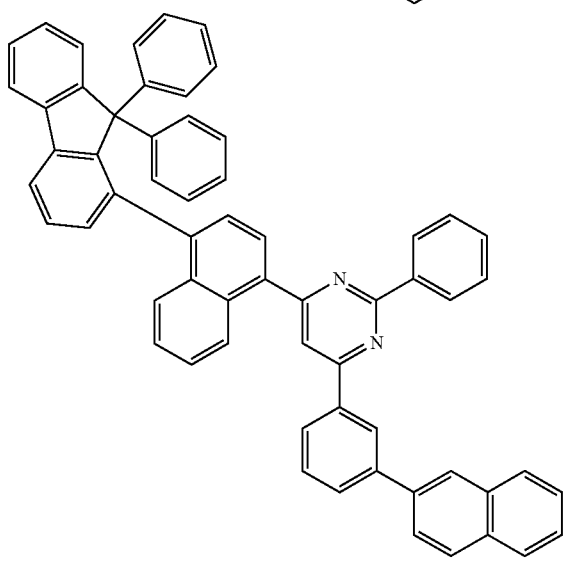
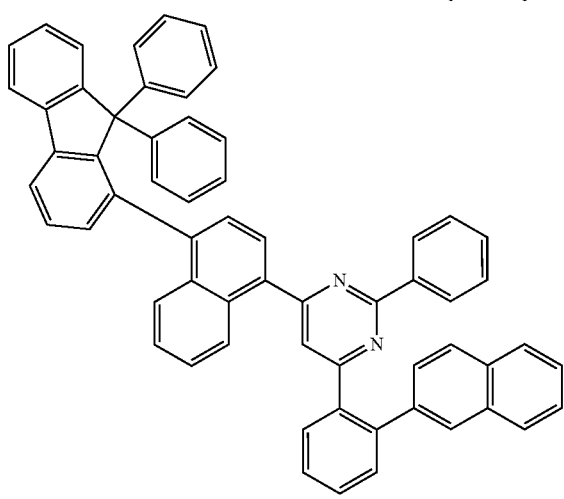
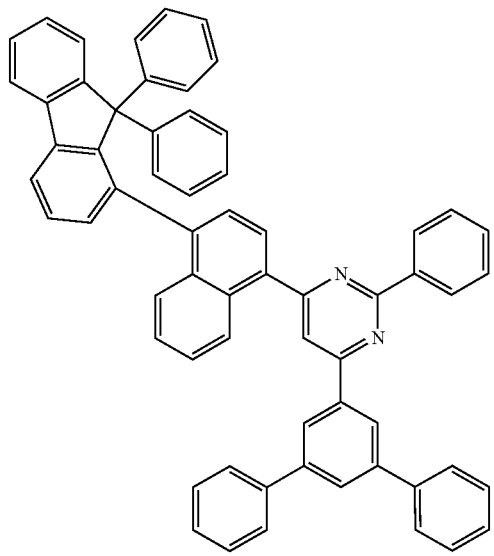

755
-continued
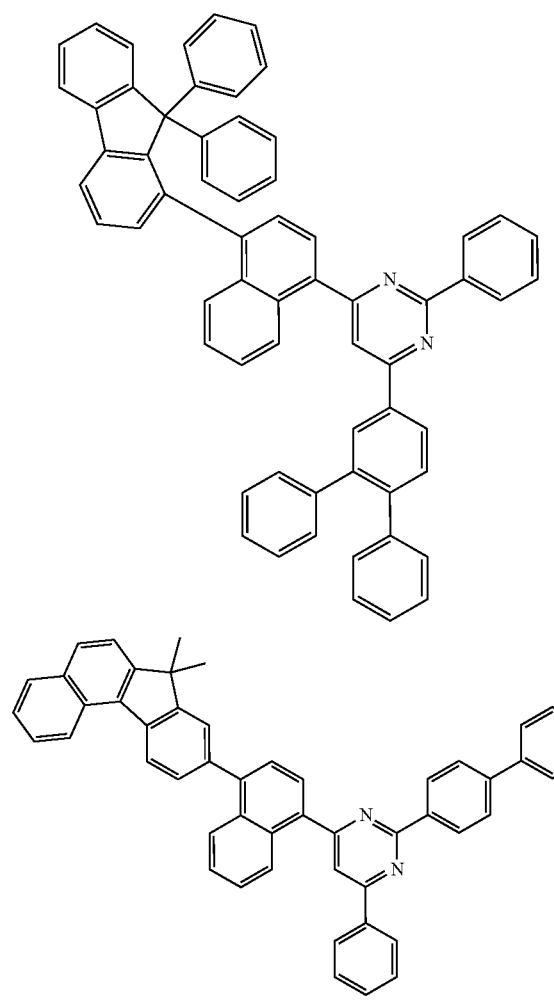
756
-continued
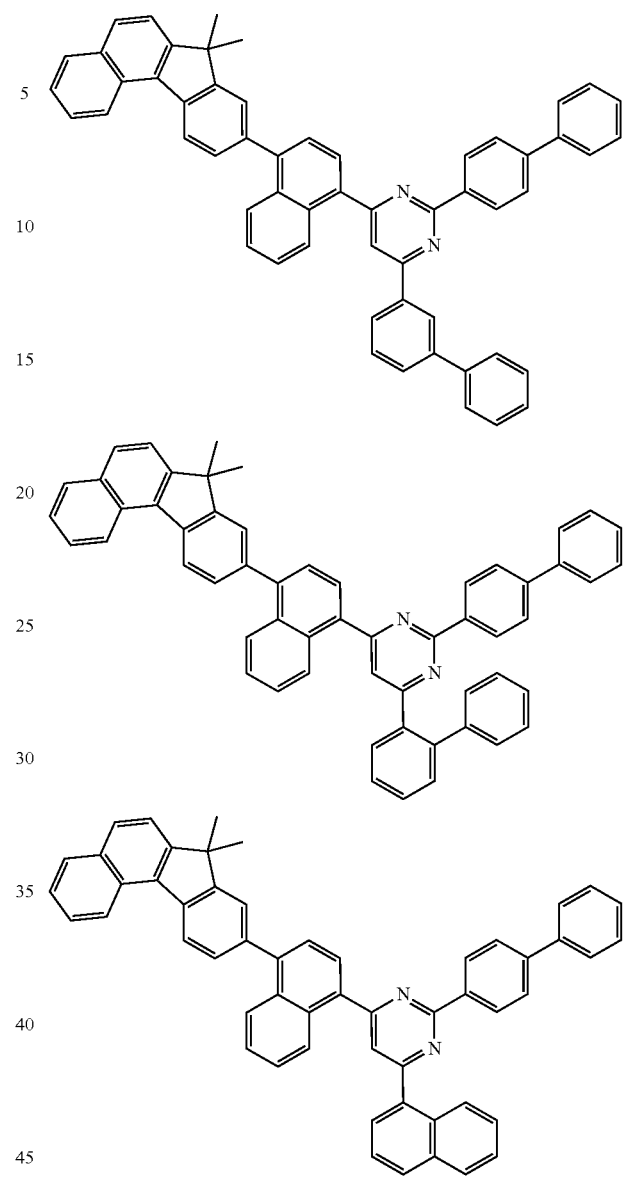
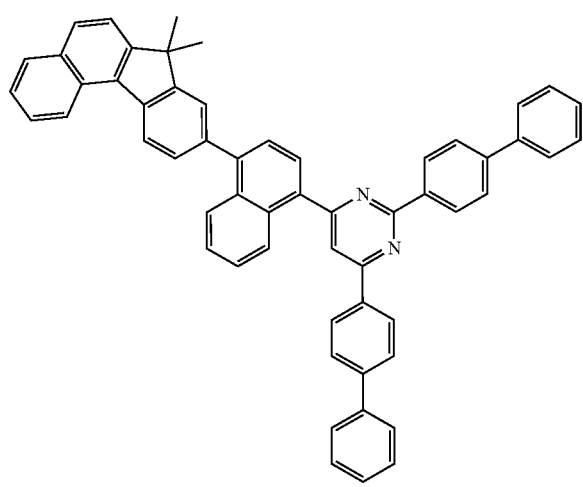

757
-continued
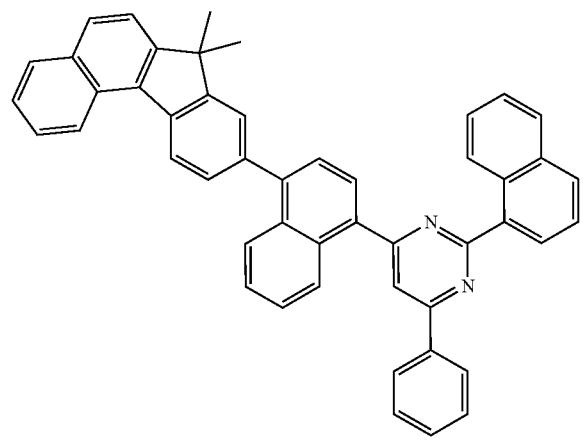
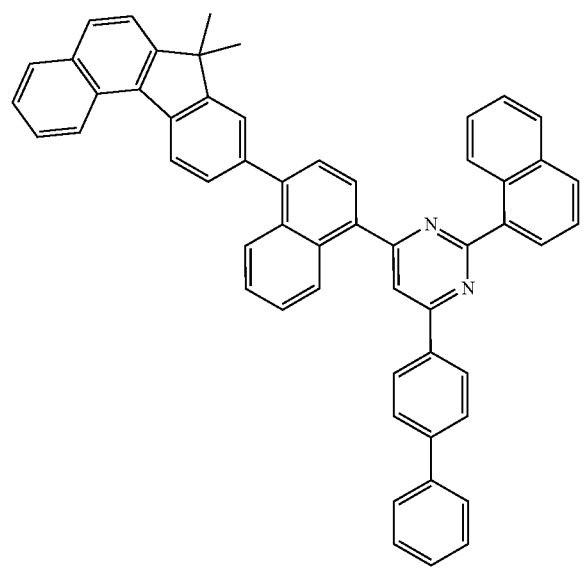
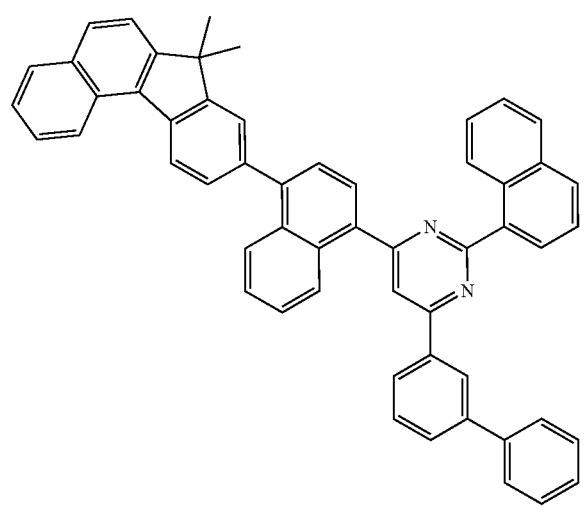
758
-continued
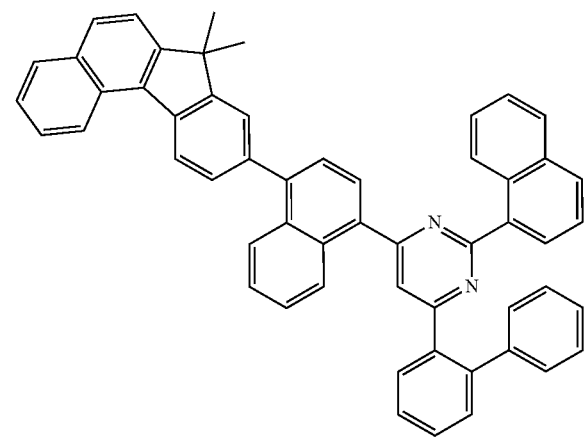
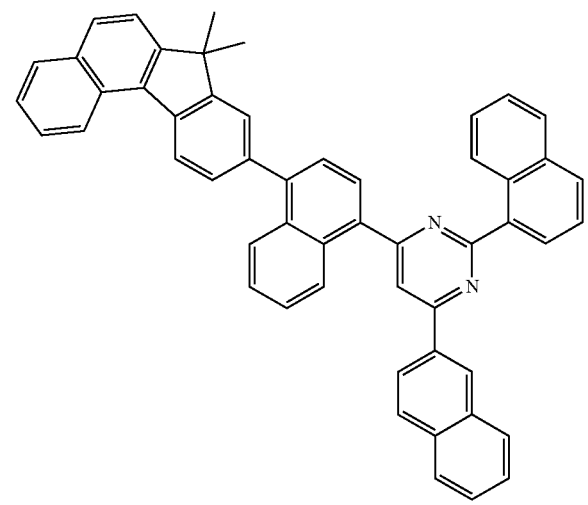

759
-continued
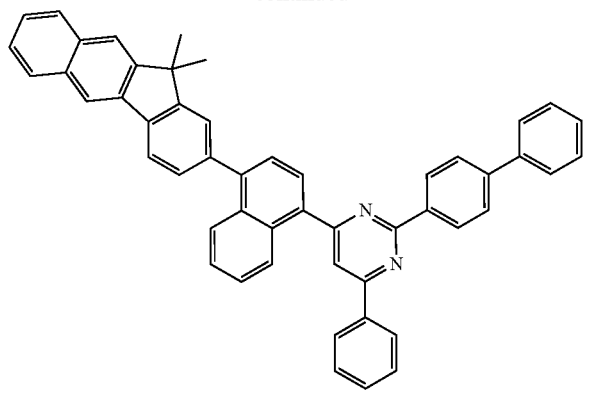
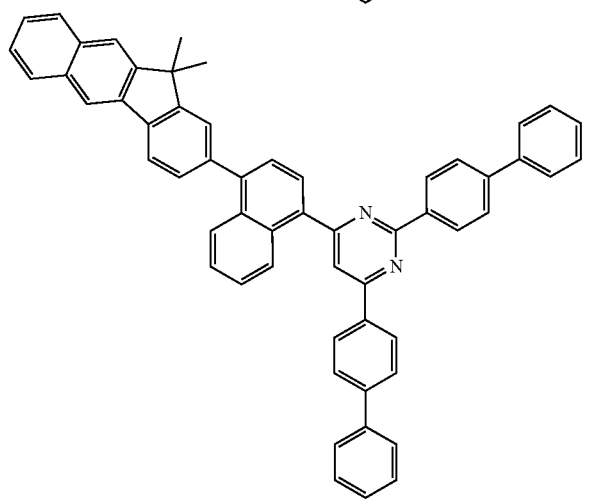
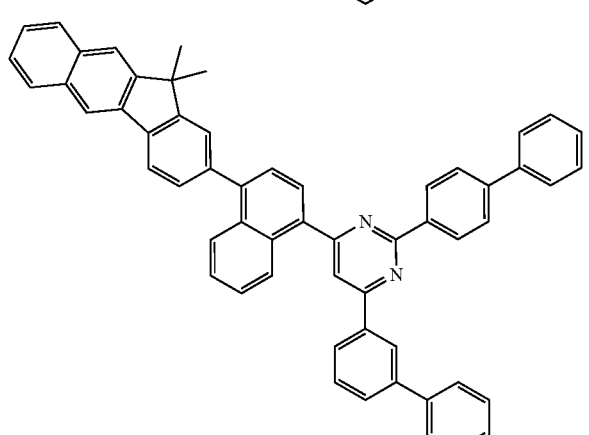
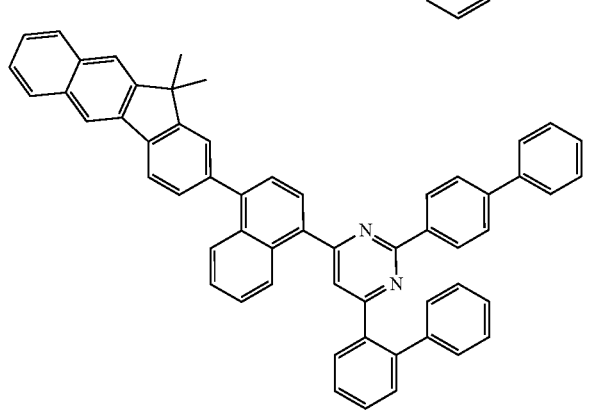
760
-continued
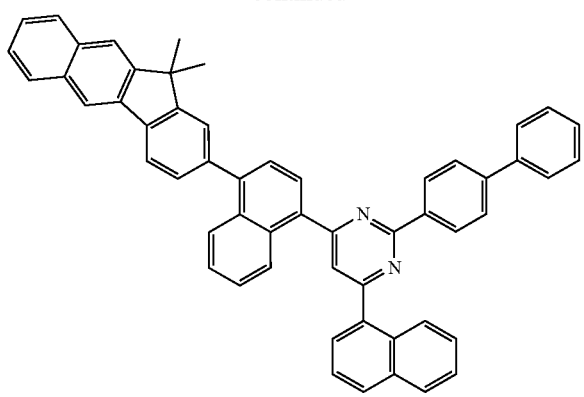
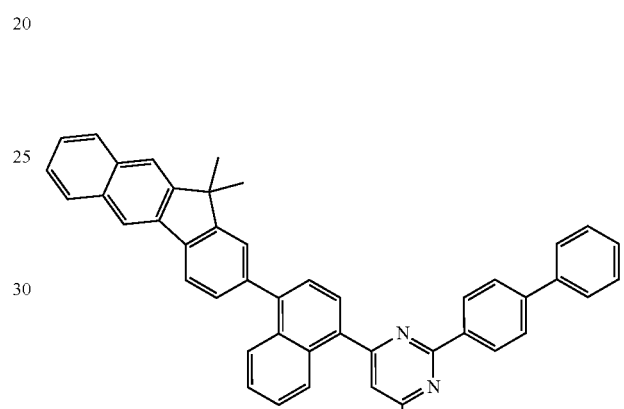
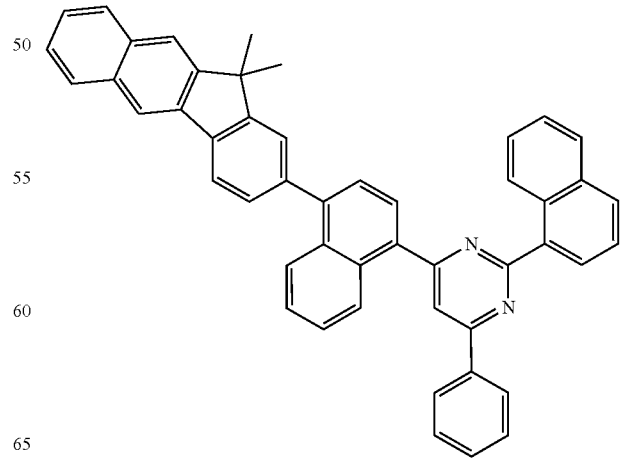

761
-continued
762
-continued
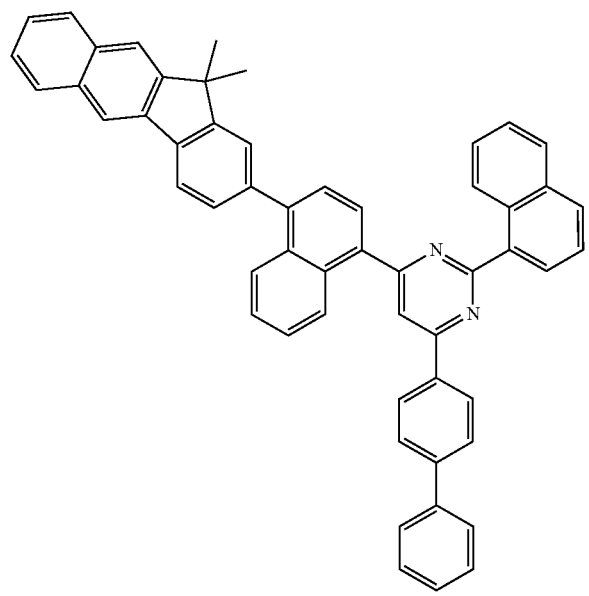
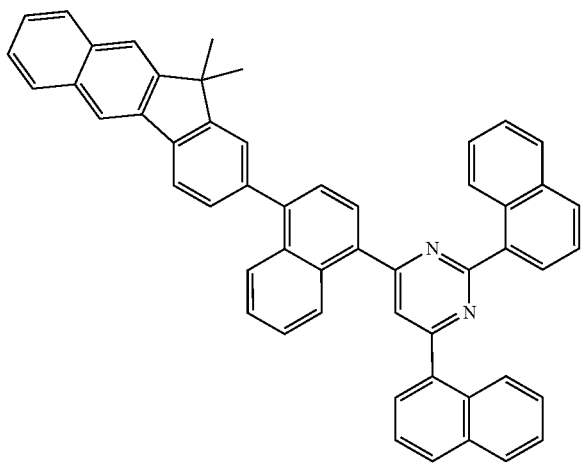
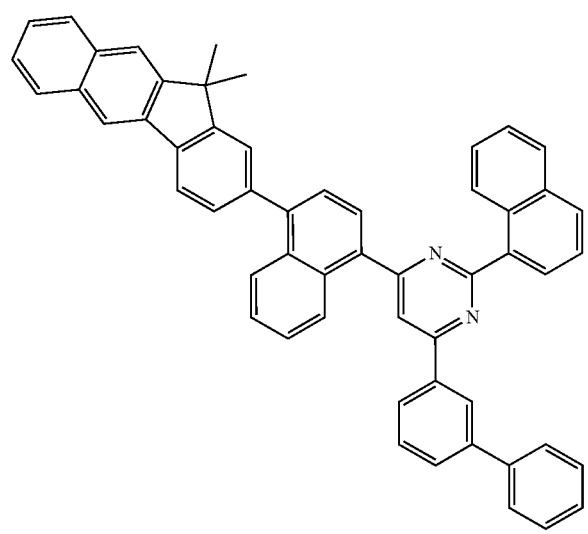
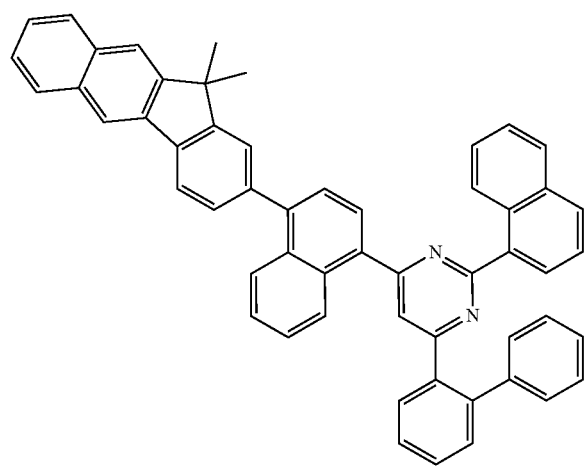
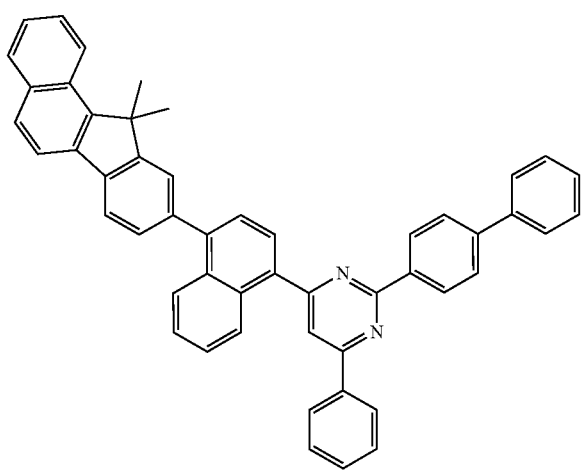

763
-continued
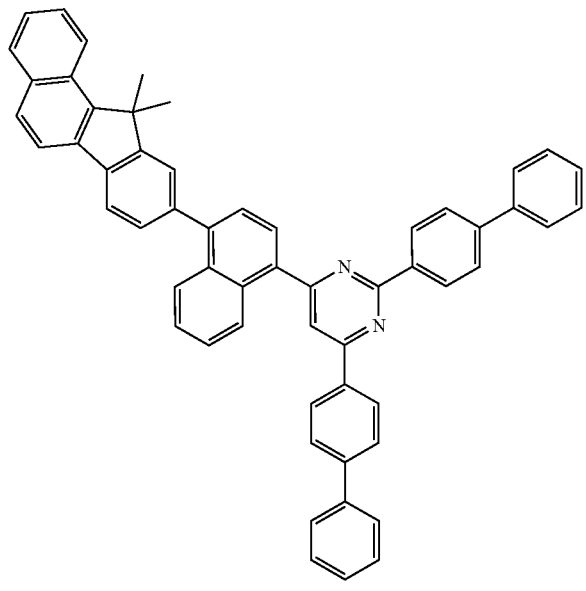
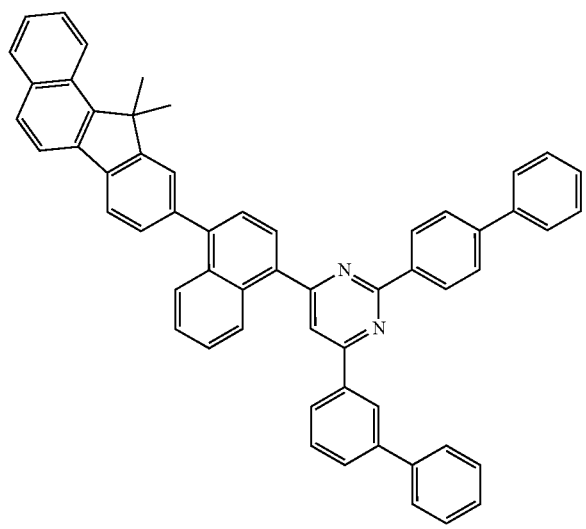
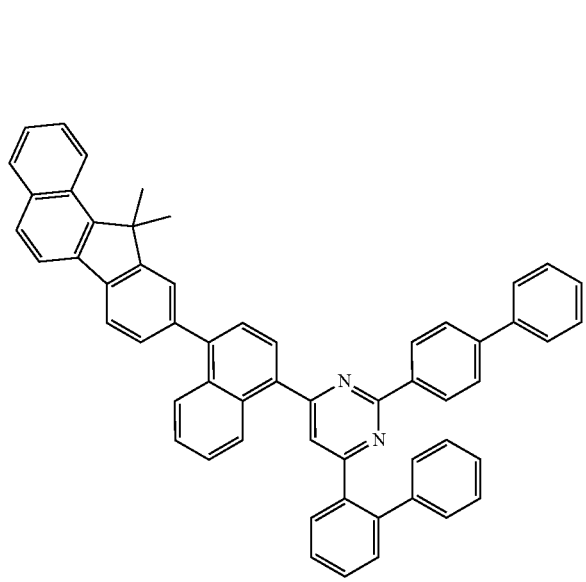
764
-continued
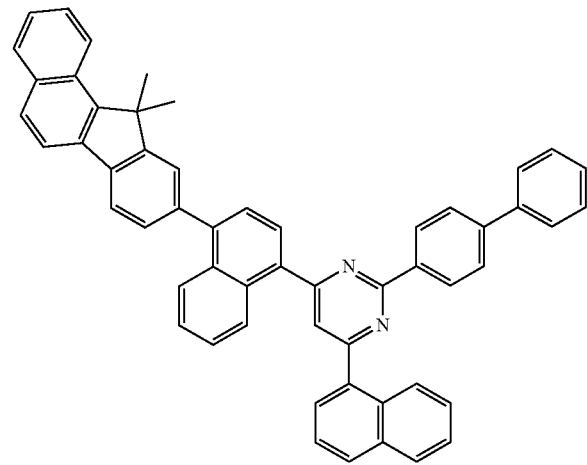
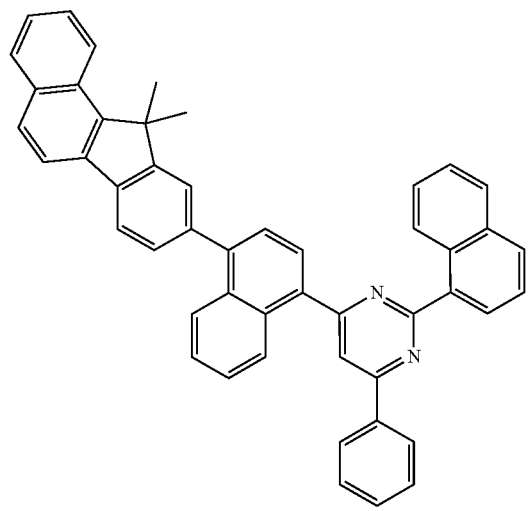

765
-continued
766
-continued
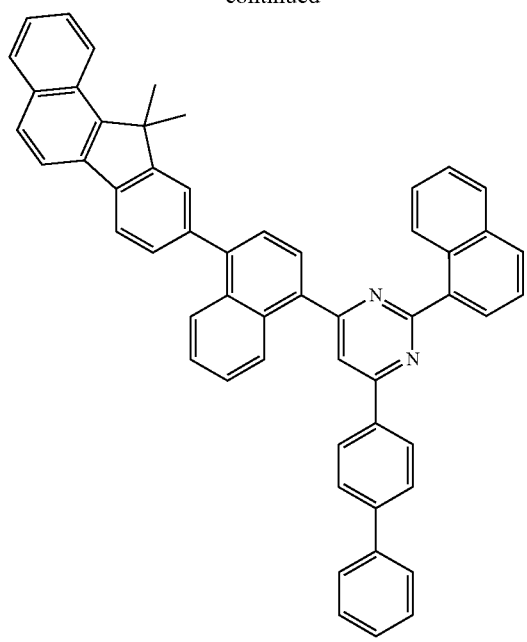
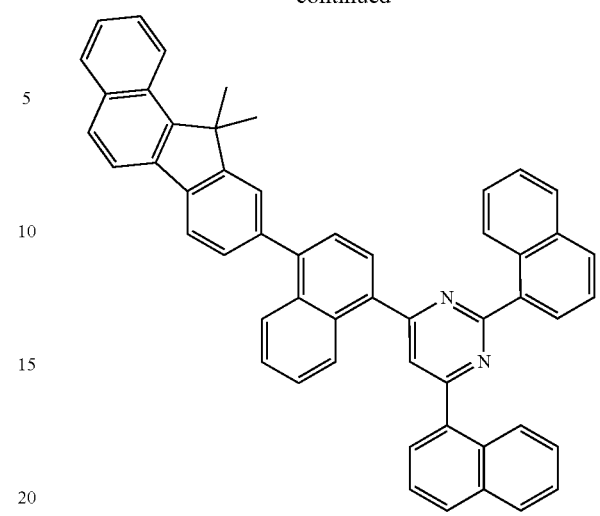
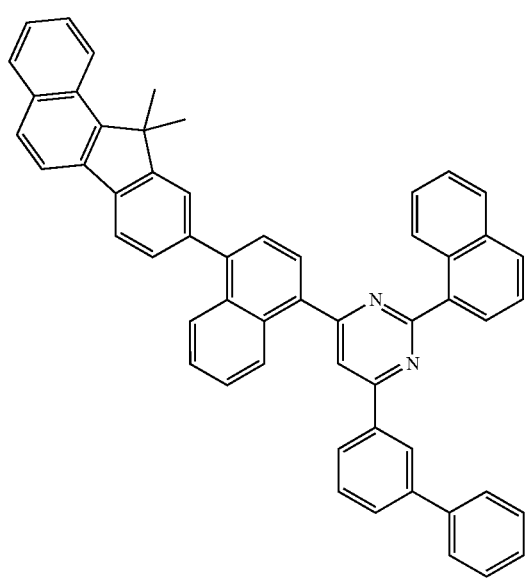
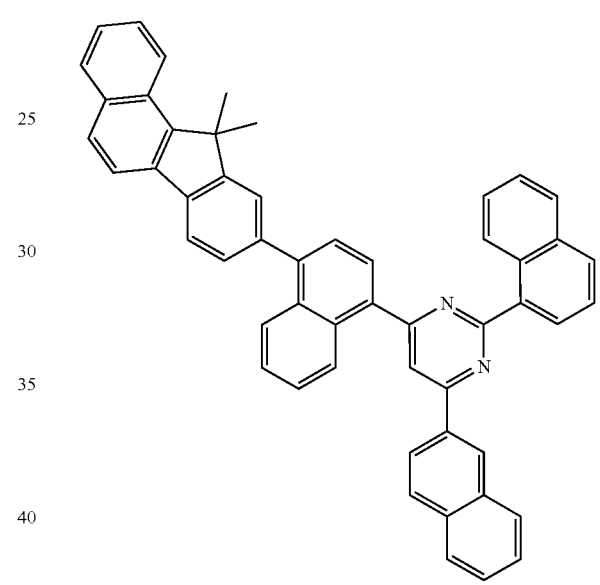
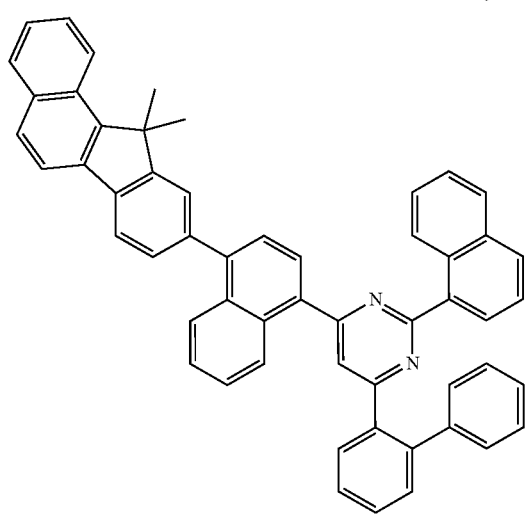
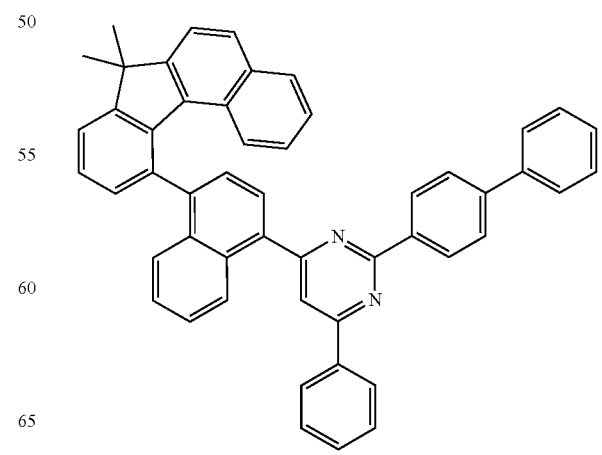

767
-continued
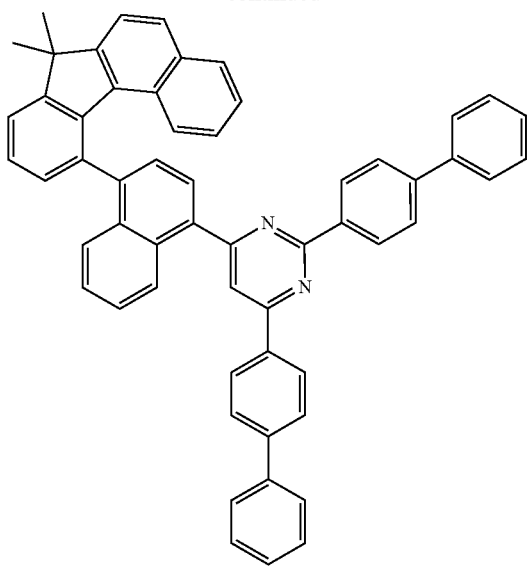
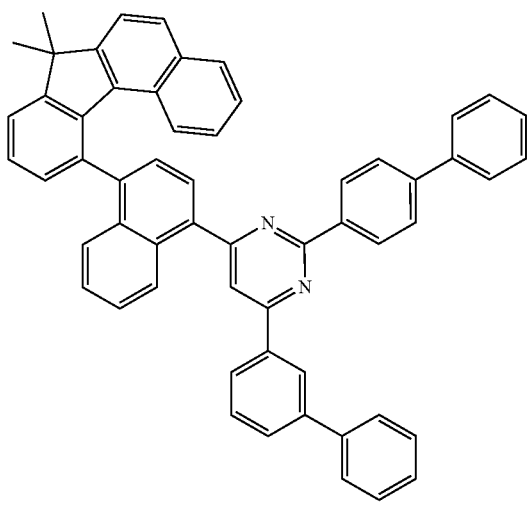
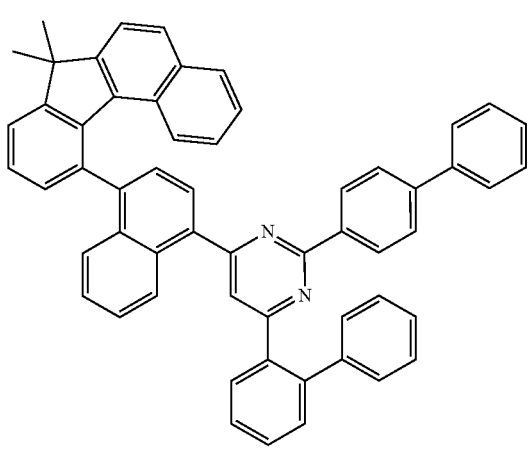
768
-continued
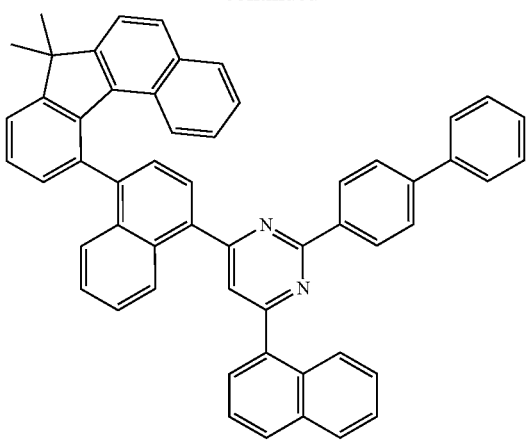
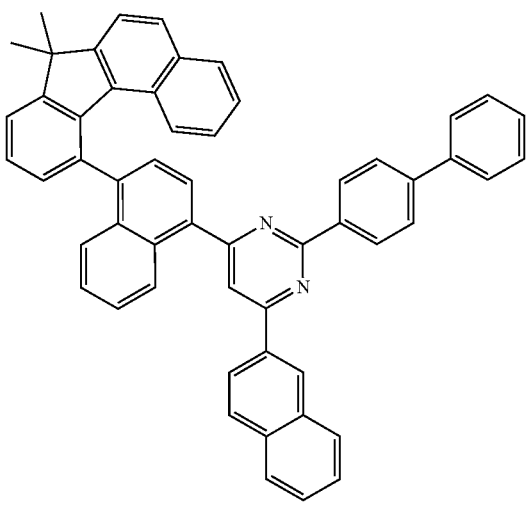
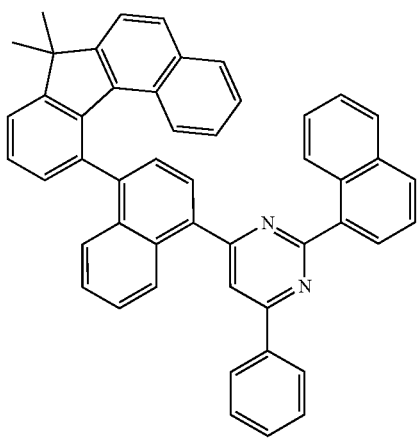

769
-continued
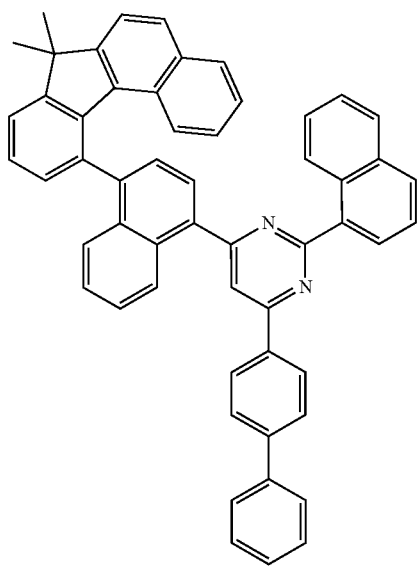
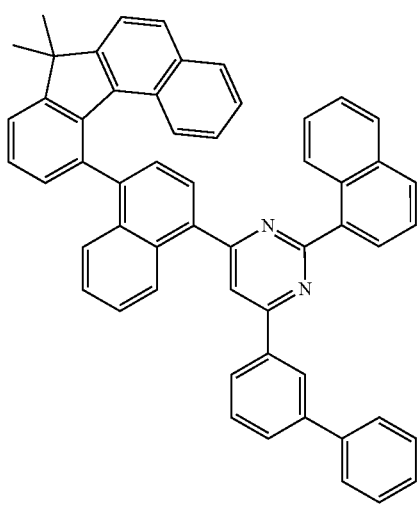
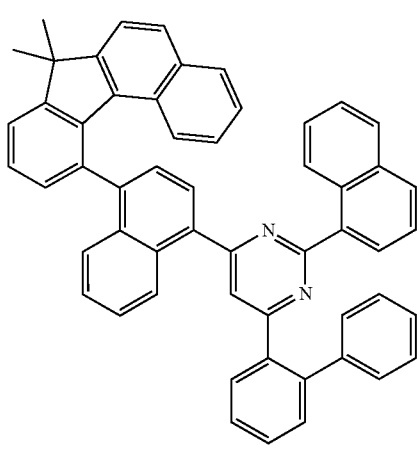
770
-continued
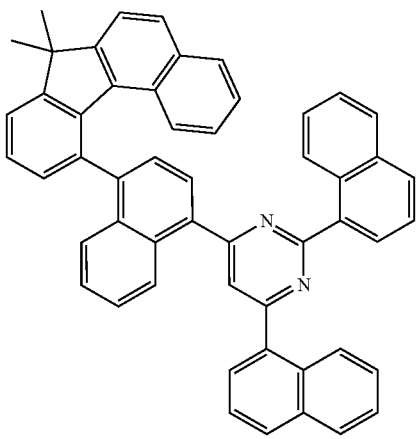
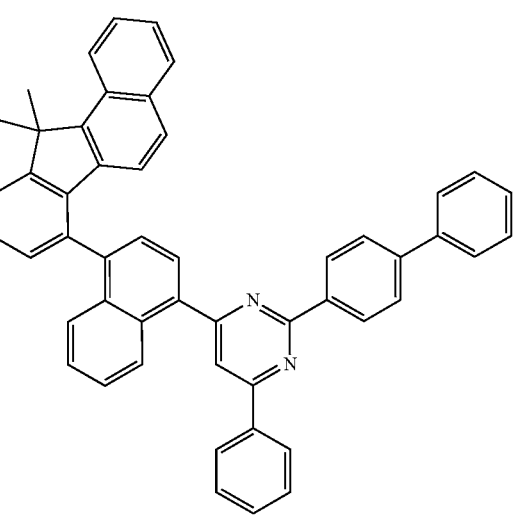

771
-continued
772
-continued
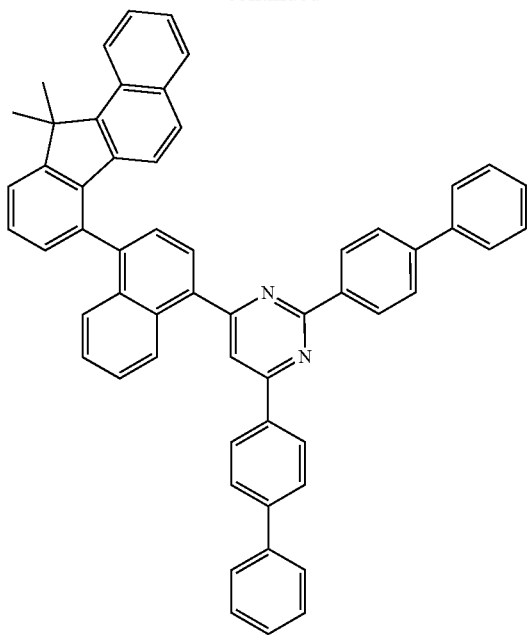
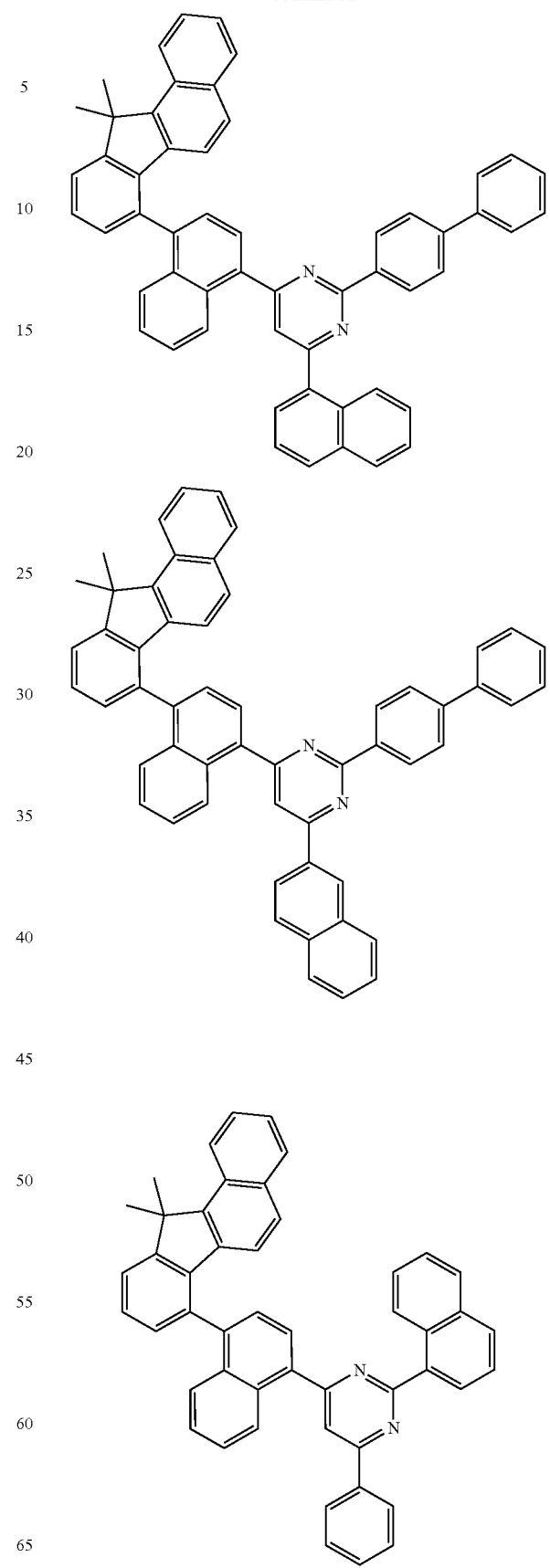

773
-continued
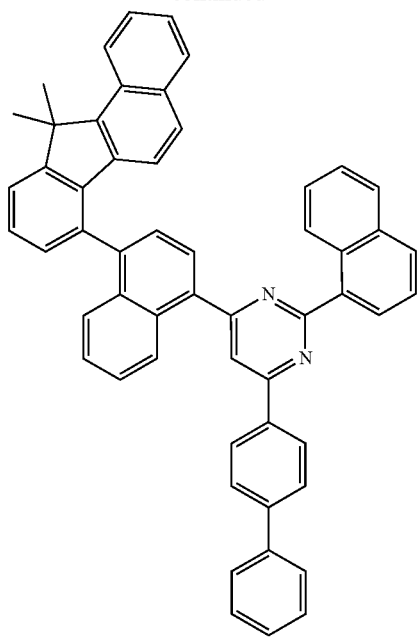
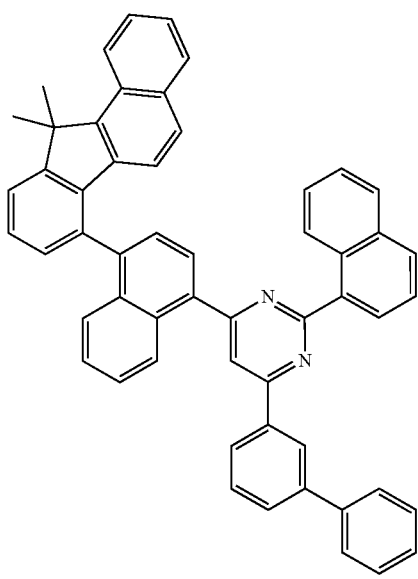
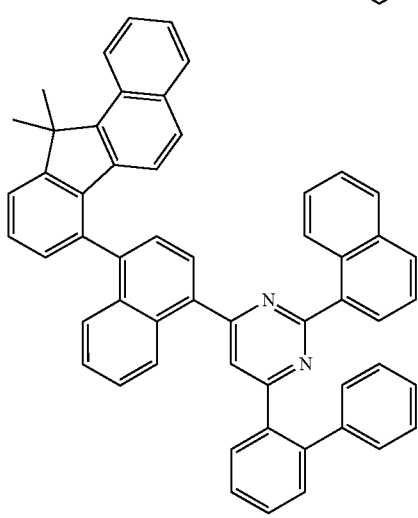
774
-continued
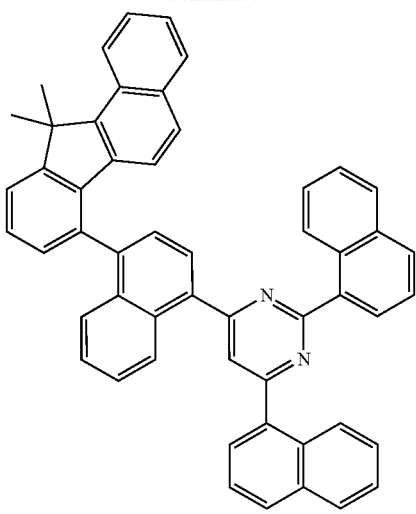
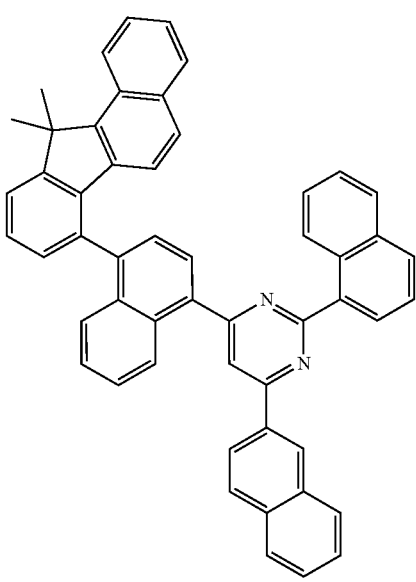 [SMILES: CC1(C)c2cccc(-c3ccc(-c4cc(-c5ccc6ccccc6c5)nc(-c5cccc6ccccc56)n4)c4ccccc34)c2-c2ccc3ccccc3c21]
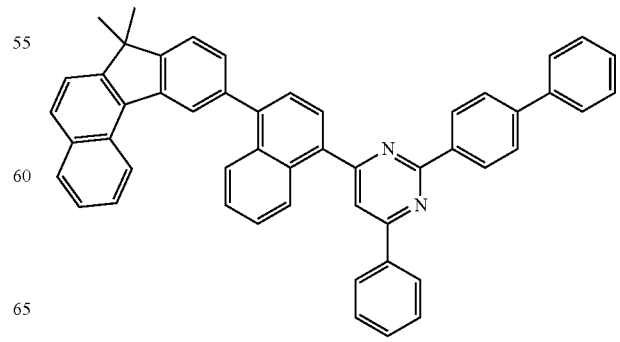

775
-continued
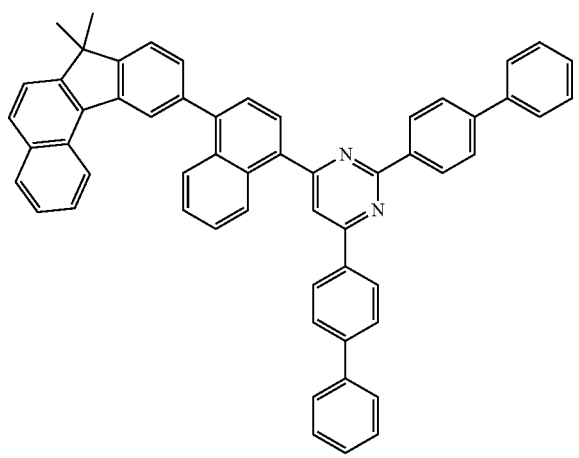
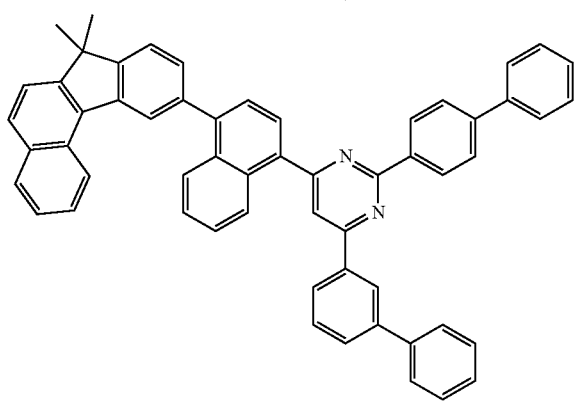
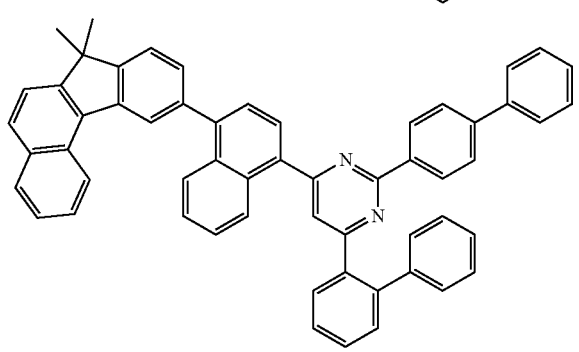
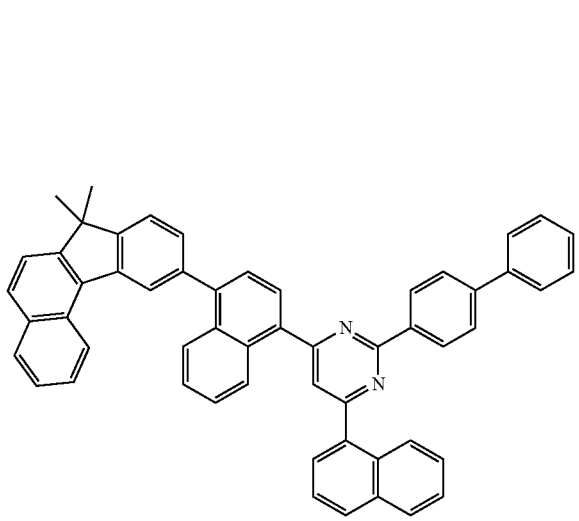
776
-continued
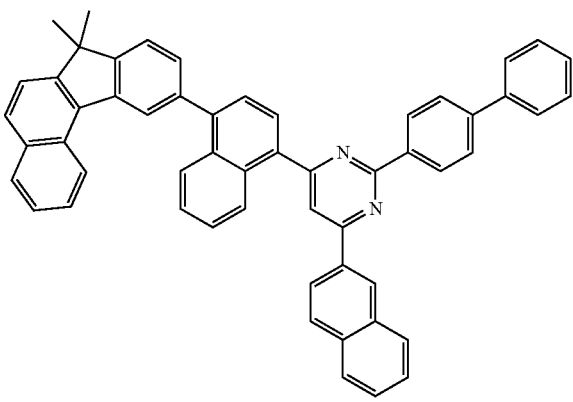
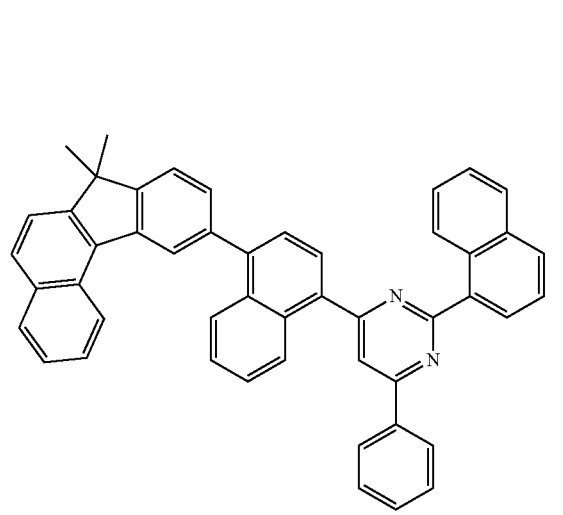
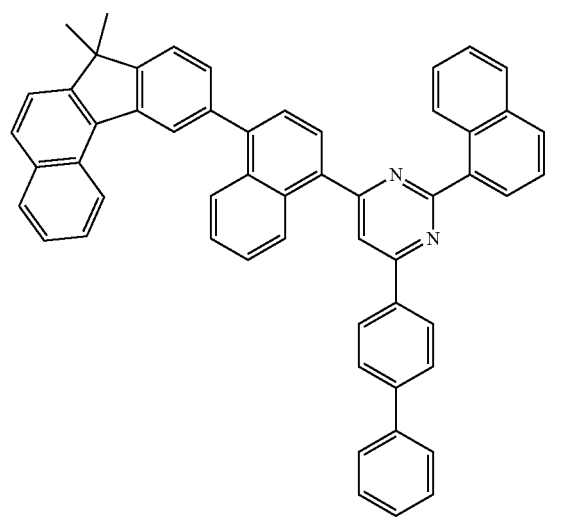

777
-continued
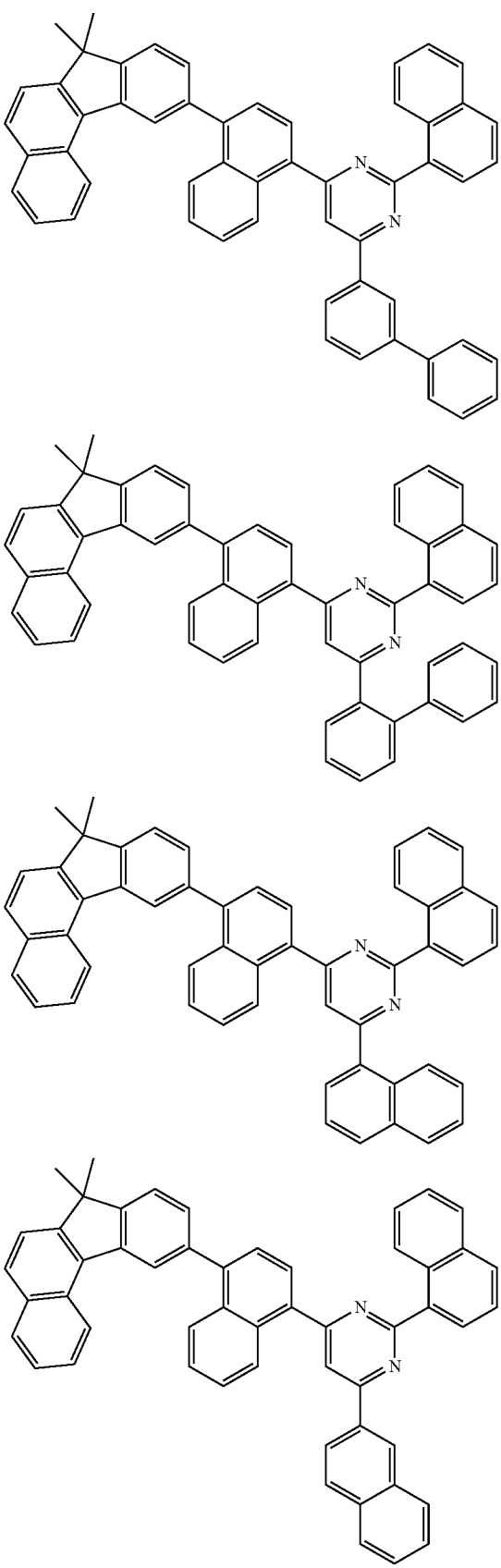
778
-continued
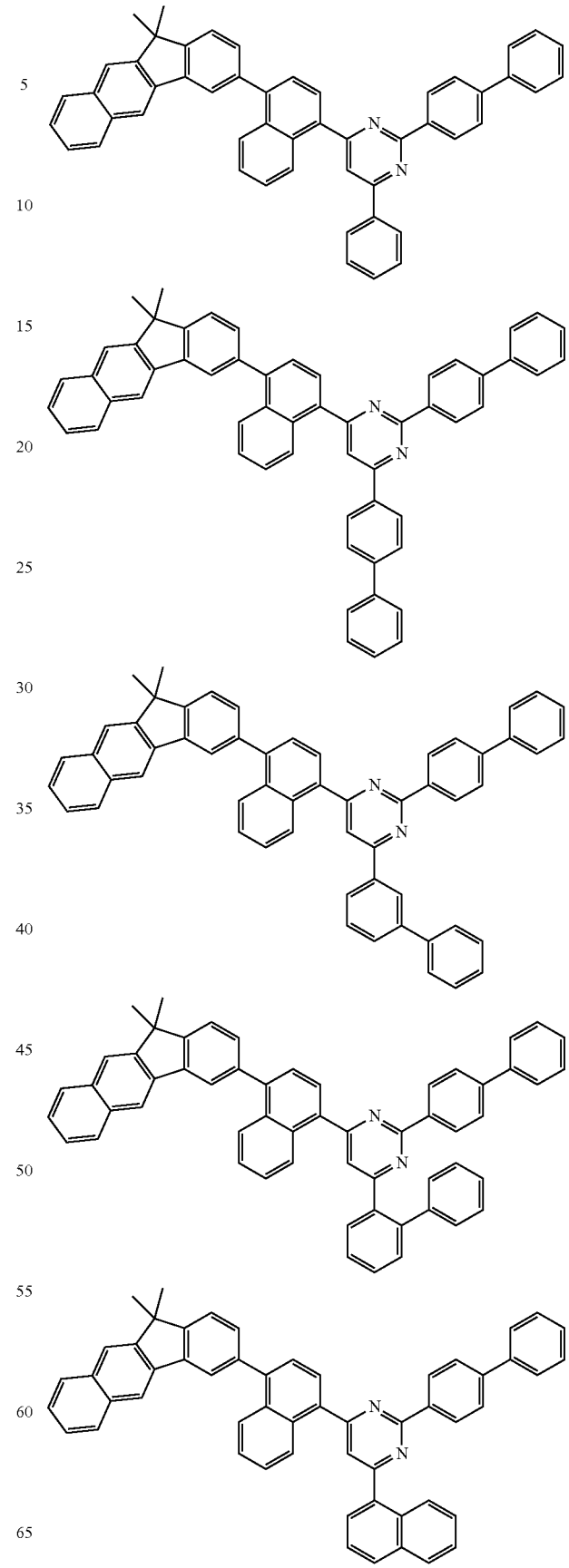

779
-continued
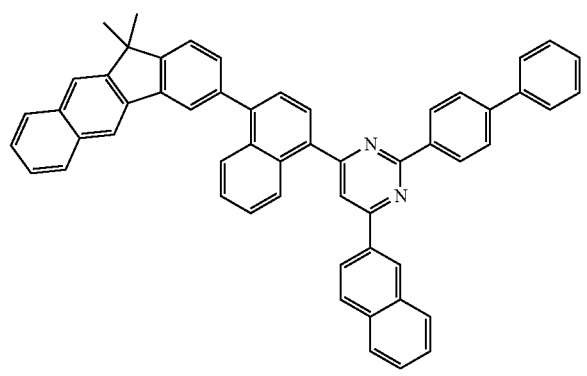
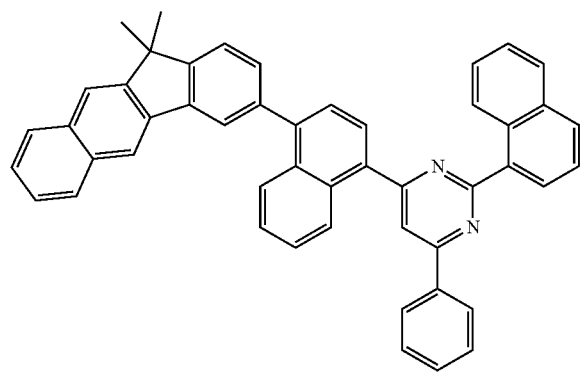
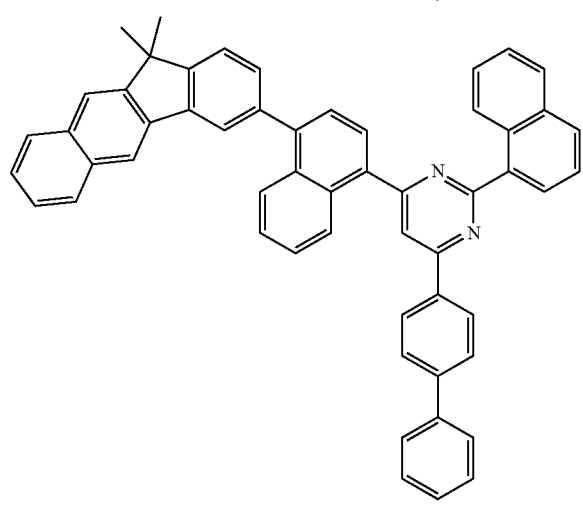
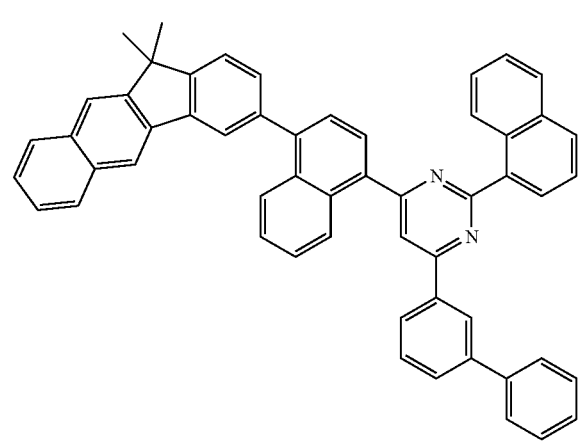
780
-continued
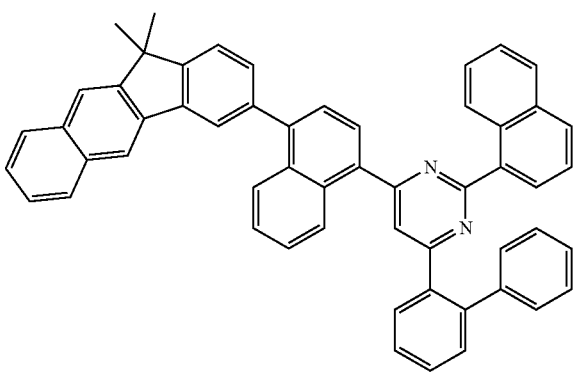
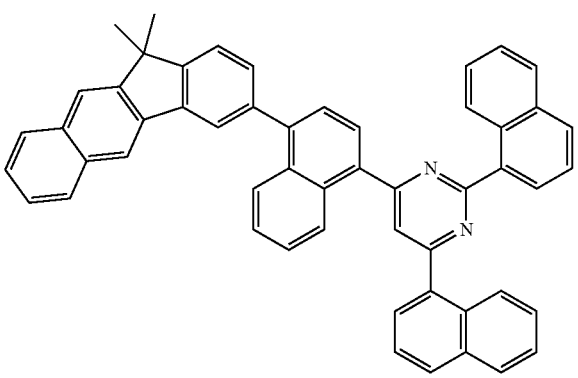
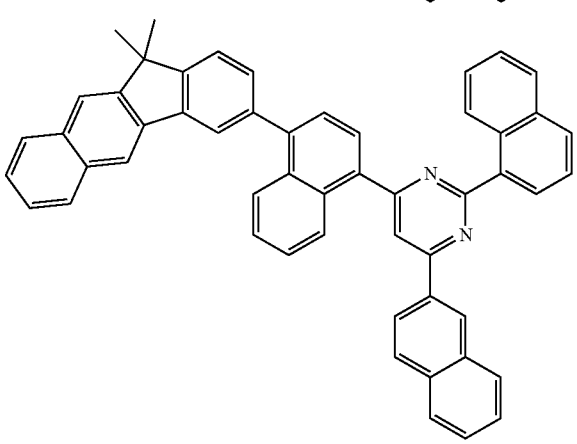
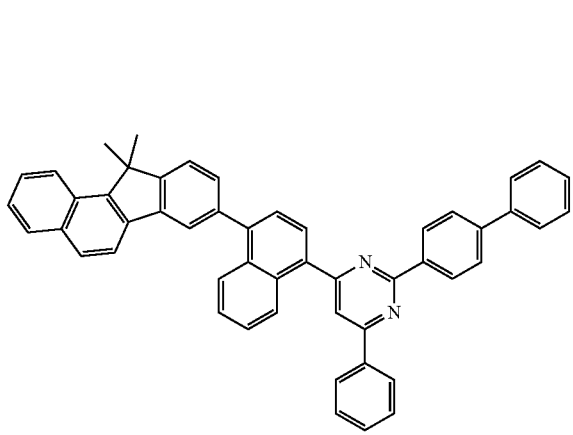

781
-continued
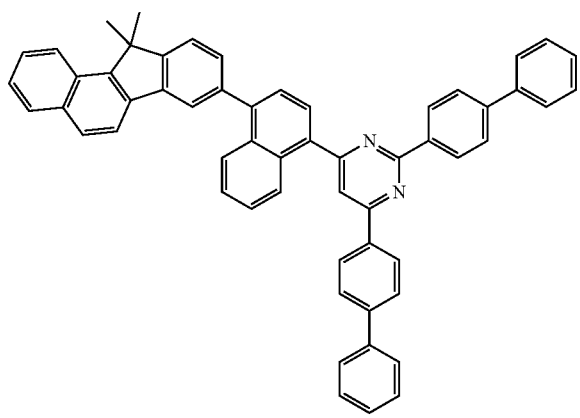
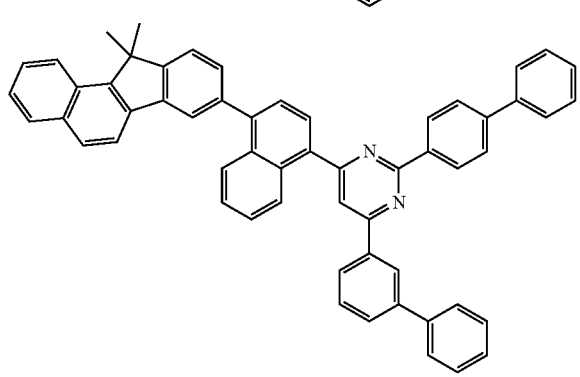
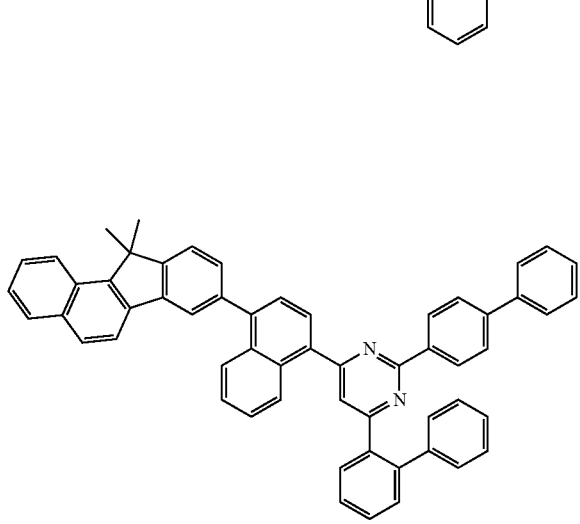
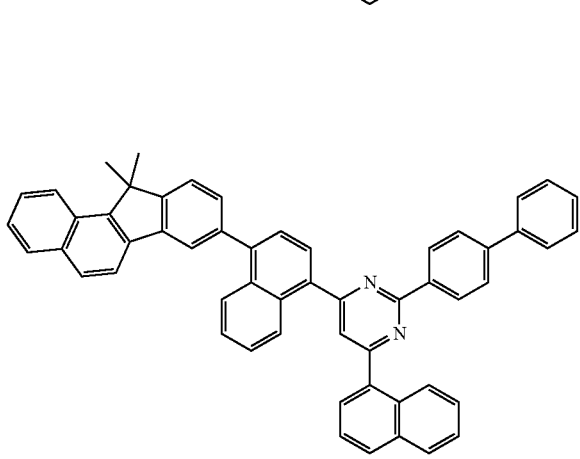
782
-continued
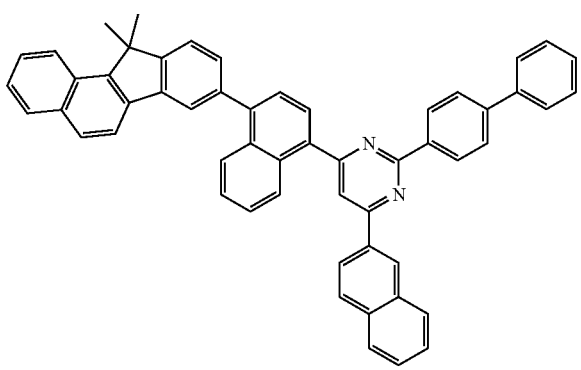
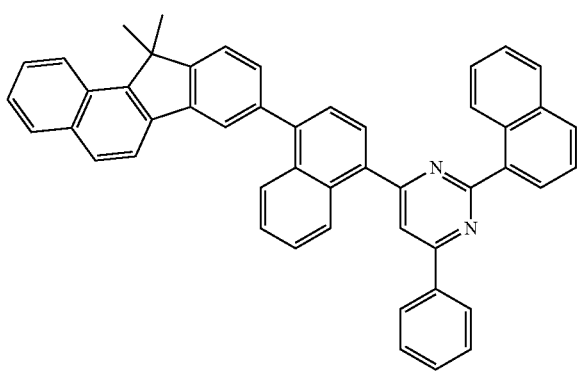
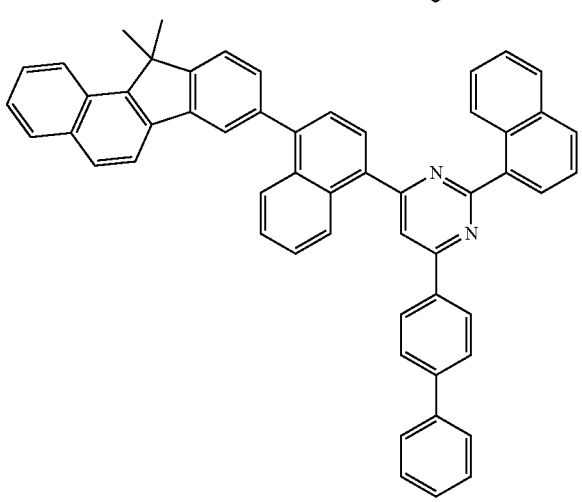
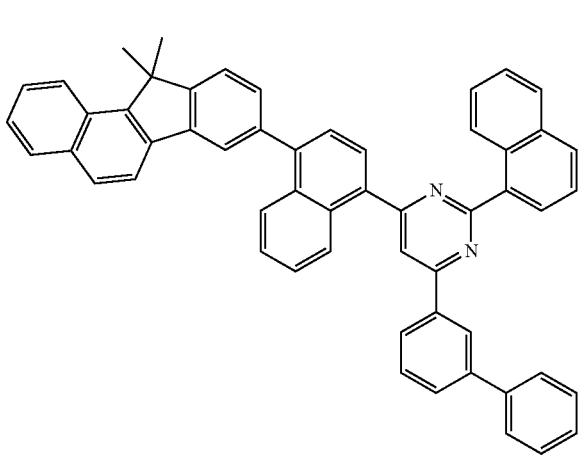

783
-continued
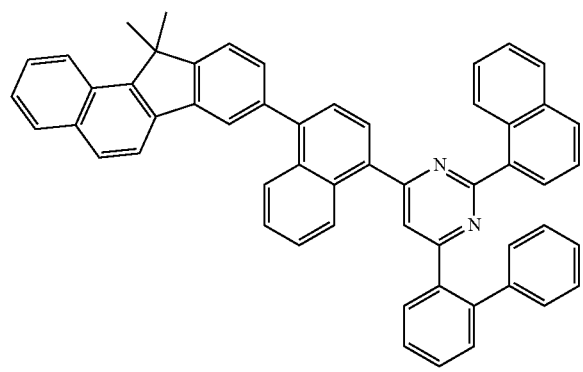
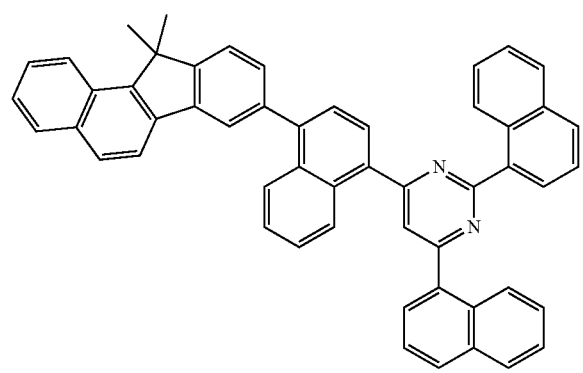
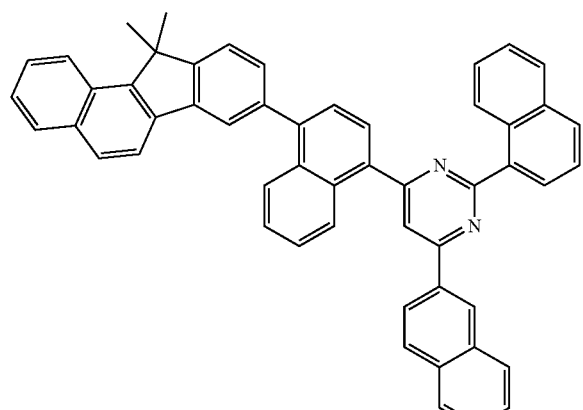
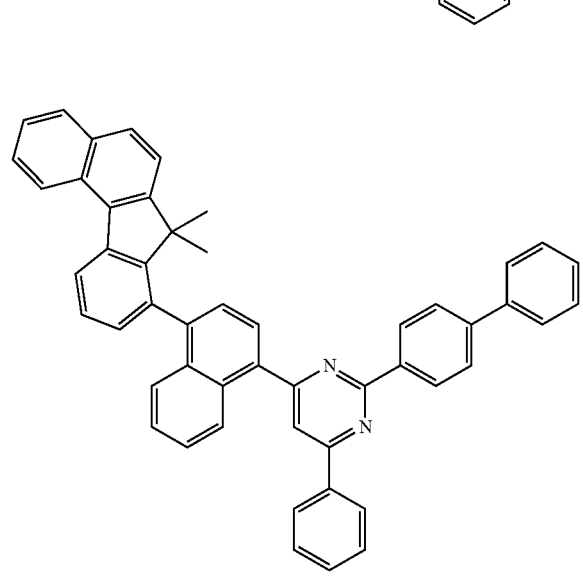
784
-continued
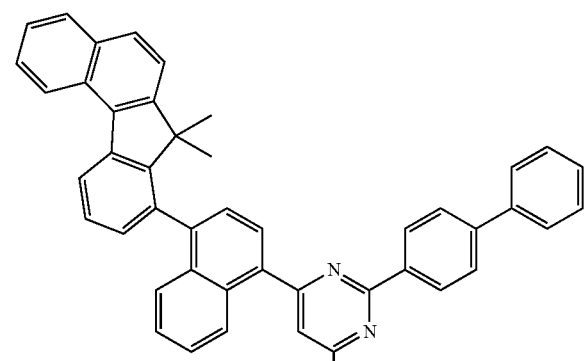
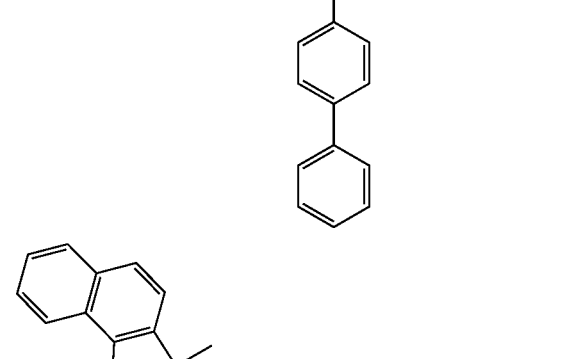
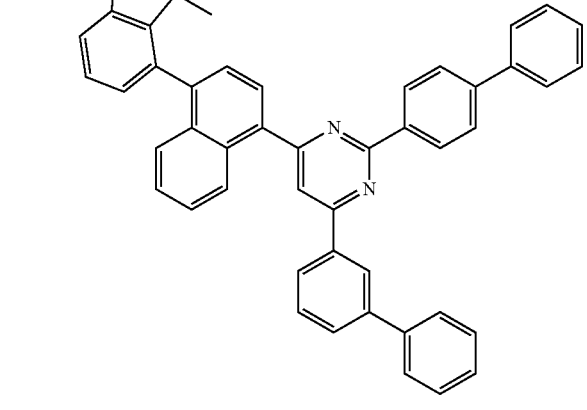
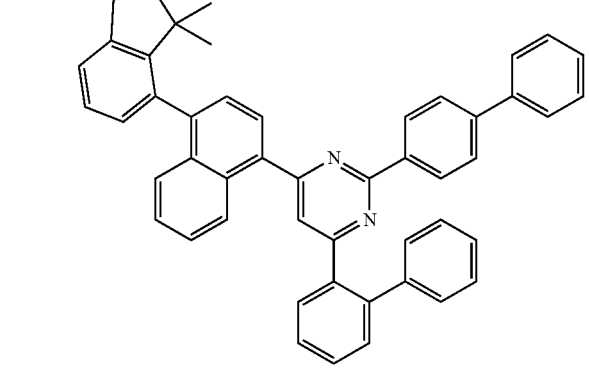

785
-continued
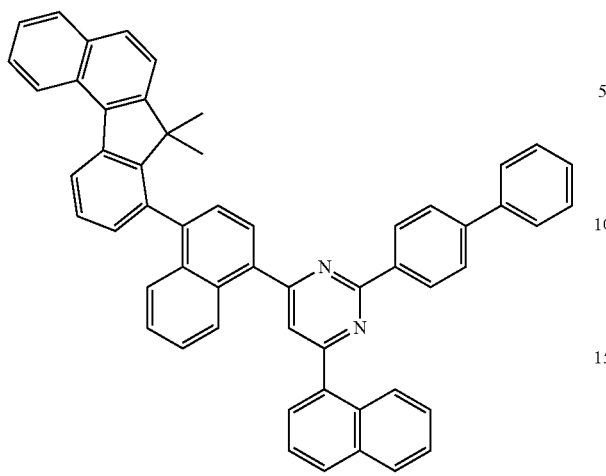
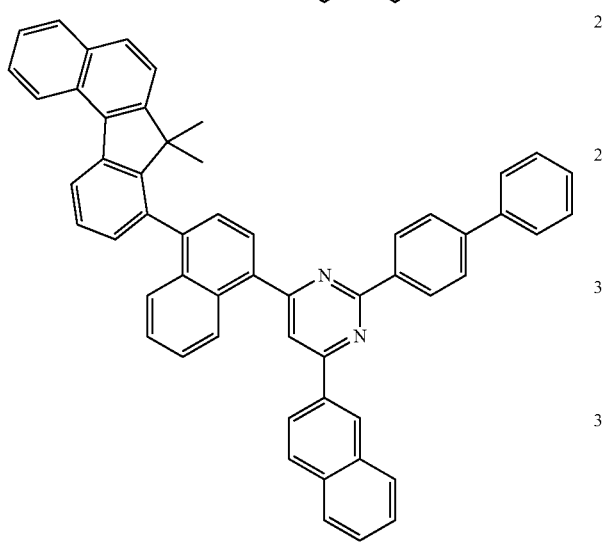
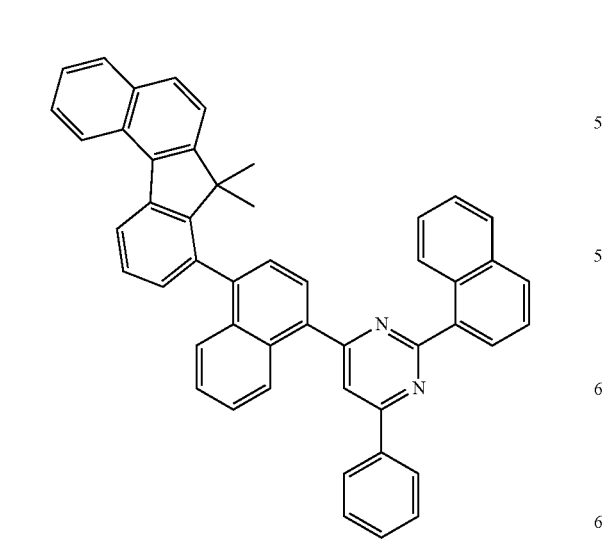
786
-continued
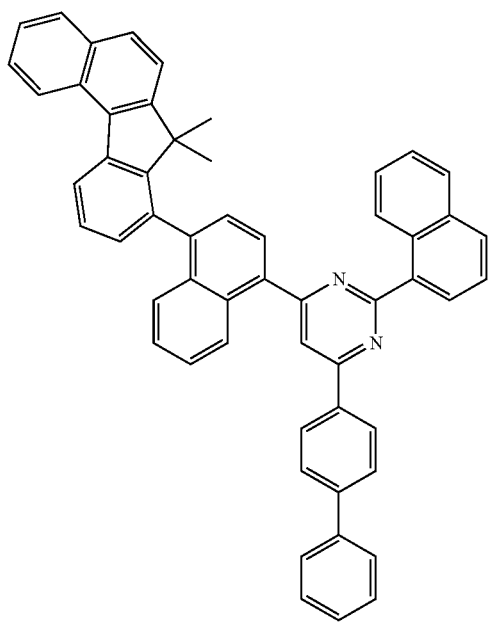
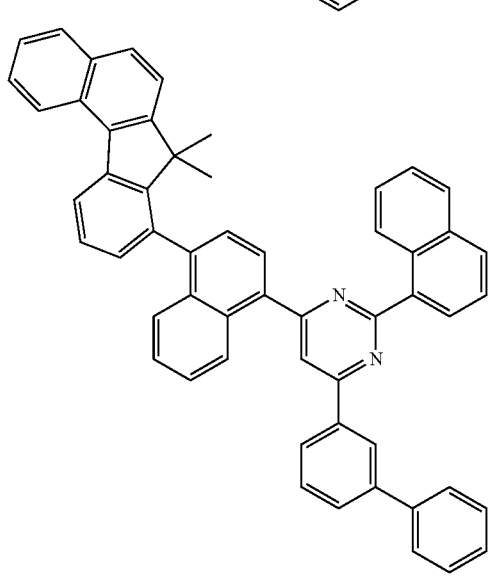
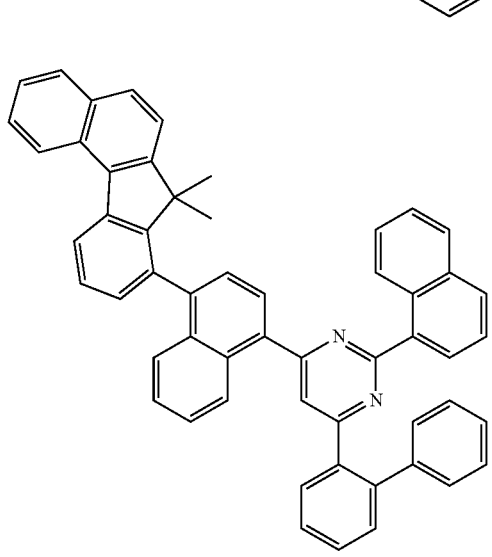

787
-continued
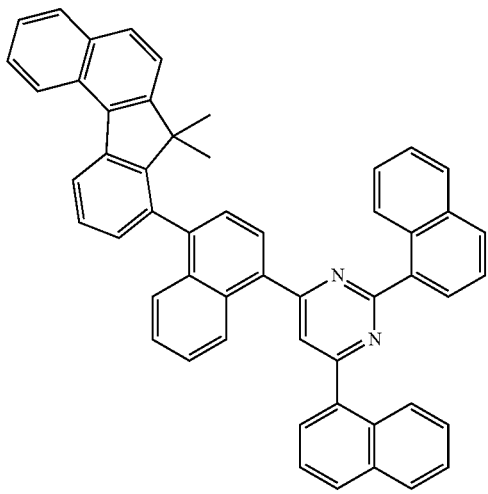
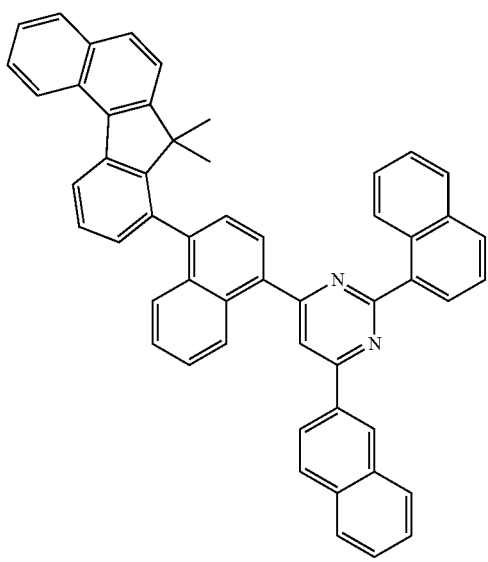
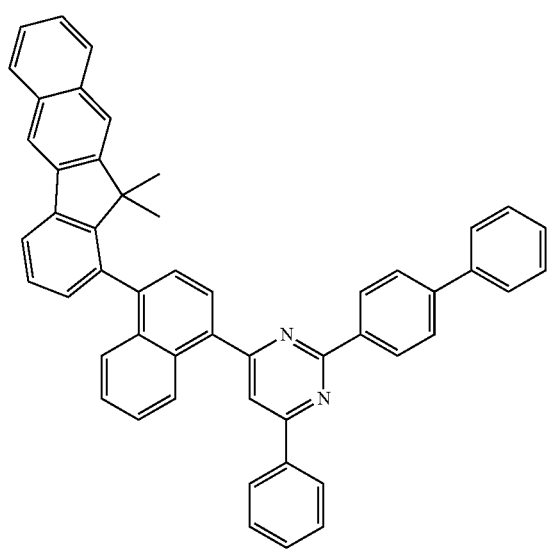
788
-continued
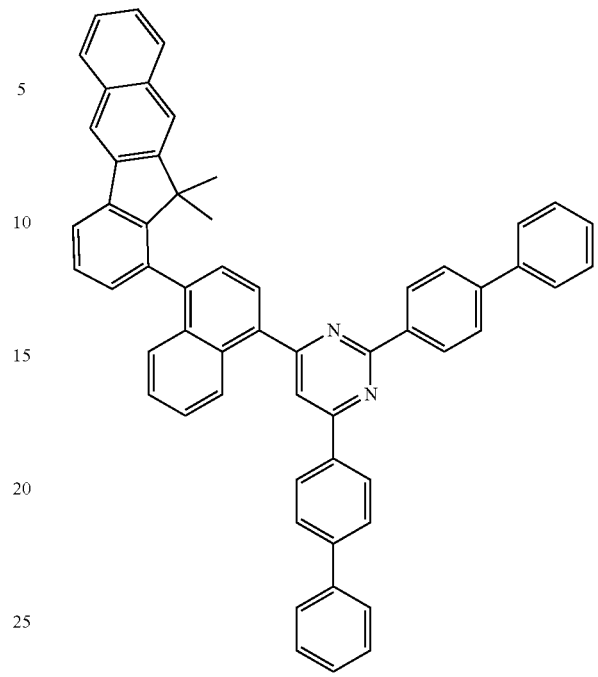
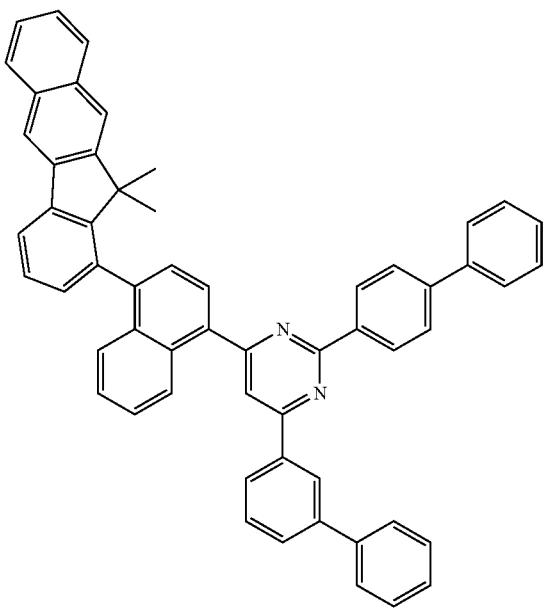

789
-continued
790
-continued
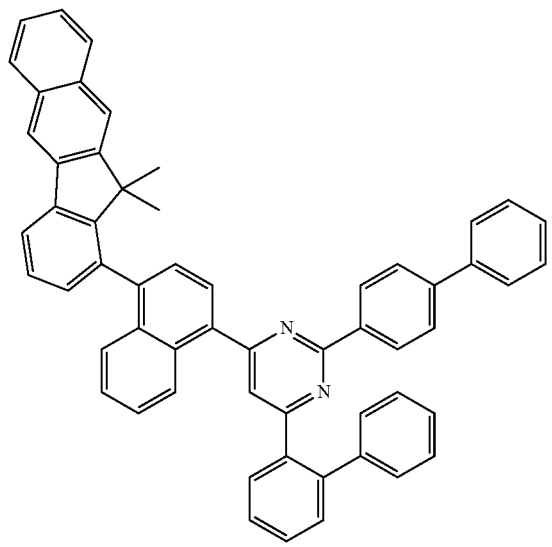

791
-continued
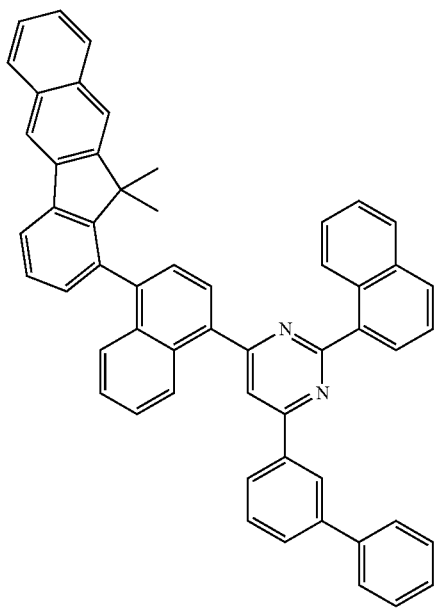
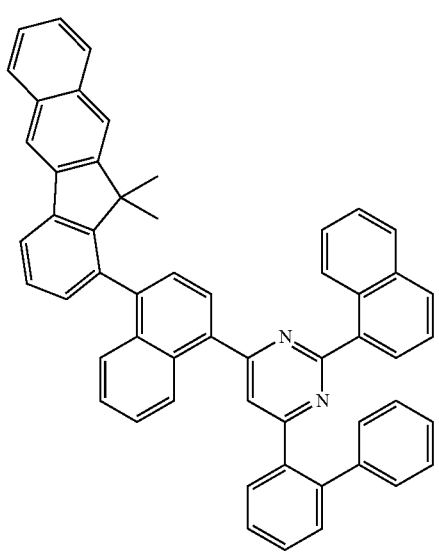
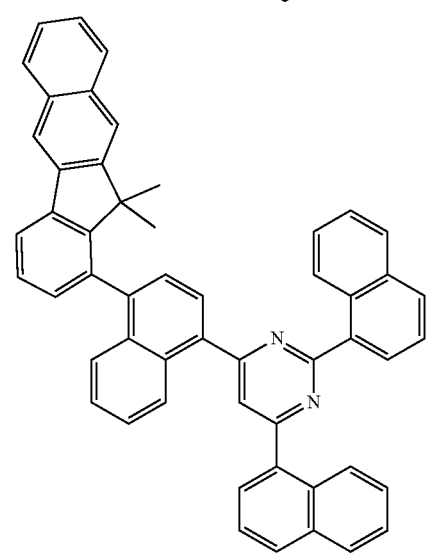
792
-continued
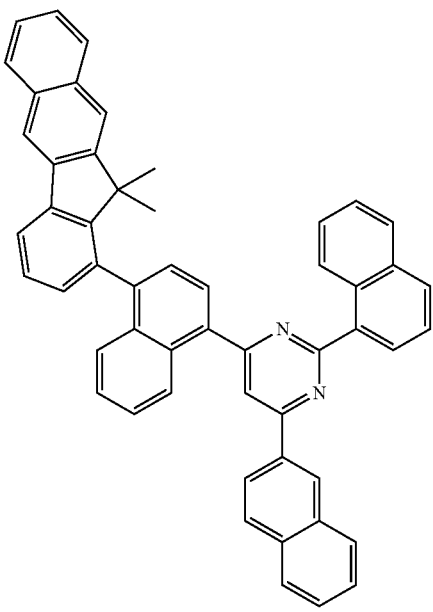
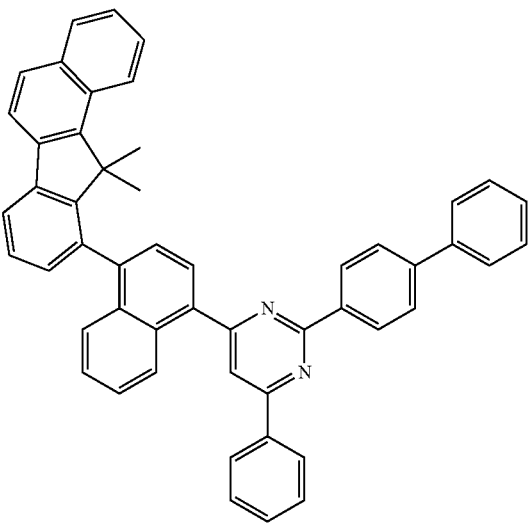

793
-continued
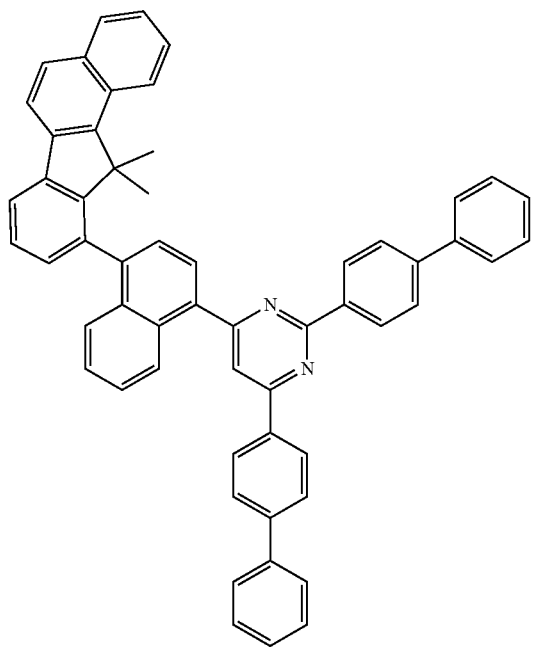
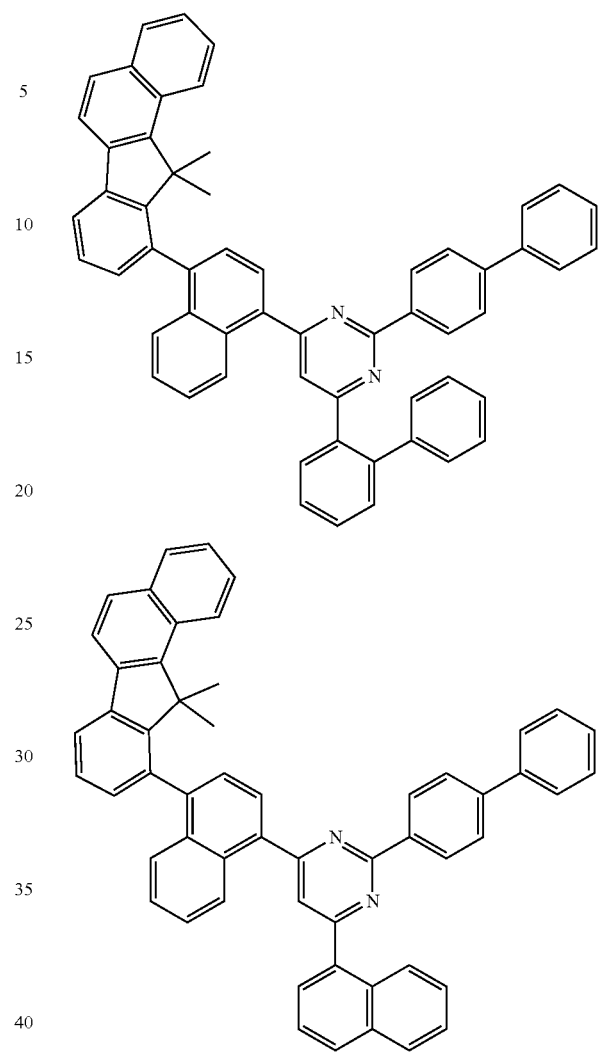
794
-continued
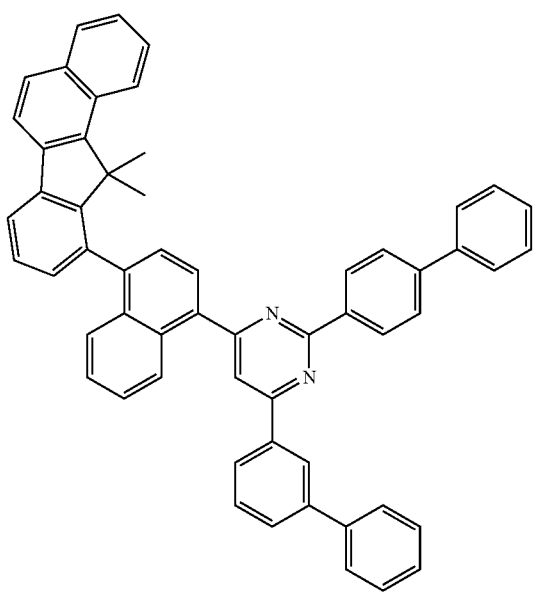
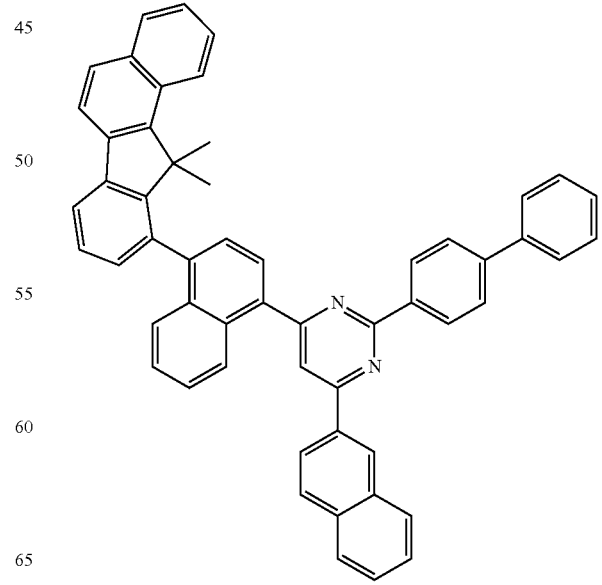

795
-continued
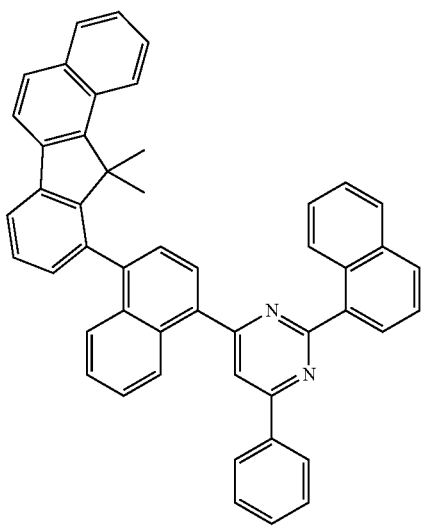
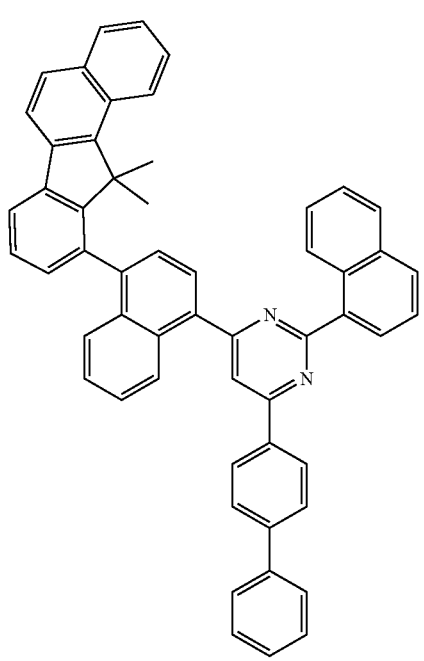
796
-continued
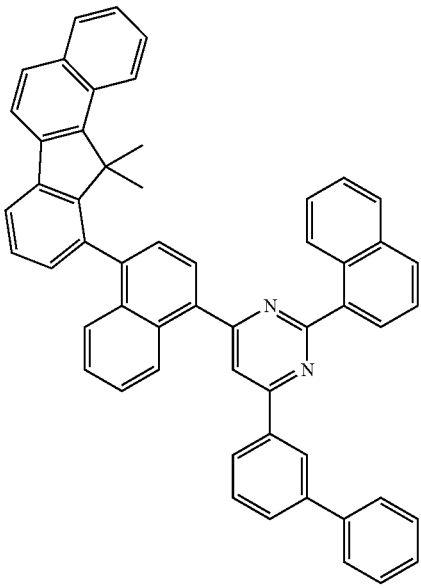
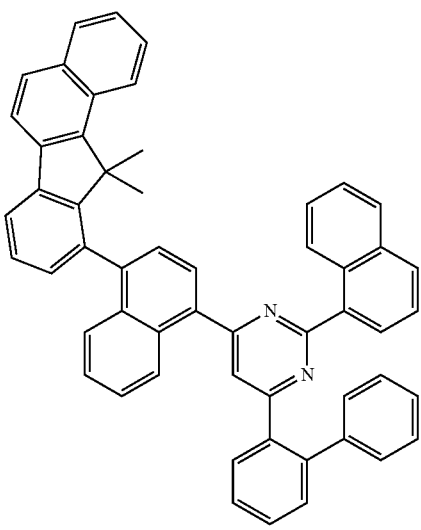
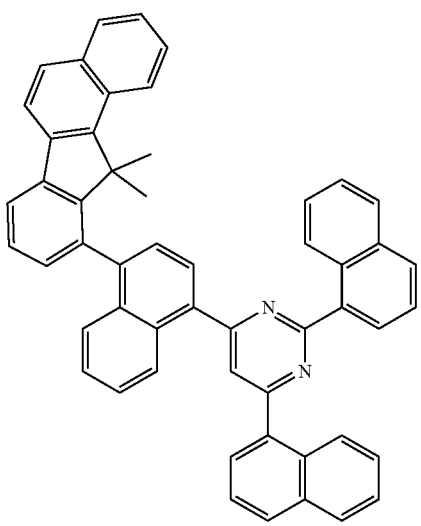

797
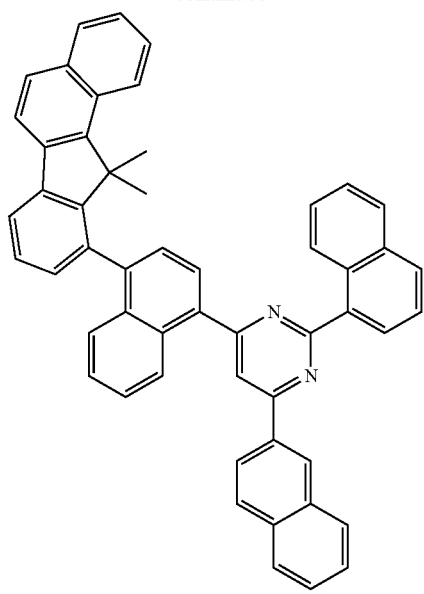
798
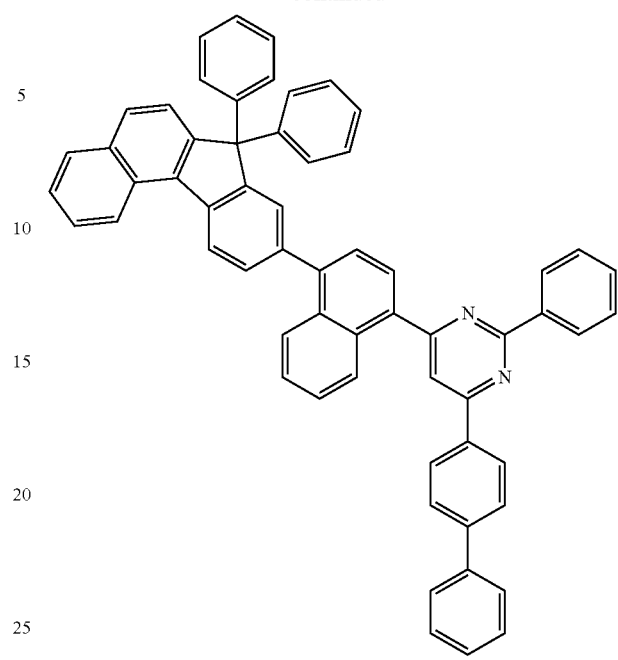
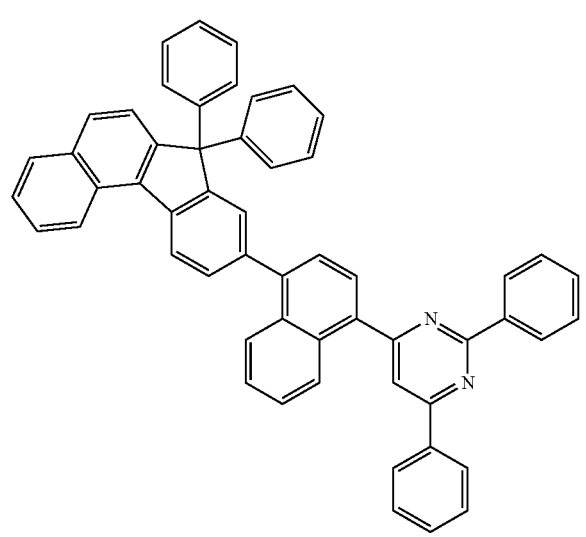

799
-continued
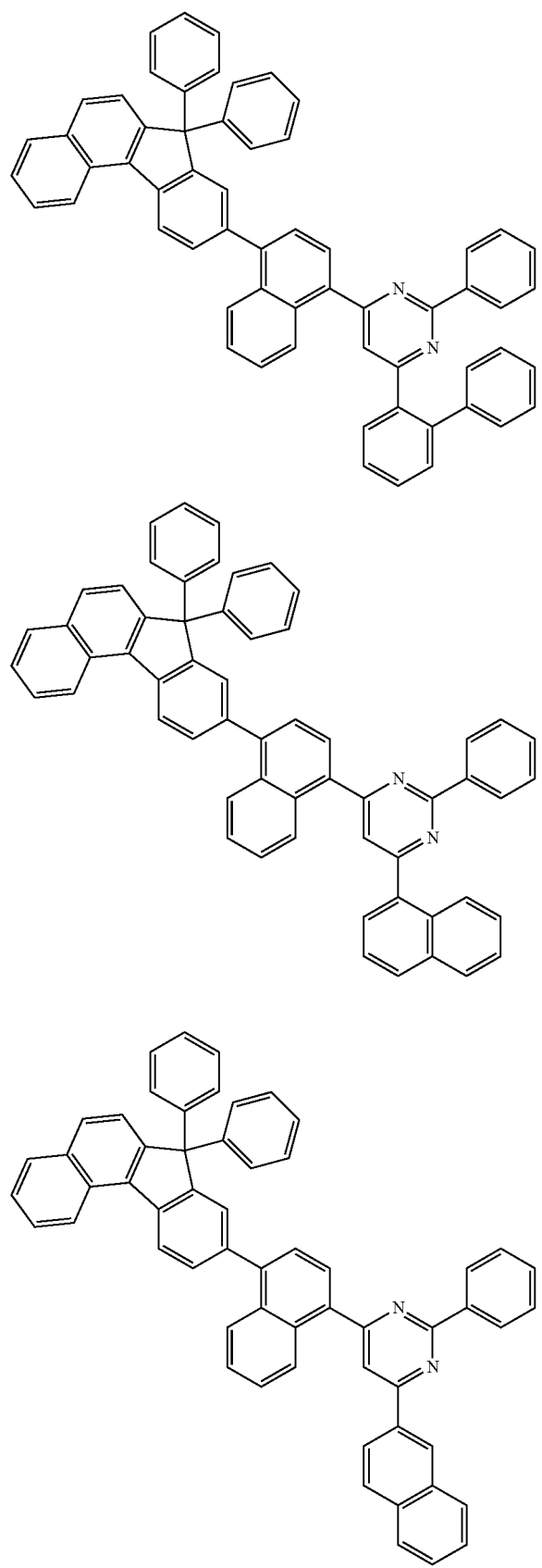
800
-continued
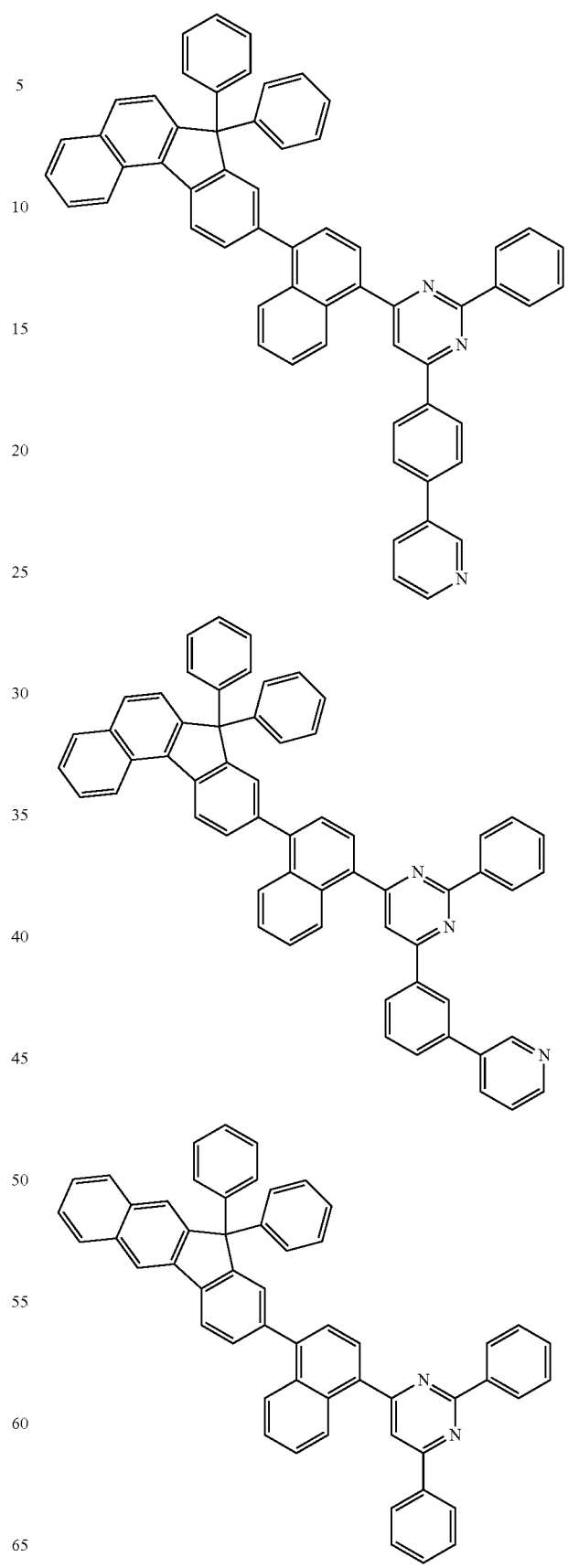

801
-continued
802
-continued
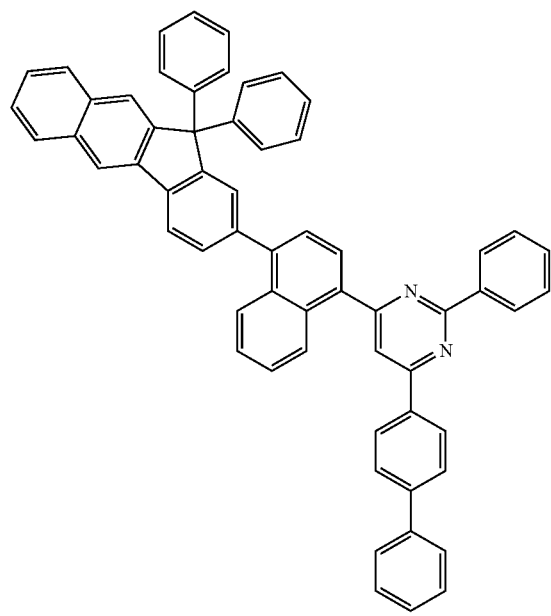
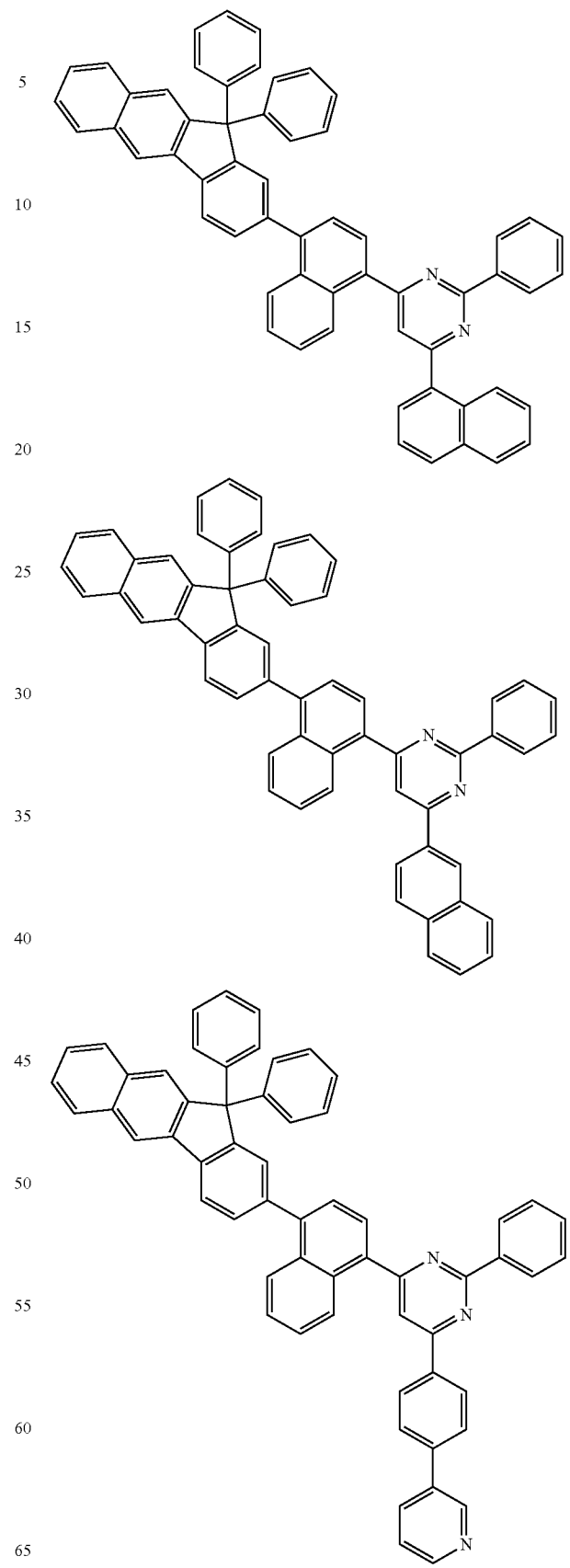

803
-continued
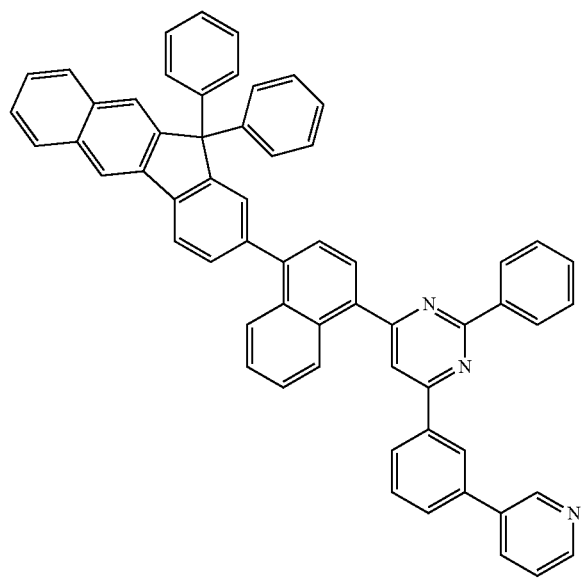
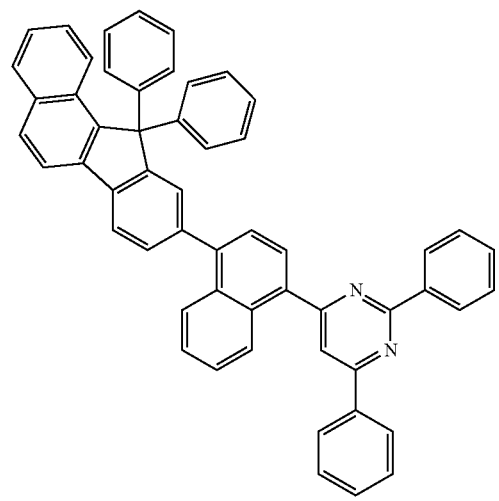
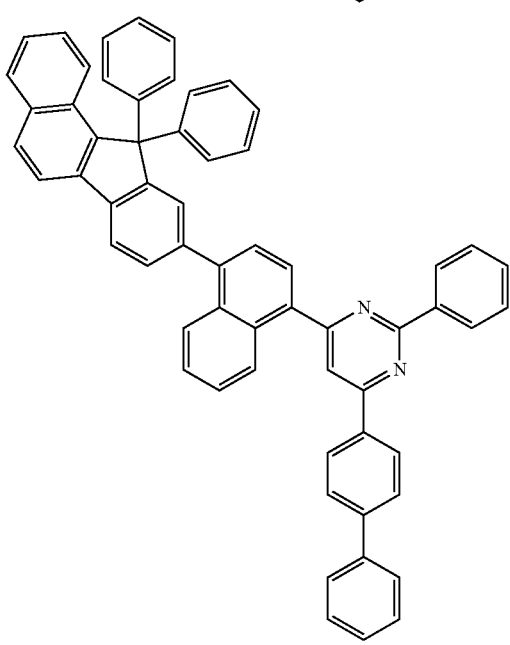
804
-continued
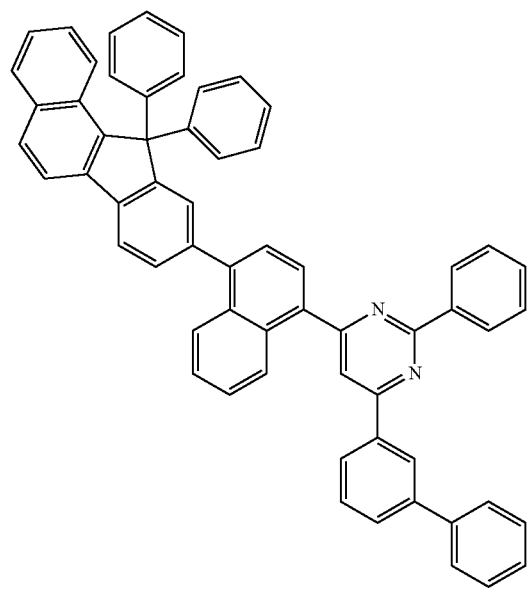
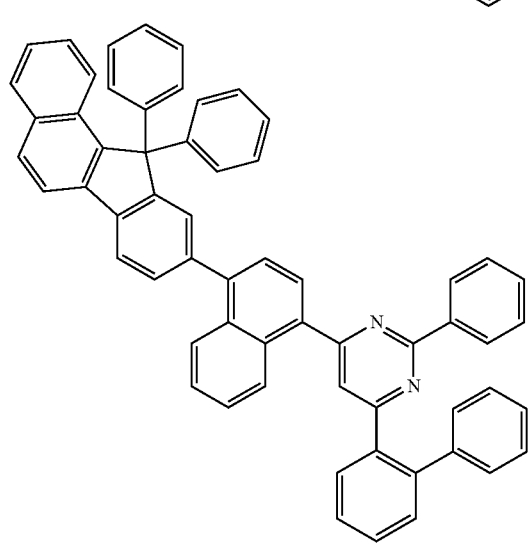
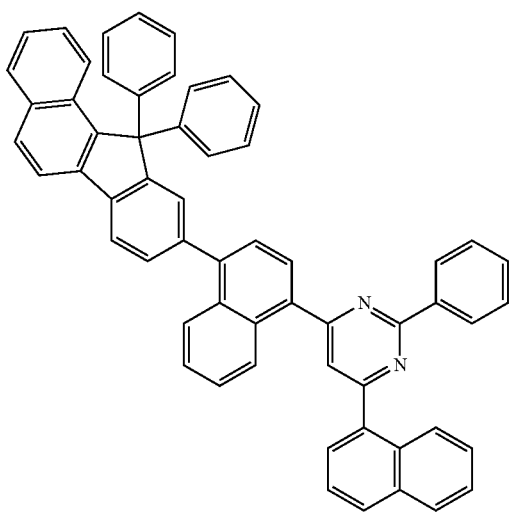

805
-continued
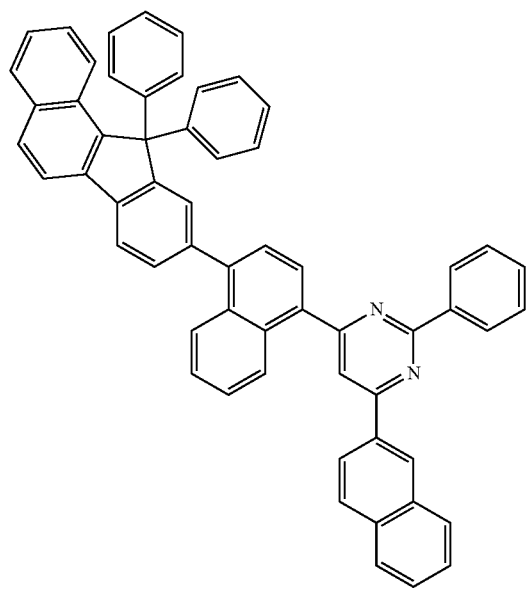
806
-continued
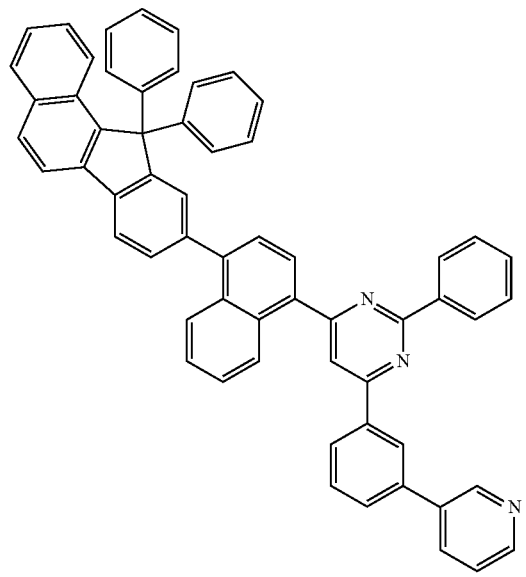
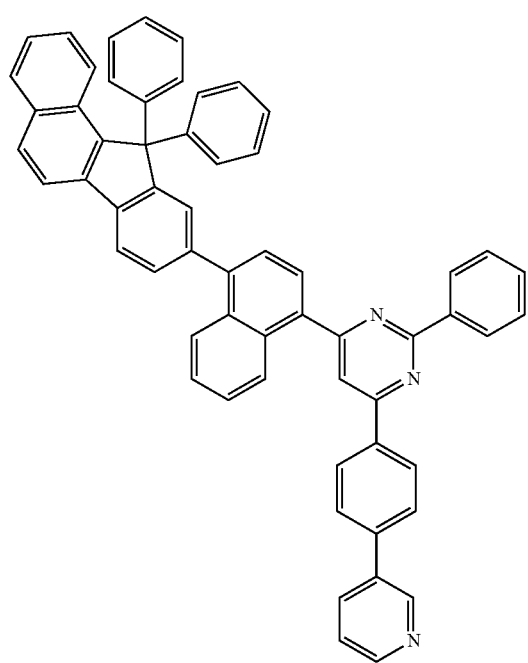
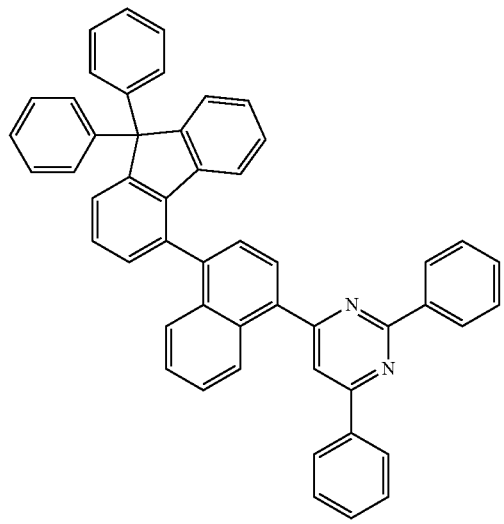

807
-continued
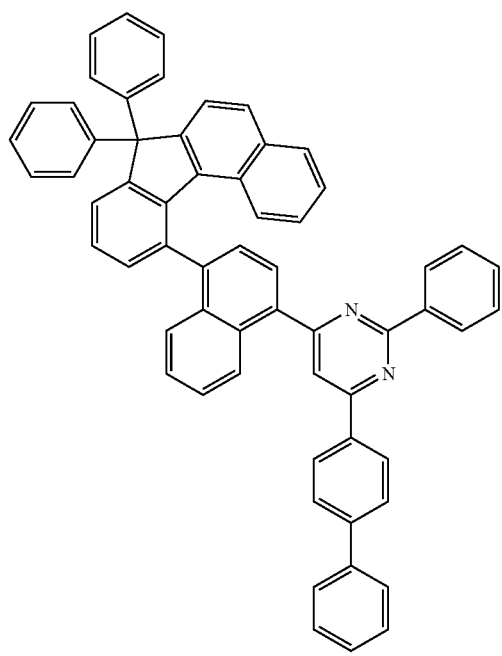
808
-continued
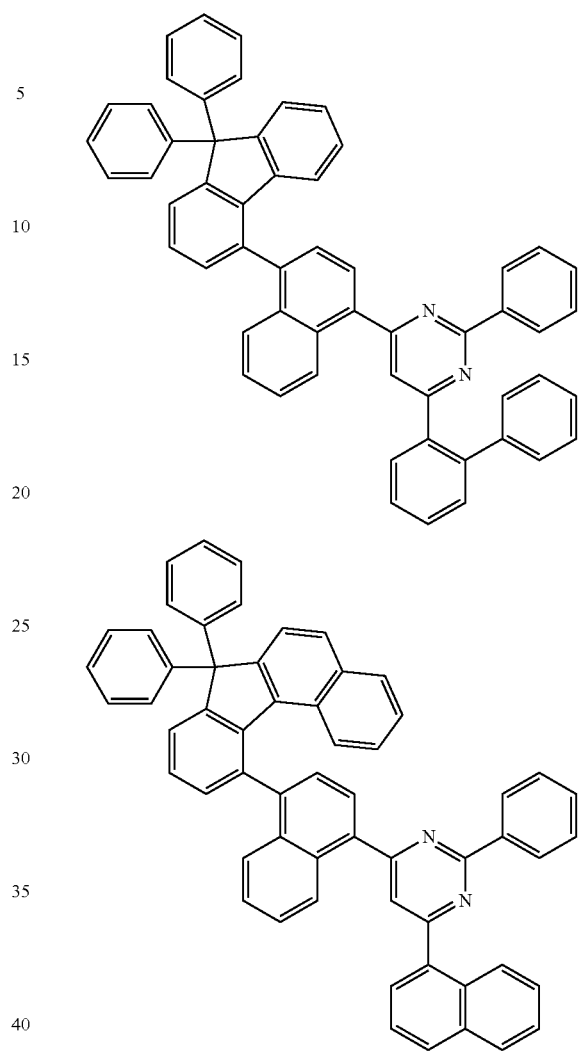
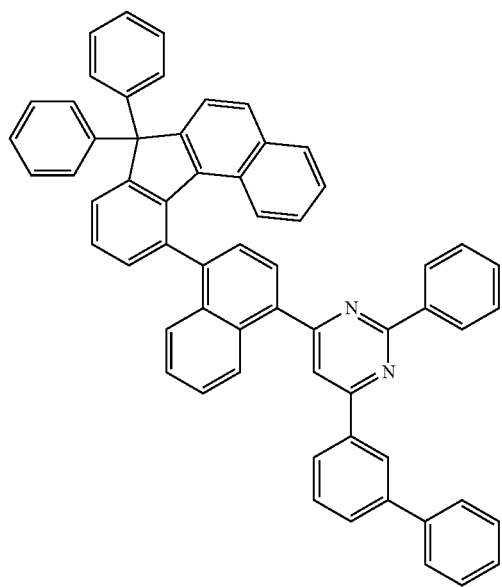
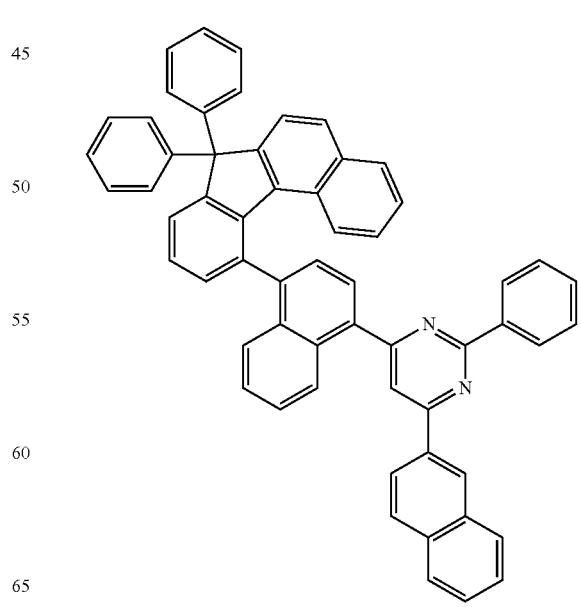

809
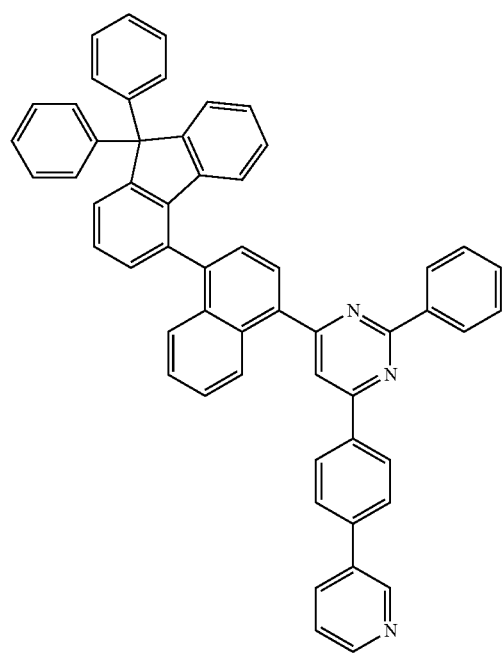
810
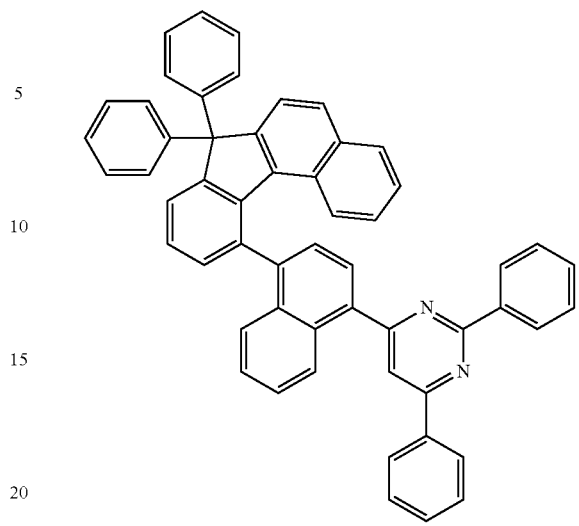
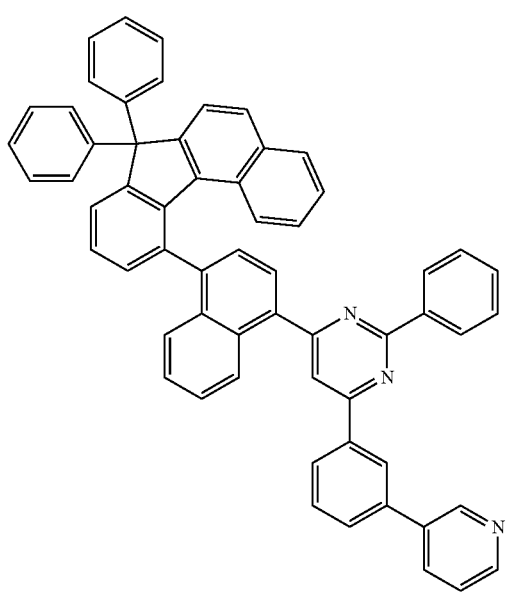
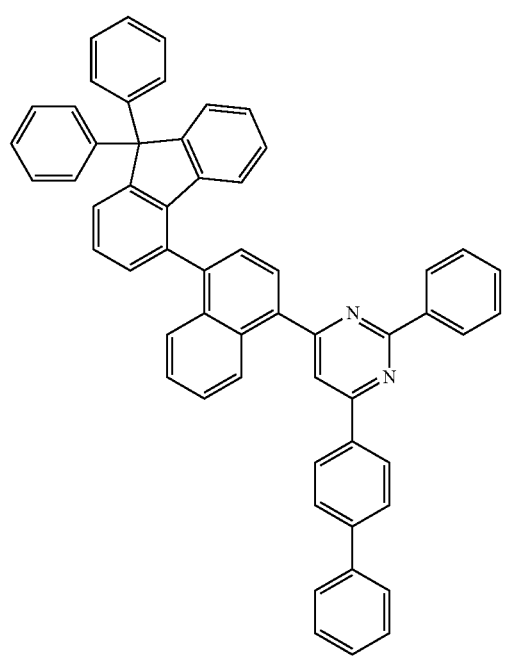

811
-continued
812
-continued
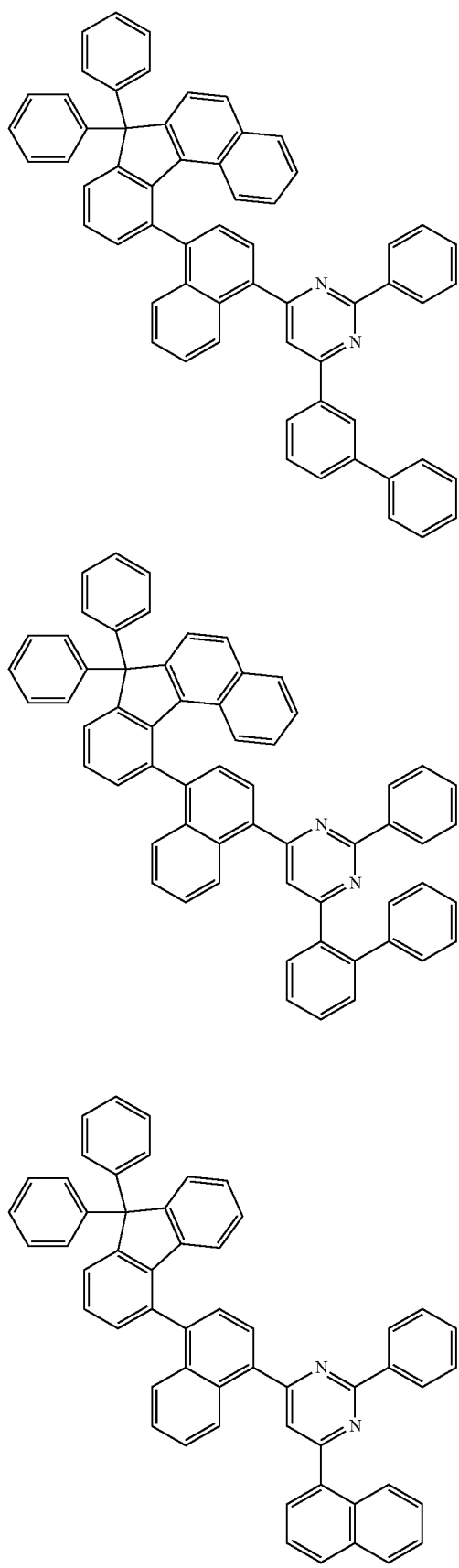
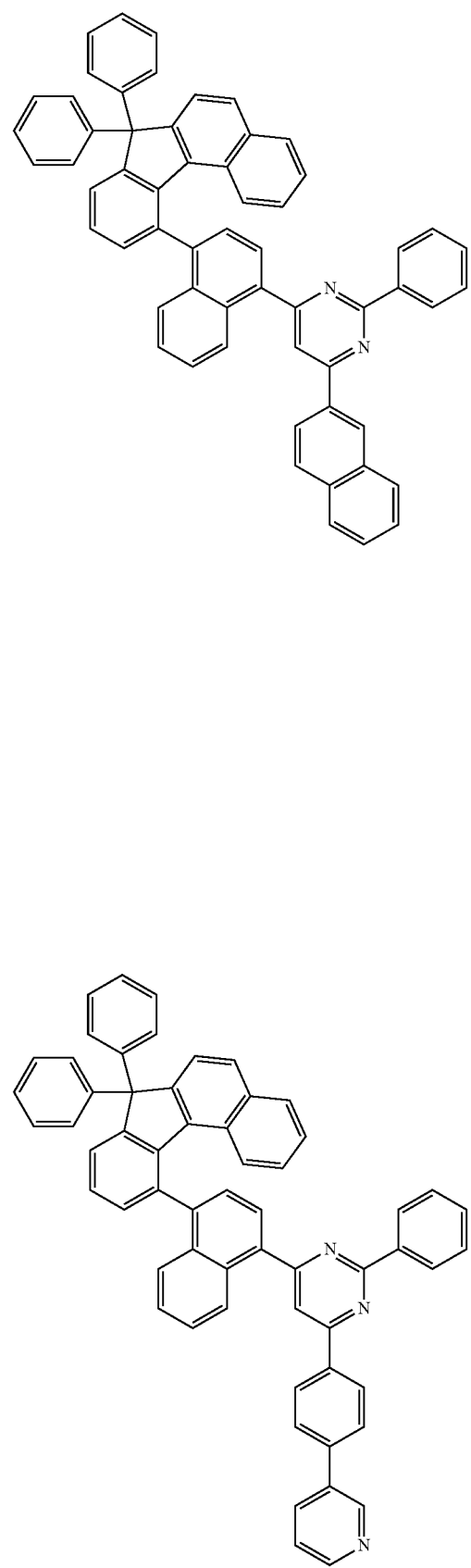

813
-continued
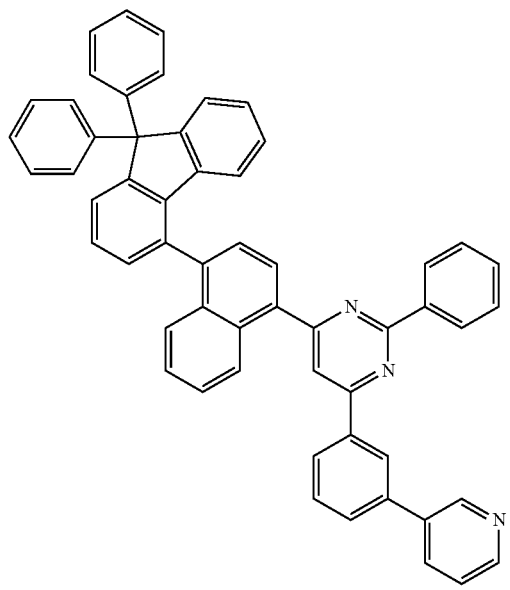
814
-continued
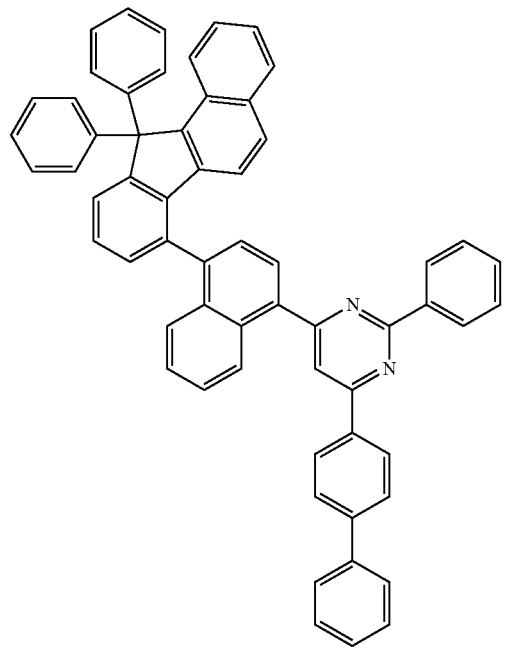
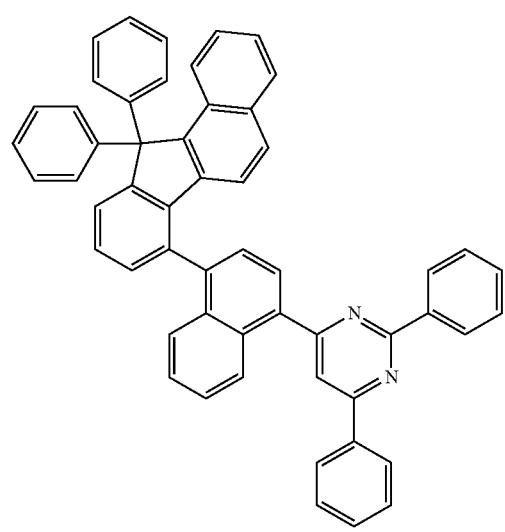
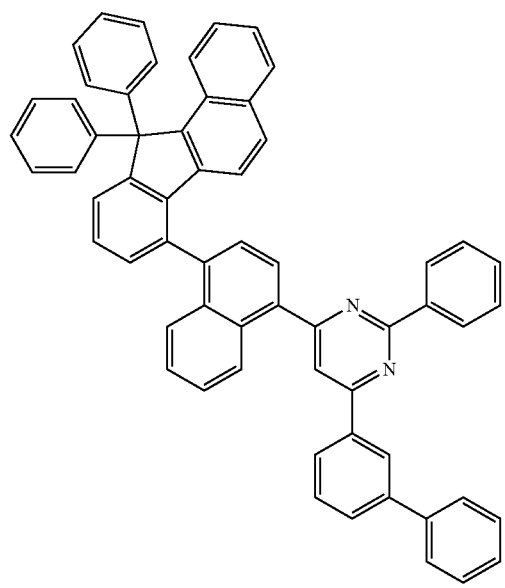

815
-continued
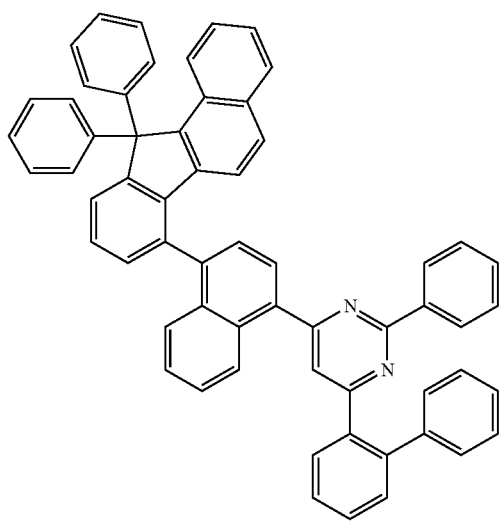
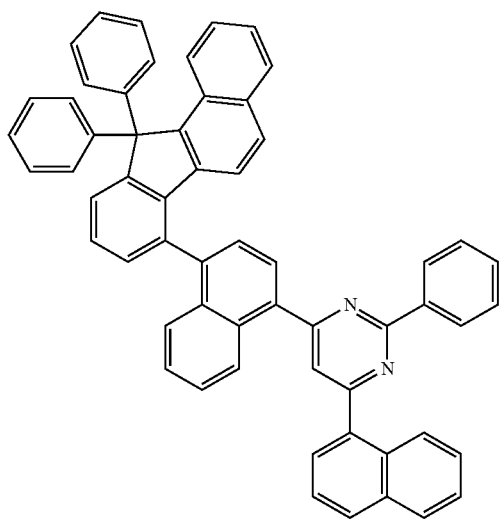
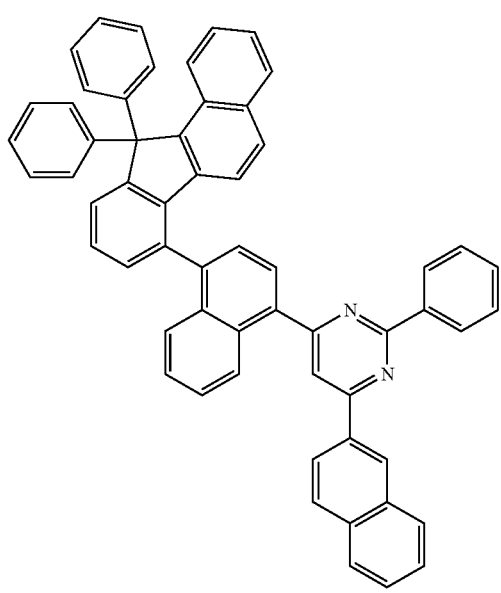
816
-continued
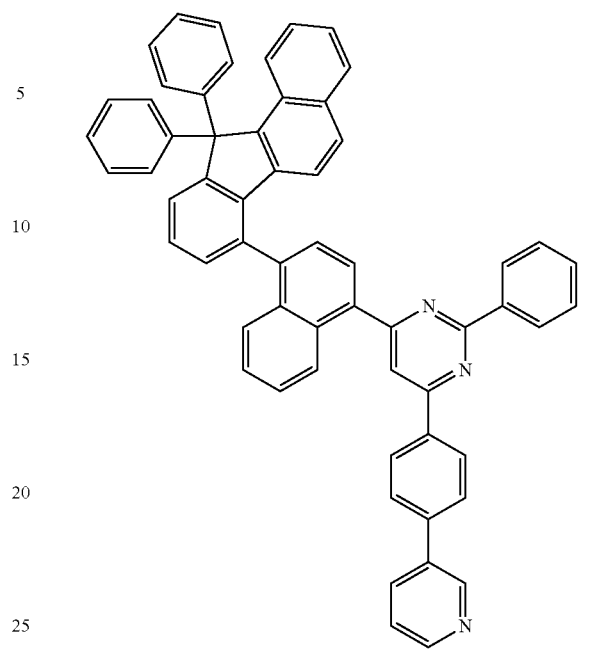
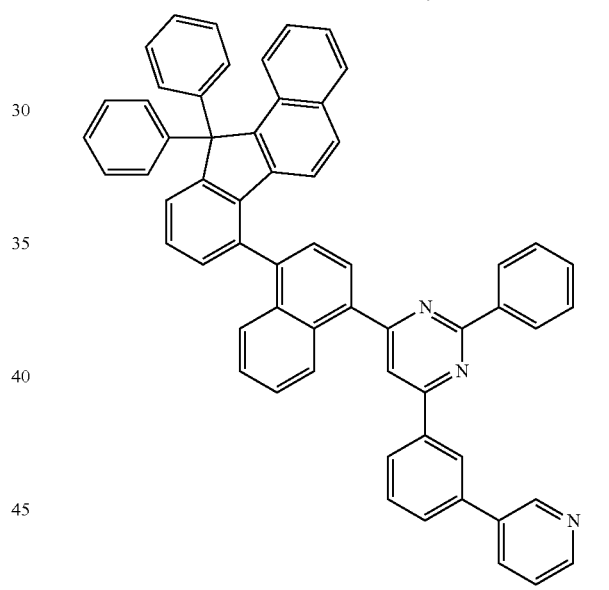
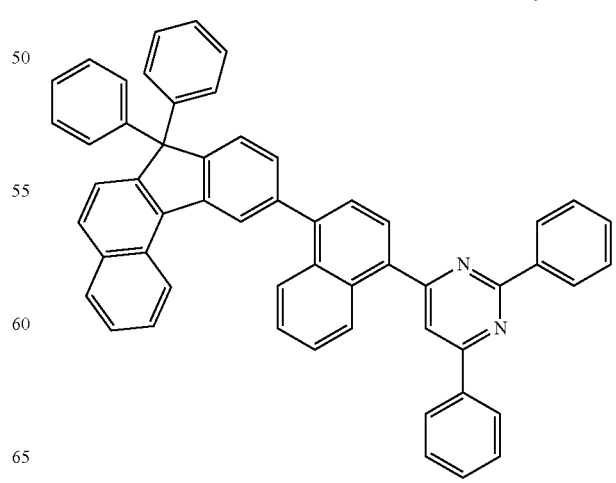

817
-continued
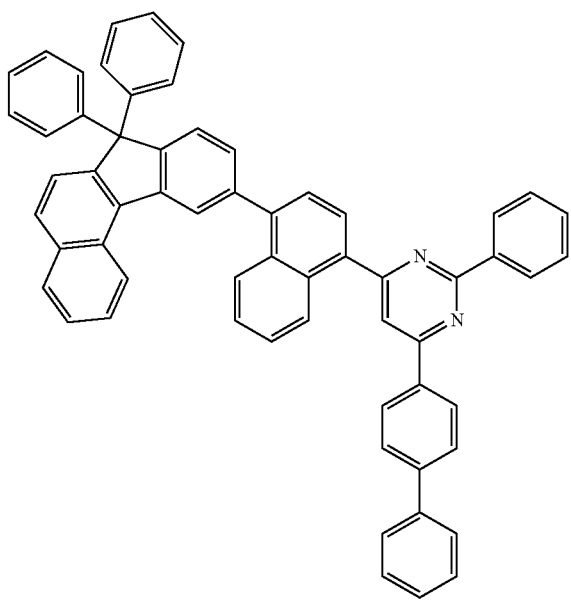
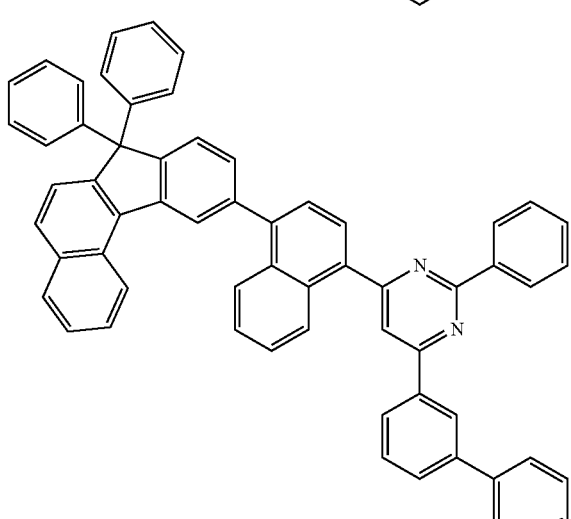
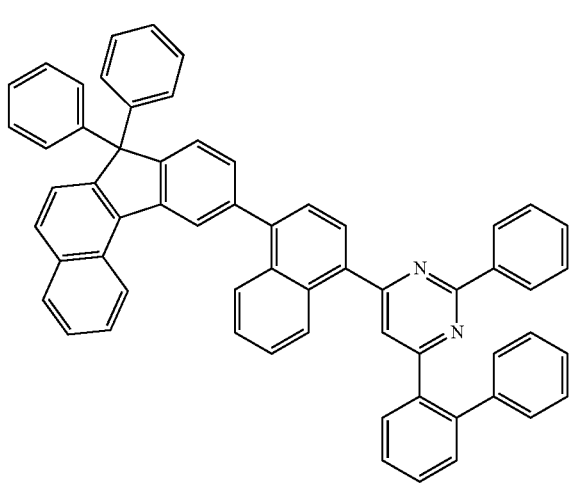
818
-continued
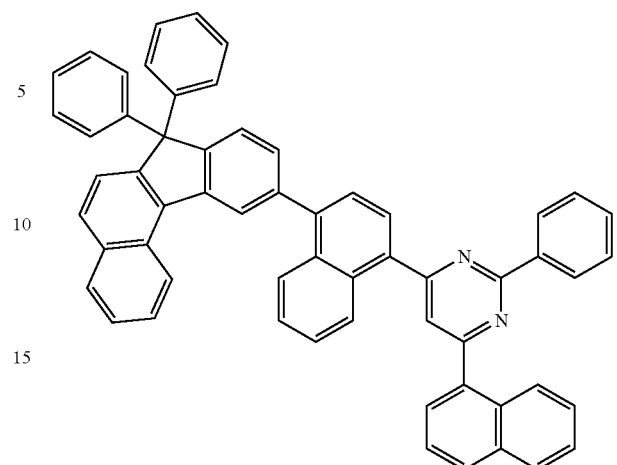
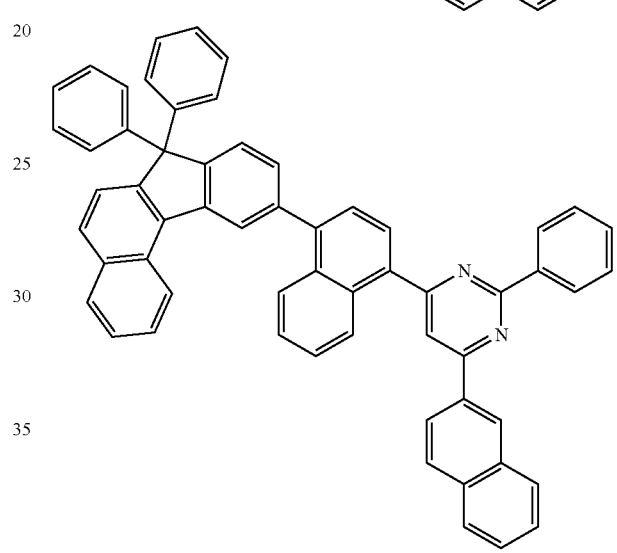
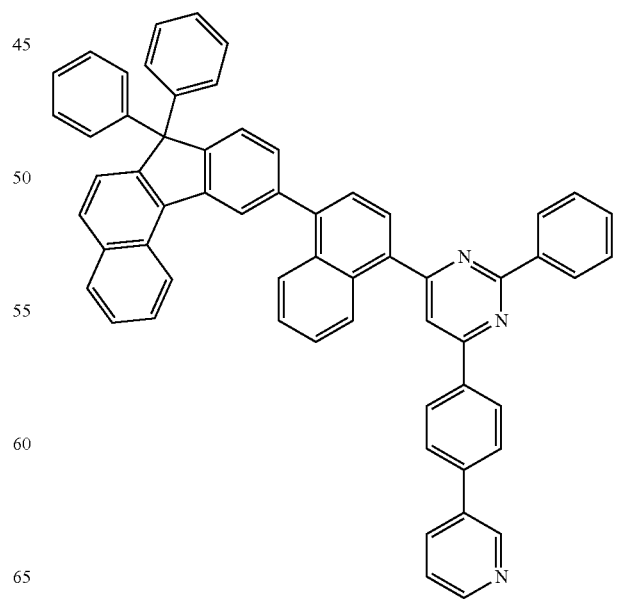

819
-continued
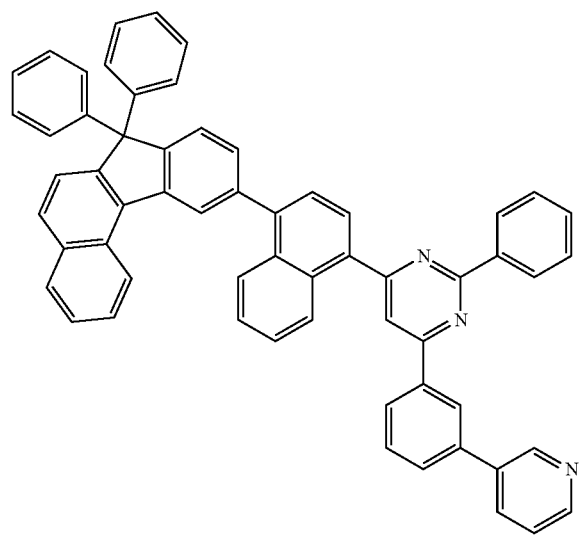
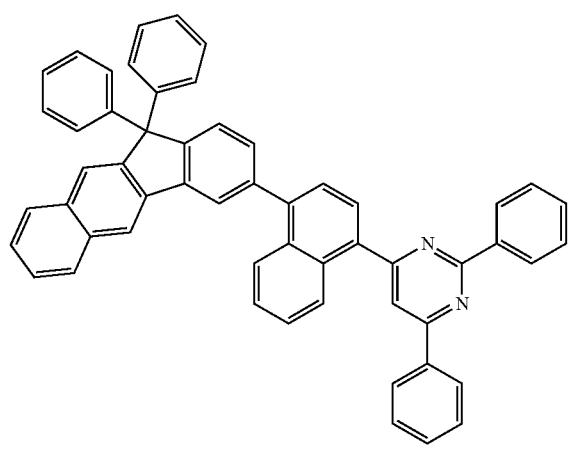
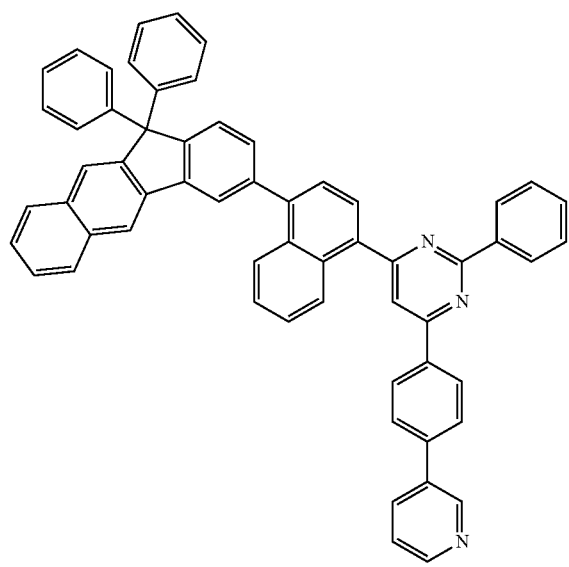
820
-continued
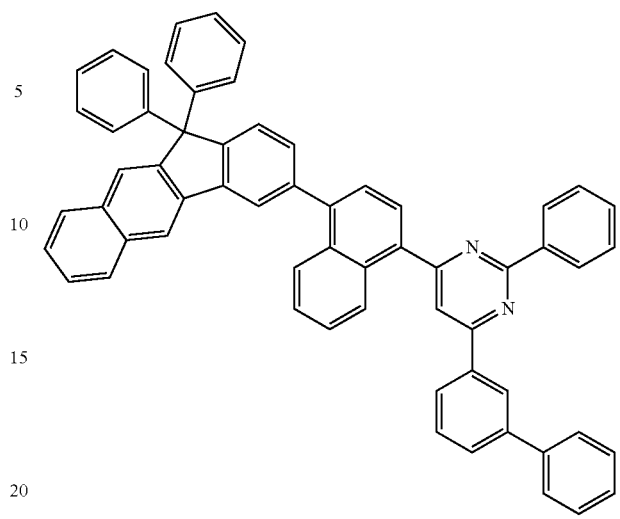
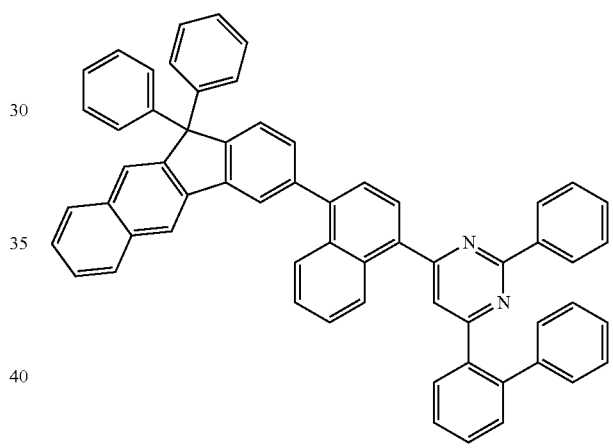
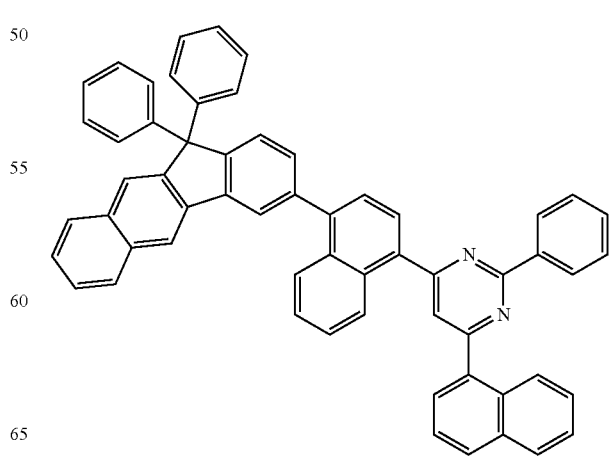

821
-continued
822
-continued
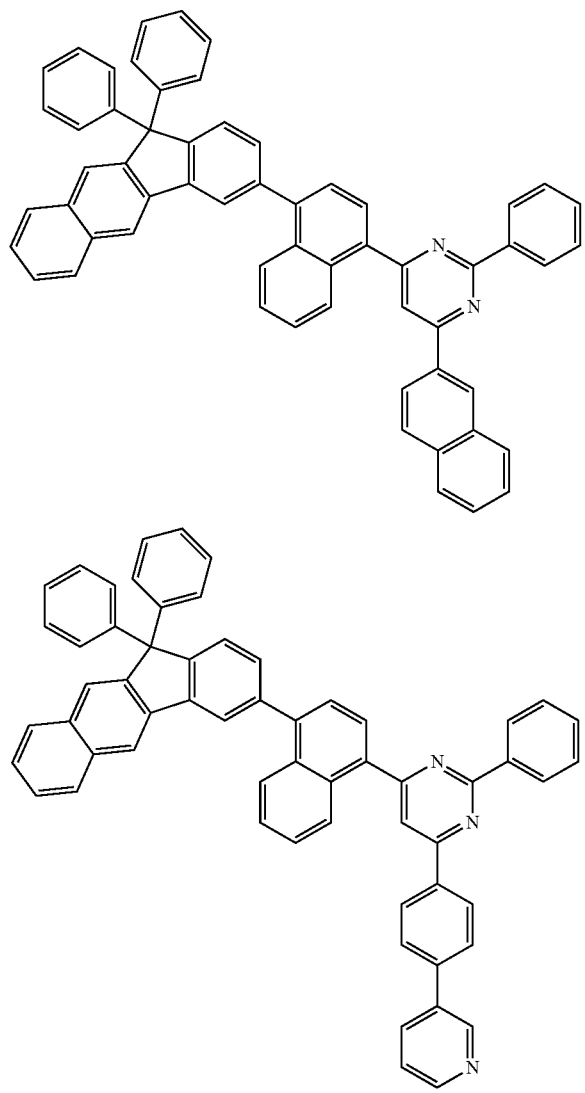
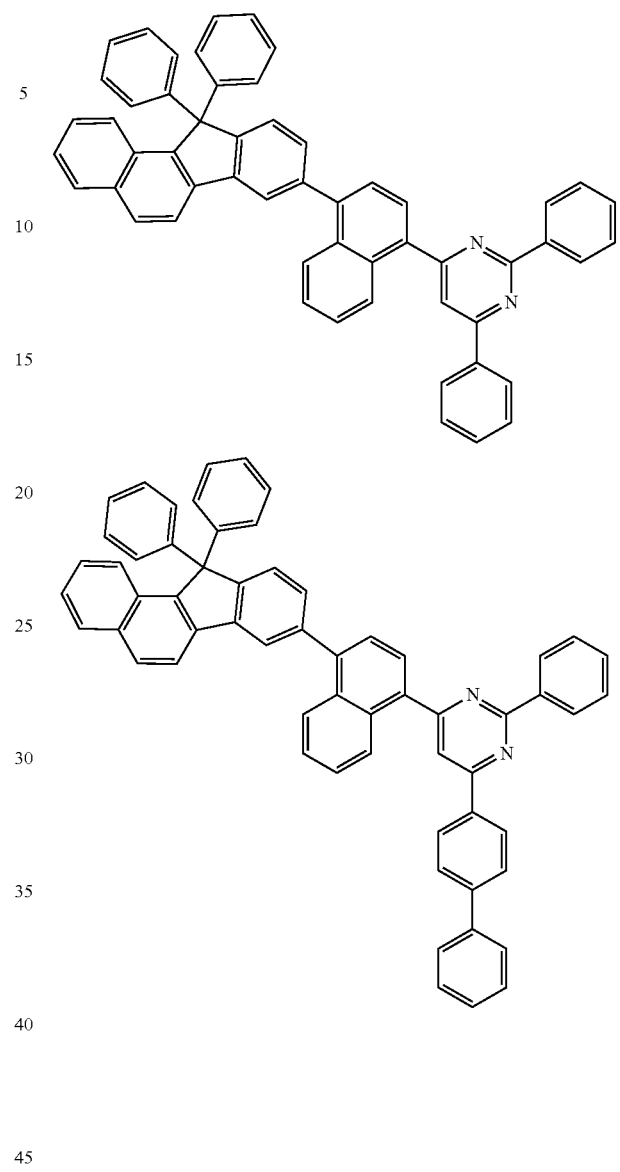
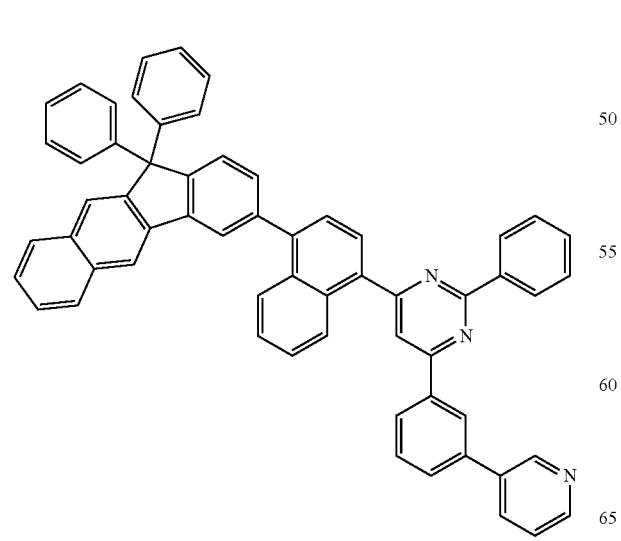

823
-continued
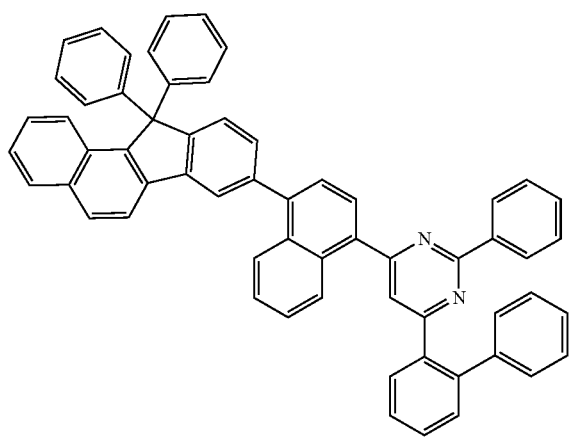
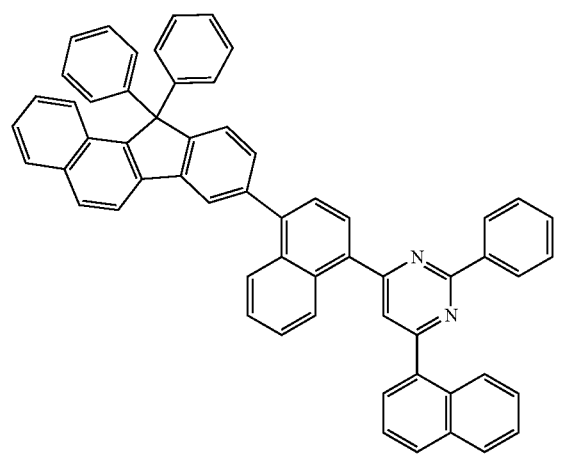
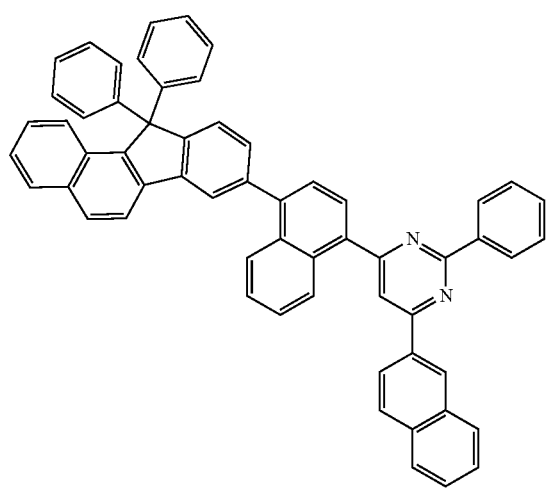
824
-continued
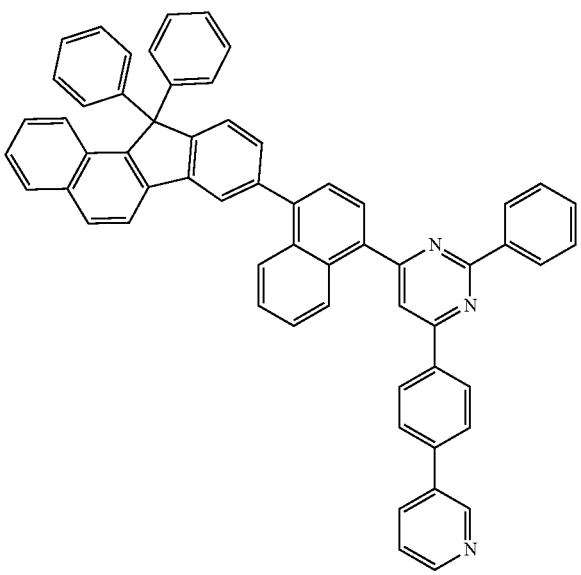
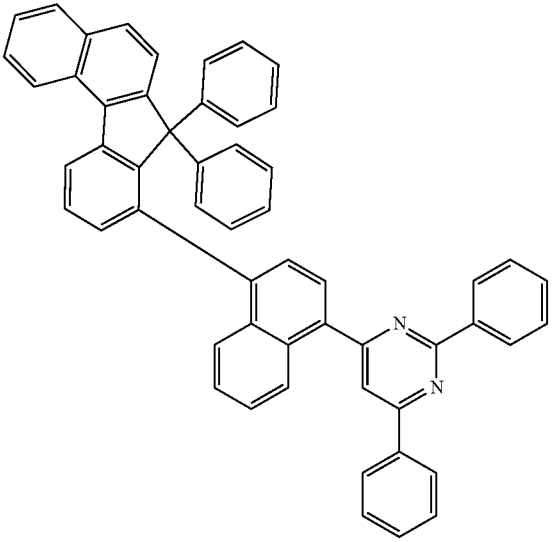

825
-continued
826
-continued
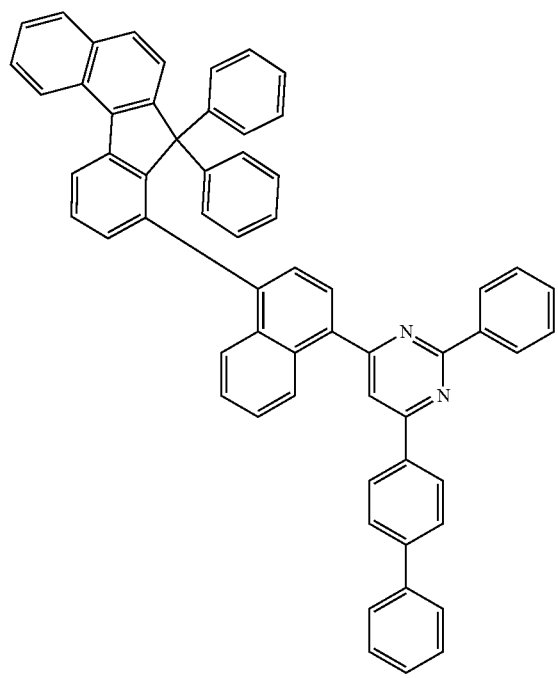
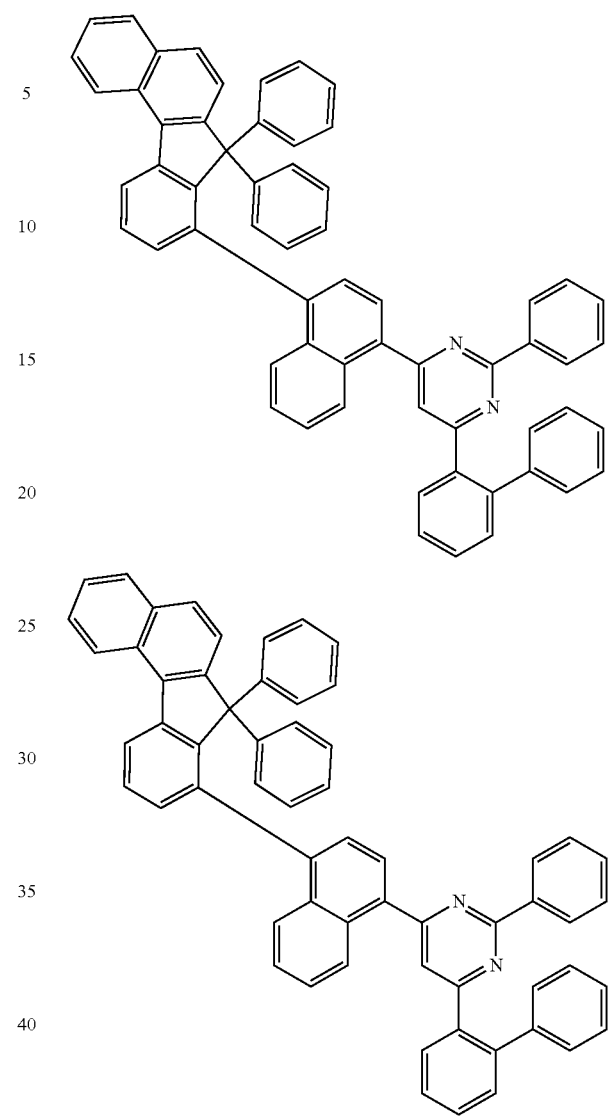
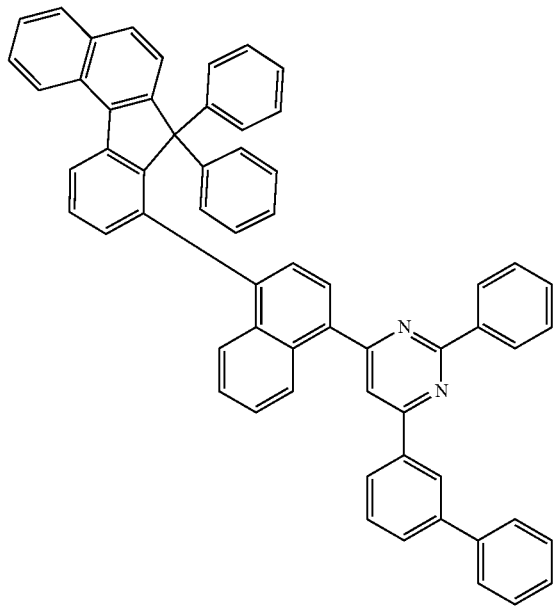

827
-continued
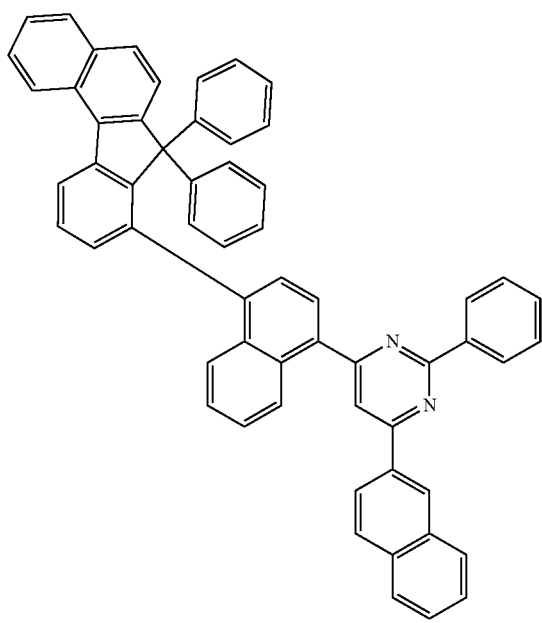
828
-continued
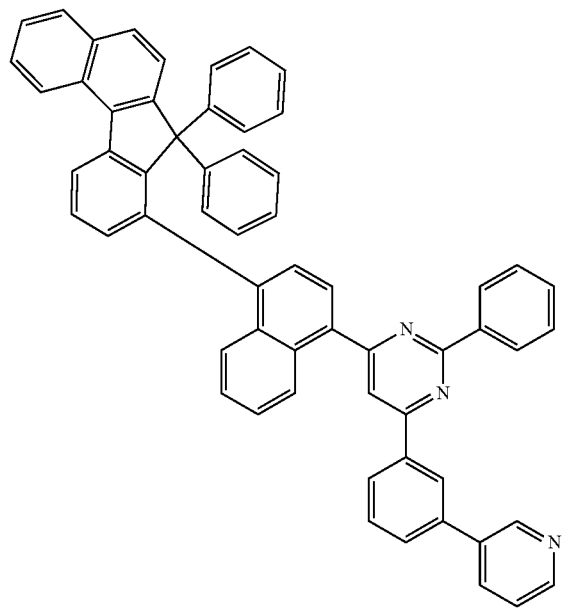
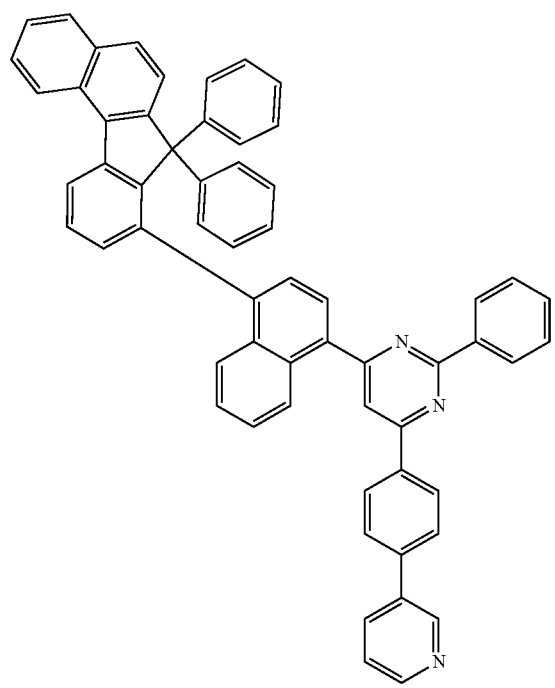
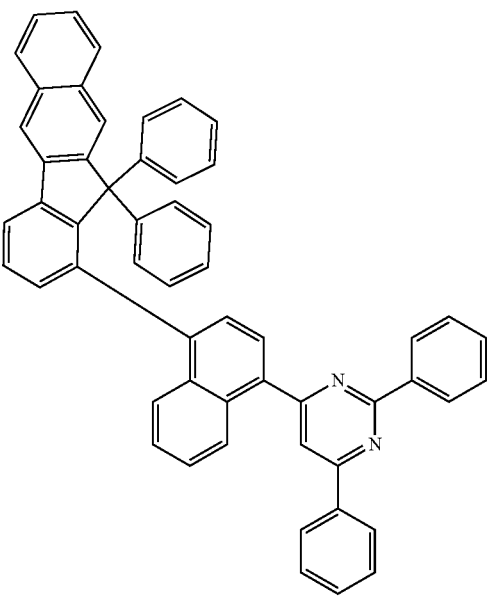

829
-continued
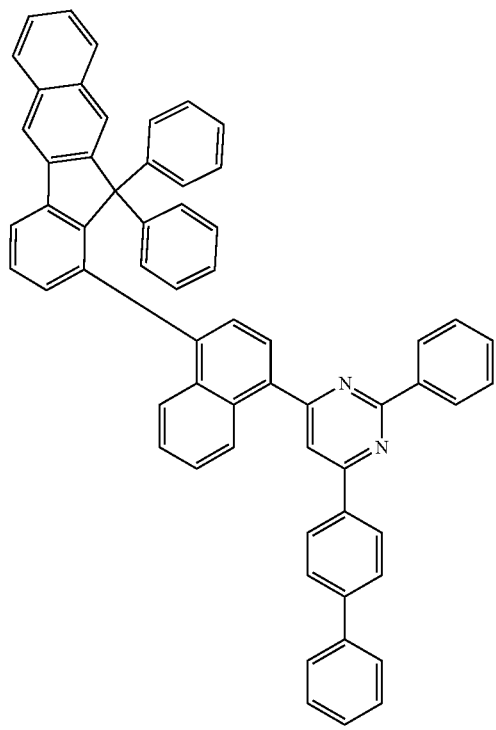
830
-continued
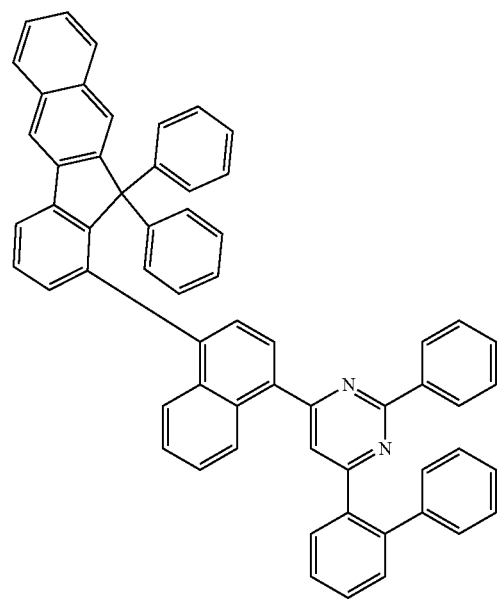
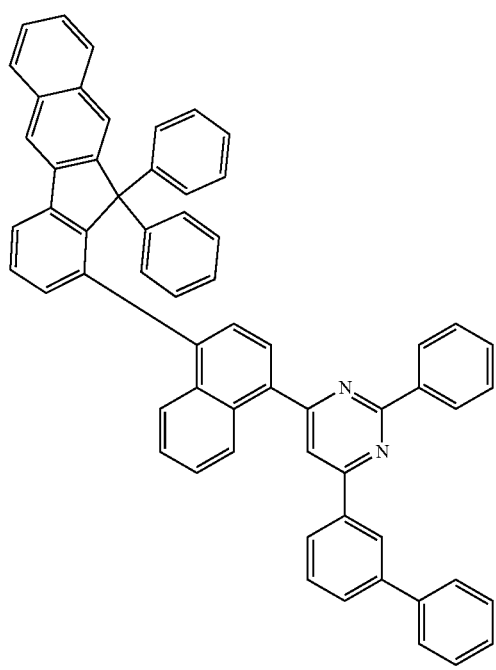
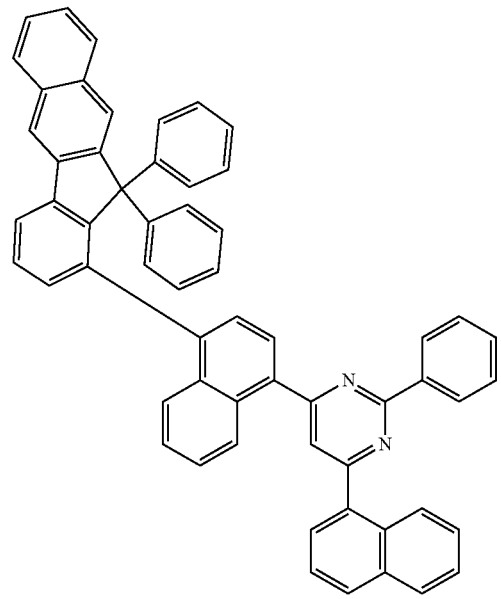

| 831 | 832 |
|---|---|
| -continued | -continued |
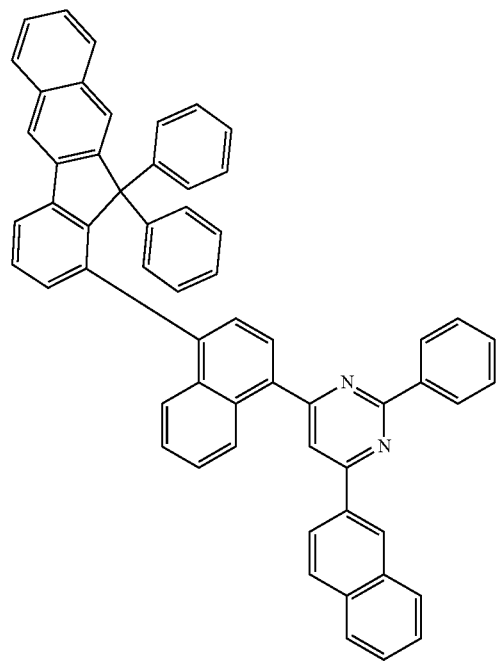
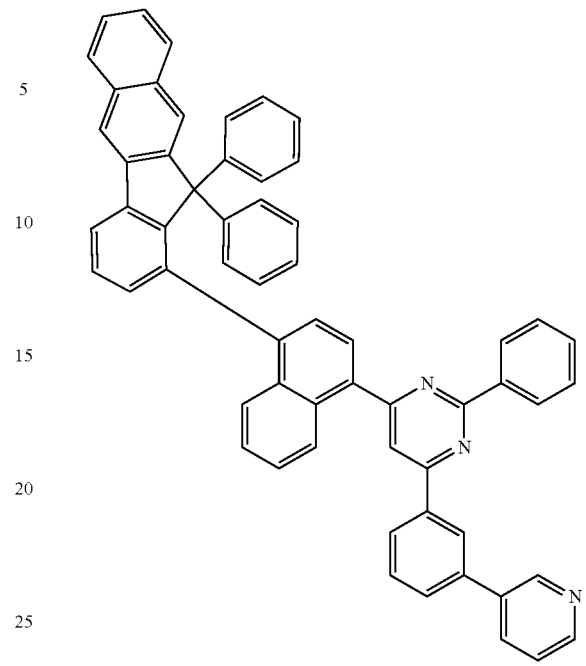
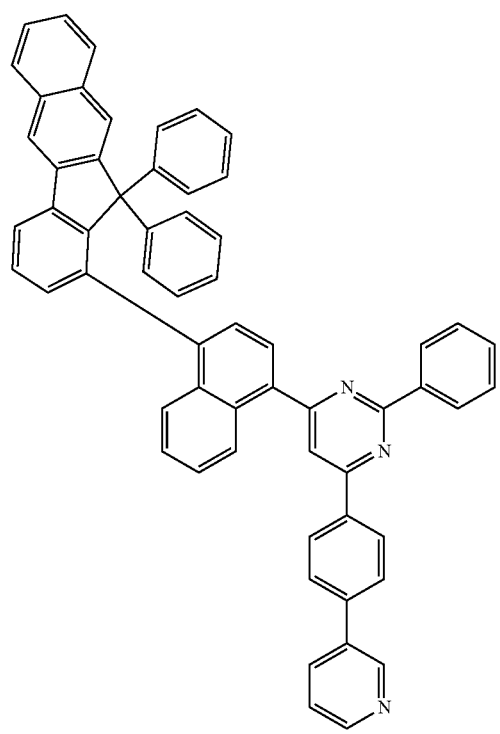
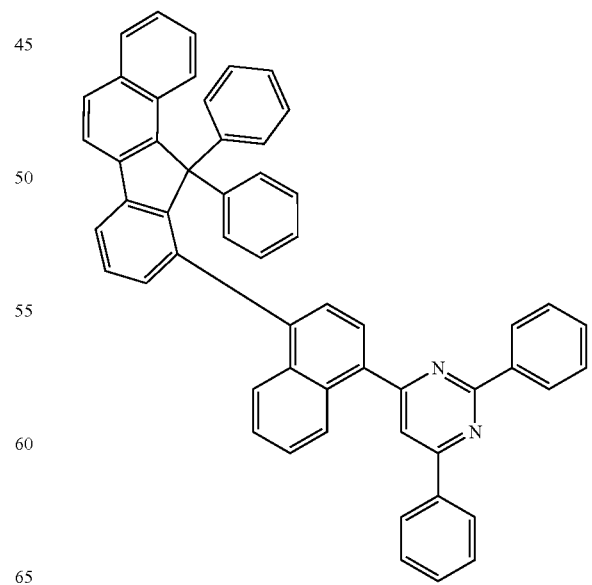

833
-continued
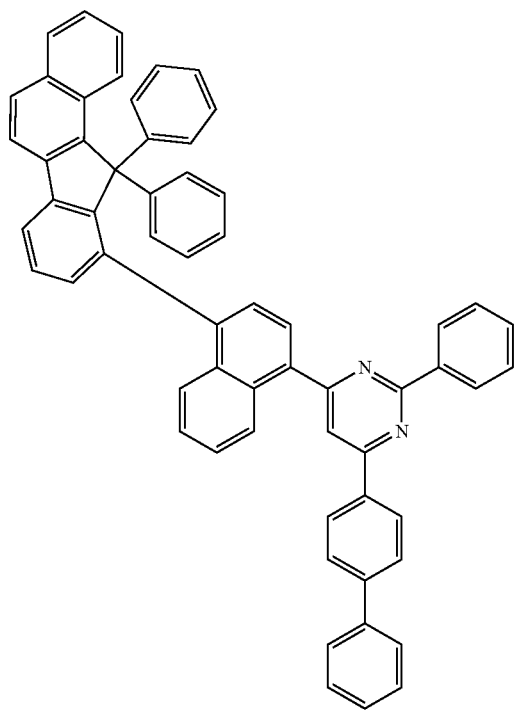
834
-continued
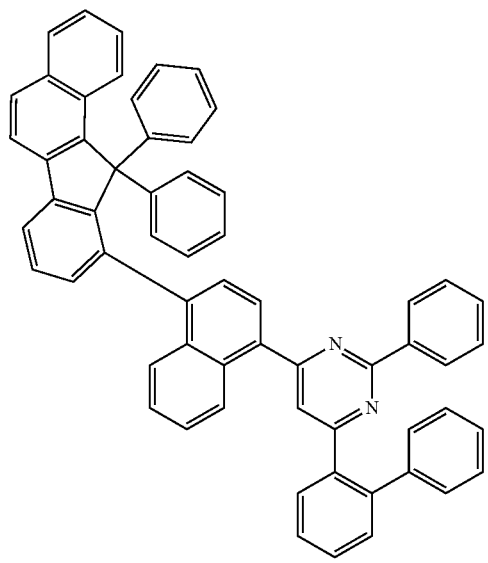
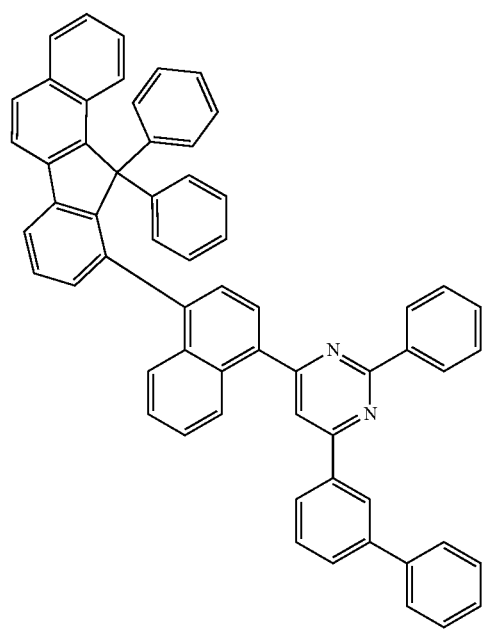
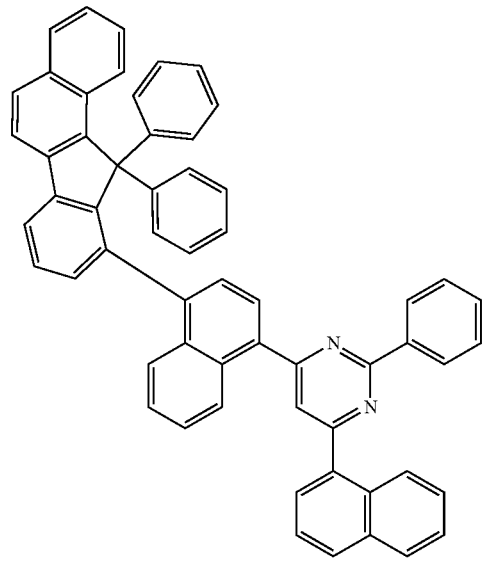

835 -continued
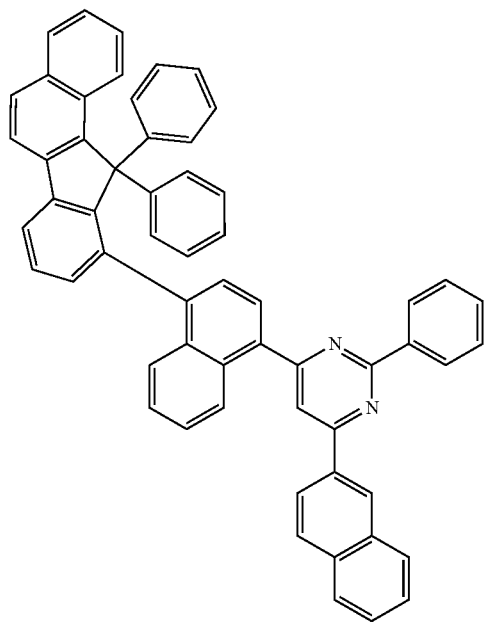
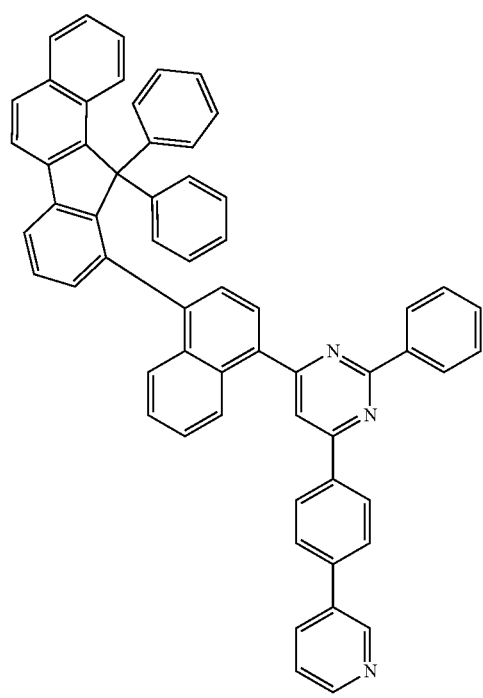
836 -continued
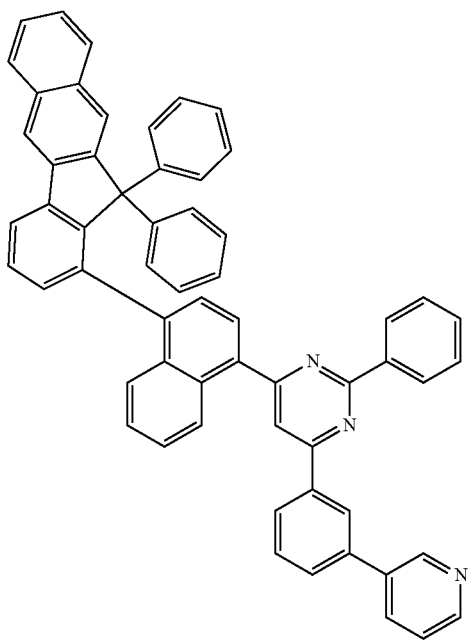
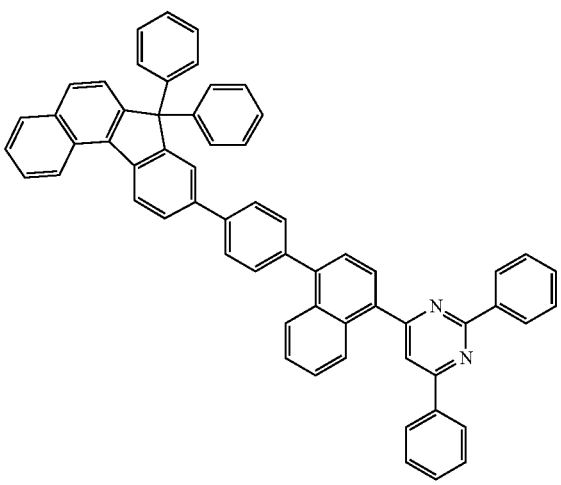

837
-continued
838
-continued
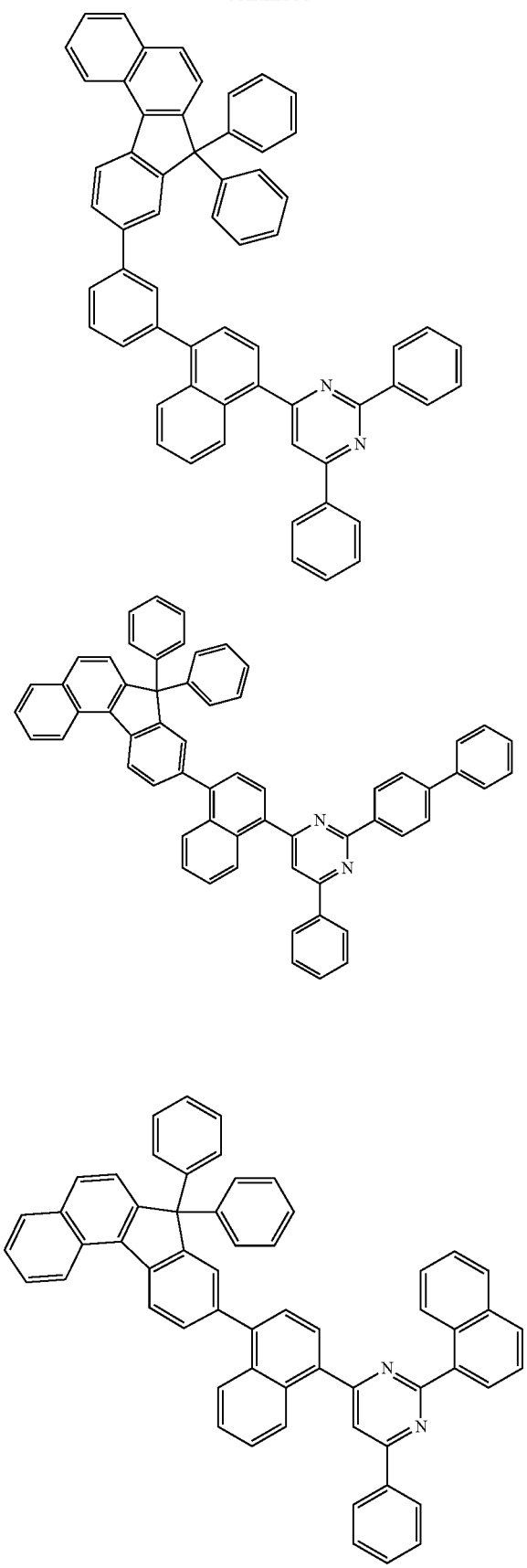
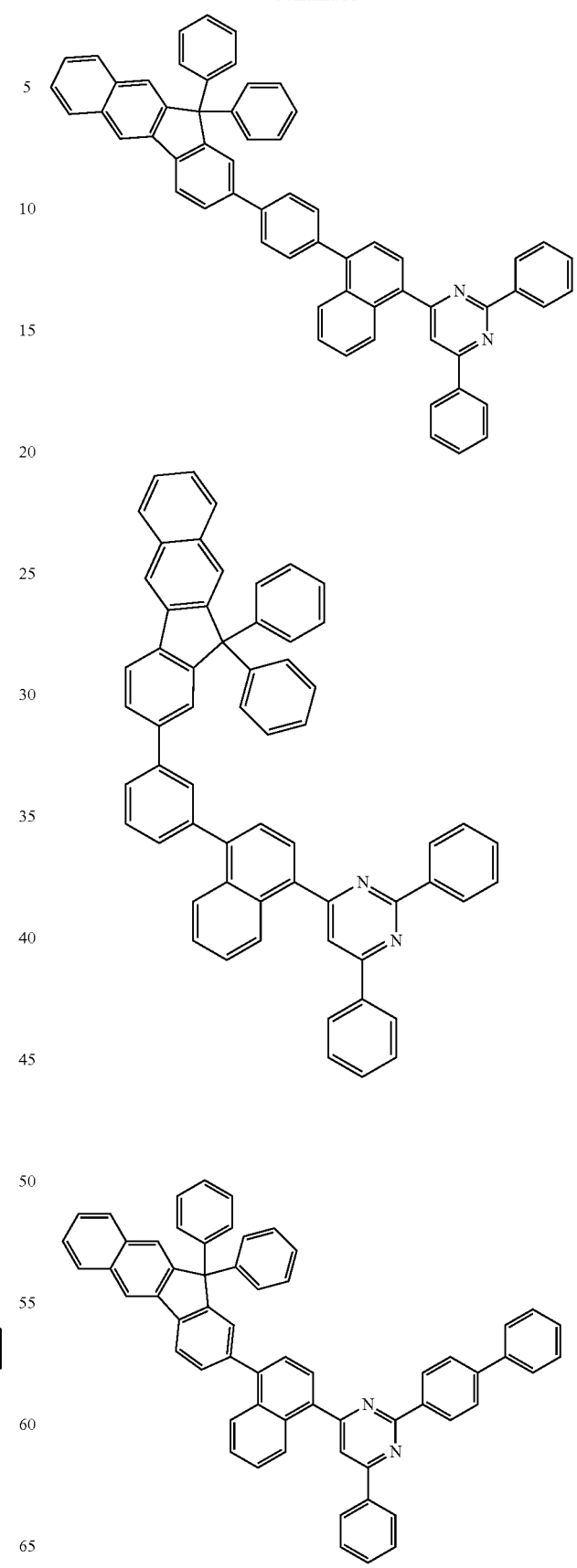

839
-continued
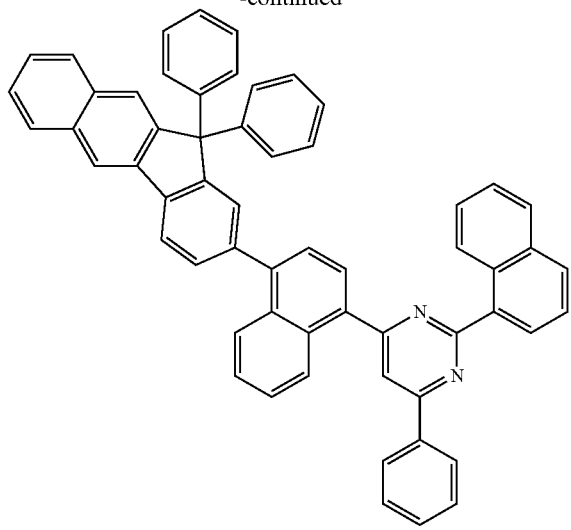
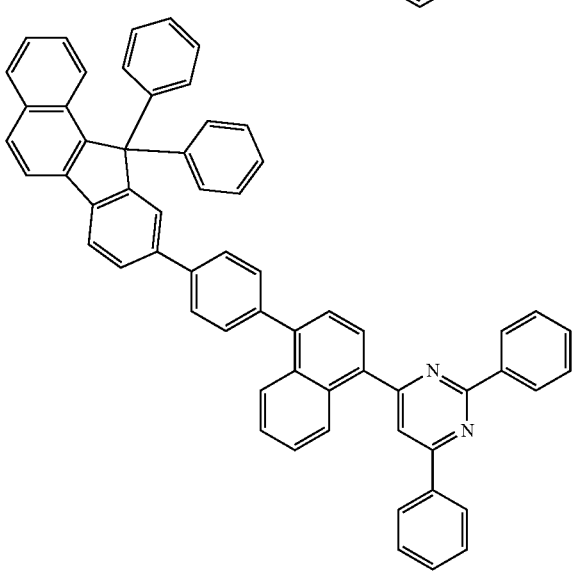
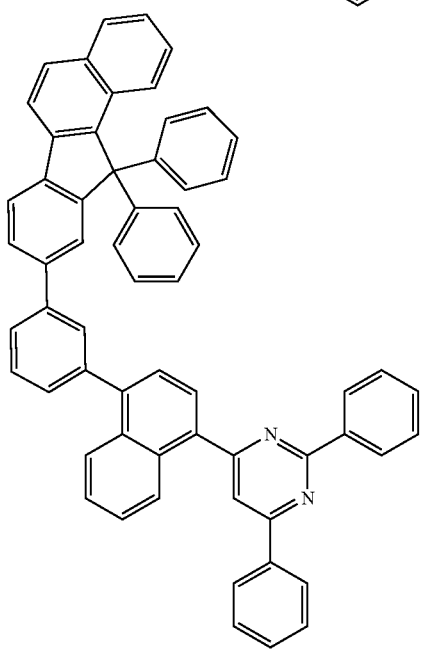
840
-continued
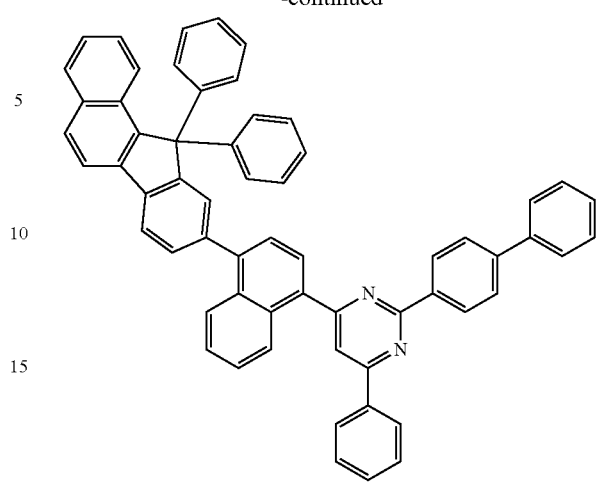
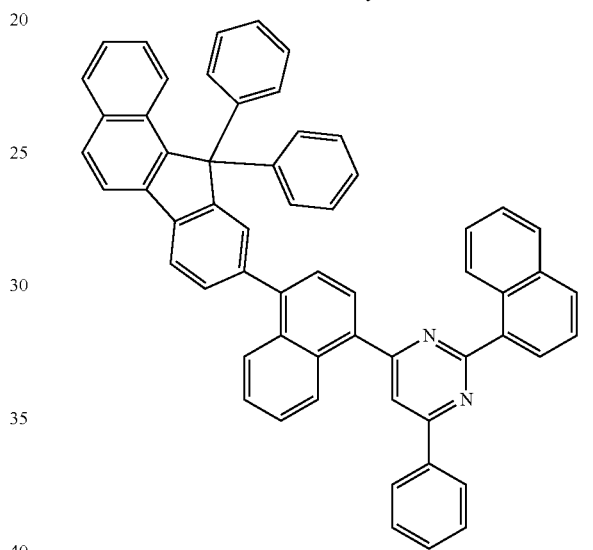
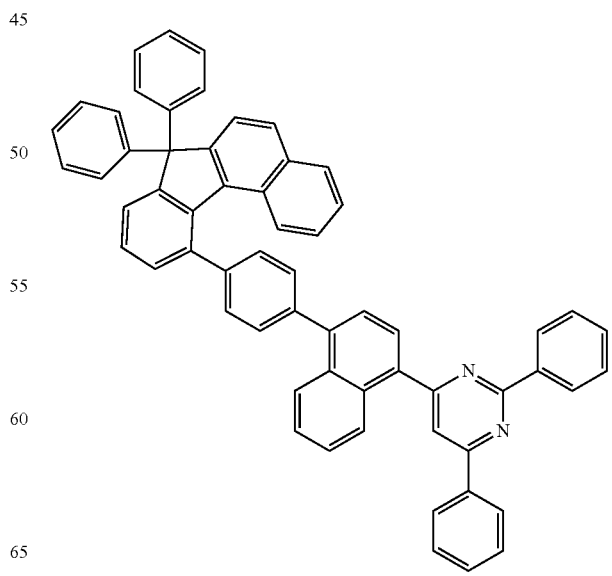

841
-continued
842
-continued
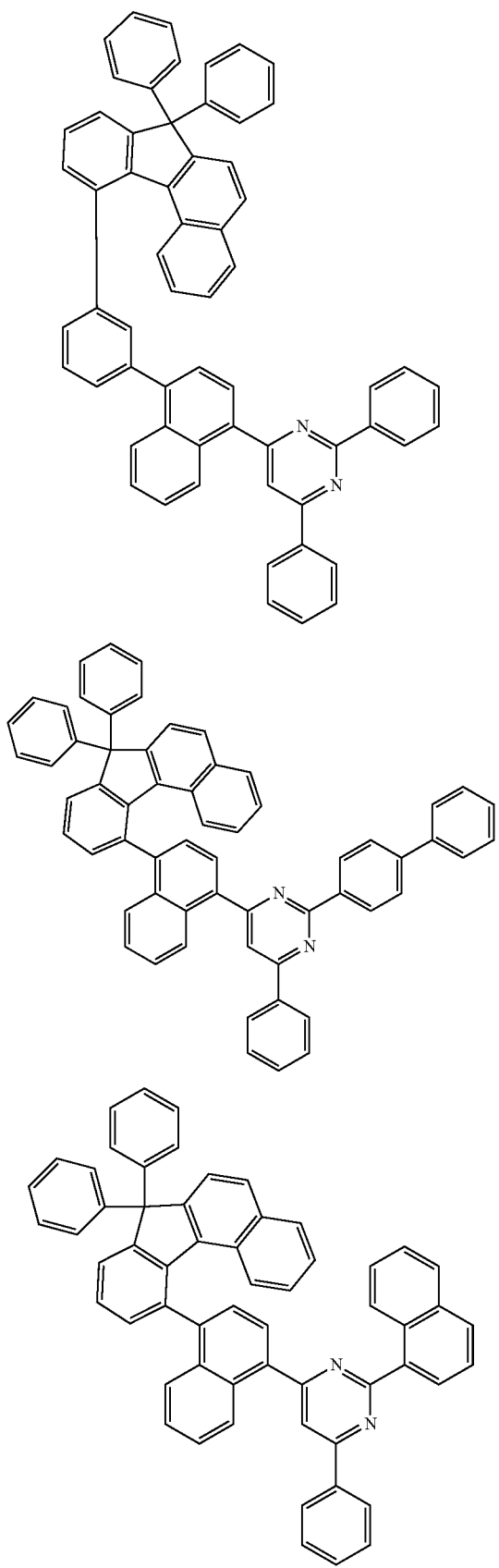
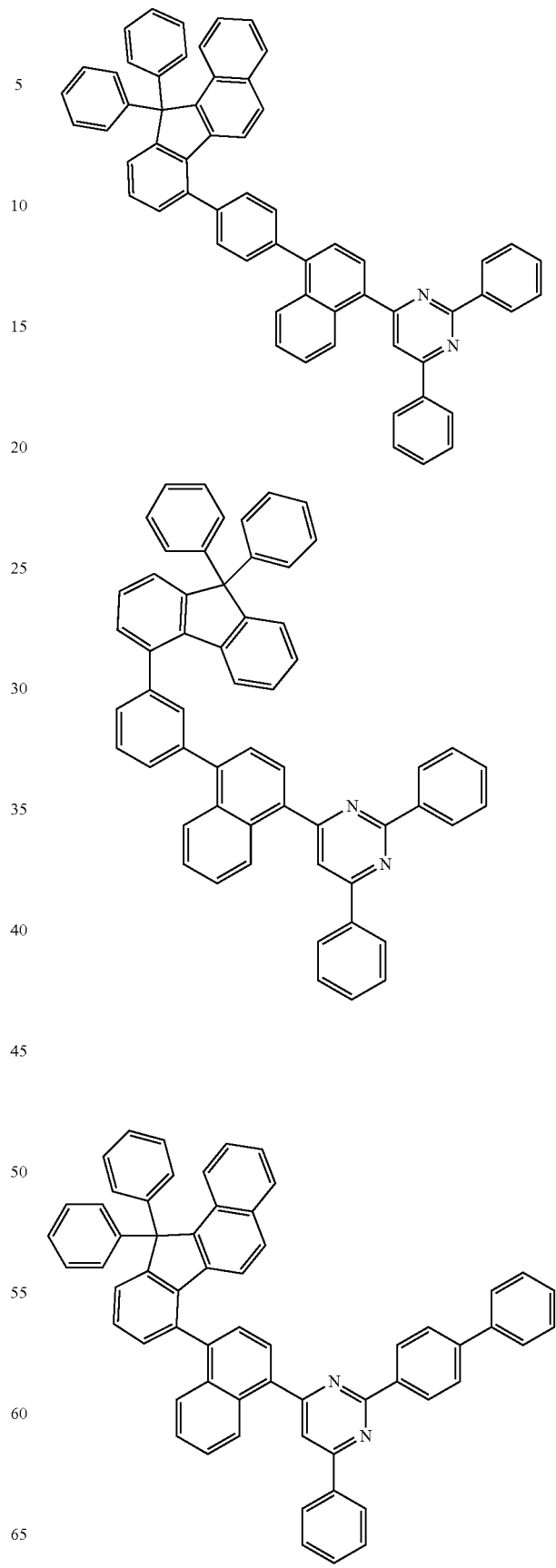

843
-continued
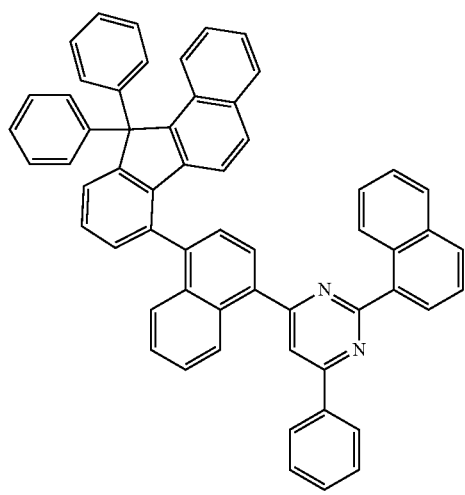
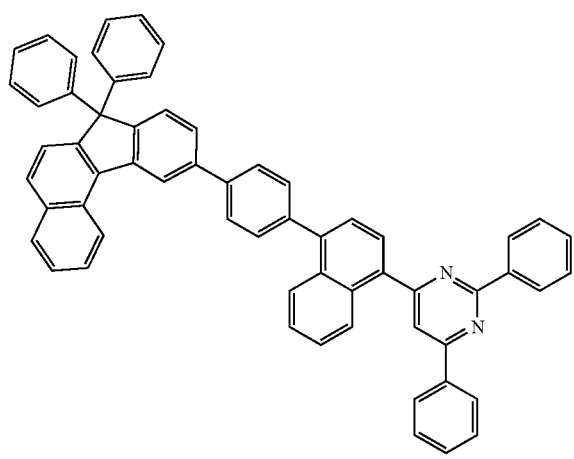
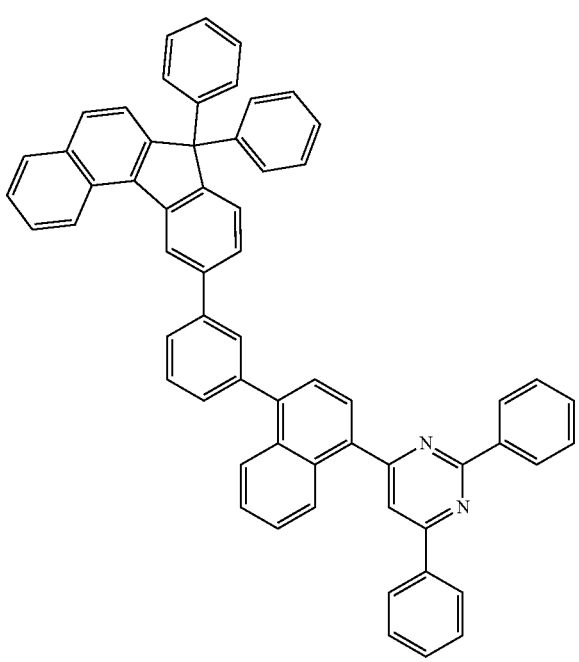
844
-continued
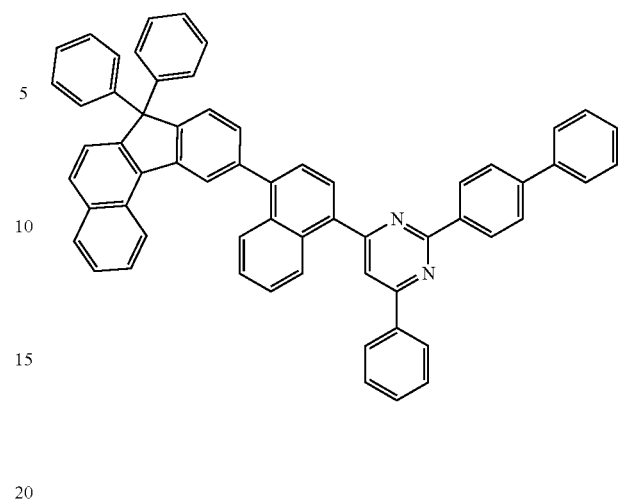

845
-continued
846
-continued
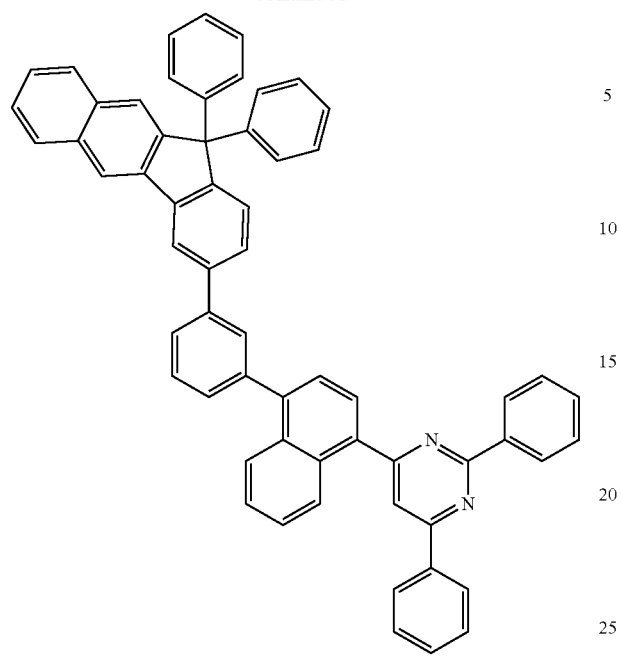
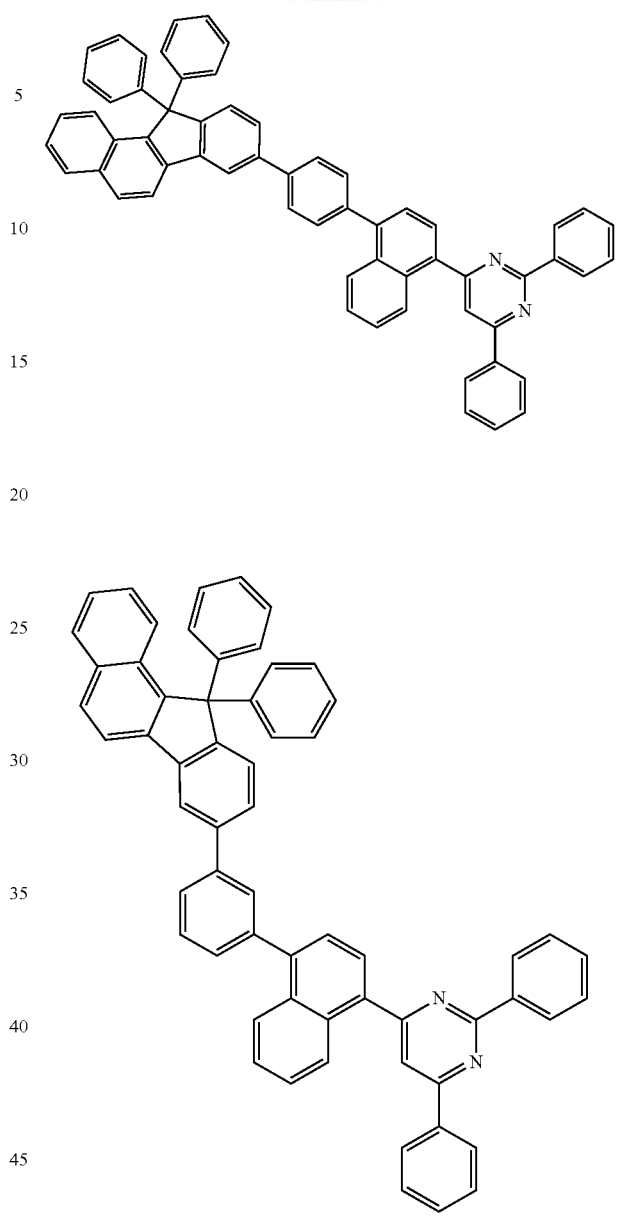
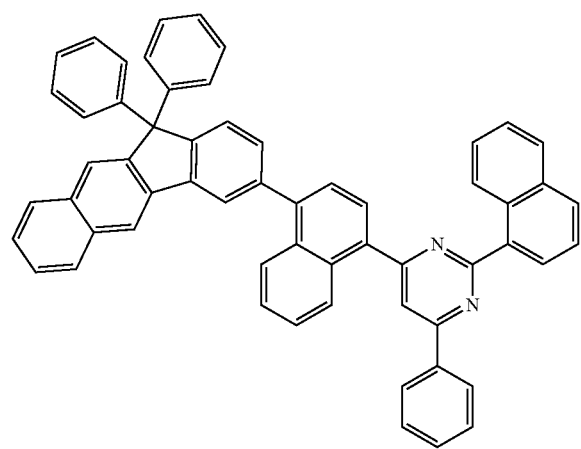

| 847 | 848 |
|---|---|
| 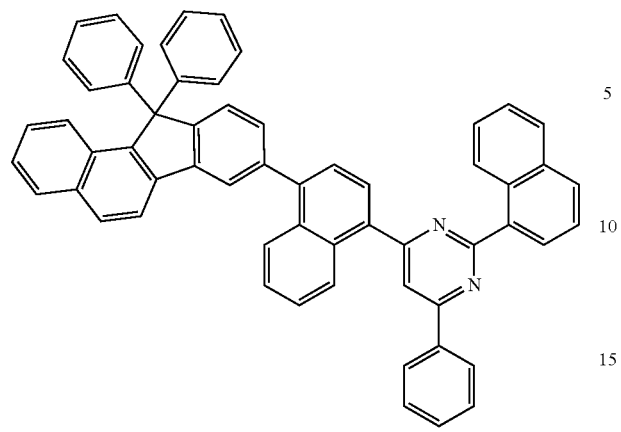<br>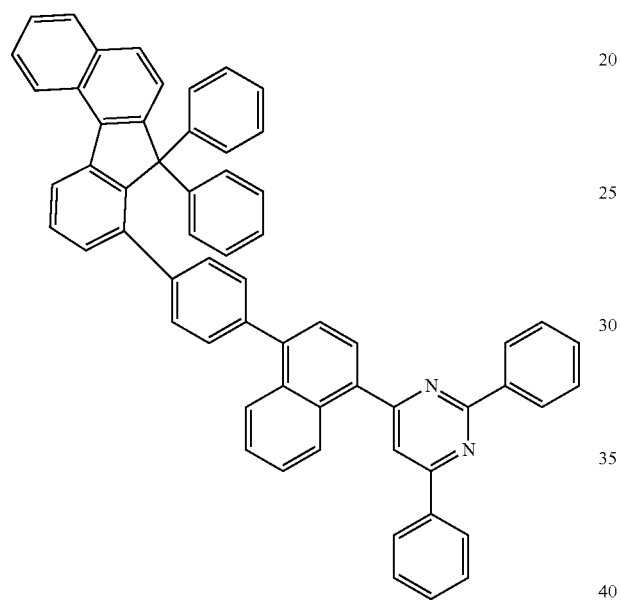<br>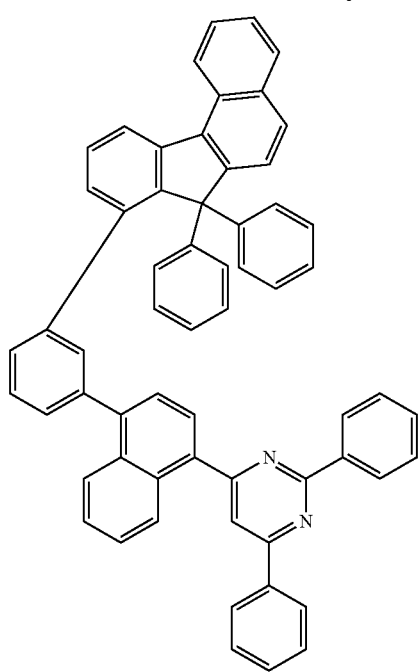 | 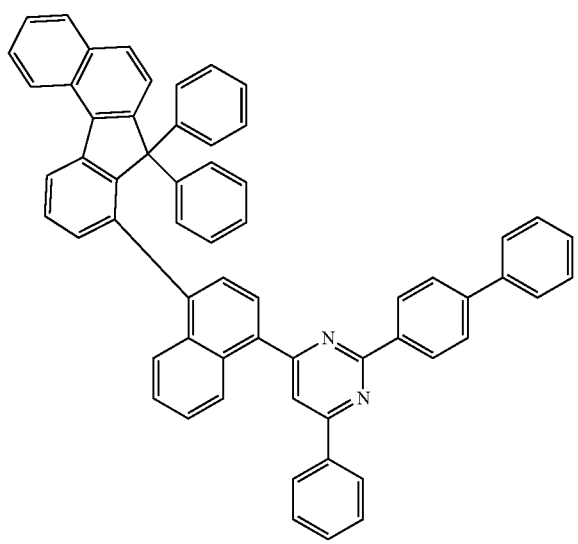<br>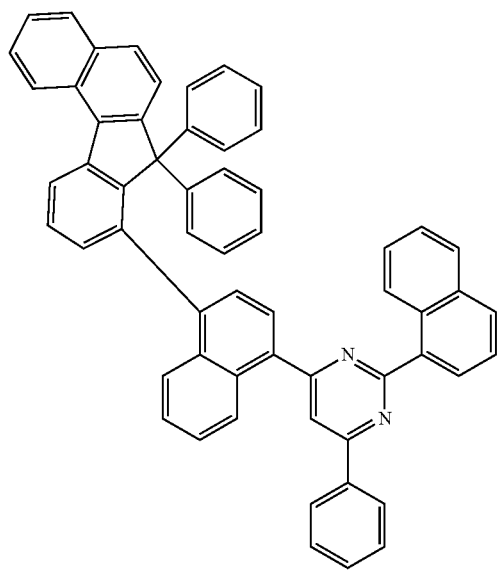 |

849
-continued
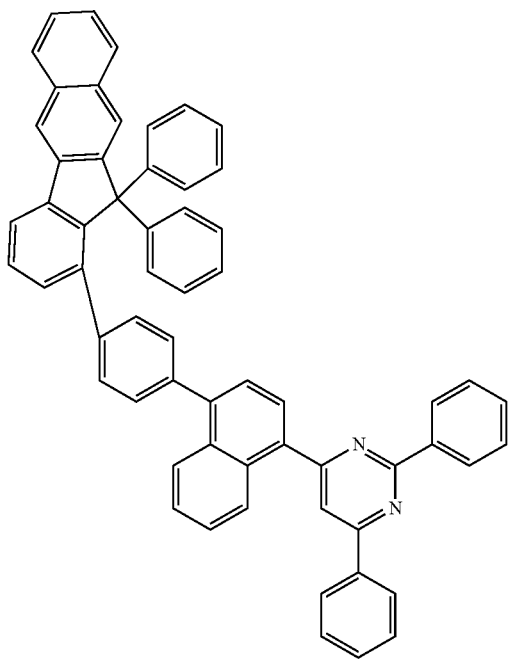
850
-continued
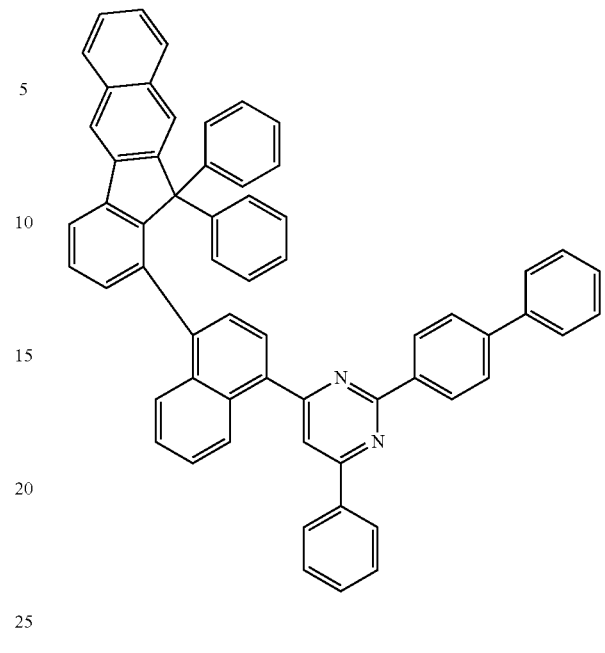
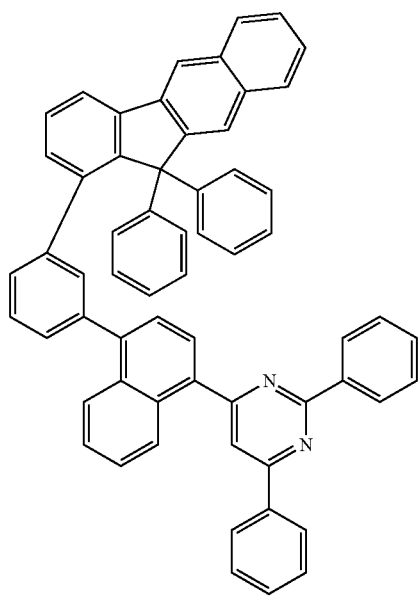
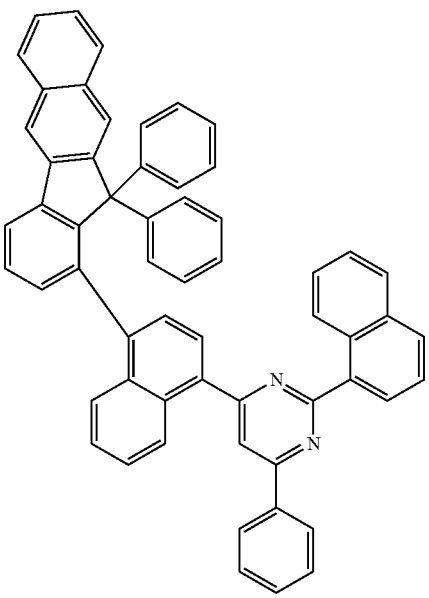

| 851 | 852 |
|---|---|
| -continued | -continued |
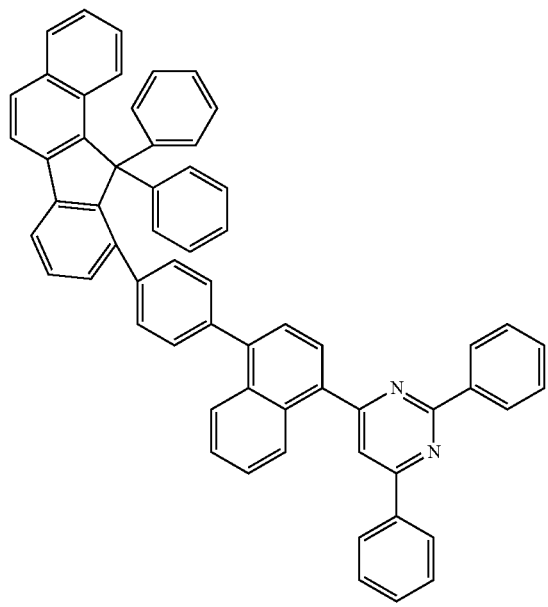
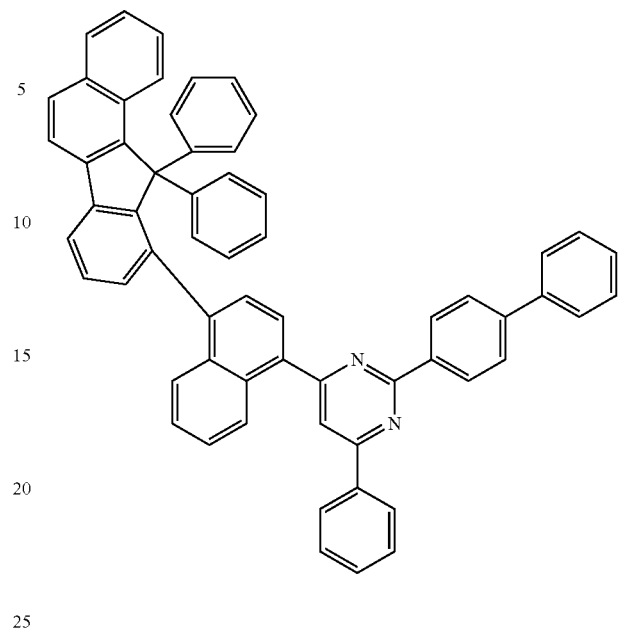
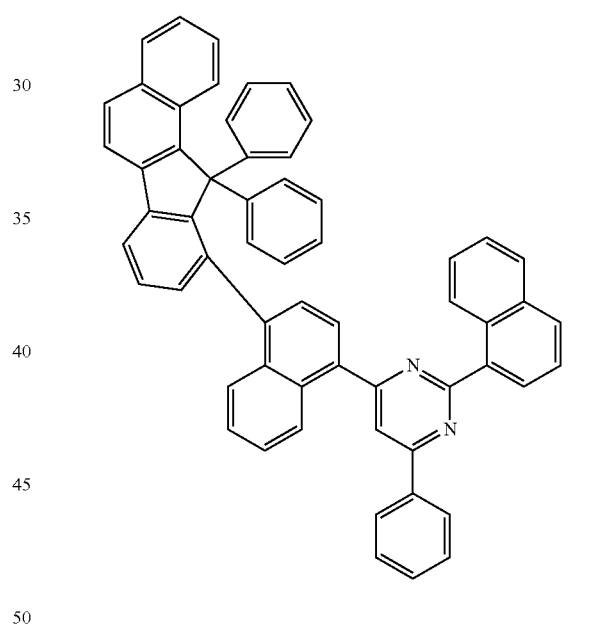
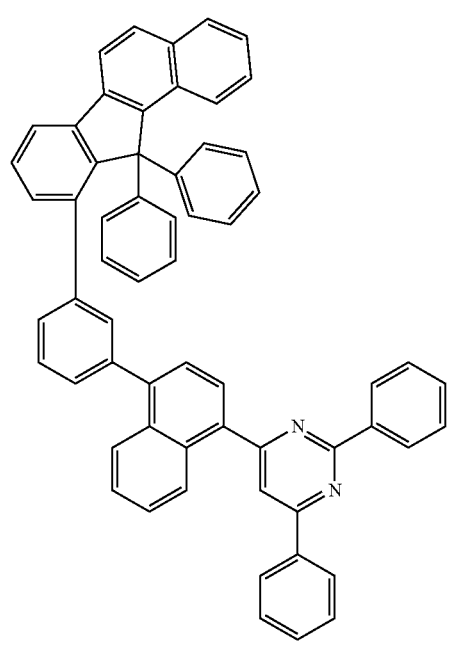
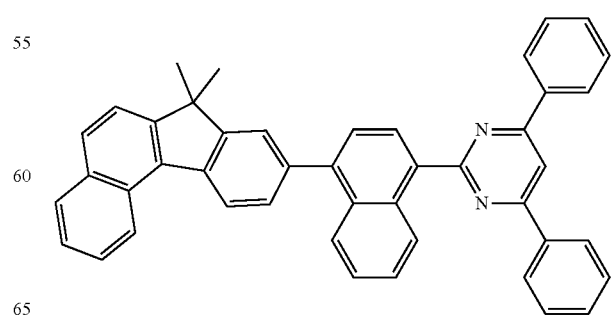

853
-continued
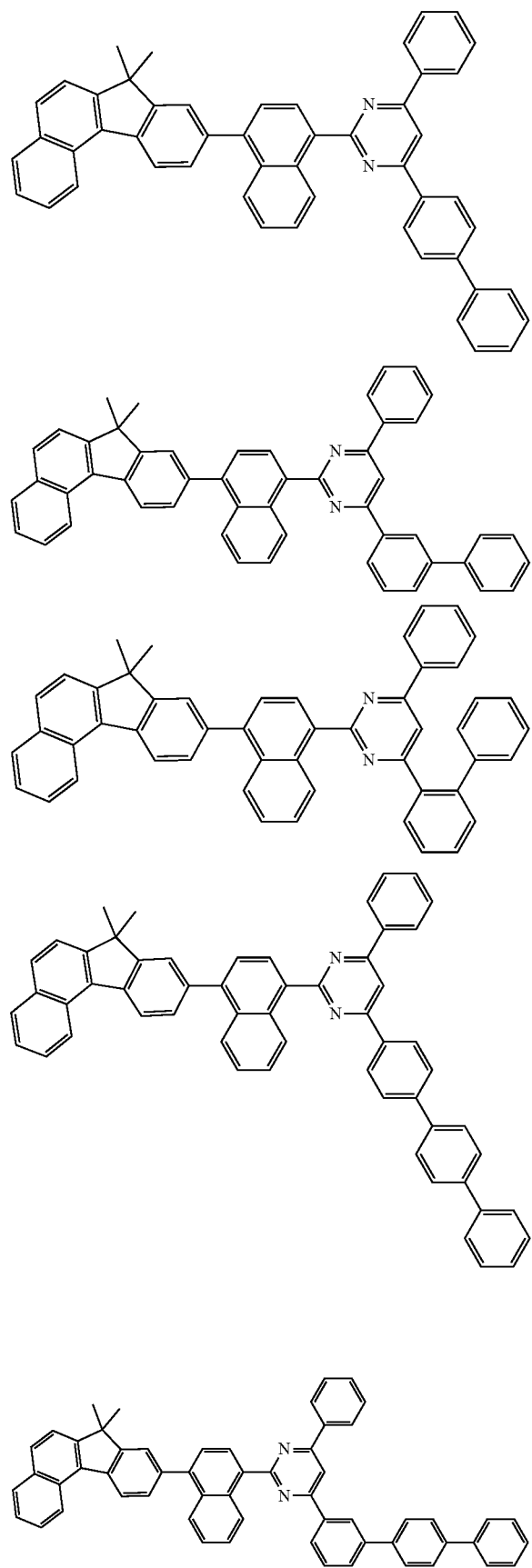
854
-continued
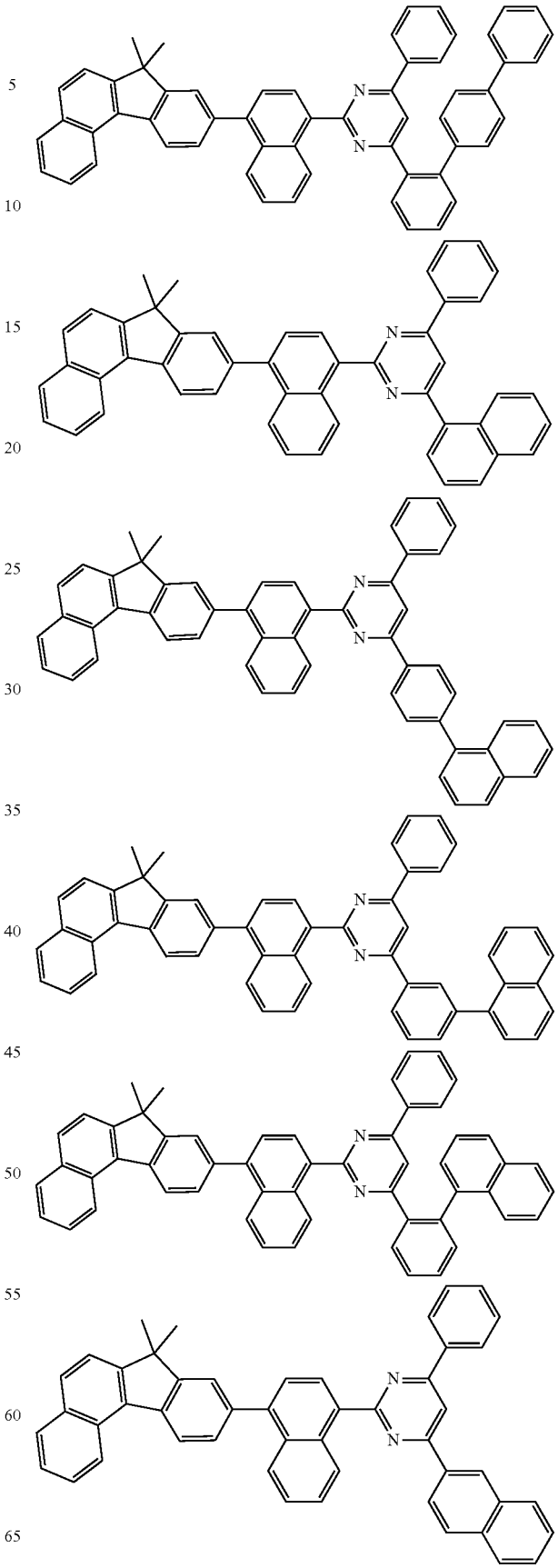

855
-continued
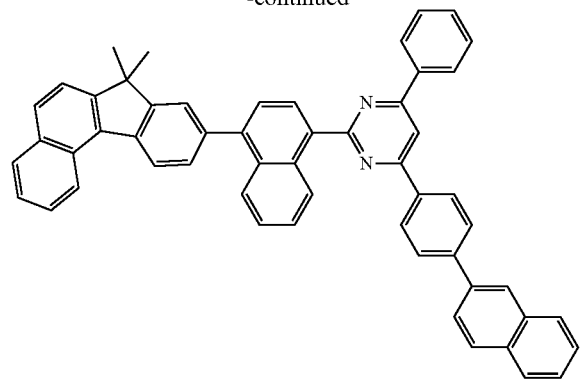
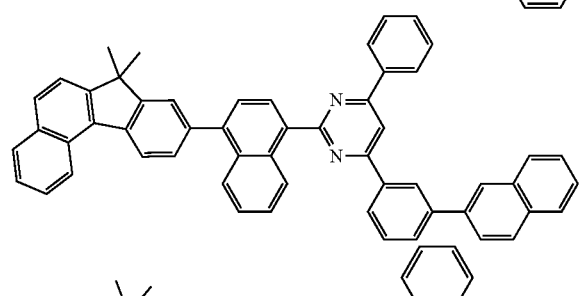
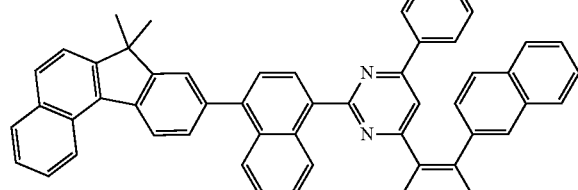
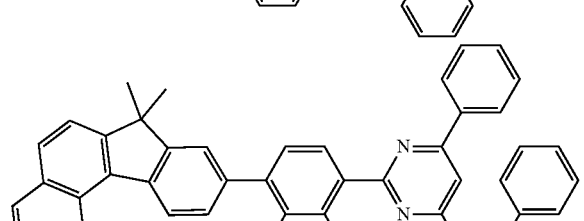
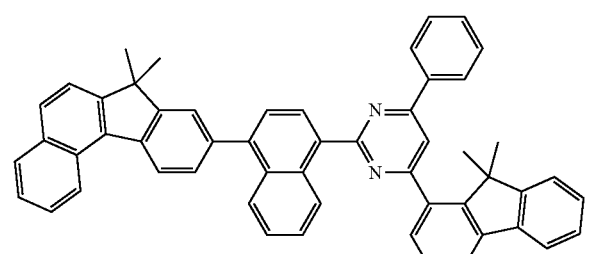
856
-continued
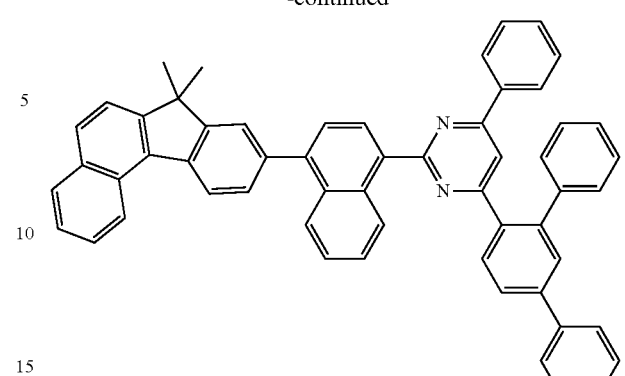
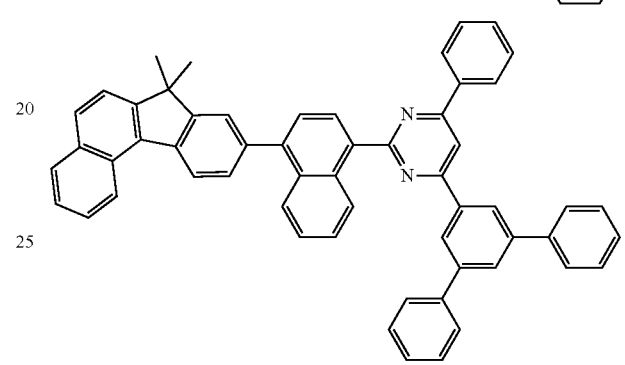
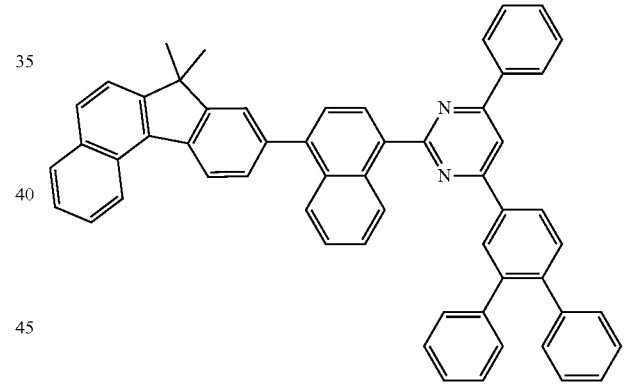
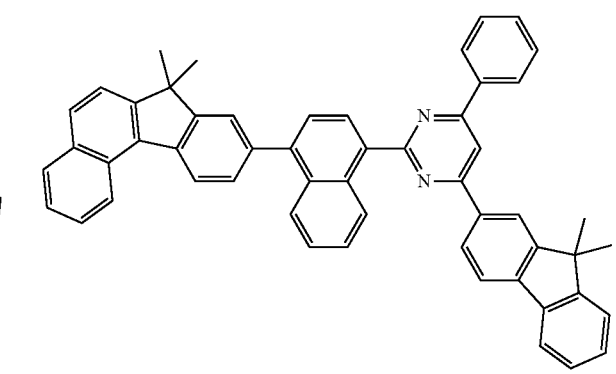

-continued
| 857 | 858 |
|---|---|
| 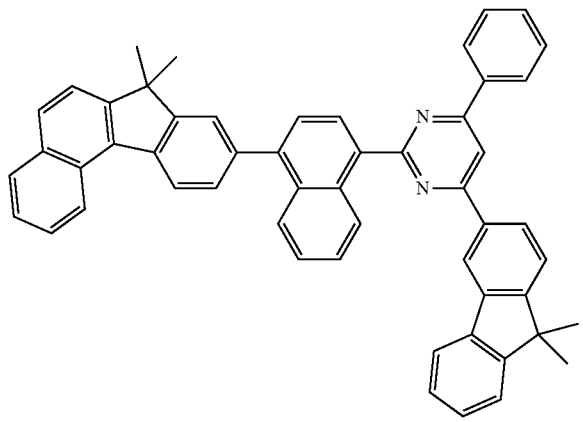 | 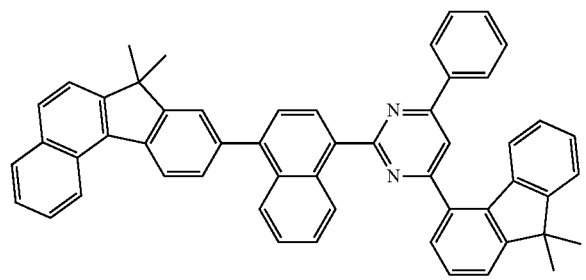 |
| 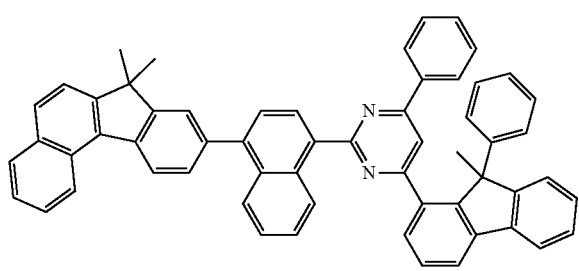 | 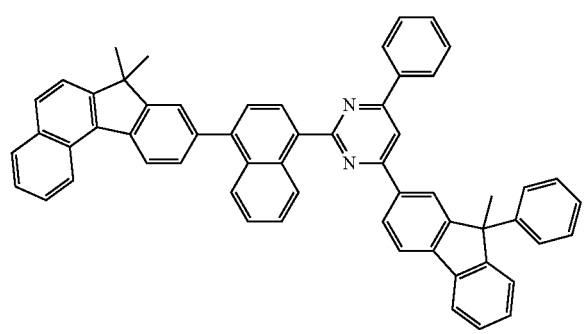 |
| 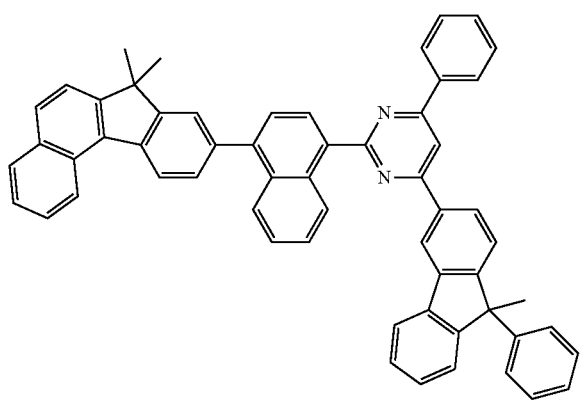 | 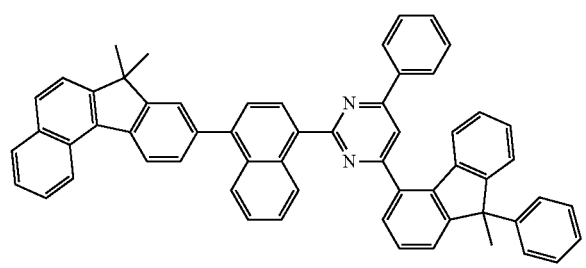 |
| 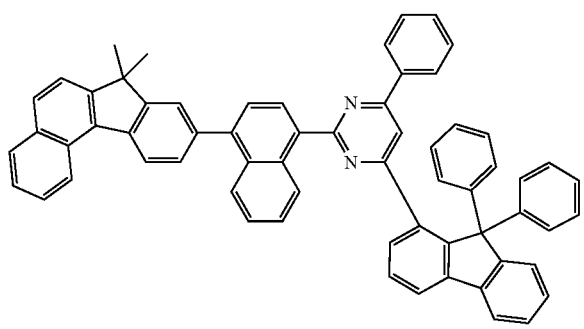 | 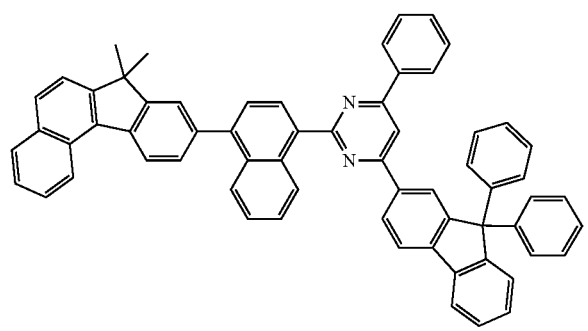 |

859
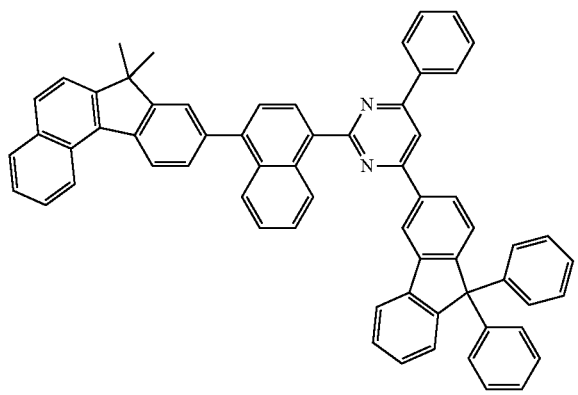
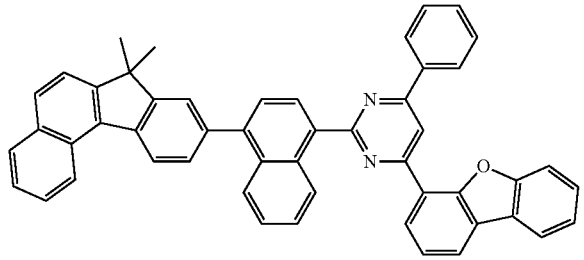
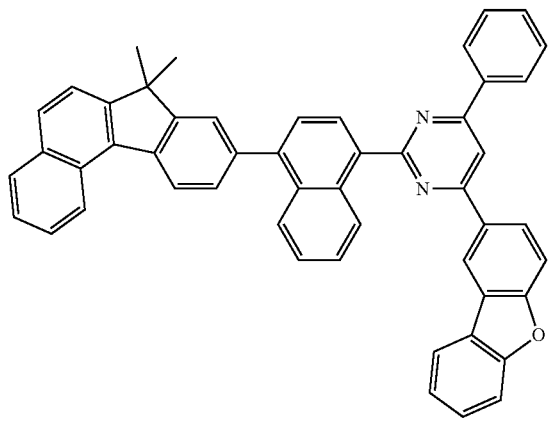
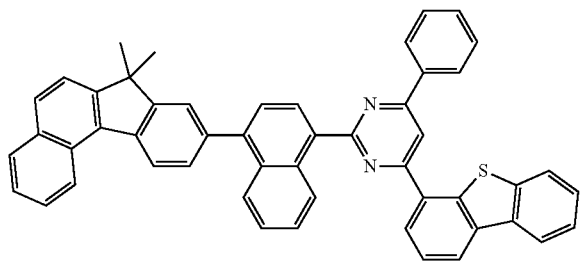
860
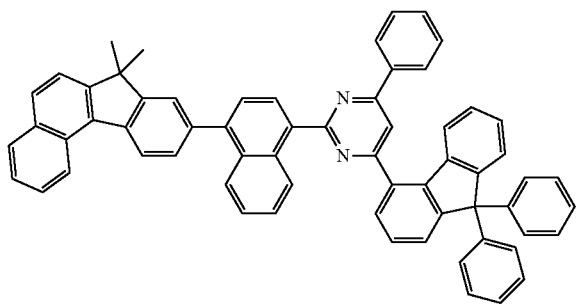
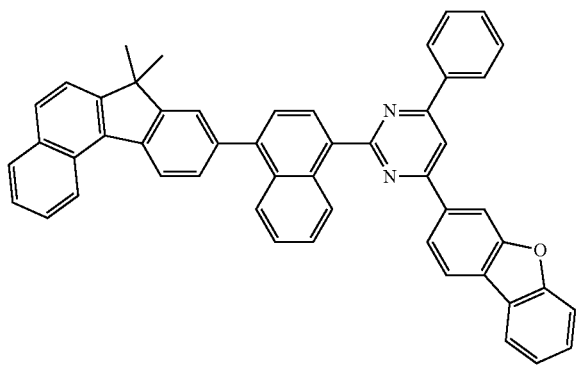
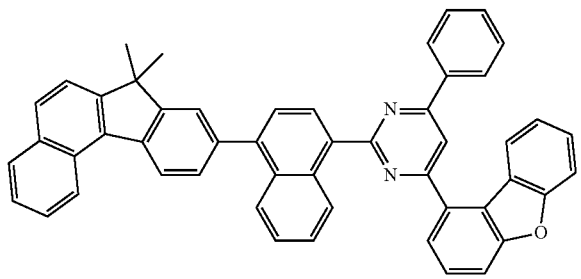
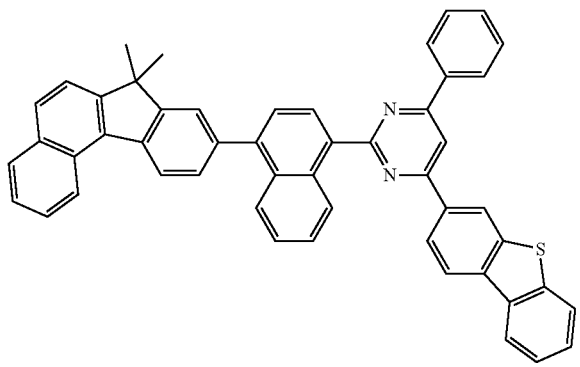

861 862
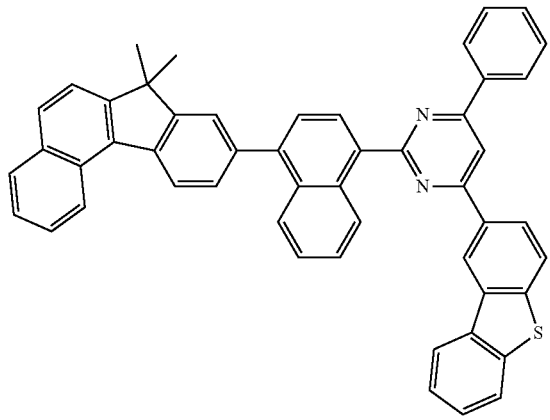
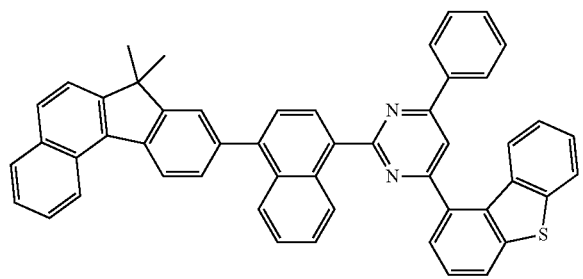
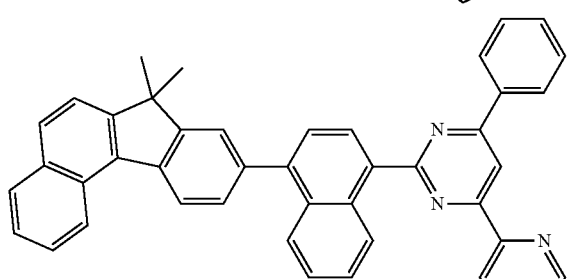
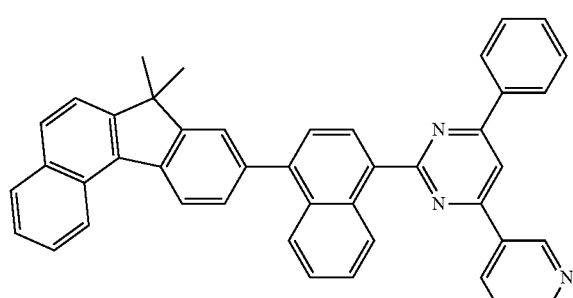
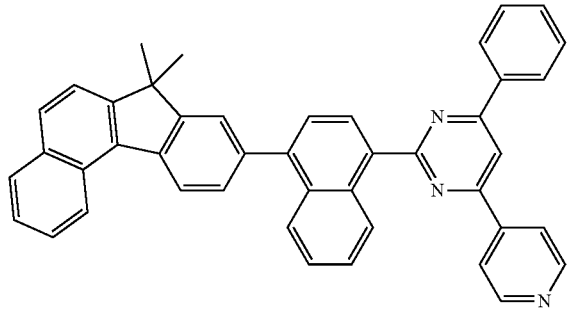
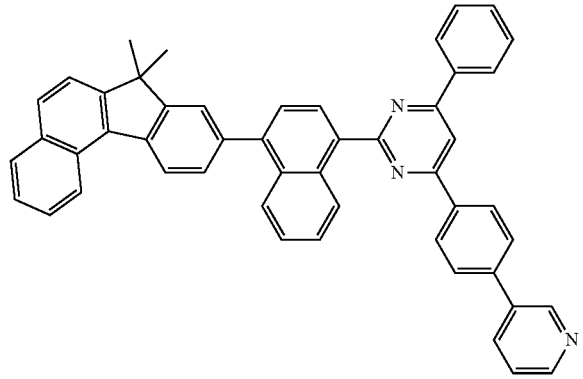
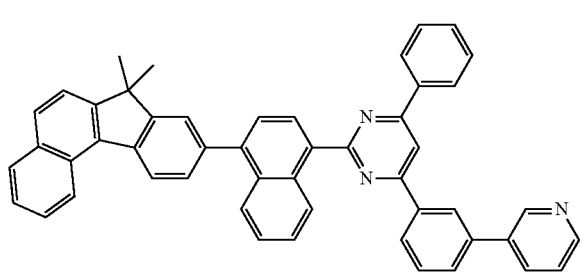
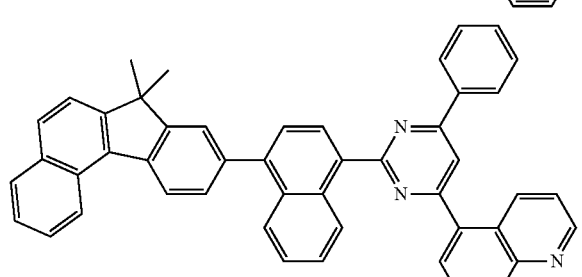
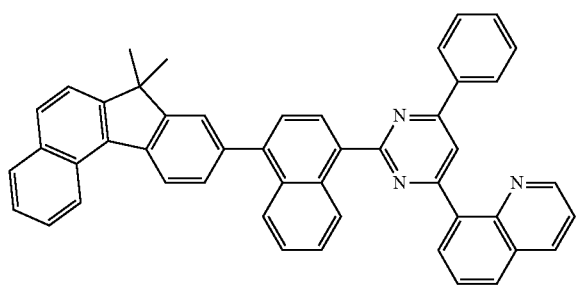
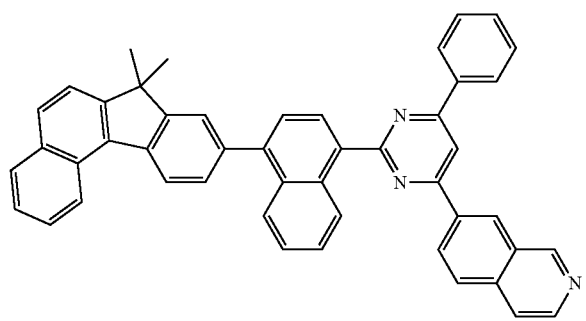

863
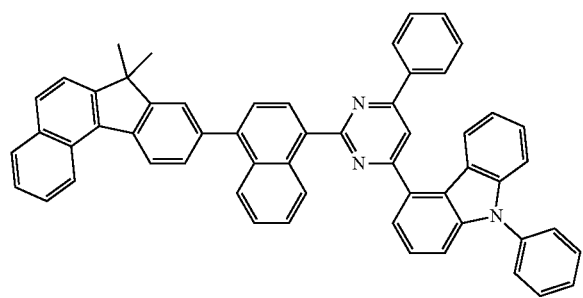
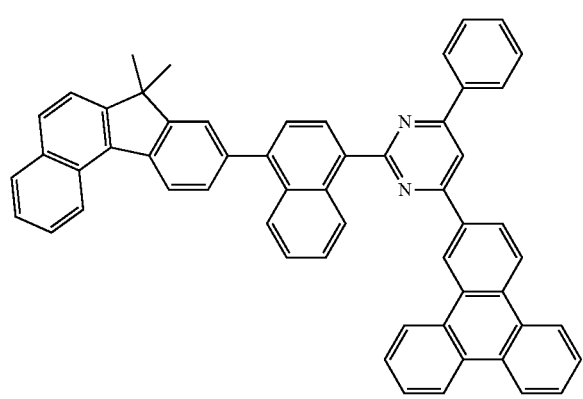
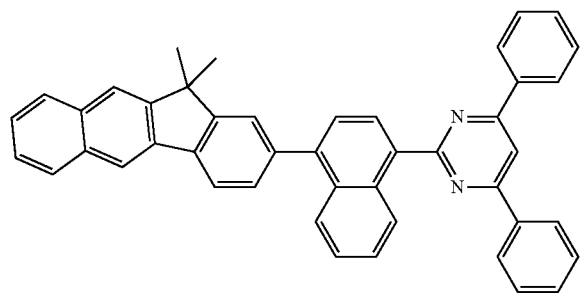
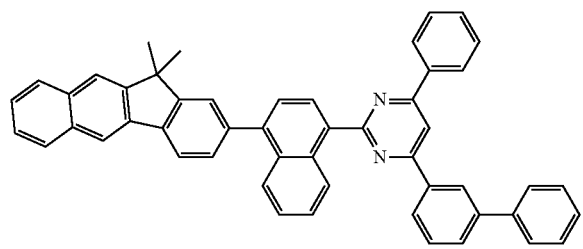
864
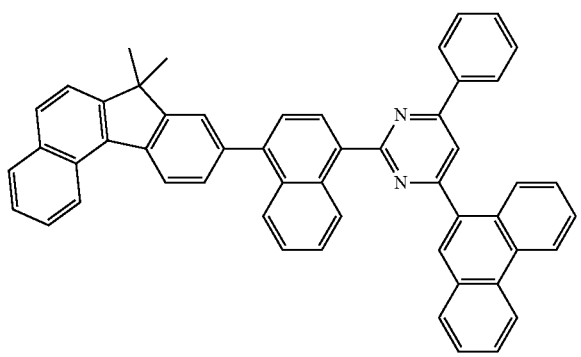
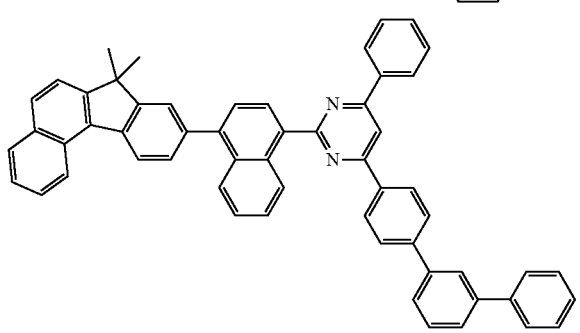
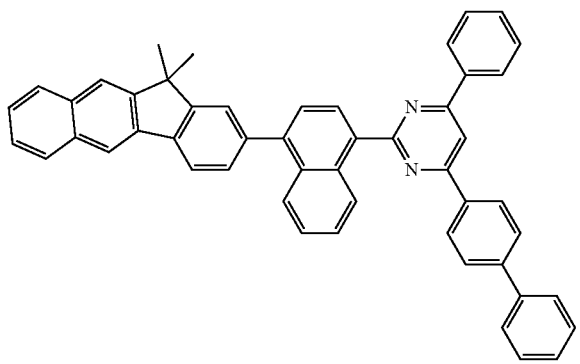
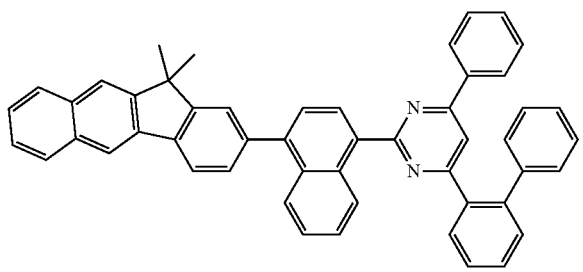

865 866
-continued
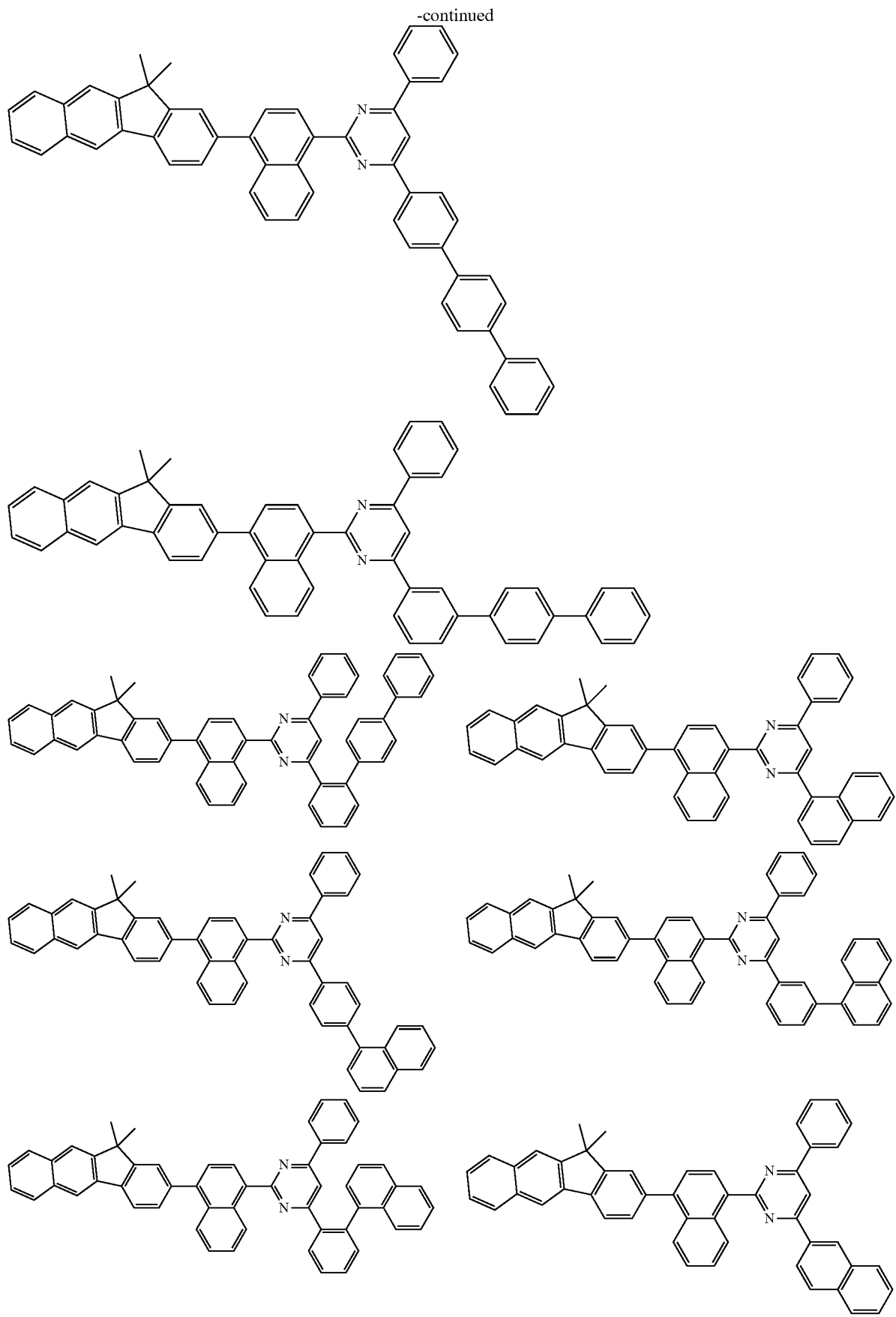

867    868
-continued
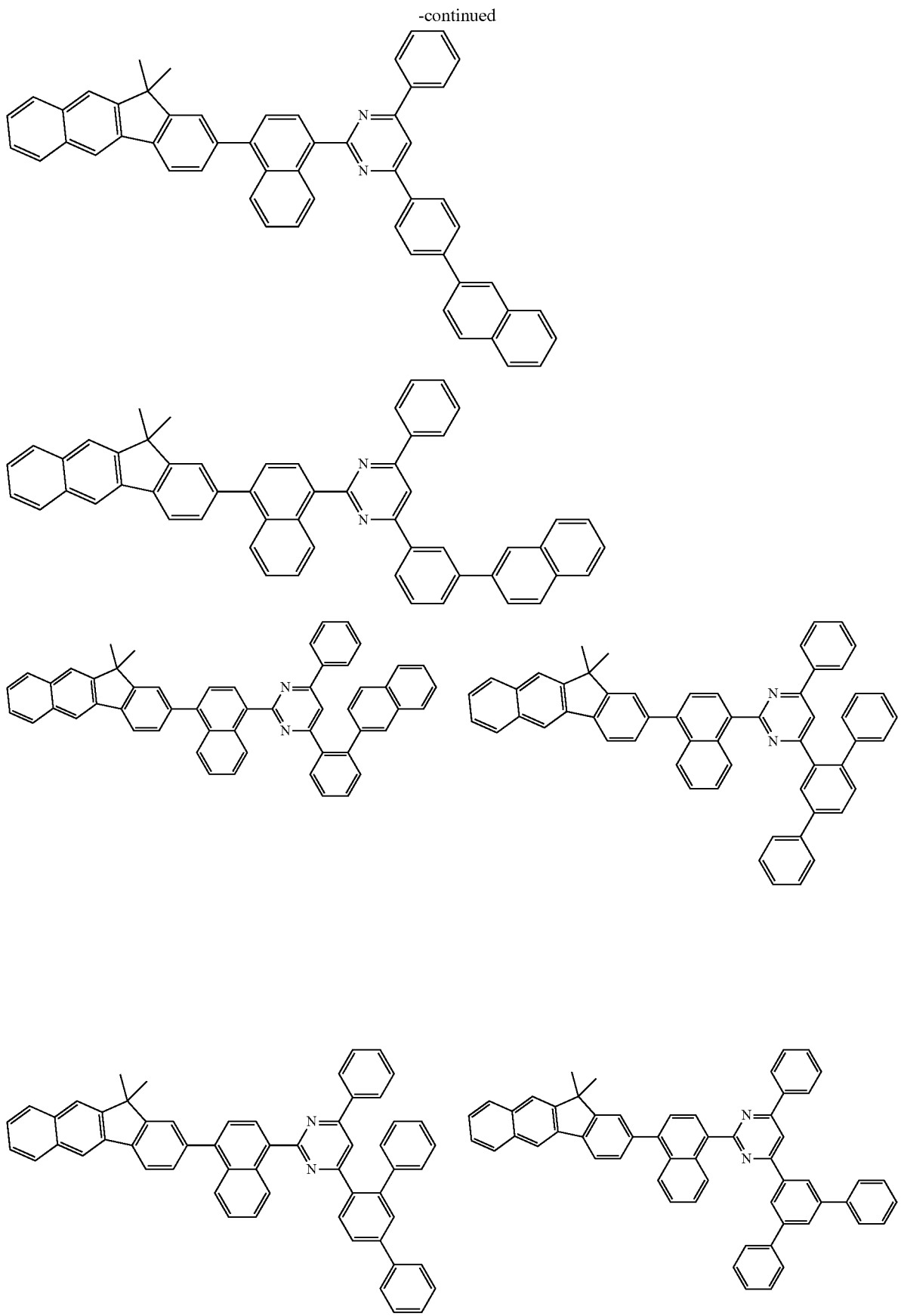

| 869 | 870 |
|---|---|
| 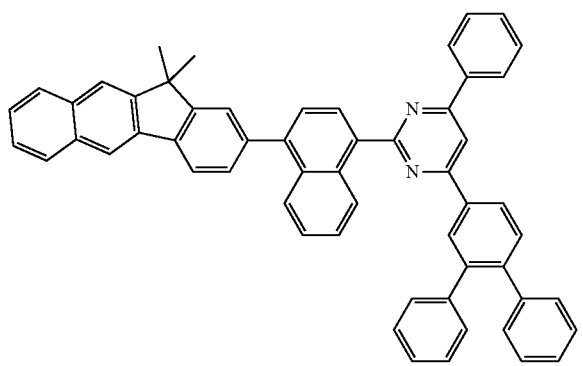 | 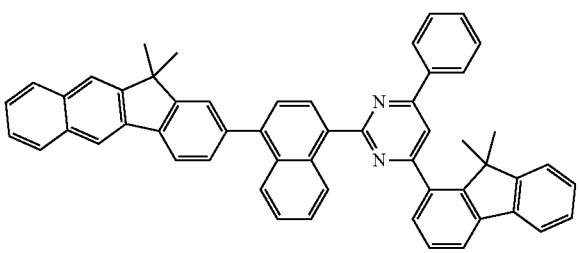 |
| 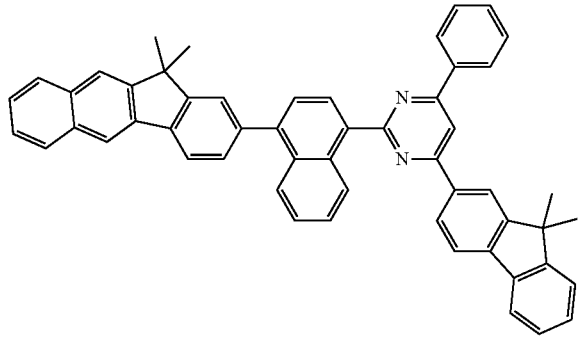 | 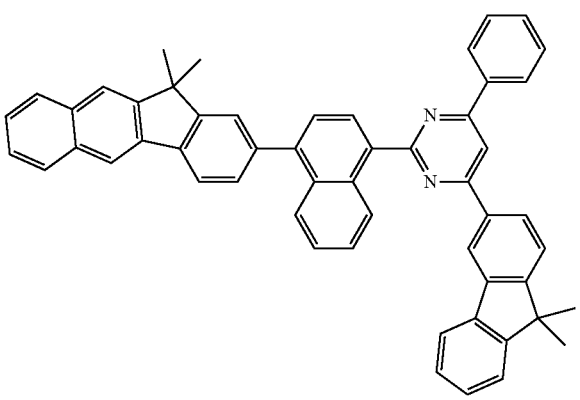 |
| 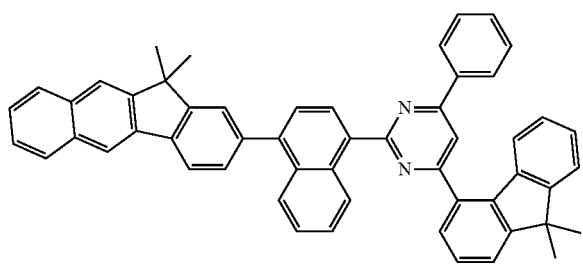 | 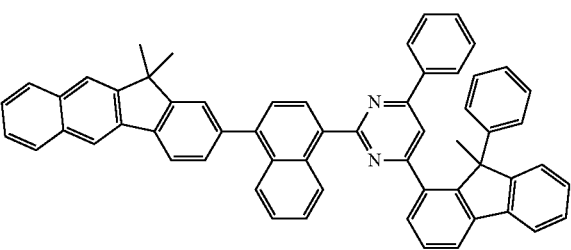 |
| 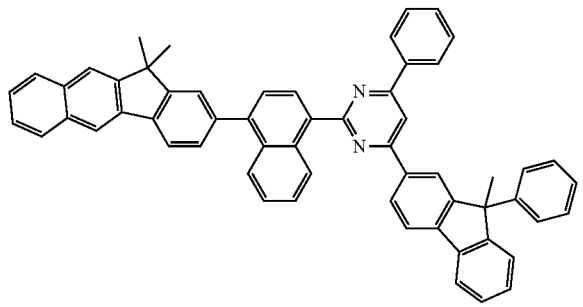 | 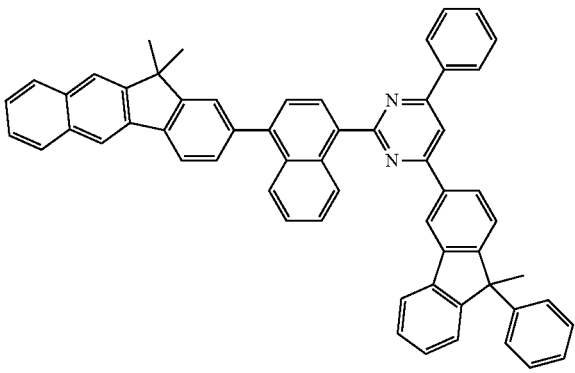 |
| 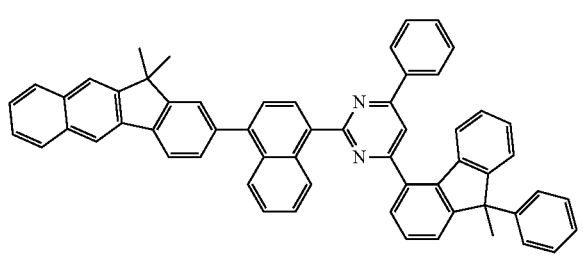 | 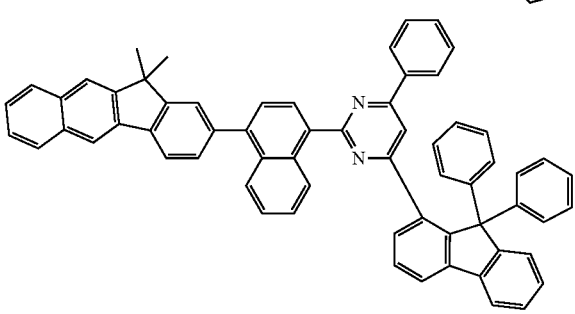 |

871 872
-continued
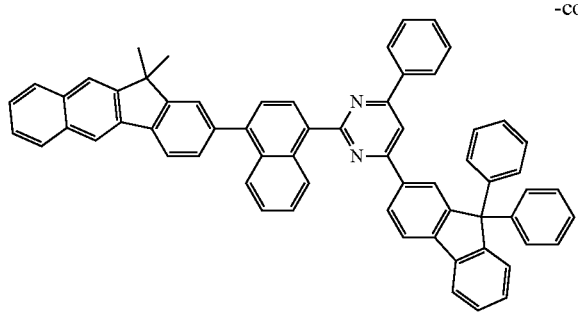
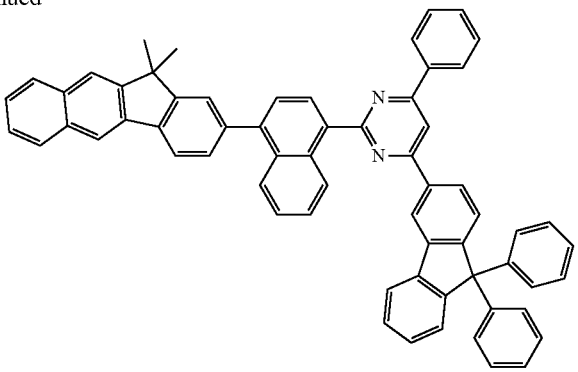
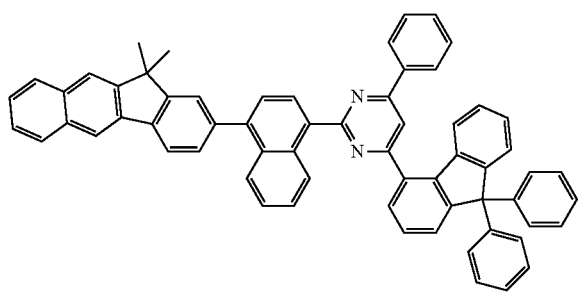
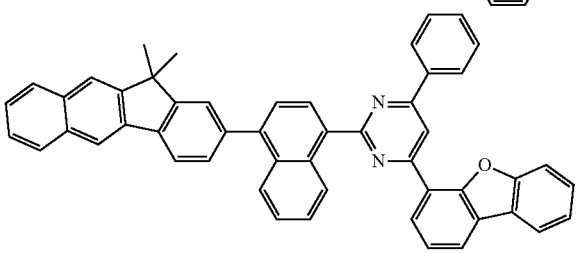
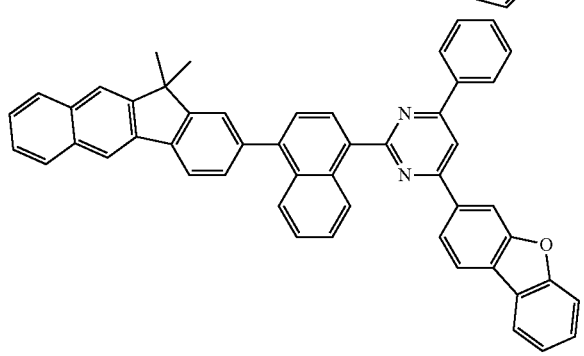
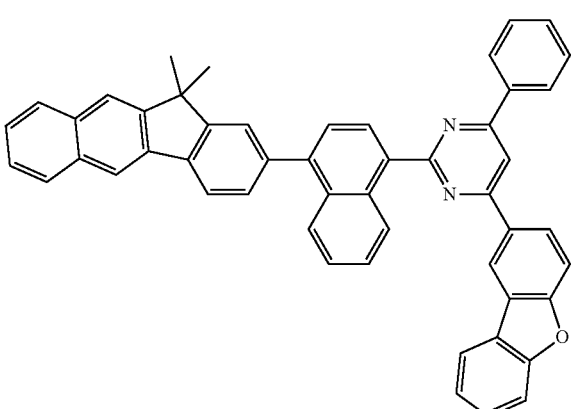
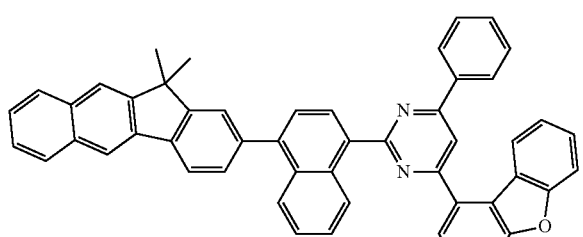
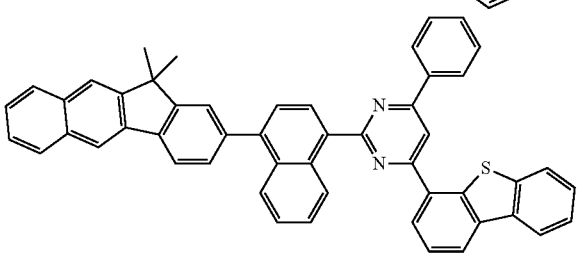
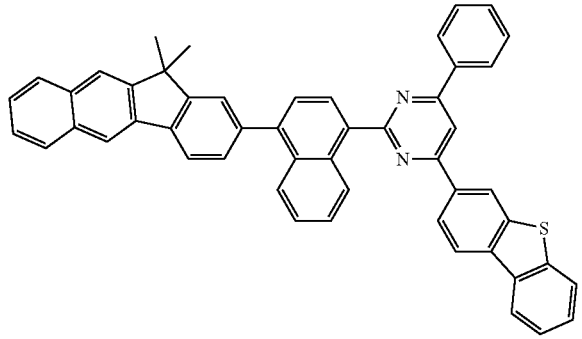
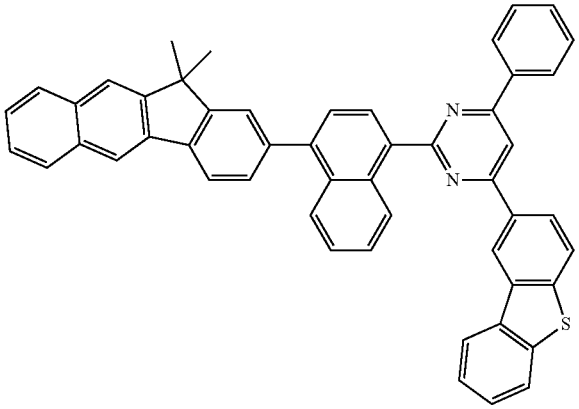

873 874
-continued
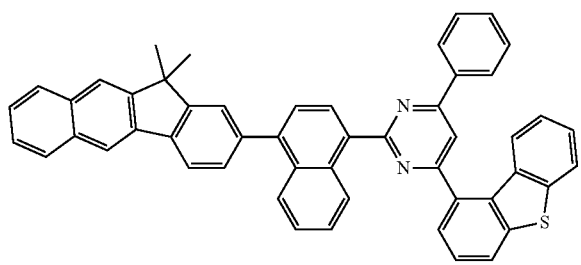
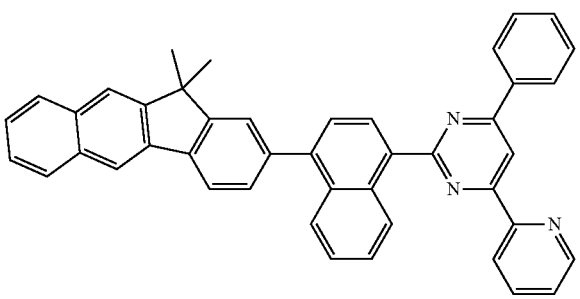
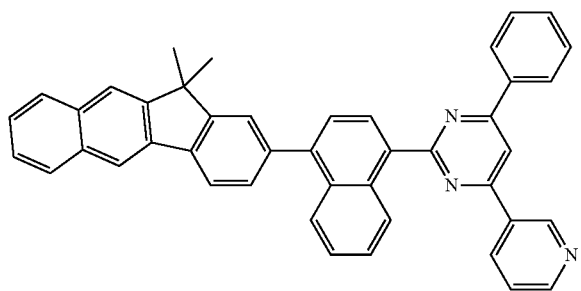
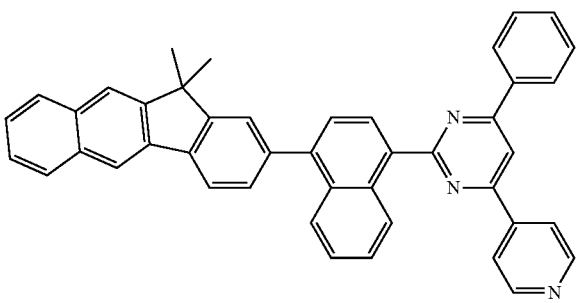
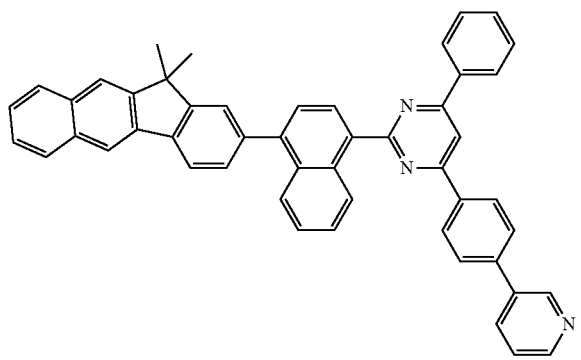
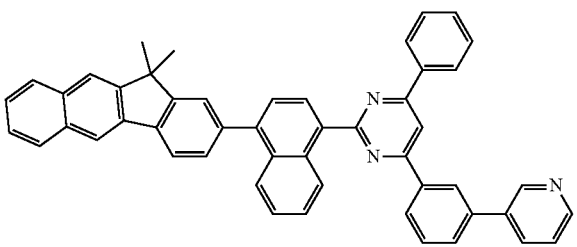
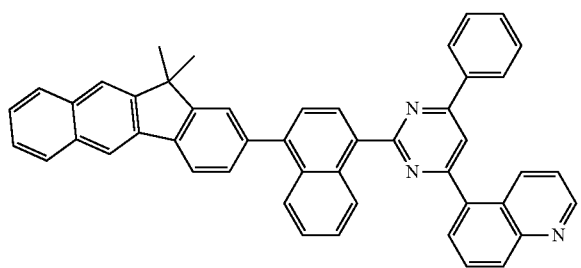
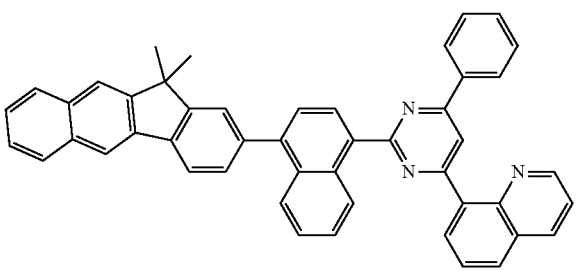
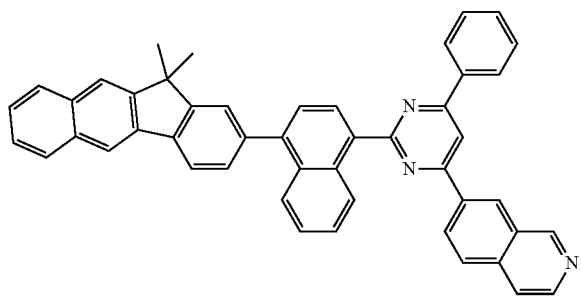
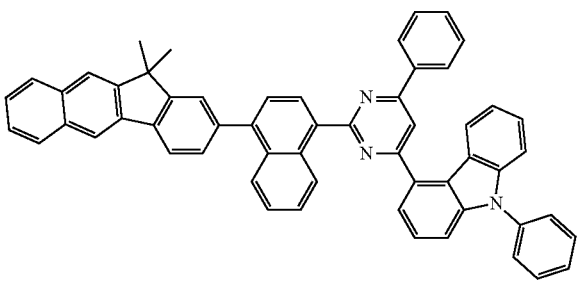

-continued
| 875 | 876 |
|---|---|
| 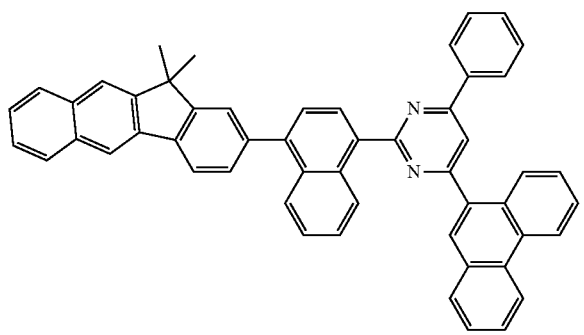 | 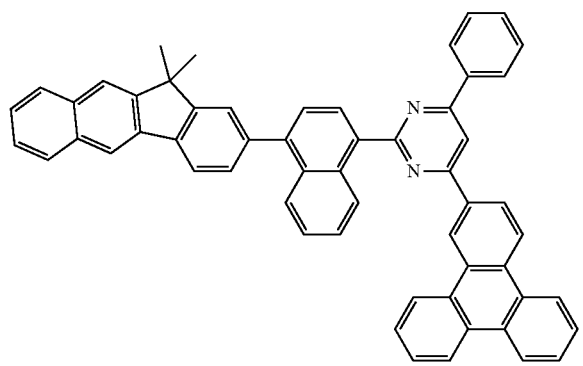 |
| 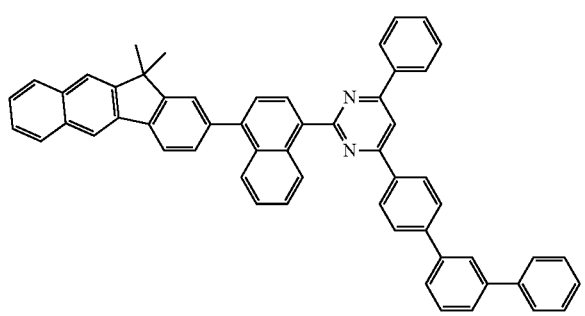 | 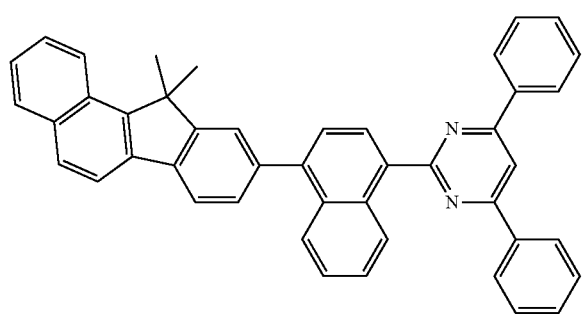 |
| 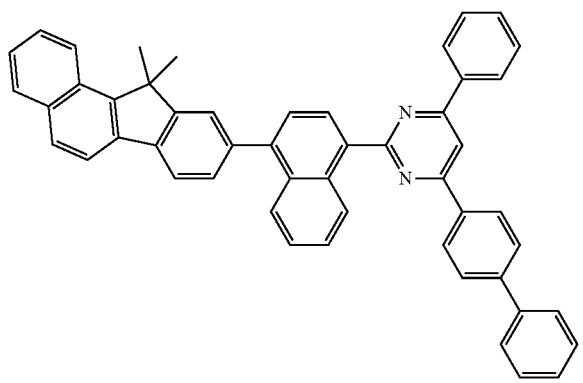 | 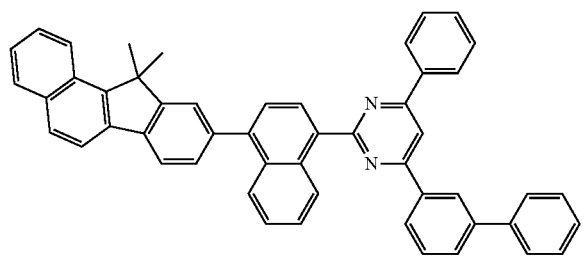 |
| 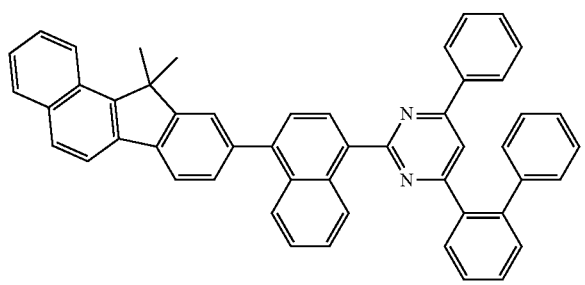 | 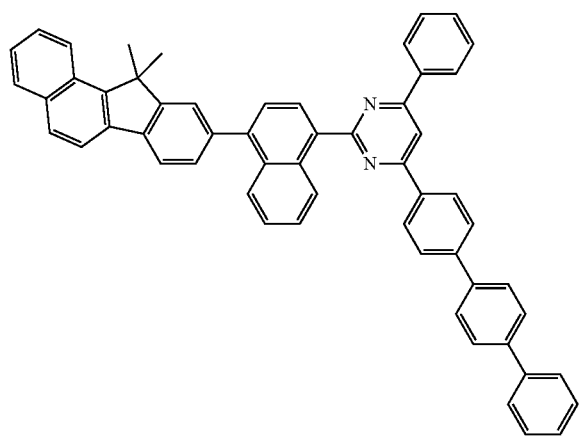 |

877
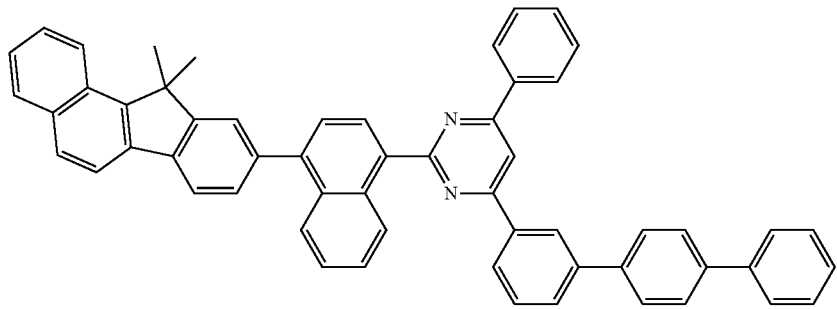
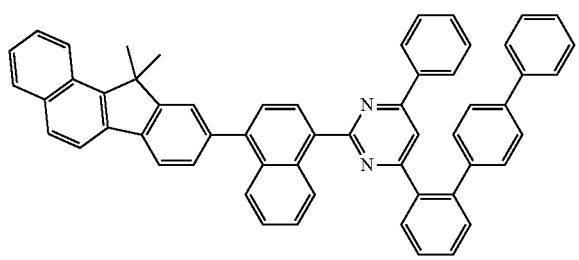
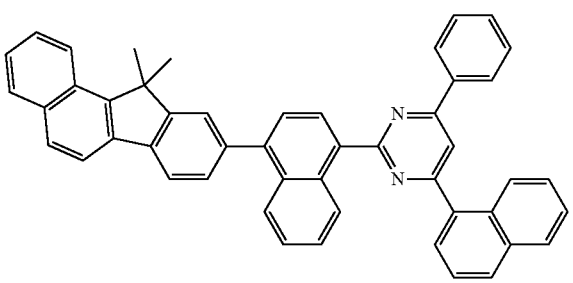
878
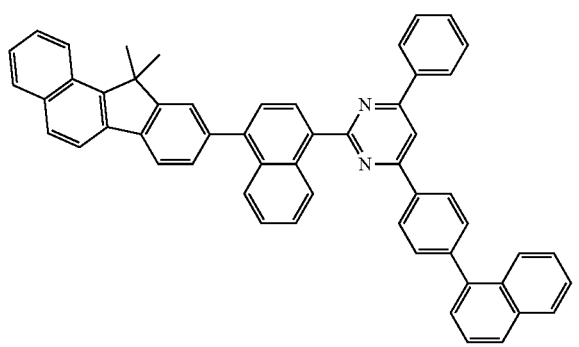
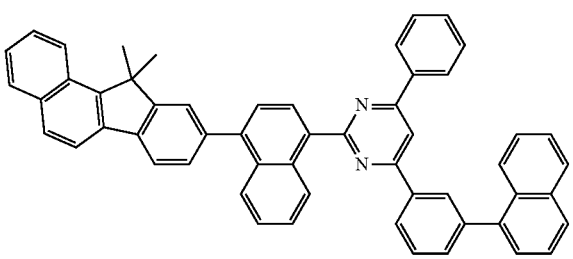
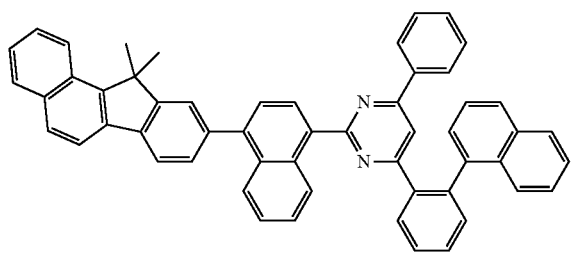
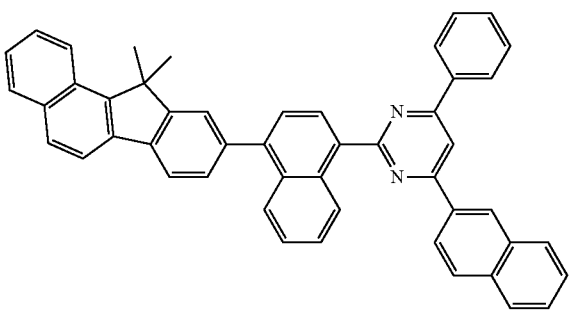
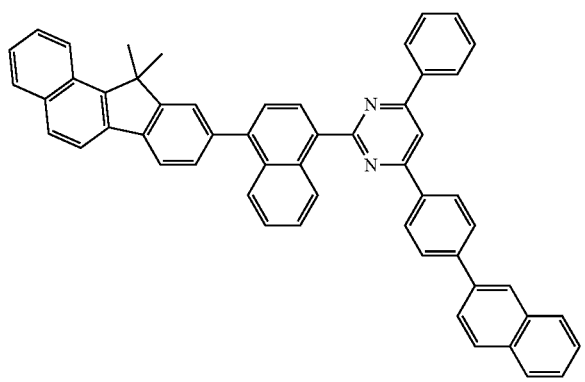
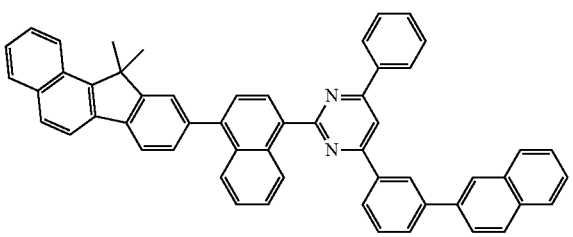

-continued
| 879 | 880 |
|---|---|
| 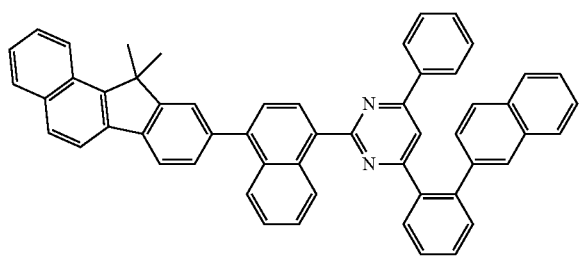 | 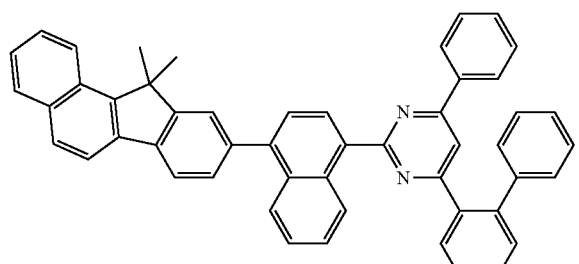 |
| 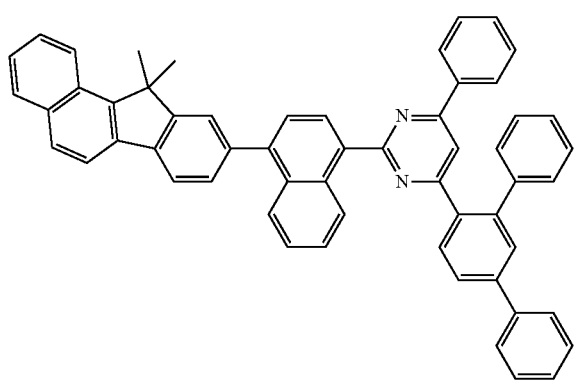 | 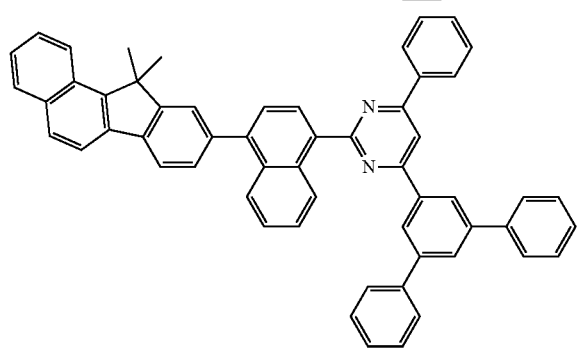 |
| 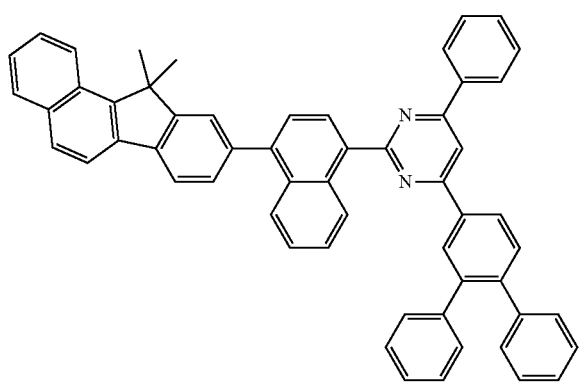 | 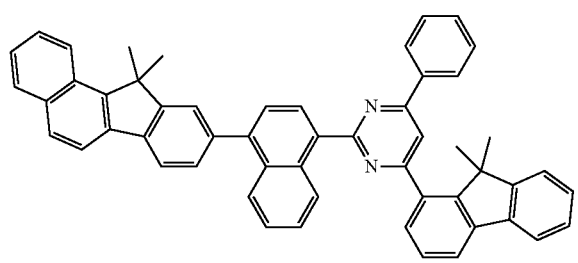 |
| 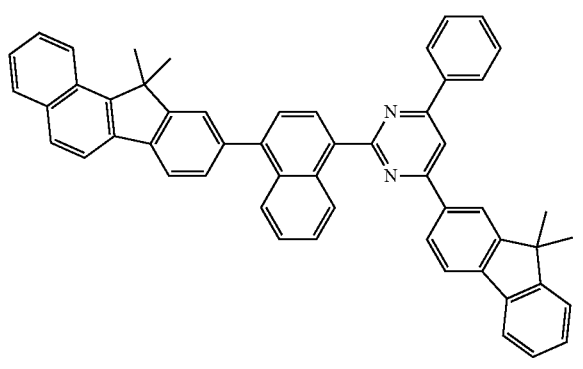 | 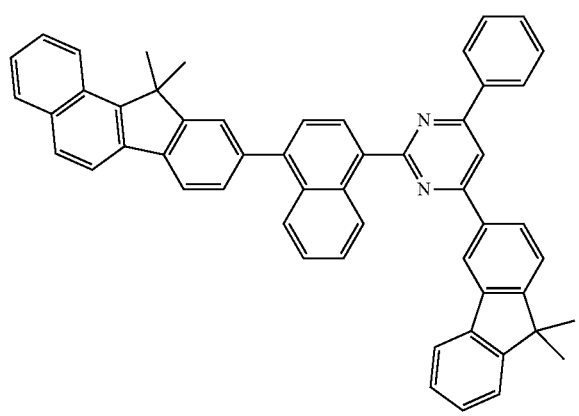 |

881 882
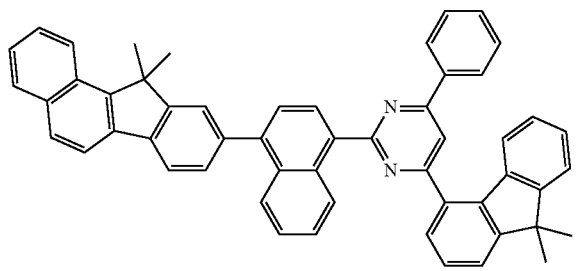
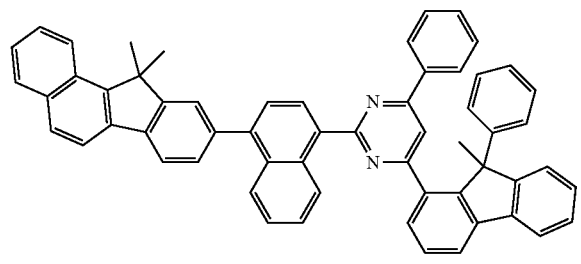
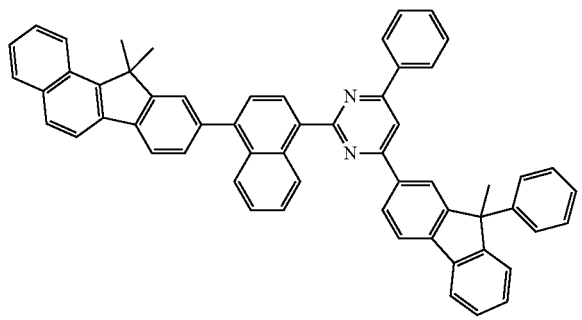
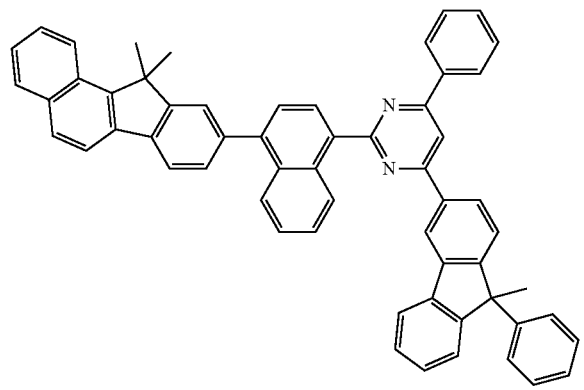
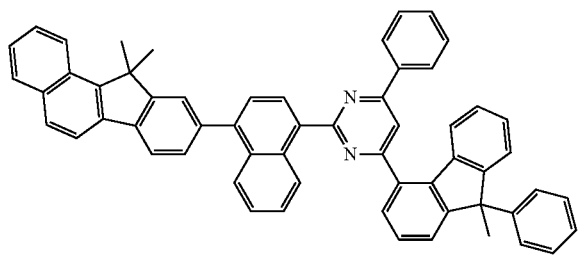
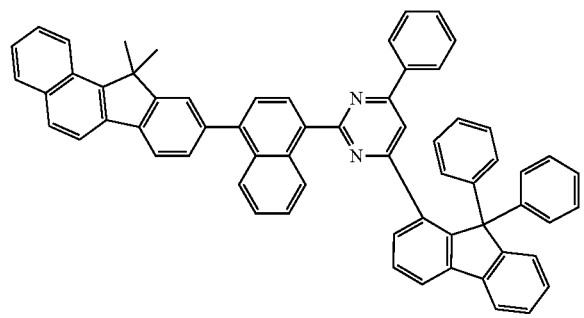
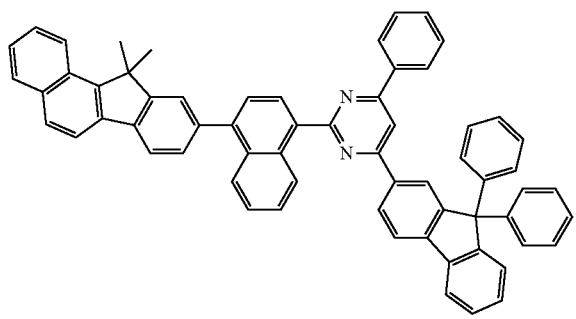
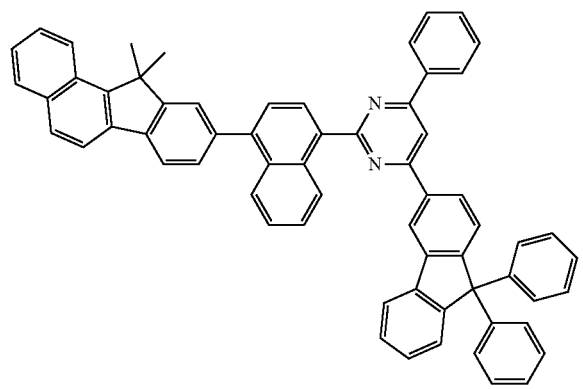
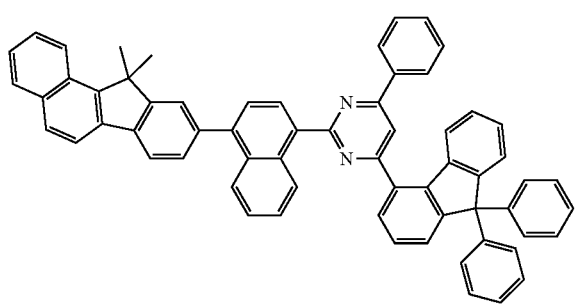
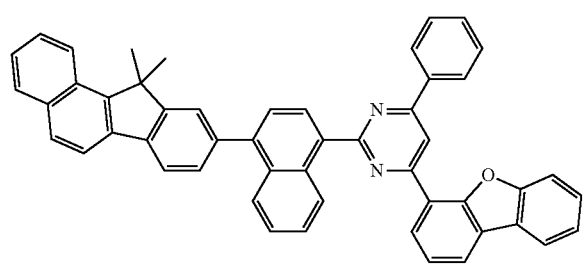

-continued
| 883 | 884 |
|---|---|
| 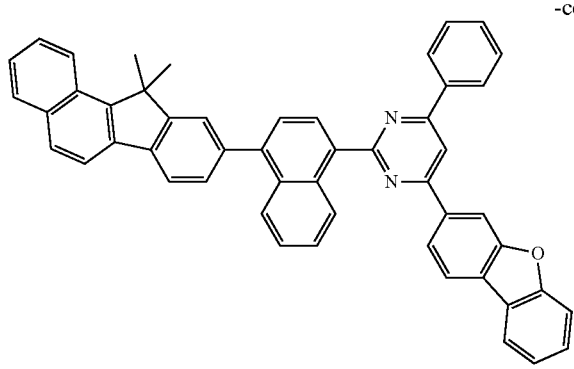 | 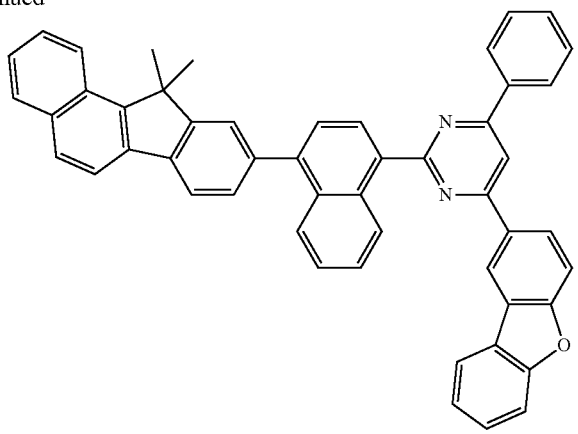 |
| 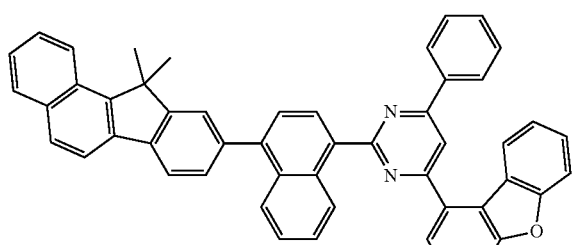 | 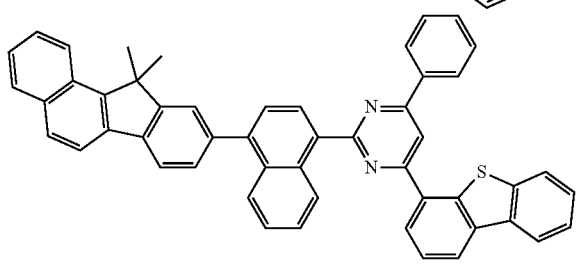 |
| 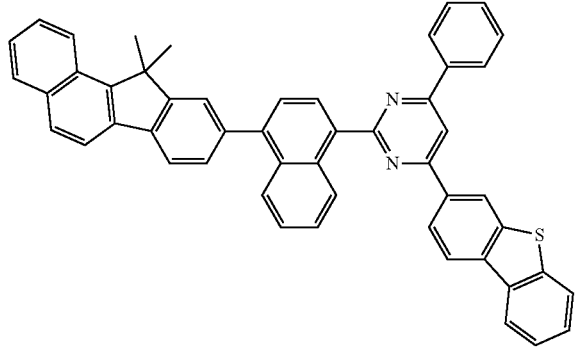 | 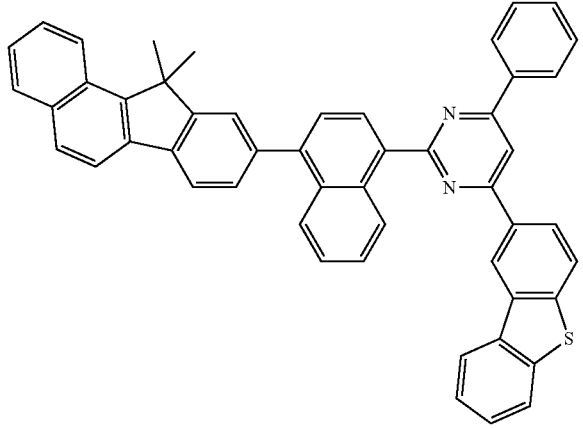 |
| 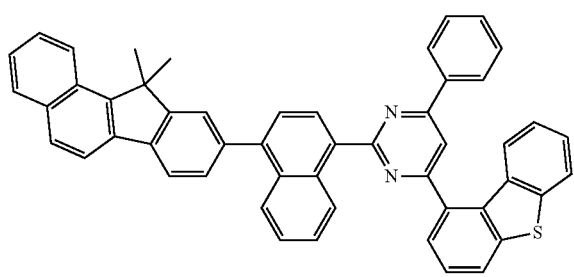 | 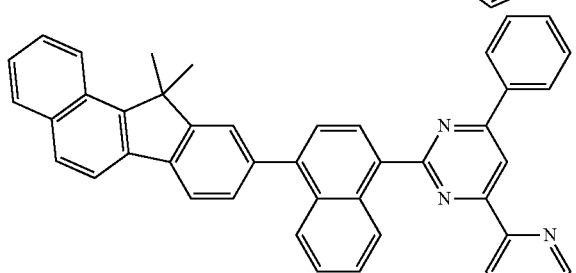 |
| 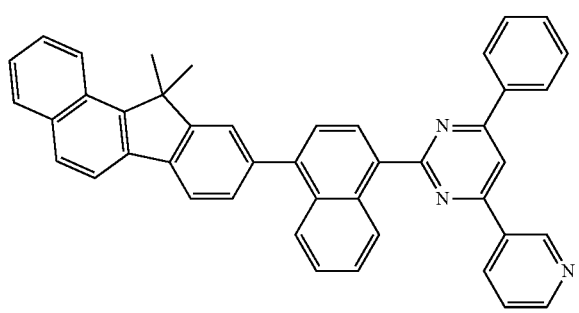 | 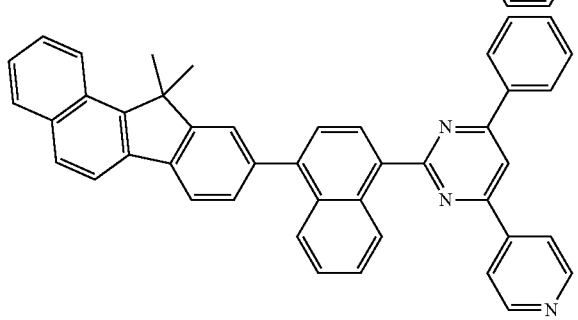 |

-continued
885
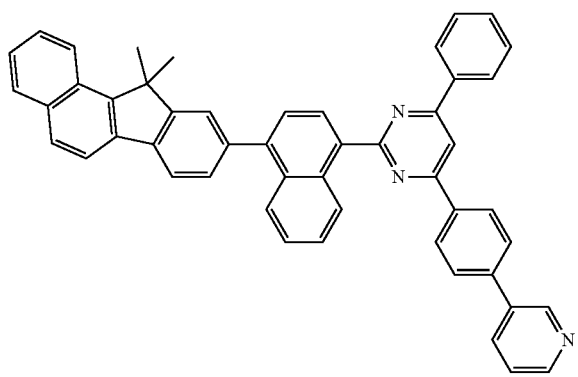
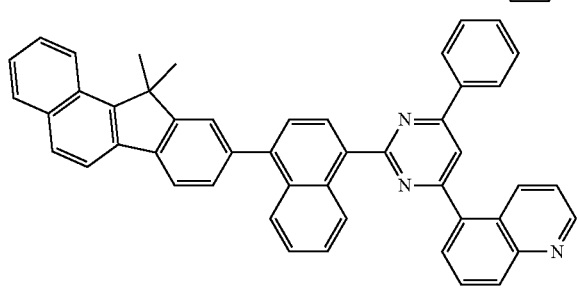
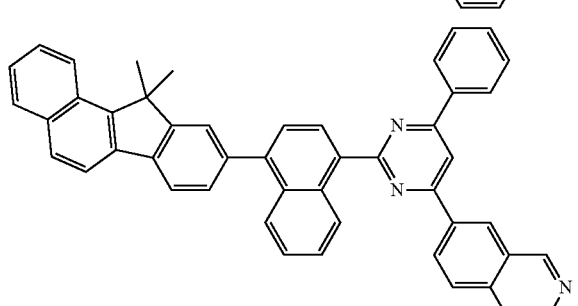
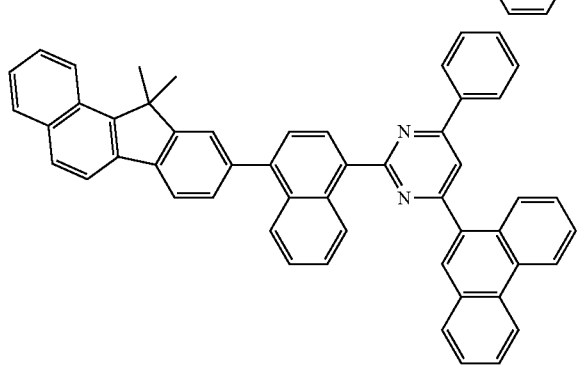
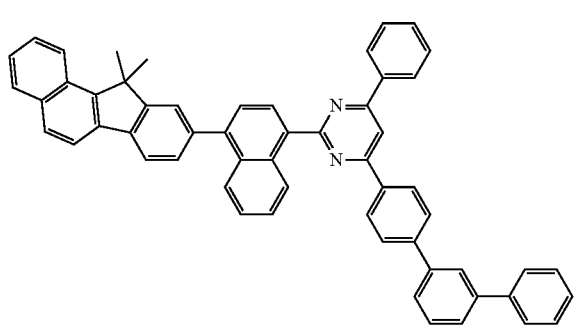
886
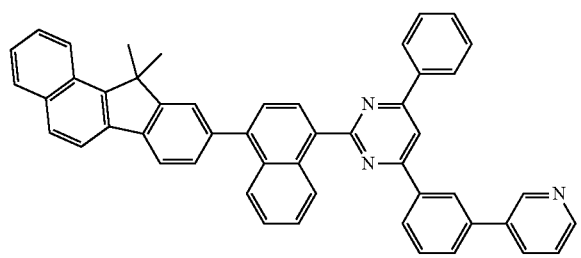
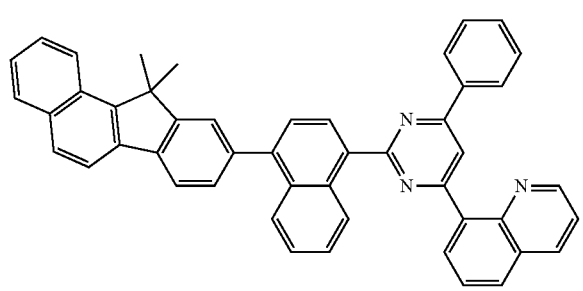
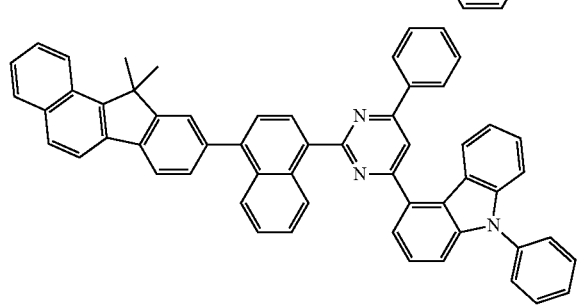
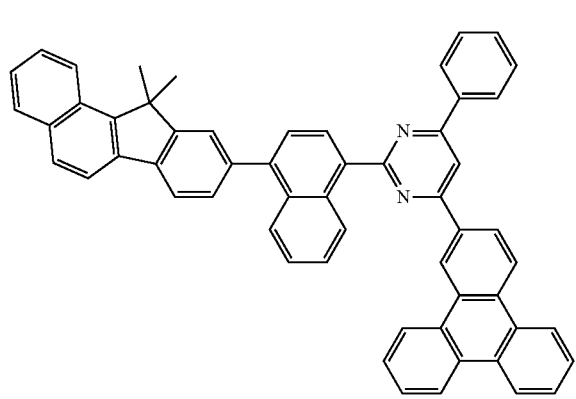
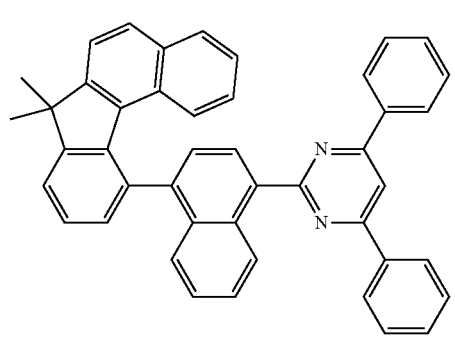

| 887 | 888 |
|---|---|
| 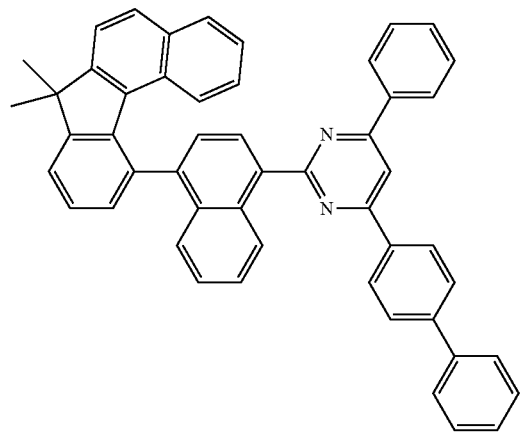 | 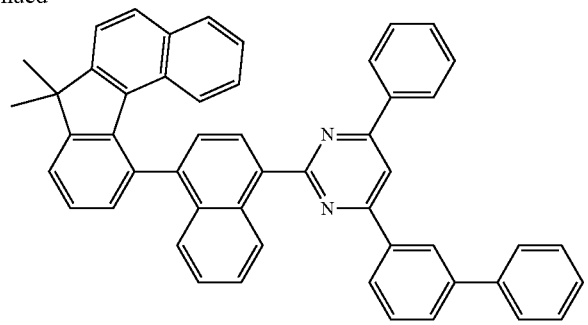 |
| 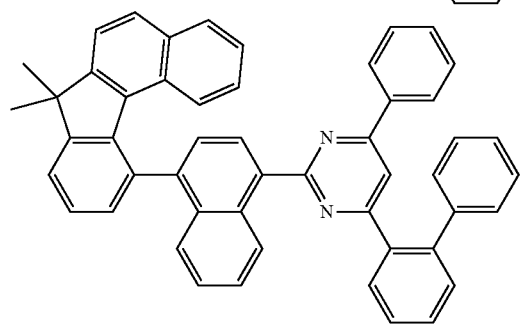 | 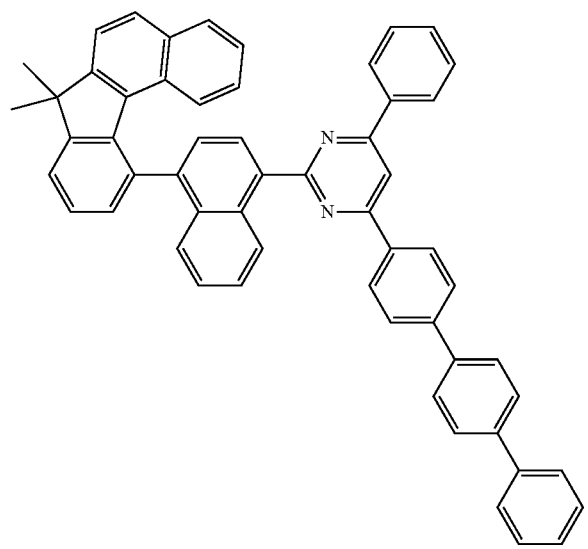 |
| 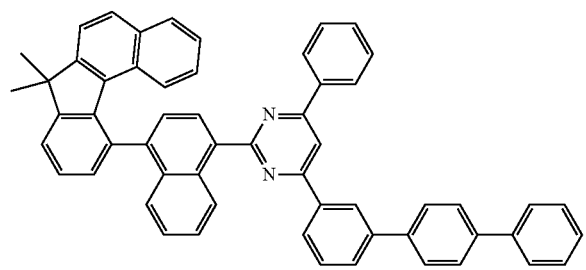 | 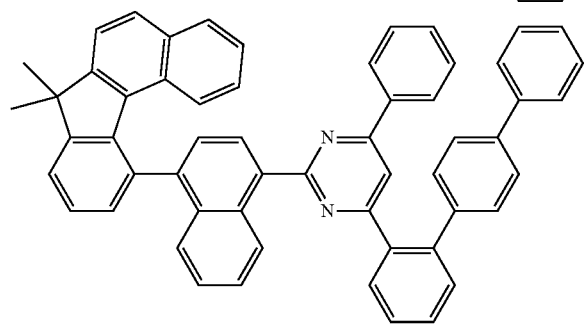 |
| 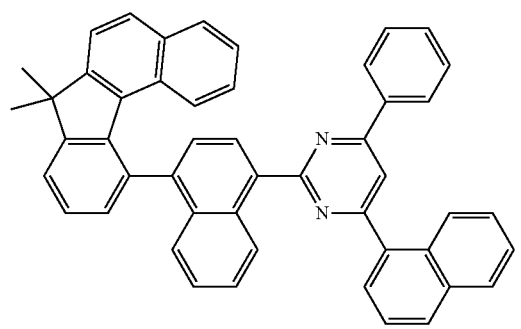 | 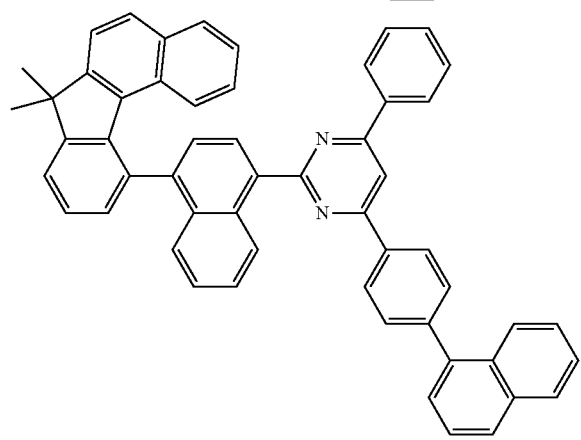 |

889
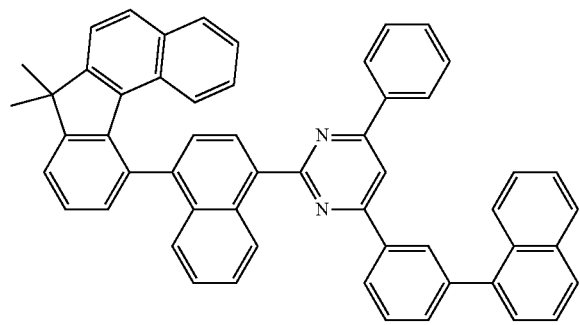
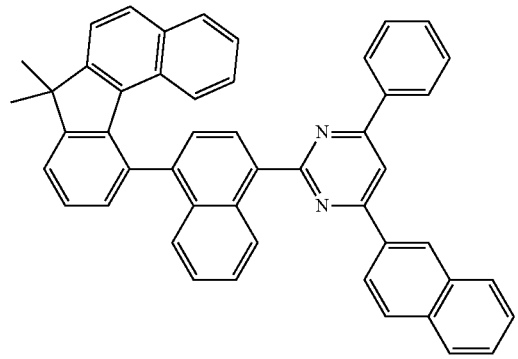
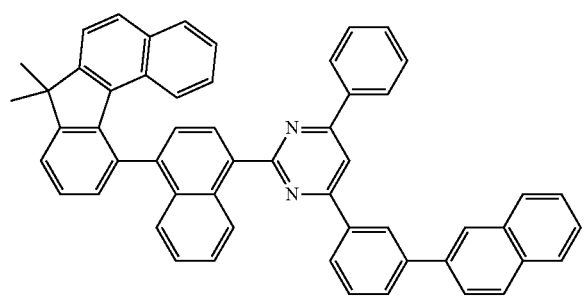
890
-continued
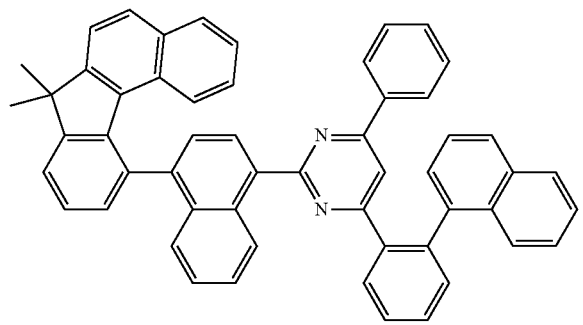
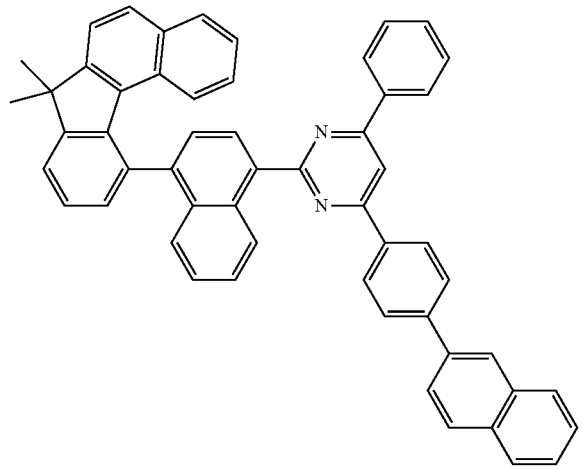
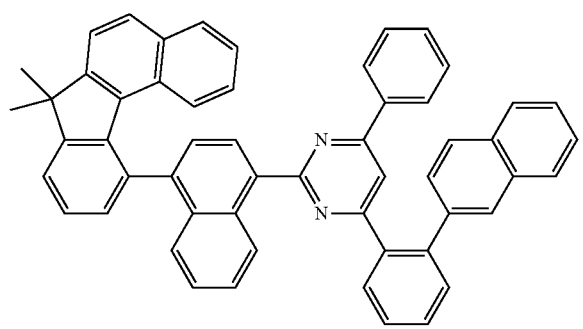
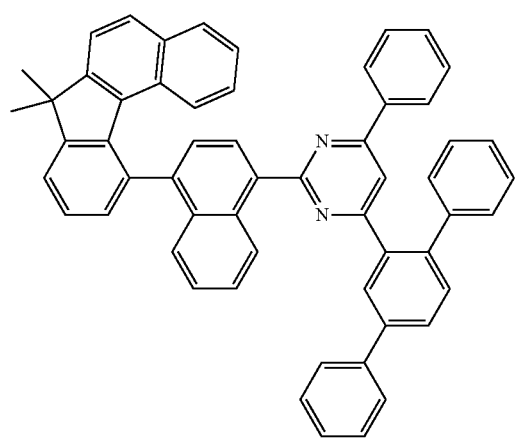
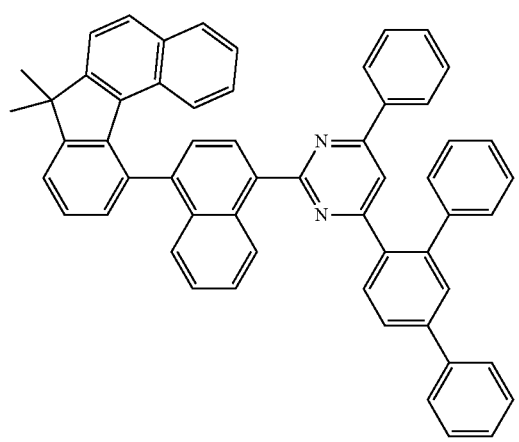

-continued
891 892
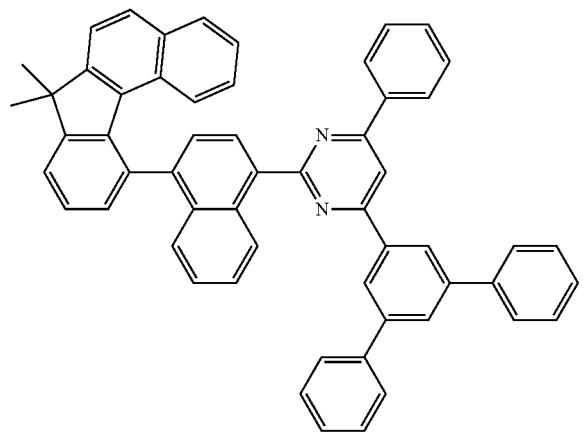
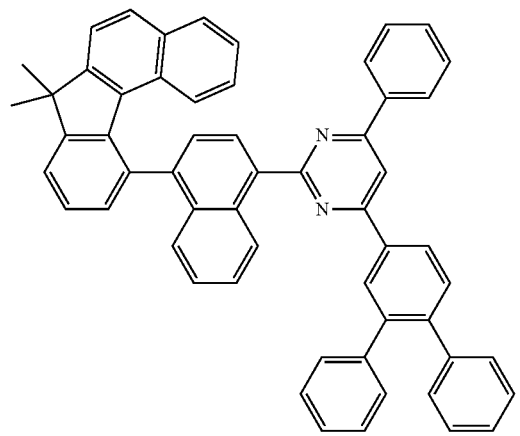
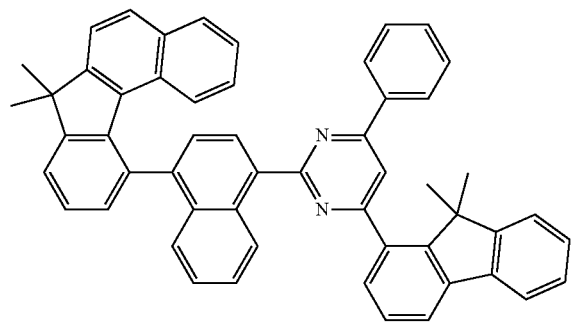
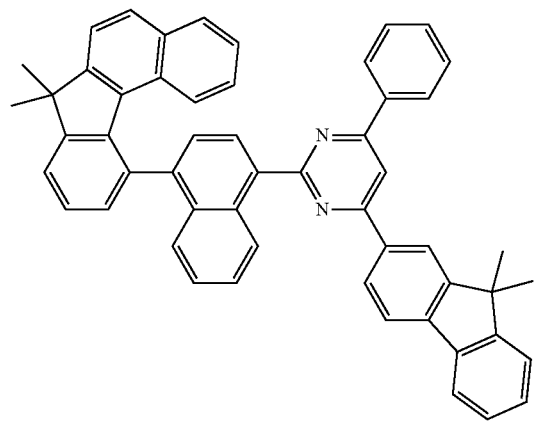
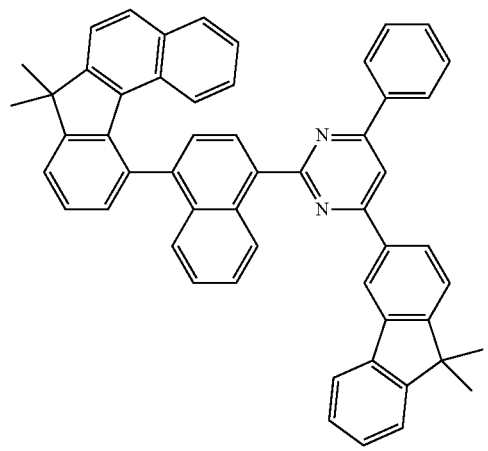
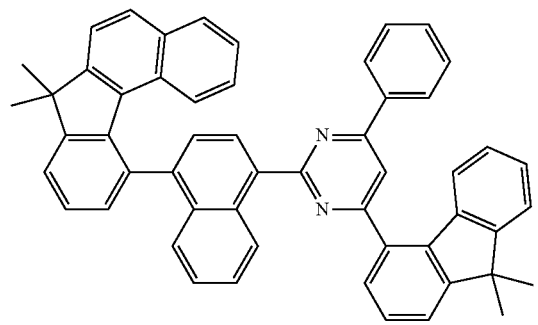
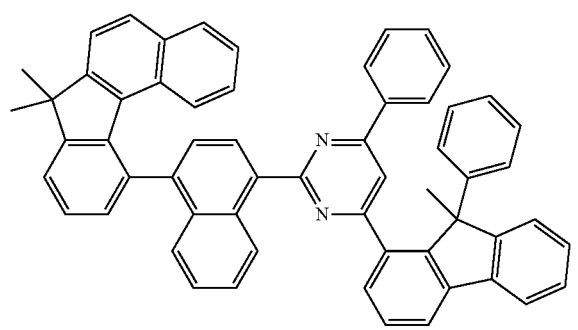
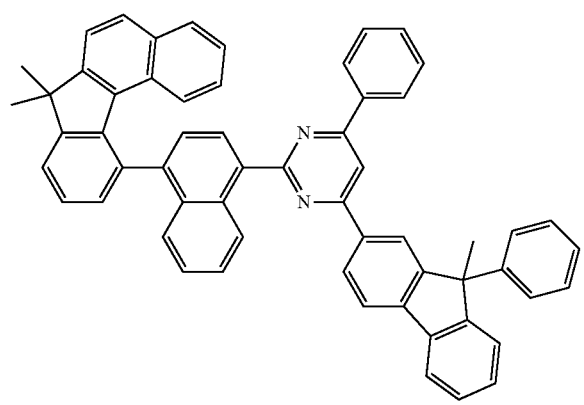

-continued
| 893 | 894 |
|---|---|
| 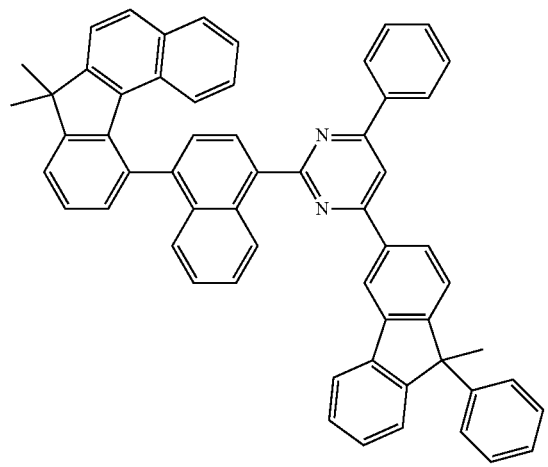 | 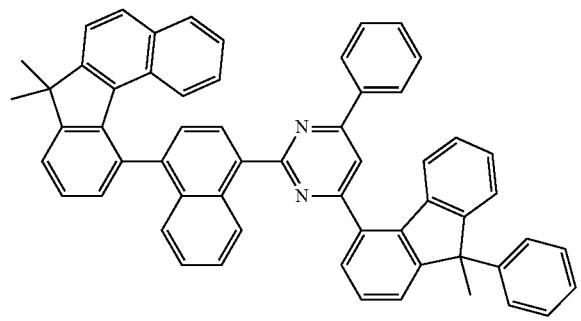 |
| 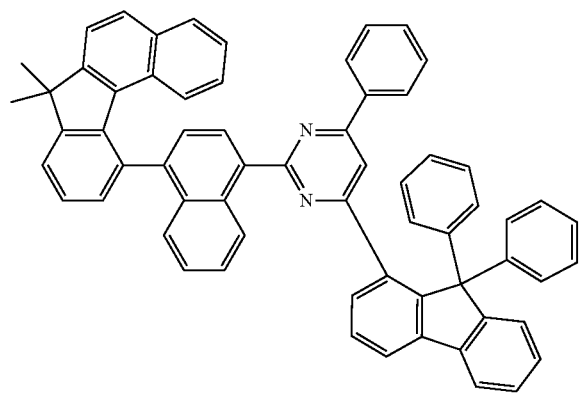 | 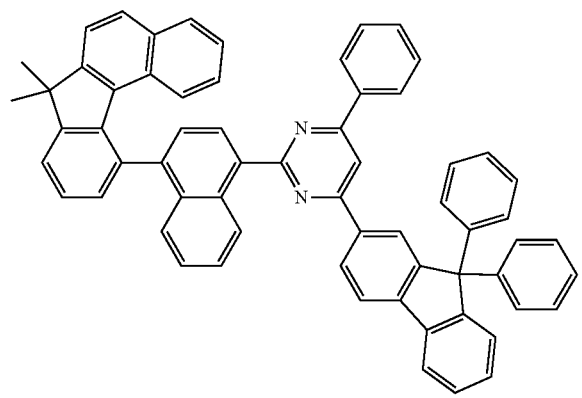 |
| 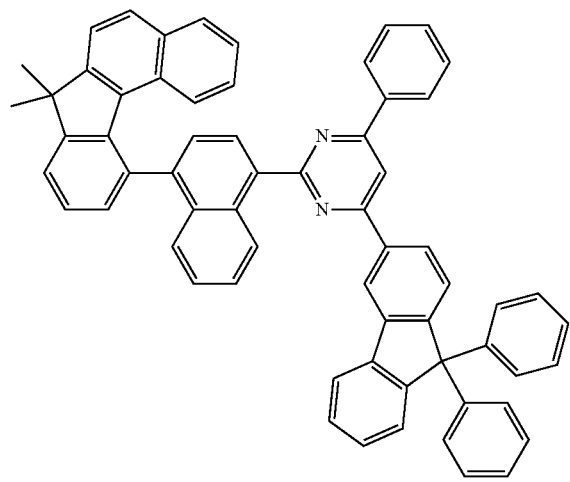 | 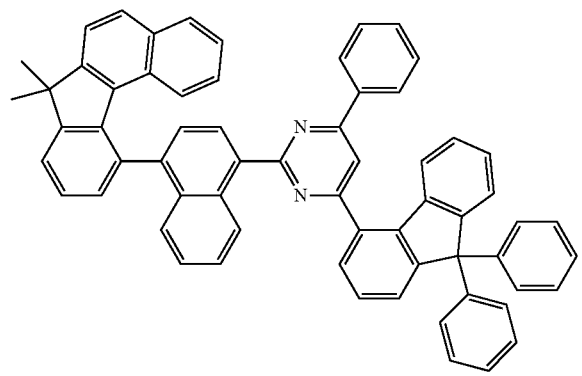 |

-continued
| 895 | 896 |
|---|---|
| 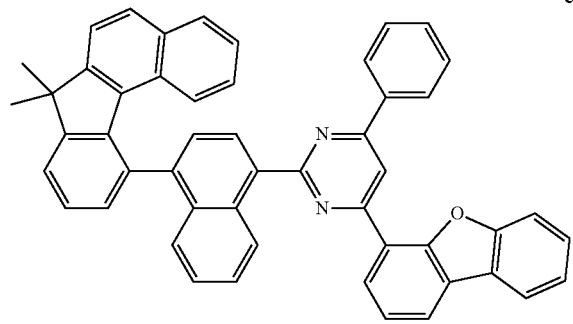 | 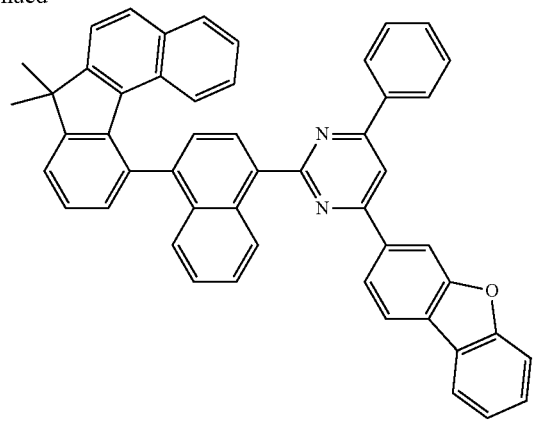 |
| 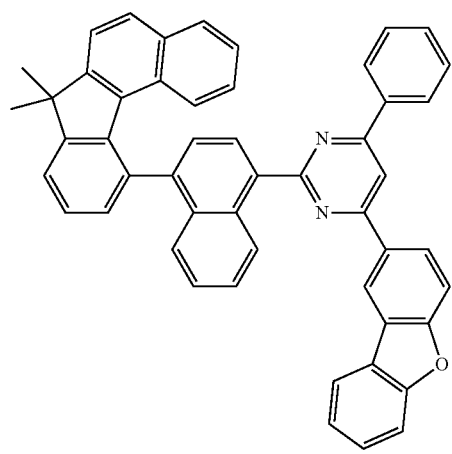 | 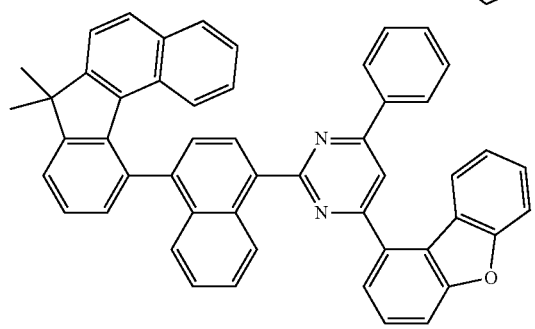 |
| 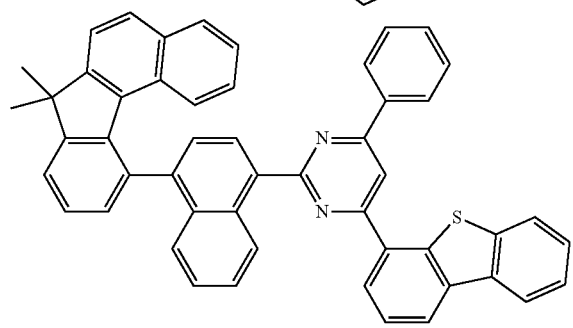 | 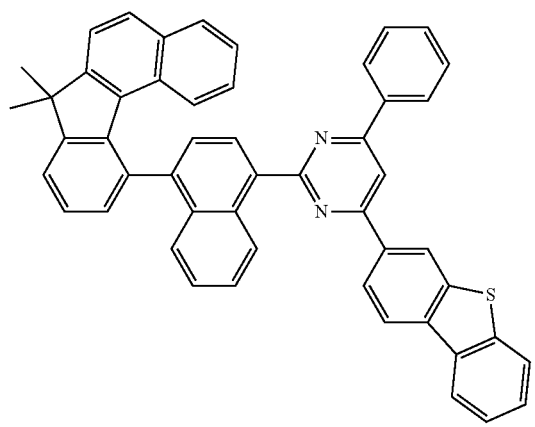 |
| 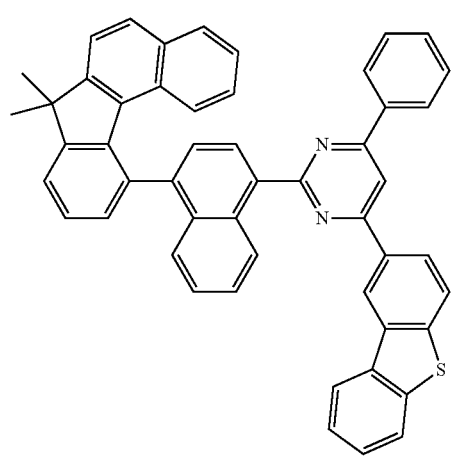 | 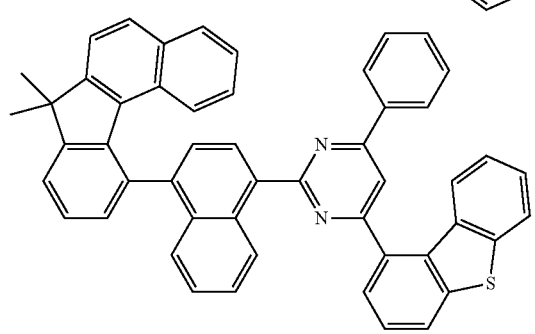 |

-continued
897 898
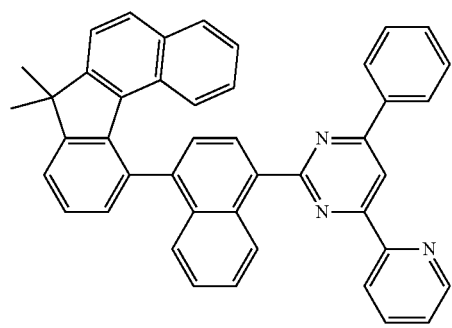 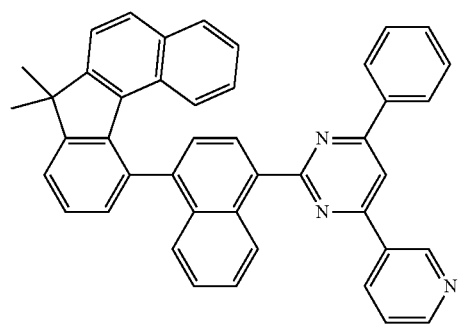
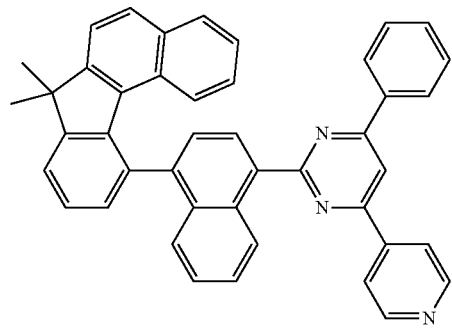 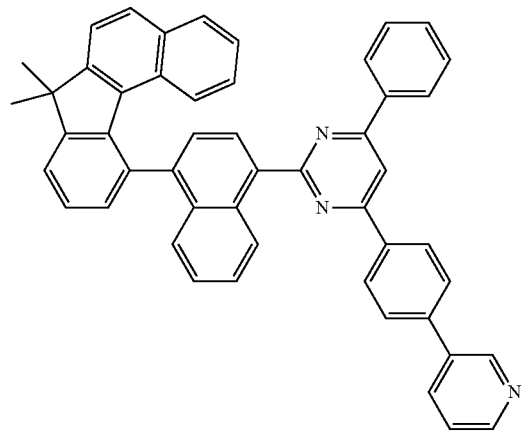
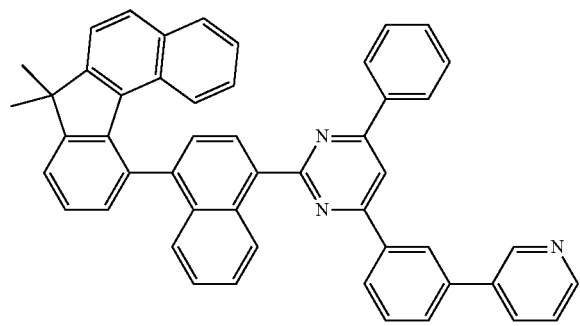 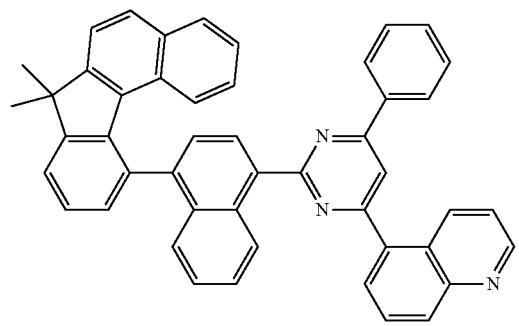
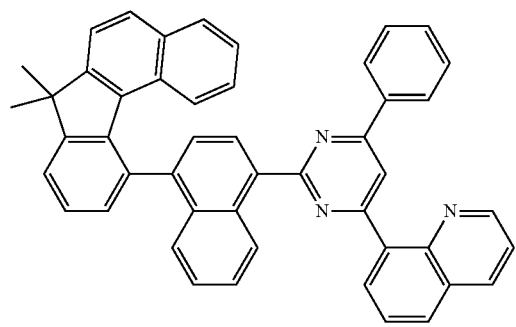 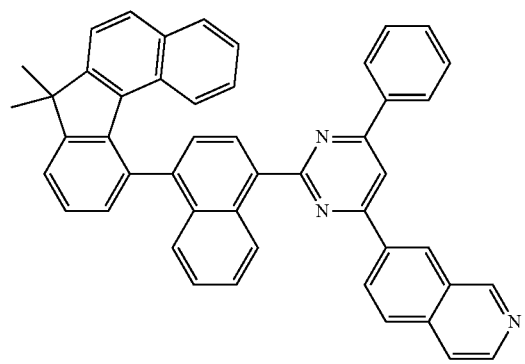

-continued
| 899 | 900 |
|---|---|
| 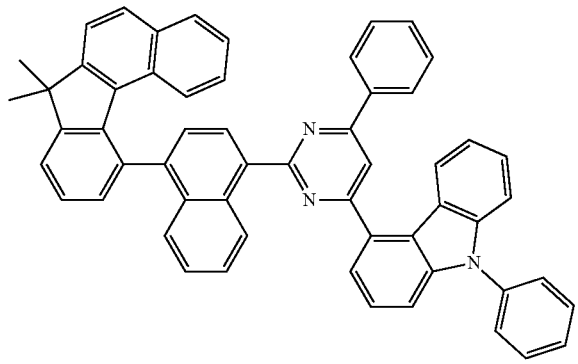 | 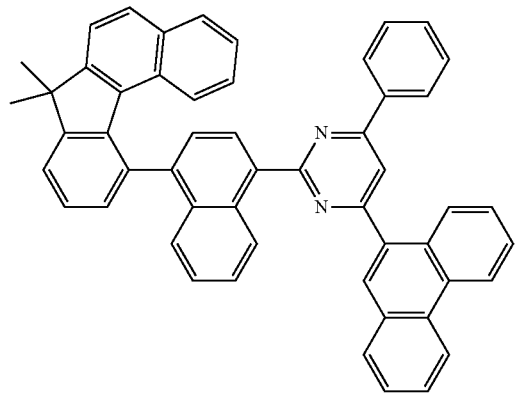 |
| 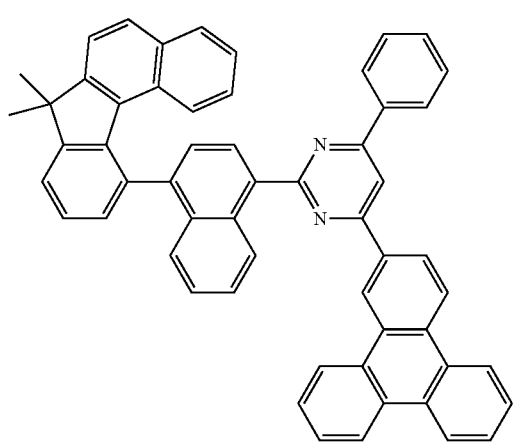 | 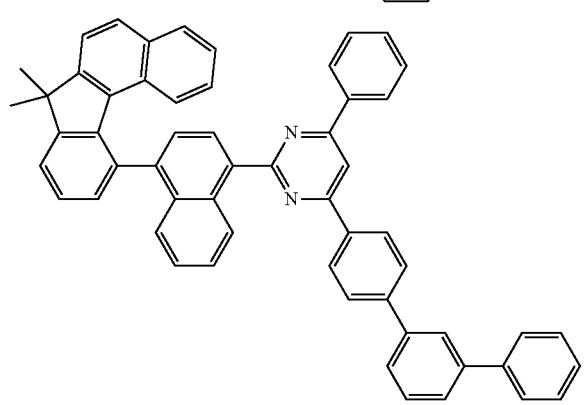 |
| 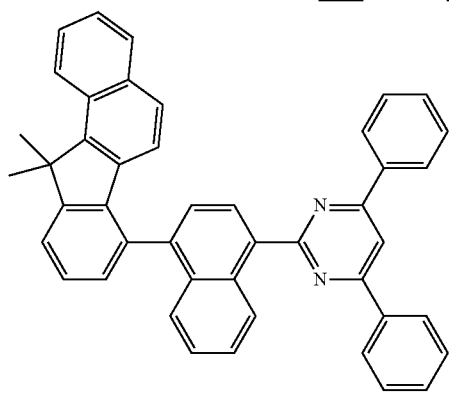 | 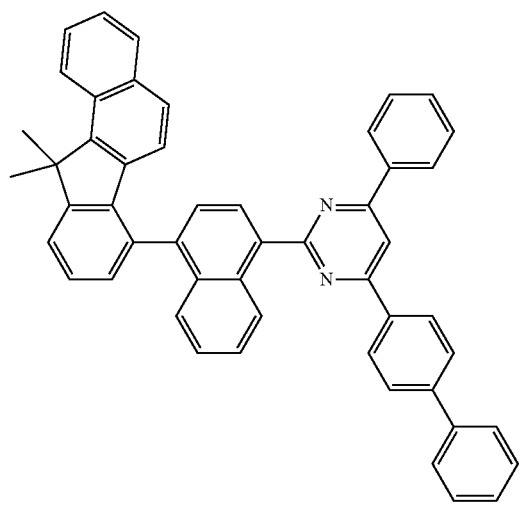 |
| 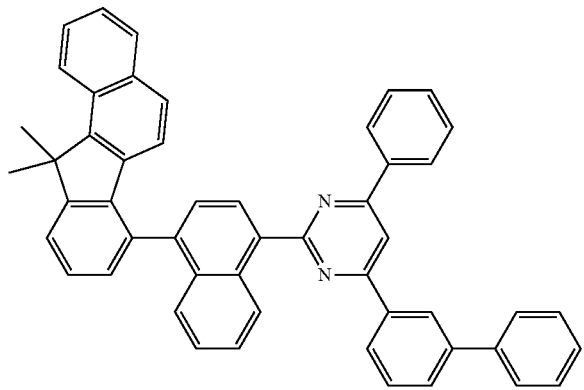 | 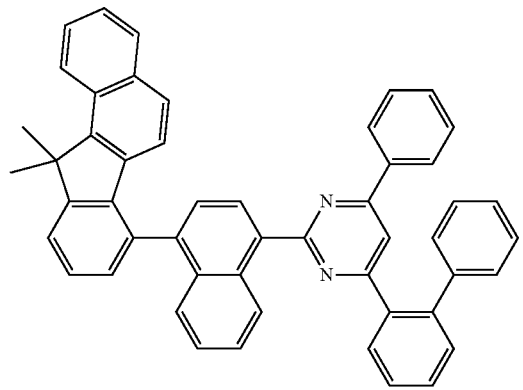 |

-continued
| 901 | 902 |
|---|---|
| 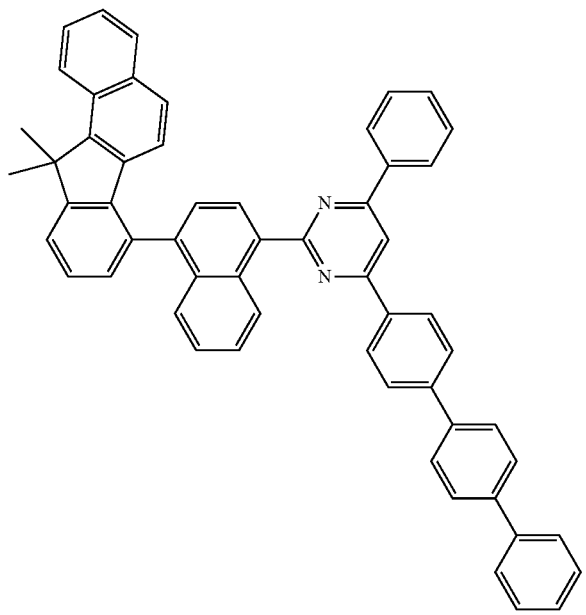 | 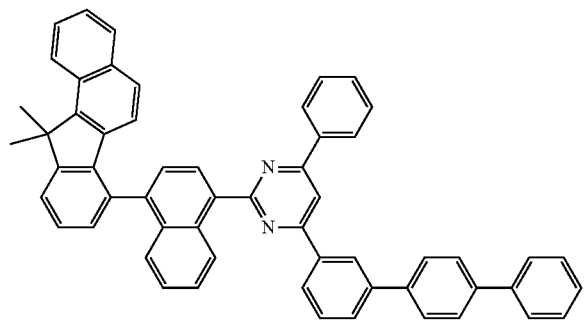 |
| 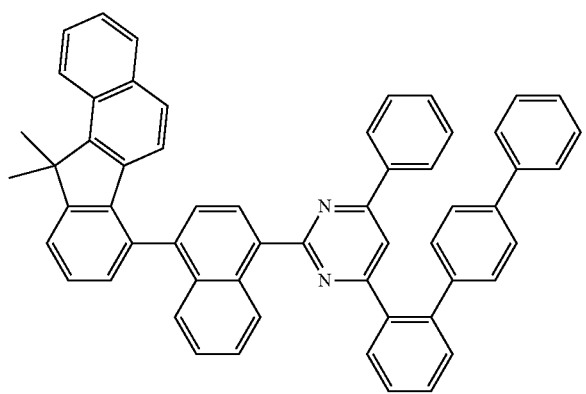 | 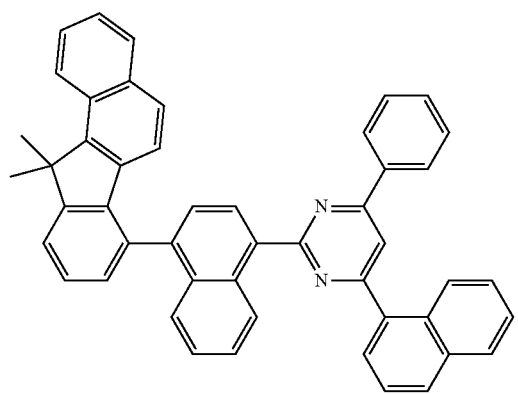 |
| 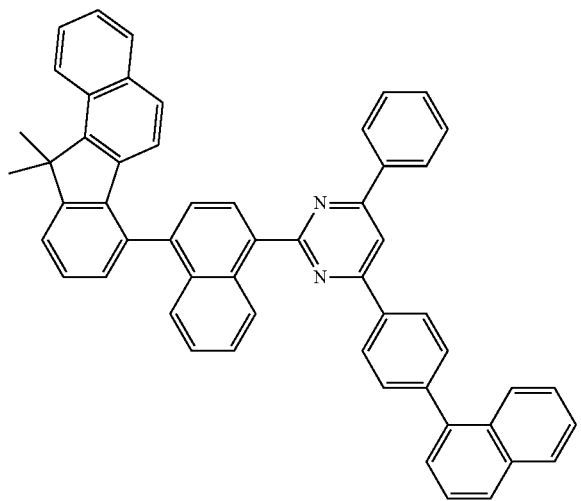 | 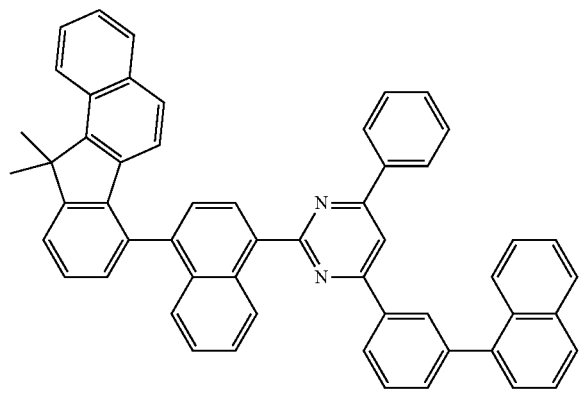 |

-continued
| 903 | 904 |
|---|---|
| 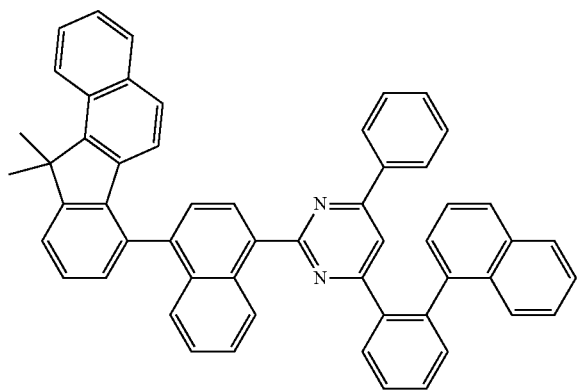 | 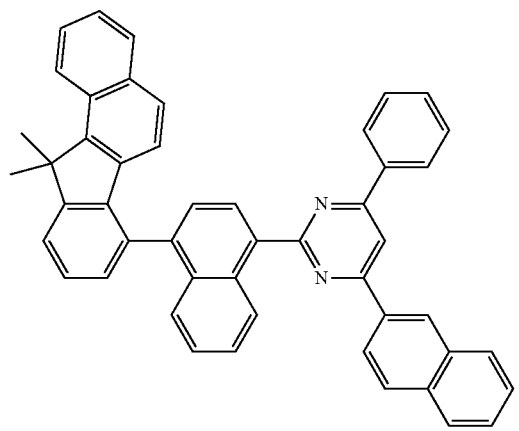 |
| 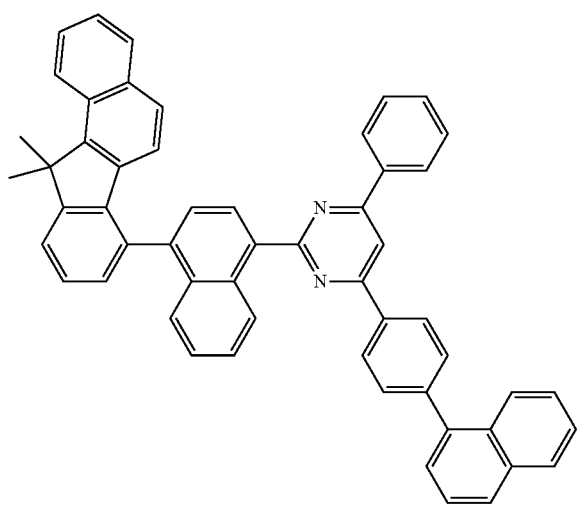 | 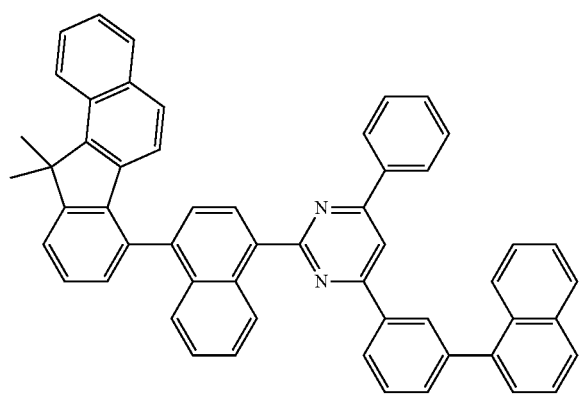 |
| 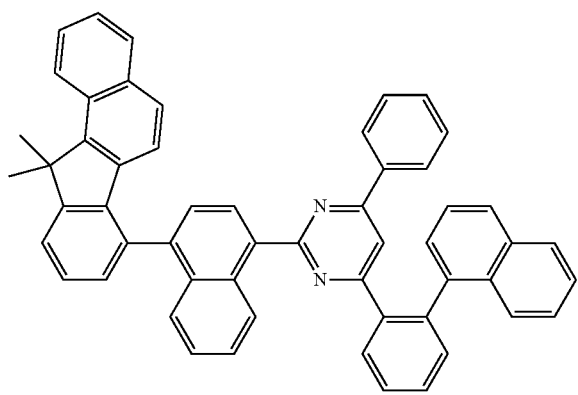 | 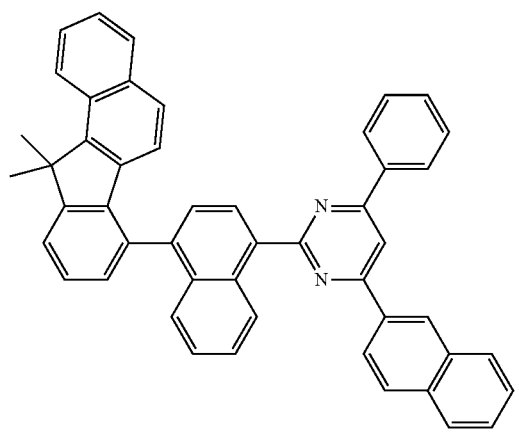 |

905 906
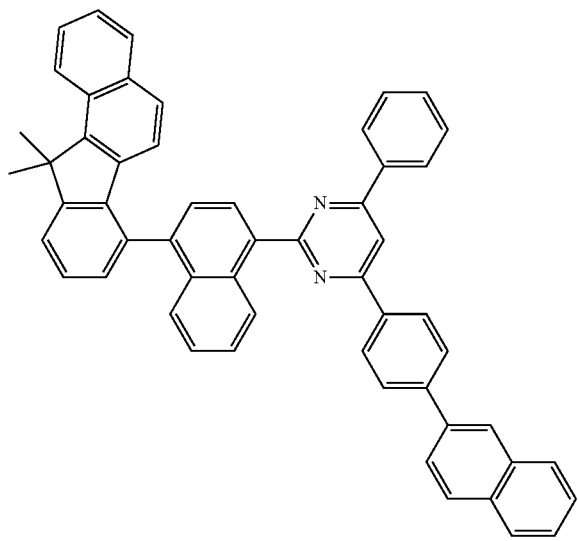
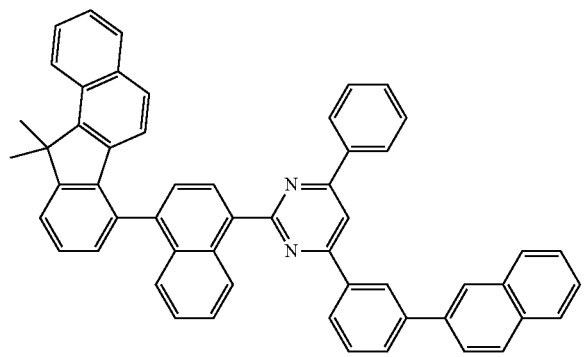
-continued
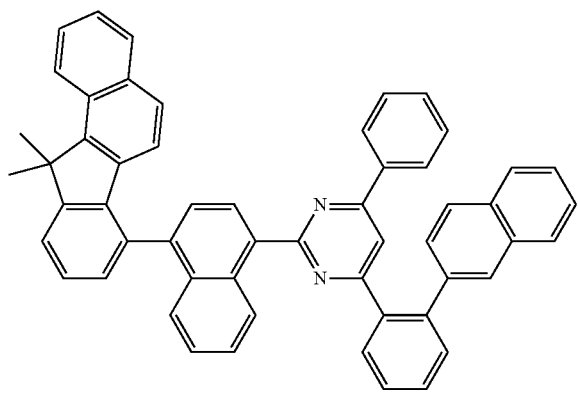
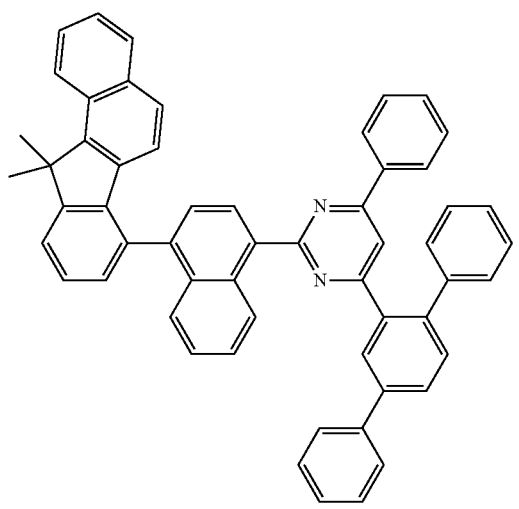
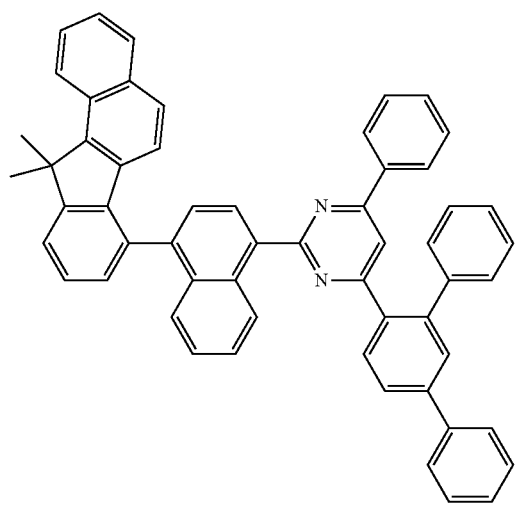

-continued
| 907 | 908 |
|---|---|
| 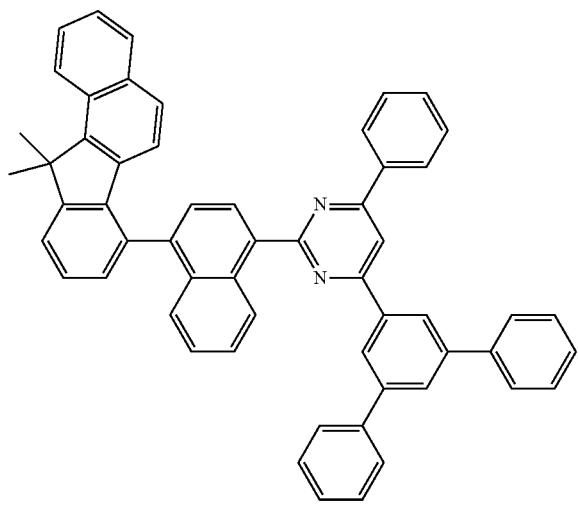 | 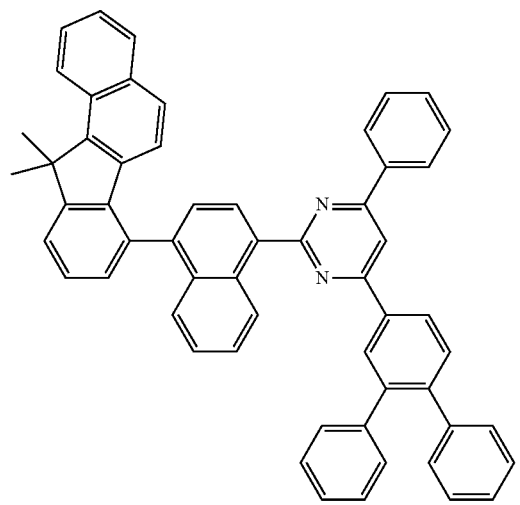 |
| 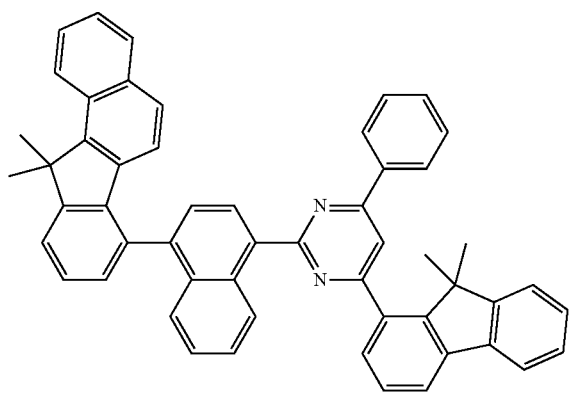 | 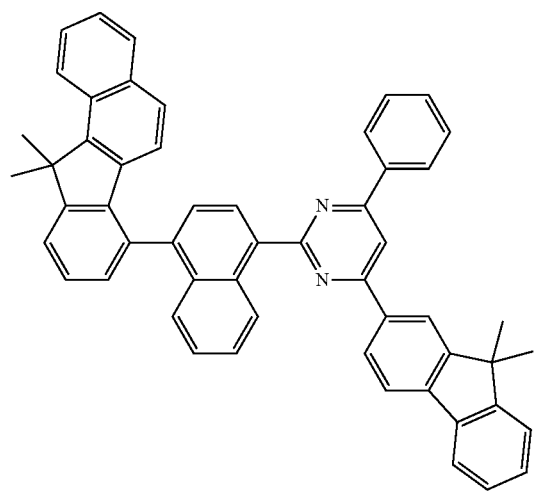 |
| 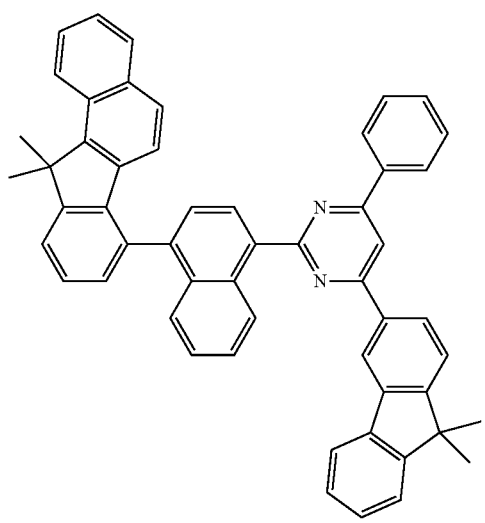 | 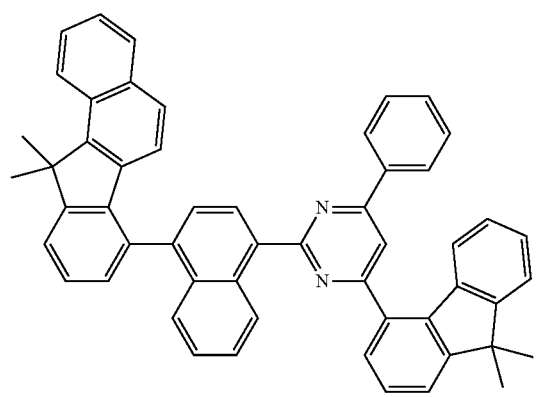 |

-continued
| 909 | 910 |
|---|---|
| 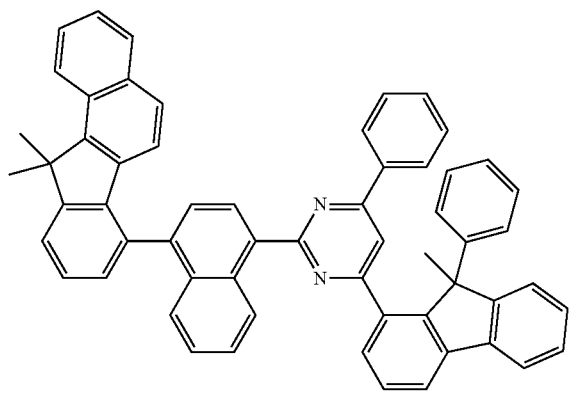 | 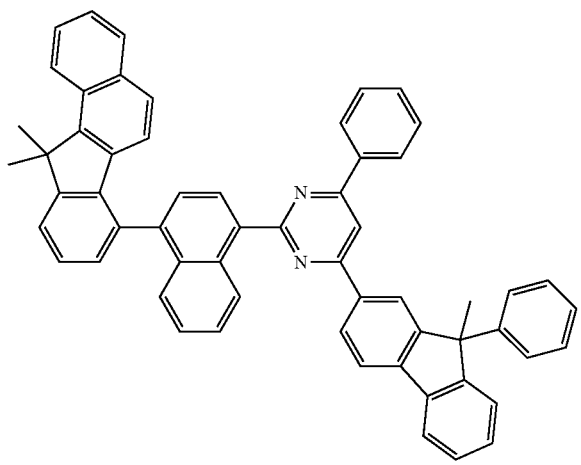 |
| 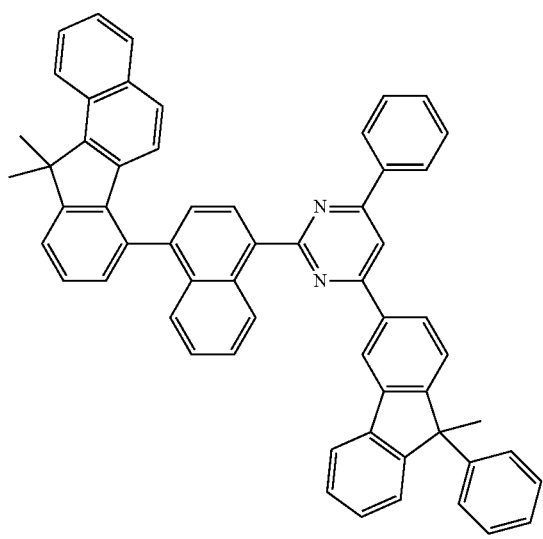 | 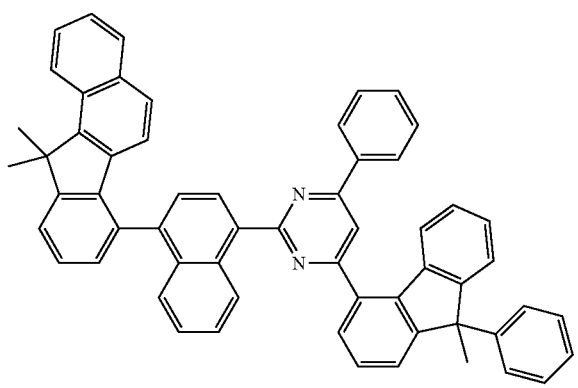 |
| 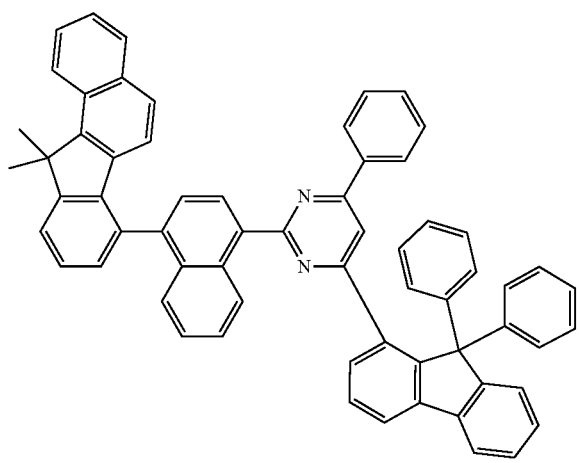 | 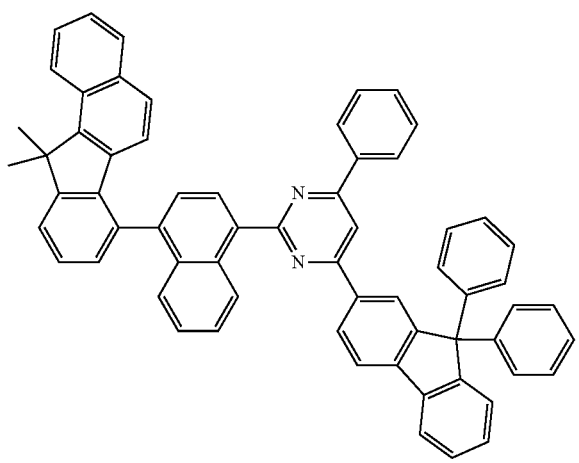 |

-continued
| 911 | 912 |
|---|---|
| 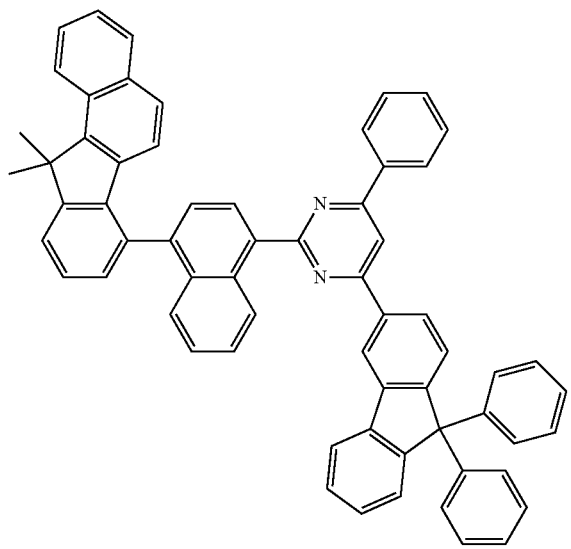 | 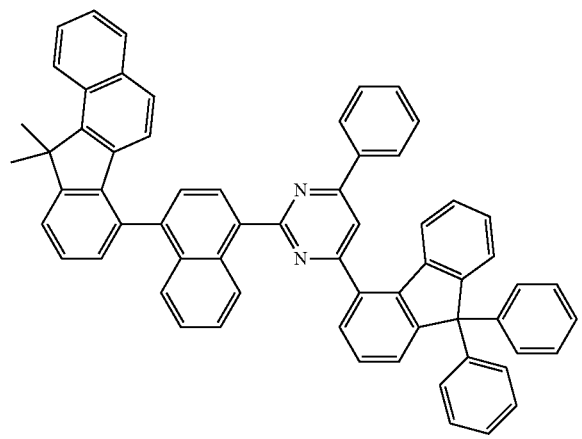 |
| 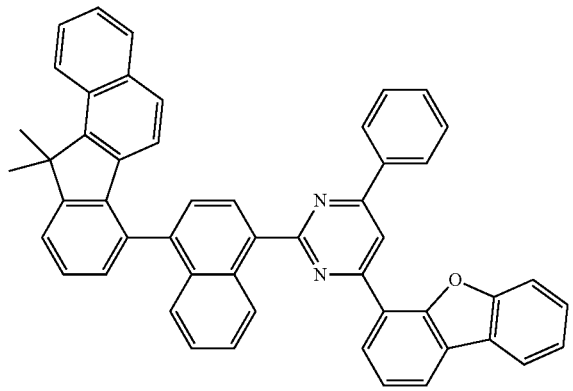 | 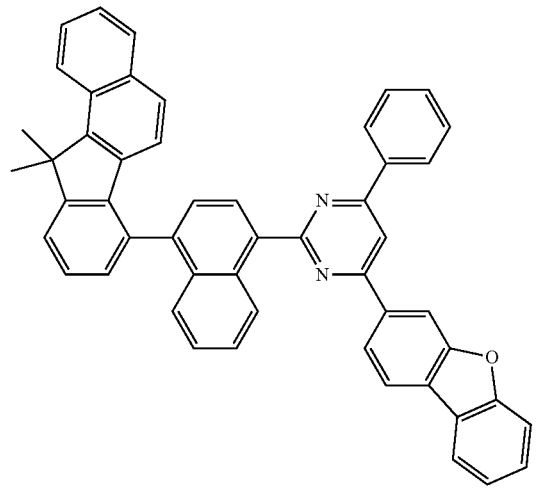 |
| 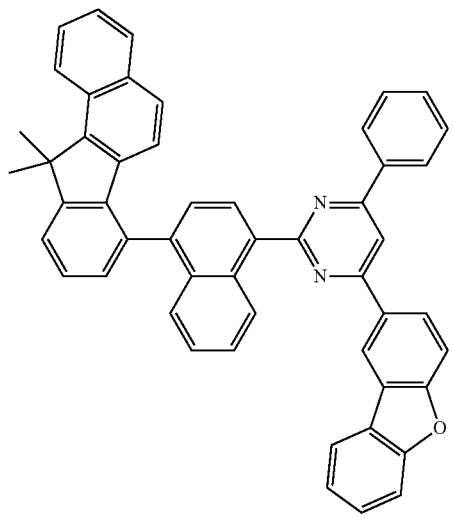 | 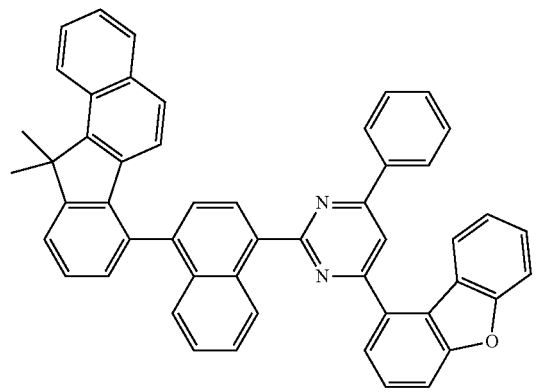 |

913
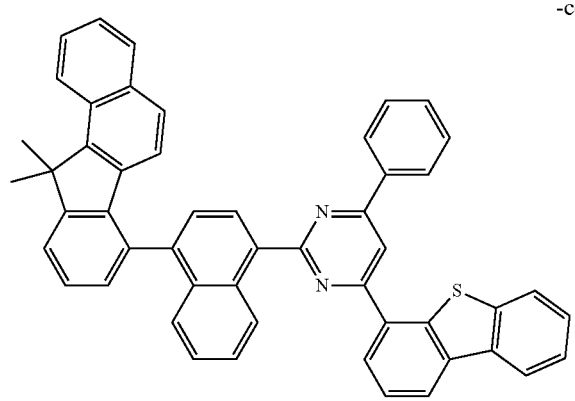
-continued
914
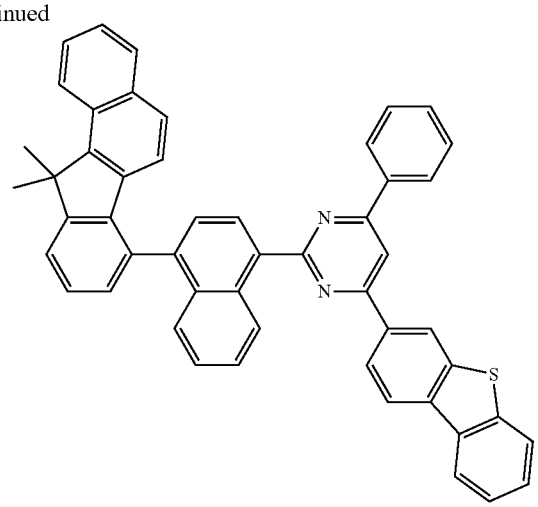
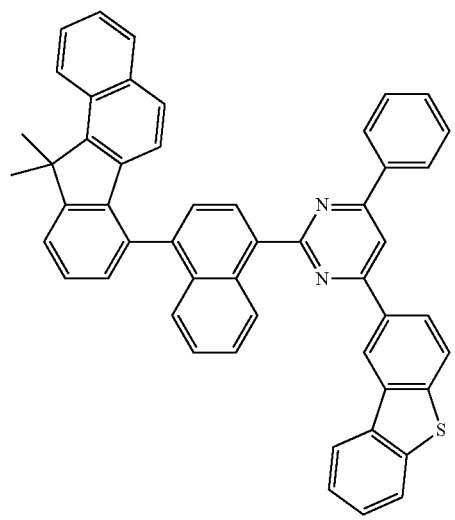
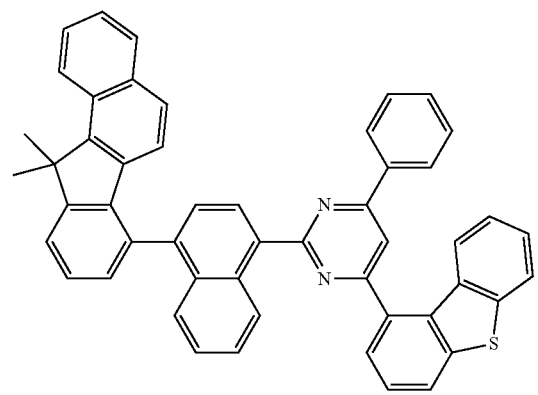
-continued
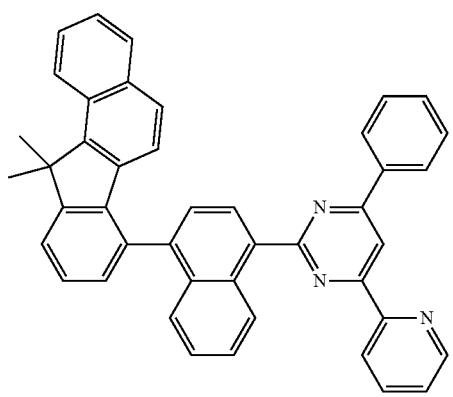
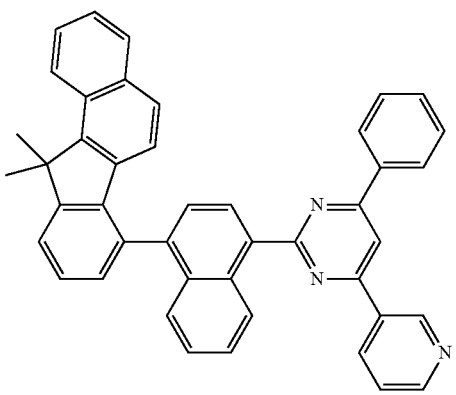

915
-continued
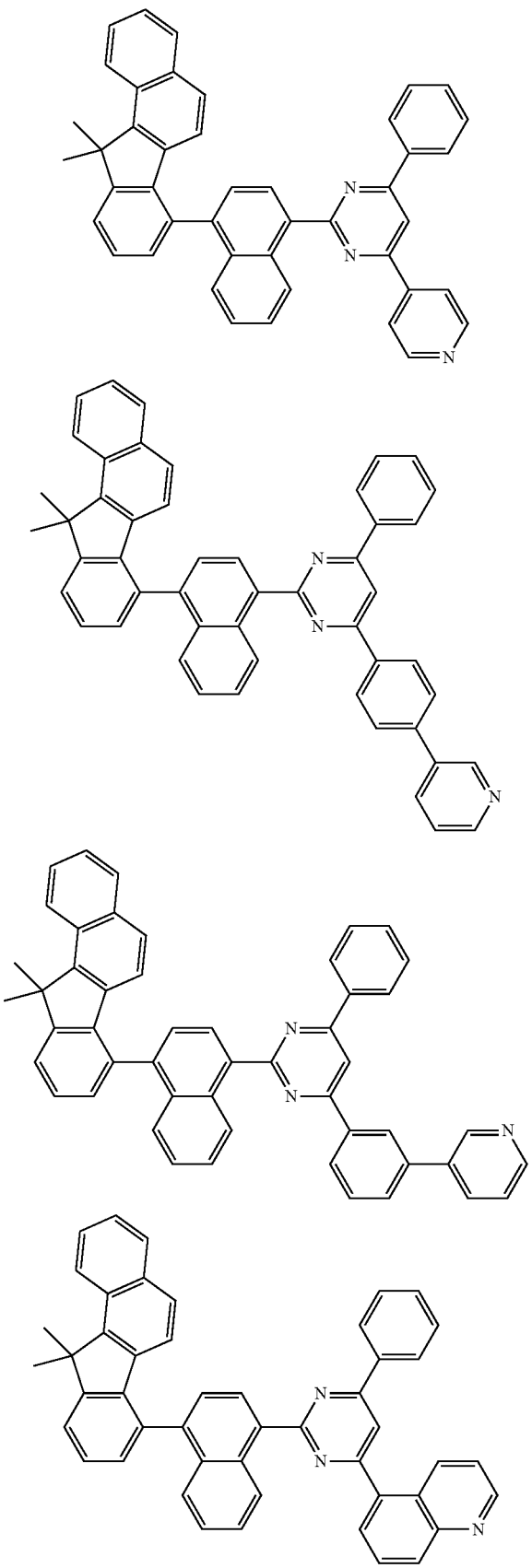
916
-continued
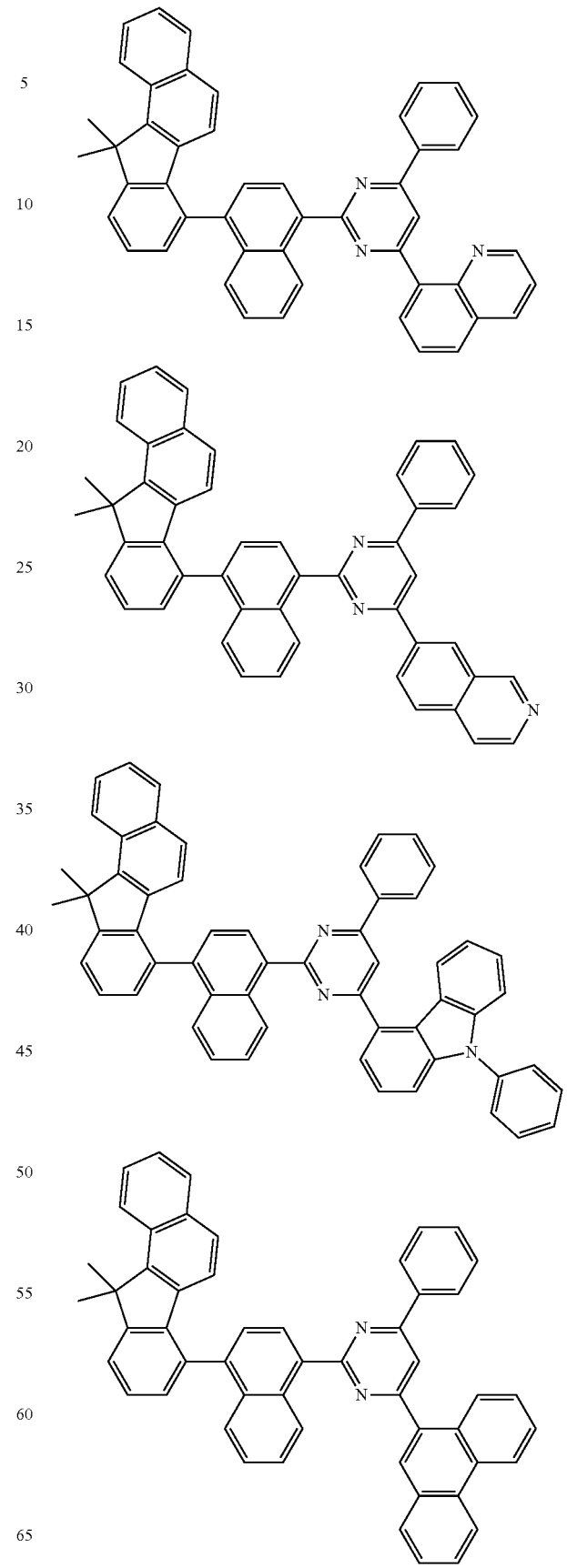

917
-continued
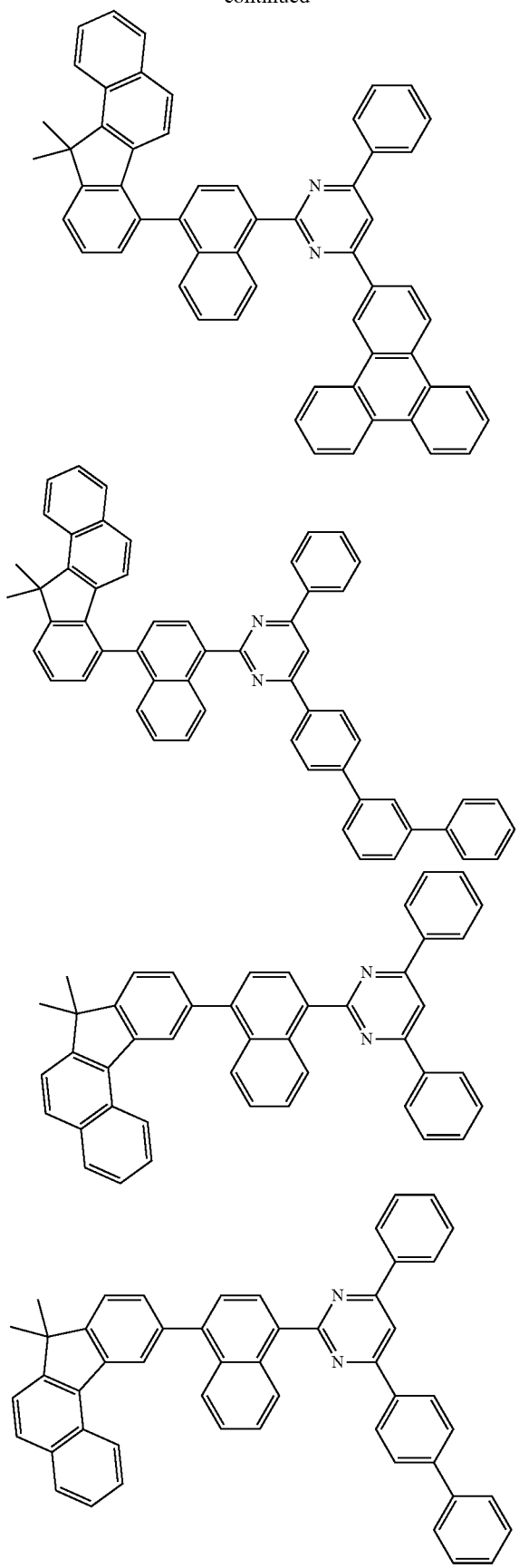
918
-continued
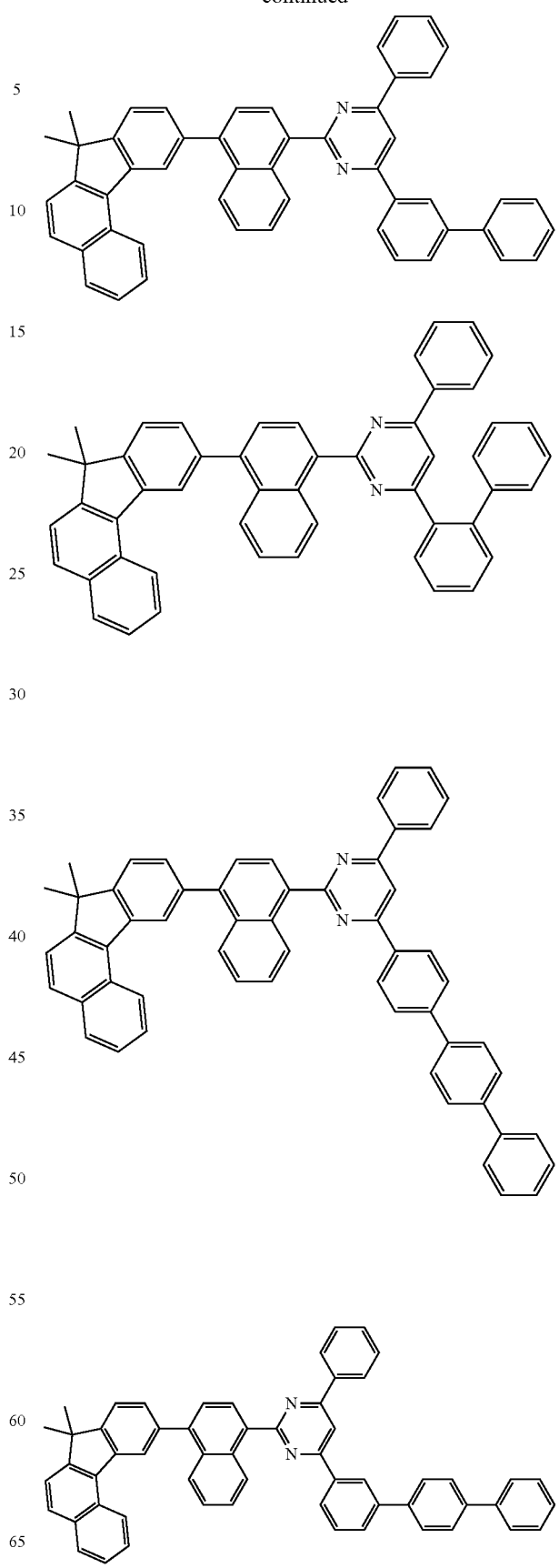

919
-continued
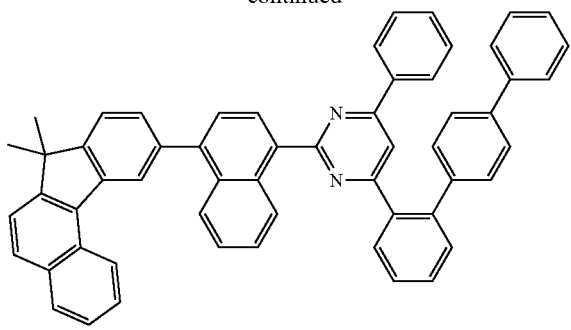
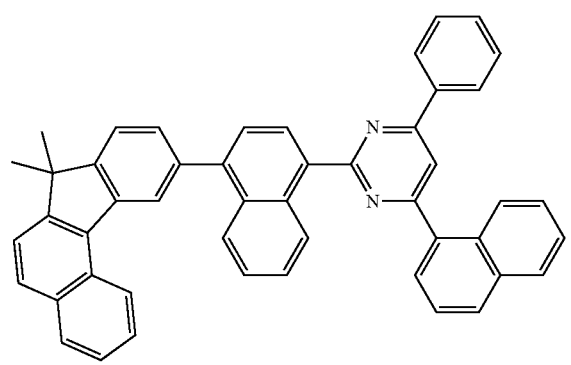
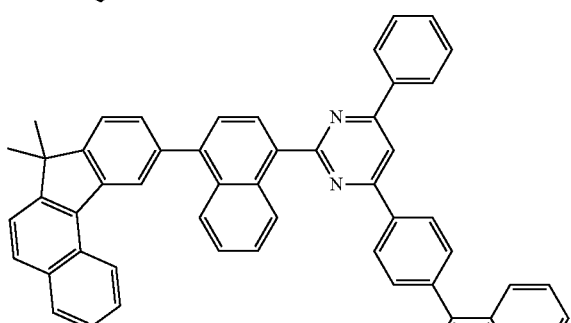
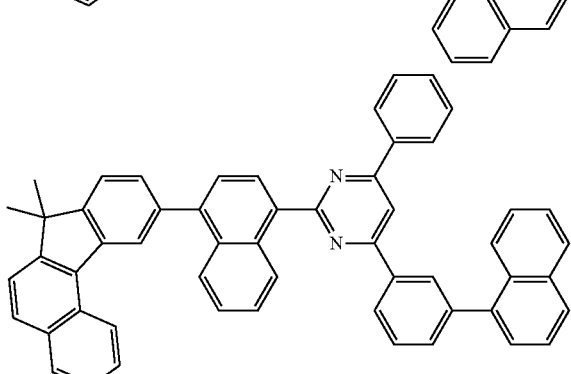
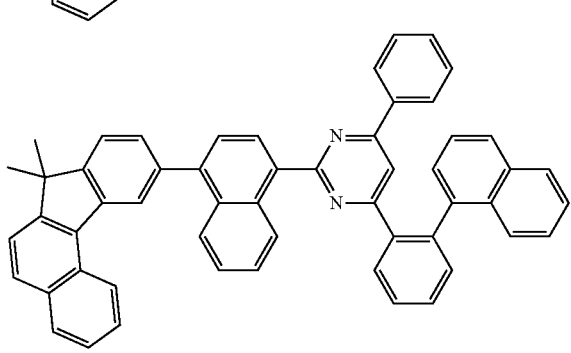
920
-continued
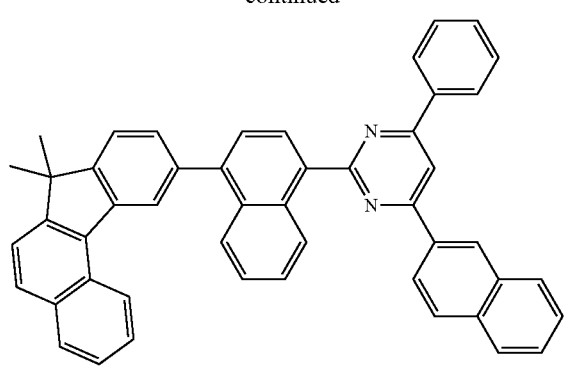
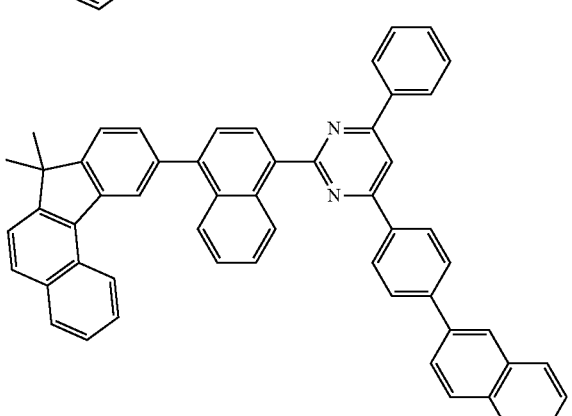
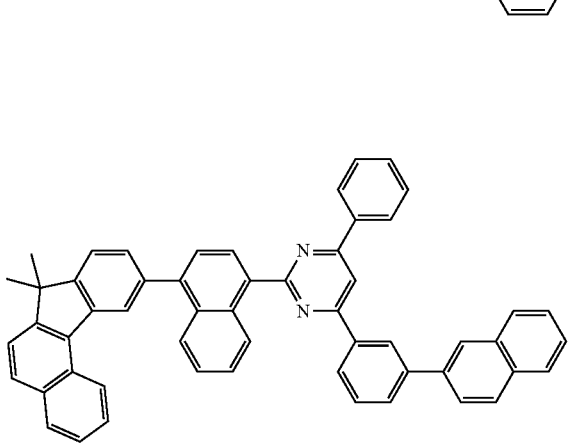
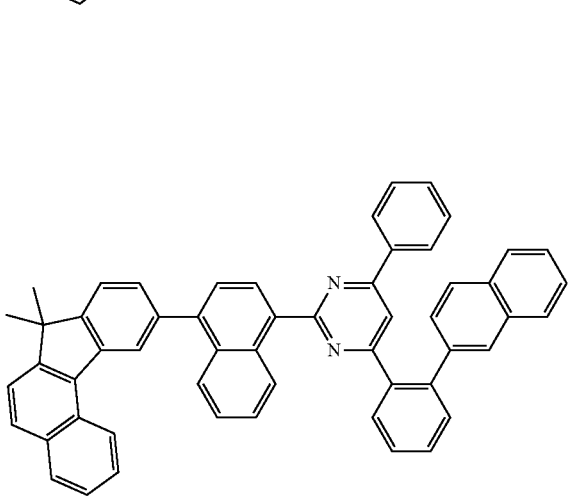

921 -continued
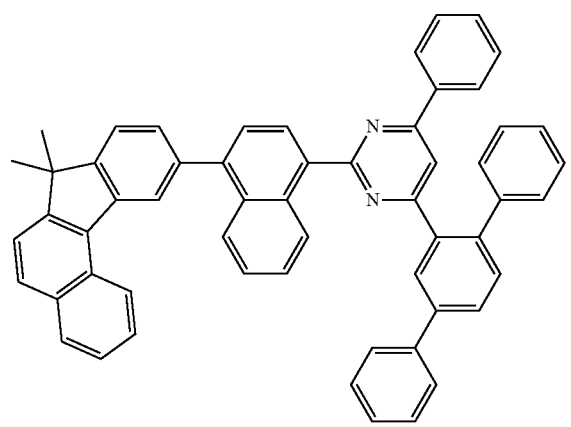
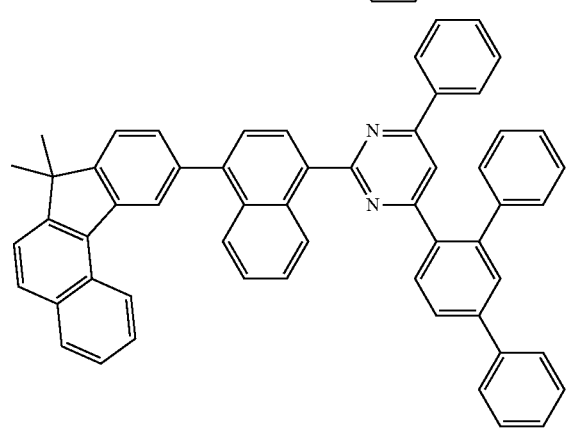
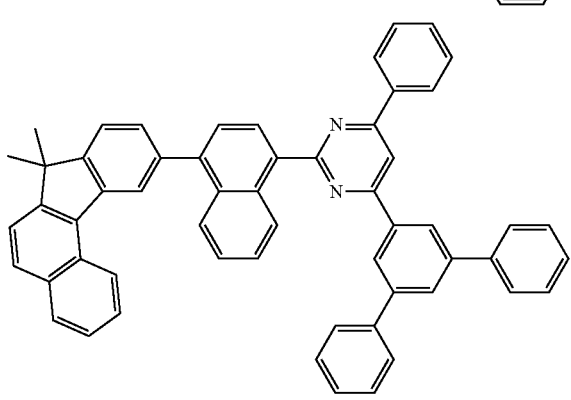
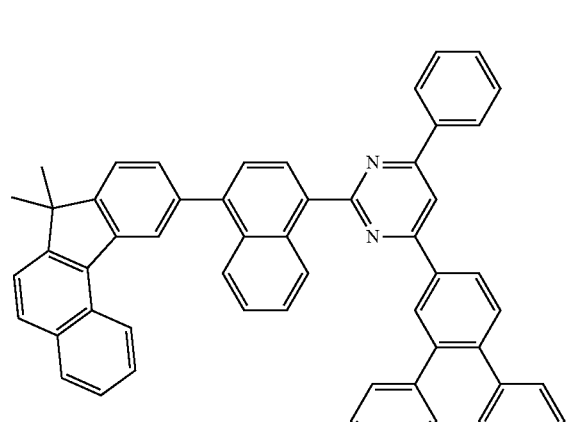
922 -continued
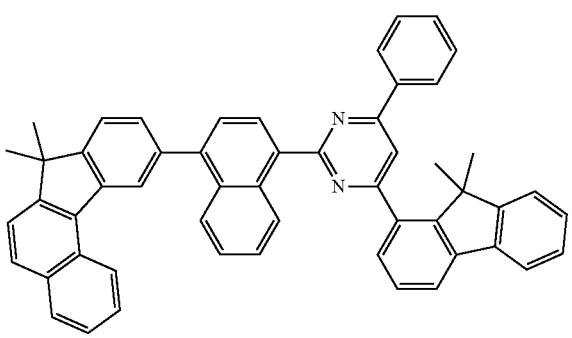
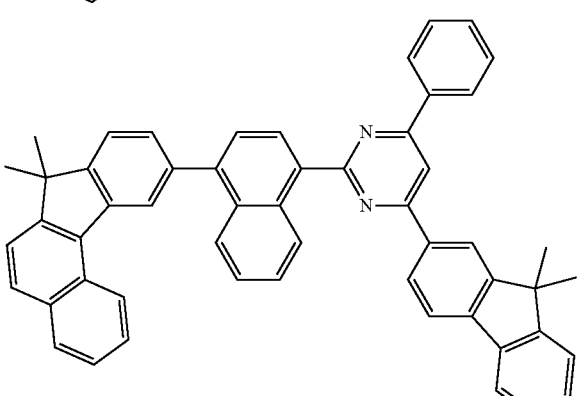
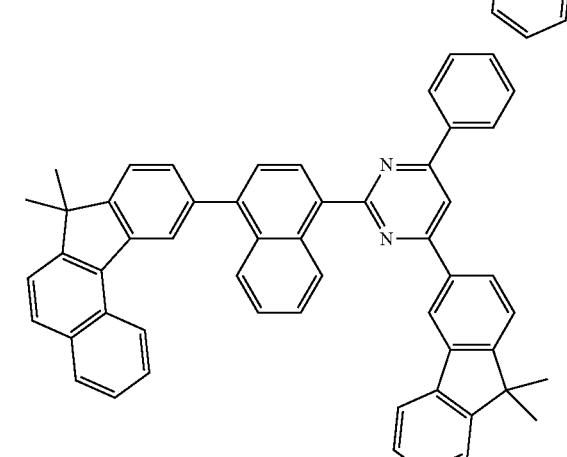
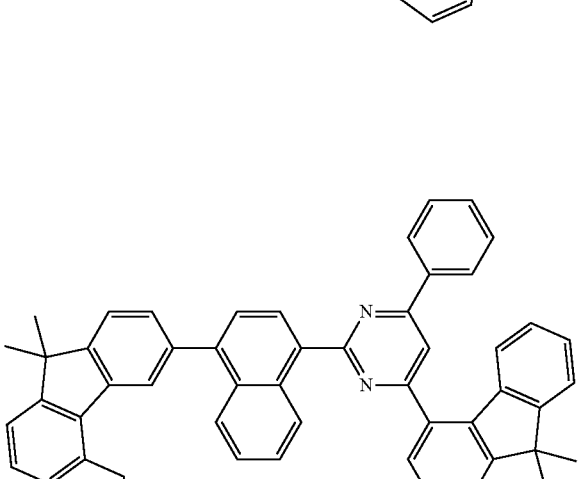

923
-continued
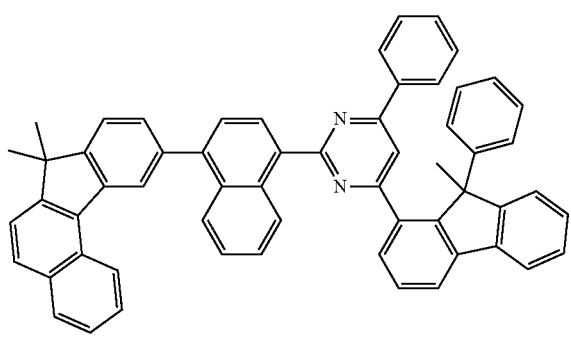
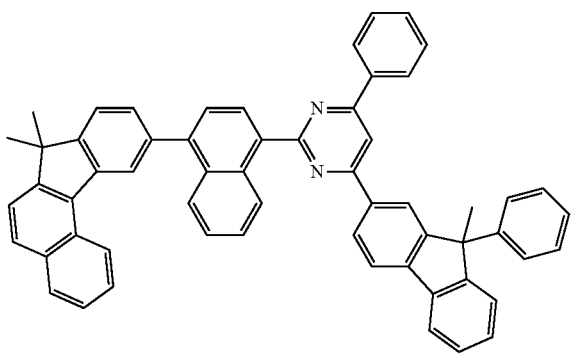
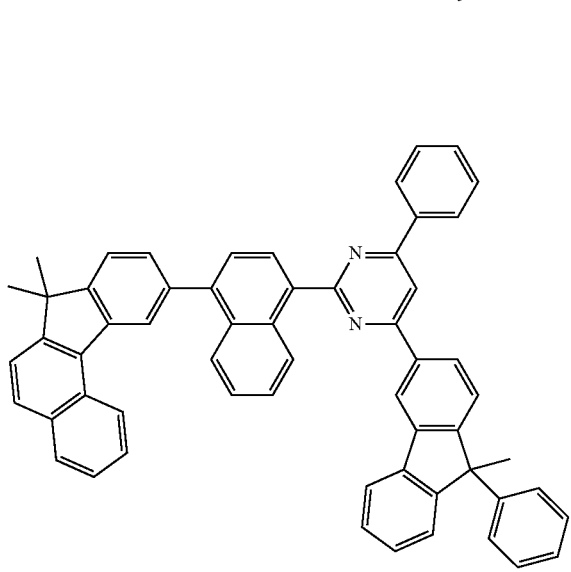
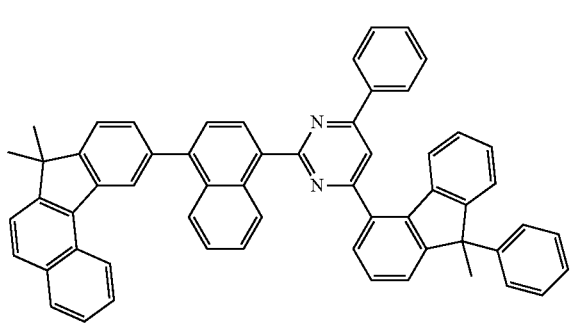
924
-continued
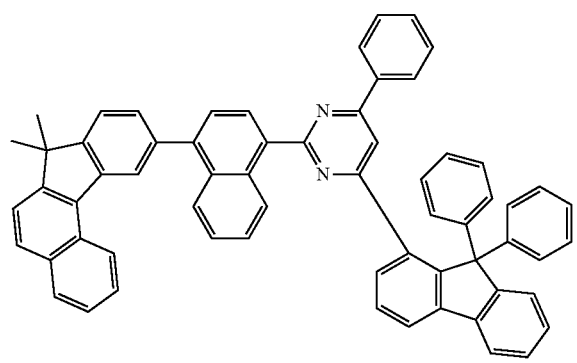
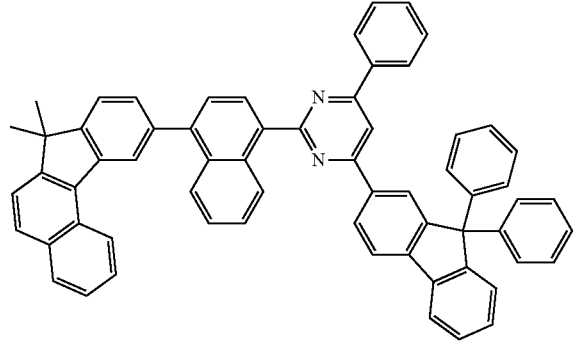
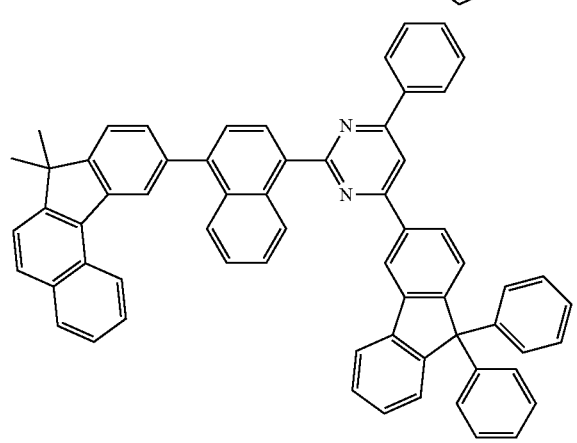
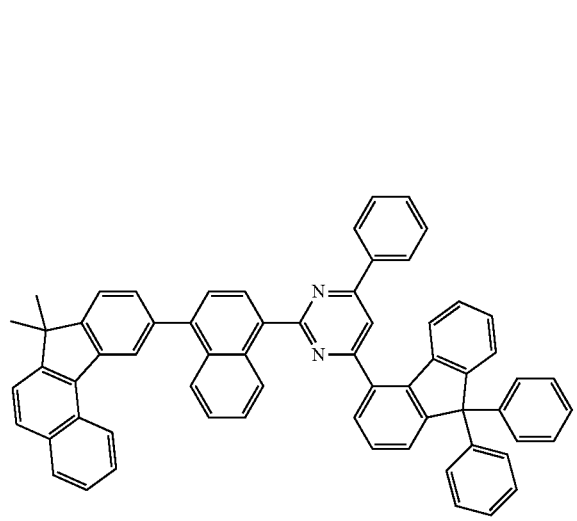

925
-continued
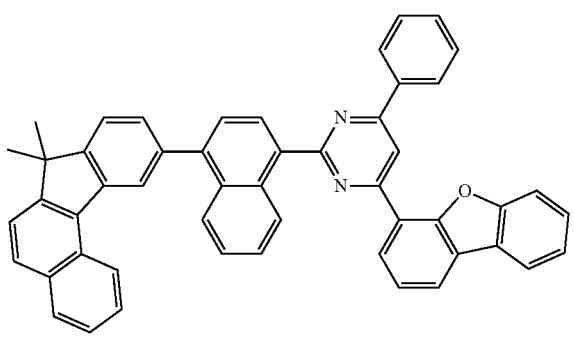
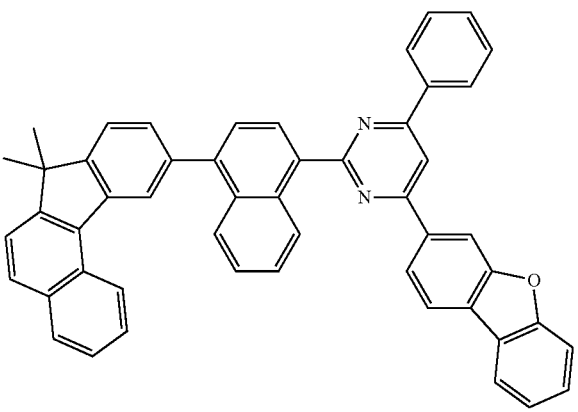
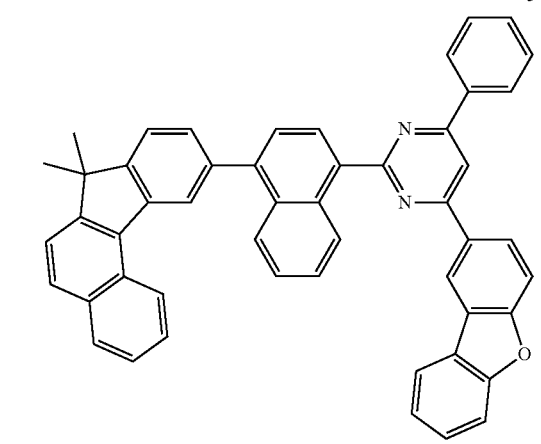
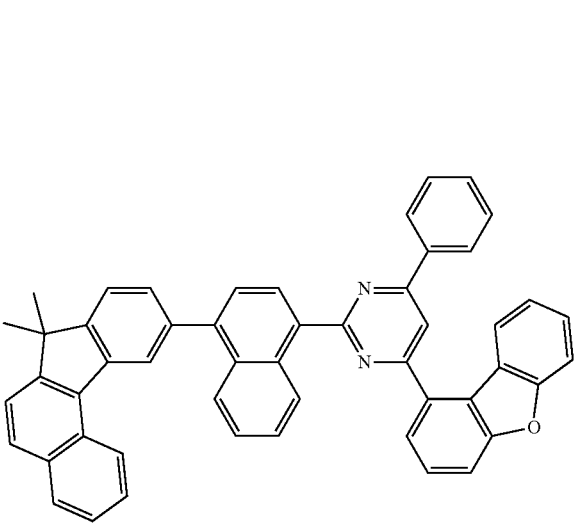
926
-continued
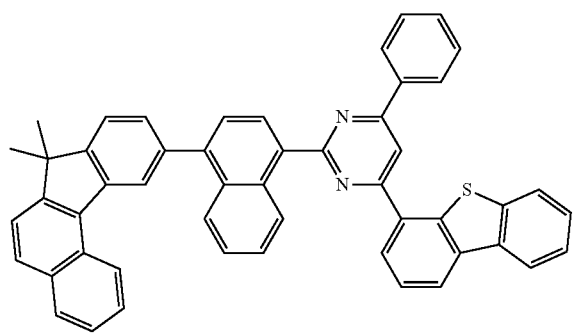
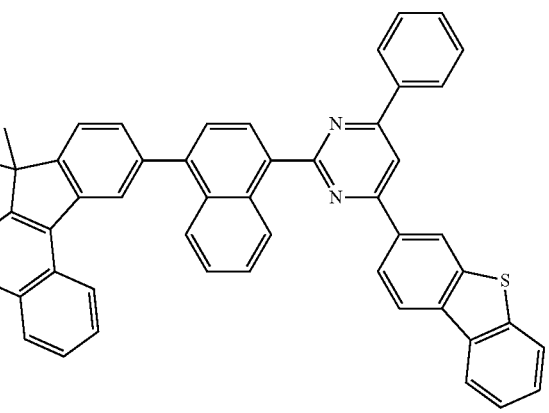
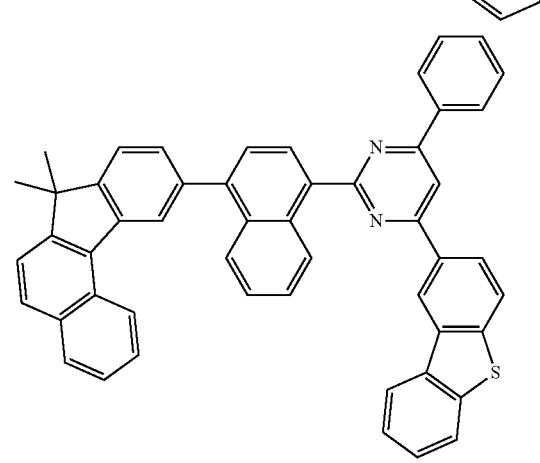
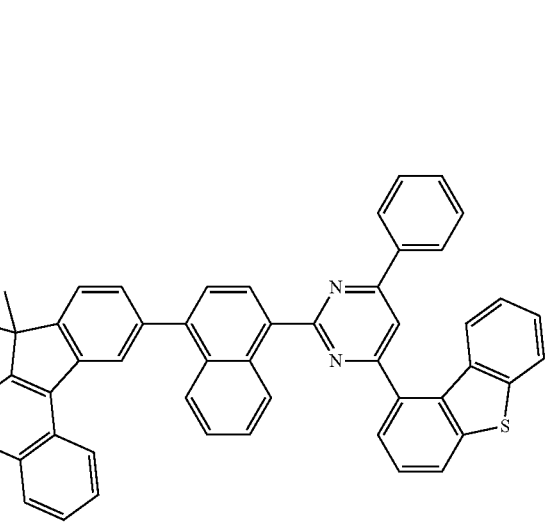

927
-continued
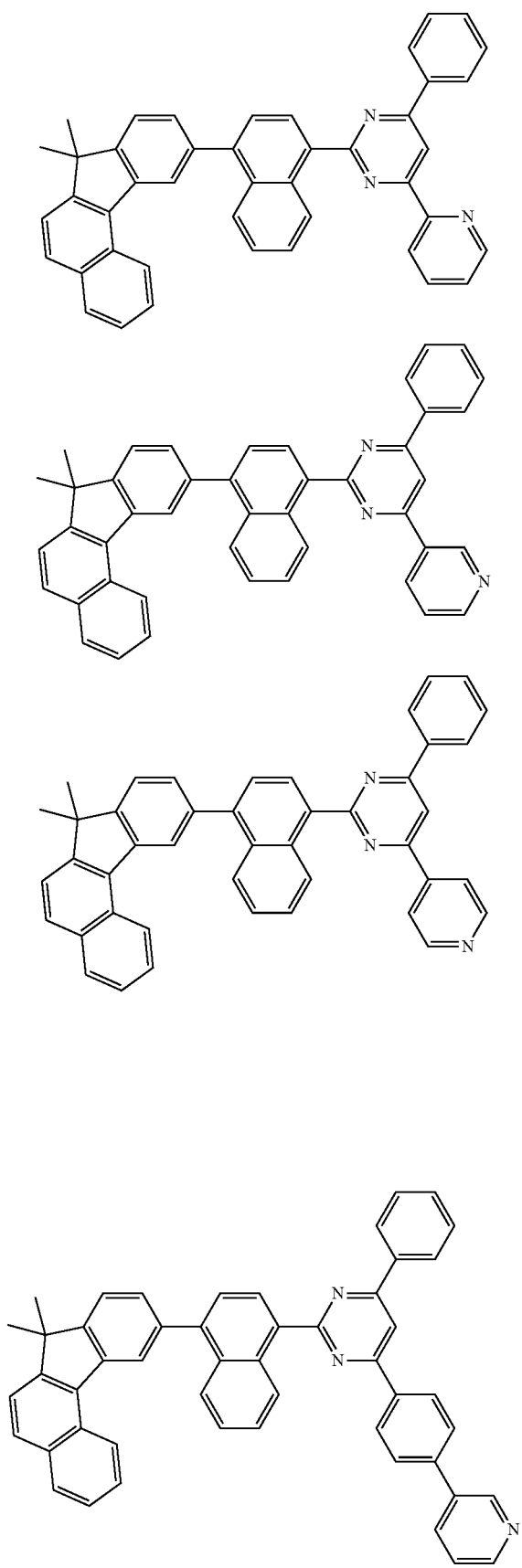
928
-continued
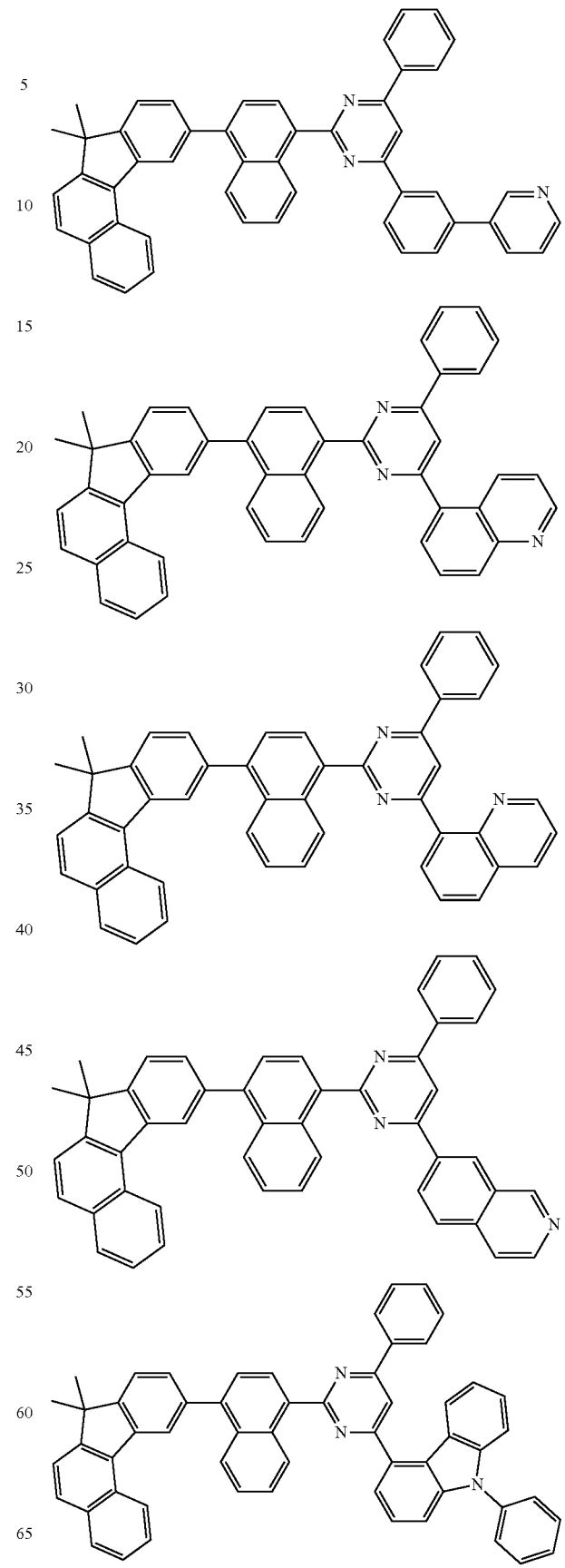

929
-continued
930
-continued
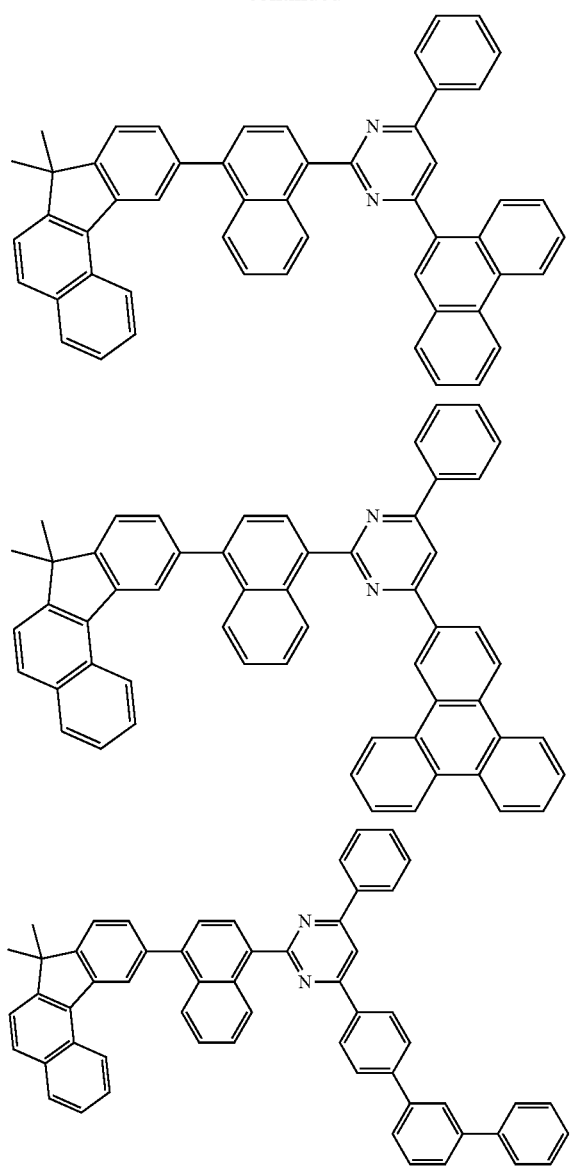
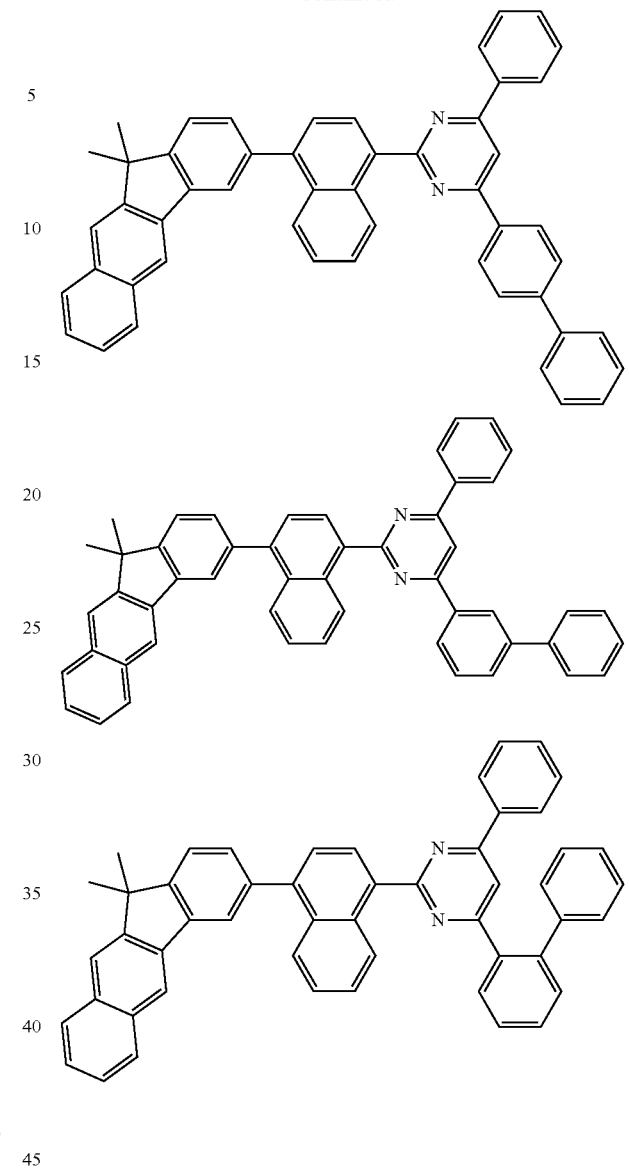
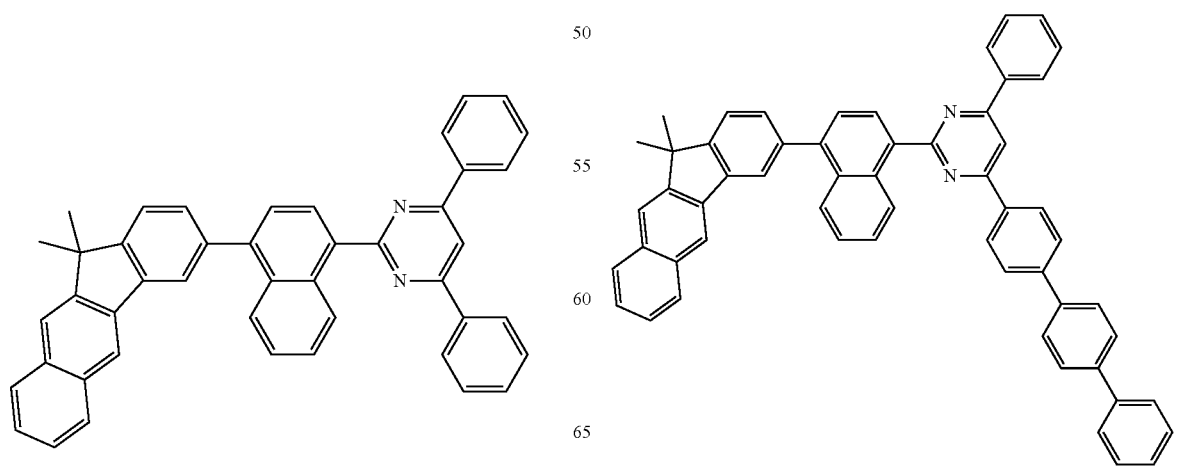

931
-continued
932
-continued
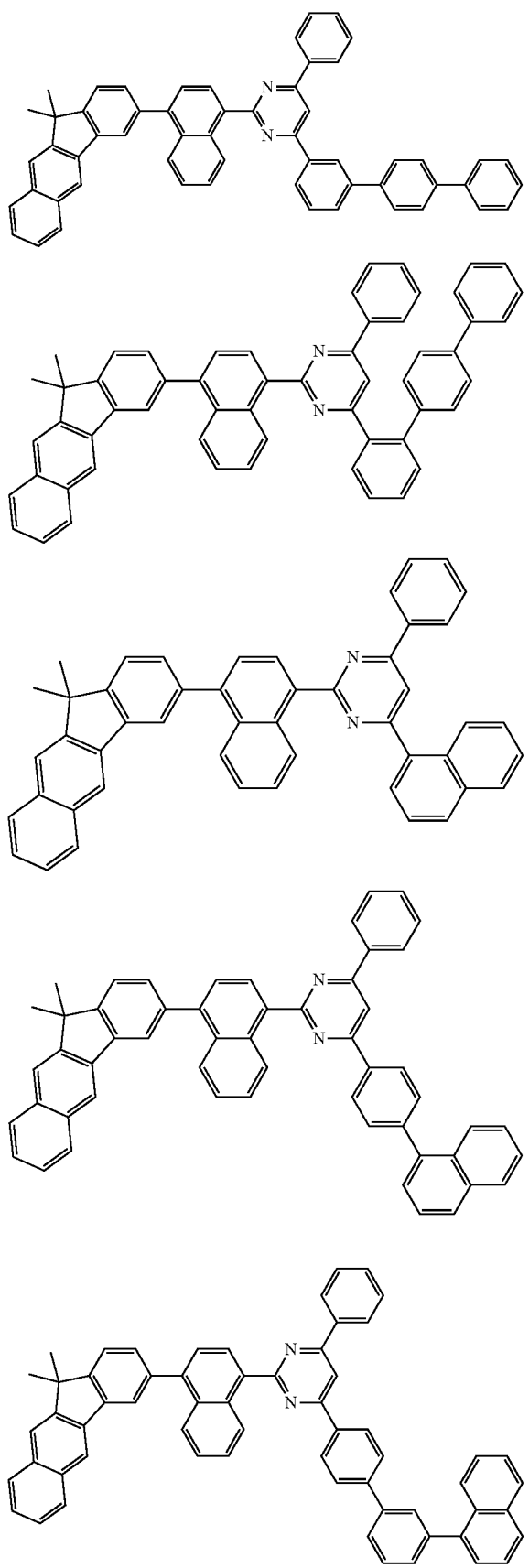
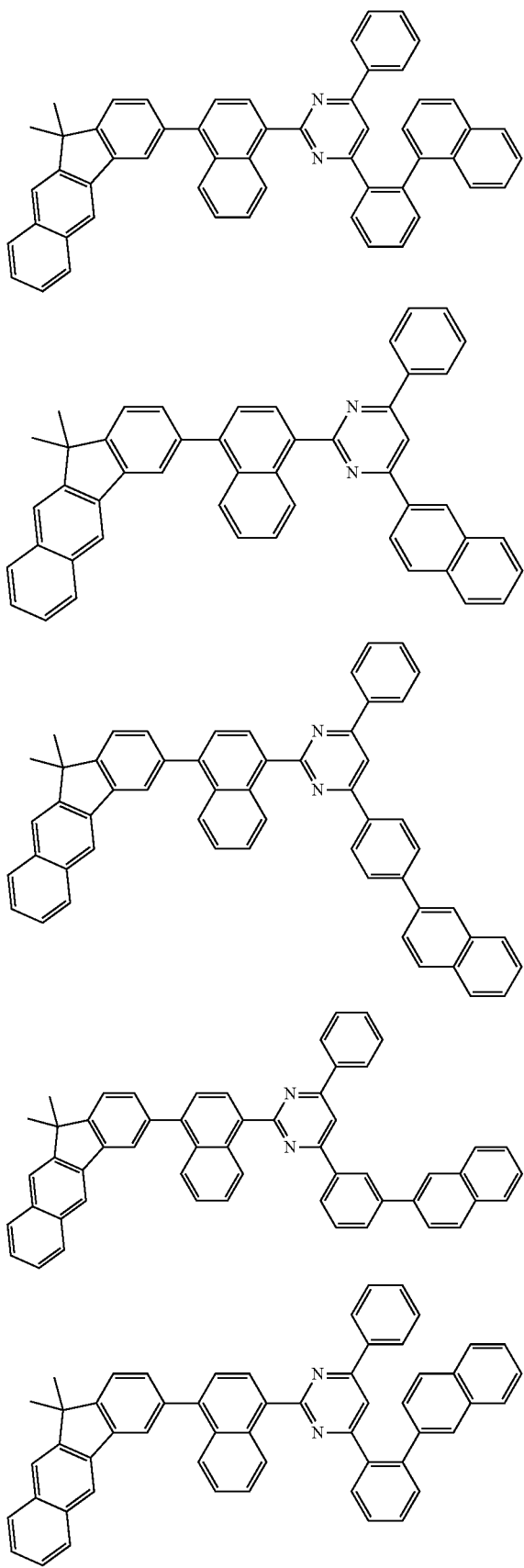

933
-continued
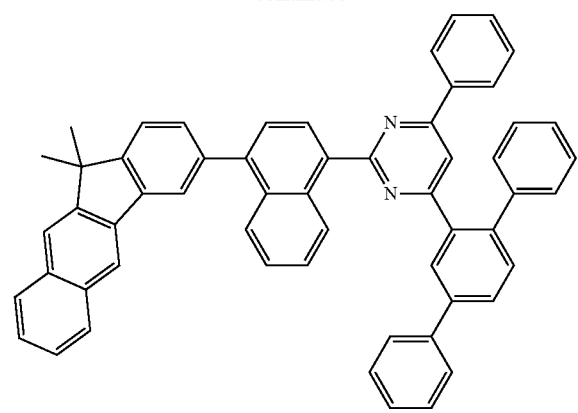
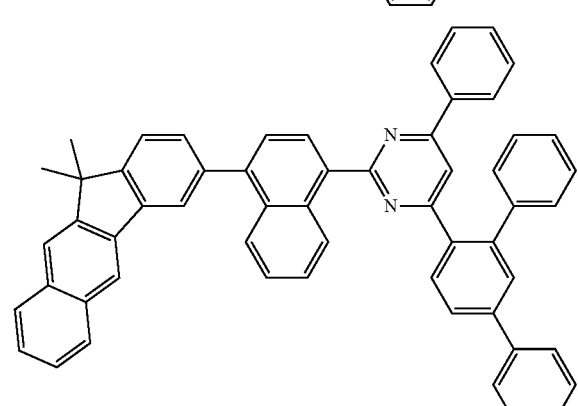
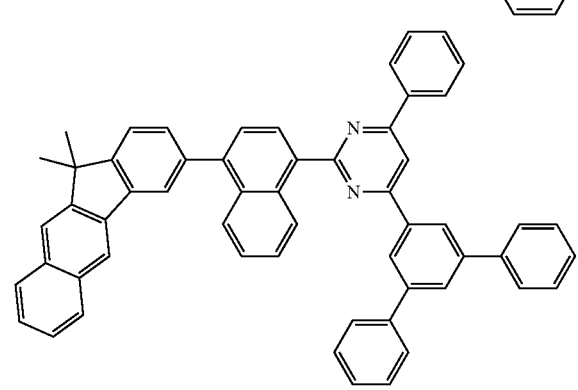
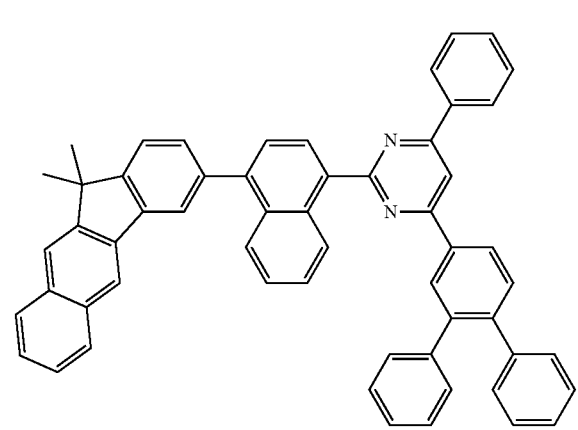
934
-continued
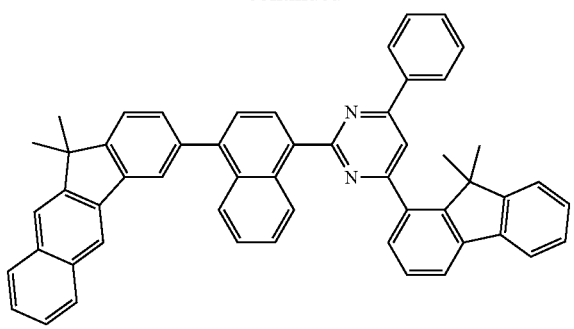
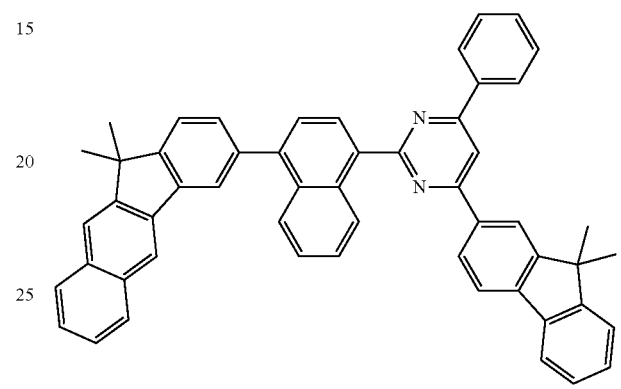
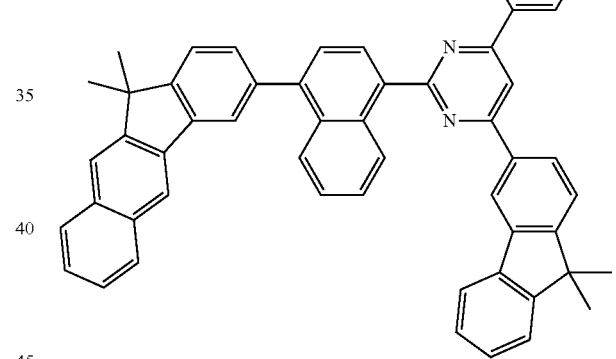
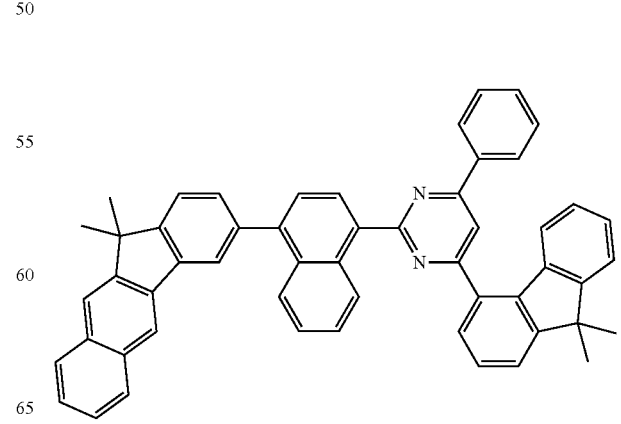

935
-continued
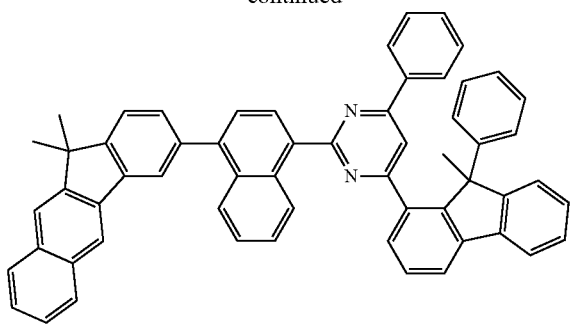
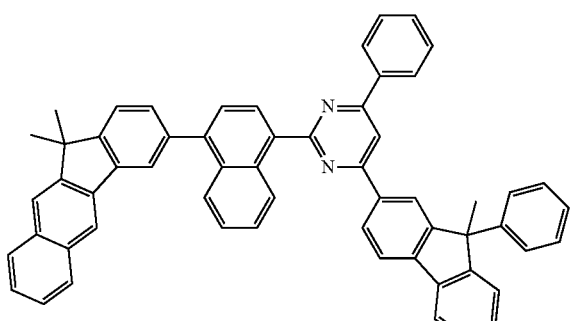
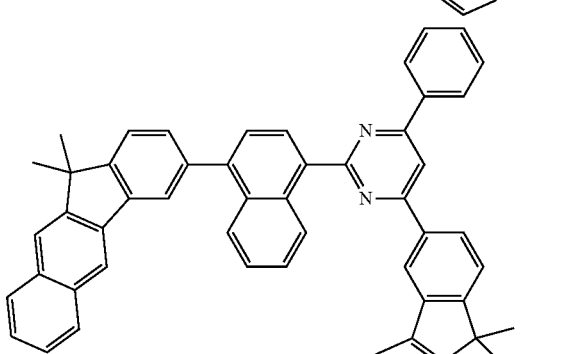
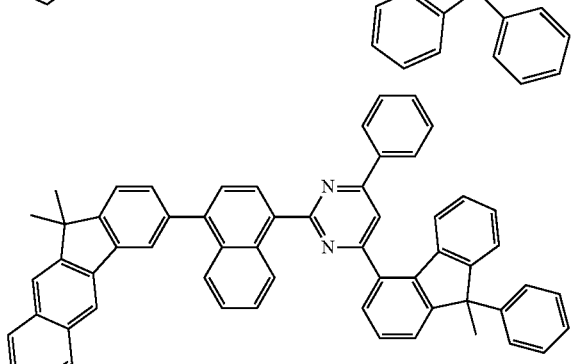
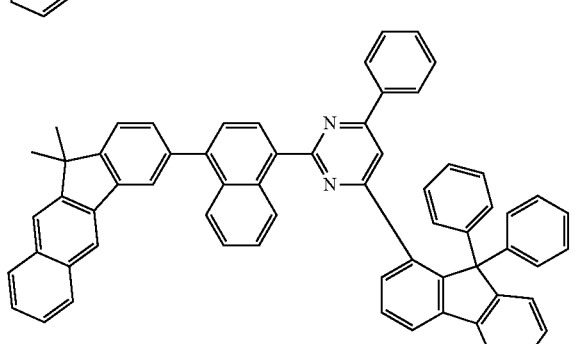
936
-continued
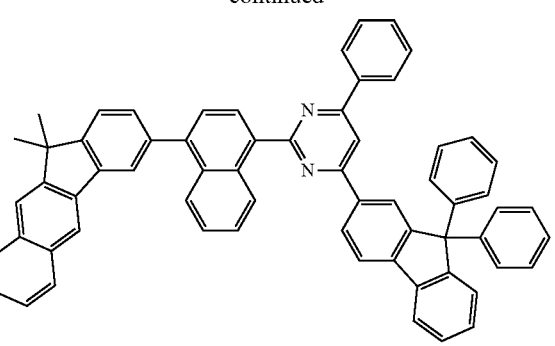
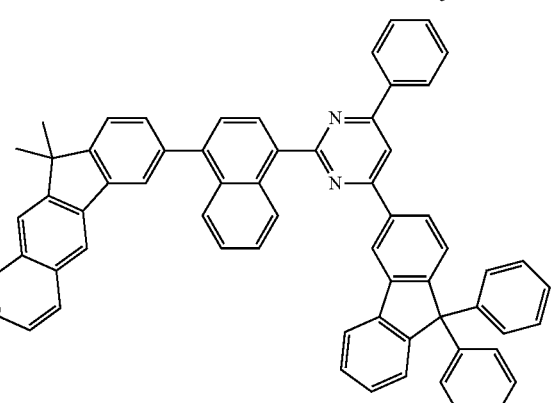
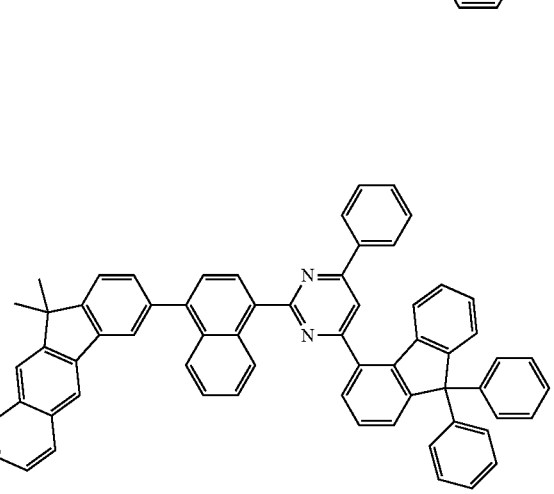
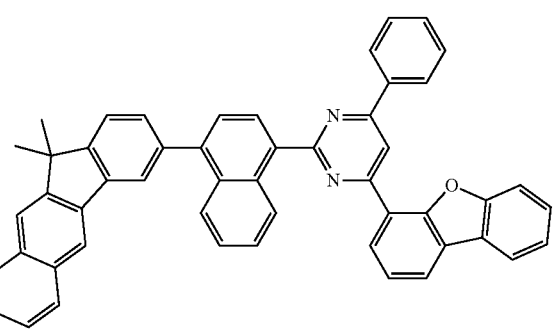

937
-continued
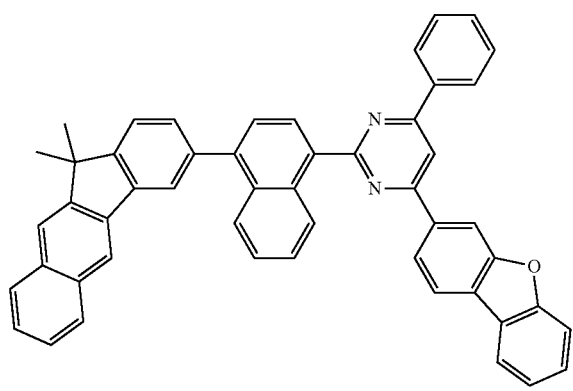
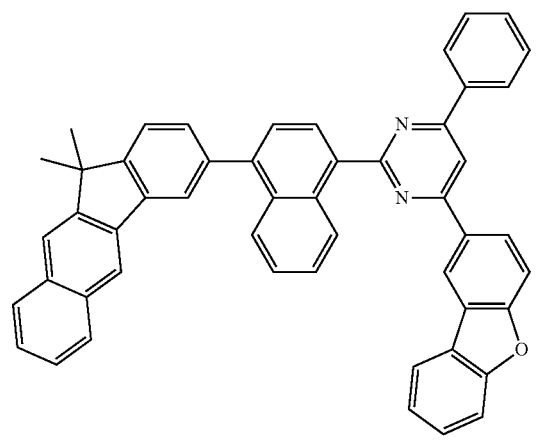
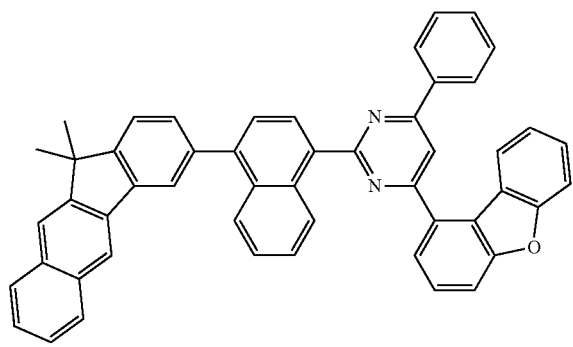
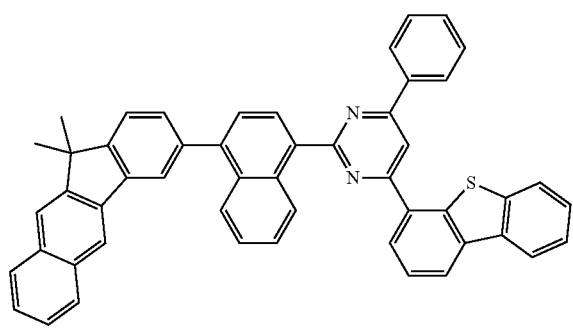
938
-continued
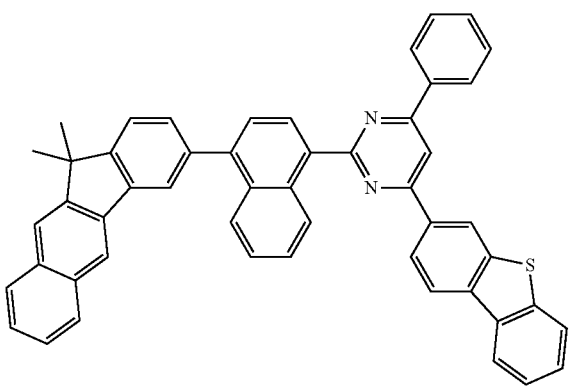
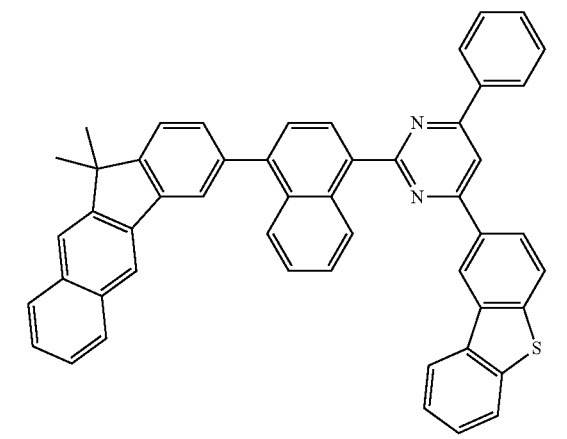
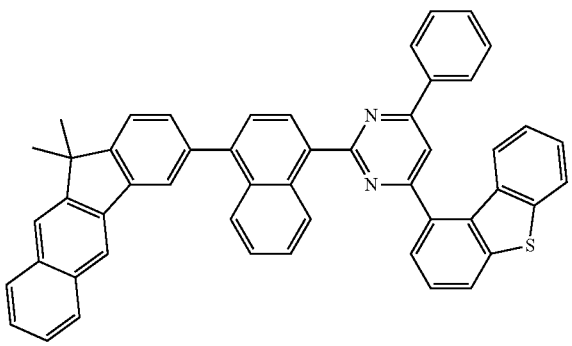
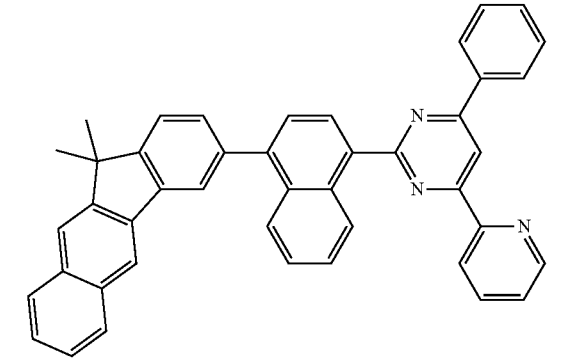

| 939 -continued | 940 -continued |
|---|---|
| 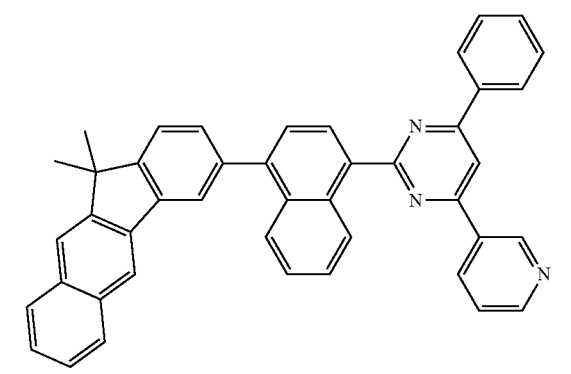 | 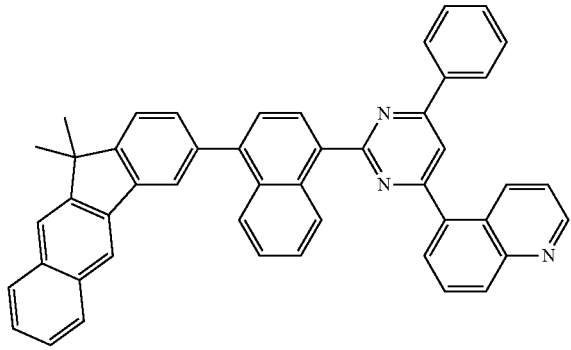 |
| 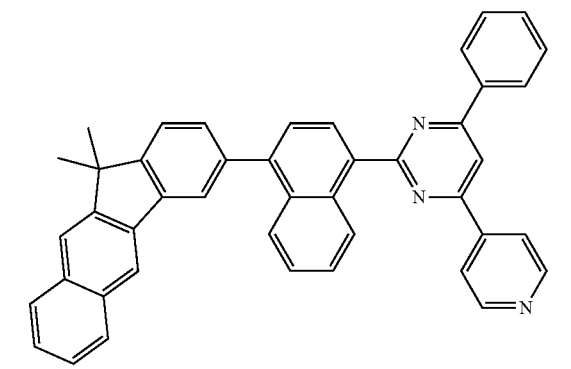 | 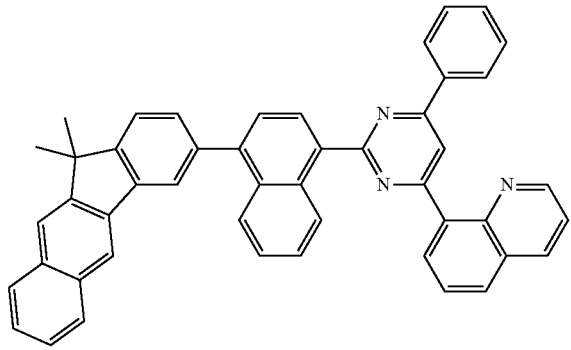 |
| 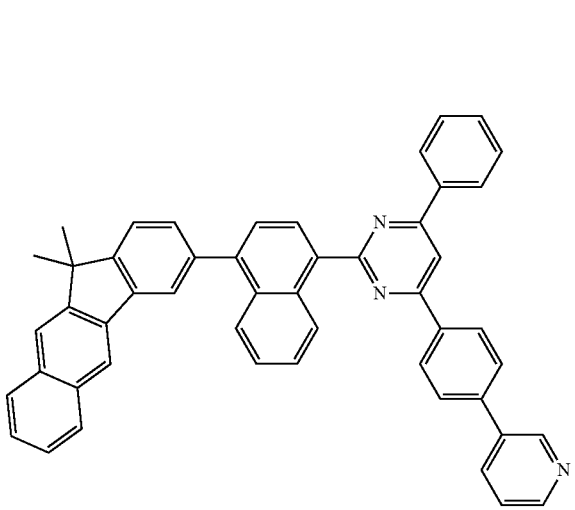 | 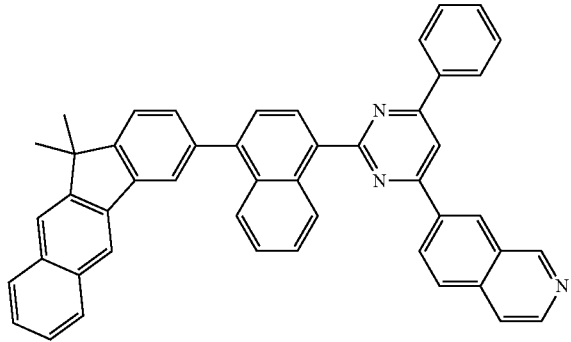 |
| 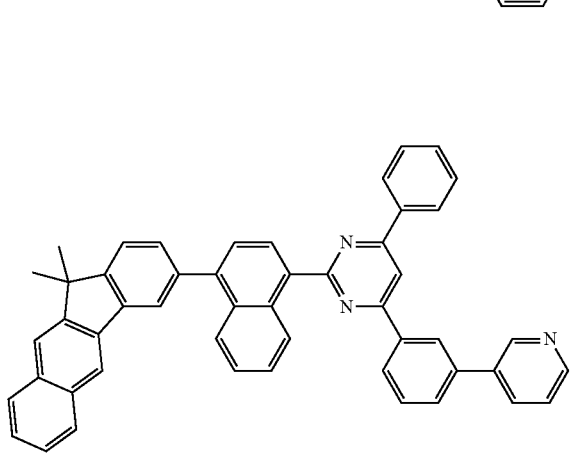 | 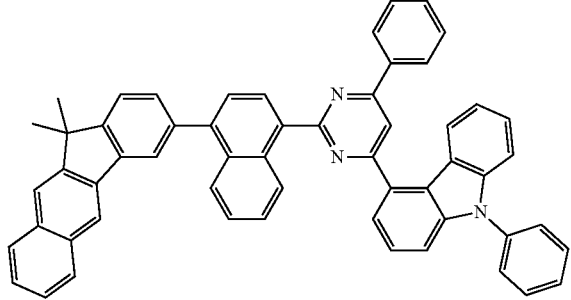 |
| | 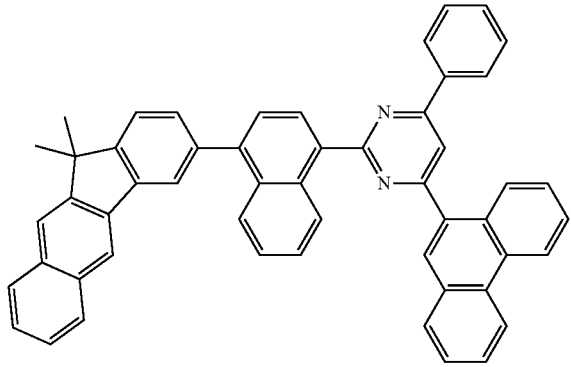 |

941
-continued
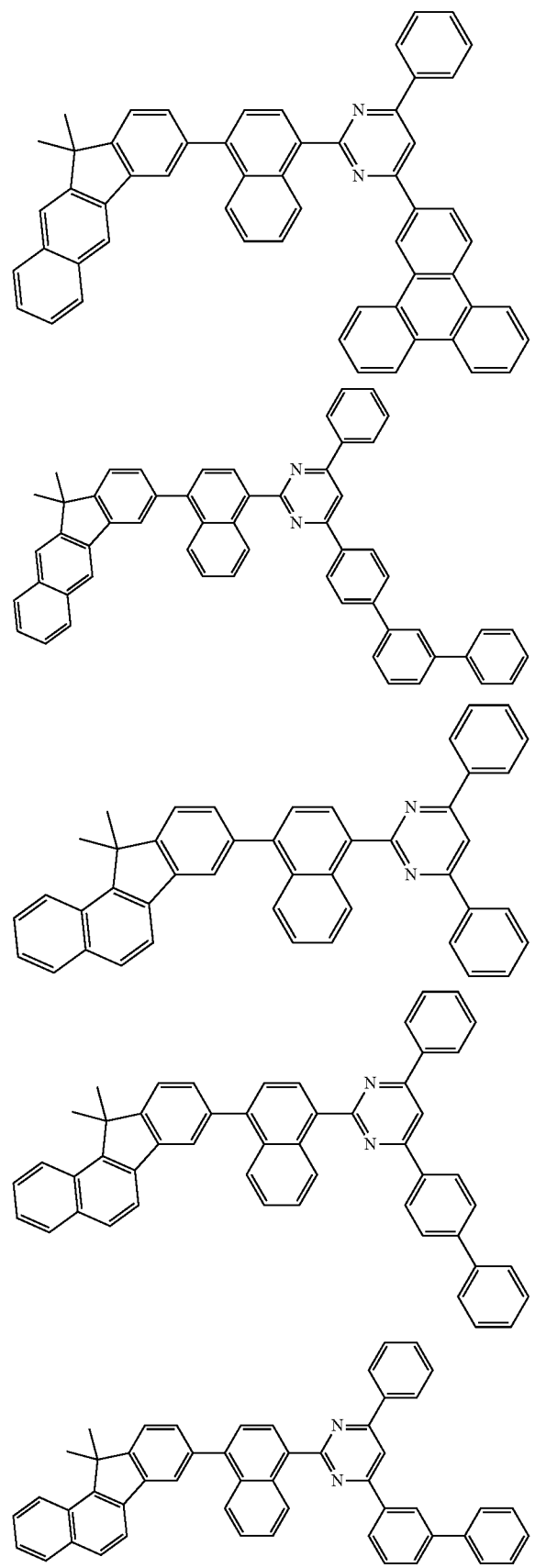
942
-continued
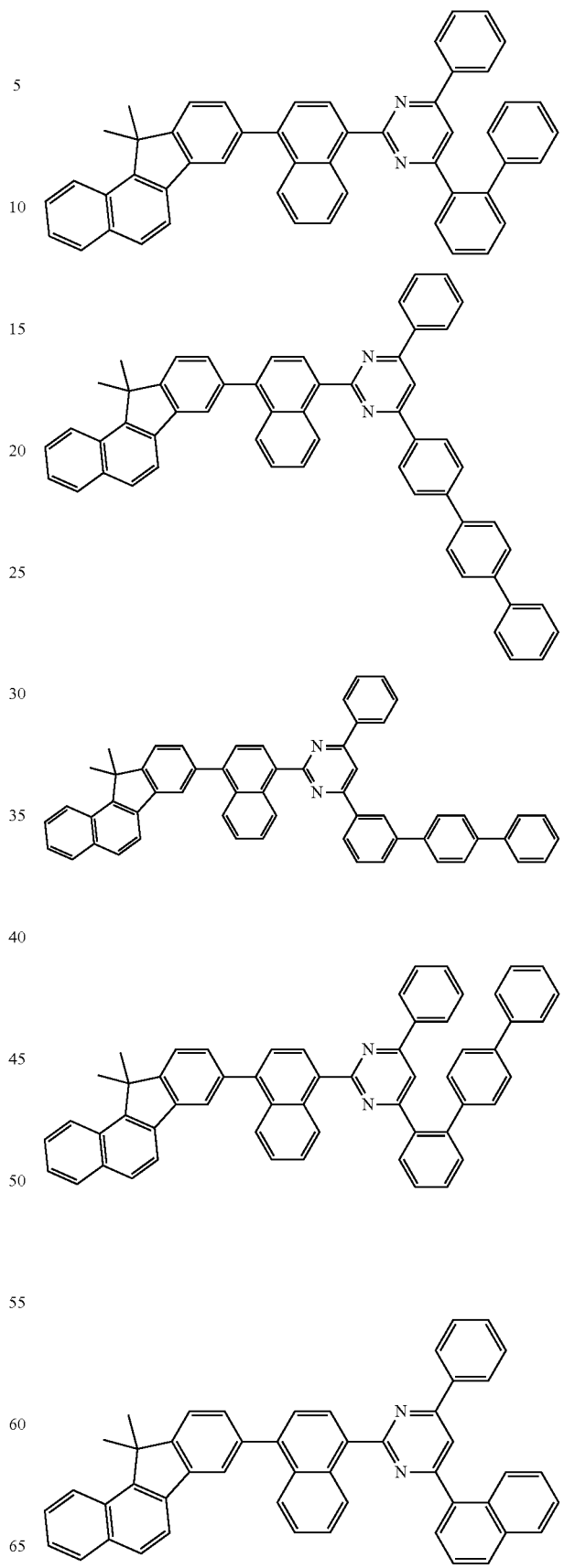

943
-continued
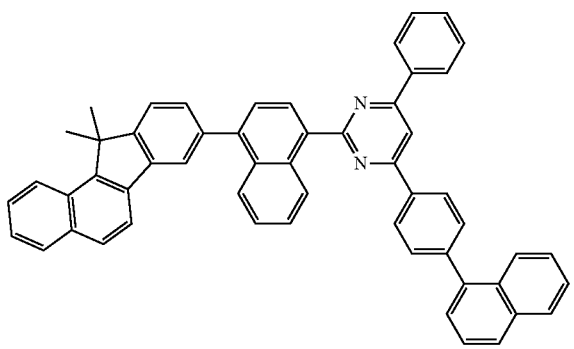
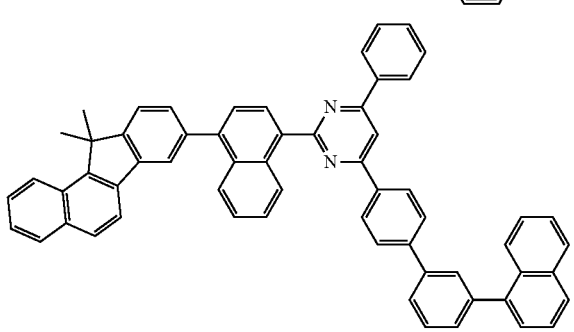
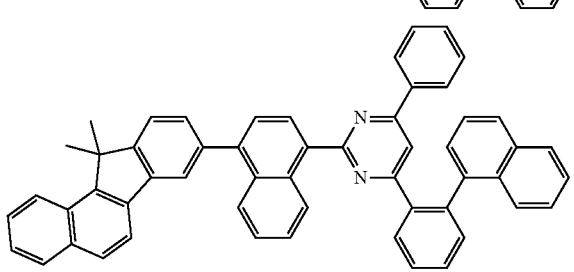
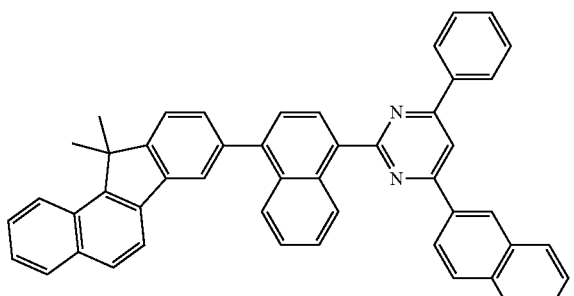
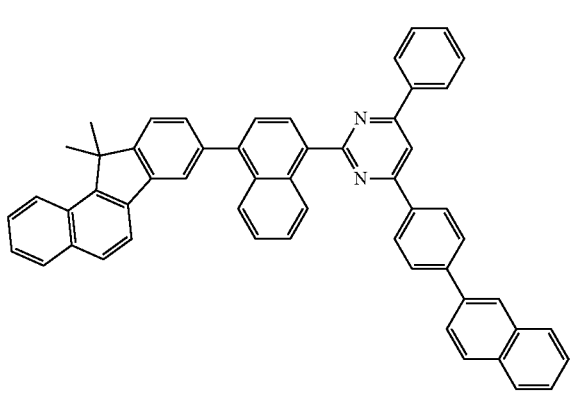
944
-continued
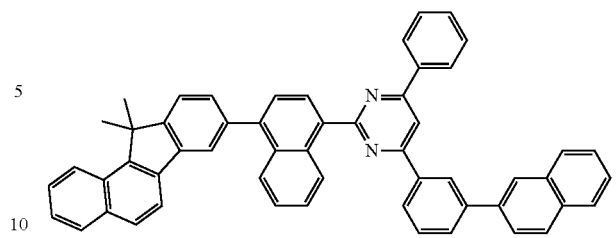
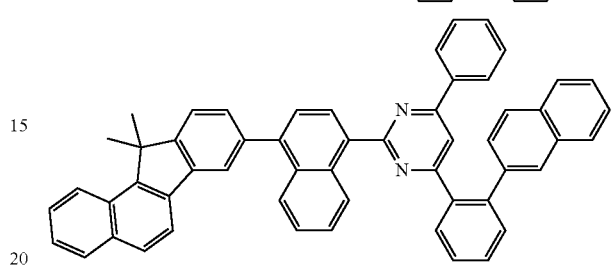
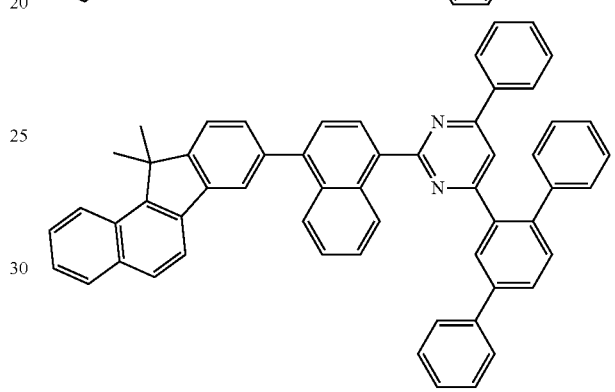
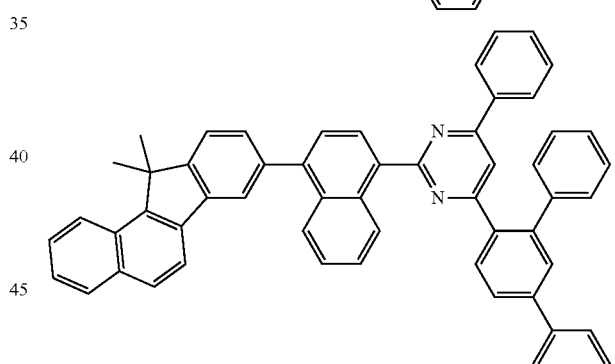
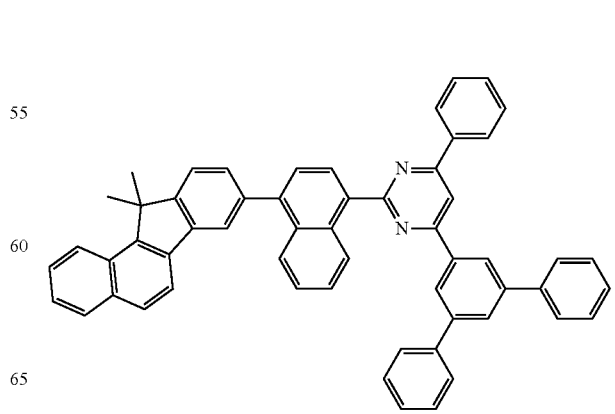

945
-continued
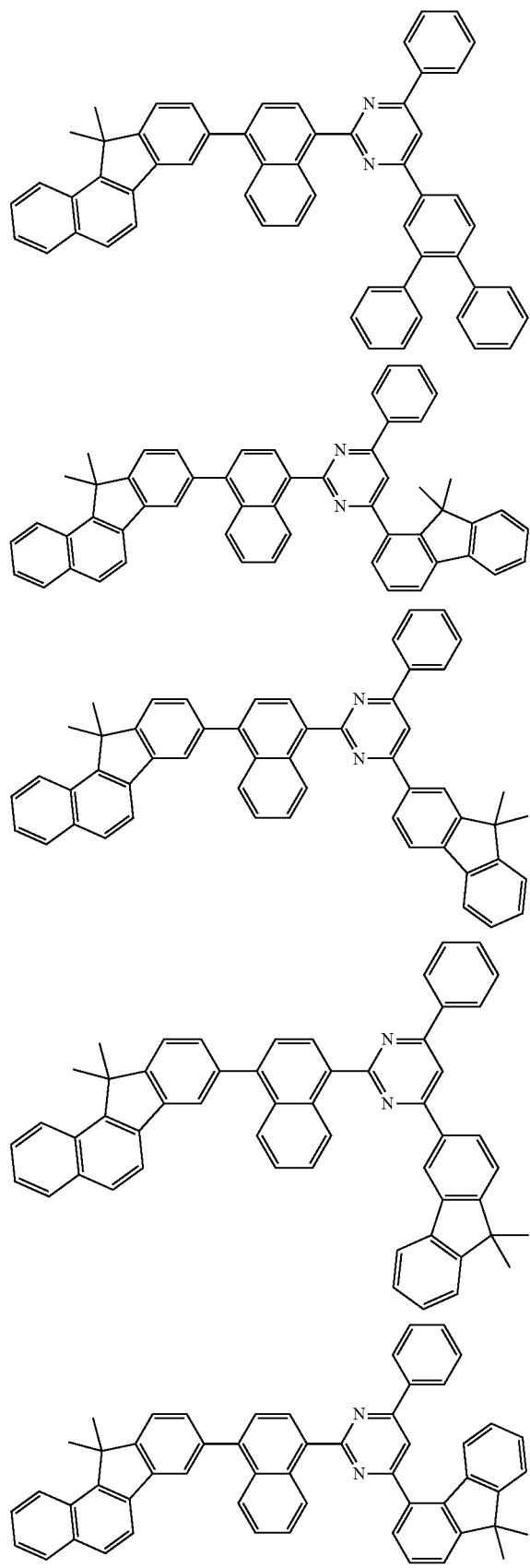
946
-continued
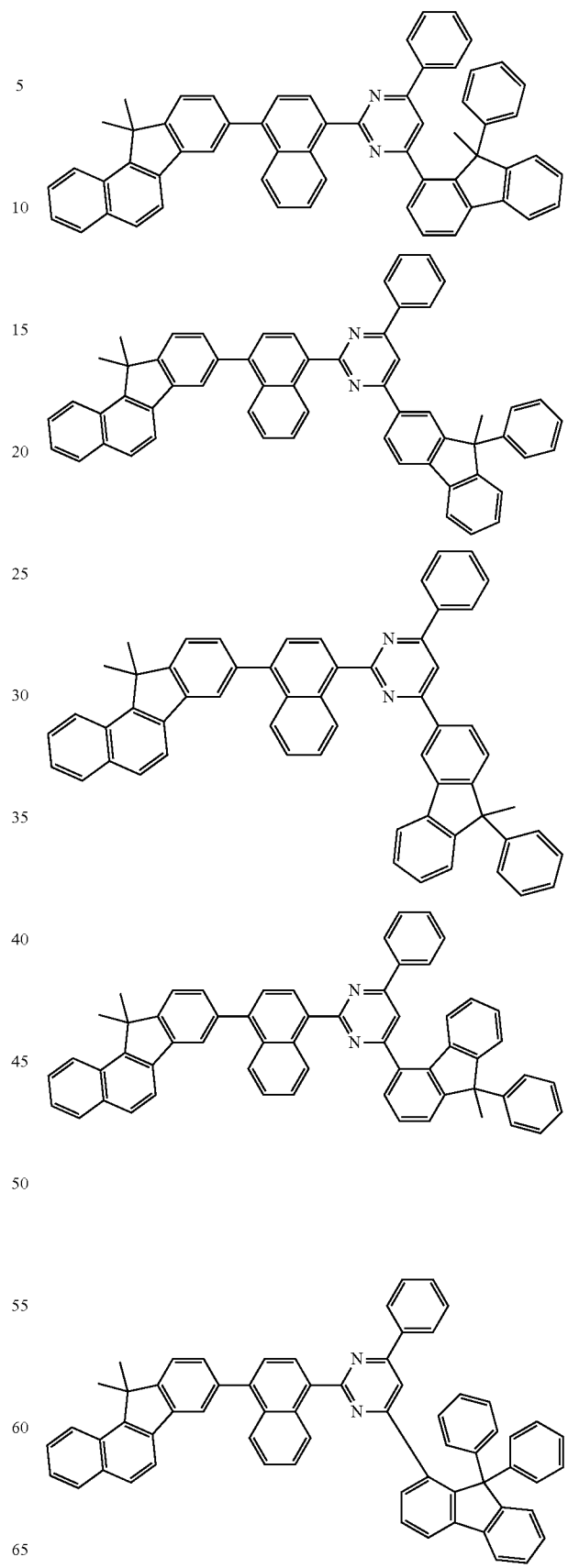

947
-continued
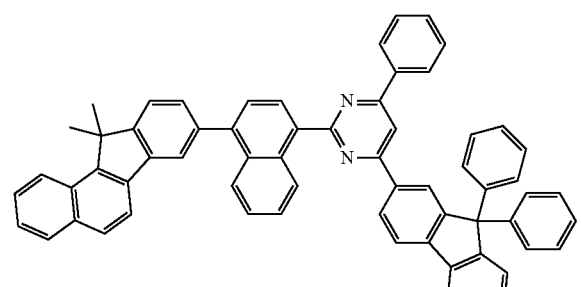
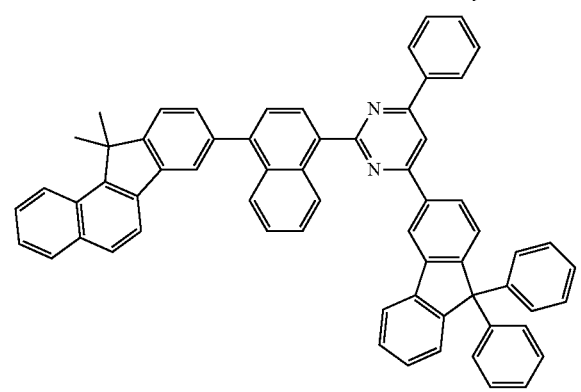
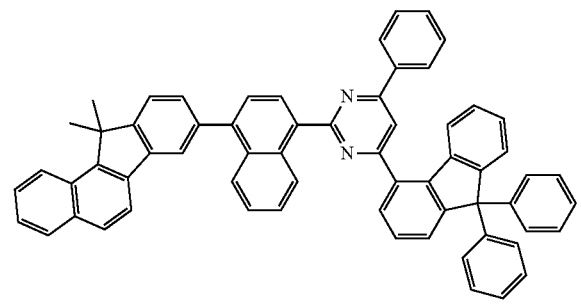
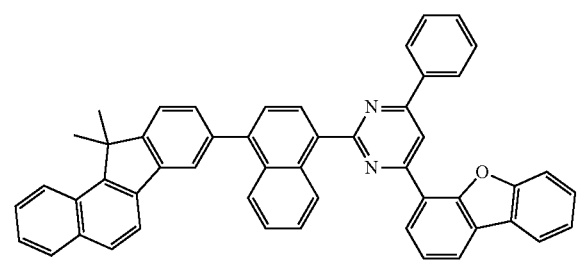
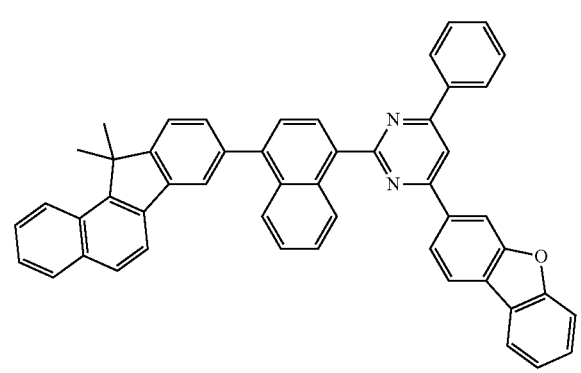
948
-continued
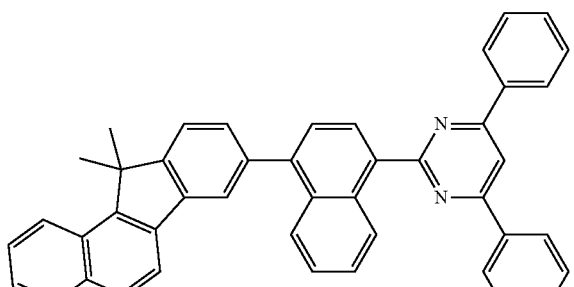
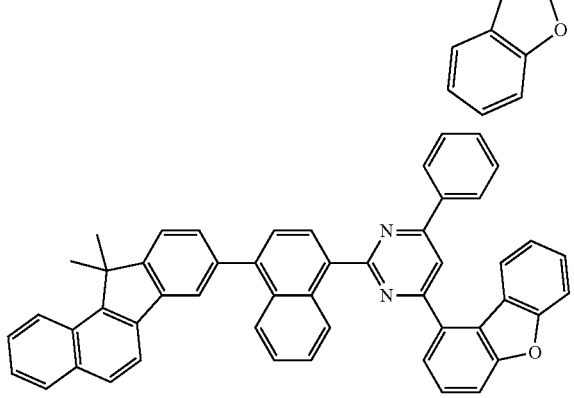
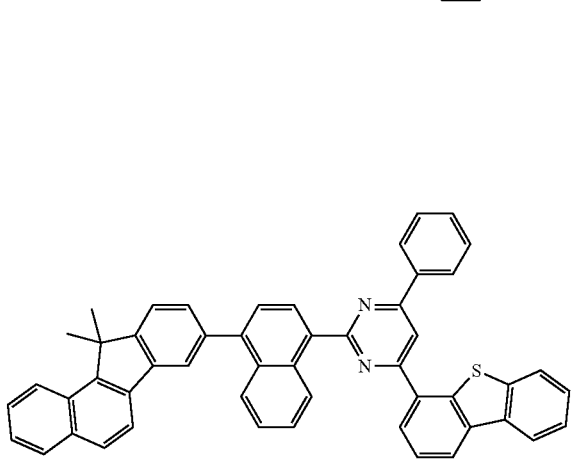
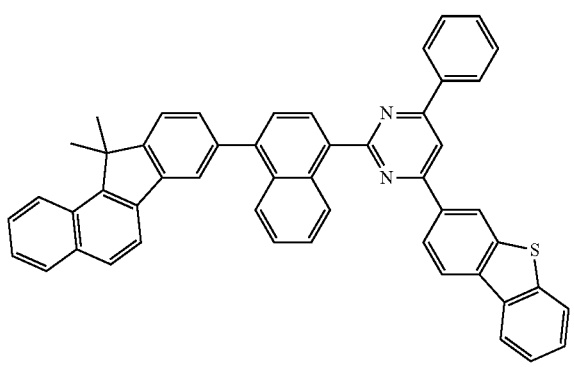

949
-continued
950
-continued
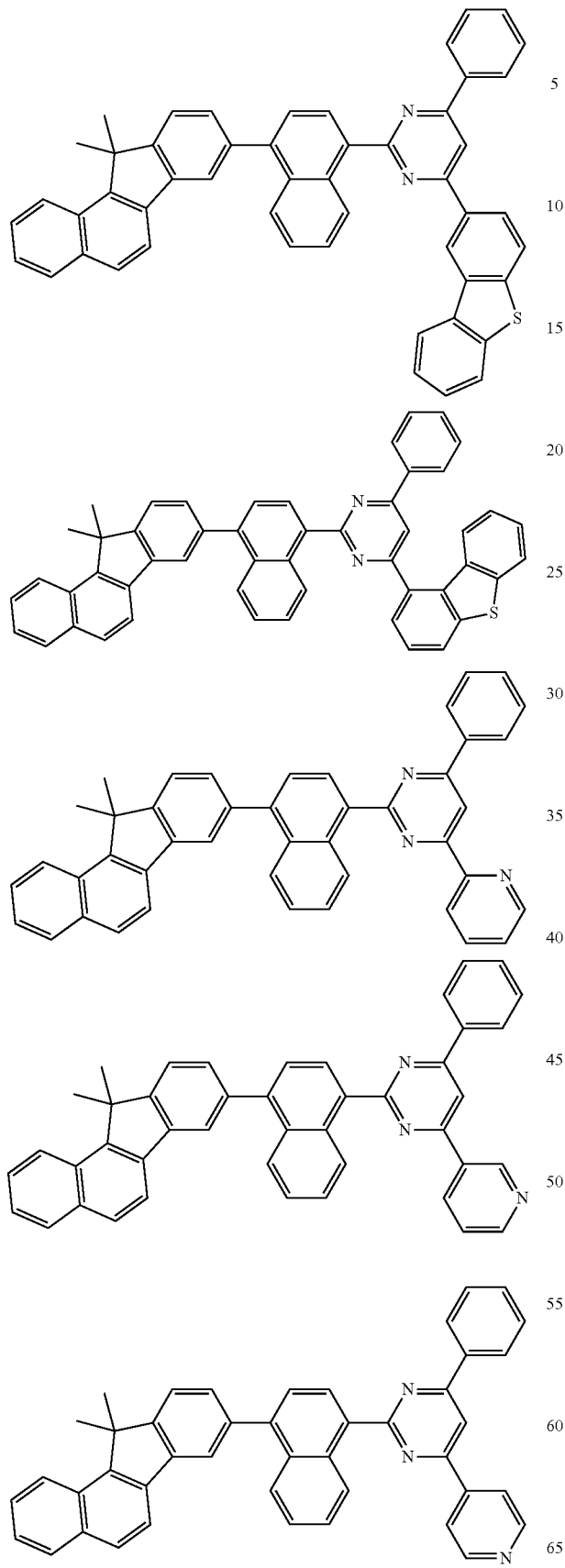
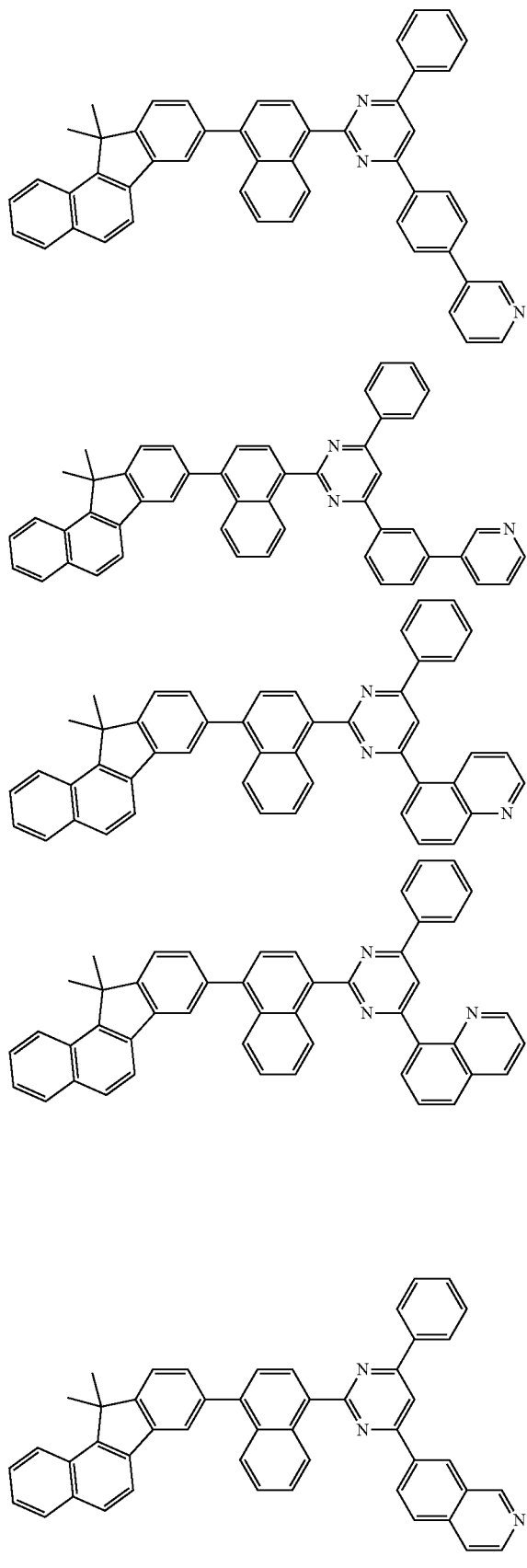

951
-continued
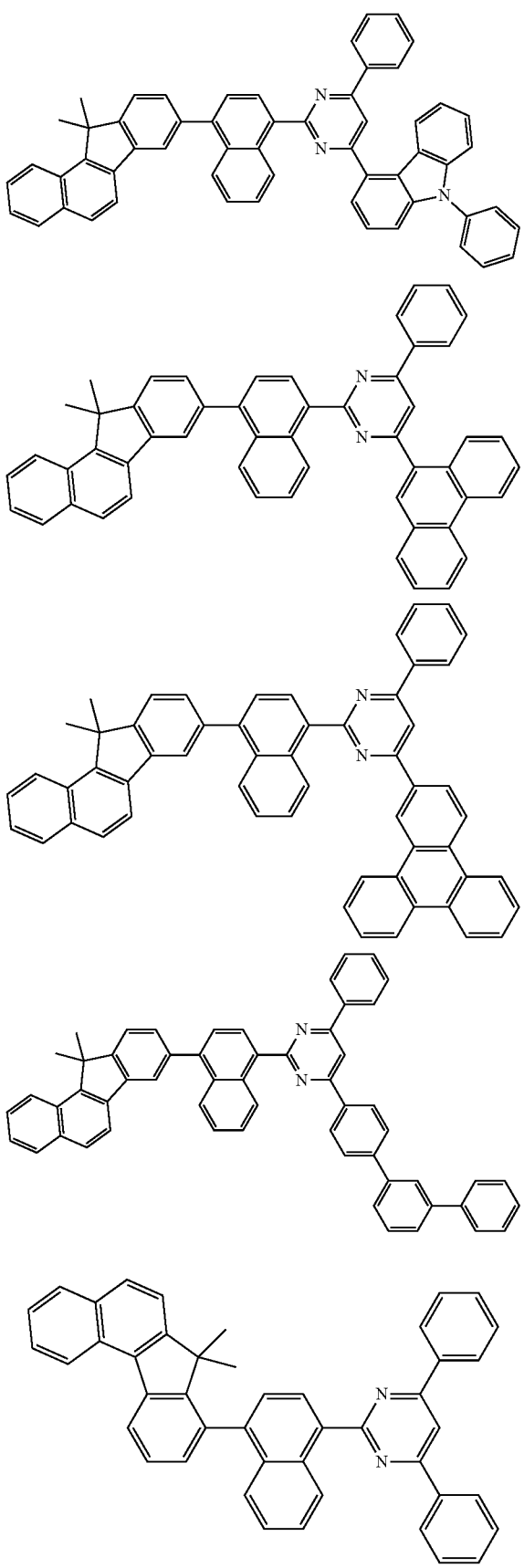
952
-continued
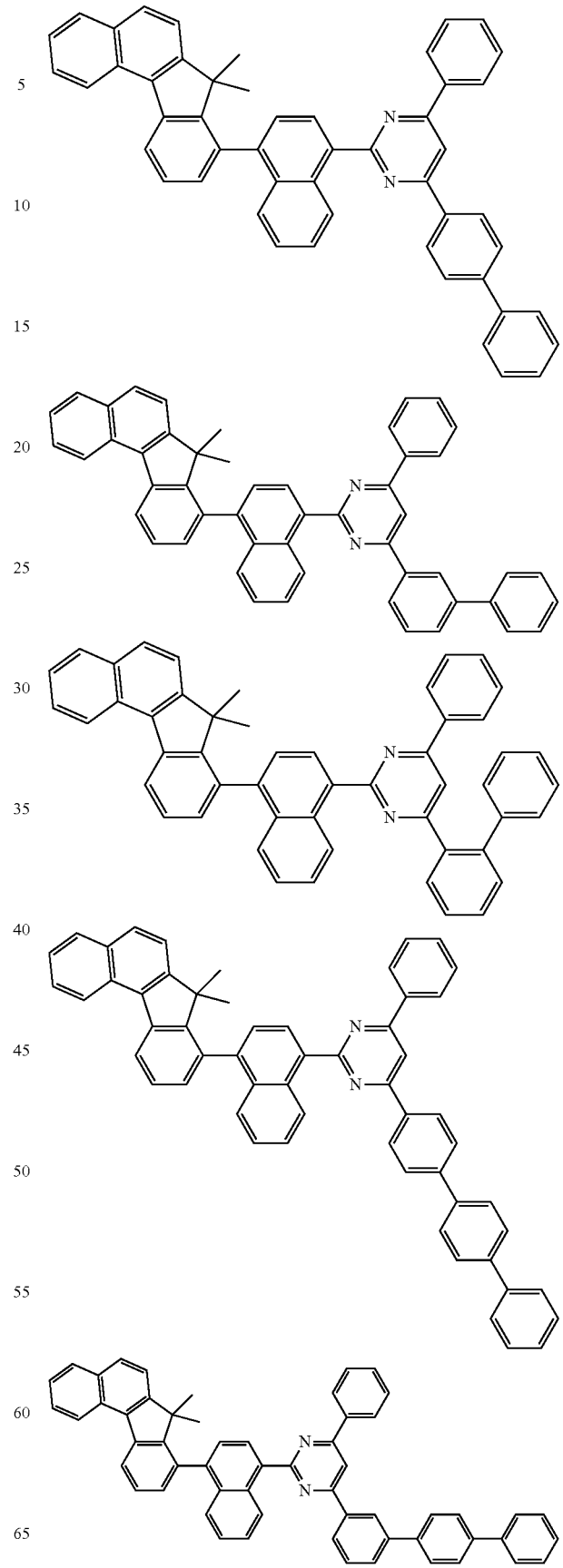

953
-continued
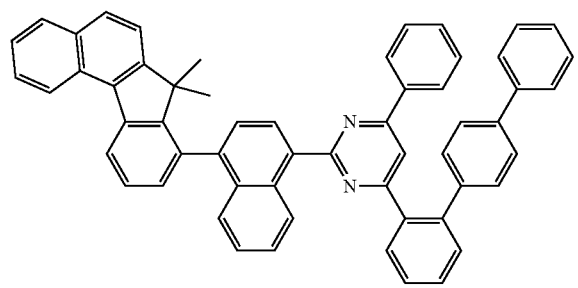
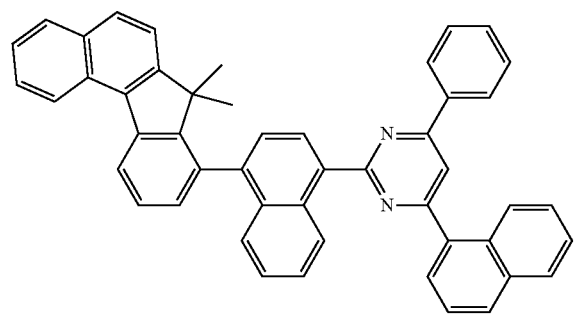
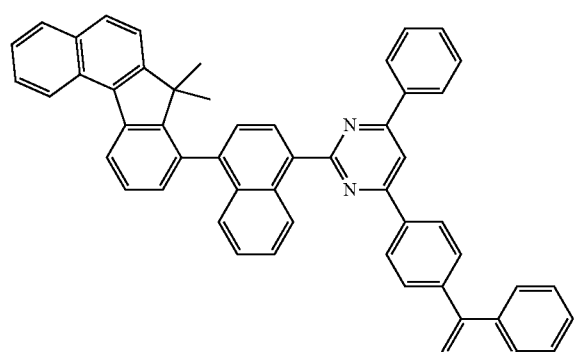
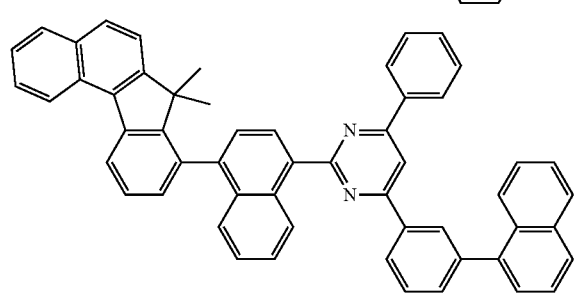
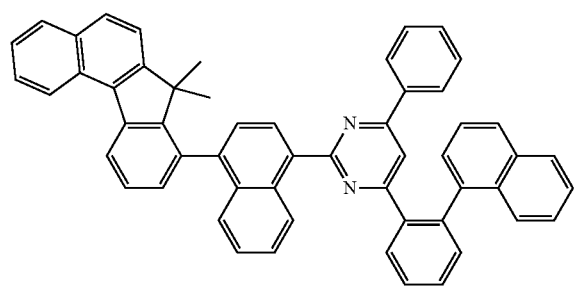
954
-continued
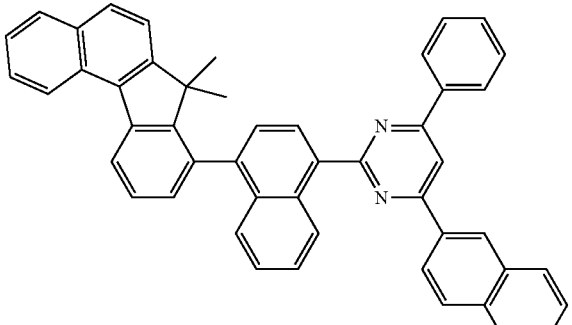
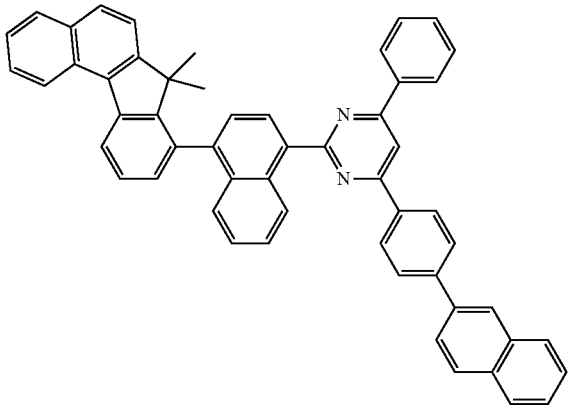
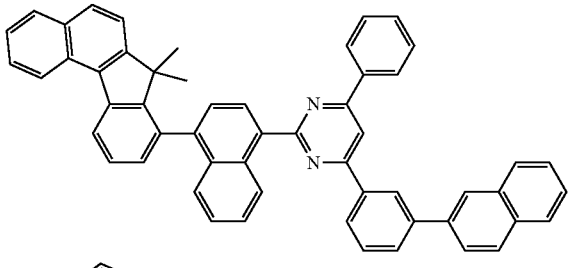
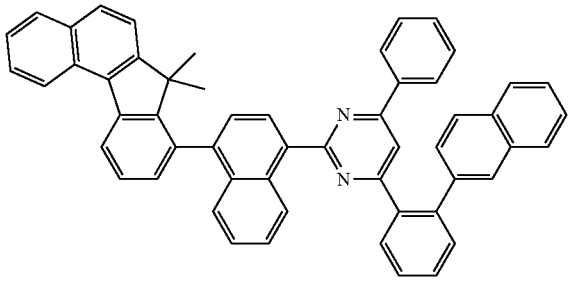
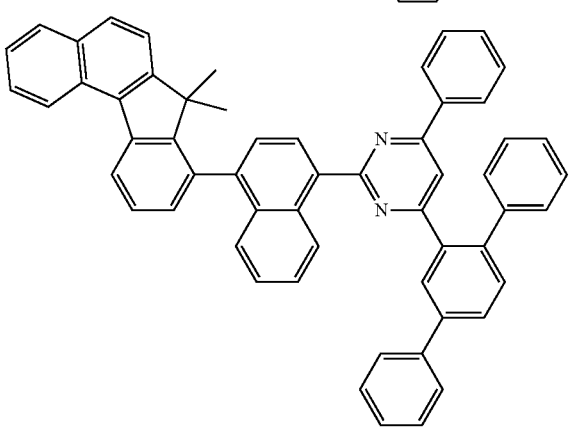

955
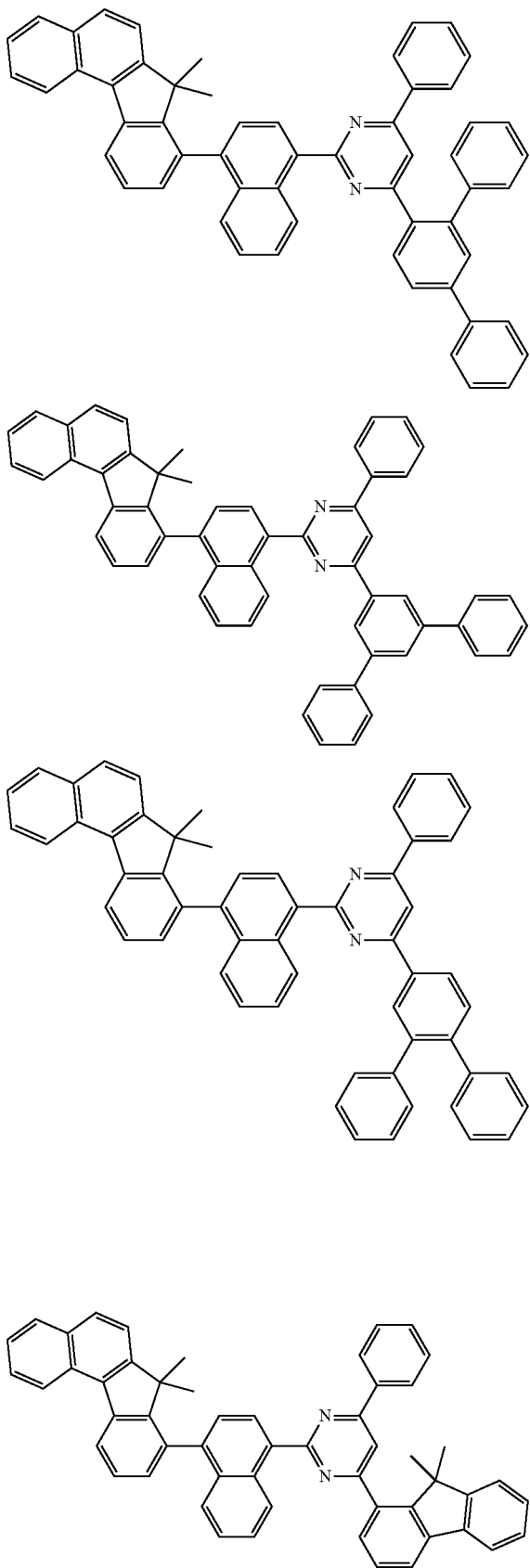
956
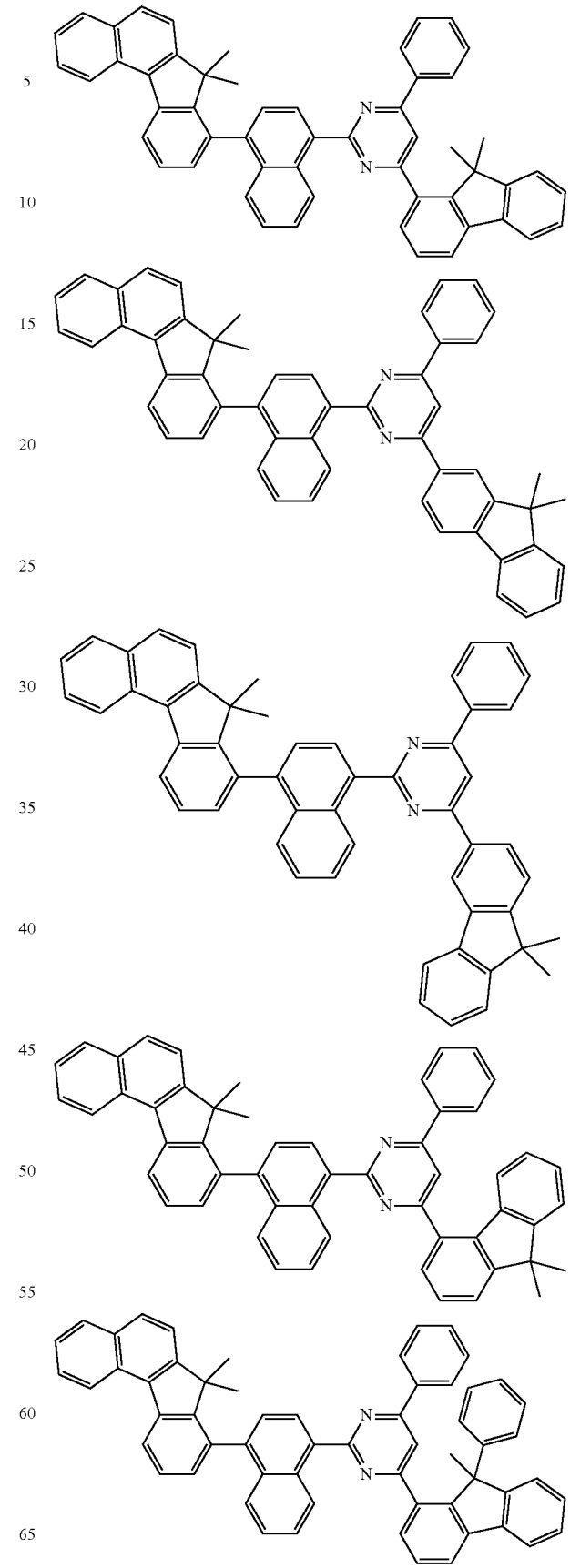

957
-continued
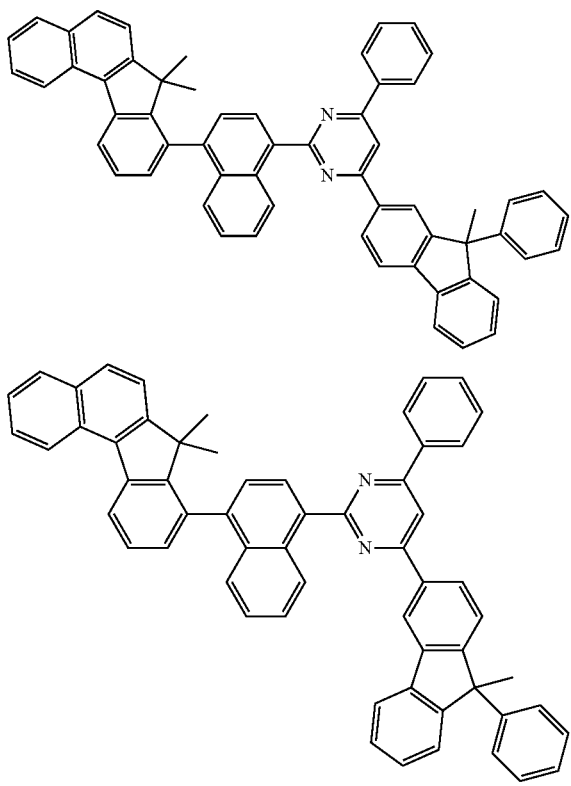
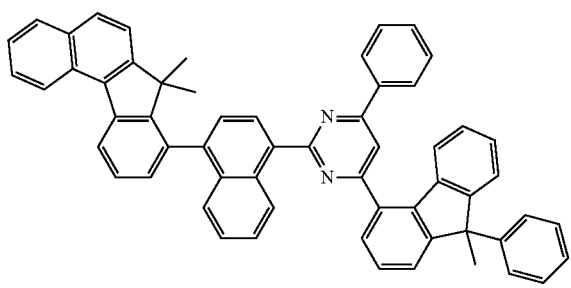
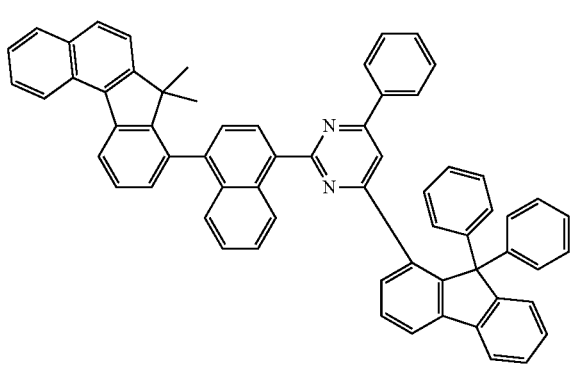
958
-continued
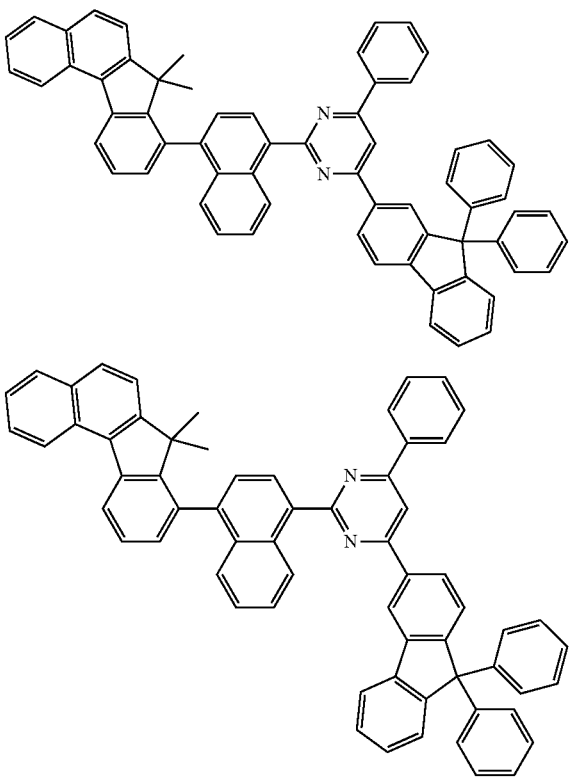
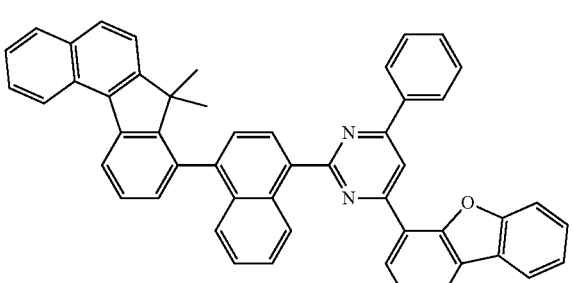

| 959 -continued | 960 -continued |
|---|---|
| 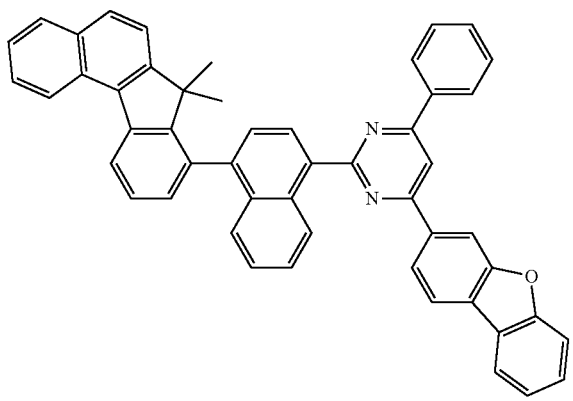 | 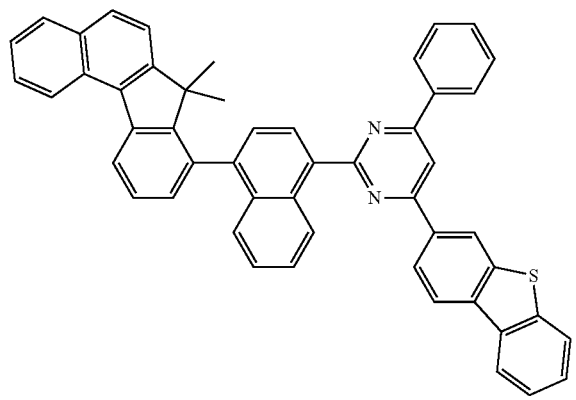 |
| 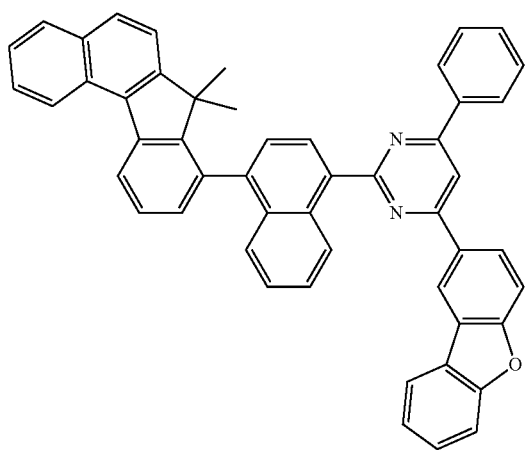 | 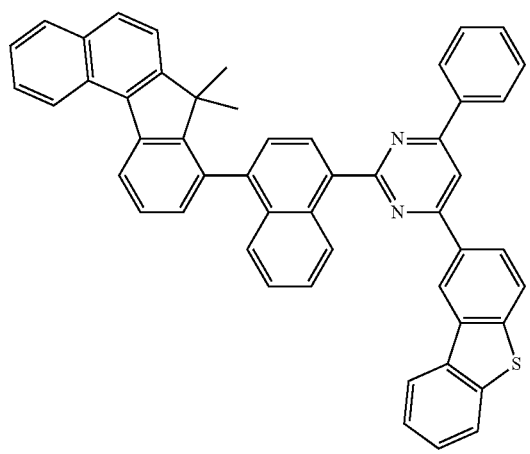 |
| 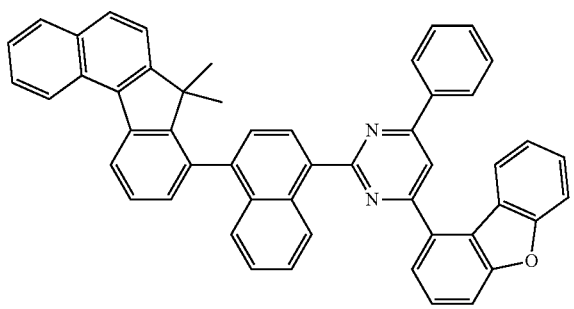 | 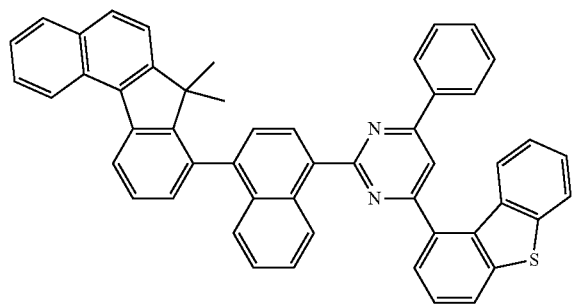 |
| 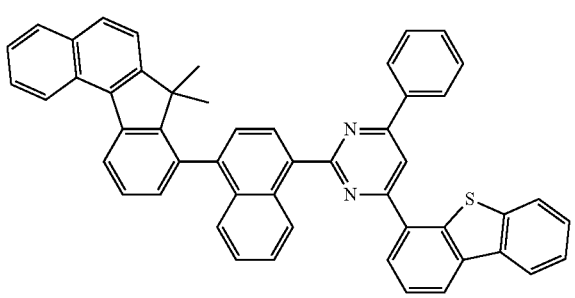 | 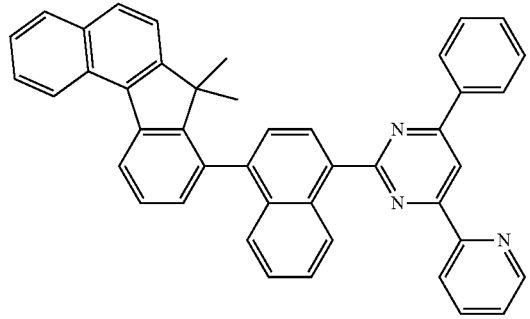 |

961
-continued
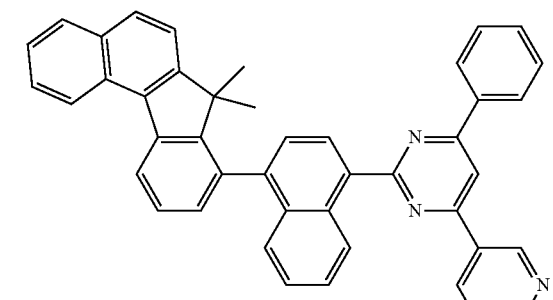
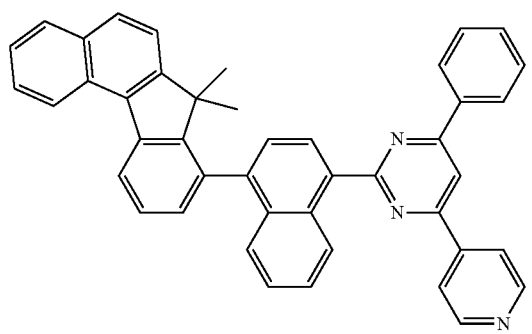
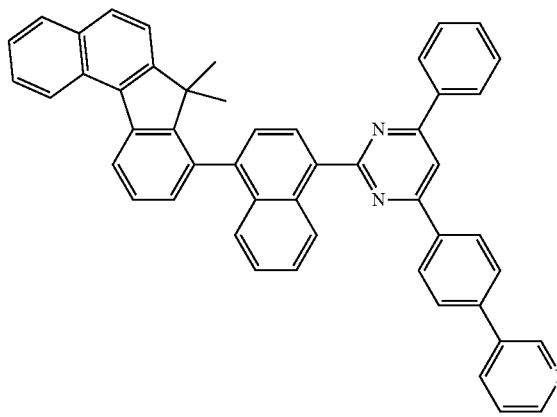
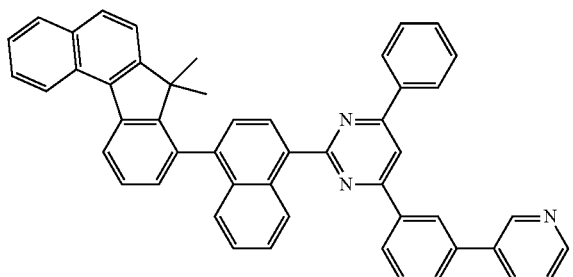
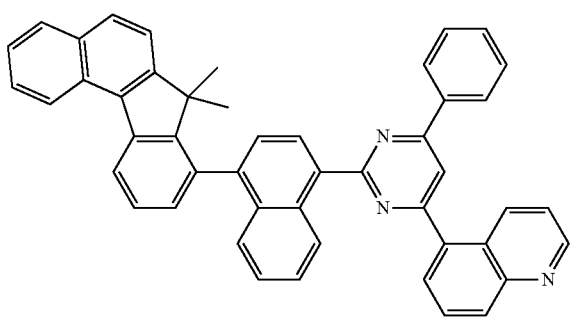
962
-continued
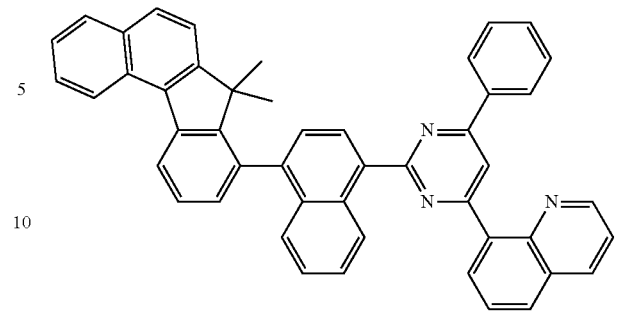
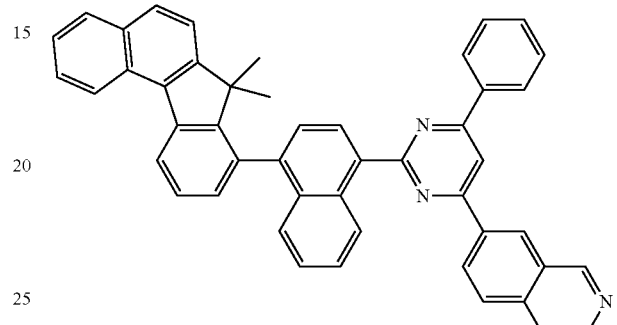
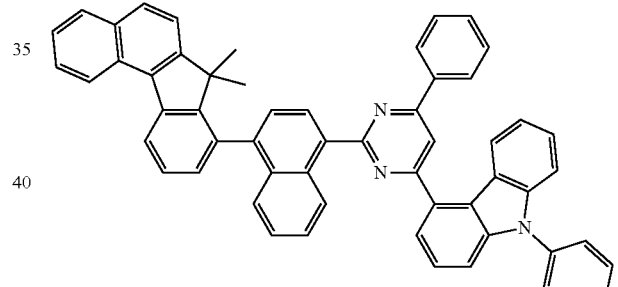
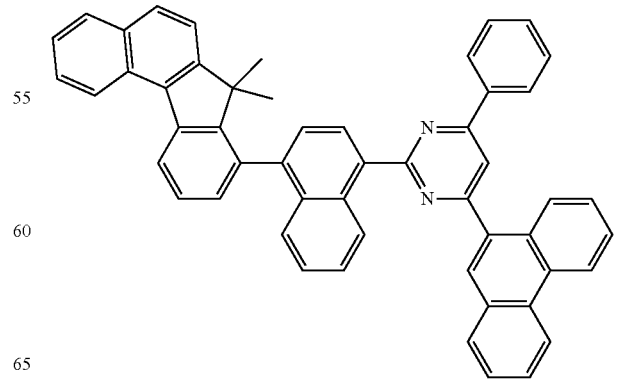
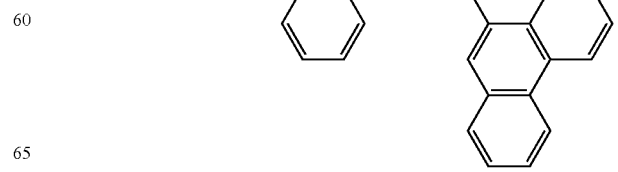

963
-continued
964
-continued
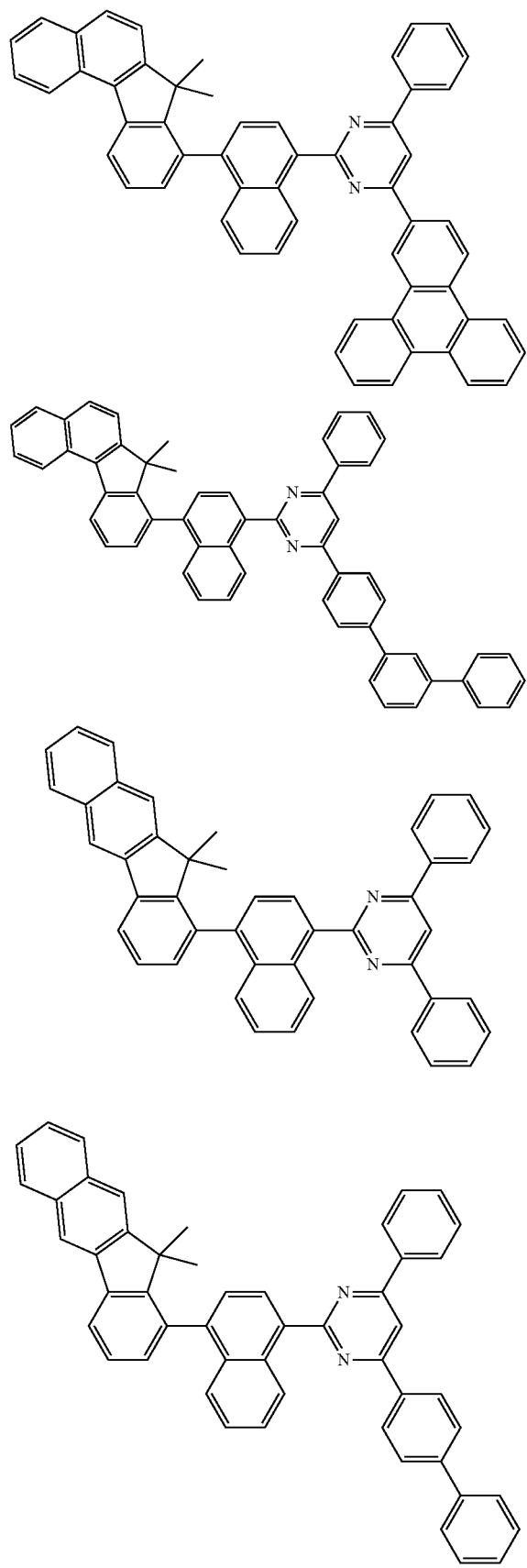
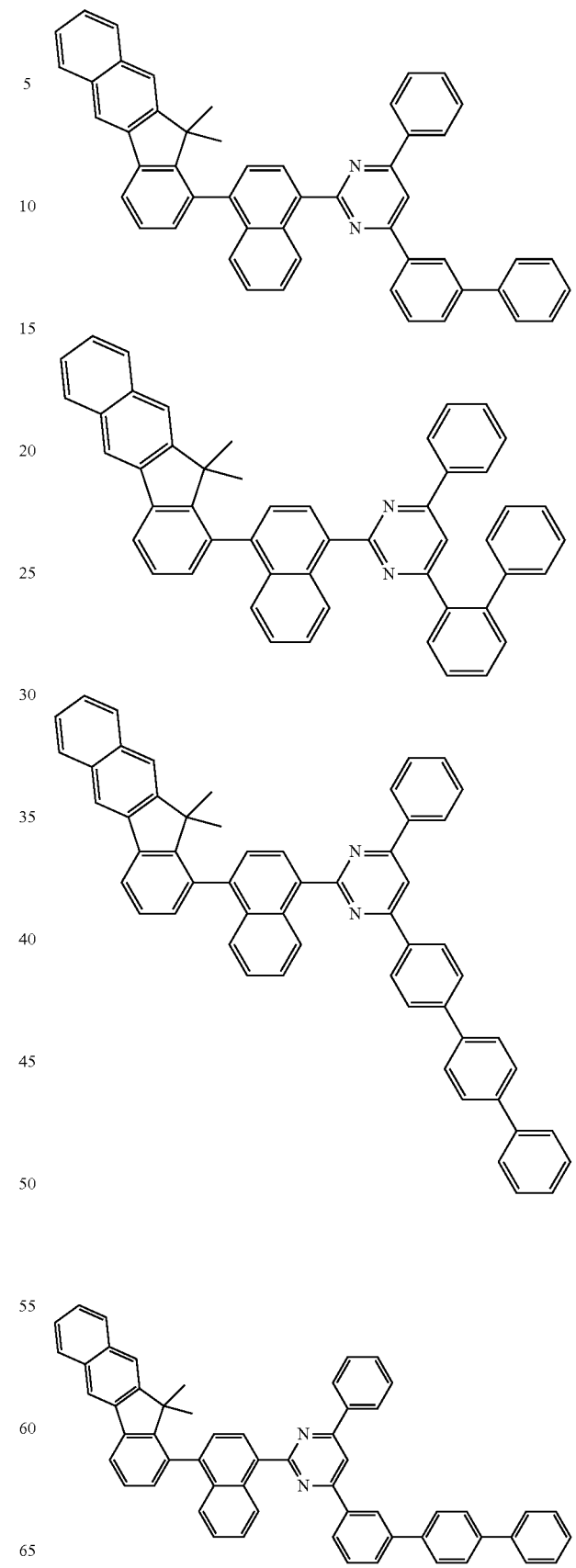

965
-continued
966
-continued
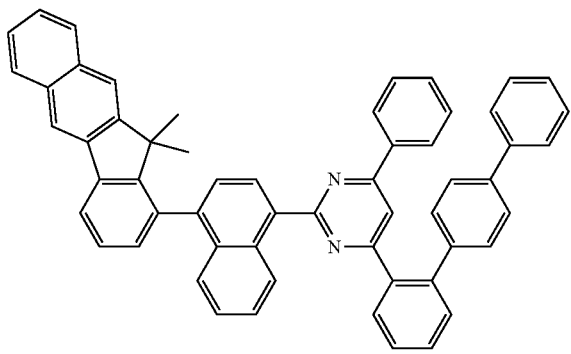
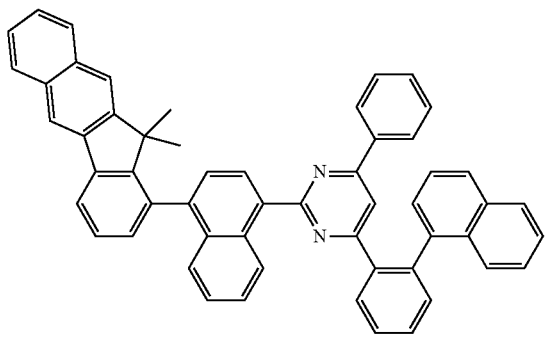
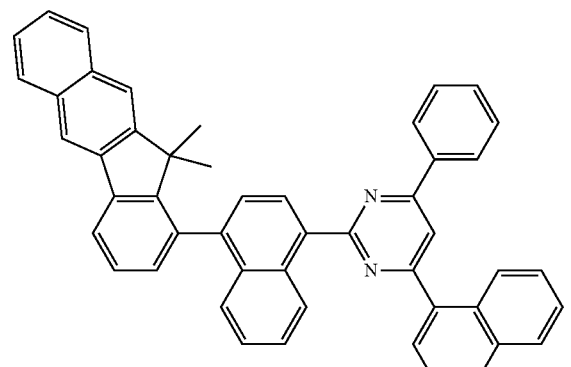
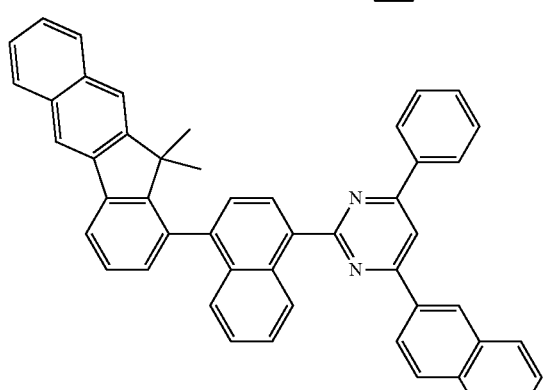
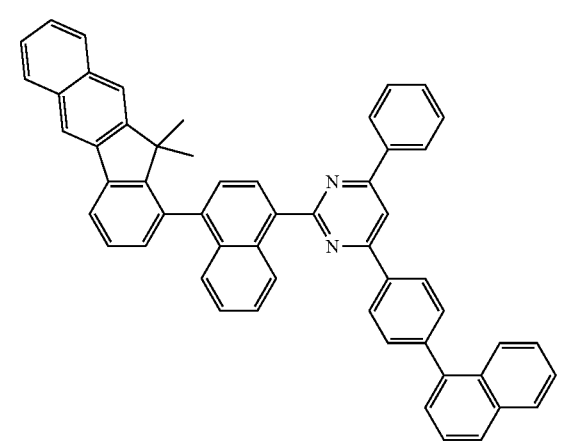
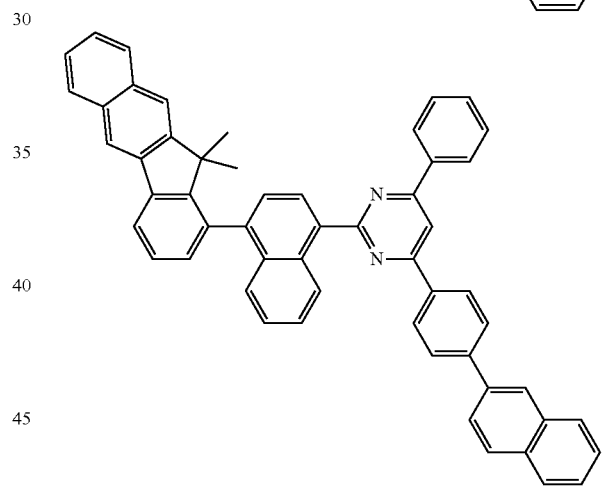
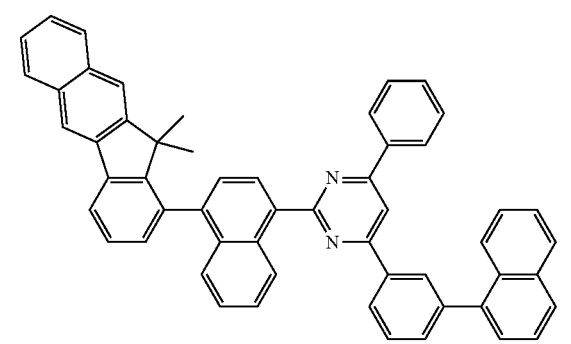
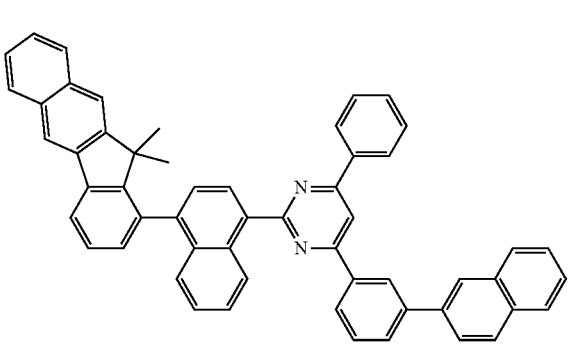

967
-continued
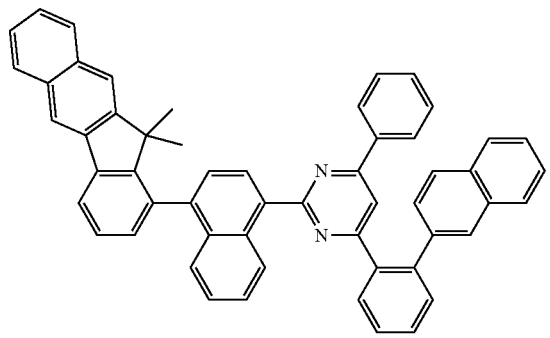
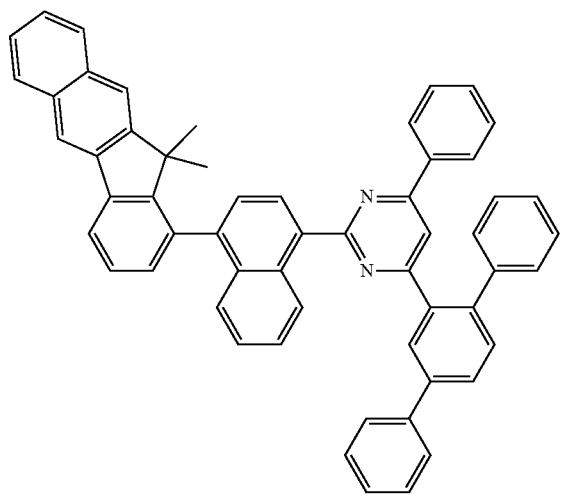
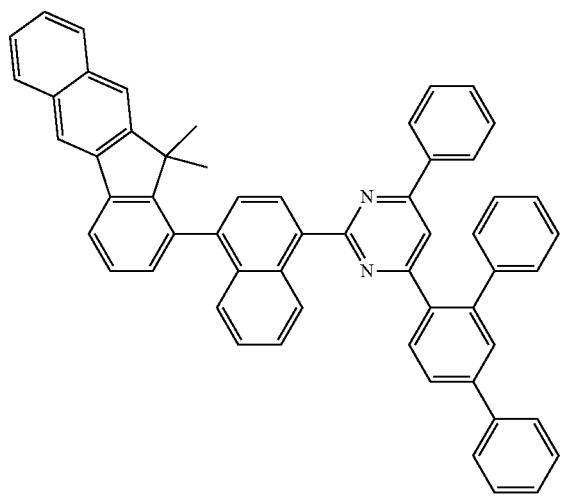
968
-continued
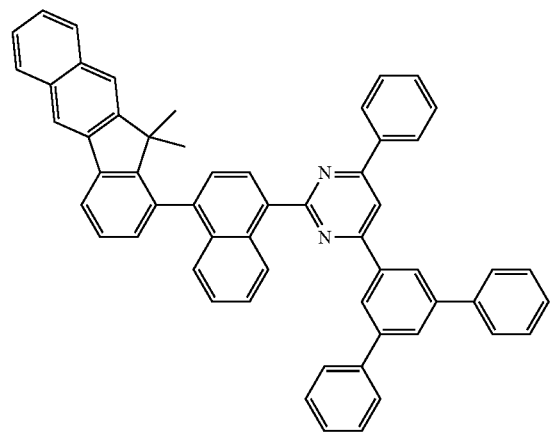
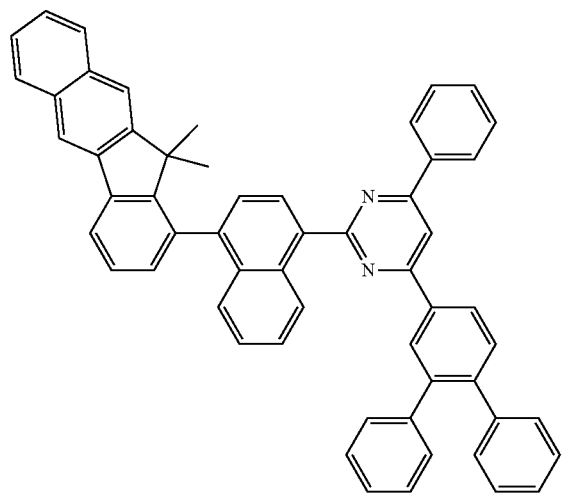
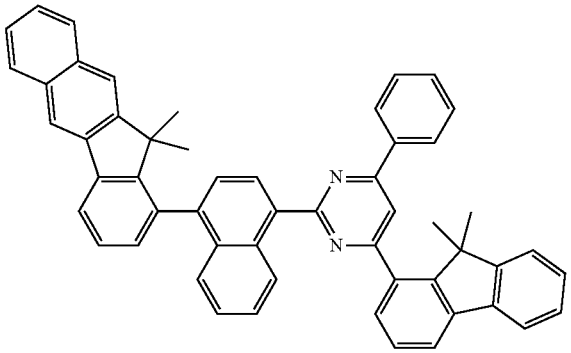

969
-continued
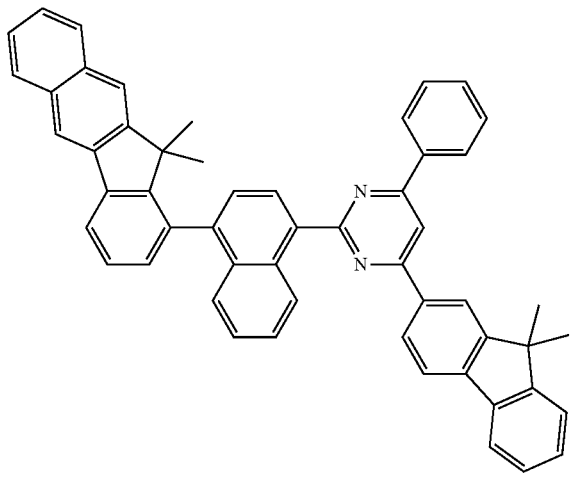
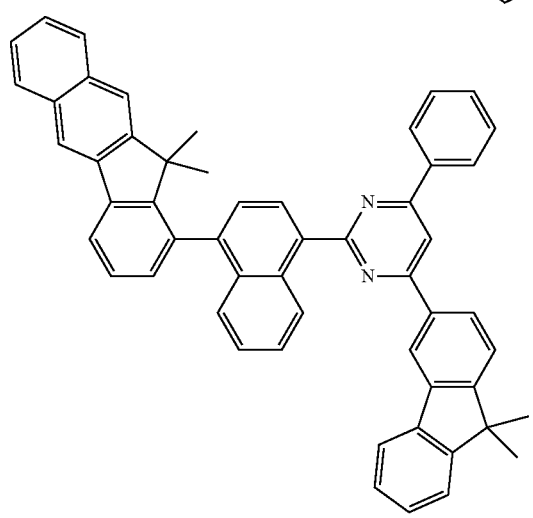
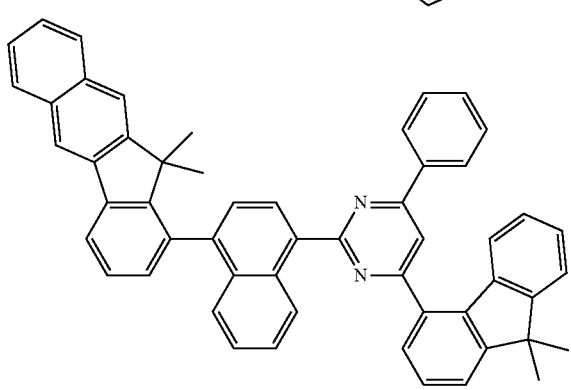
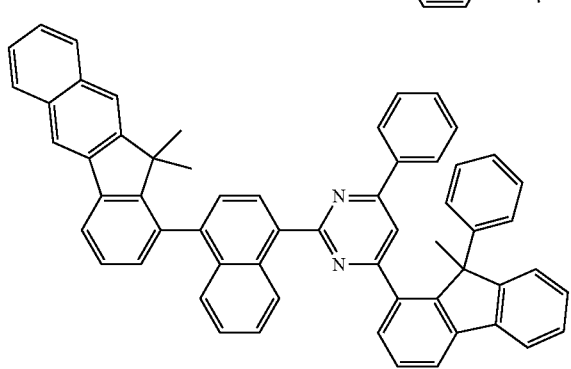
970
-continued
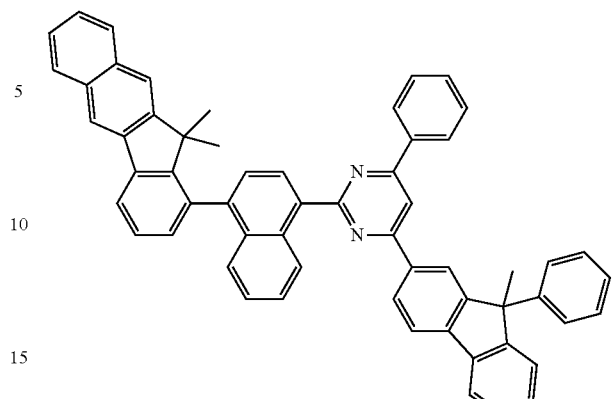
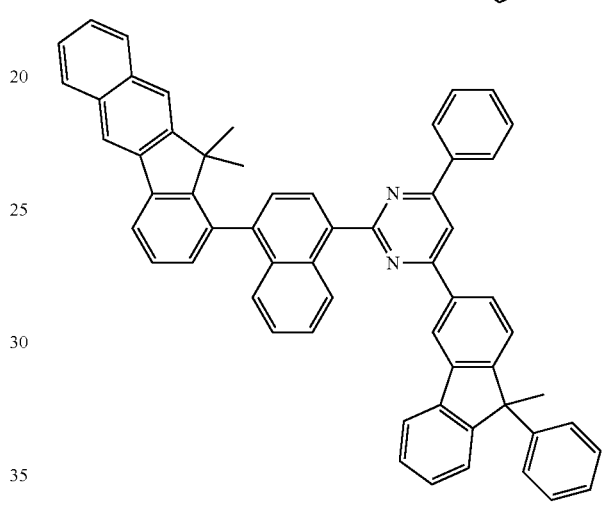
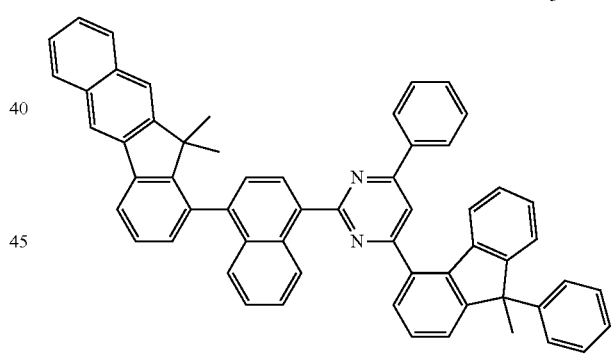
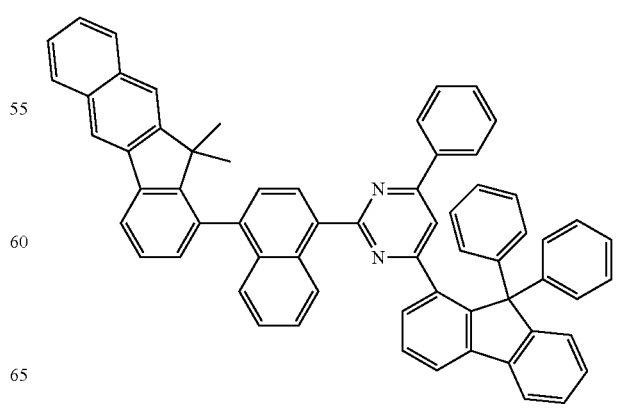

971
-continued
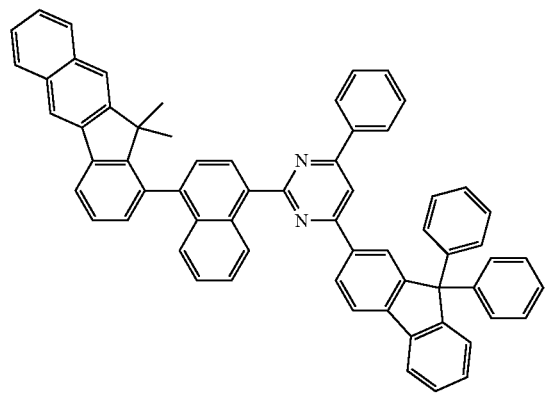
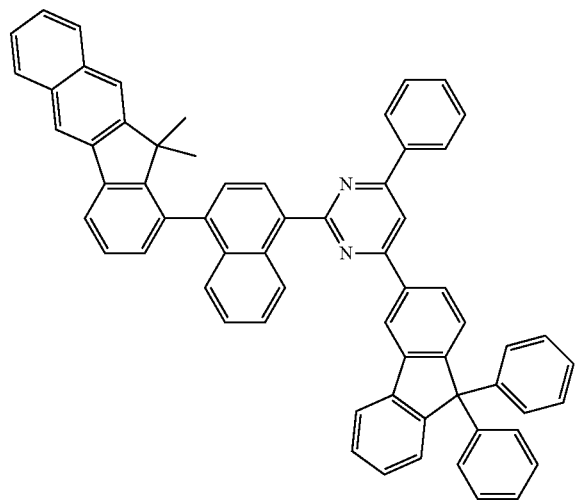
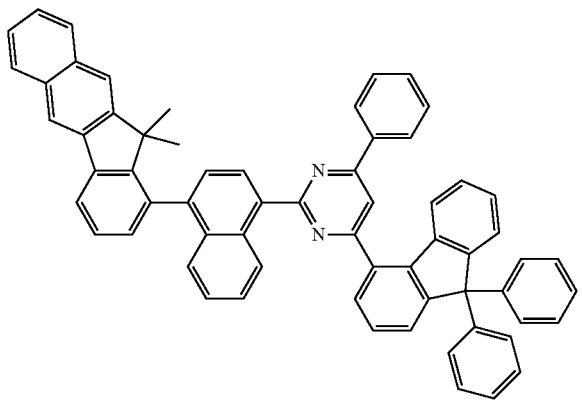
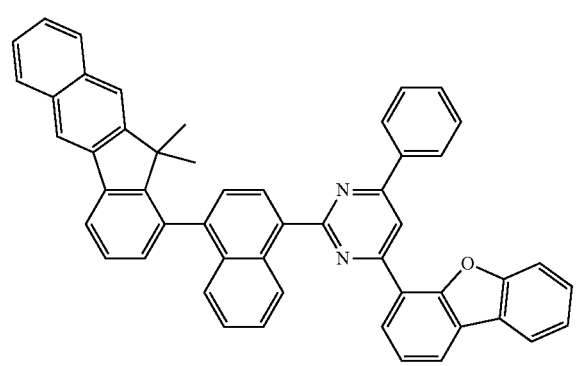
972
-continued
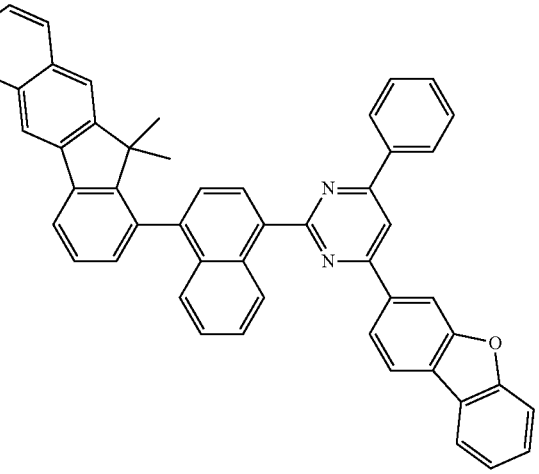
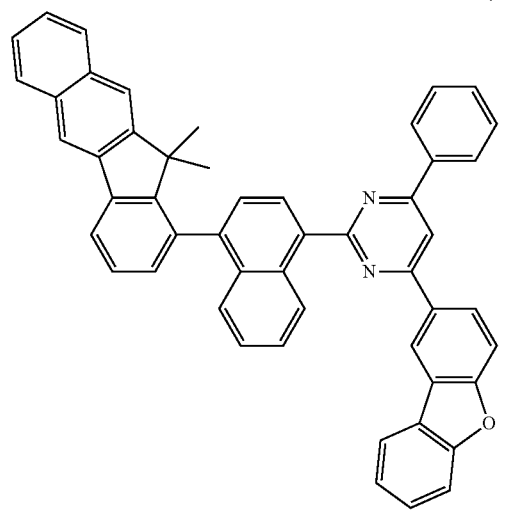
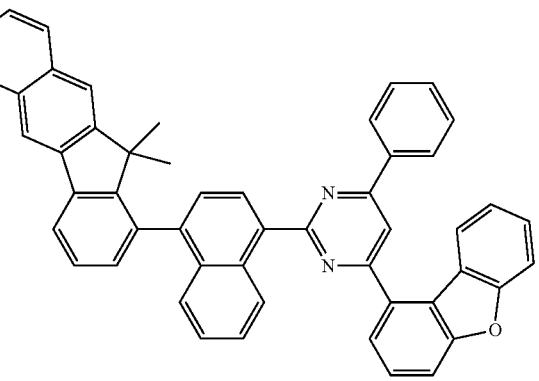
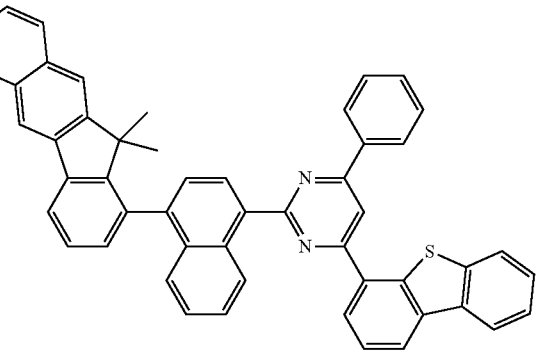

973
-continued
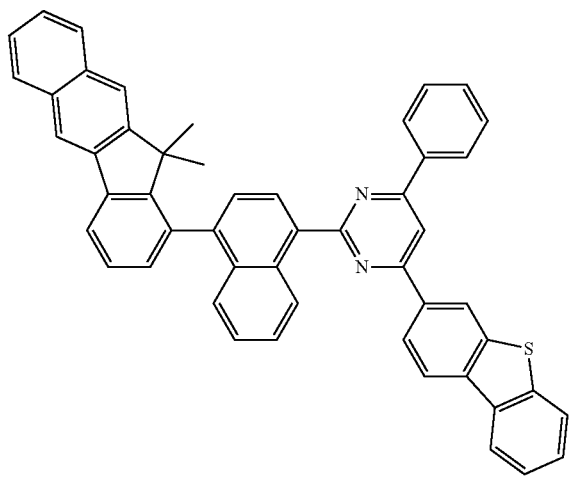
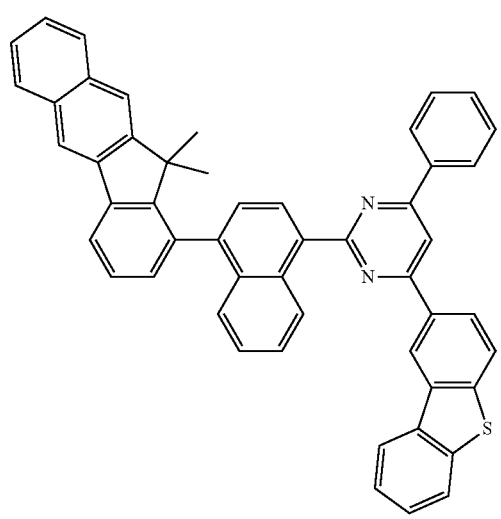
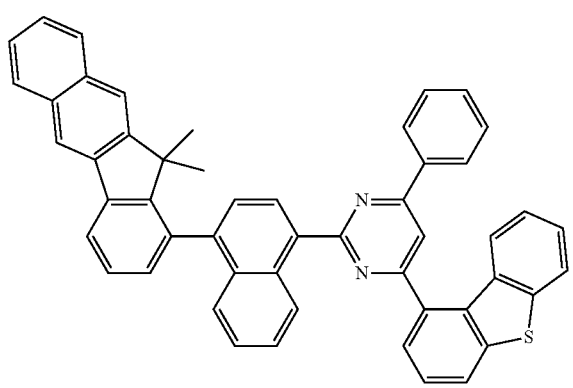
974
-continued
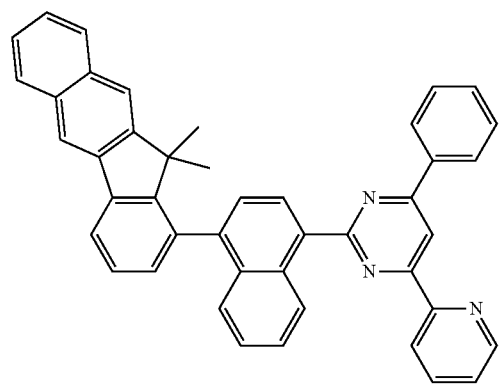
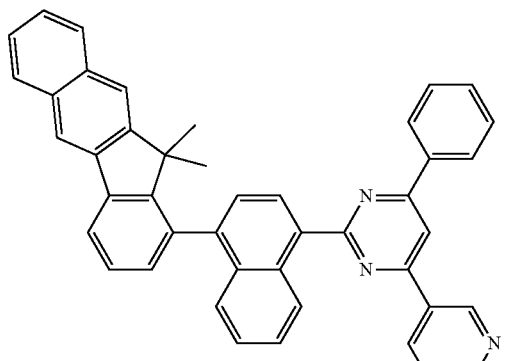
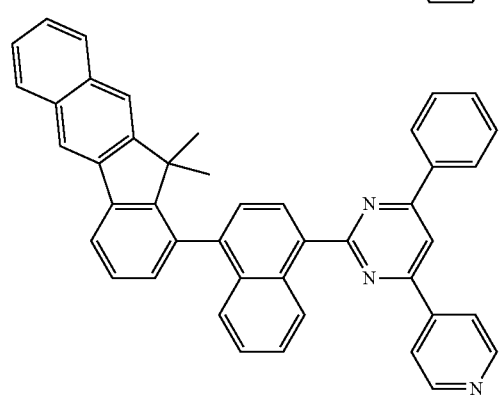
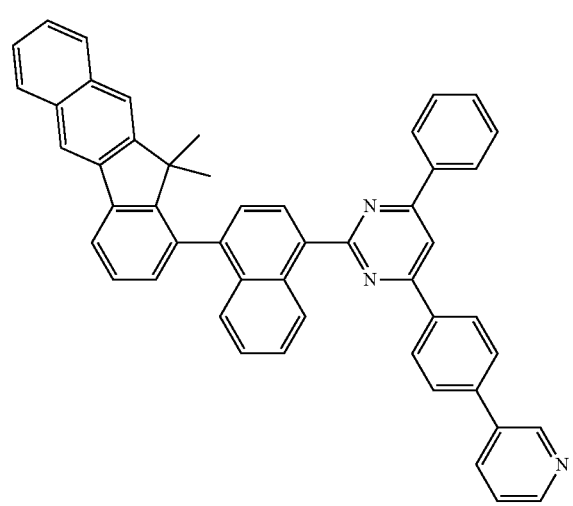

975
-continued
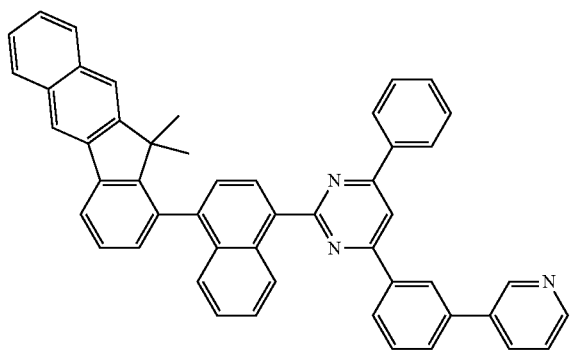
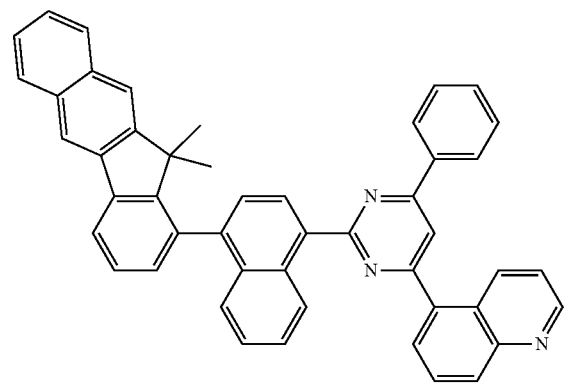
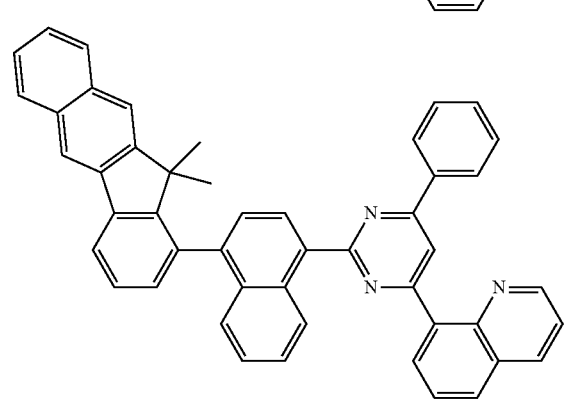
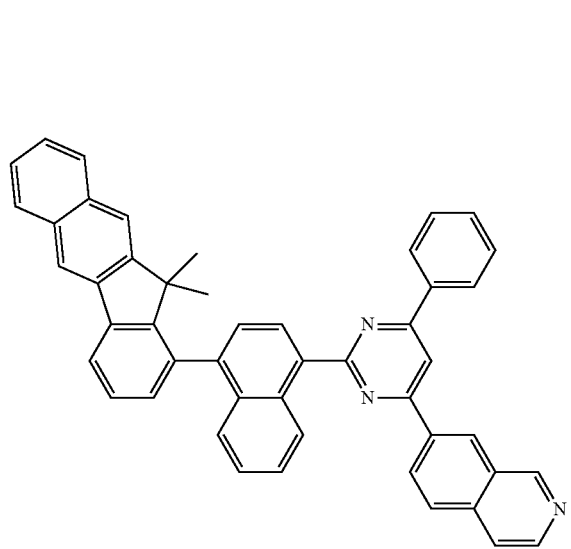
976
-continued
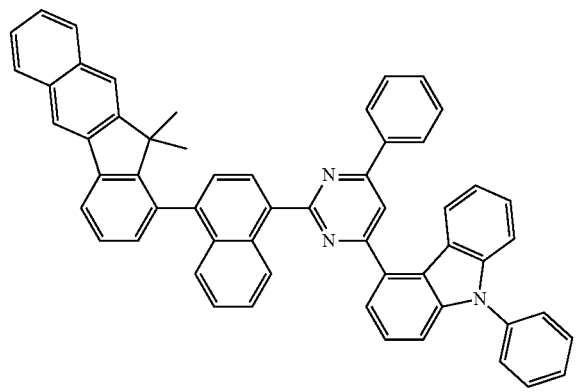
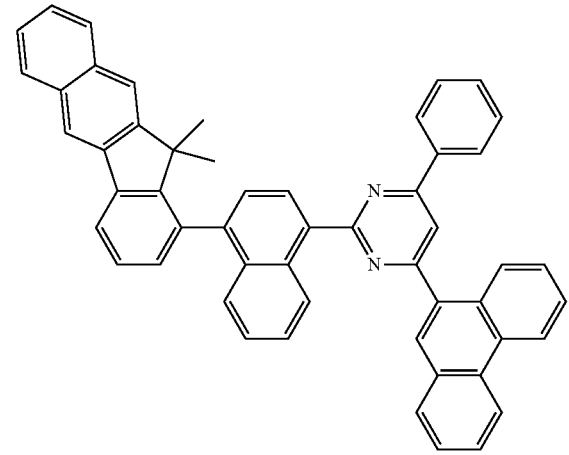
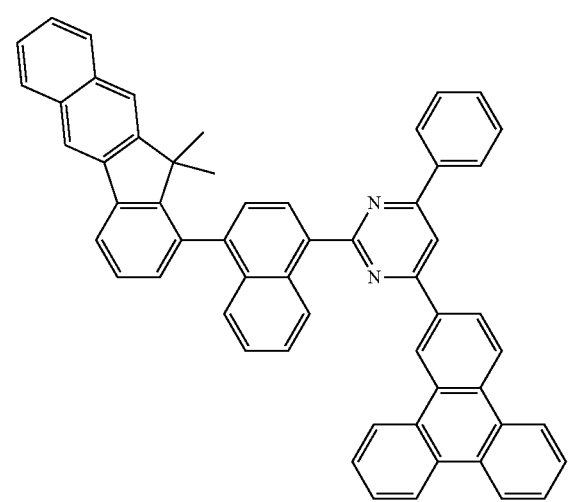

| 977 -continued | 978 -continued |
|---|---|
| 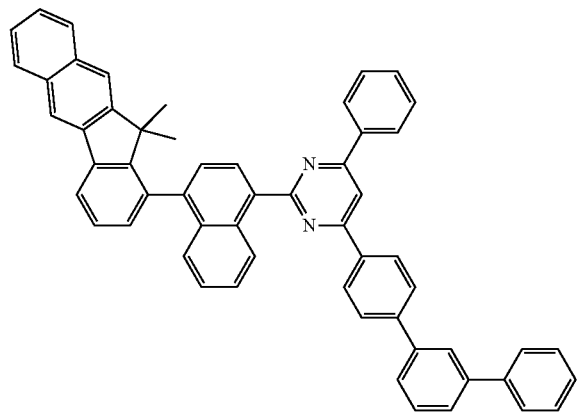 | 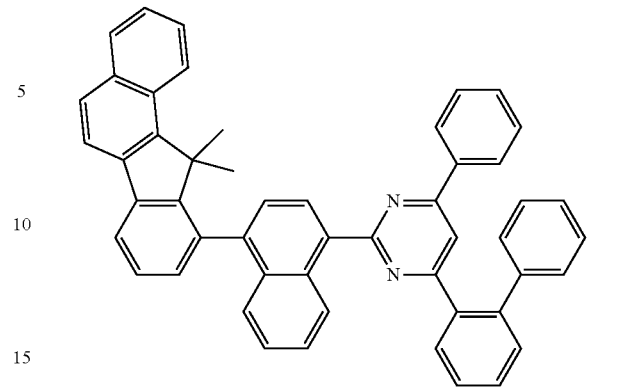 |
| 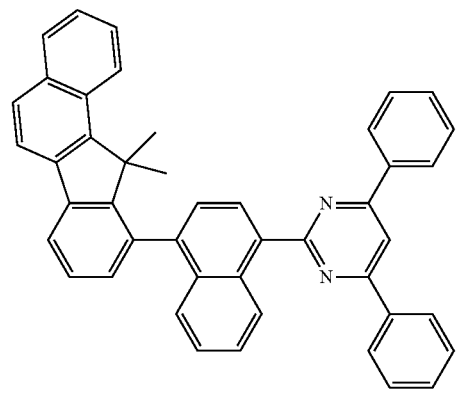 | 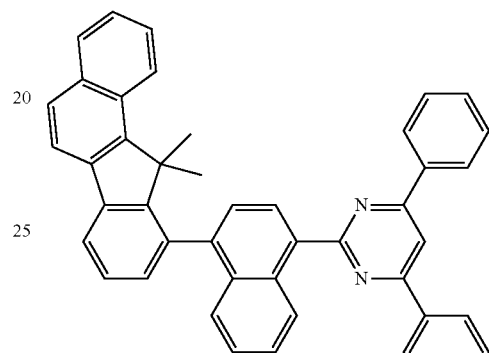 |
| 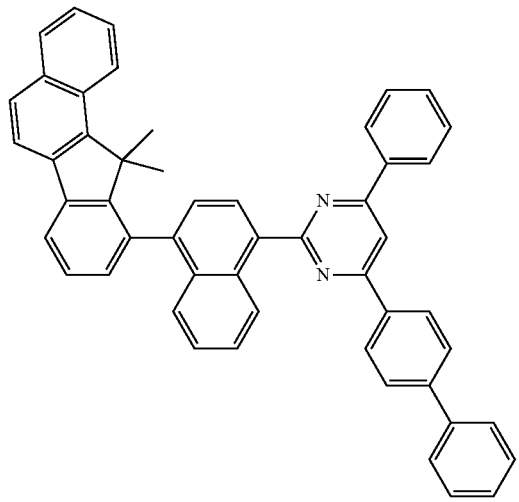 | 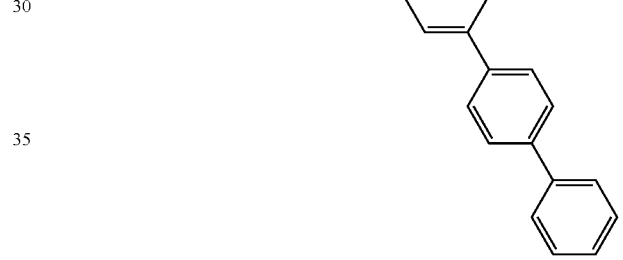 |
| 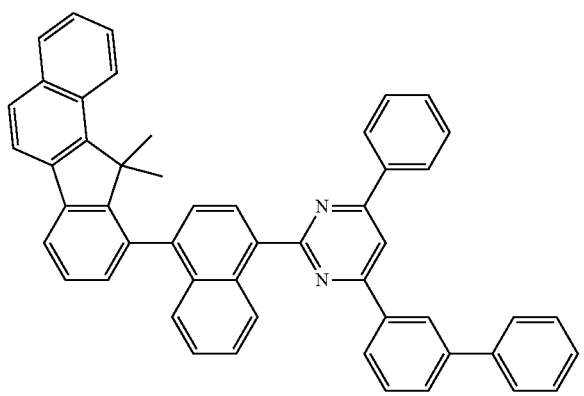 | 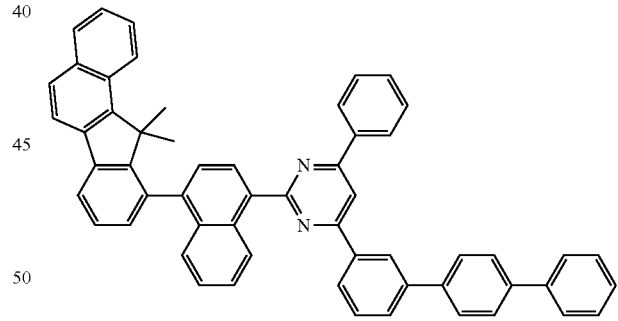 |
|  | 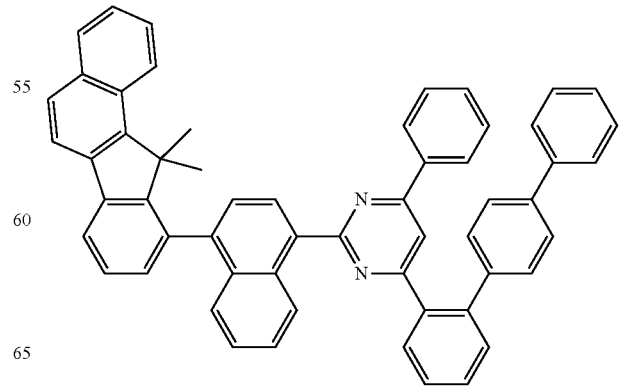 |

979
-continued
980
-continued
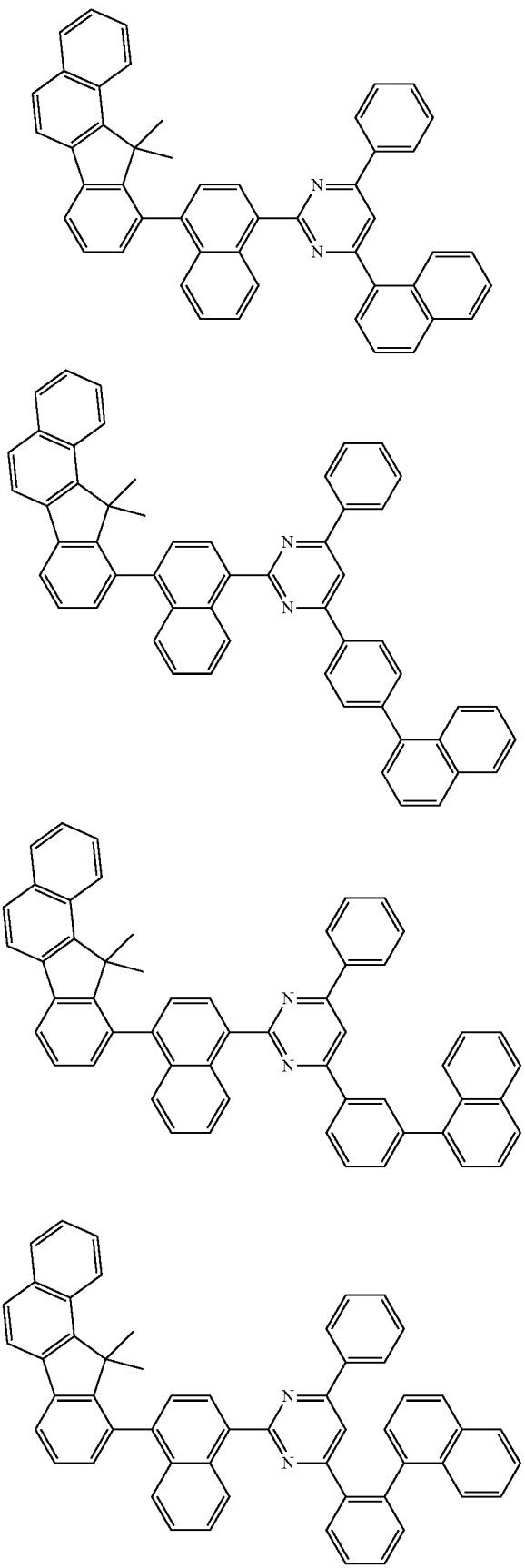
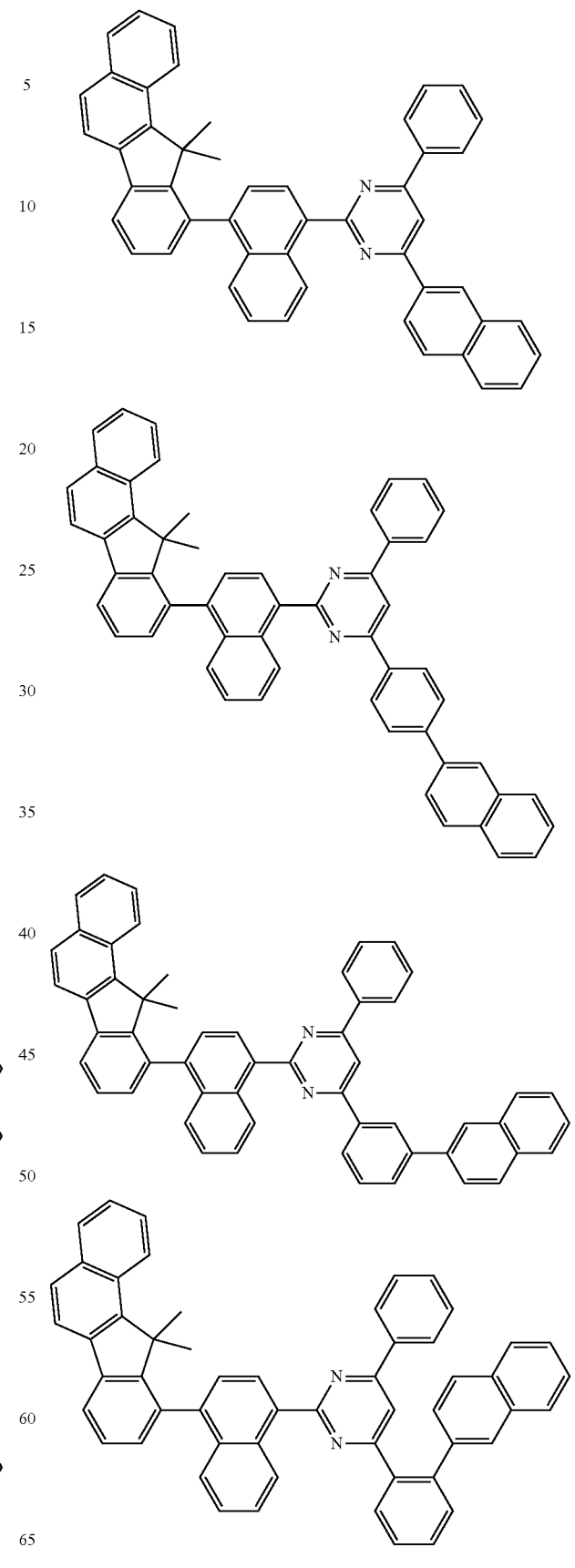

981
-continued
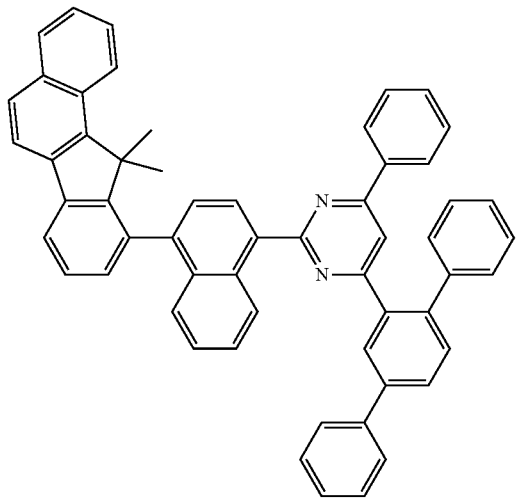
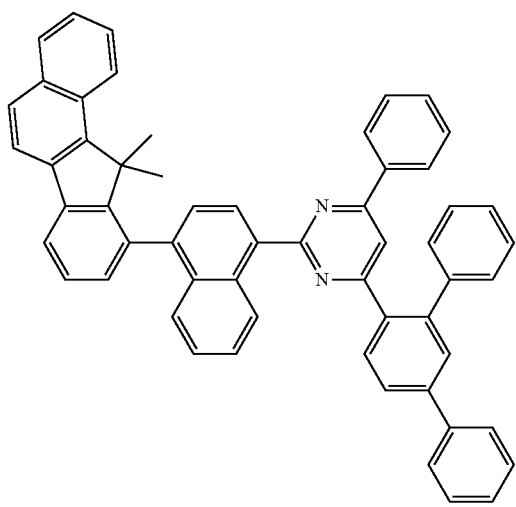
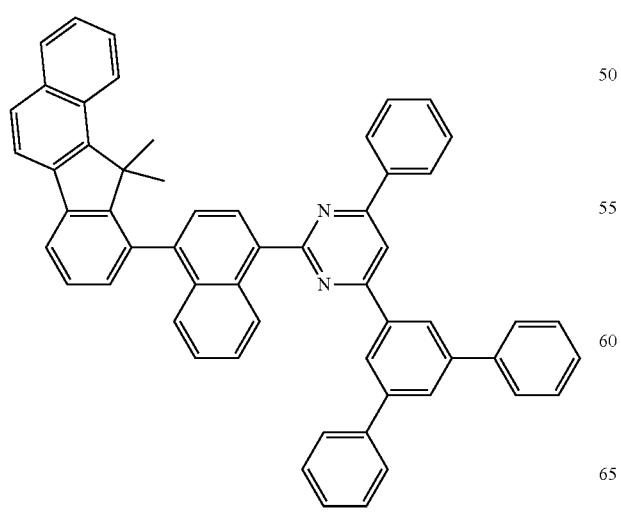
982
-continued
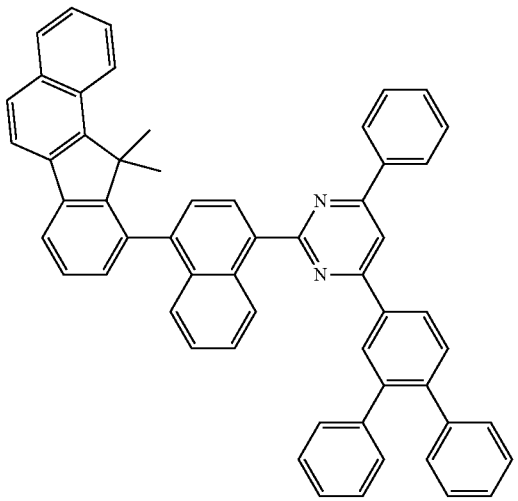
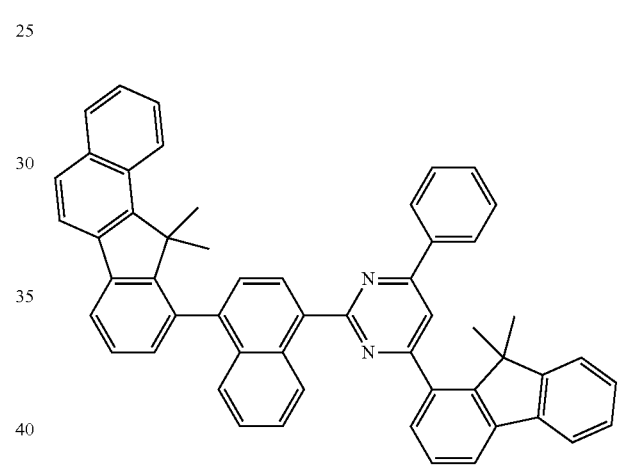
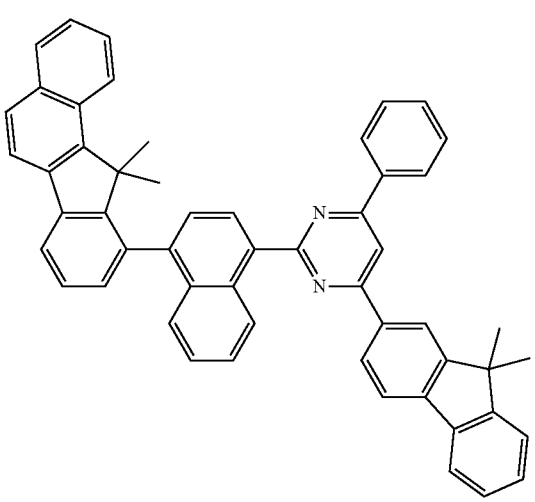

| 983 | 984 |
|---|---|
| -continued | -continued |</br>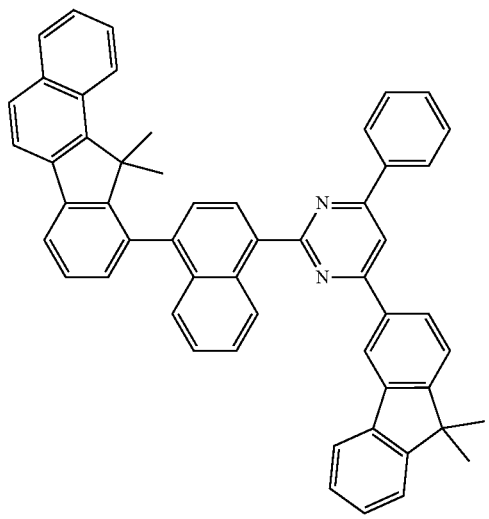 | 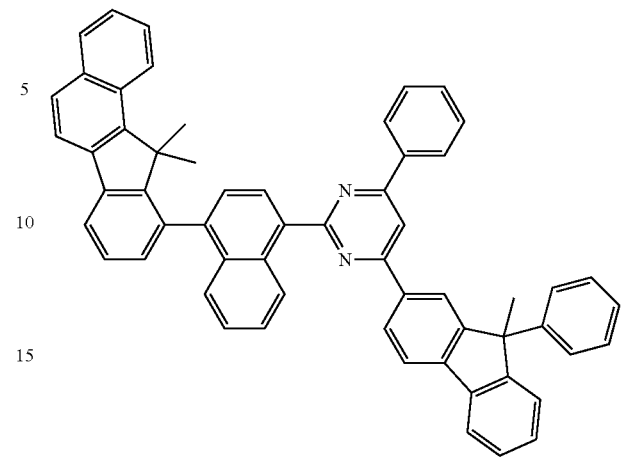 |
| 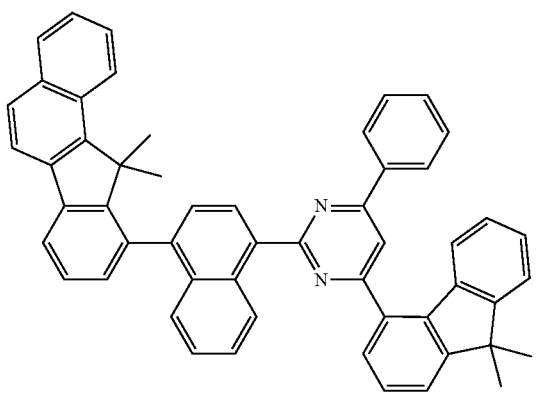 | 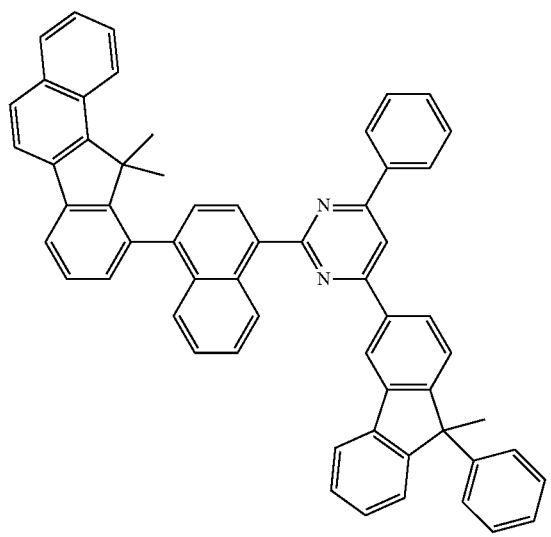 |
| 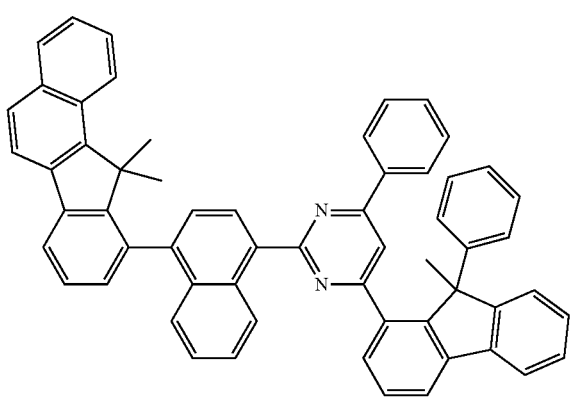 | 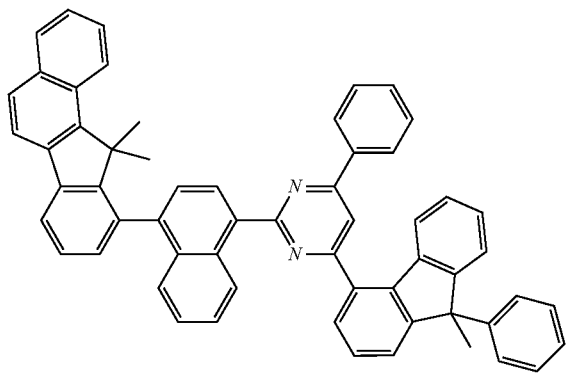 |

985
-continued
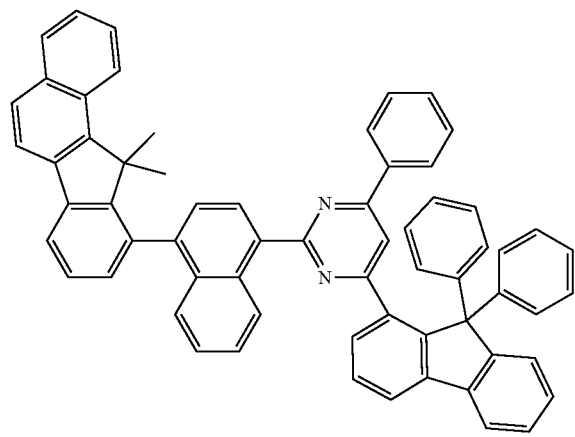
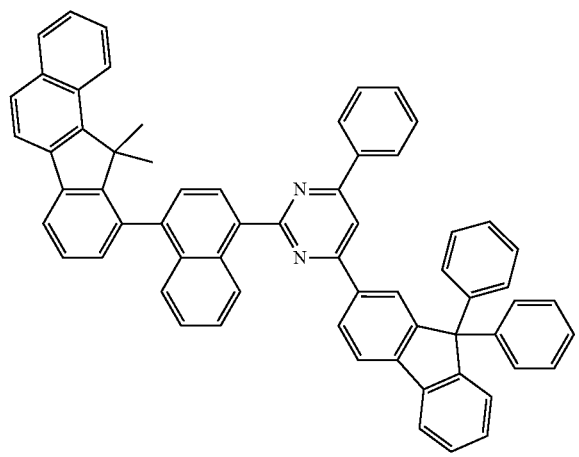
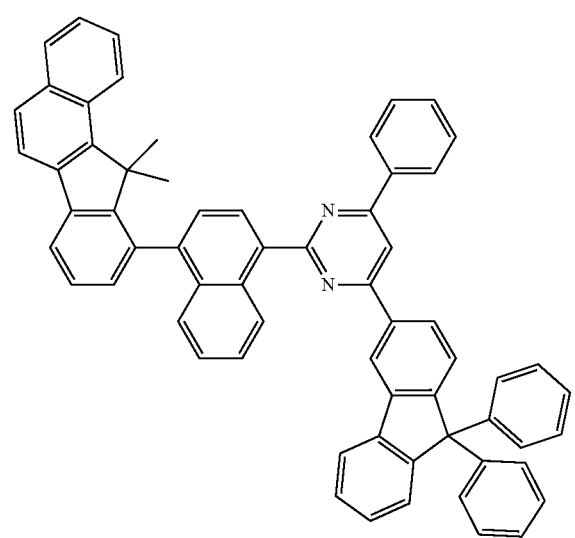
986
-continued
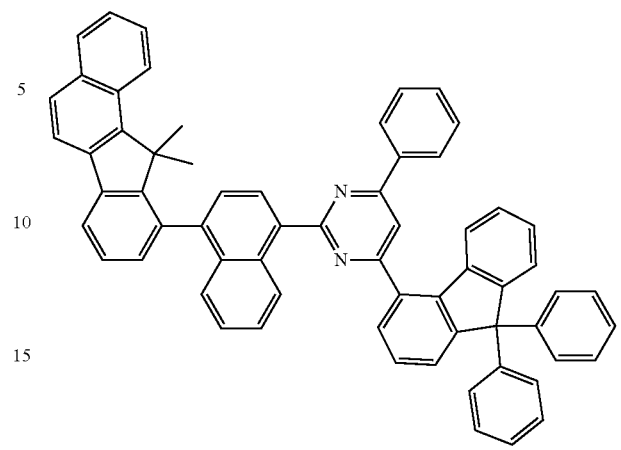
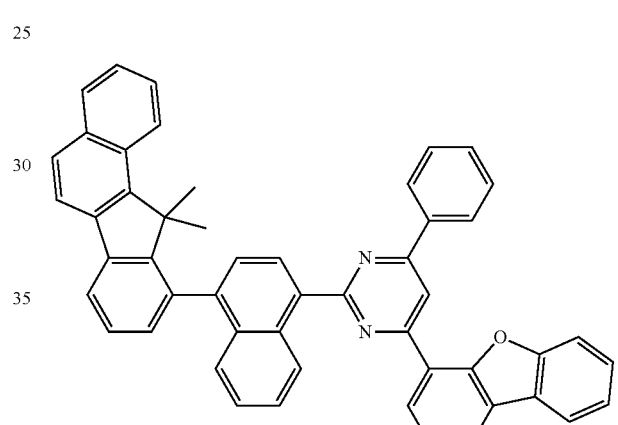
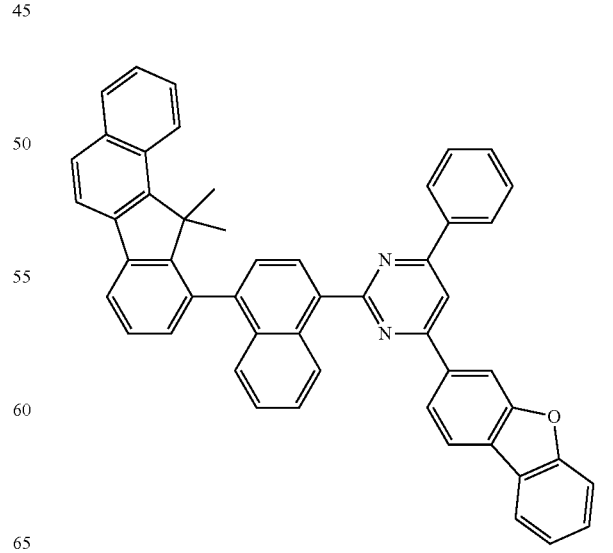

987
-continued
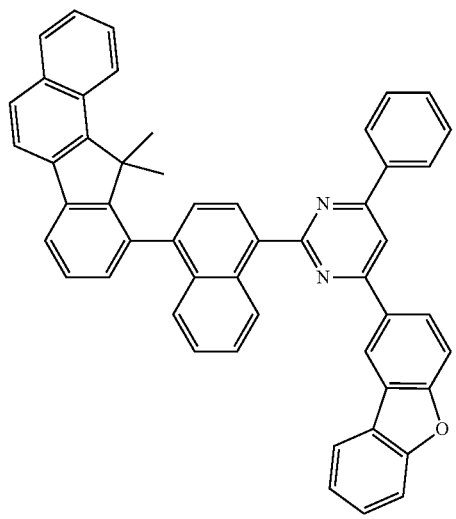
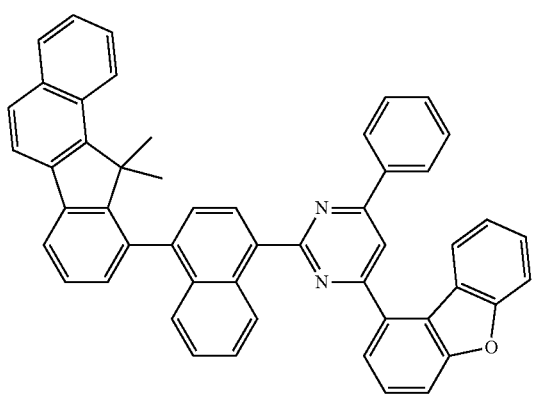
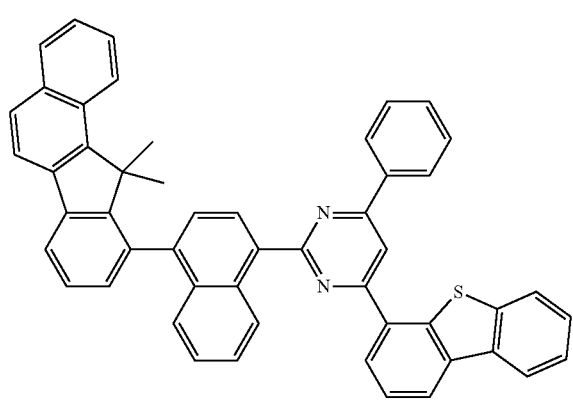
988
-continued
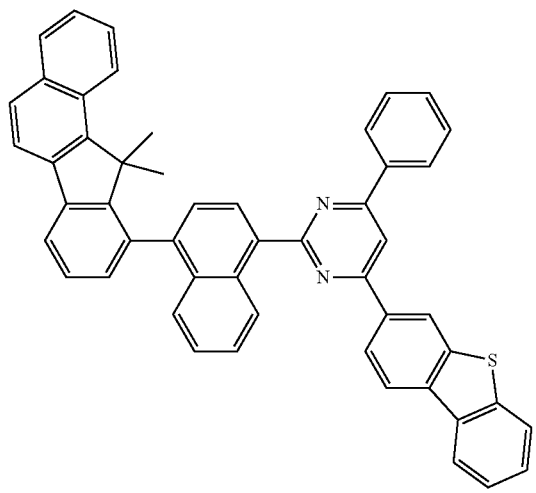
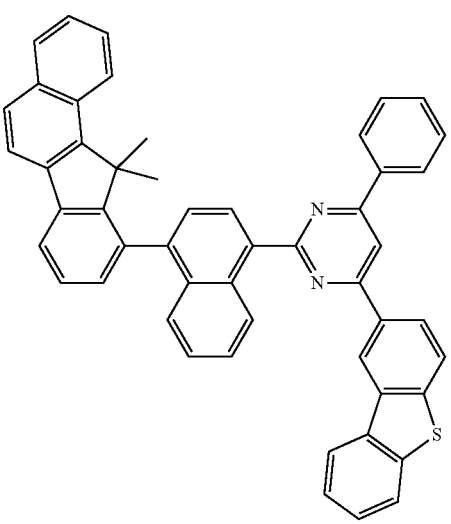
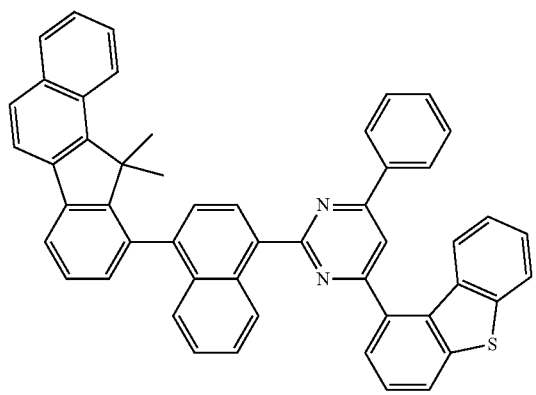

| 989 | 990 |
|---|---|
| -continued | -continued |
| 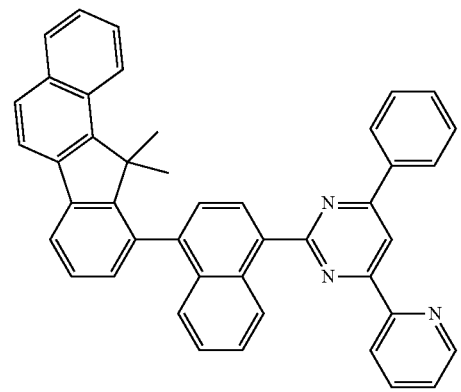 | 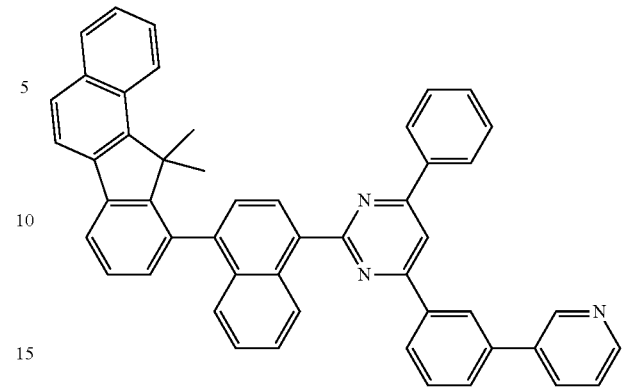 |
| 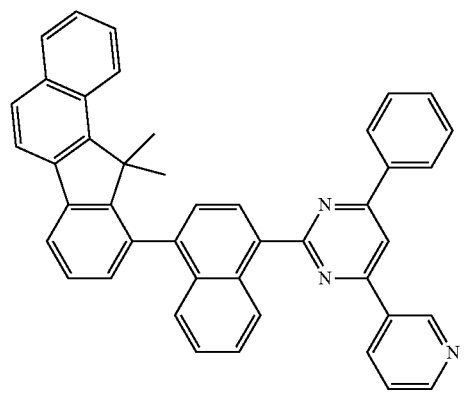 | 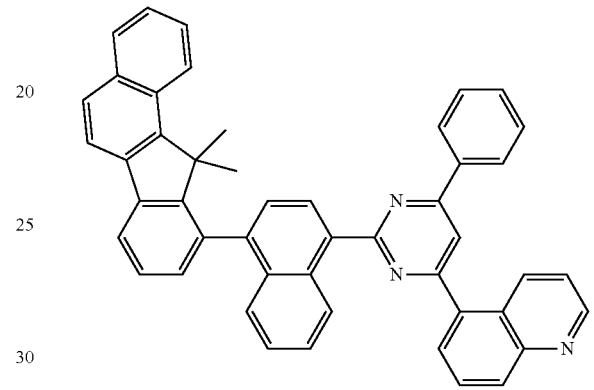 |
| 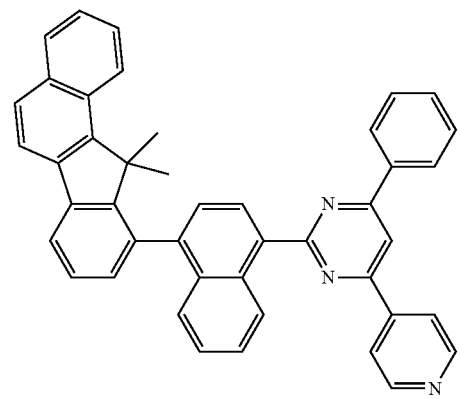 | 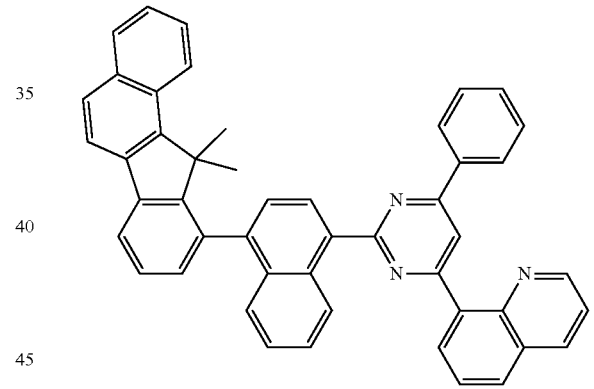 |
| 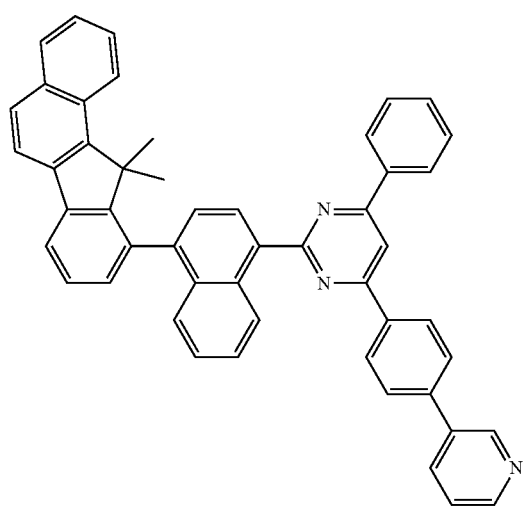 | 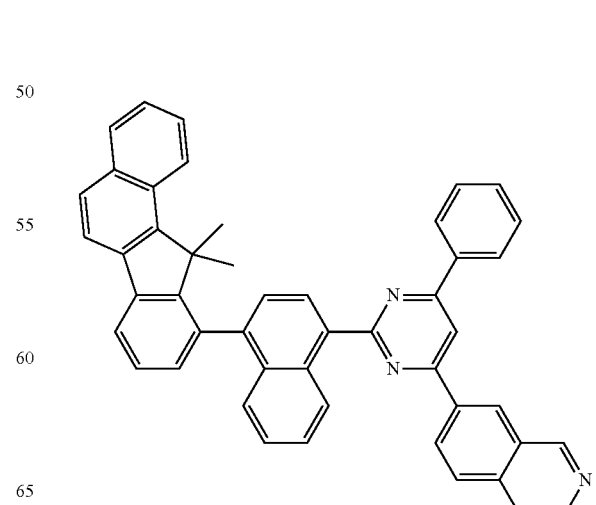 |

991
-continued
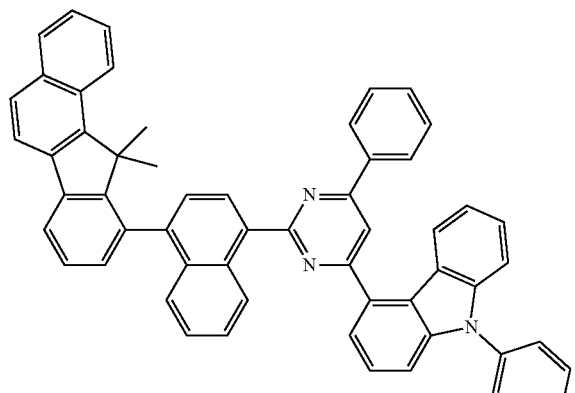
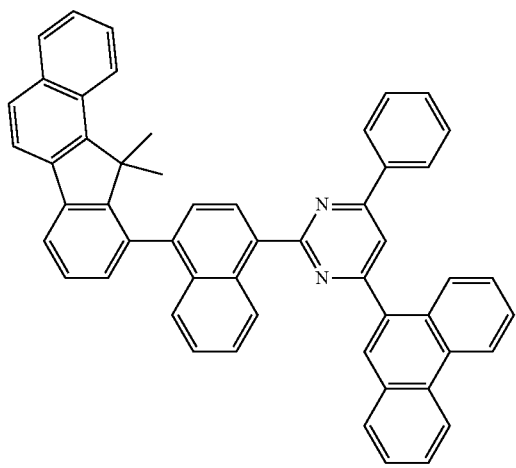
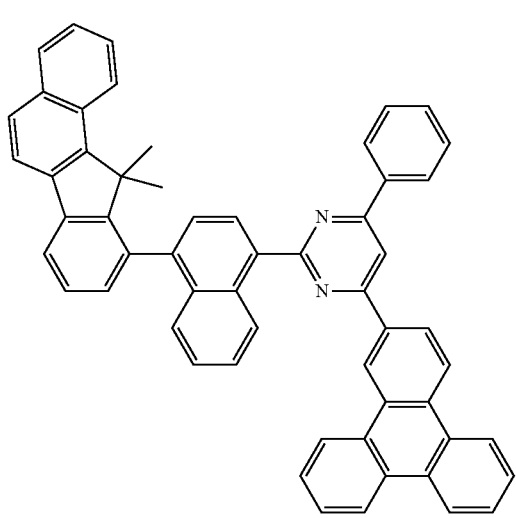
992
-continued
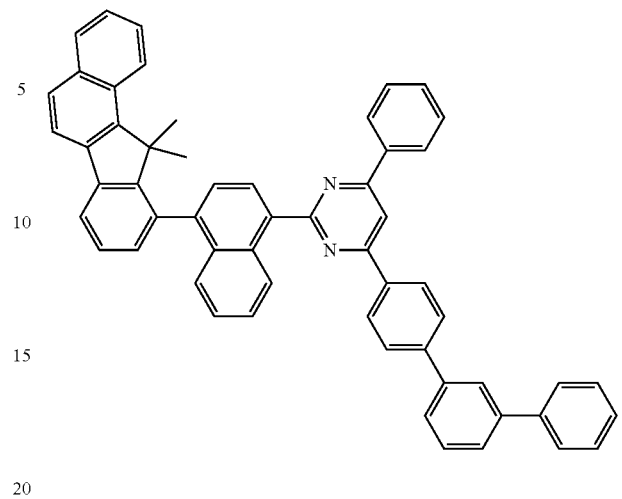
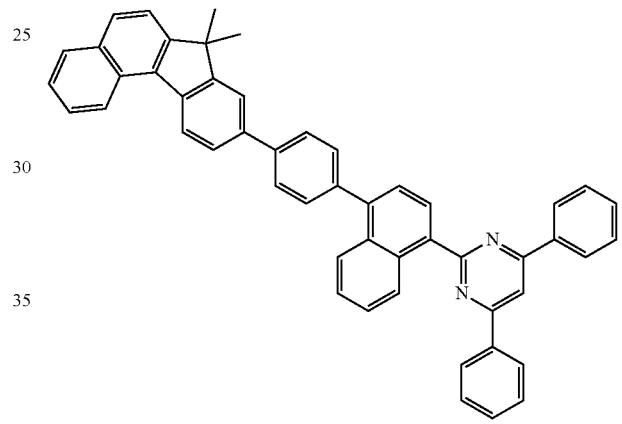
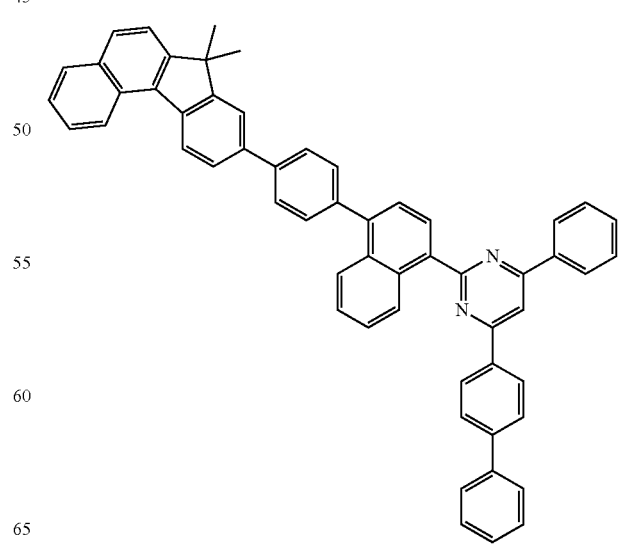

993
-continued
994
-continued
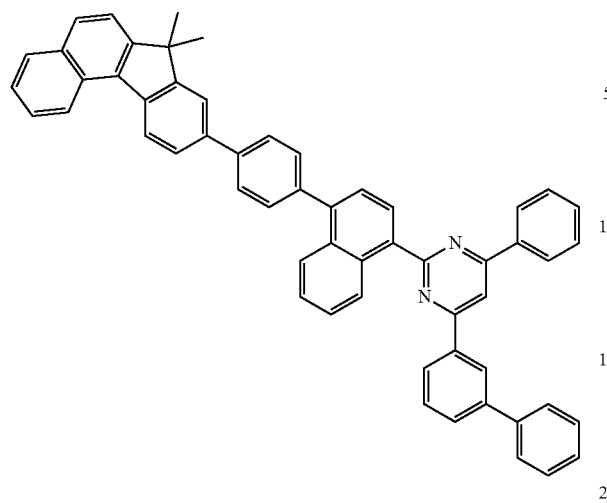
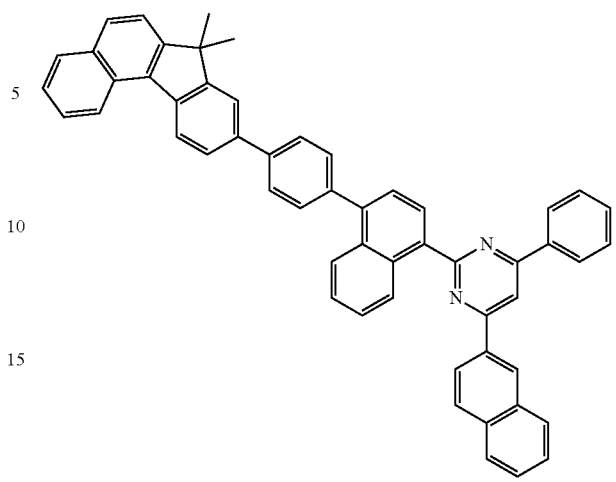
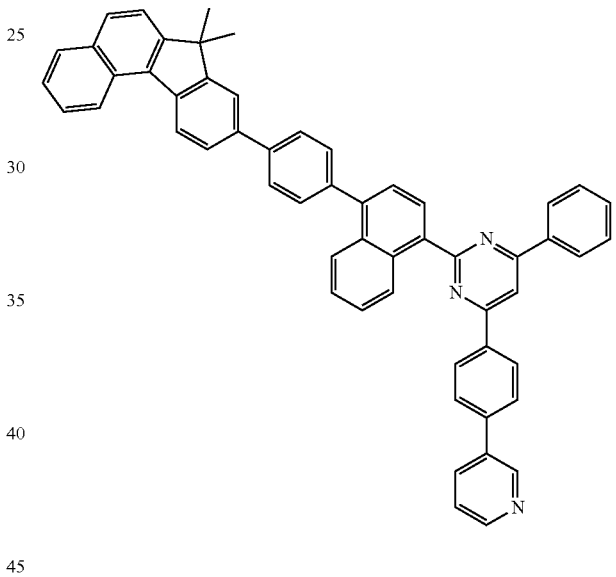
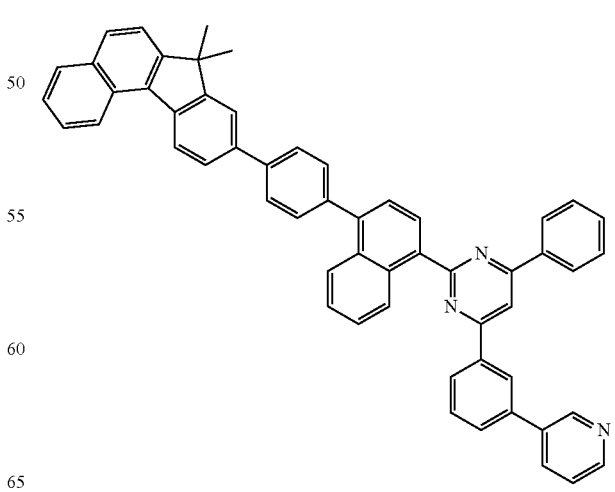

995
-continued
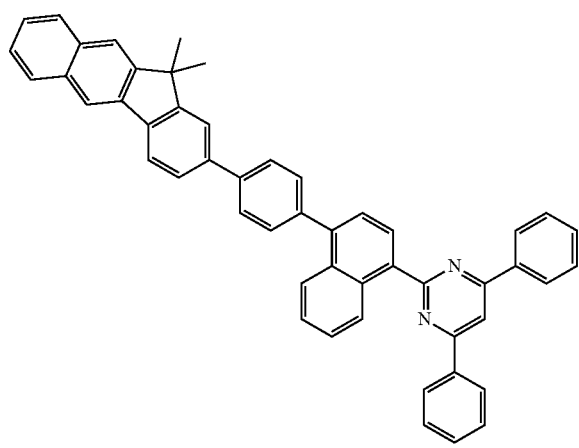
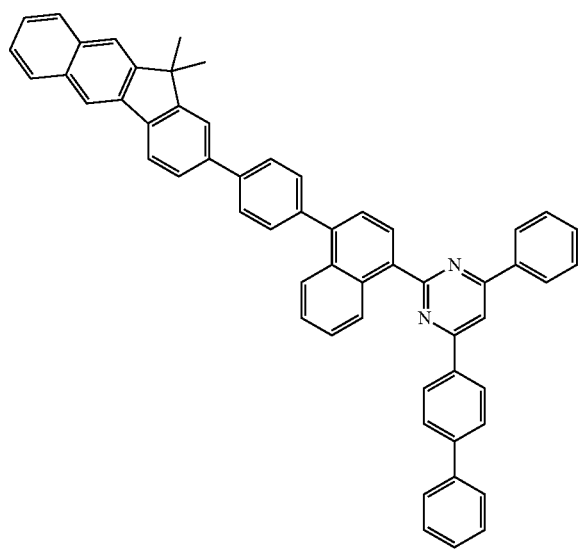
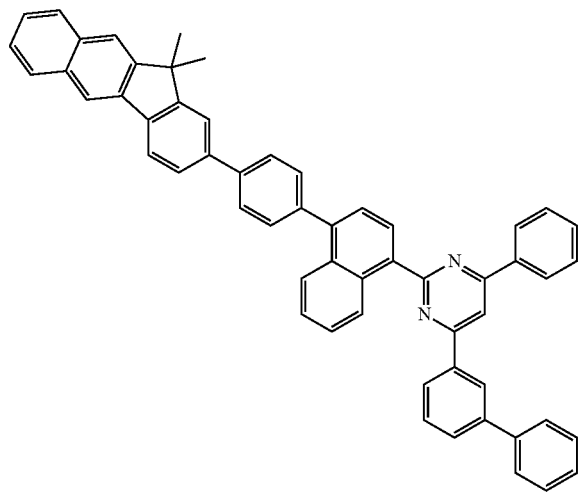
996
-continued
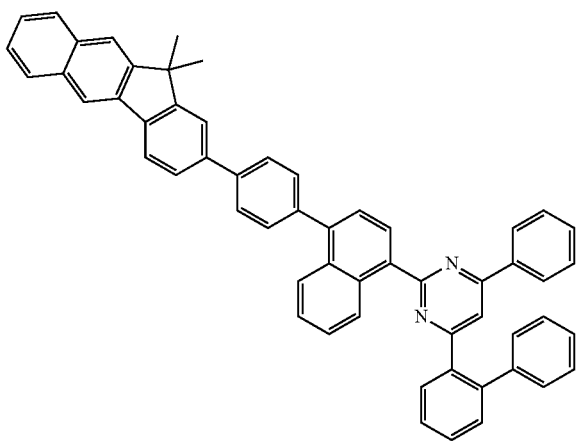
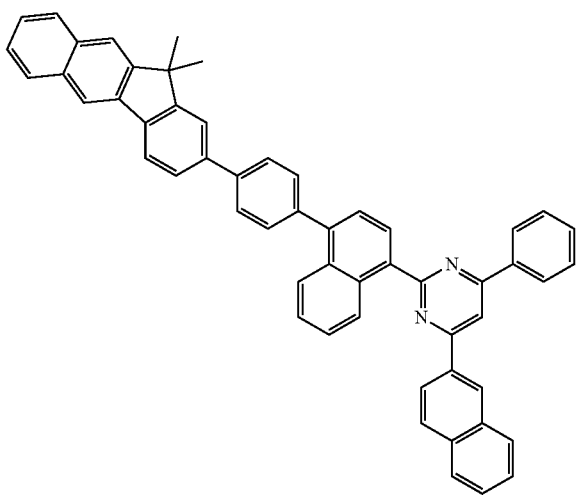

997
-continued
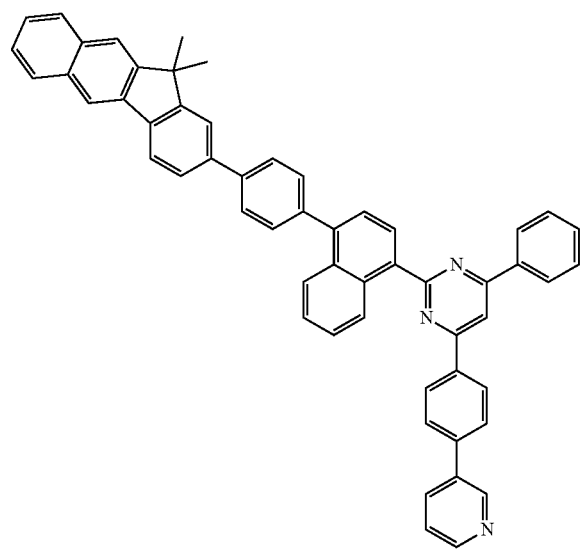
998
-continued
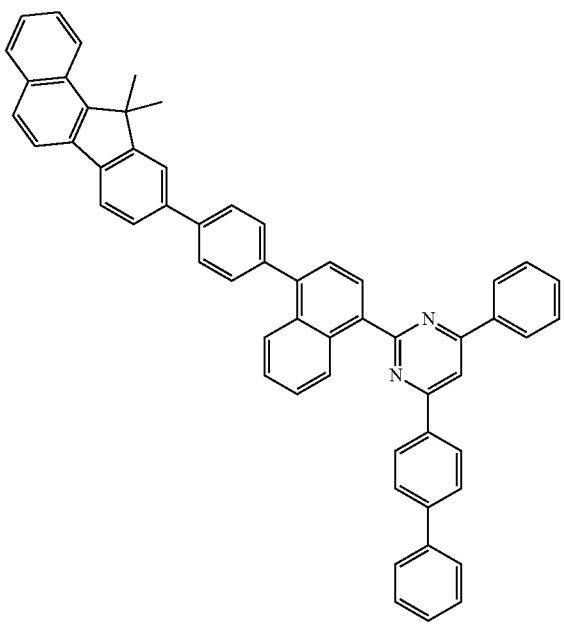
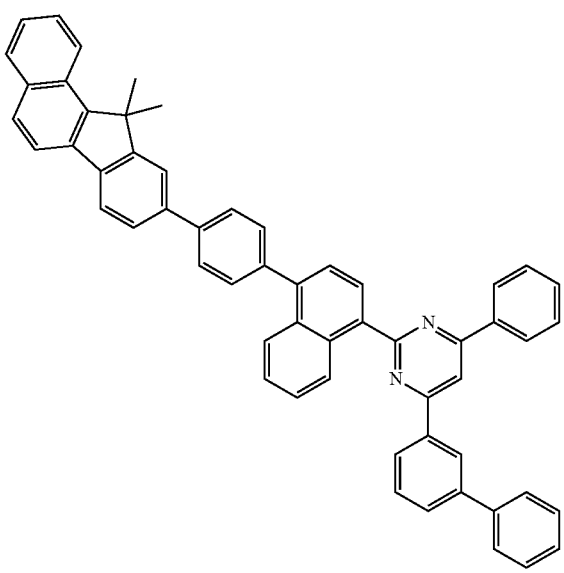
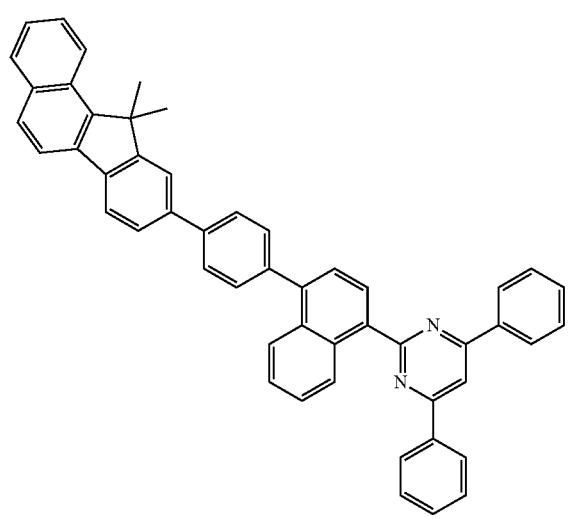
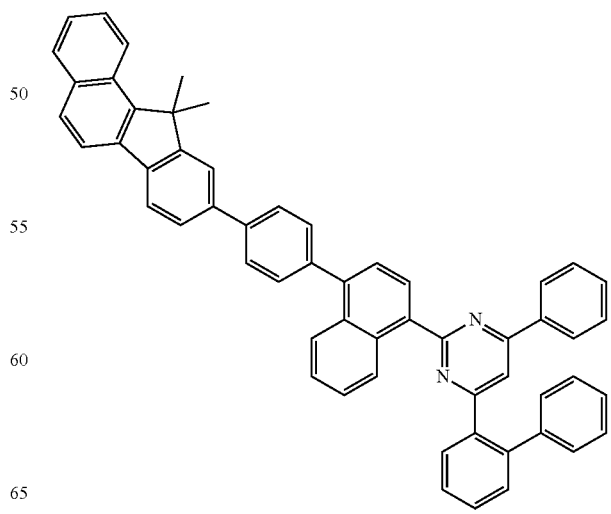

999
-continued
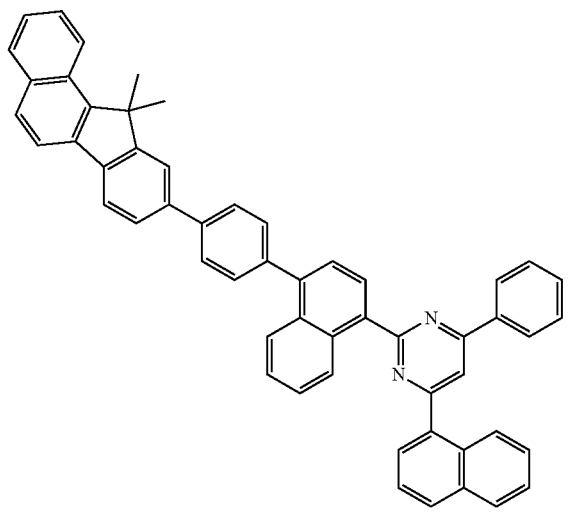
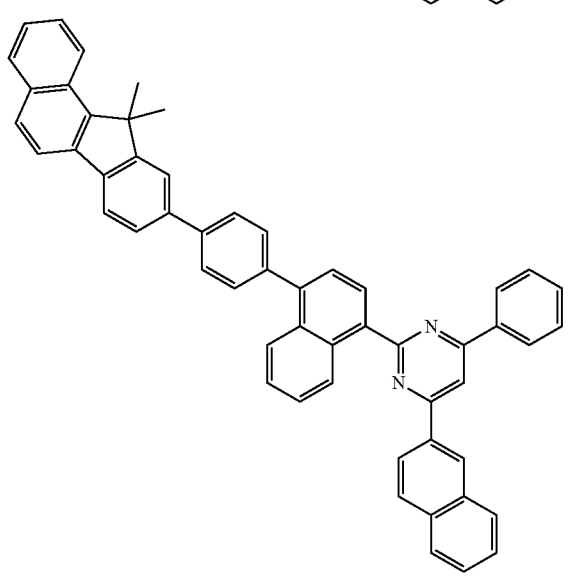
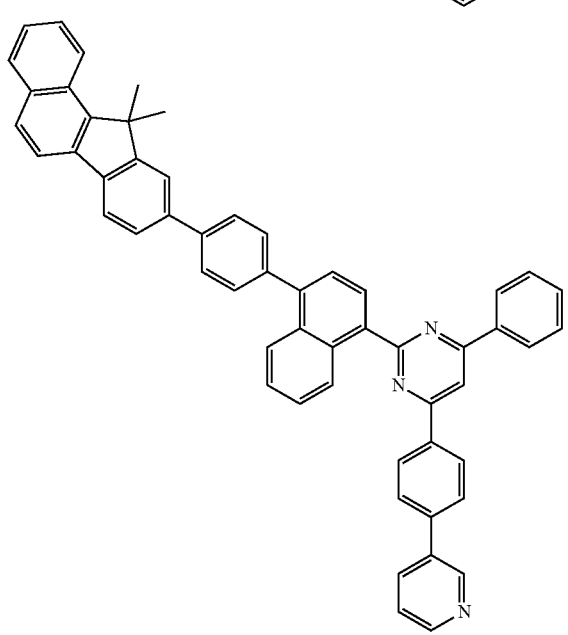
1000
-continued
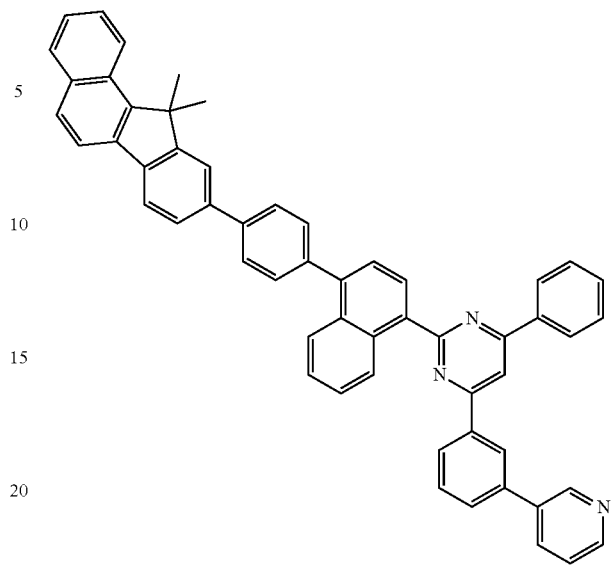
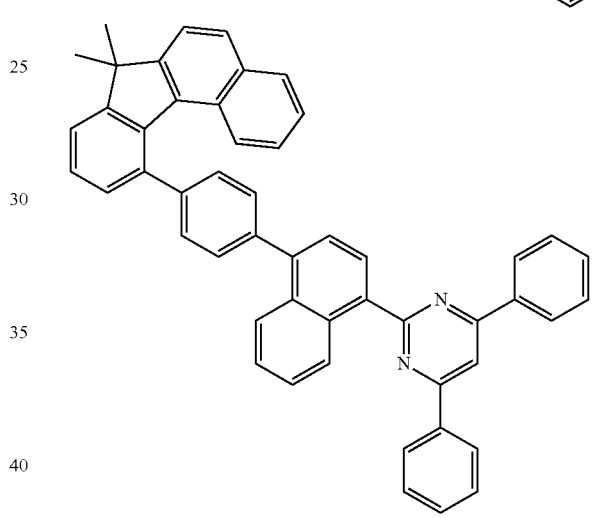
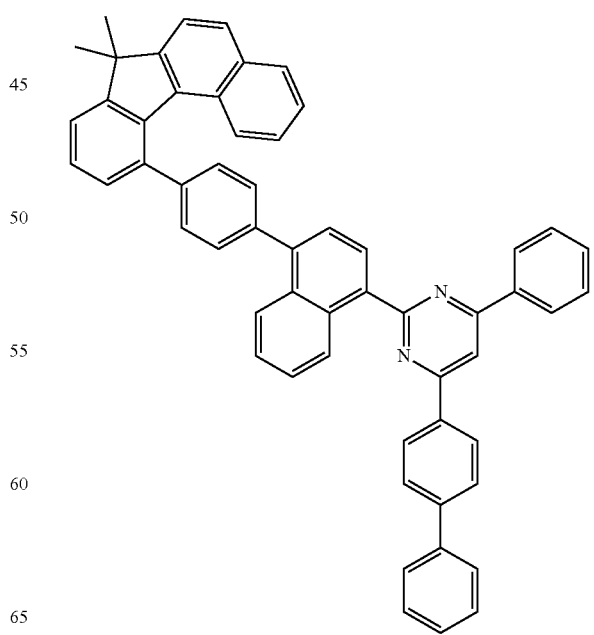

1001
-continued
1002
-continued
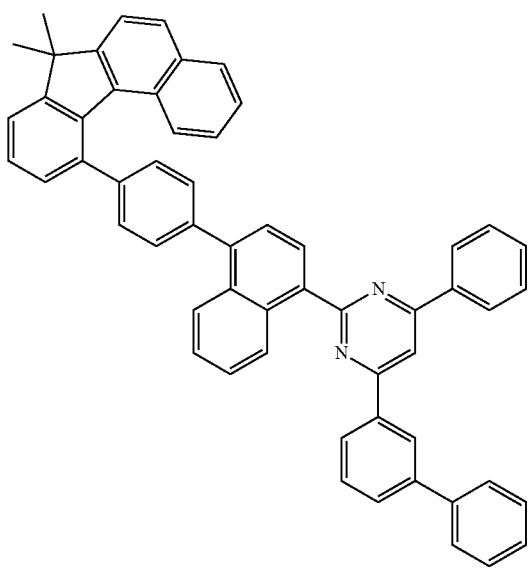
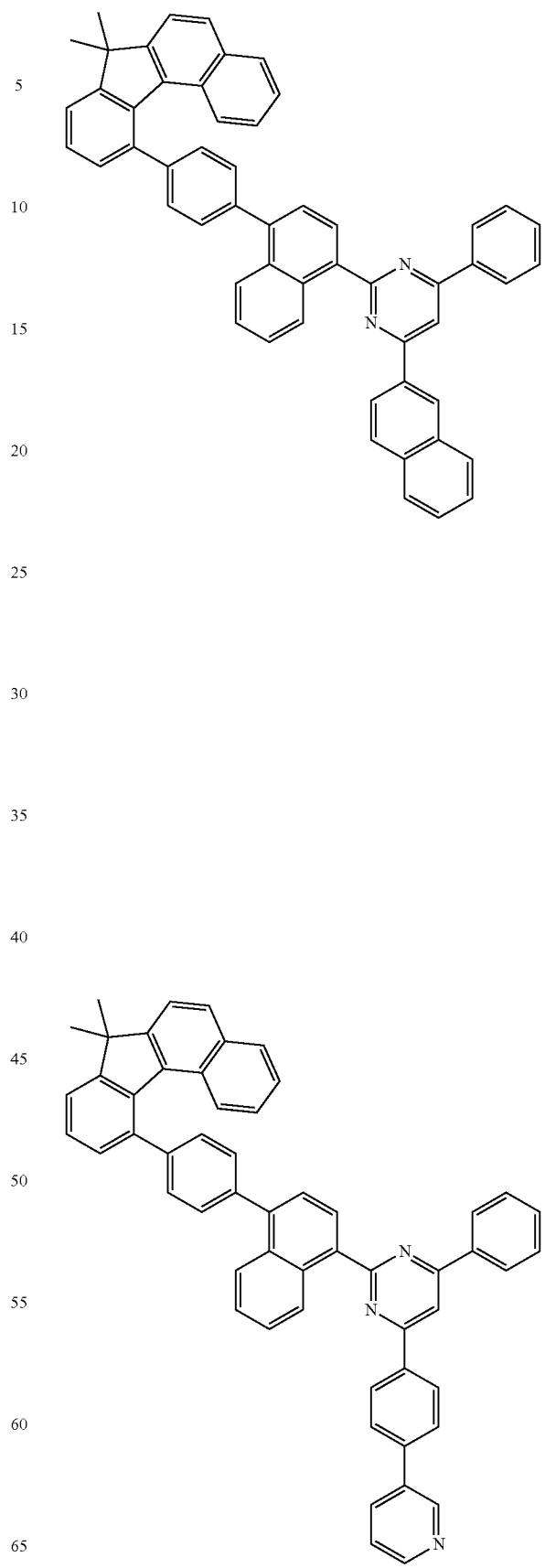

1003
-continued
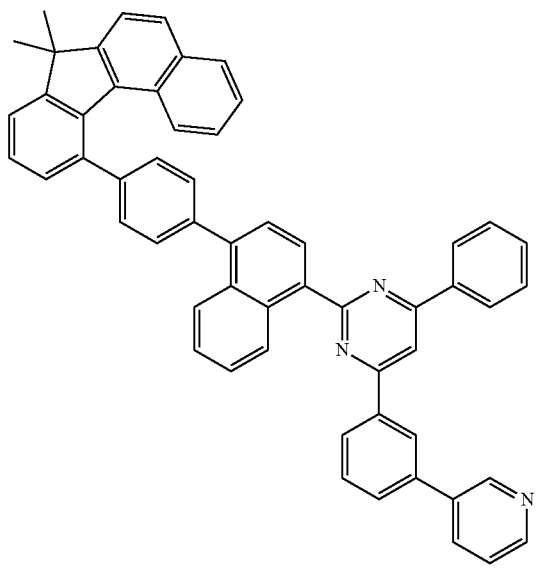
1004
-continued
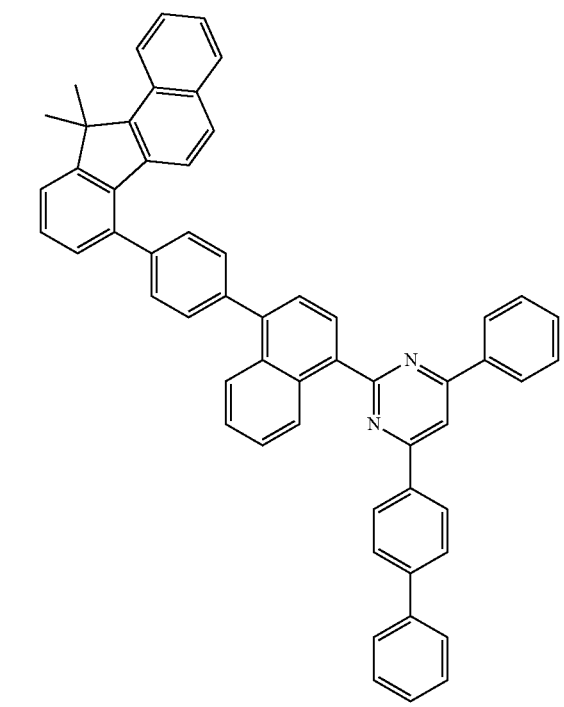
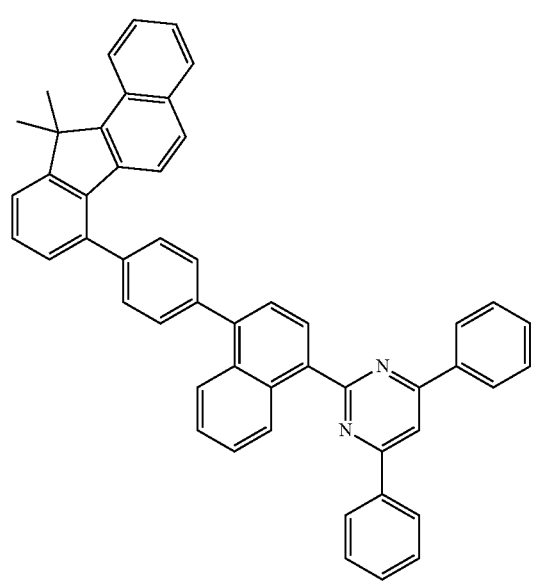
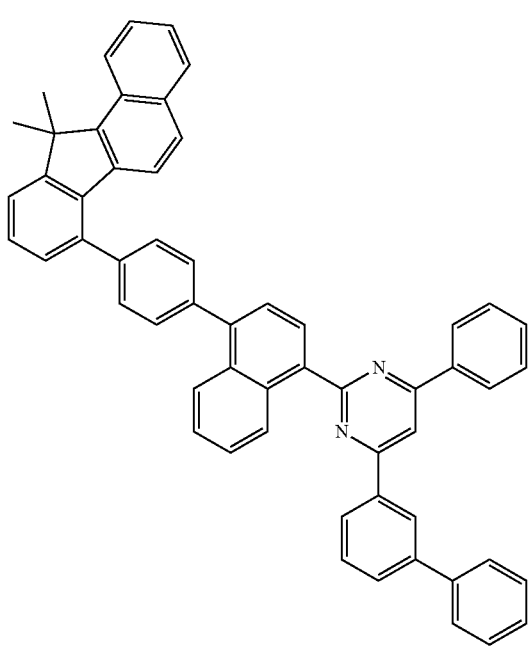

1005
-continued
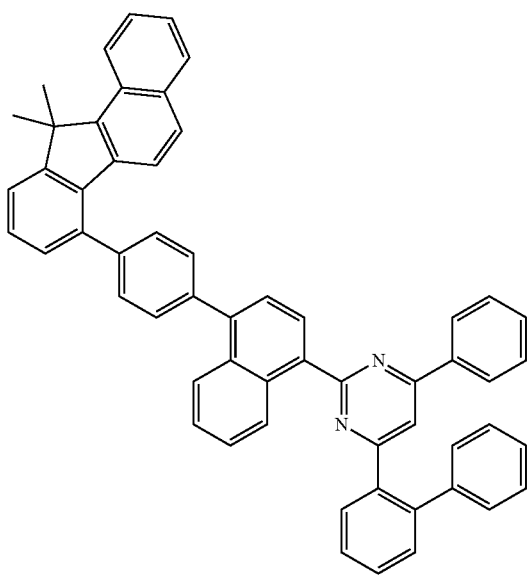
1006
-continued
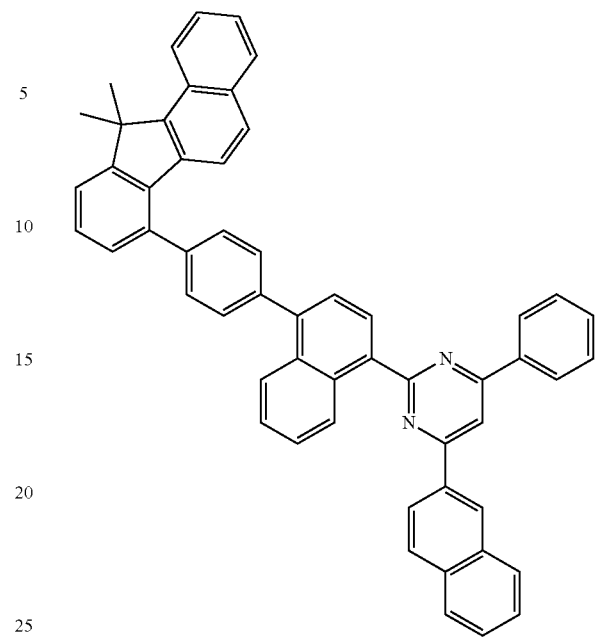
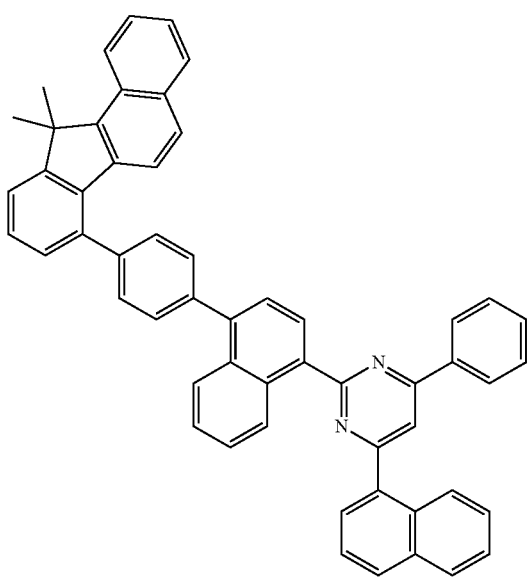
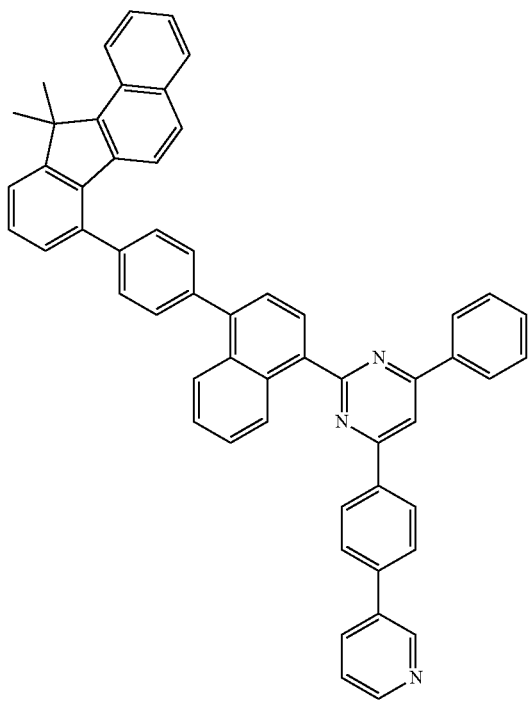

1007
-continued
1008
-continued
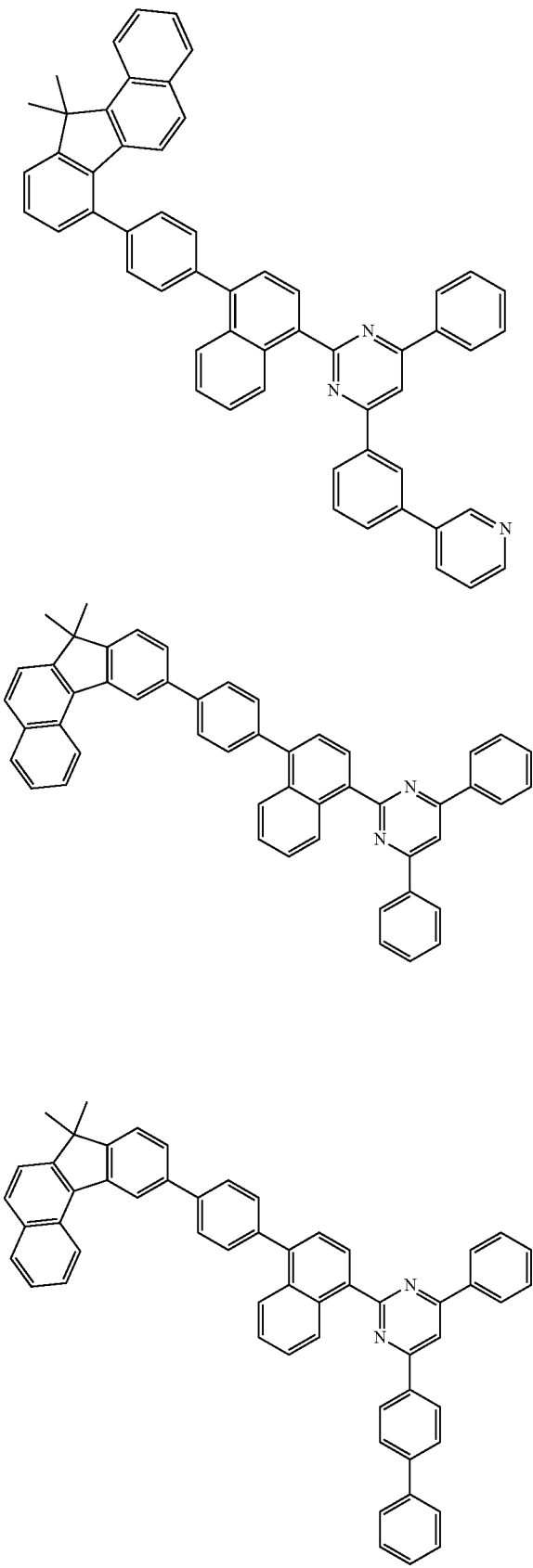
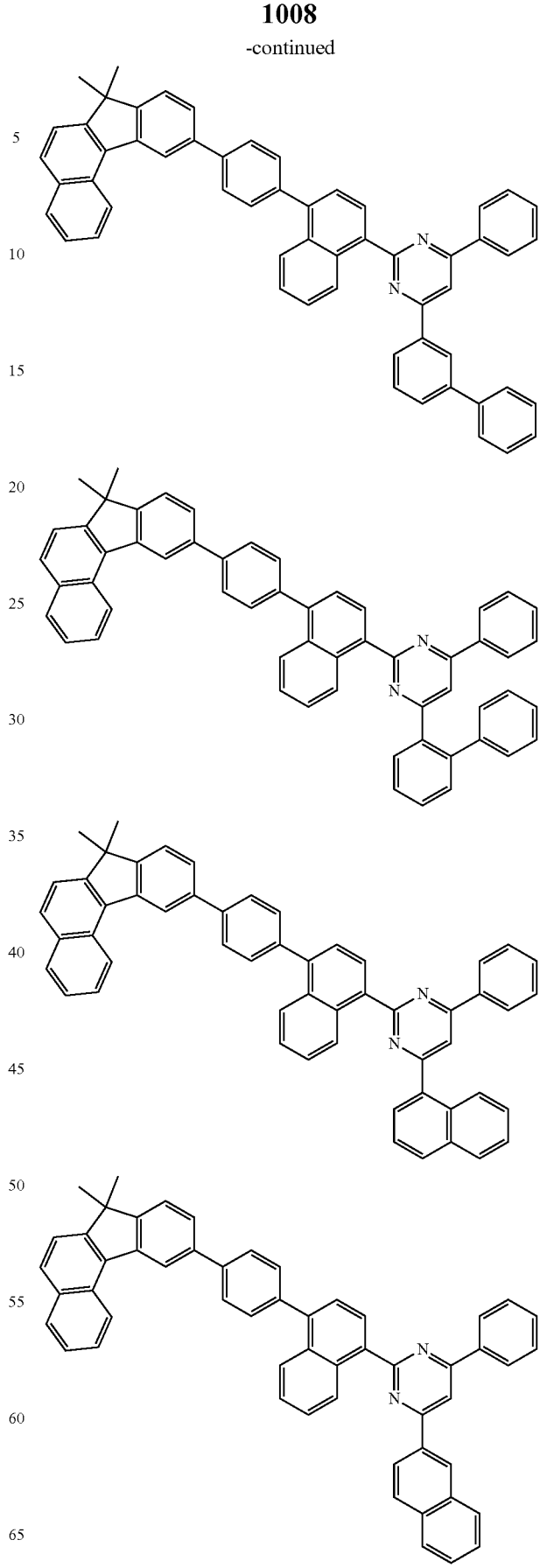

| 1009 | 1010 |
|---|---|
| -continued | -continued |
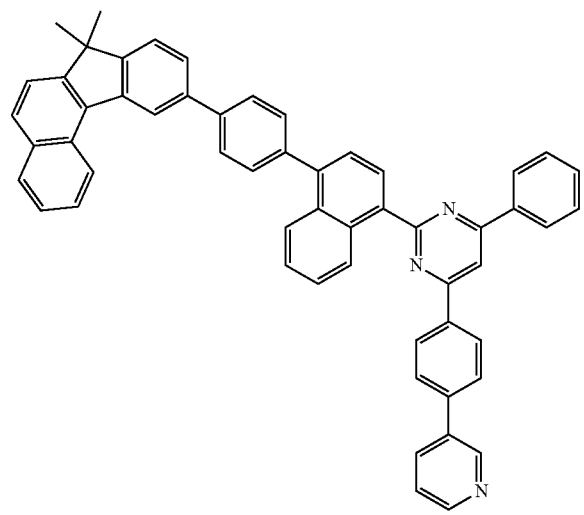
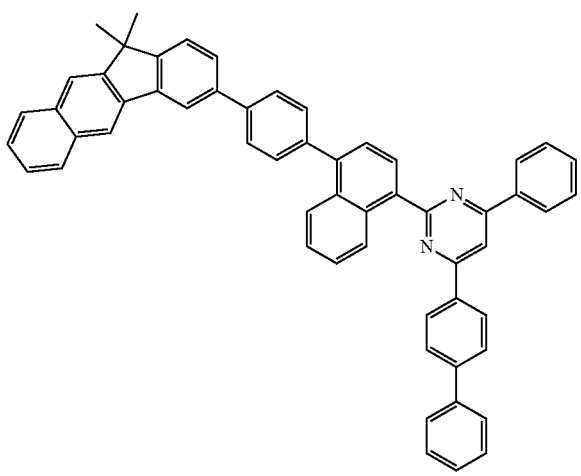
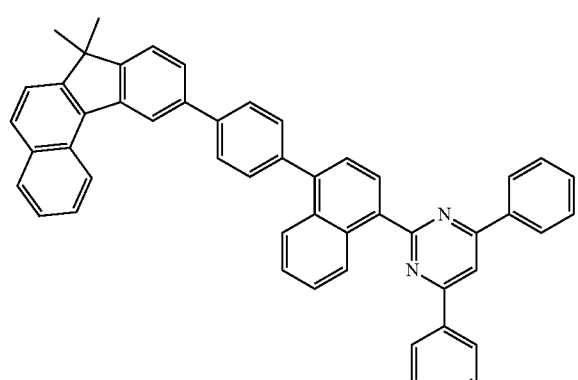
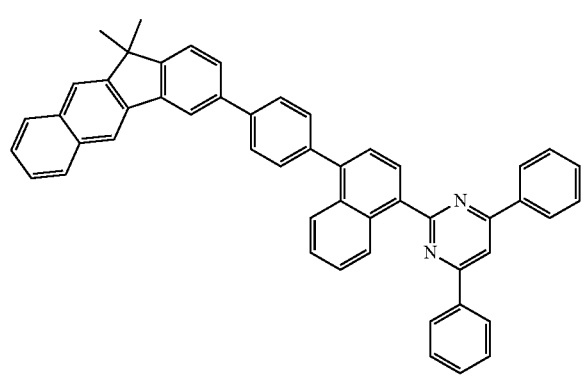
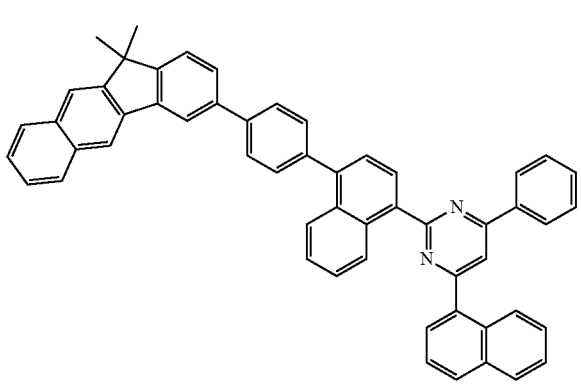

1011
-continued
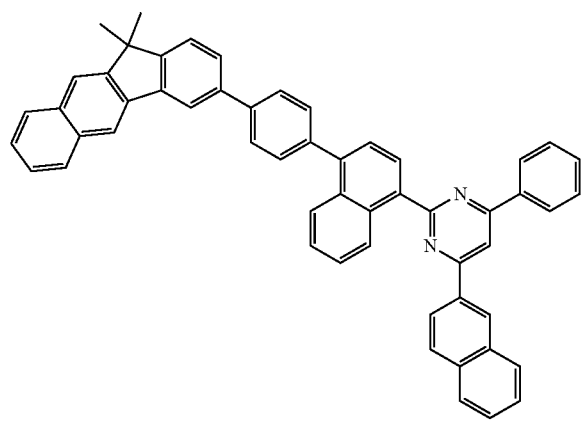
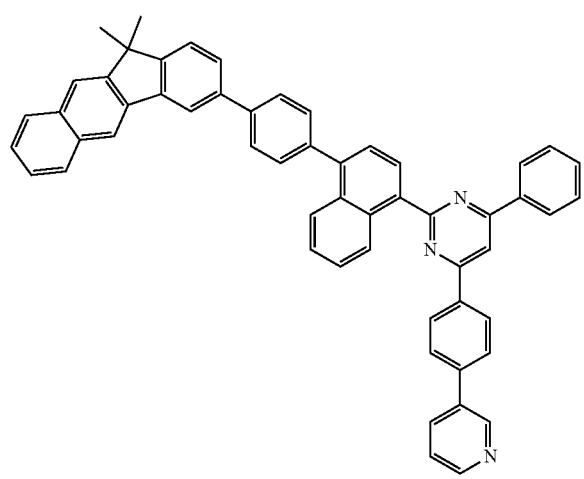
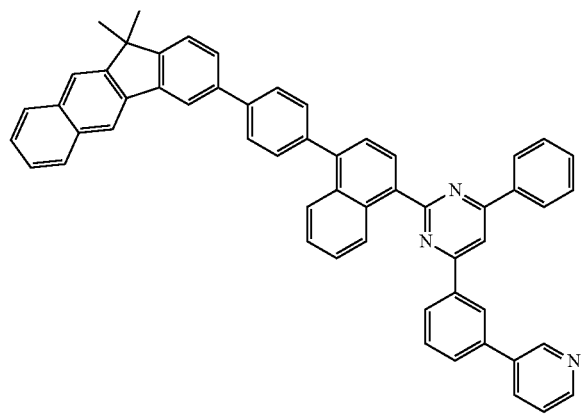
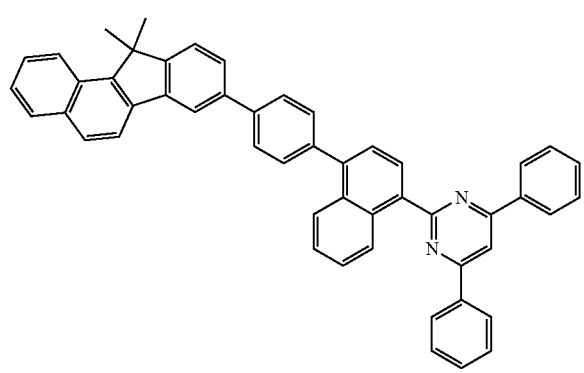
1012
-continued
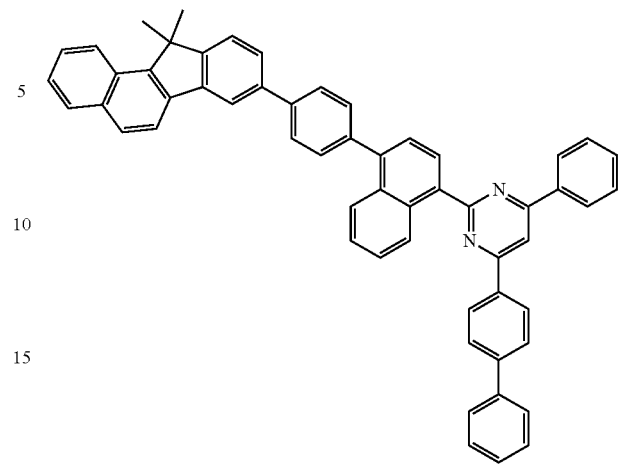
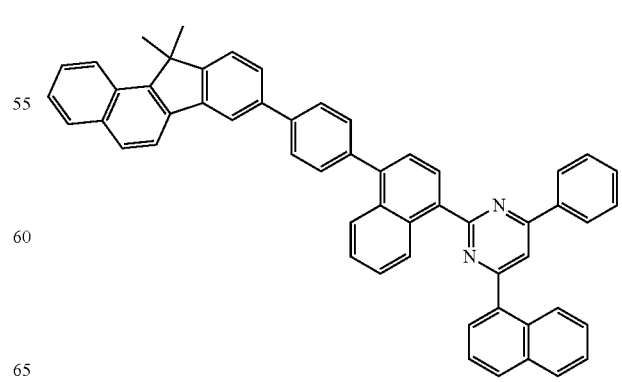

1013
-continued
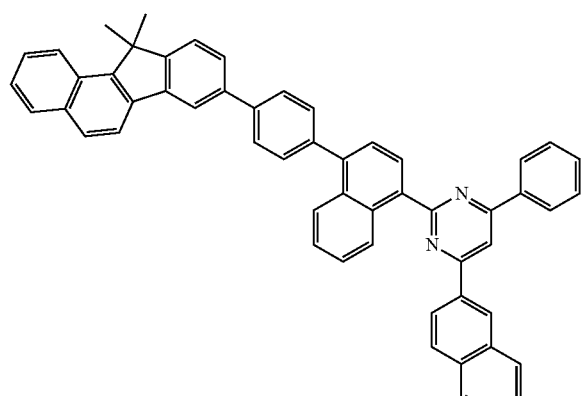
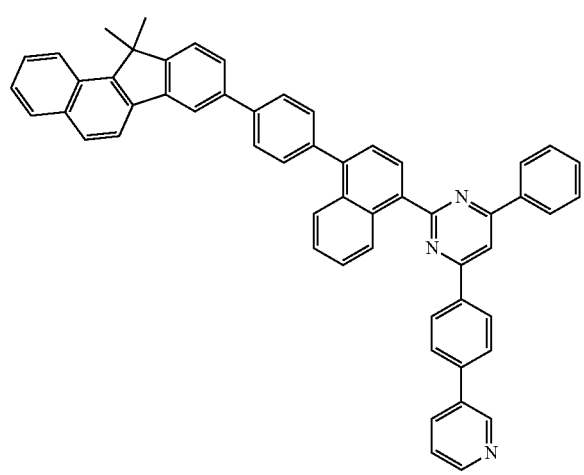
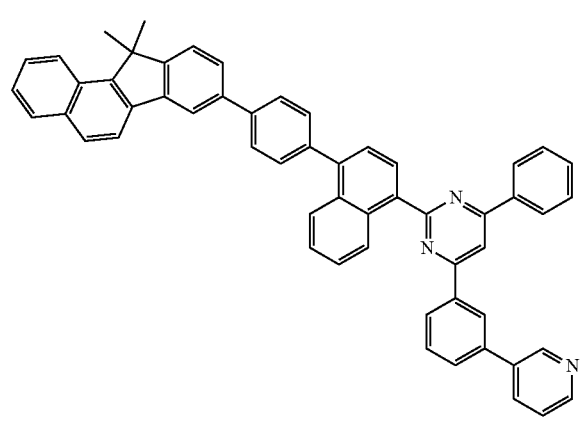
1014
-continued
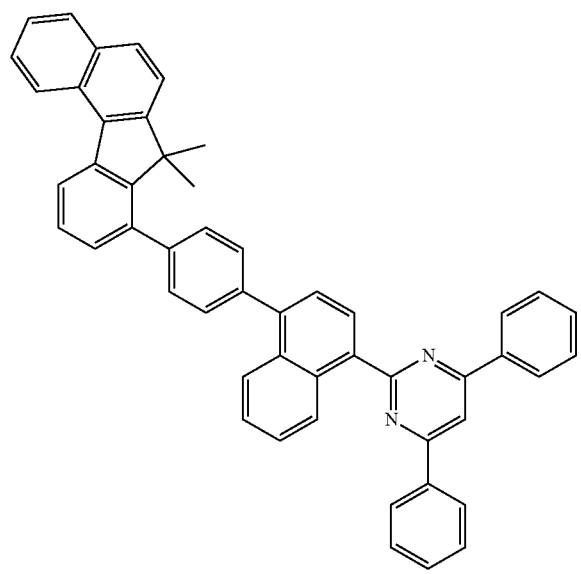
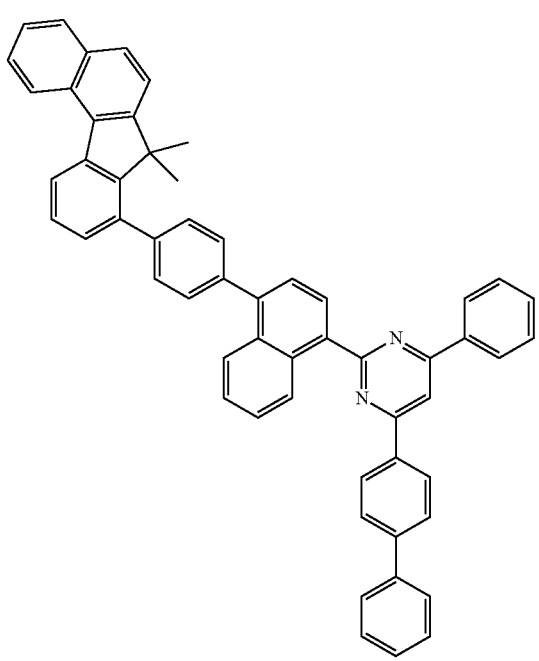

1015
-continued
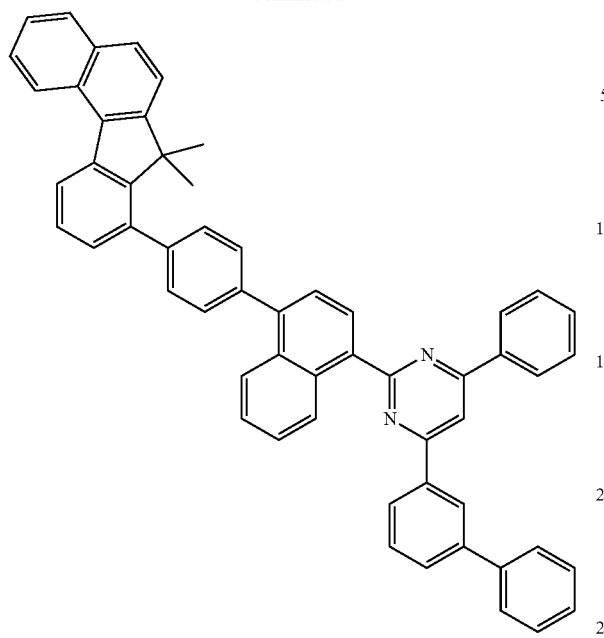
1016
-continued
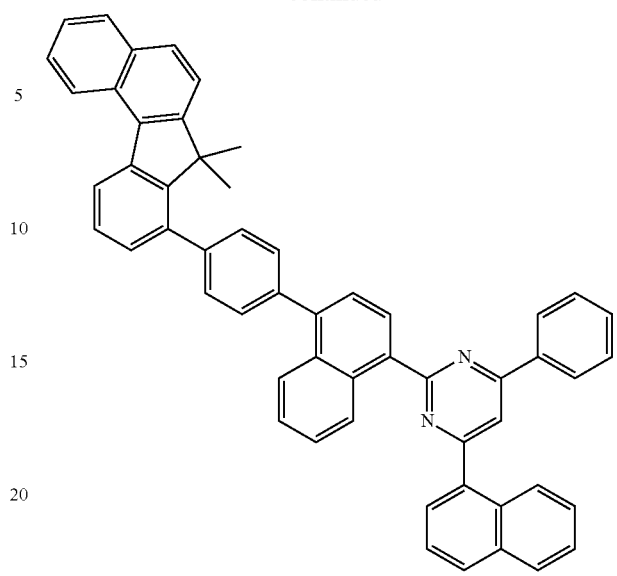
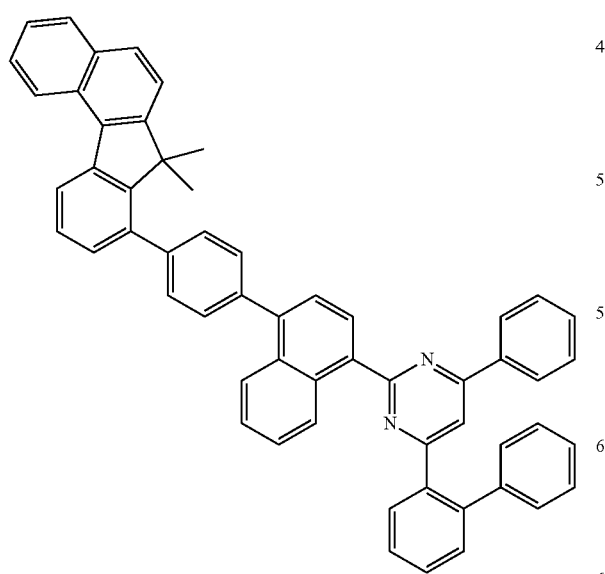
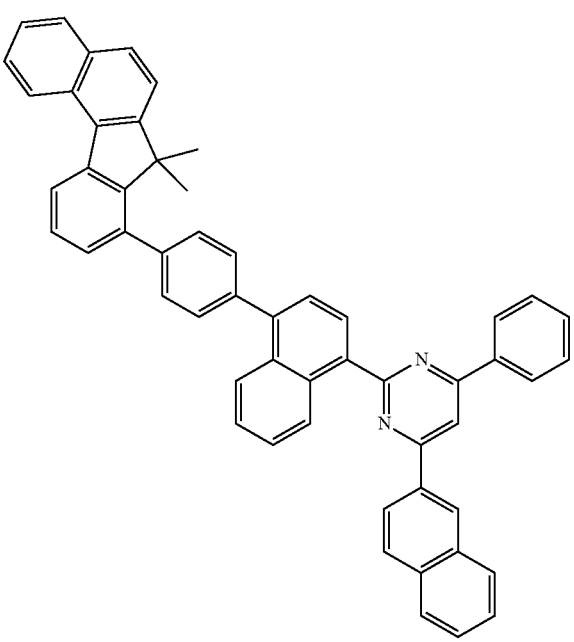

1017
-continued
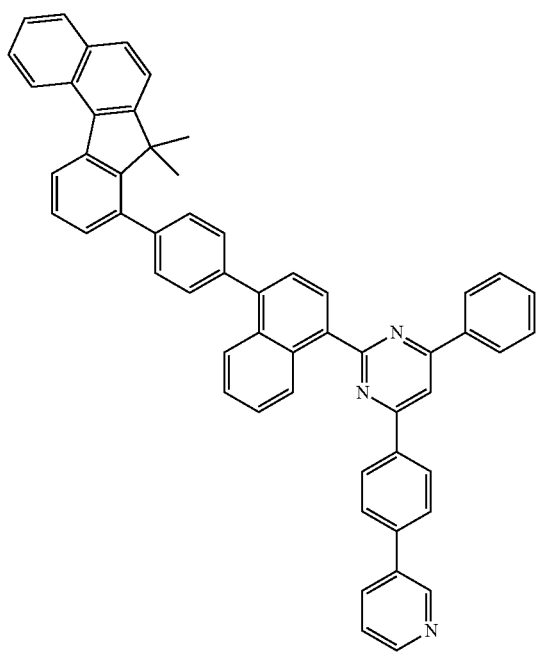
1018
-continued
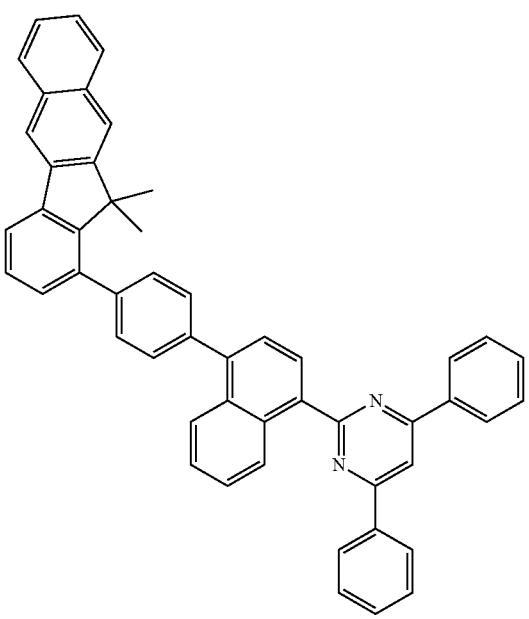
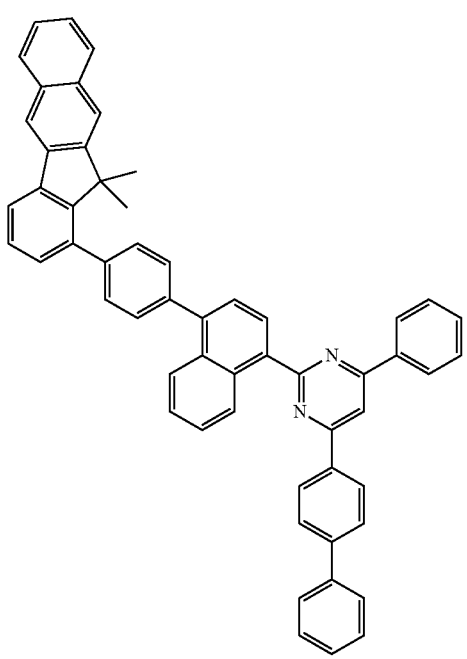

1019
-continued
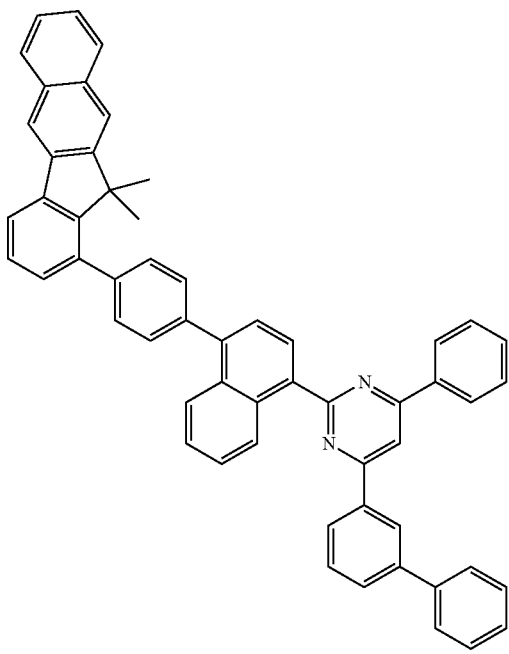
1020
-continued
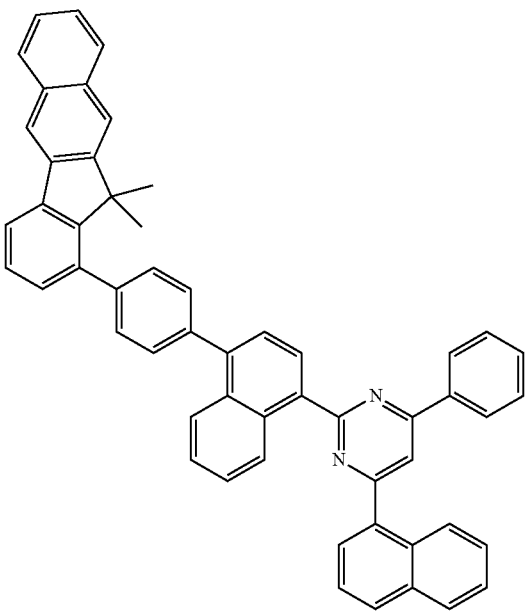
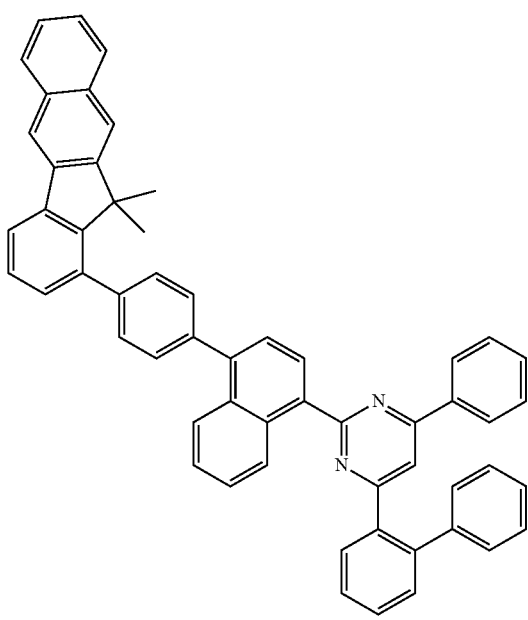
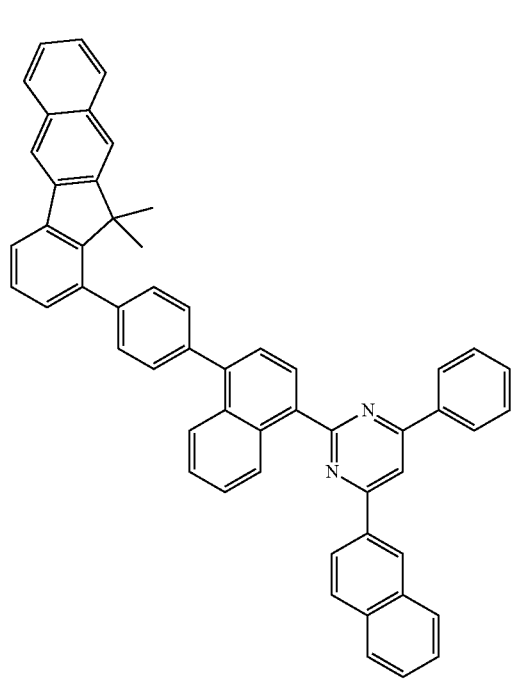

1021
-continued
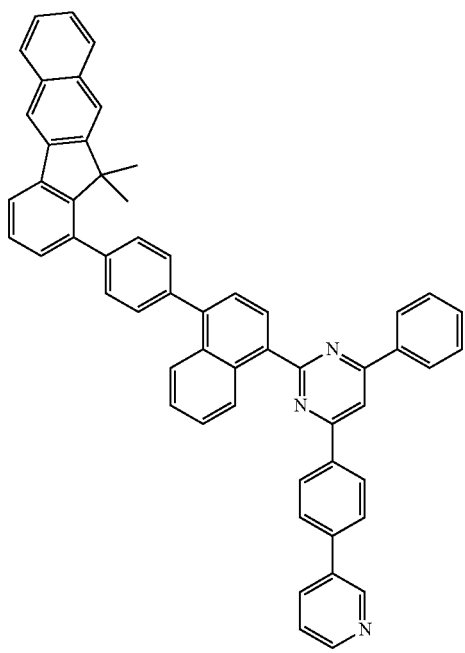
1022
-continued
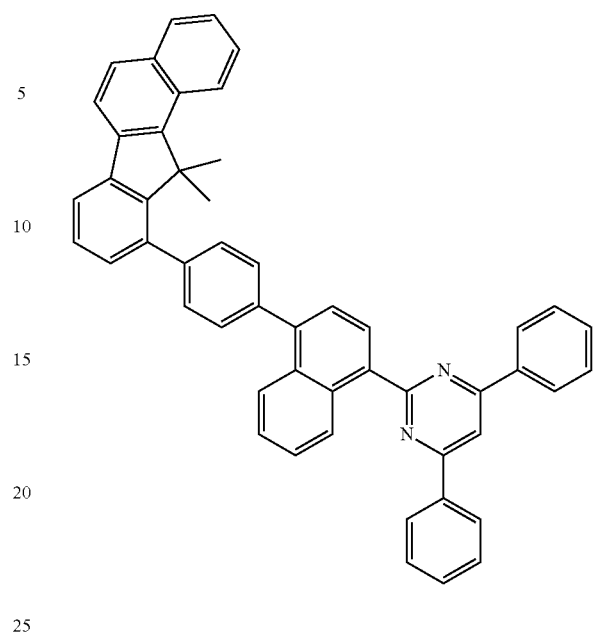
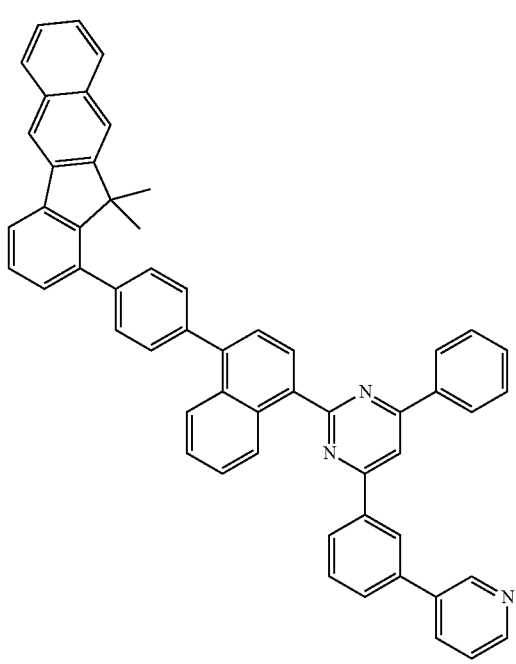 [SMILES: CC1(C)c2cc3ccccc3cc2-c2cccc(-c3ccc(-c4ccc(-c5nc(-c6ccccc6)cc(-c6cccc(-c7cccnc7)c6)n5)c5ccccc45)cc3)c21]
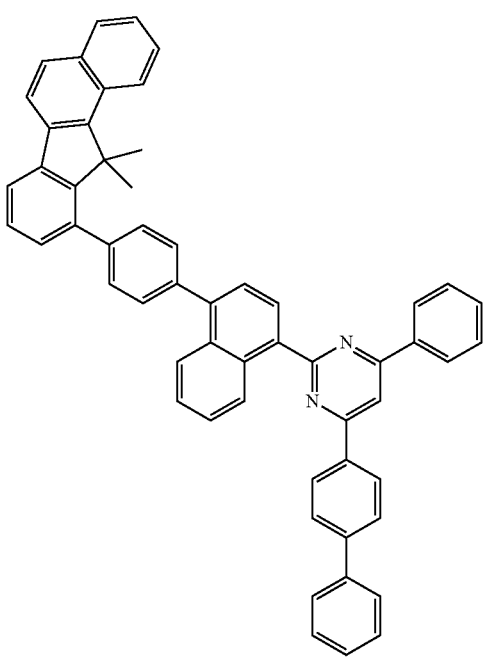

1023
-continued
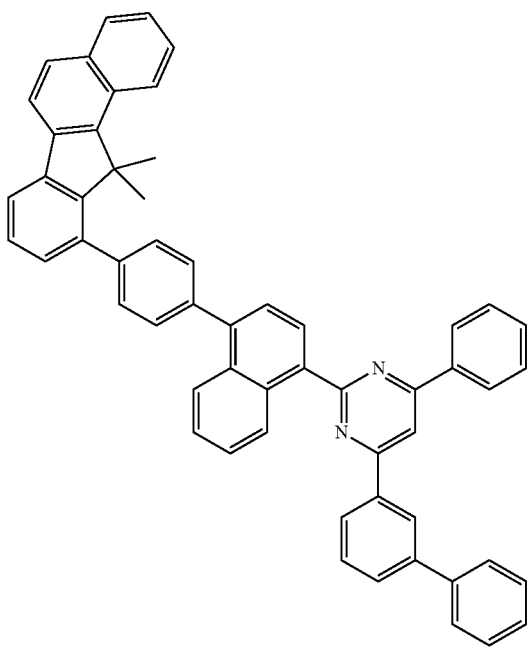
1024
-continued
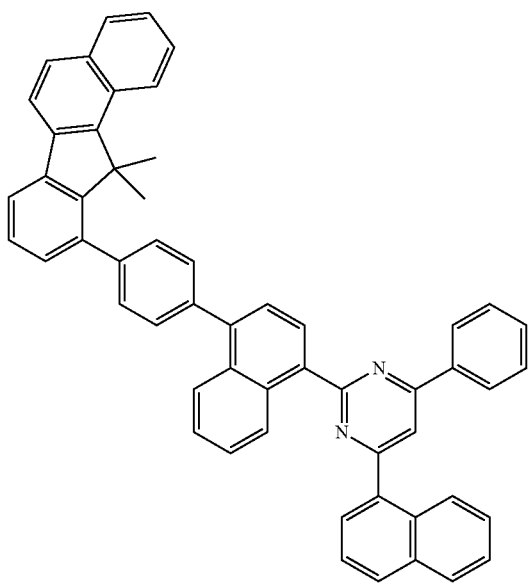
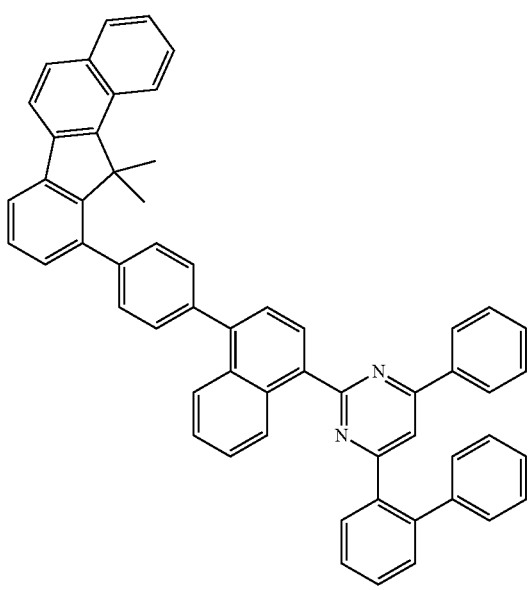
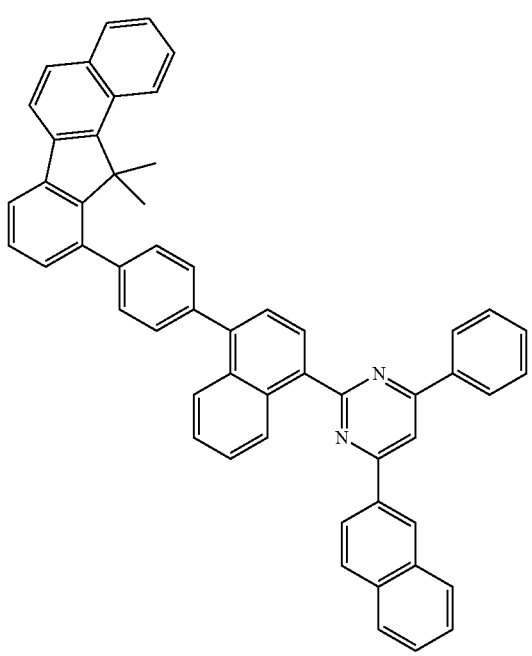

1025
-continued
1026
-continued
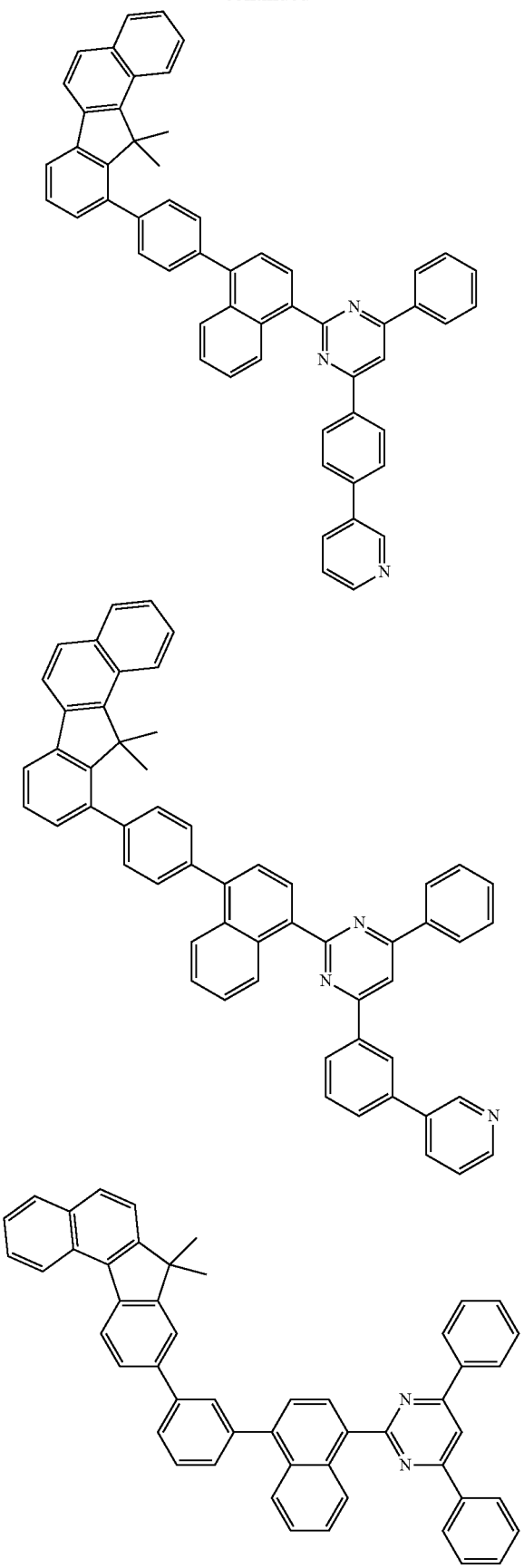
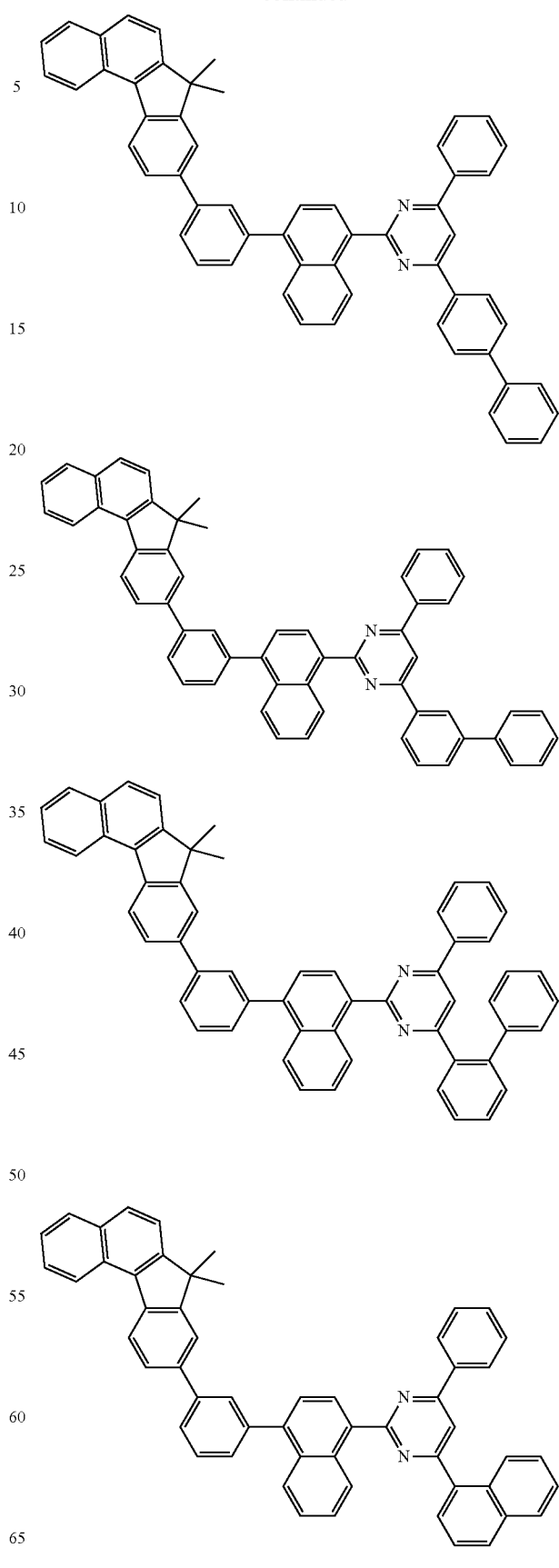

1027
-continued
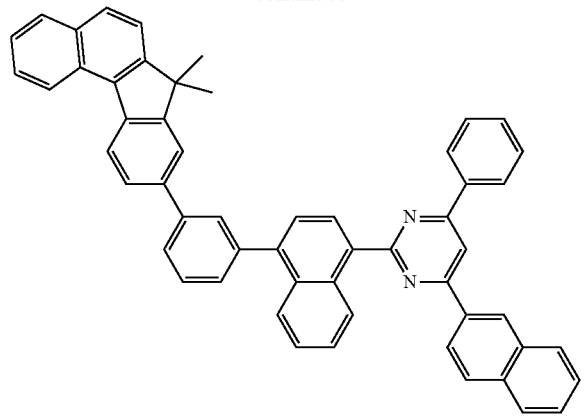
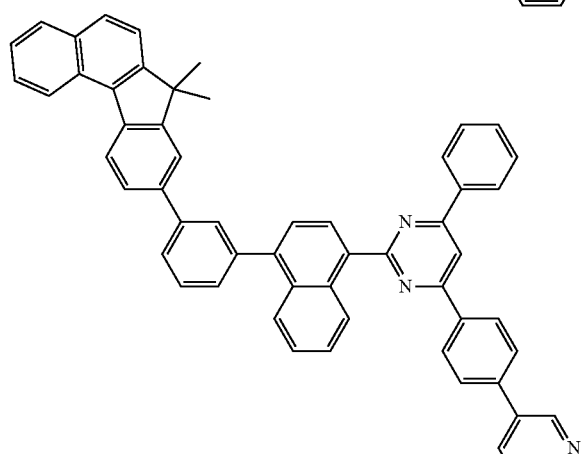
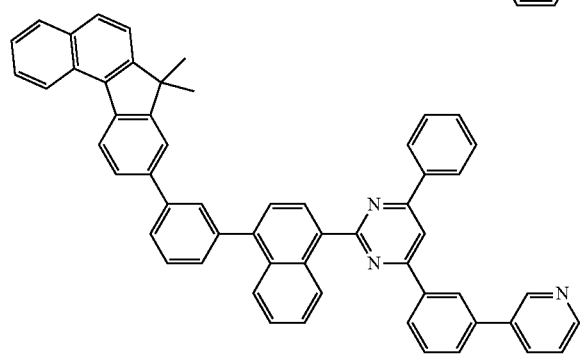
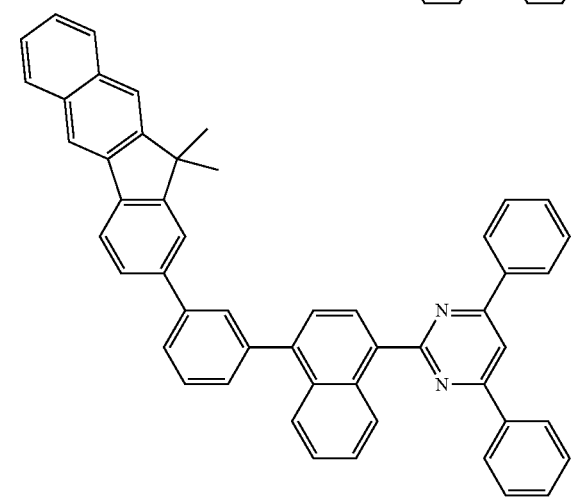
1028
-continued
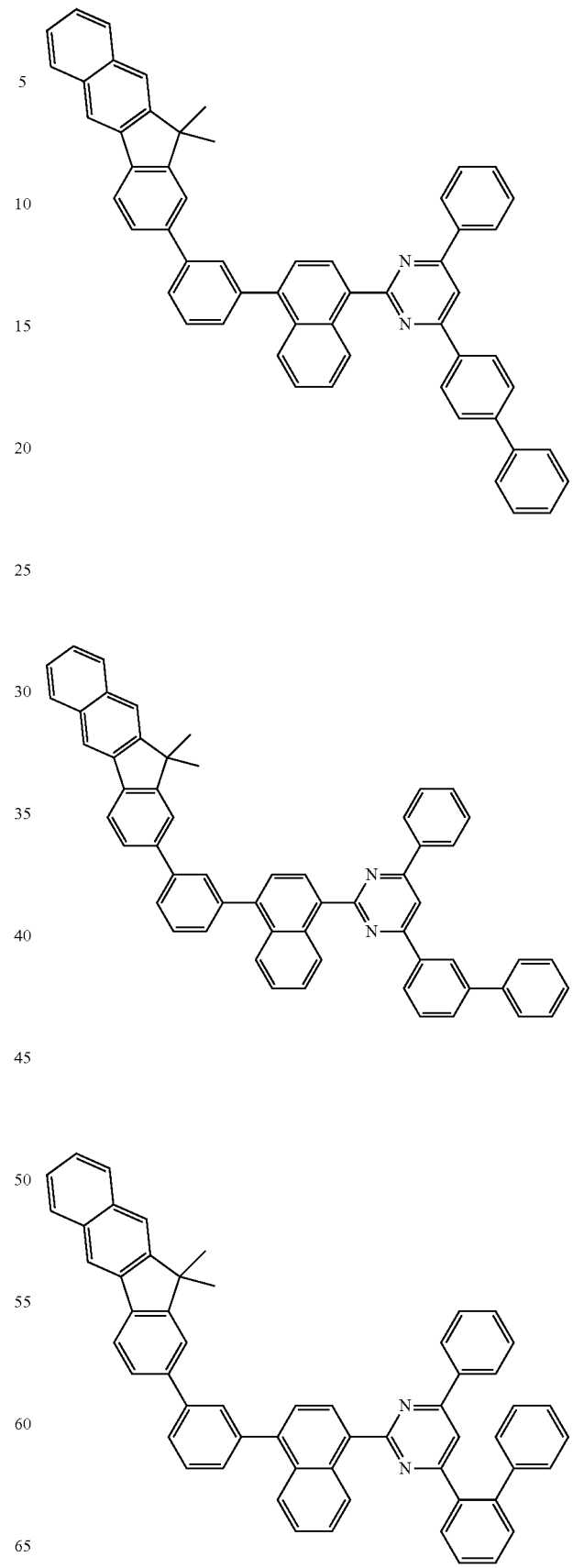

1029
-continued
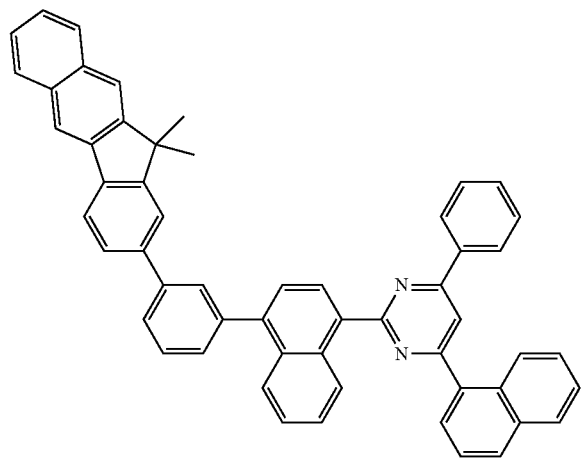
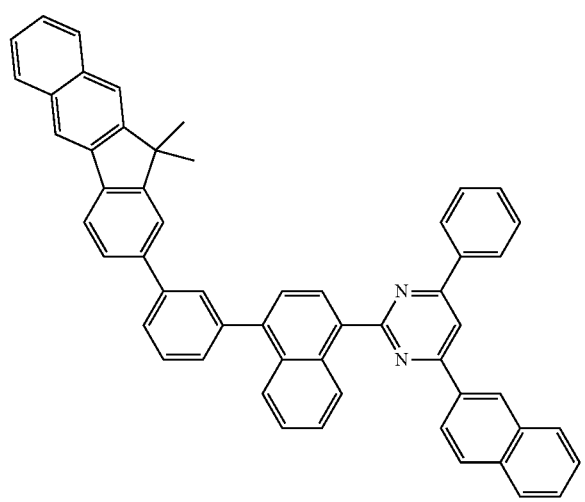
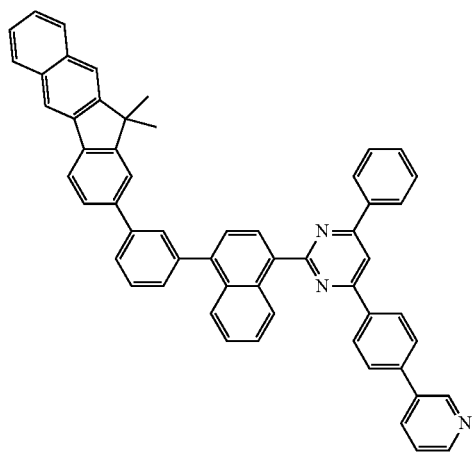
1030
-continued
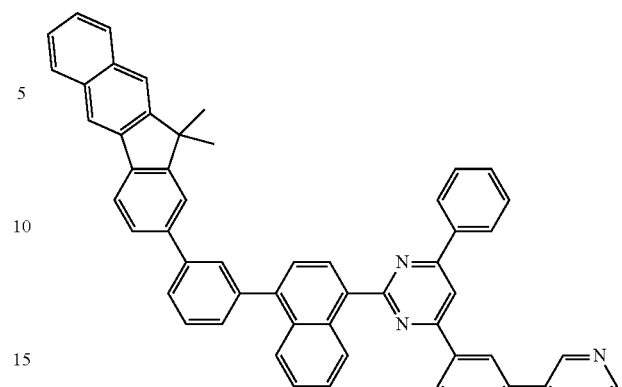
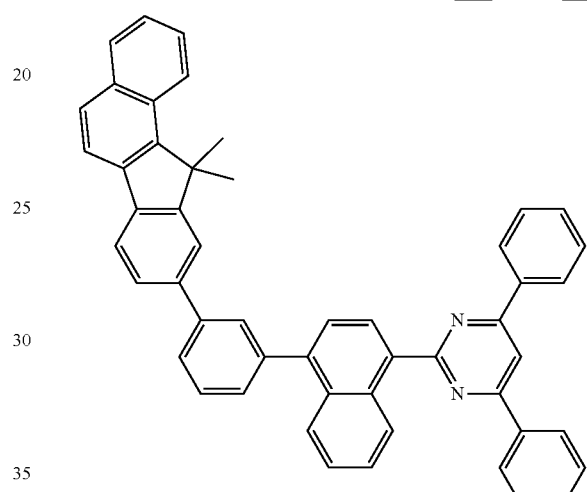
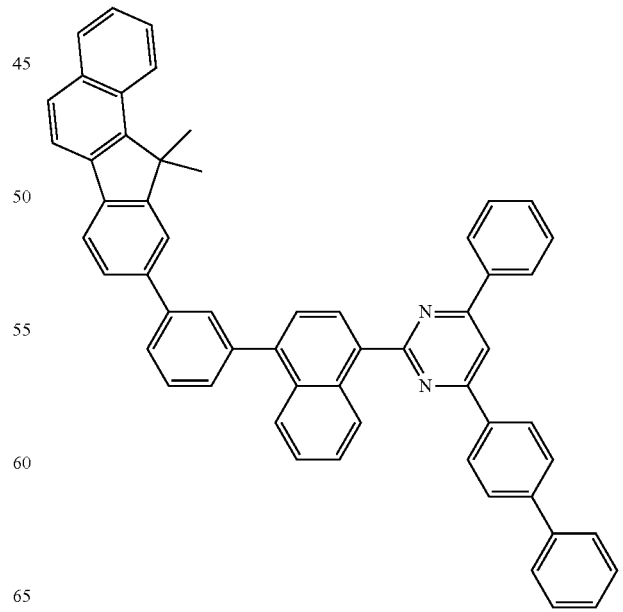

1031
-continued
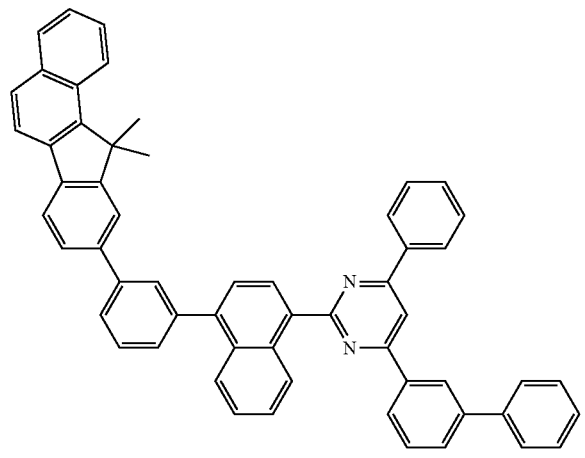
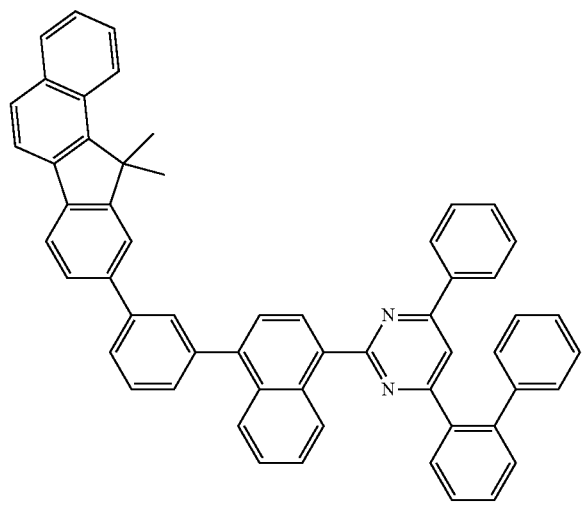
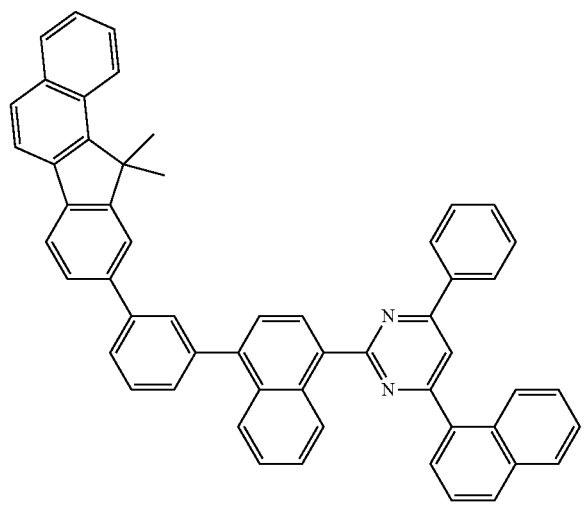
1032
-continued
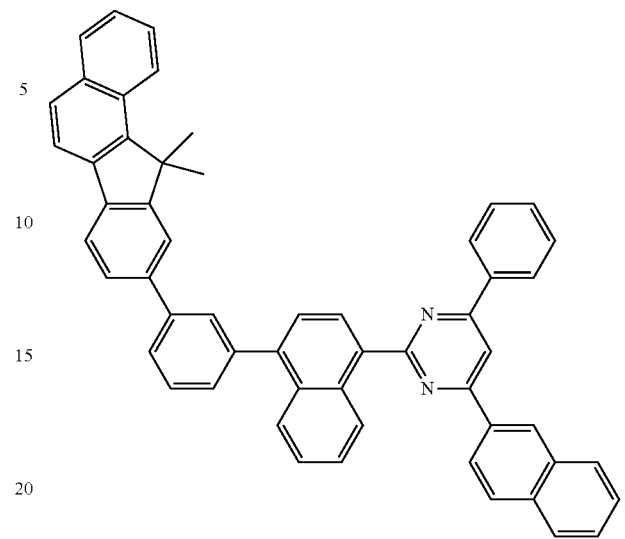
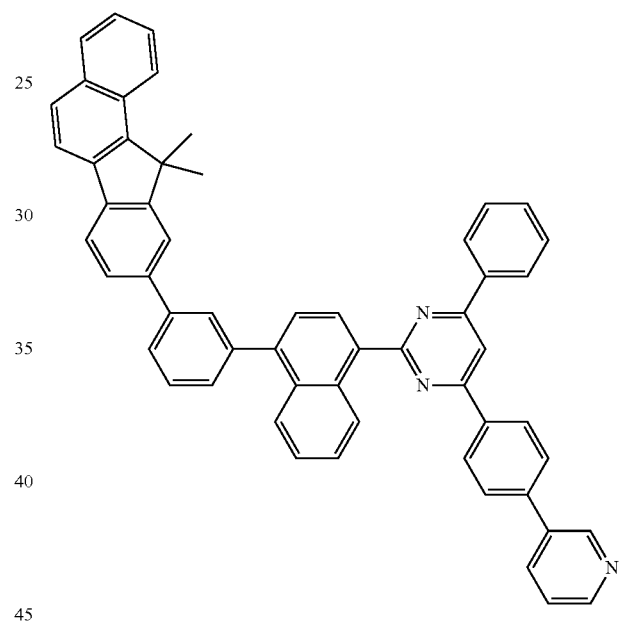
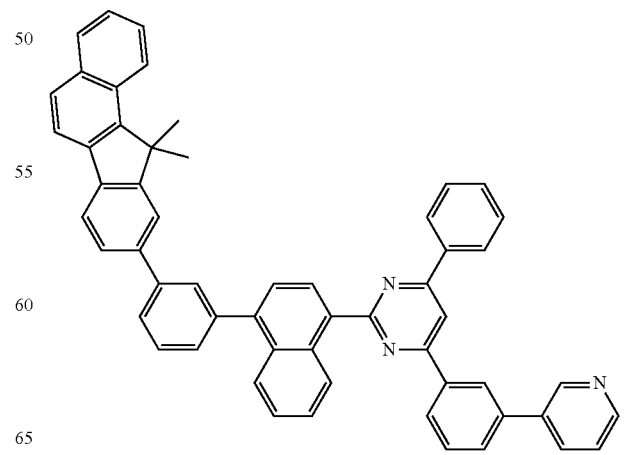

1033
-continued
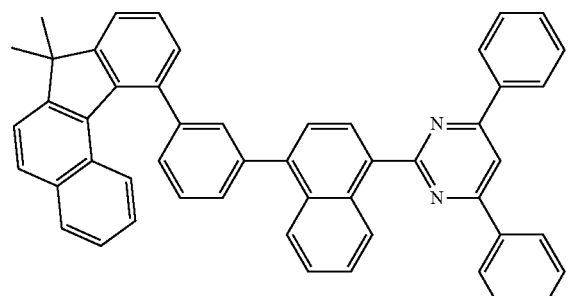
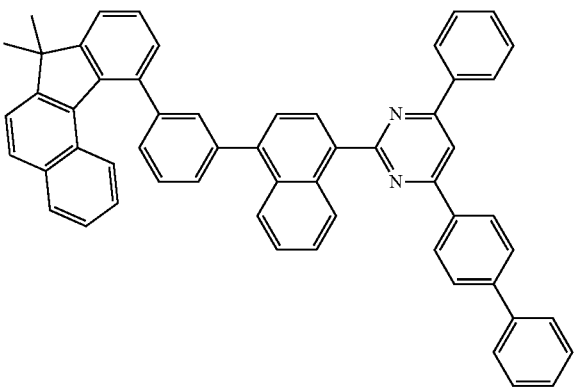
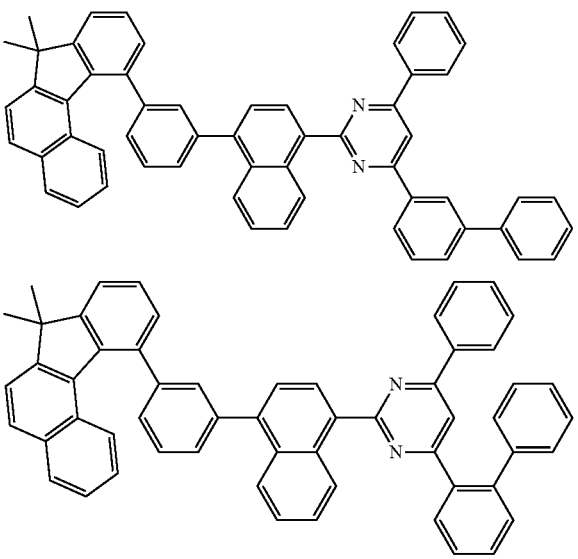
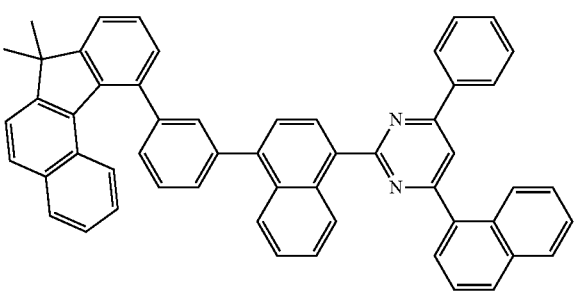
1034
-continued
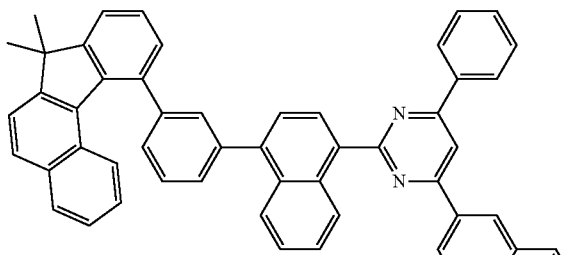
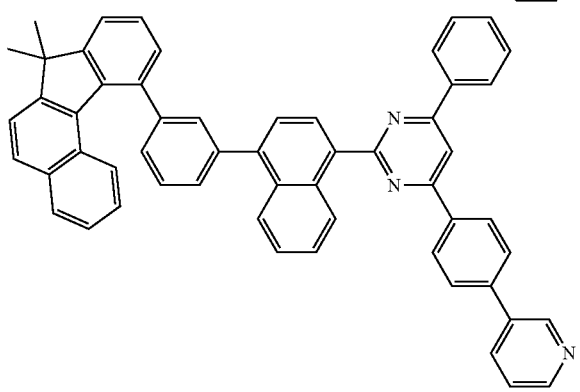
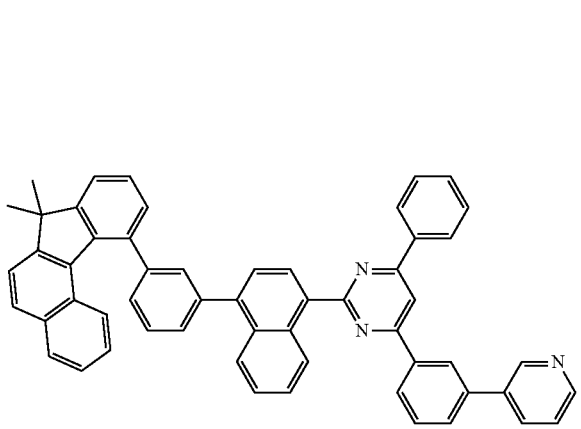
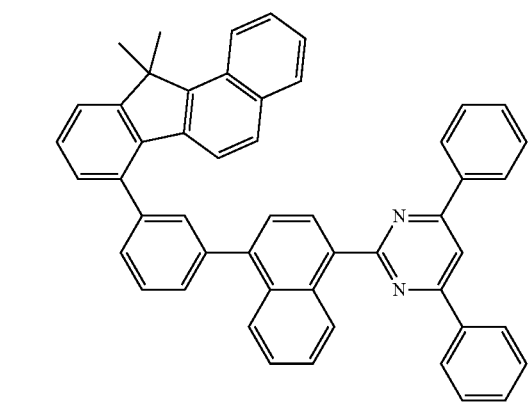

1035
-continued
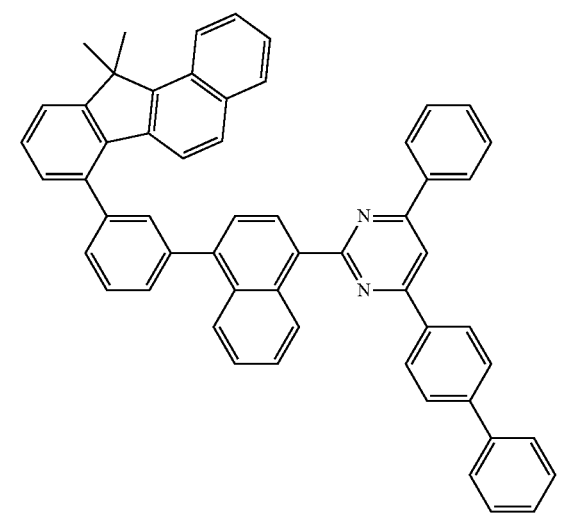
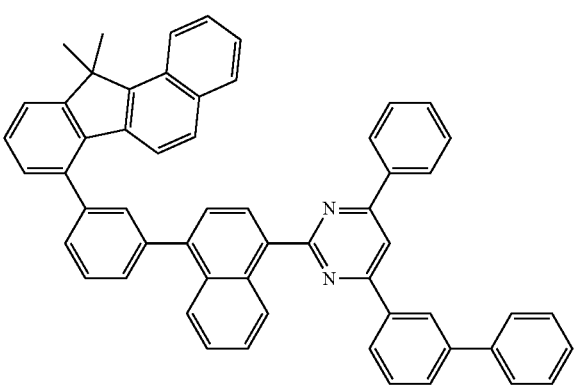 [SMILES: CC1(C)c2cccc(-c3cccc(-c4ccc(-c5nc(-c6ccccc6)cc(-c6cccc(-c7cccnc7)c6)n5)c5ccccc45)c3)c2-c2ccc3ccccc3c21]
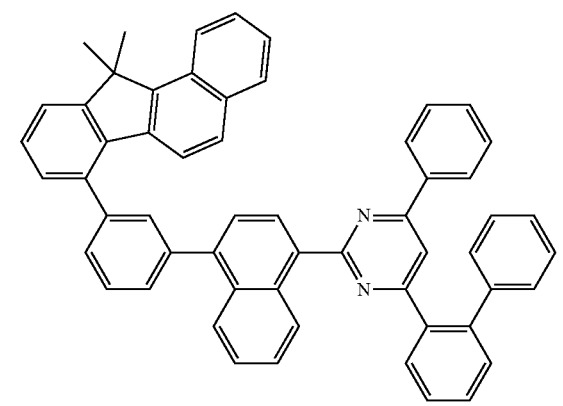
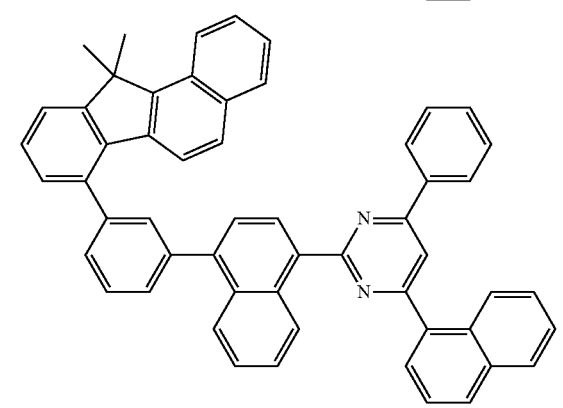
1036
-continued
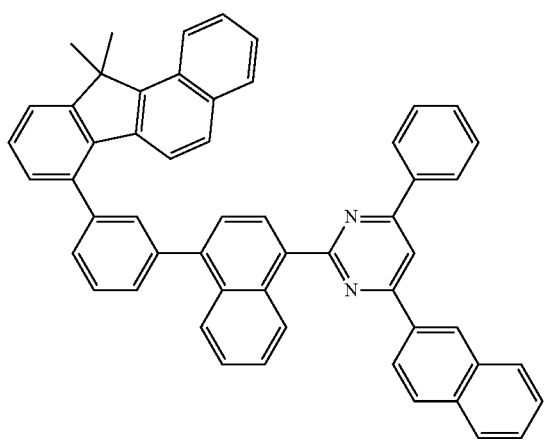
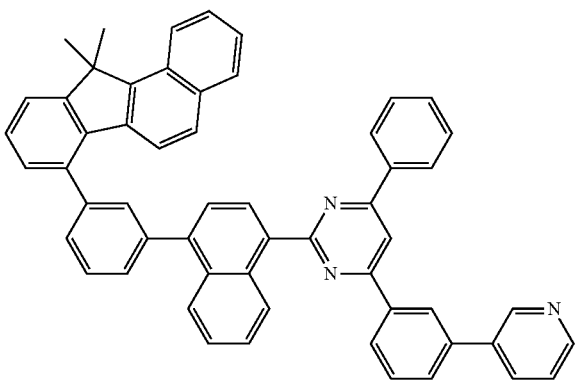
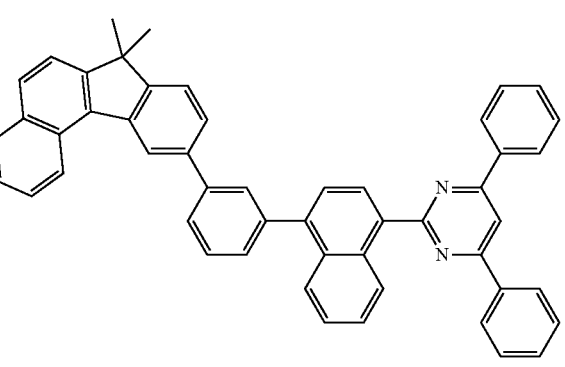

1037
-continued
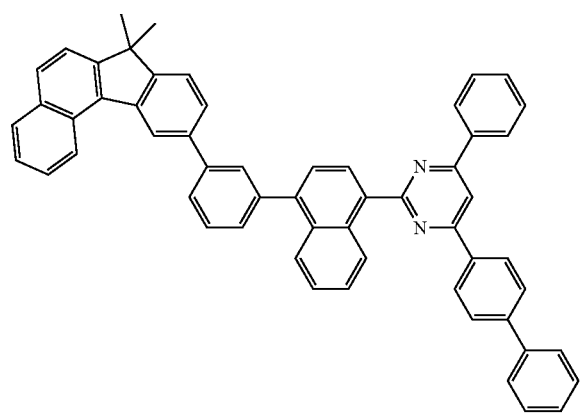
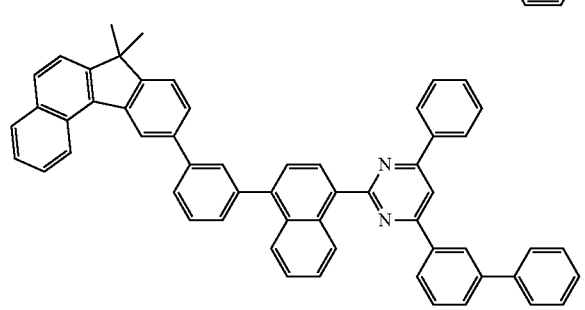
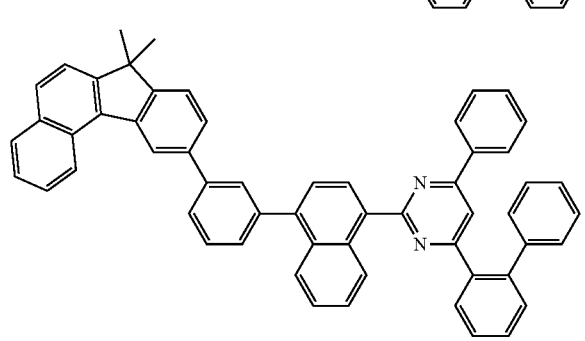
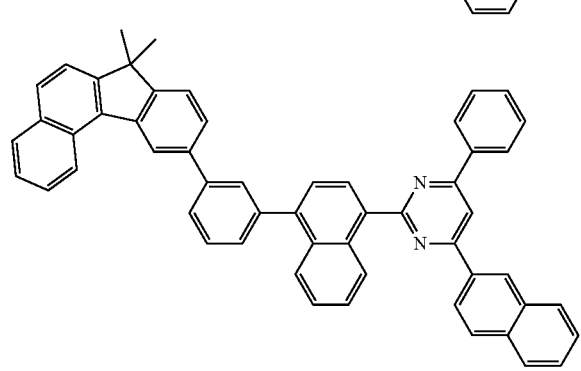
1038
-continued
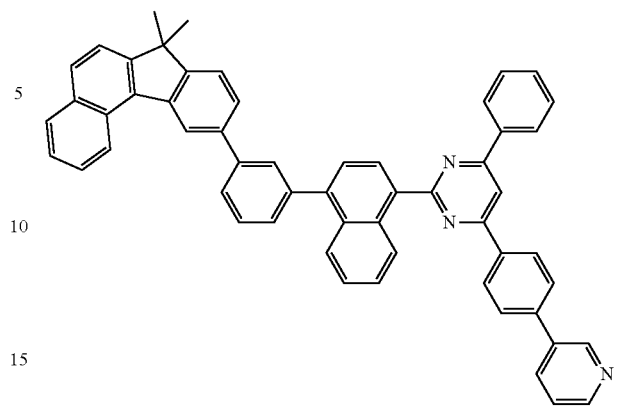
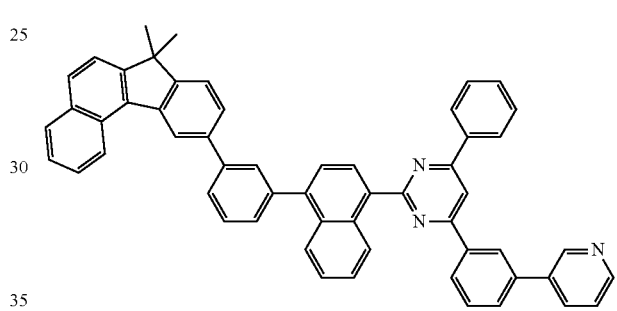
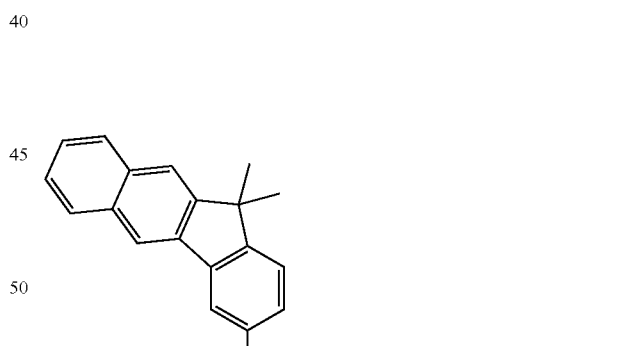
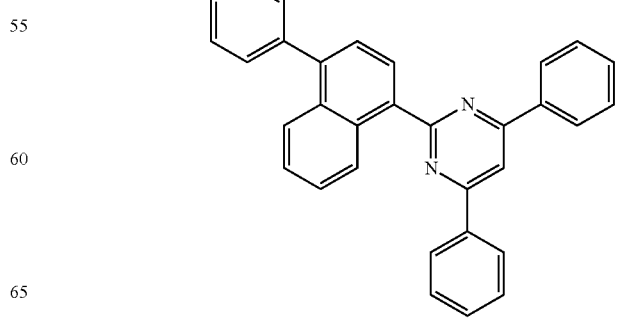

1039
-continued
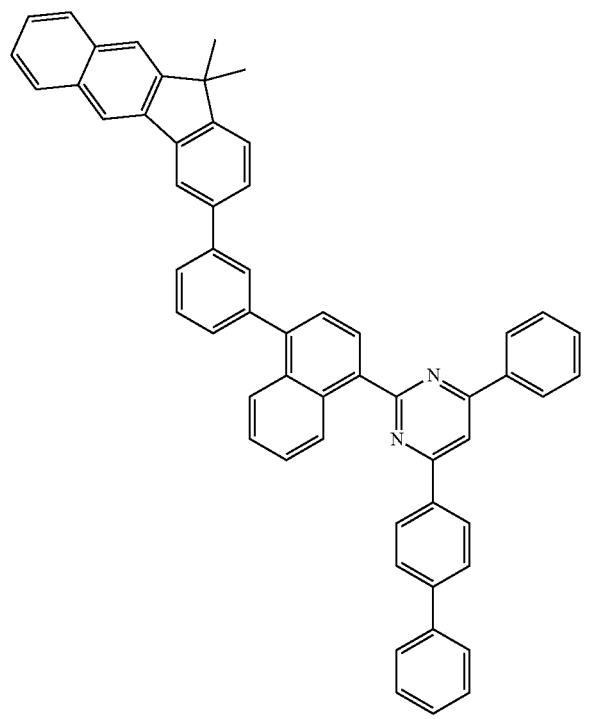
1040
-continued
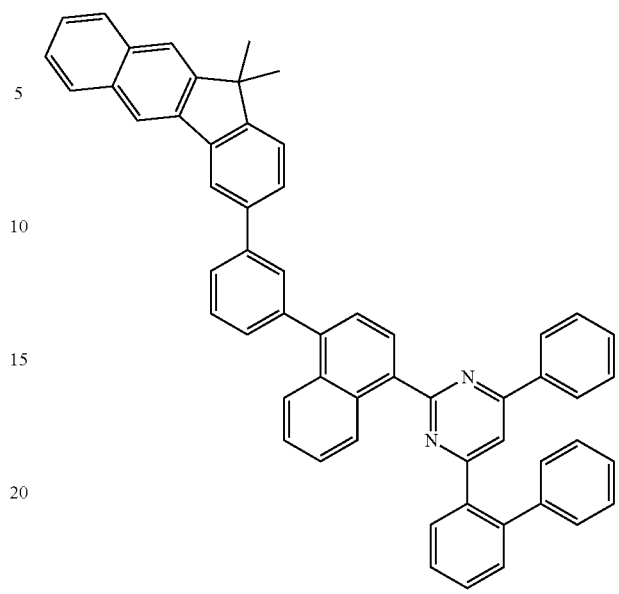
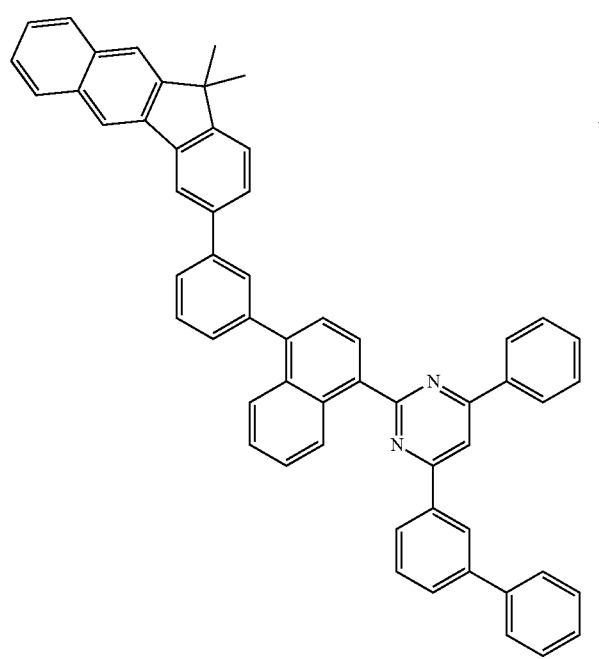
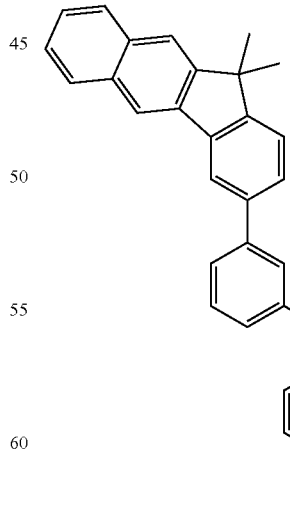
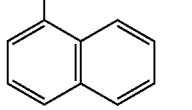

1041
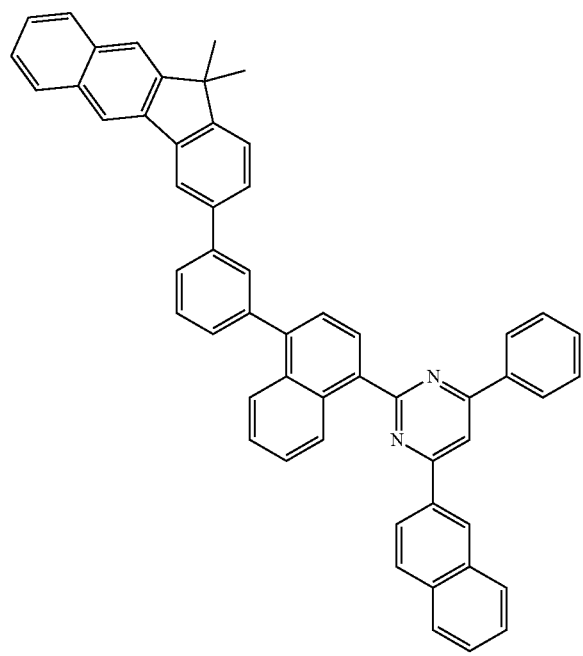
1042
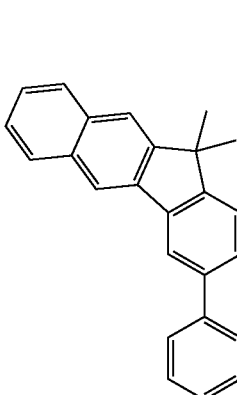
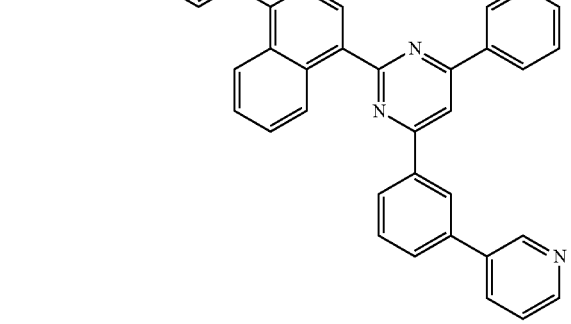
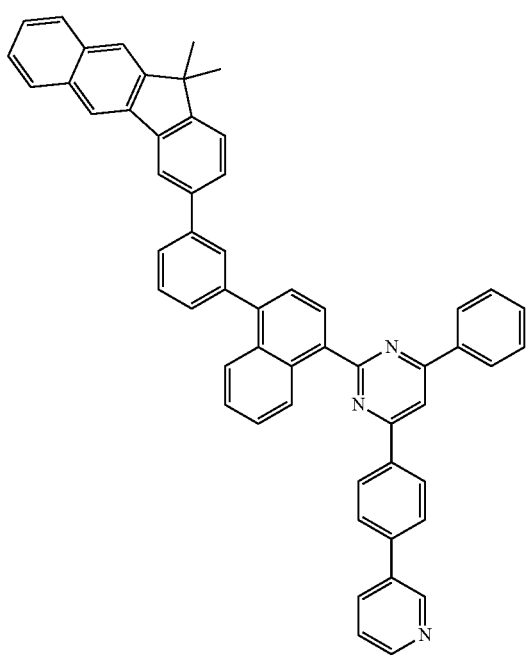
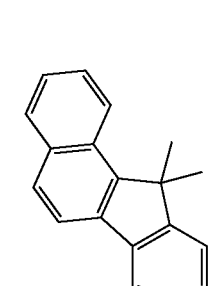

1043
-continued
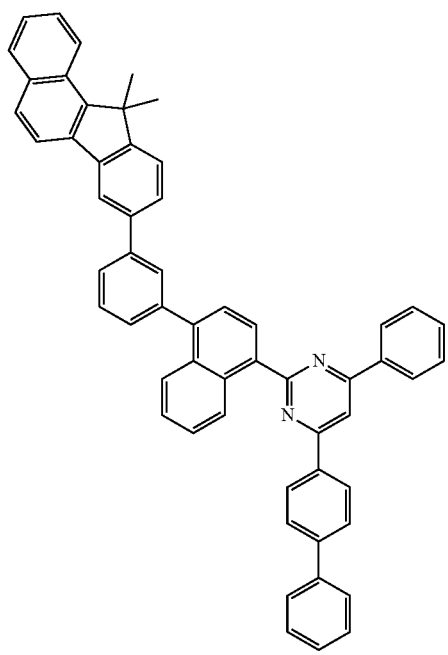
1044
-continued
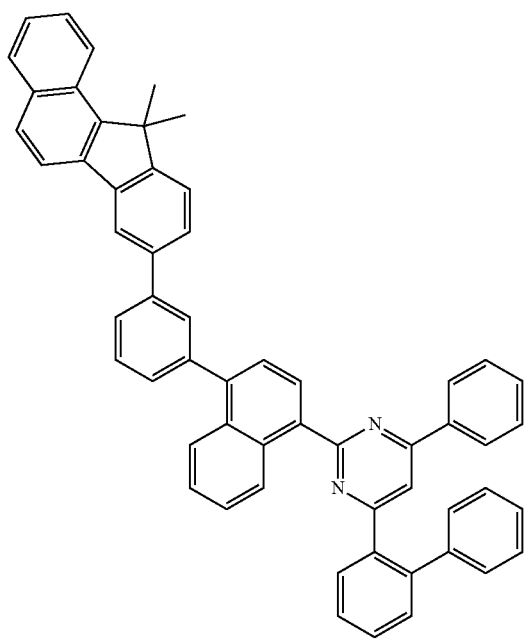
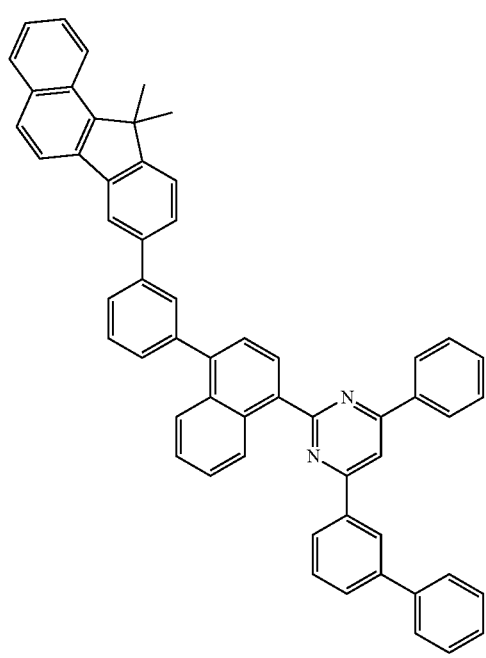
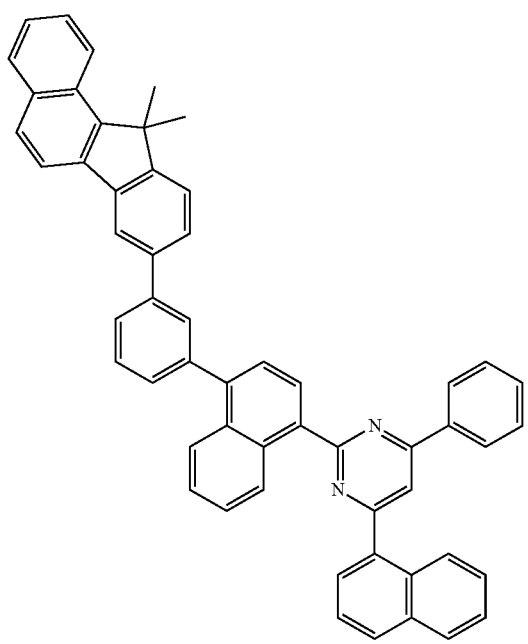

1045
-continued
1046
-continued
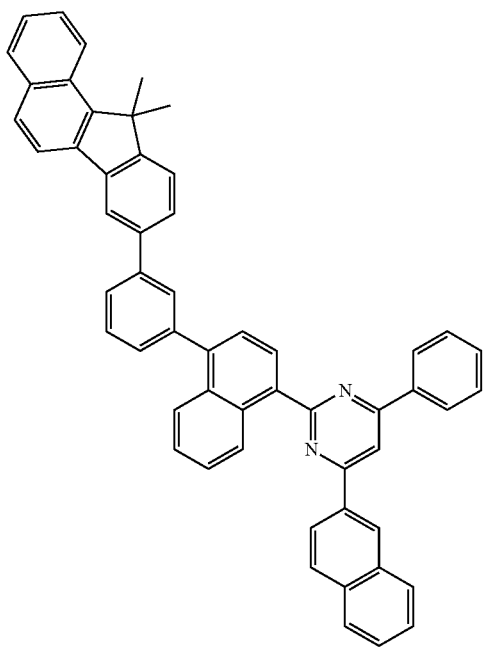
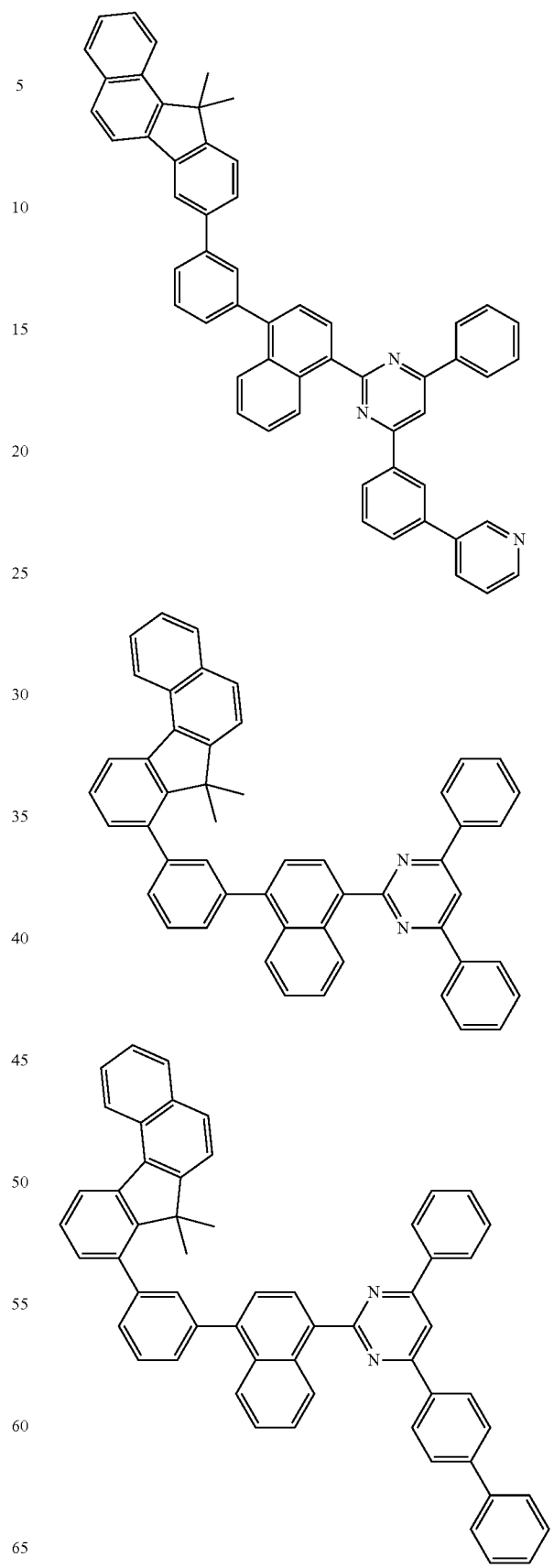

1047
-continued
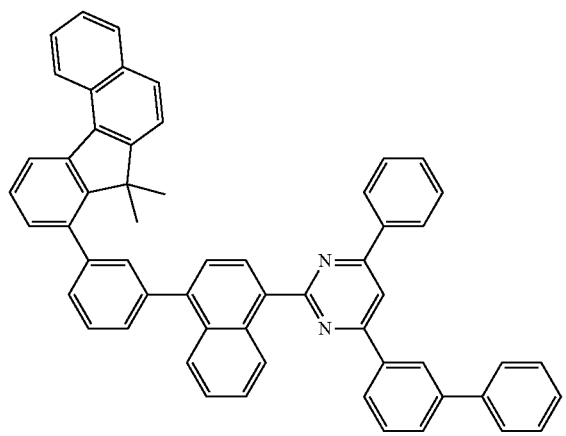
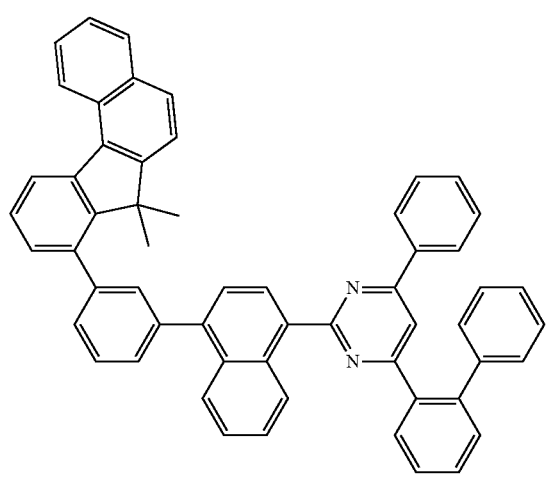
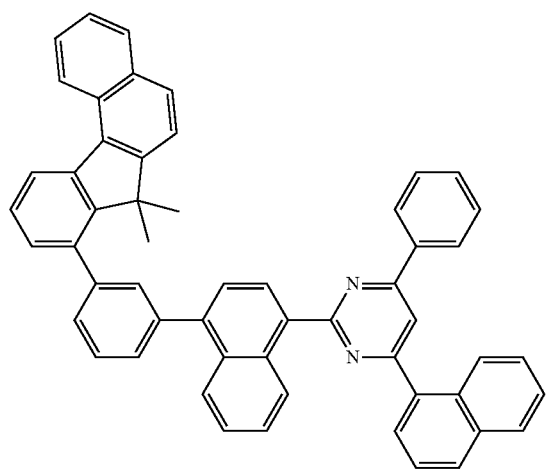
1048
-continued
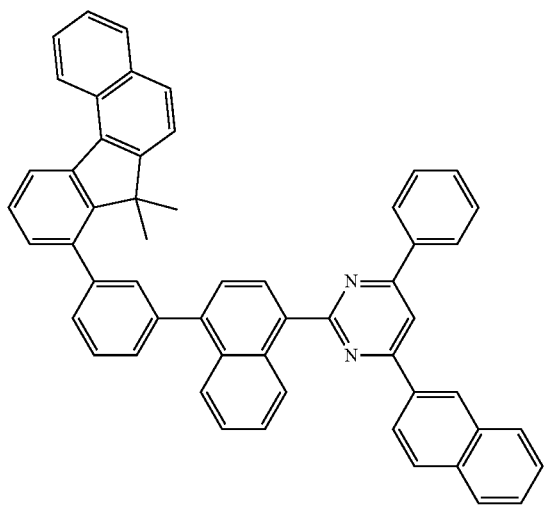
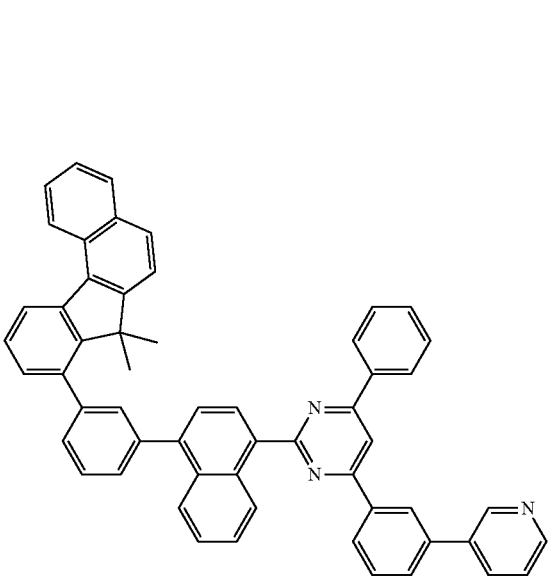

1049
-continued
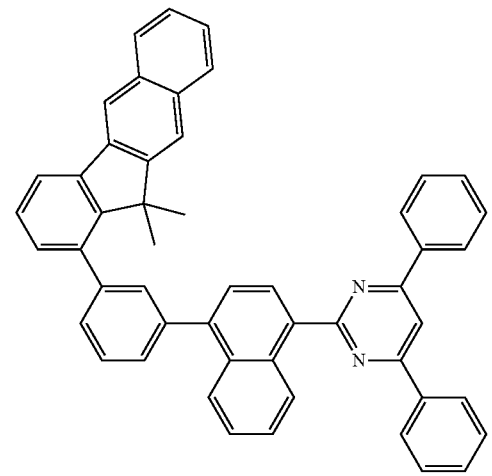
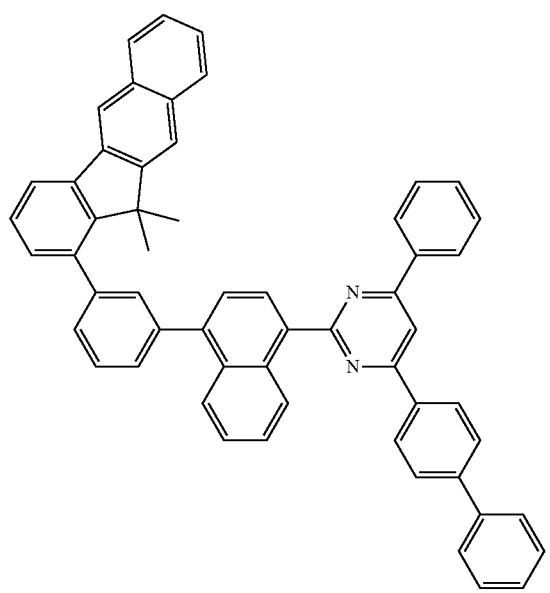
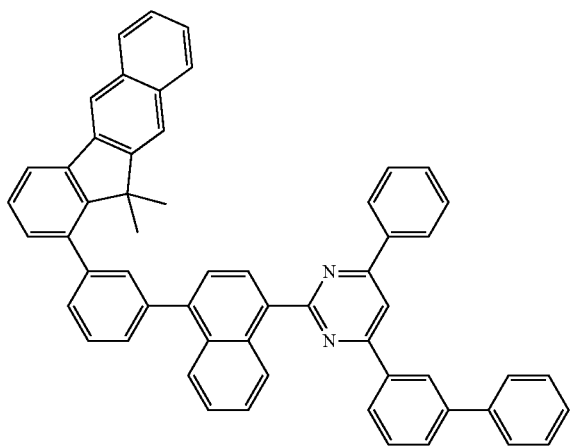
1050
-continued
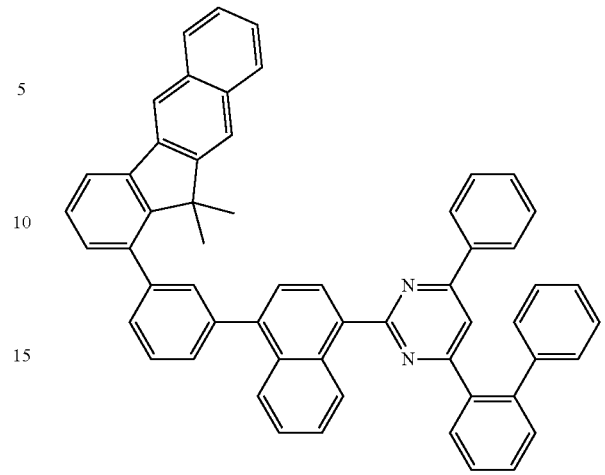
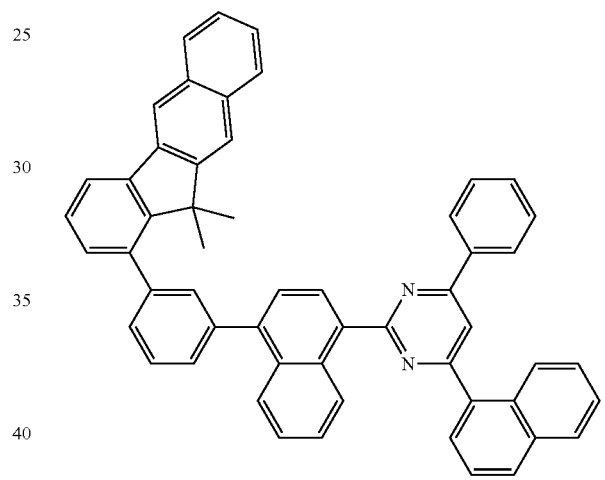
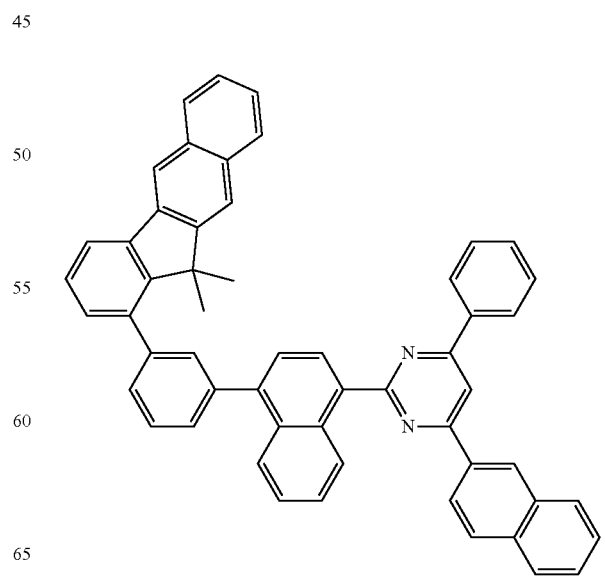

1051
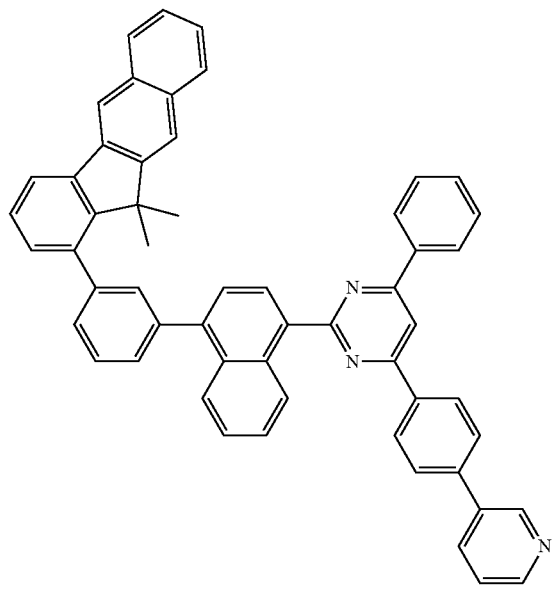
1052
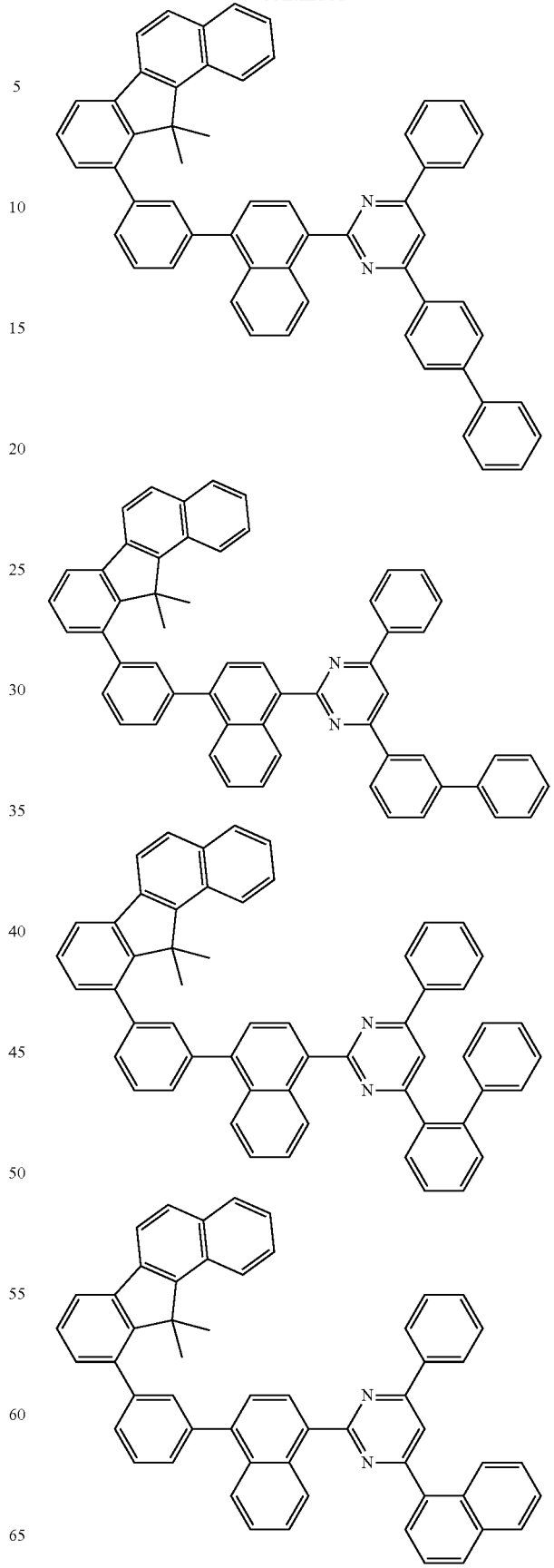

1053
-continued
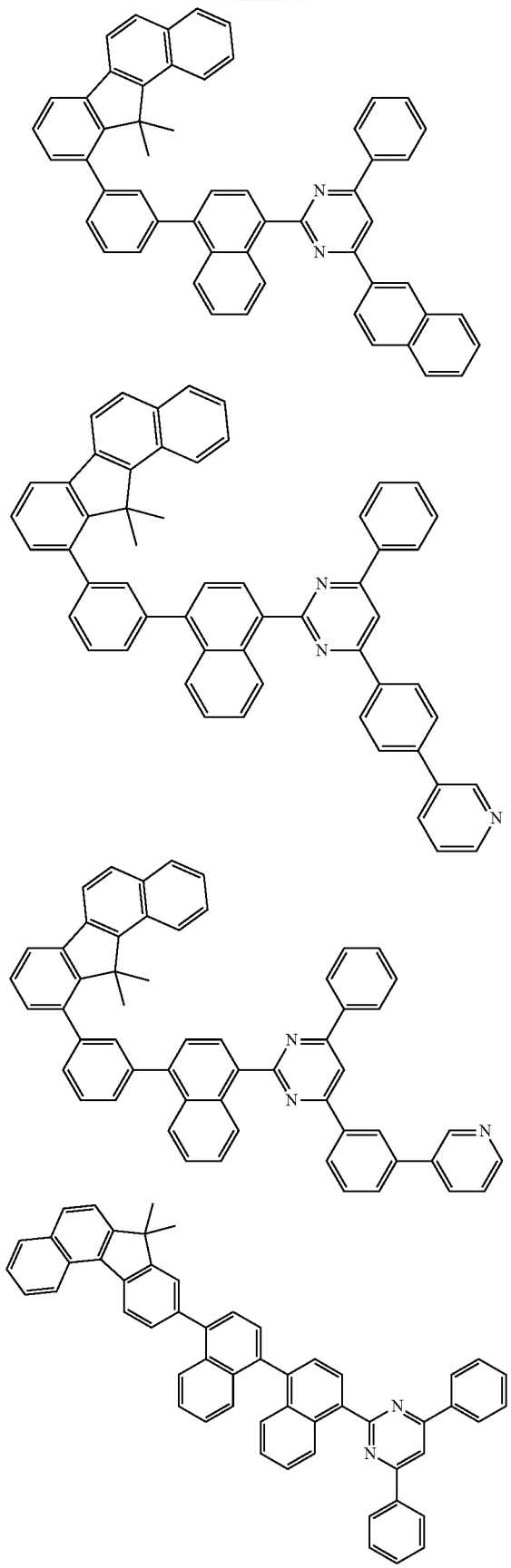
1054
-continued
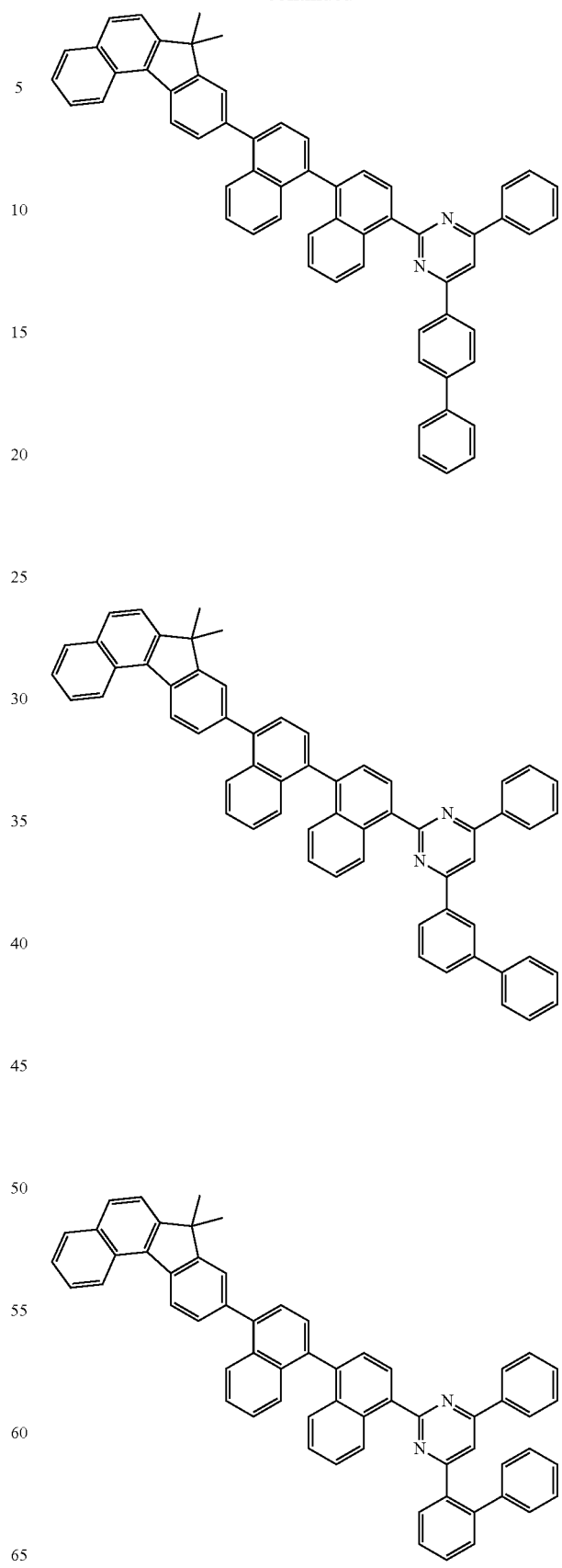

1055
-continued
1056
-continued
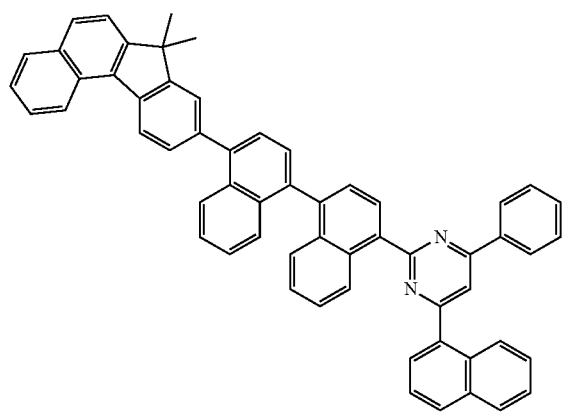
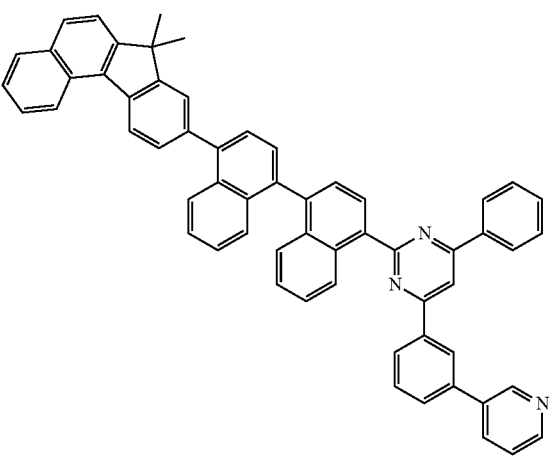
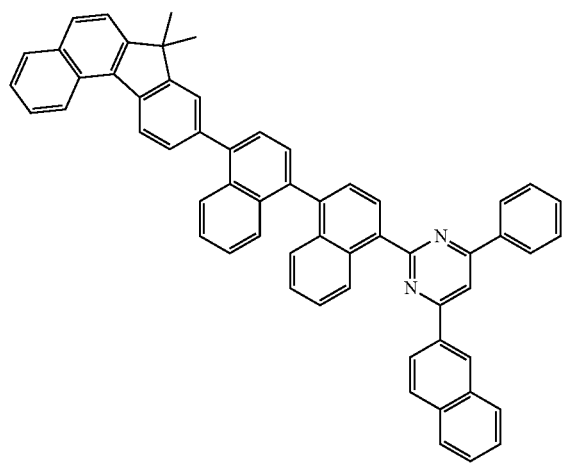
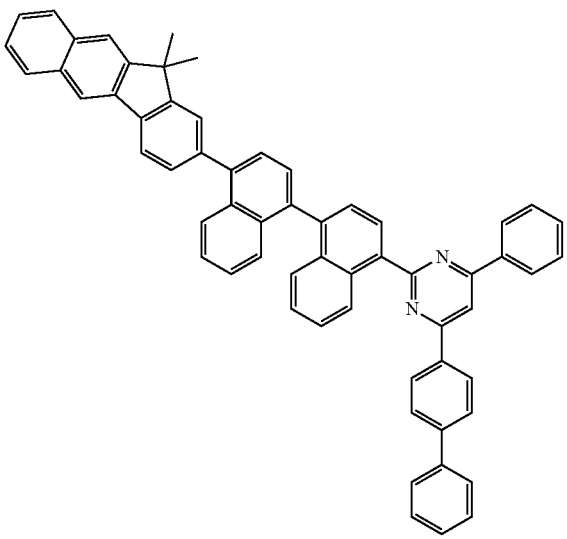

1057
-continued
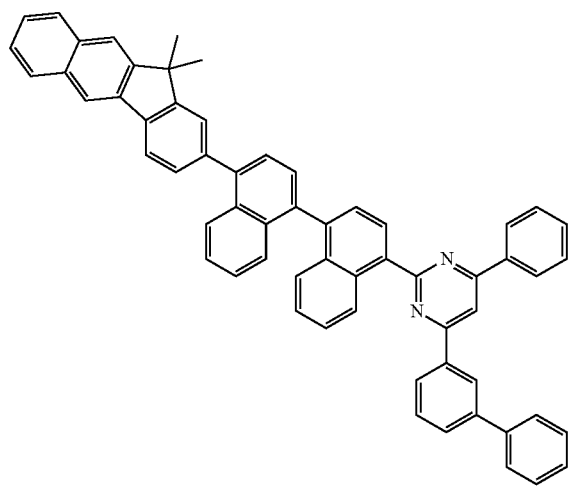
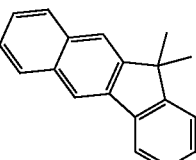
1058
-continued
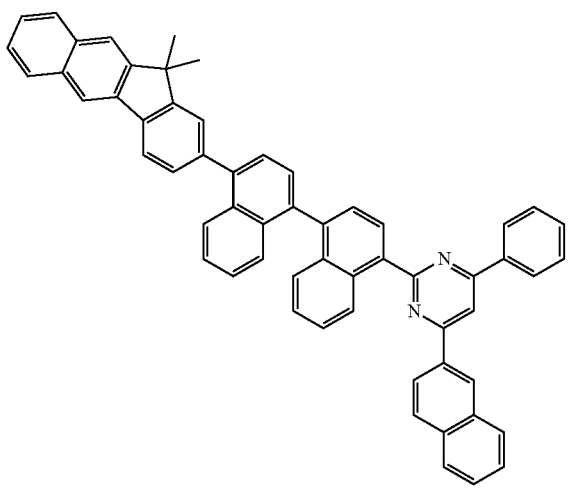
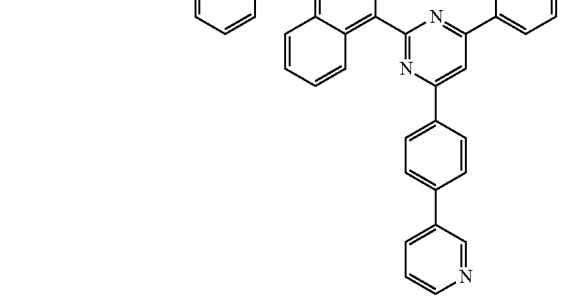
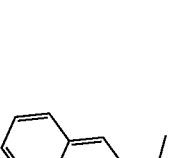
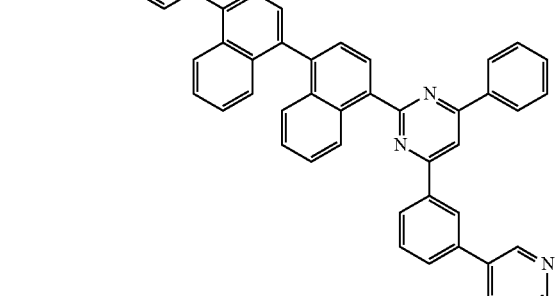

1059
-continued
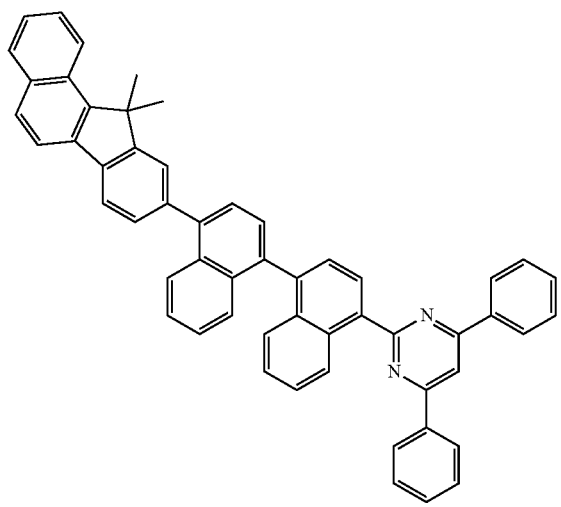
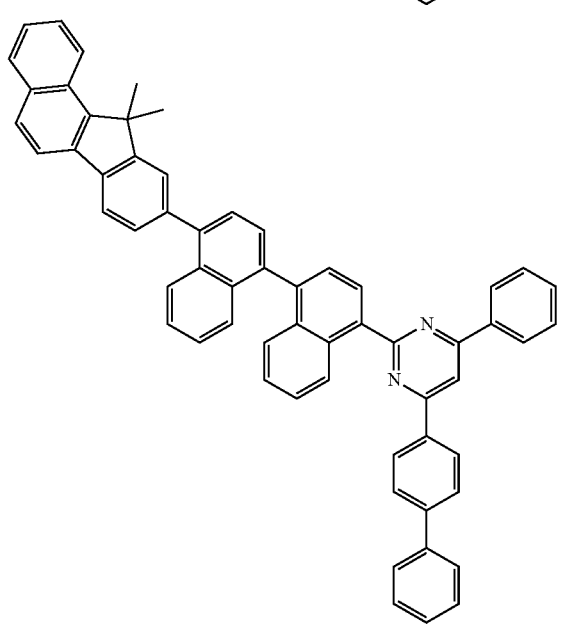
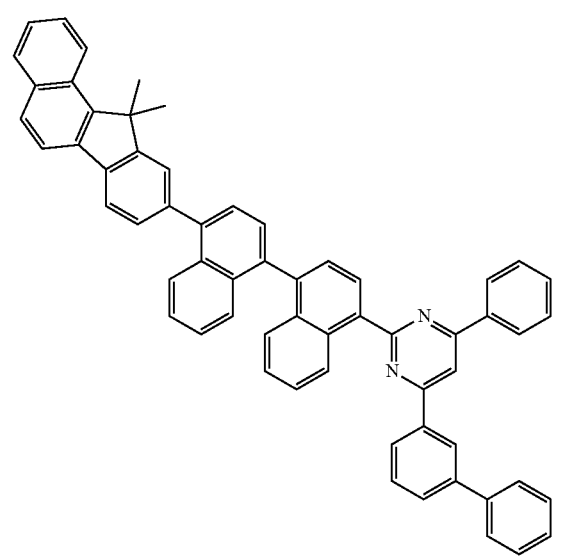
1060
-continued
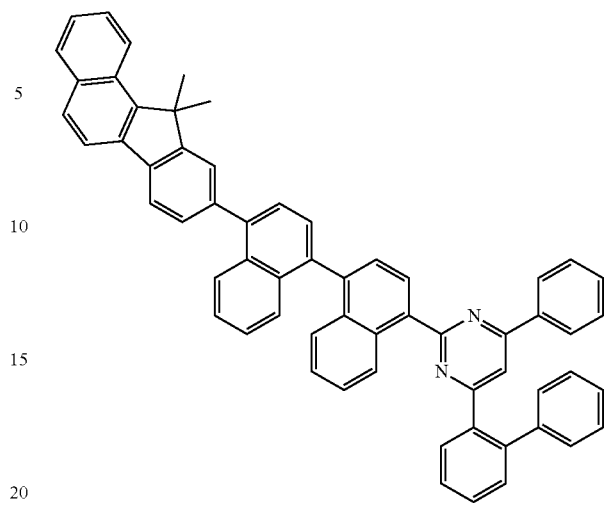
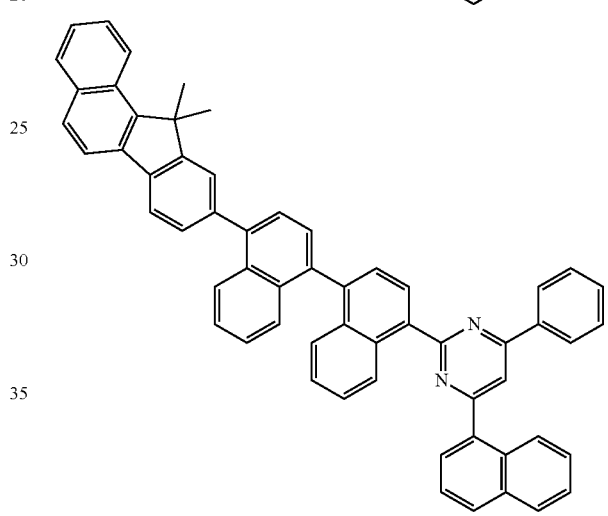
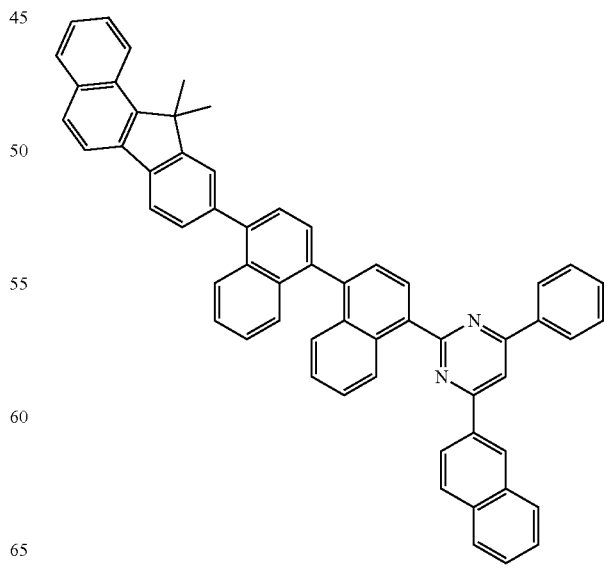

1061
-continued
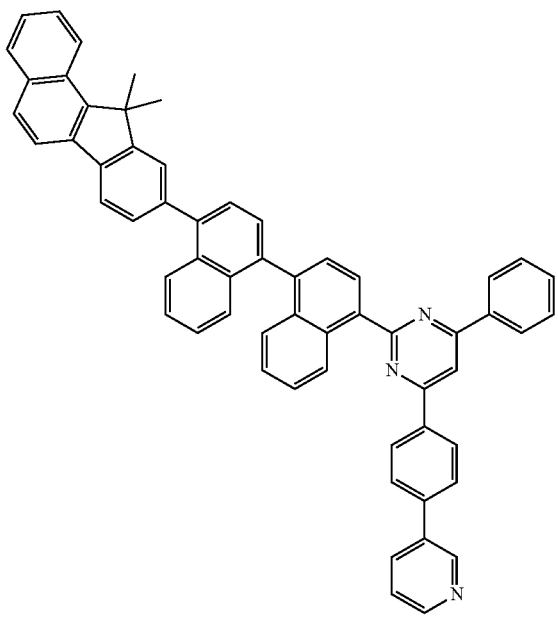
1062
-continued
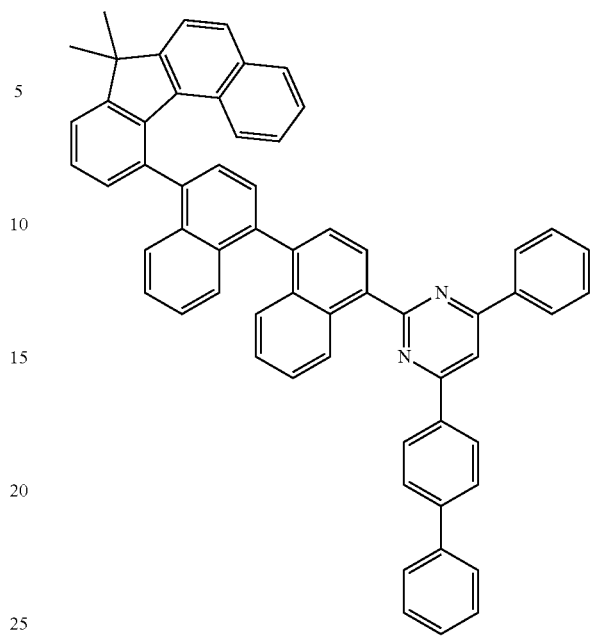
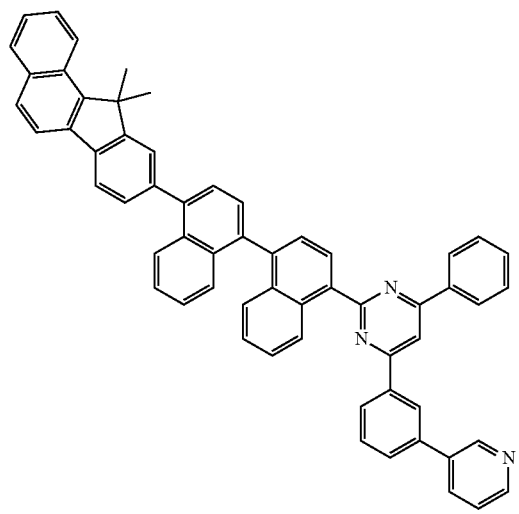
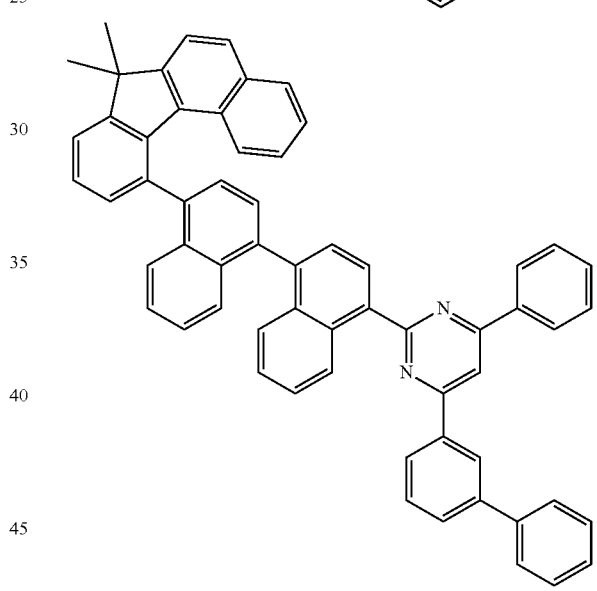
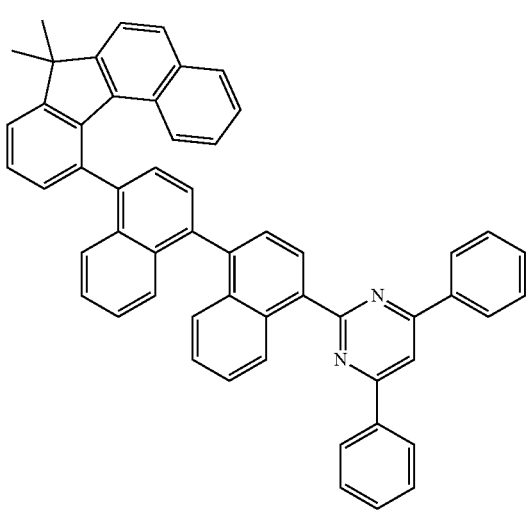
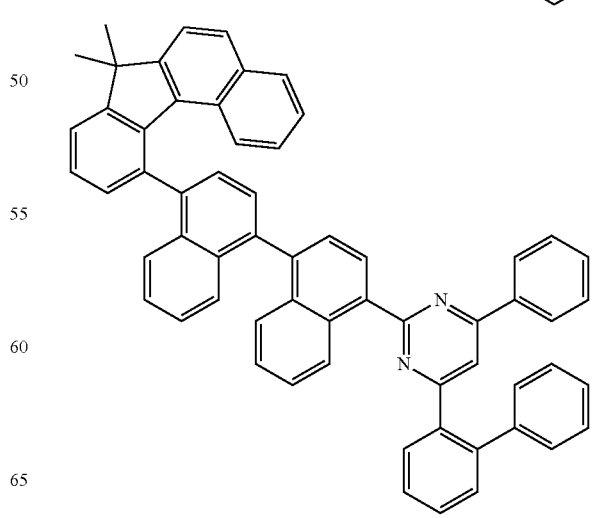

1063
-continued
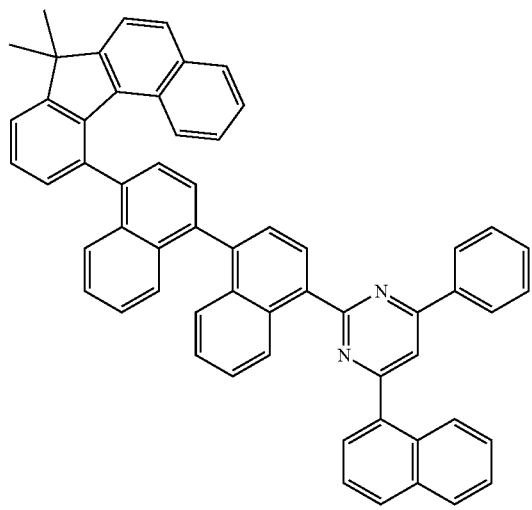
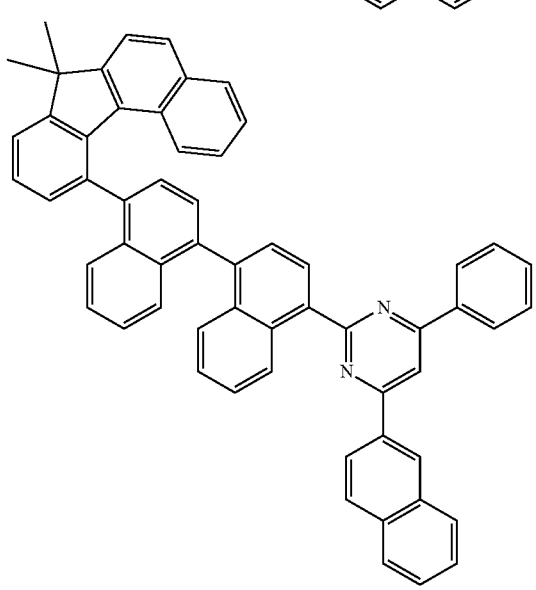
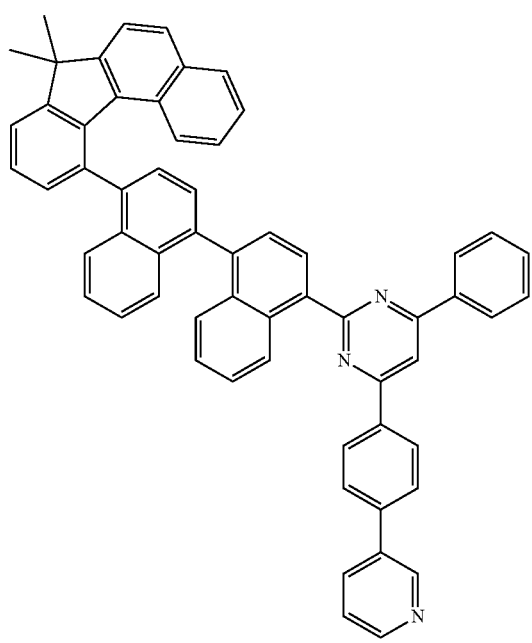
1064
-continued
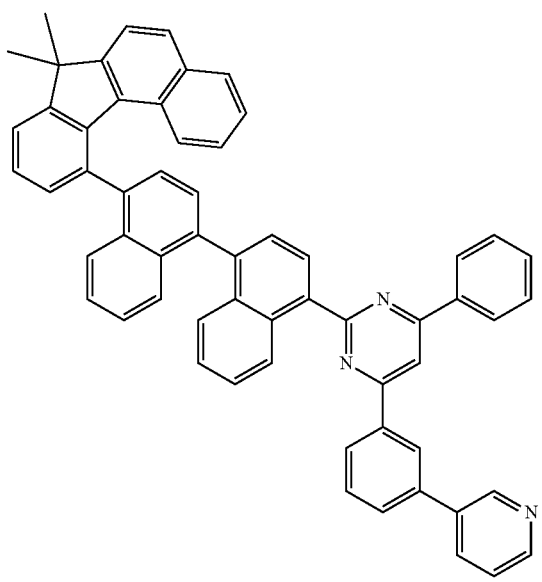
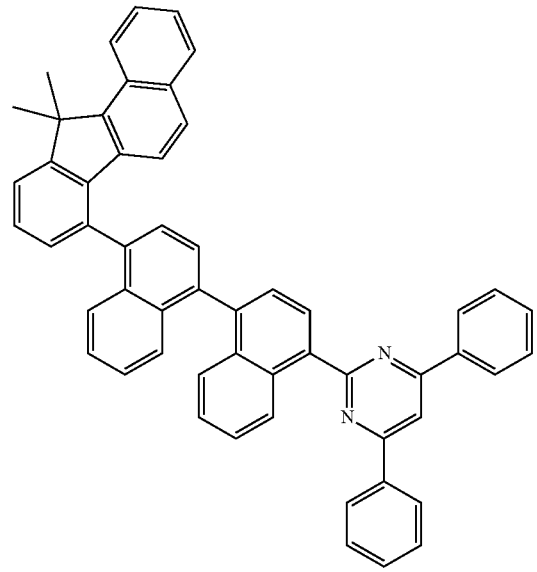

1065
-continued
1066
-continued
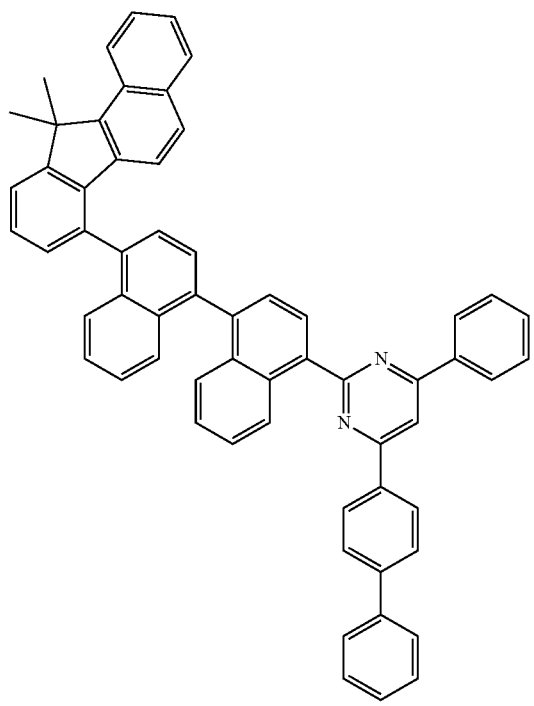
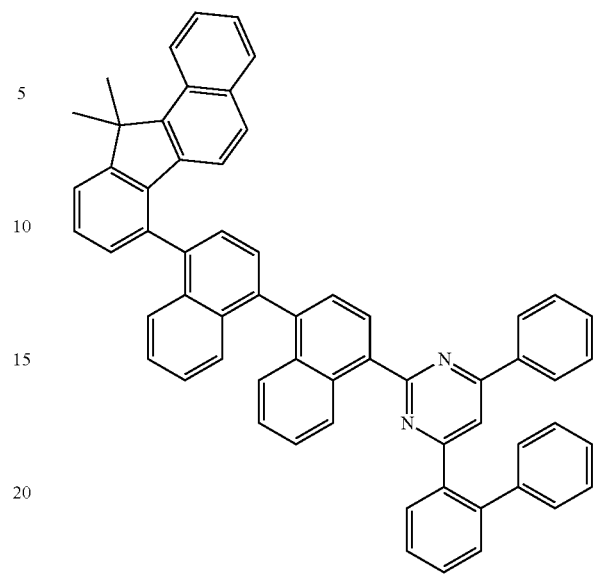
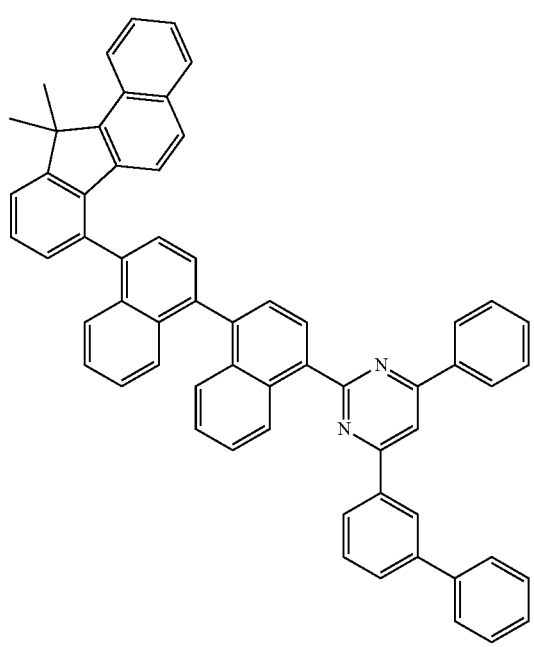

1067
-continued
1068
-continued
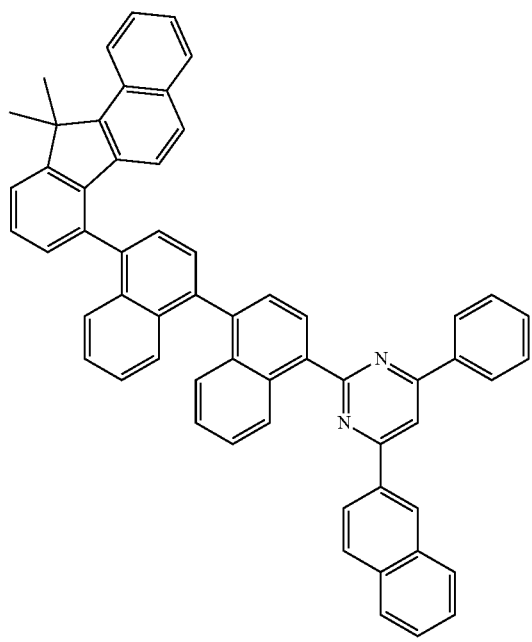
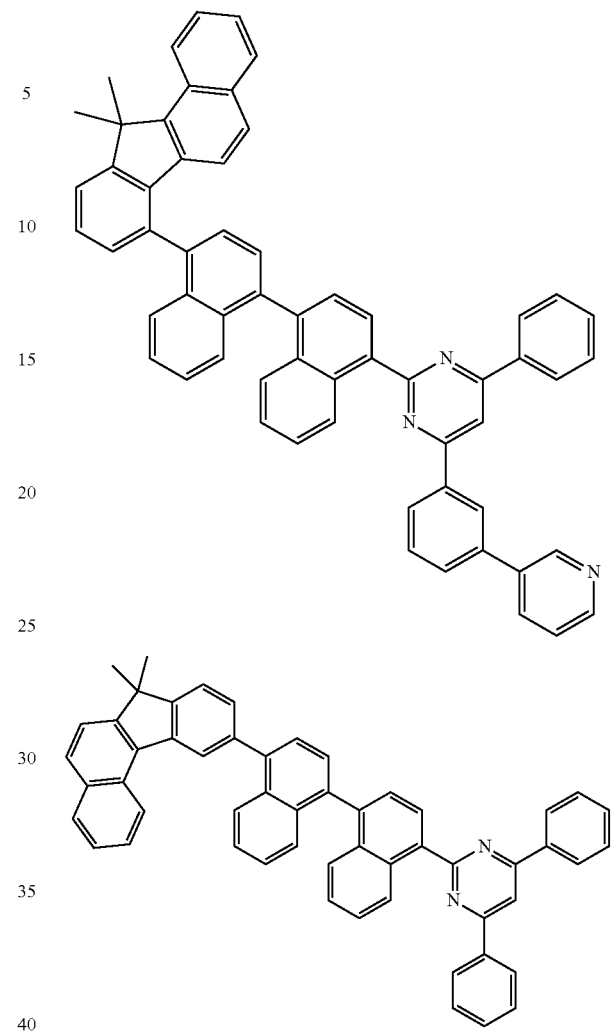
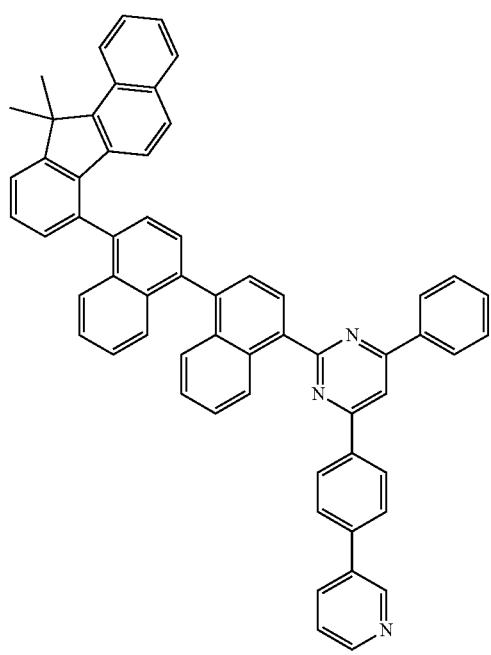

| 1069 -continued | 1070 -continued |
|---|---|
| 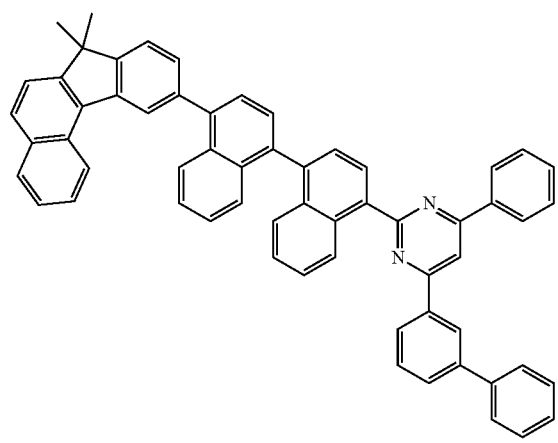 | 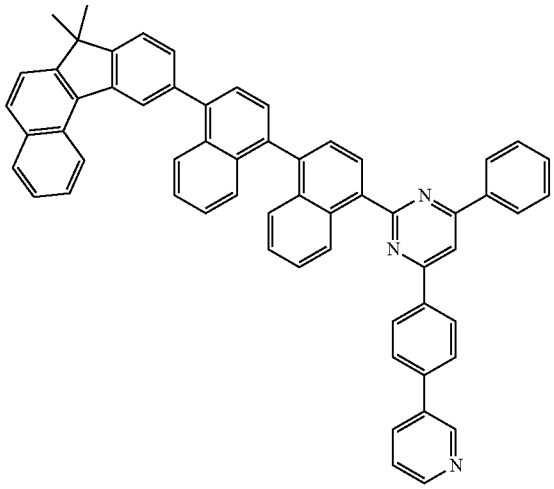 |
| | 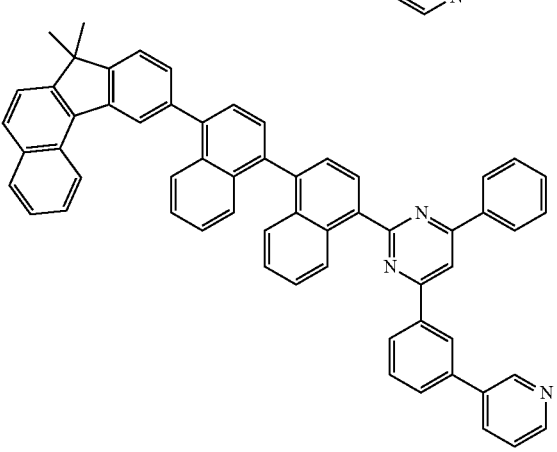 |
| | 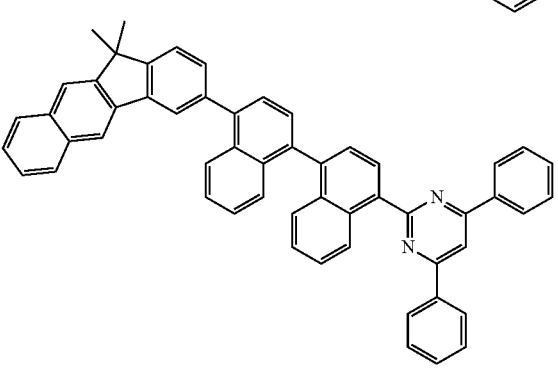 |
| | 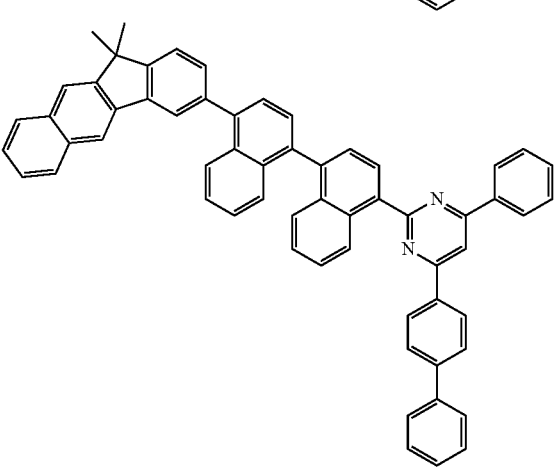 |

1071
-continued
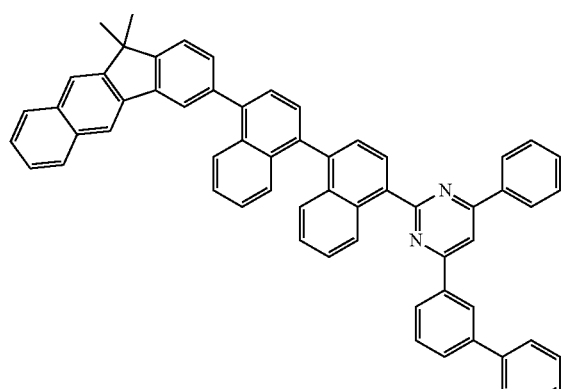
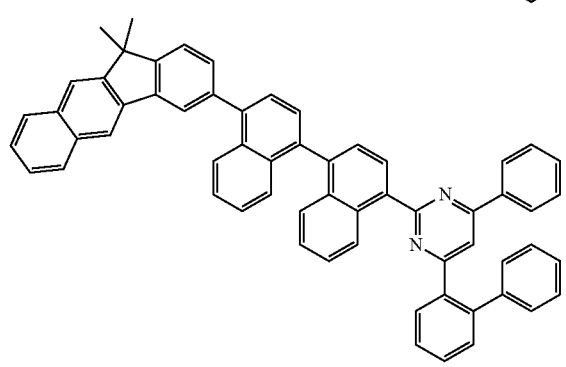
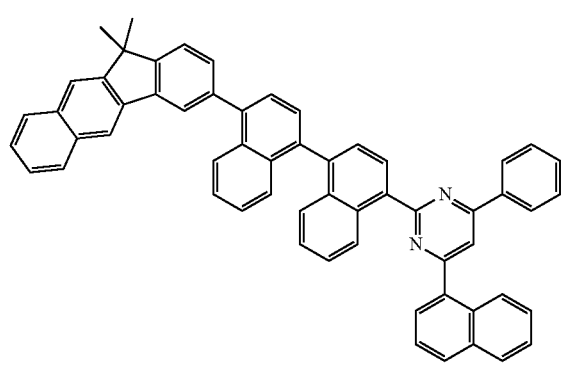
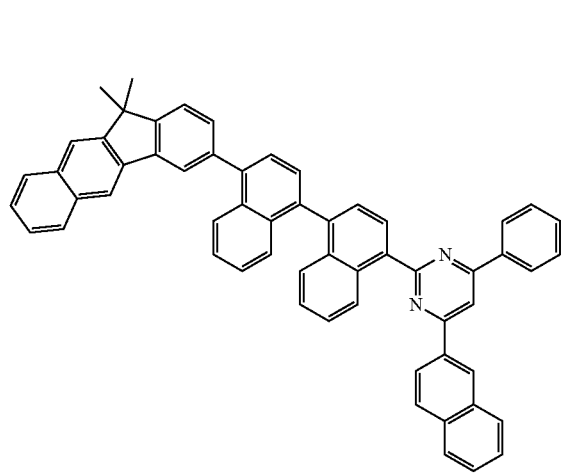
1072
-continued
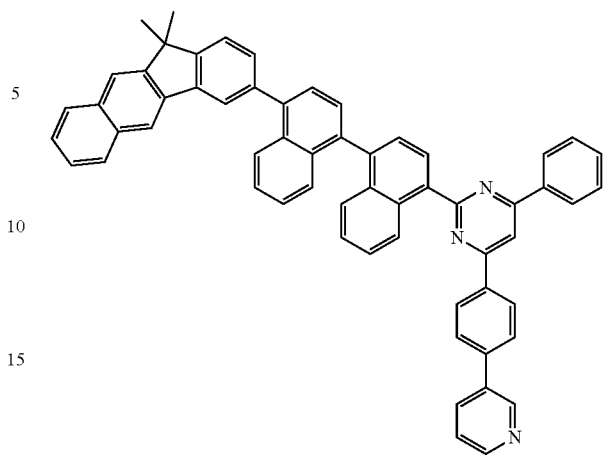
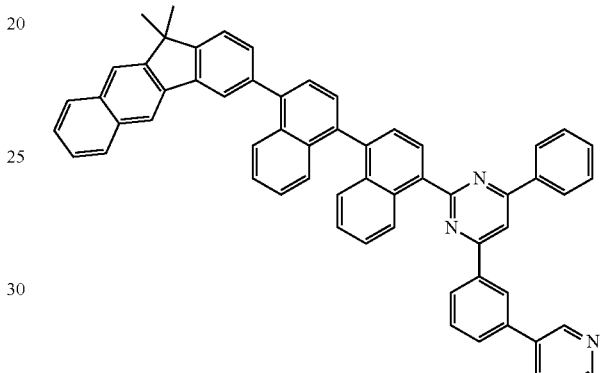
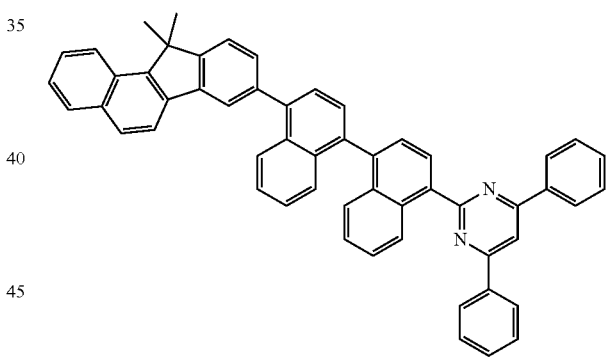

1073
-continued
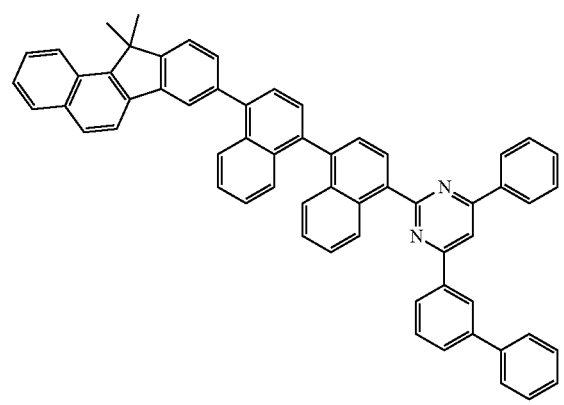
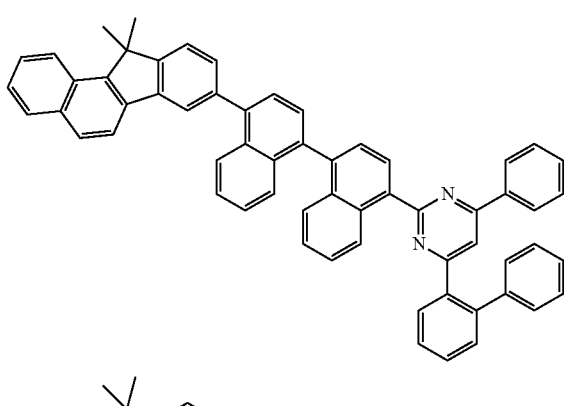
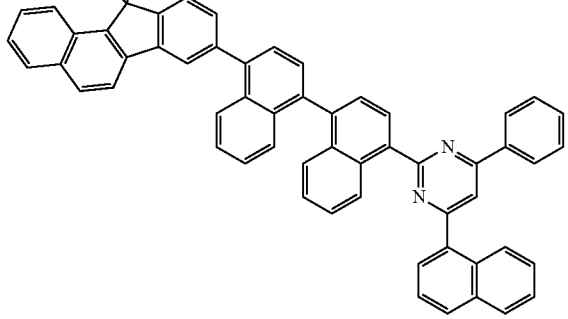
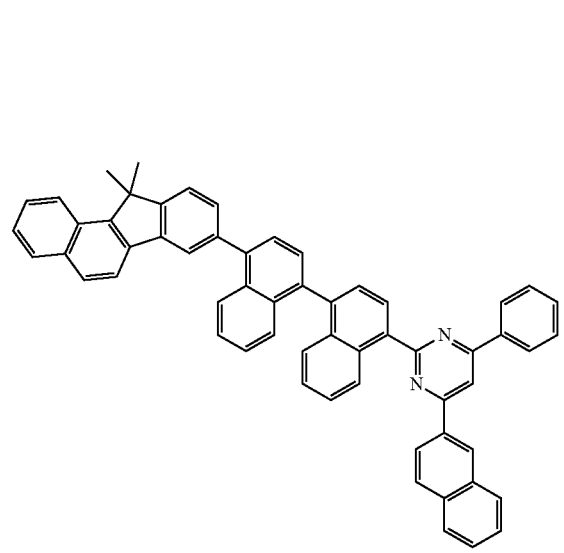
1074
-continued
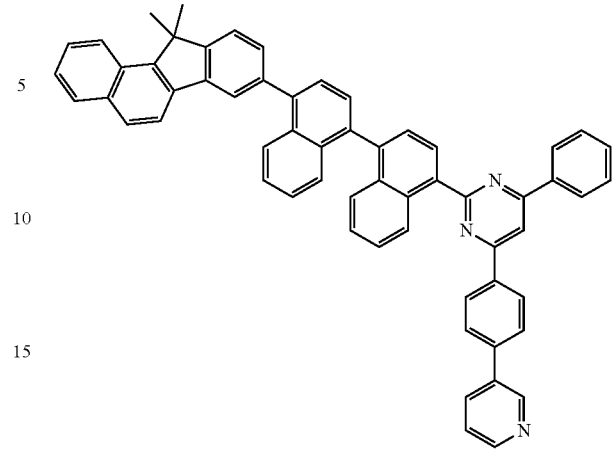
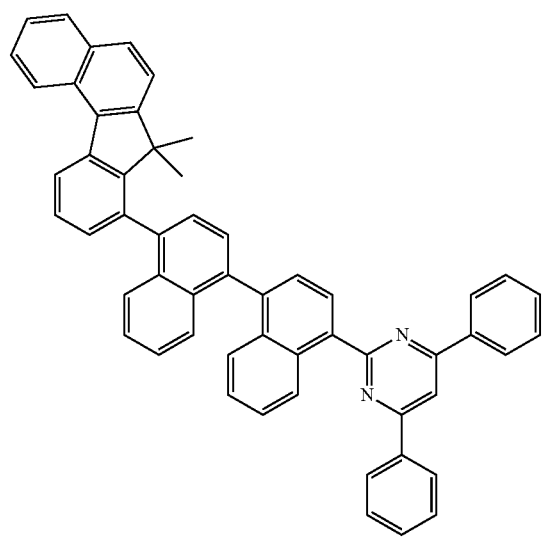

1075
-continued
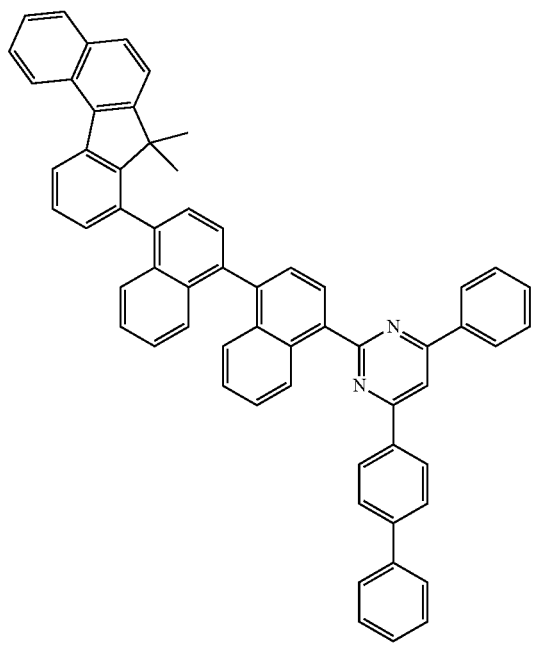
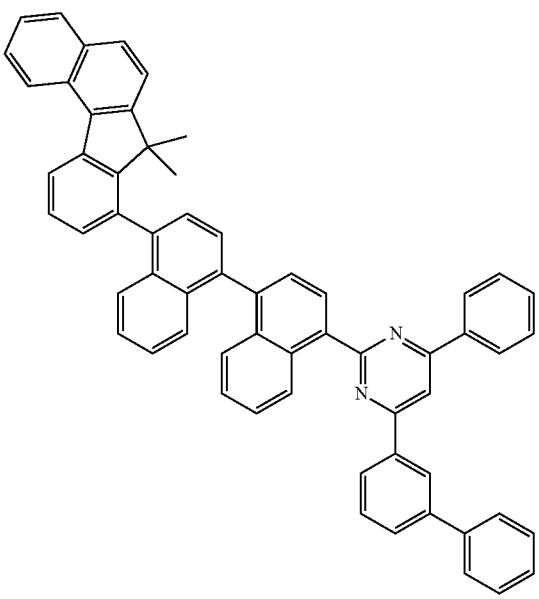
1076
-continued
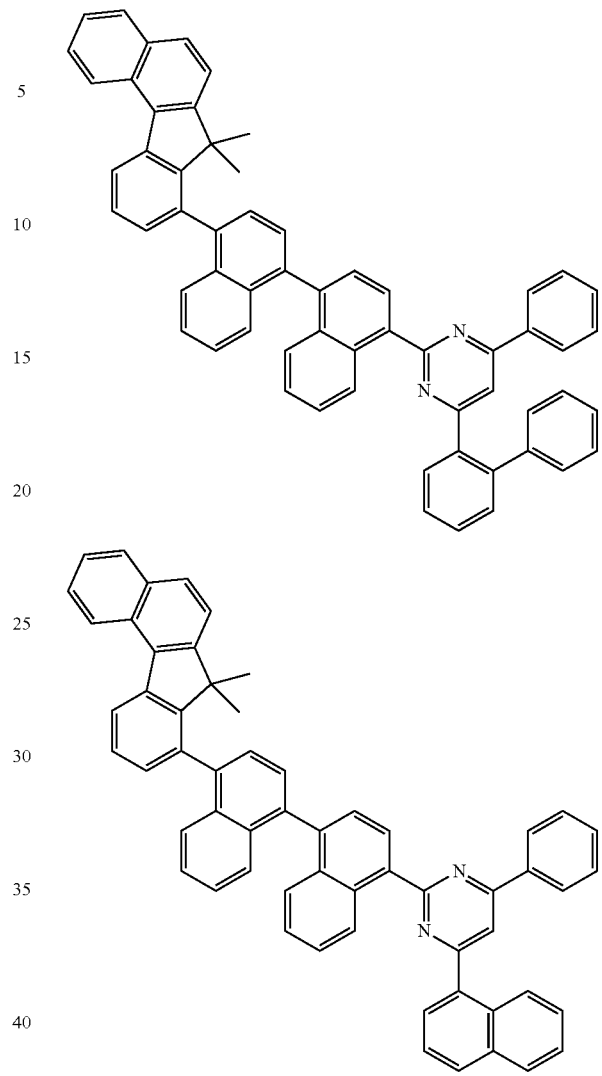
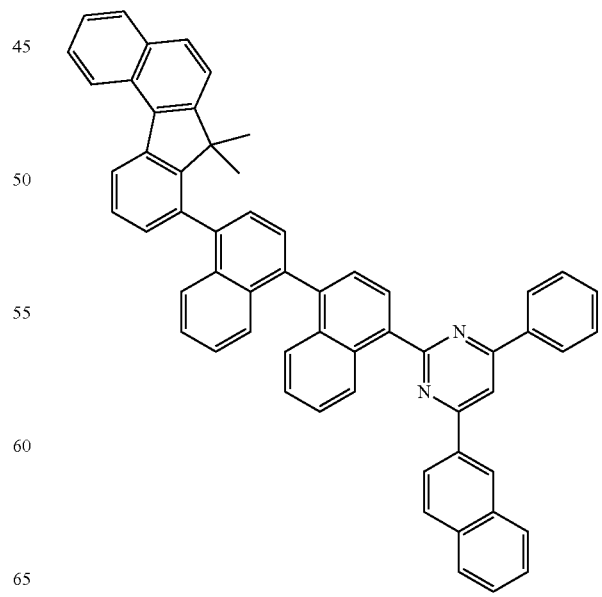

1077
-continued
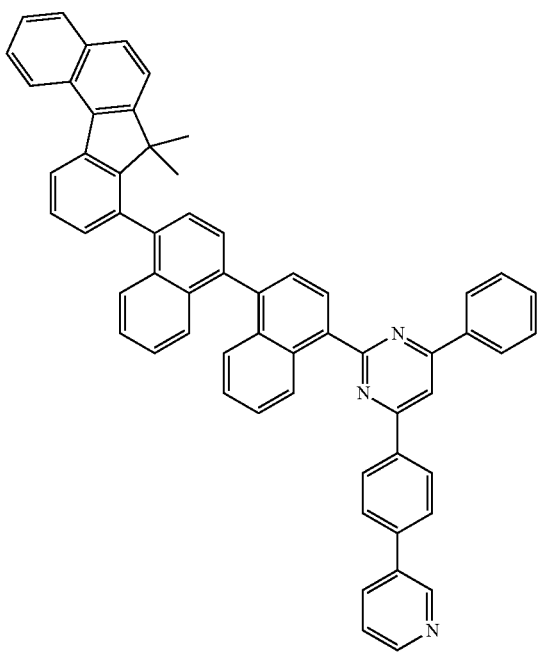
1078
-continued
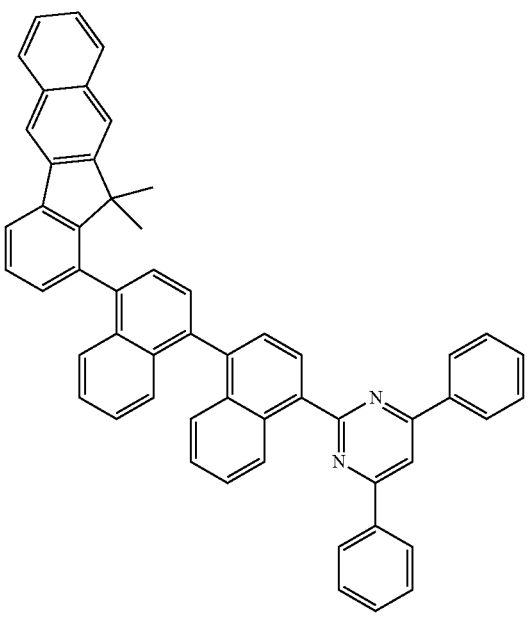
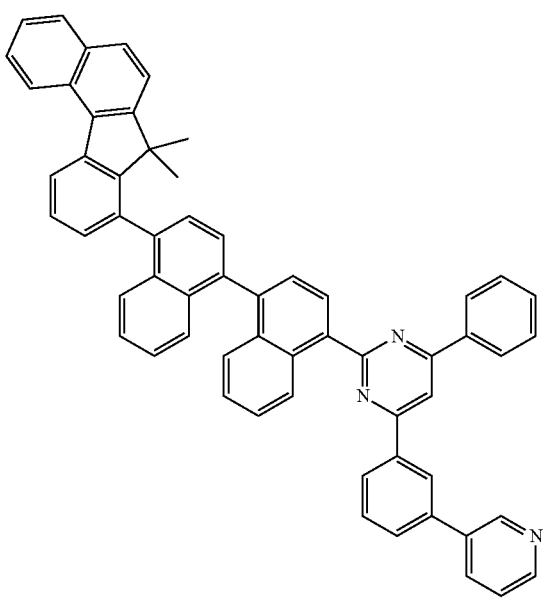
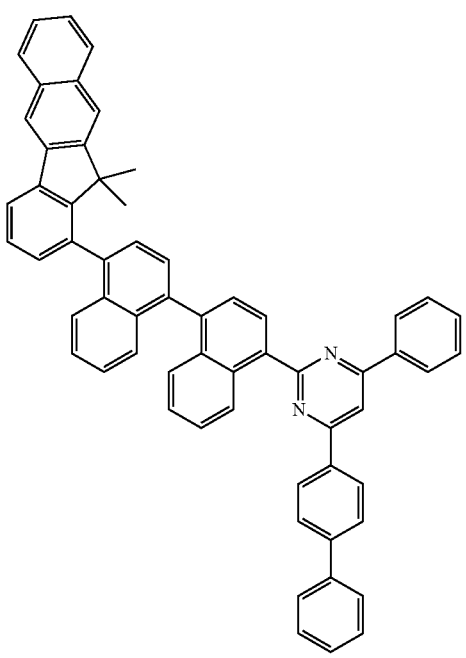

1079
-continued
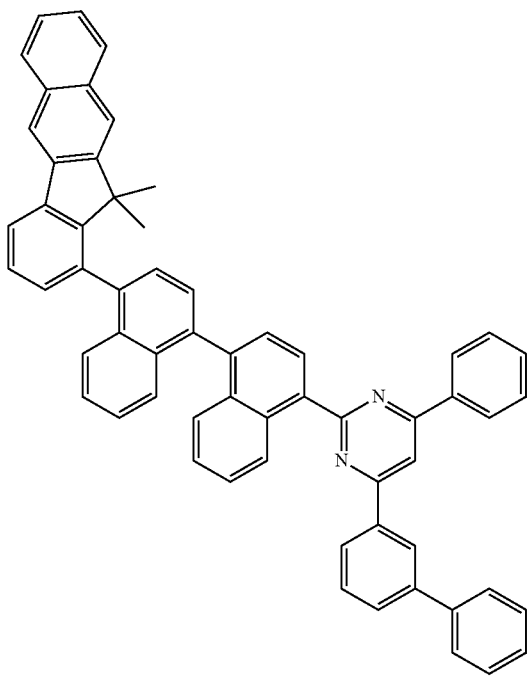
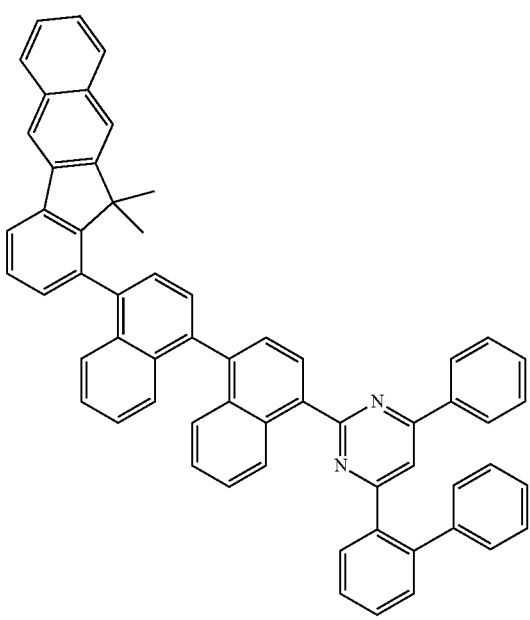
1080
-continued
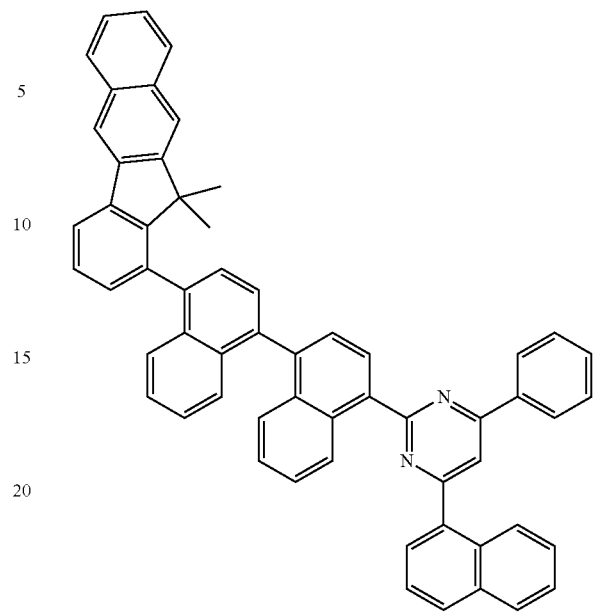
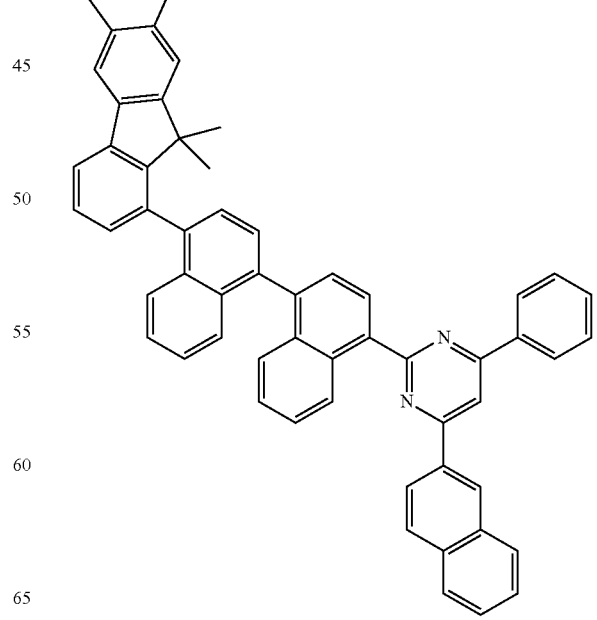

1081
-continued
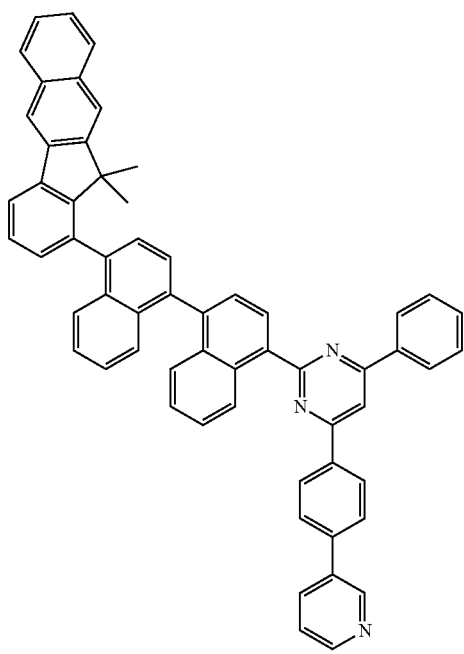
1082
-continued
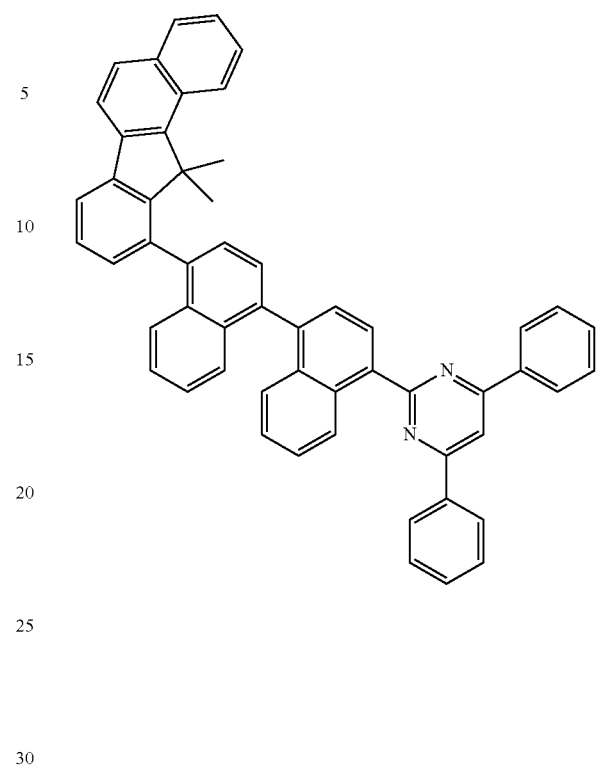
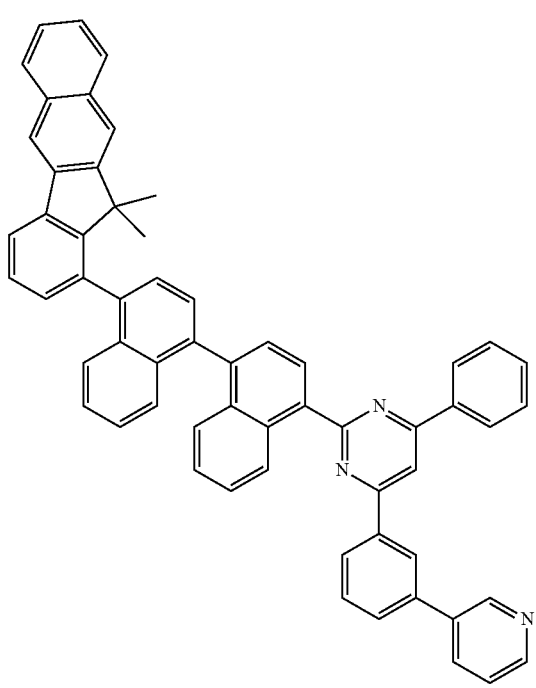
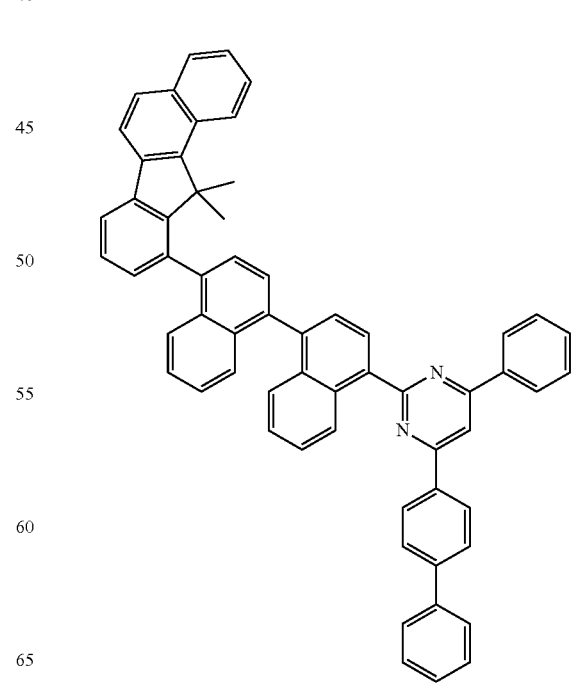

1083
-continued
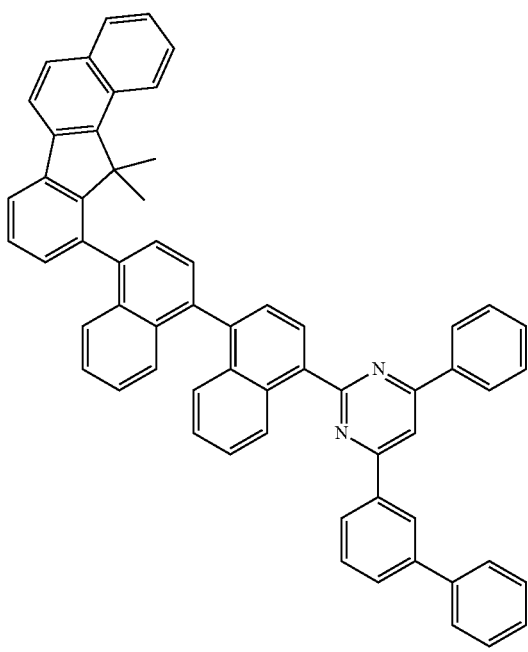
1084
-continued
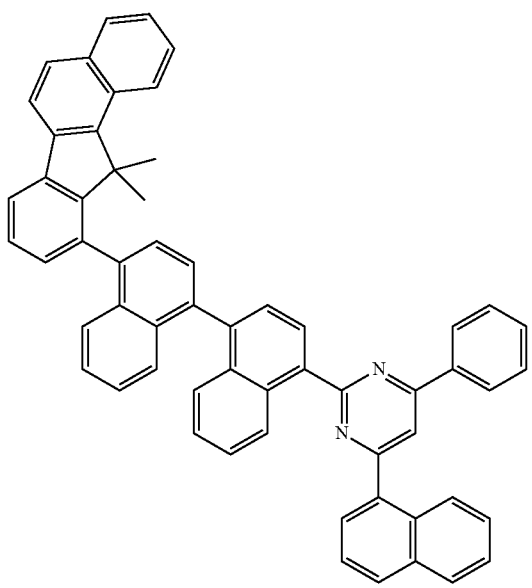
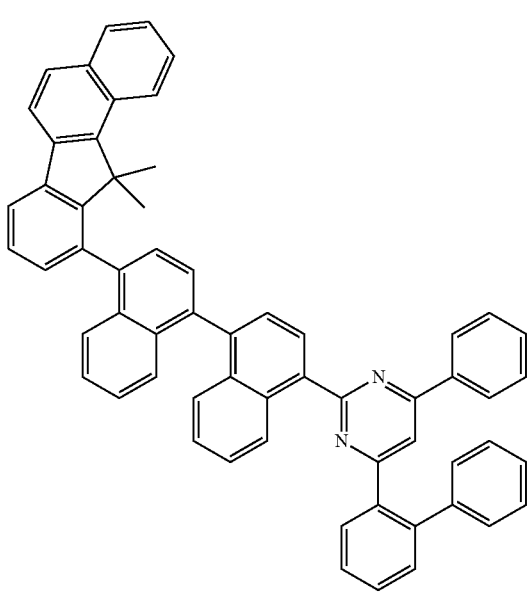
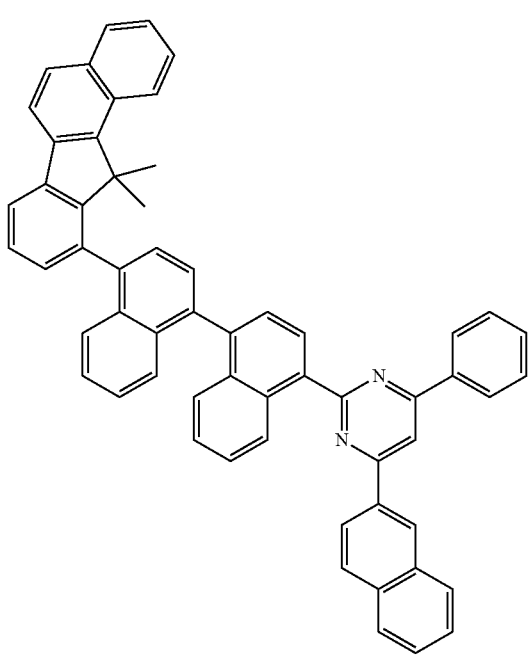

1085
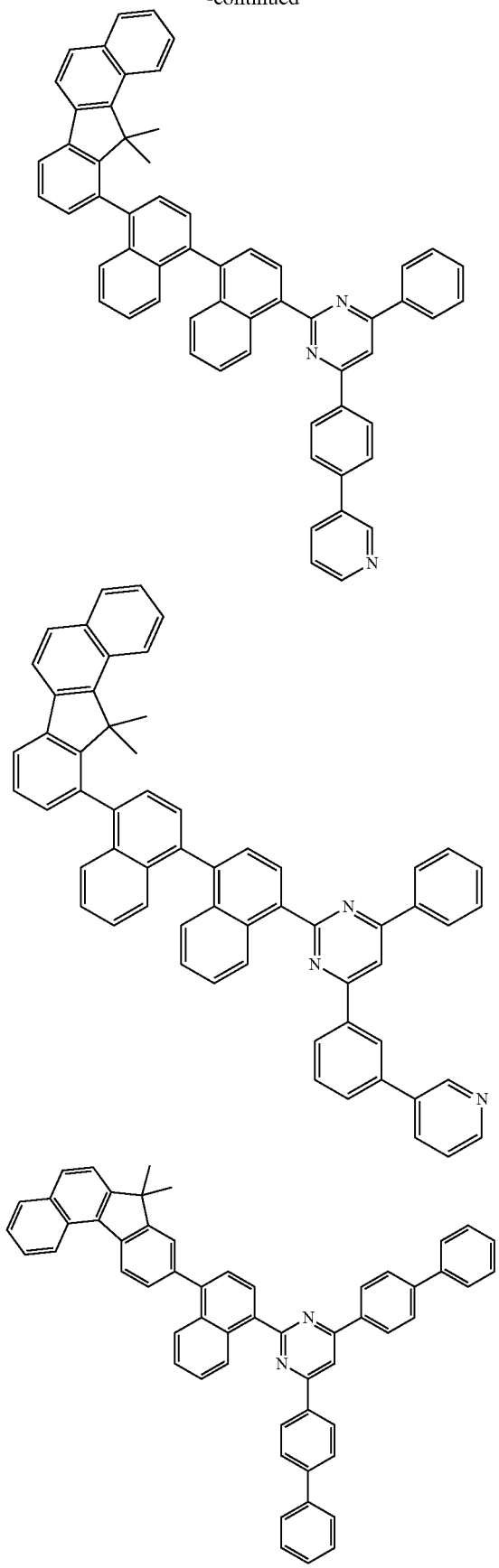
1086
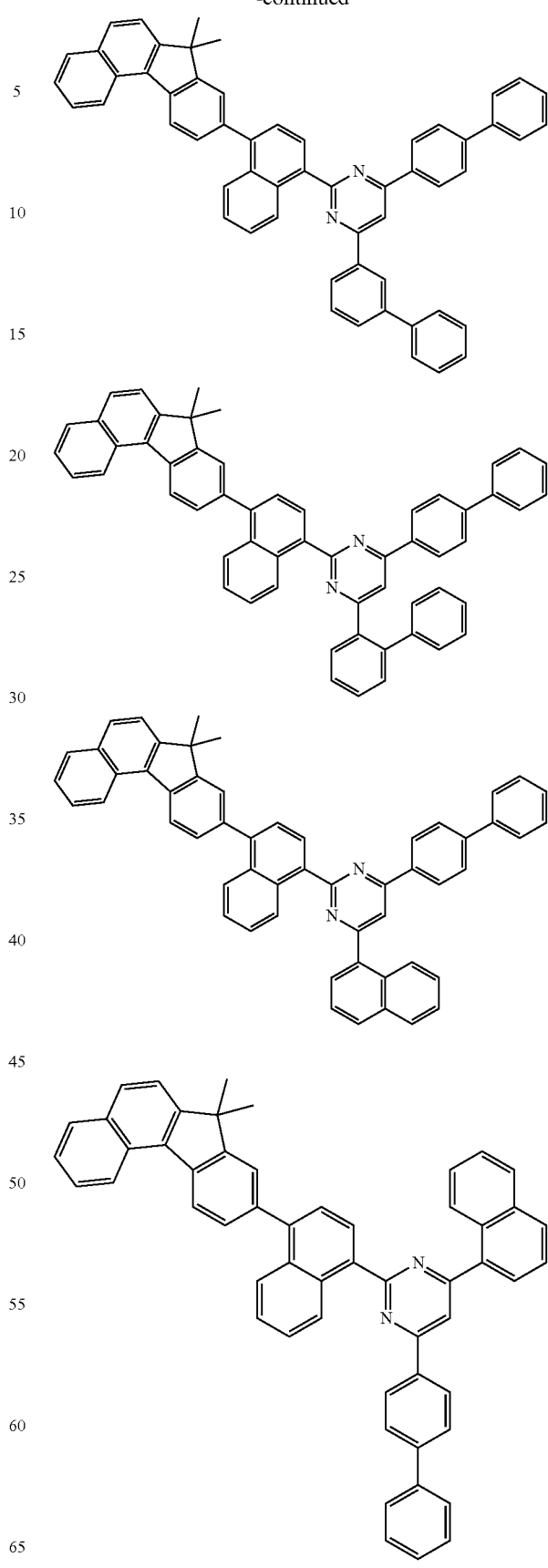

1087
-continued
1088
-continued
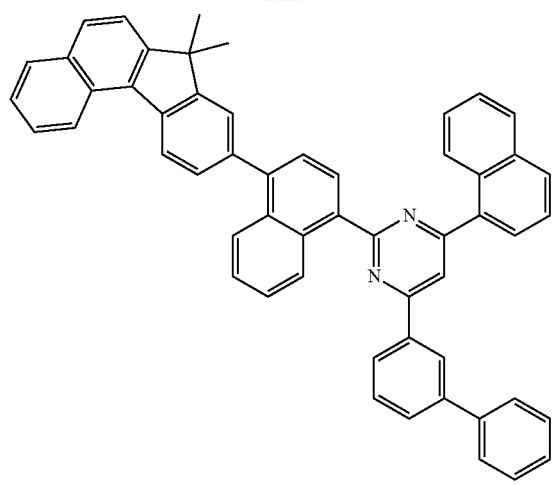
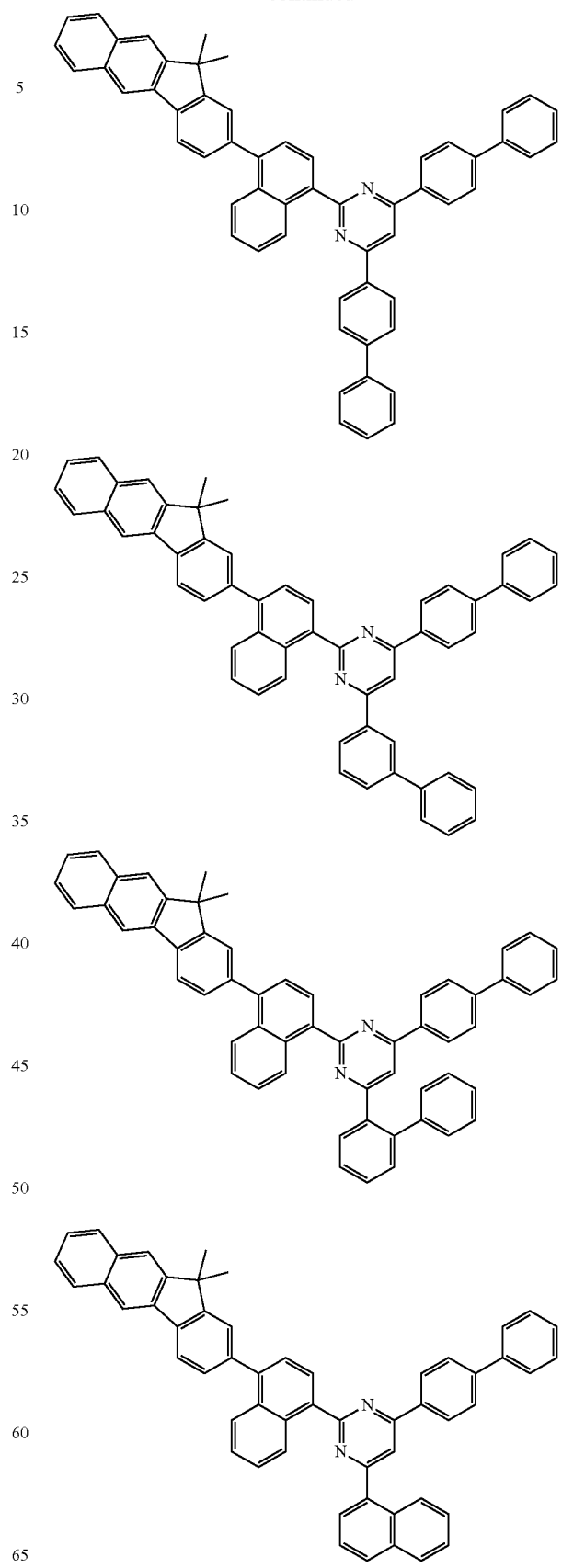

1089
-continued
1090
-continued
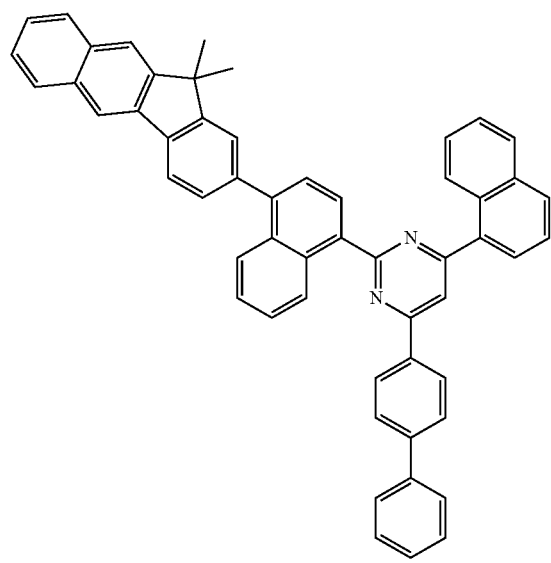
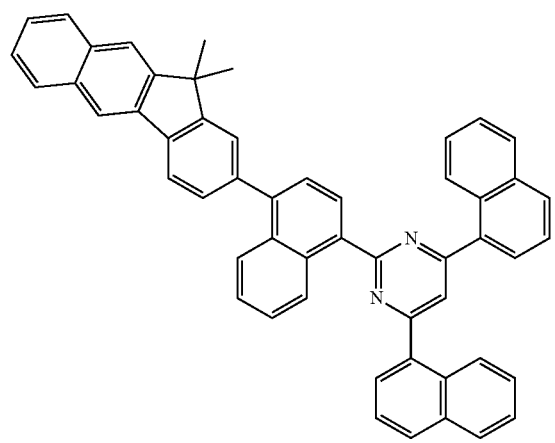
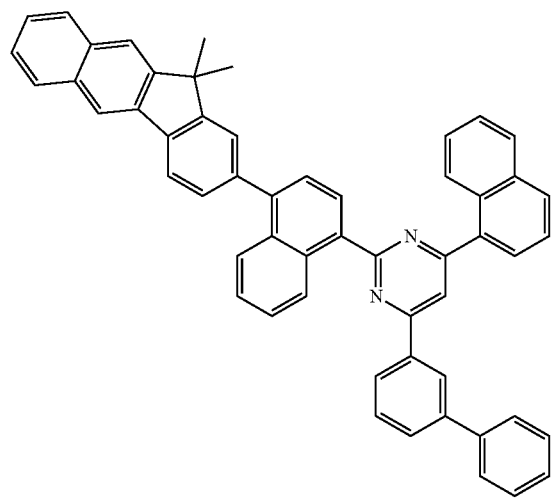
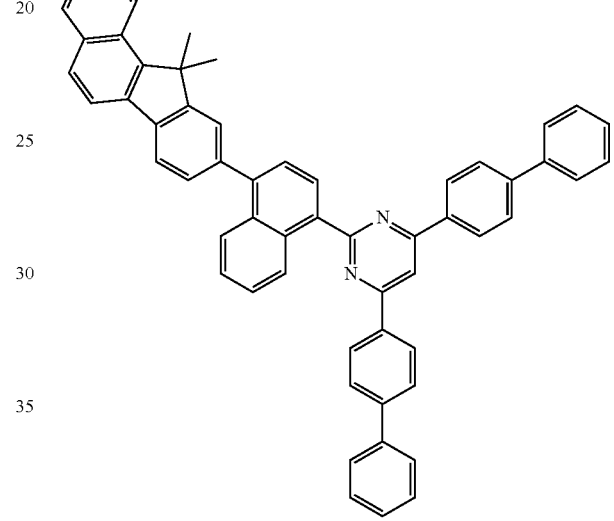
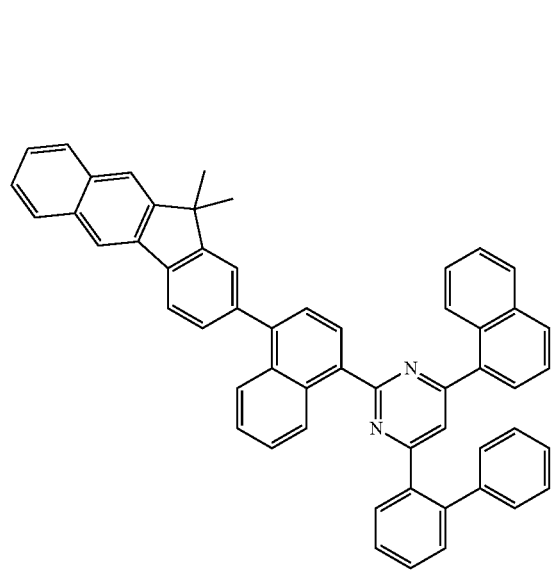
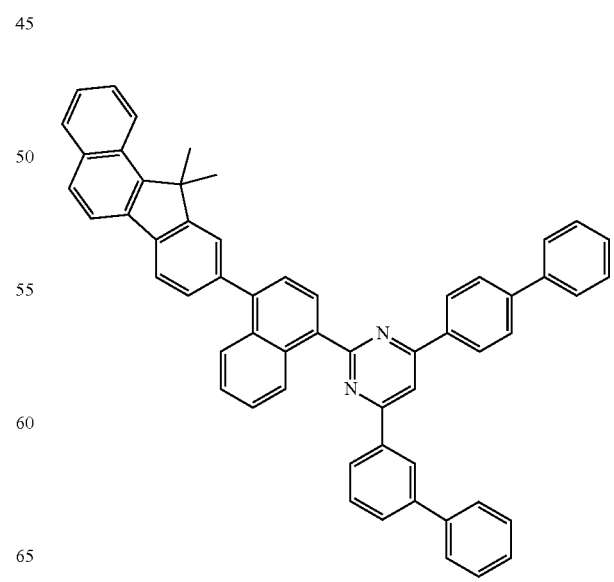

1091
-continued
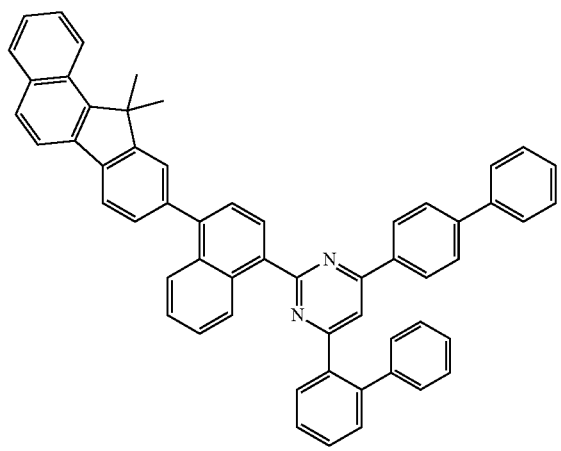
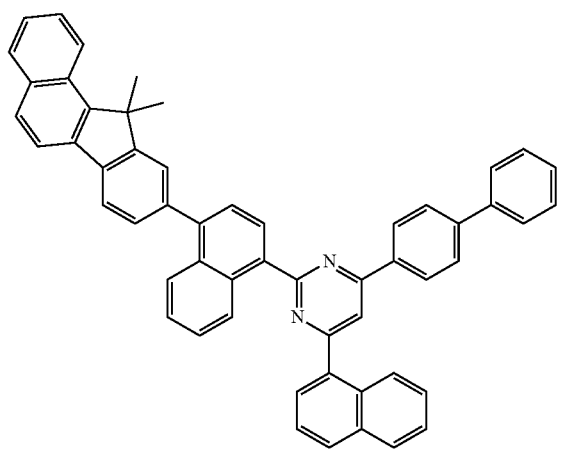
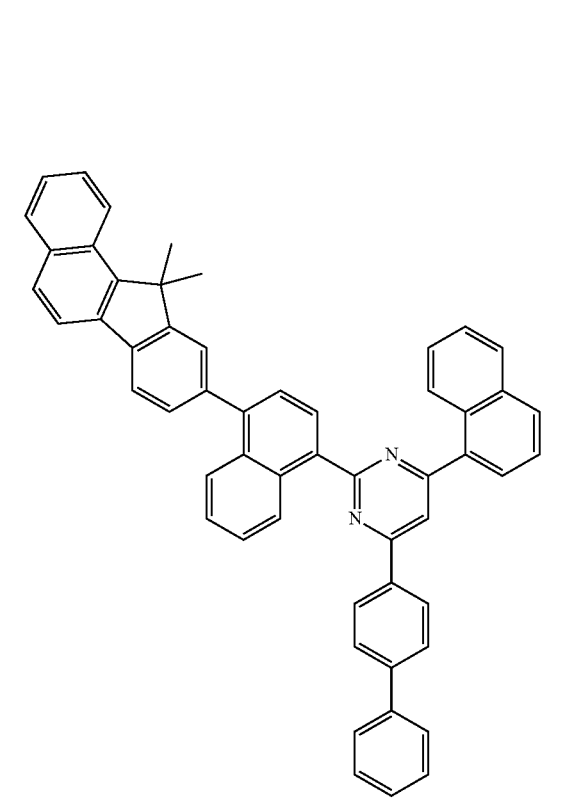
1092
-continued
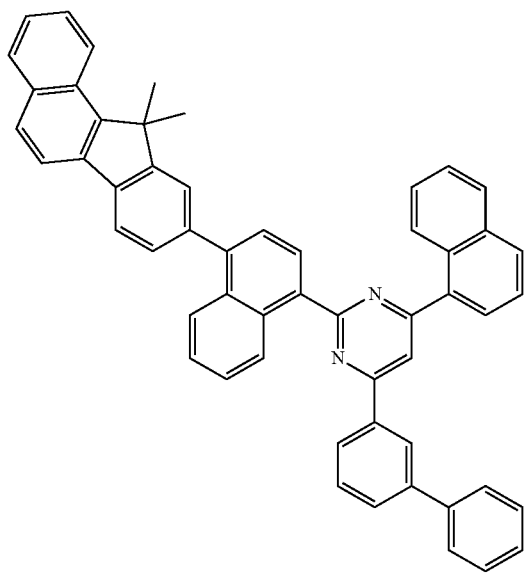
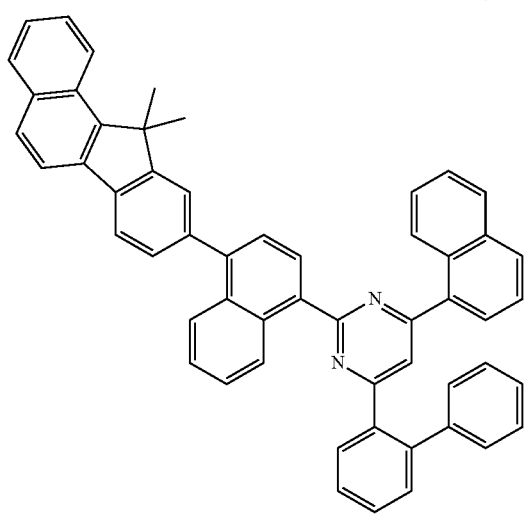
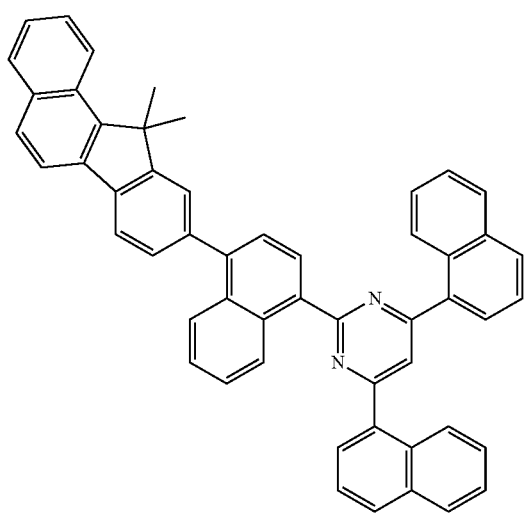

1093
-continued
1094
-continued
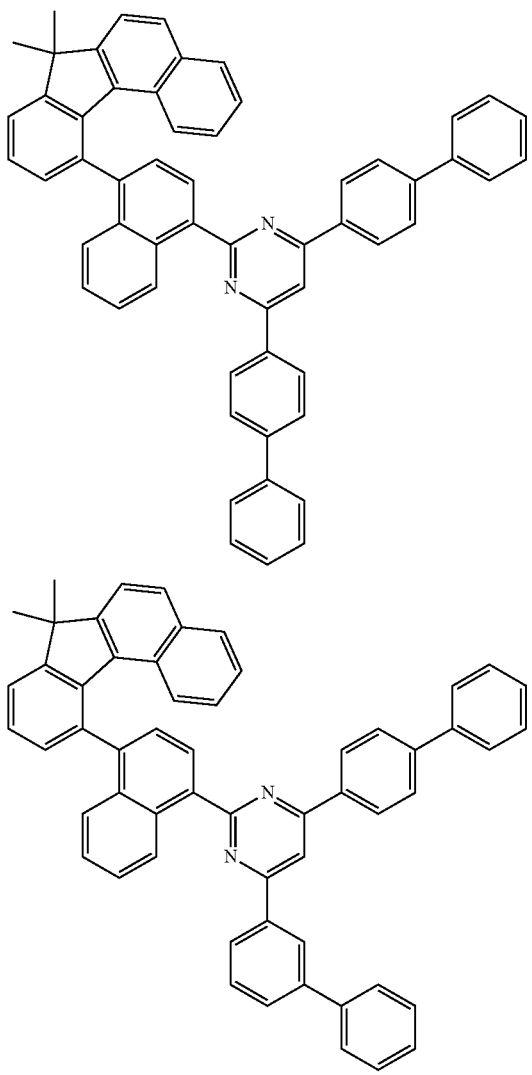
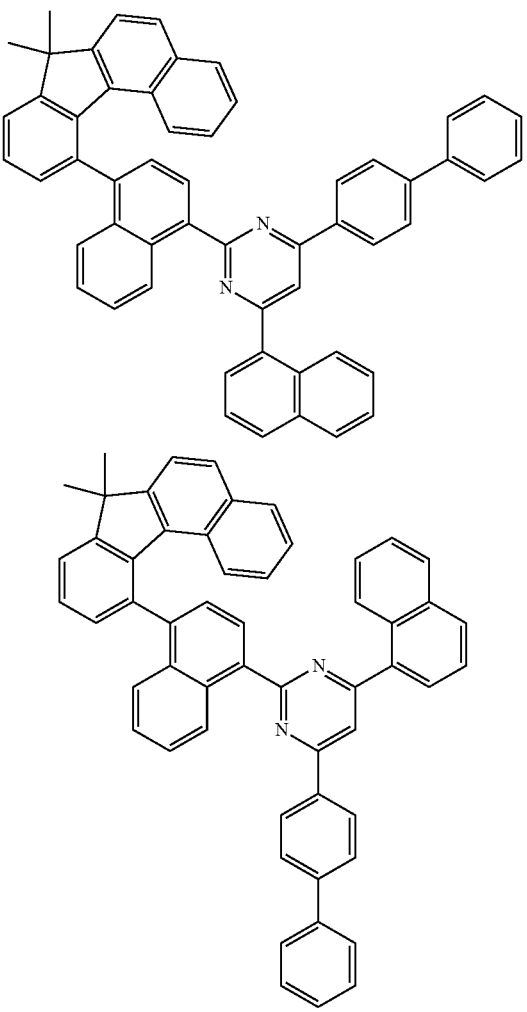
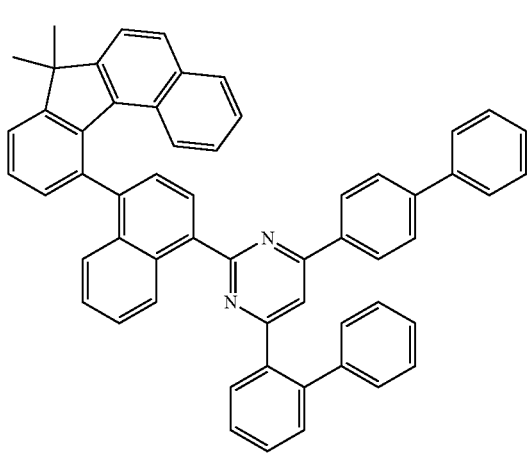
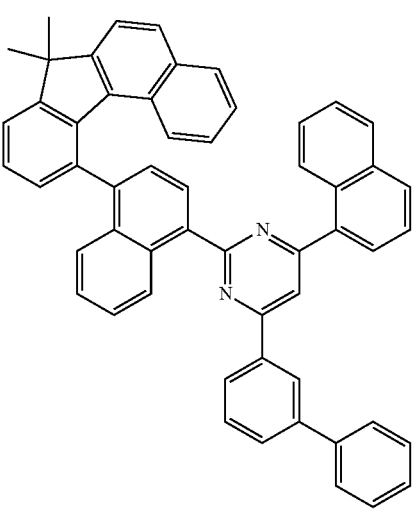

1095
-continued
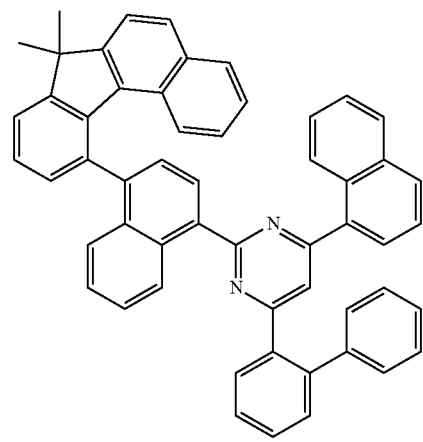
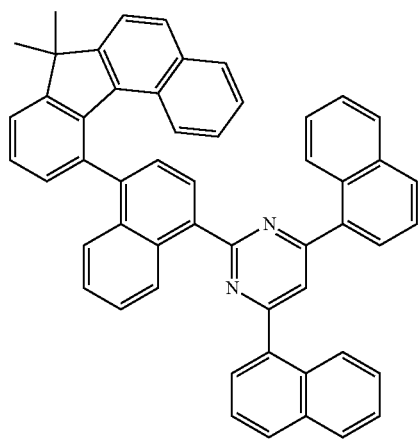
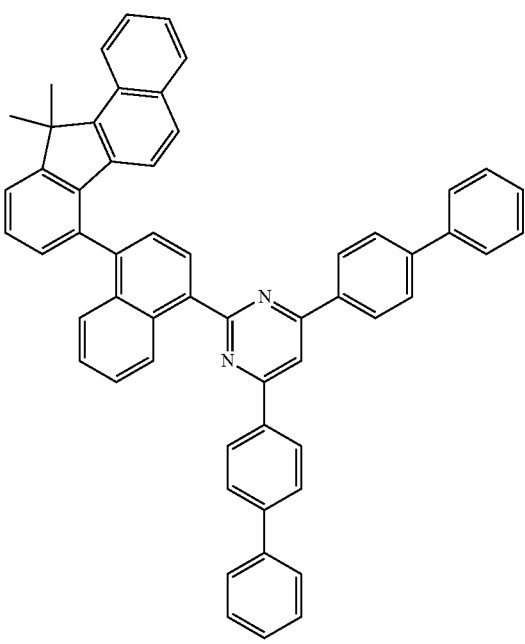
1096
-continued
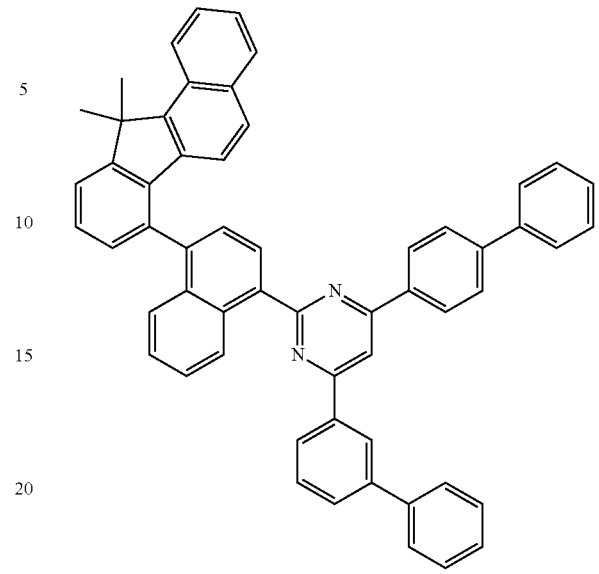
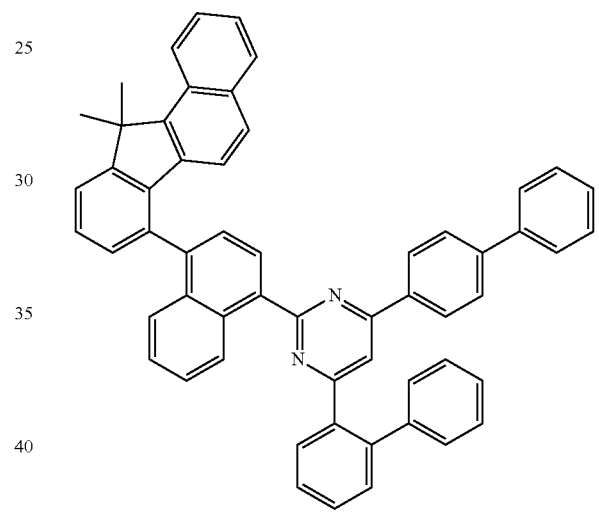
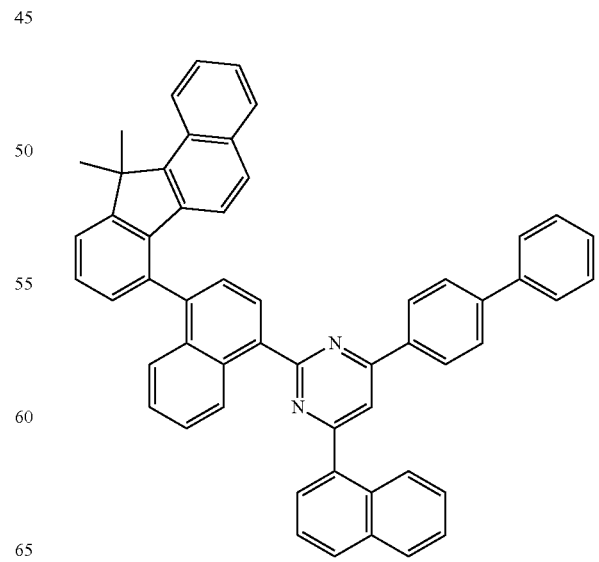

1097
-continued
1098
-continued
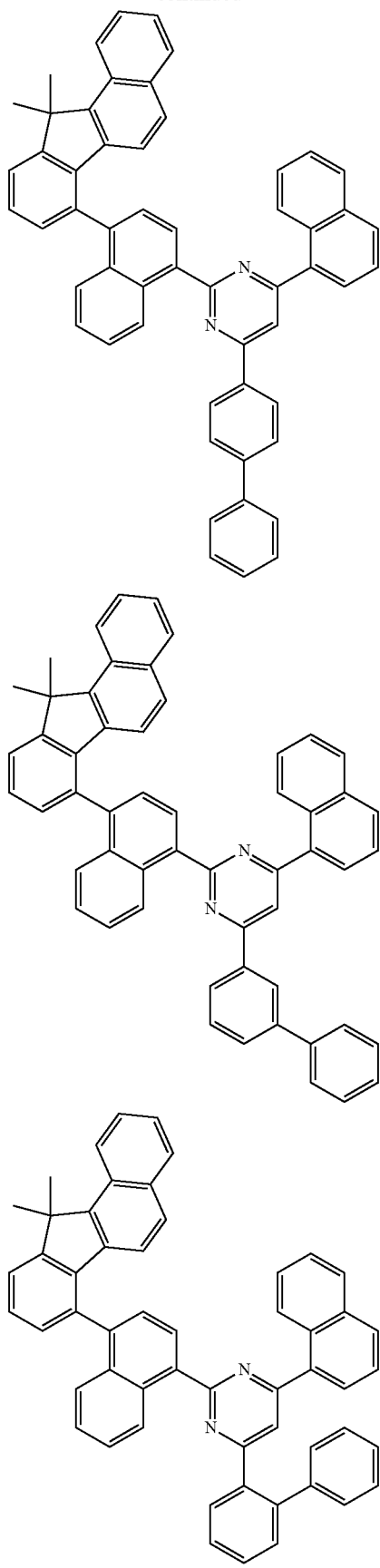
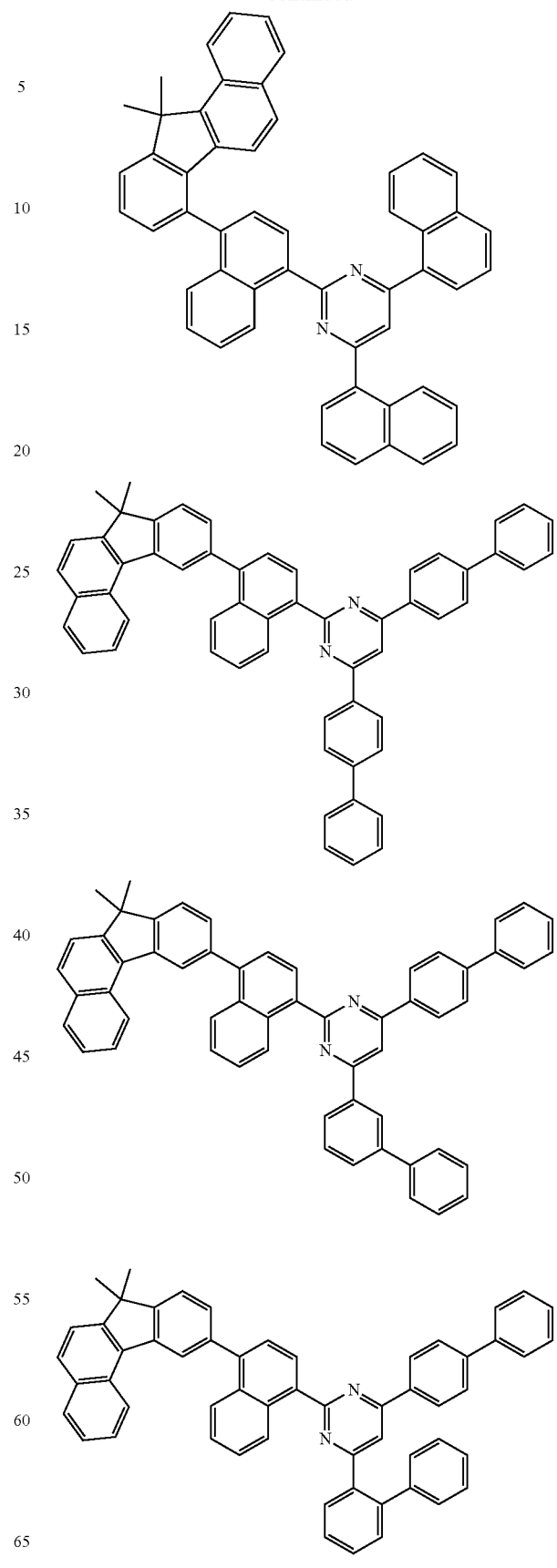

| 1099 | 1100 |
|---|---|
| -continued | -continued |
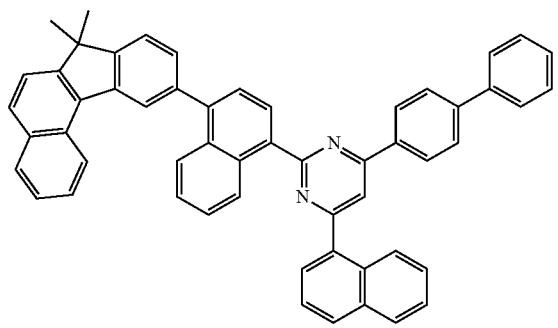
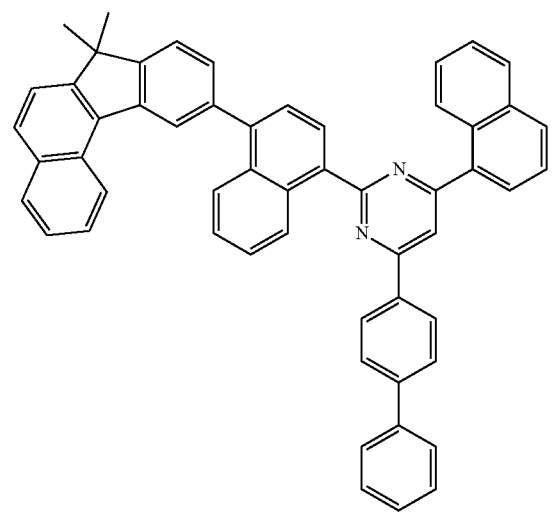
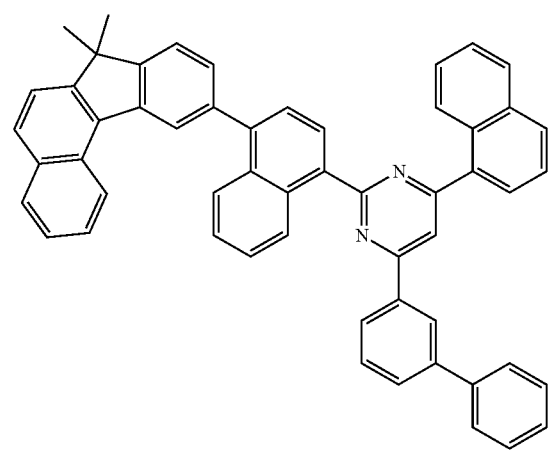
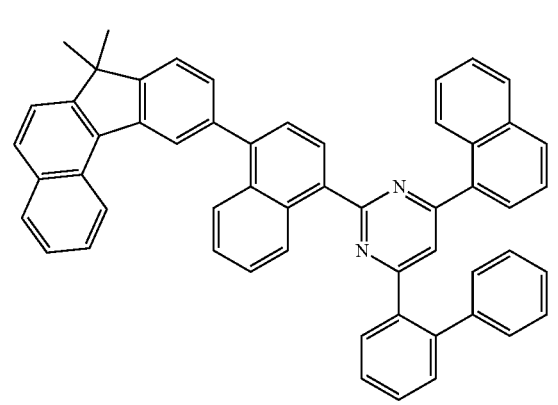
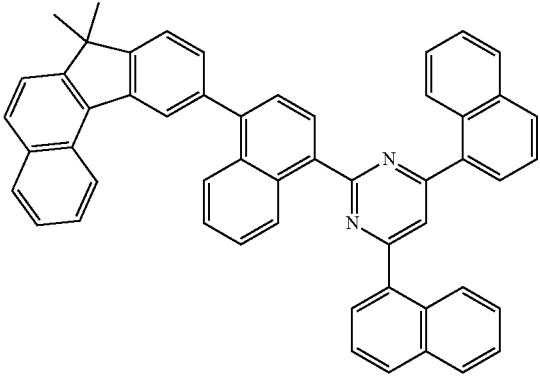
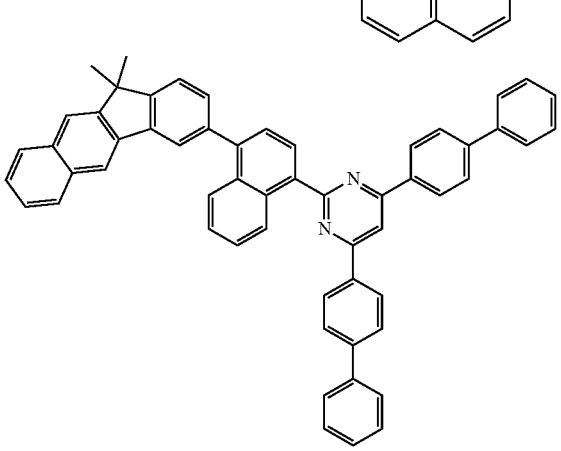
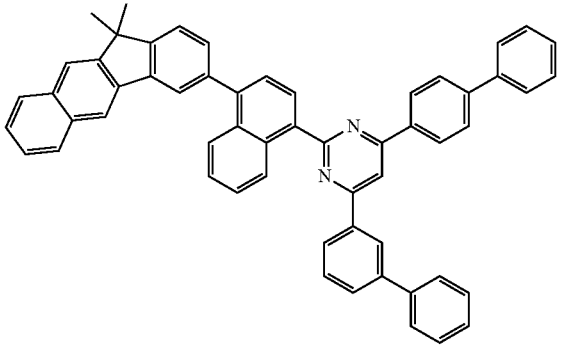
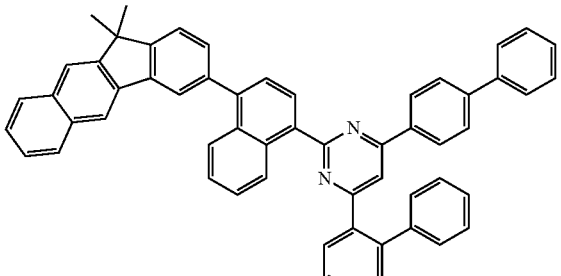
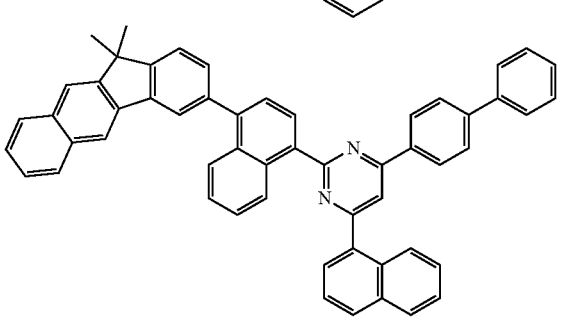

1101
-continued
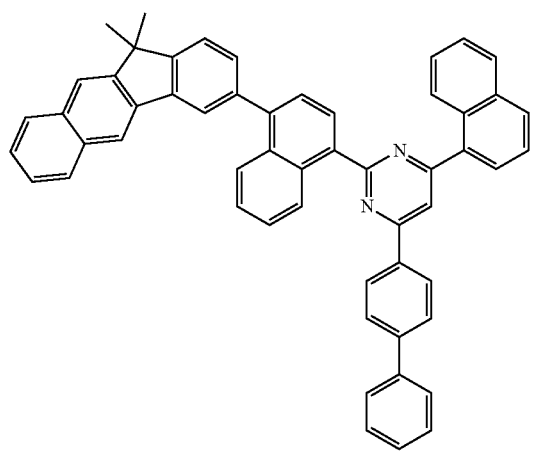
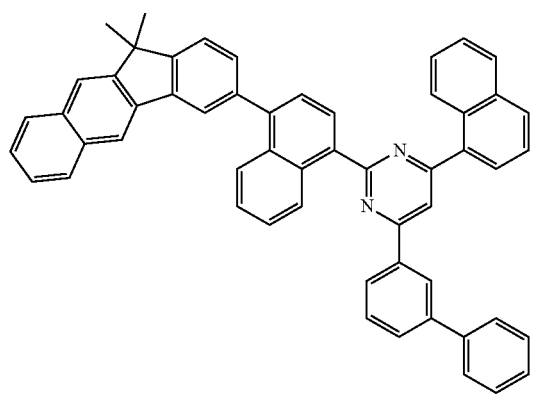
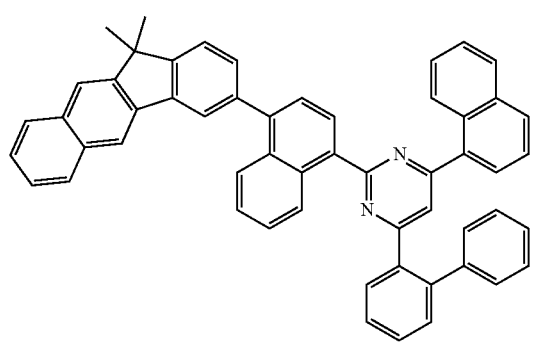
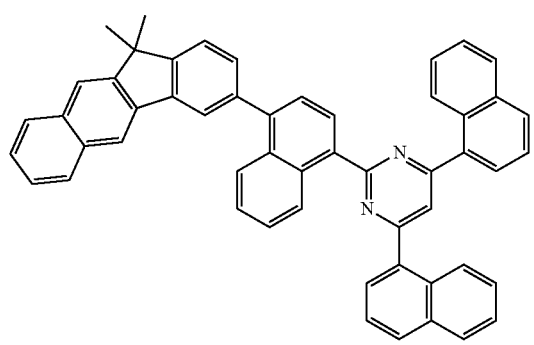
1102
-continued
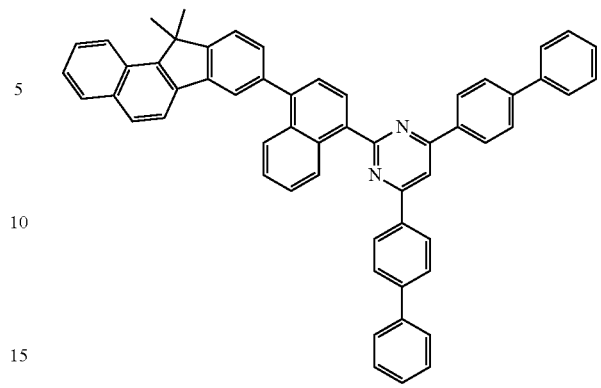
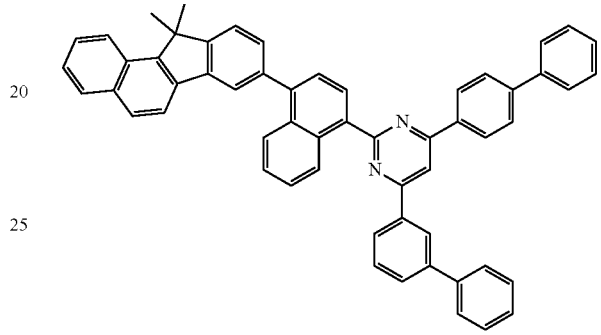
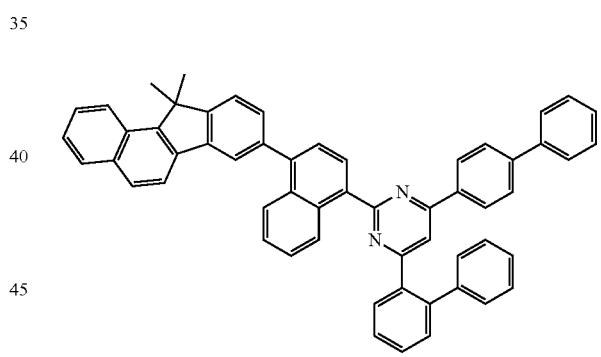
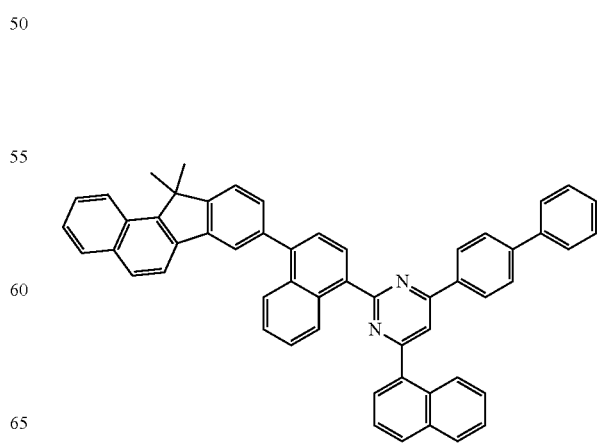

1103
-continued
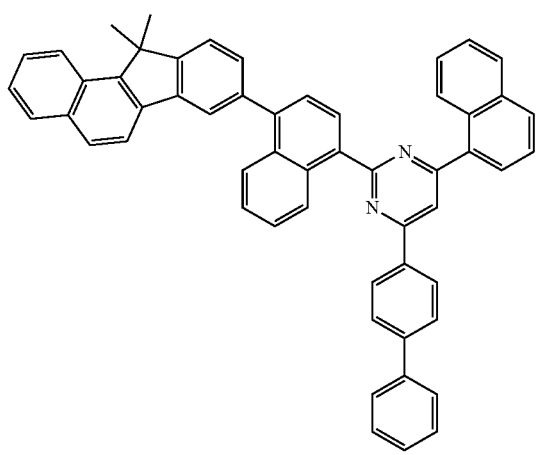
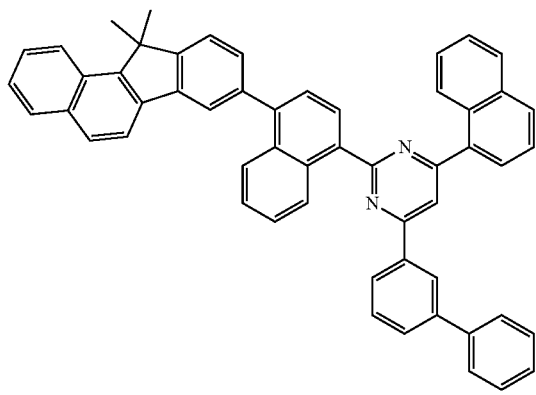
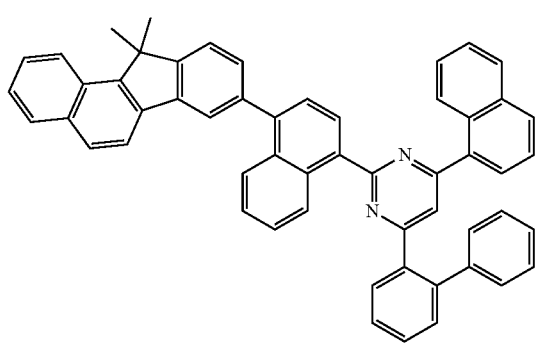
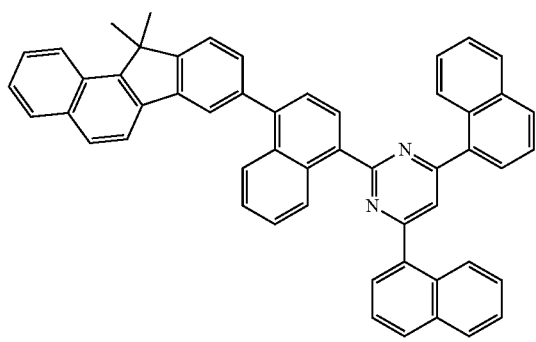
1104
-continued
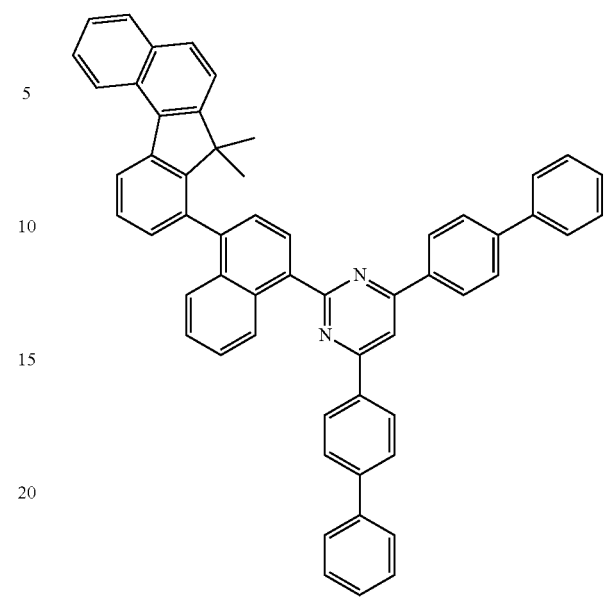
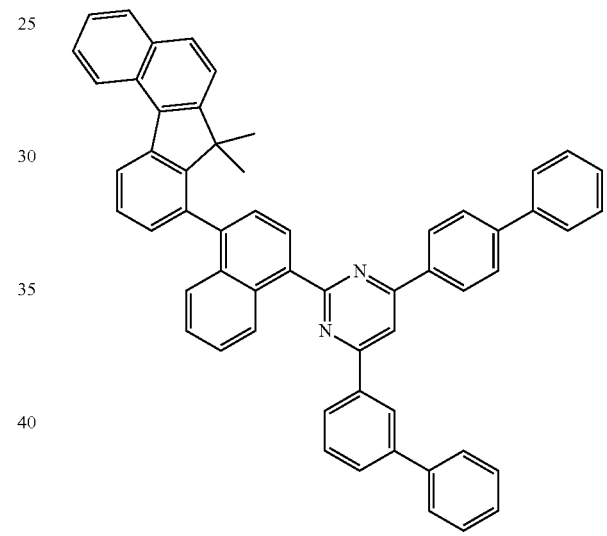
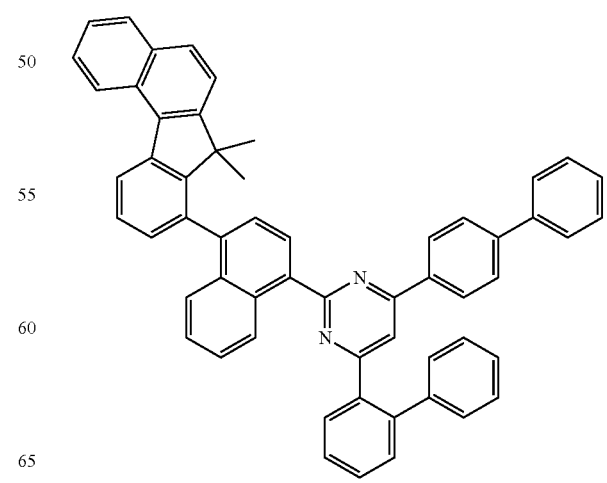

1105
-continued
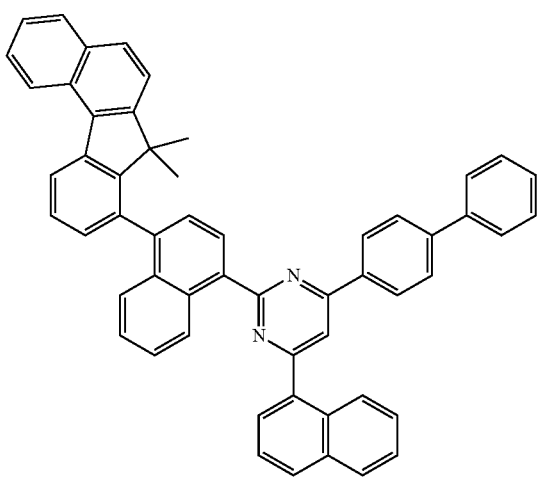
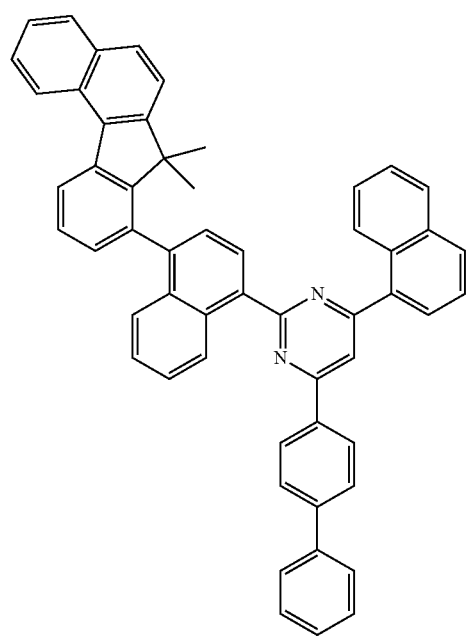
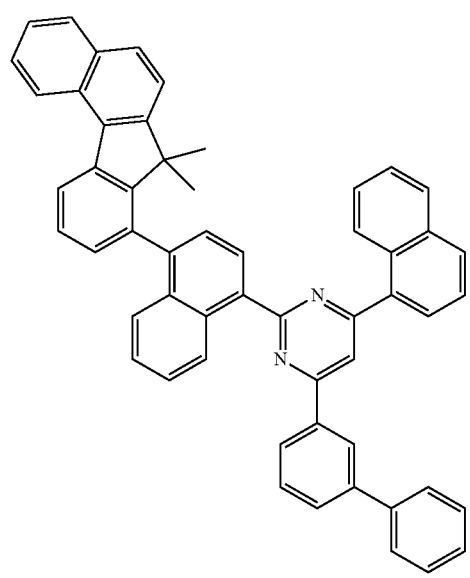
1106
-continued
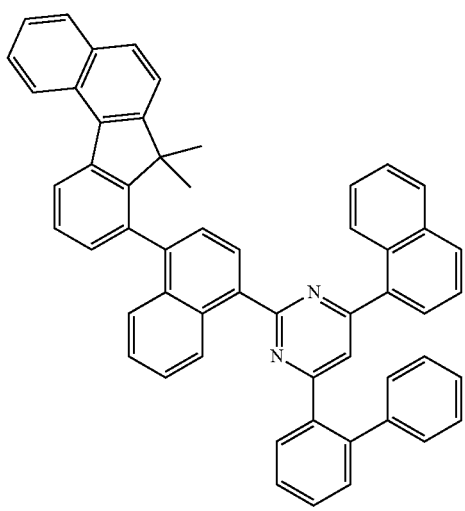
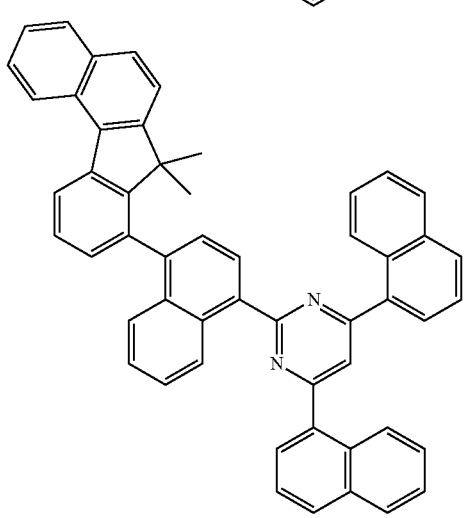
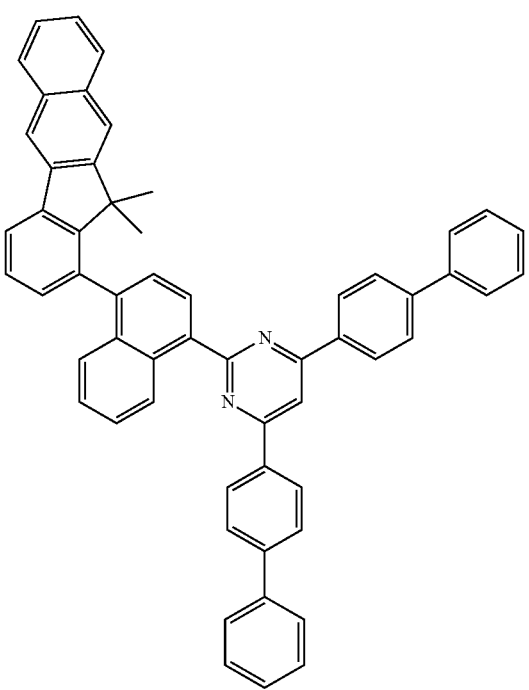

1107
-continued
1108
-continued
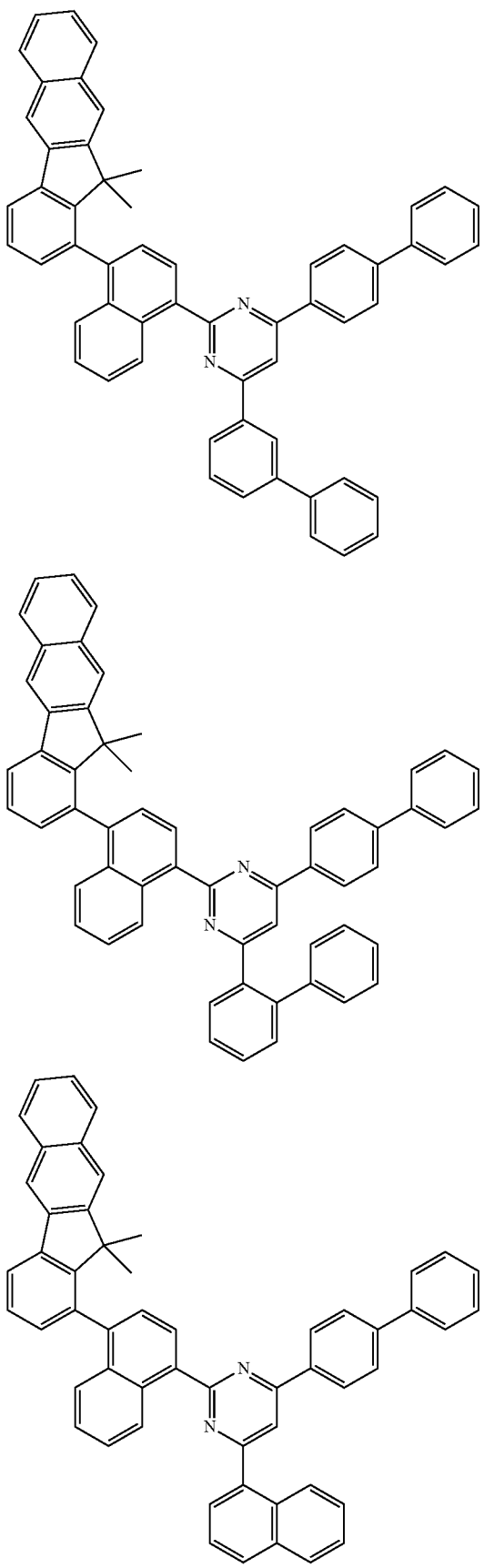
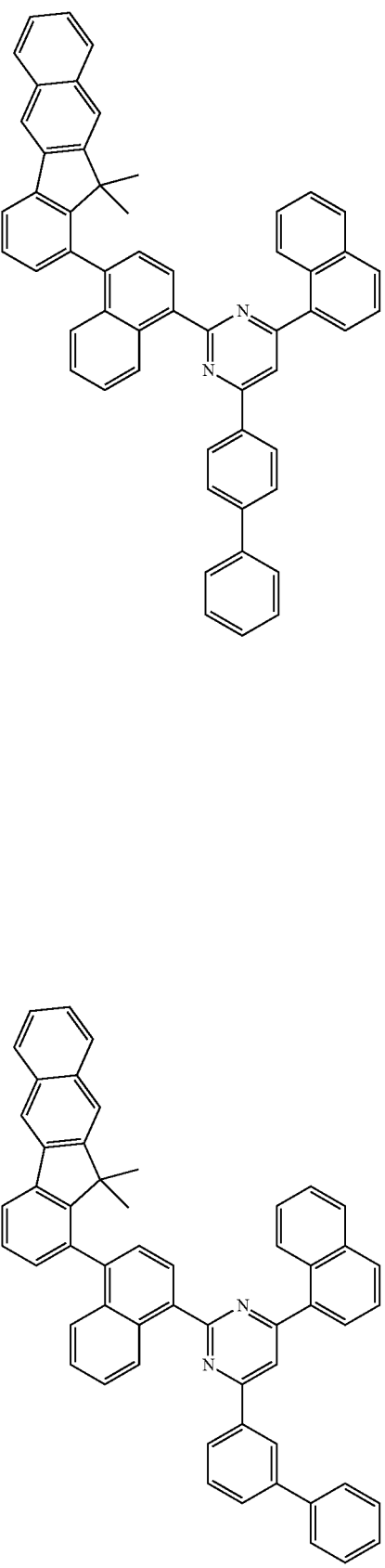

1109
-continued
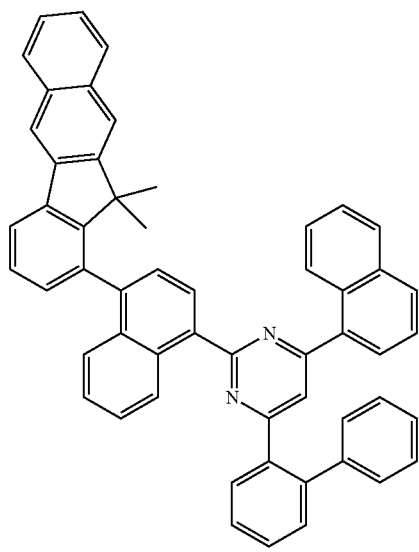
1110
-continued
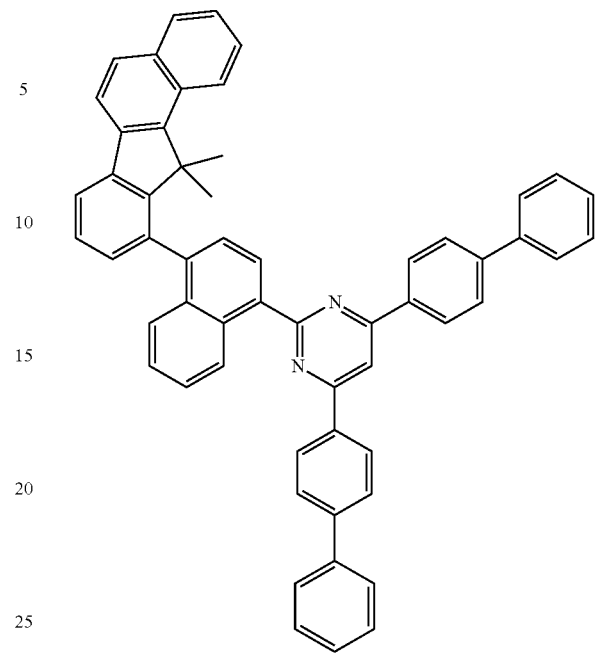
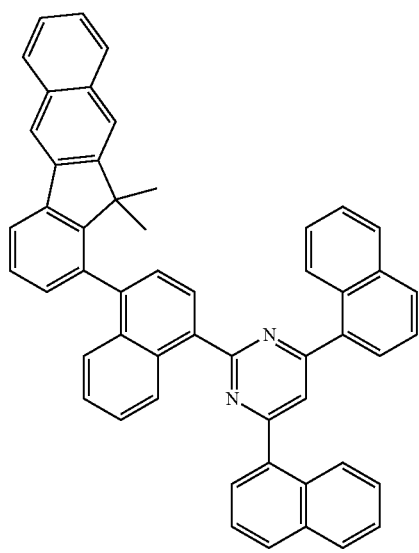
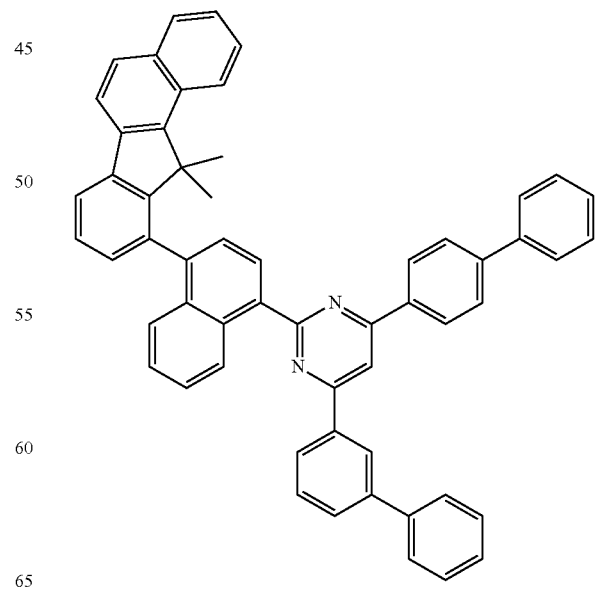

1111
-continued
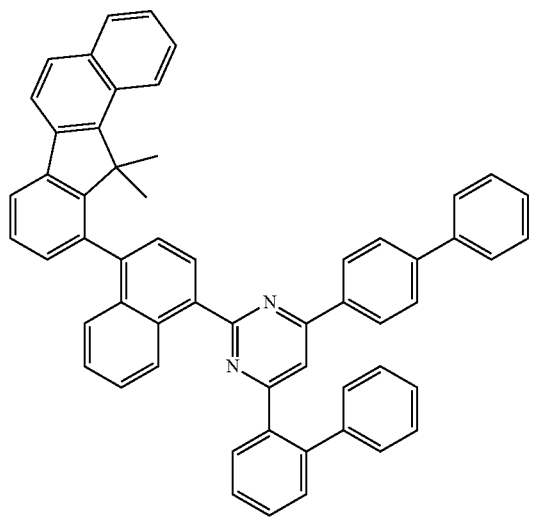
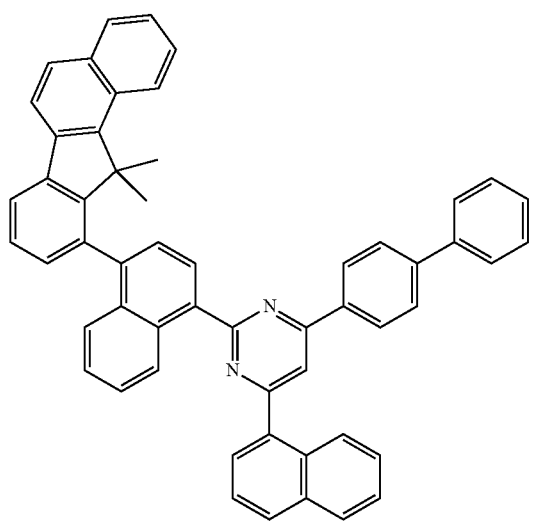
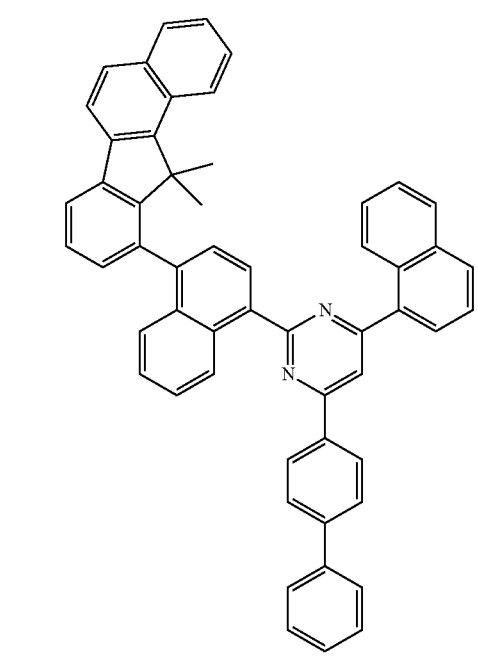
1112
-continued
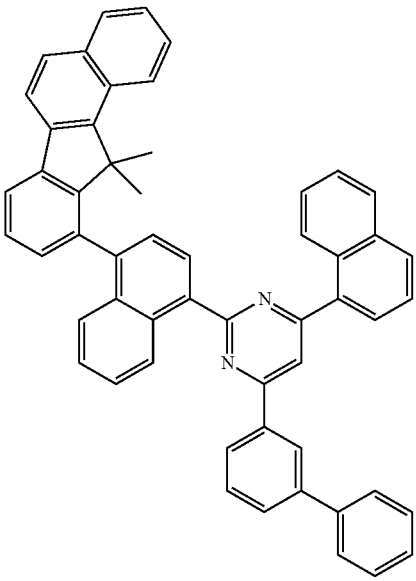
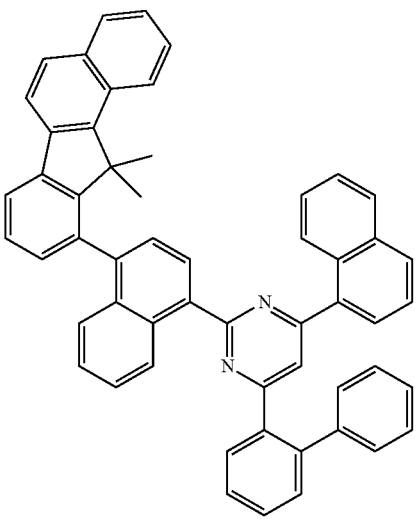
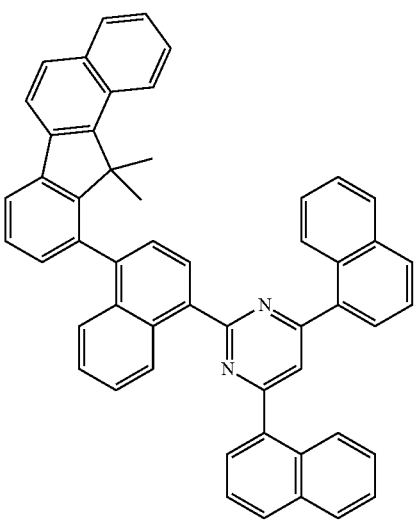

1113
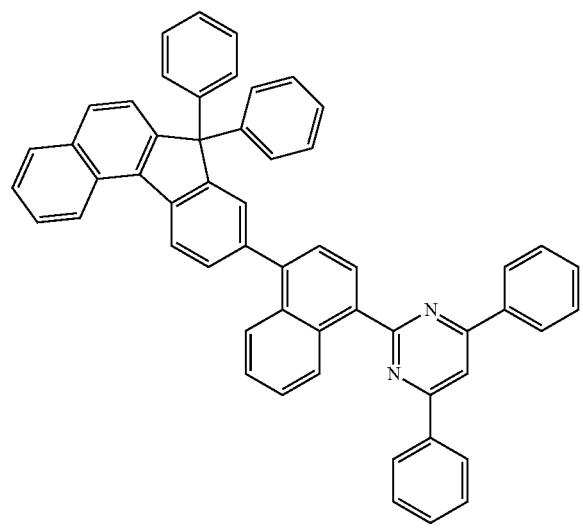
1114
-continued
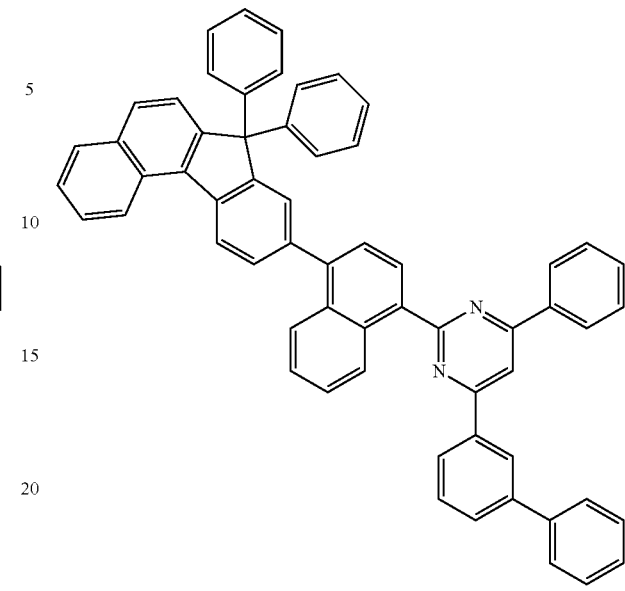
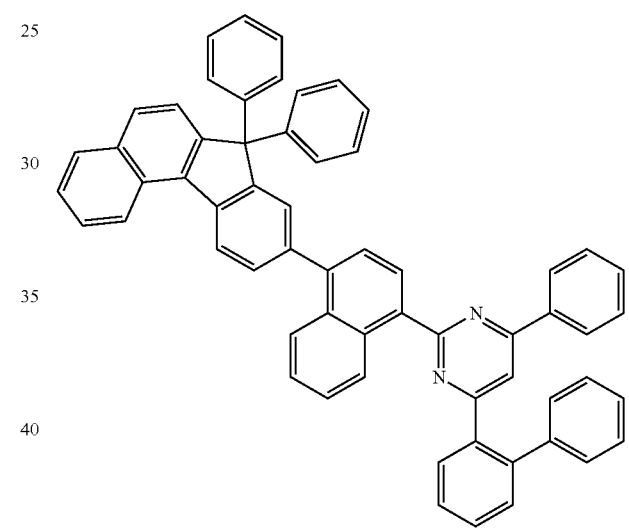
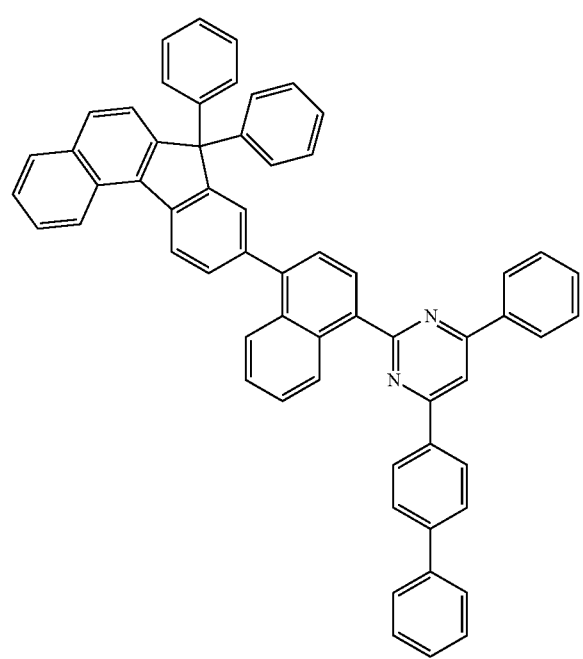

1115
-continued
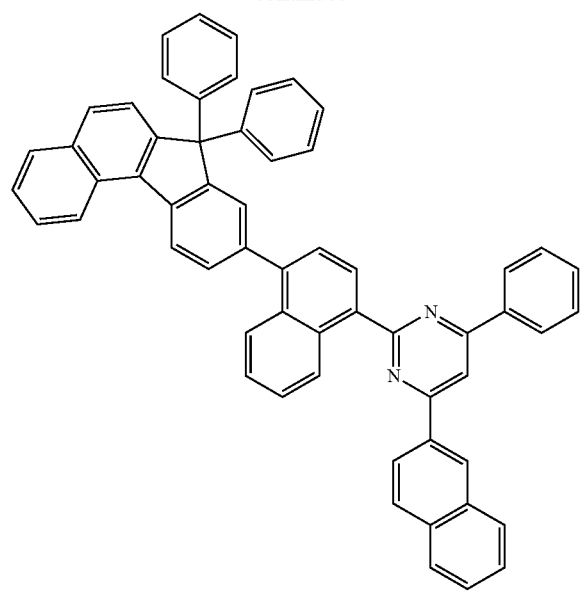
1116
-continued
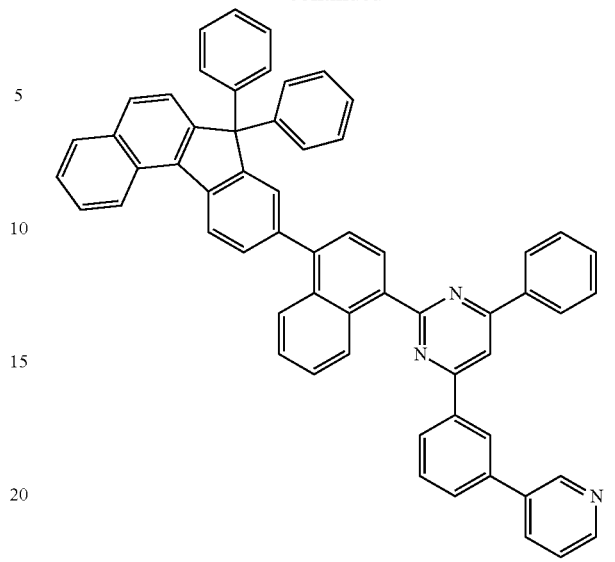
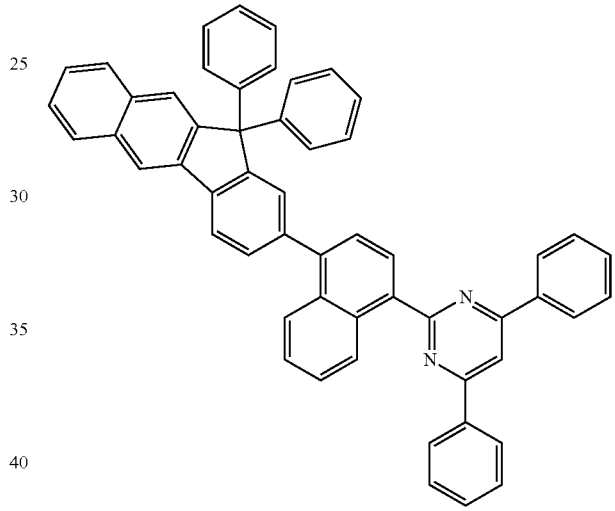
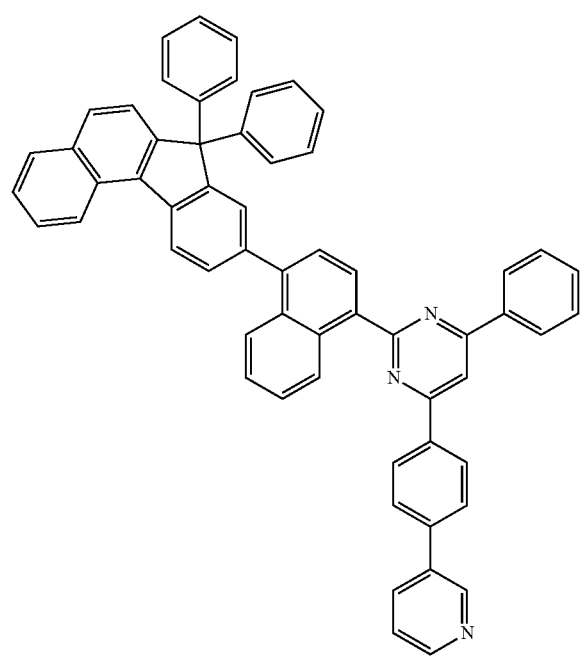

1117
-continued
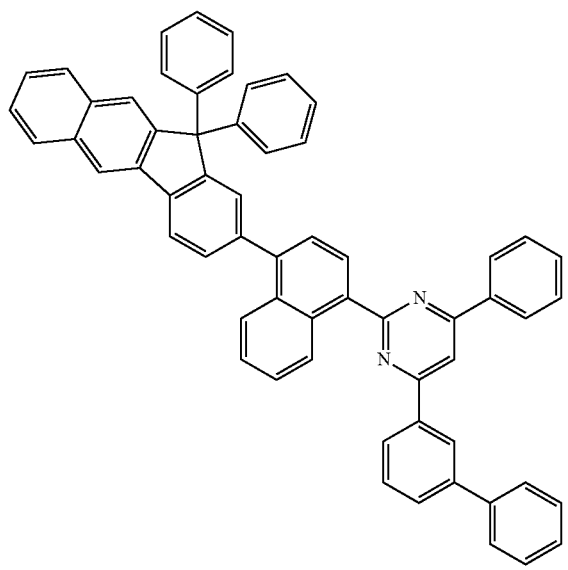
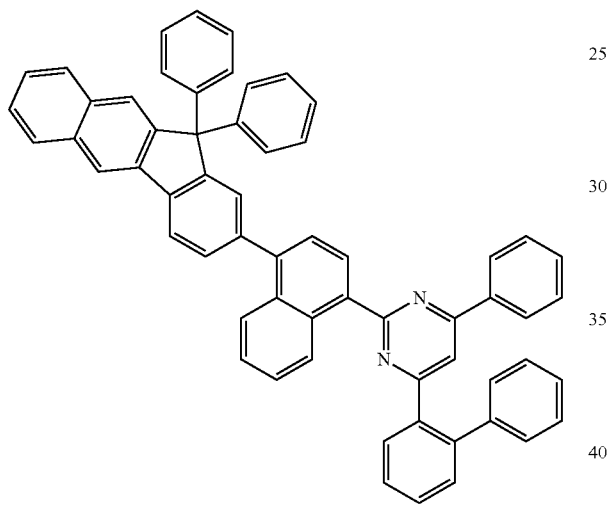
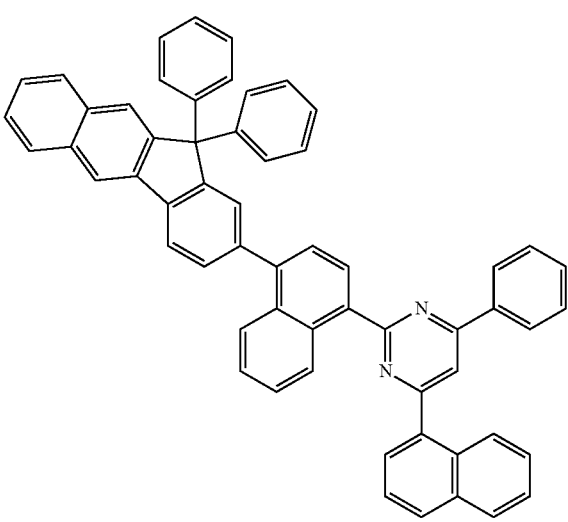
1118
-continued
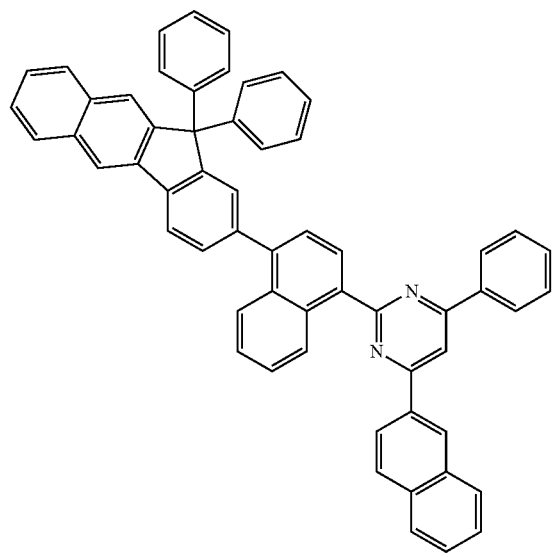
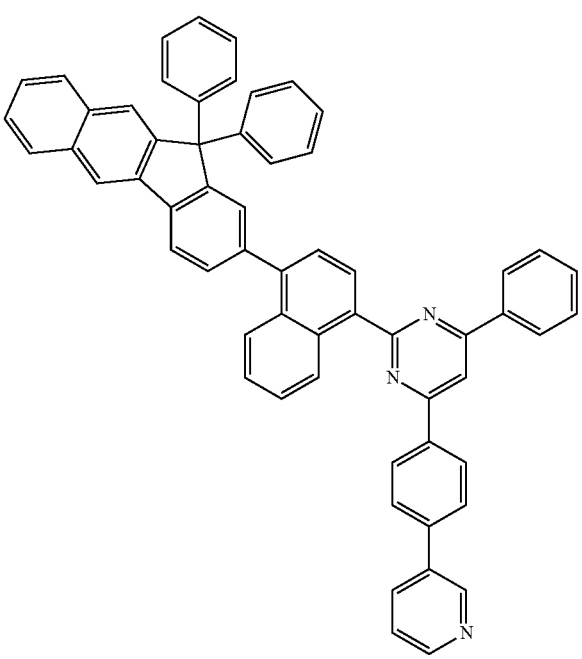

1119
-continued
1120
-continued
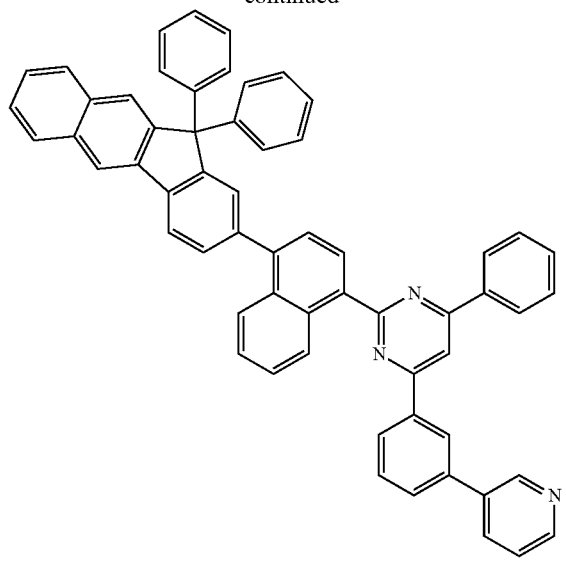
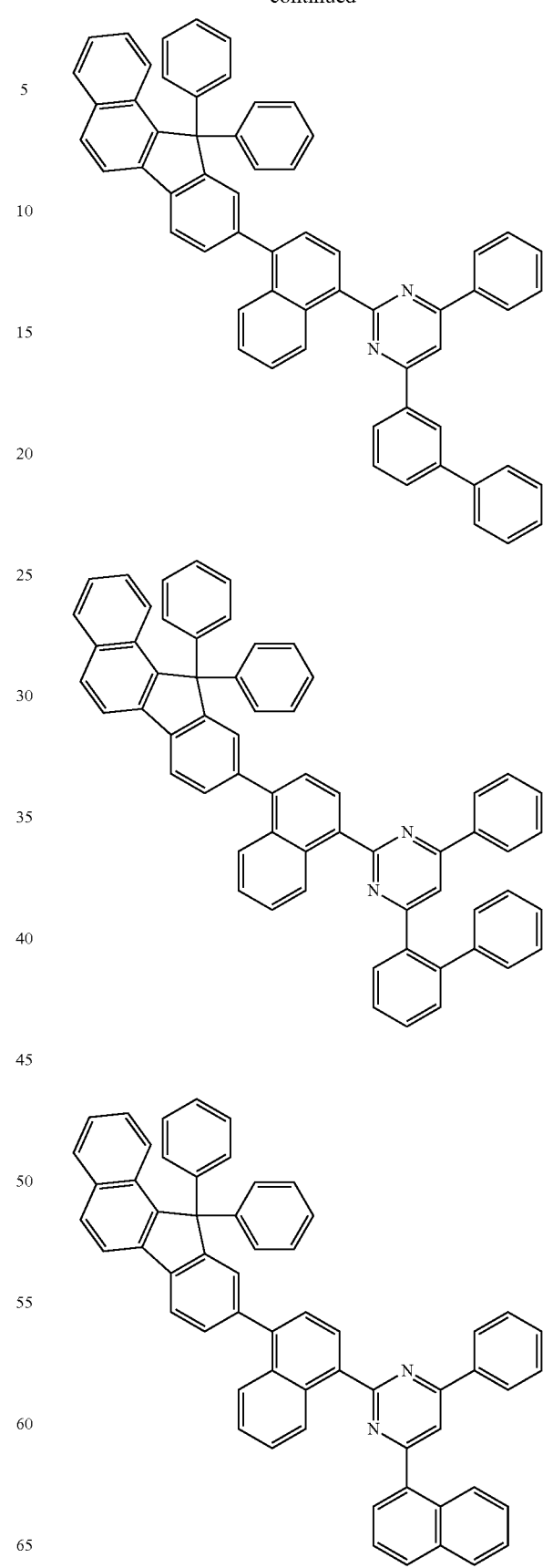

1121
-continued
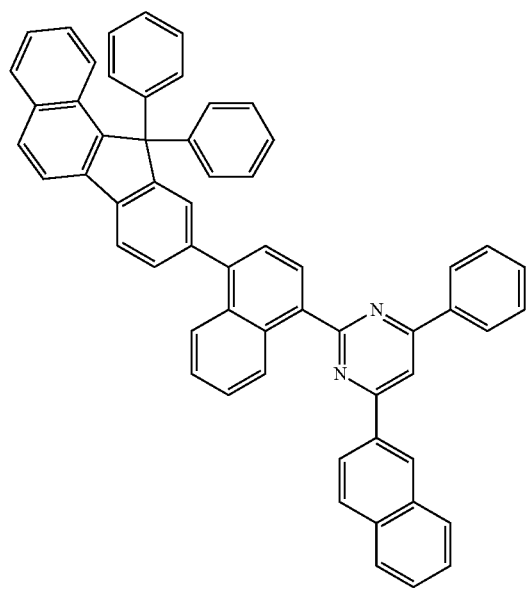
1122
-continued
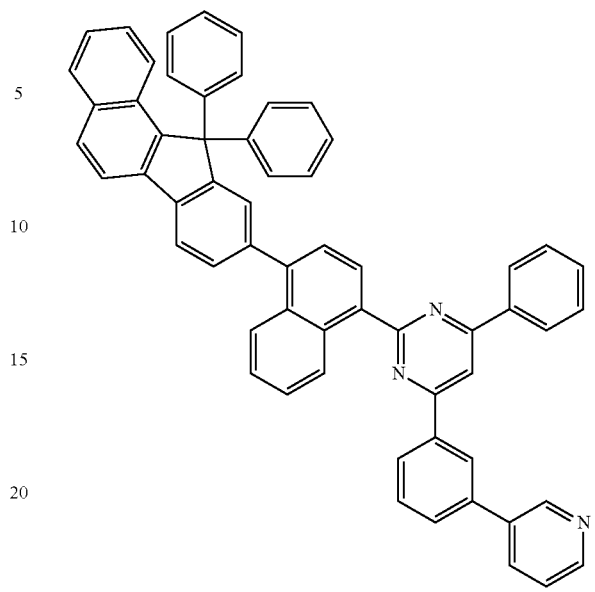
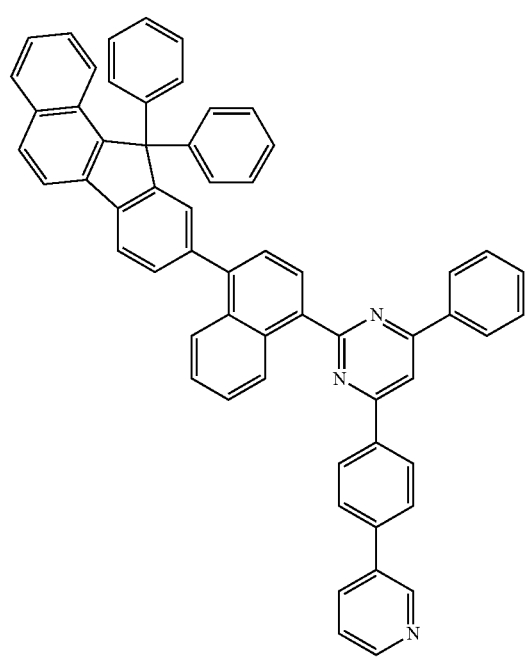
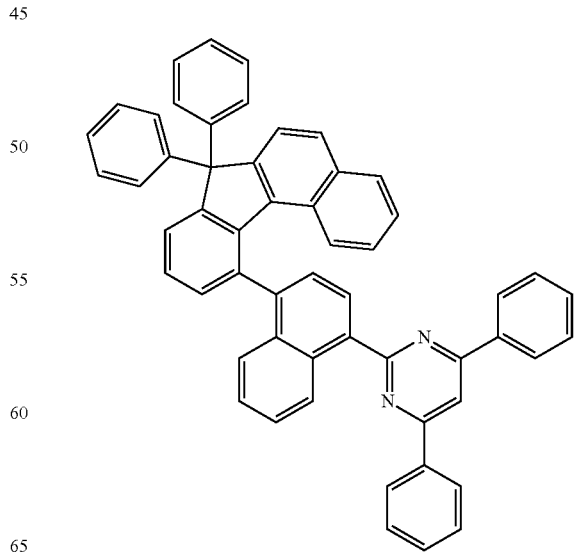

1123
-continued
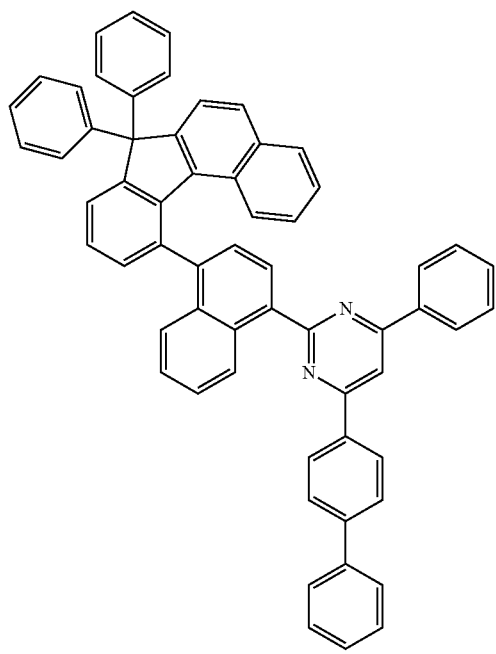
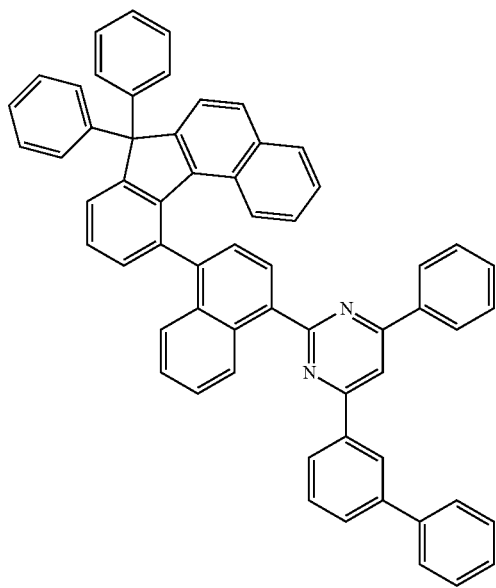
1124
-continued
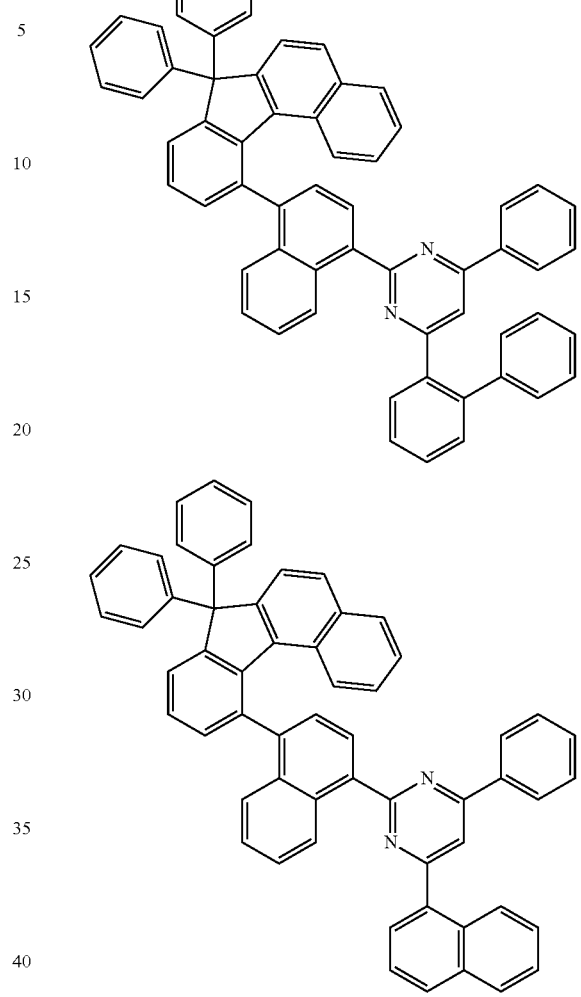
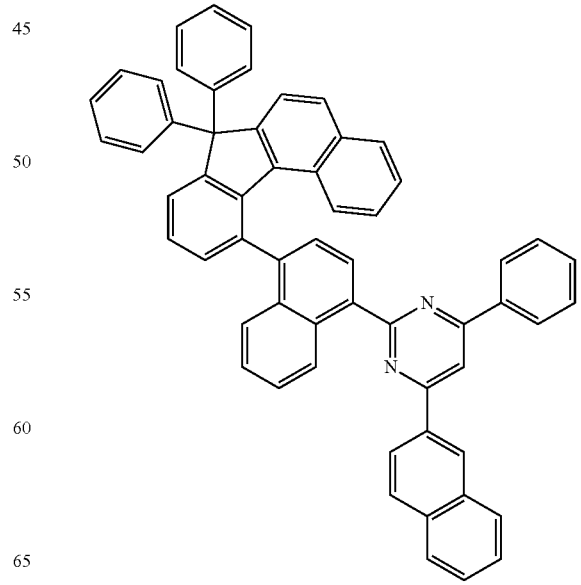

1125
-continued
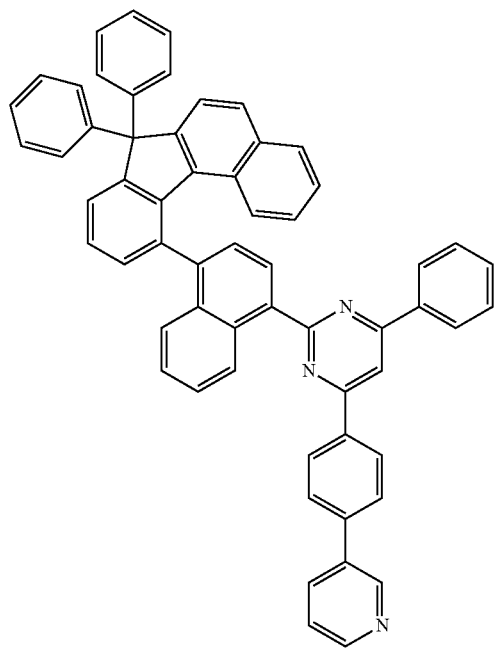
1126
-continued
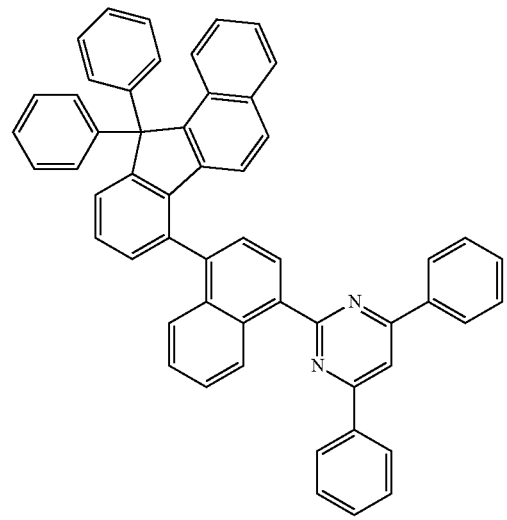
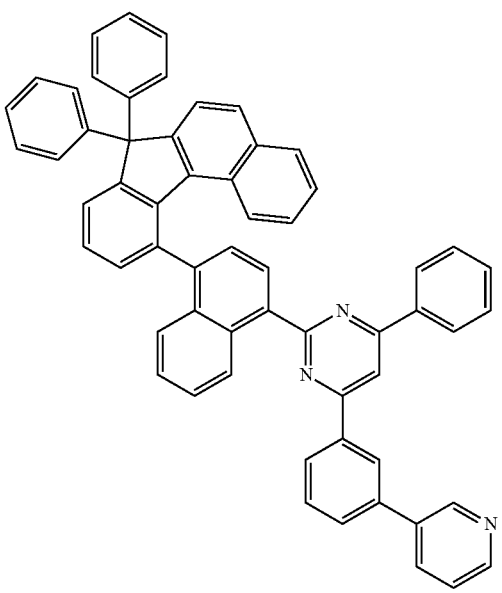
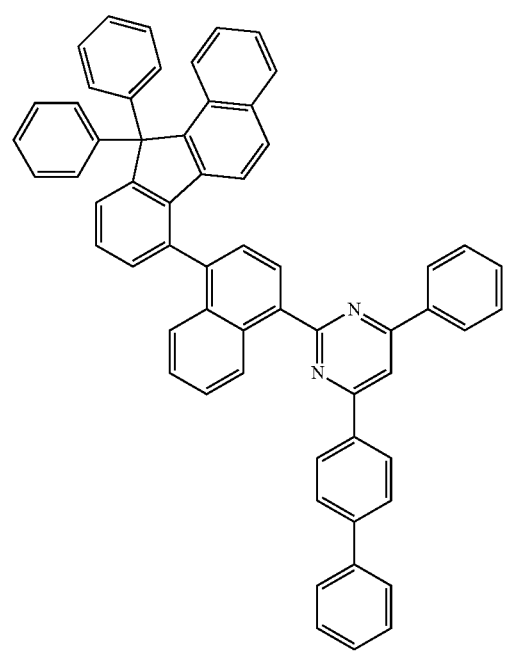

1127
-continued
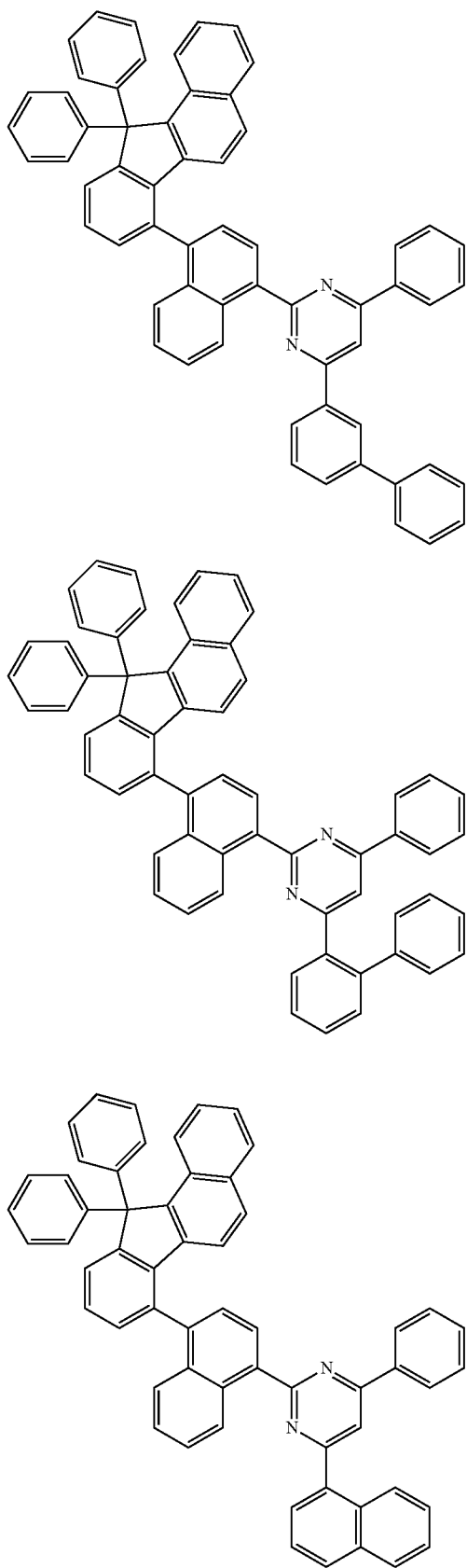
1128
-continued
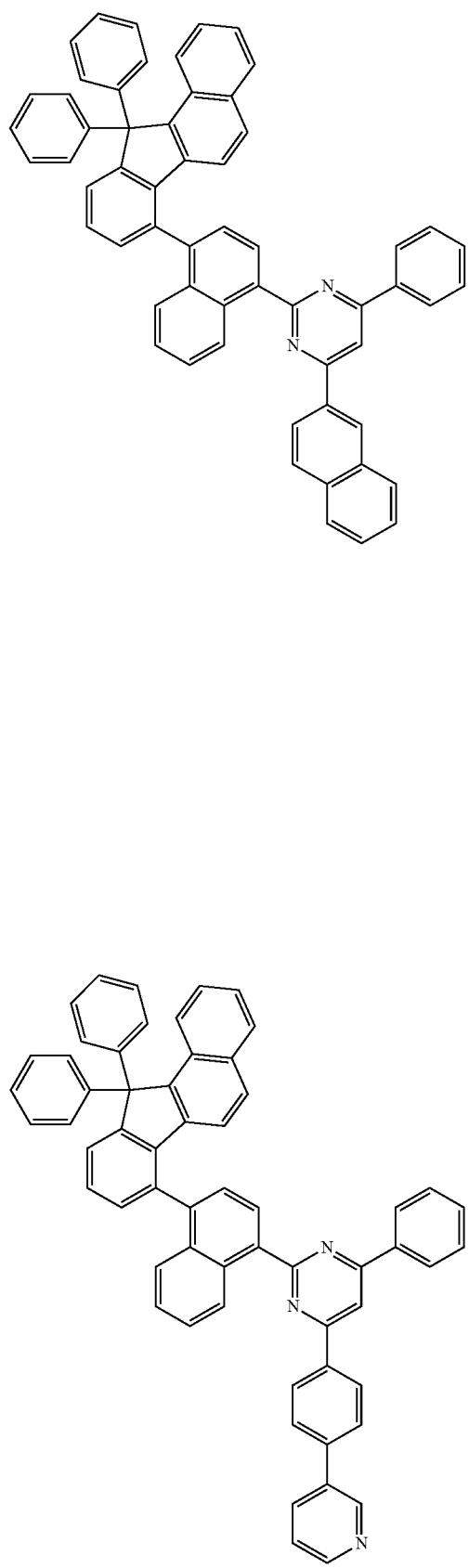

1129
-continued
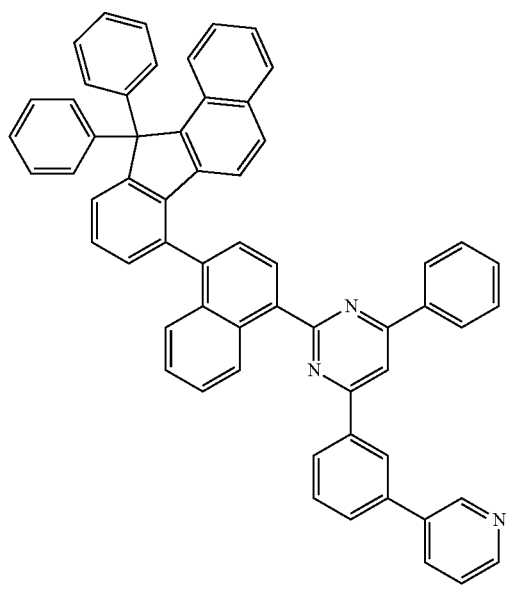
1130
-continued
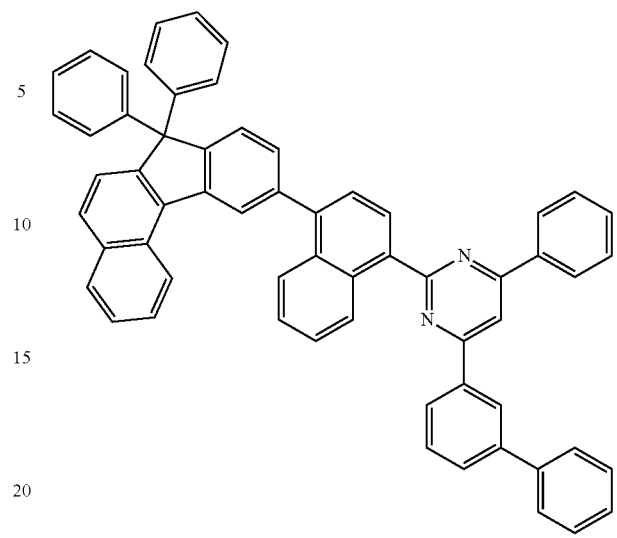
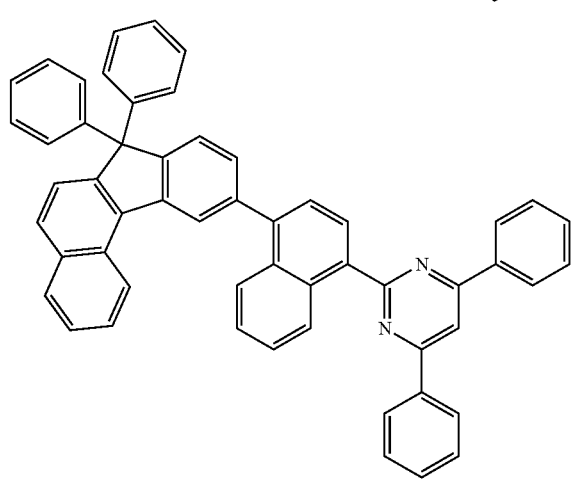
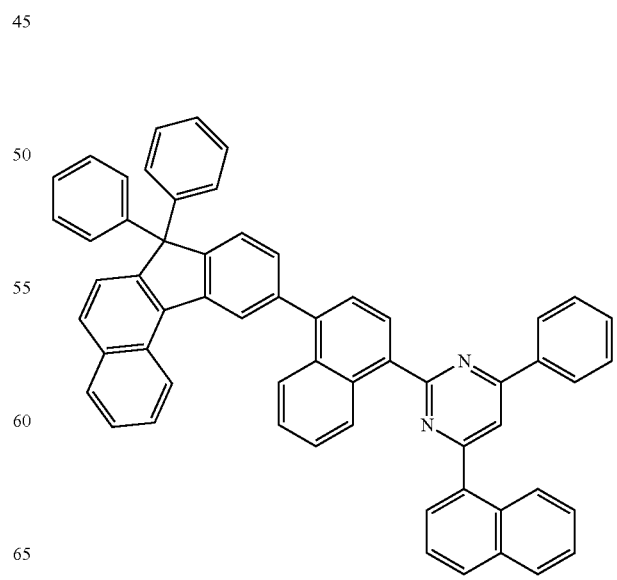
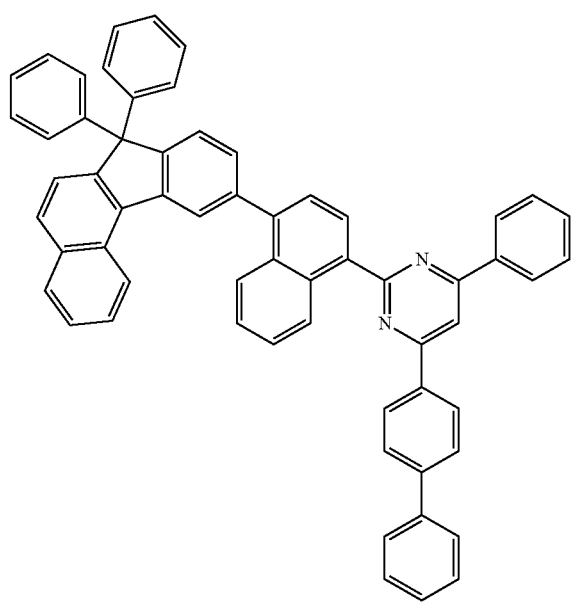

1131
-continued
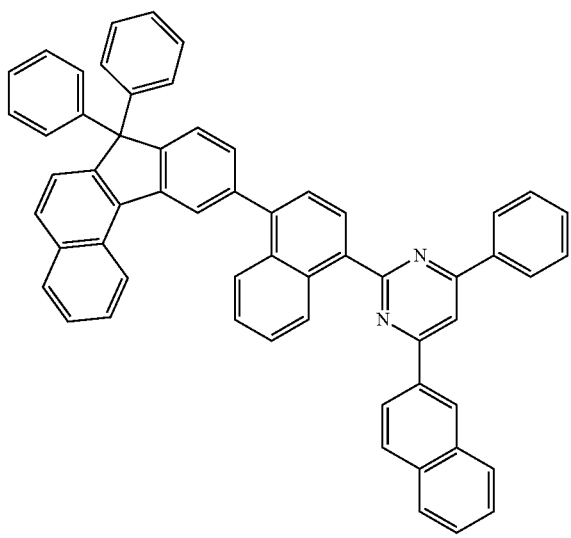
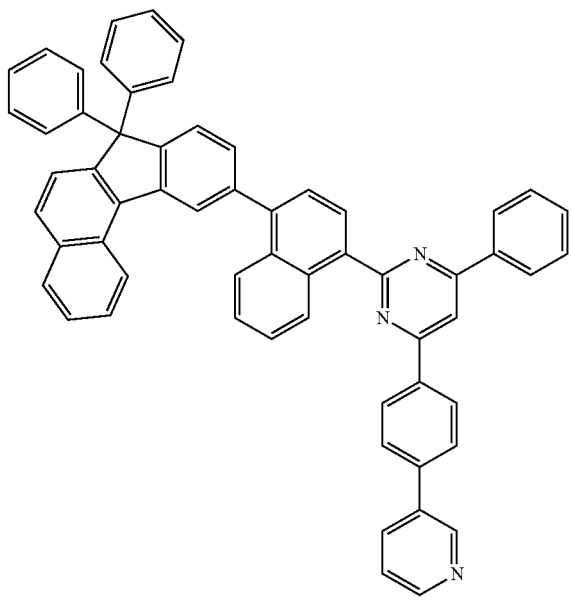
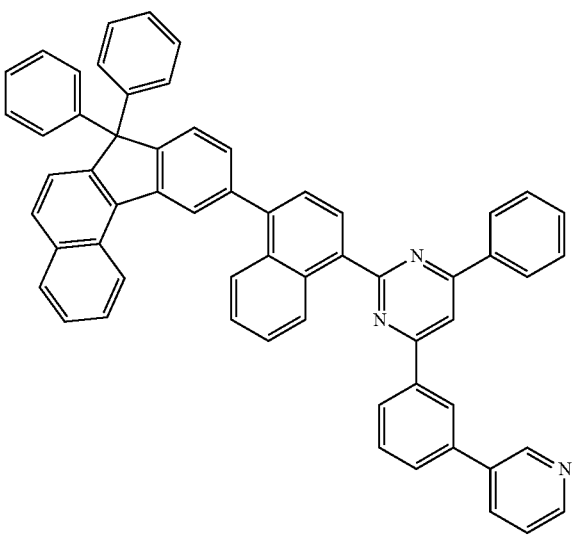
1132
-continued
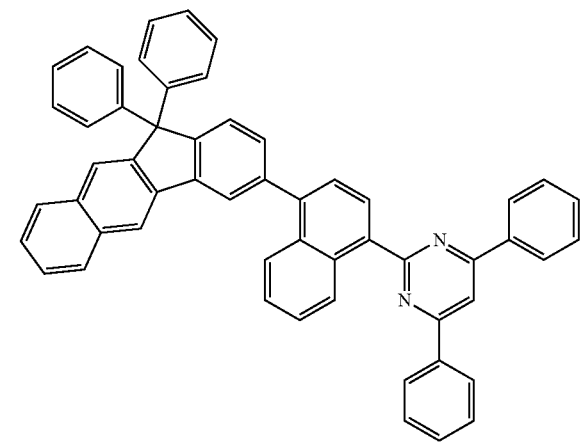

1133
-continued
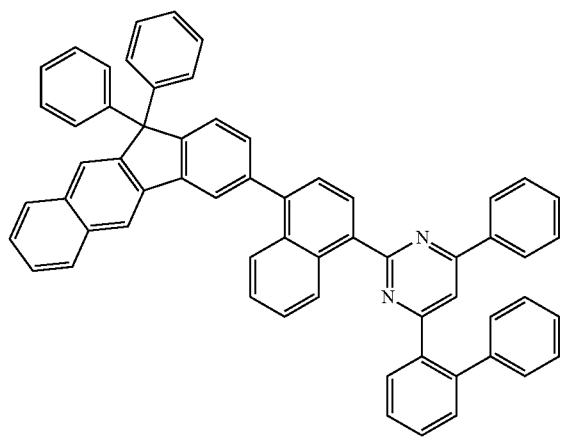
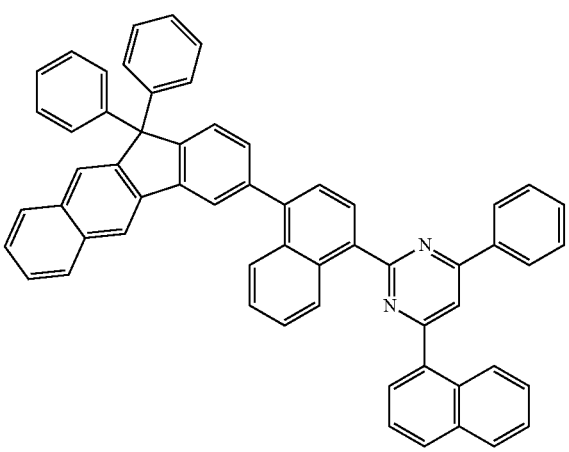
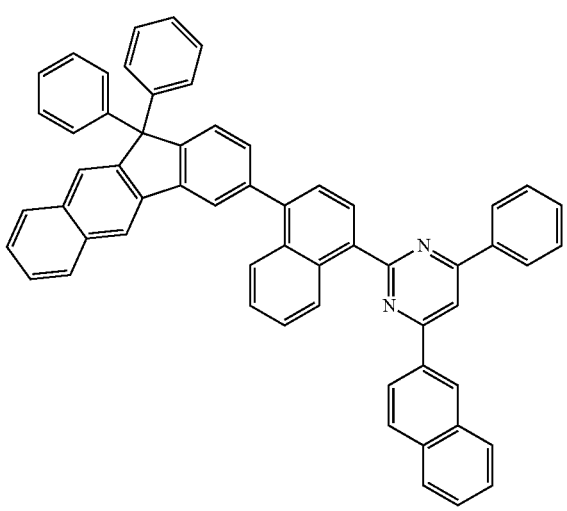
1134
-continued
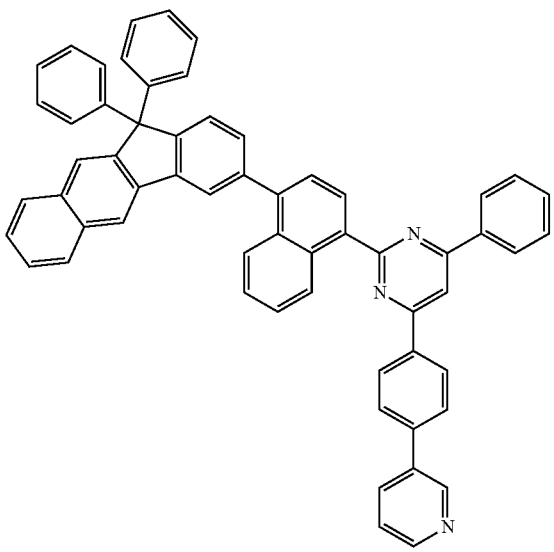
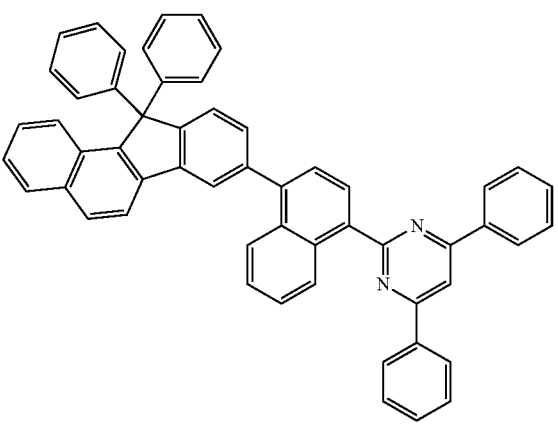

1135
-continued
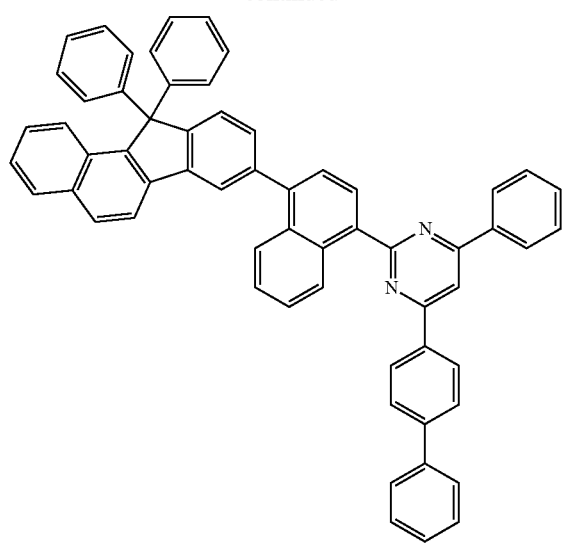
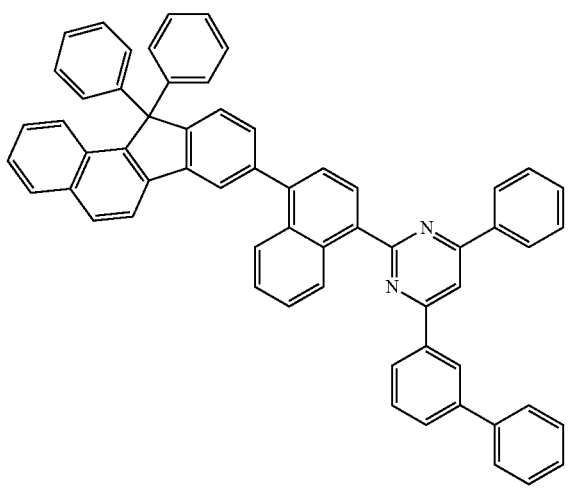
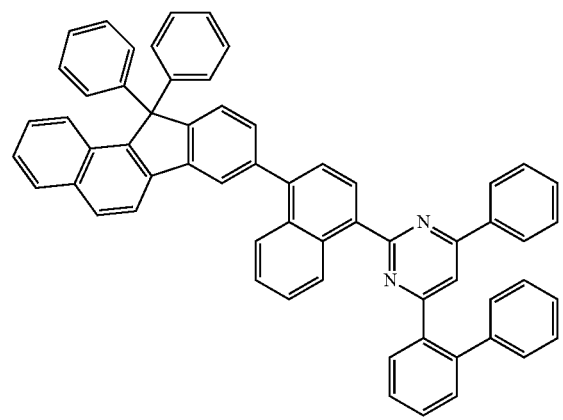
1136
-continued
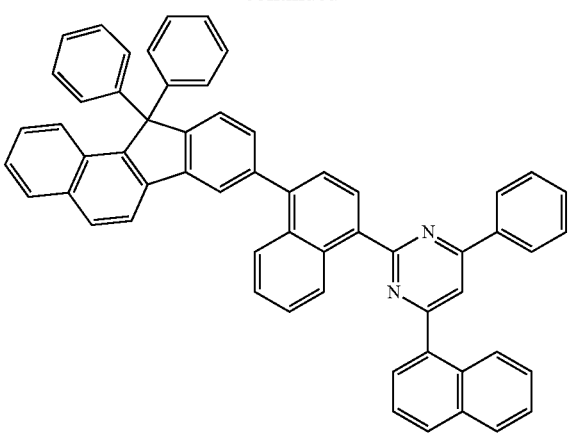
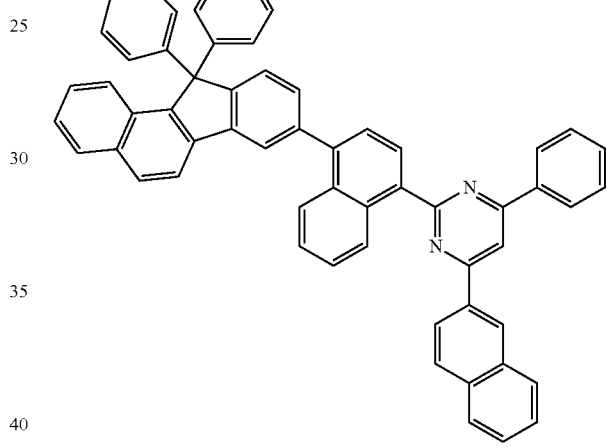
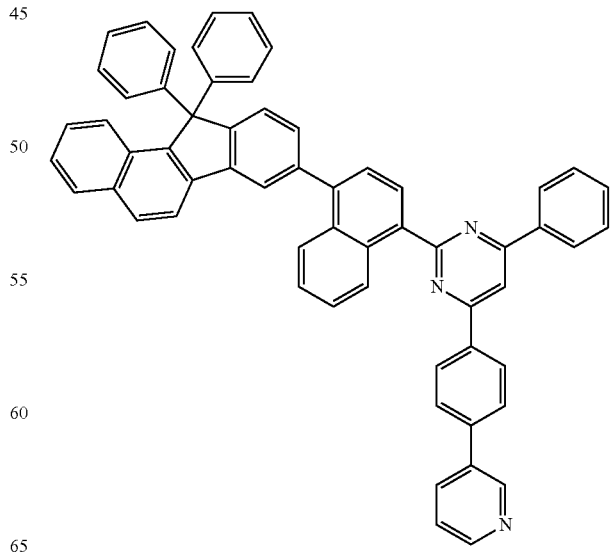

1137
-continued
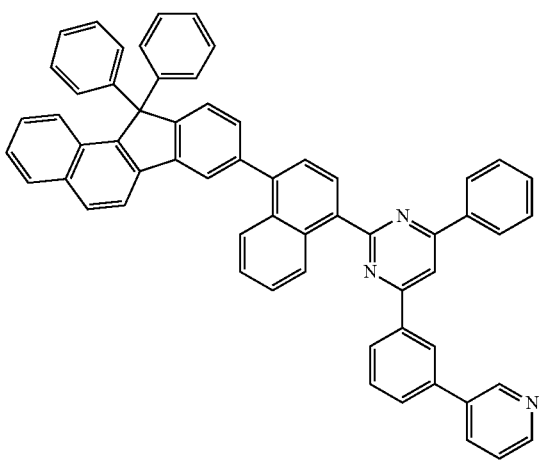
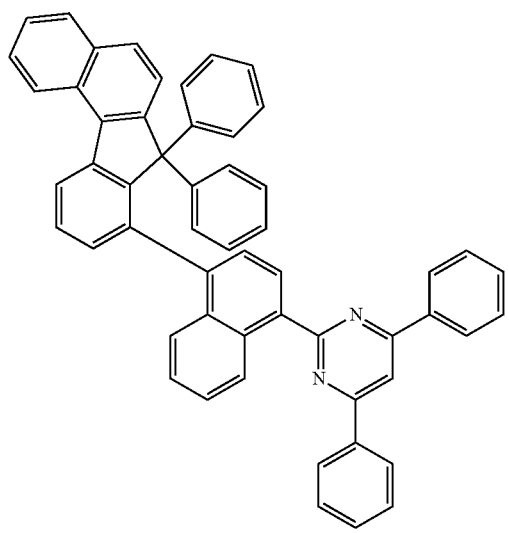
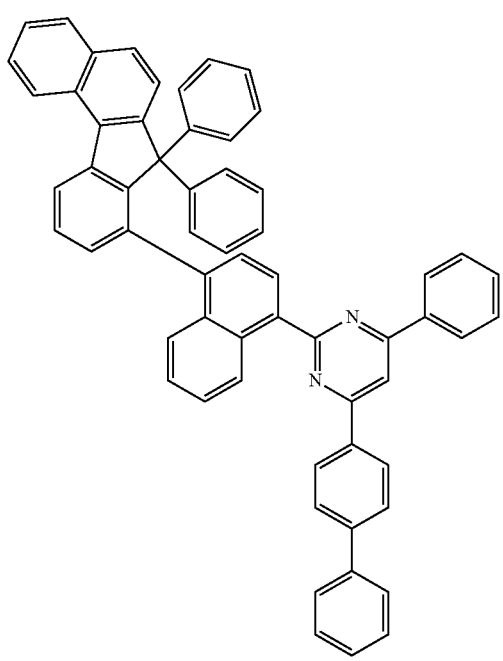
1138
-continued
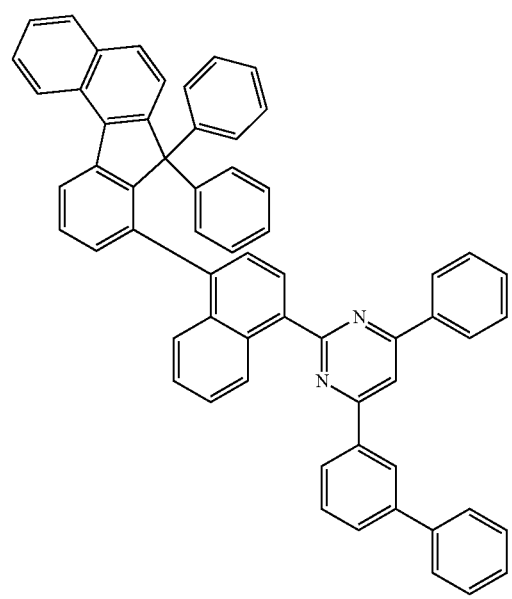
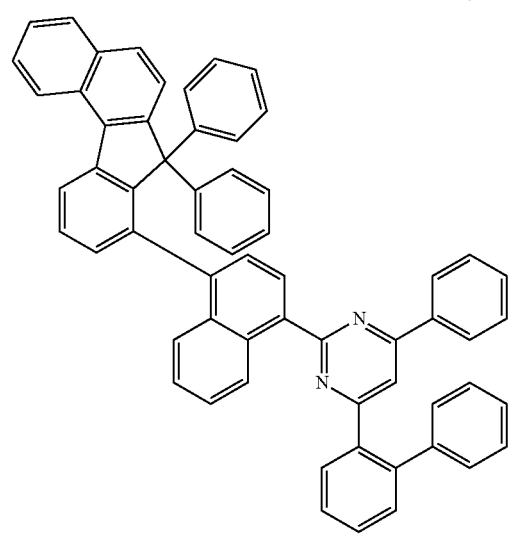
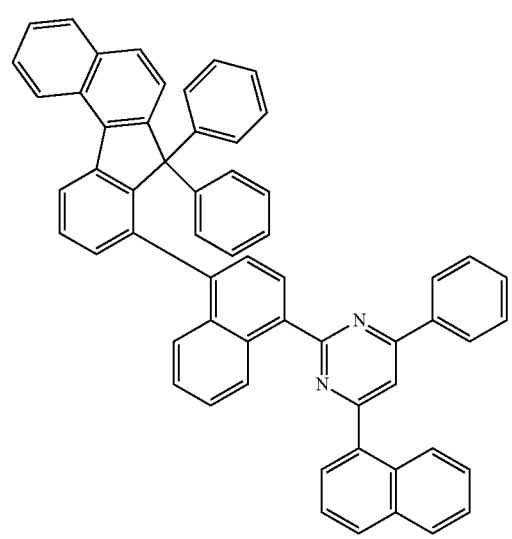

1139
-continued
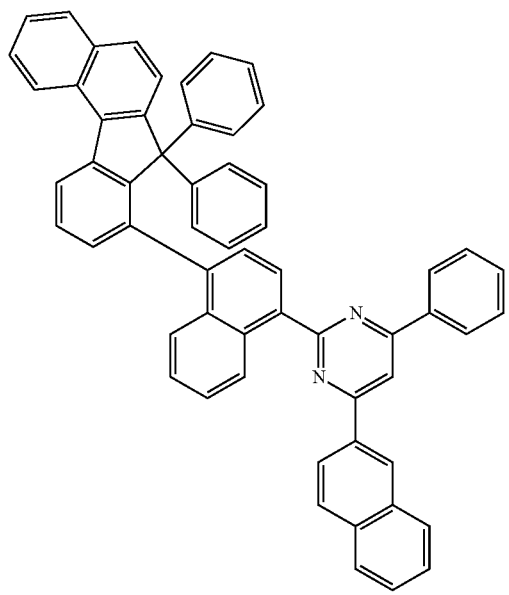
1140
-continued
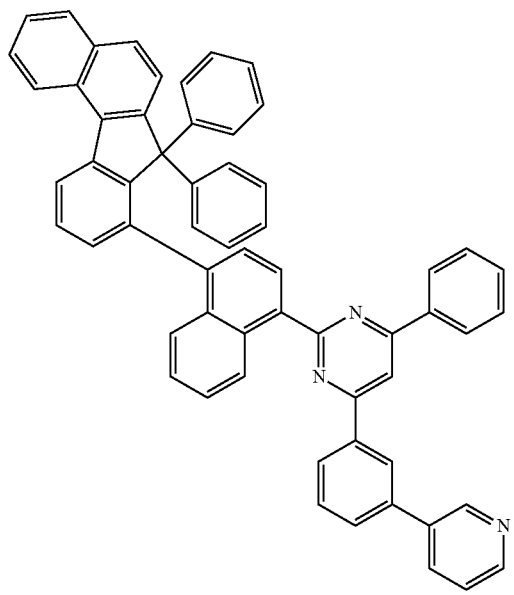
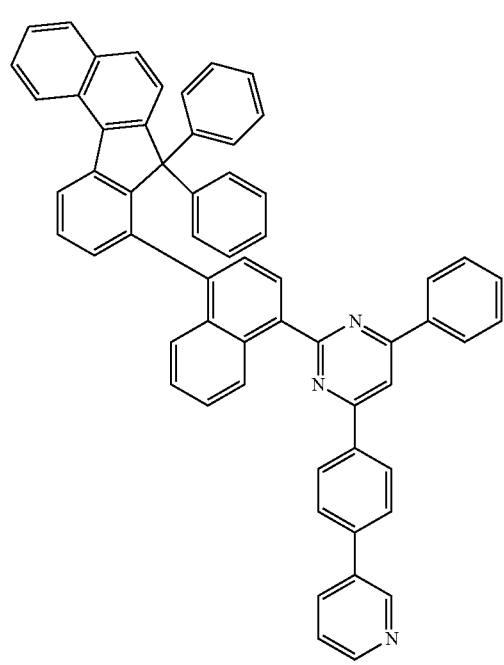

1141
-continued
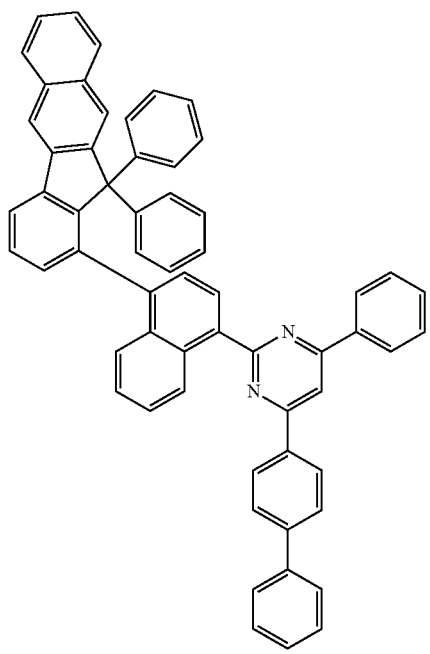
1142
-continued
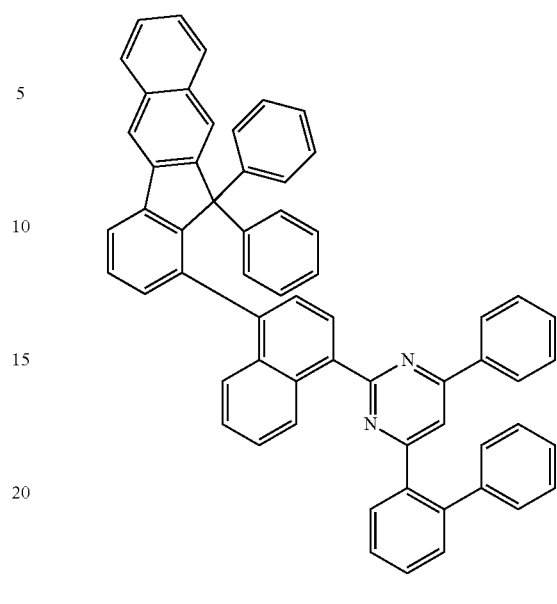
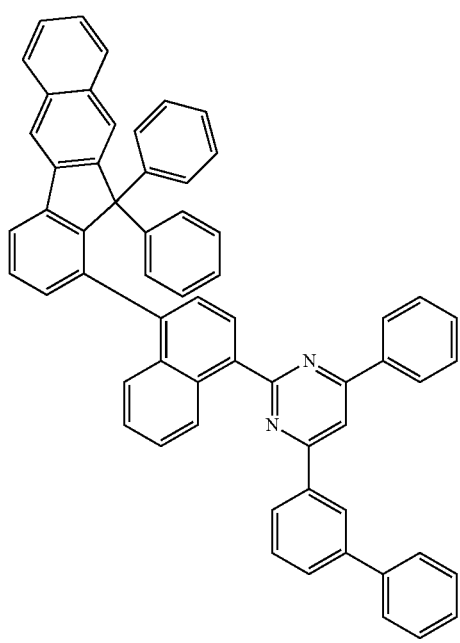
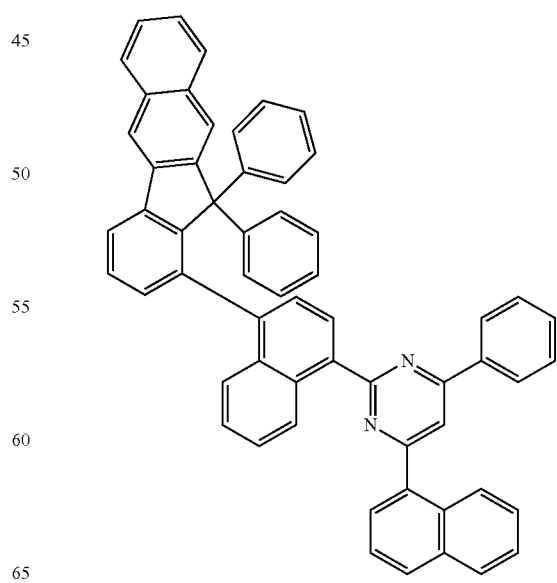

1143
-continued
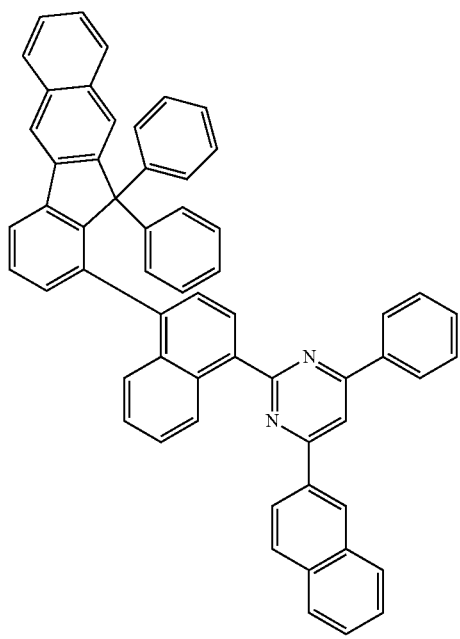
1144
-continued
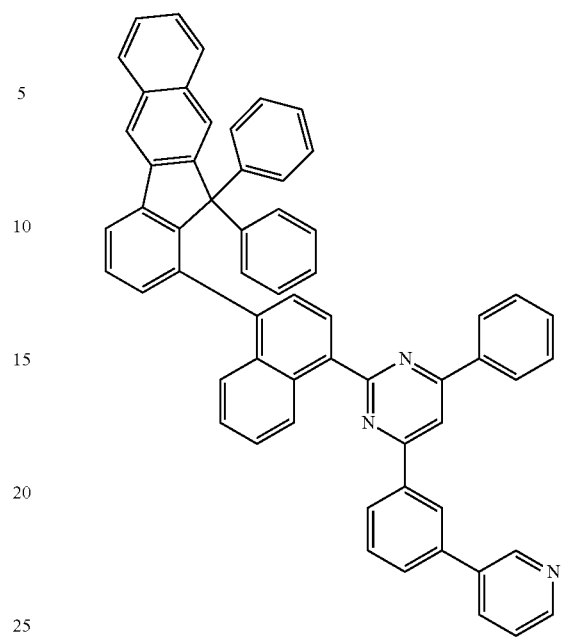
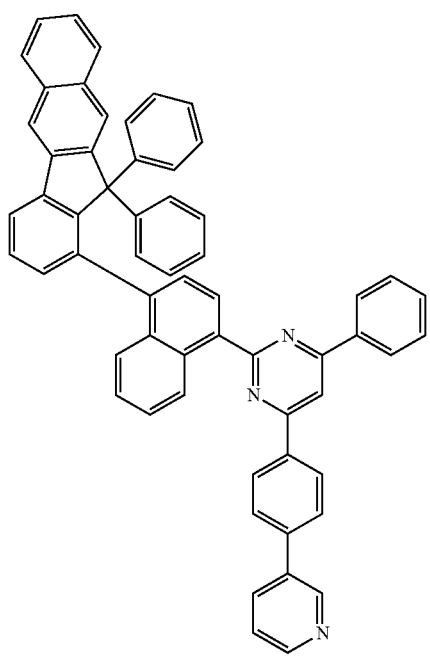
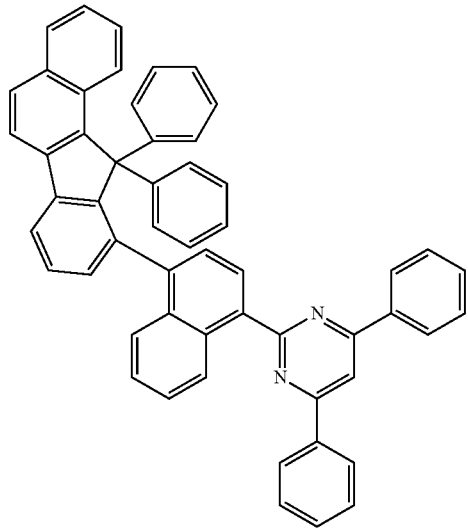

1145
-continued
1146
-continued
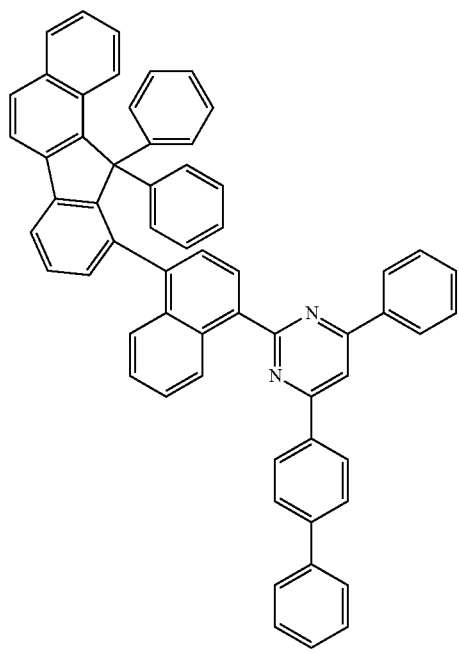
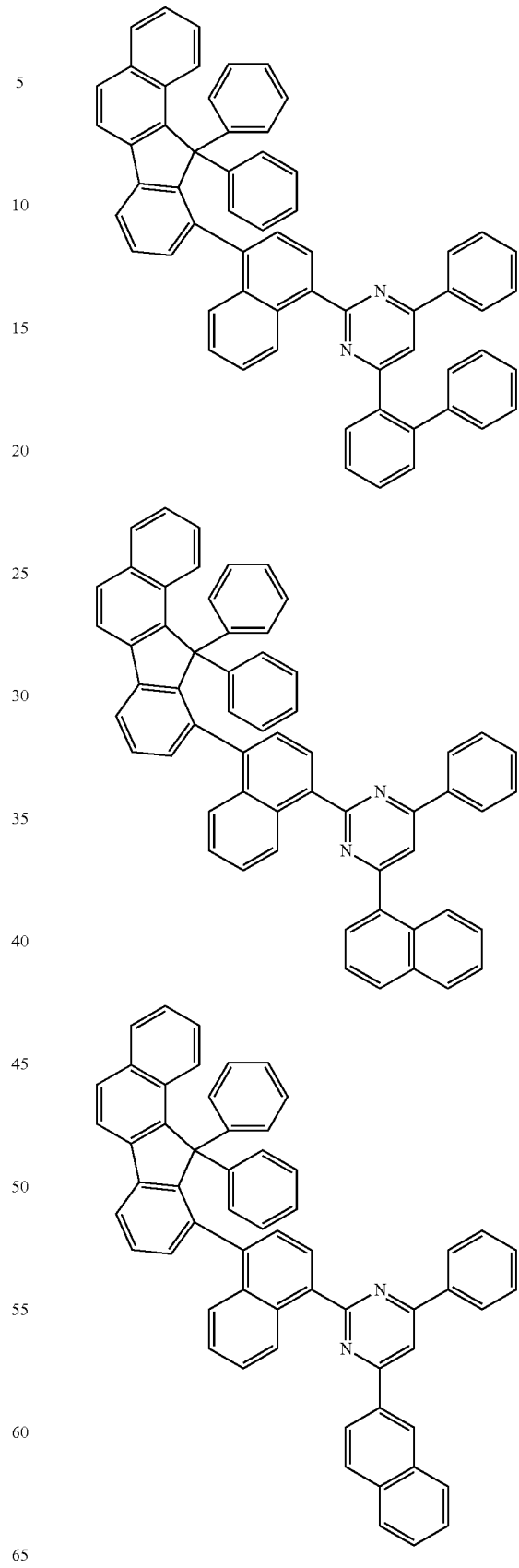

1147
-continued
1148
-continued
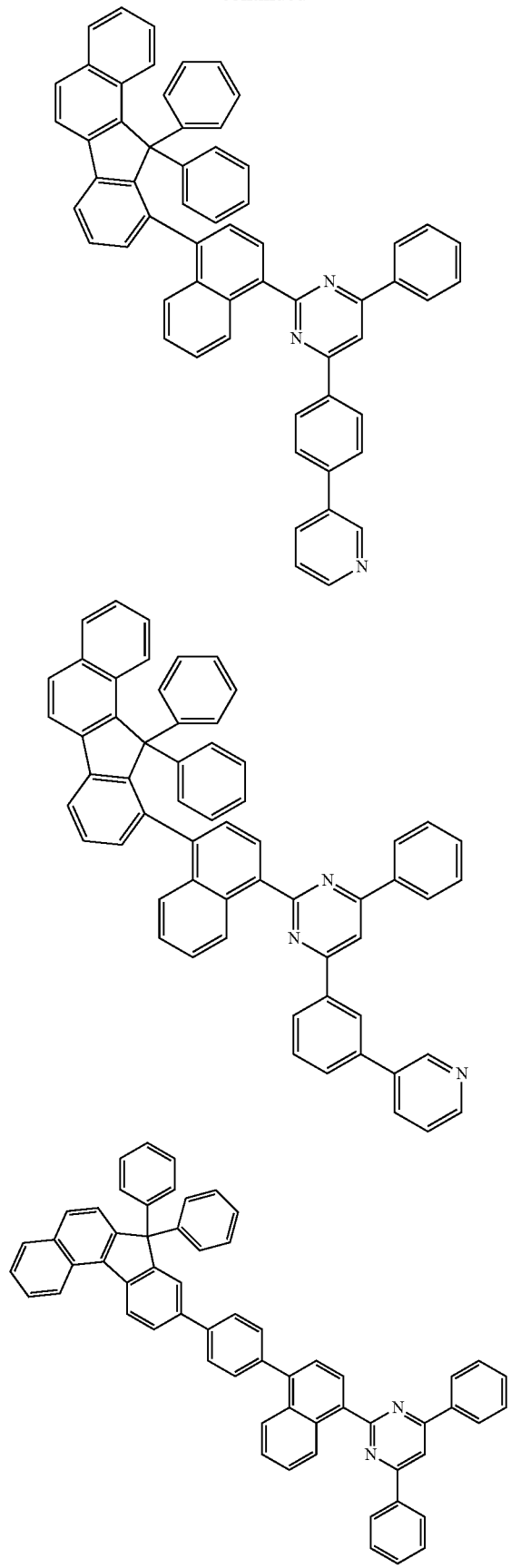
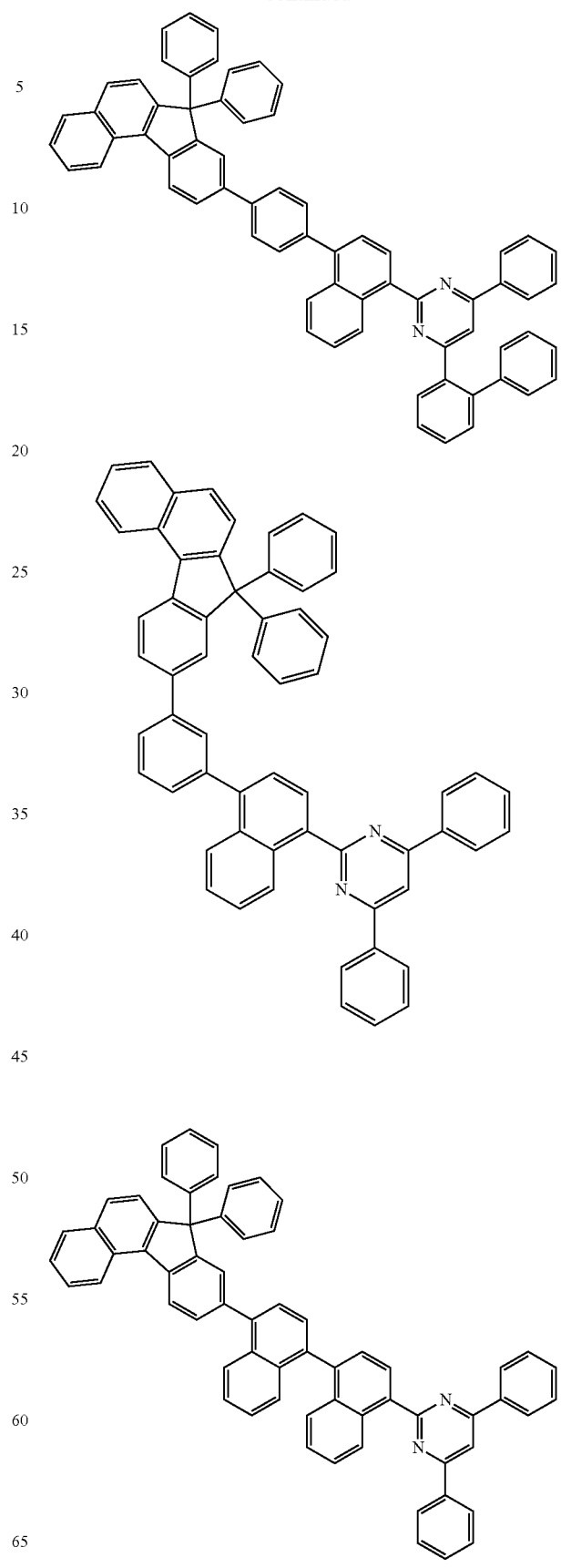

1149
-continued
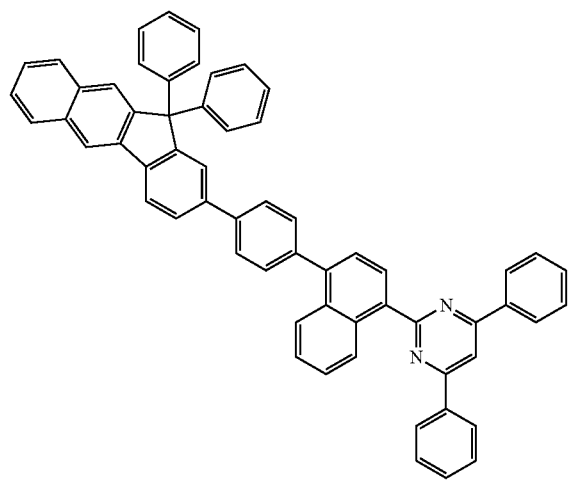
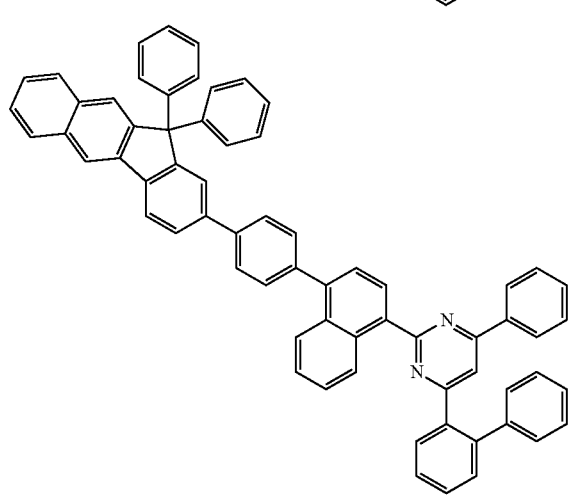
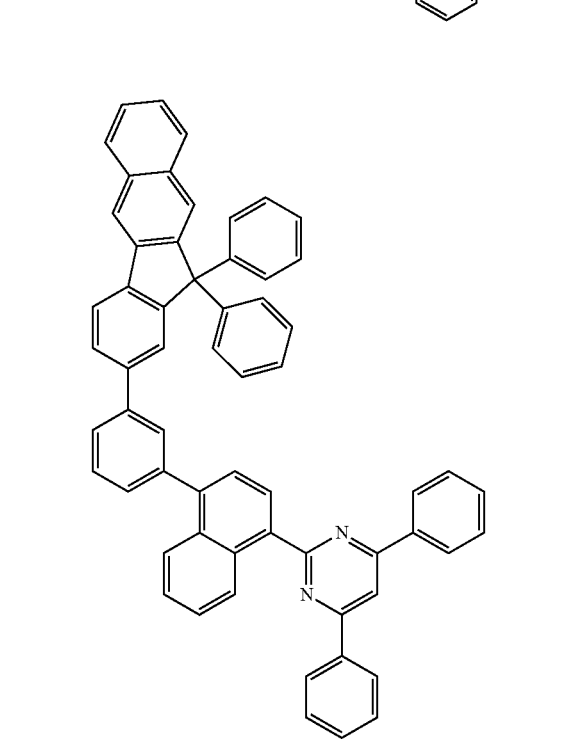
1150
-continued
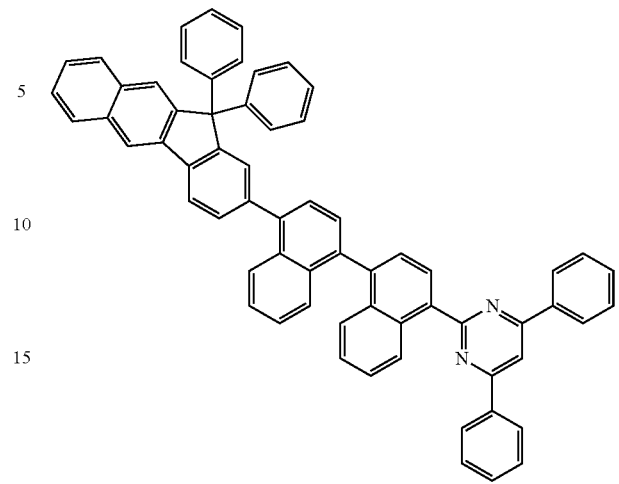
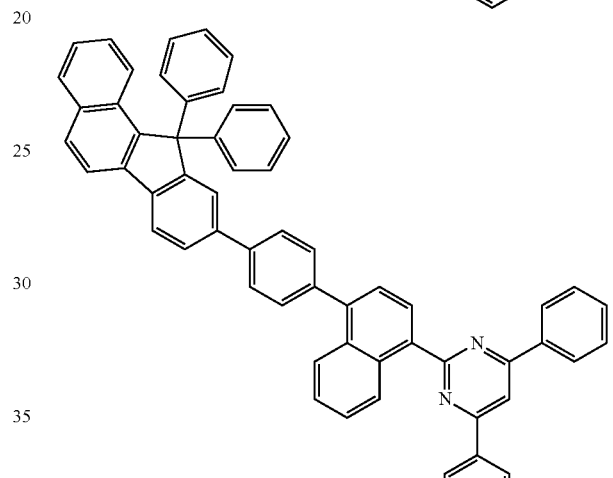
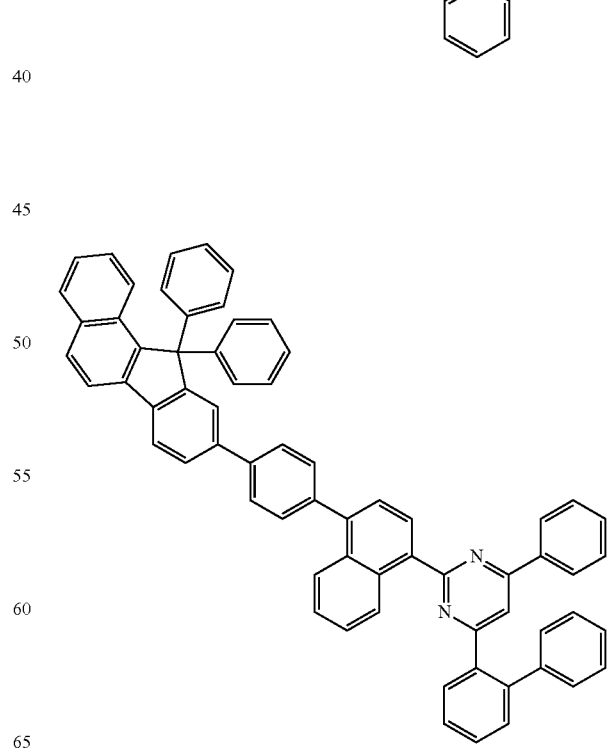

1151
-continued
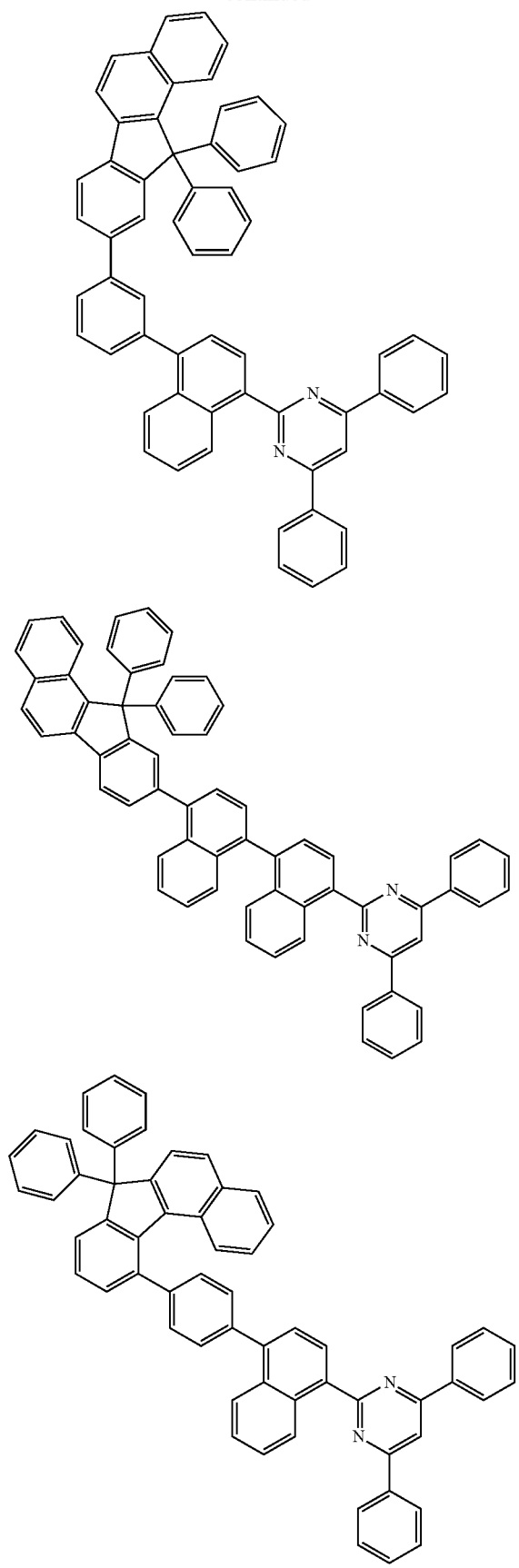
1152
-continued
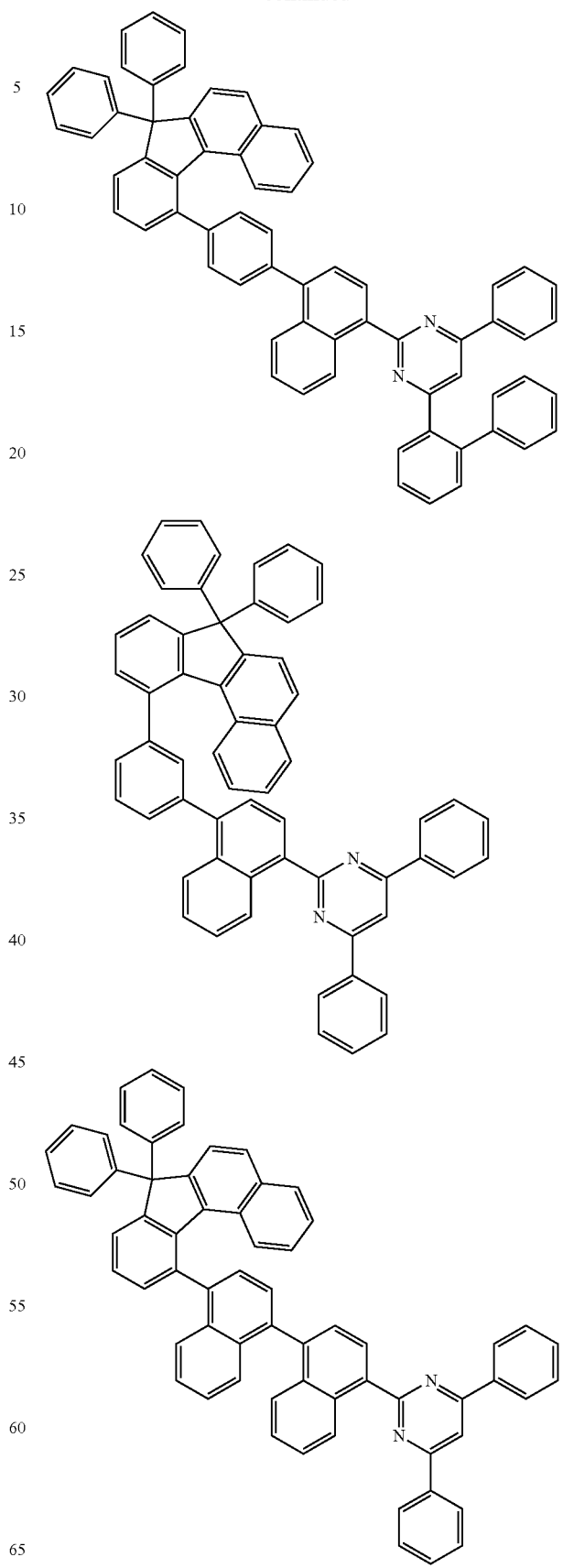

1153
-continued
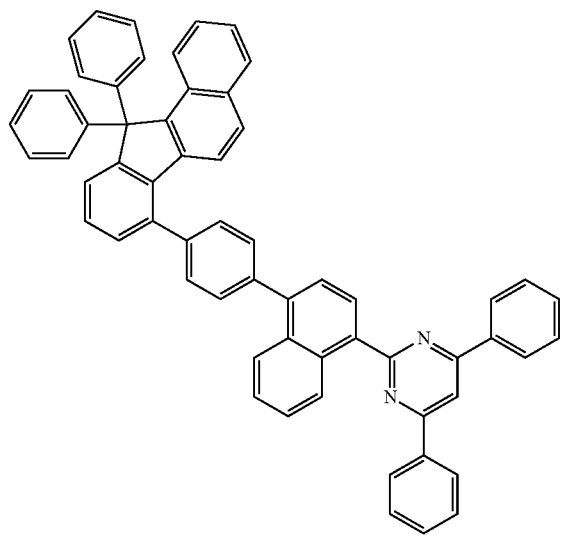
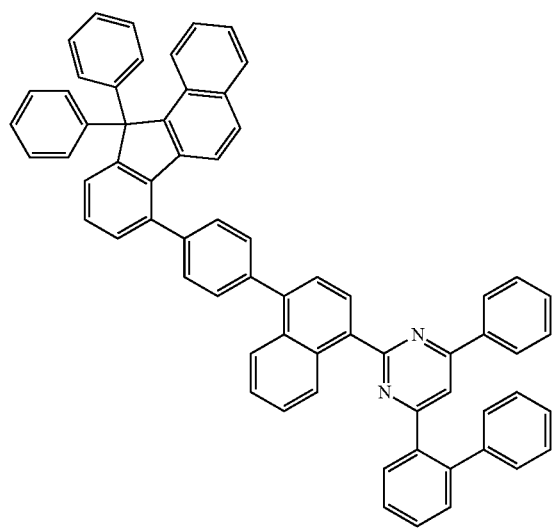
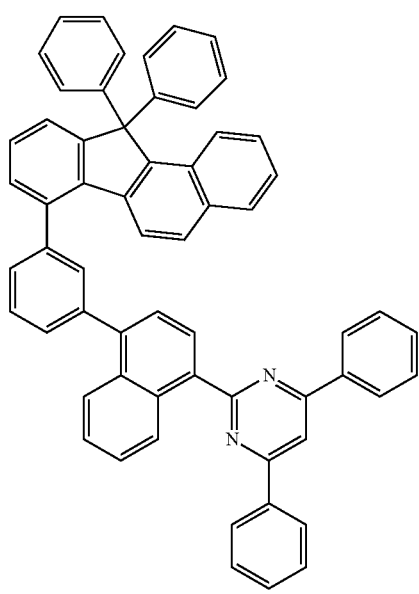
1154
-continued
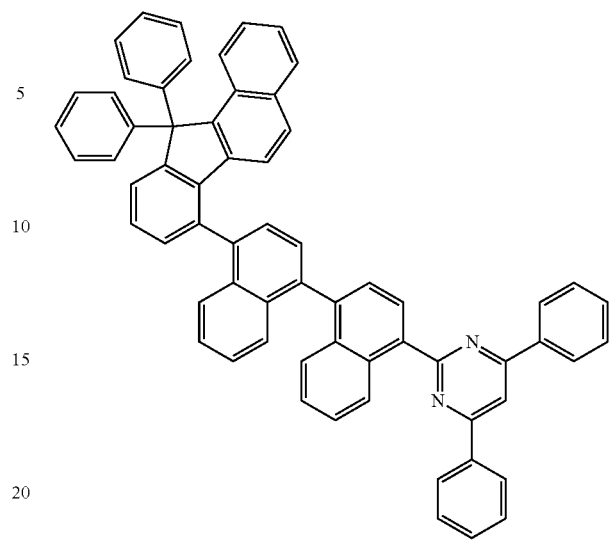
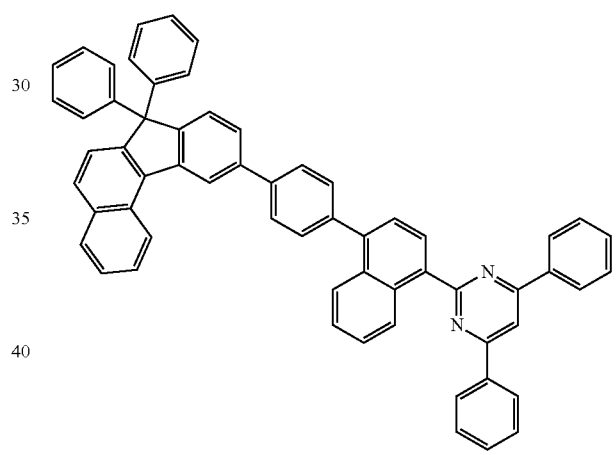
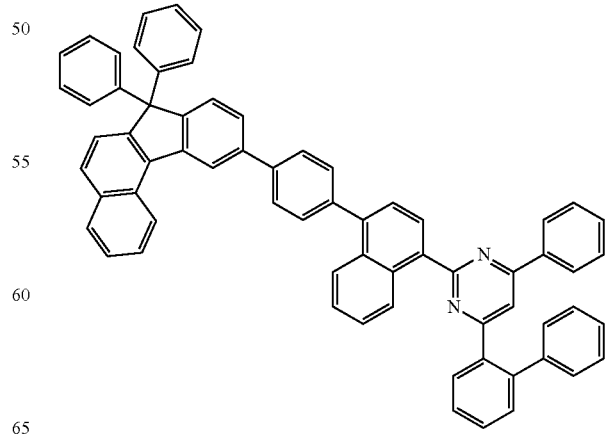

1155
-continued
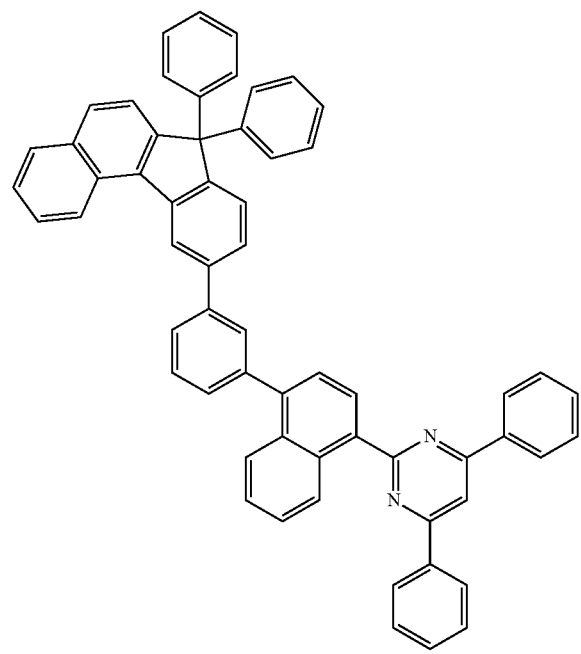
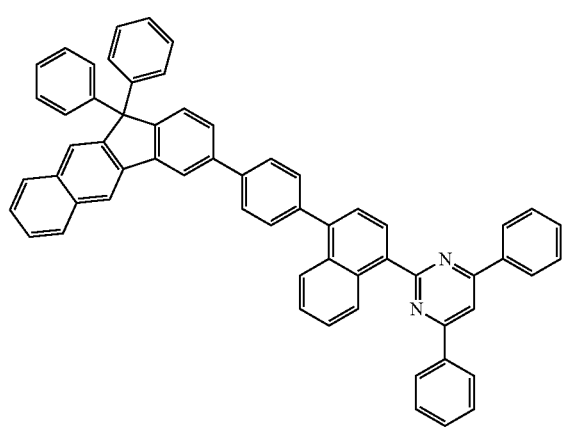
1156
-continued
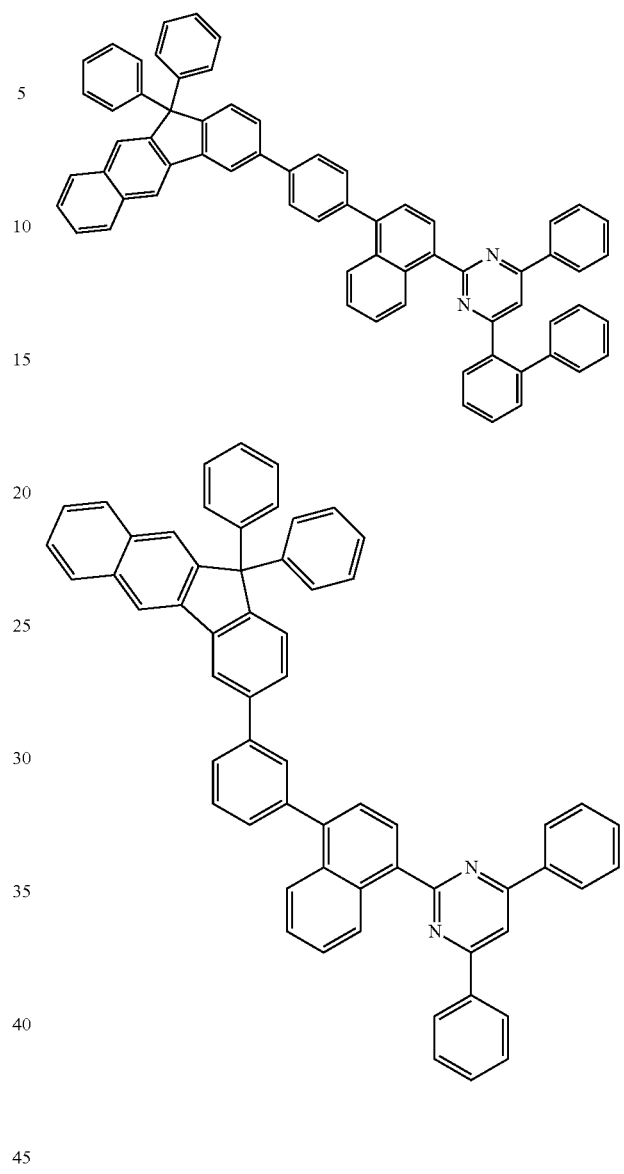
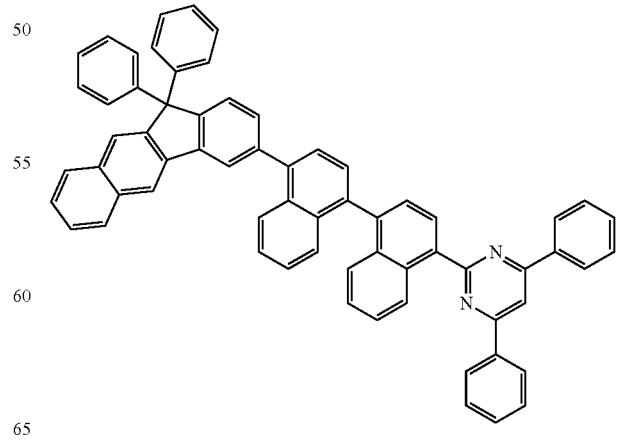

1157
-continued
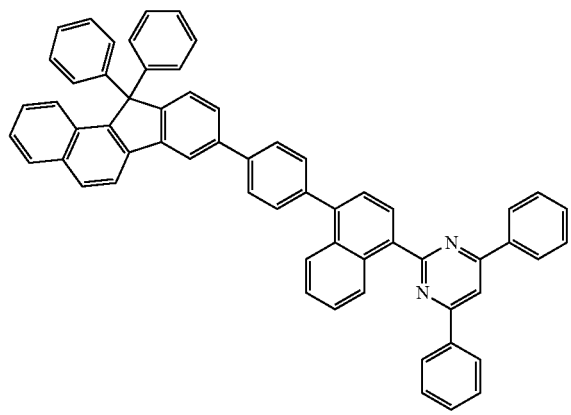
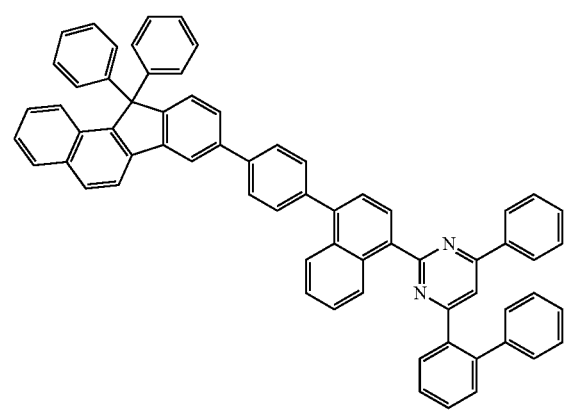
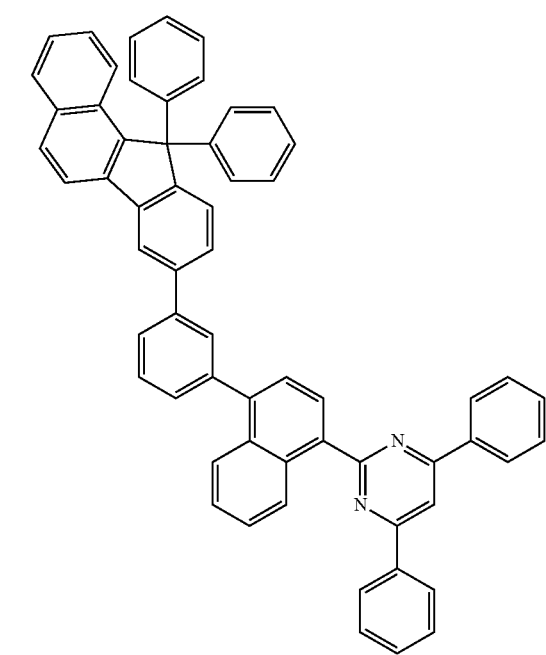
1158
-continued
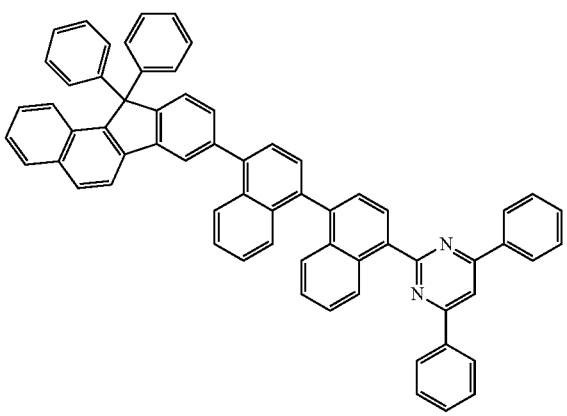
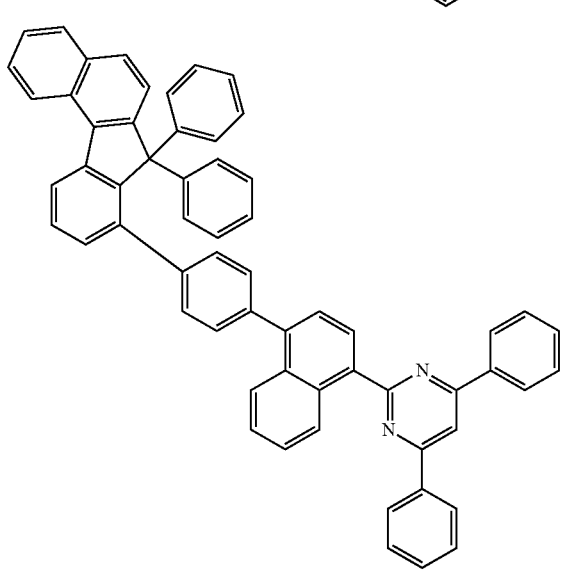

1159
-continued
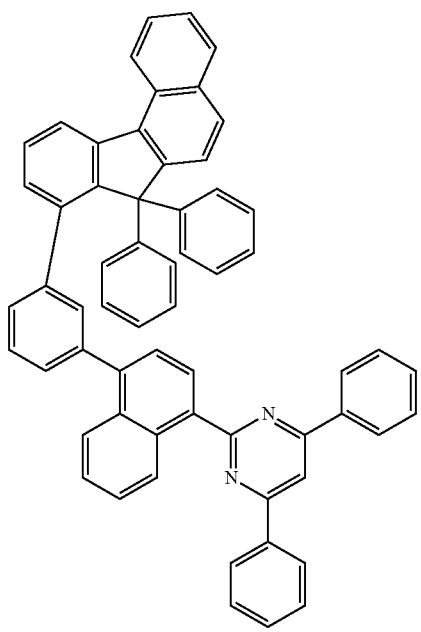
1160
-continued
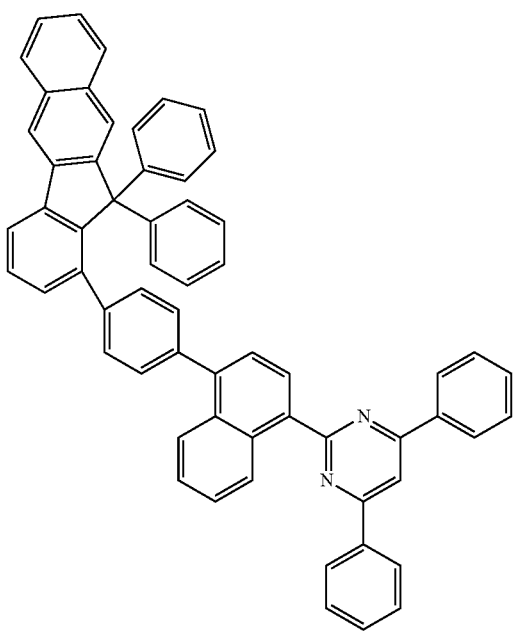
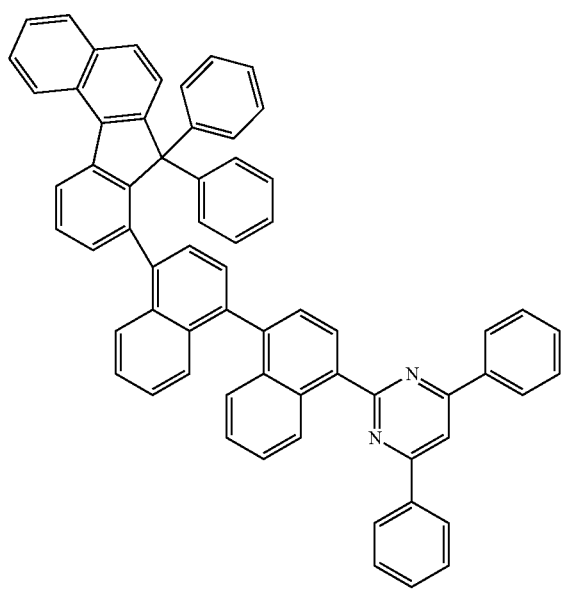

1161
-continued
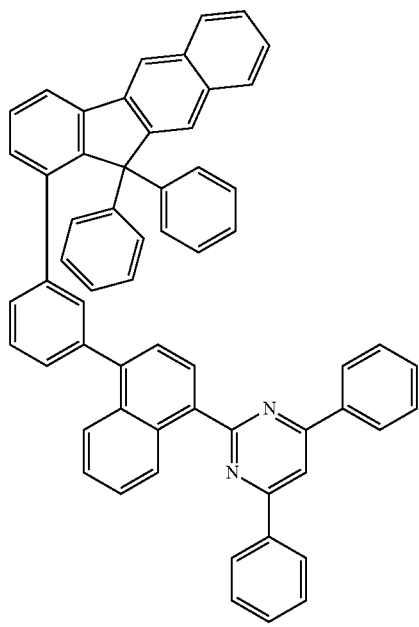
1162
-continued
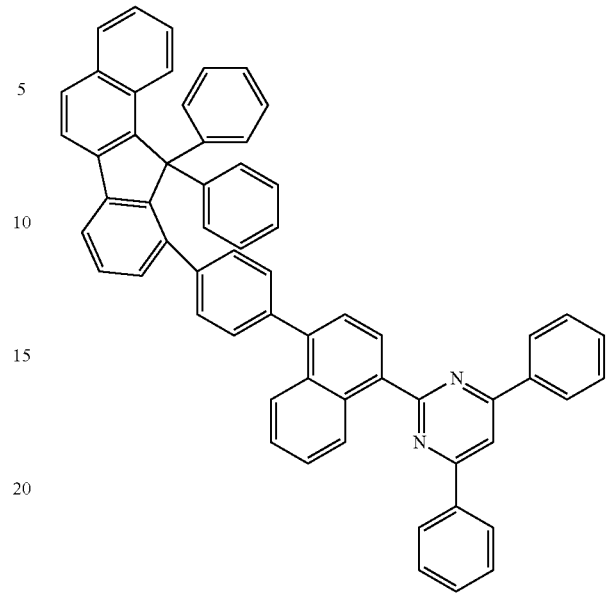
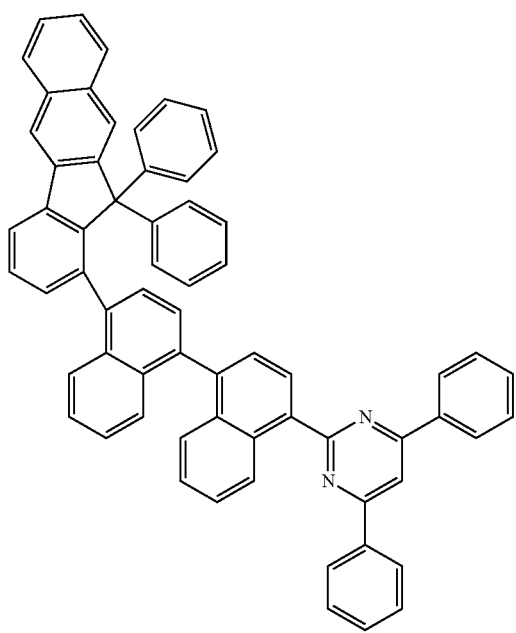
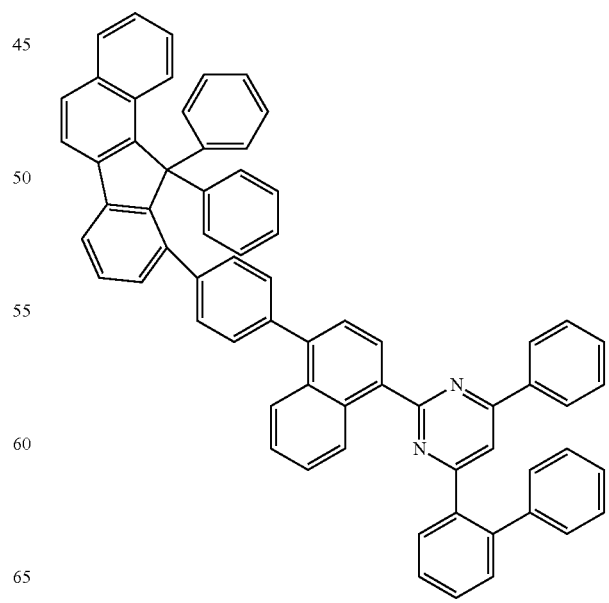

1163
-continued
1164
-continued
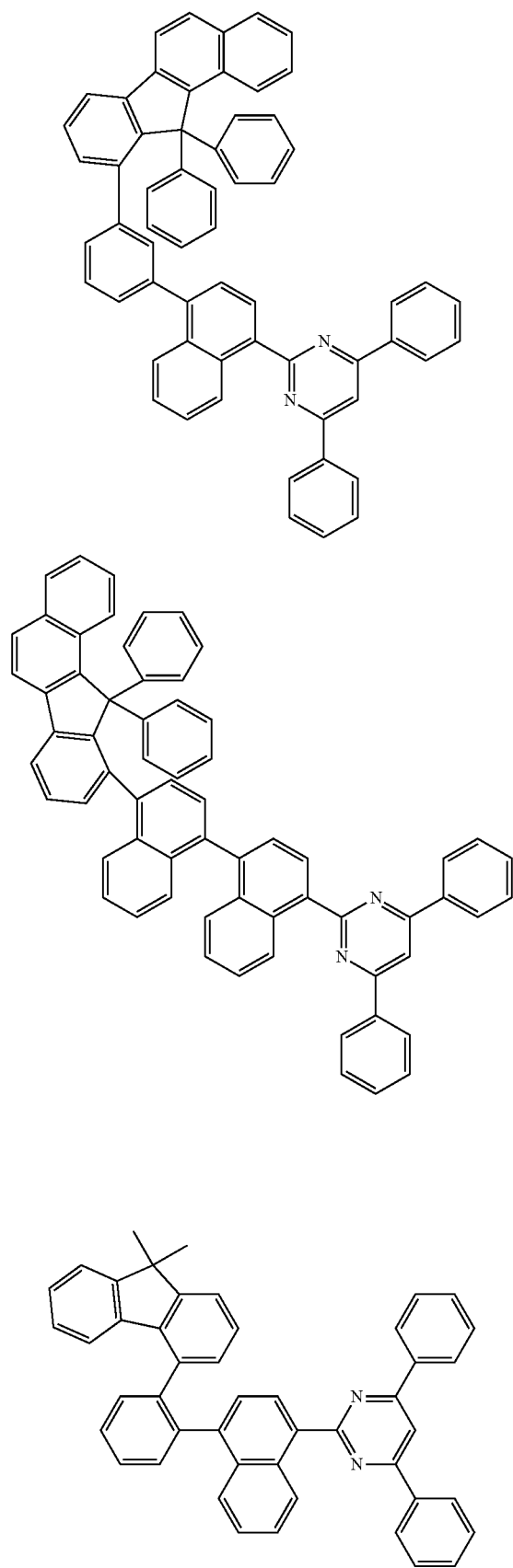
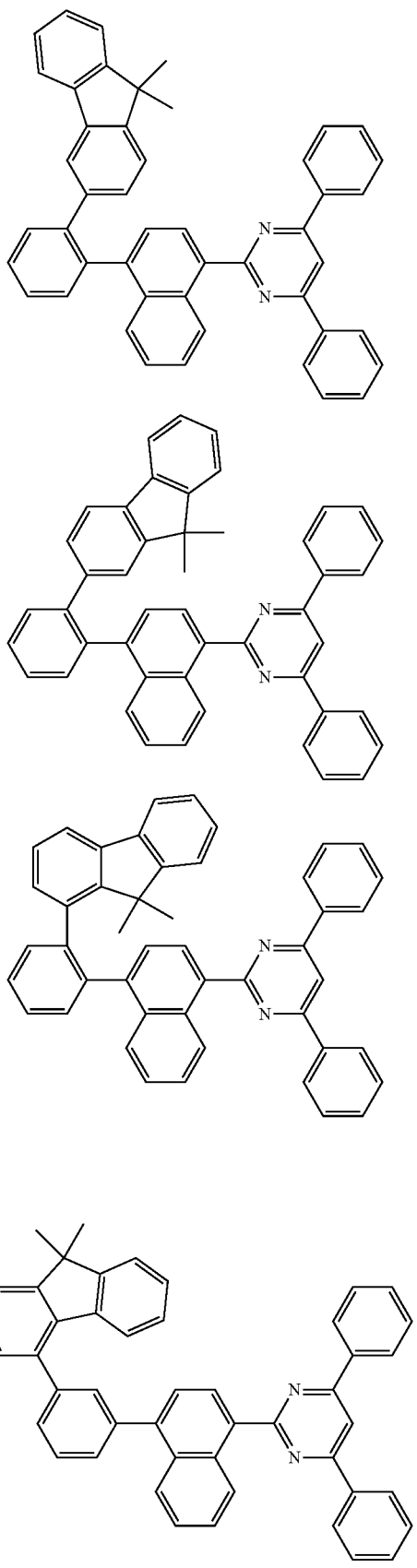

1165
-continued
1166
-continued
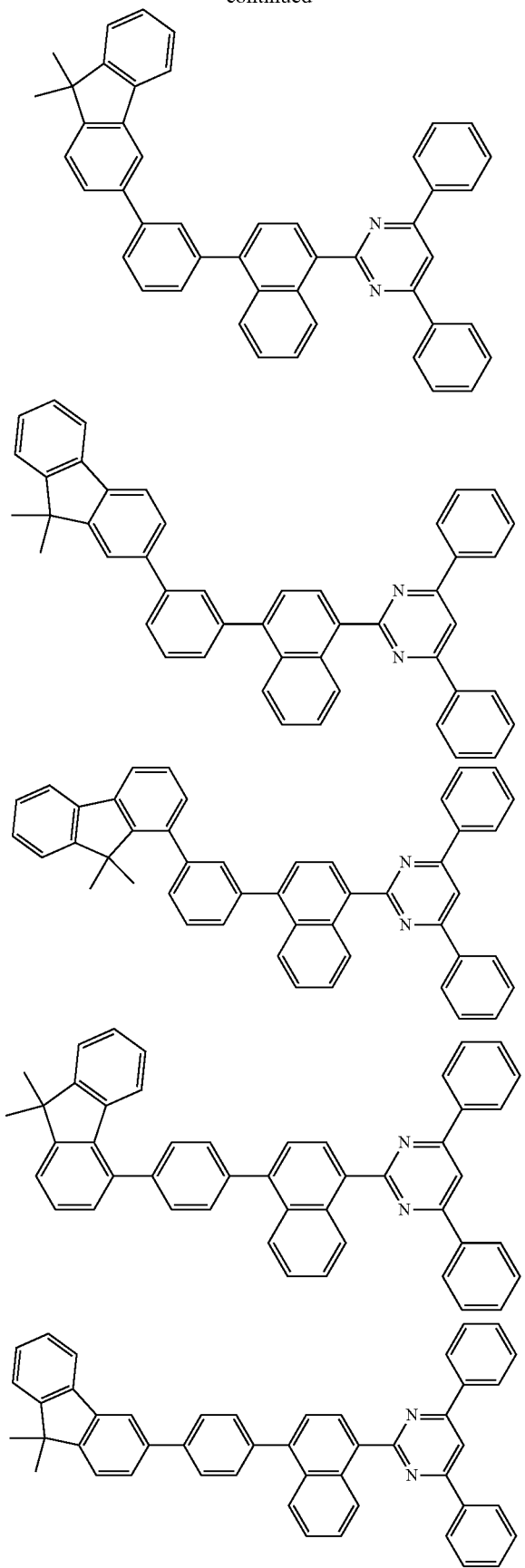
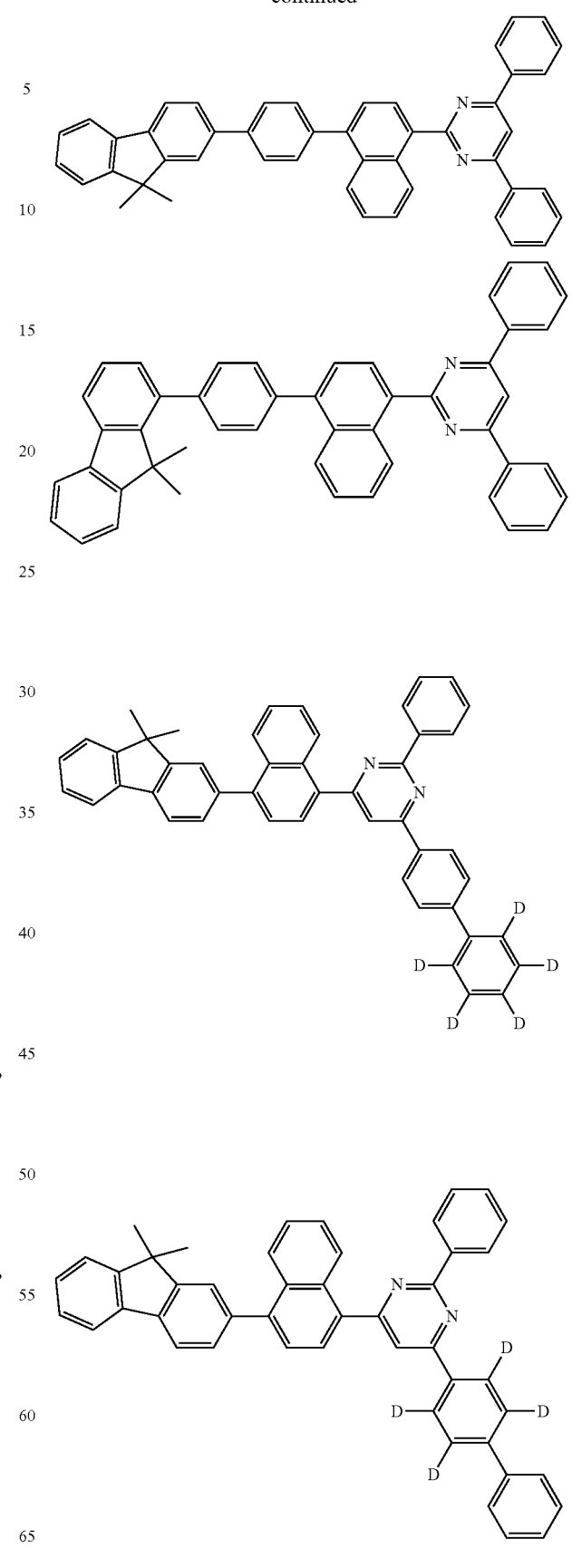

1167
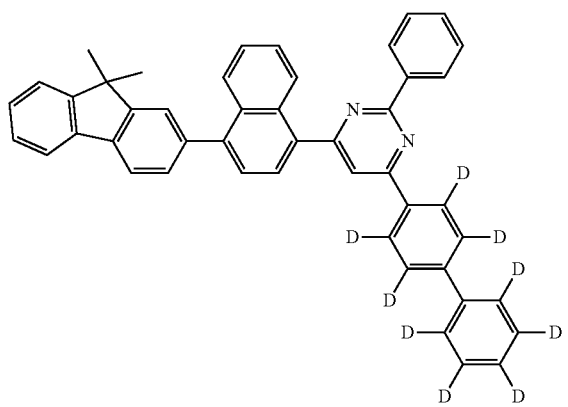
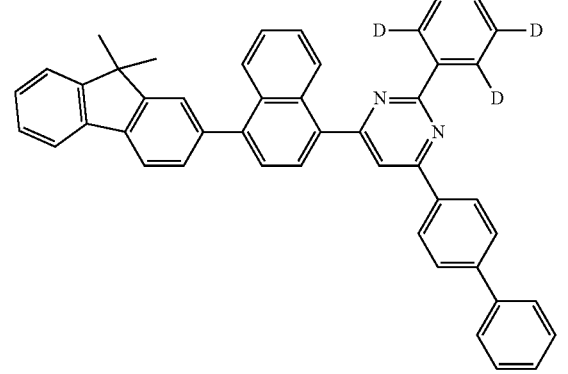
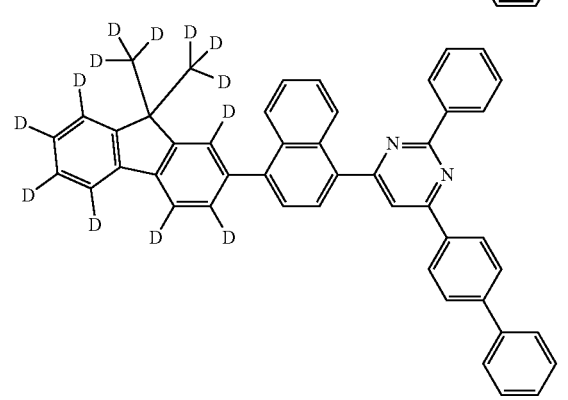
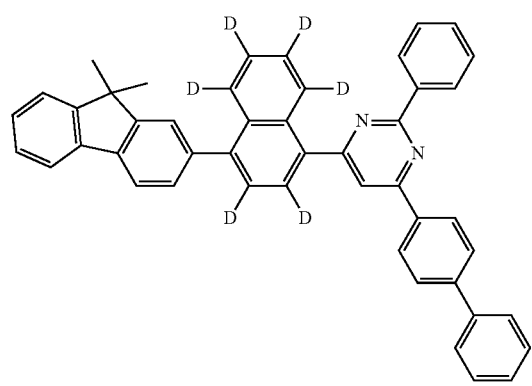
1168
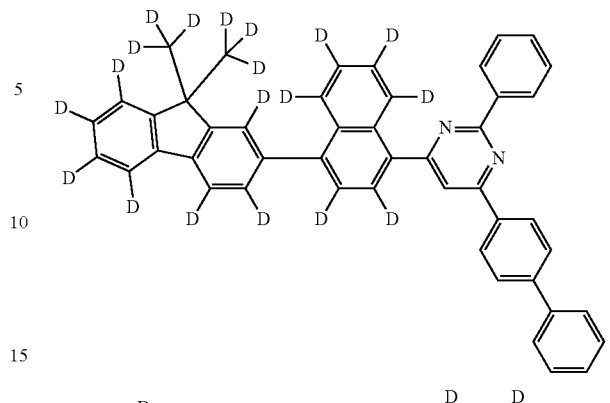
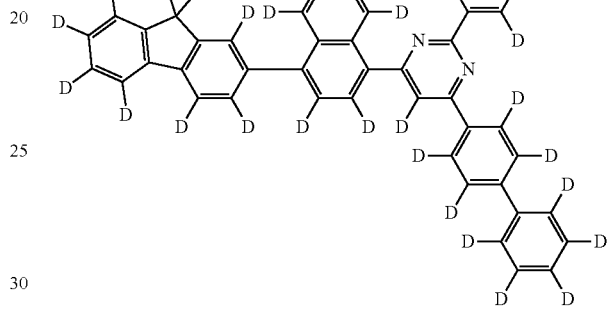
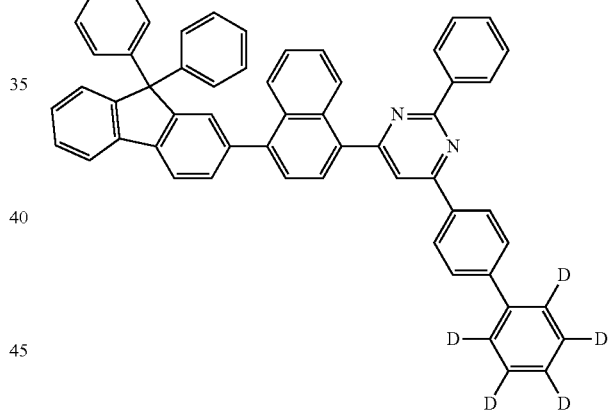
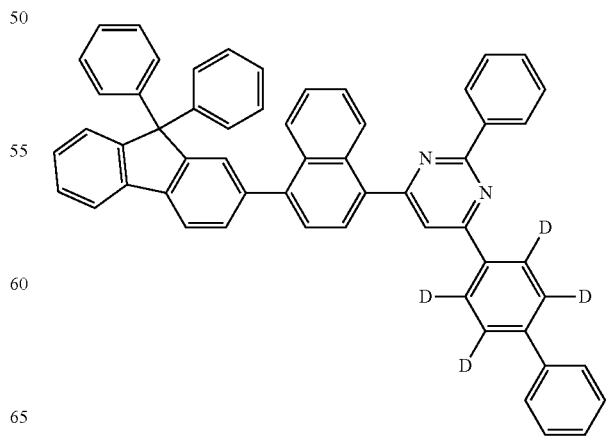

1169
-continued
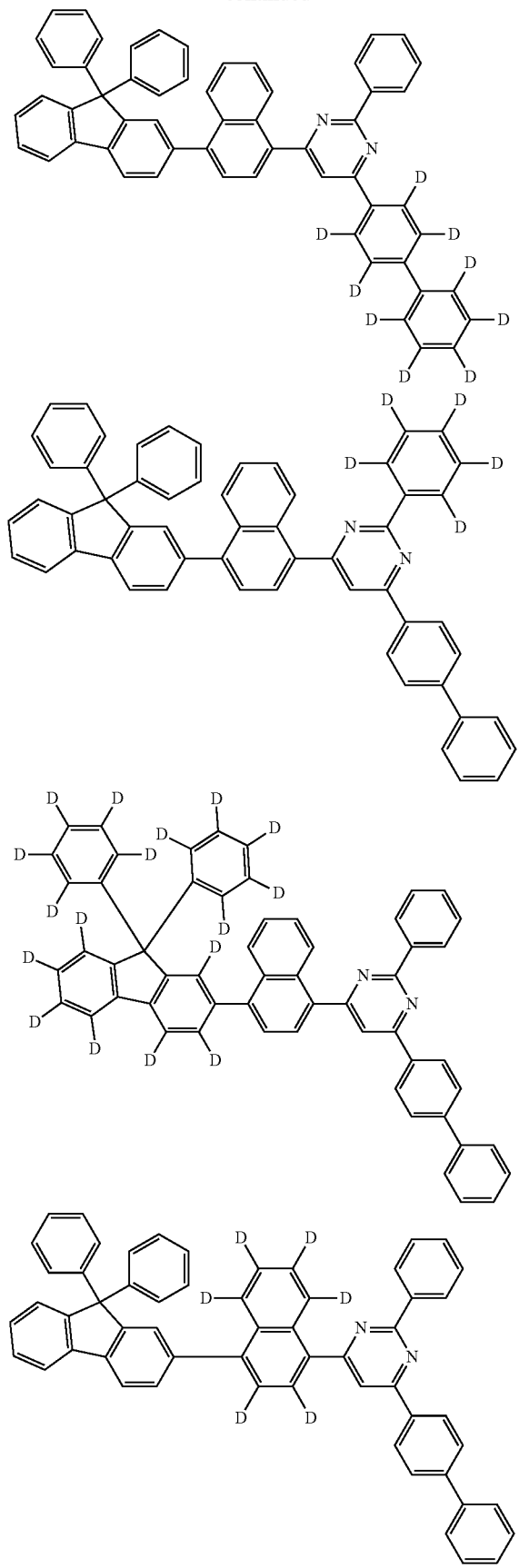
1170
-continued
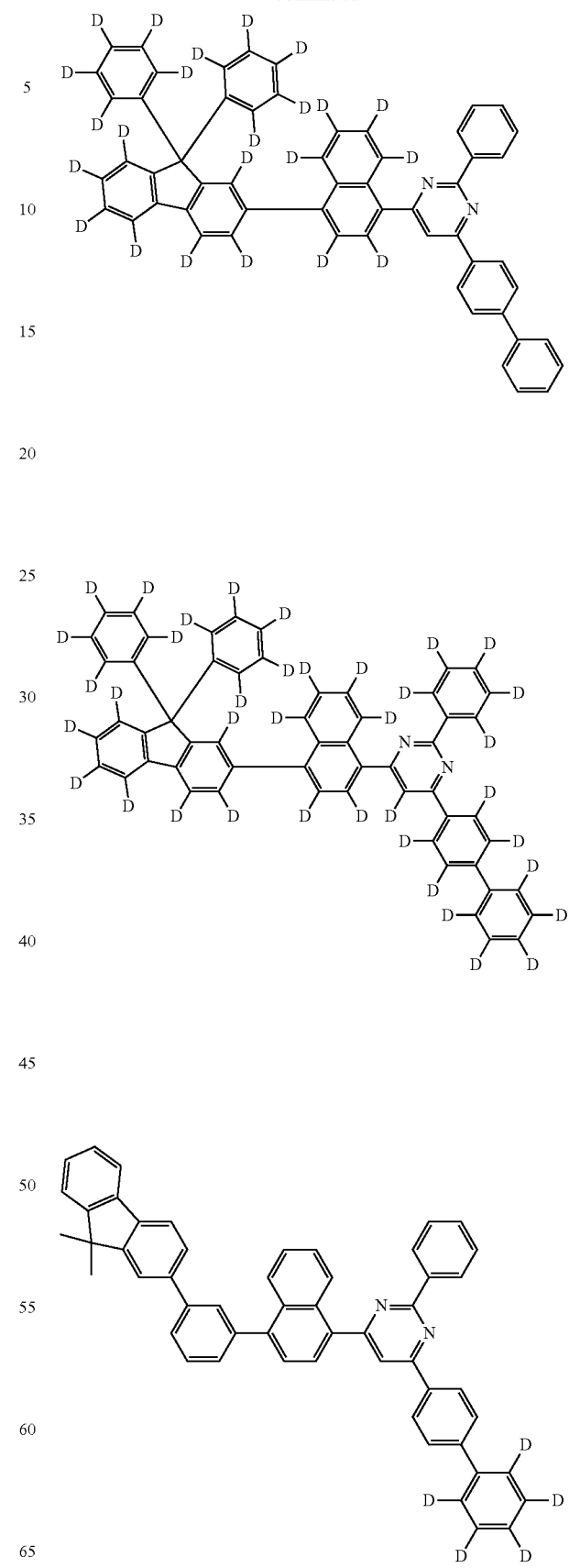

1171
-continued
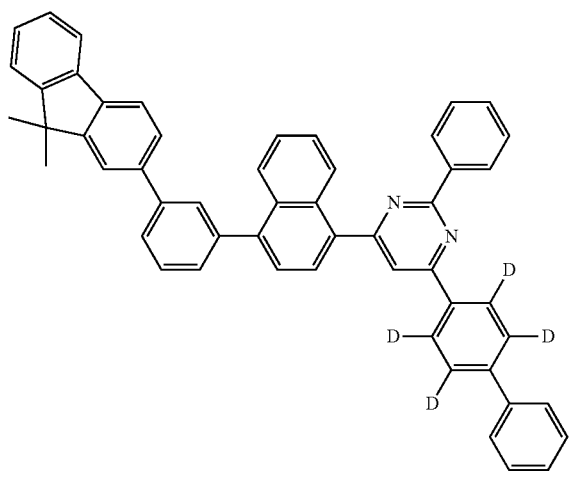
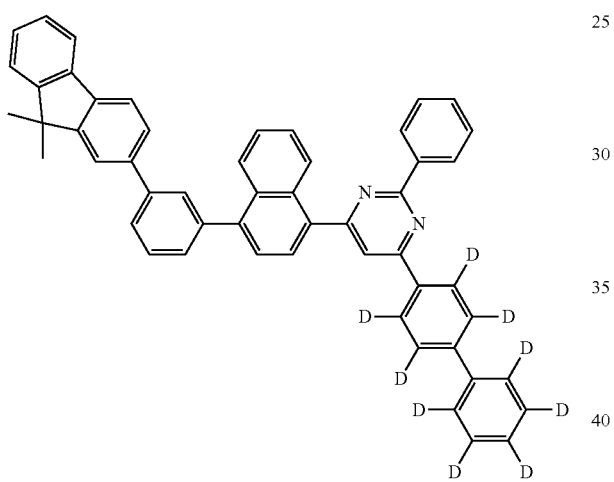
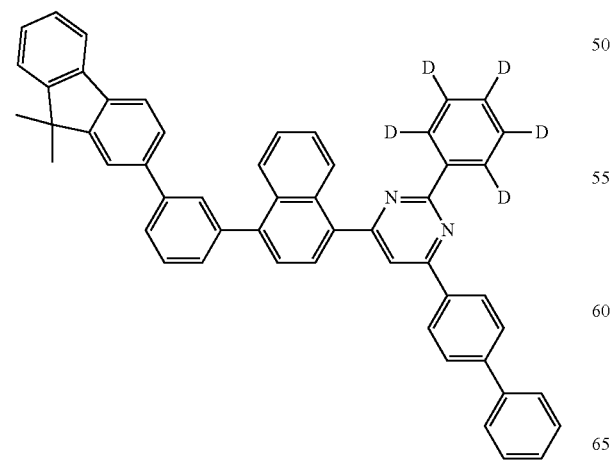
1172
-continued
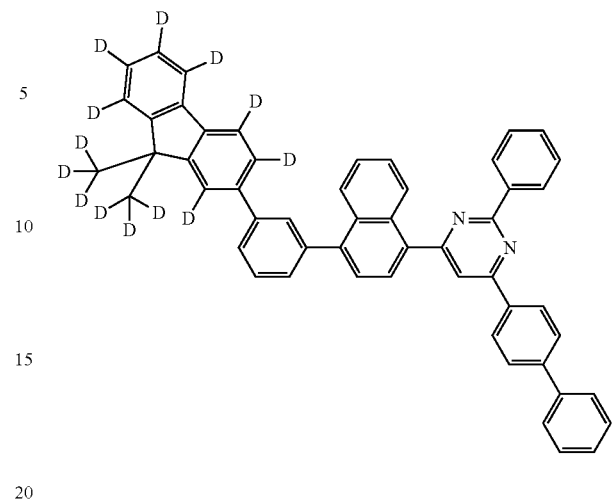
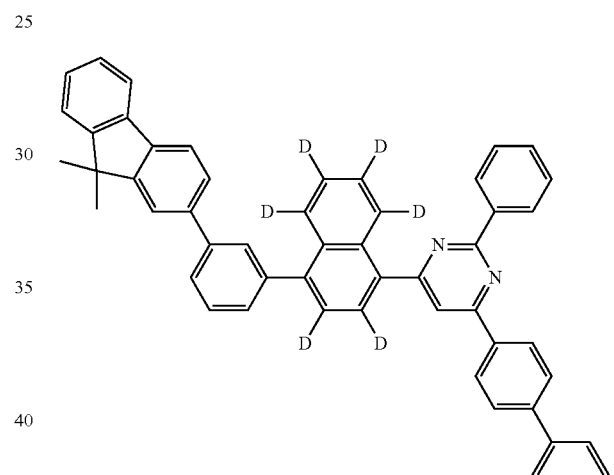
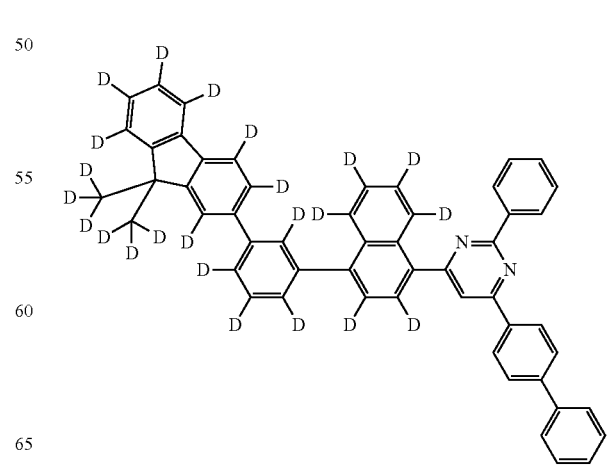

1173
-continued
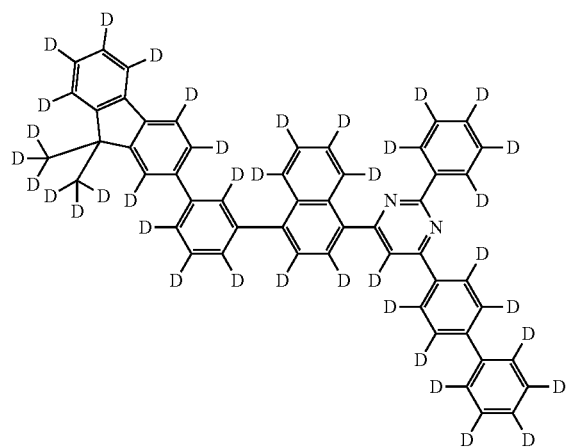
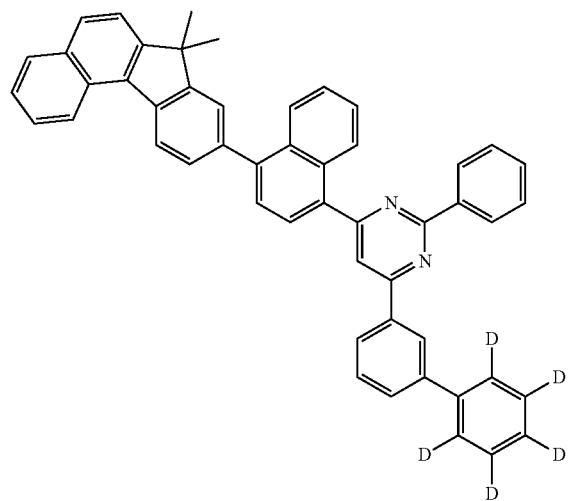
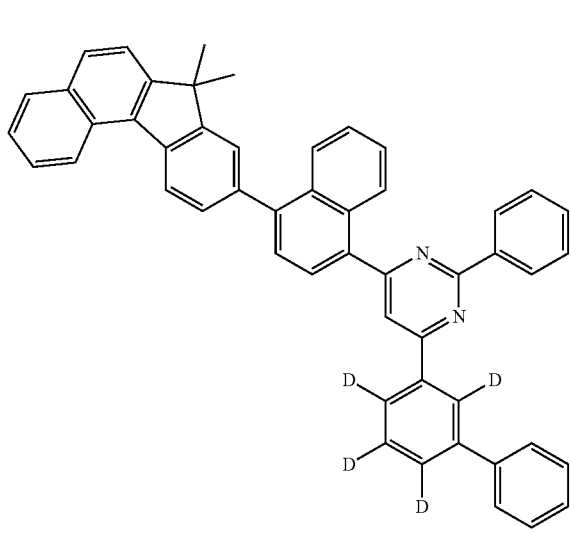
1174
-continued
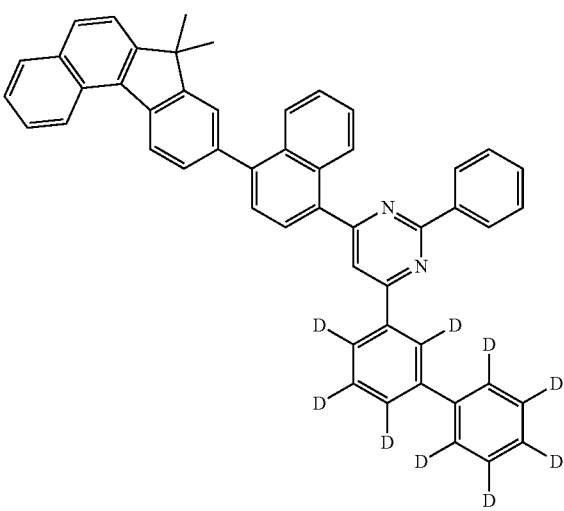
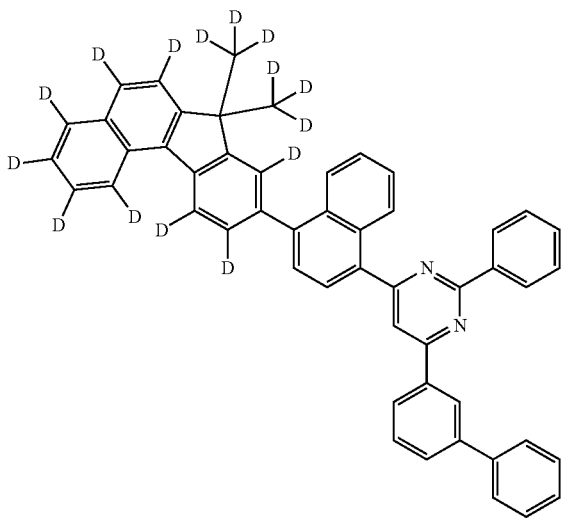

1175
-continued
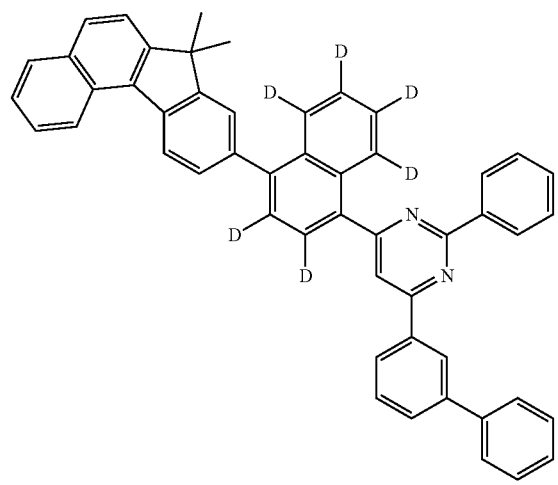
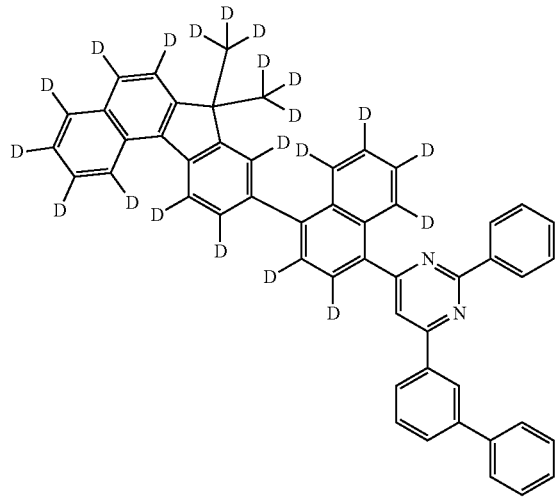
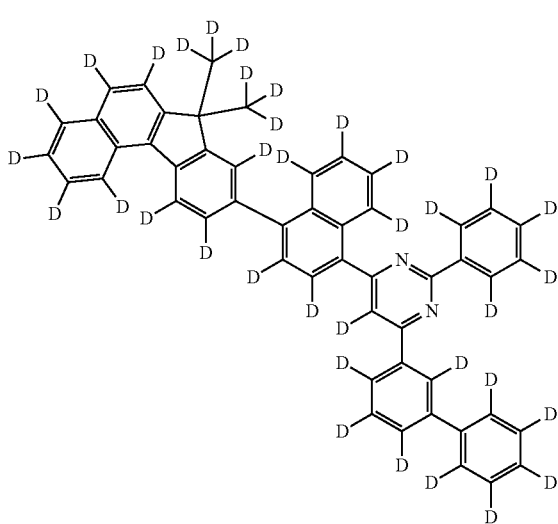
1176
-continued
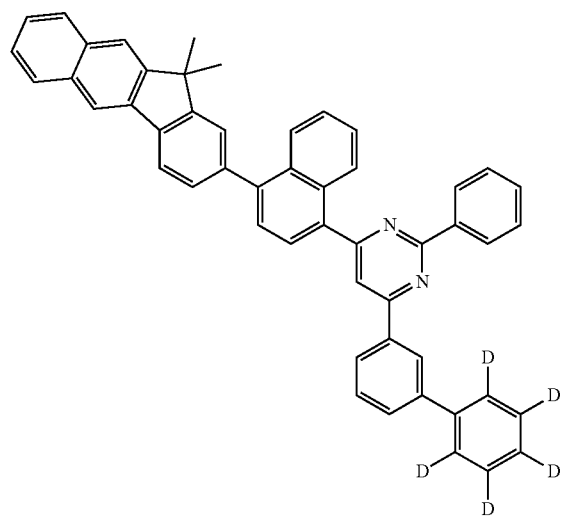
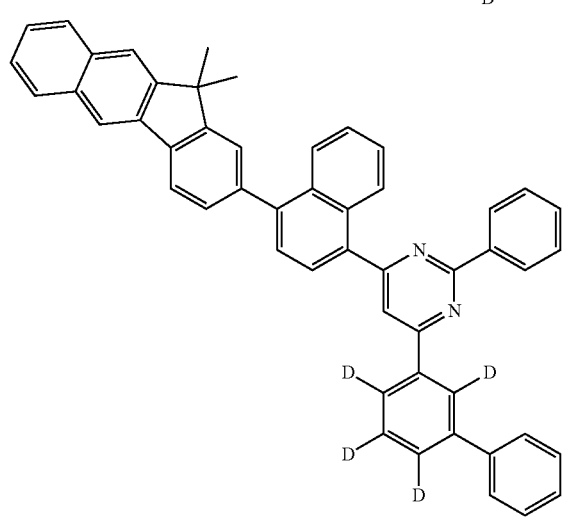

1177
-continued
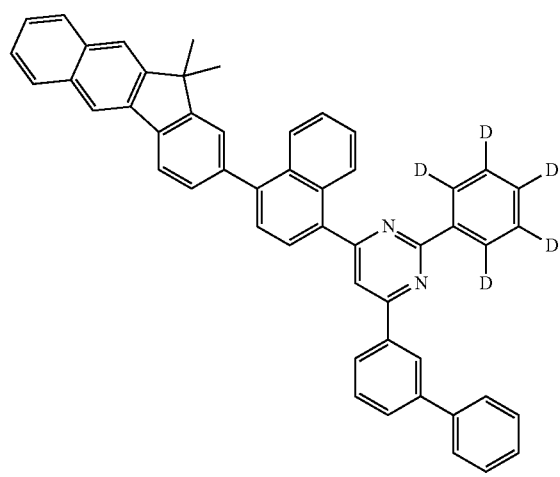
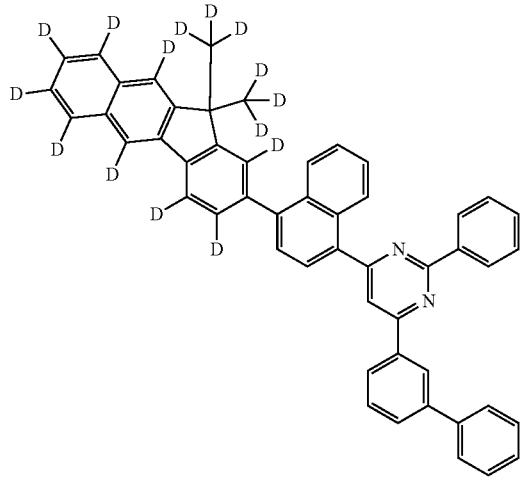
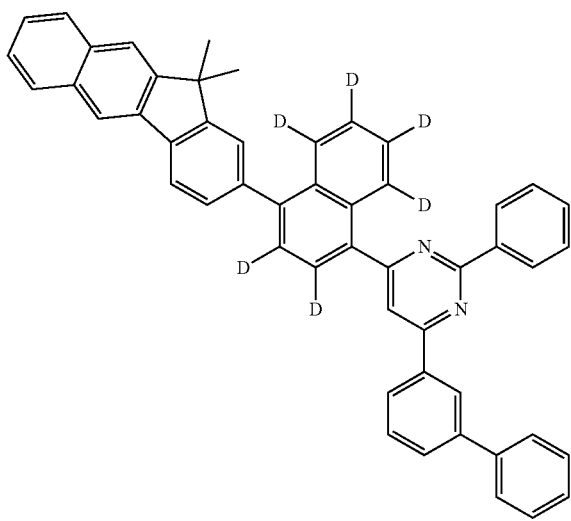
1178
-continued
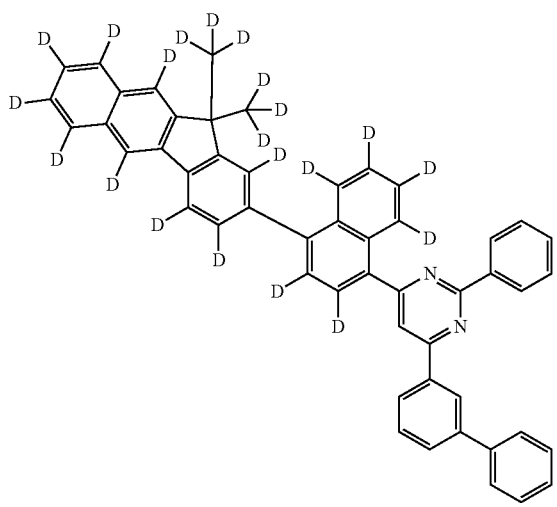
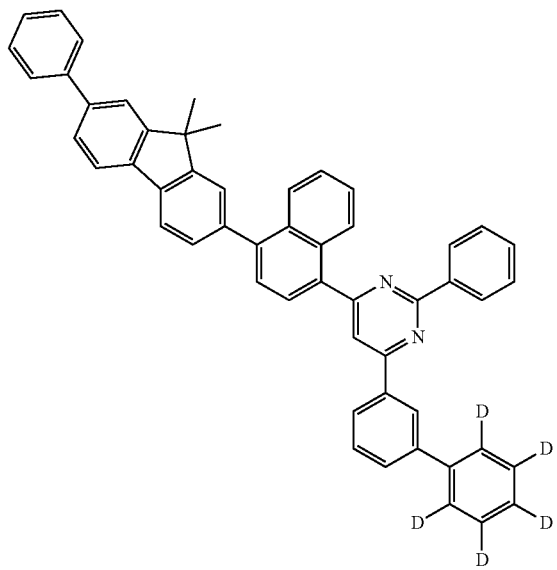

1179
-continued
1180
-continued
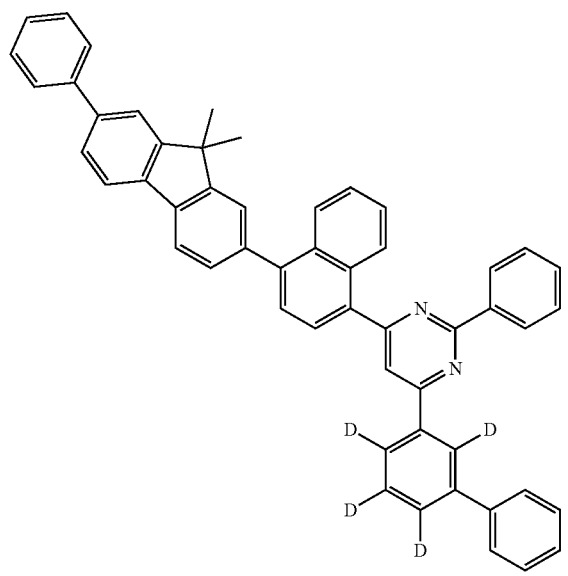
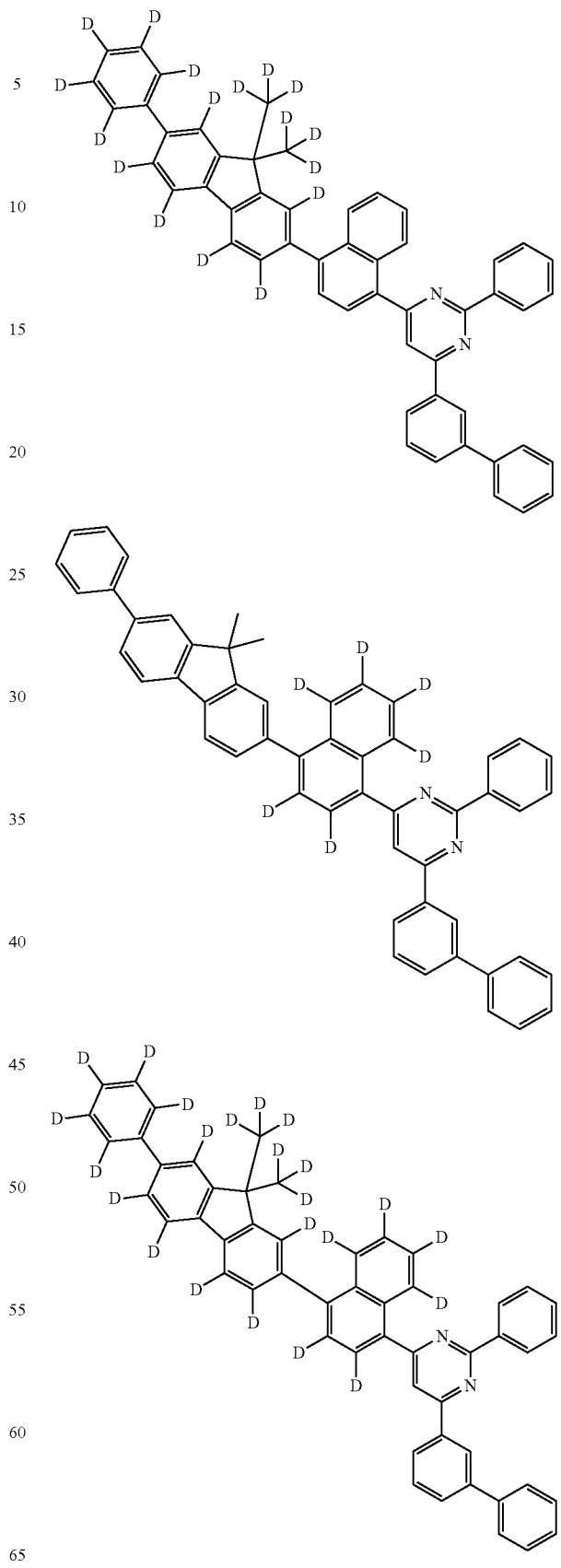

-continued

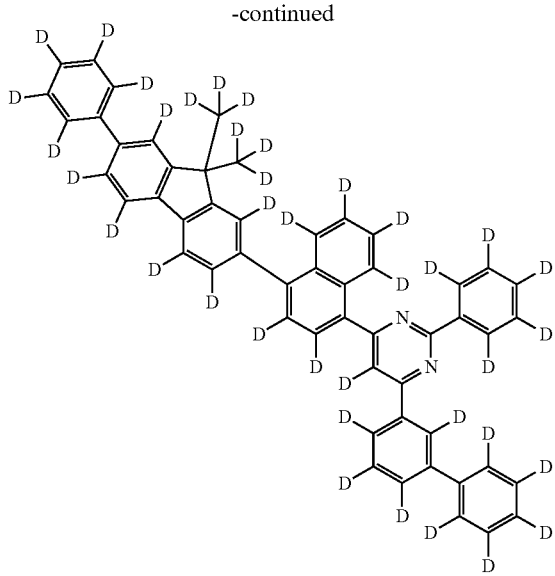

Material for Organic EL Device

The material for an organic EL device of the present invention contains the inventive compound. The content of the inventive compound in the material for an organic EL device of the present invention may be 1% by mass or more (including 100%), and is preferably 10% by mass or more (including 100%), more preferably 50% by mass or more (including 100%), further preferably 80% by mass or more (including 100%), and particularly preferably 90% by mass or more (including 100%). The material for an organic EL device of the present invention is useful for the production of an organic EL device.

Organic EL Device

The organic EL device of the present invention includes an anode, a cathode, and organic layers intervening between the anode and the cathode. The organic layers include a light emitting layer, and at least one layer of the organic layers contains the inventive compound.

Examples of the organic layer containing the inventive compound include a hole transporting zone (such as a hole injecting layer, a hole transporting layer, an electron blocking layer, and an exciton blocking layer) intervening between the anode and the light emitting layer, the light emitting layer, a space layer, and an electron transporting zone (such as an electron injecting layer, an electron transporting layer, and a hole blocking layer) intervening between the cathode and the light emitting layer, but are not limited thereto. The inventive compound is preferably used as a material for the electron transporting zone of a fluorescent or phosphorescent EL device, more preferably a material for the electron transporting layer or the hole blocking layer thereof, and particularly preferably a material for the first electron transporting layer, the second electron transporting layer, or the hole blocking layer thereof.

The organic EL device of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Above all, the fluorescent light emission-type device is preferred. The "light emitting unit" referred to herein refers to a minimum unit that emits light through recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

The light emitting unit may be a multilayer type having a plurality of phosphorescent light emitting layers or fluorescent light emitting layers. In this case, a space layer may intervene between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer/electron transporting layer (/electron injecting layer)

(b) (hole injecting layer/) hole transporting layer/phosphorescent light emitting layer/electron transporting layer (/electron injecting layer)

(c) (hole injecting layer/) hole transporting layer/first fluorescent light emitting layer/second fluorescent light emitting layer/electron transporting layer (/electron injecting layer)

(d) (hole injecting layer/) hole transporting layer/first phosphorescent light emitting layer/second phosphorescent light emitting layer/electron transporting layer (/electron injecting layer)

(e) (hole injecting layer/) hole transporting layer/phosphorescent light emitting layer/space layer/fluorescent light emitting layer/electron transporting layer (/electron injecting layer)

(f) (hole injecting layer/) hole transporting layer/first phosphorescent light emitting layer/second phosphorescent light emitting layer/space layer/fluorescent light emitting layer/electron transporting layer (/electron injecting layer)

(g) (hole injecting layer/) hole transporting layer/first phosphorescent light emitting layer/space layer/second phosphorescent light emitting layer/space layer/fluorescent light emitting layer/electron transporting layer (/electron injecting layer)

(h) (hole injecting layer/) hole transporting layer/phosphorescent light emitting layer/space layer/first fluorescent light emitting layer/second fluorescent light emitting layer/electron transporting layer (/electron injecting layer)

(i) (hole injecting layer/) hole transporting layer/electron blocking layer/fluorescent light emitting layer/electron transporting layer (/electron injecting layer)

(j) (hole injecting layer/) hole transporting layer/electron blocking layer/phosphorescent light emitting layer/ electron transporting layer (/electron injecting layer)

(k) (hole injecting layer/) hole transporting layer/exciton blocking layer/fluorescent light emitting layer/electron transporting layer (/electron injecting layer)

(l) (hole injecting layer/) hole transporting layer/exciton blocking layer/phosphorescent light emitting layer/ electron transporting layer (/electron injecting layer)

(m) (hole injecting layer/) first hole transporting layer/ second hole transporting layer/fluorescent light emitting layer/electron transporting layer (/electron injecting layer)

(n) (hole injecting layer/) first hole transporting layer/second hole transporting layer/phosphorescent light emitting layer/electron transporting layer (/electron injecting layer)
(o) (hole injecting layer/) first hole transporting layer/second hole transporting layer/fluorescent light emitting layer/first electron transporting layer/second electron transporting layer (/electron injecting layer)
(p) (hole injecting layer/) first hole transporting layer/second hole transporting layer/phosphorescent light emitting layer/first electron transporting layer/second electron transporting layer (/electron injecting layer)
(q) (hole injecting layer/) hole transporting layer/fluorescent light emitting layer/hole blocking layer/electron transporting layer (/electron injecting layer)
(r) (hole injecting layer/) hole transporting layer/phosphorescent light emitting layer/hole blocking layer/electron transporting layer (/electron injecting layer)
(s) (hole injecting layer/) hole transporting layer/fluorescent light emitting layer/exciton blocking layer/electron transporting layer (/electron injecting layer)
(t) (hole injecting layer/) hole transporting layer/phosphorescent light emitting layer/exciton blocking layer/electron transporting layer (/electron injecting layer)

The phosphorescent and fluorescent light emitting layers may emit emission colors different from each other, respectively. Specifically, in the light emitting unit (f), a layer configuration, such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer, may be exemplified.

An electron blocking layer may be properly provided between each light emitting layer and the hole transporting layer or the space layer. A hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.
(2) Anode/First Light Emitting Unit/Intermediate Layer/Second Light Emitting Unit/Cathode For example, each of the first light emitting unit and the second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration can be used, in which electrons are supplied to the first light emitting unit, and holes are supplied to the second light emitting unit.

FIG. 1 is a schematic illustration showing an example of the configuration of the organic EL device of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (such as a hole injecting layer and a hole transporting layer) is provided between the light emitting layer 5 and the anode 3, and an electron transporting zone 7 (such as an electron injecting layer and an electron transporting layer) is provided between the light emitting layer 5 and the cathode 4. In addition, an electron blocking layer (which is not shown in the figure) may be provided on the side of the anode 3 of the light emitting layer 5, and a hole blocking layer (which is not shown in the figure) may be provided on the side of the cathode 4 of the light emitting layer 5. According to the configuration, electrons and holes are trapped in the light emitting layer 5, thereby enabling one to further increase the production efficiency of excitons in the light emitting layer 5.

Figure 2:
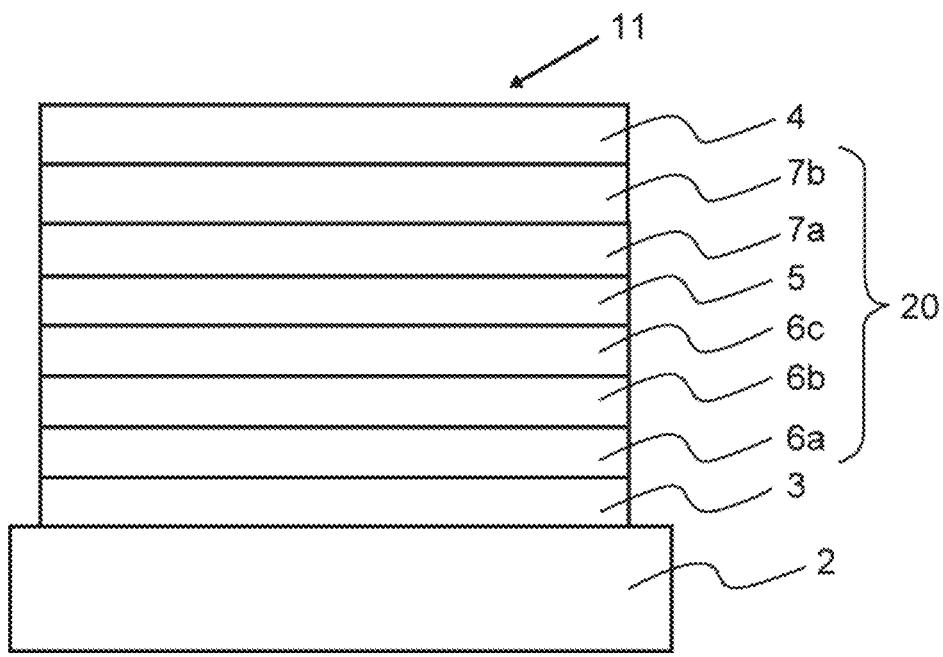
FIG. 2 is a schematic illustration showing another example of the layer configuration of the organic EL device according to one embodiment of the present invention.

FIG. 2 is a schematic illustration showing another configuration of the organic EL device of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone disposed between the anode 3 and the light emitting layer 5 includes a hole injection layer 6a, a first hole transporting layer 6b, and a second hole transporting layer 6c. An electron transporting zone disposed between the light emitting layer 5 and the cathode 4 includes a first electron transporting layer 7a and a second electron transporting layer 7b.

In the present invention, a host combined with a fluorescent dopant material (a fluorescent emitting material) is referred to as a fluorescent host, and a host combined with a phosphorescent dopant material is referred to as a phosphorescent host. The fluorescent host and the phosphorescent host are not distinguished from each other merely by the molecular structures thereof. Specifically, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. In addition, a flexible substrate may be used. Examples of the flexible substrate include a plastic substrate made of polycarbonate, polyarylate, polyether sulfone, polypropylene, polyester, polyvinyl fluoride, or polyvinyl chloride. In addition, an inorganic vapor deposition film can be used.

Anode

It is preferred that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, examples there include gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride).

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, or the like.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals, such as lithium (Li) and cesium (Cs), alkaline earth metals, such as magnesium (Mg), calcium (Ca), and strontium (Sr), and alloys containing these (such as MgAg and AlLi), and rare earth metals, such as europium (Eu), and ytterbium (Yb) and alloys containing these. When the anode is formed by using the alkali metals, the alkaline earth metals, and alloys containing these, a vacuum vapor deposition method or a sputtering method can be used. Further, when a silver paste or the like is used, a coating method, an inkjet method, or the like can be used.

Hole Injecting Layer

The hole injecting layer is a layer containing a material having a high hole injection capability (a hole injecting material) and is provided between the anode and the light emitting layer, or between the hole transporting layer, if exists, and the anode.

Examples of the hole injecting material other than the inventive compound include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Examples of the hole injecting layer material also include aromatic amine compounds as low-molecular weight organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High-molecular weight compounds (such as oligomers, dendrimers, and polymers) may also be used. Examples thereof include high-molecular weight compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). In addition, high-molecular weight compounds to which an acid is added, such as poly(3,4-ethylenedioxythiophene)/poly (styrene sulfonic acid) (PEDOT/PSS), and polyaniline/poly (styrenesulfonic acid) (PAni/PSS), can also be used.

Furthermore, it is also preferred to use an acceptor material, such as a hexaazatriphenylene (HAT) compound represented by formula (K).

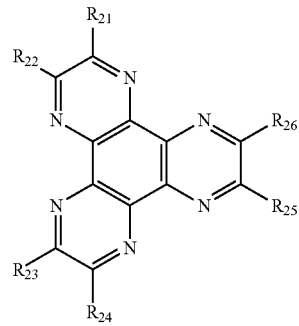

(K)

In the aforementioned formula, $R_{21}$ to $R_{26}$ each independently represent a cyano group, —$CONH_2$, a carboxy group, or —$COOR_{27}$ ($R_{27}$ represents an alkyl group having 1 to 20 carbon atoms or a cycloalkyl group having 3 to 20 carbon atoms). In addition, adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting capability (a hole transporting material) and is provided between the anode and the light emitting layer, or between the hole injecting layer, if exists, and the light emitting layer.

The hole transporting layer may have a single layer structure or a multilayer structure including two or more layers. For example, the hole transporting layer may have a two-layer structure including a first hole transporting layer (anode side) and a second hole transporting layer (cathode side). In one embodiment of the present invention, the hole transporting layer having a single layer structure is preferably disposed adjacent to the light emitting layer, and the hole transporting layer that is closest to the cathode in the multilayer structure, such as the second hole transporting layer in the two-layer structure, is preferably disposed adjacent to the light emitting layer. In another embodiment of the present invention, an electron blocking layer described later and the like may be disposed between the hole transporting layer having a single layer structure and the light emitting layer, or between the hole transporting layer that is closest to the light emitting layer in the multilayer structure and the light emitting layer.

As the hole transporting material, for example, an aromatic amine compound, a carbazole derivative, an anthracene derivative, and the like can be used.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The aforementioned compounds have a hole mobility of $10^{-6}$ cm$^2$/Vs or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High-molecular weight compounds, such as poly(N-vinylcarbazole) (abbreviation: PVK) and poly(4-vinyltriphenylamine) (abbreviation: PVTPA), can also be used.

However, compounds other than those as mentioned above can also be used so long as they are compounds high in the hole transporting capability rather than in the electron transporting capability.

Dopant Material of Light Emitting Layer

The light emitting layer is a layer containing a material having a high light emitting property (a dopant material), and various materials can be used. For example, a fluorescent emitting material or a phosphorescent emitting material can be used as the dopant material. The fluorescent emitting material is a compound that emits light from a singlet excited state, and the phosphorescent emitting material is a compound that emits from a light triplet excited state.

Examples of a blue-based fluorescent emitting material that can be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that can be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

Examples of a red-based fluorescent emitting material that can be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In one embodiment of the present invention, the light emitting layer preferably contains a fluorescent light emitting material (a fluorescent dopant material).

Examples of a blue-based phosphorescent emitting material that can be used for the light emitting layer include a metal complex, such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIrac).

Examples of a green-based phosphorescent emitting material that can be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that can be used for the light emitting layer include a metal complex, such as an iridium complex, a platinum complex, a terbium complex, and a europium complex. Specific examples thereof include organic metal complexes, such as bis[2-(2'-benzo[4,5-α]thienyl)pyridinato-N,C3']iridium(III)acetylacetonate (abbreviation: Ir(btp)2(acac)), bis(1-phenylisoquinolinato-N,C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Rare earth metal complexes, such as tris(acetylacetonate)(monophenanthroline)terbium(III) (abbreviation: Tb(acac)3(Phen)), tris(1,3-diphenyl-1,3-propanedionato)(monophenanthroline)europium(III) (abbreviation: Eu(DBM)3(Phen)), and tris[1-(2-thenoyl)-3,3,3-trifluoroacetonate](monophenanthroline)europium(III) (abbreviation: Eu(TTA)3(Phen)), emit light from rare earth metal ions (electron transition between different multiplicities), and thus may be used as the phosphorescent emitting material.

In one embodiment of the present invention, the light emitting layer preferably contains a phosphorescent light emitting material (a phosphorescent dopant material).

Host Material of Light Emitting Layer

The light emitting layer may have a configuration in which the aforementioned dopant material is dispersed in another material (a host material). The host material is preferably a material that has a higher lowest unoccupied orbital level (LUMO level) and a lower highest occupied orbital level (HOMO level) than the dopant material.

Examples of the Host Material Include:
  (1) a metal complex, such as an aluminum complex, a beryllium complex, and a zinc complex,
  (2) a heterocyclic compound, such as an oxadiazole derivative, a benzimidazole derivative, and a phenanthroline derivative,
  (3) a fused aromatic compound, such as a carbazole derivative, an anthracene derivative, a phenanthrene derivative, a pyrene derivative, and a chrysene derivative, or
  (4) an aromatic amine compound, such as a triarylamine derivative and a fused polycyclic aromatic amine derivative.

For Example, metal complexes, such as tris(8-quinolinolato)aluminum (III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ);

heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), and bathophenanthroline (abbreviation: BPhen), bathocuproine (abbreviation: BCP);

fused aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds, such as N,N-diphenyl-9-[4-(10-phenyl-9-anthryl)phenyl]-9H-carbazole-3-amine (abbreviation: CzA1PA), 4-(10-phenyl-9-anthry)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluorene-2-yl)-N-phenylamino]biphenyl (abbreviation: DFLDPBi), and 4,4'-bis[N-(spiro-9,9'-bifluorene-2-yl)-N-phenylamino]biphenyl (abbreviation: BSPB) can be used. A plurality of host materials may be used.

In particular, in the case of a blue fluorescent device, it is preferred to use the following anthracene compounds as the host material.

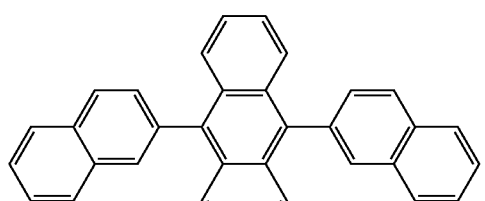

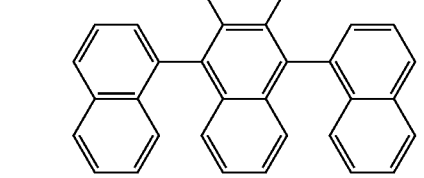

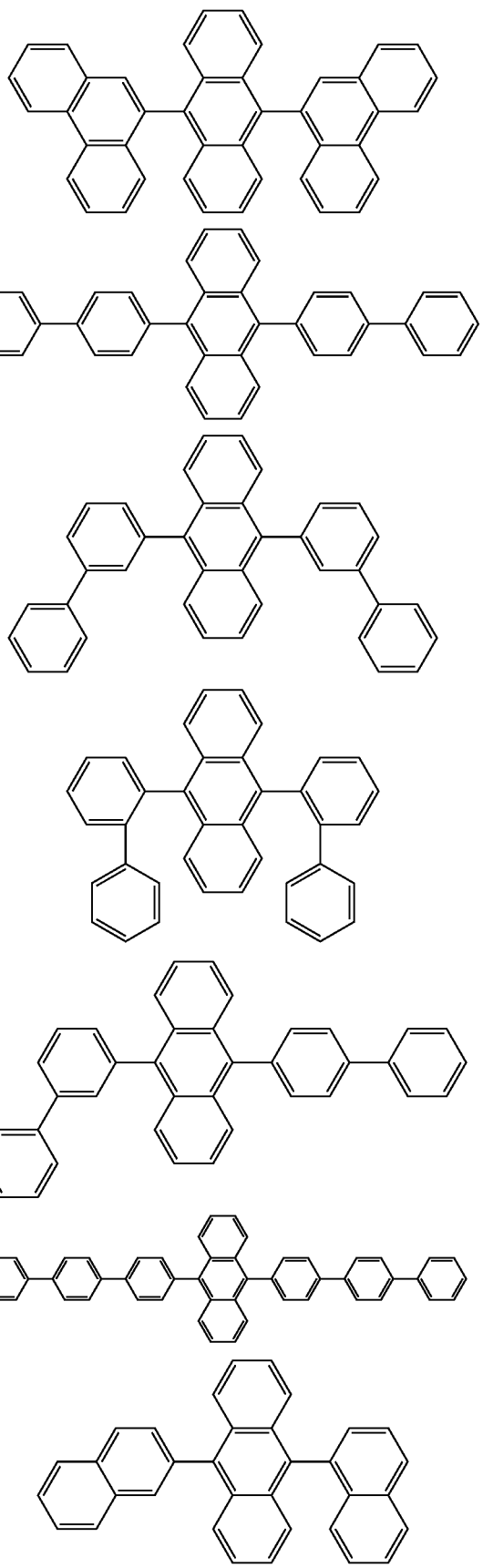

1191
-continued
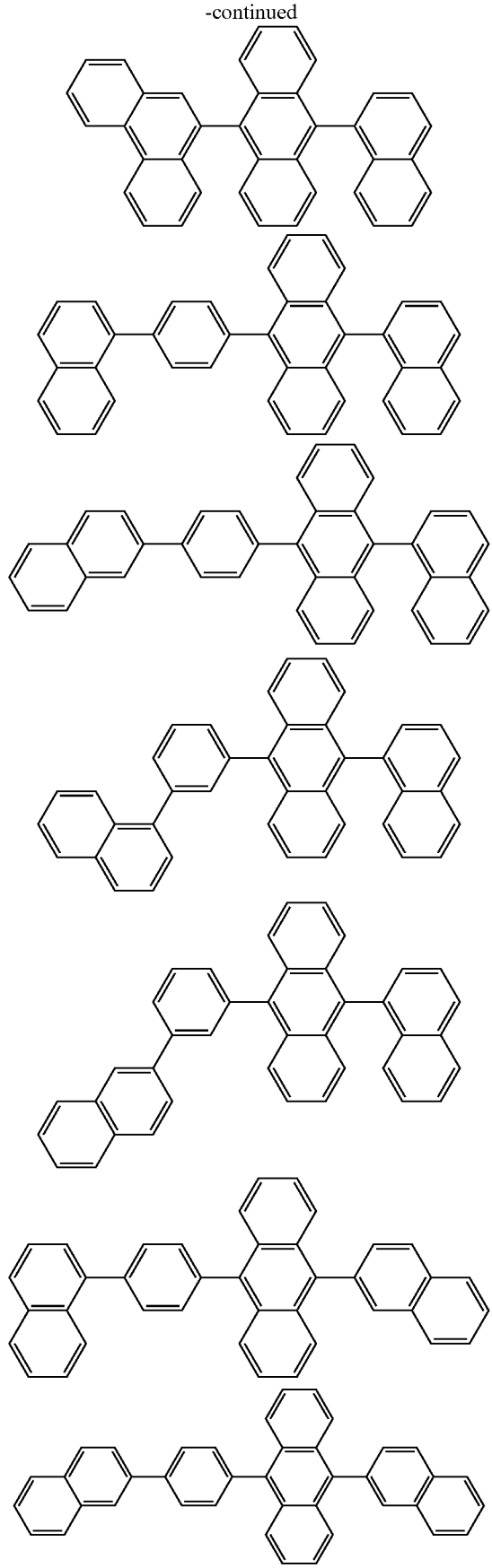
1192
-continued
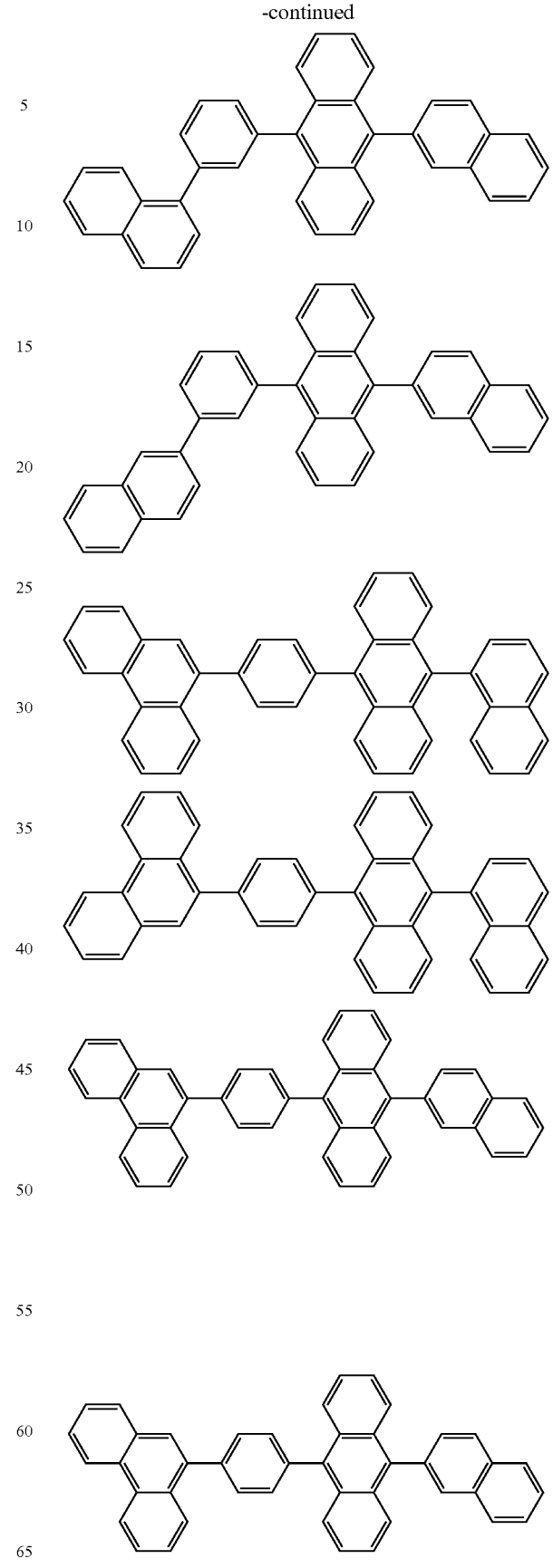

1193
-continued
1194
-continued
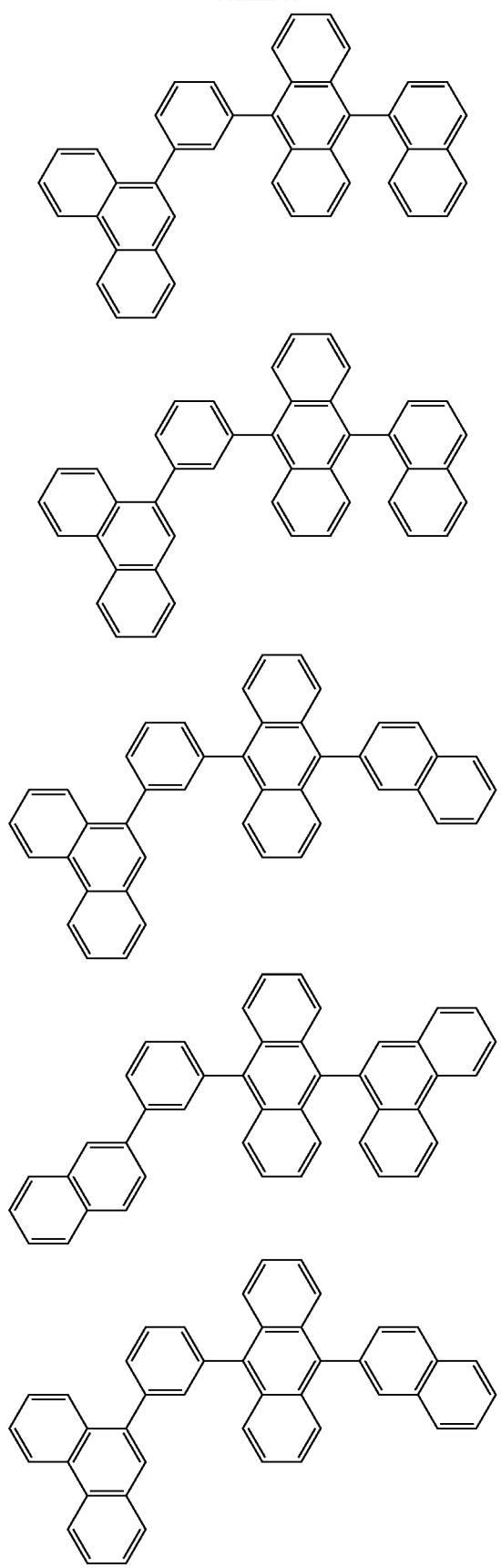
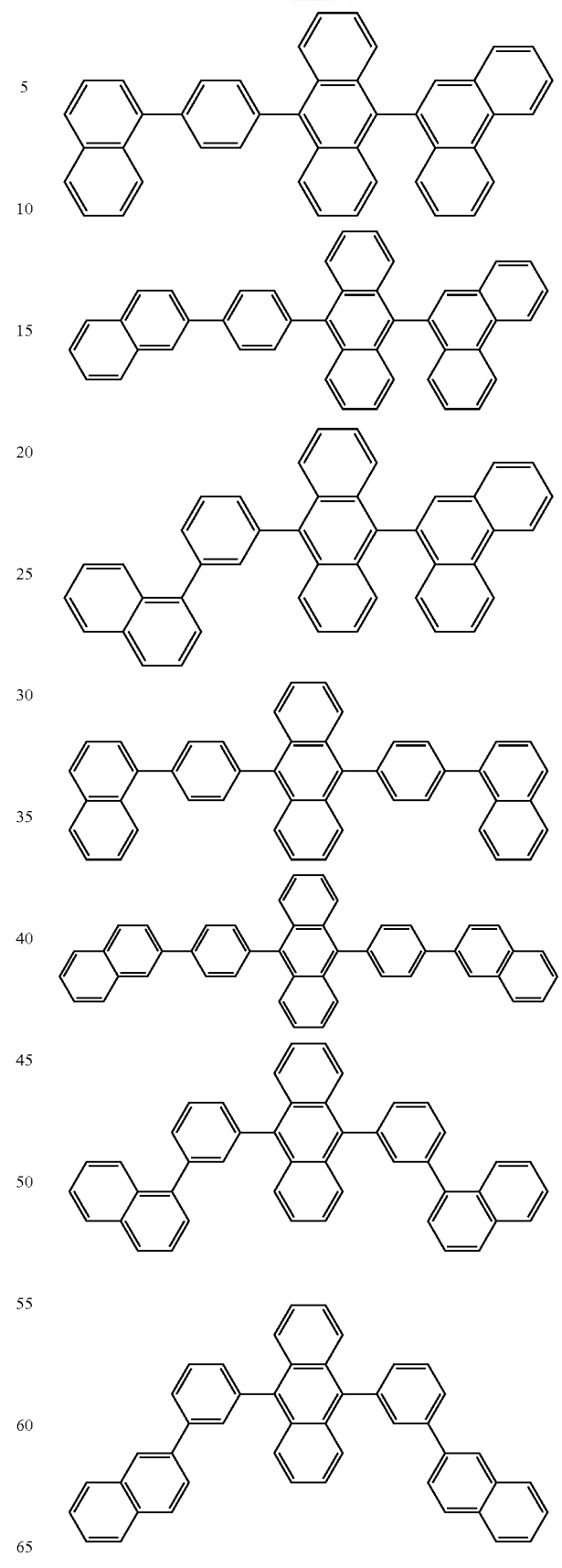

1195
-continued
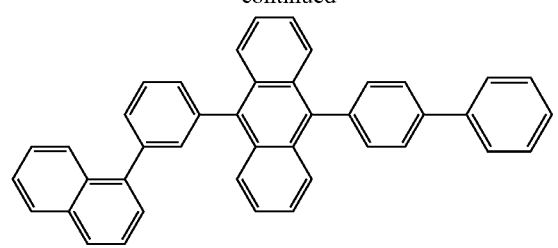
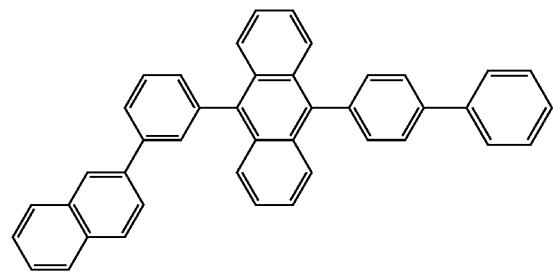
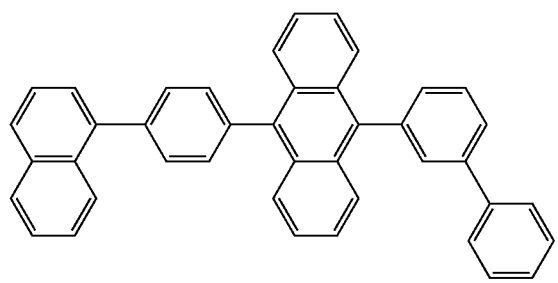
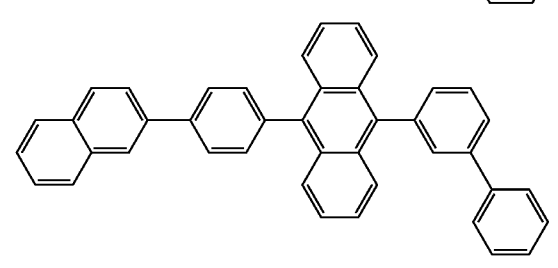
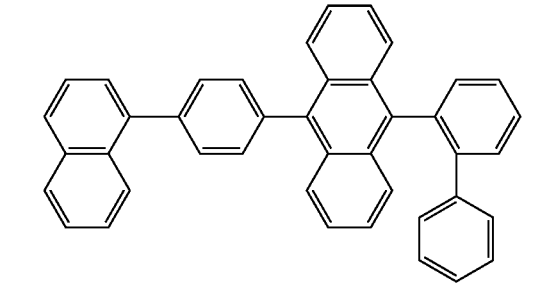
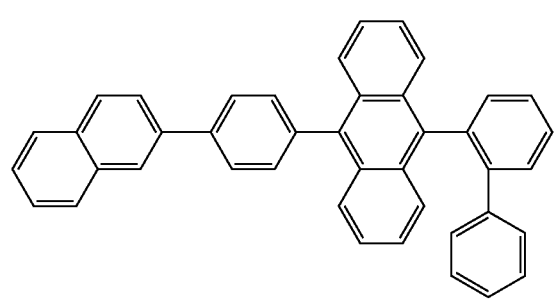
1196
-continued
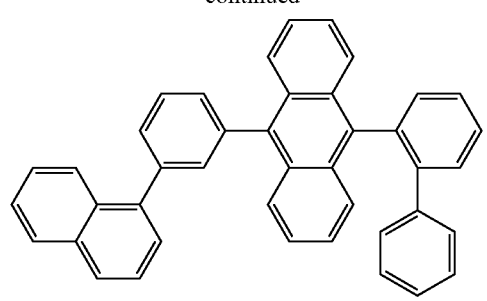
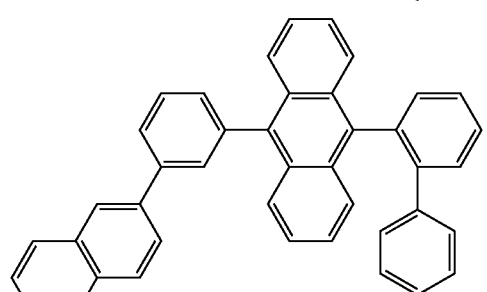
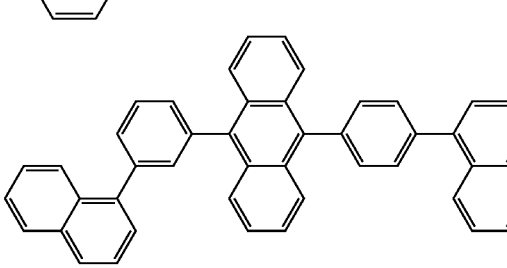
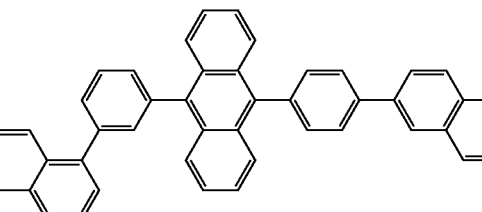
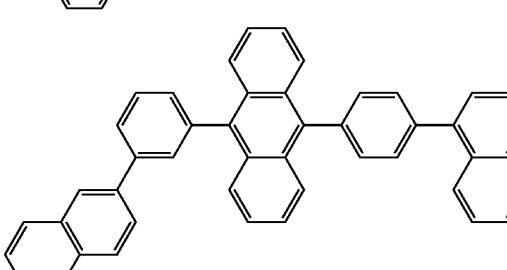
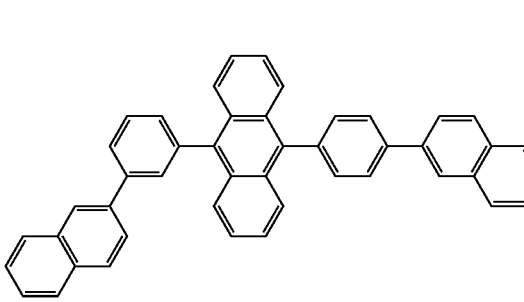

1197
-continued
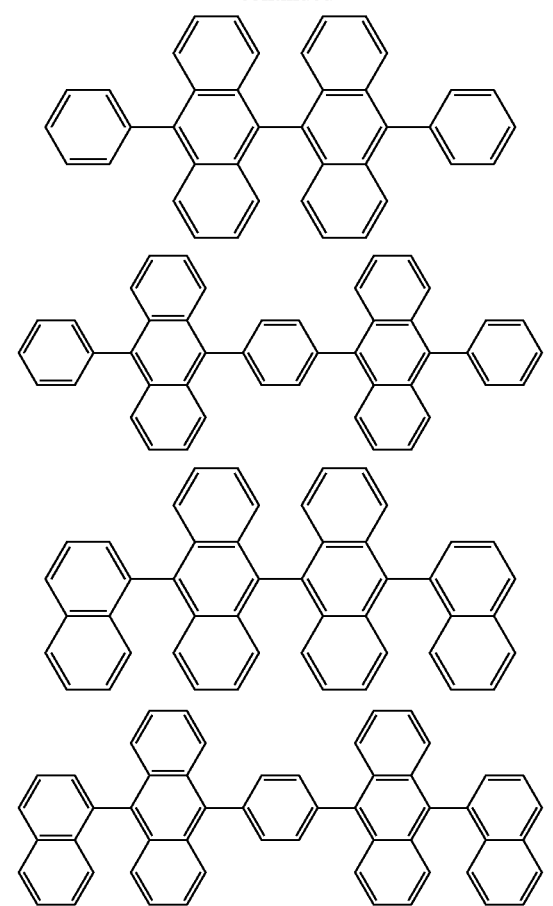
1198
-continued
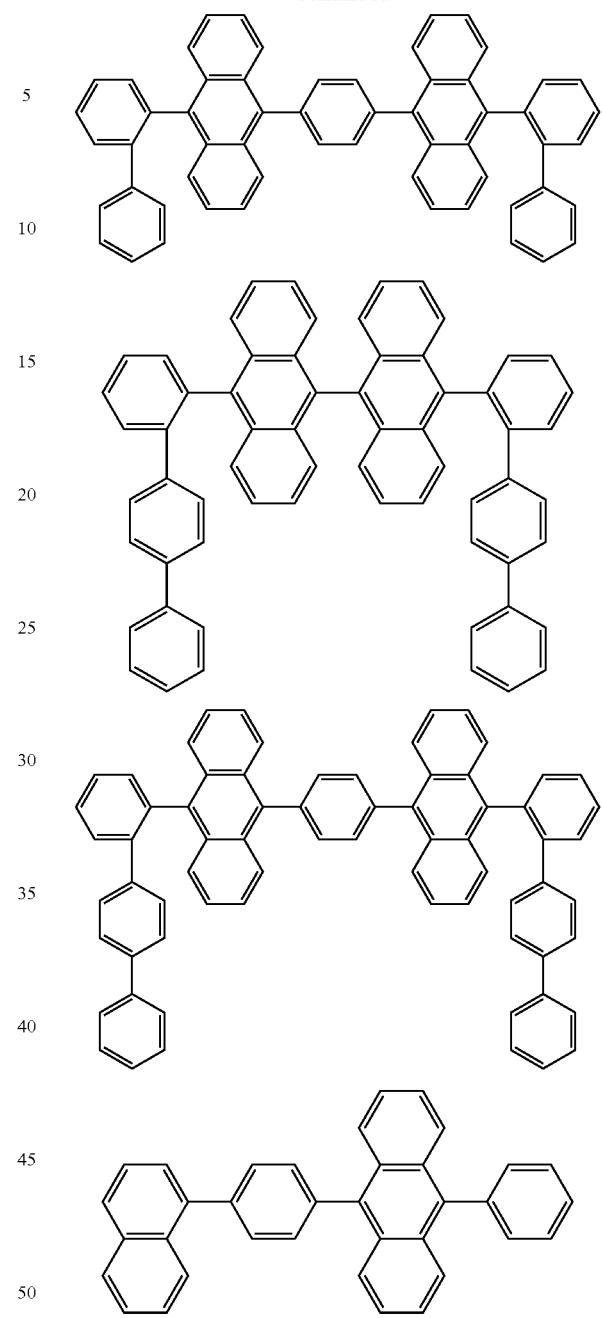
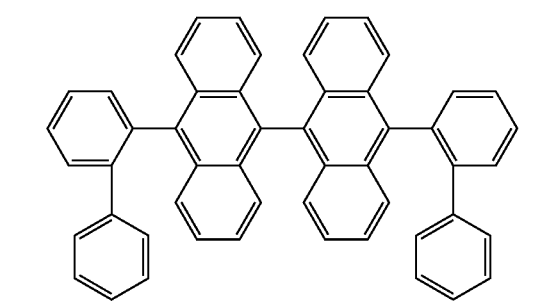
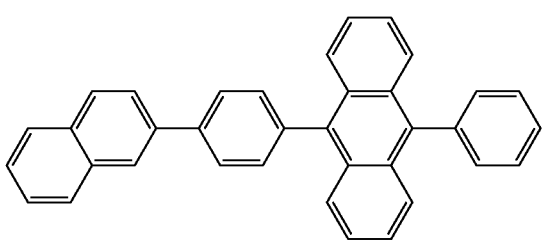

1199
-continued
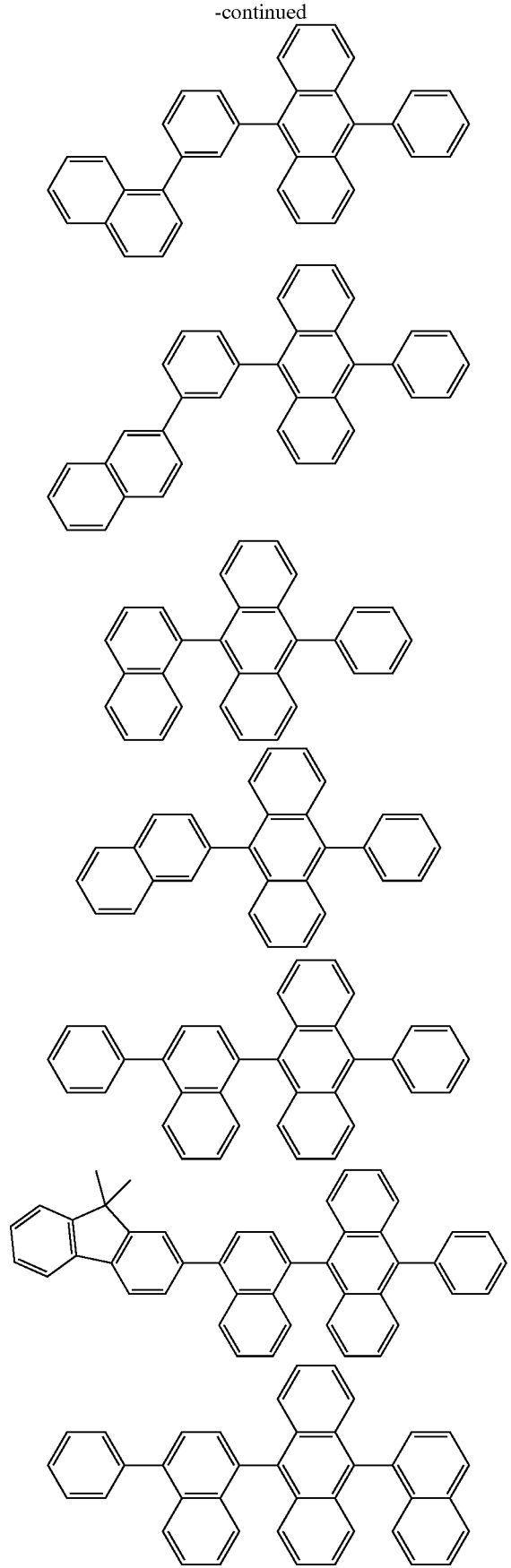
1200
-continued
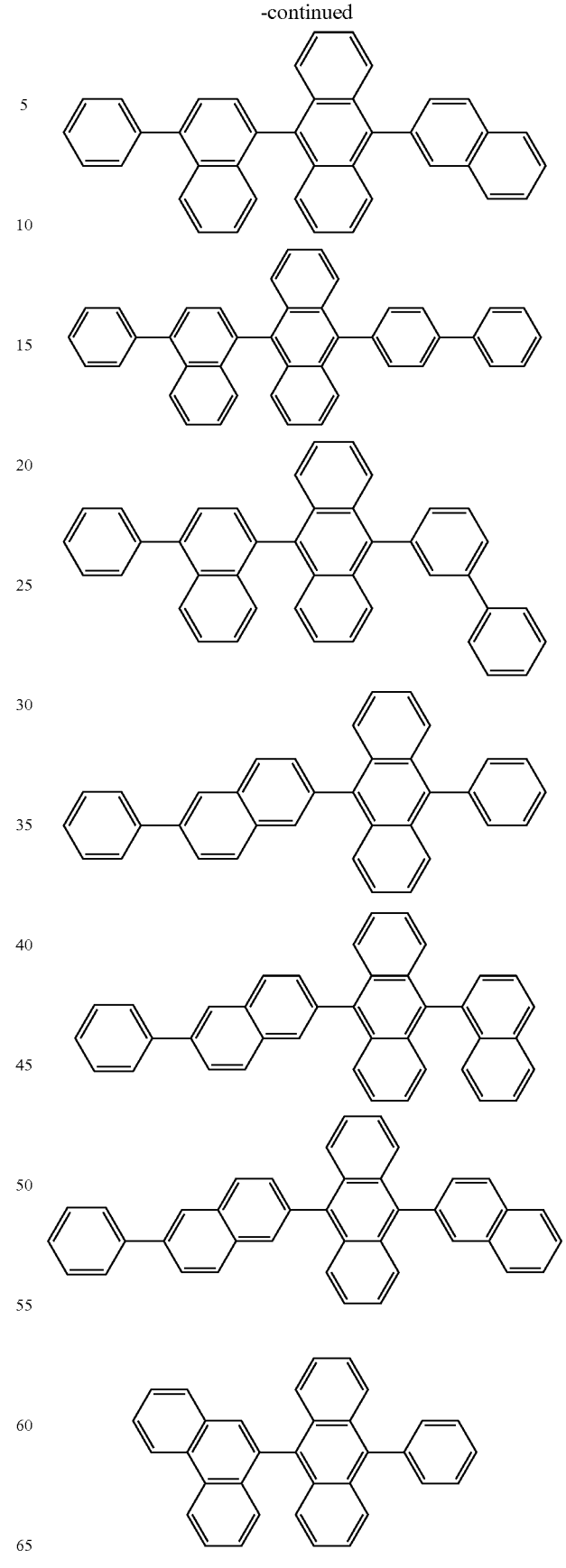

1201
-continued
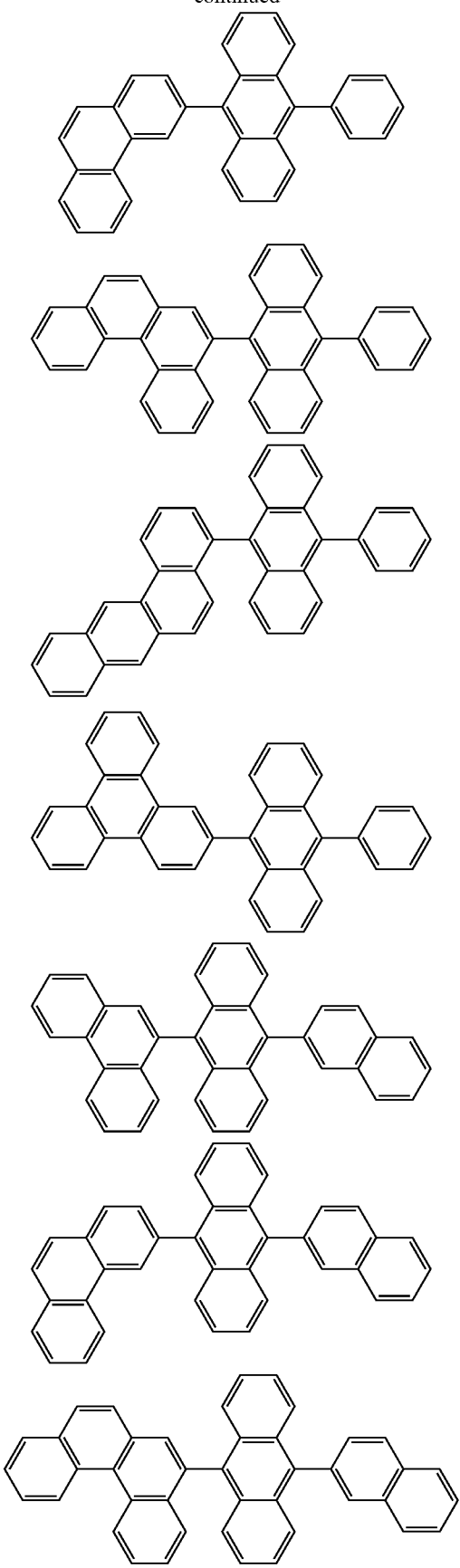
1202
-continued
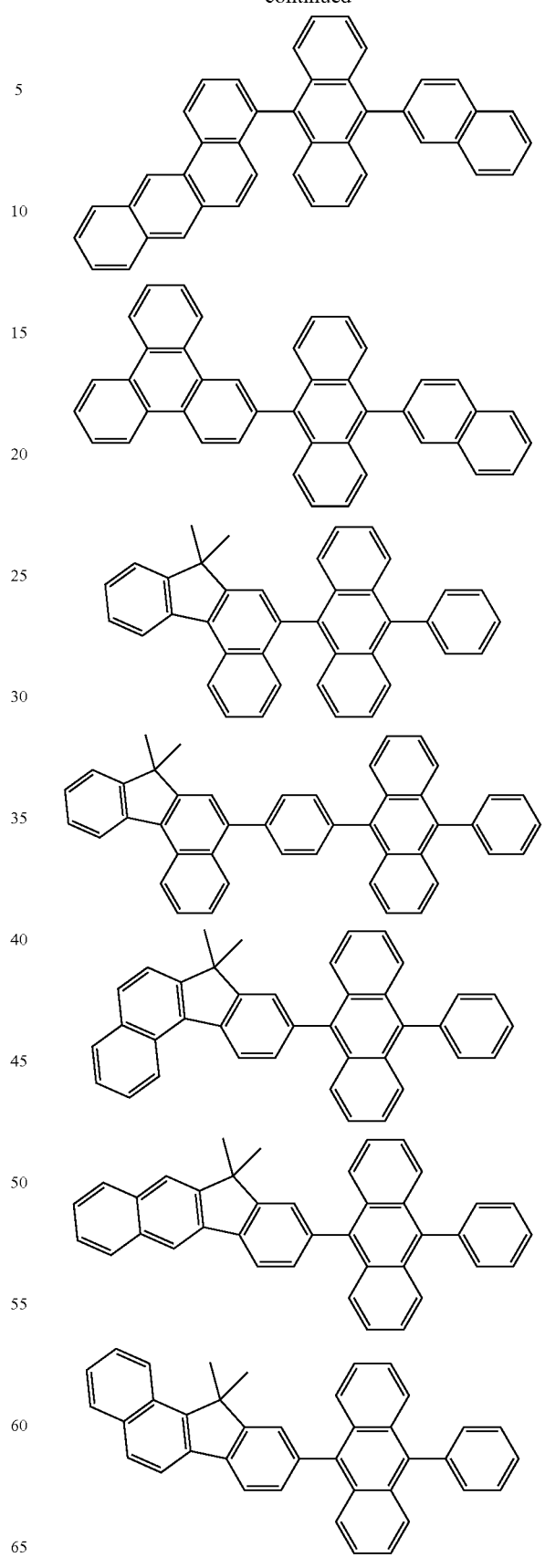

1203
-continued
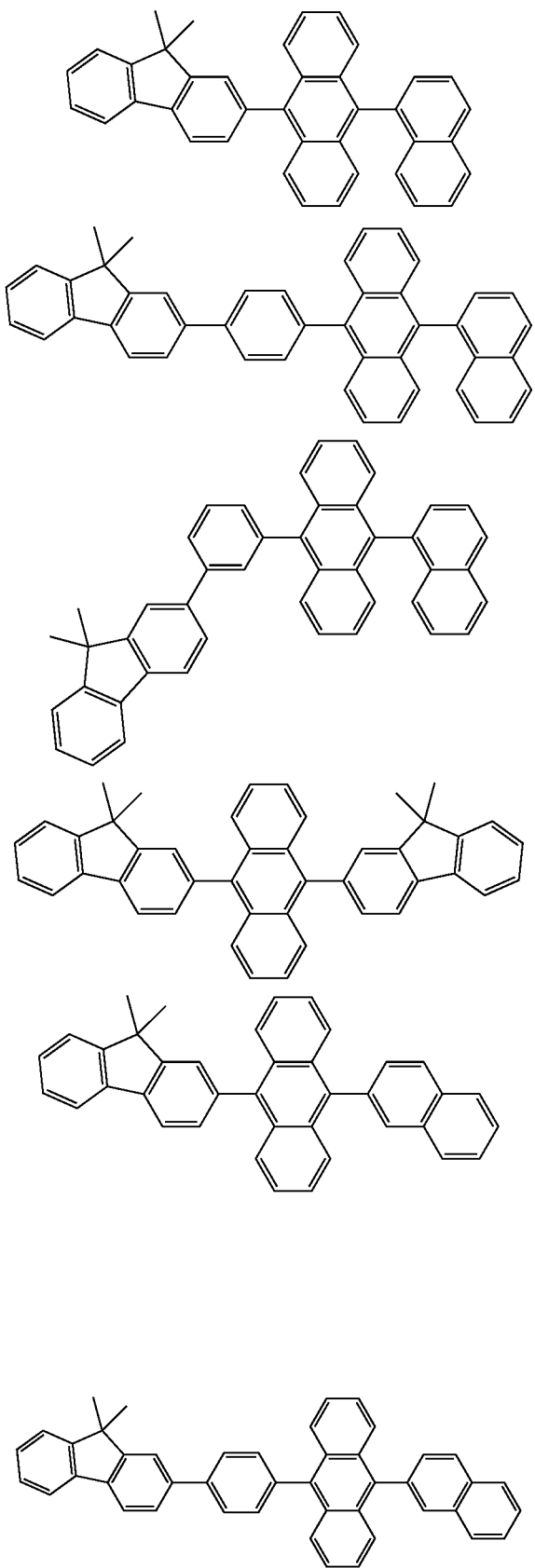
1204
-continued
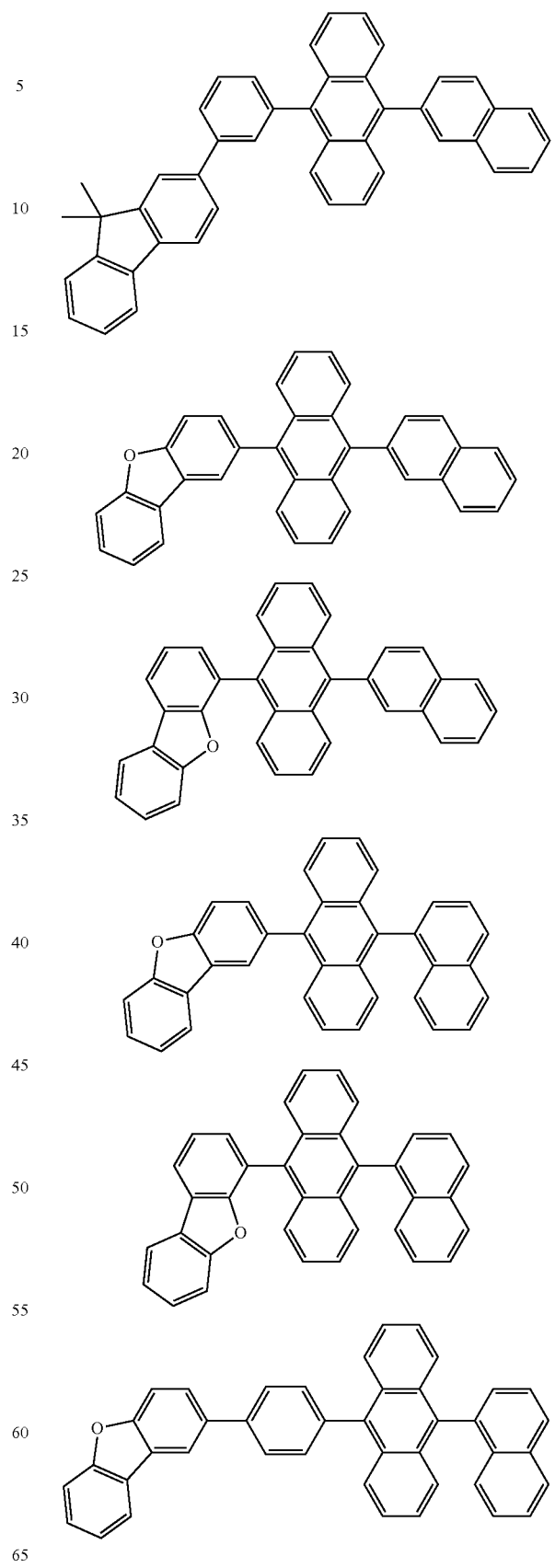

1205
-continued
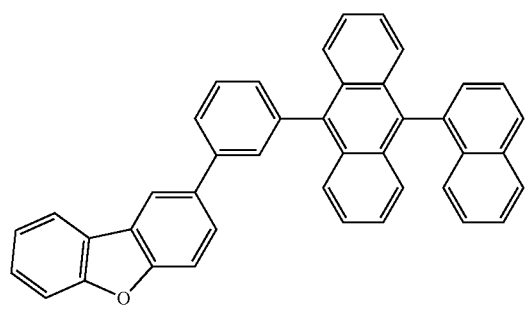
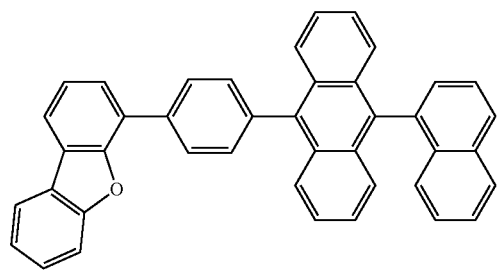
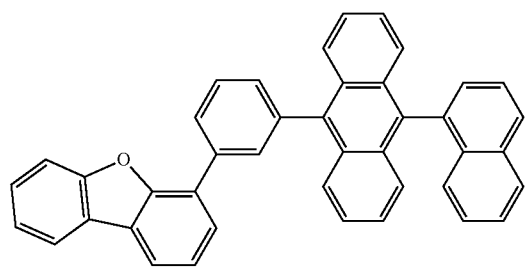
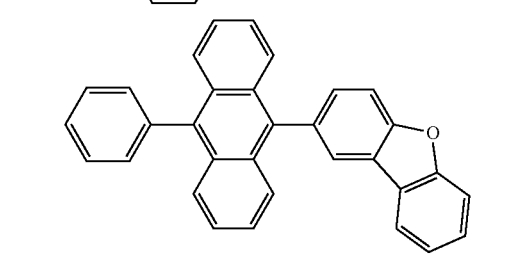
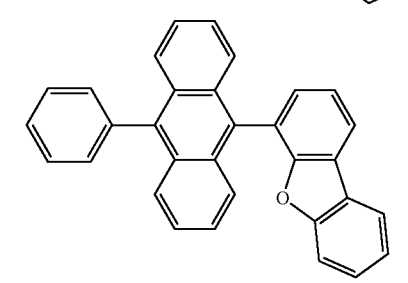
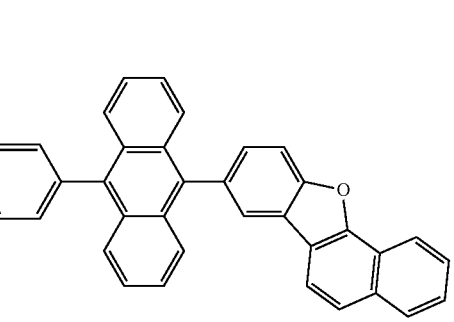
1206
-continued
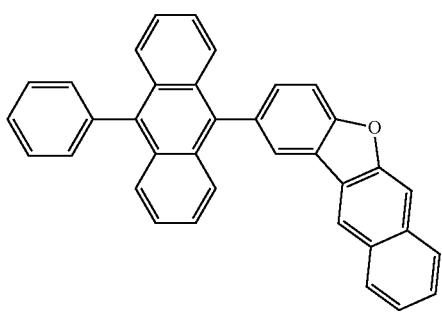
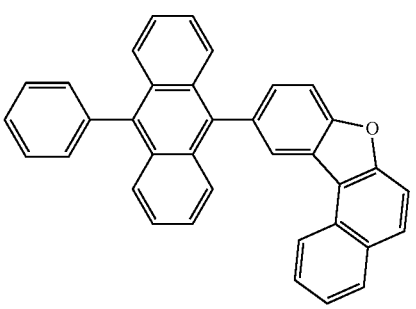
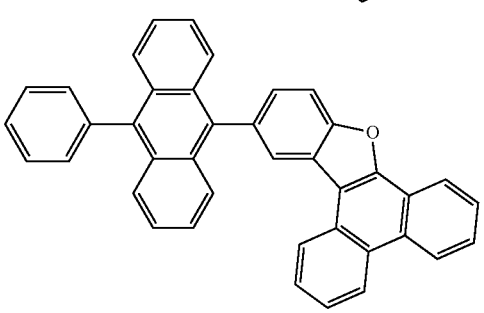
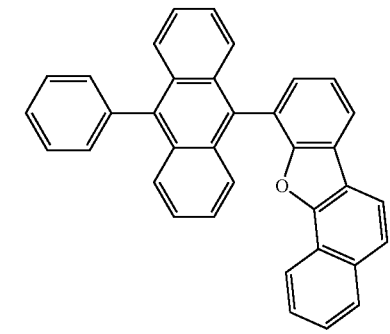
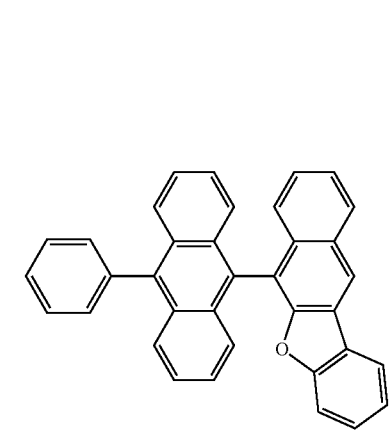

1207
-continued
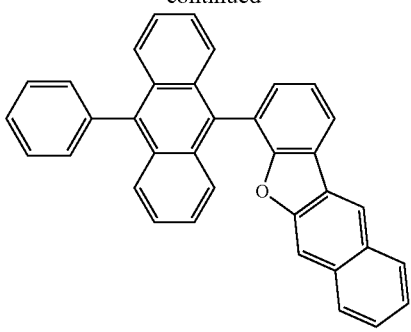
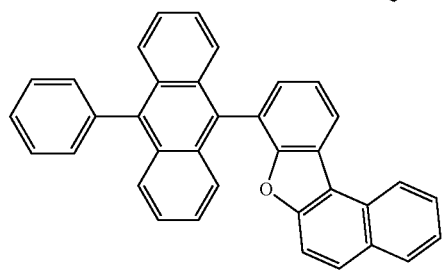
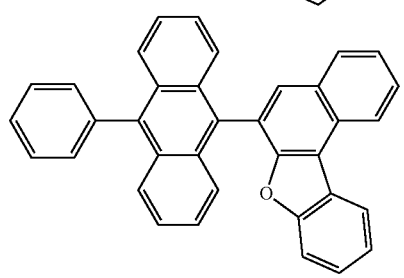
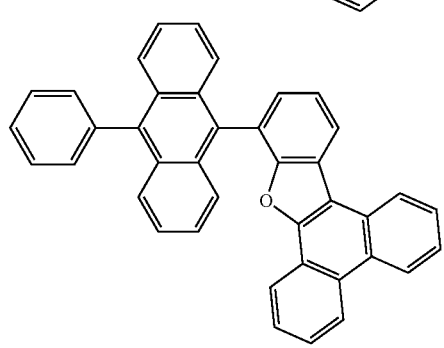
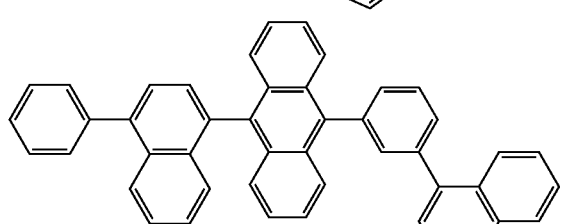
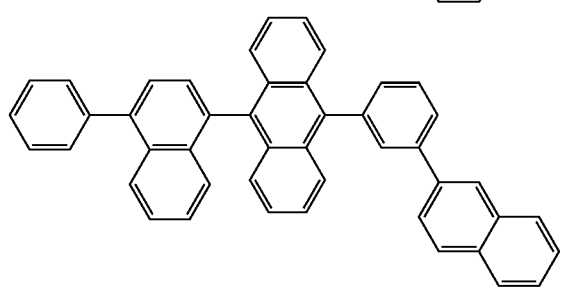
1208
-continued
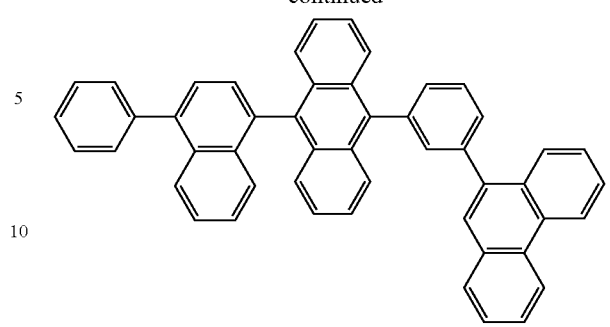
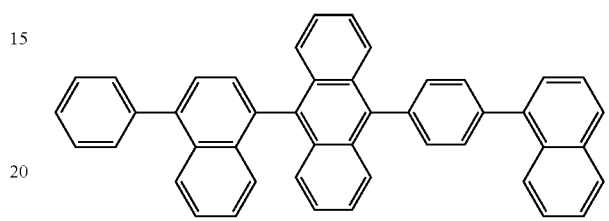
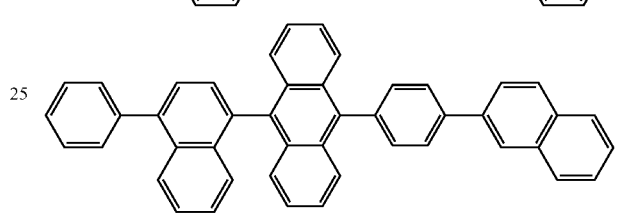
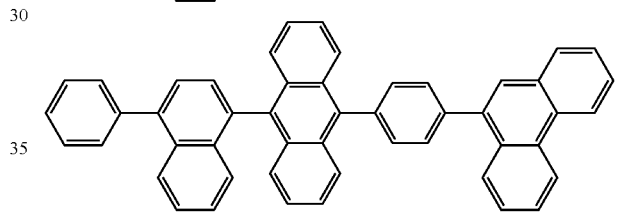
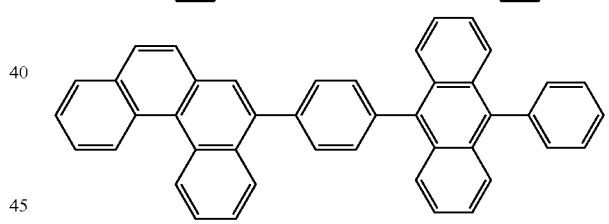
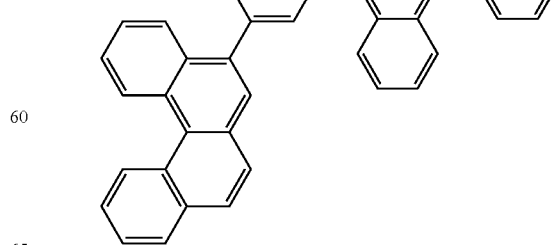

-continued

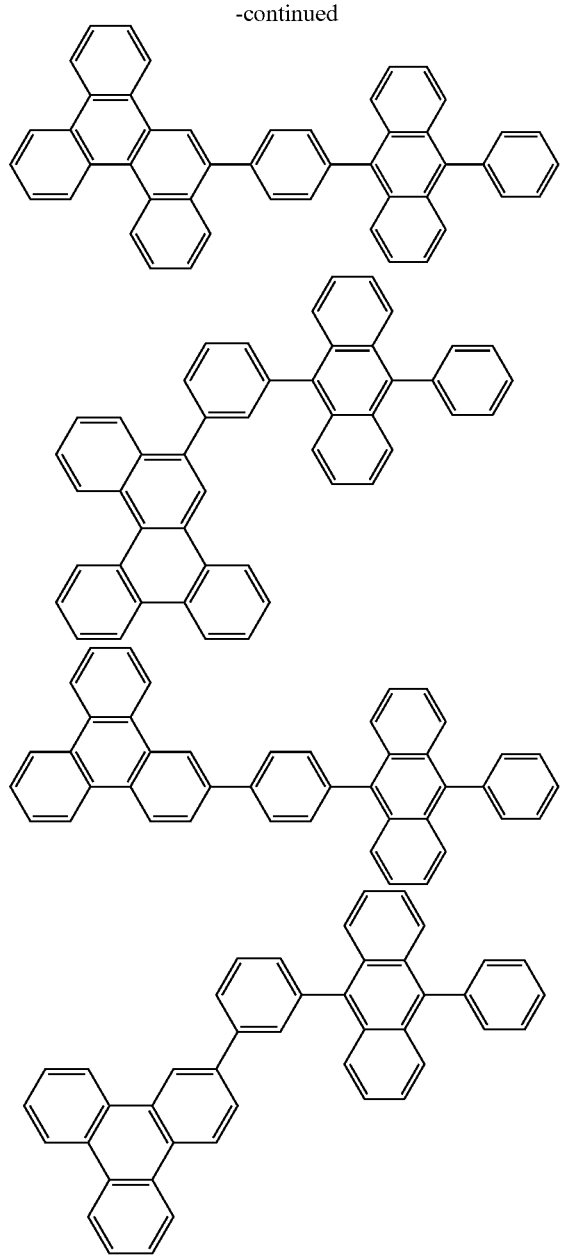

Electron Transporting Layer

The electron transporting layer is a layer containing a material having a high electron transporting capability (an electron transporting material) and is provided between the light emitting layer and the cathode, or between the electron injecting layer, if exists, and the light emitting layer. The inventive compound may be used alone or as a combination with a compound described layer in the electron transporting layer.

The electron transporting layer may have a single layer structure or a multilayer structure including two or more layers. For example, the electron transporting layer may have a two-layer structure including a first electron transporting layer (anode side) and a second electron transporting layer (cathode side). In one embodiment of the present invention, the electron transporting layer having a single layer structure is preferably disposed adjacent to the light emitting layer, and the electron transporting layer that is closest to the anode in the multilayer structure, such as the first electron transporting layer in the two-layer structure, is preferably disposed adjacent to the light emitting layer. In another embodiment of the present invention, a hole blocking layer described later and the like may be disposed between the electron transporting layer having a single layer structure and the light emitting layer, or between the electron transporting layer that is closest to the light emitting layer in the multilayer structure and the light emitting layer.

In the electron transporting layer having the two-layer structure, the inventive compound may be contained in any one of the first electron transporting layer and the second electron transporting layer, or may be contained in both the layers.

The inventive compound is preferably contained only in the first electron transporting layer in one embodiment of the present invention, the inventive compound is preferably contained only in the second electron transporting layer in another embodiment of the present invention, and the inventive compound is preferably contained in the first electron transporting layer and the second electron transporting layer in still another embodiment of the present invention.

In one embodiment of the present invention, the inventive compound contained in one of or both of the first electron transporting layer and the second electron transporting layer is preferably a protium compound from the standpoint of the production cost.

The protium compound means the inventive compound having all the hydrogen atoms in the inventive compound that are protium atoms.

Accordingly, the present invention includes an organic EL device including the first electron transporting layer and the second electron transporting layer, any one or both of which contains the inventive compound that is formed substantially only of the protium compound. The "inventive compound that is formed substantially only of the protium compound" means that the content ratio of the protium compound with respect to the total amount of the inventive compound is 90% by mol or more, preferably 95% by mol or more, and more preferably 99% by mol or more (each of which includes 100%).

Examples of the material used in the electron transporting layer include:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a high-molecular weight compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The materials are materials having an electron mobility of $10^{-6}$ cm$^2$/Vs or more. Materials other than those as mentioned above may also be used in the electron transporting layer so long as they are materials high in the electron transporting capability rather than in the hole transporting capability.

Electron Injecting Layer

The electron injecting layer is a layer containing a material having a high electron injection capability. In the electron injecting layer, alkali metals, such as lithium (Li) and cesium (Cs), alkaline earth metals, such as magnesium (Mg), calcium (Ca), and strontium (Sr), rare earth metals, such as europium (Eu) and ytterbium (Yb), and compounds containing these metals can be used. Examples of the compounds include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used as a mixture of a plurality thereof.

In addition, a material having an electron transporting capability, in which an alkali metal, an alkaline earth metal, or a compound thereof is contained, specifically Alq in which magnesium (Mg) is contained may be used. In this case, electron injection from the cathode can be more efficiently performed.

Otherwise, in the electron injecting layer, a composite material obtained by mixing an organic compound with an electron donor may be used. Such a composite material is excellent in the electron injection capability and the electron transporting capability because the organic compound receives electrons from the electron donor. In this case, the organic compound is preferably a material excellent in transporting received electrons, and specifically, examples thereof include a material constituting the aforementioned electron transporting layer (such as a metal complex and a heteroaromatic compound). As the electron donor, a material having an electron donation property for the organic compound may be used. Specifically, alkali metals, alkaline earth metals, and rare earth metals are preferred, and examples thereof include lithium, cesium, magnesium, calcium, erbium, and ytterbium. In addition, an alkali metal oxide or an alkaline earth metal oxide is preferred, and examples thereof include lithium oxide, calcium oxide, and barium oxide. In addition, a Lewis base, such as magnesium oxide, can also be used. In addition, an organic compound, such as tetrathiafulvalene (abbreviation: TTF), can also be used.

Cathode

It is preferred that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals, such as lithium (Li) and cesium (Cs), alkaline earth metals, such as magnesium (Mg), calcium (Ca), and strontium (Sr), and alloys containing these (such as MgAg, and AlLi), and rare earth metals, such as europium (Eu), and ytterbium (Yb) and alloys containing these.

When the cathode is formed by using the alkali metals, the alkaline earth metals, and the alloys containing these, a vacuum vapor deposition method or a sputtering method can be adopted. In addition, when a silver paste or the like is used, a coating method, an inkjet method, of the like can be adopted.

By providing the electron injecting layer, the cathode can be formed using various conductive materials, such as Al, Ag, ITO, graphene, and indium oxide-tin oxide containing silicon or silicon oxide regardless of the magnitude of a work function. Such a conductive material can be deposited by using a sputtering method, an inkjet method, a spin coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer can also be provided among the plurality of phosphorescent light emitting layers.

Since the space layer is provided between the light emitting layers, a material having both an electron transporting capability and a hole transporting capability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer.

In one embodiment of the present invention, it is preferred that the electron transporting zone includes a hole blocking layer of the cathode side, and the hole blocking layer contains the inventive compound. The hole blocking layer is preferably adjacent to the light emitting layer.

Each layer of the organic EL device may be formed by a conventionally known vapor deposition method, a coating method, or the like. For example, formation can be performed by a known method using a vapor deposition method such as a vacuum vapor deposition method, or a molecular beam vapor deposition method (MBE method), or a coating method using a solution of a compound for forming a layer, such as a dipping method, a spin-coating method, a casting method, a bar-coating method, and a roll-coating method.

The film thickness of each layer is not particularly limited, but is typically 5 nm to 10 µm, and more preferably 10 nm to 0.2 µm because in general, when the film thickness is too small, defects such as pinholes are likely to occur, and conversely, when the film thickness is too large, a high driving voltage is required and the efficiency decreases.

The organic EL device can be used for electronic devices, such as display components of an organic EL panel module and the like, display devices of a television, a mobile phone, a personal computer, and the like, and light emitting devices of lightings and vehicular lamps.

EXAMPLES

The present invention is hereunder described in more detail by reference to Examples, but it should be construed that the present invention is not limited to the following Examples.

Inventive Compounds Used in Production of Organic EL Device (I) of Examples 1 and 2

Compound 1

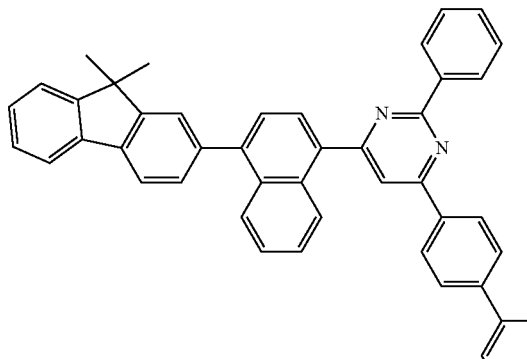

Compound 2

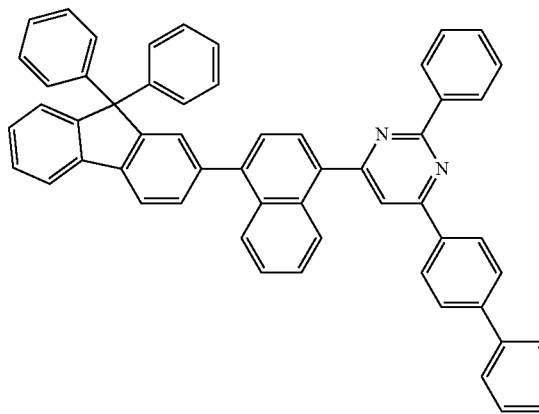

Compounds Used in Production of Organic EL Device (I)

HI-1

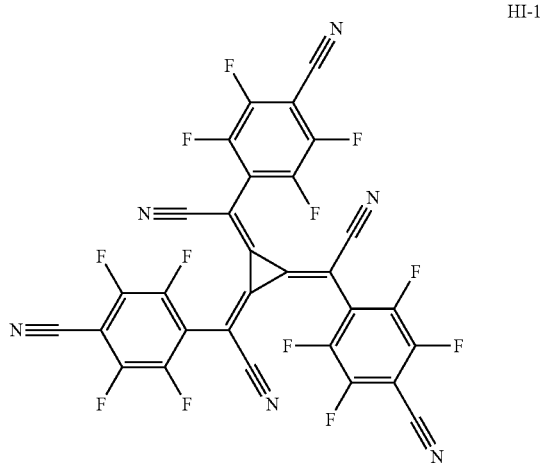 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]

HT-1

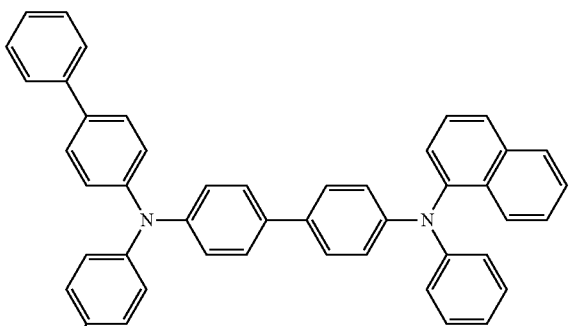

HT-2

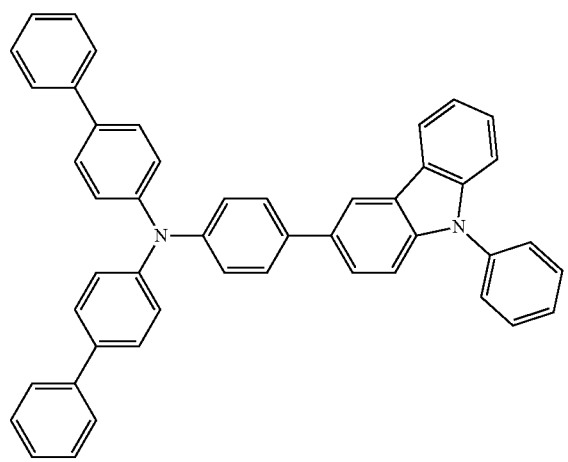

EBL-1

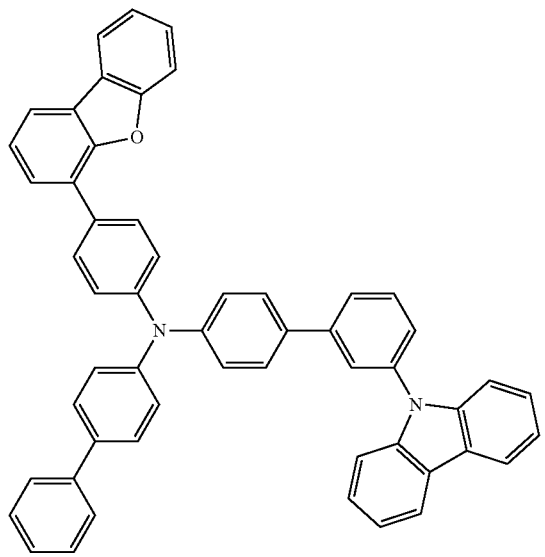

BH-1

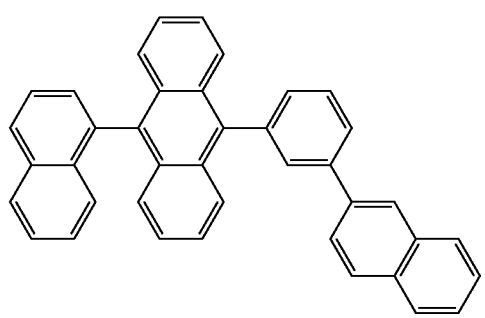

BD-1

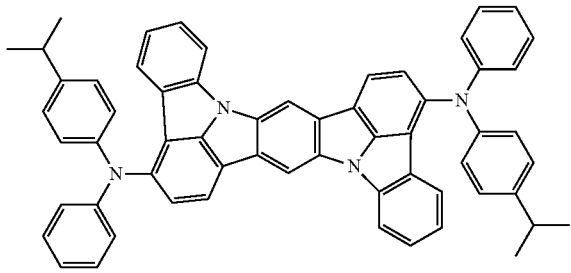

HBL-1

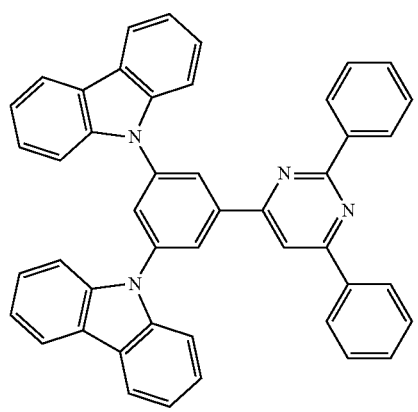

ET-1

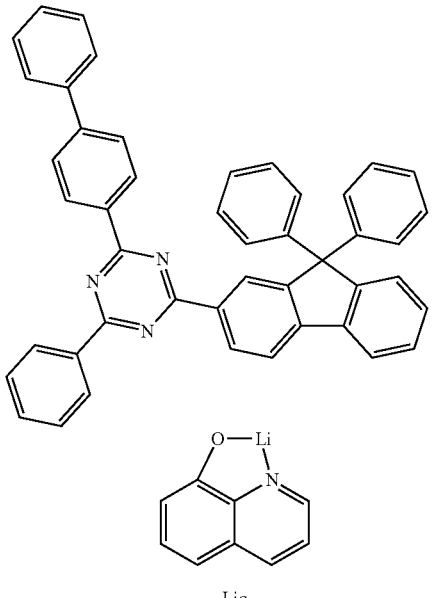

Liq

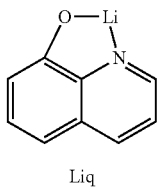

Production of Organic EL Device (I)

Example 1

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with an ITO transparent electrode was mounted on a substrate holder of a vacuum vapor deposition apparatus, and firstly, Compound HT-1 and Compound HI-1 were vapor co-deposited on the surface having the transparent electrode formed thereon, so as to cover the transparent electrode, resulting in a hole injecting layer with a film thickness of 10 nm. The mass ratio of Compound HT-1 and Compound HI-1 (HT-1/HI-1) was 97/3.

Subsequently, on the hole injecting layer, Compound HT-1 was vapor deposited to form a first hole transporting layer with a film thickness of 80 nm.

Subsequently, on the first hole transporting layer, EBL-1 was vapor deposited to form a second hole transporting layer with a film thickness of 5 nm.

Subsequently, on the second hole transporting layer, Compound BH-1 (host material) and Compound BD-1 (dopant material) were vapor co-deposited to form a light emitting layer with a film thickness of 20 nm. The mass ratio of Compound BH-1 and Compound BD-1 (BH-1/BD-1) was 99/1.

Subsequently on the light emitting layer, Compound 1 was vapor deposited to form a first electron transporting layer with a film thickness of 5 nm.

Subsequently, on the first electron transporting layer, Compound ET-1 and Liq were vapor co-deposited to form a second electron transporting layer with a film thickness of 25 nm. The mass ratio of Compound ET-1 and Liq (ET-1/Liq) was 50/50.

Subsequently, on the second electron transporting layer, Yb was vapor deposited to form an electron injecting electrode with a film thickness of 1 nm.

Then, on the electron injecting electrode, metal Al was vapor deposited to form a metal cathode with a film thickness of 80 nm.

The layer configuration of the organic EL device (I) of Example 1 thus obtained is shown below.

ITO(130)/HT-1/HI-1=97/3(10)/HT-1(80)/EBL-1(5)/
BH-1/BD-1=99/1(20)/Compound 1(5)/ET-1/
Liq=50/50(25)/Yb(1)/Al(80)

In the layer configuration, the numerals in parentheses each indicate the film thickness (nm), and the ratios each are a mass ratio.

Measurement of Device Lifetime (LT95)

The organic EL device (I) was driven with a direct current at a current density of 50 mA/cm$^2$ under a room temperature, and the period of time (h) until the luminance was decreased to 95% of the initial luminance was measured and designated as a 95% lifetime (LT95). The result is shown in Table 1.

Example 2

An organic EL device (I) was produced in the same manner as in Example 1 except that the first electron transporting layer material was changed from Compound 1 to Compound 2, and measured for LT95. The result is shown in Table 1.

TABLE 1

|  | First electron transporting layer material | LT95 (h) at 50 mA/cm$^2$ |
|---|---|---|
| Example 1 | Compound 1 | 253 |
| Example 2 | Compound 2 | 180 |

It is understood from the results in Table 1 that the compound of the present invention provides an organic EL device having an improved device lifetime.

Production of Organic EL Device (II)

Example 3

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with an ITO transparent electrode was mounted on a substrate holder of a vacuum vapor deposition apparatus, and firstly, Compound HT-2 and Compound HI-1 were vapor co-deposited on the surface having the transparent electrode formed thereon, so as to cover the transparent electrode, resulting in a hole injecting layer with a film thickness of 10 nm. The mass ratio of Compound HT-2 and Compound HI-1 (HT-2/HI-1) was 97/3.

Subsequently, on the hole injecting layer, Compound HT-2 was vapor deposited to form a first hole transporting layer with a film thickness of 80 nm.

Subsequently, on the first hole transporting layer, EBL-1 was vapor deposited to form a second hole transporting layer with a film thickness of 5 nm.

Subsequently, on the second hole transporting layer, Compound BH-1 (host material) and Compound BD-1 (dopant material) were vapor co-deposited to form a light emitting layer with a film thickness of 20 nm. The mass ratio of Compound BH-1 and Compound BD-1 (BH-1/BD-1) was 99/1.

Subsequently, on the light emitting layer, Compound 1 was vapor deposited to form a first electron transporting layer with a film thickness of 5 nm.

Subsequently, on the first electron transporting layer, Compound ET-1 and Liq were vapor co-deposited to form a second electron transporting layer with a film thickness of 25 nm. The mass ratio of Compound ET-1 and Liq (ET-1/Liq) was 50/50.

Subsequently, on the second electron transporting layer, Yb was vapor deposited to form an electron injecting electrode with a film thickness of 1 nm.

Then, on the electron injecting electrode, metal Al was vapor deposited to form a metal cathode with a film thickness of 80 nm.

The organic EL device (II) of Example 3 was measured for LT95 in the same manner as in Example 1. The result thereof is shown in Table 2, and the layer configuration of the organic EL device (II) of Example 3 thus obtained is shown below.

ITO(130)/HT-2/HI-1=97/3(10)/HT-2(80)/EBL-1(5)/
BH-1/BD-1=99/1(20)/Compound 1(5)/ET-1/
Liq=50/50(25)/Yb(1)/Al(80)

In the layer configuration, the numerals in parentheses each indicate the film thickness (nm), and the ratios each are a mass ratio.

Example 4

An organic EL device (II) was produced in the same manner as in Example 3 except that the first electron transporting layer material was changed from Compound 1 to Compound 2, and measured for LT95. The result is shown in Table 2.

TABLE 2

|  | First electron transporting layer material | LT95 (h) at 50 mA/cm$^2$ |
|---|---|---|
| Example 3 | Compound 1 | 284 |
| Example 4 | Compound 2 | 215 |

It is understood from the results in Table 2 that the compound of the present invention provides an organic EL device having an improved device lifetime.

Production of Organic EL Device (III)

Example 5

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with an ITO transparent electrode was mounted on a substrate holder of a vacuum vapor deposition apparatus, and firstly, Compound HT-1 and Compound HI-1 were vapor co-deposited on the surface having the transparent electrode formed thereon, so as to cover the transparent electrode, resulting in a hole injecting layer with a film thickness of 10 nm. The mass ratio of Compound HT-1 and Compound HI-1 (HT-1/HI-1) was 97/3.

Subsequently, on the hole injecting layer, Compound HT-1 was vapor deposited to form a first hole transporting layer with a film thickness of 80 nm.

Subsequently, on the first hole transporting layer, EBL-1 was vapor deposited to form a second hole transporting layer with a film thickness of 5 nm.

Subsequently, on the second hole transporting layer, Compound BH-1 (host material) and Compound BD-1 (dopant material) were vapor co-deposited to form a light emitting layer with a film thickness of 20 nm. The mass ratio of Compound BH-1 and Compound BD-1 (BH-1/BD-1) was 99/1.

Subsequently, on the light emitting layer, HBL-1 was vapor deposited to form a first electron transporting layer with a film thickness of 5 nm.

Subsequently, on the first electron transporting layer, Compound 1 and Liq were vapor co-deposited to form a second electron transporting layer with a film thickness of 25 nm. The mass ratio of Compound 1 and Liq (Compound 1/Liq) was 50/50.

Subsequently, on the second electron transporting layer, Yb was vapor deposited to form an electron injecting electrode with a film thickness of 1 nm.

Then, on the electron injecting electrode, metal Al was vapor deposited to form a metal cathode with a film thickness of 80 nm.

The organic EL device (III) of Example 5 was measured for LT95 in the same manner as in Example 1. The result thereof is shown in Table 3, and the layer configuration of the organic EL device (III) of Example 5 thus obtained is shown below.

ITO(130)/HT-1/HI-1=97/3(10)/HT-1(80)/EBL-1(5)/
BH-1/BD-1=99/1(20)/HBL-1(5)/Compound
1/Liq=50/50(25)/Yb(1)/Al(80)

In the layer configuration, the numerals in parentheses each indicate the film thickness (nm), and the ratios each are a mass ratio.

Example 6

An organic EL device (III) was produced in the same manner as in Example 5 except that the second electron transporting layer material was changed from Compound 1 to Compound 2, and measured for LT95. The result is shown in Table 3.

TABLE 3

| | Second electron transporting layer material | LT95 (h) at 50 mA/cm² |
|---|---|---|
| Example 5 | Compound 1 | 174 |
| Example 6 | Compound 2 | 192 |

It is understood from the results in Table 3 that the compound of the present invention provides an organic EL device having an improved device lifetime.

Inventive Compound Used in Production of Organic EL Device (IV) of Comparative Example 1 and Example 7

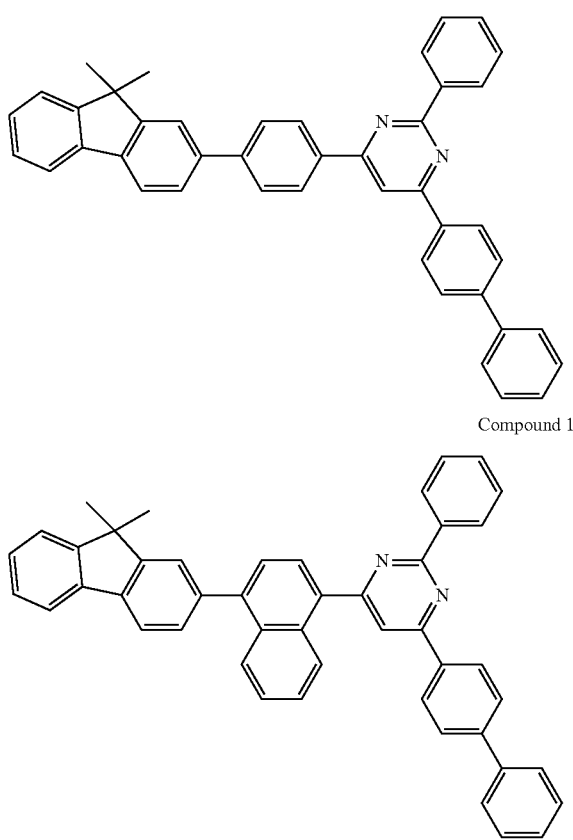

Compounds Used in Production of Organic EL Device (IV) (Compounds Other than Compound Used in Production of Organic EL Device (I) Above)

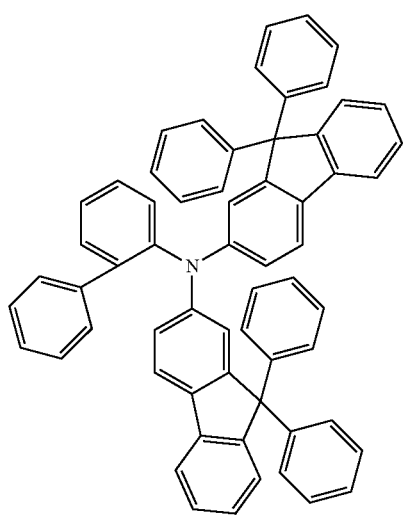

-continued

BD-2

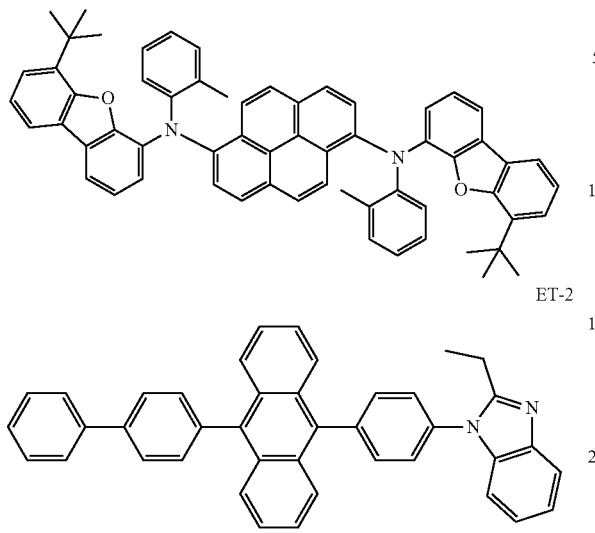

ET-2

Production of Organic EL Device (IV)

Comparative Example 1

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with an ITO transparent electrode was mounted on a substrate holder of a vacuum vapor deposition apparatus, and firstly, Compound HT-3 and Compound HI-1 were vapor co-deposited on the surface having the transparent electrode formed thereon, so as to cover the transparent electrode, resulting in a hole injecting layer with a film thickness of 10 nm. The mass ratio of Compound HT-3 and Compound HI-1 (HT-3/HI-1) was 97/3.

Subsequently, on the hole injecting layer, Compound HT-3 was vapor deposited to form a first hole transporting layer with a film thickness of 80 nm.

Subsequently, on the first hole transporting layer, EBL-1 was vapor deposited to form a second hole transporting layer with a film thickness of 10 nm.

Subsequently, on the second hole transporting layer, Compound BH-1 (host material) and Compound BD-2 (dopant material) were vapor co-deposited to form a light emitting layer with a film thickness of 25 nm. The mass ratio of Compound BH-1 and Compound BD-2 (BH-1/BD-2) was 96/4.

Subsequently, on the light emitting layer, Ref-1 was vapor deposited to form a first electron transporting layer with a film thickness of 10 nm.

Subsequently, on the first electron transporting layer, Compound ET-2 was vapor deposited to form a second electron transporting layer with a film thickness of 15 nm.

Subsequently, on the second electron transporting layer, LiF was vapor deposited to form an electron injecting electrode with a film thickness of 1 nm.

Then, on the electron injecting electrode, metal Al was vapor deposited to form a metal cathode with a film thickness of 50 nm.

The organic EL device (IV) of Comparative Example 1 was measured for LT95 in the same manner as in Example 1. The result thereof is shown in Table 4, and the layer configuration of the organic EL device (IV) of Comparative Example 1 thus obtained is shown below.

ITO(130)/HT-3/HI-1=97/3(10)/HT-3(80)/EBL-1(10)/
BH-1/BD-2=96/4(25)/Ref-1(10)/ET-2(15)/LiF
(1)/Al(50)

Example 7

An organic EL device (IV) was produced in the same manner as in Comparative Example 1 except that the first electron transporting layer material was changed from Ref-1 to Compound 1, and measured for LT95. The result is shown in Table 4.

TABLE 4

|  | First electron transporting layer material | LT95 (h) at 50 mA/cm$^2$ |
| --- | --- | --- |
| Comparative Example 1 | Ref-1 | 131 |
| Example 7 | Compound 1 | 158 |

Comparative Example 2

An organic EL device (IV) was produced in the same manner as in Comparative Example 1 except that the first electron transporting layer material was changed from Ref-1 to Ref-2, and measured for LT95. The result is shown in Table 5.

Ref-2

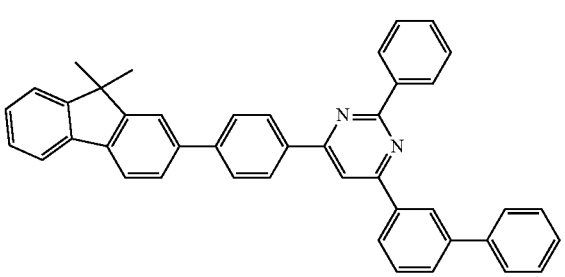

Examples 8 to 19

Organic EL devices (IV) were produced in the same manner as in Comparative Example 1 except that the first electron transporting layer material was changed from Ref-1 to any one of Compounds 12 to 20, 23, 25, 28, and 30, and measured for LT95. The results are shown in Table 5.

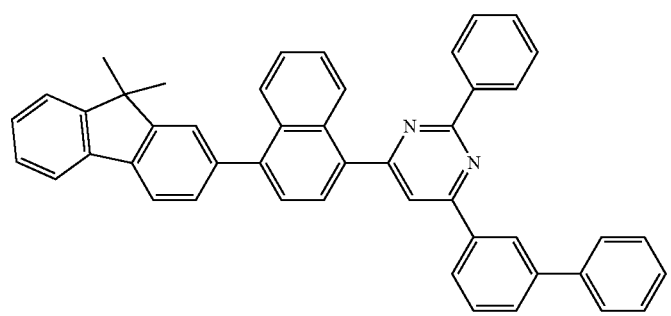
Compound 12
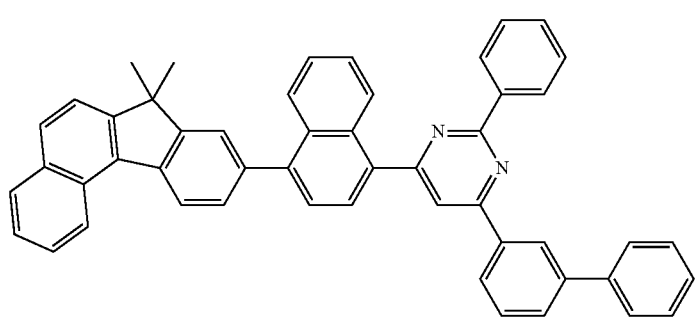
Compound 13
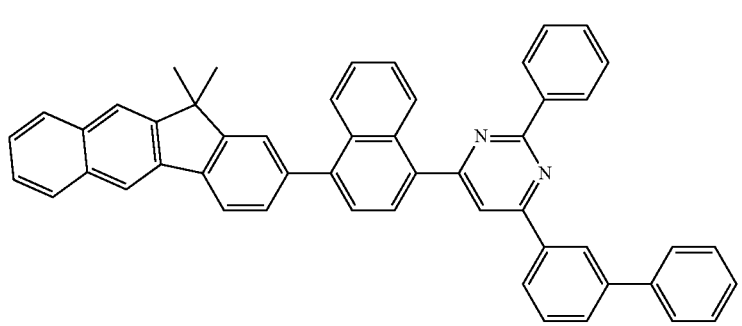
Compound 14
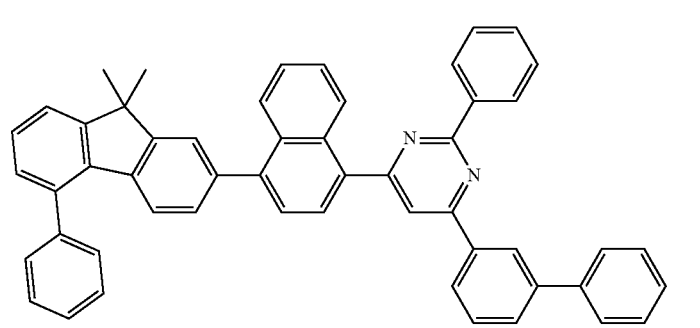
Compound 16
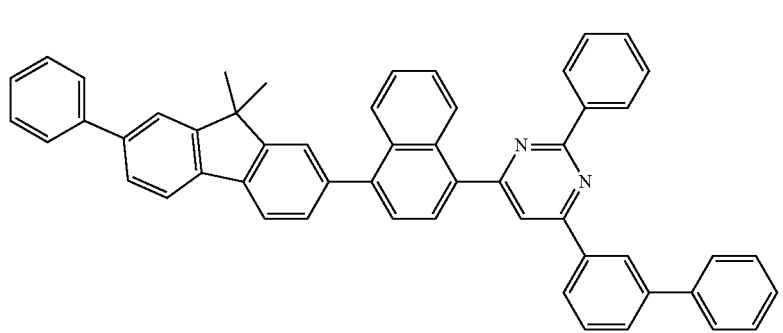
Compound 17

-continued
Compound 18
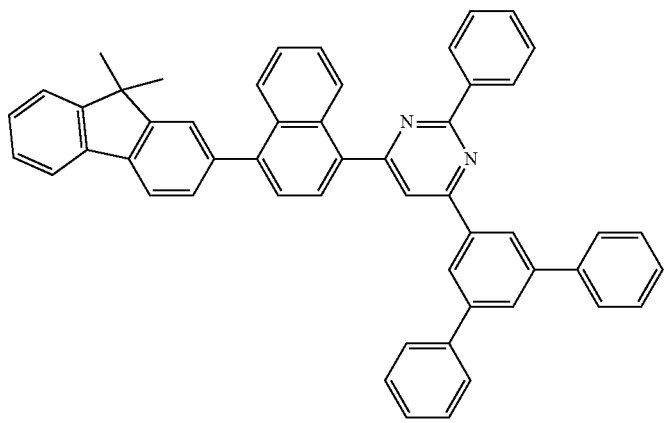
Compound 19
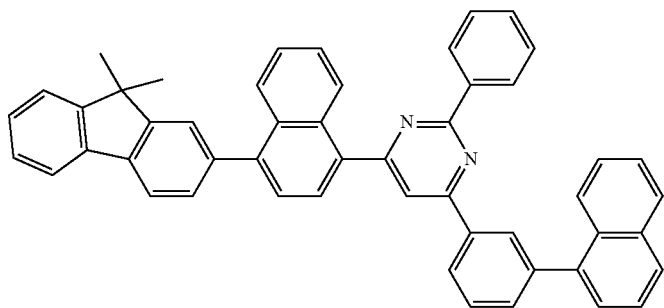
Compound 20
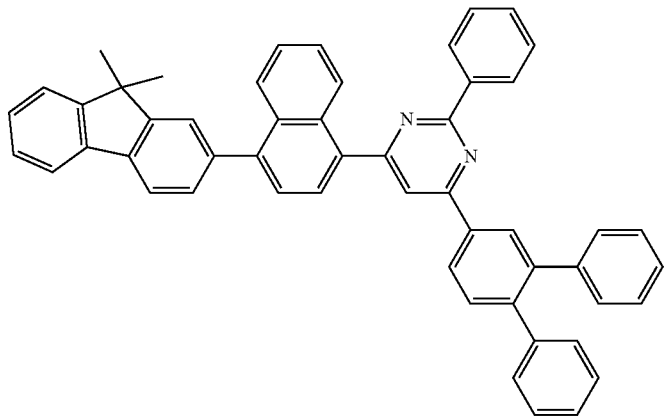
Compound 23
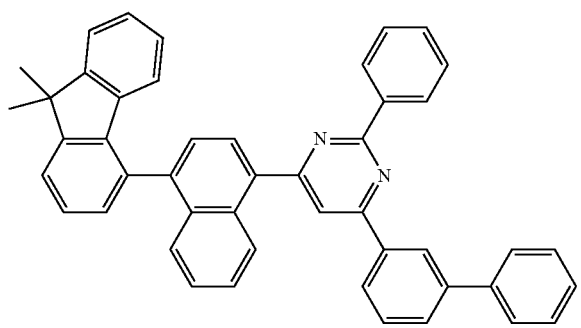

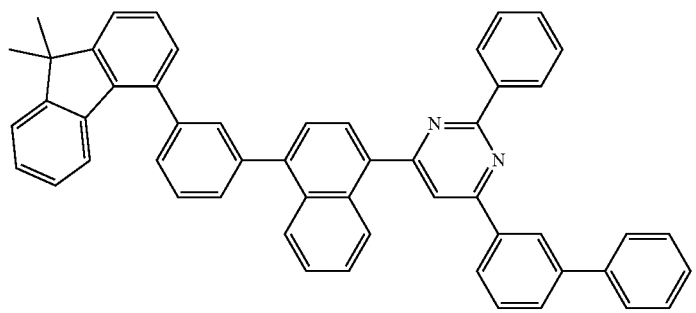
Compound 25
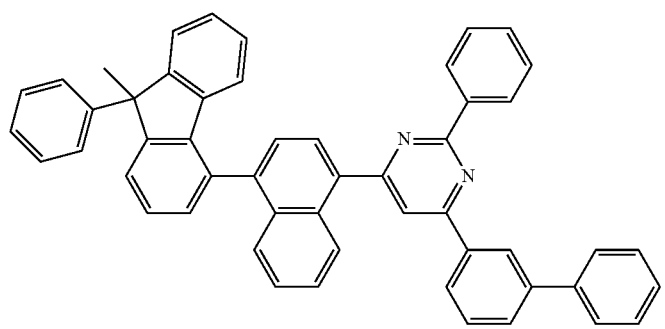
Compound 28
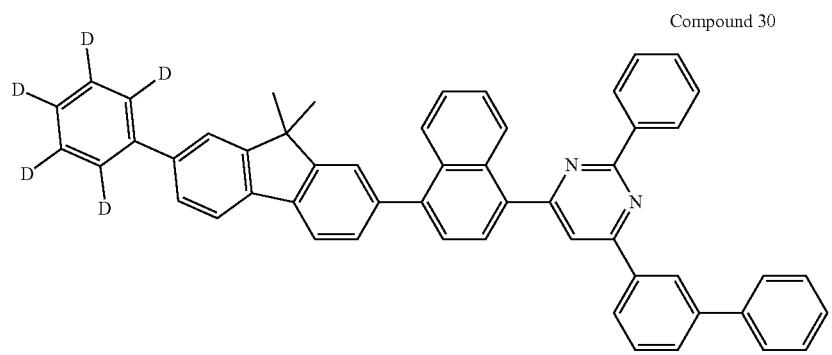
Compound 30
| | First electron transporting layer material | LT95 (h) at 50 mA/cm² |
|---|---|---|
| Comparative Example 2 | Ref-2 | 94 |
| Example 8 | Compound 12 | 133 |
| Example 9 | Compound 13 | 132 |
| Example 10 | Compound 14 | 100 |
| Example 11 | Compound 16 | 107 |
| Example 12 | Compound 17 | 110 |
| Example 13 | Compound 18 | 143 |
| Example 14 | Compound 19 | 129 |
| Example 15 | Compound 20 | 212 |
| Example 16 | Compound 23 | 141 |
| Example 17 | Compound 25 | 118 |
| Example 18 | Compound 28 | 112 |
| Example 19 | Compound 30 | 113 |

Inventive Compound Used in Production of
Organic EL Device (V) of Comparative Example 3
and Examples 20 to 49
Ref-3
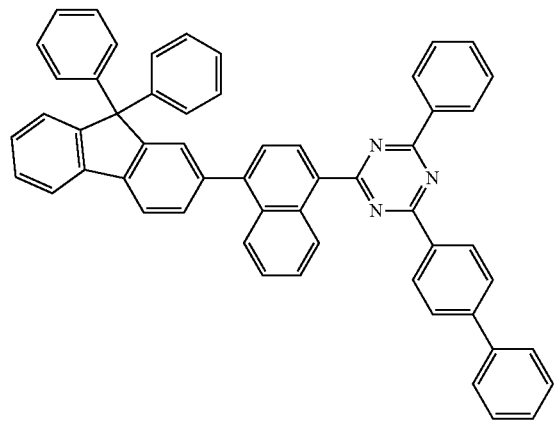
Compound 2
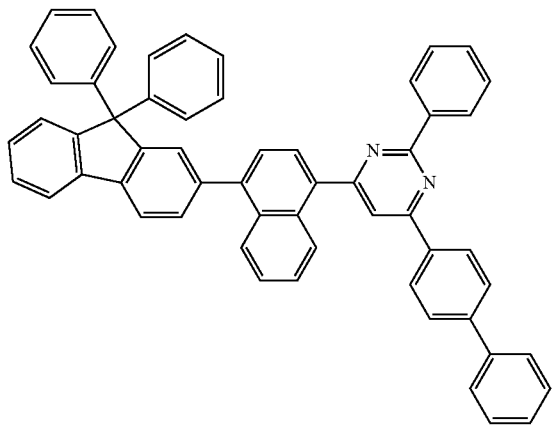
Compound 1
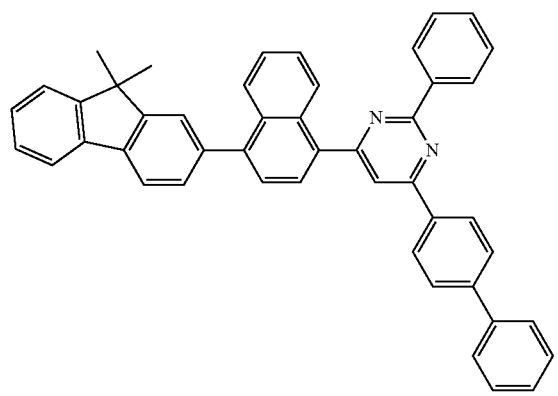
Compound 3
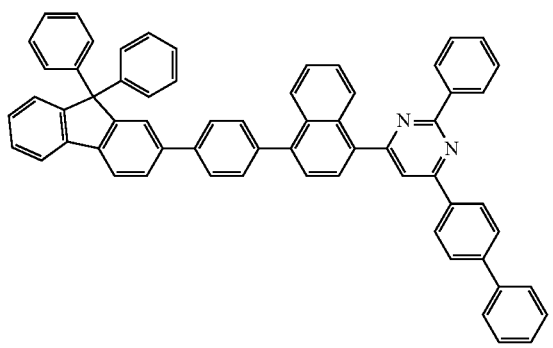
Compound 4
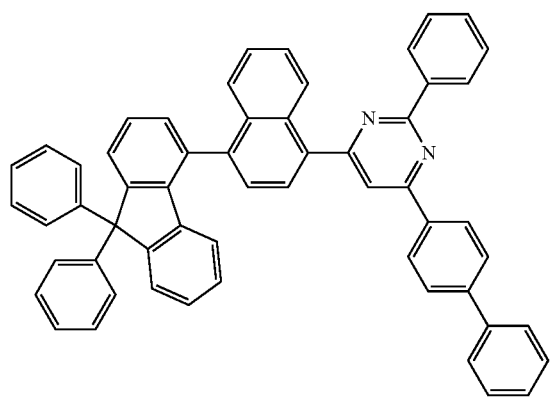
Compound 5
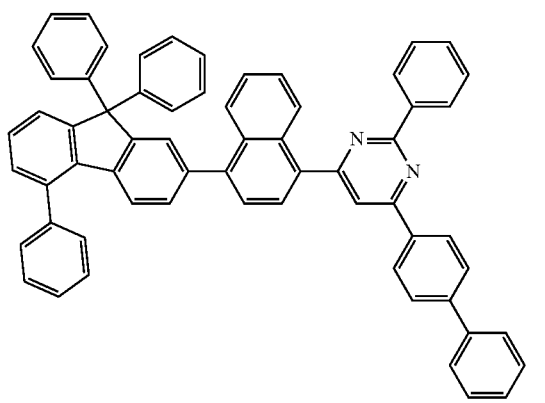

-continued
Compound 6
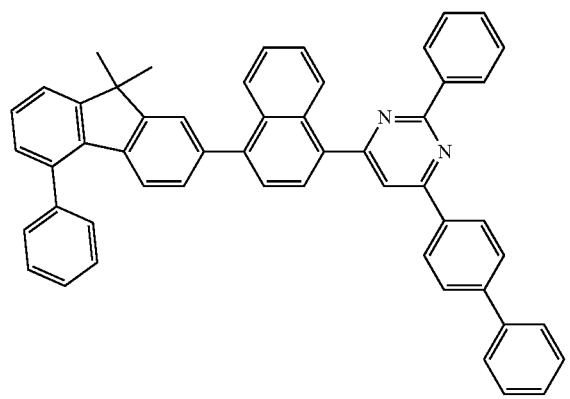
Compound 7
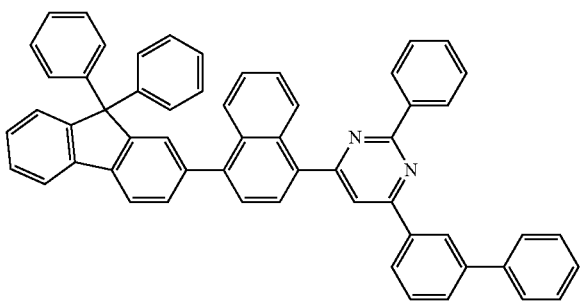
Compound 8
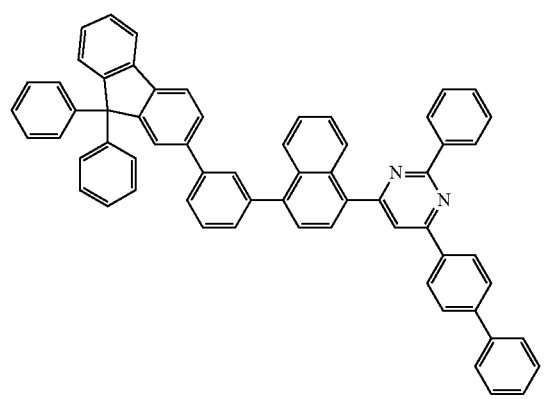
Compound 9
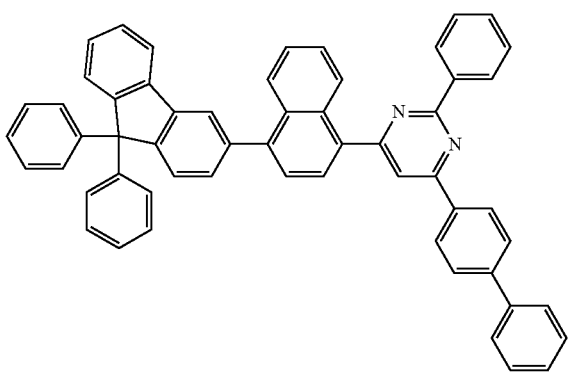
Compound 10
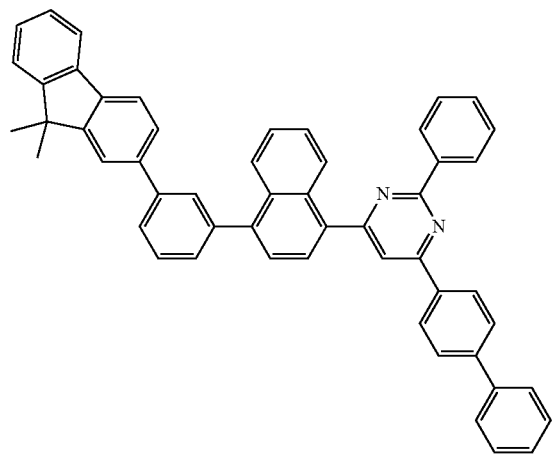
Compound 11
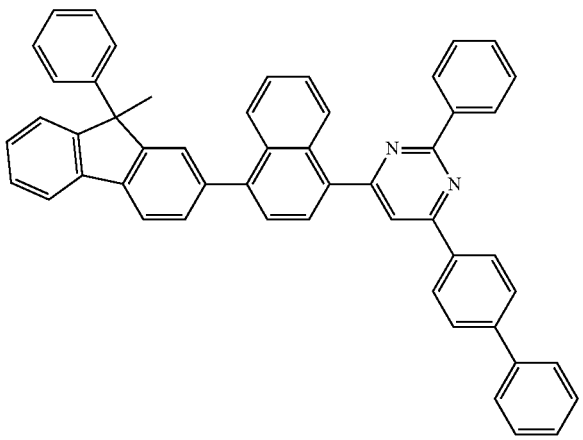
Compound 12
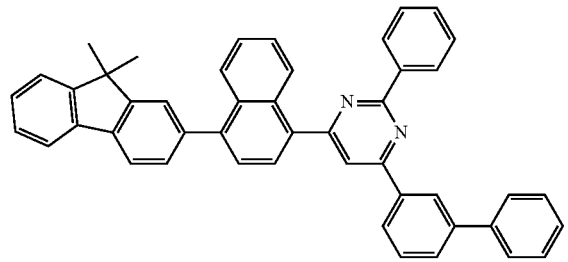
Compound 13
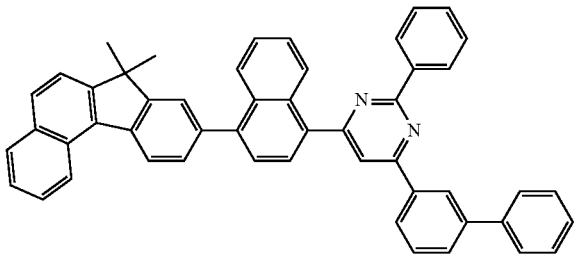

-continued
Compound 14
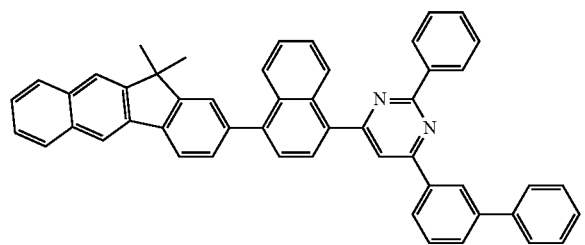
Compound 15
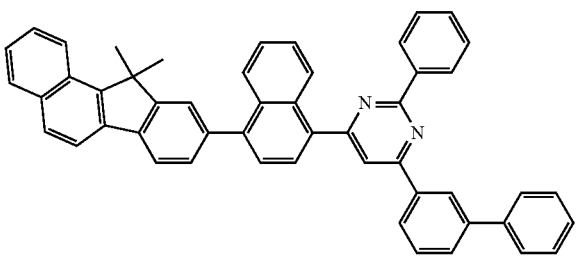
Compound 16
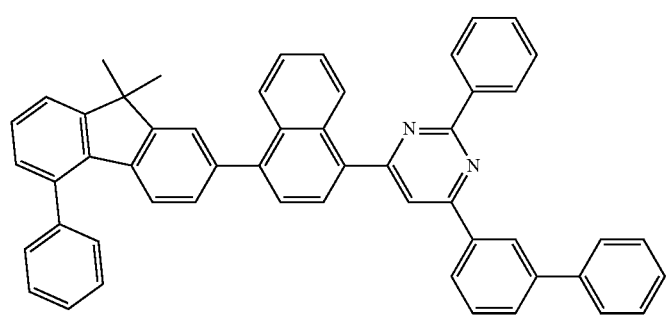
Compound 17
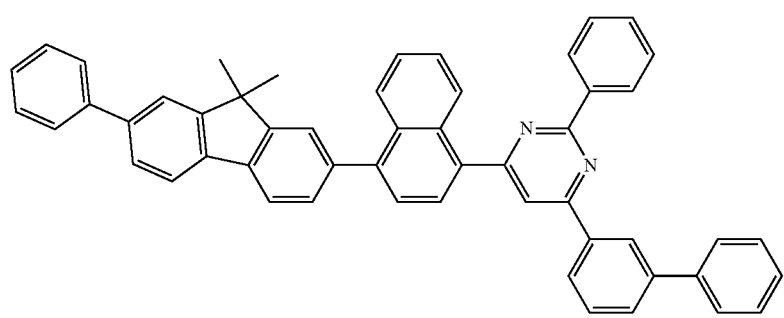
Compound 18
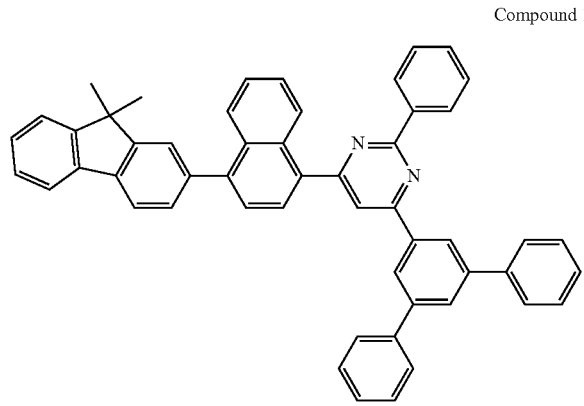
Compound 19
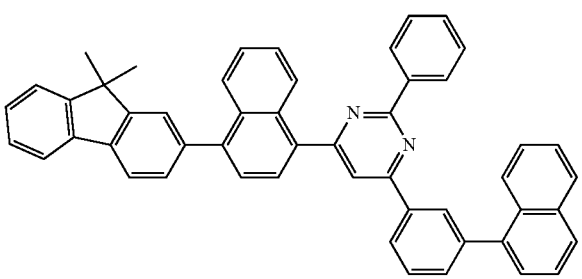

-continued
Compound 20
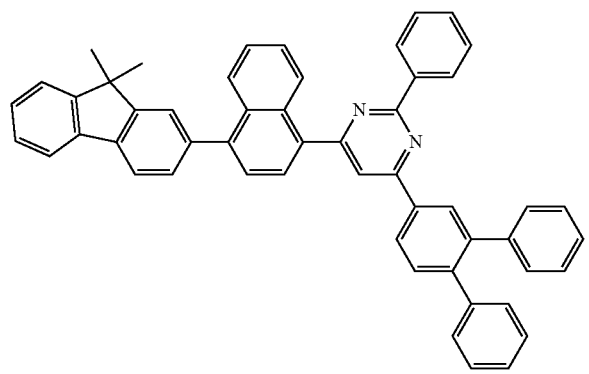
Compound 21
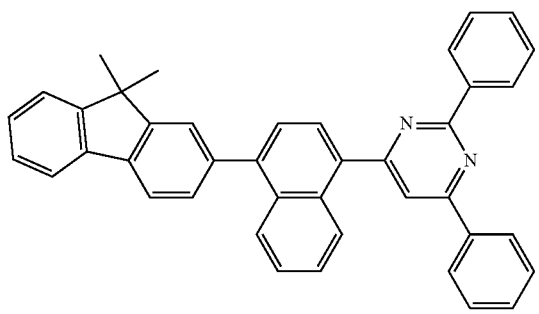
Compound 22
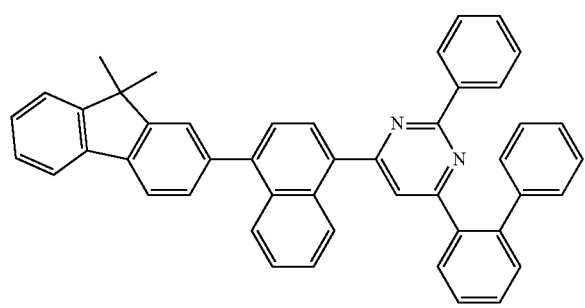
Compound 23
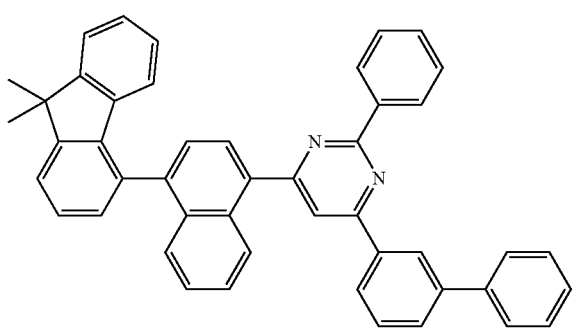
Compound 24
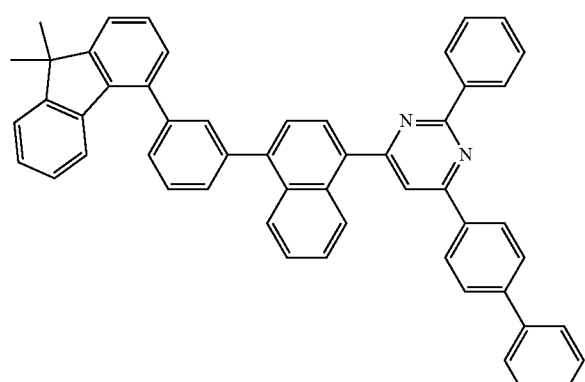
Compound 25
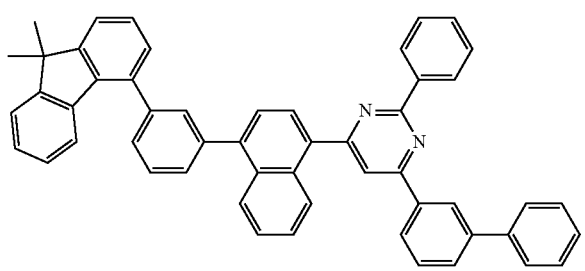
Compound 26
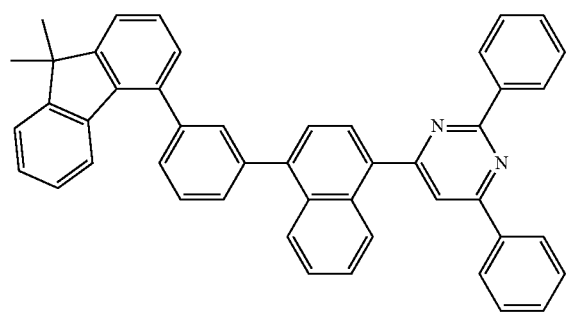
Compound 27
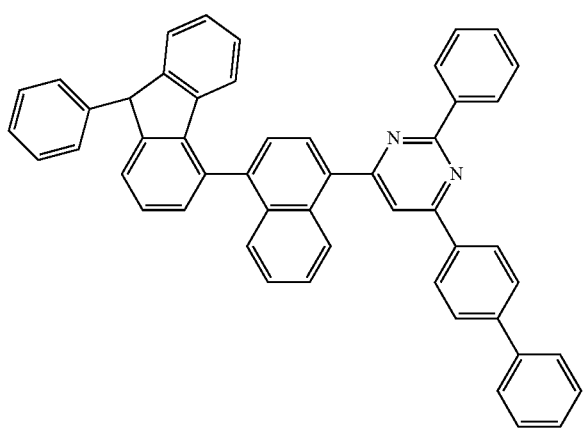

1237
Compound 28
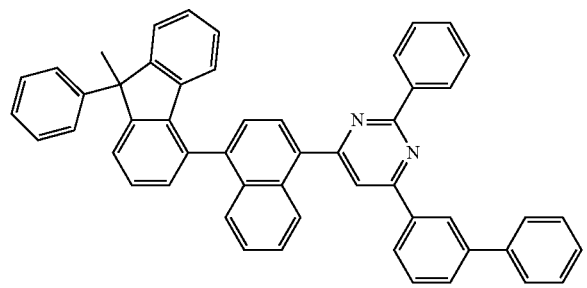
1238
-continued
Compound 29
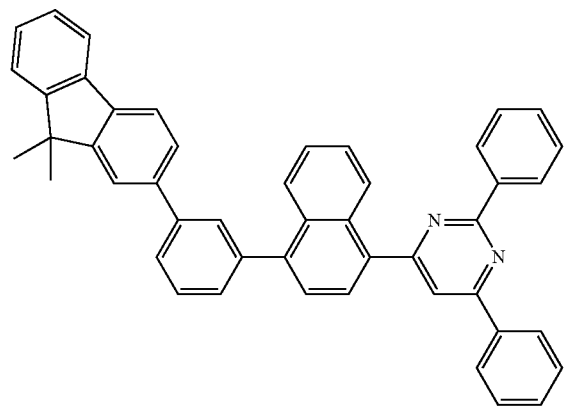
Compound 30
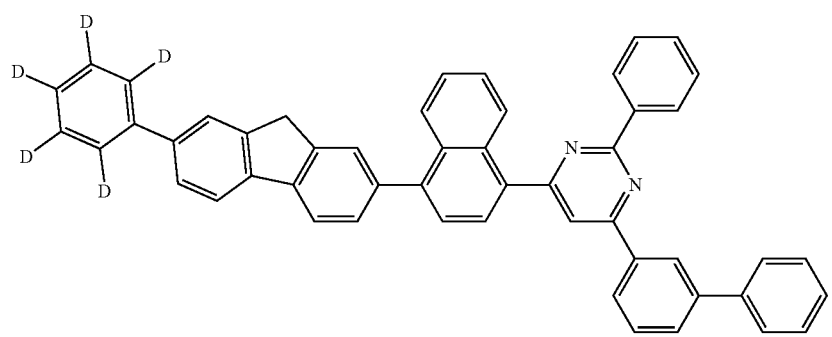
Compounds Used in Production of Organic EL Device (V)
(Compounds Other than Compound Used in Production of
Organic EL Device (V) Above)
HI-1
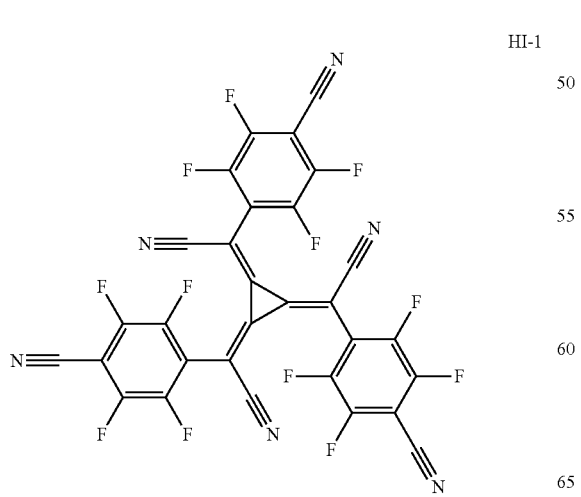
-continued
HT-3
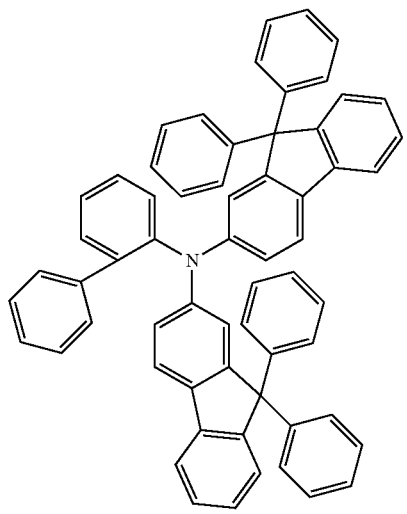

EBL-1

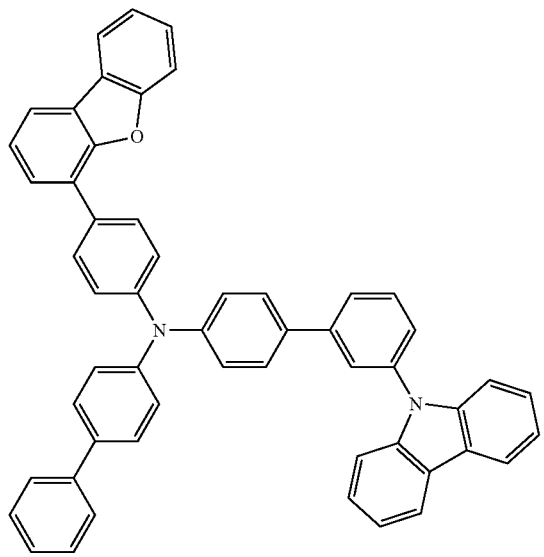

BH-2

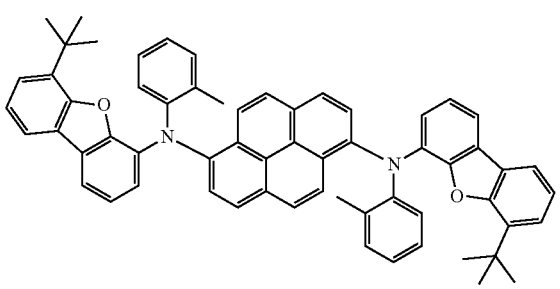

BD-2

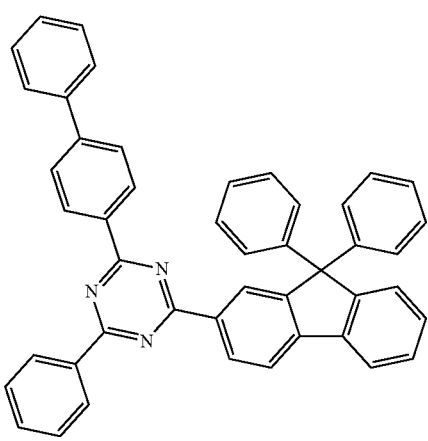

ET-1

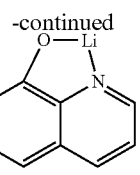

Liq

Production of Organic EL Device (V)

Comparative Example 3

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with an ITO transparent electrode was mounted on a substrate holder of a vacuum vapor deposition apparatus, and firstly, Compound HT-3 and Compound HI-1 were vapor co-deposited on the surface having the transparent electrode formed thereon, so as to cover the transparent electrode, resulting in a hole injecting layer with a film thickness of 10 nm. The mass ratio of Compound HT-3 and Compound HI-1 (HT-3/HI-1) was 97/3.

Subsequently, on the hole injecting layer, Compound HT-3 was vapor deposited to form a first hole transporting layer with a film thickness of 80 nm.

Subsequently, on the first hole transporting layer, Compound EBL-1 was vapor deposited to form a second hole transporting layer with a film thickness of 5 nm.

Subsequently, on the second hole transporting layer, Compound BH-2 (host material) and Compound BD-2 (dopant material) were vapor co-deposited to form a light emitting layer with a film thickness of 25 nm. The mass ratio of Compound BH-2 and Compound BD-2 (BH-2/BD-2) was 96/4.

Subsequently, on the light emitting layer, Ref-3 was vapor deposited to form a first electron transporting layer with a film thickness of 5 nm.

Subsequently, on the first electron transporting layer, Compound ET-1 and Compound Liq were vapor co-deposited to form a second electron transporting layer with a film thickness of 20 nm. The mass ratio of Compound ET-1 and Compound Liq (ET-1/Liq) was 50/50.

Subsequently, on the second electron transporting layer, Yb was vapor deposited to form an electron injecting electrode with a film thickness of 1 nm.

Then, on the electron injecting electrode, metal Al was vapor deposited to form a metal cathode with a film thickness of 50 nm.

The organic EL device (V) of Comparative Example 3 was measured for voltage in the following manner. The result thereof is shown in Table 6, and the layer configuration of the organic EL device (V) of Comparative Example 3 thus obtained is shown below.

<Measurement Method of Driving Voltage>

A voltage was applied to the resulting organic EL device to make a current density of 10 mA/cm$^2$, at which the voltage (unit: V) was measured. The result is shown in Table 6.

Layer Configuration of Organic EL Device (V) of Comparative Example 3

ITO(130)/HT-3/HI-1=97/3(10)/HT-3(80)/EBL-1(5)/
BH-2/BD-2=96/4(25)/Ref-3(5)/ET-1/Liq=50/50
(20)/Yb(1)/Al(50)

Examples 20 to 49

Organic EL devices (V) were produced in the same manner as in Comparative Example 3 except that the first electron transporting layer material was changed from Ref-3 to any one of Compounds 2, 1, and 3 to 30, and measured for voltage (V). The results are shown in Table 6.

TABLE 6

|  | First electron transporting layer material | Voltage (V) at 10 mA/cm$^2$ |
| --- | --- | --- |
| Comparative Example 3 | Ref-3 | 4.1 |
| Example 20 | Compound 2 | 3.4 |
| Example 21 | Compound 1 | 3.7 |
| Example 22 | Compound 3 | 3.5 |
| Example 23 | Compound 4 | 3.4 |
| Example 24 | Compound 5 | 3.4 |
| Example 25 | Compound 6 | 3.5 |
| Example 26 | Compound 7 | 3.4 |
| Example 27 | Compound 8 | 3.4 |
| Example 28 | Compound 9 | 3.5 |
| Example 29 | Compound 10 | 3.6 |
| Example 30 | Compound 11 | 3.4 |
| Example 31 | Compound 12 | 3.6 |
| Example 32 | Compound 13 | 3.6 |
| Example 33 | Compound 14 | 3.6 |
| Example 34 | Compound 15 | 3.5 |
| Example 35 | Compound 16 | 3.6 |
| Example 36 | Compound 17 | 3.6 |
| Example 37 | Compound 18 | 3.9 |
| Example 38 | Compound 19 | 3.7 |
| Example 39 | Compound 20 | 4.0 |
| Example 40 | Compound 21 | 3.5 |
| Example 41 | Compound 22 | 3.6 |
| Example 42 | Compound 23 | 3.7 |
| Example 43 | Compound 24 | 3.8 |
| Example 44 | Compound 25 | 3.7 |
| Example 45 | Compound 26 | 3.6 |
| Example 46 | Compound 27 | 3.8 |
| Example 47 | Compound 28 | 3.6 |
| Example 48 | Compound 29 | 3.5 |
| Example 49 | Compound 30 | 3.6 |

It is understood from the results in Table 6 that the compound of the present invention provides an organic EL device having an improved voltage.

Compounds Synthesized in Synthesis Examples

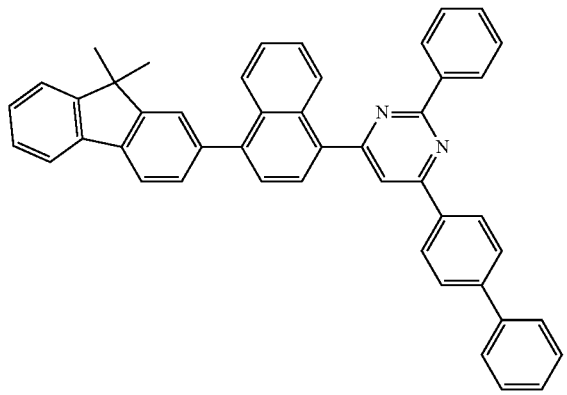

Compound 1

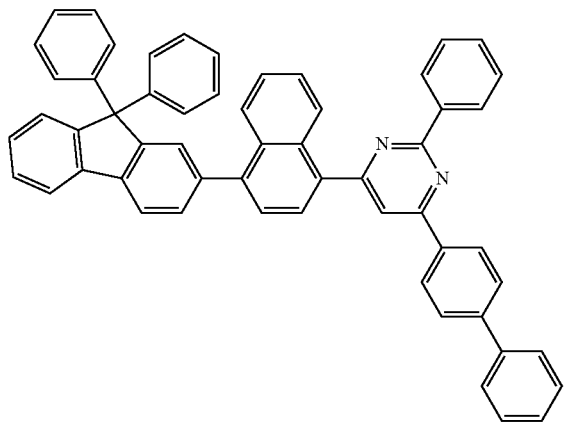

Compound 2

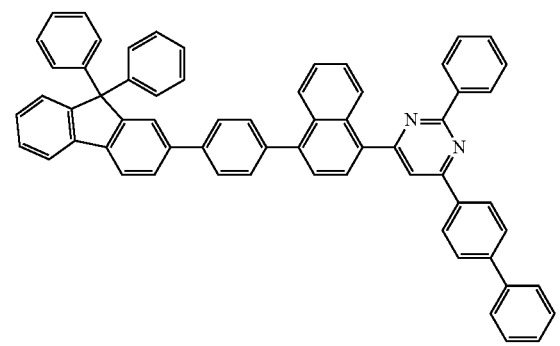

Compound 3

Compound 4
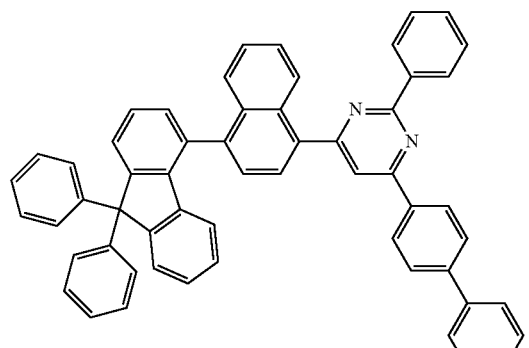
Compound 5
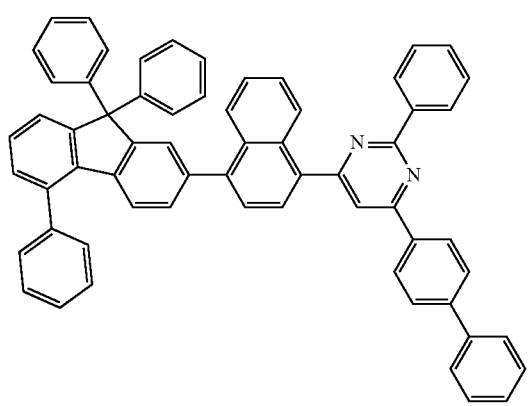
Compound 6
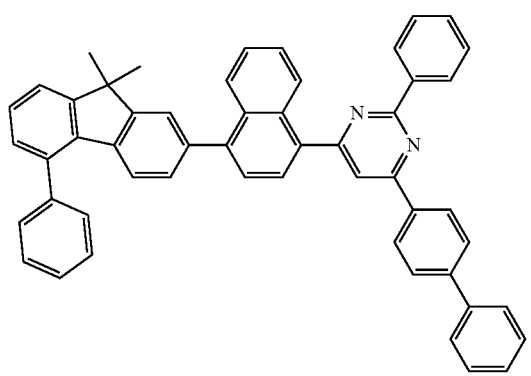
Compound 7
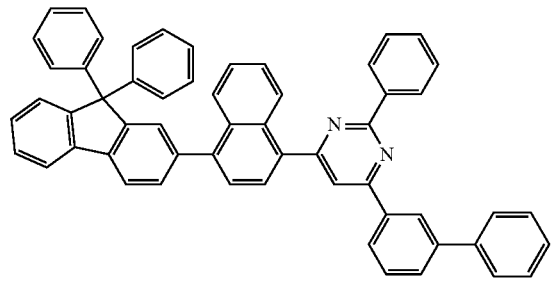
Compound 8
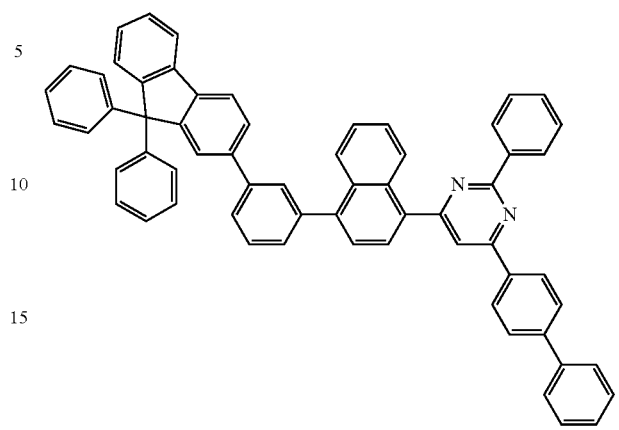
Compound 9
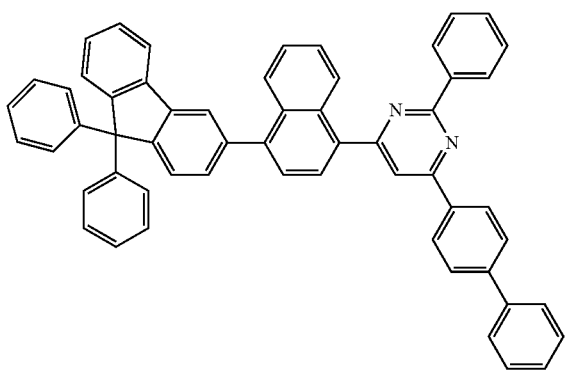
Compound 10
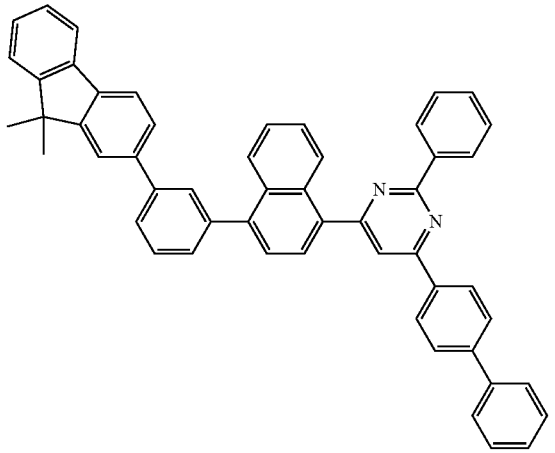

-continued
Compound 11
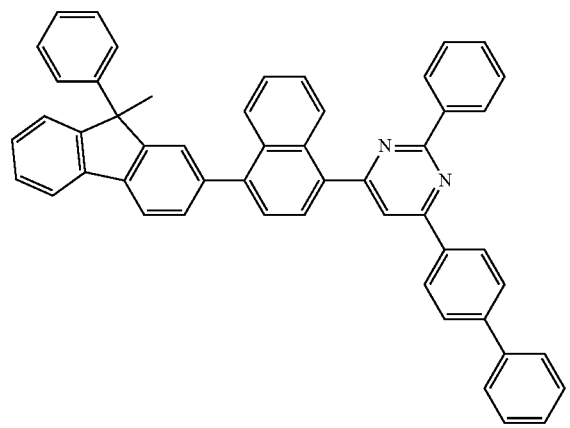
Compound 12
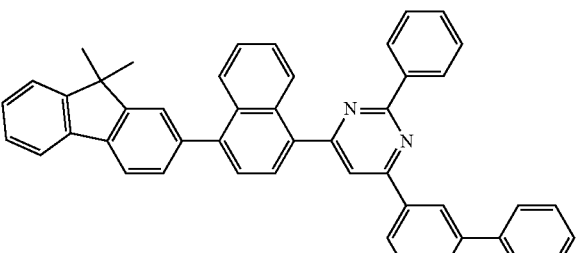
Compound 13
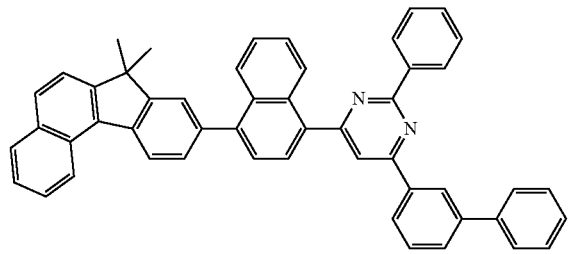
Compound 14
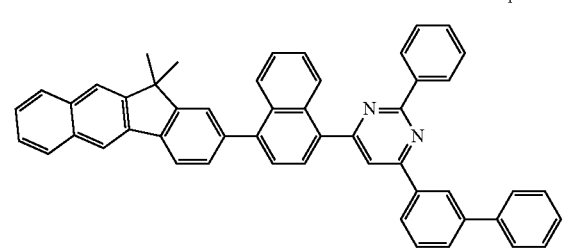
Compound 15
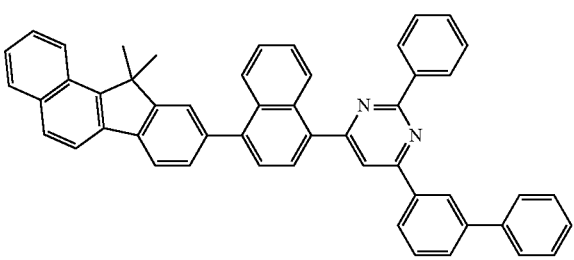
-continued
Compound 16
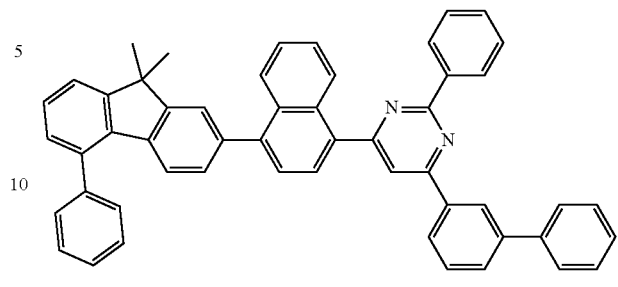
Compound 17
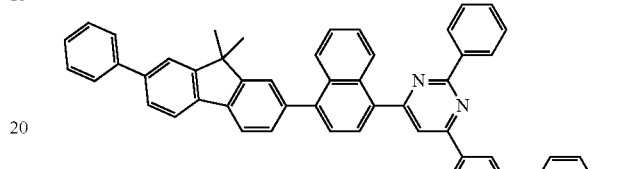
Compound 18
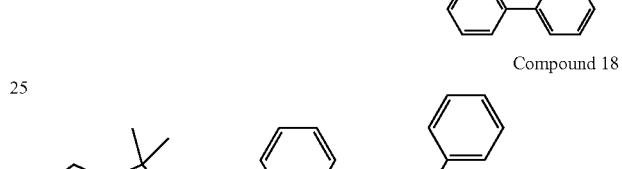
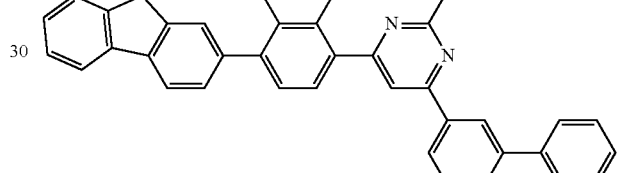
Compound 19
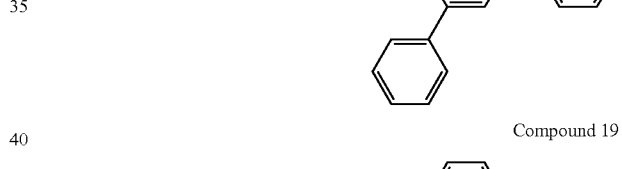
Compound 20
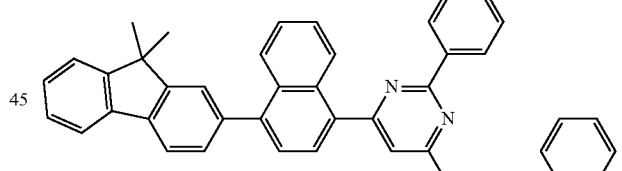
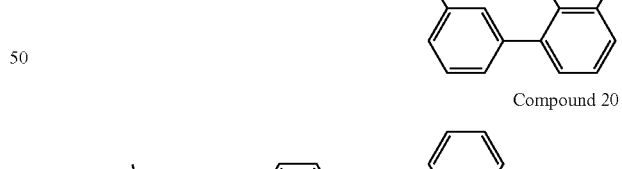

Compound 21
Compound 25
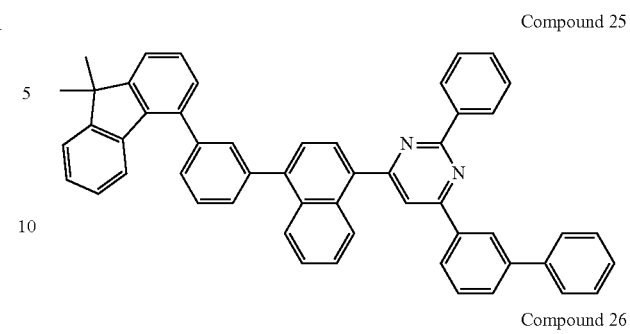
Compound 22
Compound 26
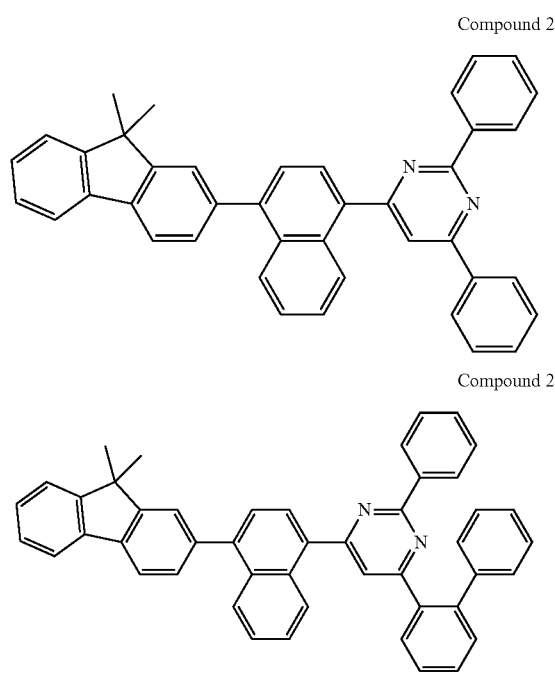
Compound 23
Compound 27
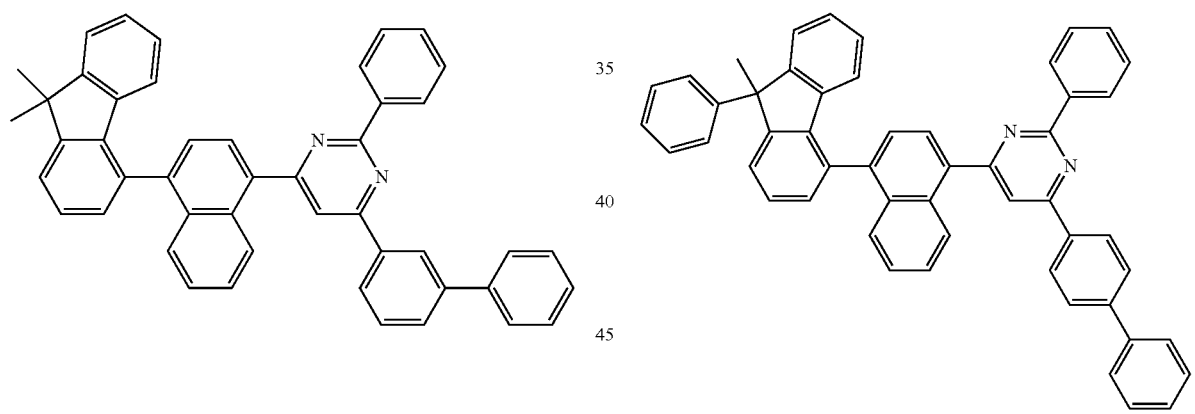
Compound 24
Compound 28
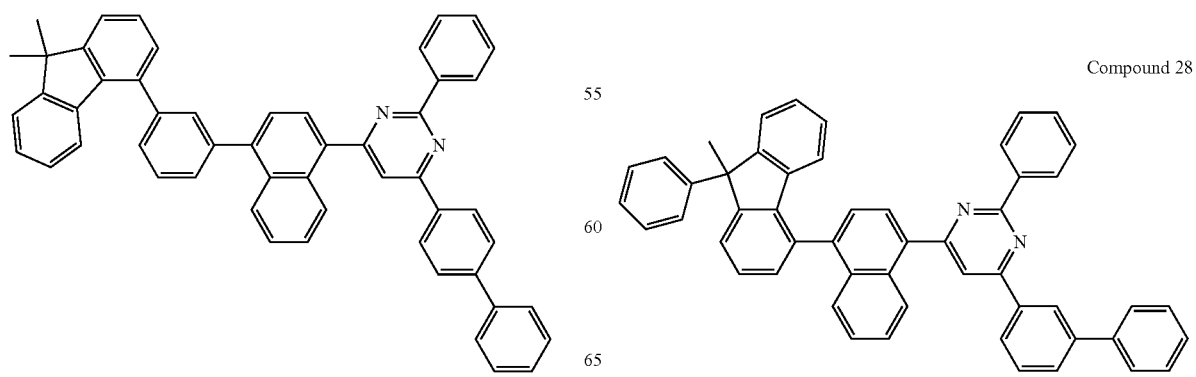

-continued

Compound 29

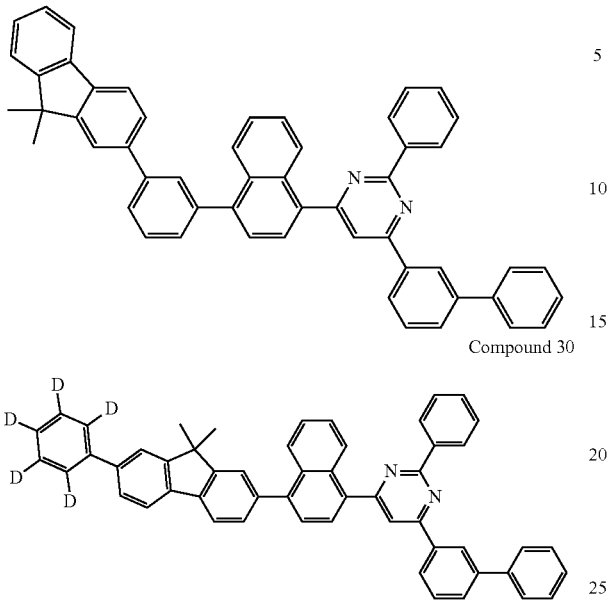

Compound 30

-continued

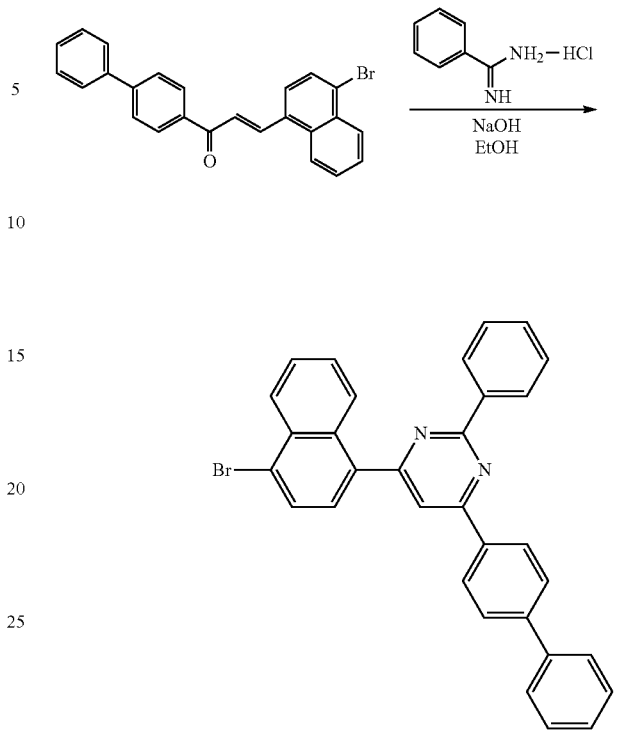

Synthesis Example 1

Synthesis of Compound 1
(1-1) Synthesis of Intermediate A

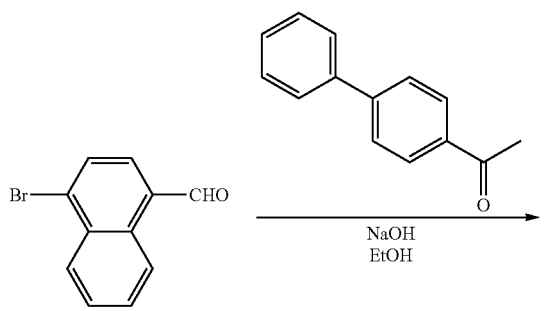

4-Bromo-1-naphthaldehyde (8.0 g), 4-acetylbiphenyl (7.0 g), and sodium hydroxide (0.27 g) were added to 600 mL of ethanol, which were agitated at room temperature for 5 hours. Subsequently, benzamidine hydrochloride (8.0 g) and sodium hydroxide (2.7 g) were added thereto, which were agitated at 70° C. for 5 hours. After completing the reaction, the deposit was filtered and purified by silica gel chromatography (developing solvent: hexane/toluene), so as to provide Intermediate A as a white solid matter (5.0 g, yield: 28%).

(1-2) Synthesis of Compound 1

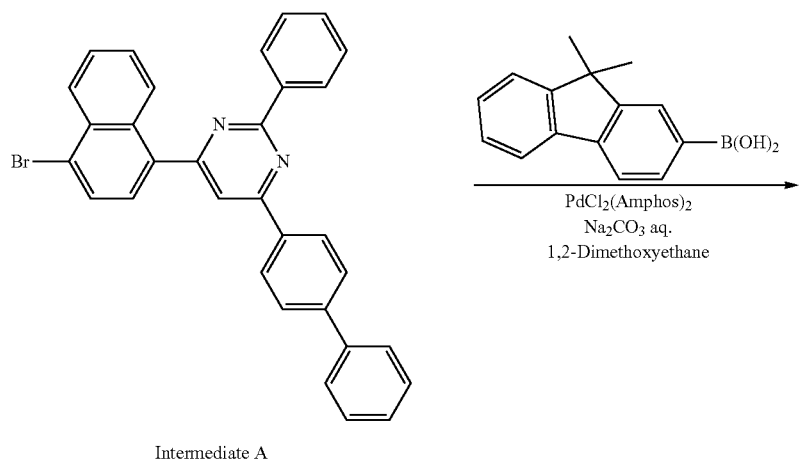

Intermediate A

-continued

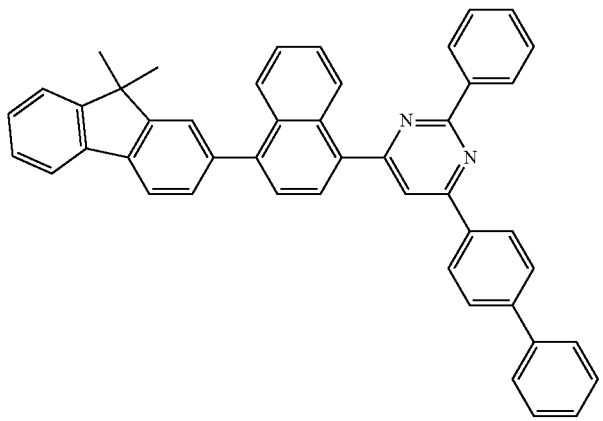

Compound 1

Intermediate A (5.0 g) and 9,9-dimethylfluorene-2-boronic acid (2.8 g) were added to 1,2-dimethoxyethane (100 mL), and argon gas was blown into the solution for 5 minutes. Dichlorobis[di-t-butyl(p-dimethylaminophenyl)phosphino] palladium(II) (PdCl$_2$(Amphos)$_2$) (0.28 g) and a sodium carbonate aqueous solution (2 M, 12 mL) were added thereto, which were heated to 75° C. for 24 hours under an argon atmosphere under agitation. The solvent was distilled off from the reaction solution, and the resulting solid matter was purified by silica gel chromatography (developing solvent: hexane/toluene), so as to provide Compound 1 as a white solid matter (5.0 g, yield: 82%).

The result of mass spectrum analysis was m/e=626 for the molecular weight of 626.80, from which the compound was identified as the target product.

Synthesis Example 2

Synthesis of Compound 2

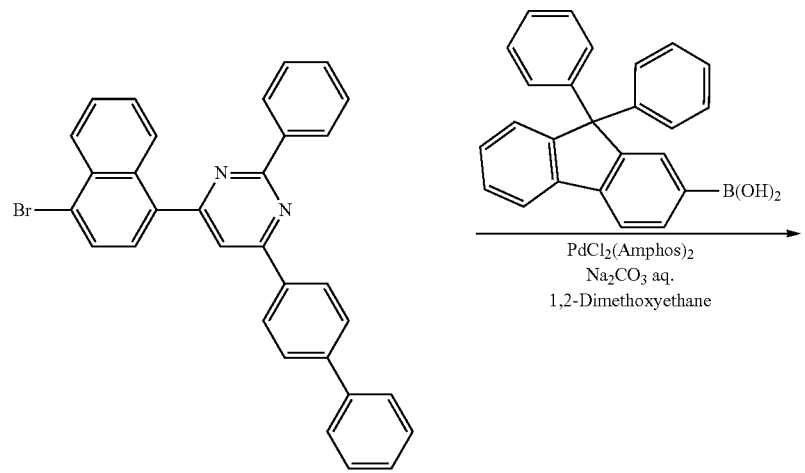

Intermediate A

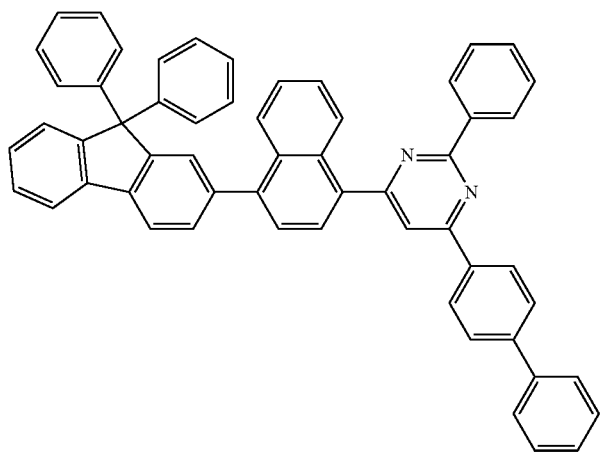

Compound 2

Compound 2 was obtained as a white solid matter (6.7 g, yield: 91%) by using Intermediate A (5.0 g) and 9,9-diphenylfluorene-2-boronic acid (4.2 g) according to the condition described in "(1-2) Synthesis of Compound 1" of Synthesis Example 1.

The result of mass spectrum analysis was m/e=750 for the molecular weight of 750.95, from which the compound was identified as the target product.

Synthesis Example 3

Synthesis of Compound 3

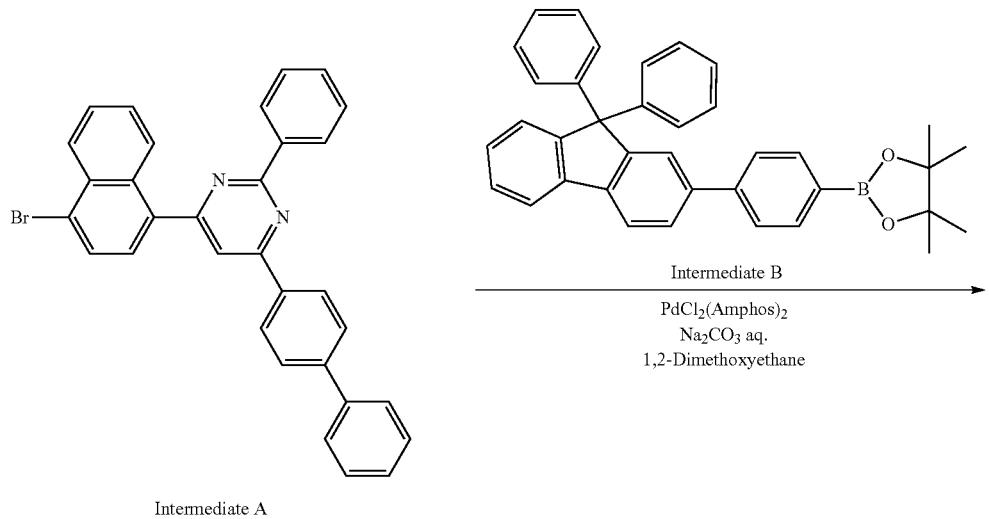

Intermediate A

Intermediate B

PdCl₂(Amphos)₂
Na₂CO₃ aq.
1,2-Dimethoxyethane

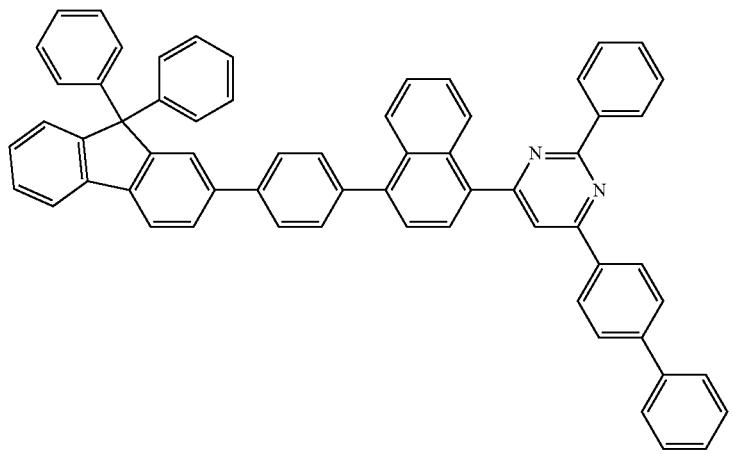

Compound 3

Compound 3 was obtained as a white solid matter (4.5 g, yield: 56%) by using Intermediate A (5.0 g) and Intermediate B synthesized by the method described in KR 10-2015-0137266 A (5.2 g) according to the condition described in "(1-2) Synthesis of Compound 1" of Synthesis Example 1.

The result of mass spectrum analysis was m/e=827 for the molecular weight of 827.04, from which the compound was identified as the target product.

Synthesis Example 4

Synthesis of Compound 4

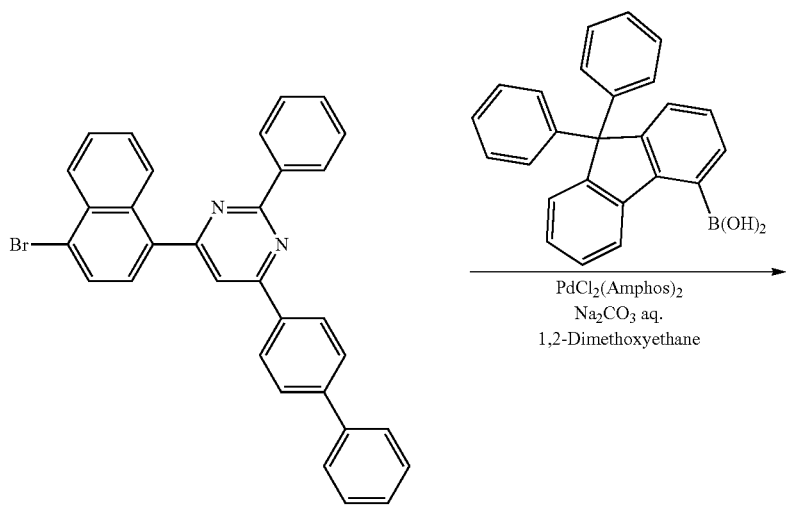

Intermediate A

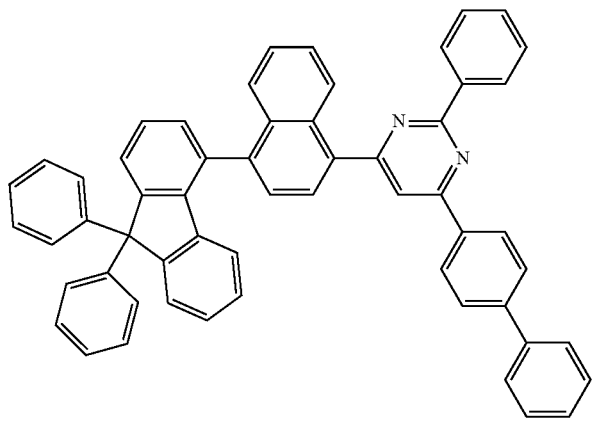

Compound 4

Compound 4 was obtained as a white solid matter (4.0 g, yield: 55%) by using Intermediate A (5.0 g) and 9,9-diphenylfluorene-4-boronic acid (4.2 g) according to the condition described in "(1-2) Synthesis of Compound 1" of Synthesis Example 1.

The result of mass spectrum analysis was m/e=750 for the molecular weight of 750.95, from which the compound was identified as the target product.

Synthesis Example 5

Synthesis of Compound 5

(5-1) Synthesis of Intermediate D

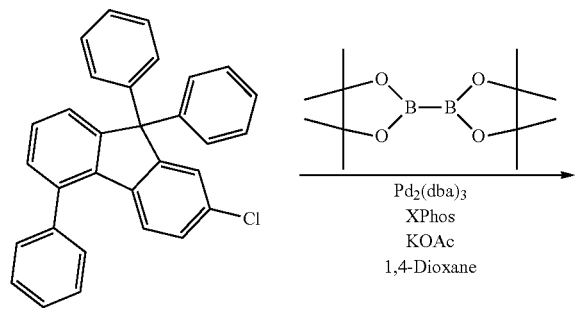

Intermediate C

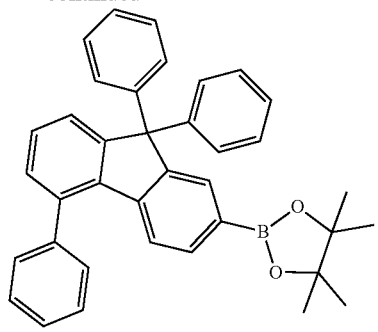

Intermediate D

Intermediate C synthesized by the method described in WO 2019/115577 (5.0 g), bis(pinacolato)diboron (3.6 g), tris(dibenzylideneacetone) dipalladium(0) ($Pd_2(dba)_3$) (0.21 g), 2-dicyclohexylphosphino-2',4',6'-triisopropylbiphenyl (XPhos) (0.45 g), and potassium acetate (2.3 g) were added to 1,4-dioxane (80 mL), and argon gas was blown into the suspension liquid for 5 minutes. The reaction solution was heated to 90° C. for 24 hours under an argon atmosphere under agitation. The solvent was distilled off from the reaction solution, and toluene and water were added thereto, followed by collecting the organic phase. The residue obtained by concentrating the organic phase was subjected to column chromatography, so as to provide Intermediate D (4.5 g, yield: 74%).

(5-2) Synthesis of Compound 5
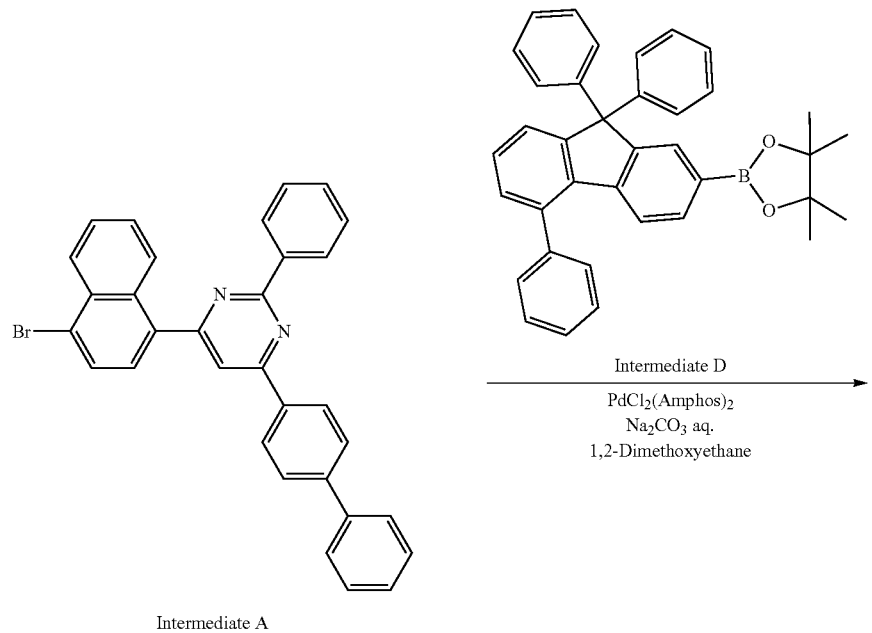
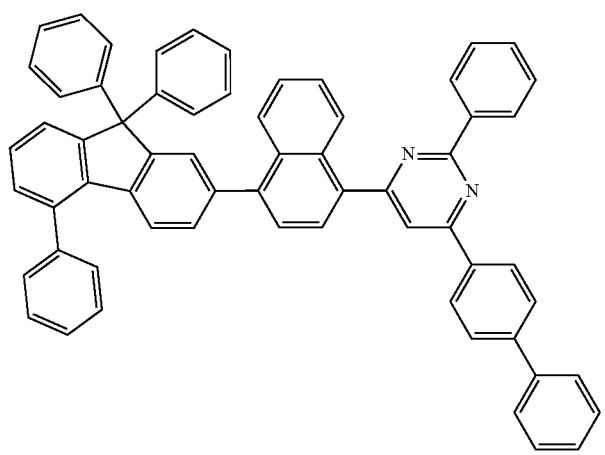
Compound 5

Compound 5 was obtained as a white solid matter (4.4 g, yield: 68%) by using Intermediate A (4.0 g) and Intermediate D (4.2 g) according to the condition described in "(1-2) Synthesis of Compound 1" of Synthesis Example 1.

The result of mass spectrum analysis was m/e=827 for the molecular weight of 827.04, from which the compound was identified as the target product.

Synthesis Example 6

Synthesis of Compound 6
(6-1) Synthesis of Intermediate F

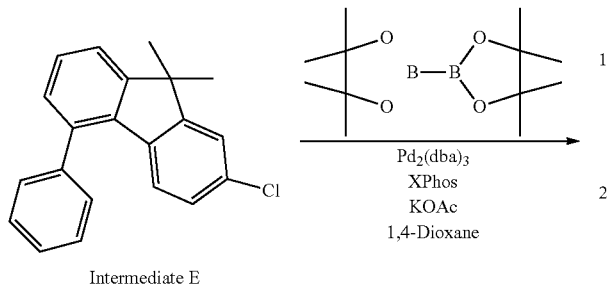

Intermediate E

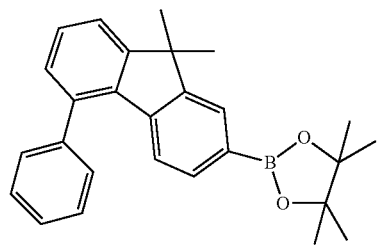

Intermediate F

Intermediate F (4.9 g, yield: 75%) was obtained by using Intermediate E synthesized by the method described in WO 2019/115577 (5.0 g) according to the condition described in "(5-1) Synthesis of Intermediate D" of Synthesis Example 5.

(6-2) Synthesis of Compound 6

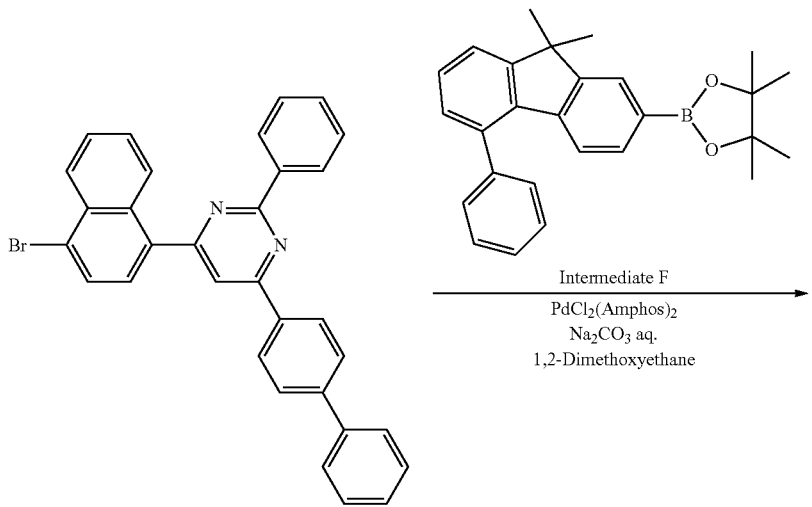

Intermediate A

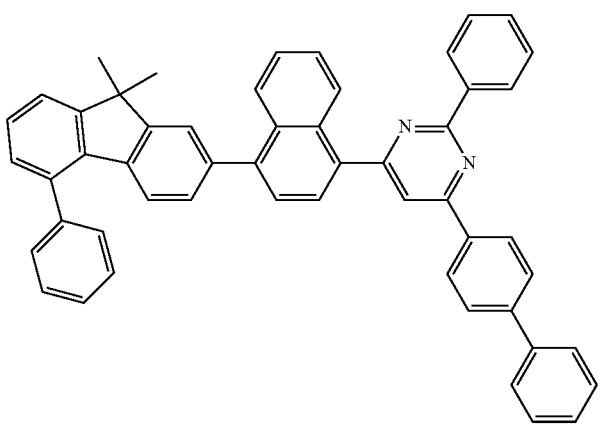

Compound 6

Compound 6 was obtained as a white solid matter (4.1 g, yield: 75%) by using Intermediate A (4.0 g) and Intermediate F (3.2 g) according to the condition described in "(1-2) Synthesis of Compound 1" of Synthesis Example 1.

The result of mass spectrum analysis was m/e=702 for the molecular weight of 702.90, from which the compound was identified as the target product.

Synthesis Example 7

Synthesis of Compound 7
(7-1) Synthesis of Intermediate G

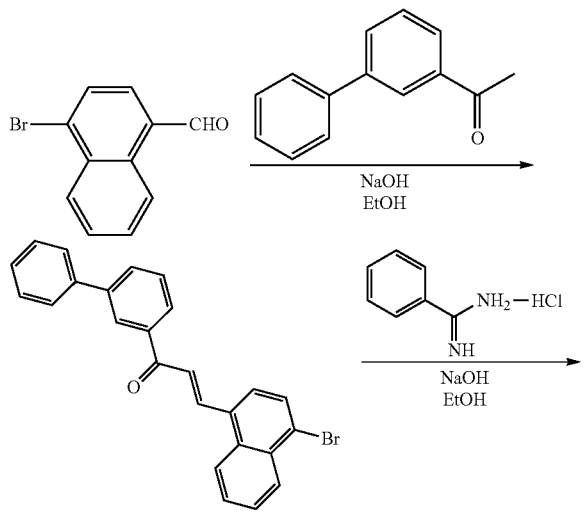

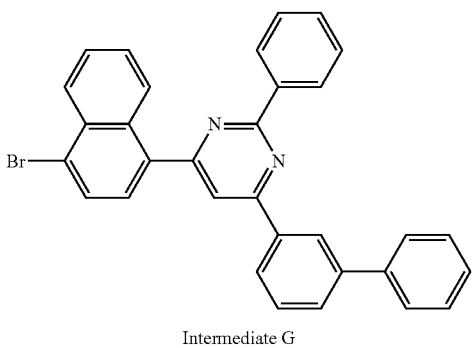

Intermediate G

4-Bromo-1-naphthaldehyde (9.0 g), 3-acetylbiphenyl (7.5 g), and sodium hydroxide (0.15 g) were added to 300 mL of ethanol, which were agitated at room temperature for 5 hours. Subsequently, benzamidine hydrochloride (6.0 g) and sodium hydroxide (1.8 g) were added thereto, which were agitated at 70° C. for 5 hours. After completing the reaction, the deposit was filtered and purified by silica gel chromatography (developing solvent: hexane/toluene), so as to provide Intermediate G as a white solid matter (5.9 g, yield: 30%).

(7-2) Synthesis of Compound 7

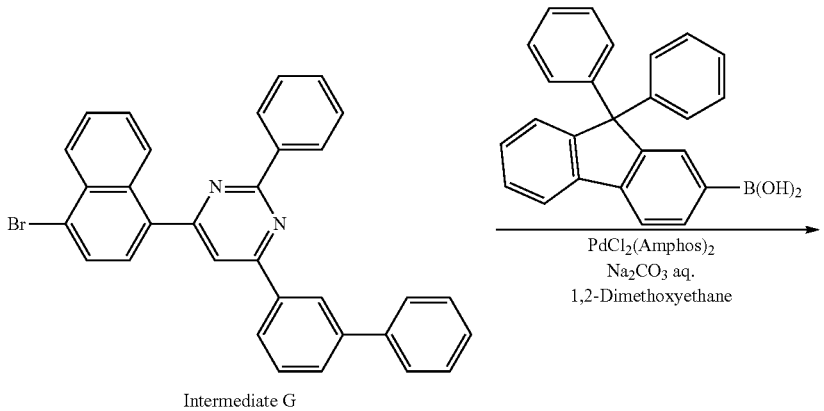

Intermediate G

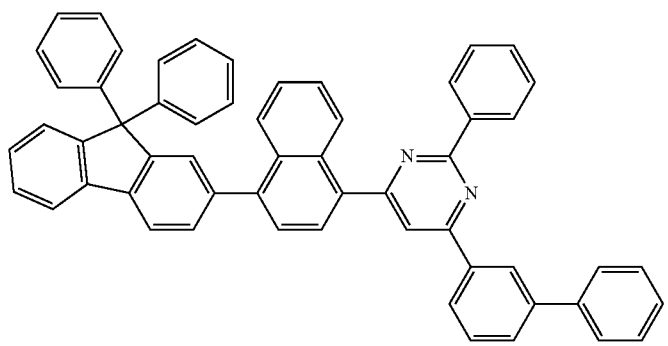

Compound 7

Compound 7 was obtained as a white solid matter (6.1 g, yield: 83%) by using Intermediate G (5.0 g) and 9,9-diphenylfluorene-2-boronic acid (4.2 g) according to the condition described in "(1-2) Synthesis of Compound 1" of Synthesis Example 1.

The result of mass spectrum analysis was m/e=750 for the molecular weight of 750.95, from which the compound was identified as the target product.

Synthesis Example 8

Synthesis of Compound 8

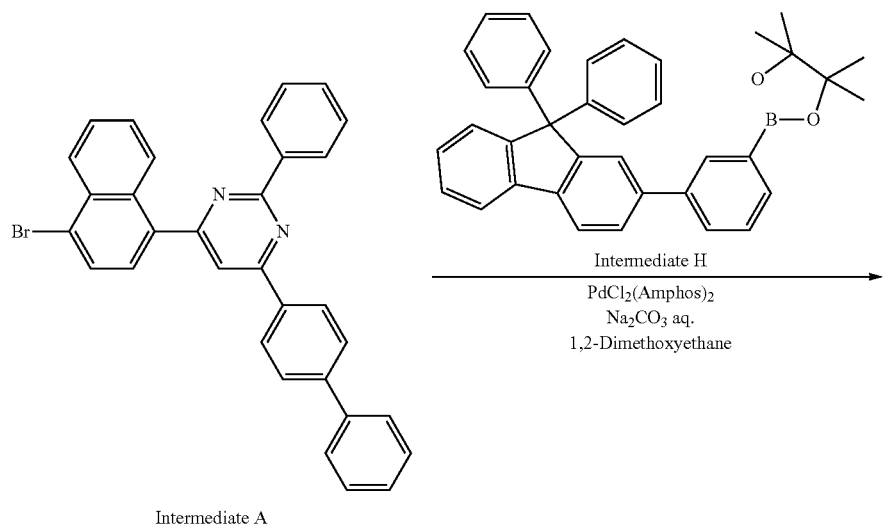

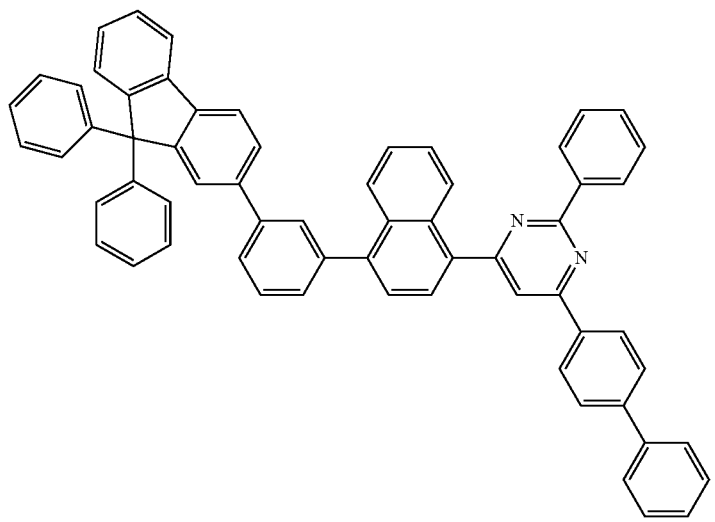

Compound 8

Compound 8 was obtained as a white solid matter (5.8 g, yield: 72%) by using Intermediate A (5.0 g) and Intermediate H (5.2 g) according to the condition described in "(1-2) Synthesis of Compound 1" of Synthesis Example 1.

The result of mass spectrum analysis was m/e=827 for the molecular weight of 827.04, from which the compound was identified as the target product.

Synthesis Example 9

Synthesis of Compound 9

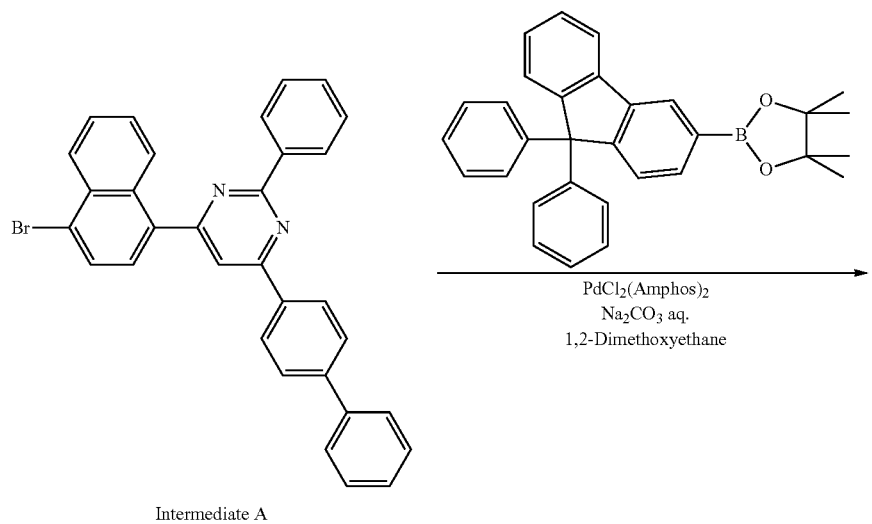

Intermediate A

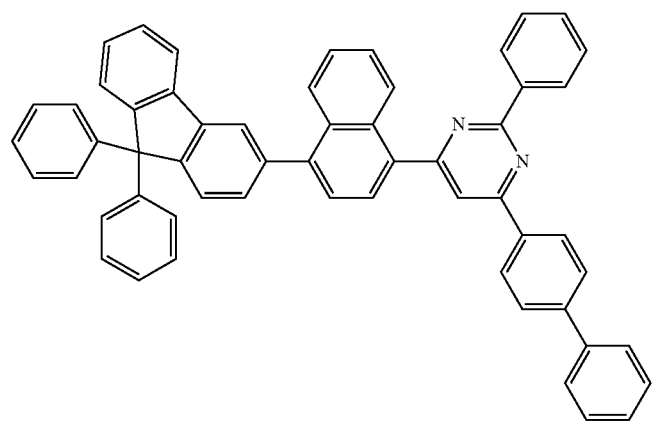

Compound 9

Compound 9 was obtained as a white solid matter (4.74 g, yield: 95%) by using Intermediate A (3.40 g) and 2-(9,9-diphenyl-9H-fluoren-3-yl)-4,4,5,5-tetramethyl-1,3,2-dioxaborolane (3.53 g) according to the condition described in "(1-2) Synthesis of Compound 1" of Synthesis Example 1.

The result of mass spectrum analysis was m/e=751 for the molecular weight of 750.95, from which the compound was identified as the target product.

Synthesis Example 10

Synthesis of Compound 10

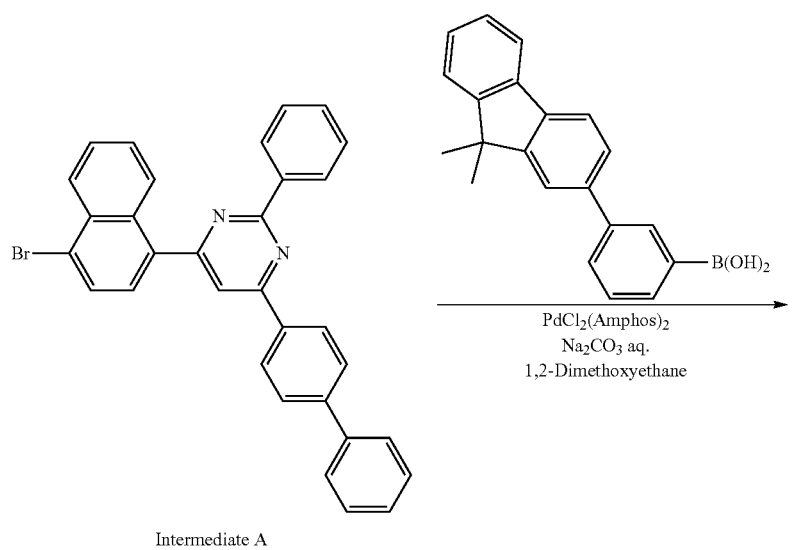

Intermediate A

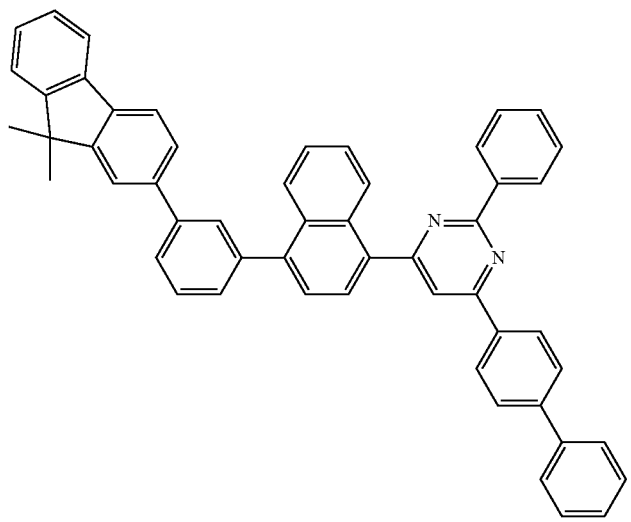

Compound 10

Compound 10 was obtained as a white solid matter (3.95 g, yield: 58%) by using Intermediate A (5.00 g) and [3-(9,9-dimethyl-9H-fluoren-2-yl)phenyl]boronic acid (3.37 g) according to the condition described in "(1-2) Synthesis of Compound 1" of Synthesis Example 1.

The result of mass spectrum analysis was m/e=703 for the molecular weight of 702.901, from which the compound was identified as the target product.

Synthesis Example 11

Synthesis of Compound 11

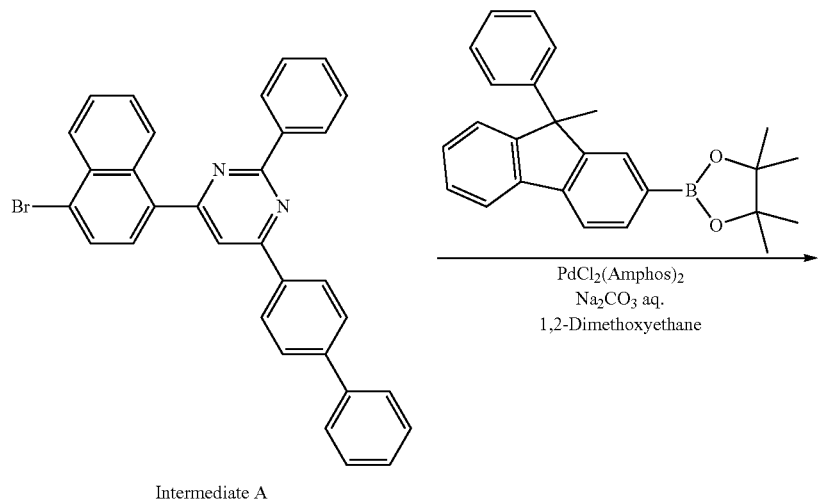

Intermediate A

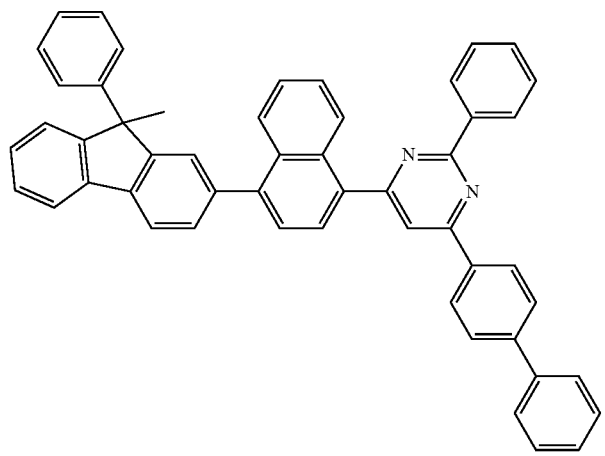

Compound 11

Compound 11 was obtained as a white solid matter (1.56 g, yield: 32%) by using Intermediate A (3.60 g) and 4,4,5,5-tetramethyl-2-(9-methyl-9-phenyl-9H-fluoren-2-yl)-1,3,2-dioxaborolane (3.22 g) according to the condition described in "(1-2) Synthesis of Compound 1" of Synthesis Example 1.

The result of mass spectrum analysis was m/e=689 for the molecular weight of 688.874, from which the compound was identified as the target product.

Synthesis Example 12

Synthesis of Compound 12

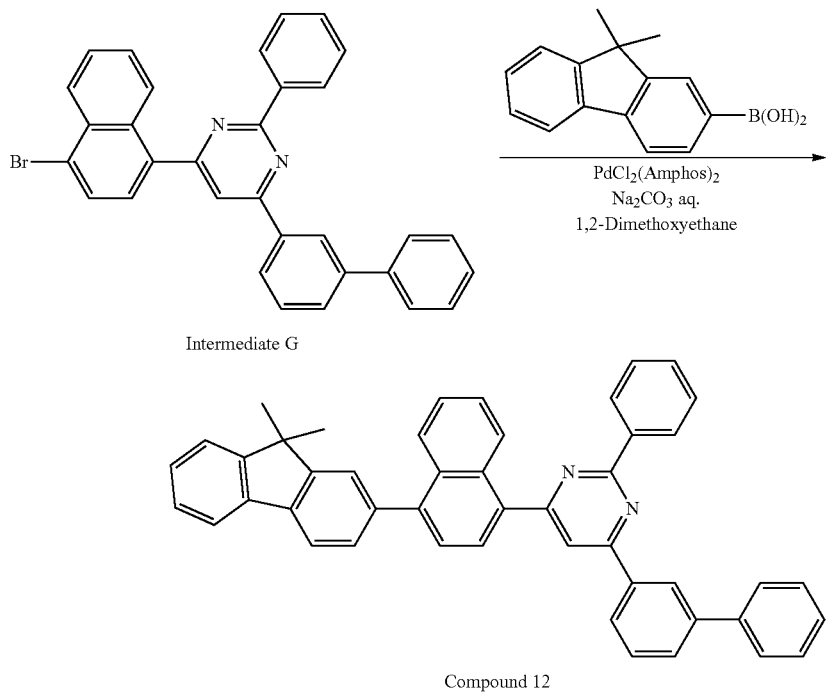

Intermediate G

Compound 12

Compound 12 was obtained as a white solid matter (4.36 g, yield: 71%) by using Intermediate G (5.00 g) and (9,9-dimethyl-9H-fluoren-2-yl)boronic acid (2.55 g) according to the condition described in "(1-2) Synthesis of Compound 1" of Synthesis Example 1.

The result of mass spectrum analysis was m/e=627 for the molecular weight of 626.803, from which the compound was identified as the target product.

Synthesis Example 13

Synthesis of Compound 13

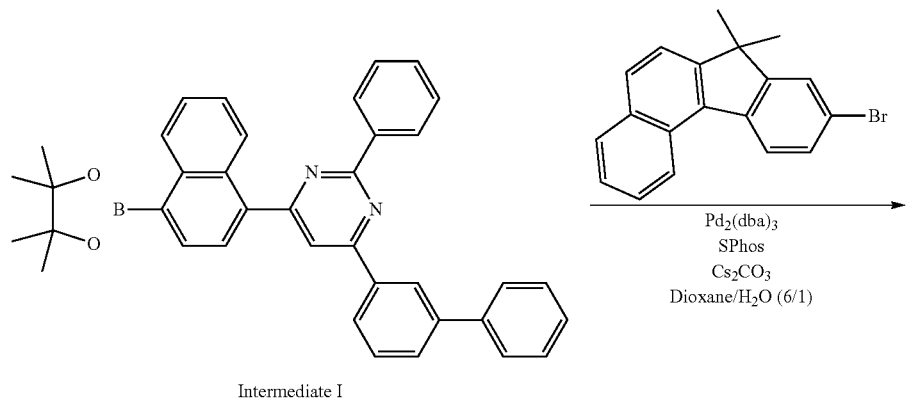

Intermediate I

-continued

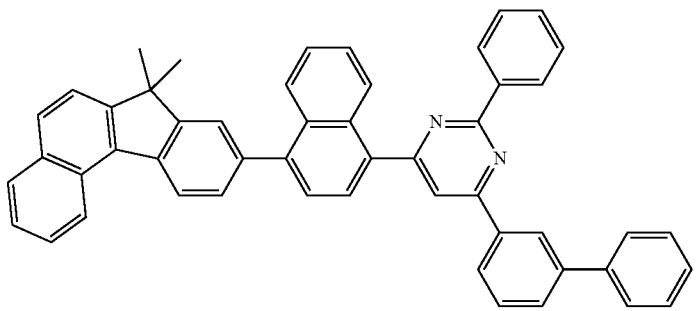

Compound 13

Intermediate I (5.00 g), 9-bromo-7,7-dimethyl-7H-benzo[c]fluorene (3.03 g), $Pd_2(dba)_3$ (0.16 g), SPhos (0.29 g), and cesium carbonate (5.81 g) were placed in a flask, and after purging with argon gas, 1,4-dioxane (38 mL) and $H_2O$ (6.3 mL) were added thereto, followed by heating and agitating at 90° C. for 18 hours. The solvent was distilled off from the reaction solution, and the resulting solid matter was purified by silica gel column chromatography (developing solvent: hexane/toluene) and washed with cyclohexane, so as to provide Compound 13 as a white solid matter (4.45 g, yield: 74%).

The result of mass spectrum analysis was m/e=677 for the molecular weight of 676.863, from which the compound was identified as the target product.

Synthesis Example 14

Synthesis of Compound 14

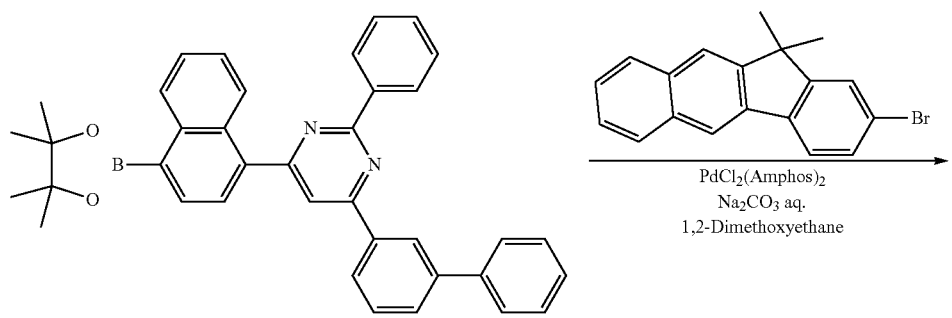

Intermediate I

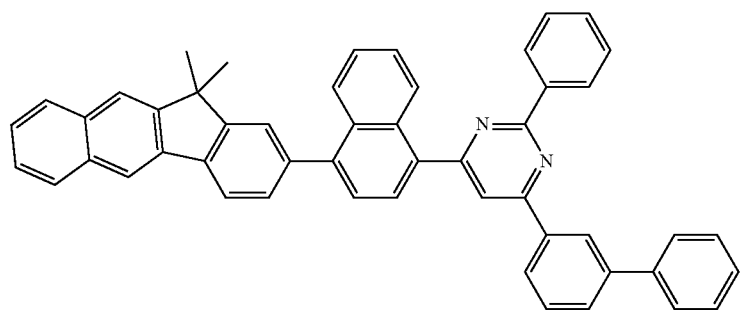

Compound 14

Compound 14 was obtained as a white solid matter (2.91 g, yield: 48%) by using Intermediate I (5.00 g) and 2-bromo-11,11-dimethyl-11H-benzo[b]fluorene (3.17 g) according to the condition described in "(1-2) Synthesis of Compound 1" of Synthesis Example 1.

The result of mass spectrum analysis was m/e=677 for the molecular weight of 676.863, from which the compound was identified as the target product.

Synthesis Example 15

Synthesis of Compound 15

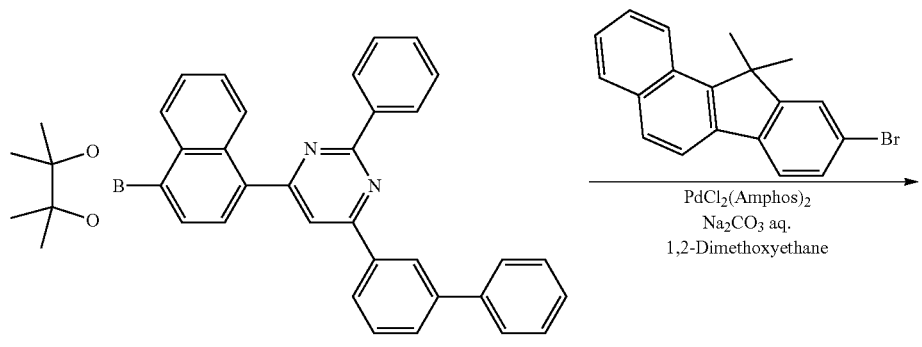

Intermediate I

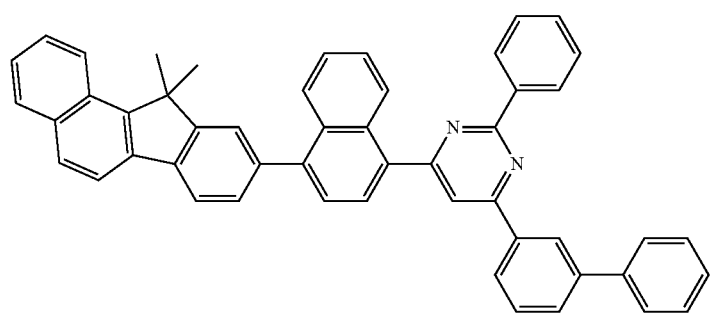

Compound 15

Compound 15 was obtained as a white solid matter (3.77 g, yield: 62%) by using Intermediate I (5.00 g) and 9-bromo-11,11-dimethyl-11H-benzo[a]fluorene (3.17 g) according to the condition described in "(1-2) Synthesis of Compound 1" of Synthesis Example 1.

The result of mass spectrum analysis was m/e=677 for the molecular weight of 676.863, from which the compound was identified as the target product.

Synthesis Example 16

Synthesis of Compound 16

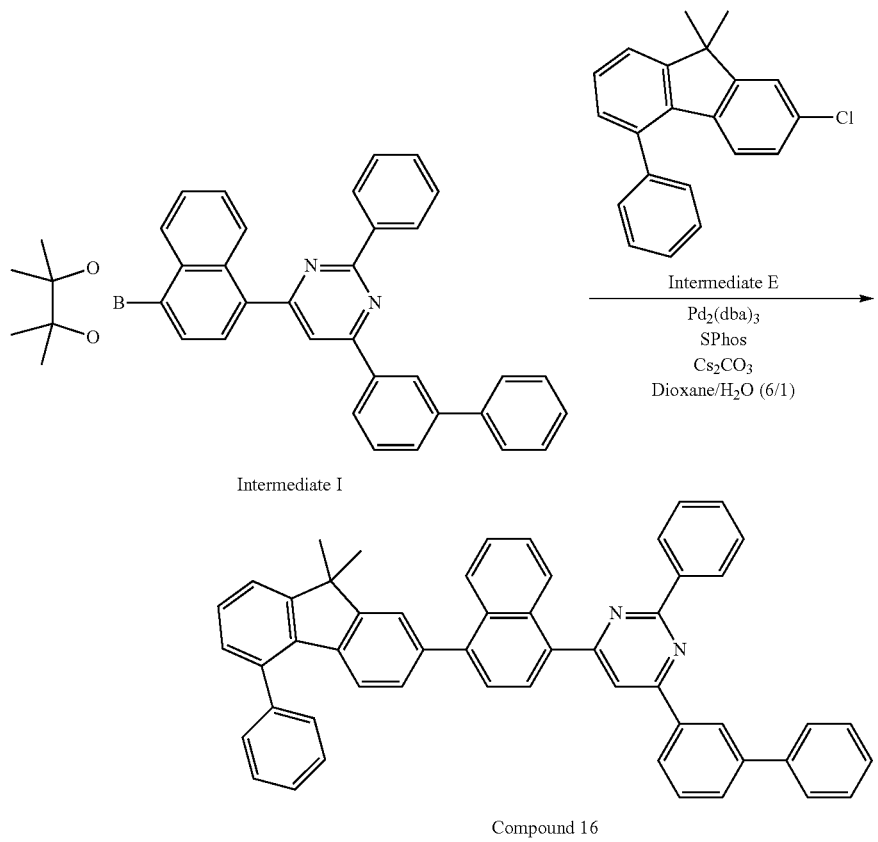

Compound 16 was obtained as a white solid matter (4.51 g, yield: 59%) by using Intermediate I (5.50 g) and 2-chloro-9,9-dimethyl-5-phenyl-9H-fluorene (3.14 g) according to the condition described in "Synthesis of Compound 13" of Synthesis Example 13.

The result of mass spectrum analysis was m/e=703 for the molecular weight of 702.901, from which the compound was identified as the target product.

Synthesis Example 17

Synthesis of Compound 17

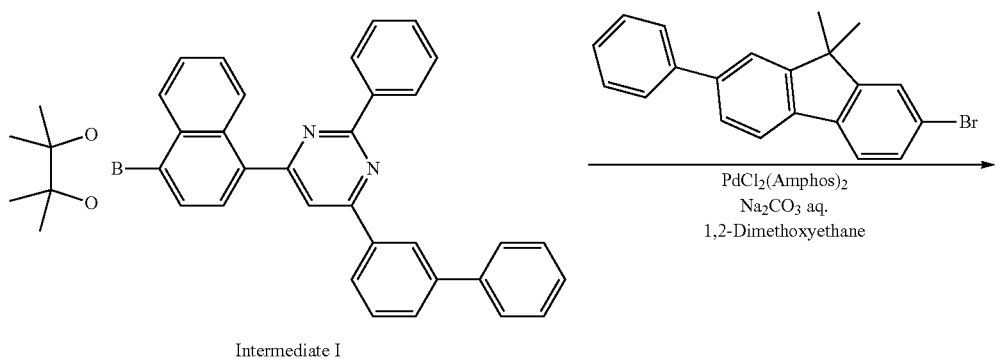

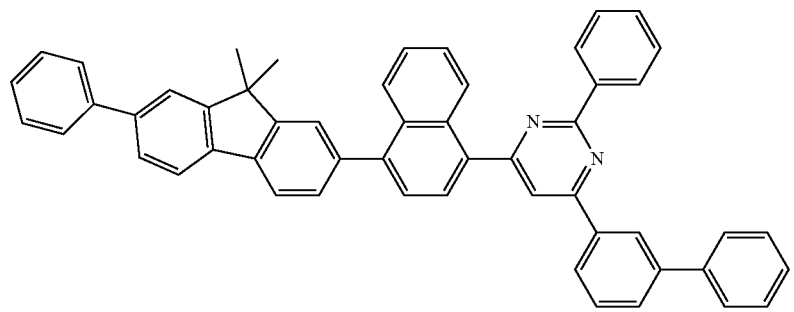

Compound 17

Compound 17 was obtained as a white solid matter (3.79 g, yield: 54%) by using Intermediate I (5.61 g) and 2-bromo-9,9-dimethyl-7-phenyl-9H-fluorene (3.84 g) according to the condition described in "(1-2) Synthesis of Compound 1" of Synthesis Example 1.

The result of mass spectrum analysis was m/e=703 for the molecular weight of 702.901, from which the compound was identified as the target product.

Synthesis Example 18

Synthesis of Compound 18

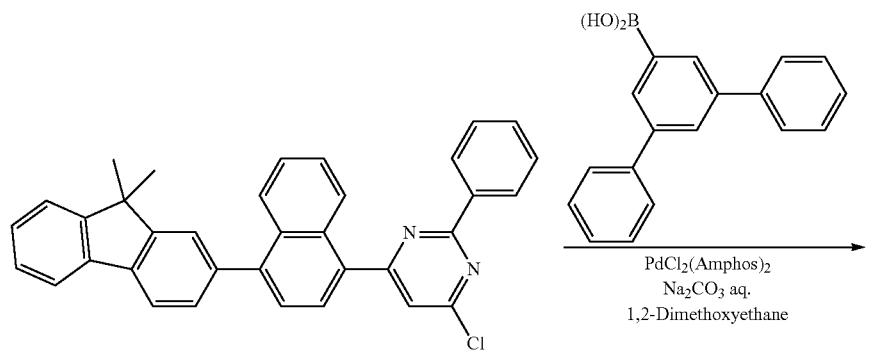

Intermediate J

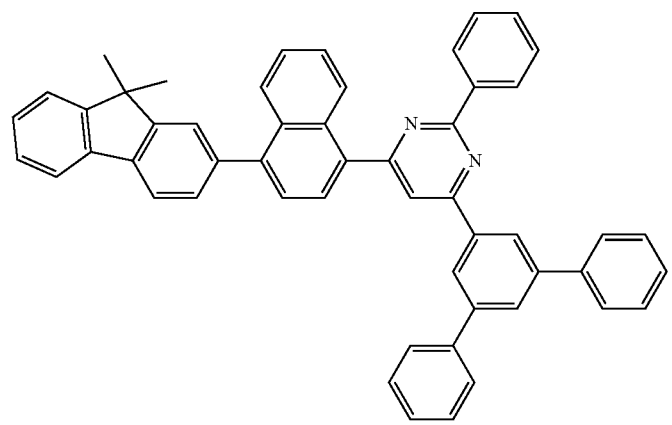

Compound 18

Compound 18 was obtained as a white solid matter (4.77 g, yield: 86%) by using Intermediate J (4.00 g) and (3,5-diphenylphenyl)boronic acid (2.37 g) according to the condition described in "(1-2) Synthesis of Compound 1" of Synthesis Example 1.

The result of mass spectrum analysis was m/e=703 for the molecular weight of 702.901, from which the compound was identified as the target product.

Synthesis Example 19

Synthesis of Compound 19

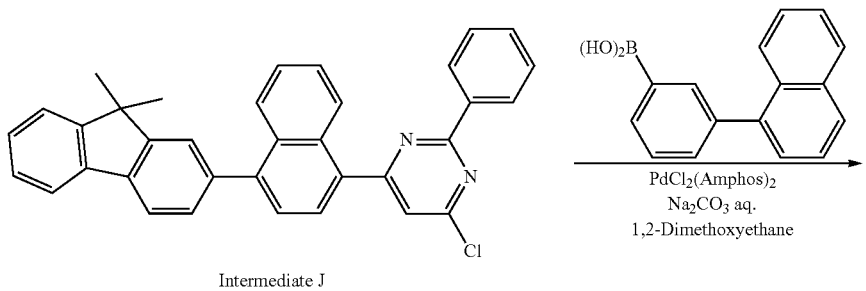

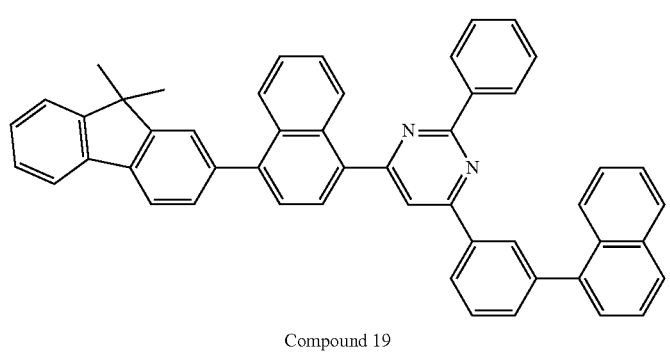

Compound 19

Compound 19 was obtained as a white solid matter (5.02 g, yield: 94%) by using Intermediate J (4.00 g) and [3-(naphthalen-1-yl)phenyl]boronic acid (2.14 g) according to the condition described in "(1-2) Synthesis of Compound 1" of Synthesis Example 1.

The result of mass spectrum analysis was m/e=677 for the molecular weight of 676.863, from which the compound was identified as the target product.

Synthesis Example 20

Synthesis of Compound 20

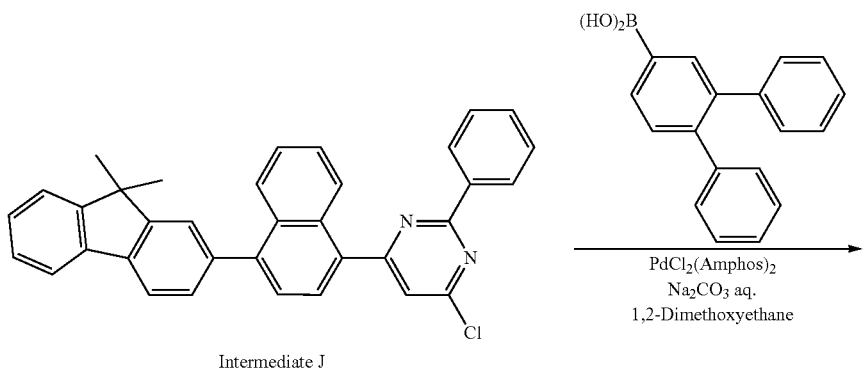

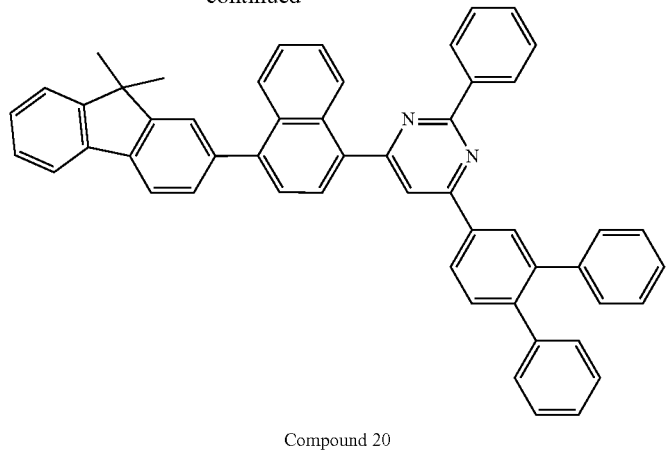

Compound 20

Compound 20 was obtained as a white solid matter (4.84 g, yield: 88%) by using Intermediate J (4.00 g) and [1,1':2,1''-terphenyl]-4-boronic acid (2.37 g) according to the condition described in "(1-2) Synthesis of Compound 1" of Synthesis Example 1.

The result of mass spectrum analysis was m/e=703 for the molecular weight of 702.901, from which the compound was identified as the target product.

Synthesis Example 21

Synthesis of Compound 21

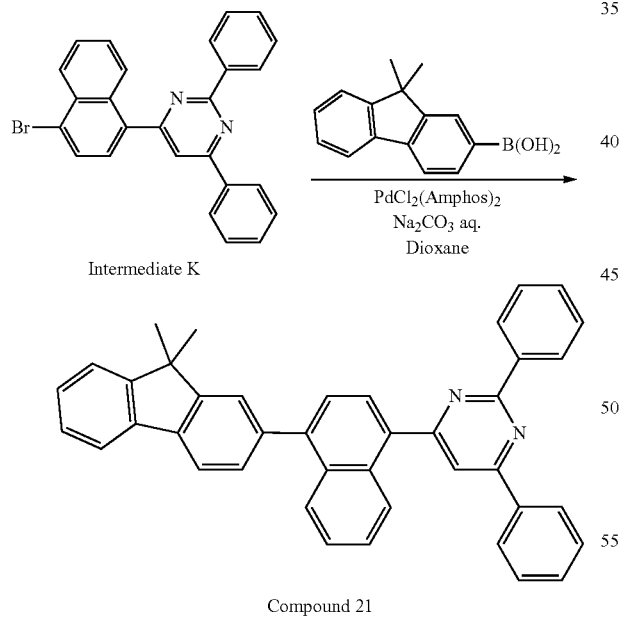

Compound 21

Compound 21 was obtained as a white solid matter (4.84 g, yield: 88%) by using Intermediate K (6.00 g) and 9,9-dimethylfluorene-2-boronic acid (4.25 g) according to the condition described in "(1-2) Synthesis of Compound 1" of Synthesis Example 1.

The result of mass spectrum analysis was m/e=551 for the molecular weight of 550.705, from which the compound was identified as the target product.

Synthesis Example 22

Synthesis of Compound 22

(22-1) Synthesis of Intermediate L

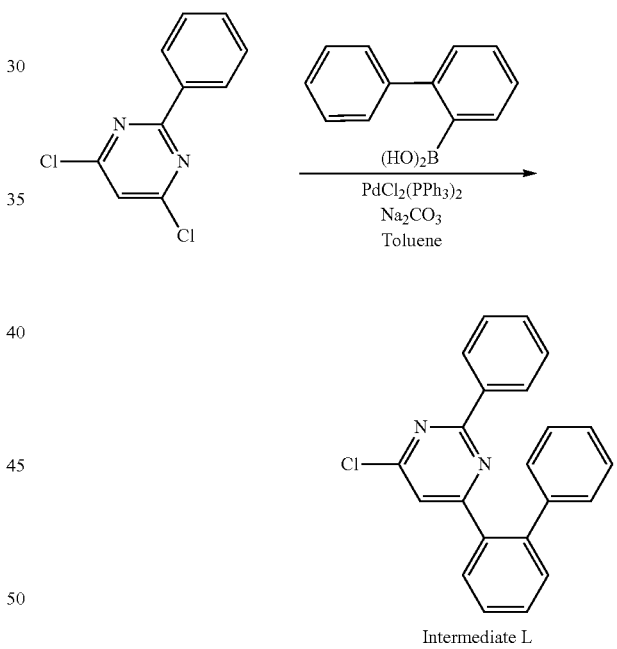

Intermediate L

A reaction vessel having added therein 4,6-dichloro-2-phenylpyrimidine (17.0 g), 2-biphenylboronic acid (19.4 g), and $PdCl_2(PPh_3)_2$ (1.3 g) was purged with argon, to which 755 mL of toluene and a sodium carbonate aqueous solution (2 M, 113 mL) were added, and the mixture was heated to 86° C. for 6 hours under agitation. After distilling off the solvent from the reaction solution, methanol was added thereto to deposit a solid matter, which was collected by filtering and washed with methanol and water. The resulting solid matter was purified by silica gel column chromatography (developing solvent: hexane/dichloromethane), so as to provide Intermediate L as a white solid matter (20.1 g, yield: 71%).

(22-2) Synthesis of Intermediate M

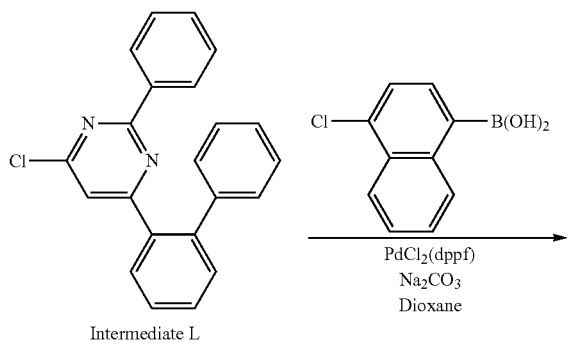

Intermediate L

Intermediate M

A reaction vessel having added therein Intermediate L (6.0 g), 9,9-dimethylfluorene-2-boronic acid (3.73 g), Pd$_2$(dba)$_3$ (0.22 g), and SPhos (0.40 g) was purged with argon, to which 120 mL of dioxane and a sodium carbonate aqueous solution (2 M, 15 mL) were added, and the mixture was heated to 80° C. for 7 hours under agitation. After distilling off the solvent from the reaction solution, the residue was purified by silica gel column chromatography (developing solvent: hexane/dichloromethane), so as to provide Intermediate M as a white solid matter (5.65 g, yield: 69%).

(22-3) Synthesis of Compound 22

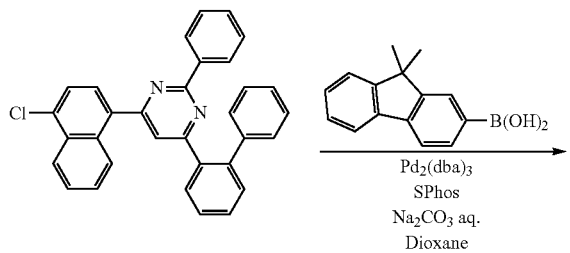

Compound 22

A reaction vessel having added therein Intermediate M (5.65 g), (4-chloronaphthalen-1-yl)boronic acid (3.8 g), PdCl$_2$(dppf) (0.52 g) was purged with argon, to which 175 mL of dioxane and a sodium carbonate aqueous solution (2 M, 22 mL) were added, and the mixture was heated to 86° C. for 7 hours under agitation. After distilling off the solvent from the reaction solution, the residue was purified by silica gel column chromatography (developing solvent: hexane/dichloromethane) and recrystallization from ethyl acetate and hexane, so as to provide Compound 22 as a white solid matter (5.83 g, yield: 77%).

The result of mass spectrum analysis was m/e=627 for the molecular weight of 626.80, from which the compound was identified as the target product.

Synthesis Example 23

Synthesis of Compound 23

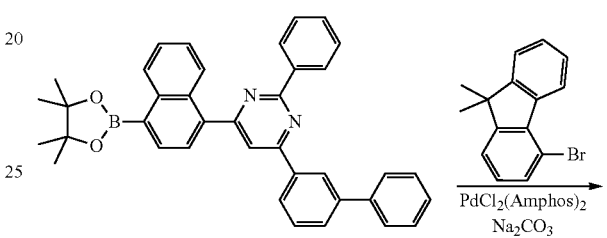

Intermediate 1

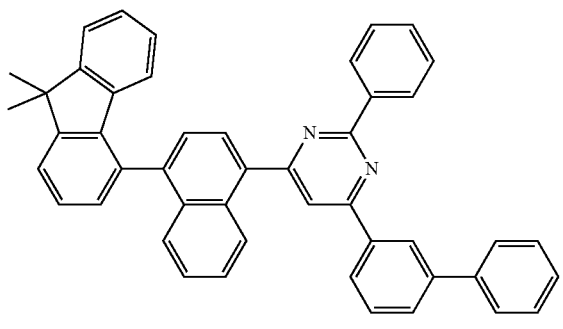

Compound 23

Compound 23 was obtained as a white solid matter (4.74 g, yield: 70%) by using Intermediate I (6.00 g) and 4-bromo-9,9-dimethyl-9H-fluorene (3.80 g) according to the condition described in "(1-2) Synthesis of Compound 1" of Synthesis Example 1.

The result of mass spectrum analysis was m/e=627 for the molecular weight of 626.80, from which the compound was identified as the target product.

Synthesis Example 24

Synthesis of Compound 24
(24-1) Synthesis of Intermediate N

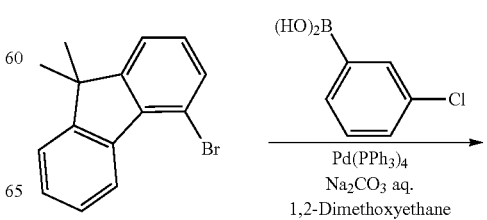

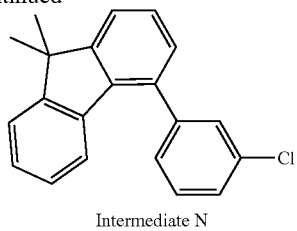

Intermediate N

A reaction vessel having added therein 4-bromo-9,9-dimethyl-9H-fluorene (10.0 g), (3-chlorophenyl)boronic acid (5.8 g), and Pd(PPh$_3$)$_4$ (0.85 g) was purged with argon, to which 366 mL of 1,2-dimethoxyethane and a sodium carbonate aqueous solution (2 M, 55 mL) were added, and the mixture was heated while refluxing for 7 hours under agitation. After distilling off the solvent from the reaction solution, methanol was added thereto to deposit a solid matter, which was collected by filtering. The resulting solid matter was purified by silica gel column chromatography (developing solvent: hexane/dichloromethane), so as to provide Intermediate N as a white solid matter (8.33 g, yield: 75%).

(24-2) Synthesis of Compound 24

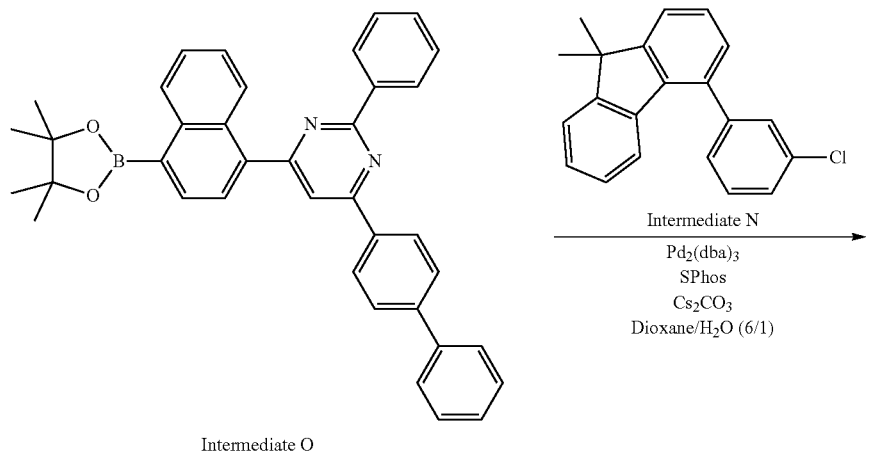

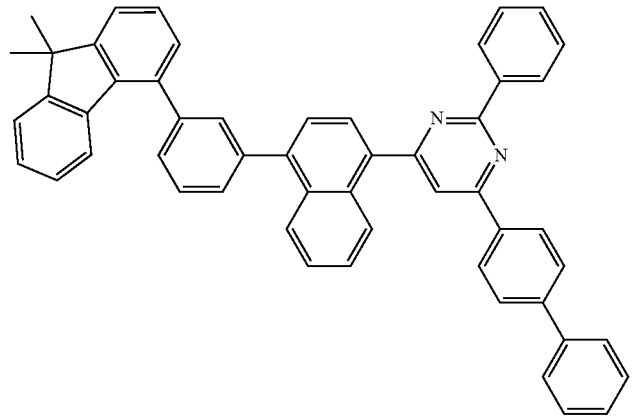

Compound 24

Compound 24 was obtained as a white solid matter (4.68 g, yield: 66%) by using Intermediate O (5.61 g) and Intermediate N (3.66 g) according to the condition described in "Synthesis of Compound 13" of Synthesis Example 13.

The result of mass spectrum analysis was m/e=703 for the molecular weight of 702.91, from which the compound was identified as the target product.

Synthesis Example 25

Synthesis of Compound 25

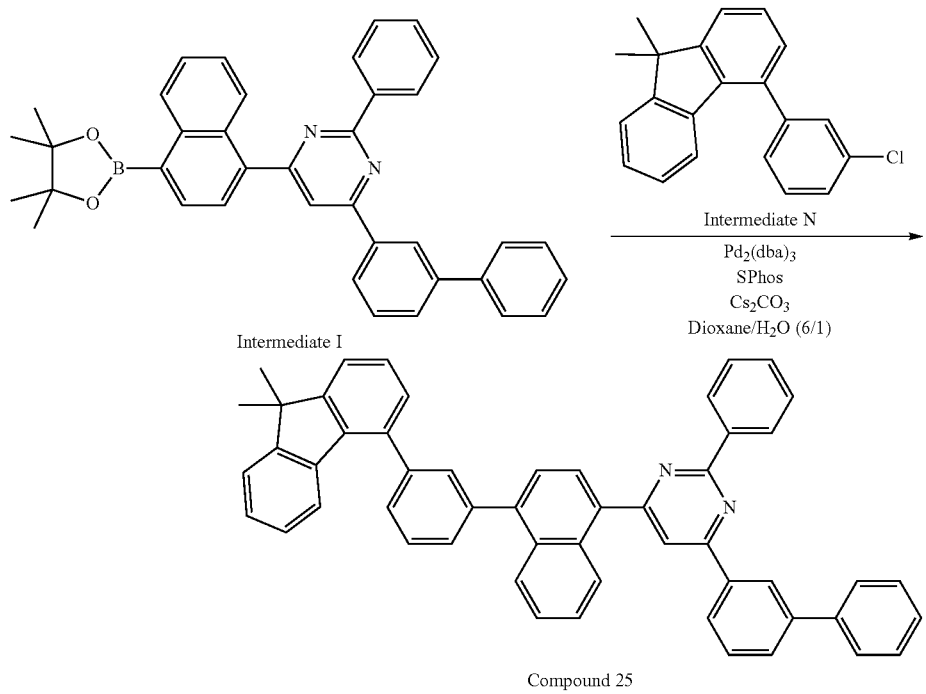

Compound 25 was obtained as a white solid matter (4.64 g, yield: 82%) by using Intermediate I (4.50 g) and Intermediate N (2.94 g) according to the condition described in "Synthesis of Compound 13" of Synthesis Example 13.

The result of mass spectrum analysis was m/e=703 for the molecular weight of 702.91, from which the compound was identified as the target product.

Synthesis Example 26

Synthesis of Compound 26

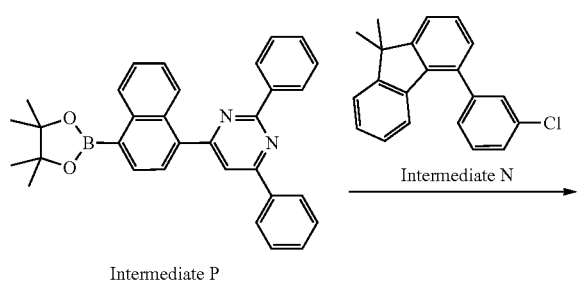

-continued

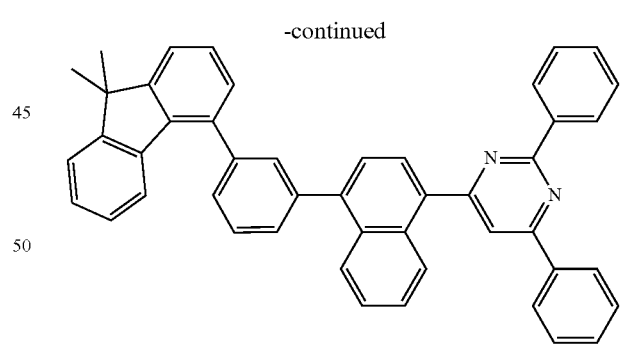

Compound 26 was obtained as a white solid matter (4.91 g, yield: 84%) by using Intermediate P (4.50 g) and Intermediate N (3.68 g) according to the condition described in "Synthesis of Compound 13" of Synthesis Example 13.

The result of mass spectrum analysis was m/e=627 for the molecular weight of 626.80, from which the compound was identified as the target product.

Synthesis Example 27

Synthesis of Compound 27

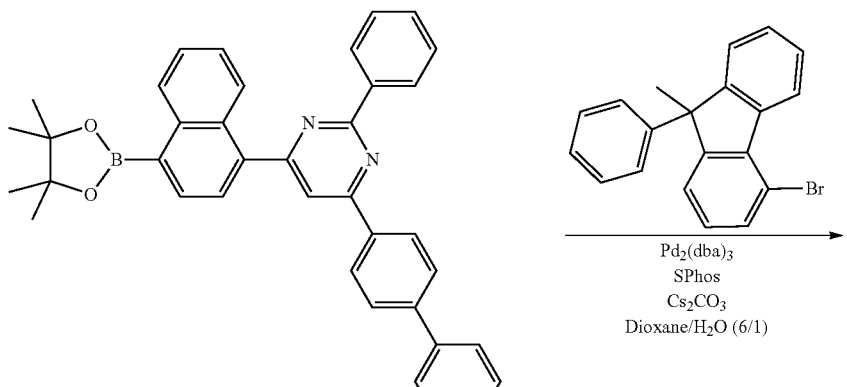

Intermediate O

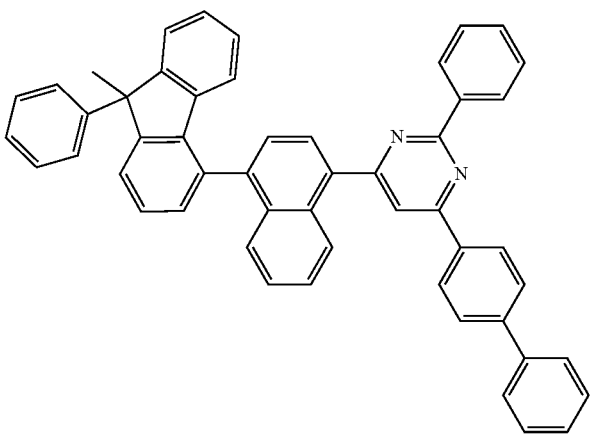

Compound 27

Compound 27 was obtained as a white solid matter (3.16 g, yield: 46%) by using Intermediate O (5.61 g) and 4-bromo-9-methyl-9-phenyl-9H-fluorene (4.02 g) according to the condition described in "Synthesis of Compound 13" of Synthesis Example 13.

The result of mass spectrum analysis was m/e=689 for the molecular weight of 688.87, from which the compound was identified as the target product.

Synthesis Example 28

Synthesis of Compound 28

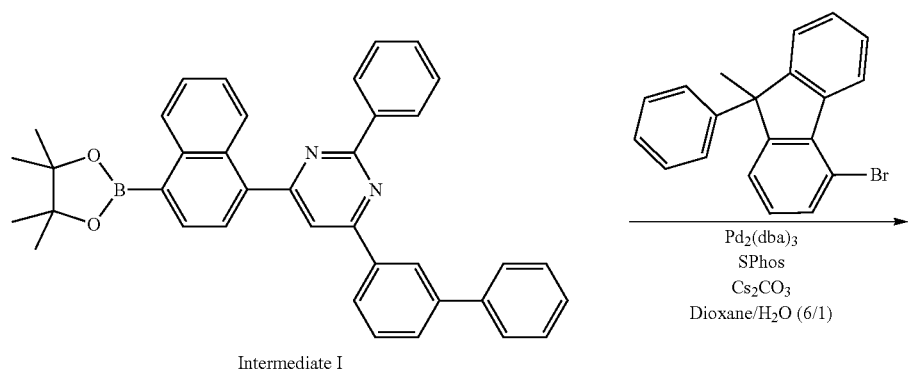

Intermediate I

-continued

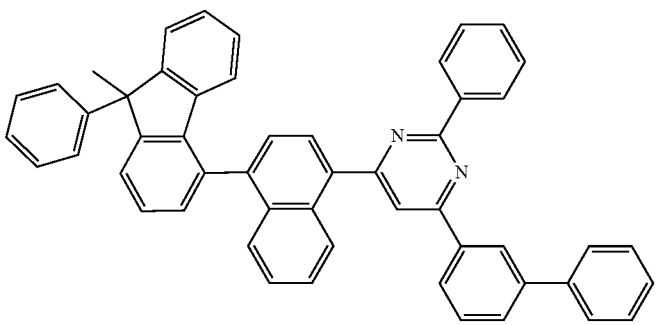

Compound 28

Compound 28 was obtained as a white solid matter (1.87 g, yield: 27%) by using Intermediate I (5.61 g) and 4-bromo-9-methyl-9-phenyl-9H-fluorene (4.02 g) according to the condition described in "Synthesis of Compound 13" of Synthesis Example 13.

The result of mass spectrum analysis was m/e=689 for the molecular weight of 688.87, from which the compound was identified as the target product.

Synthesis Example 29

Synthesis of Compound 29

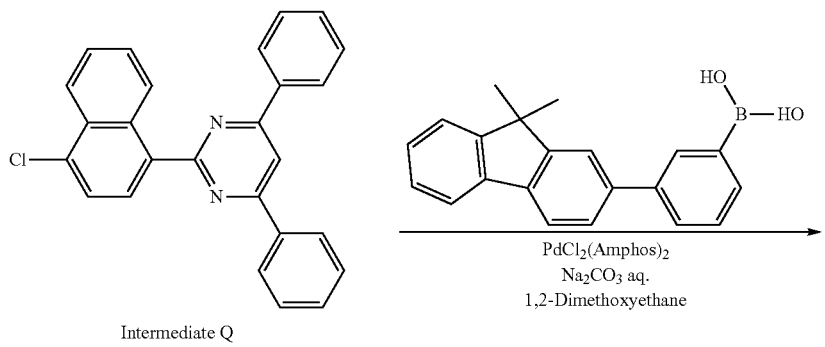

Intermediate Q

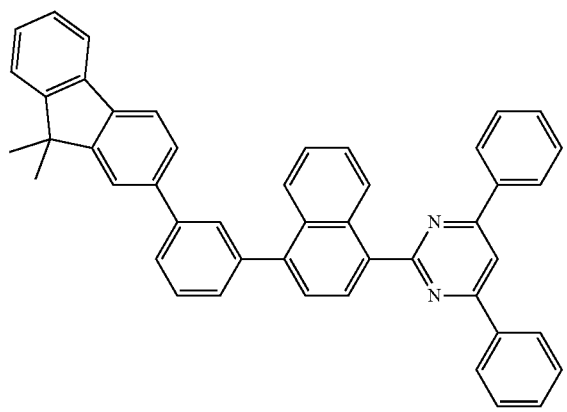

Compound 29

Compound 29 was obtained as a white solid matter (6.2 g, yield: 78%) by using Intermediate Q (5.00 g) and B-[3-(9,9-dimethyl-9H-fluoren-2-yl)phenyl]boronic acid (4.4 g) according to the condition described in "(1-2) Synthesis of Compound 1" of Synthesis Example 1.

The result of mass spectrum analysis was m/e=627 for the molecular weight of 626.8, from which the compound was identified as the target product.

Synthesis Example 30

Synthesis of Compound 30

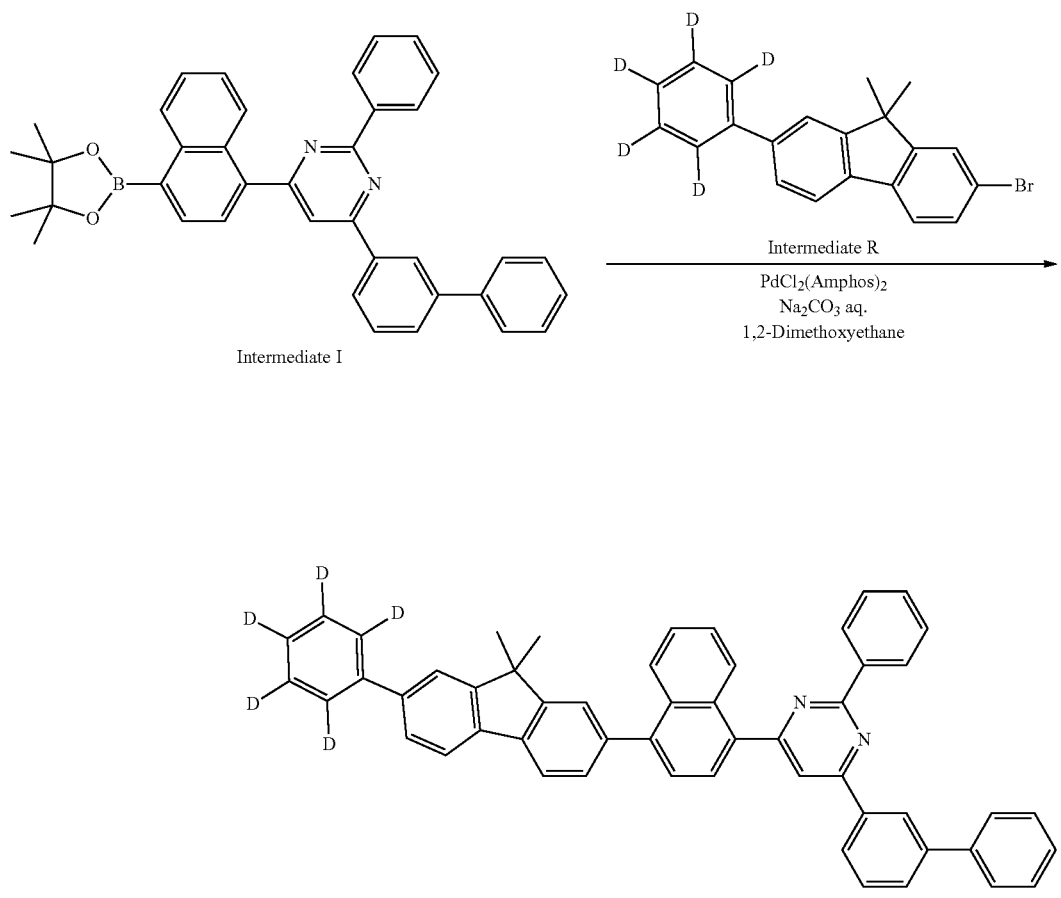

Compound 30 was obtained as a white solid matter (4.31 g, yield: 62%) by using Intermediate I (5.50 g) and Intermediate R (4.17 g) according to the condition described in "(1-2) Synthesis of Compound 1" of Synthesis Example 1.

The result of mass spectrum analysis was m/e=708 for the molecular weight of 707.93, from which the compound was identified as the target product.

REFERENCE SIGN LIST

1, 11: Organic EL device
2: Substrate
3: Anode
4: Cathode
5: Light emitting layer
6: Hole transporting zone (hole transporting layer)
6a: Hole injecting layer
6b: First hole transporting layer
6c: Second hole transporting layer
7: Electron transporting zone (electron transporting layer)
7a: First electron transporting layer
7b: Second electron transporting layer
10, 20: Light emitting unit

The invention claimed is:
1. An organic electroluminescent device, comprising:
   an anode;
   a cathode; and
   a plurality of organic layers intervening between the anode and the cathode and comprising a light emitting layer,
   wherein at least one layer of the organic layers includes at least one compound selected from the group consisting of formulae,

Compound 4

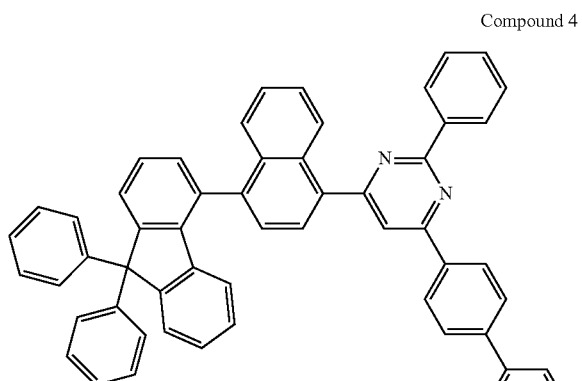

Compound 23

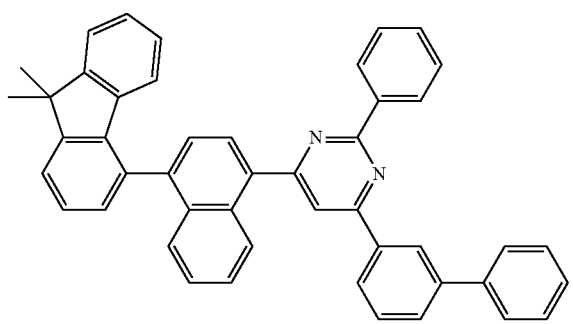

Compound 24

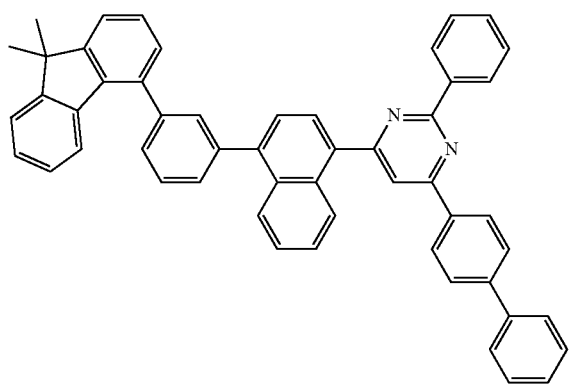

Compound 25

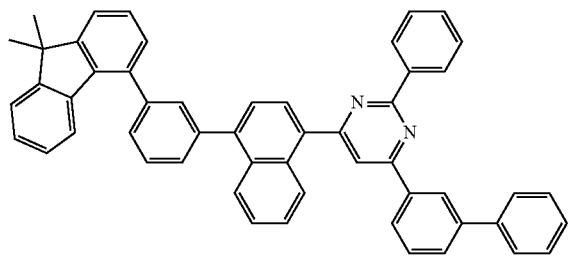

Compound 27

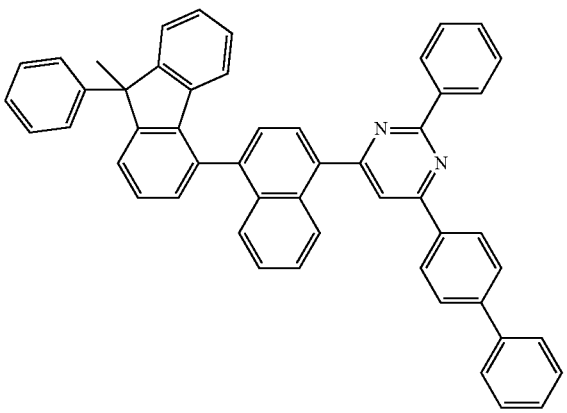

Compound 28

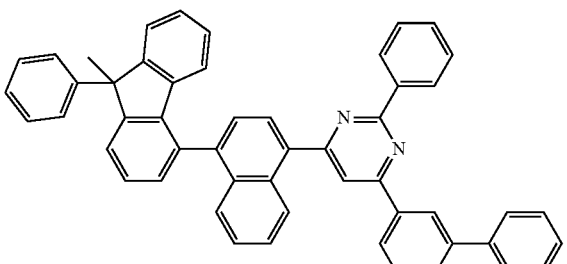

2. The organic electroluminescent device according to claim 1, wherein the organic layers include an electron transporting zone intervening between the cathode and the light emitting layer, and the electron transporting zone comprises the compound.

3. The organic electroluminescent device according to claim 2, wherein the electron transporting zone includes a first electron transporting layer on an anode side and a second electron transporting layer on a cathode side, and the first electron transporting layer, the second electron transporting layer, or both thereof comprises the compound.

4. The organic electroluminescent device according to claim 2, wherein the electron transporting zone further includes a hole blocking layer on a cathode side, and the hole blocking layer comprises the compound.

5. The organic electroluminescent device according to claim 4, wherein the hole blocking layer is adjacent to the light emitting layer.

6. An organic electroluminescent device, comprising;
an anode;
a cathode; and
a plurality of organic layers intervening between the anode and the cathode and comprising a light emitting layer,
wherein at least one layer of the organic layers includes at least one compound selected from the group consisting of formulae,

1301
Compound 2
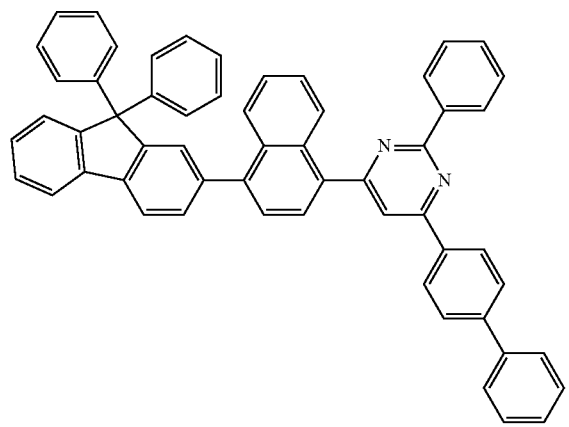
1302
Compound 3
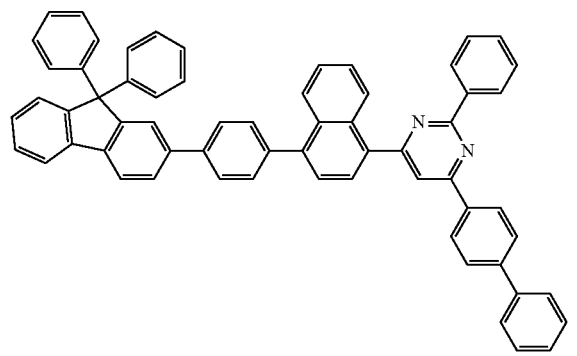
Compound 5
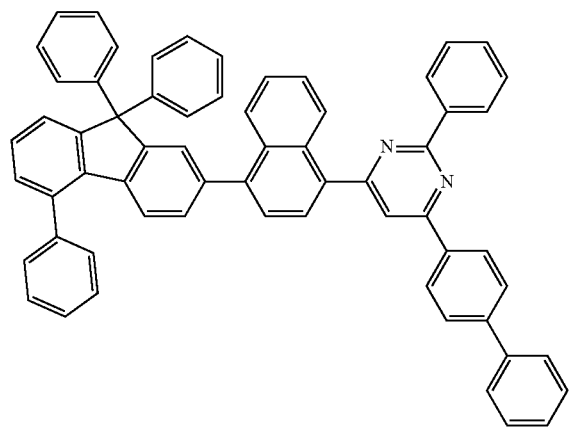
Compound 6
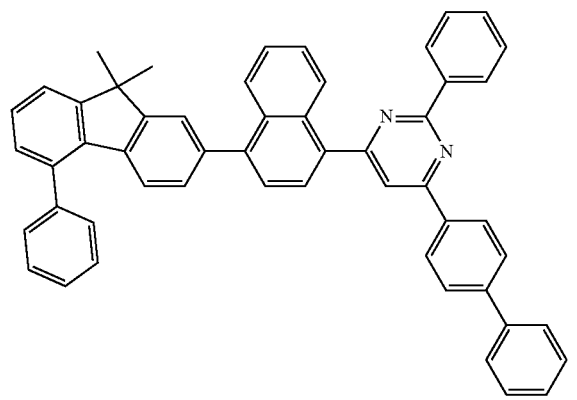
Compound 7
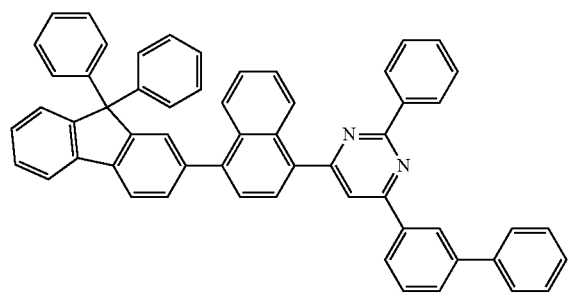
Compound 8
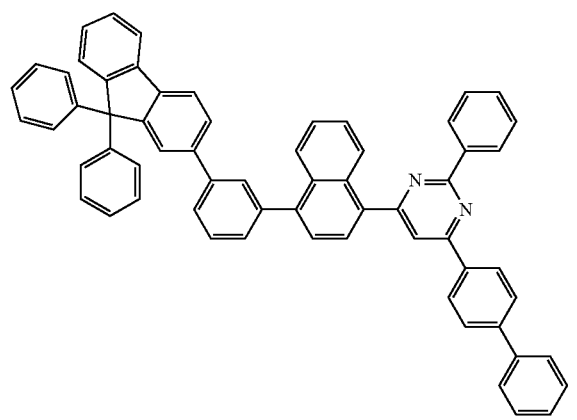

-continued
Compound 10
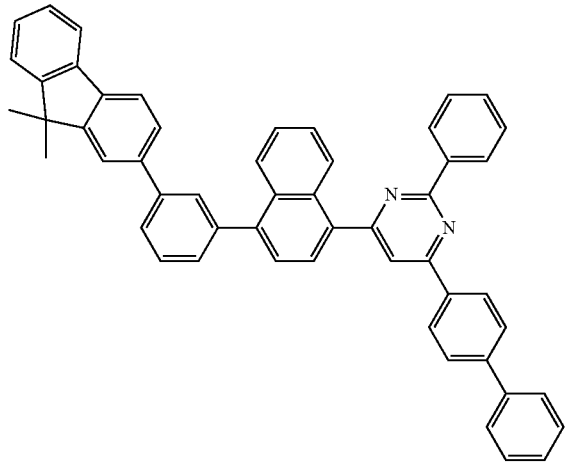
Compound 11
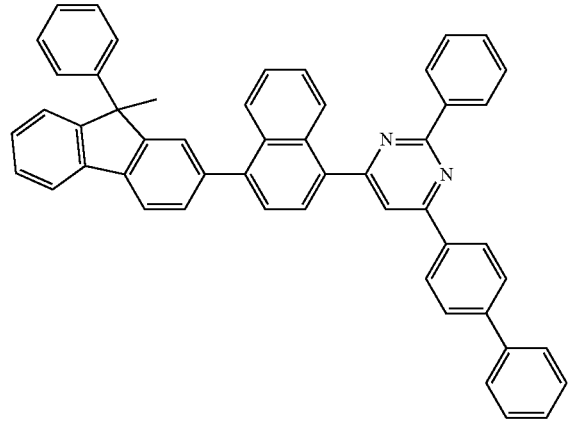
Compound 12
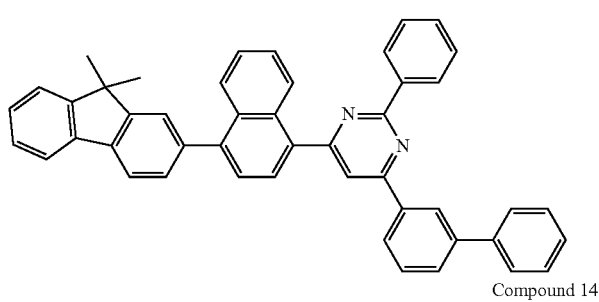
Compound 13
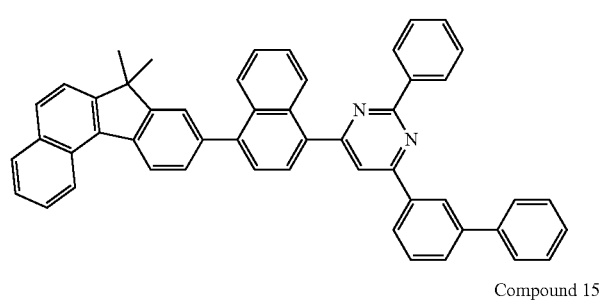
Compound 14
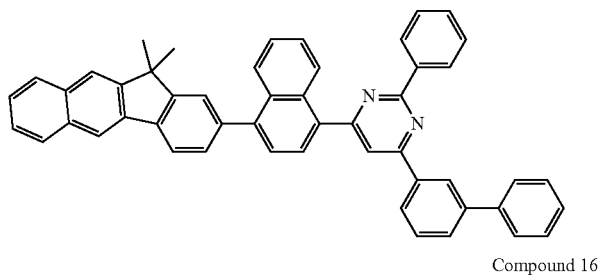
Compound 15
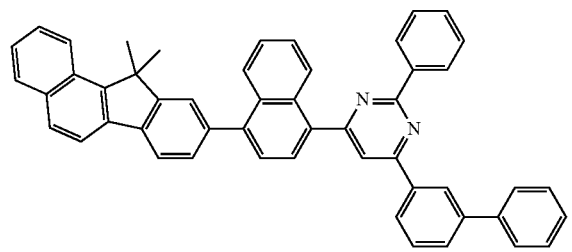
Compound 16
Compound 17
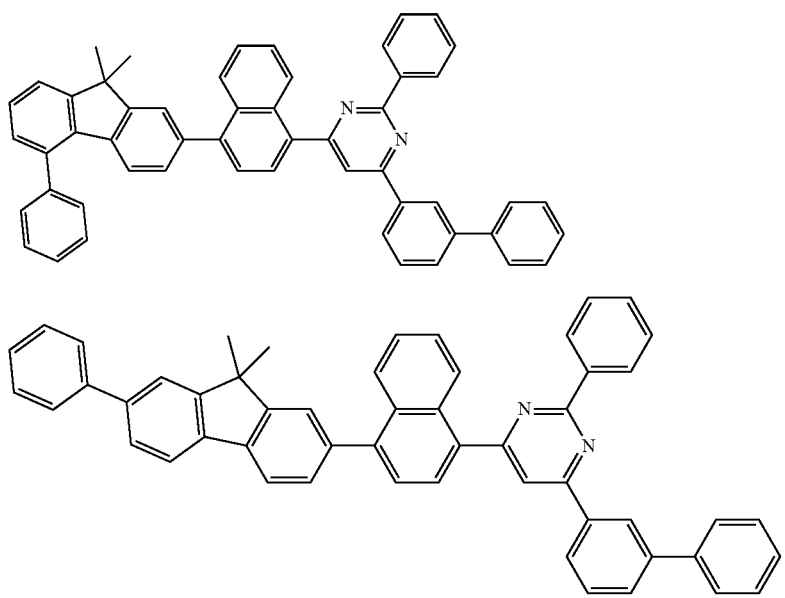

-continued

Compound 18

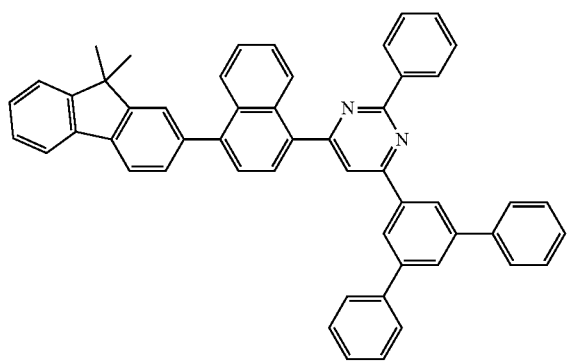

Compound 19

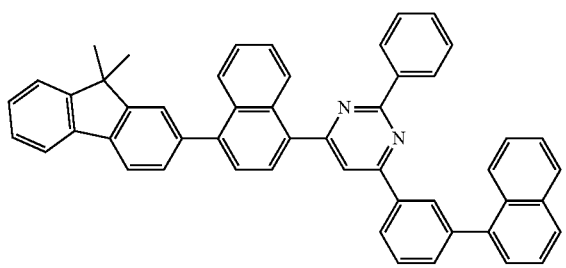

Compound 20

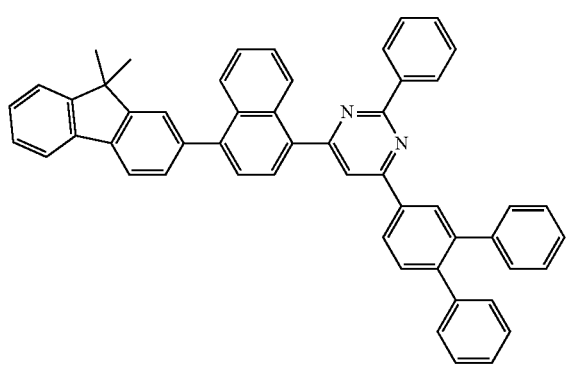

Compound 11

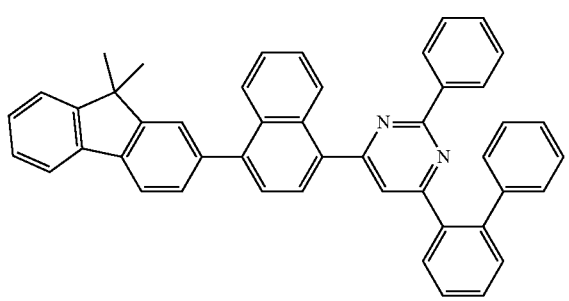

Compound 30

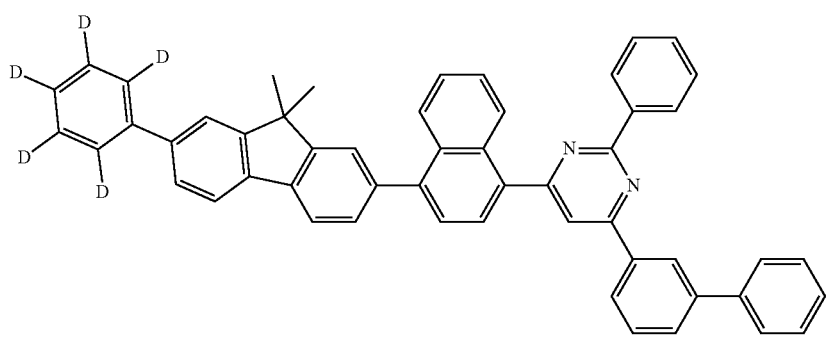

7. The organic electroluminescent device according to claim 6, wherein the organic layers include an electron transporting zone intervening between the cathode and the light emitting layer, and the electron transporting zone comprises the compound.

8. The organic electroluminescent device according to claim 7, wherein the electron transporting zone includes a first electron transporting layer on an anode side and a second electron transporting layer on a cathode side, and the first electron transporting layer, the second electron transporting layer, or both thereof comprises the compound.

9. The organic electroluminescent device according to claim 7, wherein the electron transporting zone further includes a hole blocking layer on a cathode side, and the hole blocking layer comprises the compound.

10. The organic electroluminescent device according to claim 9, wherein the hole blocking layer is adjacent to the light emitting layer.

\* \* \* \* \*

UNITED STATES PATENT AND TRADEMARK OFFICE
CERTIFICATE OF CORRECTION

PATENT NO. : 12,312,317 B2
APPLICATION NO. : 18/050171
DATED : May 27, 2025
INVENTOR(S) : Kei Yoshida et al.

Page 1 of 1

It is certified that error appears in the above-identified patent and that said Letters Patent is hereby corrected as shown below:

In the Claims

In Column 1306, above and to the right of the structure:

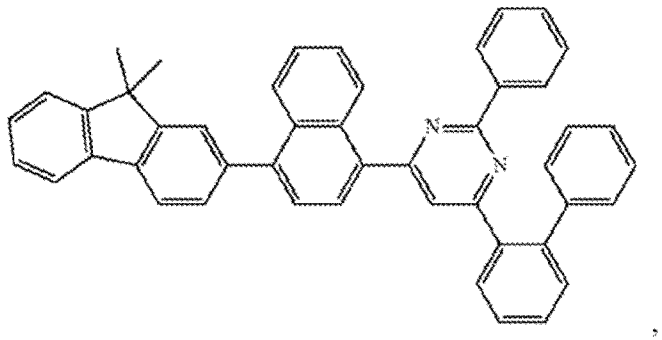

Please delete "Compound 11" and replace it with -- Compound 22 --

Signed and Sealed this
Twenty-second Day of July, 2025

Coke Morgan Stewart
*Acting Director of the United States Patent and Trademark Office*